US010308637B2

(12) United States Patent
McDonald et al.

(10) Patent No.: US 10,308,637 B2
(45) Date of Patent: *Jun. 4, 2019

(54) THERAPEUTIC INHIBITORY COMPOUNDS

(71) Applicant: LifeSci Pharmaceuticals, Inc., St. Michael (BB)

(72) Inventors: Andrew McDonald, New York, NY (US); Shawn Qian, New York, NY (US)

(73) Assignee: LIFESCI PHARMACEUTICALS, INC., Bridgetown, St. Michael (BB)

( * ) Notice: Subject to any disclaimer, the term of this patent is extended or adjusted under 35 U.S.C. 154(b) by 0 days.

This patent is subject to a terminal disclaimer.

(21) Appl. No.: 16/009,093

(22) Filed: Jun. 14, 2018

(65) Prior Publication Data

US 2019/0002437 A1 Jan. 3, 2019

Related U.S. Application Data

(63) Continuation of application No. 15/199,785, filed on Jun. 30, 2016, now Pat. No. 10,023,557.

(60) Provisional application No. 62/190,223, filed on Jul. 8, 2015, provisional application No. 62/187,786, filed on Jul. 1, 2015.

(51) Int. Cl.
C07D 401/14 (2006.01)
C07D 413/14 (2006.01)
C07D 471/04 (2006.01)
C07D 487/04 (2006.01)

(52) U.S. Cl.
CPC ......... C07D 401/14 (2013.01); C07D 413/14 (2013.01); C07D 471/04 (2013.01); C07D 487/04 (2013.01)

(58) Field of Classification Search
CPC .. C07D 401/14; C07D 413/14; C07D 487/04; C07D 471/04
See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |
| 9,533,987 B2 | 1/2017 | Davie et al. | |
| 9,611,252 B2* | 4/2017 | McDonald | C07D 401/14 |
| 1,002,355 A1 | 7/2018 | McDonald et al. | |
| 10,023,557 B2* | 7/2018 | McDonald | C07D 401/14 |
| 2007/0254894 A1 | 11/2007 | Kane et al. | |
| 2009/0099184 A1 | 4/2009 | Delombaert et al. | |
| 2009/0270407 A1 | 10/2009 | Tseng et al. | |
| 2011/0118236 A1 | 5/2011 | Mochizuki et al. | |
| 2011/0124626 A1 | 5/2011 | Pooni et al. | |
| 2012/0035168 A1 | 2/2012 | Brandl et al. | |
| 2014/0350034 A1 | 11/2014 | Brandl et al. | |
| 2014/0378474 A1 | 12/2014 | Flohr et al. | |
| 2016/0108036 A1 | 4/2016 | Davie et al. | |
| 2016/0168123 A1 | 6/2016 | Edwards et al. | |
| 2017/0260163 A1 | 9/2017 | McDonald et al. | |
| 2018/0170906 A1 | 6/2018 | McDonald et al. | |

FOREIGN PATENT DOCUMENTS

| | | |
|---|---|---|
| EP | 2269990 A1 | 1/2011 |
| WO | WO-2005079800 A1 | 9/2005 |
| WO | WO-2008071451 A1 | 6/2008 |
| WO | WO-2009083553 A1 | 7/2009 |
| WO | WO-2009119088 A1 | 10/2009 |
| WO | WO-2010051188 A1 | 5/2010 |
| WO | WO-2010108733 A1 | 9/2010 |
| WO | WO-2013017020 A1 | 2/2013 |
| WO | WO-2013040436 A2 | 3/2013 |
| WO | WO-2013111108 A1 | 8/2013 |
| WO | WO-2014086805 A1 | 6/2014 |
| WO | WO-2014188211 A1 | 11/2014 |
| WO | WO-2015022546 A1 | 2/2015 |
| WO | WO-2015103317 A1 | 7/2015 |
| WO | WO-2016011209 A1 | 1/2016 |
| WO | WO-2016083816 A1 | 6/2016 |
| WO | WO-2017001924 A1 | 1/2017 |
| WO | WO-2018011628 A1 | 1/2018 |

OTHER PUBLICATIONS

Berge et al. Pharmaceutical Salts. Journal of Pharmaceutical Sciences 66(1):1-19 (Jan. 1977).
Bork et al. Treatment of 193 episodes of laryngeal edema with C1 inhibitor concentrate in patients with hereditary angioedema. Arch. Intern. Med. 161:714-718 (2001).
Bork et al. Treatment with C1 inhibitor concentrate in abdominal pain attacks of patients with hereditary angioedema. Transfusion 45:1774-1784 (2005).
Bundgaard et al. Design of Prodrugs pp. 7-9, 21-24 (1985).
Chemical Abstracts Search (15 pgs) (Jul. 7, 2015).
Colman et al. Effect of cleavage of the heavy chain of human plasma kallikrein on its functional properties. Blood 65:311-318 (1985).
Cool. Characterization of the human blood coagulation factor XII gene. Intron/exon gene organization and analysis of the 5'-flanking region. The Journal of Biological Chemistry 262(28):13662-13673 (1987).
Co-pending U.S. Appl. No. 16/016,167, filed Jun. 22, 2018.
Cugno et al. C1-inhibitor deficiency and angioedema: molecular mechanisms and clinical progress. Trends Mol. Med. 15(2):69-78 (2009).
Cugno et al. Generation of plasmin during acute attacks of hereditary angioedema. The Journal of Laboratory and Clinical Medicine 121(1):38--43 (1993).

(Continued)

Primary Examiner — D Margaret M Seaman
(74) Attorney, Agent, or Firm — Wilson Sonsini Goodrich & Rosati

(57) ABSTRACT

Provided herein are heterocyclic derivative compounds and pharmaceutical compositions comprising said compounds that are useful for inhibiting plasma kallikrein. Furthermore, the subject compounds and compositions are useful for the treatment of diseases wherein the inhibition of plasma kallikrein inhibition has been implicated, such as angioedema and the like.

42 Claims, No Drawings

(56) References Cited

OTHER PUBLICATIONS

Evans. Synthesis of radiolabeled compounds. J Radioanal Chem 64(1-2):9-32 (1981).
Gao et al. Extracellular carbonic anhydrase mediates hemorrhagic retinal and cerebral vascular permeability through prekallikrein activation. Nat Med 13(2):181-188 (2007).
Higuchi et al. Pro-drugs as Novel Delivery Systems. A.C.S. Symposium Series vol. 14 (1975).
Kabalka et al. The Synthesis of Radiolabeled Compounds via Organometallic Intermediates. Tetrahedron 45(21):6601-6621 (1989).
Kaplan et al. Angioedema. J. Am. Acad. Dermatol. 53(3):373-388 (2005).
Kaplan et al. The intrinsic coagulation/kinin-forming cascade: assembly in plasma and cell surfaces in inflammation. Advances in Immunology 66:225-272 (1997).
Liu et al. Author response: retinal microglia. Invest. Ophthalmol. Vis. Sci. 54(2):pii (2013).
Liu et al. Hyperoxia causes regression of vitreous neovascularization by downregulating VEGF/VEGFR2 pathway. Invest. Ophthalmol. Vis. Sci. 54(2):918-931 (2013).
Liu et al. Intraocular hemorrhage causes retinal vascular dysfunction via plasma kallikrein. Invest. Ophthalmol. Vis. Sci. 54(2):1086-1094 (2013).
Liu et al. Plasma kallikrein-kinin system and diabetic retinopathy. Biol Chem 394(3):319-328 (2013).
Liu et al. TGFβ 3 signaling induces expression of Gadd45b in retinal ganglion cells. Invest. Ophthalmol. Vis. Sci. 54(2):1061-1069 (2013).
Mehta et al. Signaling mechanisms regulating endothelial permeability. Physiol. Rev. 86(1):279-367 (2006).
Mochizuki et al. Preparation of indazole derivatives as AMPA receptor function enhancing agent. Document No. 151:425739. CAPLUS Accession No. 2009:1204289 (© 2015) (15 pgs).
Muller et al. Novel roles for factor XII-driven plasma contact activation system. Curr. Opin. Hematol. 15:516-521 (2008).
Ny et al. The structure of the human tissue-type plasminogen activator gene: correlation of intron and exon structures to functional and structural domains. PNAS USA 81(17):5355-5359 (1984).
PCT/IB2016/001048 International Preliminary Report on Patentability dated Jan. 11, 2018.
PCT/IB2016/01048 International Search Report and Written Opinion dated Nov. 15, 2016.
PCT/IB2017/000984 International Search Report and Written Opinion dated Dec. 26, 2017.
PCT/US2014/072851 International Preliminary Report on Patentability dated Jul. 14, 2016.
PCT/US2014/072851 International Search Report and Written Opinion dated May 15, 2015.
PCT/US2015/040659 International Preliminary Report on Patentability dated Jan. 26, 2017.
PCT/US2015/040659 International Search Report and Written Opinion dated Oct. 16, 2015.
Phipps et al. Plasma kallikrein mediates angiotensin II type 1 receptor-stimulated retinal vascular permeability. Hypertension 53:175-181 (2009).
Pixley et al. The regulation of human factor XIIa by plasma proteinase inhibitors. The Journal of Biological Chemistry 260(3):1723-1729 (1985).
PubChem-CID-117776872, Create Date: Feb. 23, 2016 (10 pgs).
PubChem-CID-89715158, Create Date: Feb. 13, 2015 (11 pgs).
Sandoval et al. Ca(2+) signalling and PKCalpha activate increased endothelial permeability by disassembly of VE-cadherin junctions. J. Physiol. 533(pt 2):433-445 (2001).
Schapira et al. Protection of human plasma kallikrein from inactivation by C1 inhibitor and other protease inhibitors. The role of high molecular weight kininogen. Biochemistry 20:2738-2743 (1981).
Stahl et al. Handbook of Pharmaceutical Salts. Verlag Helvetica Chimica Acta, Zurich, 2002.
Stavrou. Factor XII: what does it contribute to our understanding of the physiology and pathophysiology of hemostasis & thrombosis. Thrombosis Research 125(3):210-215 (2010).
Storini et al. Selective Inhibition of Plasma Kallikrein Protects brain from Reperfusion Injury. JPET 381:849-954 (2006).
Ulven et al. 6-Acylamino-2-amino-4-methylquinolines as potent melanin-concentrating hormone 1 receptor antagonists: structure-activity exploration of eastern and western parts. Bioorg Med Chem Lett 16(4):1070-1075 (2006).
U.S. Appl. No. 14/800,631 1st Action Interview dated May 30, 2018.
U.S. Appl. No. 15/042,102 1st Action Interview dated Apr. 27, 2016.
U.S. Appl. No. 15/042,102 Office Action dated Oct. 13, 2016.
U.S. Appl. No. 15/199,785 Office Action dated Apr. 10, 2017.
U.S. Appl. No. 15/199,785 Office Action dated Nov. 24, 2017.
U.S. Appl. No. 15/470,736 Office Action dated Apr. 26, 2018.
File History for co-pending U.S. Appl. No. 14/800,631, filed Jul. 15, 2015.
File History for co-pending U.S. Appl. No. 15/470,736, filed Mar. 27, 2017.
File History for co-pending U.S. Appl. No. 16/016,167, filed Jun. 22, 2018.
File History for U.S. Pat. No. 10,023,557, issued Jul. 17, 2018 (U.S. Appl. No. 15/199,785, filed Jun. 30, 2016).
File History for U.S. Pat. No. 9,611,252, issued Apr. 4, 2017 (U.S. Appl. No. 15/042,102, filed Feb. 11, 2016).
U.S. Appl. No. 16/016,167 Office Action dated Sep. 7, 2018.

\* cited by examiner

THERAPEUTIC INHIBITORY COMPOUNDS

CROSS REFERENCE

This application is a continuation of U.S. application Ser. No. 15/199,785, filed Jun. 30, 2016, which claims the benefit of U.S. Provisional Application No. 62/190,223, filed Jul. 8, 2015, and U.S. Provisional Application No. 62/187,786, filed Jul. 1, 2015, the contents of which are hereby incorporated by reference in their entireties.

BACKGROUND

A need exists in the medicinal arts for the effective treatment of diseases and disorders related to the vascular system. Such diseases and disorders include, but are not limited to, angioedema, macular edema and brain edema.

BRIEF SUMMARY OF THE INVENTION

Provided herein are heterocyclic derivative compounds and pharmaceutical compositions comprising said compounds. The subject compounds and compositions are useful for inhibiting plasma kallikrein.

One embodiment provides a compound, or a pharmaceutically acceptable salt thereof, having the structure of Formula (I):

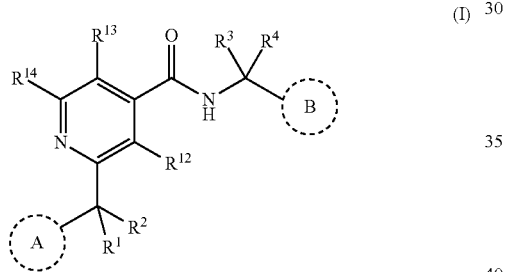

wherein,
  Ring A is an optionally substituted bicyclic heteroaryl ring;
  Ring B is an optionally substituted monocyclic heteroaryl ring or optionally substituted bicyclic heteroaryl ring;
  each $R^{12}$, $R^{13}$, or $R^{14}$ is independently selected from hydrogen, cyano, halo, hydroxy, azido, amino, nitro, —$CO_2H$, —S(O)—$R^{20}$, —S—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —C(=$NR^{22}$)—$(NR^{21})_2$, or optionally substituted alkynyl;
  each $R^1$ or $R^2$ is independently selected from hydrogen, halo, hydroxy, amino, —$CO_2H$, —S(O)—$R^{20}$, —S—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —C(=$NR^{22}$)—$(NR^{21})_2$, or optionally substituted alkynyl; or optionally, $R^1$ and $R^2$ are optionally substituted C1-C5 alkyl and join to form a ring; or optionally, $R^1$ and $R^2$ together form an oxo;
  each $R^3$ or $R^4$ is independently selected from hydrogen, —$CO_2H$, optionally substituted alkyl, optionally substituted cycloalkyl, optionally substituted alkenyl, optionally substituted aryl, optionally substituted heteroaryl, optionally substituted heterocyclyl, —CO—$R^{20}$, —$CO_2$—$R^{20}$, —$CO(NR^{21})_2$, —$SO_2(NR^{21})_2$, —C(=$NR^{22}$)—$(NR^{21})_2$, or optionally substituted alkynyl; or optionally, $R^3$ and $R^4$ are optionally substituted C1-C5 alkyl and join to form a ring;
  each $R^{20}$ is selected from optionally substituted alkyl, optionally substituted cycloalkyl, optionally substituted aryl, optionally substituted heteroaryl, or optionally substituted heterocyclyl;
  each $R^{21}$ is selected from hydrogen, optionally substituted alkyl, optionally substituted cycloalkyl, optionally substituted aryl, optionally substituted heteroaryl, or optionally substituted heterocyclyl; and
  each $R^{22}$ is selected from hydrogen, —CN, optionally substituted alkyl, optionally substituted cycloalkyl, optionally substituted aryl, optionally substituted heteroaryl, or optionally substituted heterocyclyl; with the provision that the compound of Formula (I) is not 2-[[4,5,6,7-tetrahydro-3-(trifluoromethyl)-1H-indazol-1-yl]methyl]-N-(2-thienylmethyl)-4-pyridinecarboxamide.

One embodiment provides a compound, or a pharmaceutically acceptable salt thereof, having the structure of Formula (Ia):

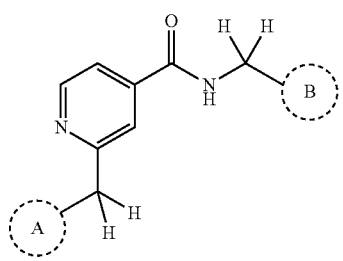

wherein,
  Ring A is an optionally substituted bicyclic heteroaryl ring; and
  Ring B is an optionally substituted monocyclic heteroaryl ring or optionally substituted bicyclic heteroaryl ring; with the provision that the compound of Formula (Ia) is not 2-[[4,5,6,7-tetrahydro-3-(trifluoromethyl)-1H-indazol-1-yl]methyl]-N-(2-thienylmethyl)-4-pyridinecarboxamide.

One embodiment provides a pharmaceutical composition comprising a compound of Formula (I), or a pharmaceutically acceptable salt thereof, and a pharmaceutically acceptable excipient.

One embodiment provides a method of inhibiting kallikrein enzyme comprising contacting the kallikrein enzyme with a compound of Formula (I).

One embodiment provides a method for treating angioedema in a patient in need thereof comprising administering to the patient a composition comprising a compound of Formula (I), or a pharmaceutically acceptable salt thereof.

One embodiment provides a pharmaceutical composition comprising a compound of Formula (Ia), or a pharmaceutically acceptable salt thereof, and a pharmaceutically acceptable excipient.

One embodiment provides a method of inhibiting kallikrein enzyme comprising contacting the kallikrein enzyme with a compound of Formula (Ia).

One embodiment provides a method for treating angioedema in a patient in need thereof comprising administering to the patient a composition comprising a compound of Formula (Ia), or a pharmaceutically acceptable salt thereof.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC (O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group is through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

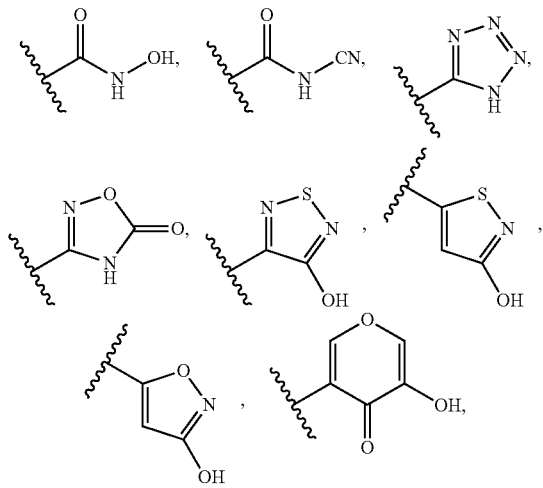

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

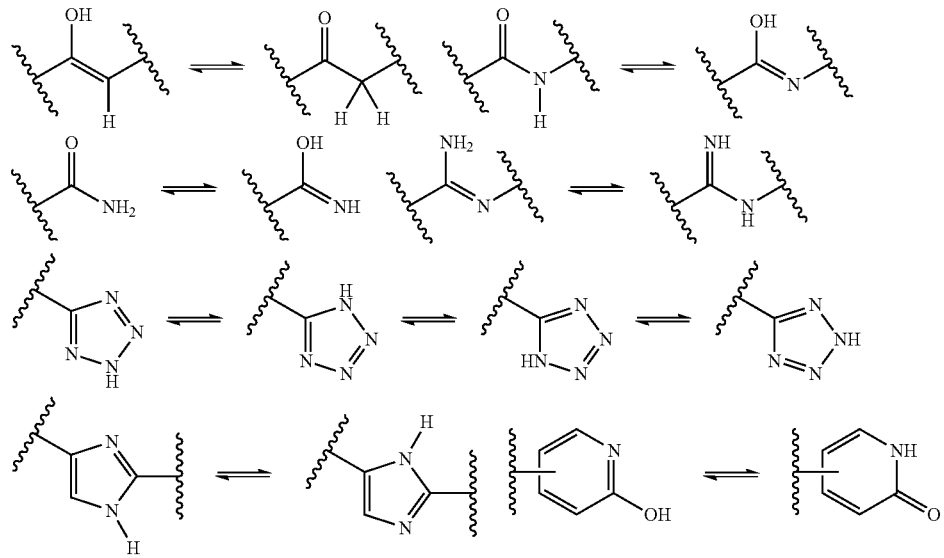

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, Deuterated starting materials are readily available and are subjected to the synthetic methods described herein to provide for the synthesis of deuterium-containing compounds. Large numbers of deuterium-containing reagents and building blocks are available commerically from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

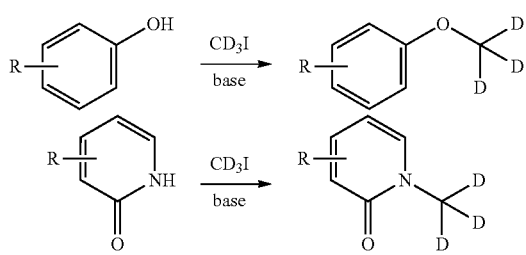

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

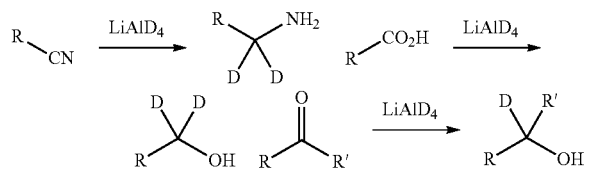

Deuterium gas and palladium catalyst are employed to reduce unsaturated carbon-carbon linkages and to perform a reductive substitution of aryl carbon-halogen bonds as illustrated, by way of example only, in the reaction schemes below.

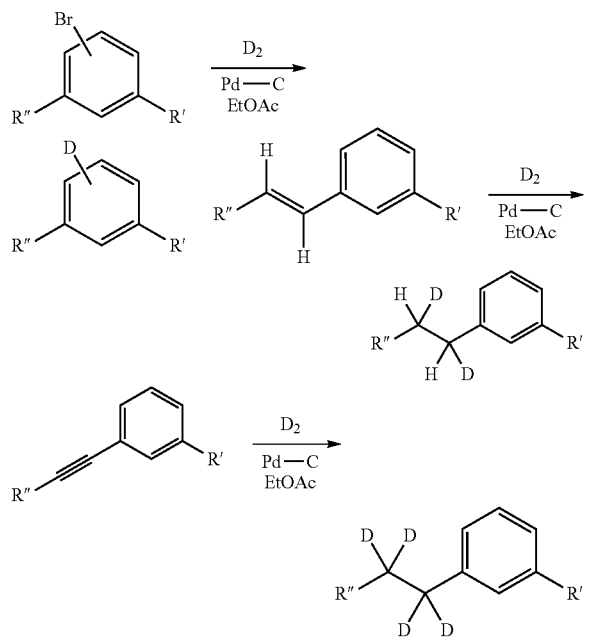

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the kallikrein inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Kallikrein Inhibitory Compounds

Provided herein are heterocyclic derivative compounds and pharmaceutical compositions comprising said compounds. The subject compounds and compositions are useful for inhibiting plasma kallikrein.

One embodiment provides a compound, or a pharmaceutically acceptable salt thereof, having the structure of Formula (I):

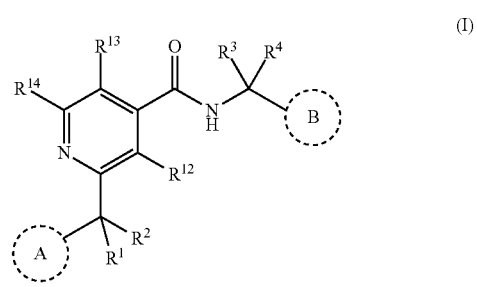

wherein

Ring A is an optionally substituted bicyclic heteroaryl ring;

Ring B is an optionally substituted monocyclic heteroaryl ring or optionally substituted bicyclic heteroaryl ring;

each $R^{12}$, $R^{13}$, or $R^{14}$ is independently selected from hydrogen, cyano, halo, hydroxy, azido, amino, nitro, —$CO_2H$, —S(O)—$R^{20}$, —S—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —C(=$NR^{22}$)—$(NR^{21})_2$, or optionally substituted alkynyl;

each $R^1$ or $R^2$ is independently selected from hydrogen, halo, hydroxy, amino, —$CO_2H$, —S(O)—$R^{20}$, —S—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —C(=$NR^{22}$)—$(NR^{21})_2$, or optionally substituted alkynyl; or optionally, $R^1$ and $R^2$ are optionally substituted C1-C5 alkyl and join to form a ring; or optionally, $R^1$ and $R^2$ together form an oxo;

each $R^3$ or $R^4$ is independently selected from hydrogen, —$CO_2H$, optionally substituted alkyl, optionally substituted cycloalkyl, optionally substituted alkenyl, optionally substituted aryl, optionally substituted heteroaryl, optionally substituted heterocyclyl, —CO—$R^{20}$, —$CO_2$—$R^{20}$, —$CO(NR^{21})_2$, —$SO_2(NR^{21})_2$, —C(=$NR^{22}$)—$(NR^{21})_2$, or optionally substituted alkynyl; or optionally, $R^3$ and $R^4$ are optionally substituted C1-C5 alkyl and join to form a ring;

each $R^{20}$ is selected from optionally substituted alkyl, optionally substituted cycloalkyl, optionally substituted aryl, optionally substituted heteroaryl, or optionally substituted heterocyclyl;

each $R^{21}$ is selected from hydrogen, optionally substituted alkyl, optionally substituted cycloalkyl, optionally substituted aryl, optionally substituted heteroaryl, or optionally substituted heterocyclyl; and each $R^{22}$ is selected from hydrogen, —CN, optionally substituted alkyl, optionally substituted cycloalkyl, optionally substituted aryl, optionally substituted heteroaryl, or optionally substituted heterocyclyl; with the provision that the compound of Formula (I) is not 2-[[4,5,6,7-tetrahydro-3-(trifluoromethyl)-1H-indazol-1-yl]methyl]-N-(2-thienylmethyl)-4-pyridinecarboxamide.

Another embodiment provides the compound, or a pharmaceutically acceptable salt thereof, having the structure of Formula (I), wherein Ring A is an optionally substituted bicyclic heteroaryl ring.

Another embodiment provides the compound, or a pharmaceutically acceptable salt thereof, having the structure of Formula (I), wherein Ring B is an optionally substituted monocyclic heteroaryl ring.

Another embodiment provides the compound, or a pharmaceutically acceptable salt thereof, having the structure of Formula (I), wherein Ring B is an optionally substituted bicyclic heteroaryl ring.

Another embodiment provides the compound, or a pharmaceutically acceptable salt thereof, having the structure of Formula (I), wherein $R^{12}$ is hydrogen.

Another embodiment provides the compound, or a pharmaceutically acceptable salt thereof, having the structure of Formula (I), wherein $R^{14}$ is independently selected from —S(O)—$R^{20}$, —S—$R^{20}$, —S(O)$_2$—$R^{20}$, optionally substituted alkoxy, optionally substituted aryloxy, optionally substituted heteroaryloxy, optionally substituted (heterocyclyl)-O—, optionally substituted heteroaryl, optionally substituted heterocyclyl, optionally substituted alkylamino, optionally substituted dialkylamino, —CO—$R^{20}$, —CO$_2$—$R^{20}$, —CO(NR$^{21}$)$_2$, —SO$_2$(NR$^{21}$)$_2$, or —C(=NR$^{22}$)—(NR$^{21}$)$_2$. Another embodiment provides the compound, or a pharmaceutically acceptable salt thereof, having the structure of Formula (I), wherein $R^{14}$ is independently selected from optionally substituted alkyl, optionally substituted cycloalkyl, optionally substituted alkenyl, optionally substituted aryl, optionally substituted heteroaryl, optionally substituted heterocyclyl, or optionally substituted alkynyl. Another embodiment provides the compound, or a pharmaceutically acceptable salt thereof, having the structure of Formula (I), wherein $R^{14}$ is hydrogen. Another embodiment provides the compound, or a pharmaceutically acceptable salt thereof, having the structure of Formula (I), wherein $R^{14}$ is optionally substituted alkyl, or optionally substituted cycloalkyl.

Another embodiment provides the compound, or a pharmaceutically acceptable salt thereof, having the structure of Formula (I), wherein $R^{13}$ is independently selected from —S(O)—$R^{20}$, —S—$R^{20}$, —S(O)$_2$—$R^{20}$, optionally substituted alkoxy, optionally substituted aryloxy, optionally substituted heteroaryloxy, optionally substituted (heterocyclyl)-O—, optionally substituted heteroaryl, optionally substituted heterocyclyl, optionally substituted alkylamino, optionally substituted dialkylamino, —CO—$R^{20}$, —CO$_2$—$R^{20}$, —CO(NR$^{21}$)$_2$, —SO$_2$(NR$^{21}$)$_2$, or —C(=NR$^{22}$)—(NR$^{21}$)$_2$. Another embodiment provides the compound, or a pharmaceutically acceptable salt thereof, having the structure of Formula (I), wherein $R^{13}$ is independently selected from optionally substituted alkyl, optionally substituted cycloalkyl, optionally substituted alkenyl, optionally substituted aryl, optionally substituted heteroaryl, optionally substituted heterocyclyl, or optionally substituted alkynyl. Another embodiment provides the compound, or a pharmaceutically acceptable salt thereof, having the structure of Formula (I), wherein $R^{13}$ is hydrogen. Another embodiment provides the compound, or a pharmaceutically acceptable salt thereof, having the structure of Formula (I), wherein $R^{13}$ is optionally substituted alkyl, or optionally substituted cycloalkyl.

Another embodiment provides the compound, or a pharmaceutically acceptable salt thereof, having the structure of Formula (I), wherein $R^3$ and $R^4$ are hydrogen. Another embodiment provides the compound, or a pharmaceutically acceptable salt thereof, having the structure of Formula (I), wherein $R^3$ is hydrogen. Another embodiment provides the compound, or a pharmaceutically acceptable salt thereof, having the structure of Formula (I), wherein $R^4$ is hydrogen. Another embodiment provides the compound, or a pharmaceutically acceptable salt thereof, having the structure of Formula (I), wherein $R^3$ is optionally substituted alkyl. Another embodiment provides the compound, or a pharmaceutically acceptable salt thereof, having the structure of Formula (I), wherein $R^4$ is optionally substituted alkyl.

Another embodiment provides the compound, or a pharmaceutically acceptable salt thereof, having the structure of Formula (I), wherein $R^1$ and $R^2$ are hydrogen. Another embodiment provides the compound, or a pharmaceutically acceptable salt thereof, having the structure of Formula (I), wherein $R^1$ is hydrogen. Another embodiment provides the compound, or a pharmaceutically acceptable salt thereof, having the structure of Formula (I), wherein $R^2$ is hydrogen. Another embodiment provides the compound, or a pharmaceutically acceptable salt thereof, having the structure of Formula (I), wherein $R^1$ is optionally substituted alkyl. Another embodiment provides the compound, or a pharmaceutically acceptable salt thereof, having the structure of Formula (I), wherein $R^2$ is optionally substituted alkyl. Another embodiment provides the compound, or a pharmaceutically acceptable salt thereof, having the structure of Formula (I), wherein $R^1$ is optionally substituted alkoxy. Another embodiment provides the compound, or a pharmaceutically acceptable salt thereof, having the structure of Formula (I), wherein $R^2$ is optionally substituted alkoxy.

One embodiment provides a compound, or a pharmaceutically acceptable salt thereof, having the structure of Formula (Ia):

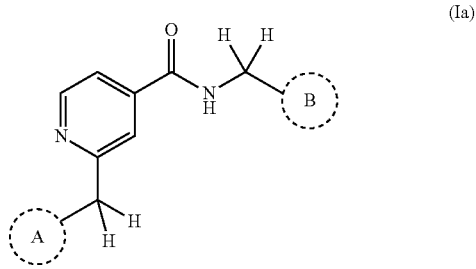

(Ia)

wherein,
  Ring A is an optionally substituted bicyclic heteroaryl ring; and
  Ring B is an optionally substituted monocyclic heteroaryl ring or optionally substituted bicyclic heteroaryl ring; with the provision that the compound of Formula (Ia) is not 2-[[4,5,6,7-tetrahydro-3-(trifluoromethyl)-1H-indazol-1-yl]methyl]-N-(2-thienylmethyl)-4-pyridinecarboxamide.

Another embodiment provides the compound, or a pharmaceutically acceptable salt thereof, having the structure of Formula (Ia), wherein Ring A is an optionally substituted bicyclic heteroaryl ring.

Another embodiment provides the compound, or a pharmaceutically acceptable salt thereof, having the structure of Formula (Ia), wherein Ring B is an optionally substituted monocyclic heteroaryl ring.

Another embodiment provides the compound, or a pharmaceutically acceptable salt thereof, having the structure of Formula (Ia), wherein Ring B is an optionally substituted bicyclic heteroaryl ring.

Another embodiment provides the compound, or a pharmaceutically acceptable salt thereof, having the structure of Formula (I) or (Ia), wherein Ring B is not thiophenyl.

Another embodiment provides the compound, or a pharmaceutically acceptable salt thereof, having the structure of Formula (I) or (Ia), wherein Ring A is not tetrahydro-1H-indazol-1-yl.

Another embodiment provides the compound, or a pharmaceutically acceptable salt thereof, having the structure of Formula (I) or (Ia), wherein Ring A is selected from optionally substituted quinolyl, optionally substituted indolyl, optionally substituted indazolyl, optionally substituted benzimidazolyl, optionally substituted isoquinolyl, optionally substituted cinnolinyl, optionally substituted phthalazinyl, optionally substituted quinazolinyl, optionally substituted naphthyridinyl, or optionally substituted benzoisoxazolyl. Another embodiment provides the compound, or a pharmaceutically acceptable salt thereof, having the structure of Formula (I) or (Ia), wherein Ring A is selected from optionally substituted benzo[d]isoxazol-7-yl, optionally substituted 4-aminoquinazolin-5-yl, optionally substituted indol-5-yl; optionally substituted quinolin-3-yl; quinoxalin-2-yl; optionally substituted isoquinolin-1(2H)-on-2-yl; or optionally substituted quinolin-6-yl. Another embodiment provides the compound, or a pharmaceutically acceptable salt thereof, having the structure of Formula (I) or (Ia), wherein Ring A is an optionally substituted quinolin-6-yl. Another embodiment provides the compound, or a pharmaceutically acceptable salt thereof, having the structure of Formula (I) or (Ia), wherein the optionally substituted quinolin-6-yl is substituted with at least one substituent selected from optionally substituted C1-C3 alkyl, halogen, —CN, —SO$_2$Me, —SO$_2$NH$_2$, —CONH$_2$, —CH$_2$NHAc, —CO$_2$Me, —CO$_2$H, —CH$_2$OH, —CH$_2$NH$_2$, —NH$_2$, —OH, or —OMe. Another embodiment provides the compound, or a pharmaceutically acceptable salt thereof, having the structure of Formula (I) or (Ia), wherein the optionally substituted quinolin-6-yl is substituted at least at the 3-position. Another embodiment provides the compound, or a pharmaceutically acceptable salt thereof, having the structure of Formula (I) or (Ia), wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl. Another embodiment provides the compound, or a pharmaceutically acceptable salt thereof, having the structure of Formula (I) or (Ia), wherein Ring A is an optionally substituted quinolin-3-yl. Another embodiment provides the compound, or a pharmaceutically acceptable salt thereof, having the structure of Formula (I) or (Ia), wherein the optionally substituted quinolin-3-yl is substituted at least at the 6-position or the 7-position. Another embodiment provides the compound, or a pharmaceutically acceptable salt thereof, having the structure of Formula (I) or (Ia), wherein the optionally substituted quinolin-3-yl is substituted with at least one substituent selected from optionally substituted C1-C3 alkyl, halogen, —CN, —SO$_2$Me, —SO$_2$NH$_2$, —CONH$_2$, —CH$_2$NHAc, —CO$_2$Me, —CO$_2$H, —CH$_2$OH, —CH$_2$NH$_2$, —NH$_2$, —OH, or —OMe.

Another embodiment provides the compound, or a pharmaceutically acceptable salt thereof, having the structure of Formula (I) or (Ia), wherein Ring B is selected from an optionally substituted monocyclic heteroaryl ring. Another embodiment provides the compound, or a pharmaceutically acceptable salt thereof, having the structure of Formula (I) or (Ia), wherein the optionally substituted monocyclic heteroaryl ring is selected from optionally substituted imidazolyl, optionally substituted pyrazolyl, optionally substituted pyridinyl, optionally substituted pyridazinyl, optionally substituted pyrimidinyl, or optionally substituted pyrazinyl. Another embodiment provides the compound, or a pharmaceutically acceptable salt thereof, having the structure of Formula (I) or (Ia), wherein the optionally substituted monocyclic heteroaryl ring is an optionally substituted pyridinyl. Another embodiment provides the compound, or a pharmaceutically acceptable salt thereof, having the structure of Formula (I) or (Ia), wherein the optionally substituted pyridinyl is an optionally substituted aminopyridinyl. Another embodiment provides the compound, or a pharmaceutically acceptable salt thereof, having the structure of Formula (I) or (Ia), wherein the optionally substituted aminopyridinyl is an optionally substituted 6-aminopyridin-3-yl. Another embodiment provides the compound, or a pharmaceutically acceptable salt thereof, having the structure of Formula (I) or (Ia), wherein Ring B is selected from an optionally substituted bicyclic heteroaryl ring. Another embodiment provides the compound, or a pharmaceutically acceptable salt thereof, having the structure of Formula (I) or (Ia), wherein the optionally substituted bicyclic heteroaryl ring is selected from optionally substituted quinolinyl, optionally substituted isoquinolinyl, optionally substituted quinazolinyl, optionally substituted indolyl, optionally substituted indazolyl, optionally substituted 1H-pyrrolo[2,3-b]pyridinyl, optionally substituted benzoxazolyl, optionally substituted benzoisoxazolyl, or optionally substituted benzimidazolyl. Another embodiment provides the compound, or a pharmaceutically acceptable salt thereof, having the structure of Formula (I) or (Ia), wherein the optionally substituted bicyclic heteroaryl ring is an optionally substituted indolyl. Another embodiment provides the compound, or a pharmaceutically acceptable salt thereof, having the structure of Formula (I) or (Ia), wherein the optionally substituted bicyclic heteroaryl ring is an optionally substituted indazolyl. Another embodiment provides the compound, or a pharmaceutically acceptable salt thereof, having the structure of Formula (I) or (Ia), wherein the optionally substituted indolyl is an optionally substituted indol-5-yl. Another embodiment provides the compound, or a pharmaceutically acceptable salt thereof, having the structure of Formula (I) or (Ia), wherein the optionally substituted indazolyl is an optionally substituted indazol-5-yl. Another embodiment provides the compound, or a pharmaceutically acceptable salt thereof, having the structure of Formula (I) or (Ia), wherein the optionally substituted bicyclic heteroaryl ring is an optionally substituted 1H-pyrrolo[2,3-b]pyridinyl. Another embodiment provides the compound, or a pharmaceutically acceptable salt thereof, having the structure of Formula (I) or (Ia), wherein the optionally substituted bicyclic heteroaryl ring is benzothiophenyl. Another embodiment provides the compound, or a pharmaceutically acceptable salt thereof, having the structure of Formula (I) or (Ia), wherein Ring A is selected from optionally substituted quinolyl; and Ring B is selected from an optionally substituted indolyl, an optionally substituted indazolyl, and an optionally substituted 1H-pyrrolo[2,3-b]pyridinyl.

One embodiment provides a compound, or a pharmaceutically acceptable salt thereof, having the structure of Formula (II):

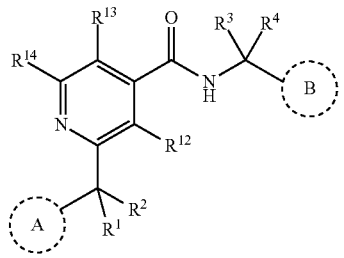

(II)

wherein,

Ring A is chosen from optionally substituted quinolyl, optionally substituted indolyl, optionally substituted indazolyl, optionally substituted benzimidazolyl, optionally substituted isoquinolyl, optionally substituted cinnolinyl, optionally substituted phthalazinyl, optionally substituted quinazolinyl, optionally substituted naphthyridinyl, or optionally substituted benzoisoxazolyl;

Ring B is an optionally substituted aryl ring;

each $R^{12}$, $R^{13}$, or $R^{14}$ is independently selected from hydrogen, cyano, halo, hydroxy, azido, amino, nitro, —$CO_2H$, —$S(O)$—$R^{20}$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl;

each $R^1$ or $R^2$ is independently selected from hydrogen, halo, hydroxy, amino, —$CO_2H$, —$S(O)$—$R^{20}$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl; or optionally, $R^1$ and $R^2$ are optionally substituted C1-C5 alkyl and join to form a ring; or optionally, $R^1$ and $R^2$ together form an oxo;

each $R^3$ or $R^4$ is independently selected from hydrogen, —$CO_2H$, optionally substituted alkyl, optionally substituted cycloalkyl, optionally substituted alkenyl, optionally substituted aryl, optionally substituted heteroaryl, optionally substituted heterocyclyl, —CO—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl; or optionally, $R^3$ and $R^4$ are optionally substituted C1-C5 alkyl and join to form a ring;

each $R^{20}$ is selected from optionally substituted alkyl, optionally substituted cycloalkyl, optionally substituted aryl, optionally substituted heteroaryl, or optionally substituted heterocyclyl;

each $R^{21}$ is selected from hydrogen, optionally substituted alkyl, optionally substituted cycloalkyl, optionally substituted aryl, optionally substituted heteroaryl, or optionally substituted heterocyclyl; and each R22 is selected from hydrogen, —CN, optionally substituted alkyl, optionally substituted cycloalkyl, optionally substituted aryl, optionally substituted heteroaryl, or optionally substituted heterocyclyl.

Another embodiment provides the compound, or a pharmaceutically acceptable salt thereof, having the structure of Formula (II), wherein Ring A is selected from optionally substituted benzo[d]isoxazol-7-yl, optionally substituted 4-aminoquinazolin-5-yl, optionally substituted indol-5-yl; optionally substituted quinolin-3-yl; quinoxalin-2-yl; optionally substituted isoquinolin-1(2H)-on-2-yl; or optionally substituted quinolin-6-yl. Another embodiment provides the compound, or a pharmaceutically acceptable salt thereof, having the structure of Formula (II), wherein Ring A is an optionally substituted quinolin-6-yl. Another embodiment provides the compound, or a pharmaceutically acceptable salt thereof, having the structure of Formula (II), wherein the optionally substituted quinolin-6-yl is substituted with at least one substituent selected from optionally substituted C1-C3 alkyl, halogen, —CN, —$SO_2Me$, —$SO_2NH_2$, —$CONH_2$, —$CH_2NHAc$, —$CO_2Me$, —$CO_2H$, —$CH_2OH$, —$CH_2NH_2$, —$NH_2$, —OH, or —OMe. Another embodiment provides the compound, or a pharmaceutically acceptable salt thereof, having the structure of Formula (II), wherein the optionally substituted quinolin-6-yl is substituted at least at the 3-position. Another embodiment provides the compound, or a pharmaceutically acceptable salt thereof, having the structure of Formula (II), wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl. Another embodiment provides the compound, or a pharmaceutically acceptable salt thereof, having the structure of Formula (II), wherein Ring A is an optionally substituted quinolin-3-yl. Another embodiment provides the compound, or a pharmaceutically acceptable salt thereof, having the structure of Formula (II), wherein the optionally substituted quinolin-3-yl is substituted at least at the 6-position or the 7-position. Another embodiment provides the compound, or a pharmaceutically acceptable salt thereof, having the structure of Formula (II), wherein the optionally substituted quinolin-3-yl is substituted with at least one substituent selected from optionally substituted C1-C3 alkyl, halogen, —CN, —$SO_2Me$, —$SO_2NH_2$, —$CONH_2$, —$CH_2NHAc$, —$CO_2Me$, —$CO_2H$, —$CH_2OH$, —$CH_2NH_2$, —$NH_2$, —OH, or —OMe.

Another embodiment provides the compound, or a pharmaceutically acceptable salt thereof, having the structure of Formula (II), wherein Ring A is a phenyl substituted with aminoalkyl. Another embodiment provides the compound, or a pharmaceutically acceptable salt thereof, having the structure of Formula (II), wherein Ring A is a phenyl substituted with aminomethyl. Another embodiment provides the compound, or a pharmaceutically acceptable salt thereof, having the structure of Formula (II), wherein Ring A is a phenyl substituted with aminoalkyl at the para-position. Another embodiment provides the compound, or a pharmaceutically acceptable salt thereof, having the structure of Formula (II), wherein Ring A is a 4-aminomethyl-2,6-dimethylphenyl group.

In some embodiments, the kallikrein inhibitory compound described herein has a structure provided in Table 1.

TABLE 1

| Chemical Synthesis Example | Structure | Name |
|---|---|---|
| 1 | 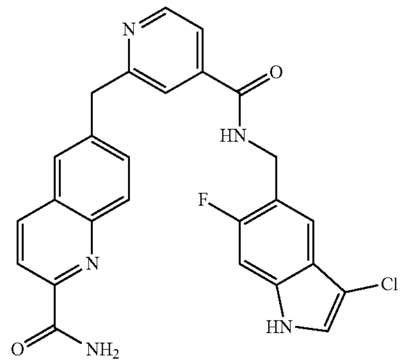 [SMILES: NC(=O)c1ccc2cc(Cc3cc(C(=O)NCc4cc5c(Cl)c[nH]c5cc4F)ccn3)ccc2n1] | 6-((4-(((3-chloro-6-fluoro-1H-indol-5-yl)methyl)carbamoyl)pyridin-2-yl)methyl)quinoline-2-carboxamide |
| 2 | 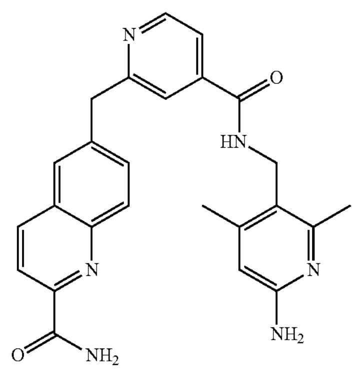 [SMILES: Cc1cc(N)nc(C)c1CNC(=O)c1ccnc(Cc2ccc3nc(C(N)=O)ccc3c2)c1] | 6-((4-(((6-amino-2,4-dimethylpyridin-3-yl)methyl)carbamoyl)pyridin-2-yl)methyl)quinoline-2-carboxamide |
| 3 | 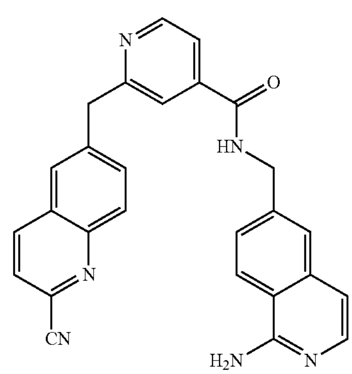 [SMILES: N#Cc1ccc2cc(Cc3cc(C(=O)NCc4ccc5c(N)nccc5c4)ccn3)ccc2n1] | N-((1-aminoisoquinolin-6-yl)methyl)-2-((2-cyanoquinolin-6-yl)methyl)isonicotinamide |

TABLE 1-continued

| Chemical Synthesis Example | Structure | Name |
|---|---|---|
| 4 | 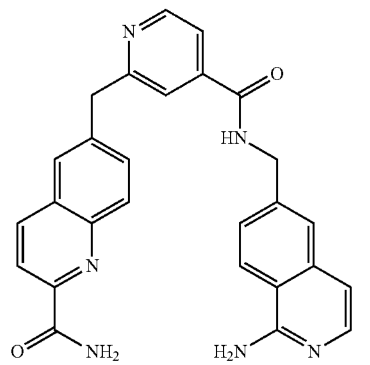 [SMILES: NC(=O)c1ccc2cc(Cc3cc(C(=O)NCc4ccc5c(N)nccc5c4)ccn3)ccc2n1] | 6-((4-(((1-aminoisoquinolin-6-yl)methyl)carbamoyl)pyridin-2-yl)methyl)quinoline-2-carboxamide |
| 5 | 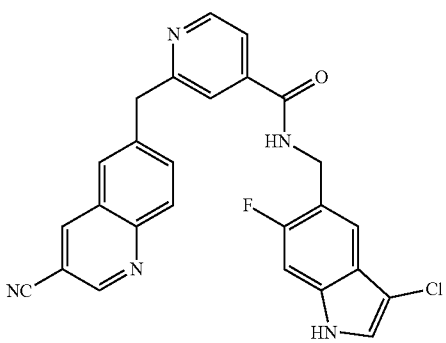 [SMILES: N#Cc1cnc2ccc(Cc3cc(C(=O)NCc4cc5c(Cl)c[nH]c5cc4F)ccn3)cc2c1] | N-((3-chloro-6-fluoro-1H-indol-5-yl)methyl)-2-((3-cyanoquinolin-6-yl)methyl)isonicotinamide |
| 6 | 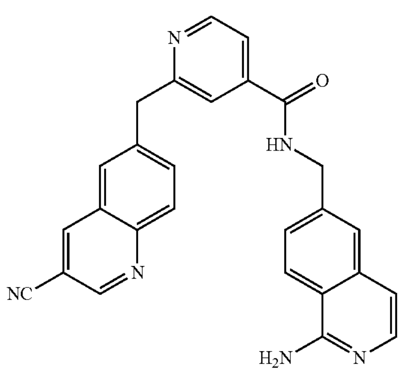 [SMILES: N#Cc1cnc2ccc(Cc3cc(C(=O)NCc4ccc5c(N)nccc5c4)ccn3)cc2c1] | N-((1-aminoisoquinolin-6-yl)methyl)-2-((3-cyanoquinolin-6-yl)methyl)isonicotinamide |
| 7 | 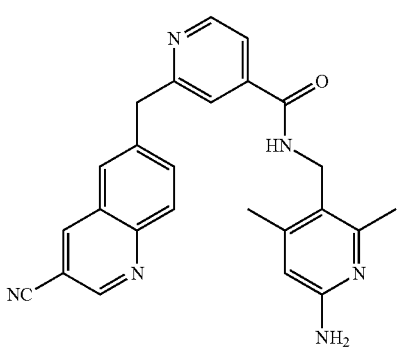 [SMILES: Cc1cc(N)nc(C)c1CNC(=O)c1ccnc(Cc2ccc3ncc(C#N)cc3c2)c1] | N((6-amino-2,4-dimethylpyridin-3-yl)methyl)-2-((3-cyanoquinolin-6-yl)methyl)isonicotinamide |

TABLE 1-continued

| Chemical Synthesis Example | Structure | Name |
|---|---|---|
| 8 | 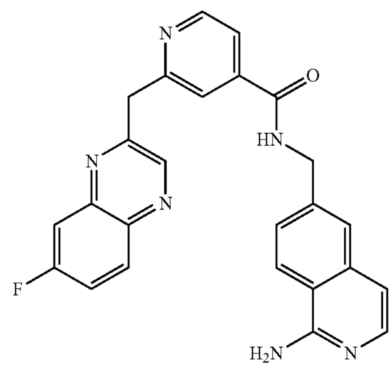 [SMILES: Nc1nccc2cc(CNC(=O)c3ccnc(Cc4cnc5ccc(F)cc5n4)c3)ccc12] | N-((1-aminoisoquinolin-6-yl)methyl)-2-((7-fluoroquinoxalin-2-yl)methyl)isonicotinamide |
| 9 | 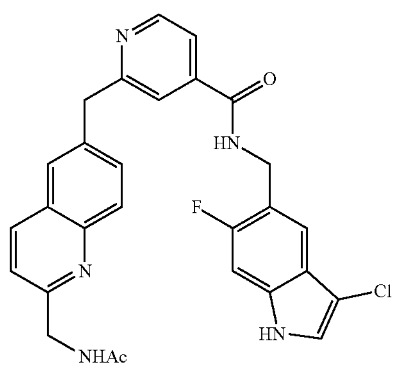 [SMILES: CC(=O)NCc1ccc2cc(Cc3cc(C(=O)NCc4cc5c(Cl)c[nH]c5cc4F)ccn3)ccc2n1] | 2-((2-(acetamidomethyl)quinolin-6-yl)methyl)-N-((3-chloro-6-fluoro-1H-indol-5-yl)methyl)isonicotinamide |
| 10 | 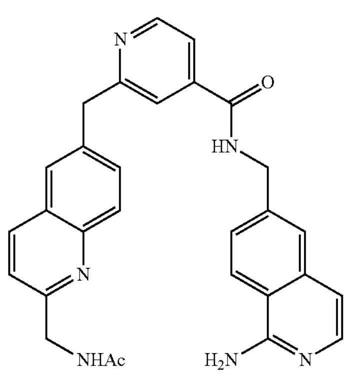 [SMILES: CC(=O)NCc1ccc2cc(Cc3cc(C(=O)NCc4ccc5c(N)nccc5c4)ccn3)ccc2n1] | 2-((2-(acetamidomethyl)quinolin-6-yl)methyl)-N-((1-aminoisoquinolin-6-yl)methyl)isonicotinamide |
| 11 | 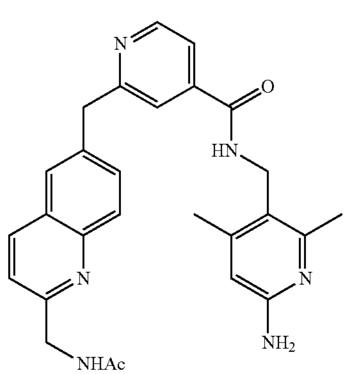 [SMILES: CC(=O)NCc1ccc2cc(Cc3cc(C(=O)NCc4c(C)cc(N)nc4C)ccn3)ccc2n1] | 2-((2-(acetamidomethyl)quinolin-6-yl)methyl)-N-((6-amino-2,4-dimethylpyridin-3-yl)methyl)isonicotinamide |

TABLE 1-continued

| Chemical Synthesis Example | Structure | Name |
|---|---|---|
| 12 | 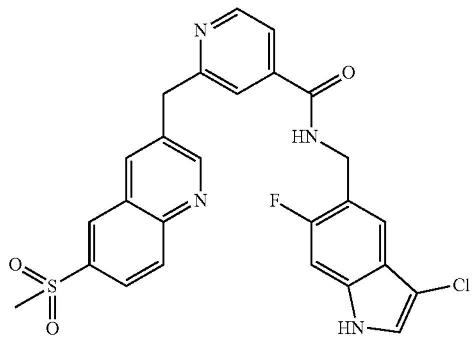 [SMILES: CS(=O)(=O)c1ccc2ncc(Cc3cc(C(=O)NCc4cc5c(Cl)c[nH]c5cc4F)ccn3)cc2c1] | N-((3-chloro-6-fluoro-1H-indol-5-yl)methyl)-2-((6-(methylsulfonyl)quinolin-3-yl)methyl)isonicotinamide |
| 13 | 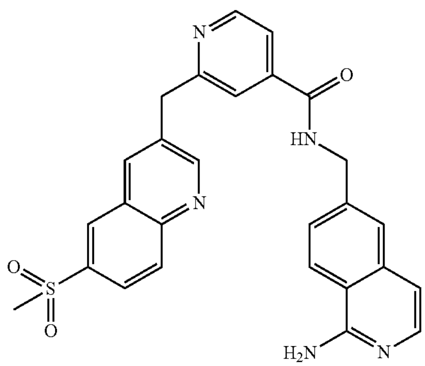 [SMILES: CS(=O)(=O)c1ccc2ncc(Cc3cc(C(=O)NCc4ccc5c(N)nccc5c4)ccn3)cc2c1] | N-((1-aminoisoquinolin-6-yl)methyl)-2-((6-(methylsulfonyl)quinolin-3-yl)methyl)isonicotinamide |
| 14 | 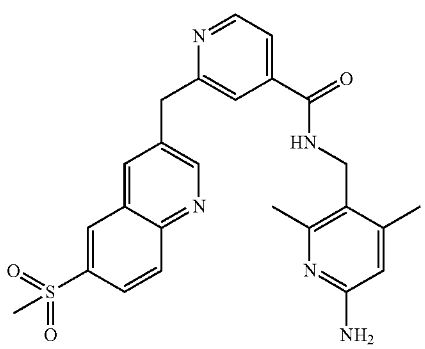 [SMILES: Cc1cc(N)nc(C)c1CNC(=O)c1ccnc(Cc2cnc3ccc(S(C)(=O)=O)cc3c2)c1] | N-((6-amino-2,4-dimethylpyridin-3-yl)methyl)-2-((6-(methylsulfonyl)quinolin-3-yl)methyl)isonicotinamide |
| 15 | 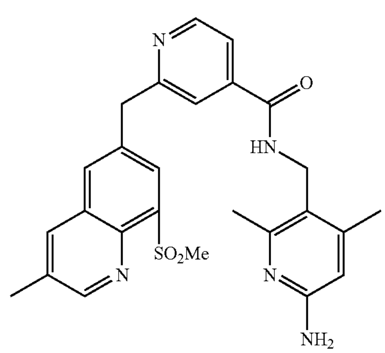 | N-((6-amino-2,4-dimethylpyridin-3-yl)methyl)-2-((3-methyl-8-(methylsulfonyl)quinolin-6-yl)methyl)isonicotinamide |

TABLE 1-continued

| Chemical Synthesis Example | Structure | Name |
|---|---|---|
| 16 | 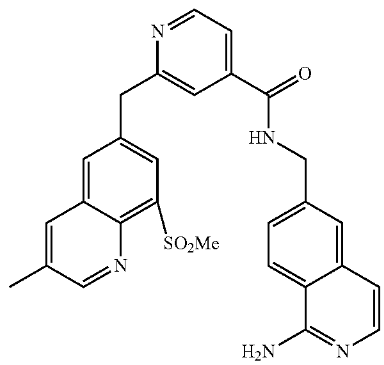 [SMILES: Cc1cnc2c(S(C)(=O)=O)cc(Cc3cc(C(=O)NCc4ccc5c(N)nccc5c4)ccn3)cc2c1] | N-((1-aminoisoquinolin-6-yl)methyl)-2-((3-methyl-8-(methylsulfonyl)quinolin-6-yl)methyl)isonicotinamide |
| 17 | 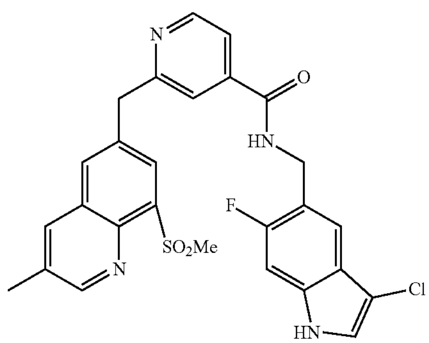 [SMILES: Cc1cnc2c(S(C)(=O)=O)cc(Cc3cc(C(=O)NCc4cc5c(Cl)c[nH]c5cc4F)ccn3)cc2c1] | N-((3-chloro-6-fluoro-1H-indol-5-yl)methyl)-2-((3-methyl-8-(methylsulfonyl)quinolin-6-yl)methyl)isonicotinamide |
| 18 | 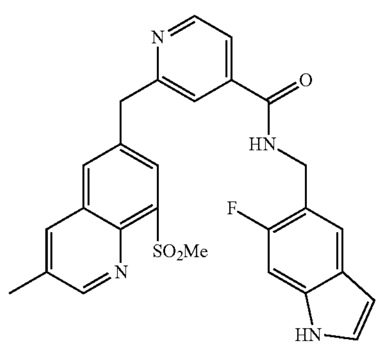 [SMILES: Cc1cnc2c(S(C)(=O)=O)cc(Cc3cc(C(=O)NCc4cc5cc[nH]c5cc4F)ccn3)cc2c1] | N-((6-fluoro-1H-indol-5-yl)methyl)-2-((3-methyl-8-(methylsulfonyl)quinolin-6-yl)methyl)isonicotinamide |
| 19 | 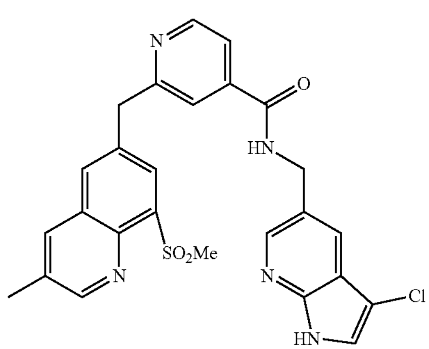 [SMILES: Cc1cnc2c(S(C)(=O)=O)cc(Cc3cc(C(=O)NCc4cnc5[nH]cc(Cl)c5c4)ccn3)cc2c1] | N-((3-chloro-1H-pyrrolo[2,3-b]pyridin-5-yl)methyl)-2-((3-methyl-8-(methylsulfonyl)quinolin-6-yl)methyl)isonicotinamide |

TABLE 1-continued

| Chemical Synthesis Example | Structure | Name |
|---|---|---|
| 20 | 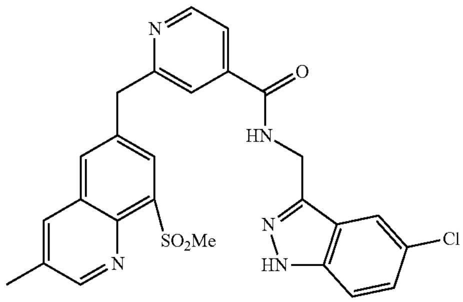 [SMILES: Cc1cnc2c(S(C)(=O)=O)cc(Cc3cc(C(=O)NCc4n[nH]c5ccc(Cl)cc45)ccn3)cc2c1] | N-((5-chloro-1H-indazol-3-yl)methyl)-2-((3-methyl-8-(methylsulfonyl)quinolin-6-yl)methyl)isonicotinamide |
| 21 | 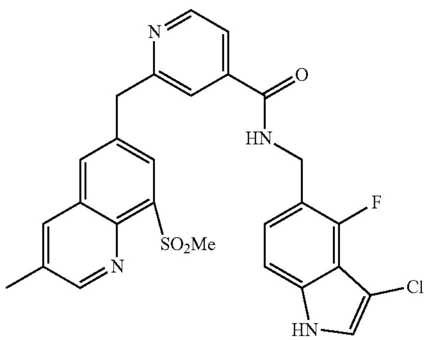 [SMILES: Cc1cnc2c(S(C)(=O)=O)cc(Cc3cc(C(=O)NCc4ccc5[nH]cc(Cl)c5c4F)ccn3)cc2c1] | N-((3-chloro-4-fluoro-1H-indol-5-yl)methyl)-2-((3-methyl-8-(methylsulfonyl)quinolin-6-yl)methyl)isonicotinamide |
| 22 | 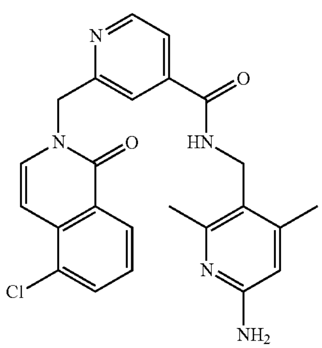 [SMILES: Cc1cc(N)nc(C)c1CNC(=O)c1ccnc(Cn2ccc3c(Cl)cccc3c2=O)c1] | N-((6-amino-2,4-dimethylpyridin-3-yl)methyl)-2-((5-chloro-1-oxoisoquinolin-2(1H)-yl)methyl)isonicotinamide |
| 23 | 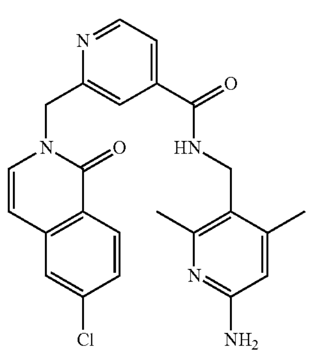 [SMILES: Cc1cc(N)nc(C)c1CNC(=O)c1ccnc(Cn2ccc3cc(Cl)ccc3c2=O)c1] | N-((6-amino-2,4-dimethylpyridin-3-yl)methyl)-2-((6-chloro-1-oxoisoquinolin-2(1H)-yl)methyl)isonicotinamide |

TABLE 1-continued

| Chemical Synthesis Example | Structure | Name |
|---|---|---|
| 24 | 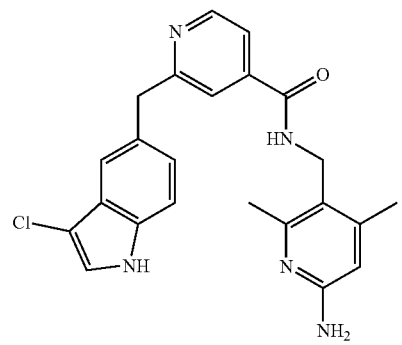 [SMILES: Cc1cc(N)nc(C)c1CNC(=O)c1ccnc(Cc2ccc3[nH]cc(Cl)c3c2)c1] | N-((6-amino-2,4-dimethylpyridin-3-yl)methyl)-2-((3-chloro-1H-indol-5-yl)methyl)isonicotinamide |
| 25 | 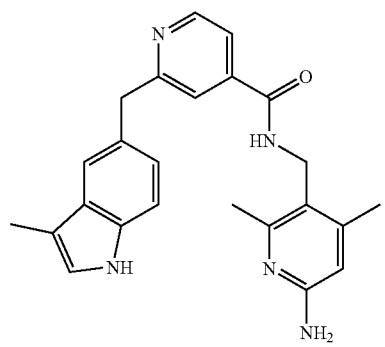 | N-((6-amino-2,4-dimethylpyridin-3-yl)methyl)-2-((3-methyl-1H-indol-5-yl)methyl)isonicotinamide |
| 26 | 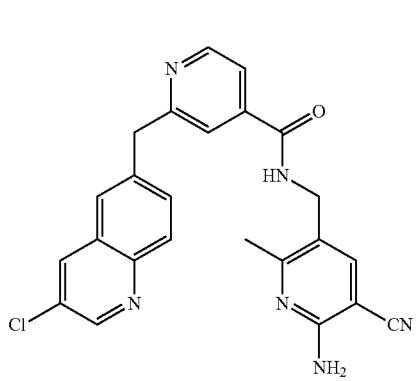 [SMILES: Cc1nc(N)c(C#N)cc1CNC(=O)c1ccnc(Cc2ccc3ncc(Cl)cc3c2)c1] | N-((6-amino-5-cyano-2-methylpyridin-3-yl)methyl)-2-((3-chloroquinolin-6-yl)methyl)isonicotinamide |
| 27 | 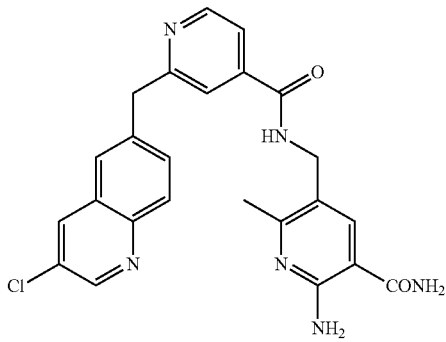 [SMILES: Cc1nc(N)c(C(N)=O)cc1CNC(=O)c1ccnc(Cc2ccc3ncc(Cl)cc3c2)c1] | 2-amino-5-((2-((3-chloroquinolin-6-yl)methyl)isonicotinamido)methyl)-6-methylnicotinamide |

TABLE 1-continued

| Chemical Synthesis Example | Structure | Name |
|---|---|---|
| 28 | 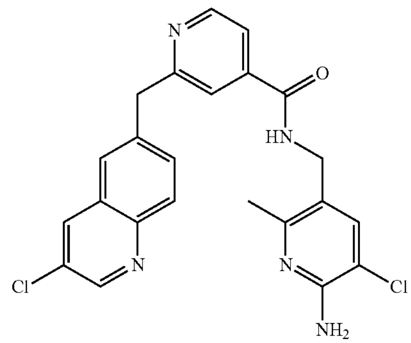 [SMILES: Cc1nc(N)c(Cl)cc1CNC(=O)c1ccnc(Cc2ccc3ncc(Cl)cc3c2)c1] | N-((6-amino-5-chloro-2-methylpyridin-3-yl)methyl)-2-((3-chloroquinolin-6-yl)methyl)isonicotinamide |
| 29 | 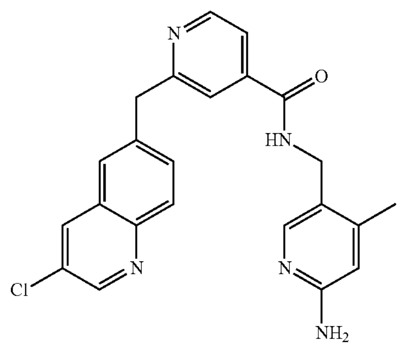 [SMILES: Cc1cc(N)ncc1CNC(=O)c1ccnc(Cc2ccc3ncc(Cl)cc3c2)c1] | N-((6-amino-4-methylpyridin-3-yl)methyl)-2-((3-chloroquinolin-6-yl)methyl)isonicotinamide |
| 30 | 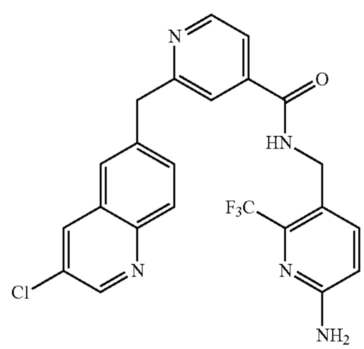 [SMILES: Nc1ccc(CNC(=O)c2ccnc(Cc3ccc4ncc(Cl)cc4c3)c2)c(C(F)(F)F)n1] | N-((6-amino-2-(trifluoromethyl)pyridin-3-yl)methyl)-2-((3-chloroquinolin-6-yl)methyl)isonicotinamide |
| 31 | 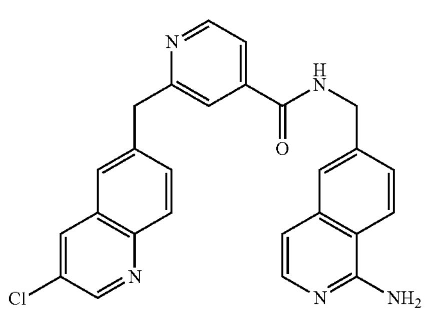 [SMILES: Nc1nccc2cc(CNC(=O)c3ccnc(Cc4ccc5ncc(Cl)cc5c4)c3)ccc12] | N-((1-aminoisoquinolin-6-yl)methyl)-2-((3-chloroquinolin-6-yl)methyl)isonicotinamide |

TABLE 1-continued

| Chemical Synthesis Example | Structure | Name |
|---|---|---|
| 32 | 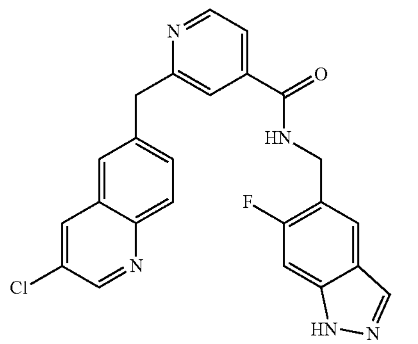 [SMILES: O=C(NCc1cc2cn[nH]c2cc1F)c1ccnc(Cc2ccc3ncc(Cl)cc3c2)c1] | 2-((3-chloroquinolin-6-yl)methyl)-N-((6-fluoro-1H-indazol-5-yl)methyl)isonicotinamide |
| 33 | 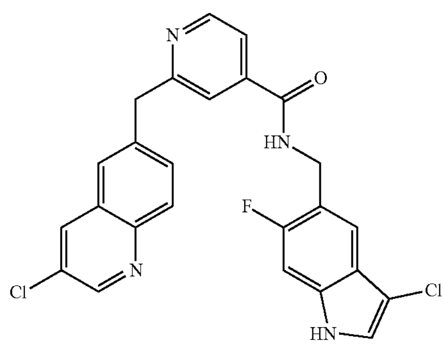 [SMILES: O=C(NCc1cc2c(Cl)c[nH]c2cc1F)c1ccnc(Cc2ccc3ncc(Cl)cc3c2)c1] | N-((3-chloro-6-fluoro-1H-indol-5-yl)methyl)-2-((3-chloroquinolin-6-yl)methyl)isonicotinamide |
| 34 | 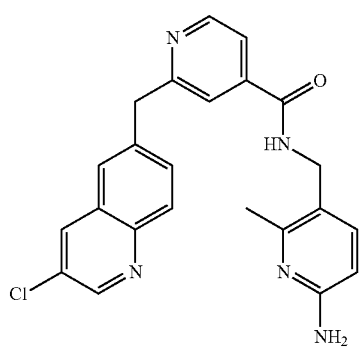 | N-((6-amino-2-methylpyridin-3-yl)methyl)-2-((3-chloroquinolin-6-yl)methyl)isonicotinamide |
| 35 | 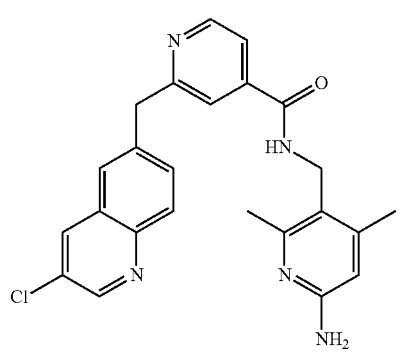 | N-((6-amino-2,4-dimethylpyridin-3-yl)methyl)-2-((3-chloroquinolin-6-yl)methyl)isonicotinamide |

TABLE 1-continued

| Chemical Synthesis Example | Structure | Name |
|---|---|---|
| 36 | 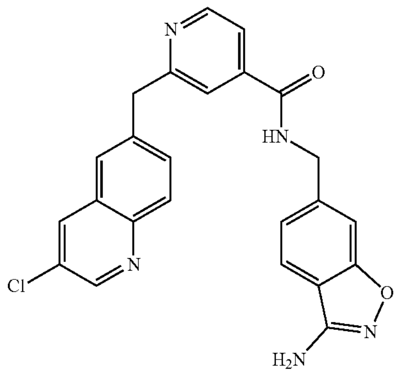 [SMILES: Nc1noc2cc(CNC(=O)c3ccnc(Cc4ccc5ncc(Cl)cc5c4)c3)ccc12] | N-((3-aminobenzo[d]isoxazol-6-yl)methyl)-2-((3-chloroquinolin-6-yl)methyl)isonicotinamide |
| 37 | 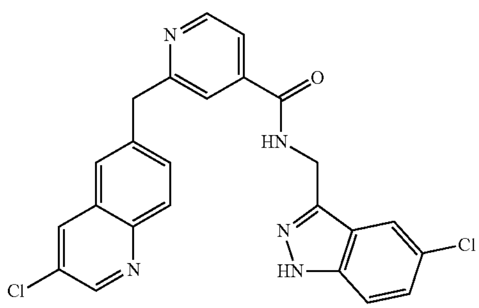 [SMILES: O=C(NCc1n[nH]c2ccc(Cl)cc12)c1ccnc(Cc2ccc3ncc(Cl)cc3c2)c1] | N-((5-chloro-1H-indazol-3-yl)methyl)-2-((3-chloroquinolin-6-yl)methyl)isonicotinamide |
| 38 | 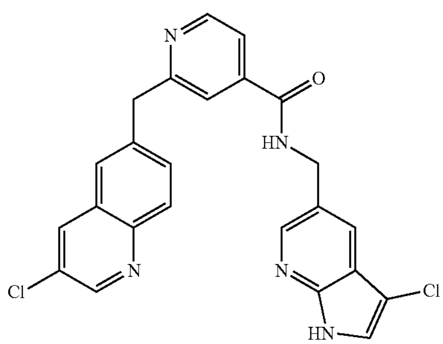 [SMILES: O=C(NCc1cnc2[nH]cc(Cl)c2c1)c1ccnc(Cc2ccc3ncc(Cl)cc3c2)c1] | N-((3-chloro-1H-pyrrolo[2,3-b]pyridin-5-yl)methyl)-2-((3-chloroquinolin-6-yl)methyl)isonicotinamide |
| 39 | 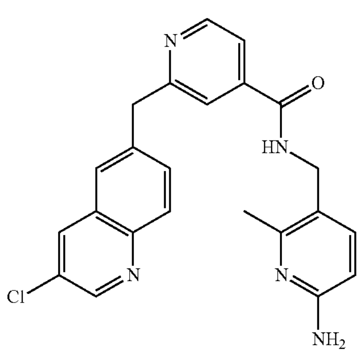 [SMILES: Cc1nc(N)ccc1CNC(=O)c1ccnc(Cc2ccc3ncc(Cl)cc3c2)c1] | N-((6-amino-2-methylpyridin-3-yl)methyl)-2-((3-chloroquinolin-6-yl)methyl)isonicotinamide |

TABLE 1-continued

| Chemical Synthesis Example | Structure | Name |
|---|---|---|
| 40 | 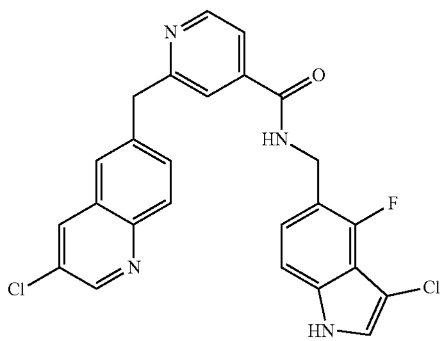 [SMILES: O=C(NCc1ccc2[nH]cc(Cl)c2c1F)c1ccnc(Cc2ccc3ncc(Cl)cc3c2)c1] | N-((3-chloro-4-fluoro-1H-indol-5-yl)methyl)-2-((3-chloroquinolin-6-yl)methyl)isonicotinamide |
| 41 | 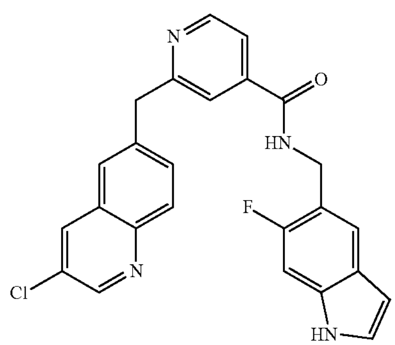 [SMILES: O=C(NCc1cc2cc[nH]c2cc1F)c1ccnc(Cc2ccc3ncc(Cl)cc3c2)c1] | 2-((3-chloroquinolin-6-yl)methyl)-N-((6-fluoro-1H-indol-5-yl)methyl)isonicotinamide |
| 42 | 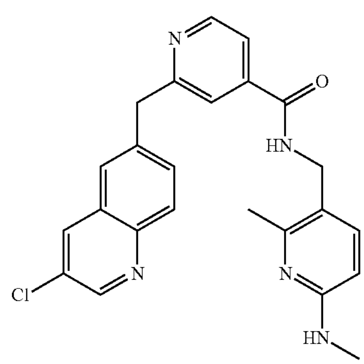 [SMILES: CNc1ccc(CNC(=O)c2ccnc(Cc3ccc4ncc(Cl)cc4c3)c2)c(C)n1] | 2-((3-chloroquinolin-6-yl)methyl)-N-((2-methyl-6-(methylamino)pyridin-3-yl)methyl)isonicotinamide |
| 43 | 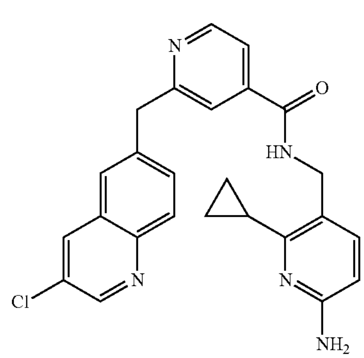 [SMILES: Nc1ccc(CNC(=O)c2ccnc(Cc3ccc4ncc(Cl)cc4c3)c2)c(C2CC2)n1] | N-((6-amino-2-cyclopropylpyridin-3-yl)methyl)-2-((3-chloroquinolin-6-yl)methyl)isonicotinamide |

TABLE 1-continued

| Chemical Synthesis Example | Structure | Name |
|---|---|---|
| 44 | 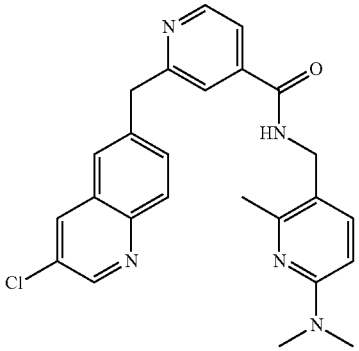 [SMILES: Cc1nc(N(C)C)ccc1CNC(=O)c1ccnc(Cc2ccc3ncc(Cl)cc3c2)c1] | 2-((3-chloroquinolin-6-yl)methyl)-N-((6-(dimethylamino)-2-methylpyridin-3-yl)methyl)isonicotinamide |
| 45 | 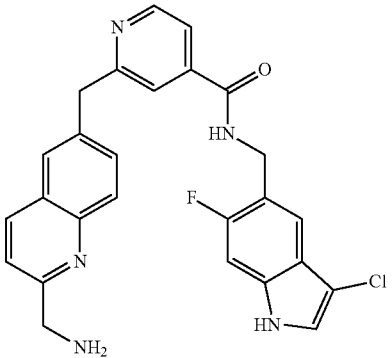 [SMILES: NCc1ccc2cc(Cc3cc(C(=O)NCc4cc5c(Cl)c[nH]c5cc4F)ccn3)ccc2n1] | 2-((2-(aminomethyl)quinolin-6-yl)methyl)-N-((3-chloro-6-fluoro-1H-indol-5-yl)methyl)isonicotinamide |
| 46 | 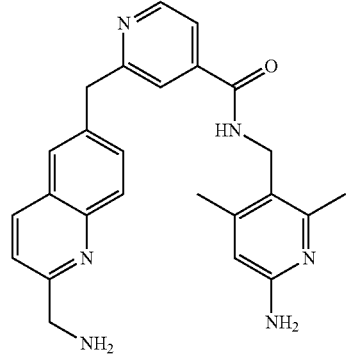 [SMILES: Cc1cc(N)nc(C)c1CNC(=O)c1ccnc(Cc2ccc3nc(CN)ccc3c2)c1] | N-((6-amino-2,4-dimethylpyridin-3-yl)methyl)-2-((2-(aminomethyl)quinolin-6-yl)methyl)isonicotinamide |
| 47 | 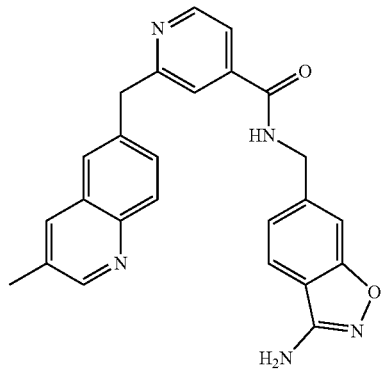 [SMILES: Cc1cnc2ccc(Cc3cc(C(=O)NCc4ccc5c(N)noc5c4)ccn3)cc2c1] | N-((3-aminobenzo[d]isoxazol-6-yl)methyl)-2-((3-methylquinolin-6-yl)methyl)isonicotinamide |

TABLE 1-continued

| Chemical Synthesis Example | Structure | Name |
|---|---|---|
| 48 | 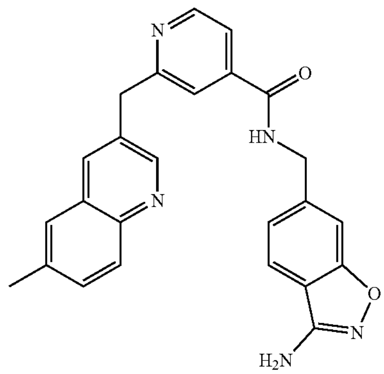 [SMILES: Cc1ccc2ncc(Cc3cc(C(=O)NCc4ccc5c(N)noc5c4)ccn3)cc2c1] | N-((3-aminobenzo[d]isoxazol-6-yl)methyl)-2-((6-methylquinolin-3-yl)methyl)isonicotinamide |
| 49 | 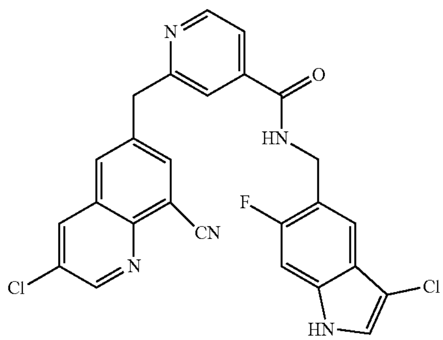 [SMILES: N#Cc1cc(Cc2cc(C(=O)NCc3cc4c(Cl)c[nH]c4cc3F)ccn2)cc2cc(Cl)cnc12] | N-((3-chloro-6-fluoro-1H-indol-5-yl)methyl)-2-((3-chloro-8-cyanoquinolin-6-yl)methyl)isonicotinamide |
| 50 | 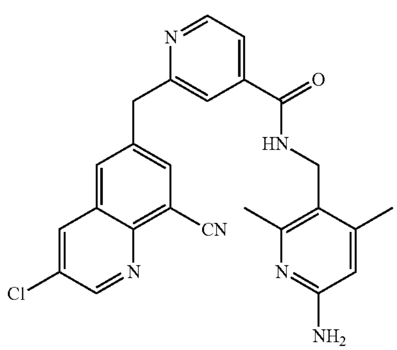 | N-((6-amino-2,4-dimethylpyridin-3-yl)methyl)-2-((3-chloro-8-cyanoquinolin-6-yl)methyl)isonicotinamide |
| 51 | 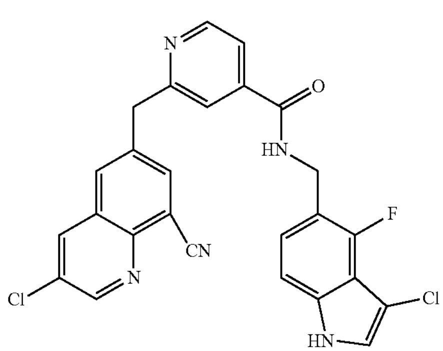 [SMILES: N#Cc1cc(Cc2cc(C(=O)NCc3ccc4[nH]cc(Cl)c4c3F)ccn2)cc2cc(Cl)cnc12] | N-((3-chloro-4-fluoro-1H-indol-5-yl)methyl)-2-((3-chloro-8-cyanoquinolin-6-yl)methyl)isonicotinamide |

TABLE 1-continued

| Chemical Synthesis Example | Structure | Name |
|---|---|---|
| 52 | 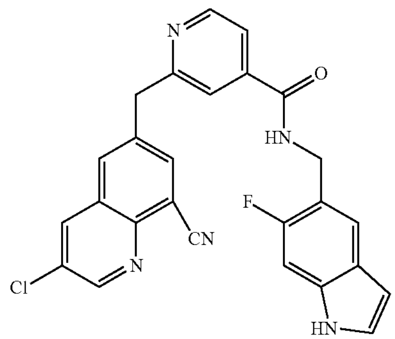 [SMILES: N#Cc1cc(Cc2cc(C(=O)NCc3cc4cc[nH]c4cc3F)ccn2)cc2cc(Cl)cnc12] | 2-((3-chloro-8-cyanoquinolin-6-yl)methyl)-N-((6-fluoro-1H-indol-5-yl)methyl)isonicotinamide |
| 53 | 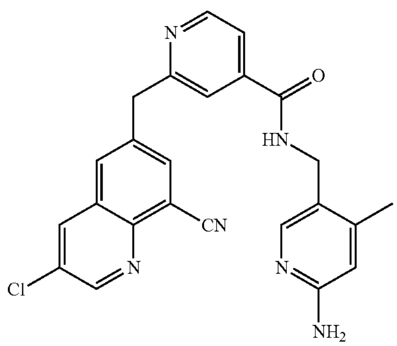 [SMILES: Cc1cc(N)ncc1CNC(=O)c1ccnc(Cc2cc(C#N)c3ncc(Cl)cc3c2)c1] | N-((6-amino-4-methylpyridin-3-yl)methyl)-2-((3-chloro-8-cyanoquinolin-6-yl)methyl)isonicotinamide |
| 54 | 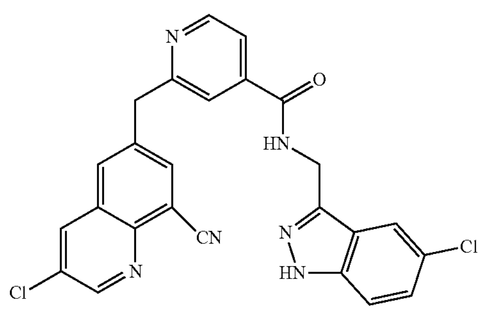 [SMILES: N#Cc1cc(Cc2cc(C(=O)NCc3n[nH]c4ccc(Cl)cc34)ccn2)cc2cc(Cl)cnc12] | N-((5-chloro-1H-indazol-3-yl)methyl)-2-((3-chloro-8-cyanoquinolin-6-yl)methyl)isonicotinamide |
| 55 | 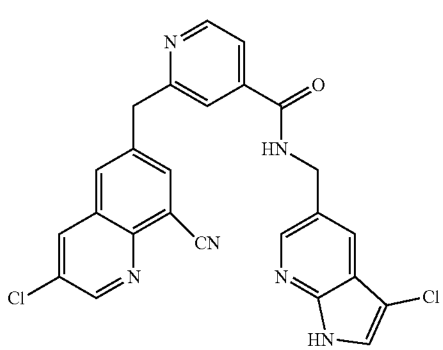 [SMILES: N#Cc1cc(Cc2cc(C(=O)NCc3cnc4[nH]cc(Cl)c4c3)ccn2)cc2cc(Cl)cnc12] | N-((3-chloro-1H-pyrrolo[2,3-b]pyridin-5-yl)methyl)-2-((3-chloro-8-cyanoquinolin-6-yl)methyl)isonicotinamide |

TABLE 1-continued

| Chemical Synthesis Example | Structure | Name |
|---|---|---|
| 56 | 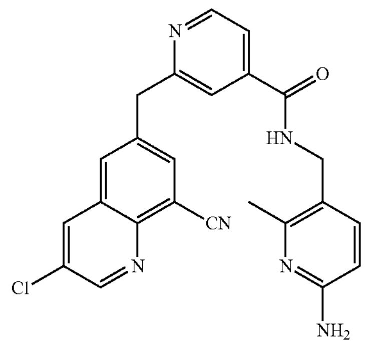 | N-((6-amino-2-methylpyridin-3-yl)methyl)-2-((3-chloro-8-cyanoquinolin-6-yl)methyl)isonicotinamide |
| 57 | 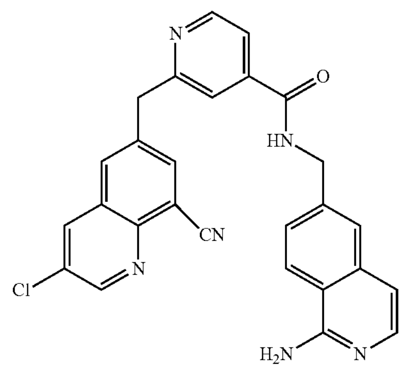 [SMILES: N#Cc1cc(Cc2cc(C(=O)NCc3ccc4c(N)nccc4c3)ccn2)cc2cc(Cl)cnc12] | N-((1-aminoisoquinolin-6-yl)methyl)-2-((3-chloro-8-cyanoquinolin-6-yl)methyl)isonicotinamide |
| 58 | 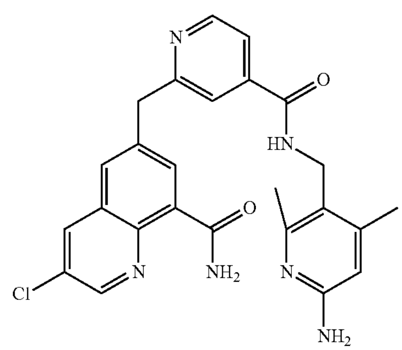 [SMILES: Cc1cc(N)nc(C)c1CNC(=O)c1ccnc(Cc2cc(C(N)=O)c3ncc(Cl)cc3c2)c1] | 6-((4-(((6-amino-2,4-dimethylpyridin-3-yl)methyl)carbamoyl)pyridin-2-yl)methyl)-3-chloroquinoline-8-carboxamide |
| 59 | 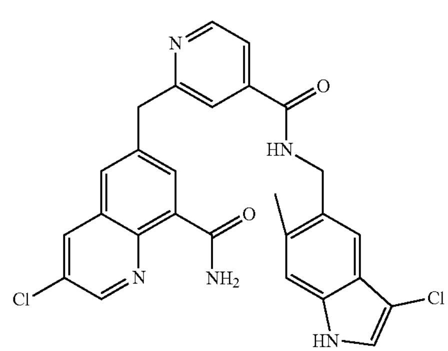 [SMILES: Cc1cc2[nH]cc(Cl)c2cc1CNC(=O)c1ccnc(Cc2cc(C(N)=O)c3ncc(Cl)cc3c2)c1] | 3-chloro-6-((4-(((3-chloro-6-fluoro-1H-indol-5-yl)methyl)carbamoyl)pyridin-2-yl)methyl)quinoline-8-carboxamide |

TABLE 1-continued

| Chemical Synthesis Example | Structure | Name |
|---|---|---|
| 60 | 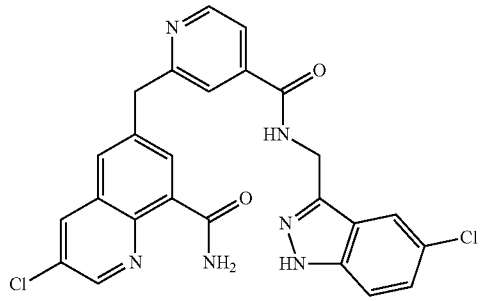 [SMILES: NC(=O)c1cc(Cc2cc(C(=O)NCc3n[nH]c4ccc(Cl)cc34)ccn2)cc2cc(Cl)cnc12] | 3-chloro-6-((4-((((5-chloro-1H-indazol-3-yl)methyl)carbamoyl)pyridin-2-yl)methyl)quinoline-8-carboxamide |
| 61 | 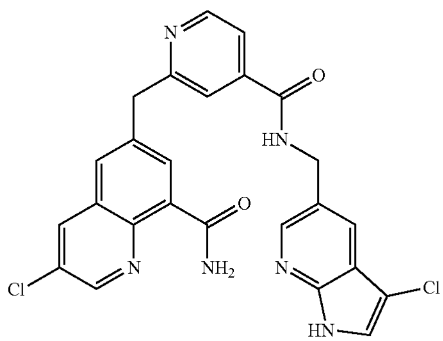 [SMILES: NC(=O)c1cc(Cc2cc(C(=O)NCc3cnc4[nH]cc(Cl)c4c3)ccn2)cc2cc(Cl)cnc12] | 3-chloro-6-((4-((((3-chloro-1H-pyrrolo[2,3-b]pyridin-5-yl)methyl)carbamoyl)pyridin-2-yl)methyl)quinoline-8-carboxamide |
| 62 | 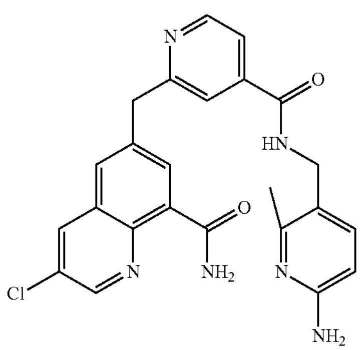 [SMILES: Cc1nc(N)ccc1CNC(=O)c1ccnc(Cc2cc(C(N)=O)c3ncc(Cl)cc3c2)c1] | 6-((4-((((6-amino-2-methylpyridin-3-yl)methyl)carbamoyl)pyridin-2-yl)methyl)-3-chloroquinoline-8-carboxamide |
| 63 | 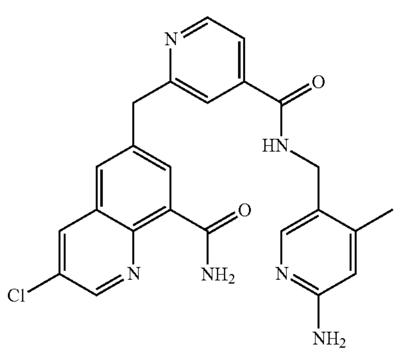 [SMILES: Cc1cc(N)ncc1CNC(=O)c1ccnc(Cc2cc(C(N)=O)c3ncc(Cl)cc3c2)c1] | 6-((4-((((6-amino-4-methylpyridin-3-yl)methyl)carbamoyl)pyridin-2-yl)methyl)-3-chloroquinoline-8-carboxamide |

TABLE 1-continued

| Chemical Synthesis Example | Structure | Name |
|---|---|---|
| 64 | 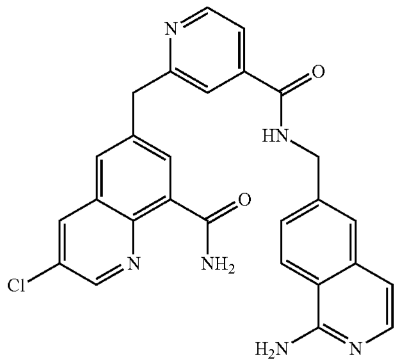 [SMILES: NC(=O)c1cc(Cc2cc(C(=O)NCc3ccc4c(N)nccc4c3)ccn2)cc2cc(Cl)cnc12] | 6-((4-(((1-aminoisoquinolin-6-yl)methyl)carbamoyl)pyridin-2-yl)methyl)-3-chloroquinoline-8-carboxamide |
| 65 | 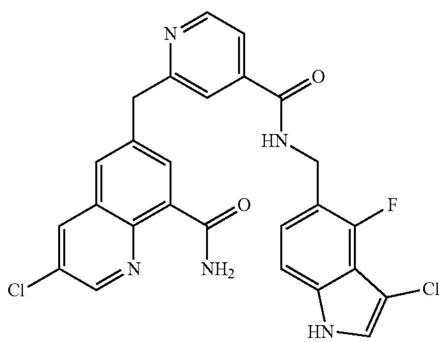 [SMILES: NC(=O)c1cc(Cc2cc(C(=O)NCc3ccc4[nH]cc(Cl)c4c3F)ccn2)cc2cc(Cl)cnc12] | 3-chloro-6-((4-(((3-chloro-4-fluoro-1H-indol-5-yl)methyl)carbamoyl)pyridin-2-yl)methyl)quinoline-8-carboxamide |
| 66 | 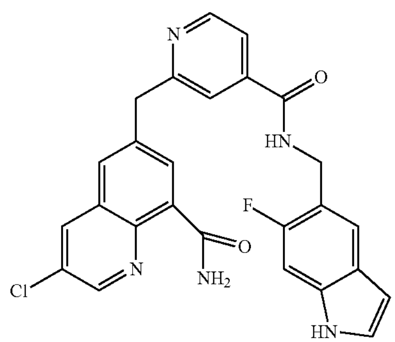 [SMILES: NC(=O)c1cc(Cc2cc(C(=O)NCc3cc4cc[nH]c4cc3F)ccn2)cc2cc(Cl)cnc12] | 3-chloro-6-((4-(((6-fluoro-1H-indol-5-yl)methyl)carbamoyl)pyridin-2-yl)methyl)quinoline-8-carboxamide |
| 67 | 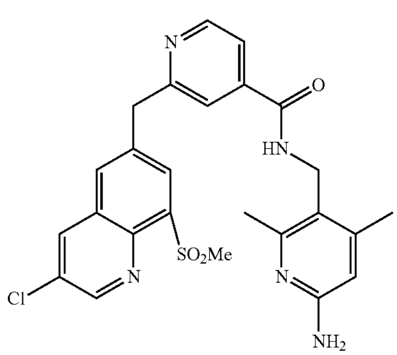 [SMILES: Cc1cc(N)nc(C)c1CNC(=O)c1ccnc(Cc2cc(S(C)(=O)=O)c3ncc(Cl)cc3c2)c1] | N-((6-amino-2,4-dimethylpyridin-3-yl)methyl)-2-((3-chloro-8-(methylsulfonyl)quinolin-6-yl)methyl)isonicotinamide |

TABLE 1-continued

| Chemical Synthesis Example | Structure | Name |
|---|---|---|
| 68 | 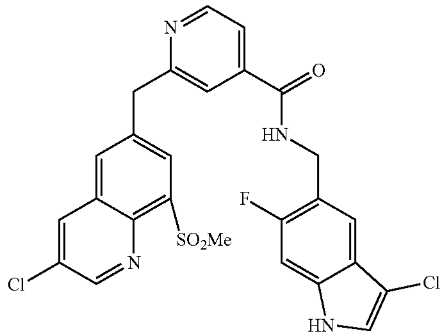 [SMILES: CS(=O)(=O)c1cc(Cc2cc(C(=O)NCc3cc4c(Cl)c[nH]c4cc3F)ccn2)cc2cc(Cl)cnc12] | N-((3-chloro-6-fluoro-1H-indol-5-yl)methyl)-2-((3-chloro-8-(methylsulfonyl)quinolin-6-yl)methyl)isonicotinamide |
| 69 | 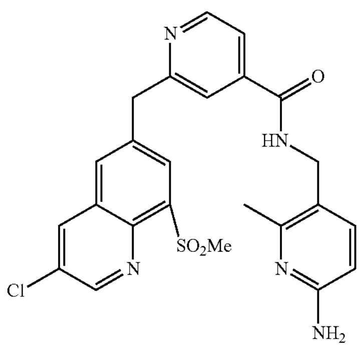 [SMILES: Cc1nc(N)ccc1CNC(=O)c1ccnc(Cc2cc(S(C)(=O)=O)c3ncc(Cl)cc3c2)c1] | N-((6-amino-2-methylpyridin-3-yl)methyl)-2-((3-chloro-8-(methylsulfonyl)quinolin-6-yl)methyl)isonicotinamide |
| 70 | 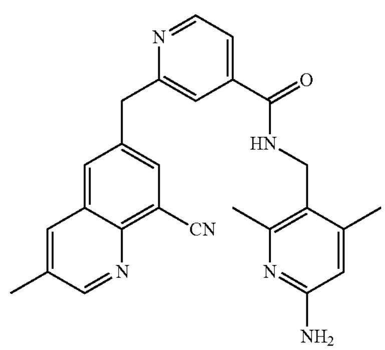 | N-((6-amino-2,4-dimethylpyridin-3-yl)methyl)-2-((8-cyano-3-methylquinolin-6-yl)methyl)isonicotinamide |
| 71 | 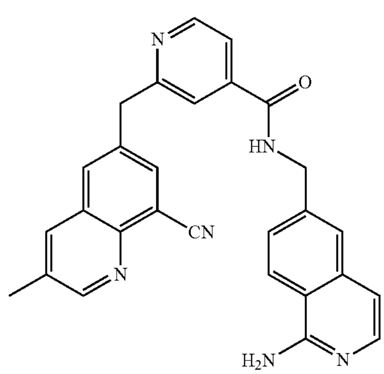 [SMILES: Cc1cnc2c(C#N)cc(Cc3cc(C(=O)NCc4ccc5c(N)nccc5c4)ccn3)cc2c1] | N-((1-aminoisoquinolin-6-yl)methyl)-2-((8-cyano-3-methylquinolin-6-yl)methyl)isonicotinamide |

TABLE 1-continued

| Chemical Synthesis Example | Structure | Name |
|---|---|---|
| 72 | 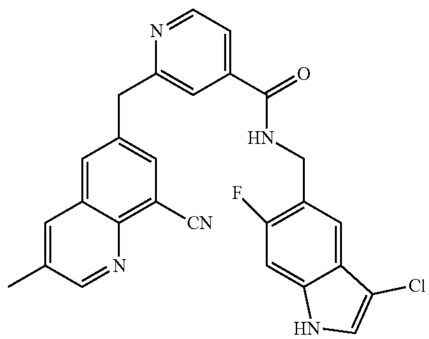 [SMILES: Cc1cnc2c(C#N)cc(Cc3cc(C(=O)NCc4cc5c(Cl)c[nH]c5cc4F)ccn3)cc2c1] | N-((3-chloro-6-fluoro-1H-indol-5-yl)methyl)-2-((8-cyano-3-methylquinolin-6-yl)methyl)isonicotinamide |
| 73 | 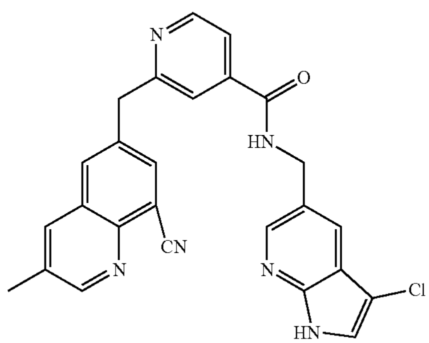 [SMILES: Cc1cnc2c(C#N)cc(Cc3cc(C(=O)NCc4cnc5[nH]cc(Cl)c5c4)ccn3)cc2c1] | N-((3-chloro-1H-pyrrolo[2,3-b]pyridin-5-yl)methyl)-2-((8-cyano-3-methylquinolin-6-yl)methyl)isonicotinamide |
| 74 | 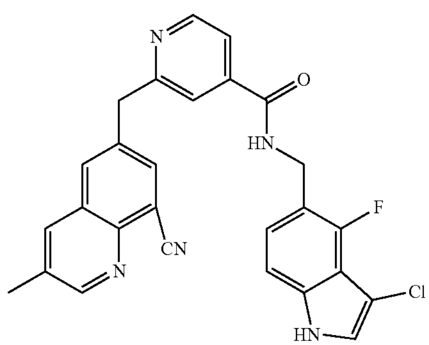 [SMILES: Cc1cnc2c(C#N)cc(Cc3cc(C(=O)NCc4ccc5[nH]cc(Cl)c5c4F)ccn3)cc2c1] | N-((3-chloro-4-fluoro-1H-indol-5-yl)methyl)-2-((8-cyano-3-methylquinolin-6-yl)methyl)isonicotinamide |
| 75 | 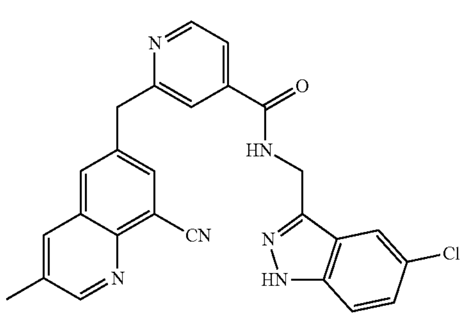 [SMILES: Cc1cnc2c(C#N)cc(Cc3cc(C(=O)NCc4n[nH]c5ccc(Cl)cc45)ccn3)cc2c1] | N-((5-chloro-1H-indazol-3-yl)methyl)-2-((8-cyano-3-methylquinolin-6-yl)methyl)isonicotinamide |

TABLE 1-continued

| Chemical Synthesis Example | Structure | Name |
|---|---|---|
| 76 | 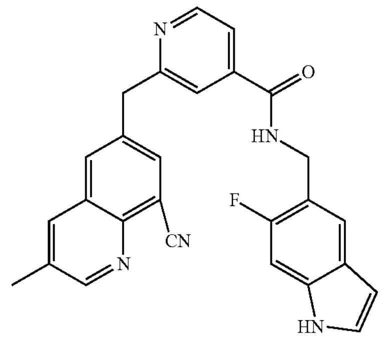 [SMILES: Cc1cnc2c(C#N)cc(Cc3cc(C(=O)NCc4cc5cc[nH]c5cc4F)ccn3)cc2c1] | 2-((8-cyano-3-methylquinolin-6-yl)methyl)-N-((6-fluoro-1H-indol-5-yl)methyl)isonicotinamide |
| 77 | 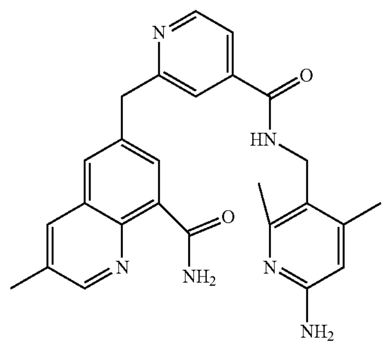 | 6-((4-(((6-amino-2,4-dimethylpyridin-3-yl)methyl)carbamoyl)pyridin-2-yl)methyl)-3-methylquinoline-8-carboxamide |
| 78 | 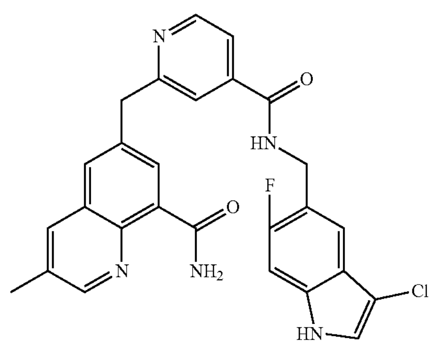 [SMILES: Cc1cnc2c(C(N)=O)cc(Cc3cc(C(=O)NCc4cc5c(Cl)c[nH]c5cc4F)ccn3)cc2c1] | 6-((4-(((3-chloro-6-fluoro-1H-indol-5-yl)methyl)carbamoyl)pyridin-2-yl)methyl)-3-methylquinoline-8-carboxamide |
| 79 | 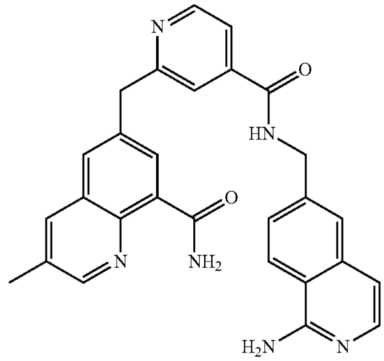 [SMILES: Cc1cnc2c(C(N)=O)cc(Cc3cc(C(=O)NCc4ccc5c(N)nccc5c4)ccn3)cc2c1] | 6-((4-(((1-aminoisoquinolin-6-yl)methyl)carbamoyl)pyridin-2-yl)methyl)-3-methylquinoline-8-carboxamide |

TABLE 1-continued

| Chemical Synthesis Example | Structure | Name |
|---|---|---|
| 80 | 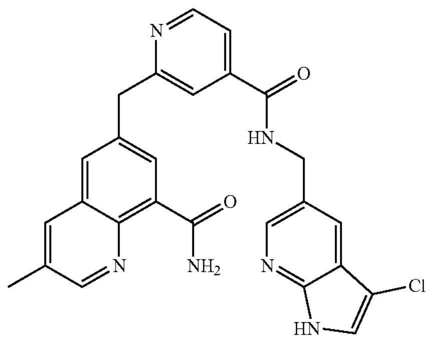 [SMILES: Cc1cnc2c(C(N)=O)cc(Cc3cc(C(=O)NCc4cnc5[nH]cc(Cl)c5c4)ccn3)cc2c1] | 6-((4-(((3-chloro-1H-pyrrolo[2,3-b]pyridin-5-yl)methyl)carbamoyl)pyridin-2-yl)methyl)-3-methylquinoline-8-carboxamide |
| 81 | 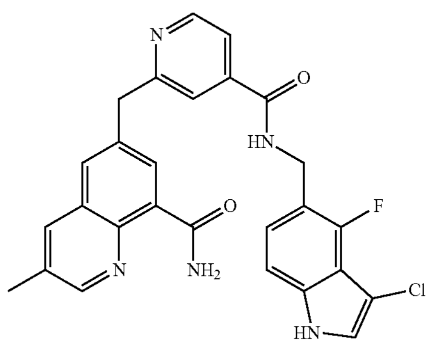 [SMILES: Cc1cnc2c(C(N)=O)cc(Cc3cc(C(=O)NCc4ccc5[nH]cc(Cl)c5c4F)ccn3)cc2c1] | 6-((4-(((3-chloro-4-fluoro-1H-indol-5-yl)methyl)carbamoyl)pyridin-2-yl)methyl)-3-methylquinoline-8-carboxamide |
| 82 | 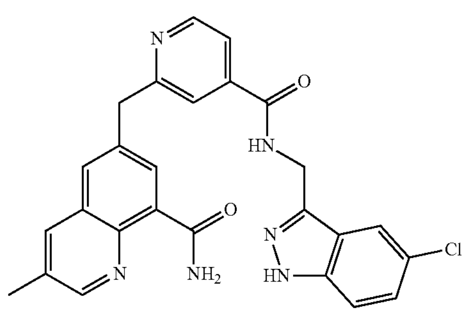 [SMILES: Cc1cnc2c(C(N)=O)cc(Cc3cc(C(=O)NCc4n[nH]c5ccc(Cl)cc45)ccn3)cc2c1] | 6-((4-(((5-chloro-1H-indazol-3-yl)methyl)carbamoyl)pyridin-2-yl)methyl)-3-methylquinoline-8-carboxamide |
| 83 | 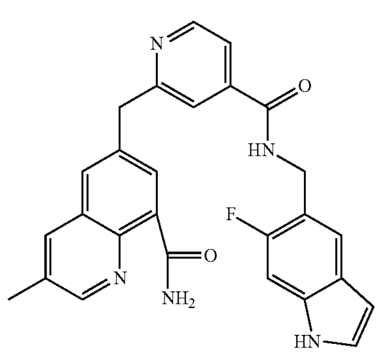 [SMILES: Cc1cnc2c(C(N)=O)cc(Cc3cc(C(=O)NCc4cc5cc[nH]c5cc4F)ccn3)cc2c1] | 6-((4-(((6-fluoro-1H-indol-5-yl)methyl)carbamoyl)pyridin-2-yl)methyl)-3-methylquinoline-8-carboxamide |

TABLE 1-continued

| Chemical Synthesis Example | Structure | Name |
|---|---|---|
| 84 | 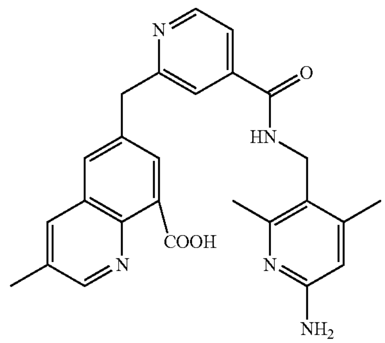 | 6-((4-(((6-amino-2,4-dimethylpyridin-3-yl)methyl)carbamoyl)pyridin-2-yl)methyl)-3-methylquinoline-8-carboxylic acid |
| 85 | 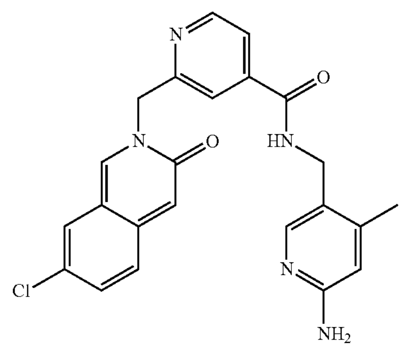 [SMILES: Cc1cc(N)ncc1CNC(=O)c1ccnc(Cn2cc3cc(Cl)ccc3cc2=O)c1] | N-((6-amino-4-methylpyridin-3-yl)methyl)-2-((7-chloro-3-oxoisoquinolin-2(3H)-yl)methyl)isonicotinamide |
| 86 | 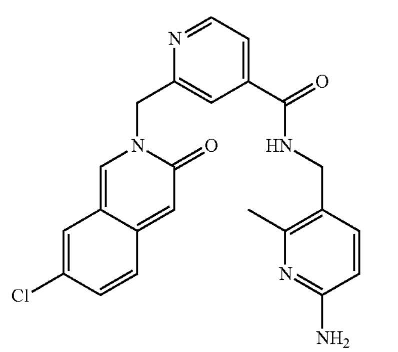 [SMILES: Cc1nc(N)ccc1CNC(=O)c1ccnc(Cn2cc3cc(Cl)ccc3cc2=O)c1] | N-((6-amino-2-methylpyridin-3-yl)methyl)-2-((7-chloro-3-oxoisoquinolin-2(3H)-yl)methyl)isonicotinamide |
| 87 | 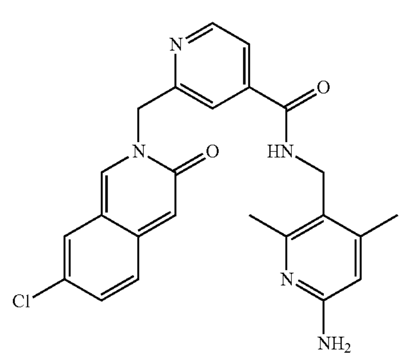 [SMILES: Cc1cc(N)nc(C)c1CNC(=O)c1ccnc(Cn2cc3cc(Cl)ccc3cc2=O)c1] | N-((6-amino-2,4-dimethylpyridin-3-yl)methyl)-2-((7-chloro-3-oxoisoquinolin-2(3H)-yl)methyl)isonicotinamide |

TABLE 1-continued

| Chemical Synthesis Example | Structure | Name |
|---|---|---|
| 88 | 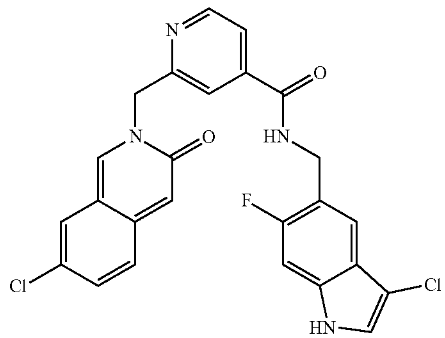 [SMILES: O=C(NCc1cc2c(Cl)c[nH]c2cc1F)c1ccnc(Cn2cc3cc(Cl)ccc3cc2=O)c1] | 2-((7-chloro-3-oxoisoquinolin-2(3H)-yl)methyl)-N-((3-chloro-6-fluoro-1H-indol-5-yl)methyl)isonicotinamide |
| 89 | 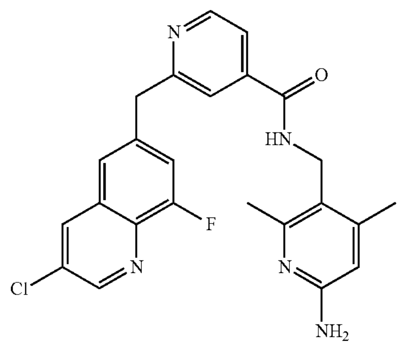 [SMILES: Cc1cc(N)nc(C)c1CNC(=O)c1ccnc(Cc2cc(F)c3ncc(Cl)cc3c2)c1] | N-((6-amino-2,4-dimethylpyridin-3-yl)methyl)-2-((3-chloro-8-fluoroquinolin-6-yl)methyl)isonicotinamide |
| 90 | 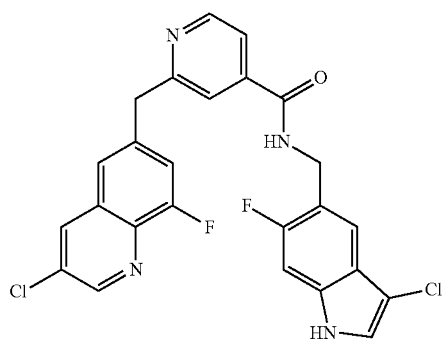 [SMILES: O=C(NCc1cc2c(Cl)c[nH]c2cc1F)c1ccnc(Cc2cc(F)c3ncc(Cl)cc3c2)c1] | N-((3-chloro-6-fluoro-1H-indol-5-yl)methyl)-2-((3-chloro-8-fluoroquinolin-6-yl)methyl)isonicotinamide |
| 91 | 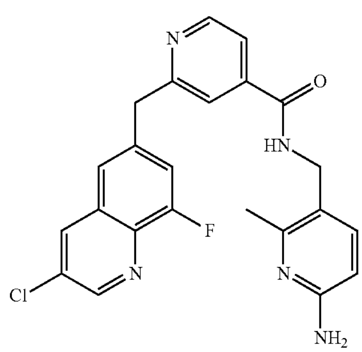 [SMILES: Cc1nc(N)ccc1CNC(=O)c1ccnc(Cc2cc(F)c3ncc(Cl)cc3c2)c1] | N-((6-amino-2-methylpyridin-3-yl)methyl)-2-((3-chloro-8-fluoroquinolin-6-yl)methyl)isonicotinamide |

TABLE 1-continued

| Chemical Synthesis Example | Structure | Name |
|---|---|---|
| 92 | 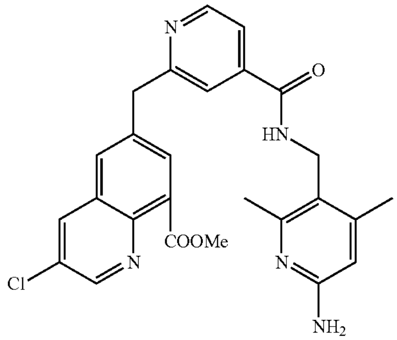 [SMILES: COC(=O)c1cc(Cc2cc(C(=O)NCc3c(C)cc(N)nc3C)ccn2)cc2cc(Cl)cnc12] | methyl 6-((4-(((6-amino-2,4-dimethylpyridin-3-yl)methyl)carbamoyl)pyridin-2-yl)methyl)-3-chloroquinoline-8-carboxylate |
| 93 | 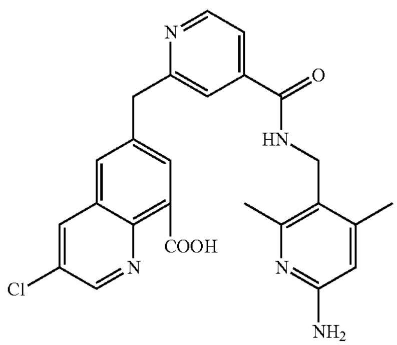 [SMILES: Cc1cc(N)nc(C)c1CNC(=O)c1ccnc(Cc2cc(C(=O)O)c3ncc(Cl)cc3c2)c1] | 6-((4-(((6-amino-2,4-dimethylpyridin-3-yl)methyl)carbamoyl)pyridin-2-yl)methyl)-3-chloroquinoline-8-carboxylic acid |
| 94 | 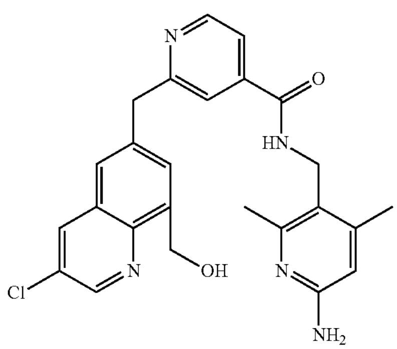 [SMILES: Cc1cc(N)nc(C)c1CNC(=O)c1ccnc(Cc2cc(CO)c3ncc(Cl)cc3c2)c1] | N-((6-amino-2,4-dimethylpyridin-3-yl)methyl)-2-((3-chloro-8-(hydroxymethyl)quinolin-6-yl)methyl)isonicotinamide |
| 95 | 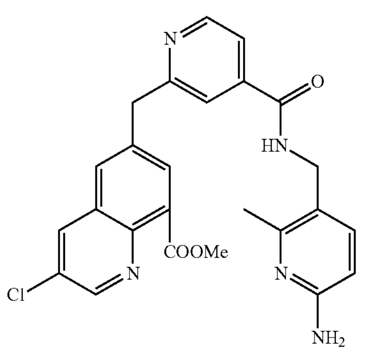 [SMILES: COC(=O)c1cc(Cc2cc(C(=O)NCc3ccc(N)nc3C)ccn2)cc2cc(Cl)cnc12] | methyl 6-((4-(((6-amino-2-methylpyridin-3-yl)methyl)carbamoyl)pyridin-2-yl)methyl)-3-chloroquinoline-8-carboxylate |

TABLE 1-continued

| Chemical Synthesis Example | Structure | Name |
|---|---|---|
| 96 | 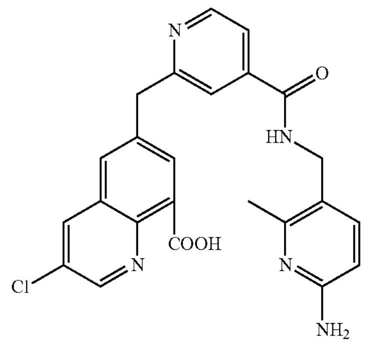 [SMILES: Cc1nc(N)ccc1CNC(=O)c1ccnc(Cc2cc(C(=O)O)c3ncc(Cl)cc3c2)c1] | 6-((4-(((6-amino-2-methylpyridin-3-yl)methyl)carbamoyl)pyridin-2-yl)methyl)-3-chloroquinoline-8-carboxylic acid |
| 97 | 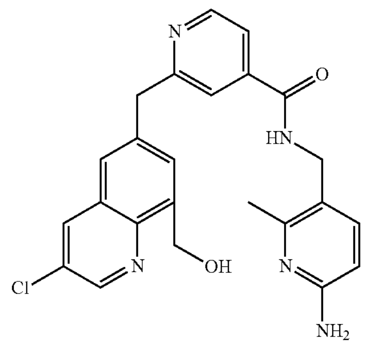 [SMILES: Cc1nc(N)ccc1CNC(=O)c1ccnc(Cc2cc(CO)c3ncc(Cl)cc3c2)c1] | N-((6-amino-2-methylpyridin-3-yl)methyl)-2-((3-chloro-8-(hydroxymethyl)quinolin-6-yl)methyl)isonicotinamide |
| 98 | 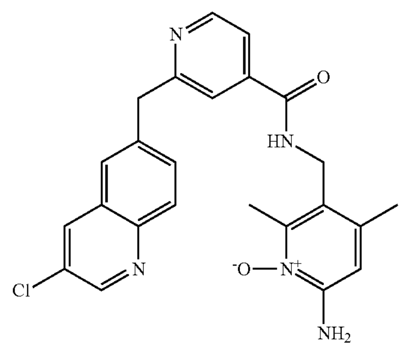 | 6-amino-3-((2-((3-chloroquinolin-6-yl)methyl)isonicotinamido)methyl)-2,4-dimethylpyridine 1-oxide |
| 99 | 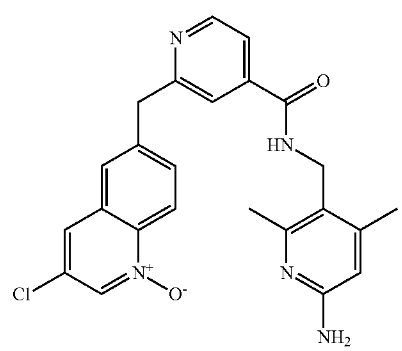 [SMILES: Cc1cc(N)nc(C)c1CNC(=O)c1ccnc(Cc2ccc3c(cc(Cl)c[n+]3[O-])c2)c1] | 6-((4-(((6-amino-2,4-dimethylpyridin-3-yl)methyl)carbamoyl)pyridin-2-yl)methyl)-3-chloroquinoline 1-oxide |

TABLE 1-continued

| Chemical Synthesis Example | Structure | Name |
|---|---|---|
| 100 | 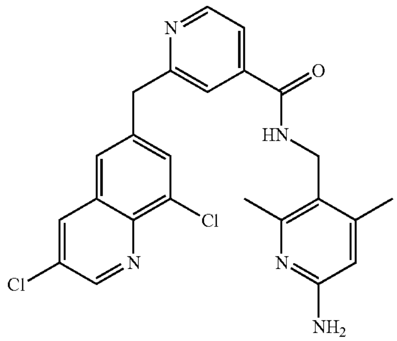 [SMILES: Cc1cc(N)nc(C)c1CNC(=O)c1ccnc(Cc2cc(Cl)c3ncc(Cl)cc3c2)c1] | N-((6-amino-2,4-dimethylpyridin-3-yl)methyl)-2-((3,8-dichloroquinolin-6-yl)methyl)isonicotinamide |
| 101 | 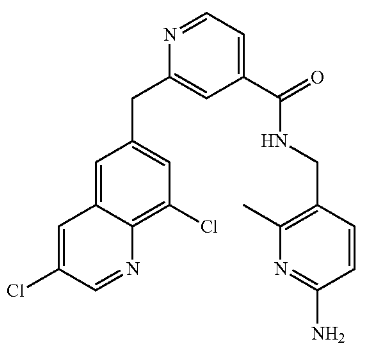 [SMILES: Cc1nc(N)ccc1CNC(=O)c1ccnc(Cc2cc(Cl)c3ncc(Cl)cc3c2)c1] | N-((6-amino-2-methylpyridin-3-yl)methyl)-2-((3,8-dichloroquinolin-6-yl)methyl)isonicotinamide |
| 102 | 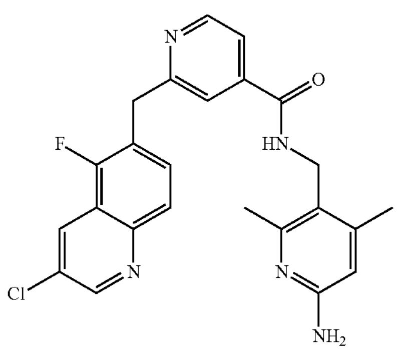 [SMILES: Cc1cc(N)nc(C)c1CNC(=O)c1ccnc(Cc2ccc3ncc(Cl)cc3c2F)c1] | N-((6-amino-2,4-dimethylpyridin-3-yl)methyl)-2-((3-chloro-5-fluoroquinolin-6-yl)methyl)isonicotinamide |
| 103 | 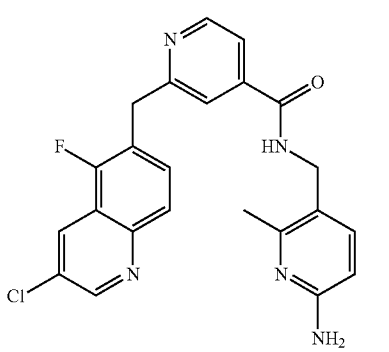 [SMILES: Cc1nc(N)ccc1CNC(=O)c1ccnc(Cc2ccc3ncc(Cl)cc3c2F)c1] | N-((6-amino-2-methylpyridin-3-yl)methyl)-2-((3-chloro-5-fluoroquinolin-6-yl)methyl)isonicotinamide |

TABLE 1-continued

| Chemical Synthesis Example | Structure | Name |
|---|---|---|
| 104 | 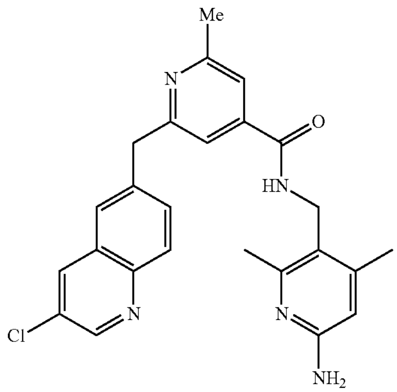 [SMILES: Cc1cc(C(=O)NCc2c(C)cc(N)nc2C)cc(Cc2ccc3ncc(Cl)cc3c2)n1] | N-((6-amino-2,4-dimethylpyridin-3-yl)methyl)-2-((3-chloroquinolin-6-yl)methyl)-6-methylisonicotinamide |
| 105 | 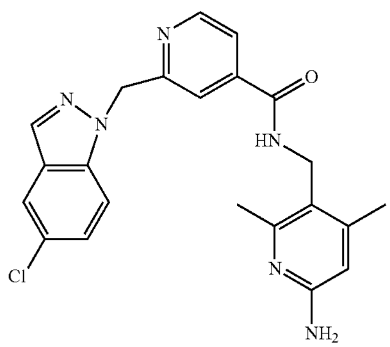 [SMILES: Cc1cc(N)nc(C)c1CNC(=O)c1ccnc(Cn2ncc3cc(Cl)ccc32)c1] | N-((6-amino-2,4-dimethylpyridin-3-yl)methyl)-2-((5-chloro-1H-indazol-1-yl)methyl)isonicotinamide |
| 106 | 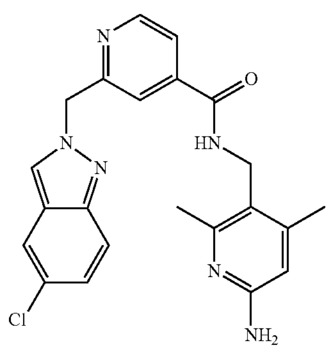 [SMILES: Cc1cc(N)nc(C)c1CNC(=O)c1ccnc(Cn2cc3cc(Cl)ccc3n2)c1] | N-((6-amino-2,4-dimethylpyridin-3-yl)methyl)-2-((5-chloro-2H-indazol-2-yl)methyl)isonicotinamide |
| 107 | 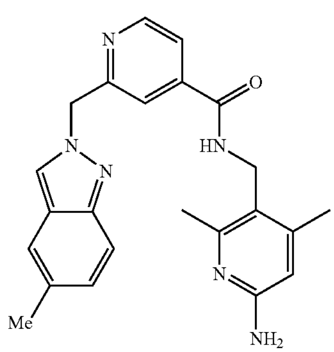 [SMILES: Cc1ccc2nn(Cc3cc(C(=O)NCc4c(C)cc(N)nc4C)ccn3)cc2c1] | N-((6-amino-2,4-dimethylpyridin-3-yl)methyl)-2-((5-methyl-2H-indazol-2-yl)methyl)isonicotinamide |

TABLE 1-continued

| Chemical Synthesis Example | Structure | Name |
|---|---|---|
| 108 | 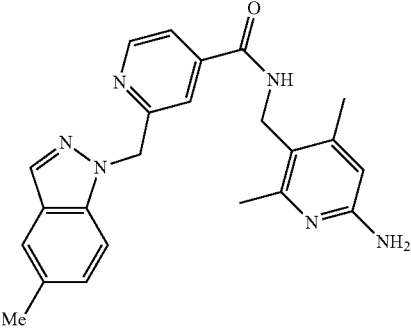 [SMILES: Cc1ccc2c(cnn2Cc2cc(C(=O)NCc3c(C)cc(N)nc3C)ccn2)c1] | N-((6-amino-2,4-dimethylpyridin-3-yl)methyl)-2-((5-methyl-1H-indazol-1-yl)methyl)isonicotinamide |
| 109 | 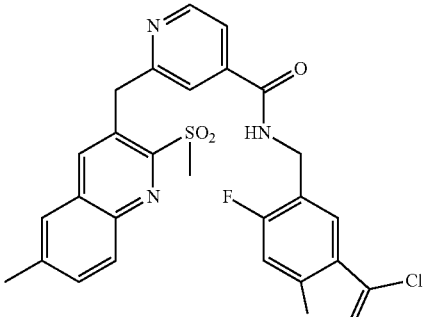 | N-((3-chloro-6-fluoro-1H-indol-5-yl)methyl)-2-((6-methyl-2-(methylsulfonyl)quinolin-3-yl)methyl)isonicotinamide |
| 110 | 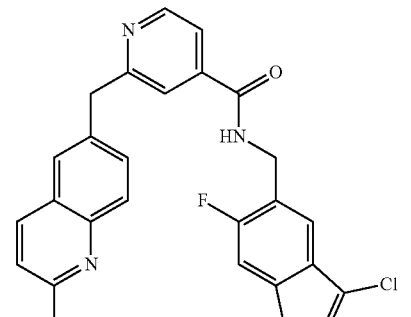 | N-((3-chloro-6-fluoro-1H-indol-5-yl)methyl)-2-((2-methylquinolin-6-yl)methyl)isonicotinamide |
| 111 | 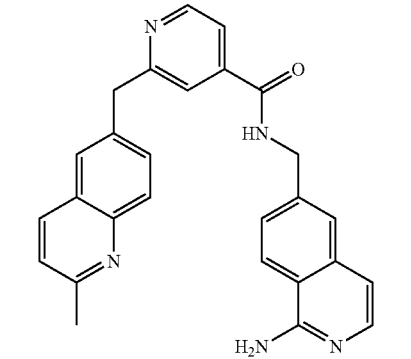 [SMILES: Cc1ccc2cc(Cc3cc(C(=O)NCc4ccc5c(N)nccc5c4)ccn3)ccc2n1] | N-((1-aminoisoquinolin-6-yl)methyl)-2-((2-methylquinolin-6-yl)methyl)isonicotinamide |

TABLE 1-continued

| Chemical Synthesis Example | Structure | Name |
|---|---|---|
| 112 | 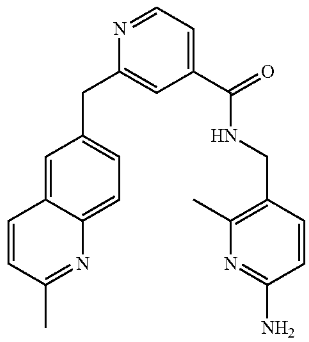 [SMILES: Cc1ccc2cc(Cc3cc(C(=O)NCc4ccc(N)nc4C)ccn3)ccc2n1] | N-((6-amino-2-methylpyridin-3-yl)methyl)-2-((2-methylquinolin-6-yl)methyl)isonicotinamide |
| 113 | 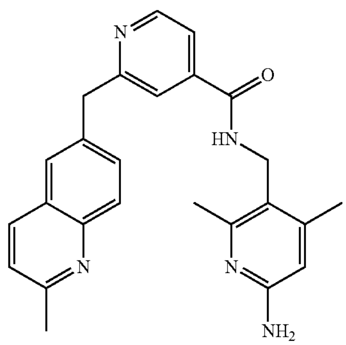 [SMILES: Cc1ccc2cc(Cc3cc(C(=O)NCc4c(C)cc(N)nc4C)ccn3)ccc2n1] | N-((6-amino-2,4-dimethylpyridin-3-yl)methyl)-2-((2-methylquinolin-6-yl)methyl)isonicotinamide |
| 114 | 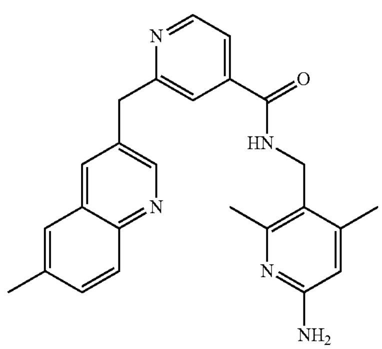 | N-((6-amino-2,4-dimethylpyridin-3-yl)methyl)-2-((6-methylquinolin-3-yl)methyl)isonicotinamide |
| 115 | 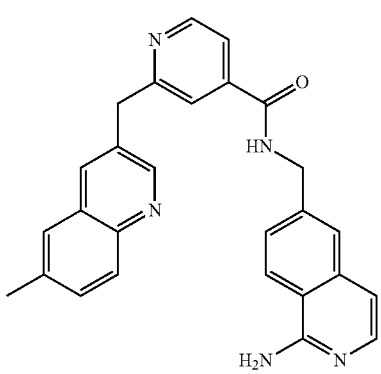 [SMILES: Cc1ccc2ncc(Cc3cc(C(=O)NCc4ccc5c(N)nccc5c4)ccn3)cc2c1] | N-((1-aminoisoquinolin-6-yl)methyl)-2-((6-methylquinolin-3-yl)methyl)isonicotinamide |

TABLE 1-continued

| Chemical Synthesis Example | Structure | Name |
|---|---|---|
| 116 | 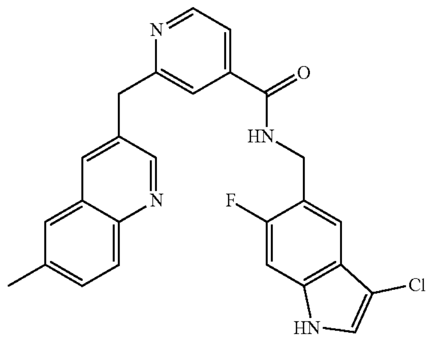 [SMILES: Cc1ccc2ncc(Cc3cc(C(=O)NCc4cc5c(Cl)c[nH]c5cc4F)ccn3)cc2c1] | N-((3-chloro-6-fluoro-1H-indol-5-yl)methyl)-2-((6-methylquinolin-3-yl)methyl)isonicotinamide |
| 117 | 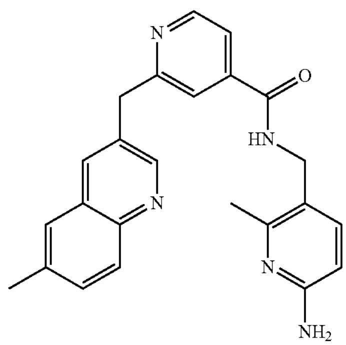 [SMILES: Cc1ccc2ncc(Cc3cc(C(=O)NCc4ccc(N)nc4C)ccn3)cc2c1] | N-((6-amino-2-methylpyridin-3-yl)methyl)-2-((6-methylquinolin-3-yl)methyl)isonicotinamide |
| 118 | 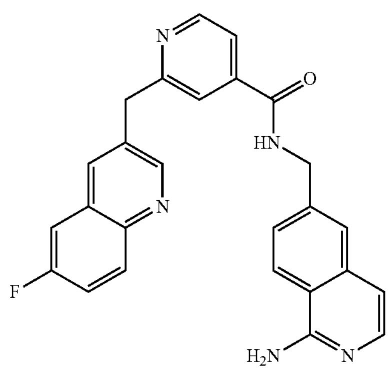 [SMILES: Nc1nccc2cc(CNC(=O)c3ccnc(Cc4cnc5ccc(F)cc5c4)c3)ccc12] | N-((1-aminoisoquinolin-6-yl)methyl)-2-((6-fluoroquinolin-3-yl)methyl)isonicotinamide |
| 119 | 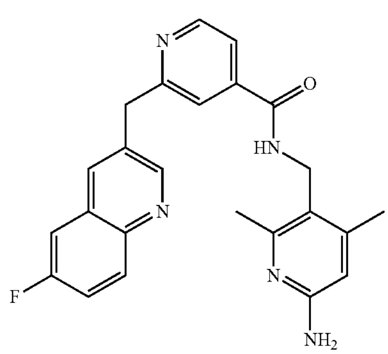 [SMILES: Cc1cc(N)nc(C)c1CNC(=O)c1ccnc(Cc2cnc3ccc(F)cc3c2)c1] | N-((6-amino-2,4-dimethylpyridin-3-yl)methyl)-2-((6-fluoroquinolin-3-yl)methyl)isonicotinamide |

| Chemical Synthesis Example | Structure | Name |
|---|---|---|
| 120 | 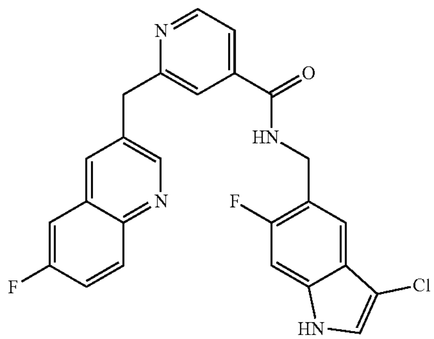 [SMILES: O=C(NCc1cc2c(Cl)c[nH]c2cc1F)c1ccnc(Cc2cnc3ccc(F)cc3c2)c1] | N-((3-chloro-6-fluoro-1H-indol-5-yl)methyl)-2-((6-fluoroquinolin-3-yl)methyl)isonicotinamide |
| 121 | 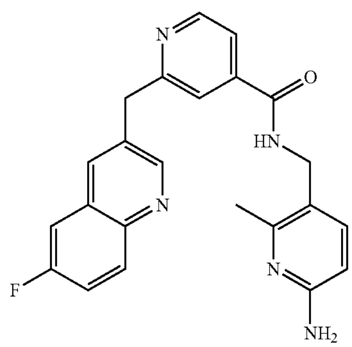 [SMILES: Cc1nc(N)ccc1CNC(=O)c1ccnc(Cc2cnc3ccc(F)cc3c2)c1] | N-((6-amino-2-methylpyridin-3-yl)methyl)-2-((6-fluoroquinolin-3-yl)methyl)isonicotinamide |
| 122 | 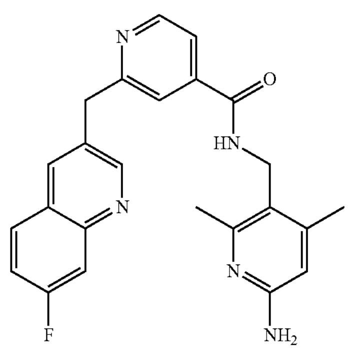 [SMILES: Cc1cc(N)nc(C)c1CNC(=O)c1ccnc(Cc2cnc3cc(F)ccc3c2)c1] | N-((6-amino-2,4-dimethylpyridin-3-yl)methyl)-2-((7-fluoroquinolin-3-yl)methyl)isonicotinamide |
| 123 | 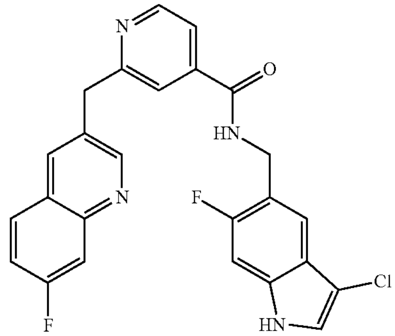 | N-((3-chloro-6-fluoro-1H-indol-5-yl)methyl)-2-((7-fluoroquinolin-3-yl)methyl)isonicotinamide |

TABLE 1-continued
| Chemical Synthesis Example | Structure | Name |
|---|---|---|
| 124 | 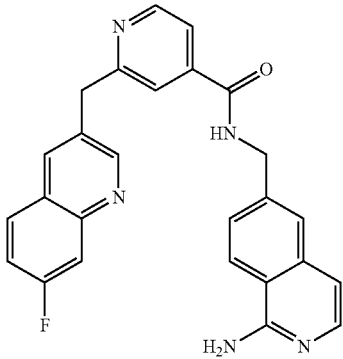 [SMILES: Nc1nccc2cc(CNC(=O)c3ccnc(Cc4cnc5cc(F)ccc5c4)c3)ccc12] | N-((1-aminoisoquinolin-6-yl)methyl)-2-((7-fluoroquinolin-3-yl)methyl)isonicotinamide |
| 125 | 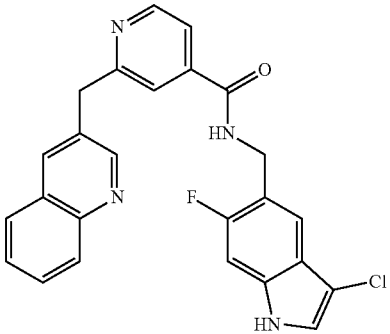 [SMILES: O=C(NCc1cc2c(Cl)c[nH]c2cc1F)c1ccnc(Cc2cnc3ccccc3c2)c1] | N-((3-chloro-6-fluoro-1H-indol-5-yl)methyl)-2-(quinolin-3-ylmethyl)isonicotinamide |
| 126 | 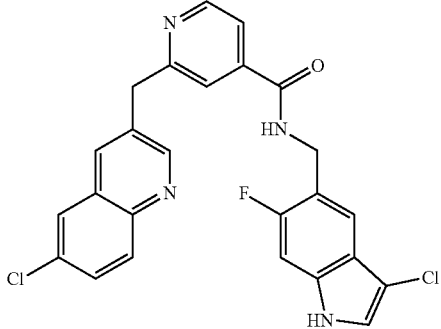 [SMILES: O=C(NCc1cc2c(Cl)c[nH]c2cc1F)c1ccnc(Cc2cnc3ccc(Cl)cc3c2)c1] | N-((3-chloro-6-fluoro-1H-indol-5-yl)methyl)-2-((6-chloroquinolin-3-yl)methyl)isonicotinamide |
| 127 | 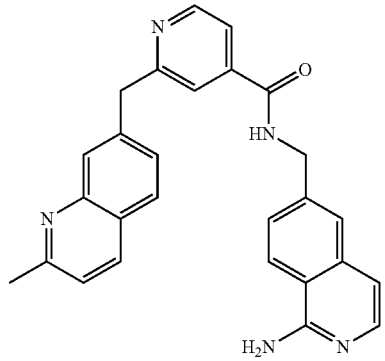 [SMILES: Cc1ccc2ccc(Cc3cc(C(=O)NCc4ccc5c(N)nccc5c4)ccn3)cc2n1] | N-((1-aminoisoquinolin-6-yl)methyl)-2-((2-methylquinolin-7-yl)methyl)isonicotinamide |

| Chemical Synthesis Example | Structure | Name |
|---|---|---|
| 128 | 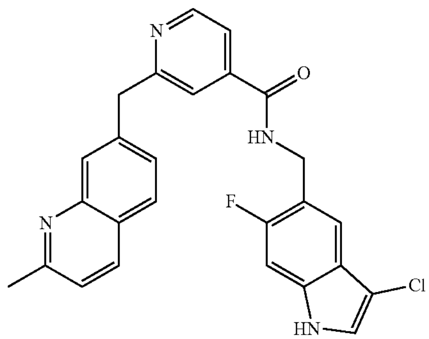 [SMILES: Cc1ccc2ccc(Cc3cc(C(=O)NCc4cc5c(Cl)c[nH]c5cc4F)ccn3)cc2n1] | N-((3-chloro-6-fluoro-1H-indol-5-yl)methyl)-2-((2-methylquinolin-7-yl)methyl)isonicotinamide |
| 129 | 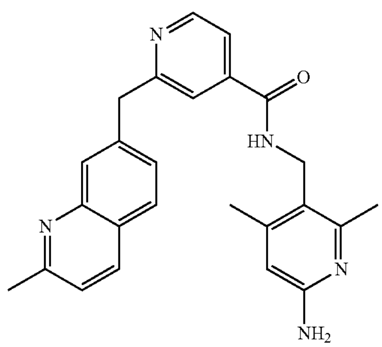 | N-((6-amino-2,4-dimethylpyridin-3-yl)methyl)-2-((2-methylquinolin-7-yl)methyl)isonicotinamide |
| 130 | 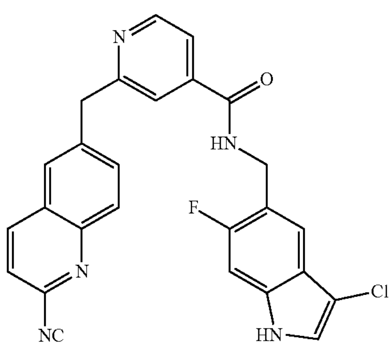 | N-((3-chloro-6-fluoro-1H-indol-5-yl)methyl)-2-((2-isocyanoquinolin-6-yl)methyl)isonicotinamide |
| 131 | 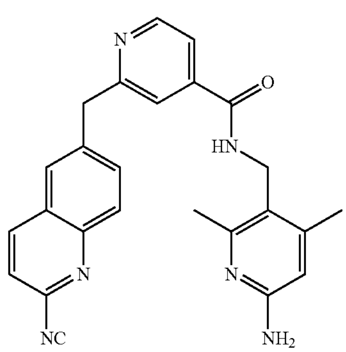 | N-((6-amino-2,4-dimethylpyridin-3-yl)methyl)-2-((2-isocyanoquinolin-6-yl)methyl)isonicotinamide |

TABLE 1-continued

| Chemical Synthesis Example | Structure | Name |
|---|---|---|
| 132 | 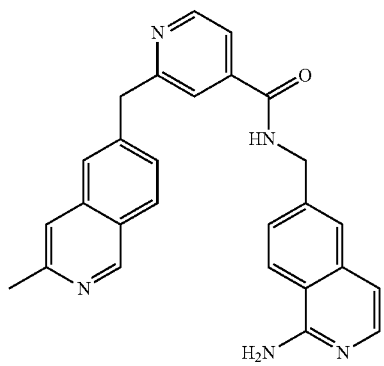 [SMILES: Cc1cc2cc(Cc3cc(C(=O)NCc4ccc5c(N)nccc5c4)ccn3)ccc2cn1] | N-((1-aminoisoquinolin-6-yl)methyl)-2-((3-methylisoquinolin-6-yl)methyl)isonicotinamide |
| 133 | 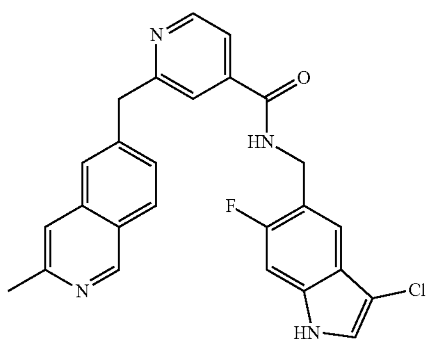 [SMILES: Cc1cc2cc(Cc3cc(C(=O)NCc4cc5c(Cl)c[nH]c5cc4F)ccn3)ccc2cn1] | N-((3-chloro-6-fluoro-1H-indol-5-yl)methyl)-2-((3-methylisoquinolin-6-yl)methyl)isonicotinamide |
| 134 | 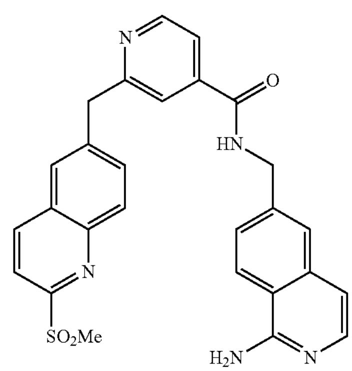 [SMILES: CS(=O)(=O)c1ccc2cc(Cc3cc(C(=O)NCc4ccc5c(N)nccc5c4)ccn3)ccc2n1] | N-((1-aminoisoquinolin-6-yl)methyl)-2-((2-(methylsulfonyl)quinolin-6-yl)methyl)isonicotinamide |
| 135 | 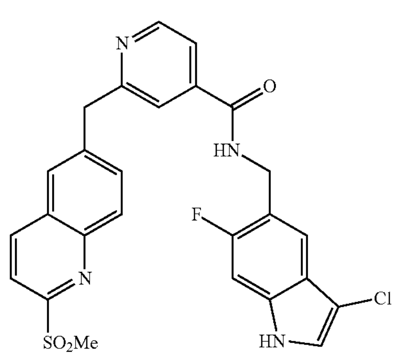 [SMILES: CS(=O)(=O)c1ccc2cc(Cc3cc(C(=O)NCc4cc5c(Cl)c[nH]c5cc4F)ccn3)ccc2n1] | N-((3-chloro-6-fluoro-1H-indol-5-yl)methyl)-2-((2-(methylsulfonyl)quinolin-6-yl)methyl)isonicotinamide |

TABLE 1-continued

| Chemical Synthesis Example | Structure | Name |
|---|---|---|
| 136 | 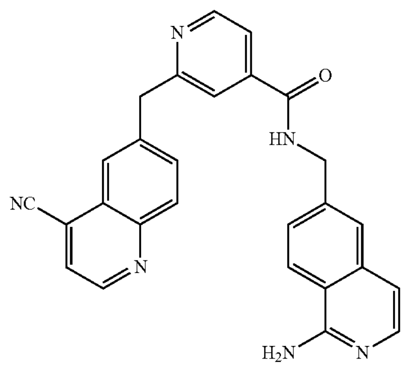 [SMILES: N#Cc1ccnc2ccc(Cc3cc(C(=O)NCc4ccc5c(N)nccc5c4)ccn3)cc12] | N-((1-aminoisoquinolin-6-yl)methyl)-2-((4-cyanoquinolin-6-yl)methyl)isonicotinamide |
| 137 | 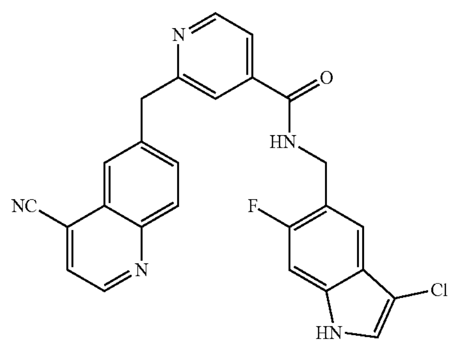 [SMILES: N#Cc1ccnc2ccc(Cc3cc(C(=O)NCc4cc5c(Cl)c[nH]c5cc4F)ccn3)cc12] | N-((3-chloro-6-fluoro-1H-indol-5-yl)methyl)-2-((4-cyanoquinolin-6-yl)methyl)isonicotinamide |
| 138 | 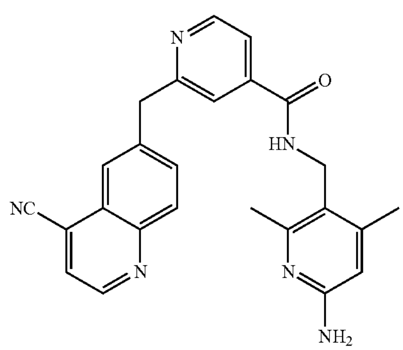 [SMILES: Cc1cc(N)nc(C)c1CNC(=O)c1ccnc(Cc2ccc3nccc(C#N)c3c2)c1] | N-((6-amino-2,4-dimethylpyridin-3-yl)methyl)-2-((4-cyanoquinolin-6-yl)methyl)isonicotinamide |
| 139 | 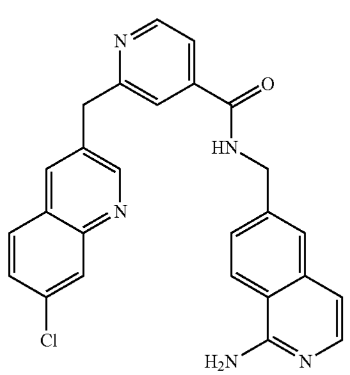 [SMILES: Nc1nccc2cc(CNC(=O)c3ccnc(Cc4cnc5cc(Cl)ccc5c4)c3)ccc12] | N-((1-aminoisoquinolin-6-yl)methyl)-2-((7-chloroquinolin-3-yl)methyl)isonicotinamide |

TABLE 1-continued

| Chemical Synthesis Example | Structure | Name |
|---|---|---|
| 140 | 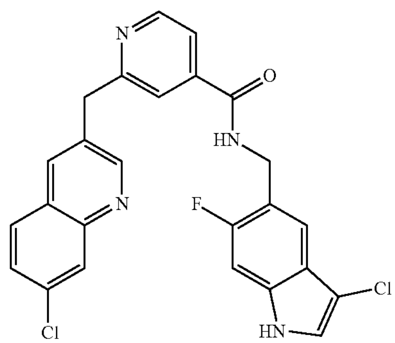 [SMILES: O=C(NCc1cc2c(Cl)c[nH]c2cc1F)c1ccnc(Cc2cnc3cc(Cl)ccc3c2)c1] | N-((3-chloro-6-fluoro-1H-indol-5-yl)methyl)-2-((7-chloroquinolin-3-yl)methyl)isonicotinamide |
| 141 | 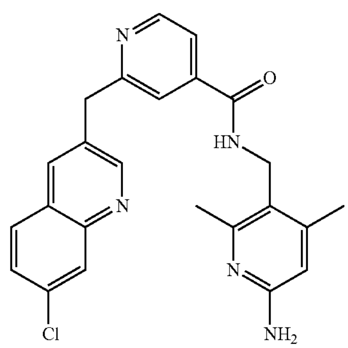 [SMILES: Cc1cc(N)nc(C)c1CNC(=O)c1ccnc(Cc2cnc3cc(Cl)ccc3c2)c1] | N-((6-amino-2,4-dimethylpyridin-3-yl)methyl)-2-((7-chloroquinolin-3-yl)methyl)isonicotinamide |
| 142 | 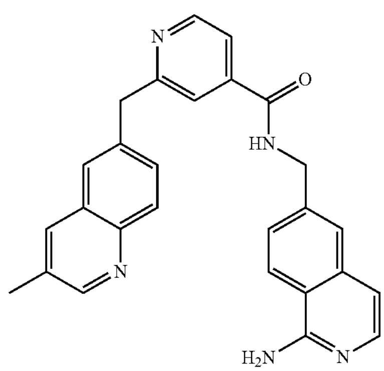 [SMILES: Cc1cnc2ccc(Cc3cc(C(=O)NCc4ccc5c(N)nccc5c4)ccn3)cc2c1] | N-((1-aminoisoquinolin-6-yl)methyl)-2-((3-methylquinolin-6-yl)methyl)isonicotinamide |
| 143 | 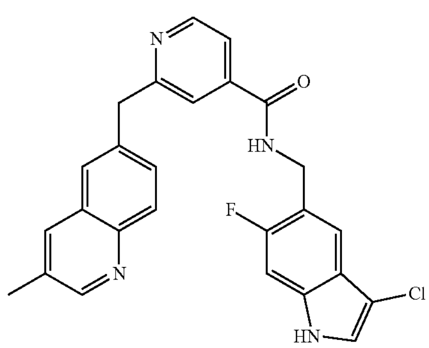 [SMILES: Cc1cnc2ccc(Cc3cc(C(=O)NCc4cc5c(Cl)c[nH]c5cc4F)ccn3)cc2c1] | N-((3-chloro-6-fluoro-1H-indol-5-yl)methyl)-2-((3-methylquinolin-6-yl)methyl)isonicotinamide |

TABLE 1-continued

| Chemical Synthesis Example | Structure | Name |
|---|---|---|
| 144 | 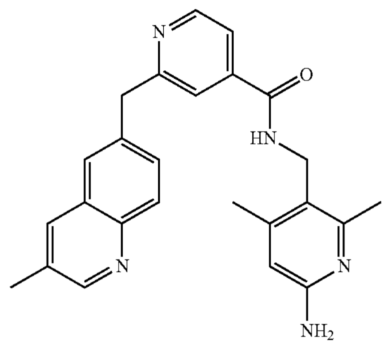 | N-((6-amino-2,4-dimethylpyridin-3-yl)methyl)-2-((3-methylquinolin-6-yl)methyl)isonicotinamide |
| 145 | 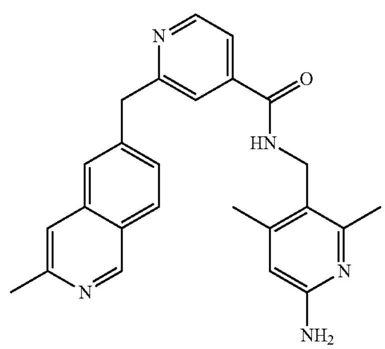 | N-((6-amino-2,4-dimethylpyridin-3-yl)methyl)-2-((3-methylisoquinolin-6-yl)methyl)isonicotinamide |
| 146 | 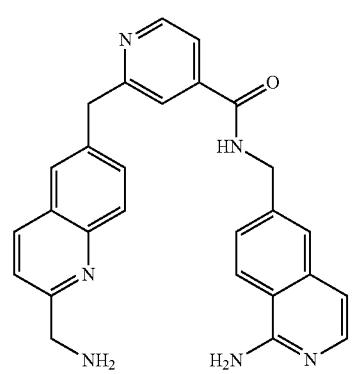 [SMILES: NCc1ccc2cc(Cc3cc(C(=O)NCc4ccc5c(N)nccc5c4)ccn3)ccc2n1] | N-((1-aminoisoquinolin-6-yl)methyl)-2-((2-(aminomethyl)quinolin-6-yl)methyl)isonicotinamide |
| 147 | 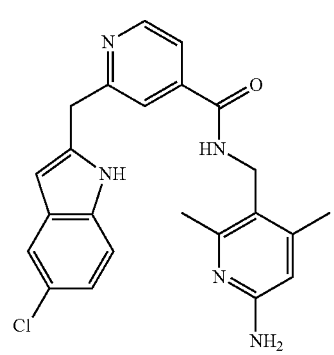 [SMILES: Cc1cc(N)nc(C)c1CNC(=O)c1ccnc(Cc2cc3cc(Cl)ccc3[nH]2)c1] | N-((6-amino-2,4-dimethylpyridin-3-yl)methyl)-2-((5-chloro-1H-indol-2-yl)methyl)isonicotinamide |

TABLE 1-continued

| Chemical Synthesis Example | Structure | Name |
|---|---|---|
| 148 | 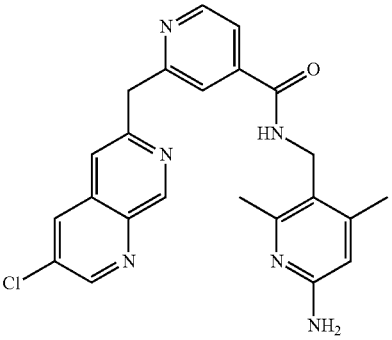 [SMILES: Cc1cc(N)nc(C)c1CNC(=O)c1ccnc(Cc2cc3cc(Cl)cnc3cn2)c1] | N-((6-amino-2,4-dimethylpyridin-3-yl)methyl)-2-((3-chloro-1,7-naphthyridin-6-yl)methyl)isonicotinamide |
| 149 | 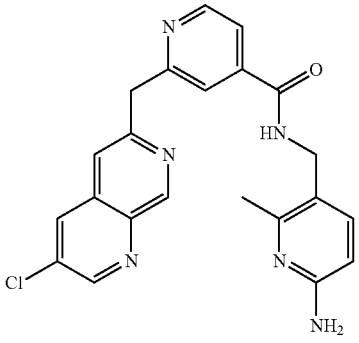 [SMILES: Cc1nc(N)ccc1CNC(=O)c1ccnc(Cc2cc3cc(Cl)cnc3cn2)c1] | N-((6-amino-2-methylpyridin-3-yl)methyl)-2-((3-chloro-1,7-naphthyridin-6-yl)methyl)isonicotinamide |
| 150 | 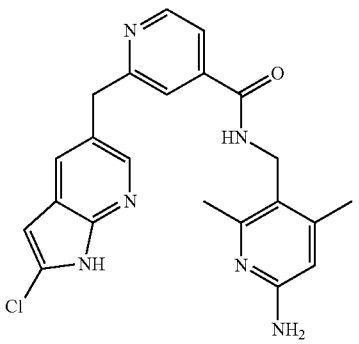 [SMILES: Cc1cc(N)nc(C)c1CNC(=O)c1ccnc(Cc2cnc3[nH]c(Cl)cc3c2)c1] | N-((6-amino-2,4-dimethylpyridin-3-yl)methyl)-2-((2-chloro-1H-pyrrolo[2,3-b]pyridin-5-yl)methyl)isonicotinamide |
| 151 | 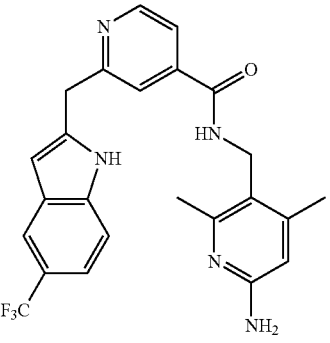 | N-((6-amino-2,4-dimethylpyridin-3-yl)methyl)-2-((5-(trifluoromethyl)-1H-indol-2-yl)methyl)isonicotinamide |

TABLE 1-continued

| Chemical Synthesis Example | Structure | Name |
|---|---|---|
| 152 | 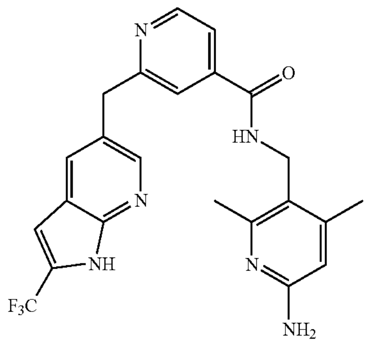 [SMILES: Cc1cc(N)nc(C)c1CNC(=O)c1ccnc(Cc2cnc3[nH]c(C(F)(F)F)cc3c2)c1] | N-((6-amino-2,4-dimethylpyridin-3-yl)methyl)-2-((2-(trifluoromethyl)-1H-pyrrolo[2,3-b]pyridin-5-yl)methyl)isonicotinamide |
| 153 | 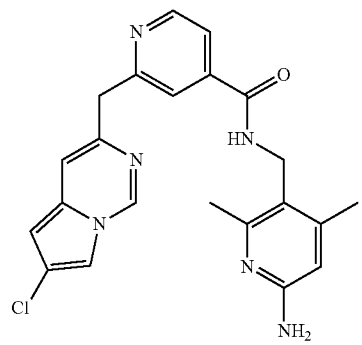 [SMILES: Cc1cc(N)nc(C)c1CNC(=O)c1ccnc(Cc2cc3cc(Cl)cn3cn2)c1] | N-((6-amino-2,4-dimethylpyridin-3-yl)methyl)-2-((6-chloropyrrolo[1,2-c]pyrimidin-3-yl)methyl)isonicotinamide |
| 154 | 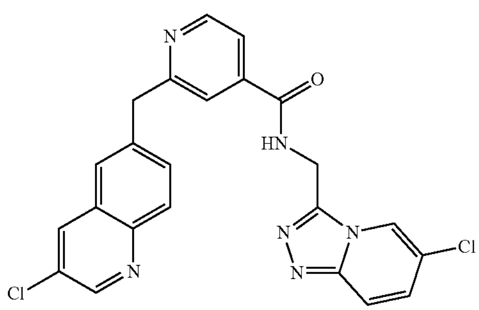 [SMILES: O=C(NCc1nnc2ccc(Cl)cn12)c1ccnc(Cc2ccc3ncc(Cl)cc3c2)c1] | N-((6-chloro-[1,2,4]triazolo[4,3-a]pyridin-3-yl)methyl)-2-((3-chloroquinolin-6-yl)methyl)isonicotinamide |
| 155 | 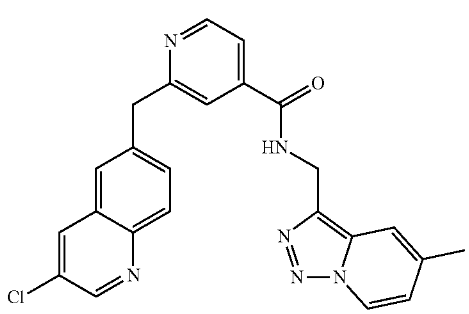 [SMILES: Cc1ccn2nnc(CNC(=O)c3ccnc(Cc4ccc5ncc(Cl)cc5c4)c3)c2c1] | 2-((3-chloroquinolin-6-yl)methyl)-N-((5-methyl-[1,2,3]triazolo[1,5-a]pyridin-3-yl)methyl)isonicotinamide |

TABLE 1-continued

| Chemical Synthesis Example | Structure | Name |
|---|---|---|
| 156 | 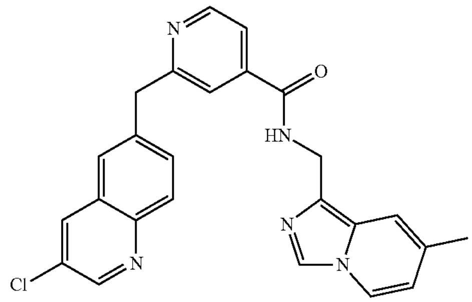 [SMILES: Cc1ccn2cnc(CNC(=O)c3ccnc(Cc4ccc5ncc(Cl)cc5c4)c3)c2c1] | 2-((3-chloroquinolin-6-yl)methyl)-N-((7-methylimidazo[1,5-a]pyridin-1-yl)methyl)isonicotinamide |
| 157 | 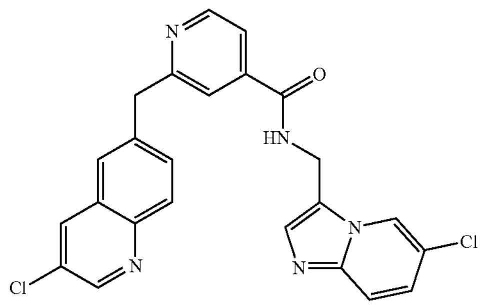 [SMILES: O=C(NCc1cnc2ccc(Cl)cn12)c1ccnc(Cc2ccc3ncc(Cl)cc3c2)c1] | N-((6-chloroimidazo[1,2-a]pyridin-3-yl)methyl)-2-((3-chloroquinolin-6-yl)methyl)isonicotinamide |
| 158 | 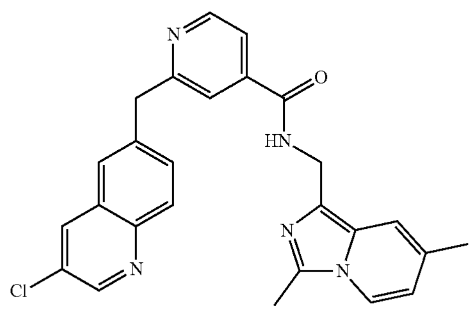 [SMILES: Cc1ccn2c(C)nc(CNC(=O)c3ccnc(Cc4ccc5ncc(Cl)cc5c4)c3)c2c1] | 2-((3-chloroquinolin-6-yl)methyl)-N-((3,7-dimethylimidazo[1,5-a]pyridin-1-yl)methyl)isonicotinamide |
| 159 | 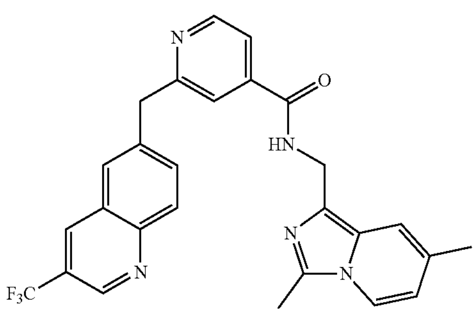 [SMILES: Cc1ccn2c(C)nc(CNC(=O)c3ccnc(Cc4ccc5ncc(C(F)(F)F)cc5c4)c3)c2c1] | N-((3,7-dimethylimidazo[1,5-a]pyridin-1-yl)methyl)-2-((3-(trifluoromethyl)quinolin-6-yl)methyl)isonicotinamide |
| 160 | 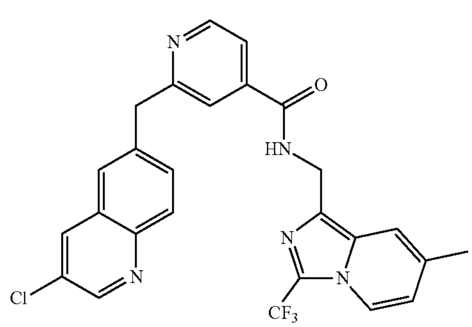 [SMILES: Cc1ccn2c(C(F)(F)F)nc(CNC(=O)c3ccnc(Cc4ccc5ncc(Cl)cc5c4)c3)c2c1] | 2-((3-chloroquinolin-6-yl)methyl)-N-((7-methyl-3-(trifluoromethyl)imidazo[1,5-a]pyridin-1-yl)methyl)isonicotinamide |

TABLE 1-continued

| Chemical Synthesis Example | Structure | Name |
|---|---|---|
| 161 | 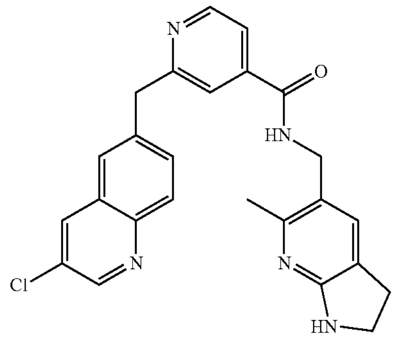 [SMILES: Cc1nc2c(cc1CNC(=O)c1ccnc(Cc3ccc4ncc(Cl)cc4c3)c1)CCN2] | 2-((3-chloroquinolin-6-yl)methyl)-N-((6-methyl-2,3-dihydro-1H-pyrrolo[2,3-b]pyridin-5-yl)methyl)isonicotinamide |
| 162 | 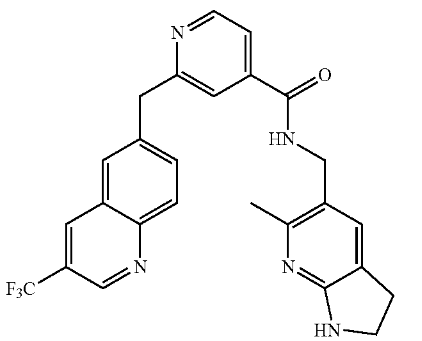 [SMILES: Cc1nc2c(cc1CNC(=O)c1ccnc(Cc3ccc4ncc(C(F)(F)F)cc4c3)c1)CCN2] | N-((6-methyl-2,3-dihydro-1H-pyrrolo[2,3-b]pyridin-5-yl)methyl)-2-((3-(trifluoromethyl)quinolin-6-yl)methyl)isonicotinamide |
| 163 | 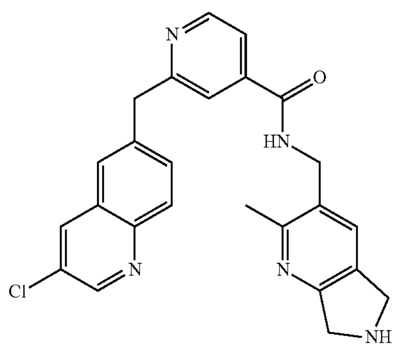 [SMILES: Cc1nc2c(cc1CNC(=O)c1ccnc(Cc3ccc4ncc(Cl)cc4c3)c1)CNC2] | 2-((3-chloroquinolin-6-yl)methyl)-N-((2-methyl-6,7-dihydro-5H-pyrrolo[3,4-b]pyridin-3-yl)methyl)isonicotinamide |
| 164 | 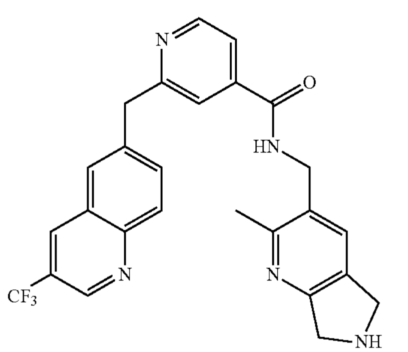 [SMILES: Cc1nc2c(cc1CNC(=O)c1ccnc(Cc3ccc4ncc(C(F)(F)F)cc4c3)c1)CNC2] | N-((2-methyl-6,7-dihydro-5H-pyrrolo[3,4-b]pyridin-3-yl)methyl)-2-((3-(trifluoromethyl)quinolin-6-yl)methyl)isonicotinamide |

TABLE 1-continued

| Chemical Synthesis Example | Structure | Name |
|---|---|---|
| 165 | 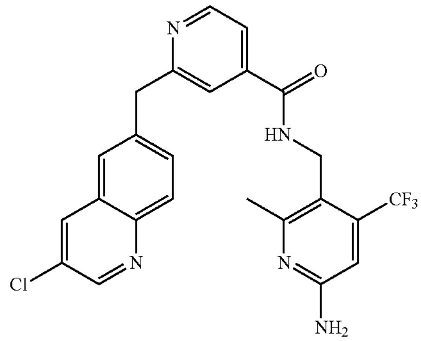 [SMILES: Cc1nc(N)cc(C(F)(F)F)c1CNC(=O)c1ccnc(Cc2ccc3ncc(Cl)cc3c2)c1] | N-((6-amino-2-methyl-4-(trifluoromethyl)pyridin-3-yl)methyl)-2-((3-chloroquinolin-6-yl)methyl)isonicotinamide |
| 166 | 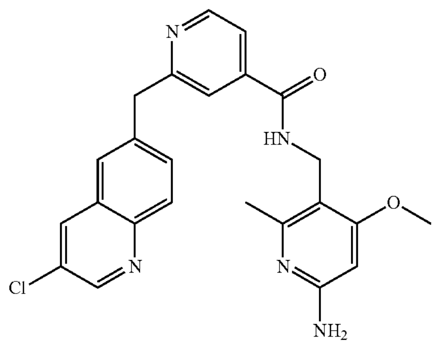 [SMILES: COc1cc(N)nc(C)c1CNC(=O)c1ccnc(Cc2ccc3ncc(Cl)cc3c2)c1] | N-((6-amino-4-methoxy-2-methylpyridin-3-yl)methyl)-2-((3-chloroquinolin-6-yl)methyl)isonicotinamide |
| 167 | 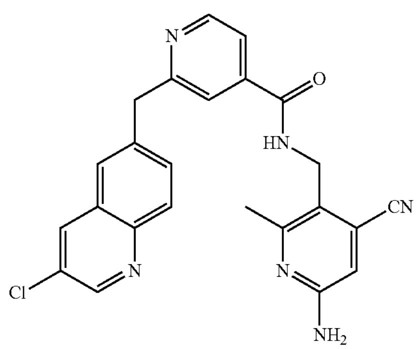 [SMILES: Cc1nc(N)cc(C#N)c1CNC(=O)c1ccnc(Cc2ccc3ncc(Cl)cc3c2)c1] | N-((6-amino-4-cyano-2-methylpyridin-3-yl)methyl)-2-((3-chloroquinolin-6-yl)methyl)isonicotinamide |
| 168 | 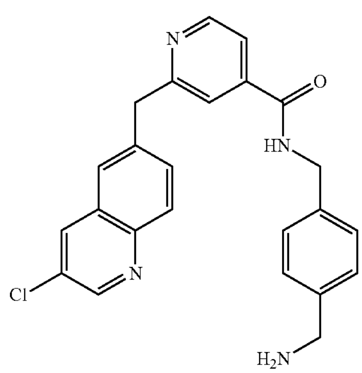 [SMILES: NCc1ccc(CNC(=O)c2ccnc(Cc3ccc4ncc(Cl)cc4c3)c2)cc1] | N-(4-(aminomethyl)benzyl)-2-((3-chloroquinolin-6-yl)methyl)isonicotinamide |

TABLE 1-continued

| Chemical Synthesis Example | Structure | Name |
|---|---|---|
| 169 | 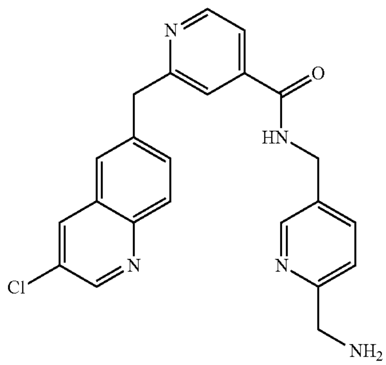 [SMILES: NCc1ccc(CNC(=O)c2ccnc(Cc3ccc4ncc(Cl)cc4c3)c2)cn1] | N-((6-(aminomethyl)pyridin-3-yl)methyl)-2-((3-chloroquinolin-6-yl)methyl)isonicotinamide |
| 170 | 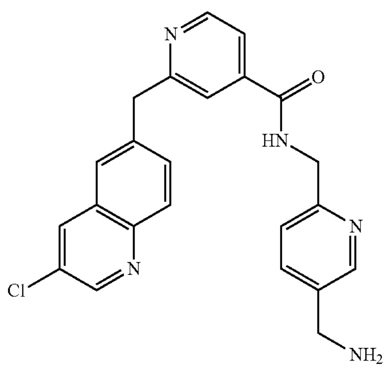 [SMILES: NCc1ccc(CNC(=O)c2ccnc(Cc3ccc4ncc(Cl)cc4c3)c2)nc1] | N-((5-(aminomethyl)pyridin-2-yl)methyl)-2-((3-chloroquinolin-6-yl)methyl)isonicotinamide |
| 171 | 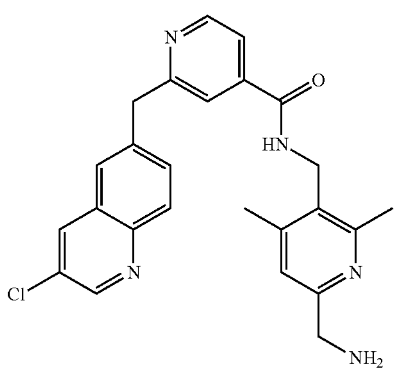 [SMILES: Cc1cc(CN)nc(C)c1CNC(=O)c1ccnc(Cc2ccc3ncc(Cl)cc3c2)c1] | N-((6-(aminomethyl)-2,4-dimethylpyridin-3-yl)methyl)-2-((3-chloroquinolin-6-yl)methyl)isonicotinamide |
| 172 | 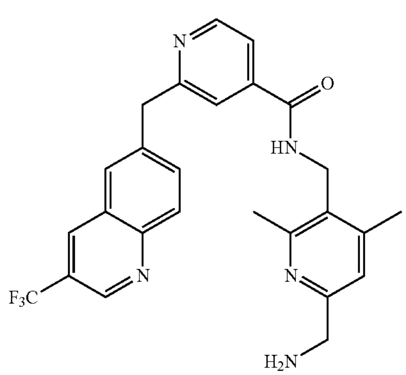 [SMILES: Cc1cc(CN)nc(C)c1CNC(=O)c1ccnc(Cc2ccc3ncc(C(F)(F)F)cc3c2)c1] | N-((6-(aminomethyl)-2,4-dimethylpyridin-3-yl)methyl)-2-((3-(trifluoromethyl)quinolin-6-yl)methyl)isonicotinamide |

TABLE 1-continued

| Chemical Synthesis Example | Structure | Name |
|---|---|---|
| 173 | 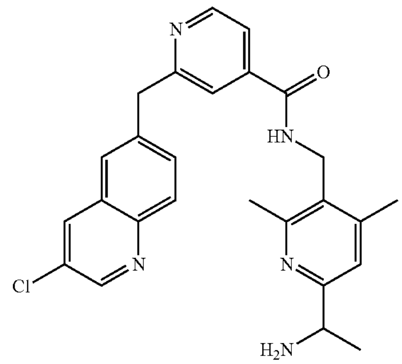 [SMILES: Cc1cc(C(C)N)nc(C)c1CNC(=O)c1ccnc(Cc2ccc3ncc(Cl)cc3c2)c1] | N-((6-(1-aminoethyl)-2,4-dimethylpyridin-3-yl)methyl)-2-((3-chloroquinolin-6-yl)methyl)isonicotinamide |
| 174 | 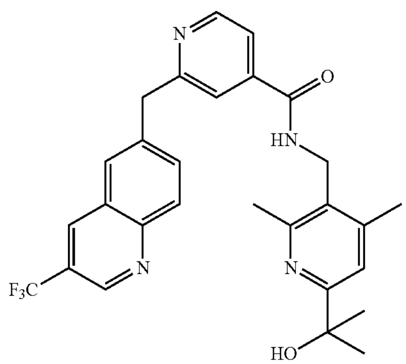 [SMILES: Cc1cc(C(C)(C)O)nc(C)c1CNC(=O)c1ccnc(Cc2ccc3ncc(C(F)(F)F)cc3c2)c1] | N-((6-(2-hydroxypropan-2-yl)-2,4-dimethylpyridin-3-yl)methyl)-2-((3-(trifluoromethyl)quinolin-6-yl)methyl)isonicotinamide |
| 175 | 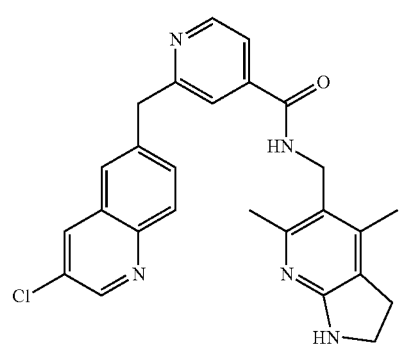 [SMILES: Cc1nc2c(c(C)c1CNC(=O)c1ccnc(Cc3ccc4ncc(Cl)cc4c3)c1)CCN2] | 2-((3-chloroquinolin-6-yl)methyl)-N-((4,6-dimethyl-2,3-dihydro-1H-pyrrolo[2,3-b]pyridin-5-yl)methyl)isonicotinamide |
| 176 | 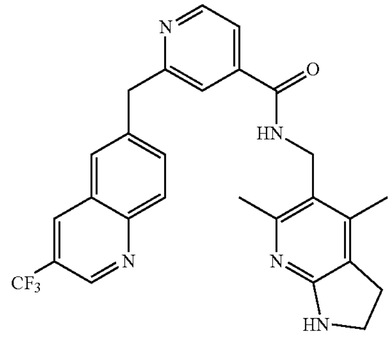 [SMILES: Cc1nc2c(c(C)c1CNC(=O)c1ccnc(Cc3ccc4ncc(C(F)(F)F)cc4c3)c1)CCN2] | N-((4,6-dimethyl-2,3-dihydro-1H-pyrrolo[2,3-b]pyridin-5-yl)methyl)-2-((3-(trifluoromethyl)quinolin-6-yl)methyl)isonicotinamide |

TABLE 1-continued

| Chemical Synthesis Example | Structure | Name |
|---|---|---|
| 177 | 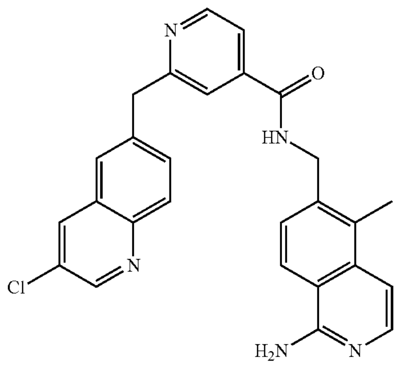 [SMILES: Cc1c(CNC(=O)c2ccnc(Cc3ccc4ncc(Cl)cc4c3)c2)ccc2c(N)nccc12] | N-((1-amino-5-methylisoquinolin-6-yl)methyl)-2-((3-chloroquinolin-6-yl)methyl)isonicotinamide |
| 178 | 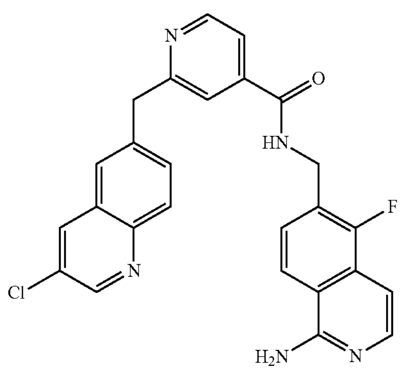 [SMILES: Nc1nccc2c(F)c(CNC(=O)c3ccnc(Cc4ccc5ncc(Cl)cc5c4)c3)ccc12] | N-((1-amino-5-fluoroisoquinolin-6-yl)methyl)-2-((3-chloroquinolin-6-yl)methyl)isonicotinamide |
| 179 | 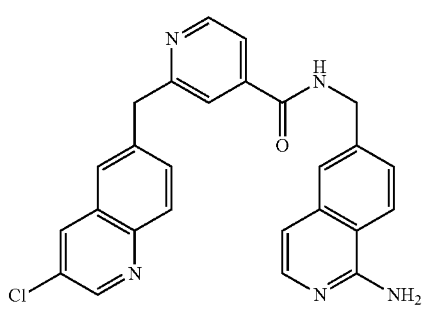 [SMILES: Nc1nccc2cc(CNC(=O)c3ccnc(Cc4ccc5ncc(Cl)cc5c4)c3)ccc12] | N-((1-aminoisoquinolin-6-yl)methyl)-2-((3-chloroquinolin-6-yl)methyl)isonicotinamide |
| 180 | 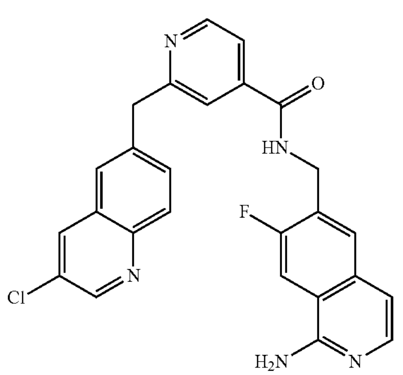 [SMILES: Nc1nccc2cc(CNC(=O)c3ccnc(Cc4ccc5ncc(Cl)cc5c4)c3)c(F)cc12] | N-((1-amino-7-fluoroisoquinolin-6-yl)methyl)-2-((3-chloroquinolin-6-yl)methyl)isonicotinamide |

TABLE 1-continued

| Chemical Synthesis Example | Structure | Name |
|---|---|---|
| 181 | 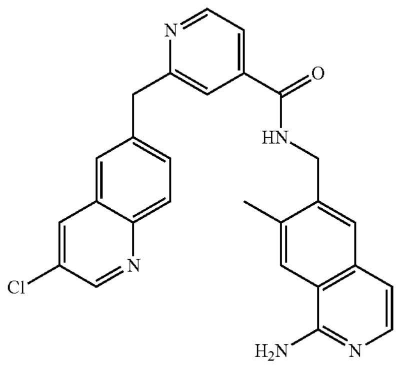 [SMILES: Cc1cc2c(N)nccc2cc1CNC(=O)c1ccnc(Cc2ccc3ncc(Cl)cc3c2)c1] | N-((1-amino-7-methylisoquinolin-6-yl)methyl)-2-((3-chloroquinolin-6-yl)methyl)isonicotinamide |
| 182 | 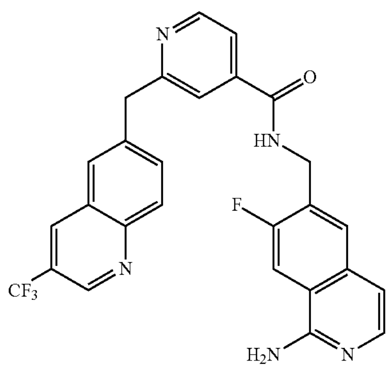 [SMILES: Nc1nccc2cc(CNC(=O)c3ccnc(Cc4ccc5ncc(C(F)(F)F)cc5c4)c3)c(F)cc12] | N-((1-amino-7-fluoroisoquinolin-6-yl)methyl)-2-((3-(trifluoromethyl)quinolin-6-yl)methyl)isonicotinamide |
| 183 | 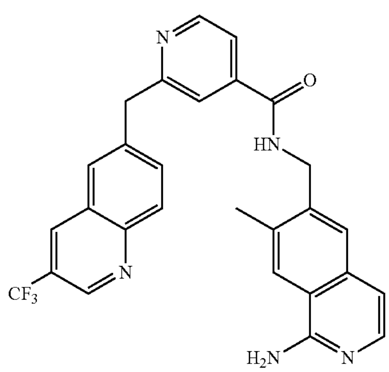 [SMILES: Cc1cc2c(N)nccc2cc1CNC(=O)c1ccnc(Cc2ccc3ncc(C(F)(F)F)cc3c2)c1] | N-((1-amino-7-methylisoquinolin-6-yl)methyl)-2-((3-(trifluoromethyl)quinolin-6-yl)methyl)isonicotinamide |
| 184 | 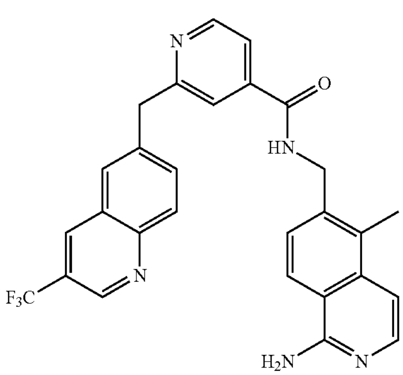 [SMILES: Cc1c(CNC(=O)c2ccnc(Cc3ccc4ncc(C(F)(F)F)cc4c3)c2)ccc2c(N)nccc12] | N-((1-amino-5-methylisoquinolin-6-yl)methyl)-2-((3-(trifluoromethyl)quinolin-6-yl)methyl)isonicotinamide |

TABLE 1-continued

| Chemical Synthesis Example | Structure | Name |
|---|---|---|
| 185 | 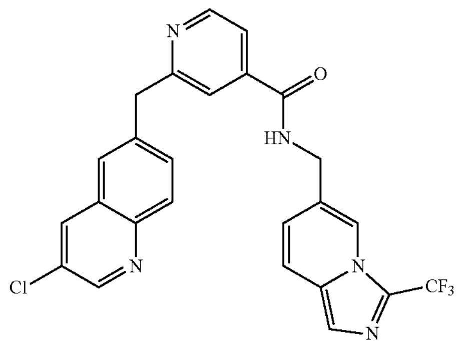 [SMILES: O=C(NCc1ccc2cnc(C(F)(F)F)n2c1)c1ccnc(Cc2ccc3ncc(Cl)cc3c2)c1] | 2-((3-chloroquinolin-6-yl)methyl)-N-((3-(trifluoromethyl)imidazo[1,5-a]pyridin-6-yl)methyl)isonicotinamide |
| 186 | 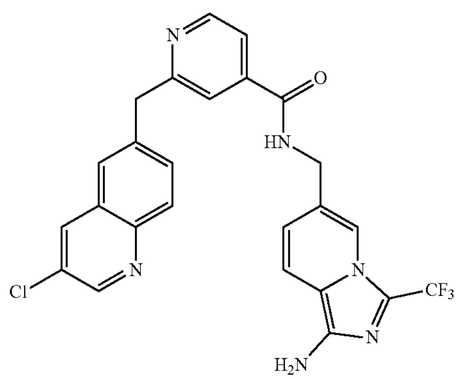 [SMILES: Nc1nc(C(F)(F)F)n2cc(CNC(=O)c3ccnc(Cc4ccc5ncc(Cl)cc5c4)c3)ccc12] | N-((1-amino-3-(trifluoromethyl)imidazo[1,5-a]pyridin-6-yl)methyl)-2-((3-chloroquinolin-6-yl)methyl)isonicotinamide |
| 187 | 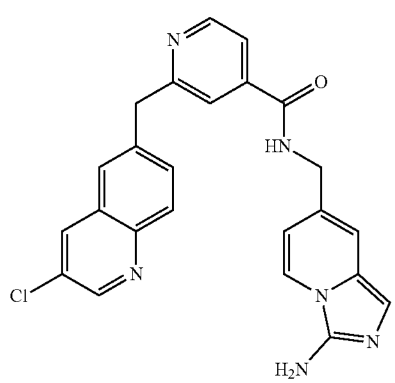 | N-((3-aminoimidazo[1,5-a]pyridin-7-yl)methyl)-2-((3-chloroquinolin-6-yl)methyl)isonicotinamide |
| 188 | 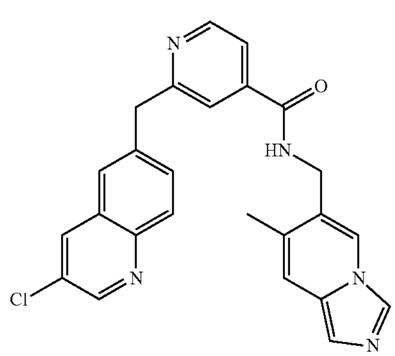 [SMILES: Cc1cc2cncn2cc1CNC(=O)c1ccnc(Cc2ccc3ncc(Cl)cc3c2)c1] | 2-((3-chloroquinolin-6-yl)methyl)-N-((7-methylimidazo[1,5-a]pyridin-6-yl)methyl)isonicotinamide |

TABLE 1-continued

| Chemical Synthesis Example | Structure | Name |
|---|---|---|
| 189 | 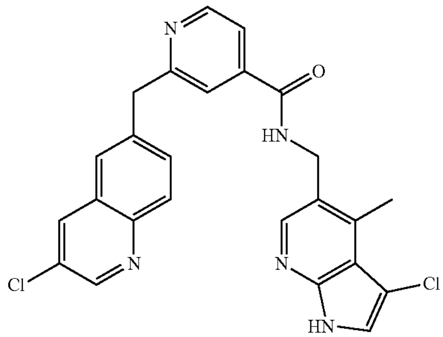 [SMILES: Cc1c(CNC(=O)c2ccnc(Cc3ccc4ncc(Cl)cc4c3)c2)cnc2[nH]cc(Cl)c12] | N-((3-chloro-4-methyl-1H-pyrrolo[2,3-b]pyridin-5-yl)methyl)-2-((3-chloroquinolin-6-yl)methyl)isonicotinamide |
| 190 | 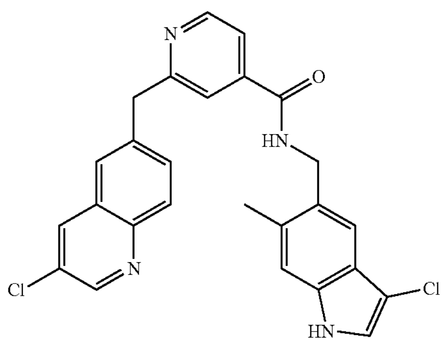 [SMILES: Cc1cc2[nH]cc(Cl)c2cc1CNC(=O)c1ccnc(Cc2ccc3ncc(Cl)cc3c2)c1] | N-((3-chloro-6-methyl-1H-indol-5-yl)methyl)-2-((3-chloroquinolin-6-yl)methyl)isonicotinamide |
| 191 | 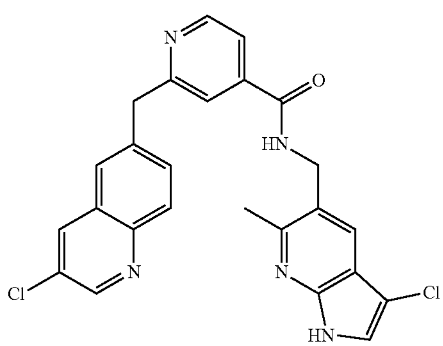 [SMILES: Cc1nc2[nH]cc(Cl)c2cc1CNC(=O)c1ccnc(Cc2ccc3ncc(Cl)cc3c2)c1] | N-((3-chloro-6-methyl-1H-pyrrolo[2,3-b]pyridin-5-yl)methyl)-2-((3-chloroquinolin-6-yl)methyl)isonicotinamide |
| 192 | 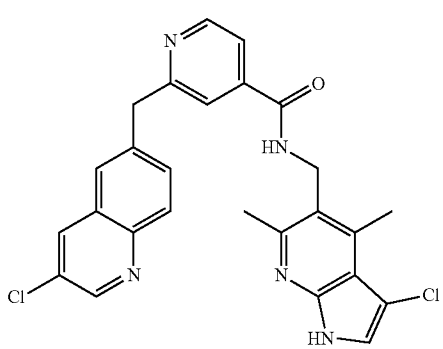 [SMILES: Cc1nc2[nH]cc(Cl)c2c(C)c1CNC(=O)c1ccnc(Cc2ccc3ncc(Cl)cc3c2)c1] | N-((3-chloro-4,6-dimethyl-1H-pyrrolo[2,3-b]pyridin-5-yl)methyl)-2-((3-chloroquinolin-6-yl)methyl)isonicotinamide |

TABLE 1-continued

| Chemical Synthesis Example | Structure | Name |
|---|---|---|
| 193 | 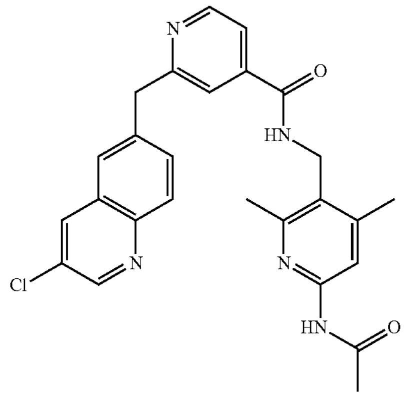 [SMILES: CC(=O)Nc1cc(C)c(CNC(=O)c2ccnc(Cc3ccc4ncc(Cl)cc4c3)c2)c(C)n1] | N-((6-acetamido-2,4-dimethylpyridin-3-yl)methyl)-2-((3-chloroquinolin-6-yl)methyl)isonicotinamide |
| 194 | 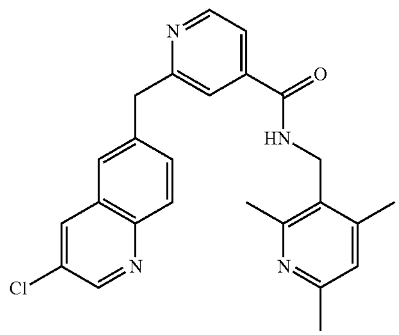 [SMILES: Cc1cc(C)c(CNC(=O)c2ccnc(Cc3ccc4ncc(Cl)cc4c3)c2)c(C)n1] | 2-((3-chloroquinolin-6-yl)methyl)-N-((2,4,6-trimethylpyridin-3-yl)methyl)isonicotinamide |
| 195 | 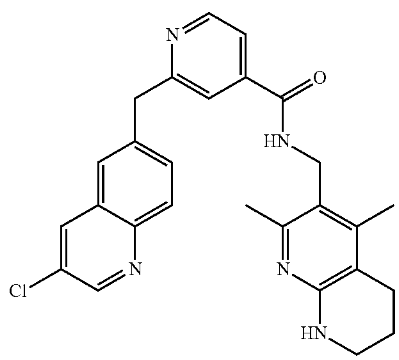 [SMILES: Cc1nc2c(c(C)c1CNC(=O)c1ccnc(Cc3ccc4ncc(Cl)cc4c3)c1)CCCN2] | 2-((3-chloroquinolin-6-yl)methyl)-N-((2,4-dimethyl-5,6,7,8-tetrahydro-1,8-naphthyridin-3-yl)methyl)isonicotinamide |
| 196 | 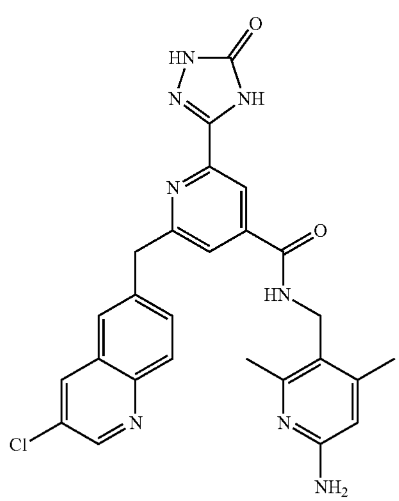 [SMILES: Cc1cc(N)nc(C)c1CNC(=O)c1cc(Cc2ccc3ncc(Cl)cc3c2)nc(-c2n[nH]c(=O)[nH]2)c1] | N-((6-amino-2,4-dimethylpyridin-3-yl)methyl)-2-((3-chloroquinolin-6-yl)methyl)-6-(5-oxo-4,5-dihydro-1H-1,2,4-triazol-3-yl)isonicotinamide |

TABLE 1-continued

| Chemical Synthesis Example | Structure | Name |
|---|---|---|
| 197 | 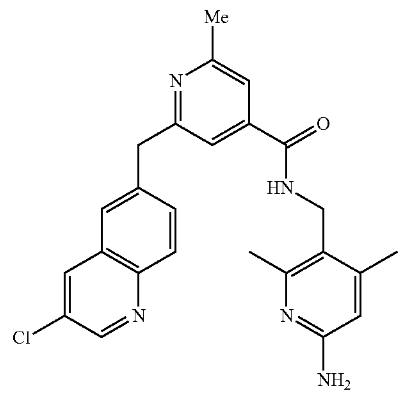 [SMILES: Cc1cc(C(=O)NCc2c(C)cc(N)nc2C)cc(Cc2ccc3ncc(Cl)cc3c2)n1] | N-((6-amino-2-methylpyridin-3-yl)methyl)-2-((3-chloroquinolin-6-yl)methyl)isonicotinamide |
| 198 | 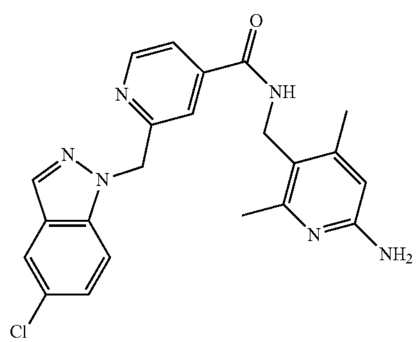 [SMILES: Cc1cc(N)nc(C)c1CNC(=O)c1ccnc(Cn2ncc3cc(Cl)ccc32)c1] | N-((6-amino-2,4-dimethylpyridin-3-yl)methyl)-2-((5-chloro-1H-indazol-1-yl)methyl)isonicotinamide |
| 199 | 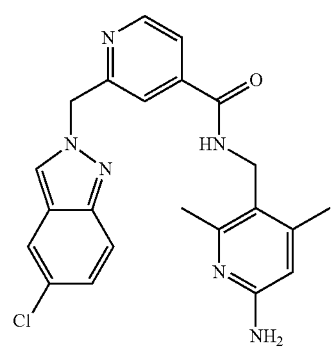 [SMILES: Cc1cc(N)nc(C)c1CNC(=O)c1ccnc(Cn2cc3cc(Cl)ccc3n2)c1] | N-((6-amino-2,4-dimethylpyridin-3-yl)methyl)-2-((5-chloro-2H-indazol-2-yl)methyl)isonicotinamide |
| 200 | 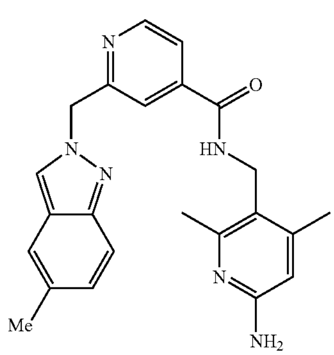 [SMILES: Cc1ccc2nn(Cc3cc(C(=O)NCc4c(C)cc(N)nc4C)ccn3)cc2c1] | N-((6-amino-2,4-dimethylpyridin-3-yl)methyl)-2-((5-methyl-2H-indazol-2-yl)methyl)isonicotinamide |

TABLE 1-continued

| Chemical Synthesis Example | Structure | Name |
|---|---|---|
| 201 | 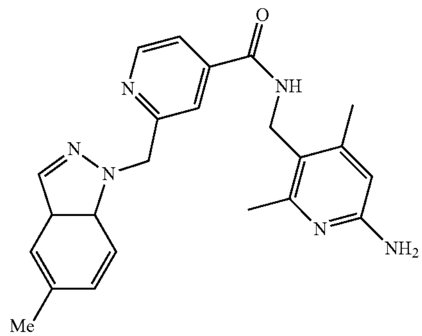 [SMILES: CC1=CC2C=NN(Cc3cc(C(=O)NCc4c(C)cc(N)nc4C)ccn3)C2C=C1] | N-((6-amino-2,4-dimethylpyridin-3-yl)methyl)-2-((5-methyl-3a,7a-dihydro-1H-indazol-1-yl)methyl)isonicotinamide |
| 202 | 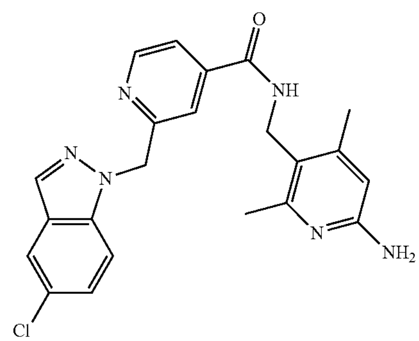 [SMILES: Cc1cc(N)nc(C)c1CNC(=O)c1ccnc(Cn2ncc3cc(Cl)ccc32)c1] | N-((6-amino-2,4-dimethylpyridin-3-yl)methyl)-2-((5-chloro-1H-pyrazolo[3,4-b]pyridin-1-yl)methyl)isonicotinamide |
| 203 | 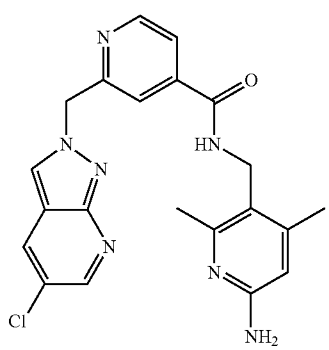 [SMILES: Cc1cc(N)nc(C)c1CNC(=O)c1ccnc(Cn2cc3cc(Cl)cnc3n2)c1] | N-((6-amino-2,4-dimethylpyridin-3-yl)methyl)-2-((5-chloro-2H-pyrazolo[3,4-b]pyridin-2-yl)methyl)isonicotinamide |
| 204 | 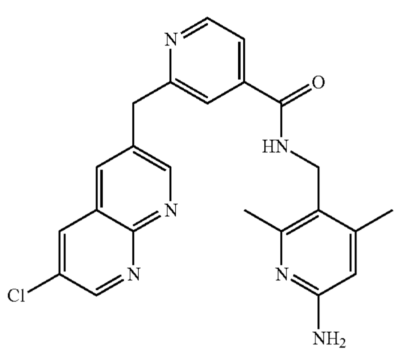 [SMILES: Cc1cc(N)nc(C)c1CNC(=O)c1ccnc(Cc2cnc3ncc(Cl)cc3c2)c1] | N-((6-amino-2,4-dimethylpyridin-3-yl)methyl)-2-((6-chloro-1,8-naphthyridin-3-yl)methyl)isonicotinamide |

TABLE 1-continued

| Chemical Synthesis Example | Structure | Name |
|---|---|---|
| 205 | 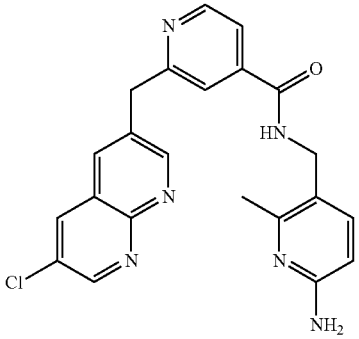 [SMILES: Cc1nc(N)ccc1CNC(=O)c1ccnc(Cc2cnc3ncc(Cl)cc3c2)c1] | N-((6-amino-2-methylpyridin-3-yl)methyl)-2-((6-chloro-1,8-naphthyridin-3-yl)methyl)isonicotinamide |
| 206 | 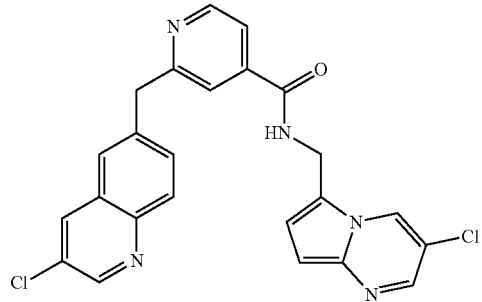 | N-((3-chloropyrrolo[1,2-a]pyrimidin-6-yl)methyl)-2-((3-chloroquinolin-6-yl)methyl)isonicotinamide |
| 207 | 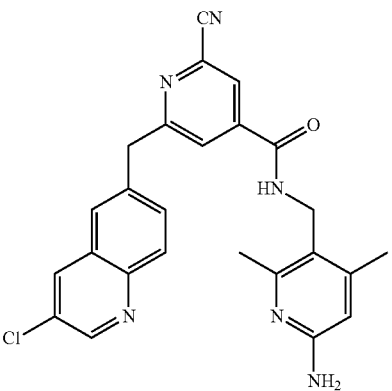 | N-((6-amino-2,4-dimethylpyridin-3-yl)methyl)-2-((3-chloroquinolin-6-yl)methyl)-6-cyanoisonicotinamide |
| 208 | 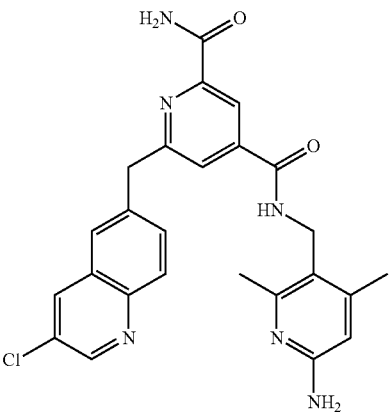 [SMILES: Cc1cc(N)nc(C)c1CNC(=O)c1cc(Cc2ccc3ncc(Cl)cc3c2)nc(C(N)=O)c1] | $N^4$-((6-amino-2,4-dimethylpyridin-3-yl)methyl)-6-((3-chloroquinolin-6-yl)methyl)pyridine-2,4-dicarboxamide |

TABLE 1-continued

| Chemical Synthesis Example | Structure | Name |
|---|---|---|
| 209 | 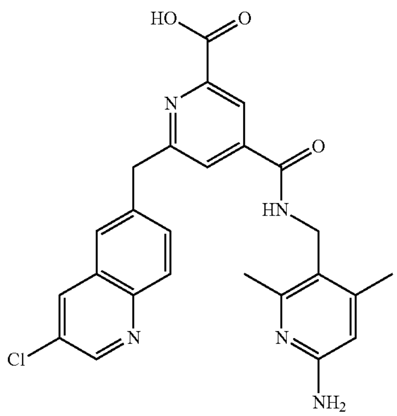 [SMILES: Cc1cc(N)nc(C)c1CNC(=O)c1cc(Cc2ccc3ncc(Cl)cc3c2)nc(C(=O)O)c1] | 4-((6-amino-2,4-dimethylpyridin-3-yl)methylcarbamoyl)-6-((3-chloroquinolin-6-yl)methyl)picolinic acid |
| 210 | 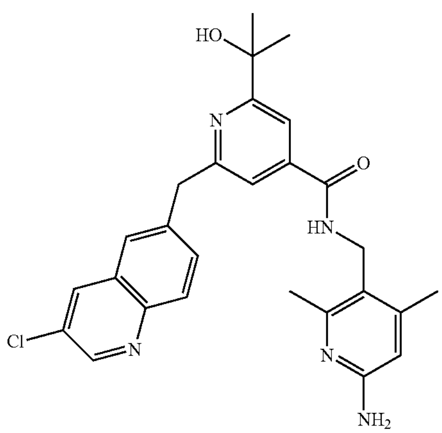 [SMILES: Cc1cc(N)nc(C)c1CNC(=O)c1cc(Cc2ccc3ncc(Cl)cc3c2)nc(C(C)(C)O)c1] | N-((6-amino-2,4-dimethylpyridin-3-yl)methyl)-2-((3-chloroquinolin-6-yl)methyl)-6-(2-hydroxypropan-2-yl)isonicotinamide |
| 211 | 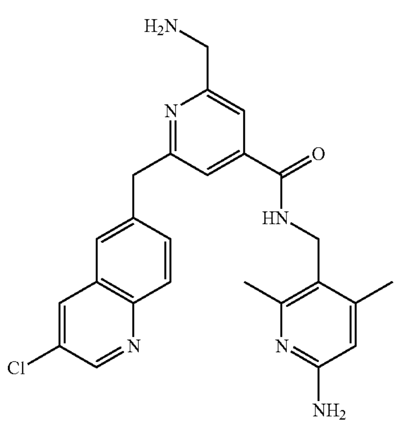 [SMILES: Cc1cc(N)nc(C)c1CNC(=O)c1cc(CN)nc(Cc2ccc3ncc(Cl)cc3c2)c1] | N-((6-amino-2,4-dimethylpyridin-3-yl)methyl)-2-(aminomethyl)-6-((3-chloroquinolin-6-yl)methyl)isonicotinamide |

| Chemical Synthesis Example | Structure | Name |
|---|---|---|
| 212 | 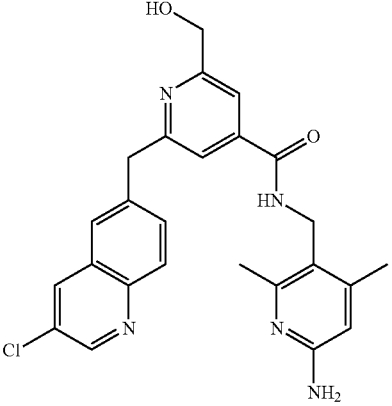 [SMILES: Cc1cc(N)nc(C)c1CNC(=O)c1cc(CO)nc(Cc2ccc3ncc(Cl)cc3c2)c1] | N-((6-amino-2,4-dimethylpyridin-3-yl)methyl)-2-((3-chloroquinolin-6-yl)methyl)-6-(hydroxymethyl)isonicotinamide |
| 213 | 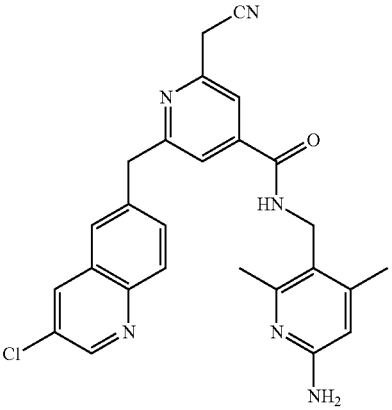 [SMILES: Cc1cc(N)nc(C)c1CNC(=O)c1cc(CC#N)nc(Cc2ccc3ncc(Cl)cc3c2)c1] | N-((6-amino-2,4-dimethylpyridin-3-yl)methyl)-2-((3-chloroquinolin-6-yl)methyl)-6-(cyanomethyl)isonicotinamide |
| 214 | 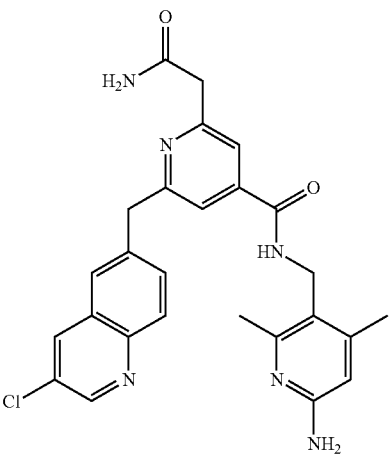 [SMILES: Cc1cc(N)nc(C)c1CNC(=O)c1cc(CC(N)=O)nc(Cc2ccc3ncc(Cl)cc3c2)c1] | N-((6-amino-2,4-dimethylpyridin-3-yl)methyl)-2-(2-amino-2-oxoethyl)-6-((3-chloroquinolin-6-yl)methyl)isonicotinamide |

TABLE 1-continued

| Chemical Synthesis Example | Structure | Name |
|---|---|---|
| 215 | 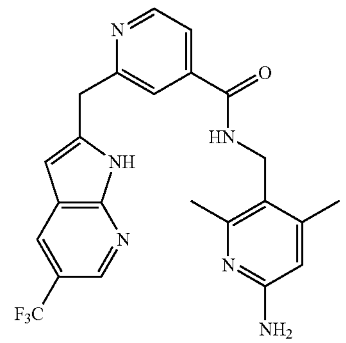 [SMILES: Cc1cc(N)nc(C)c1CNC(=O)c1ccnc(Cc2cc3cc(C(F)(F)F)cnc3[nH]2)c1] | N-((6-amino-2,4-dimethylpyridin-3-yl)methyl)-2-((5-(trifluoromethyl)-1H-pyrrolo[2,3-b]pyridin-2-yl)methyl)isonicotinamide |
| 216 | 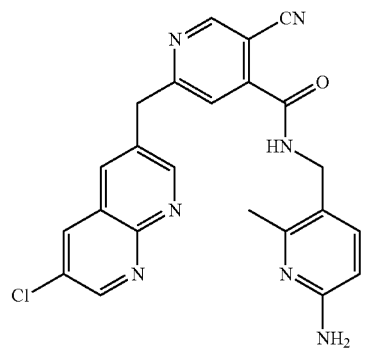 [SMILES: Cc1nc(N)ccc1CNC(=O)c1cc(Cc2cnc3ncc(Cl)cc3c2)ncc1C#N] | N-((6-amino-2-methylpyridin-3-yl)methyl)-2-((6-chloro-1,8-naphthyridin-3-yl)methyl)-5-cyanoisonicotinamide |
| 217 | 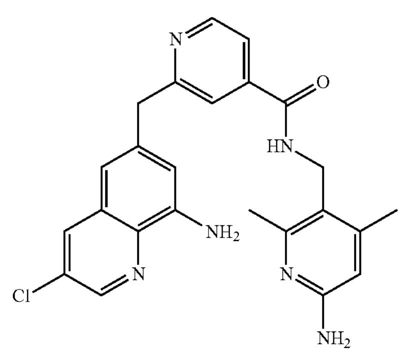 [SMILES: Cc1cc(N)nc(C)c1CNC(=O)c1ccnc(Cc2cc(N)c3ncc(Cl)cc3c2)c1] | N-((6-amino-2,4-dimethylpyridin-3-yl)methyl)-2-((8-amino-3-chloroquinolin-6-yl)methyl)isonicotinamide |
| 218 | 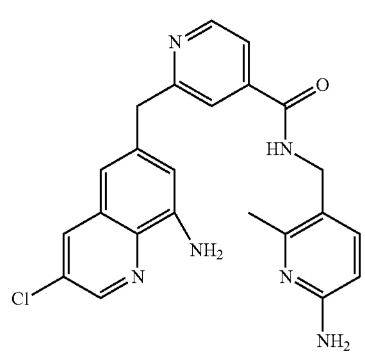 [SMILES: Cc1nc(N)ccc1CNC(=O)c1ccnc(Cc2cc(N)c3ncc(Cl)cc3c2)c1] | N-((6-amino-2-methylpyridin-3-yl)methyl)-2-((8-amino-3-chloroquinolin-6-yl)methyl)isonicotinamide |

TABLE 1-continued

| Chemical Synthesis Example | Structure | Name |
|---|---|---|
| 219 | 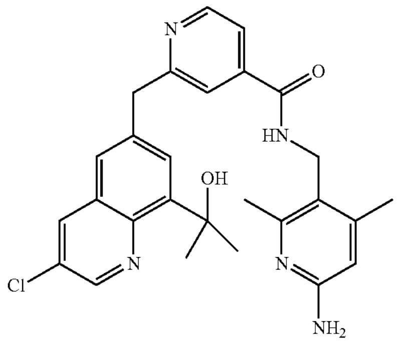 [SMILES: Cc1cc(N)nc(C)c1CNC(=O)c1ccnc(Cc2cc(C(C)(C)O)c3ncc(Cl)cc3c2)c1] | N-((6-amino-2,4-dimethylpyridin-3-yl)methyl)-2-((3-chloro-8-(2-hydroxypropan-2-yl)quinolin-6-yl)methyl)isonicotinamide |
| 220 | 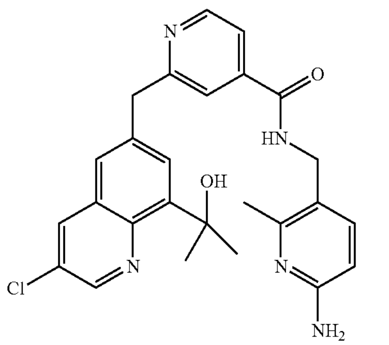 [SMILES: Cc1nc(N)ccc1CNC(=O)c1ccnc(Cc2cc(C(C)(C)O)c3ncc(Cl)cc3c2)c1] | N-((6-amino-2-methylpyridin-3-yl)methyl)-2-((3-chloro-8-(2-hydroxypropan-2-yl)quinolin-6-yl)methyl)isonicotinamide |
| 221 | 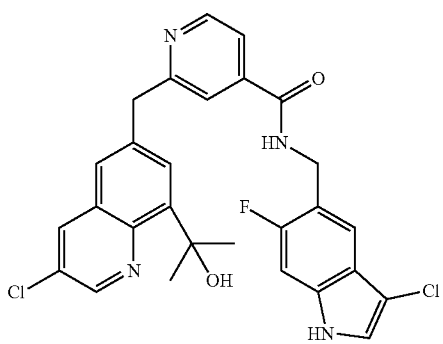 [SMILES: CC(C)(O)c1cc(Cc2cc(C(=O)NCc3cc4c(Cl)c[nH]c4cc3F)ccn2)cc2cc(Cl)cnc12] | N-((3-chloro-6-fluoro-1H-indol-5-yl)methyl)-2-((3-chloro-8-(2-hydroxypropan-2-yl)quinolin-6-yl)methyl)isonicotinamide |
| 222 | 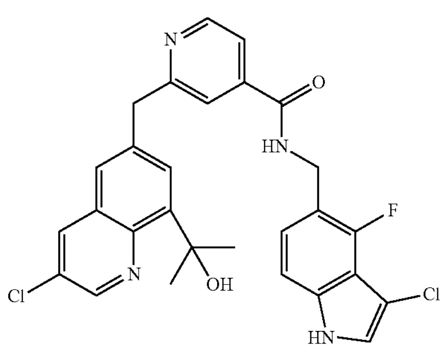 [SMILES: CC(C)(O)c1cc(Cc2cc(C(=O)NCc3ccc4[nH]cc(Cl)c4c3F)ccn2)cc2cc(Cl)cnc12] | N-((3-chloro-4-fluoro-1H-indol-5-yl)methyl)-2-((3-chloro-8-(2-hydroxypropan-2-yl)quinolin-6-yl)methyl)isonicotinamide |

TABLE 1-continued

| Chemical Synthesis Example | Structure | Name |
|---|---|---|
| 223 | 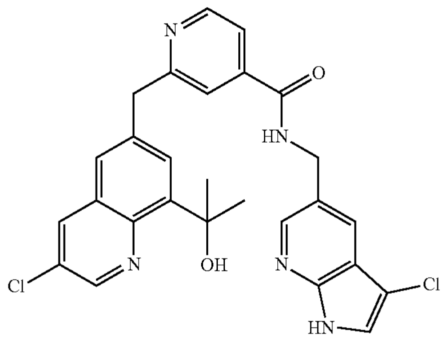 [SMILES: CC(C)(O)c1cc(Cc2cc(C(=O)NCc3cnc4[nH]cc(Cl)c4c3)ccn2)cc2cc(Cl)cnc12] | N-((3-chloro-1H-pyrrolo[2,3-b]pyridin-5-yl)methyl)-2-((3-chloro-8-(2-hydroxypropan-2-yl)quinolin-6-yl)methyl)isonicotinamide |
| 224 | 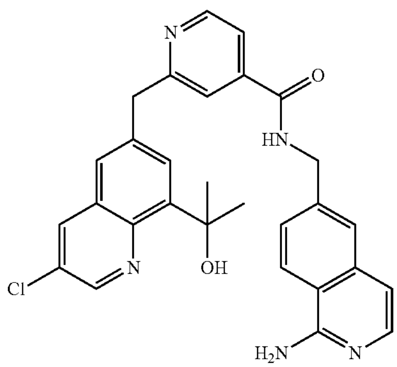 [SMILES: CC(C)(O)c1cc(Cc2cc(C(=O)NCc3ccc4c(N)nccc4c3)ccn2)cc2cc(Cl)cnc12] | N-((1-aminoisoquinolin-6-yl)methyl)-2-((3-chloro-8-(2-hydroxypropan-2-yl)quinolin-6-yl)methyl)isonicotinamide |
| 225 | 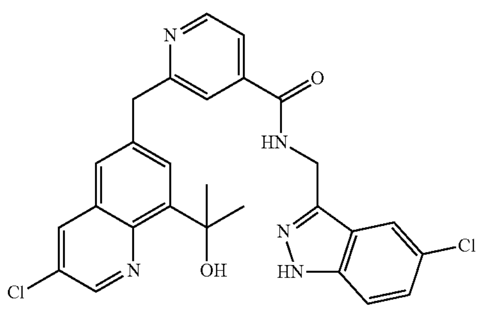 [SMILES: CC(C)(O)c1cc(Cc2cc(C(=O)NCc3n[nH]c4ccc(Cl)cc34)ccn2)cc2cc(Cl)cnc12] | N-((5-chloro-1H-indazol-3-yl)methyl)-2-((3-chloro-8-(2-hydroxypropan-2-yl)quinolin-6-yl)methyl)isonicotinamide |
| 226 | 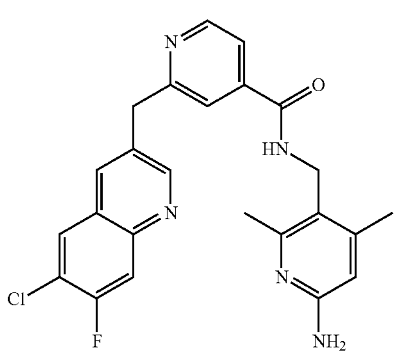 [SMILES: Cc1cc(N)nc(C)c1CNC(=O)c1ccnc(Cc2cnc3cc(F)c(Cl)cc3c2)c1] | N-((6-amino-2,4-dimethylpyridin-3-yl)methyl)-2-((6-chloro-7-fluoroquinolin-3-yl)methyl)isonicotinamide |

TABLE 1-continued

| Chemical Synthesis Example | Structure | Name |
|---|---|---|
| 227 | 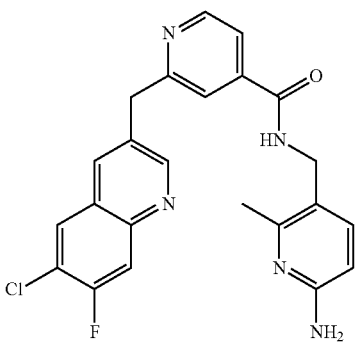 [SMILES: Cc1nc(N)ccc1CNC(=O)c1ccnc(Cc2cnc3cc(F)c(Cl)cc3c2)c1] | N-((6-amino-2-methylpyridin-3-yl)methyl)-2-((6-chloro-7-fluoroquinolin-3-yl)methyl)isonicotinamide |
| 228 | 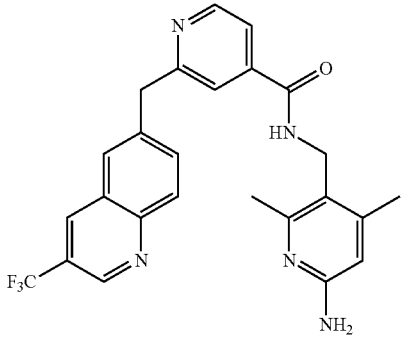 [SMILES: Cc1cc(N)nc(C)c1CNC(=O)c1ccnc(Cc2ccc3ncc(C(F)(F)F)cc3c2)c1] | N-((6-amino-2,4-dimethylpyridin-3-yl)methyl)-2-((3-(trifluoromethyl)quinolin-6-yl)methyl)isonicotinamide |
| 229 | 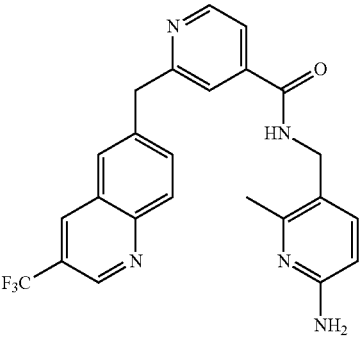 [SMILES: Cc1nc(N)ccc1CNC(=O)c1ccnc(Cc2ccc3ncc(C(F)(F)F)cc3c2)c1] | N-((6-amino-2-methylpyridin-3-yl)methyl)-2-((3-(trifluoromethyl)quinolin-6-yl)methyl)isonicotinamide |
| 230 | 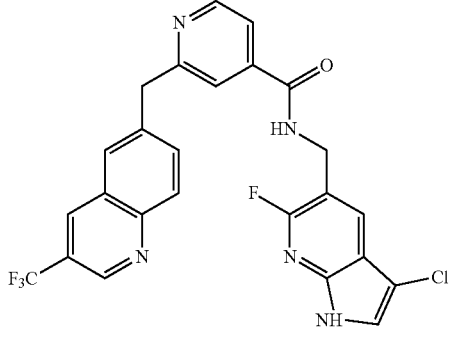 | N-((3-chloro-6-fluoro-1H-indol-5-yl)methyl)-2-((3-(trifluoromethyl)quinolin-6-yl)methyl)isonicotinamide |

TABLE 1-continued

| Chemical Synthesis Example | Structure | Name |
|---|---|---|
| 231 | 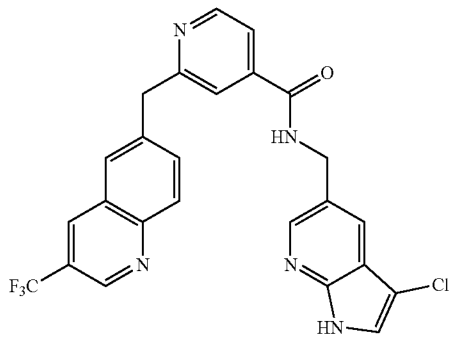 [SMILES: O=C(NCc1cnc2[nH]cc(Cl)c2c1)c1ccnc(Cc2ccc3ncc(C(F)(F)F)cc3c2)c1] | N-((3-chloro-1H-pyrrolo[2,3-b]pyridin-5-yl)methyl)-2-((3-(trifluoromethyl)quinolin-6-yl)methyl)isonicotinamide |
| 232 | 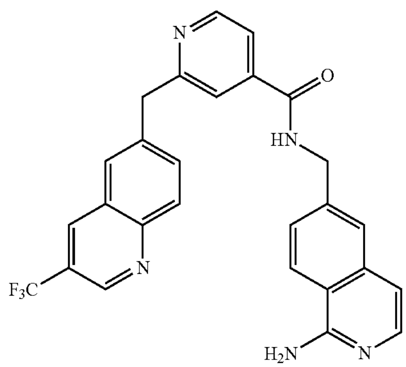 [SMILES: Nc1nccc2cc(CNC(=O)c3ccnc(Cc4ccc5ncc(C(F)(F)F)cc5c4)c3)ccc12] | N-((1-aminoisoquinolin-6-yl)methyl)-2-((3-(trifluoromethyl)quinolin-6-yl)methyl)isonicotinamide |
| 233 | 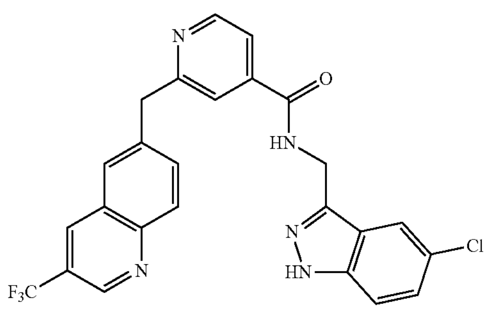 [SMILES: O=C(NCc1n[nH]c2ccc(Cl)cc12)c1ccnc(Cc2ccc3ncc(C(F)(F)F)cc3c2)c1] | N-((5-chloro-1H-indazol-3-yl)methyl)-2-((3-(trifluoromethyl)quinolin-6-yl)methyl)isonicotinamide |
| 234 | 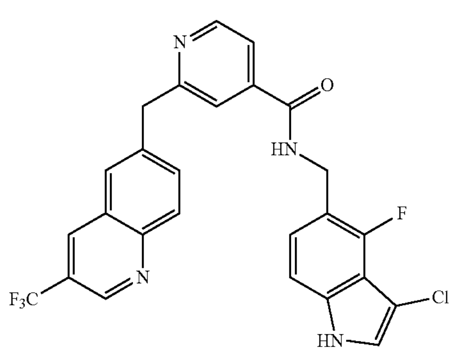 [SMILES: O=C(NCc1ccc2[nH]cc(Cl)c2c1F)c1ccnc(Cc2ccc3ncc(C(F)(F)F)cc3c2)c1] | N-((3-chloro-4-fluoro-1H-indol-5-yl)methyl)-2-((3-(trifluoromethyl)quinolin-6-yl)methyl)isonicotinamide |

TABLE 1-continued

| Chemical Synthesis Example | Structure | Name |
|---|---|---|
| 235 | 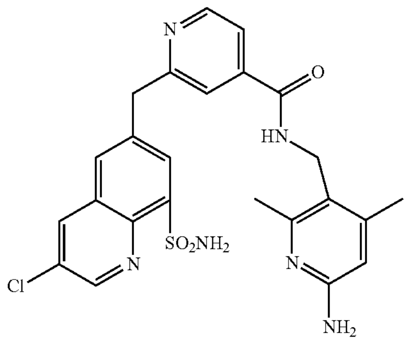 [SMILES: Cc1cc(N)nc(C)c1CNC(=O)c1ccnc(Cc2cc(S(N)(=O)=O)c3ncc(Cl)cc3c2)c1] | N-((6-amino-2,4-dimethylpyridin-3-yl)methyl)-2-((3-chloro-8-sulfamoylquinolin-6-yl)methyl)isonicotinamide |
| 236 | 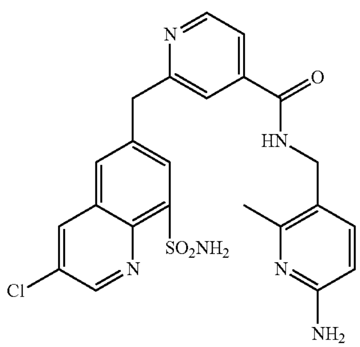 [SMILES: Cc1nc(N)ccc1CNC(=O)c1ccnc(Cc2cc(S(N)(=O)=O)c3ncc(Cl)cc3c2)c1] | N-((6-amino-2-methylpyridin-3-yl)methyl)-2-((3-chloro-8-sulfamoylquinolin-6-yl)methyl)isonicotinamide |
| 237 | 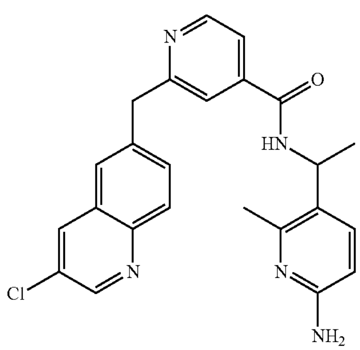 [SMILES: Cc1nc(N)ccc1C(C)NC(=O)c1ccnc(Cc2ccc3ncc(Cl)cc3c2)c1] | N-(1-(6-amino-2-methylpyridin-3-yl)ethyl)-2-((3-chloroquinolin-6-yl)methyl)isonicotinamide |
| 238 | 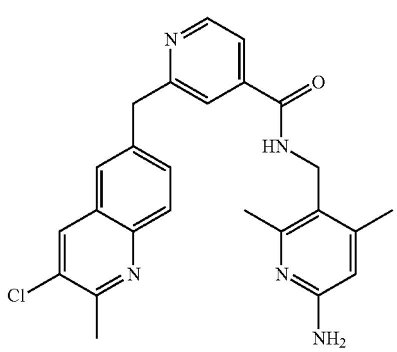 [SMILES: Cc1cc(N)nc(C)c1CNC(=O)c1ccnc(Cc2ccc3nc(C)c(Cl)cc3c2)c1] | N-((6-amino-2,4-dimethylpyridin-3-yl)methyl)-2-((3-chloro-2-methylquinolin-6-yl)methyl)isonicotinamide |

TABLE 1-continued

| Chemical Synthesis Example | Structure | Name |
|---|---|---|
| 239 | 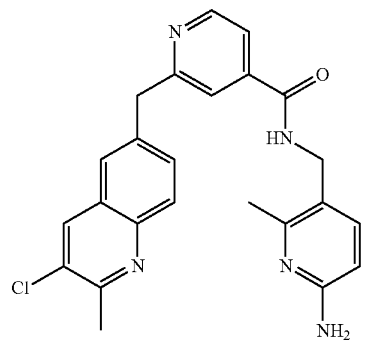 [SMILES: Cc1nc2ccc(Cc3cc(C(=O)NCc4ccc(N)nc4C)ccn3)cc2cc1Cl] | N-((6-amino-2-methylpyridin-3-yl)methyl)-2-((3-chloro-2-methylquinolin-6-yl)methyl)isonicotinamide |
| 240 | 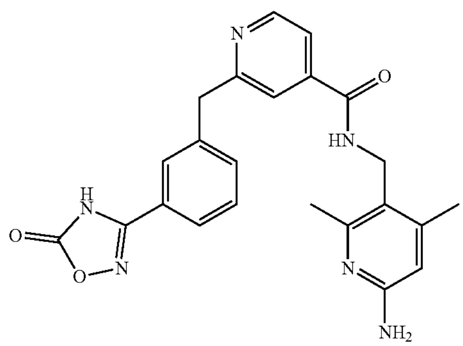 [SMILES: Cc1cc(N)nc(C)c1CNC(=O)c1ccnc(Cc2cccc(-c3noc(=O)[nH]3)c2)c1] | N-((6-amino-2,4-dimethylpyridin-3-yl)methyl)-2-(3-(5-oxo-4,5-dihydro-1,2,4-oxadiazol-3-yl)benzyl)isonicotinamide |
| 241 | 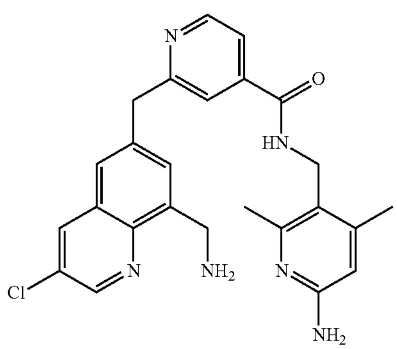 [SMILES: Cc1cc(N)nc(C)c1CNC(=O)c1ccnc(Cc2cc(CN)c3ncc(Cl)cc3c2)c1] | N-((6-amino-2,4-dimethylpyridin-3-yl)methyl)-2-((8-(aminomethyl)-3-chloroquinolin-6-yl)methyl)isonicotinamide |
| 242 | 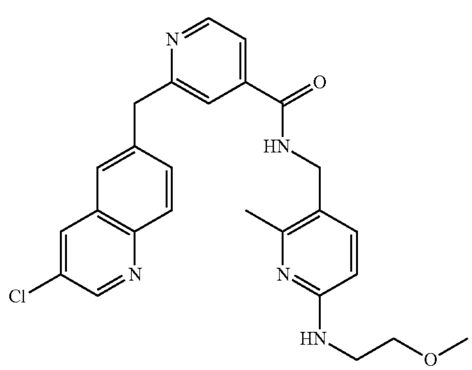 [SMILES: COCCNc1ccc(CNC(=O)c2ccnc(Cc3ccc4ncc(Cl)cc4c3)c2)c(C)n1] | 2-((3-chloroquinolin-6-yl)methyl)-N-((6-((2-methoxyethyl)amino)-2-methylpyridin-3-yl)methyl)isonicotinamide |

TABLE 1-continued

| Chemical Synthesis Example | Structure | Name |
|---|---|---|
| 243 | 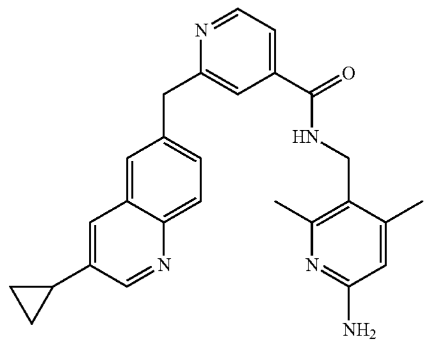 [SMILES: Cc1cc(N)nc(C)c1CNC(=O)c1ccnc(Cc2ccc3ncc(C4CC4)cc3c2)c1] | N-((6-amino-2,4-dimethylpyridin-3-yl)methyl)-2-((3-cyclopropylquinolin-6-yl)methyl)isonicotinamide |
| 244 | 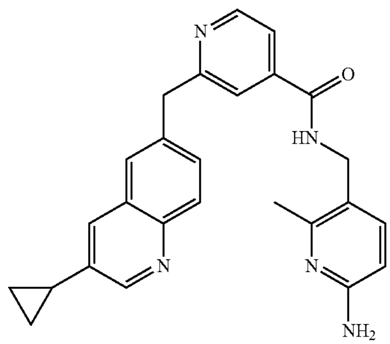 [SMILES: Cc1nc(N)ccc1CNC(=O)c1ccnc(Cc2ccc3ncc(C4CC4)cc3c2)c1] | N-((6-amino-2-methylpyridin-3-yl)methyl)-2-((3-cyclopropylquinolin-6-yl)methyl)isonicotinamide |
| 245 | 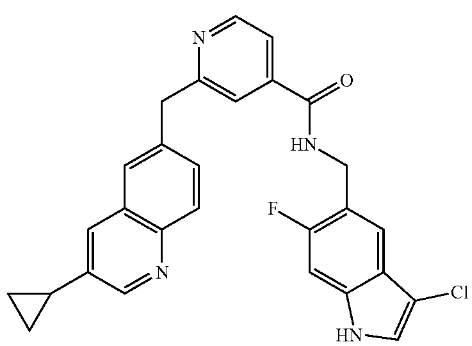 [SMILES: O=C(NCc1cc2c(Cl)c[nH]c2cc1F)c1ccnc(Cc2ccc3ncc(C4CC4)cc3c2)c1] | N-((3-chloro-6-fluoro-1H-indol-5-yl)methyl)-2-((3-cyclopropylquinolin-6-yl)methyl)isonicotinamide |
| 246 | 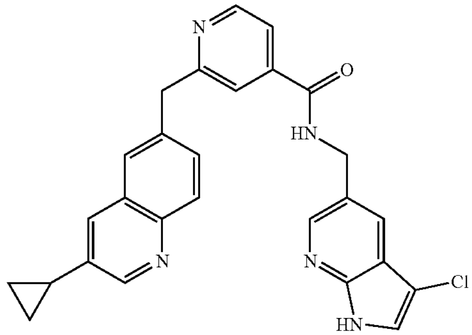 [SMILES: O=C(NCc1cnc2[nH]cc(Cl)c2c1)c1ccnc(Cc2ccc3ncc(C4CC4)cc3c2)c1] | N-((3-chloro-1H-pyrrolo[2,3-b]pyridin-5-yl)methyl)-2-((3-cyclopropylquinolin-6-yl)methyl)isonicotinamide |

TABLE 1-continued

| Chemical Synthesis Example | Structure | Name |
|---|---|---|
| 247 | 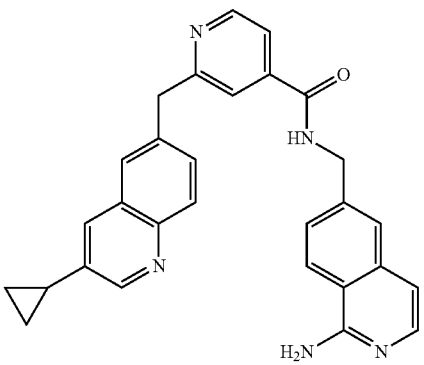 [SMILES: Nc1nccc2cc(CNC(=O)c3ccnc(Cc4ccc5ncc(C6CC6)cc5c4)c3)ccc12] | N-((1-aminoisoquinolin-6-yl)methyl)-2-((3-cyclopropylquinolin-6-yl)methyl)isonicotinamide |
| 248 | 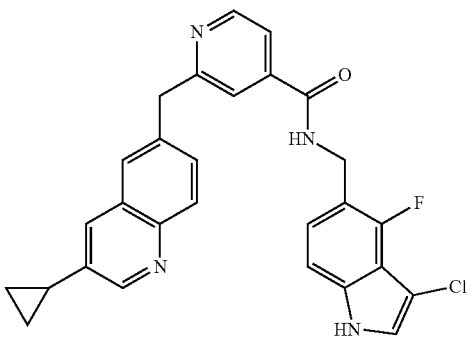 [SMILES: O=C(NCc1ccc2[nH]cc(Cl)c2c1F)c1ccnc(Cc2ccc3ncc(C4CC4)cc3c2)c1] | N-((3-chloro-4-fluoro-1H-indol-5-yl)methyl)-2-((3-cyclopropylquinolin-6-yl)methyl)isonicotinamide |
| 249 | 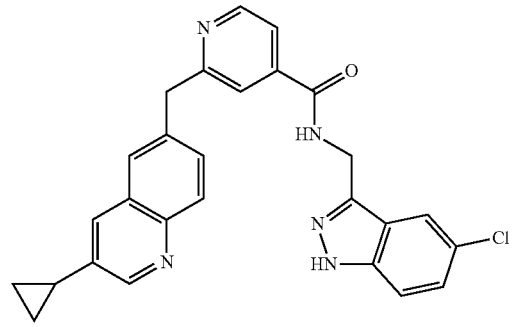 [SMILES: O=C(NCc1n[nH]c2ccc(Cl)cc12)c1ccnc(Cc2ccc3ncc(C4CC4)cc3c2)c1] | N-((5-chloro-1H-indazol-3-yl)methyl)-2-((3-cyclopropylquinolin-6-yl)methyl)isonicotinamide |
| 250 | 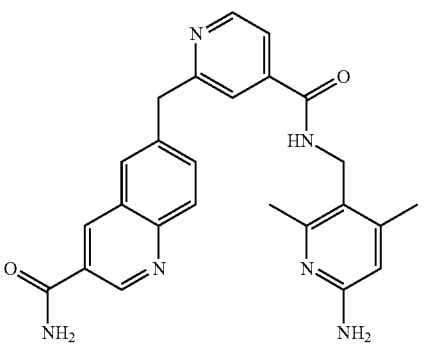 [SMILES: Cc1cc(N)nc(C)c1CNC(=O)c1ccnc(Cc2ccc3ncc(C(N)=O)cc3c2)c1] | 6-((4-(((6-amino-2,4-dimethylpyridin-3-yl)methyl)carbamoyl)pyridin-2-yl)methyl)quinoline-3-carboxamide |

TABLE 1-continued

| Chemical Synthesis Example | Structure | Name |
|---|---|---|
| 251 | 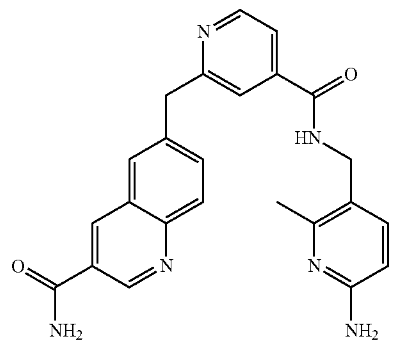 [SMILES: Cc1nc(N)ccc1CNC(=O)c1ccnc(Cc2ccc3ncc(C(N)=O)cc3c2)c1] | 6-((4-(((6-amino-2-methylpyridin-3-yl)methyl)carbamoyl)pyridin-2-yl)methyl)quinoline-3-carboxamide |
| 252 | 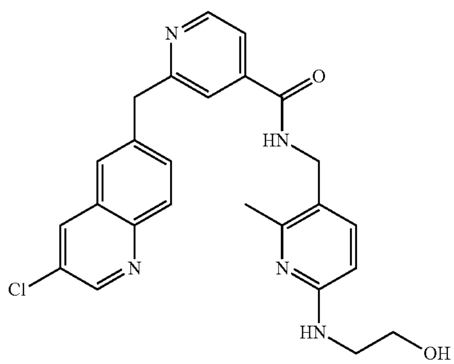 [SMILES: Cc1nc(NCCO)ccc1CNC(=O)c1ccnc(Cc2ccc3ncc(Cl)cc3c2)c1] | 2-((3-chloroquinolin-6-yl)methyl)-N-((6-((2-hydroxyethyl)amino)-2-methylpyridin-3-yl)methyl)isonicotinamide |
| 253 | 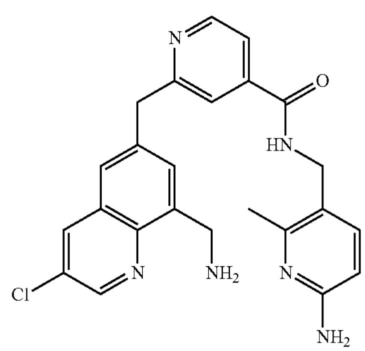 [SMILES: Cc1nc(N)ccc1CNC(=O)c1ccnc(Cc2cc(CN)c3ncc(Cl)cc3c2)c1] | N-((6-amino-2-methylpyridin-3-yl)methyl)-2-((8-(aminomethyl)-3-chloroquinolin-6-yl)methyl)isonicotinamide |
| 254 | 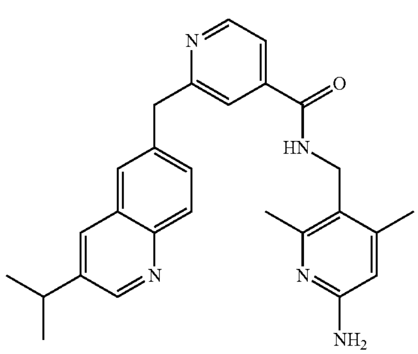 [SMILES: Cc1cc(N)nc(C)c1CNC(=O)c1ccnc(Cc2ccc3ncc(C(C)C)cc3c2)c1] | N-((6-amino-2,4-dimethylpyridin-3-yl)methyl)-2-((3-isopropylquinolin-6-yl)methyl)isonicotinamide |

TABLE 1-continued

| Chemical Synthesis Example | Structure | Name |
|---|---|---|
| 255 | 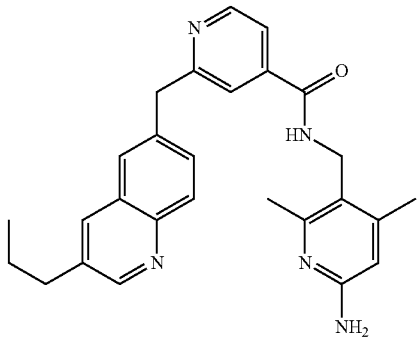 [SMILES: CCCc1cnc2ccc(Cc3cc(C(=O)NCc4c(C)cc(N)nc4C)ccn3)cc2c1] | N-((6-amino-2,4-dimethylpyridin-3-yl)methyl)-2-((3-propylquinolin-6-yl)methyl)isonicotinamide |
| 256 | 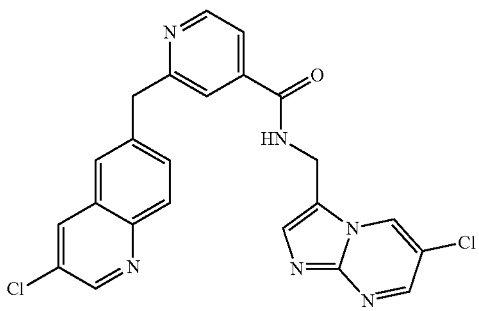 [SMILES: O=C(NCc1cnc2ncc(Cl)cn12)c1ccnc(Cc2ccc3ncc(Cl)cc3c2)c1] | N-((6-chloroimidazo[1,2-a]pyrimidin-3-yl)methyl)-2-((3-chloroquinolin-6-yl)methyl)isonicotinamide |
| 257 | 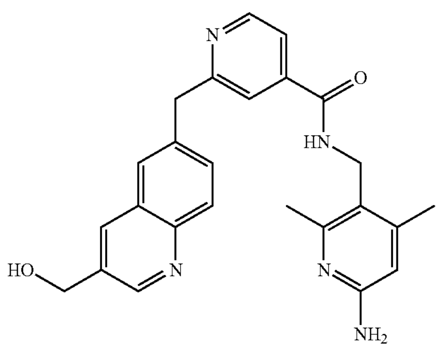 [SMILES: Cc1cc(N)nc(C)c1CNC(=O)c1ccnc(Cc2ccc3ncc(CO)cc3c2)c1] | N-((6-amino-2,4-dimethylpyridin-3-yl)methyl)-2-((3-(hydroxymethyl)quinolin-6-yl)methyl)isonicotinamide |
| 258 | 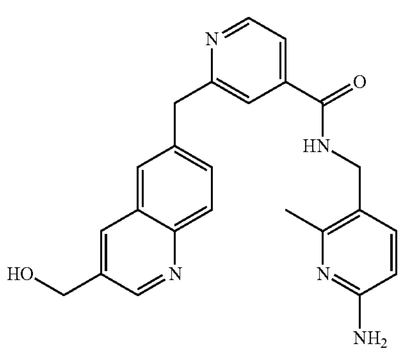 [SMILES: Cc1nc(N)ccc1CNC(=O)c1ccnc(Cc2ccc3ncc(CO)cc3c2)c1] | N-((6-amino-2-methylpyridin-3-yl)methyl)-2-((3-(hydroxymethyl)quinolin-6-yl)methyl)isonicotinamide |

TABLE 1-continued

| Chemical Synthesis Example | Structure | Name |
|---|---|---|
| 259 | 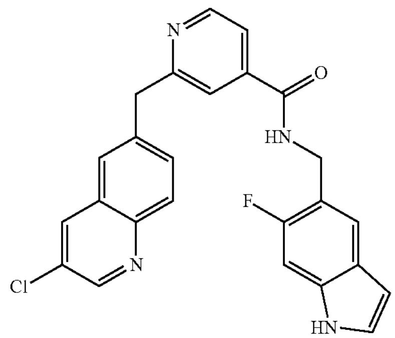 [SMILES: O=C(NCc1cc2cc[nH]c2cc1F)c1ccnc(Cc2ccc3ncc(Cl)cc3c2)c1] | 2-((3-chloroquinolin-6-yl)methyl)-N-((6-fluoro-1H-indol-5-yl)methyl)isonicotinamide |
| 260 | 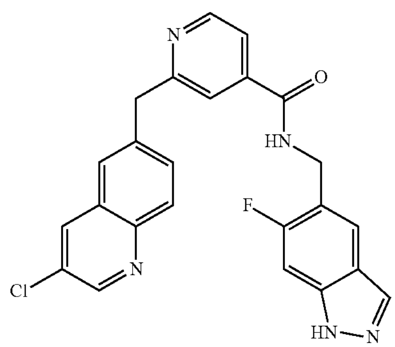 [SMILES: O=C(NCc1cc2cn[nH]c2cc1F)c1ccnc(Cc2ccc3ncc(Cl)cc3c2)c1] | 2-((3-chloroquinolin-6-yl)methyl)-N-((6-fluoro-1H-indazol-5-yl)methyl)isonicotinamide |
| 261 | 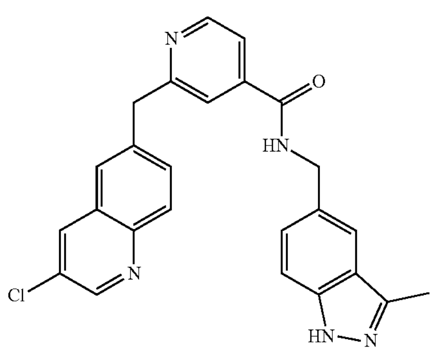 [SMILES: Cc1n[nH]c2ccc(CNC(=O)c3ccnc(Cc4ccc5ncc(Cl)cc5c4)c3)cc12] | 2-((3-chloroquinolin-6-yl)methyl)-N-((3-methyl-1H-indazol-5-yl)methyl)isonicotinamide |
| 262 | 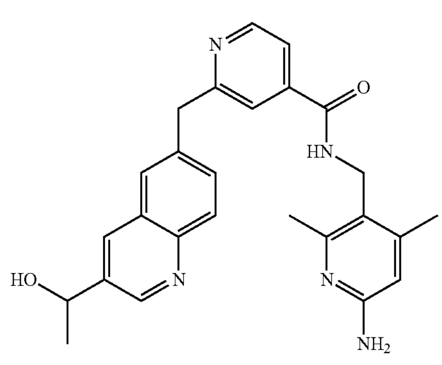 [SMILES: Cc1cc(N)nc(C)c1CNC(=O)c1ccnc(Cc2ccc3ncc(C(C)O)cc3c2)c1] | N-((6-amino-2,4-dimethylpyridin-3-yl)methyl)-2-((3-(1-hydroxyethyl)quinolin-6-yl)methyl)isonicotinamide |

TABLE 1-continued

| Chemical Synthesis Example | Structure | Name |
|---|---|---|
| 263 | 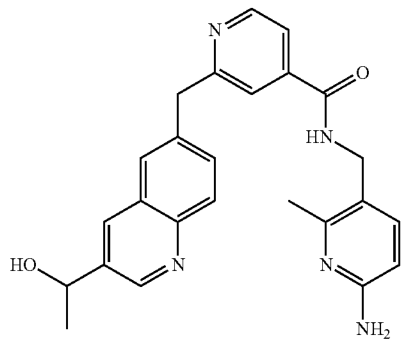 [SMILES: Cc1nc(N)ccc1CNC(=O)c1ccnc(Cc2ccc3ncc(C(C)O)cc3c2)c1] | N-((6-amino-2-methylpyridin-3-yl)methyl)-2-((3-(1-hydroxyethyl)quinolin-6-yl)methyl)isonicotinamide |
| 264 | 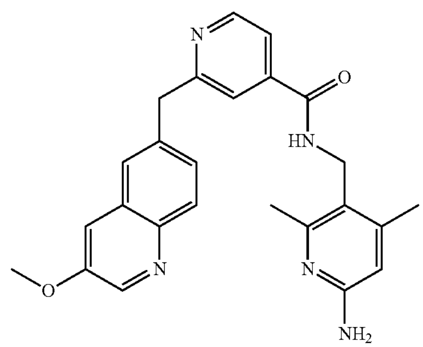 | N-((6-amino-2,4-dimethylpyridin-3-yl)methyl)-2-((3-methoxyquinolin-6-yl)methyl)isonicotinamide |
| 265 | 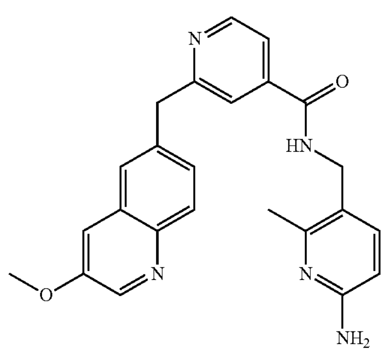 [SMILES: COc1cnc2ccc(Cc3cc(C(=O)NCc4ccc(N)nc4C)ccn3)cc2c1] | N-((6-amino-2-methylpyridin-3-yl)methyl)-2-((3-methoxyquinolin-6-yl)methyl)isonicotinamide |
| 266 | 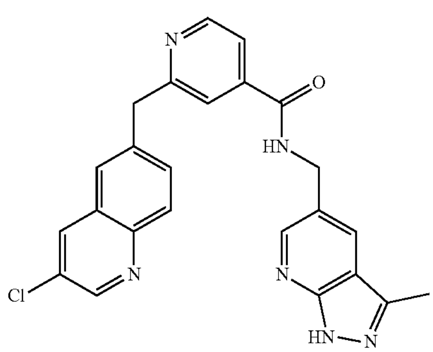 [SMILES: Cc1n[nH]c2ncc(CNC(=O)c3ccnc(Cc4ccc5ncc(Cl)cc5c4)c3)cc12] | 2-((3-chloroquinolin-6-yl)methyl)-N-((3-methyl-1H-pyrazolo[3,4-b]pyridin-5-yl)methyl)isonicotinamide |

TABLE 1-continued

| Chemical Synthesis Example | Structure | Name |
|---|---|---|
| 267 | 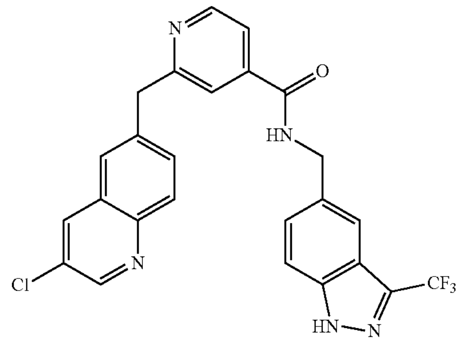 [SMILES: O=C(NCc1ccc2[nH]nc(C(F)(F)F)c2c1)c1ccnc(Cc2ccc3ncc(Cl)cc3c2)c1] | 2-((3-chloroquinolin-6-yl)methyl)-N-((3-(trifluoromethyl)-1H-indazol-5-yl)methyl)isonicotinamide |
| 268 | 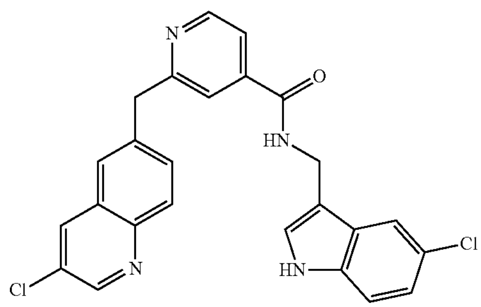 [SMILES: O=C(NCc1c[nH]c2ccc(Cl)cc12)c1ccnc(Cc2ccc3ncc(Cl)cc3c2)c1] | N-((5-chloro-1H-indol-3-yl)methyl)-2-((3-chloroquinolin-6-yl)methyl)isonicotinamide |
| 269 | 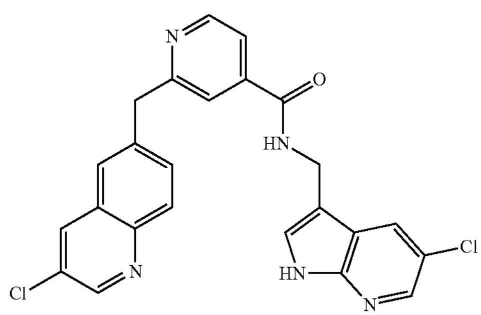 [SMILES: O=C(NCc1c[nH]c2ncc(Cl)cc12)c1ccnc(Cc2ccc3ncc(Cl)cc3c2)c1] | N-((5-chloro-1H-pyrrolo[2,3-b]pyridin-3-yl)methyl)-2-((3-chloroquinolin-6-yl)methyl)isonicotinamide |
| 270 | 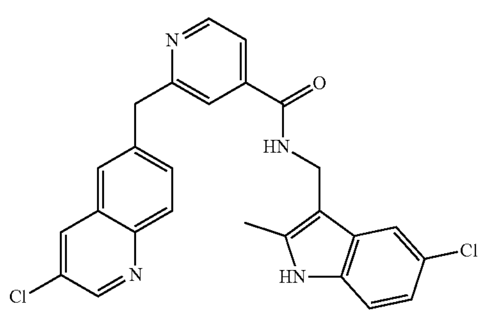 [SMILES: Cc1[nH]c2ccc(Cl)cc2c1CNC(=O)c1ccnc(Cc2ccc3ncc(Cl)cc3c2)c1] | N-((5-chloro-2-methyl-1H-indol-3-yl)methyl)-2-((3-chloroquinolin-6-yl)methyl)isonicotinamide |

TABLE 1-continued

| Chemical Synthesis Example | Structure | Name |
|---|---|---|
| 271 | 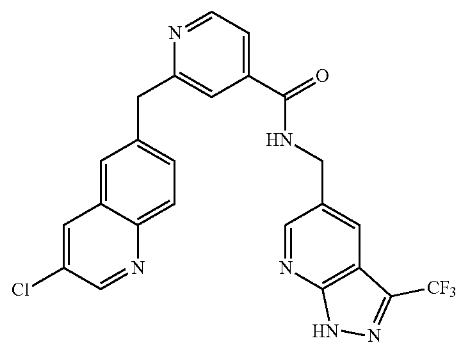 [SMILES: O=C(NCc1cnc2[nH]nc(C(F)(F)F)c2c1)c1ccnc(Cc2ccc3ncc(Cl)cc3c2)c1] | 2-((3-chloroquinolin-6-yl)methyl)-N-((3-(trifluoromethyl)-1H-pyrazolo[3,4-b]pyridin-5-yl)methyl)isonicotinamide |
| 272 | 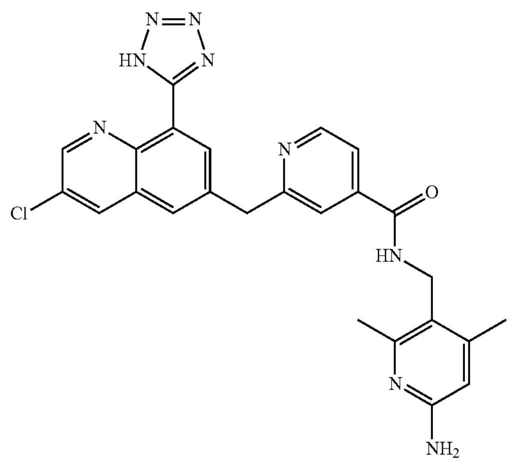 [SMILES: Cc1cc(N)nc(C)c1CNC(=O)c1ccnc(Cc2cc(-c3nnn[nH]3)c3ncc(Cl)cc3c2)c1] | N-((6-amino-2,4-dimethylpyridin-3-yl)methyl)-2-((3-chloro-8-(1H-tetrazol-5-yl)quinolin-6-yl)methyl)isonicotinamide |
| 273 | 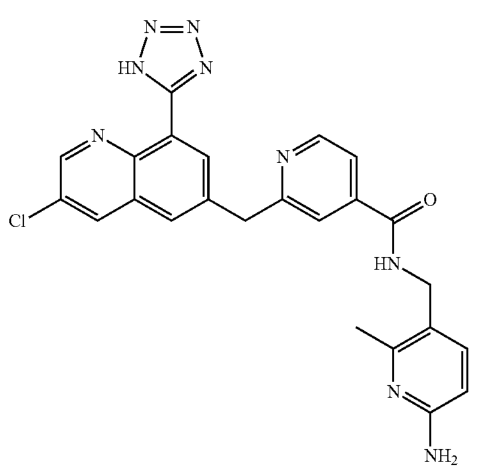 [SMILES: Cc1nc(N)ccc1CNC(=O)c1ccnc(Cc2cc(-c3nnn[nH]3)c3ncc(Cl)cc3c2)c1] | N-((6-amino-2-methylpyridin-3-yl)methyl)-2-((3-chloro-8-(1H-tetrazol-5-yl)quinolin-6-yl)methyl)isonicotinamide |

TABLE 1-continued

| Chemical Synthesis Example | Structure | Name |
|---|---|---|
| 274 | 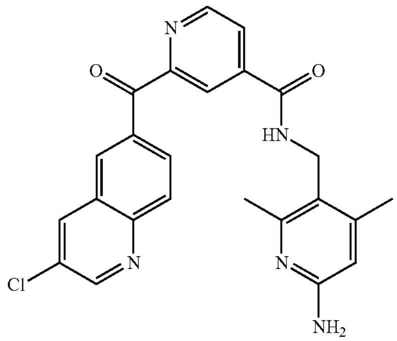 [SMILES: Cc1cc(N)nc(C)c1CNC(=O)c1ccnc(C(=O)c2ccc3ncc(Cl)cc3c2)c1] | N-((6-amino-2,4-dimethylpyridin-3-yl)methyl)-2-(3-chloroquinoline-6-carbonyl)isonicotinamide |
| 275 | 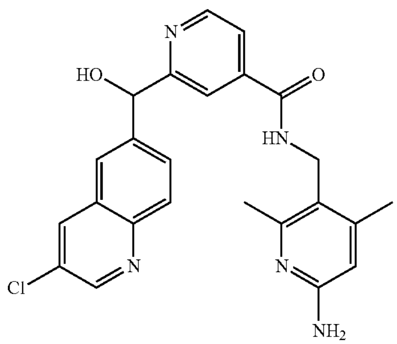 [SMILES: Cc1cc(N)nc(C)c1CNC(=O)c1ccnc(C(O)c2ccc3ncc(Cl)cc3c2)c1] | N-((6-amino-2,4-dimethylpyridin-3-yl)methyl)-2-((3-chloroquinolin-6-yl)(hydroxy)methyl)isonicotinamide |
| 276 | 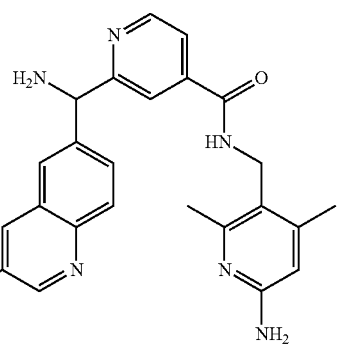 | 2-[Amino-(3-chloro-quinolin-6-yl)-methyl]-N-(6-amino-2,4-dimethyl-pyridin-3-ylmethyl)-isonicotinamide |
| 277 | 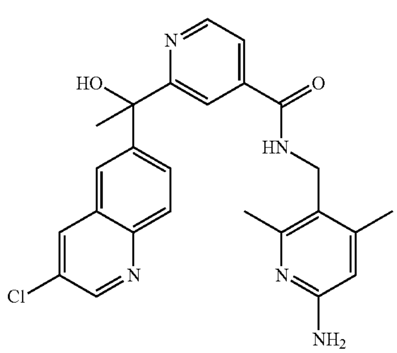 [SMILES: Cc1cc(N)nc(C)c1CNC(=O)c1ccnc(C(C)(O)c2ccc3ncc(Cl)cc3c2)c1] | N-((6-amino-2,4-dimethylpyridin-3-yl)methyl)-2-(1-(3-chloroquinolin-6-yl)-1-hydroxyethyl)isonicotinamide |

TABLE 1-continued

| Chemical Synthesis Example | Structure | Name |
|---|---|---|
| 278 | 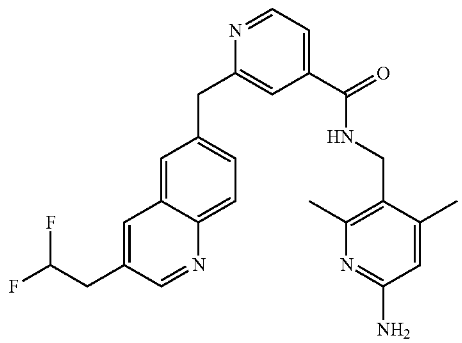 [SMILES: Cc1cc(N)nc(C)c1CNC(=O)c1ccnc(Cc2ccc3ncc(CC(F)F)cc3c2)c1] | N-((6-amino-2,4-dimethylpyridin-3-yl)methyl)-2-((3-(2,2-difluoroethyl)quinolin-6-yl)methyl)isonicotinamide |
| 279 | 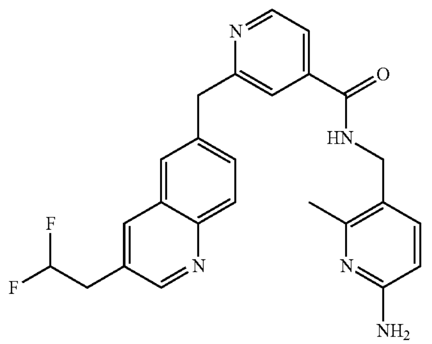 [SMILES: Cc1nc(N)ccc1CNC(=O)c1ccnc(Cc2ccc3ncc(CC(F)F)cc3c2)c1] | N-((6-amino-2-methylpyridin-3-yl)methyl)-2-((3-(2,2-difluoroethyl)quinolin-6-yl)methyl)isonicotinamide |
| 280 | 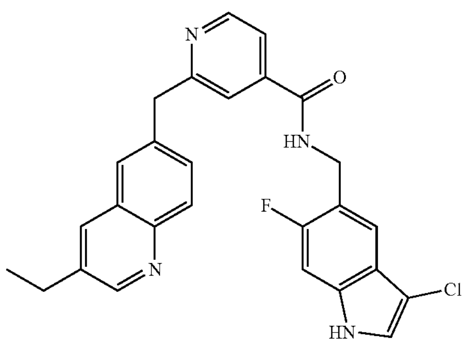 [SMILES: CCc1cnc2ccc(Cc3cc(C(=O)NCc4cc5c(Cl)c[nH]c5cc4F)ccn3)cc2c1] | N-((3-chloro-6-fluoro-1H-indol-5-yl)methyl)-2-((3-ethylquinolin-6-yl)methyl)isonicotinamide |
| 281 | 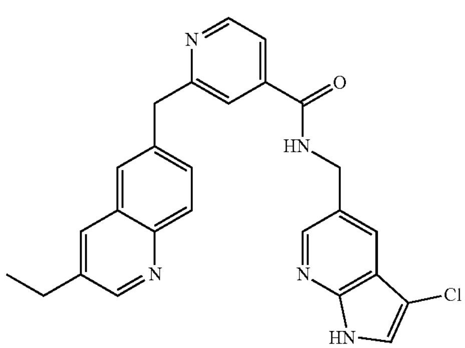 [SMILES: CCc1cnc2ccc(Cc3cc(C(=O)NCc4cnc5[nH]cc(Cl)c5c4)ccn3)cc2c1] | N-((3-chloro-1H-pyrrolo[2,3-b]pyridin-5-yl)methyl)-2-((3-ethylquinolin-6-yl)methyl)isonicotinamide |

TABLE 1-continued

| Chemical Synthesis Example | Structure | Name |
|---|---|---|
| 282 | 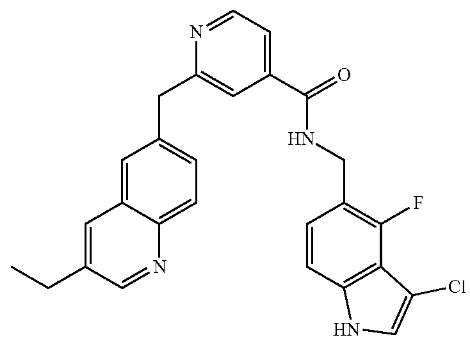 [SMILES: CCc1cnc2ccc(Cc3cc(C(=O)NCc4ccc5[nH]cc(Cl)c5c4F)ccn3)cc2c1] | N-((3-chloro-4-fluoro-1H-indol-5-yl)methyl)-2-((3-ethylquinolin-6-yl)methyl)isonicotinamide |
| 283 | 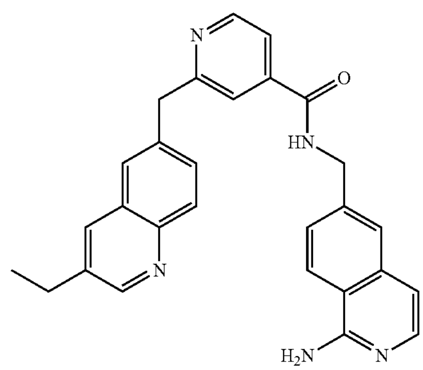 [SMILES: CCc1cnc2ccc(Cc3cc(C(=O)NCc4ccc5c(N)nccc5c4)ccn3)cc2c1] | N-((1-aminoisoquinolin-6-yl)methyl)-2-((3-ethylquinolin-6-yl)methyl)isonicotinamide |
| 284 | 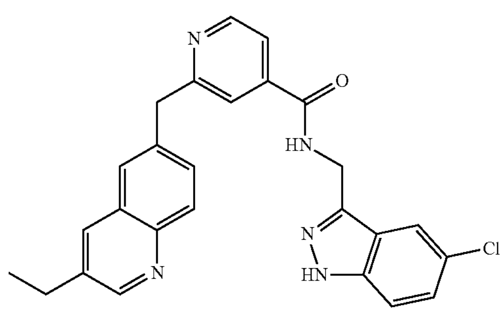 [SMILES: CCc1cnc2ccc(Cc3cc(C(=O)NCc4n[nH]c5ccc(Cl)cc45)ccn3)cc2c1] | N-((5-chloro-1H-indazol-3-yl)methyl)-2-((3-ethylquinolin-6-yl)methyl)isonicotinamide |
| 285 | 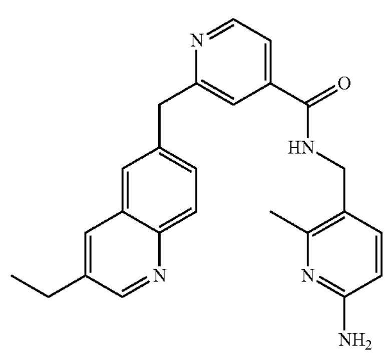 [SMILES: CCc1cnc2ccc(Cc3cc(C(=O)NCc4ccc(N)nc4C)ccn3)cc2c1] | N-((6-amino-2-methylpyridin-3-yl)methyl)-2-((3-ethylquinolin-6-yl)methyl)isonicotinamide |

TABLE 1-continued

| Chemical Synthesis Example | Structure | Name |
|---|---|---|
| 286 | 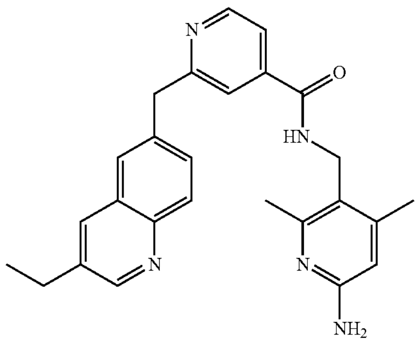 [SMILES: CCc1cnc2ccc(Cc3cc(C(=O)NCc4c(C)cc(N)nc4C)ccn3)cc2c1] | N-((6-amino-2,4-dimethylpyridin-3-yl)methyl)-2-((3-ethylquinolin-6-yl)methyl)isonicotinamide |
| 287 | 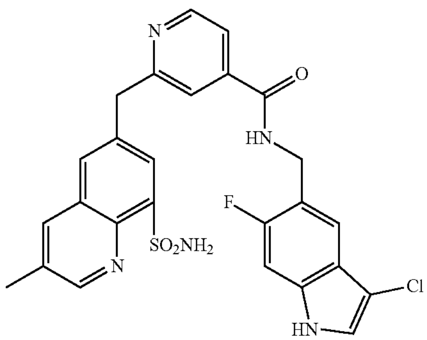 [SMILES: Cc1cnc2c(S(N)(=O)=O)cc(Cc3cc(C(=O)NCc4cc5c(Cl)c[nH]c5cc4F)ccn3)cc2c1] | N-((3-chloro-6-fluoro-1H-indol-5-yl)methyl)-2-((3-methyl-8-sulfamoylquinolin-6-yl)methyl)isonicotinamide |
| 288 | 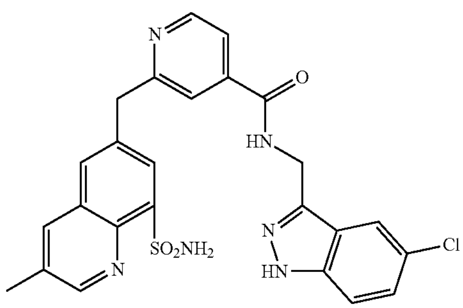 [SMILES: Cc1cnc2c(S(N)(=O)=O)cc(Cc3cc(C(=O)NCc4n[nH]c5ccc(Cl)cc45)ccn3)cc2c1] | N-((5-chloro-1H-indazol-3-yl)methyl)-2-((3-methyl-8-sulfamoylquinolin-6-yl)methyl)isonicotinamide |
| 289 | 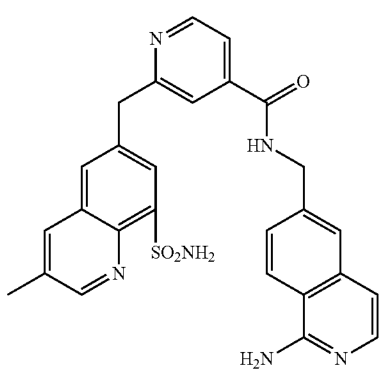 [SMILES: Cc1cnc2c(S(N)(=O)=O)cc(Cc3cc(C(=O)NCc4ccc5c(N)nccc5c4)ccn3)cc2c1] | N-((1-aminoisoquinolin-6-yl)methyl)-2-((3-methyl-8-sulfamoylquinolin-6-yl)methyl)isonicotinamide |

TABLE 1-continued

| Chemical Synthesis Example | Structure | Name |
|---|---|---|
| 290 | 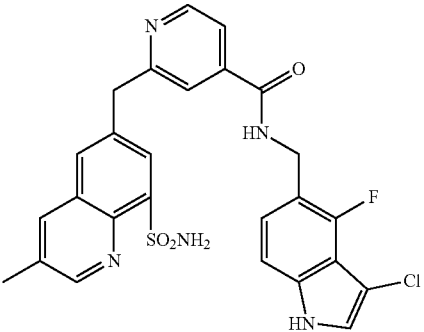 [SMILES: Cc1cnc2c(S(N)(=O)=O)cc(Cc3cc(C(=O)NCc4ccc5[nH]cc(Cl)c5c4F)ccn3)cc2c1] | N-((3-chloro-4-fluoro-1H-indol-5-yl)methyl)-2-((3-methyl-8-sulfamoylquinolin-6-yl)methyl)isonicotinamide |
| 291 | 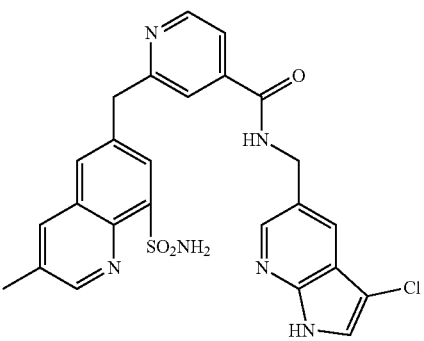 [SMILES: Cc1cnc2c(S(N)(=O)=O)cc(Cc3cc(C(=O)NCc4cnc5[nH]cc(Cl)c5c4)ccn3)cc2c1] | N-((3-chloro-1H-pyrrolo[2,3-b]pyridin-5-yl)methyl)-2-((3-methyl-8-sulfamoylquinolin-6-yl)methyl)isonicotinamide |
| 292 | 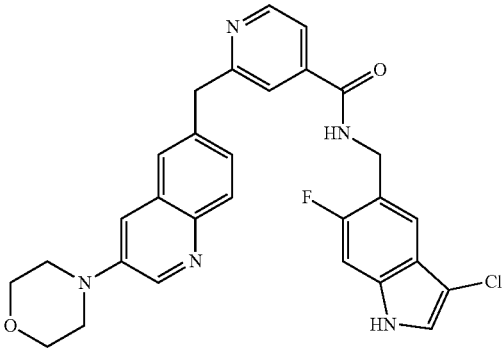 [SMILES: O=C(NCc1cc2c(Cl)c[nH]c2cc1F)c1ccnc(Cc2ccc3ncc(N4CCOCC4)cc3c2)c1] | N-((3-chloro-6-fluoro-1H-indol-5-yl)methyl)-2-((3-morpholinoquinolin-6-yl)methyl)isonicotinamide |
| 293 | 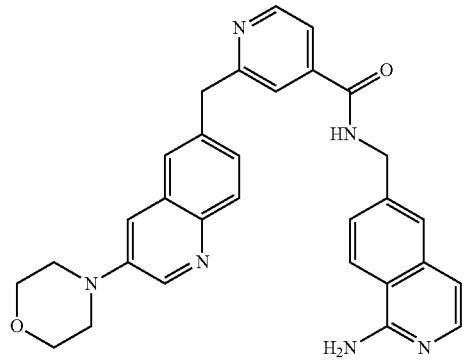 [SMILES: Nc1nccc2cc(CNC(=O)c3ccnc(Cc4ccc5ncc(N6CCOCC6)cc5c4)c3)ccc12] | N-((1-aminoisoquinolin-6-yl)methyl)-2-((3-morpholinoquinolin-6-yl)methyl)isonicotinamide |

TABLE 1-continued

| Chemical Synthesis Example | Structure | Name |
|---|---|---|
| 294 | 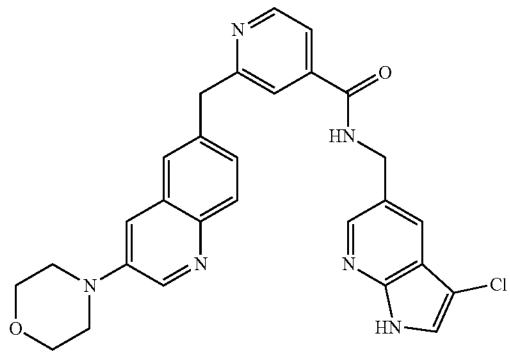 [SMILES: O=C(NCc1cnc2[nH]cc(Cl)c2c1)c1ccnc(Cc2ccc3ncc(N4CCOCC4)cc3c2)c1] | N-((3-chloro-1H-pyrrolo[2,3-b]pyridin-5-yl)methyl)-2-((3-morpholinoquinolin-6-yl)methyl)isonicotinamide |
| 295 | 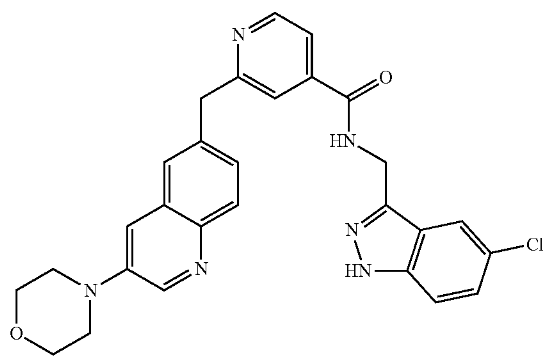 [SMILES: O=C(NCc1n[nH]c2ccc(Cl)cc12)c1ccnc(Cc2ccc3ncc(N4CCOCC4)cc3c2)c1] | N-((5-chloro-1H-indazol-3-yl)methyl)-2-((3-morpholinoquinolin-6-yl)methyl)isonicotinamide |
| 296 | 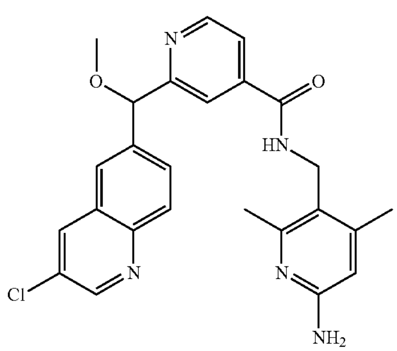 [SMILES: COC(c1ccc2ncc(Cl)cc2c1)c1cc(C(=O)NCc2c(C)cc(N)nc2C)ccn1] | N-((6-amino-2,4-dimethylpyridin-3-yl)methyl)-2-((3-chloroquinolin-6-yl)(methoxy)methyl)isonicotinamide |
| 297 | 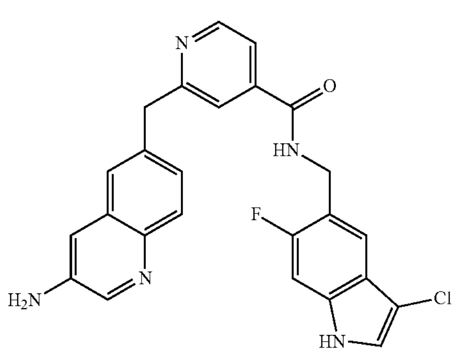 [SMILES: Nc1cnc2ccc(Cc3cc(C(=O)NCc4cc5c(Cl)c[nH]c5cc4F)ccn3)cc2c1] | 2-((3-aminoquinolin-6-yl)methyl)-N-((3-chloro-6-fluoro-1H-indol-5-yl)methyl)isonicotinamide |

TABLE 1-continued

| Chemical Synthesis Example | Structure | Name |
|---|---|---|
| 298 | 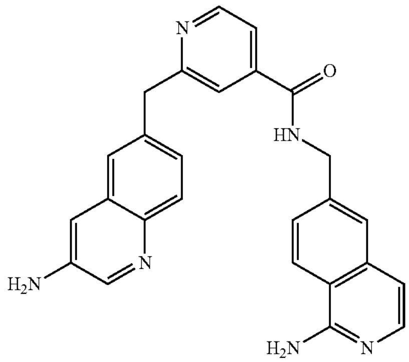 [SMILES: Nc1cnc2ccc(Cc3cc(C(=O)NCc4ccc5c(N)nccc5c4)ccn3)cc2c1] | N-((1-aminoisoquinolin-6-yl)methyl)-2-((3-aminoquinolin-6-yl)methyl)isonicotinamide |
| 299 | 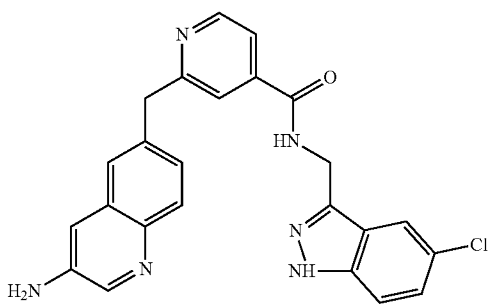 [SMILES: Nc1cnc2ccc(Cc3cc(C(=O)NCc4n[nH]c5ccc(Cl)cc45)ccn3)cc2c1] | 2-((3-aminoquinolin-6-yl)methyl)-N-((5-chloro-1H-indazol-3-yl)methyl)isonicotinamide |
| 300 | 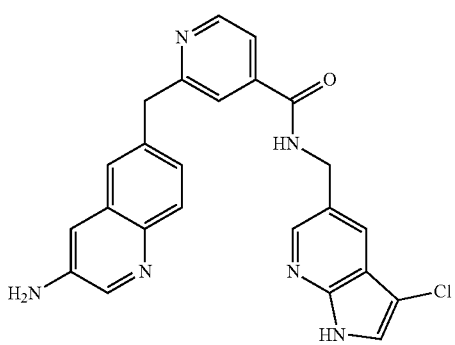 [SMILES: Nc1cnc2ccc(Cc3cc(C(=O)NCc4cnc5[nH]cc(Cl)c5c4)ccn3)cc2c1] | 2-((3-aminoquinolin-6-yl)methyl)-N-((3-chloro-1H-pyrrolo[2,3-b]pyridin-5-yl)methyl)isonicotinamide |
| 301 | 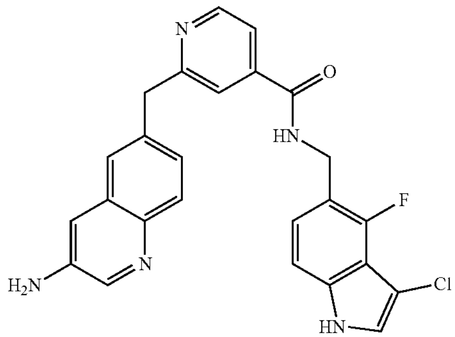 [SMILES: Nc1cnc2ccc(Cc3cc(C(=O)NCc4ccc5[nH]cc(Cl)c5c4F)ccn3)cc2c1] | 2-((3-aminoquinolin-6-yl)methyl)-N-((3-chloro-4-fluoro-1H-indol-5-yl)methyl)isonicotinamide |

TABLE 1-continued

| Chemical Synthesis Example | Structure | Name |
|---|---|---|
| 302 | 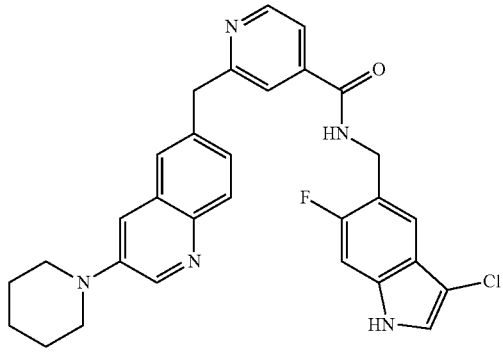 [SMILES: O=C(NCc1cc2c(Cl)c[nH]c2cc1F)c1ccnc(Cc2ccc3ncc(N4CCCCC4)cc3c2)c1] | N-((3-chloro-6-fluoro-1H-indol-5-yl)methyl)-2-((3-(piperidin-1-yl)quinolin-6-yl)methyl)isonicotinamide |
| 303 | 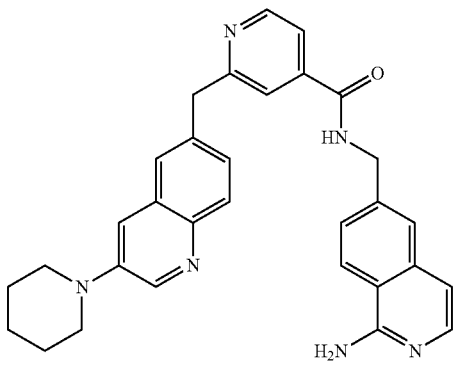 [SMILES: Nc1nccc2cc(CNC(=O)c3ccnc(Cc4ccc5ncc(N6CCCCC6)cc5c4)c3)ccc12] | N-((1-aminoisoquinolin-6-yl)methyl)-2-((3-(piperidin-1-yl)quinolin-6-yl)methyl)isonicotinamide |
| 304 | 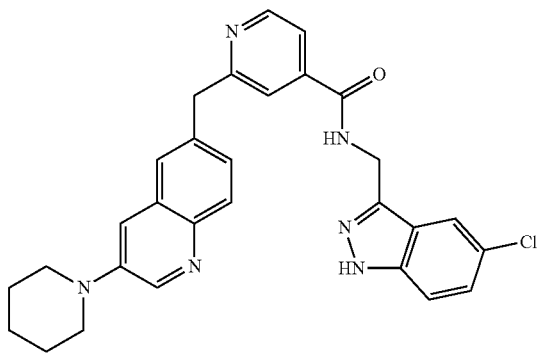 [SMILES: O=C(NCc1n[nH]c2ccc(Cl)cc12)c1ccnc(Cc2ccc3ncc(N4CCCCC4)cc3c2)c1] | N-((5-chloro-1H-indazol-3-yl)methyl)-2-((3-(piperidin-1-yl)quinolin-6-yl)methyl)isonicotinamide |
| 305 | 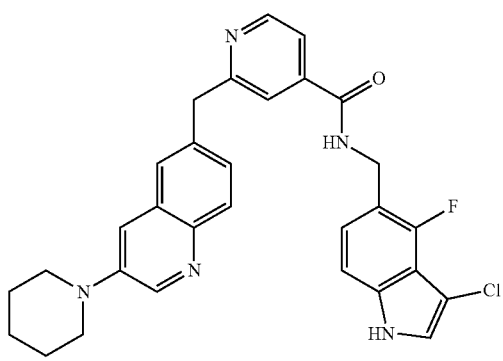 [SMILES: O=C(NCc1ccc2[nH]cc(Cl)c2c1F)c1ccnc(Cc2ccc3ncc(N4CCCCC4)cc3c2)c1] | N-((3-chloro-4-fluoro-1H-indol-5-yl)methyl)-2-((3-(piperidin-1-yl)quinolin-6-yl)methyl)isonicotinamide |

TABLE 1-continued

| Chemical Synthesis Example | Structure | Name |
|---|---|---|
| 306 | 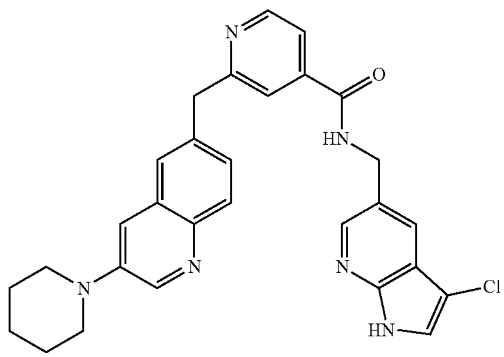 [SMILES: O=C(NCc1cnc2[nH]cc(Cl)c2c1)c1ccnc(Cc2ccc3ncc(N4CCCCC4)cc3c2)c1] | N-((3-chloro-1H-pyrrolo[2,3-b]pyridin-5-yl)methyl)-2-((3-(piperidin-1-yl)quinolin-6-yl)methyl)isonicotinamide |
| 307 | 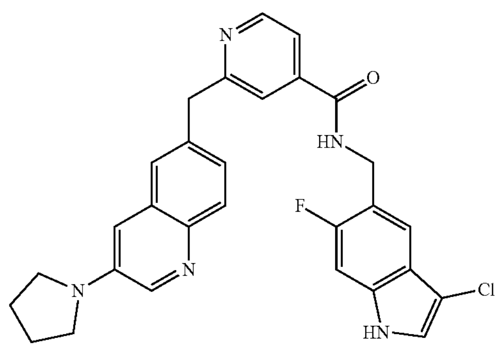 [SMILES: O=C(NCc1cc2c(Cl)c[nH]c2cc1F)c1ccnc(Cc2ccc3ncc(N4CCCC4)cc3c2)c1] | N-((3-chloro-6-fluoro-1H-indol-5-yl)methyl)-2-((3-(pyrrolidin-1-yl)quinolin-6-yl)methyl)isonicotinamide |
| 308 | 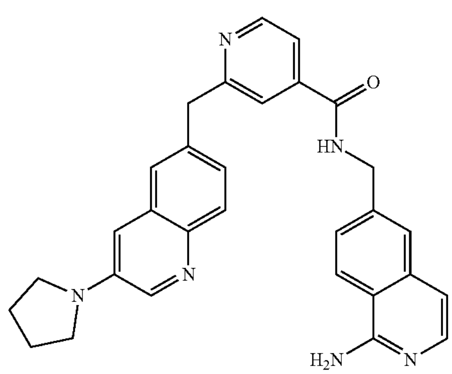 [SMILES: Nc1nccc2cc(CNC(=O)c3ccnc(Cc4ccc5ncc(N6CCCC6)cc5c4)c3)ccc12] | N-((1-aminoisoquinolin-6-yl)methyl)-2-((3-(pyrrolidin-1-yl)quinolin-6-yl)methyl)isonicotinamide |
| 309 | 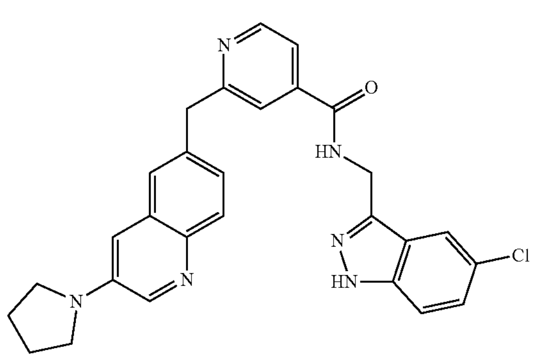 [SMILES: O=C(NCc1n[nH]c2ccc(Cl)cc12)c1ccnc(Cc2ccc3ncc(N4CCCC4)cc3c2)c1] | N-((5-chloro-1H-indazol-3-yl)methyl)-2-((3-(pyrrolidin-1-yl)quinolin-6-yl)methyl)isonicotinamide |

TABLE 1-continued

| Chemical Synthesis Example | Structure | Name |
|---|---|---|
| 310 | 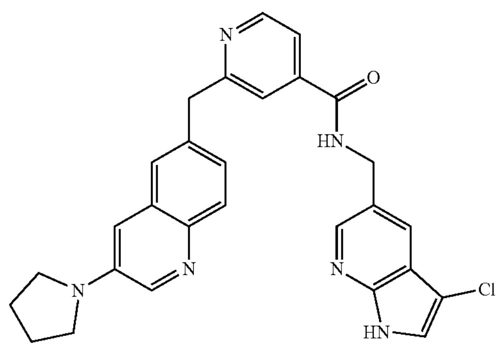 [SMILES: O=C(NCc1cnc2[nH]cc(Cl)c2c1)c1ccnc(Cc2ccc3ncc(N4CCCC4)cc3c2)c1] | N-((3-chloro-1H-pyrrolo[2,3-b]pyridin-5-yl)methyl)-2-((3-(pyrrolidin-1-yl)quinolin-6-yl)methyl)isonicotinamide |
| 311 | 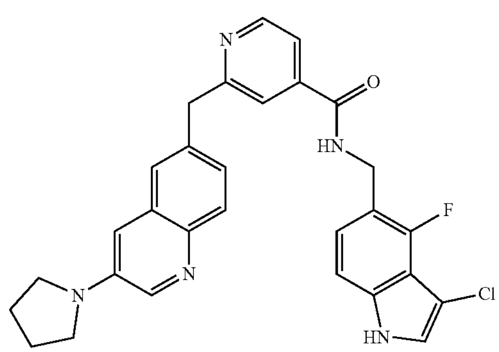 [SMILES: O=C(NCc1ccc2[nH]cc(Cl)c2c1F)c1ccnc(Cc2ccc3ncc(N4CCCC4)cc3c2)c1] | N-((3-chloro-4-fluoro-1H-indol-5-yl)methyl)-2-((3-(pyrrolidin-1-yl)quinolin-6-yl)methyl)isonicotinamide |
| 312 | 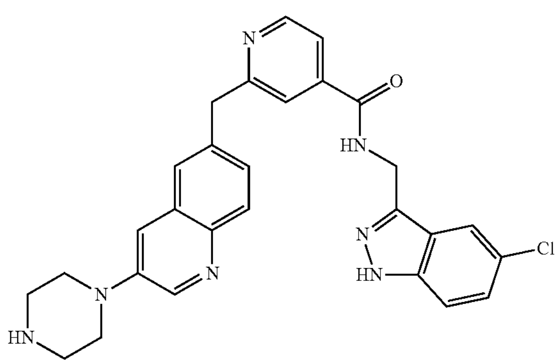 [SMILES: O=C(NCc1n[nH]c2ccc(Cl)cc12)c1ccnc(Cc2ccc3ncc(N4CCNCC4)cc3c2)c1] | N-((5-chloro-1H-indazol-3-yl)methyl)-2-((3-(piperazin-1-yl)quinolin-6-yl)methyl)isonicotinamide |
| 313 | 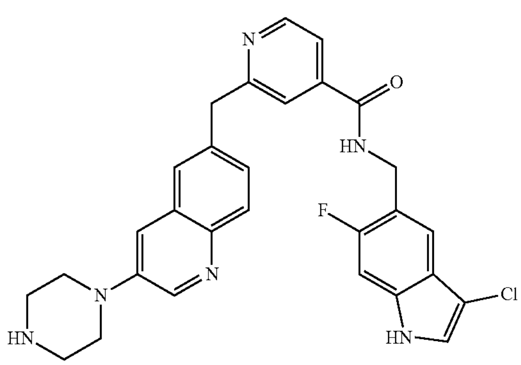 [SMILES: O=C(NCc1cc2c(Cl)c[nH]c2cc1F)c1ccnc(Cc2ccc3ncc(N4CCNCC4)cc3c2)c1] | N-((3-chloro-6-fluoro-1H-indol-5-yl)methyl)-2-((3-(piperazin-1-yl)quinolin-6-yl)methyl)isonicotinamide |

TABLE 1-continued

| Chemical Synthesis Example | Structure | Name |
|---|---|---|
| 314 | 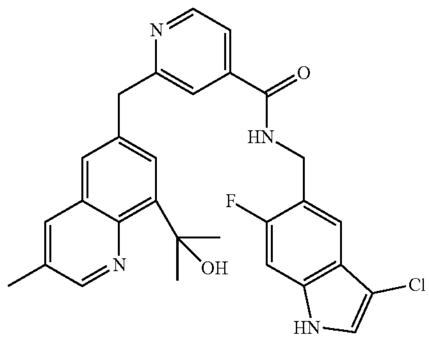 [SMILES: Cc1cnc2c(C(C)(C)O)cc(Cc3cc(C(=O)NCc4cc5c(Cl)c[nH]c5cc4F)ccn3)cc2c1] | N-((3-chloro-6-fluoro-1H-indol-5-yl)methyl)-2-((8-(2-hydroxypropan-2-yl)-3-methylquinolin-6-yl)methyl)isonicotinamide |
| 315 | 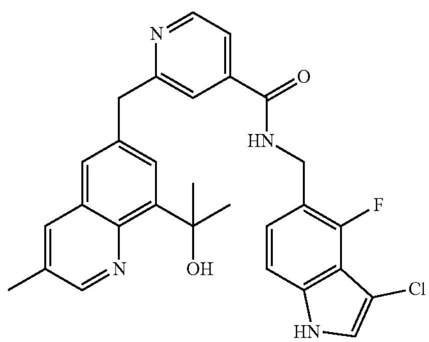 [SMILES: Cc1cnc2c(C(C)(C)O)cc(Cc3cc(C(=O)NCc4ccc5[nH]cc(Cl)c5c4F)ccn3)cc2c1] | N-((3-chloro-4-fluoro-1H-indol-5-yl)methyl)-2-((8-(2-hydroxypropan-2-yl)-3-methylquinolin-6-yl)methyl)isonicotinamide |
| 316 | 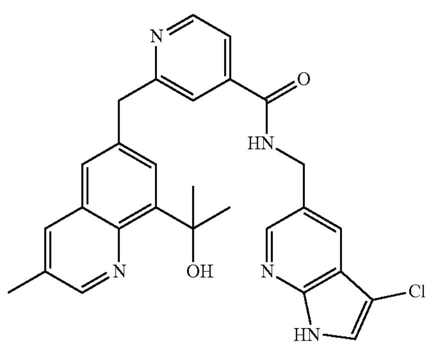 [SMILES: Cc1cnc2c(C(C)(C)O)cc(Cc3cc(C(=O)NCc4cnc5[nH]cc(Cl)c5c4)ccn3)cc2c1] | N-((3-chloro-1H-pyrrolo[2,3-b]pyridin-5-yl)methyl)-2-((8-(2-hydroxypropan-2-yl)-3-methylquinolin-6-yl)methyl)isonicotinamide |
| 317 | 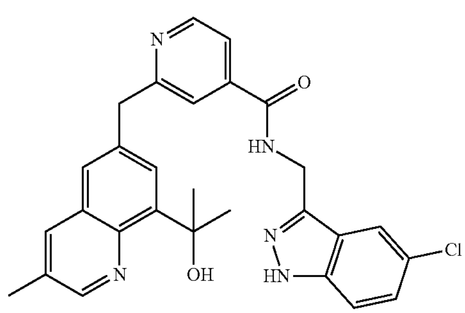 [SMILES: Cc1cnc2c(C(C)(C)O)cc(Cc3cc(C(=O)NCc4n[nH]c5ccc(Cl)cc45)ccn3)cc2c1] | N-((5-chloro-1H-indazol-3-yl)methyl)-2-((8-(2-hydroxypropan-2-yl)-3-methylquinolin-6-yl)methyl)isonicotinamide |

TABLE 1-continued

| Chemical Synthesis Example | Structure | Name |
|---|---|---|
| 318 | 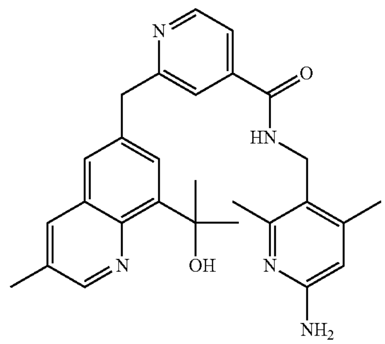 | N-((6-amino-2,4-dimethylpyridin-3-yl)methyl)-2-((8-(2-hydroxypropan-2-yl)-3-methylquinolin-6-yl)methyl)isonicotinamide |
| 319 | 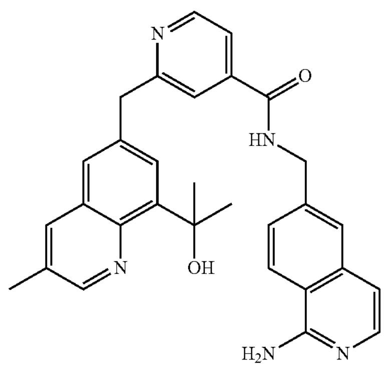 [SMILES: Cc1cnc2c(C(C)(C)O)cc(Cc3cc(C(=O)NCc4ccc5c(N)nccc5c4)ccn3)cc2c1] | N-((1-aminoisoquinolin-6-yl)methyl)-2-((8-(2-hydroxypropan-2-yl)-3-methylquinolin-6-yl)methyl)isonicotinamide |
| 320 | 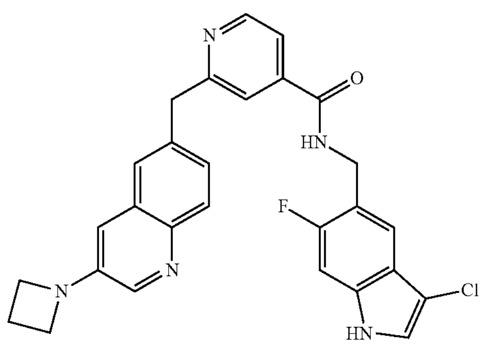 [SMILES: O=C(NCc1cc2c(Cl)c[nH]c2cc1F)c1ccnc(Cc2ccc3ncc(N4CCC4)cc3c2)c1] | 2-((3-(azetidin-1-yl)quinolin-6-yl)methyl)-N-((3-chloro-6-fluoro-1H-indol-5-yl)methyl)isonicotinamide |
| 321 | 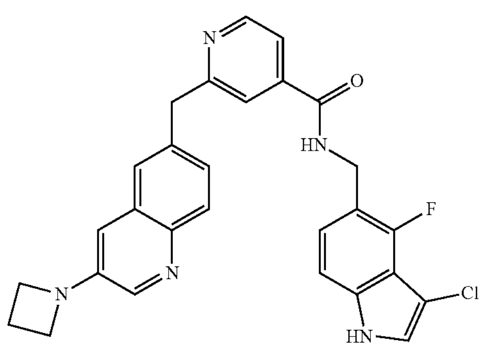 [SMILES: O=C(NCc1ccc2[nH]cc(Cl)c2c1F)c1ccnc(Cc2ccc3ncc(N4CCC4)cc3c2)c1] | 2-((3-(azetidin-1-yl)quinolin-6-yl)methyl)-N-((3-chloro-4-fluoro-1H-indol-5-yl)methyl)isonicotinamide |

TABLE 1-continued

| Chemical Synthesis Example | Structure | Name |
|---|---|---|
| 322 | 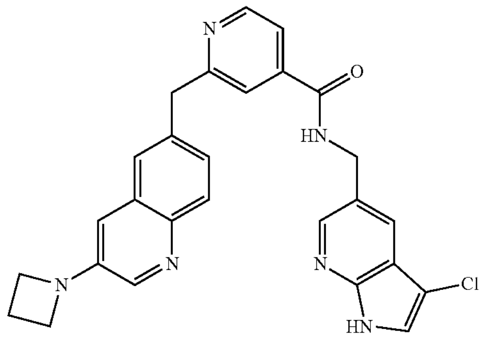 [SMILES: O=C(NCc1cnc2[nH]cc(Cl)c2c1)c1ccnc(Cc2ccc3ncc(N4CCC4)cc3c2)c1] | 2-((3-(azetidin-1-yl)quinolin-6-yl)methyl)-N-((3-chloro-1H-pyrrolo[2,3-b]pyridin-5-yl)methyl)isonicotinamide |
| 323 | 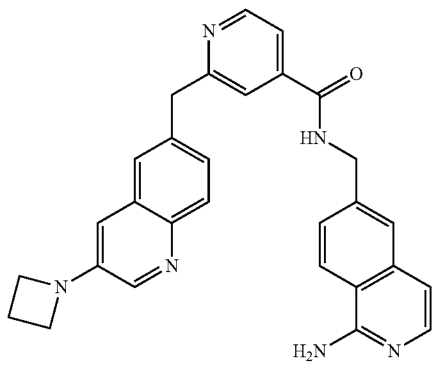 [SMILES: Nc1nccc2cc(CNC(=O)c3ccnc(Cc4ccc5ncc(N6CCC6)cc5c4)c3)ccc12] | N-((1-aminoisoquinolin-6-yl)methyl)-2-((3-(azetidin-1-yl)quinolin-6-yl)methyl)isonicotinamide |
| 324 | 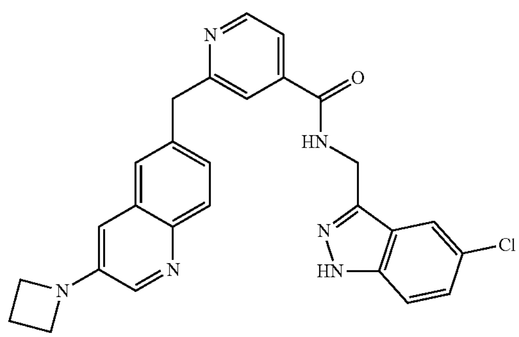 [SMILES: O=C(NCc1n[nH]c2ccc(Cl)cc12)c1ccnc(Cc2ccc3ncc(N4CCC4)cc3c2)c1] | 2-((3-(azetidin-1-yl)quinolin-6-yl)methyl)-N-((5-chloro-1H-indazol-3-yl)methyl)isonicotinamide |

In some embodiments, the compound described herein has the structure provided in Table 2.

TABLE 2

| Name | Structure |
|---|---|
| N-((1-aminoisoquinolin-6-yl)methyl)-2-((3-fluoroquinolin-6-yl)methyl)isonicotinamide | 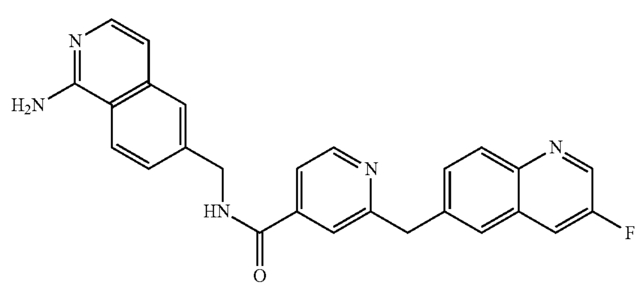 [SMILES: Nc1nccc2cc(CNC(=O)c3ccnc(Cc4ccc5ncc(F)cc5c4)c3)ccc12] |

TABLE 2-continued

| Name | Structure |
|---|---|
| N((1-aminoisoquinolin-6-yl)methyl)-2-((6-cyanoquinolin-3-yl)methyl)isonicotinamide | 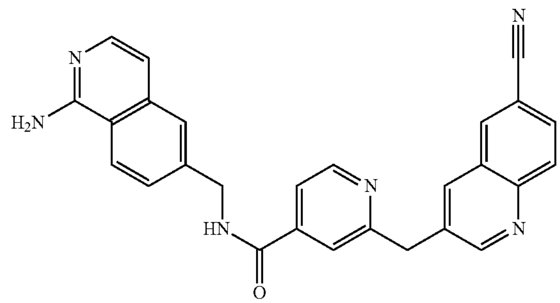 [SMILES: N#Cc1ccc2ncc(Cc3cc(C(=O)NCc4ccc5c(N)nccc5c4)ccn3)cc2c1] |
| 3-((4-(((1-aminoisoquinolin-6-yl)methyl)carbamoyl)pyridin-2-yl)methyl)quinoline-6-carboxamide | 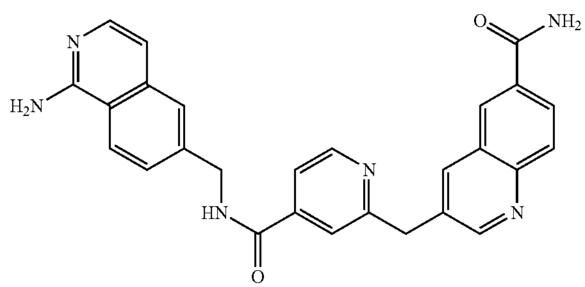 [SMILES: NC(=O)c1ccc2ncc(Cc3cc(C(=O)NCc4ccc5c(N)nccc5c4)ccn3)cc2c1] |
| N-((1-aminoisoquinolin-6-yl)methyl)-2-((6-chloroquinolin-3-yl)methyl)isonicotinamide | 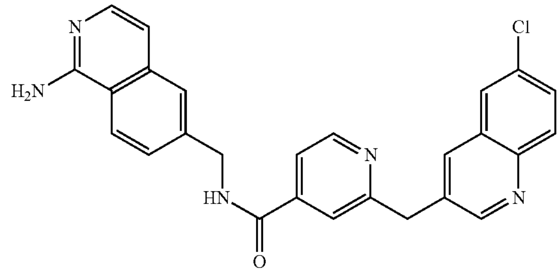 [SMILES: Nc1nccc2cc(CNC(=O)c3ccnc(Cc4cnc5ccc(Cl)cc5c4)c3)ccc12] |
| N-((1-aminoisoquinolin-6-yl)methyl)-2-((6-(hydroxymethyl)quinolin-3-yl)methyl)isonicotinamide | 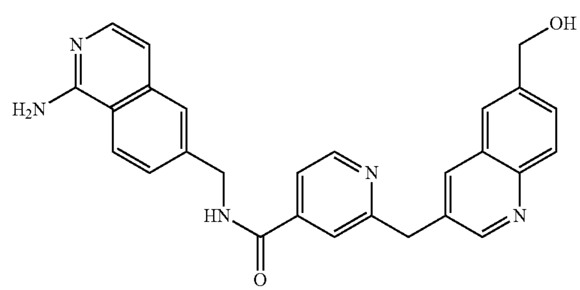 [SMILES: Nc1nccc2cc(CNC(=O)c3ccnc(Cc4cnc5ccc(CO)cc5c4)c3)ccc12] |
| N-((1-aminoisoquinolin-6-yl)methyl)-2-((6-(aminomethyl)quinolin-3-yl)methyl)isonicotinamide | 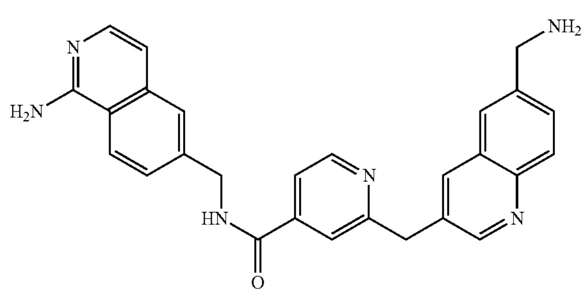 [SMILES: NCc1ccc2ncc(Cc3cc(C(=O)NCc4ccc5c(N)nccc5c4)ccn3)cc2c1] |

TABLE 2-continued

| Name | Structure |
|------|-----------|
| 6-((4-(((1-aminoisoquinolin-6-yl)methyl)carbamoyl)pyridin-2-yl)methyl)quinoline-3-carboxamide | 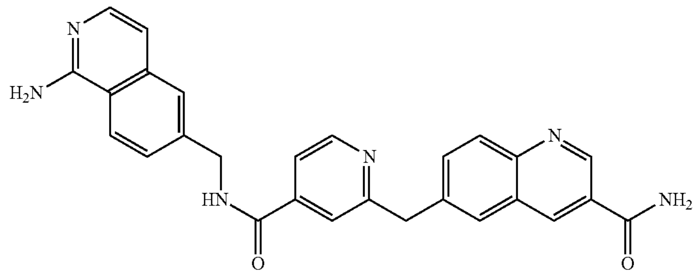 [SMILES: NC(=O)c1cnc2ccc(Cc3cc(C(=O)NCc4ccc5c(N)nccc5c4)ccn3)cc2c1] |
| N-((1-aminoisoquinolin-6-yl)methyl)-2-((3-(hydroxymethyl)quinolin-6-yl)methyl)isonicotinamide | 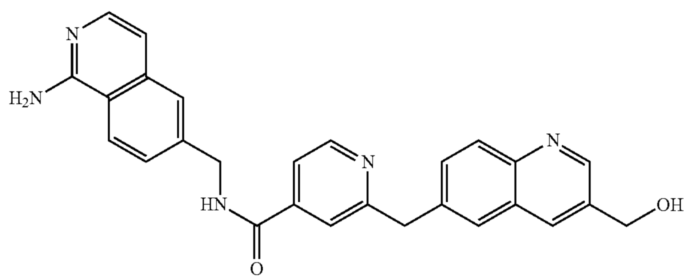 [SMILES: Nc1nccc2cc(CNC(=O)c3ccnc(Cc4ccc5ncc(CO)cc5c4)c3)ccc12] |
| N-((1-aminoisoquinolin-6-yl)methyl)-2-((3-(aminomethyl)quinolin-6-yl)methyl)isonicotinamide | 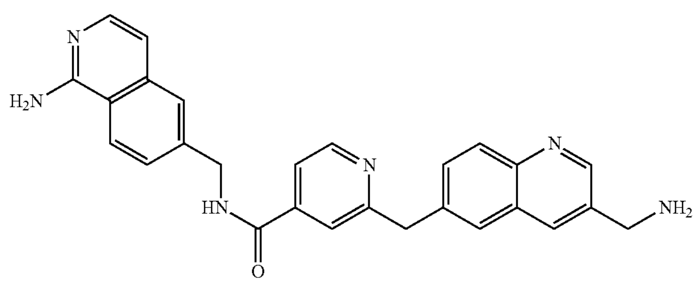 [SMILES: NCc1cnc2ccc(Cc3cc(C(=O)NCc4ccc5c(N)nccc5c4)ccn3)cc2c1] |
| N-((1-aminoisoquinolin-6-yl)methyl)-2-((3-methyl-8-sulfamoylquinolin-6-yl)methyl)isonicotinamide | 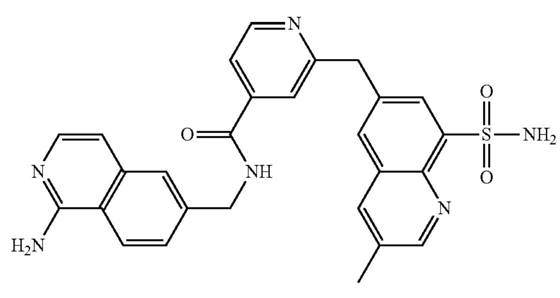 [SMILES: Cc1cnc2c(S(N)(=O)=O)cc(Cc3cc(C(=O)NCc4ccc5c(N)nccc5c4)ccn3)cc2c1] |
| 6-((4-(((1-aminoisoquinolin-6-yl)methyl)carbamoyl)pyridin-2-yl)methyl)-3-methylquinoline-8-carboxylic acid | 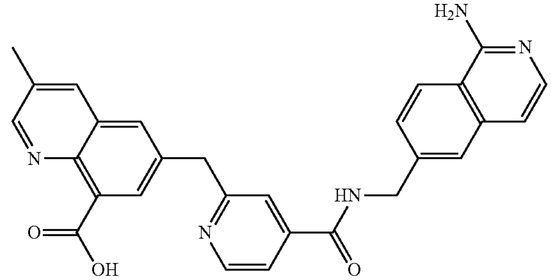 [SMILES: Cc1cnc2c(C(=O)O)cc(Cc3cc(C(=O)NCc4ccc5c(N)nccc5c4)ccn3)cc2c1] |

TABLE 2-continued

| Name | Structure |
|---|---|
| N-((6-amino-2-methylpyridin-3-yl)methyl)-2-((3-methyl-8-(methylsulfonyl)quinolin-6-yl)methyl)isonicotinamide | 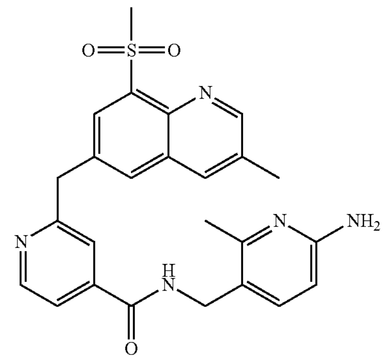 [SMILES: Cc1cnc2c(S(C)(=O)=O)cc(Cc3cc(C(=O)NCc4ccc(N)nc4C)ccn3)cc2c1] |
| N-((6-amino-4-methylpyridin-3-yl)methyl)-2-((3-methyl-8-(methylsulfonyl)quinolin-6-yl)methyl)isonicotinamide | 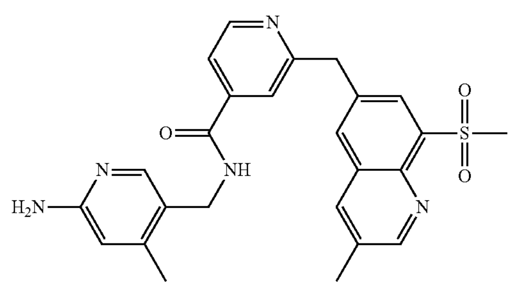 [SMILES: Cc1cnc2c(S(C)(=O)=O)cc(Cc3cc(C(=O)NCc4cnc(N)cc4C)ccn3)cc2c1] |
| N-((6-amino-2-methyl-4-(trifluoromethyl)pyridin-3-yl)methyl)-2-((3-methyl-8-(methylsulfonyl)quinolin-6-yl)methyl)isonicotinamide | 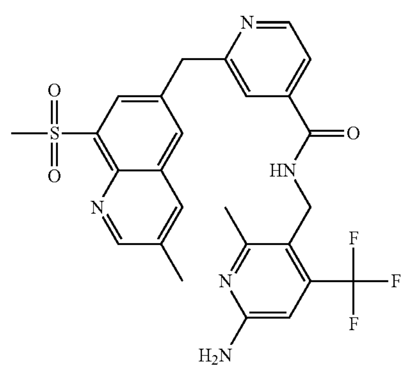 [SMILES: Cc1cnc2c(S(C)(=O)=O)cc(Cc3cc(C(=O)NCc4c(C(F)(F)F)cc(N)nc4C)ccn3)cc2c1] |
| N-((6-amino-4-cyano-2-methylpyridin-3-yl)methyl)-2-((3-methyl-8-(methylsulfonyl)quinolin-6-yl)methyl)isonicotinamide | 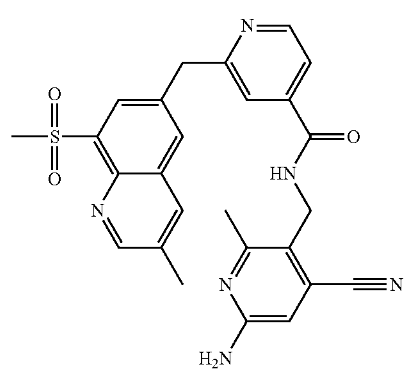 [SMILES: Cc1cnc2c(S(C)(=O)=O)cc(Cc3cc(C(=O)NCc4c(C#N)cc(N)nc4C)ccn3)cc2c1] |

TABLE 2-continued

| Name | Structure |
|---|---|
| N-((6-amino-4-methyl-2-(trifluoromethyl)pyridin-3-yl)methyl)-2-((3-methyl-8-(methylsulfonyl)quinolin-6-yl)methyl)isonicotinamide | 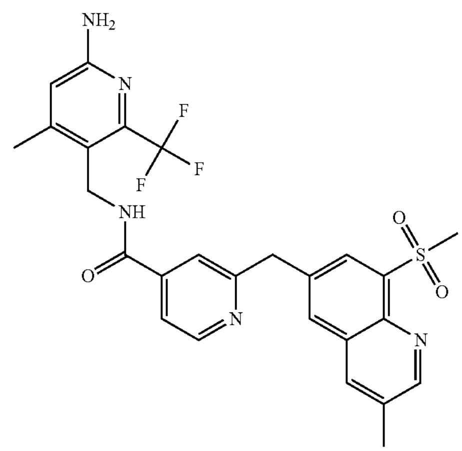 |
| N-((6-amino-2-cyano-4-methylpyridin-3-yl)methyl)-2-((3-methyl-8-(methylsulfonyl)quinolin-6-yl)methyl)isonicotinamide | 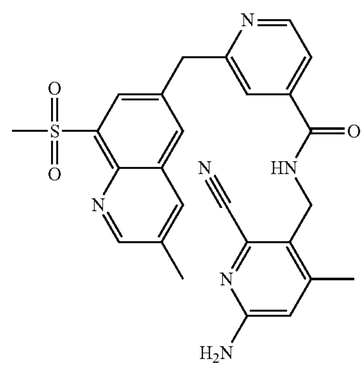 [SMILES: Cc1cnc2c(S(C)(=O)=O)cc(Cc3cc(C(=O)NCc4c(C)cc(N)nc4C#N)ccn3)cc2c1] |
| N-((6-amino-5-fluoro-2-methylpyridin-3-yl)methyl)-2-((3-methyl-8-(methylsulfonyl)quinolin-6-yl)methyl)isonicotinamide | 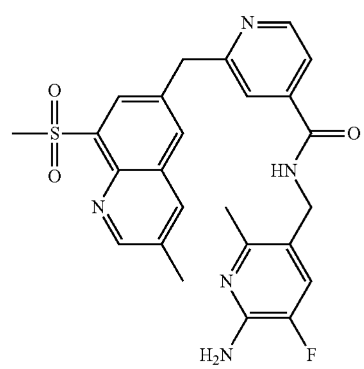 [SMILES: Cc1cnc2c(S(C)(=O)=O)cc(Cc3cc(C(=O)NCc4cc(F)c(N)nc4C)ccn3)cc2c1] |
| N-((6-amino-5-chloro-2-methylpyridin-3-yl)methyl)-2-((3-methyl-8-(methylsulfonyl)quinolin-6-yl)methyl)isonicotinamide | 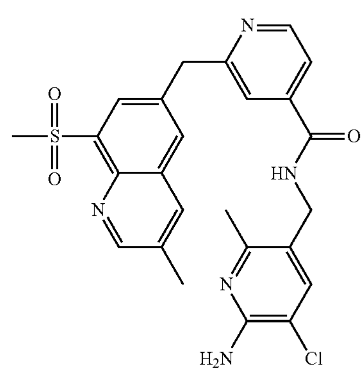 [SMILES: Cc1cnc2c(S(C)(=O)=O)cc(Cc3cc(C(=O)NCc4cc(Cl)c(N)nc4C)ccn3)cc2c1] |

TABLE 2-continued

| Name | Structure |
|---|---|
| N-((6-amino-5-cyano-2-methylpyridin-3-yl)methyl)-2-((3-methyl-8-(methylsulfonyl)quinolin-6-yl)methyl)isonicotinamide | 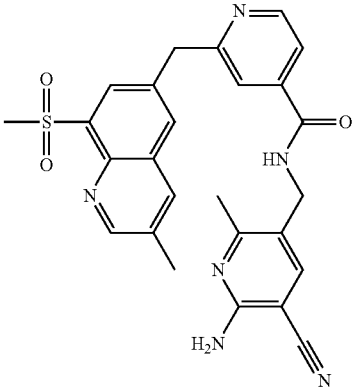 [SMILES: Cc1cnc2c(S(C)(=O)=O)cc(Cc3cc(C(=O)NCc4cc(C#N)c(N)nc4C)ccn3)cc2c1] |
| N-((6-amino-2-methyl-5-(trifluoromethyl)pyridin-3-yl)methyl)-2-((3-methyl-8-(methylsulfonyl)quinolin-6-yl)methyl)isonicotinamide | 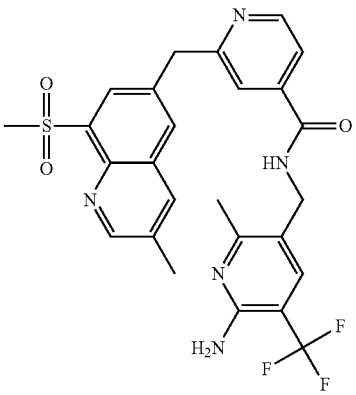 [SMILES: Cc1cnc2c(S(C)(=O)=O)cc(Cc3cc(C(=O)NCc4cc(C(F)(F)F)c(N)nc4C)ccn3)cc2c1] |
| N-((1-aminoisoquinolin-6-yl)methyl)-2-((3-fluoro-8-(methylsulfonyl)quinolin-6-yl)methyl)isonicotinamide | 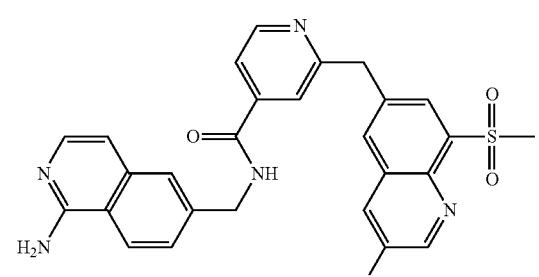 |
| N-((1-aminoisoquinolin-6-yl)methyl)-2-((3-fluoro-8-sulfamoylquinolin-6-yl)methyl)isonicotinamide | 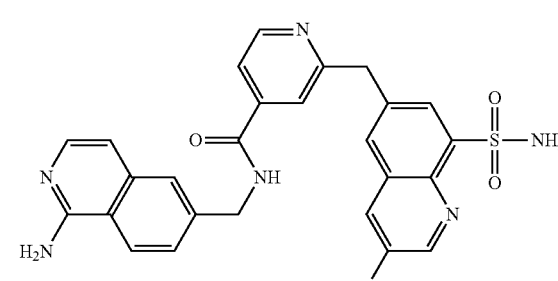 |

TABLE 2-continued

| Name | Structure |
|---|---|
| 6-((4-(((1-aminoisoquinolin-6-yl)methyl)carbamoyl)pyridin-2-yl)methyl)-3-fluoroquinoline-8-carboxylic acid | 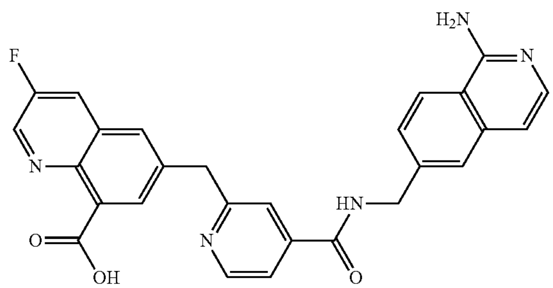 [SMILES: Nc1nccc2cc(CNC(=O)c3ccnc(Cc4cc(C(=O)O)c5ncc(F)cc5c4)c3)ccc12] |
| N-((3-chloro-1H-pyrrolo[2,3-b]pyridin-5-yl)methyl)-2-((3-fluoro-8-(methylsulfonyl)quinolin-6-yl)methyl)isonicotinamide | 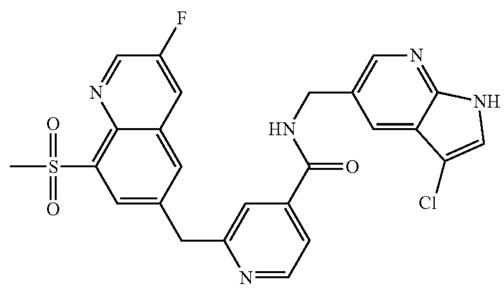 [SMILES: CS(=O)(=O)c1cc(Cc2cc(C(=O)NCc3cnc4[nH]cc(Cl)c4c3)ccn2)cc2cc(F)cnc12] |
| N-((3-chloro-6-fluoro-1H-indol-5-yl)methyl)-2-((3-fluoro-8-(methylsulfonyl)quinolin-6-yl)methyl)isonicotinamide | 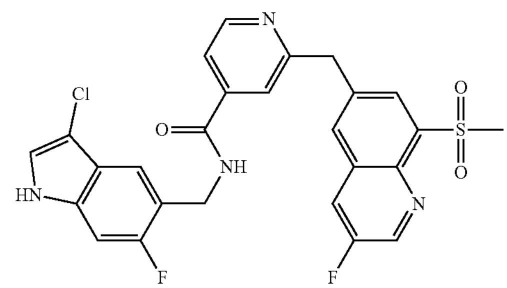 [SMILES: CS(=O)(=O)c1cc(Cc2cc(C(=O)NCc3cc4c(Cl)c[nH]c4cc3F)ccn2)cc2cc(F)cnc12] |
| N-((6-amino-2,4-dimethylpyridin-3-yl)methyl)-2-((3-fluoro-8-(methylsulfonyl)quinolin-6-yl)methyl)isonicotinamide | 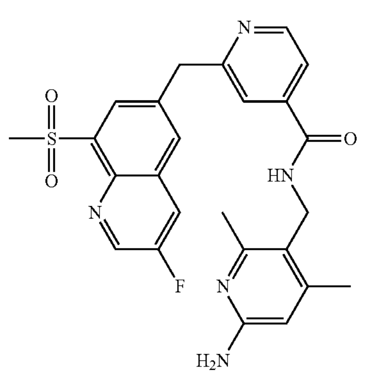 |
| N-((5-chloro-1H-indazol-3-yl)methyl)-2-((3-fluoro-8-(methylsulfonyl)quinolin-6-yl)methyl)isonicotinamide | 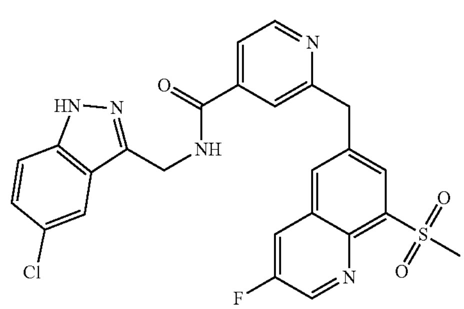 |

TABLE 2-continued

| Name | Structure |
|---|---|
| N-((6-amino-2-methylpyridin-3-yl)methyl)-2-((3-fluoro-8-(methylsulfonyl)quinolin-6-yl)methyl)isonicotinamide | 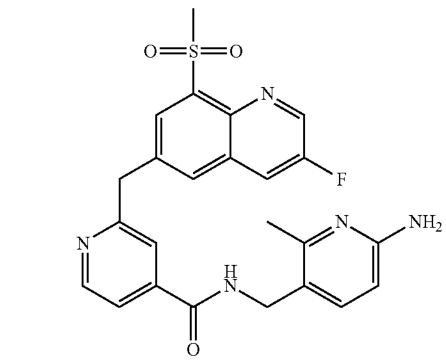 [SMILES: Cc1nc(N)ccc1CNC(=O)c1ccnc(Cc2cc(S(C)(=O)=O)c3ncc(F)cc3c2)c1] |
| N-((6-amino-4-methylpyridin-3-yl)methyl)-2-((3-fluoro-8-(methylsulfonyl)quinolin-6-yl)methyl)isonicotinamide | 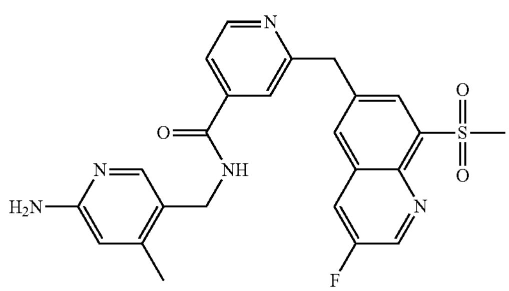 [SMILES: Cc1cc(N)ncc1CNC(=O)c1ccnc(Cc2cc(S(C)(=O)=O)c3ncc(F)cc3c2)c1] |
| N-((6-amino-2-methyl-4-(trifluoromethyl)pyridin-3-yl)methyl)-2-((3-fluoro-8-(methylsulfonyl)quinolin-6-yl)methyl)isonicotinamide | 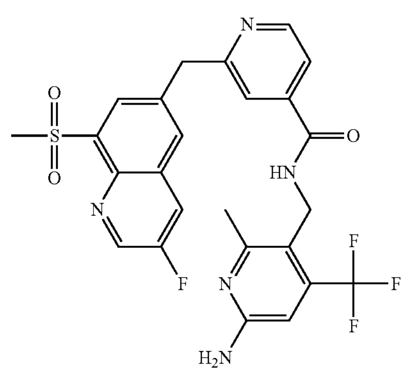 |
| N-((6-amino-4-cyano-2-methylpyridin-3-yl)methyl)-2-((3-fluoro-8-(methylsulfonyl)quinolin-6-yl)methyl)isonicotinamide | 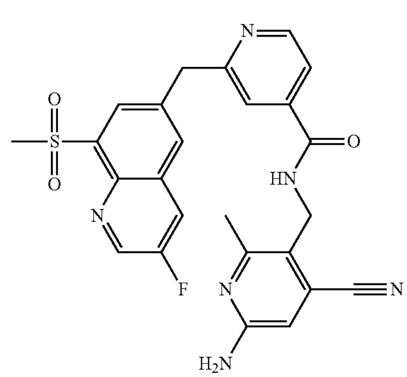 |

TABLE 2-continued

| Name | Structure |
|---|---|
| N-((6-amino-4-methyl-2-(trifluoromethyl)pyridin-3-yl)methyl)-2-((3-fluoro-8-(methylsulfonyl)quinolin-6-yl)methyl)isonicotinamide | 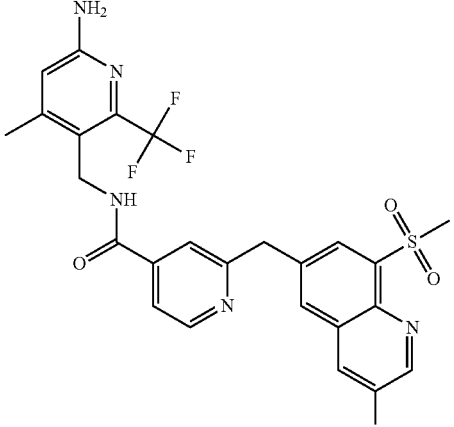 |
| N-((6-amino-2-cyano-4-methylpyridin-3-yl)methyl)-2-((3-fluoro-8-(methylsulfonyl)quinolin-6-yl)methyl)isonicotinamide | 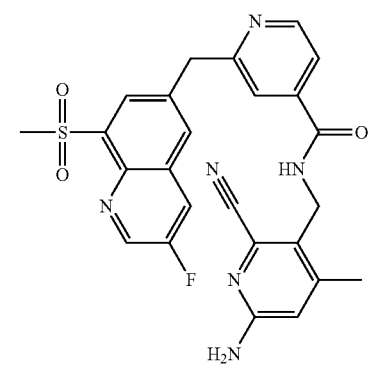 |
| N-((6-amino-5-fluoro-2-methylpyridin-3-yl)methyl)-2-((3-fluoro-8-(methylsulfonyl)quinolin-6-yl)methyl)isonicotinamide | 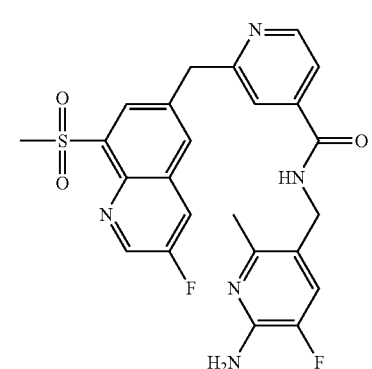 |
| N-((6-amino-5-chloro-2-methylpyridin-3-yl)methyl)-2-((3-fluoro-8-(methylsulfonyl)quinolin-6-yl)methyl)isonicotinamide | 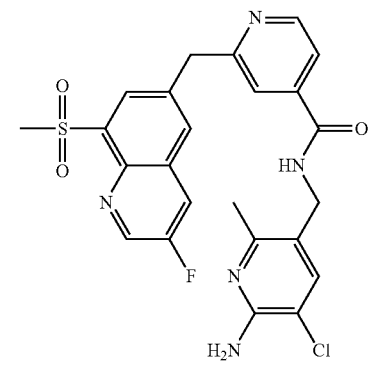 [SMILES: Cc1nc(N)c(Cl)cc1CNC(=O)c1ccnc(Cc2cc(S(C)(=O)=O)c3ncc(F)cc3c2)c1] |

TABLE 2-continued

| Name | Structure |
|---|---|
| N-((6-amino-5-cyano-2-methylpyridin-3-yl)methyl)-2-((3-fluoro-8-(methylsulfonyl)quinolin-6-yl)methyl)isonicotinamide | 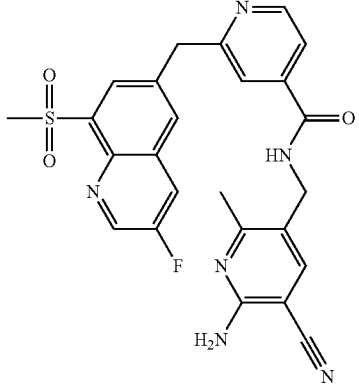 [SMILES: Cc1nc(N)c(C#N)cc1CNC(=O)c1ccnc(Cc2cc(S(C)(=O)=O)c3ncc(F)cc3c2)c1] |
| N-((6-amino-2-methyl-5-(trifluoromethyl)pyridin-3-yl)methyl)-2-((3-fluoro-8-(methylsulfonyl)quinolin-6-yl)methyl)isonicotinamide | 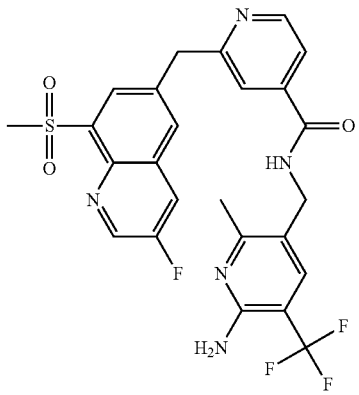 [SMILES: Cc1nc(N)c(C(F)(F)F)cc1CNC(=O)c1ccnc(Cc2cc(S(C)(=O)=O)c3ncc(F)cc3c2)c1] |
| N-((3-chloro-4-fluoro-1H-indol-5-yl)methyl)-2-((3-fluoro-8-(methylsulfonyl)quinolin-6-yl)methyl)isonicotinamide | 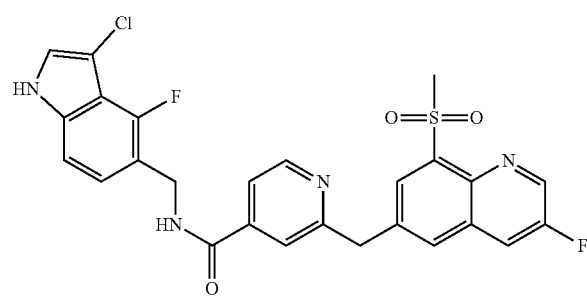 [SMILES: CS(=O)(=O)c1cc(Cc2cc(C(=O)NCc3ccc4[nH]cc(Cl)c4c3F)ccn2)cc2cc(F)cnc12] |
| N-((6-amino-2-methylpyridin-3-yl)methyl)-2-((3-methylquinolin-6-yl)methyl)isonicotinamide | 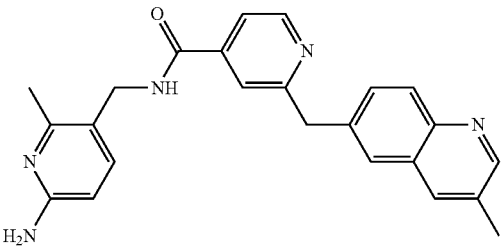 |
| N-((6-amino-4-methylpyridin-3-yl)methyl)-2-((3-methylquinolin-6-yl)methyl)isonicotinamide | 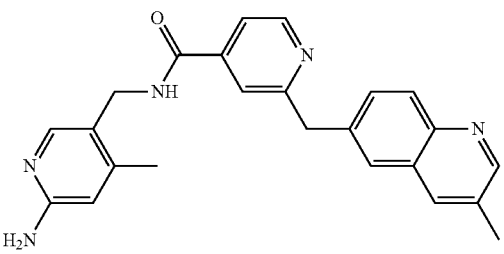 |

TABLE 2-continued

| Name | Structure |
|---|---|
| N-((3-chloro-1H-pyrrolo[2,3-b]pyridin-5-yl)methyl)-2-((3-methylquinolin-6-yl)methyl)isonicotinamide | 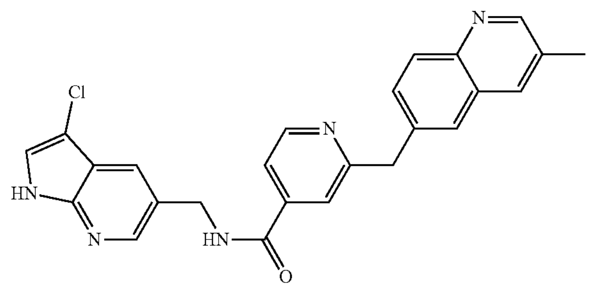 |
| N-((5-chloro-1H-indazol-3-yl)methyl)-2-((3-methylquinolin-6-yl)methyl)isonicotinamide | 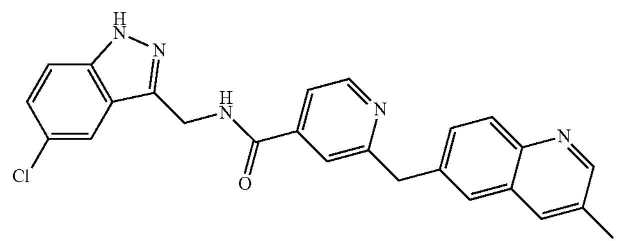 [SMILES: Cc1cnc2ccc(Cc3cc(C(=O)NCc4n[nH]c5ccc(Cl)cc45)ccn3)cc2c1] |
| N-((3-chloro-4-fluoro-1H-indol-5-yl)methyl)-2-((3-methylquinolin-6-yl)methyl)isonicotinamide | 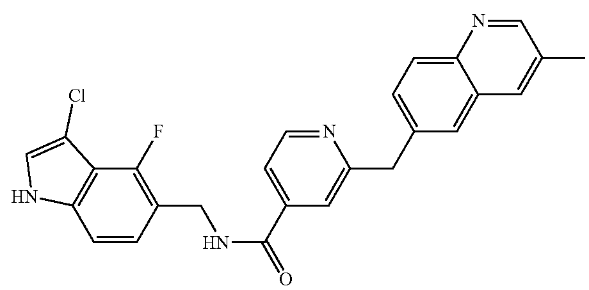 [SMILES: Cc1cnc2ccc(Cc3cc(C(=O)NCc4ccc5[nH]cc(Cl)c5c4F)ccn3)cc2c1] |
| N-((6-fluoro-1H-indol-5-yl)methyl)-2-((3-methylquinolin-6-yl)methyl)isonicotinamide | 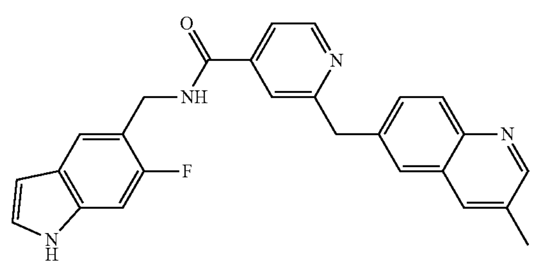 [SMILES: Cc1cnc2ccc(Cc3cc(C(=O)NCc4cc5cc[nH]c5cc4F)ccn3)cc2c1] |
| N-((6-fluoro-1H-indazol-5-yl)methyl)-2-((3-methylquinolin-6-yl)methyl)isonicotinamide | 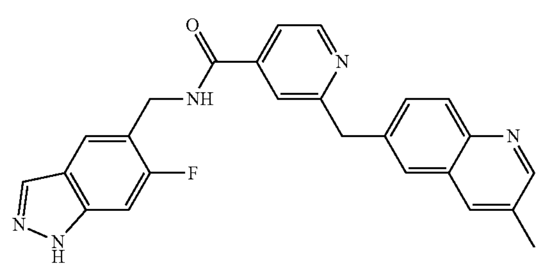 [SMILES: Cc1cnc2ccc(Cc3cc(C(=O)NCc4cc5cn[nH]c5cc4F)ccn3)cc2c1] |
| N-((1H-pyrrolo[2,3-b]pyridin-5-yl)methyl)-2-((3-methylquinolin-6-yl)methyl)isonicotinamide | 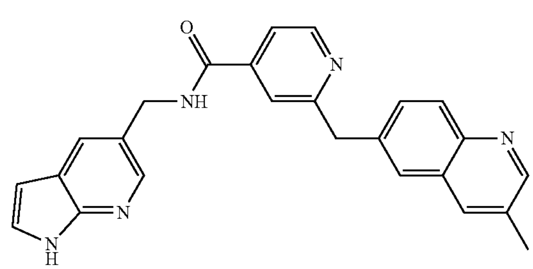 [SMILES: Cc1cnc2ccc(Cc3cc(C(=O)NCc4cnc5[nH]ccc5c4)ccn3)cc2c1] |

TABLE 2-continued

| Name | Structure |
|---|---|
| N-((3-chloro-1H-indol-5-yl)methyl)-2-((3-methylquinolin-6-yl)methyl)isonicotinamide | 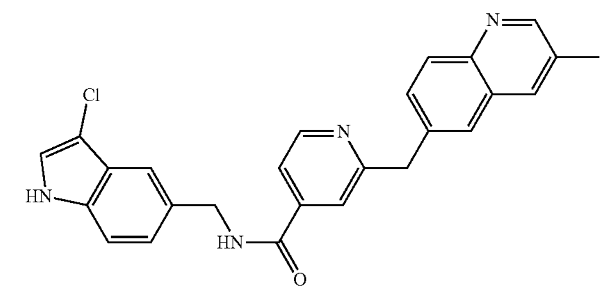 [SMILES: Cc1cnc2ccc(Cc3cc(C(=O)NCc4ccc5[nH]cc(Cl)c5c4)ccn3)cc2c1] |
| N-((5-chloro-1H-indol-3-yl)methyl)-2-((3-methylquinolin-6-yl)methyl)isonicotinamide | 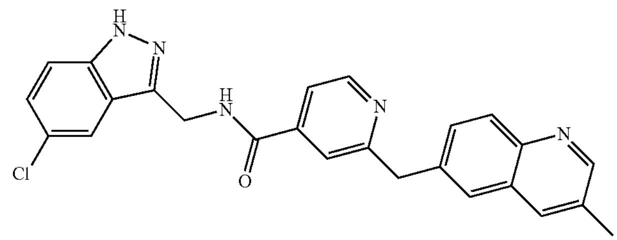 [SMILES: Cc1cnc2ccc(Cc3cc(C(=O)NCc4n[nH]c5ccc(Cl)cc45)ccn3)cc2c1] |
| N-((3-chloro-6-methyl-1H-indol-5-yl)methyl)-2-((3-methylquinolin-6-yl)methyl)isonicotinamide | 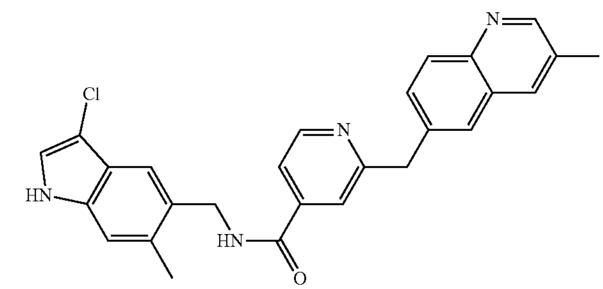 [SMILES: Cc1cnc2ccc(Cc3cc(C(=O)NCc4cc5c(Cl)c[nH]c5cc4C)ccn3)cc2c1] |
| N-((3-chloro-6-methyl-1H-pyrrolo[2,3-b]pyridin-5-yl)methyl)-2-((3-methylquinolin-6-yl)methyl)isonicotinamide | 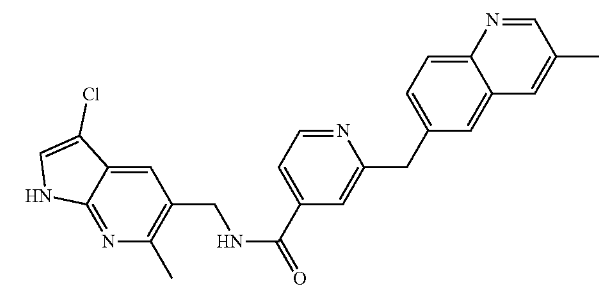 [SMILES: Cc1cnc2ccc(Cc3cc(C(=O)NCc4cc5c(Cl)c[nH]c5nc4C)ccn3)cc2c1] |
| N-((3-chloro-1H-pyrrolo[3,2-b]pyridin-5-yl)methyl)-2-((3-methylquinolin-6-yl)methyl)isonicotinamide | 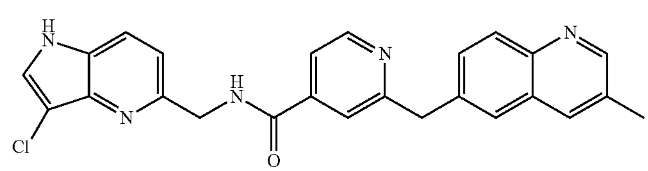 [SMILES: Cc1cnc2ccc(Cc3cc(C(=O)NCc4ccc5[nH]cc(Cl)c5n4)ccn3)cc2c1] |
| N-((1H-pyrrolo[3,2-b]pyridin-5-yl)methyl)-2-((3-methylquinolin-6-yl)methyl)isonicotinamide | 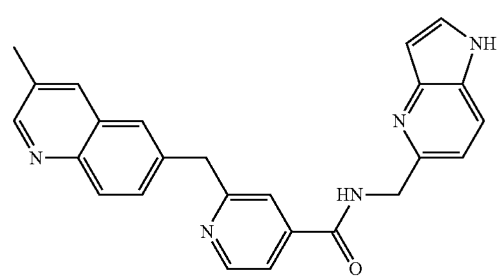 [SMILES: Cc1cnc2ccc(Cc3cc(C(=O)NCc4ccc5[nH]ccc5n4)ccn3)cc2c1] |

TABLE 2-continued

| Name | Structure |
|---|---|
| N-((6-amino-2-methylpyridin-3-yl)methyl)-2-((3-fluoroquinolin-6-yl)methyl)isonicotinamide | 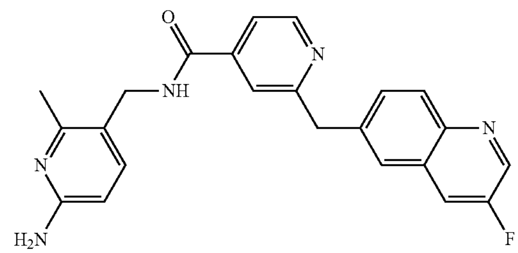 |
| N-((6-amino-4-methylpyridin-3-yl)methyl)-2-((3-fluoroquinolin-6-yl)methyl)isonicotinamide | 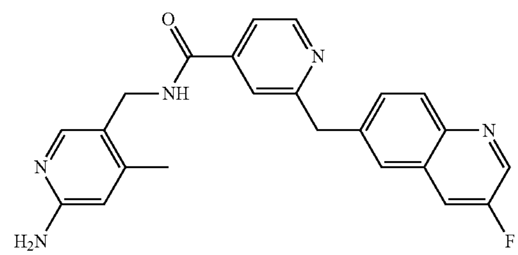 [SMILES: Cc1cc(N)ncc1CNC(=O)c1ccnc(Cc2ccc3ncc(F)cc3c2)c1] |
| N-((6-amino-2,4-dimethylpyridin-3-yl)methyl)-2-((3-fluoroquinolin-6-yl)methyl)isonicotinamide | 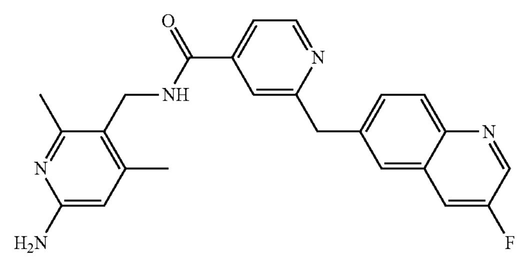 [SMILES: Cc1cc(N)nc(C)c1CNC(=O)c1ccnc(Cc2ccc3ncc(F)cc3c2)c1] |
| N-((3-chloro-1H-pyrrolo[2,3-b]pyridin-5-yl)methyl)-2-((3-fluoroquinolin-6-yl)methyl)isonicotinamide | 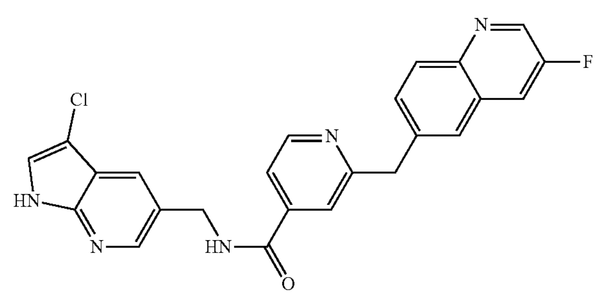 [SMILES: O=C(NCc1cnc2[nH]cc(Cl)c2c1)c1ccnc(Cc2ccc3ncc(F)cc3c2)c1] |
| N-((5-chloro-1H-indazol-3-yl)methyl)-2-((3-fluoroquinolin-6-yl)methyl)isonicotinamide | 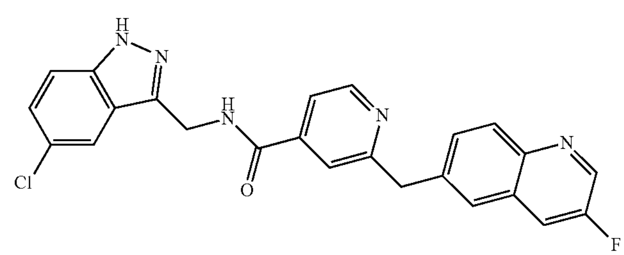 [SMILES: O=C(NCc1n[nH]c2ccc(Cl)cc12)c1ccnc(Cc2ccc3ncc(F)cc3c2)c1] |
| N-((3-chloro-4-fluoro-1H-indol-5-yl)methyl)-2-((3-fluoroquinolin-6-yl)methyl)isonicotinamide | 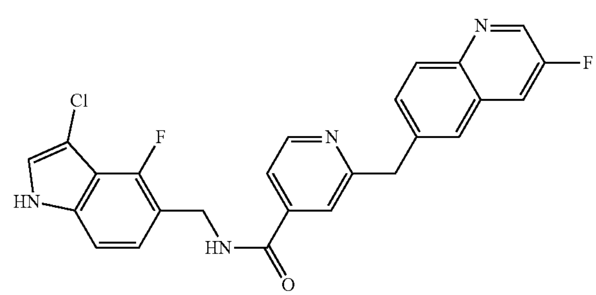 [SMILES: O=C(NCc1ccc2[nH]cc(Cl)c2c1F)c1ccnc(Cc2ccc3ncc(F)cc3c2)c1] |

TABLE 2-continued

| Name | Structure |
|---|---|
| N-((3-chloro-1H-pyrrolo[2,3-b]pyridin-5-yl)methyl)-2-((3-chloro-8-(methylsulfonyl)quinolin-6-yl)methyl)isonicotinamide | 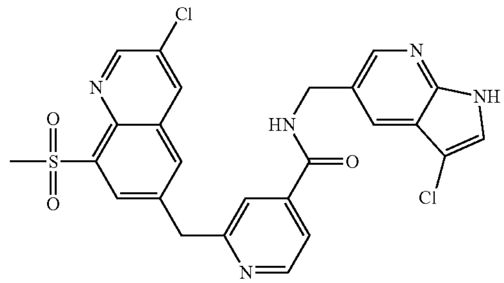 |
| N-((5-chloro-1H-indazol-3-yl)methyl)-2-((3-chloro-8-(methylsulfonyl)quinolin-6-yl)methyl)isonicotinamide | 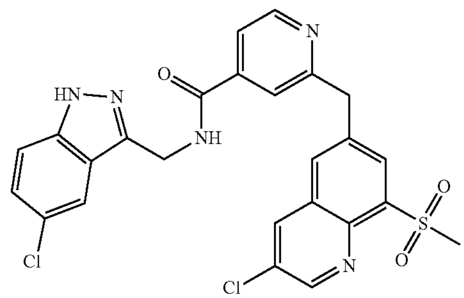 [SMILES: CS(=O)(=O)c1cc(Cc2cc(C(=O)NCc3n[nH]c4ccc(Cl)cc34)ccn2)cc2cc(Cl)cnc12] |
| N-((6-fluoro-1H-indol-5-yl)methyl)-2-((3-fluoroquinolin-6-yl)methyl)isonicotinamide | 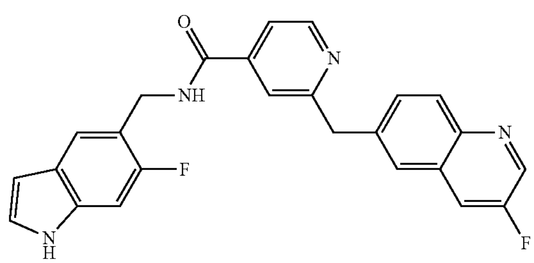 [SMILES: O=C(NCc1cc2cc[nH]c2cc1F)c1ccnc(Cc2ccc3ncc(F)cc3c2)c1] |
| N-((6-fluoro-1H-indazol-5-yl)methyl)-2-((3-fluoroquinolin-6-yl)methyl)isonicotinamide | 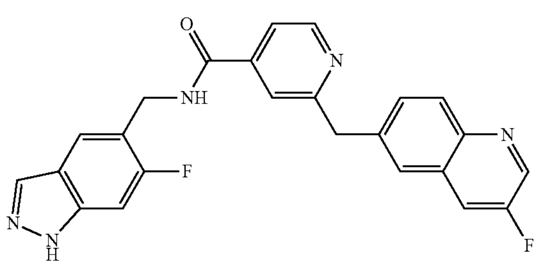 [SMILES: O=C(NCc1cc2cn[nH]c2cc1F)c1ccnc(Cc2ccc3ncc(F)cc3c2)c1] |
| N-((1H-pyrrolo[2,3-b]pyridin-5-yl)methyl)-2-((3-fluoroquinolin-6-yl)methyl)isonicotinamide | 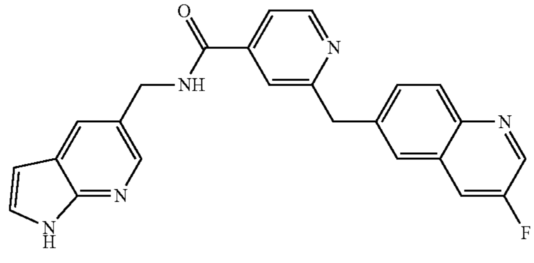 [SMILES: O=C(NCc1cnc2[nH]ccc2c1)c1ccnc(Cc2ccc3ncc(F)cc3c2)c1] |

TABLE 2-continued

| Name | Structure |
|---|---|
| N-((3-chloro-1H-indol-5-yl)methyl)-2-((3-fluoroquinolin-6-yl)methyl)isonicotinamide | 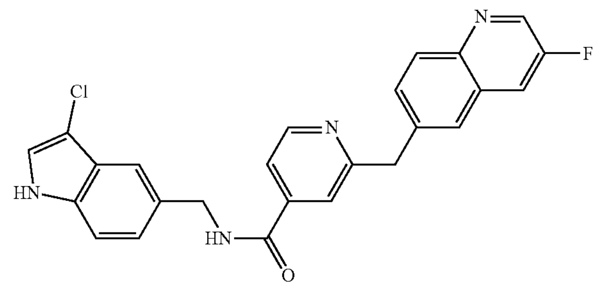 [SMILES: O=C(NCc1ccc2[nH]cc(Cl)c2c1)c1ccnc(Cc2ccc3ncc(F)cc3c2)c1] |
| N-((5-chloro-1H-indol-3-yl)methyl)-2-((3-fluoroquinolin-6-yl)methyl)isonicotinamide | 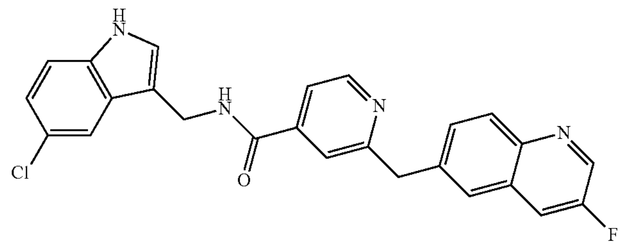 [SMILES: O=C(NCc1c[nH]c2ccc(Cl)cc12)c1ccnc(Cc2ccc3ncc(F)cc3c2)c1] |
| N-((3-chloro-6-methyl-1H-indol-5-yl)methyl)-2-((3-fluoroquinolin-6-yl)methyl)isonicotinamide | 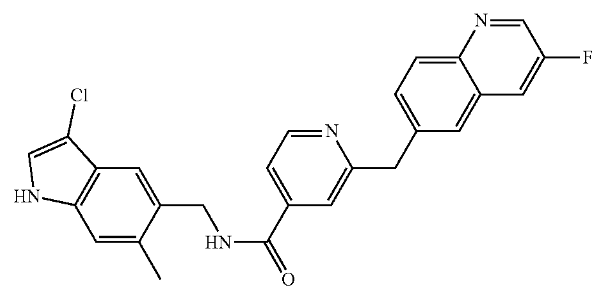 [SMILES: Cc1cc2[nH]cc(Cl)c2cc1CNC(=O)c1ccnc(Cc2ccc3ncc(F)cc3c2)c1] |
| N-((3-chloro-6-methyl-1H-pyrrolo[2,3-b]pyridin-5-yl)methyl)-2-((3-fluoroquinolin-6-yl)methyl)isonicotinamide | 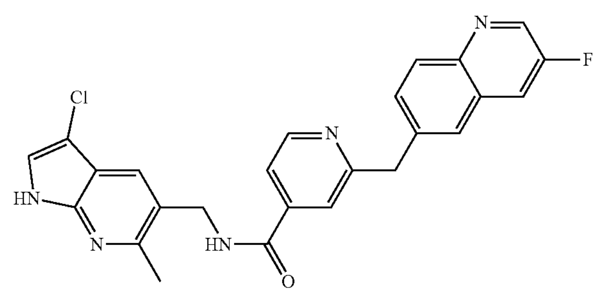 [SMILES: Cc1nc2[nH]cc(Cl)c2cc1CNC(=O)c1ccnc(Cc2ccc3ncc(F)cc3c2)c1] |
| N-((3-chloro-1H-pyrrolo[3,2-b]pyridin-5-yl)methyl)-2-((3-fluoroquinolin-6-yl)methyl)isonicotinamide | 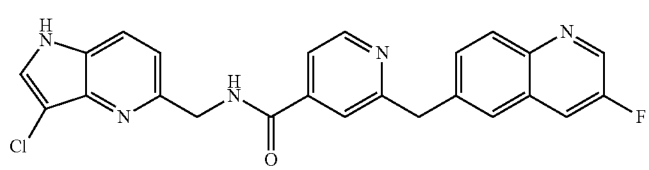 [SMILES: O=C(NCc1ccc2[nH]cc(Cl)c2n1)c1ccnc(Cc2ccc3ncc(F)cc3c2)c1] |
| N-((1H-pyrrolo[3,2-b]pyridin-5-yl)methyl)-2-((3-fluoroquinolin-6-yl)methyl)isonicotinamide | 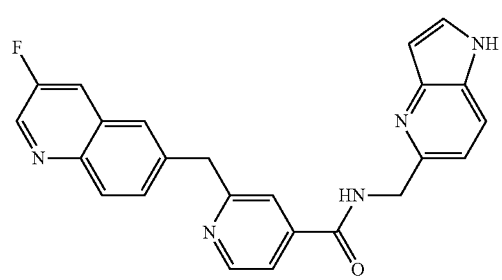 [SMILES: O=C(NCc1ccc2[nH]ccc2n1)c1ccnc(Cc2ccc3ncc(F)cc3c2)c1] |

TABLE 2-continued

| Name | Structure |
|---|---|
| N-((1H-benzo[d]imidazol-5-yl)methyl)-2-((3-methylquinolin-6-yl)methyl)isonicotinamide | 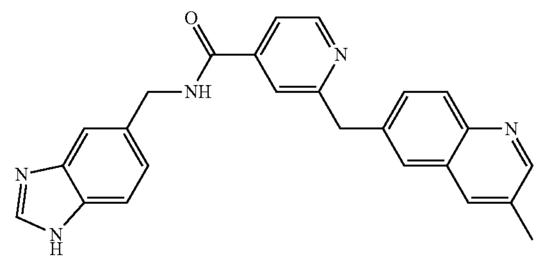 [SMILES: Cc1cnc2ccc(Cc3cc(C(=O)NCc4ccc5[nH]cnc5c4)ccn3)cc2c1] |
| N-((3-amino-1H-indazol-6-yl)methyl)-2-((3-methylquinolin-6-yl)methyl)isonicotinamide | 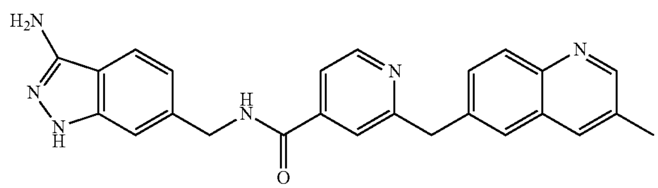 [SMILES: Cc1cnc2ccc(Cc3cc(C(=O)NCc4ccc5c(N)n[nH]c5c4)ccn3)cc2c1] |
| N-((2-aminobenzo[d]oxazol-6-yl)methyl)-2-((3-methylquinolin-6-yl)methyl)isonicotinamide | 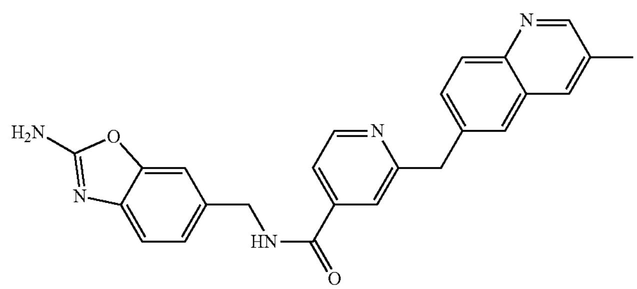 [SMILES: Cc1cnc2ccc(Cc3cc(C(=O)NCc4ccc5nc(N)oc5c4)ccn3)cc2c1] |
| N-((2-aminobenzo[d]oxazol-5-yl)methyl)-2-((3-methylquinolin-6-yl)methyl)isonicotinamide | 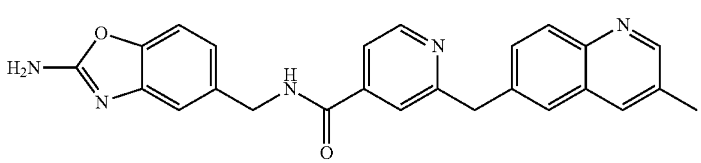 [SMILES: Cc1cnc2ccc(Cc3cc(C(=O)NCc4ccc5oc(N)nc5c4)ccn3)cc2c1] |
| N-((1-aminoisoquinolin-6-yl)methyl)-2-((3-methyl-8-(methylsulfonyl)isoquinolin-6-yl)methyl)isonicotinamide | 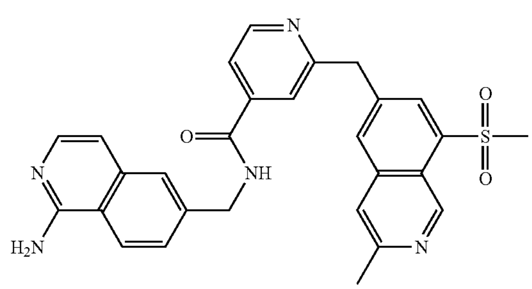 [SMILES: Cc1cc2cc(Cc3cc(C(=O)NCc4ccc5c(N)nccc5c4)ccn3)cc(S(C)(=O)=O)c2cn1] |
| N-((1-aminoisoquinolin-6-yl)methyl)-2-((3-methyl-8-sulfamoylisoquinolin-6-yl)methyl)isonicotinamide | 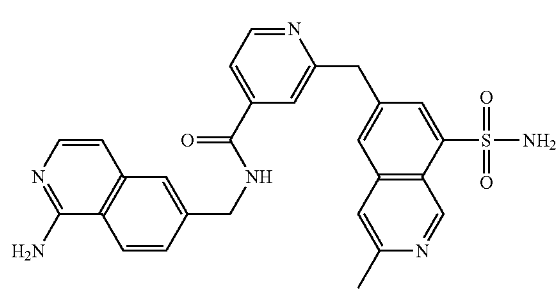 [SMILES: Cc1cc2cc(Cc3cc(C(=O)NCc4ccc5c(N)nccc5c4)ccn3)cc(S(N)(=O)=O)c2cn1] |

TABLE 2-continued

| Name | Structure |
|---|---|
| 6-((4-(((1-aminoisoquinolin-6-yl)methyl)carbamoyl)pyridin-2-yl)methyl)-3-methylisoquinoline-8-carboxylic acid | 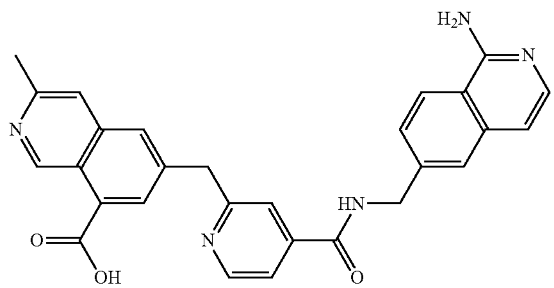 [SMILES: Cc1cc2cc(Cc3cc(C(=O)NCc4ccc5c(N)nccc5c4)ccn3)cc(C(=O)O)c2cn1] |
| N-((3-chloro-1H-pyrrolo[2,3-b]pyridin-5-yl)methyl)-2-((3-methyl-8-(methylsulfonyl)isoquinolin-6-yl)methyl)isonicotinamide | 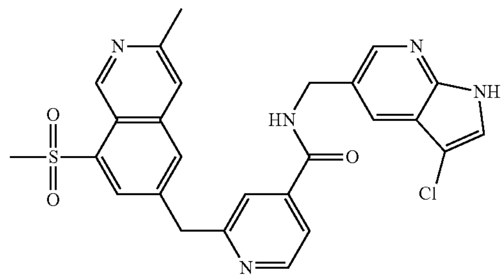 [SMILES: Cc1cc2cc(Cc3cc(C(=O)NCc4cnc5[nH]cc(Cl)c5c4)ccn3)cc(S(C)(=O)=O)c2cn1] |
| N-((3-chloro-6-fluoro-1H-indol-5-yl)methyl)-2-((3-methyl-8-(methylsulfonyl)isoquinolin-6-yl)methyl)isonicotinamide | 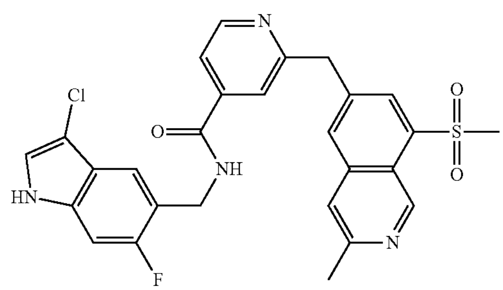 [SMILES: Cc1cc2cc(Cc3cc(C(=O)NCc4cc5c(Cl)c[nH]c5cc4F)ccn3)cc(S(C)(=O)=O)c2cn1] |
| N-((6-amino-2,4-dimethylpyridin-3-yl)methyl)-2-((3-methyl-8-(methylsulfonyl)isoquinolin-6-yl)methyl)isonicotinamide | 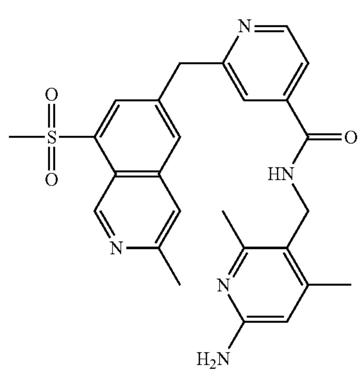 |
| N-((5-chloro-1H-indazol-3-yl)methyl)-2-((3-methyl-8-(methylsulfonyl)isoquinolin-6-yl)methyl)isonicotinamide | 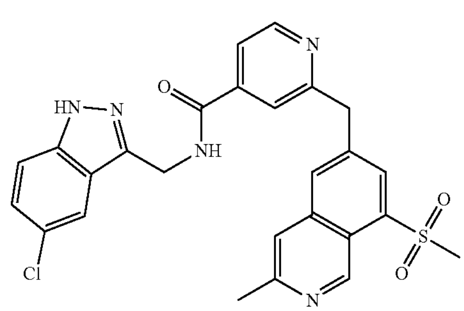 [SMILES: Cc1cc2cc(Cc3cc(C(=O)NCc4n[nH]c5ccc(Cl)cc45)ccn3)cc(S(C)(=O)=O)c2cn1] |

TABLE 2-continued

| Name | Structure |
|---|---|
| N-((3-chloro-4-fluoro-1H-indol-5-yl)methyl)-2-((3-methyl-8-(methylsulfonyl)isoquinolin-6-yl)methyl)isonicotinamide | 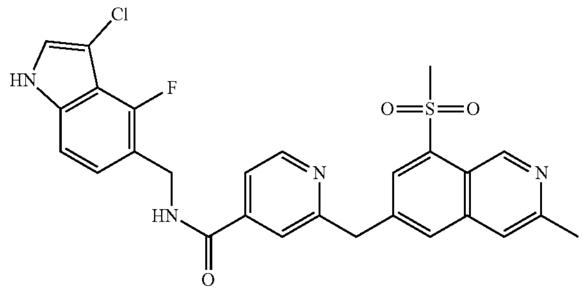 [SMILES: Cc1cc2cc(Cc3cc(C(=O)NCc4ccc5[nH]cc(Cl)c5c4F)ccn3)cc(S(C)(=O)=O)c2cn1] |
| N-((1-aminoisoquinolin-6-yl)methyl)-2-((2-methyl-8-(methylsulfonyl)quinolin-6-yl)methyl)isonicotinamide | 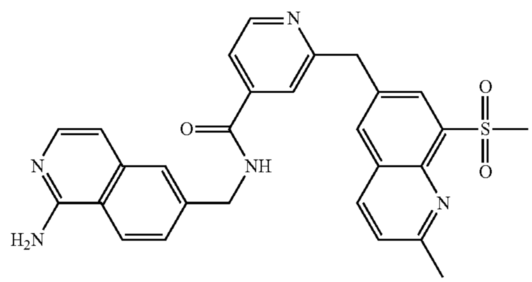 [SMILES: Cc1ccc2cc(Cc3cc(C(=O)NCc4ccc5c(N)nccc5c4)ccn3)cc(S(C)(=O)=O)c2n1] |
| N-((1-aminoisoquinolin-6-yl)methyl)-2-((2-methyl-8-sulfamoylquinolin-6-yl)methyl)isonicotinamide | 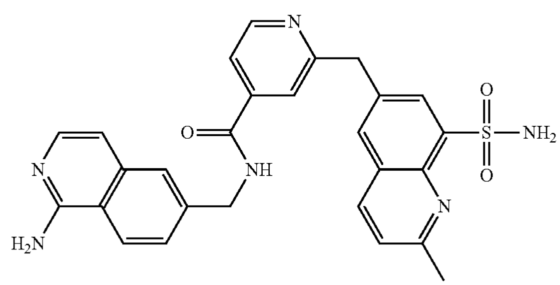 [SMILES: Cc1ccc2cc(Cc3cc(C(=O)NCc4ccc5c(N)nccc5c4)ccn3)cc(S(N)(=O)=O)c2n1] |
| 6-((4-(((1-aminoisoquinolin-6-yl)methyl)carbamoyl)pyridin-2-yl)methyl)-2-methylquinoline-8-carboxylic acid | 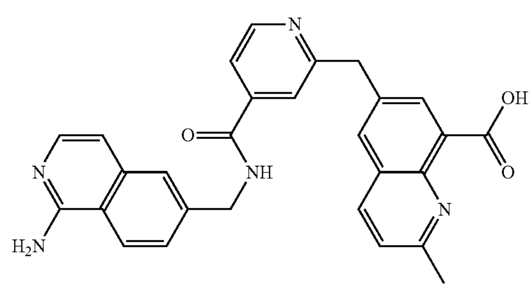 [SMILES: Cc1ccc2cc(Cc3cc(C(=O)NCc4ccc5c(N)nccc5c4)ccn3)cc(C(=O)O)c2n1] |
| N-((3-chloro-1H-pyrrolo[2,3-b]pyridin-5-yl)methyl)-2-((2-methyl-8-(methylsulfonyl)quinolin-6-yl)methyl)isonicotinamide | 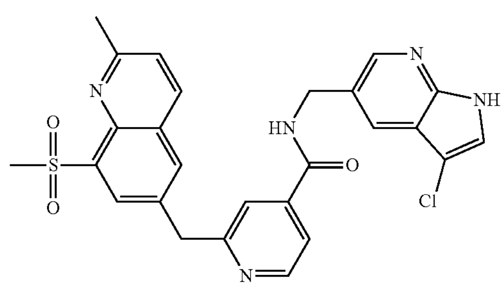 [SMILES: Cc1ccc2cc(Cc3cc(C(=O)NCc4cnc5[nH]cc(Cl)c5c4)ccn3)cc(S(C)(=O)=O)c2n1] |

TABLE 2-continued

| Name | Structure |
|---|---|
| N-((3-chloro-6-fluoro-1H-indol-5-yl)methyl)-2-((2-methyl-8-(methylsulfonyl)quinolin-6-yl)methyl)isonicotinamide | 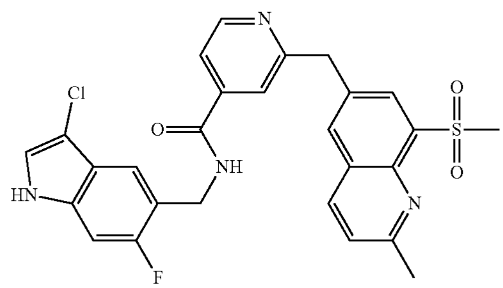 [SMILES: Cc1ccc2cc(Cc3cc(C(=O)NCc4cc5c(Cl)c[nH]c5cc4F)ccn3)cc(S(C)(=O)=O)c2n1] |
| N-((6-amino-2,4-dimethylpyridin-3-yl)methyl)-2-((2-methyl-8-(methylsulfonyl)quinolin-6-yl)methyl)isonicotinamide | 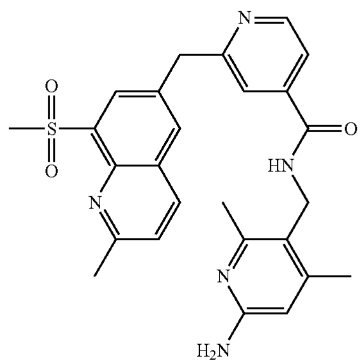 |
| N-((5-chloro-1H-indazol-3-yl)methyl)-2-((2-methyl-8-(methylsulfonyl)quinolin-6-yl)methyl)isonicotinamide | 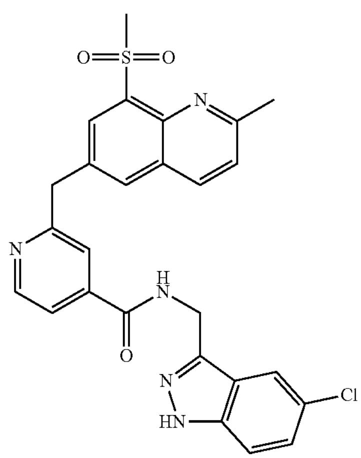 [SMILES: Cc1ccc2cc(Cc3cc(C(=O)NCc4n[nH]c5ccc(Cl)cc45)ccn3)cc(S(C)(=O)=O)c2n1] |
| N-((3-chloro-4-fluoro-1H-indol-5-yl)methyl)-2-((2-methyl-8-(methylsulfonyl)quinolin-6-yl)methyl)isonicotinamide | 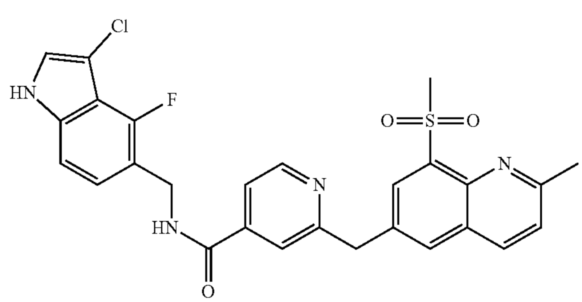 [SMILES: Cc1ccc2cc(Cc3cc(C(=O)NCc4ccc5[nH]cc(Cl)c5c4F)ccn3)cc(S(C)(=O)=O)c2n1] |

TABLE 2-continued

| Name | Structure |
|---|---|
| N-((6-amino-4-cyano-2-methylpyridin-3-yl)methyl)-2-((3-methylquinolin-6-yl)methyl)isonicotinamide | 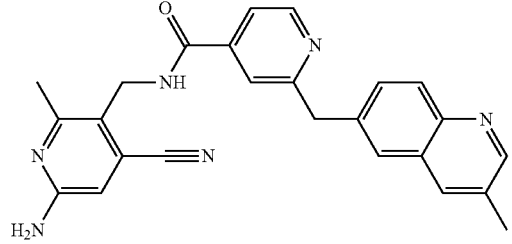 |
| N-((6-amino-2-methyl-4-(trifluoromethyl)pyridin-3-yl)methyl)-2-((3-methylquinolin-6-yl)methyl)isonicotinamide | 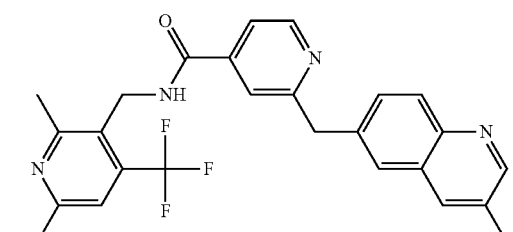 |
| N-((6-amino-5-fluoro-2-methylpyridin-3-yl)methyl)-2-((3-methylquinolin-6-yl)methyl)isonicotinamide | 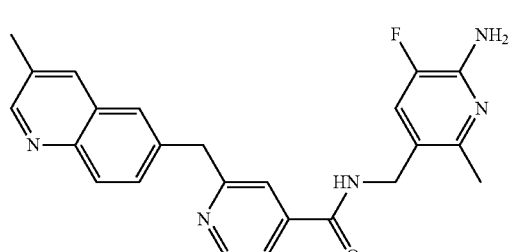 |
| N-((6-amino-5-chloro-2-methylpyridin-3-yl)methyl)-2-((3-methylquinolin-6-yl)methyl)isonicotinamide | 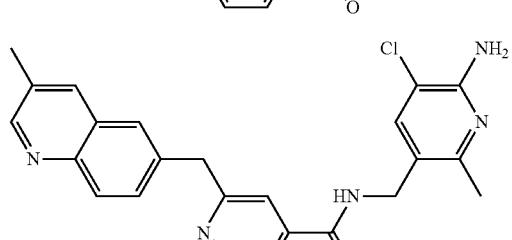 |
| N-((6-amino-2-methyl-5-(trifluoromethyl)pyridin-3-yl)methyl)-2-((3-methylquinolin-6-yl)methyl)isonicotinamide | 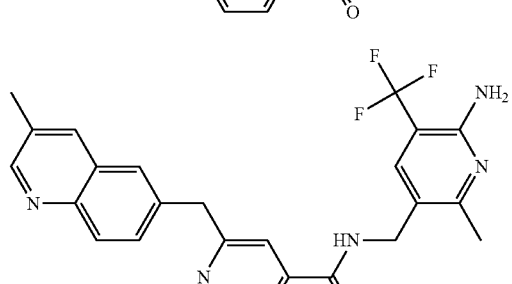 |
| N-((6-amino-5-cyano-2-methylpyridin-3-yl)methyl)-2-((3-methylquinolin-6-yl)methyl)isonicotinamide | 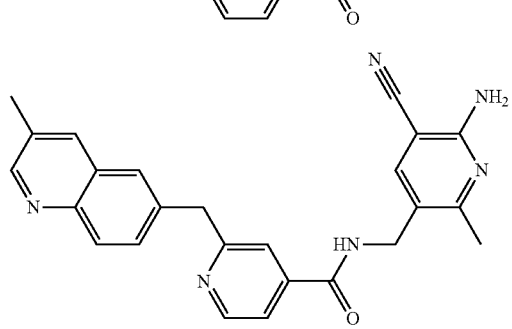 |

TABLE 2-continued

| Name | Structure |
|---|---|
| N-((6-amino-2-cyano-4-methylpyridin-3-yl)methyl)-2-((3-methylquinolin-6-yl)methyl)isonicotinamide | 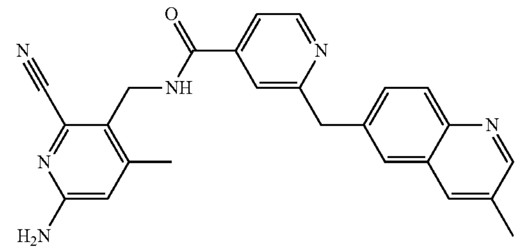 [SMILES: Cc1cnc2ccc(Cc3cc(C(=O)NCc4c(C)cc(N)nc4C#N)ccn3)cc2c1] |
| N-((6-amino-4-methyl-2-(trifluoromethyl)pyridin-3-yl)methyl)-2-((3-methylquinolin-6-yl)methyl)isonicotinamide | 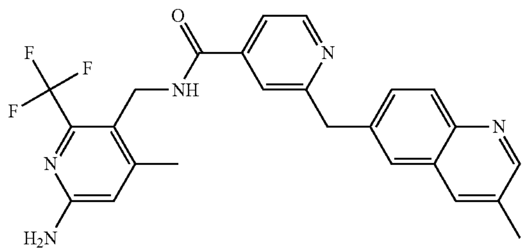 [SMILES: Cc1cnc2ccc(Cc3cc(C(=O)NCc4c(C)cc(N)nc4C(F)(F)F)ccn3)cc2c1] |
| N-((6-amino-4-cyano-2-methylpyridin-3-yl)methyl)-2-((3-fluoroquinolin-6-yl)methyl)isonicotinamide | 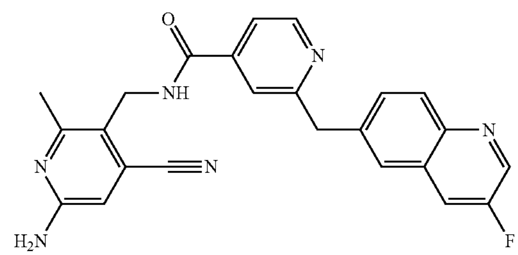 [SMILES: Cc1nc(N)cc(C#N)c1CNC(=O)c1ccnc(Cc2ccc3ncc(F)cc3c2)c1] |
| N-((6-amino-2-methyl-4-(trifluoromethyl)pyridin-3-yl)methyl)-2-((3-fluoroquinolin-6-yl)methyl)isonicotinamide | 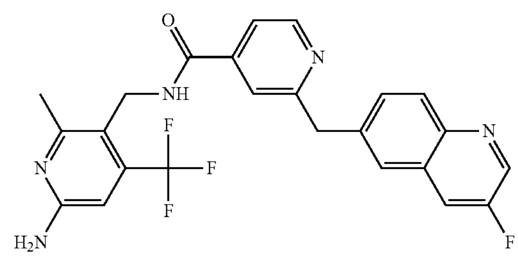 |
| N-((6-amino-5-fluoro-2-methylpyridin-3-yl)methyl)-2-((3-fluoroquinolin-6-yl)methyl)isonicotinamide | 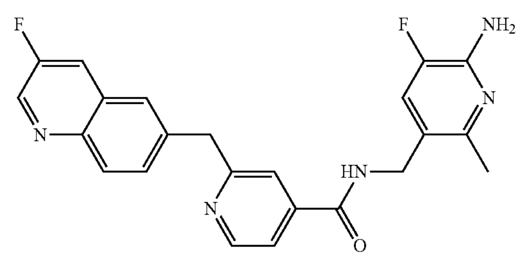 [SMILES: Cc1nc(N)c(F)cc1CNC(=O)c1ccnc(Cc2ccc3ncc(F)cc3c2)c1] |
| N-((6-amino-5-chloro-2-methylpyridin-3-yl)methyl)-2-((3-fluoroquinolin-6-yl)methyl)isonicotinamide | 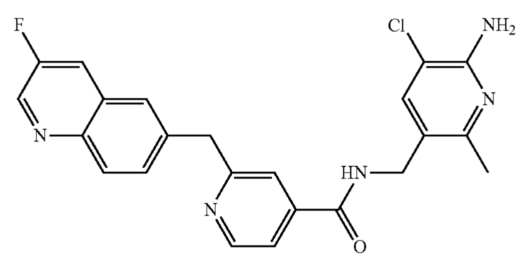 |

TABLE 2-continued

| Name | Structure |
|---|---|
| N-((6-amino-2-methyl-5-(trifluoromethyl)pyridin-3-yl)methyl)-2-((3-fluoroquinolin-6-yl)methyl)isonicotinamide | 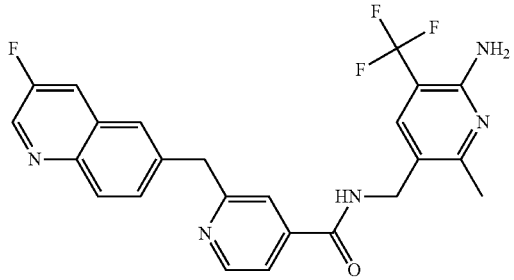 [SMILES: Cc1nc(N)c(C(F)(F)F)cc1CNC(=O)c1ccnc(Cc2ccc3ncc(F)cc3c2)c1] |
| N-((6-amino-5-cyano-2-methylpyridin-3-yl)methyl)-2-((3-fluoroquinolin-6-yl)methyl)isonicotinamide | 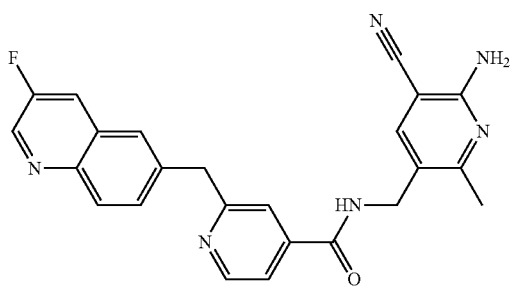 [SMILES: Cc1nc(N)c(C#N)cc1CNC(=O)c1ccnc(Cc2ccc3ncc(F)cc3c2)c1] |
| N-((6-amino-2-cyano-4-methylpyridin-3-yl)methyl)-2-((3-fluoroquinolin-6-yl)methyl)isonicotinamide | 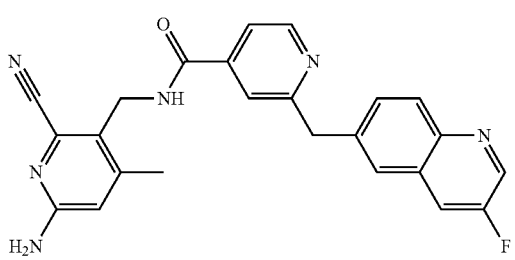 [SMILES: Cc1cc(N)nc(C#N)c1CNC(=O)c1ccnc(Cc2ccc3ncc(F)cc3c2)c1] |
| N-((6-amino-4-methyl-2-(trifluoromethyl)pyridin-3-yl)methyl)-2-((3-fluoroquinolin-6-yl)methyl)isonicotinamide | 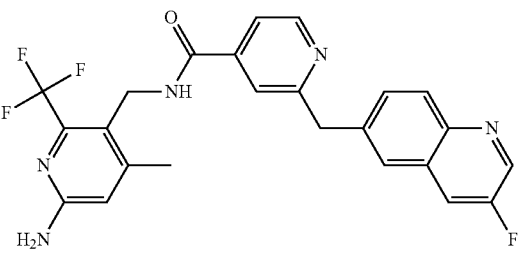 [SMILES: Cc1cc(N)nc(C(F)(F)F)c1CNC(=O)c1ccnc(Cc2ccc3ncc(F)cc3c2)c1] |
| N-((1-aminoimidazo[1,5-a]pyridin-6-yl)methyl)-2-((3-chloroquinolin-6-yl)methyl)isonicotinamide | 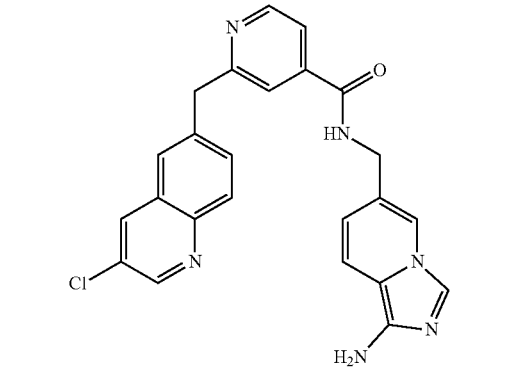 |

| Name | Structure |
|---|---|
| N-((8-aminoimidazo[1,5-a]pyrimidin-3-yl)methyl)-2-((3-chloroquinolin-6-yl)methyl)isonicotinamide | 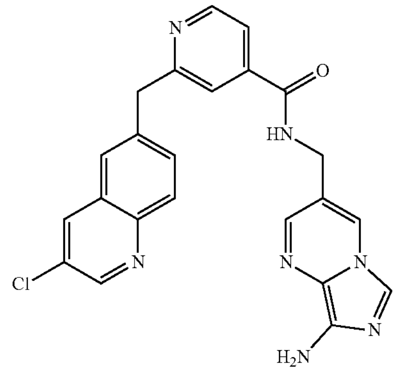 [SMILES: Nc1ncn2cc(CNC(=O)c3ccnc(Cc4ccc5ncc(Cl)cc5c4)c3)ccc12] |
| N-((3-aminoimidazo[1,5-a]pyridin-7-yl)methyl)-2-((3-chloroquinolin-6-yl)methyl)isonicotinamide | 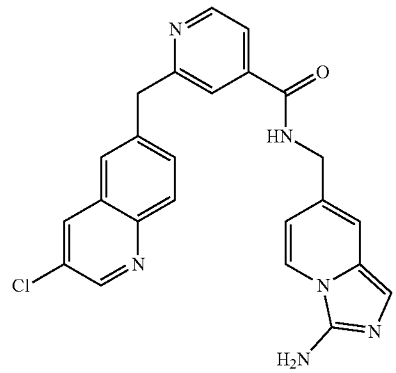 [SMILES: Nc1ncc2cc(CNC(=O)c3ccnc(Cc4ccc5ncc(Cl)cc5c4)c3)ccn12] |
| N-((6-aminoimidazo[1,5-a]pyrimidin-2-yl)methyl)-2-((3-chloroquinolin-6-yl)methyl)isonicotinamide | 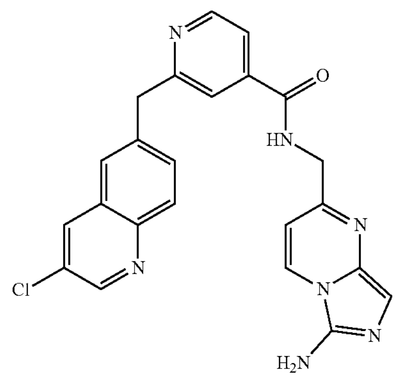 [SMILES: Nc1ncc2nc(CNC(=O)c3ccnc(Cc4ccc5ncc(Cl)cc5c4)c3)ccn12] |
| N-((3-aminoimidazo[1,5-c]pyrimidin-7-yl)methyl)-2-((3-chloroquinolin-6-yl)methyl)isonicotinamide | 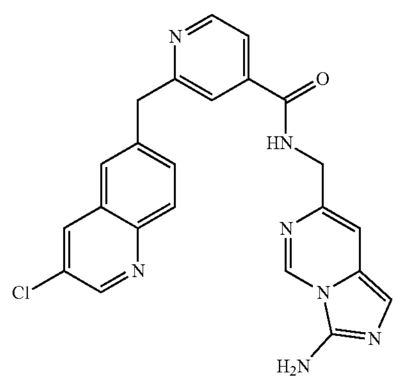 [SMILES: Nc1ncc2cc(CNC(=O)c3ccnc(Cc4ccc5ncc(Cl)cc5c4)c3)ncn12] |

TABLE 2-continued

| Name | Structure |
|---|---|
| N-((7-aminoimidazo[1,5-b]pyridazin-3-yl)methyl)-2-((3-chloroquinolin-6-yl)methyl)isonicotinamide | 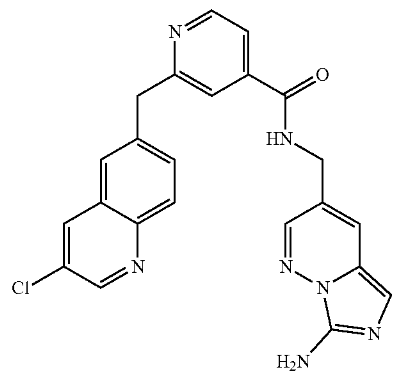 |
| N-((1-amino-3-methylimidazo[1,5-a]pyridin-6-yl)methyl)-2-((3-chloroquinolin-6-yl)methyl)isonicotinamide | 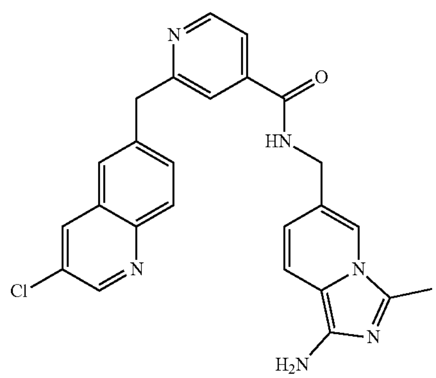 |
| N-((8-amino-6-methylimidazo[1,5-a]pyrimidin-3-yl)methyl)-2-((3-chloroquinolin-6-yl)methyl)isonicotinamide | 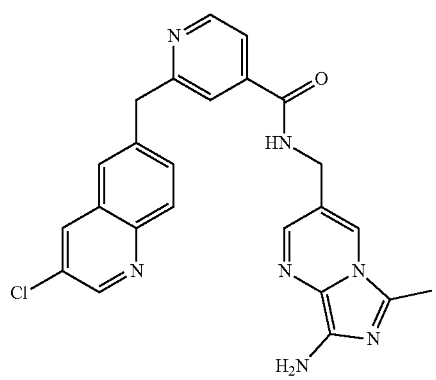 [SMILES: Cc1nc(N)c2ccc(CNC(=O)c3ccnc(Cc4ccc5ncc(Cl)cc5c4)c3)cn12] |
| N-((1-amino-3-methyl-2H-isoindol-5-yl)methyl)-2-((3-chloroquinolin-6-yl)methyl)isonicotinamide | 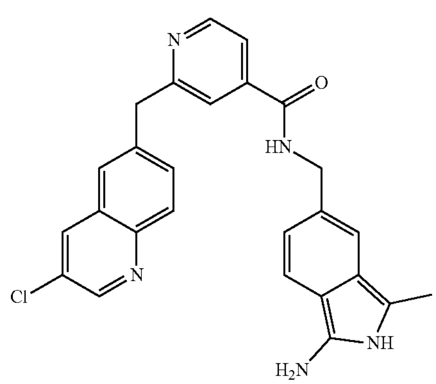 [SMILES: Cc1[nH]c(N)c2ccc(CNC(=O)c3ccnc(Cc4ccc5ncc(Cl)cc5c4)c3)cc12] |

TABLE 2-continued

| Name | Structure |
|---|---|
| N-((3-amino-1-methylimidazo[1,5-a]pyridin-7-yl)methyl)-2-((3-chloroquinolin-6-yl)methyl)isonicotinamide | 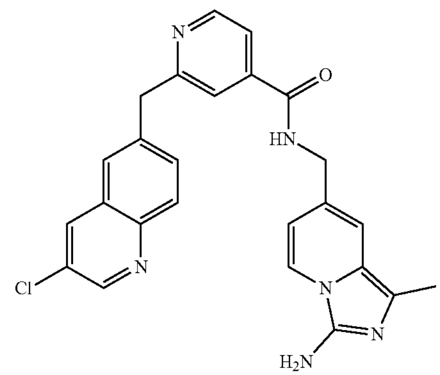 [SMILES: Cc1nc(N)n2ccc(CNC(=O)c3ccnc(Cc4ccc5ncc(Cl)cc5c4)c3)cc12] |
| N-((6-amino-8-methylimidazo[1,5-a]pyrimidin-2-yl)methyl)-2-((3-chloroquinolin-6-yl)methyl)isonicotinamide | 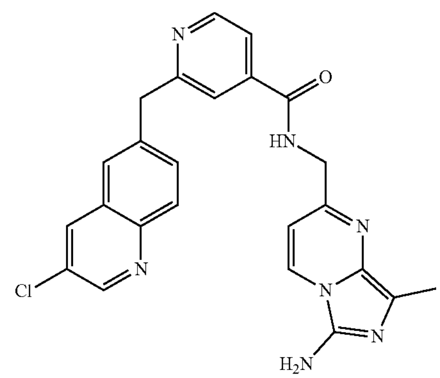 [SMILES: Cc1nc(N)n2ccc(CNC(=O)c3ccnc(Cc4ccc5ncc(Cl)cc5c4)c3)nc12] |
| N-((3-amino-1-methylimidazo[1,5-c]pyrimidin-7-yl)methyl)-2-((3-chloroquinolin-6-yl)methyl)isonicotinamide | 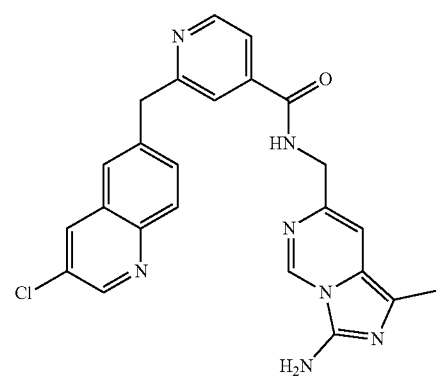 [SMILES: Cc1nc(N)n2cnc(CNC(=O)c3ccnc(Cc4ccc5ncc(Cl)cc5c4)c3)cc12] |
| N-((7-amino-5-methylimidazo[1,5-b]pyridazin-3-yl)methyl)-2-((3-chloroquinolin-6-yl)methyl)isonicotinamide | 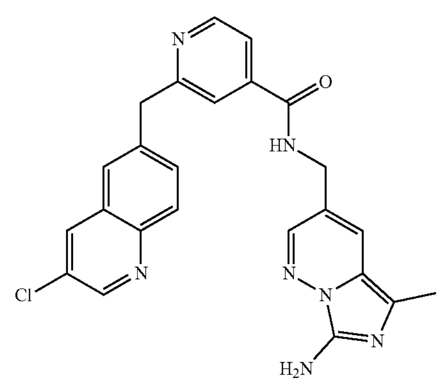 [SMILES: Cc1nc(N)n2ncc(CNC(=O)c3ccnc(Cc4ccc5ncc(Cl)cc5c4)c3)cc12] |

TABLE 2-continued

| Name | Structure |
|---|---|
| N-((2-amino-3-methyl-1H-pyrrolo[2,3-b]pyridin-5-yl)methyl)-2-((3-chloroquinolin-6-yl)methyl)isonicotinamide | 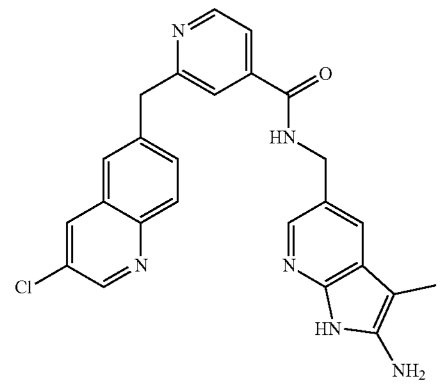 [SMILES: Cc1c(N)[nH]c2ncc(CNC(=O)c3ccnc(Cc4ccc5ncc(Cl)cc5c4)c3)cc12] |
| N-((2-amino-3-chloro-1H-pyrrolo[2,3-b]pyridin-5-yl)methyl)-2-((3-chloroquinolin-6-yl)methyl)isonicotinamide | 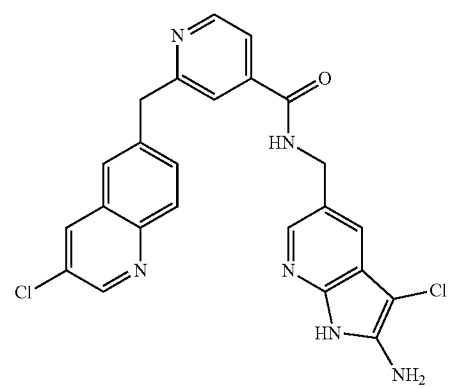 [SMILES: Nc1[nH]c2ncc(CNC(=O)c3ccnc(Cc4ccc5ncc(Cl)cc5c4)c3)cc2c1Cl] |
| N-((6-chloroimidazo[1,2-a]pyridin-3-yl)methyl)-2-((3-chloroquinolin-6-yl)methyl)isonicotinamide | 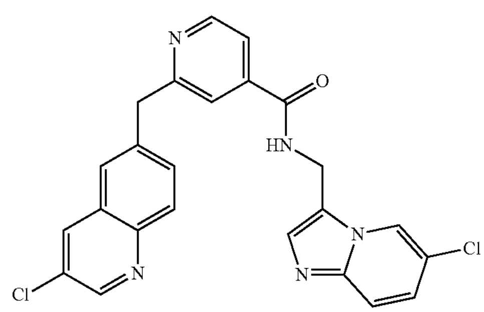 [SMILES: O=C(NCc1cnc2ccc(Cl)cn12)c1ccnc(Cc2ccc3ncc(Cl)cc3c2)c1] |
| N-((3-chloropyrrolo[1,2-a]pyrimidin-6-yl)methyl)-2-((3-chloroquinolin-6-yl)methyl)isonicotinamide | 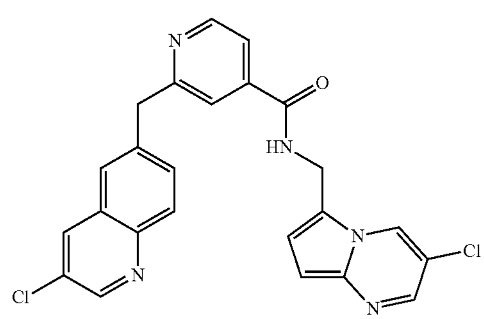 [SMILES: O=C(NCc1ccc2ncc(Cl)cn12)c1ccnc(Cc2ccc3ncc(Cl)cc3c2)c1] |

TABLE 2-continued

| Name | Structure |
|---|---|
| N-((6-chloroimidazo[1,2-a]pyrimidin-3-yl)methyl)-2-((3-chloroquinolin-6-yl)methyl)isonicotinamide | 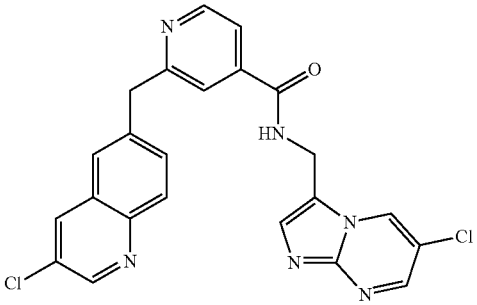 |
| N-((6-chloro-[1,2,4]triazolo[4,3-a]pyridin-3-yl)methyl)-2-((3-chloroquinolin-6-yl)methyl)isonicotinamide | 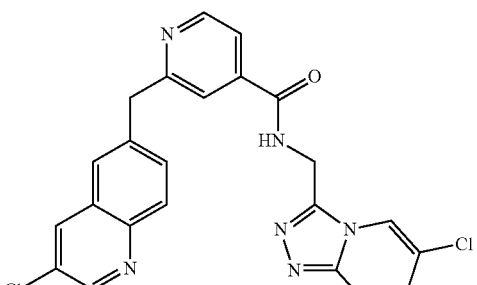 |
| N-((7-chloroimidazo[1,5-a]pyridin-1-yl)methyl)-2-((3-chloroquinolin-6-yl)methyl)isonicotinamide | 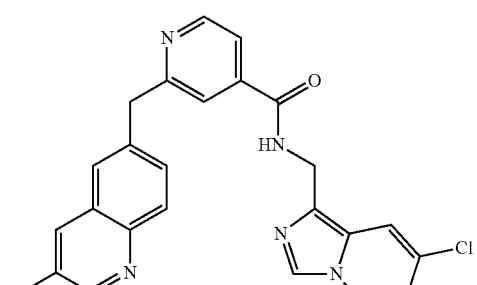 |
| N-((5-chloro-[1,2,3]triazolo[1,5-a]pyridin-3-yl)methyl)-2-((3-chloroquinolin-6-yl)methyl)isonicotinamide | 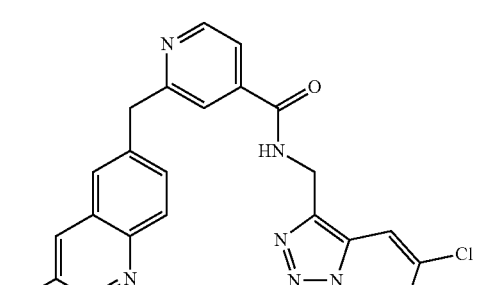 |
| N-((1-aminoimidazo[1,5-a]pyridin-6-yl)methyl)-2-((3-chloroquinolin-6-yl)methyl)isonicotinamide | 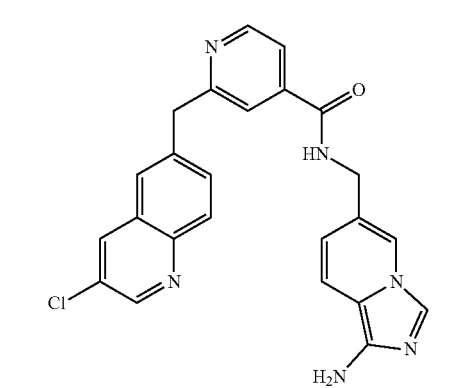 |

TABLE 2-continued

| Name | Structure |
|---|---|
| N-((3-aminoimidazo[1,5-a]pyridin-7-yl)methyl)-2-((3-chloroquinolin-6-yl)methyl)isonicotinamide | 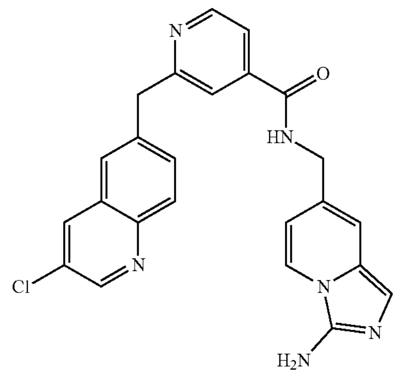 [SMILES: Nc1ncc2cc(CNC(=O)c3ccnc(Cc4ccc5ncc(Cl)cc5c4)c3)ccn12] |
| N-((3-amino-1-methylimidazo[1,5-a]pyridin-7-yl)methyl)-2-((3-chloroquinolin-6-yl)methyl)isonicotinamide | 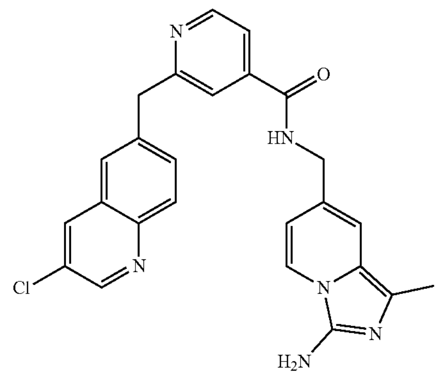 |
| N-((3-chloropyrrolo[1,2-a]pyrimidin-6-yl)methyl)-2-((3-chloroquinolin-6-yl)methyl)isonicotinamide | 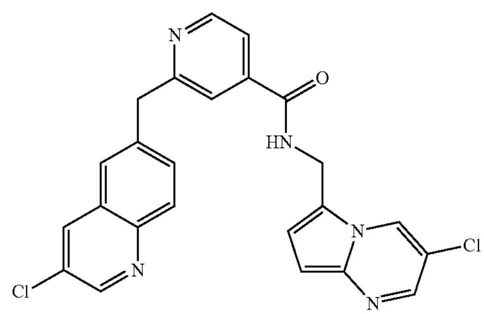 [SMILES: O=C(NCc1ccc2ncc(Cl)cn12)c1ccnc(Cc2ccc3ncc(Cl)cc3c2)c1] |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the kallikrein inhibitory compound described herein is P. H. Stahl & C. G. Wermuth "Handbook of Pharmaceutical Salts", Verlag Helvetica Chimica Acta, Zurich, 2002.

Pharmaceutical Compositions

In certain embodiments, the kallikrein inhibitory compound as described herein is administered as a pure chemical. In other embodiments, the kallikrein inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one kallikrein inhibitory compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (Ia), or a pharmaceutically acceptable salt thereof, and a pharmaceutically acceptable excipient. One embodiment provides a pharmaceutical composition comprising a compound of Formula (II), or a pharmaceutically acceptable salt thereof, and a pharmaceutically acceptable excipient.

In certain embodiments, the kallikrein inhibitory compound as described by Formula (I), (Ia) or (II) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The dose of the composition comprising at least one kallikrein inhibitory compound as described herein differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Kallikrein-Kinin System

Modulation of vascular permeability is important in regulating the passage of small molecules or blood cells between blood vessels and surrounding tissues. Vascular permeability depends upon the physiological states of tissues such as during inflammation, changes in blood pressure, and fluctuations in ion and nutrient gradients. The junctions between the endothelial cells that line blood vessels are the immediate controllers of vascular permeability. The strength of these junctions is tightly regulated by the kinin-kallikrein system of polypeptides and enzymes. Abnormalities in the kinin-kallikrein system lead to a range of pathologies including angioedema, macular edema and brain edema. Angioedema is a potentially fatal blood disorder characterized by swelling that may occur in the face, gastrointestinal tract, extremities, genitals and upper airways. Genetic hereditary angioedema attacks result from the unregulated activation of the kallikrein system with uncontrolled increases in vascular permeability. Currently there is a need for agents that are useful for the treatment of angioedema and for agents that inhibit plasma kallikrein.

The kallikrein-kinin system represents a metabolic cascade that, when activated, triggers the release of vasoactive kinins. The kinin-kallikrein system (KKS) consists of serine proteases involved in the production of kinins, principally bradykinin and Lys-bradykinin (kallidin). The KKS contributes to a variety of physiological processes including inflammation, blood pressure control and coagulation. The activation of this system is particularly important in blood pressure regulation and in inflammatory reactions, due to the ability of bradykinin to elevate vascular permeability and to cause vasodilatation of arteries and veins of the gut, aorta, uterus and urethra. The kinin-kallikrein system, also referred to as the contact system, consists of three serine proenzymes (factor XII (FXII) or Hageman factor, factor IX (FIX), and prekallikrein), and the kinin precursor high molecular weight kinin (HK). Contact activation is triggered by the binding of FXII to a negatively charged surface and involves the formation of α-FXIIa via autocatalysis. Bound α-FXIIa converts prekallikrein into kallikrein. Kallikrein can further convert α-FXIIa to β-FXIIa by an additional cleavage at R334-N335, a positive feedback mechanism that leads to sufficient kallikrein production to drive downstream processes. α-FXIIa consists of a heavy and light chain that are disulphide linked, whereas β-FXIIa lacks the heavy chain and loses its capacity to bind to negatively charged surfaces (Stavrou E, Schmaier A H., *Thrombosis Research*, 2010, 125(3) pp. 210-215). The N-terminal region of FXII (α-FXIIa heavy chain) shows strong homology with tissue-type plasminogen activator (tPA), with the presence of fibronectin type I, epidermal growth factor, and Kringle domains (Ny et al., *Proc Natl Acad Sci USA*, 1984, 81(17) pp. 5355-5359; Cool D E, MacGillivray R T, *The Journal of Biological Chemistry*, 1987, 262(28) pp. 13662-13673). Kallikrein is a trypsin-like serine protease enzyme that cleaves high molecular weight kinin (HK) to produce bradykinin. Bradykinin then binds to the bradykinin 2R receptors (BK2R) on endothelial cells to trigger an increase in vascular permeability.

Protease inhibitors regulate the activation of the contact system. Several known serpins of plasma are C1-inhibitor (C1INH), antithrombin III, α2-macroglobulin, α1-protease inhibitor, and α2-antiplasmin (Kaplan et al., *Advances in Immunology*, 1997 (66) pp. 225-72; Pixley et al., *The Journal of Biological Chemistry*, 1985, 260(3) pp. 1723-9). However, C1INH is the major regulator of the intrinsic system, interfering with the activities of factor XIIa and of kallikrein (Cugno et al., *The Journal of Laboratory and Clinical Medicine*, 1993, 121(1) pp. 38-43). Both C1INH and α2-macroglobulin account for more than 90% of the kallikrein inhibitory activity of plasma. Thus, the FXII-dependent kallikrein-kinin system is tightly regulated by the CINH and when regulation of the FXII-dependent kallikrein-kinin system fails, in a subject, the subject is believed to suffer from hereditary angioedema (HAE) that is characterized by invalidating edema attacks.

Angioedema is a potentially fatal blood disorder characterized by swelling that may occur in the face, gastrointestinal tract, extremities, genitals and upper airways. Angioedema attacks begin in the deeper layers of the skin and mucous membranes with localized blood vessel dilatation and increased permeability. Symptoms of the disease result from the leakage of plasma from blood vessels into surrounding tissues. Genetic hereditary angioedema attacks result from unregulated activation of the kallikrein system with consequent overproduction of bradykinin and uncontrolled increases in vascular permeability. As vascular permeability rises beyond normal, plasma leaks out of the vasculature into surrounding tissue, causing swelling (Mehta D and Malik A B, *Physiol. Rev.*, 86 (1), 279-367, 2006; Sandoval R et al., *J. Physiol.*, 533 (pt 2), 433-45, 2001; Kaplan A P and Greaves M W, Angioedema. *J. Am. Acad. Dermatol.*, 2005).

HAE results from mutations in the genes that code for elements of the coagulation and inflammation pathways. The three forms of HAE are distinguished by their underlying causes and levels of the C1-esterase inhibitor (CINH, serpin peptidase inhibitor, clade G, member 1) protein in the blood, which inhibits the activity of plasma kallikrein. In type I, patients have insufficient levels of functional C1INH, while type II patients have dysfunctional C1INH. While type I and II affect men and women at equal rates, type III, which primarily affects women, results from a mutation in coagulation factor XII (Hageman factor; HAE-FXII). The underlying causes of type I and II HAE are autosomal dominant mutations in C1INH gene (SERPING1 gene) on chromosome 11 (11q12-q13.1).

C1INH accounts for 90% of inhibition of FXIIa and 50% of inhibition of plasma kallikrein (Pixley R A et al., *J. Biol. Chem.*, 260, 1723-9, 1985; Schapira M et al., *Biochemistry*, 20, 2738-43, 1981). In addition, C1INH also inactivates prekallikrein (Colman R W et al, *Blood*, 65, 311-8, 1985). When C1INH levels are normal, its activity blocks FXIIa from converting prekallikrein to kallikrein and blocks kallikrein's conversion to HK, thus preventing the production of bradykinin and the edemic episodes. When CINH levels are low, or levels of dysfunctional C1INH are high, this inhibition fails and the pathogenic process ensues.

In addition to HAE, plasma kallikrein also contributes to non-hereditary angioedema, high altitude cerebral edema, cytotoxic cerebral edema, osmotic cerebral edema, diabetic macular edema (DME), clinically significant macular edema, cystoid macular edema (CME, Gao B B, *Nat Med.*, 13(2), 181-8, 2007), retinal edema, radiation induced edema, lymph edema, glioma-associated edema, allergic edema e.g. airflow obstruction in chronic allergic sinusitis or perennial rhinitis. Other disorders of the plasma kallikrein system include retinopathy and diabetic retinopathy (Liu J and Feener E P, *Biol. Chem.* 394(3), 319-28, 2013), proliferative and non-proliferative retinopathy (Liu J et al, *Invest. Ophthalmol. Vis. Sci.*, 54(2), 2013), CME following cataract extraction, CME induced by cryotherapy, CME induced by uveitis, CME following vascular occlusion (e.g., central retinal vein occlusion, branch retinal vein occlusion or hemiretinal vein occlusion), complications related to cataract surgery in diabetic retinopathy, hypertensive retinopathy (J A Phillips et al., *Hypertension*, 53, 175-181, 2009), retinal trauma, dry and wet age-related macular degeneration (AMD), ischemic reperfusion injuries (C Storoni et al., *JPET*, 381, 849-954, 2006), e.g., in a variety of contexts associated with tissue and/or organ transplantation.

Current treatments for angioedema, and those under development, target different elements in the HAE pathway. Three classes of therapies are currently available: (a) replacement therapy with C1INH concentrates (e.g., Cinryze, Berinert), (b) administration of selective kallikrein inhibitors (e.g., Ecallantide) and (c) bradykinin receptors antagonists (e.g., Firazyr).

Replacement therapies have proven useful for both acute attacks, including emergency situations, such as laryngeal edema (Bork K et al., *Transfusion*, 45, 1774-1784, 2005; Bork K and Barnstedt S E, *Arch. Intern. Med.*, 161, 714-718, 2001) and prophylaxis. Selective C1INH inhibitors inactivate both α-FXIIa and β-FXIIa molecules active early in the HAE pathway that catalyze the production of kallikrein (Muller F and Renne T, *Curr. Opin. Hematol.*, 15, 516-21, 2008; Cugno M et al., *Trends Mol. Med.* 15(2):69-78, 2009). In addition to HAE, plasma kallikrein inhibitors are considered to be useful in the treatment of other edemas such as macular edema and brain edema, and retinopathy, e.g., retinopathy associated with diabetes and/or hypertension. There is evidence that plasma kallikrein inhibitors are also effective in the treatment of edema formation in diseases, e.g., edema formation related to ischemic reperfusion injuries. The bradykinin receptors antagonists prevent bradykinin from activating the vascular permeability pathway and stop the initiation of swelling.

Methods of Treatment

Disclosed herein are methods of treating diseases or disorders wherein the inhibition of plasma kallikrein is indicated. Such diseases and disorders include but are not limited to angioedema, including hereditary and non-hereditary.

In some embodiments, the methods disclosed herein are useful for the treatment of angioedema. In some embodiments, the angioedema is hereditary angioedema (HAE).

One embodiment provides a method of treating angioedema in a patient in need thereof comprising administration of a composition comprising a compound of Formula (I), or a pharmaceutically acceptable salt thereof. Another embodiment provides the method wherein the angioedema is hereditary angioedema.

One embodiment provides a method of treating angioedema in a patient in need thereof comprising administration of a composition comprising a compound of Formula (Ia), or a pharmaceutically acceptable salt thereof. Another embodiment provides the method wherein the angioedema is hereditary angioedema.

One embodiment provides a method of treating angioedema in a patient in need thereof comprising administration of a composition comprising a compound of Formula (II), or a pharmaceutically acceptable salt thereof. Another embodiment provides the method wherein the angioedema is hereditary angioedema.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

The following abbreviations and terms have the indicated meanings throughout:

AcOH=acetic acid
$B_2pin_2$=bis(pinacolato)diboron
Boc=tert-butoxycarbonyl
DCC=dicyclohexylcarbodiimide
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min=minute
mL=milliliter
mmol=millimole
NaOAc=sodium acetate
PE=petroleum ether
Ph=phenyl
Prep=preparative
quant.=quantitative
RP-HPLC=reverse phase-high pressure liquid chromatography
rt or RT=room temperature
THF=tetrahydrofuran
UV=ultraviolet Intermediate 1: Preparation of 5-(aminomethyl)-4,6-dimethylpyridin-2-amine Hydrochloride

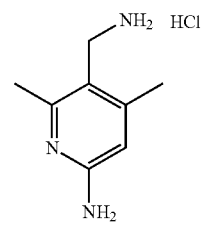

Step 1: Preparation of 5-iodo-4,6-dimethyl-pyridin-2-ylamine

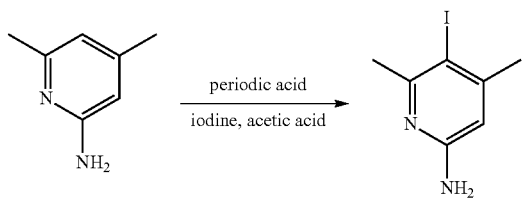

A mixture of 4,6-dimethyl-pyridin-2-ylamine (6 g, 49.1 mmol, 1.0 eq), periodic acid (1.6 g, 7.37 mmol, 0.15 eq) and iodine (6.2 g, 24.5 mmol, 0.5 eq) was added in a mixed solution of acetic acid (120 mL), $H_2O_2$ (6 mL) and $H_2SO_4$ (1 mL) at 80° C. for 4 h, then reaction mixture was poured into 10% aqueous Na₂S₂O₃ solution to quench any unreacted iodine and extracted with ether. The extract was washed with 10% aqueous NaOH, dried over Na₂SO₄ and concentrated, the resulting residue was purified by silica gel chromatography (DCM/MeOH=100/1, v/v) to afford 5-iodo-4,6-dimethyl-pyridin-2-ylamine (10 g, 80%) as a yellow solid.

Step 2: Preparation of 6-amino-2,4-dimethyl-nicotinonitrile

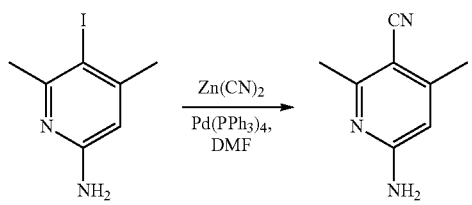

To a solution of 5-iodo-4,6-dimethyl-pyridin-2-ylamine (10 g, 40.3 mmol, 1.0 eq) in DMF (300 mL) was added Zn(CN)₂ (14 g, 120.9 mmol, 3.0 eq) and Pd(PPh₃)₄ (4.65 g, 4.03 mmol, 0.1 eq) carefully. The mixture was stirred at 90° C. overnight under N₂. EA and water was added. The organic layer was separated and concentrated. The resulting residue was purified by silica gel chromatography (DCM/MeOH=100/1, v/v) to afford 6-amino-2,4-dimethyl-nicotinonitrile (5 g, 84%) as a yellow solid.

Step 3: Preparation of tert-butyl (6-amino-2,4-dimethylpyridin-3-yl)methylcarbamate

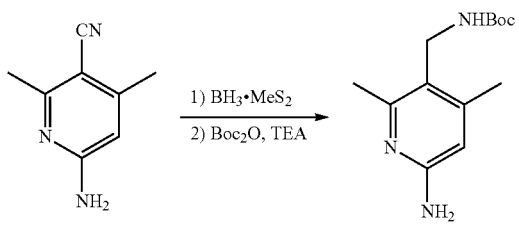

To a solution of 6-amino-2,4-dimethyl-nicotinonitrile (8.1 g, 55 mmol, 1.0 eq) in THF (300 mL) was added BH3.MeS2 (10 M, 55 mL, 550 mmol, 10.0 eq) at rt slowly. The mixture was stirred under reflux for 48 h. After cooling to rt, the mixture was quenched by the addition of concentrated HCl. The mixture was basified to pH 8 with sat. NaHCO₃ solution. To the mixture were added TEA (9.2 mL, 66 mmol, 1.2 eq) and Boc2O (14.4 g, 66 mmol, 1.2 eq). The reaction mixture was stirred at rt for 1 h and then extracted with EA. The combined organic layers were dried over Na2SO4, filtered, and concentrated. The residue was purified on silica gel column (PE/EA=1/1) to give tert-butyl (6-amino-2,4-dimethylpyridin-3-yl)methylcarbamate (4.1 g, 30%) as a yellow solid.

Step 4: Preparation of 5-aminomethyl-4,6-dimethyl-pyridin-2-ylamine Hydrochloride

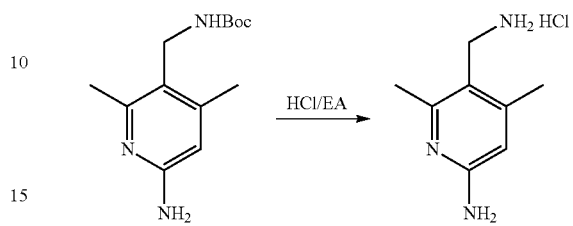

To a solution of (6-amino-2,4-dimethyl-pyridin-3-ylmethyl)-carbamic acid tert-butyl ester (4.1 g, 16.3 mmol, 1.0 eq) in EA (20 mL) was added a solution of HCl in EA (10 M, 50 mL). The mixture was stirred at rt for 1 h, and the precipitate was collected by filtration to afford 5-aminomethyl-4,6-dimethyl-pyridin-2-ylamine hydrochloride (2.0 g, 66%) as a white solid.

Example 1: Preparation of 6-((4-(((3-chloro-6-fluoro-1H-indol-5-yl)methyl)carbamoyl)pyridin-2-yl)methyl)quinoline-2-carboxamide

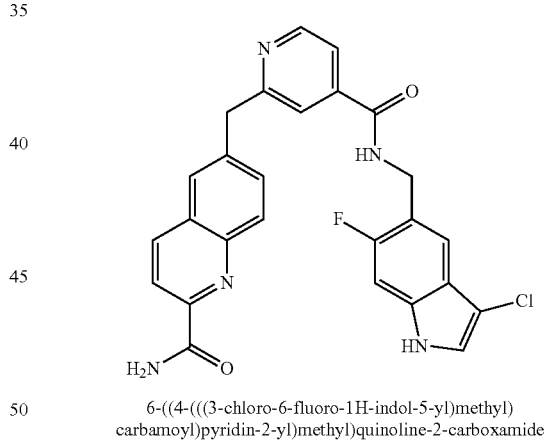

6-((4-(((3-chloro-6-fluoro-1H-indol-5-yl)methyl)carbamoyl)pyridin-2-yl)methyl)quinoline-2-carboxamide

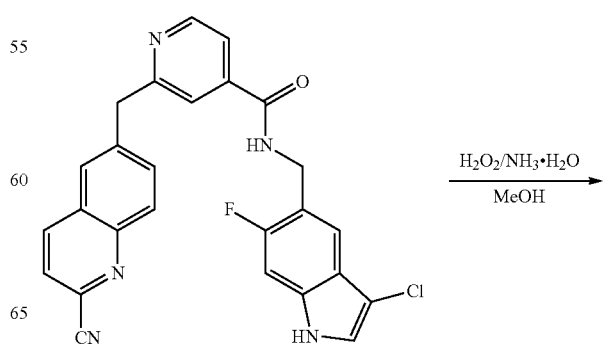

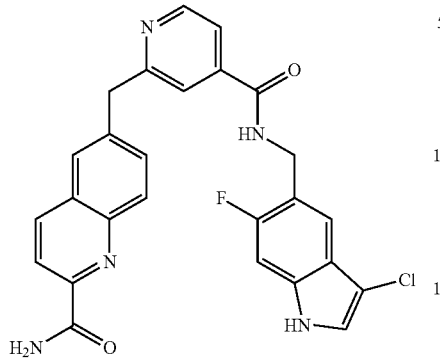

To a solution of N-(3-chloro-6-fluoro-1H-indol-5-ylmethyl)-2-(2-cyano-quinolin-6-ylmethyl)-isonicotinamide (synthesized as described in Example 3) 70 mg, 0.15 mmol, 1.0 eq) in MeOH (1.5 mL)/H₂O (0.6 mL) was added ammonium hydroxide (2.1 mL) and hydrogen peroxide (0.1 mL). The mixture was stirred at 30° C. for 3 h. The mixture was concentrated in vacuum and the residue was purified by prep-HPLC to give 6-((4-(((3-chloro-6-fluoro-1H-indol-5-yl) methyl) carbamoyl)pyridin-2-yl)methyl)quinoline-2-carboxamide (18 mg, 25%) as a white solid. LRMS (M+H⁺) m/z calculated 488.1, found 487.8.

¹H NMR (DMSO-d₆, 400 MHz) δ 11.41 (s, 1H), 9.27 (s, 1H), 8.67 (d, 1H), 8.49 (d, 1H), 8.26 (s, 1H), 8.13 (d, 1H), 8.01 (d, 1H), 7.95 (s, 1H), 7.82 (s, 1H), 7.78 (d, 2H), 7.67 (d, 1H), 7.51 (s, 1H), 7.46 (d, 1H), 7.24 (d, 1H), 4.59 (d, 2H), 4.40 (s, 2H).

Example 2: Preparation of 6-((4-(((6-amino-2,4-dimethylpyridin-3-yl)methyl)carbamoyl)pyridin-2-yl)methyl)quinoline-2-carboxamide

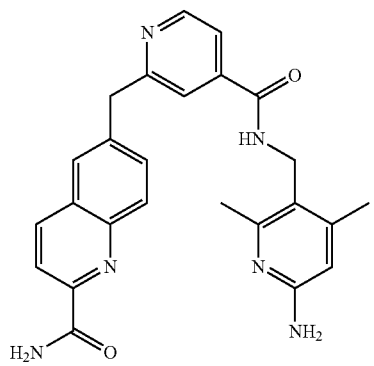

6-((4-(((6-amino-2,4-dimethylpyridin-3-yl)methyl)carbamoyl)pyridin-2-yl)methyl)quinoline-2-carboxmaide

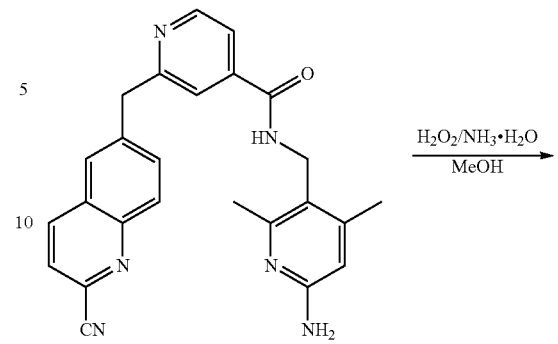

6-((4-(((6-Amino-2,4-dimethylpyridin-3-yl)methyl)carbamoyl)pyridin-2-yl)methyl)quinoline-2-carboxamide (18 mg, 19%) was prepared as described for 6-((4-(((3-chloro-6-fluoro-1H-indol-5-yl)methyl) carbamoyl)pyridin-2-yl)methyl)quinoline-2-carboxamide (Example 1) as a white solid. LRMS (M+H⁺) m/z calculated 441.2, found 440.9.

¹H NMR (DMSO-d₆, 400 MHz) δ 8.66-8.61 (m, 2H), 8.49 (d, 1H), 8.27 (s, 1H), 8.13 (d, 1H), 8.06 (d, 1H), 7.94 (s, 1H), 7.80 (s, 1H), 7.78 (s, 1H), 7.62 (d, 1H), 6.13 (s, 1H), 5.71 (s, 2H), 4.38 (s, 1H), 4.35 (d, 2H), 2.30 (s, 3H), 2.17 (s, 3H).

Example 3: Preparation of N-((1-aminoisoquinolin-6-yl)methyl)-2-((2-cyanoquinolin-6-yl)methyl)isonicotinamide

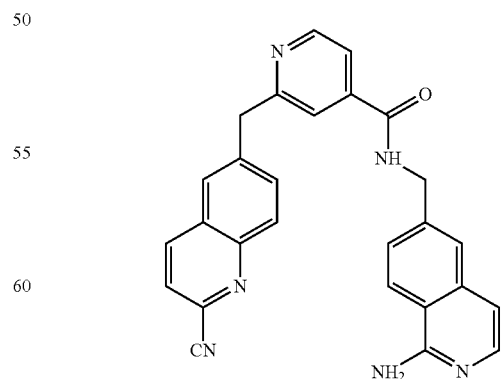

N-((1-aminoisoquinolin-6-yl)methyl)-2-((2-cyanoquinolin-6-yl)methyl)isonicotinamide

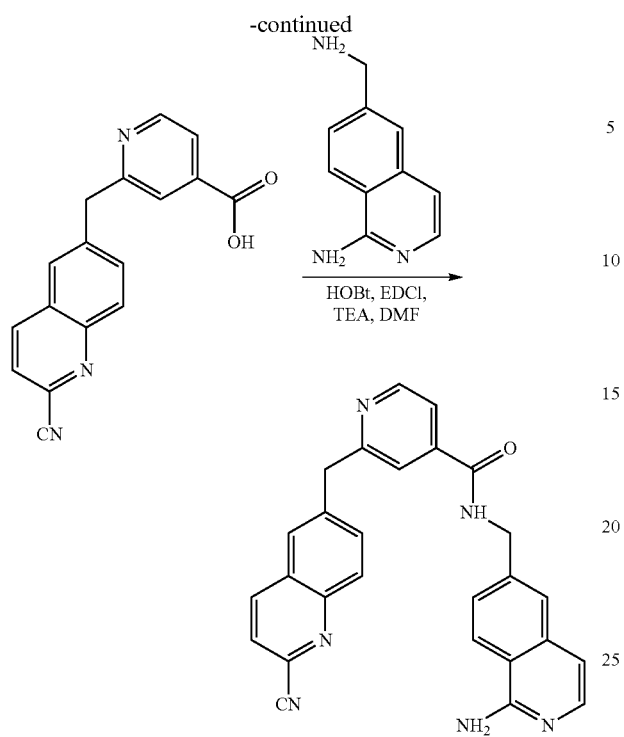

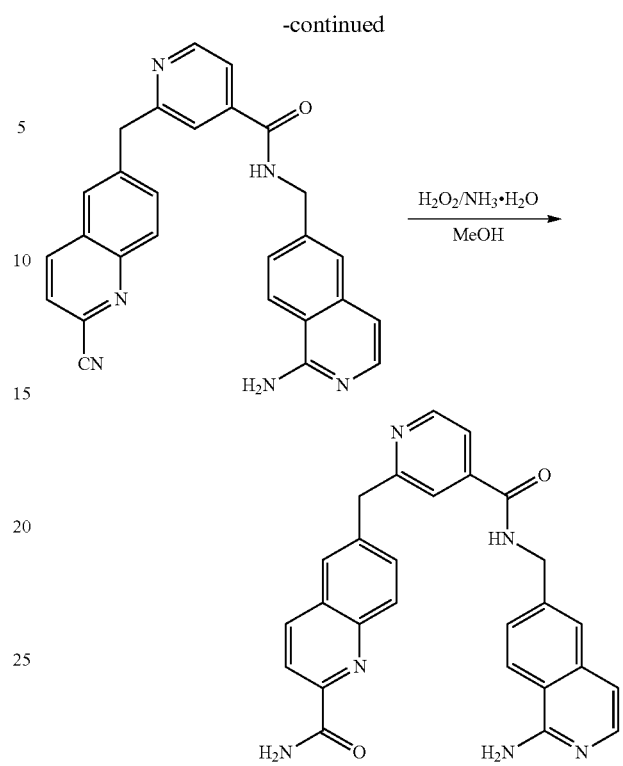

To a solution of 2-(2-cyano-quinolin-6-ylmethyl)-isonicotinic acid (250 mg, 0.86 mmol, 1.0 eq) in DMF (10 mL) was added 6-aminomethyl-isoquinolin-1-ylamine (148.7 mg, 0.86 mmol, 1.0 eq) followed by EDCI (280.7 mg, 1.46 mmol, 1.7 eq), HOBT (174.2 mg, 1.29 mmol, 1.5 eq) and TEA (0.47 mL, 3.4 mmol, 4.0 eq). The reaction mixture was heated to 45° C. kept stirring overnight. Water was added, and the mixture was extracted with DCM. The organic layer was washed with water, dried over $Na_2SO_4$, filtered and concentrated. The residue was purified by prep-HPLC to give N-((1-aminoisoquinolin-6-yl) methyl)-2-((2-cyanoquinolin-6-yl) methyl) isonicotinamide (95 mg, 25%) as a yellow solid. LRMS (M+H$^+$) m/z calculated 445.2, found 445.2.

$^1$H NMR (DMSO-$d_6$, 400 MHz): δ 9.41 (t, 1H), 8.58 (d, 1H), 8.62 (d, 1H), 8.15 (d, 1H), 8.09 (d, 1H), 8.01 (t, 2H), 7.91 (d, 1H), 7.89 (d, 1H), 7.84 (s, 1H), 7.77 (d, 1H), 7.70 (dd, 1H), 7.56 (s, 1H), 7.41 (dd, 1H), 6.85 (d, 1H), 6.76 (s, 2H), 4.62 (d, 2H), 4.44 (s, 2H).

Example 4: Preparation of 6-((4-(((6-amino-2,4-dimethylpyridin-3-yl)methyl)carbamoyl)pyridin-2-yl)methyl)quinoline-2-carboxamide

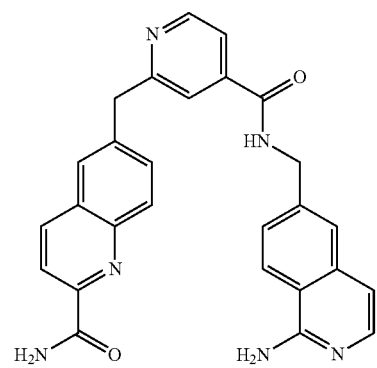

6-((4-(((1-aminoisoquinolin-6-yl)methyl)carbamoyl)pyridin-2-yl)methyl)quinoline-2-carboxamide 6-((4-(((6-Amino-2,4-dimethylpyridin-3-yl)methyl)carbamoyl)pyridin-2-yl)methyl)quinoline-2-carboxamide (17 mg, 23%) was prepared as described for 6-((4-(((3-chloro-6-fluoro-1H-indol-5-yl)methyl)carbamoyl)pyridin-2-yl)methyl) quinoline-2-carboxamide (Example 1) as a white solid. LRMS (M+H$^+$) m/z calculated 463.2, found 462.8.

$^1$H NMR (DMSO-$d_6$, 400 MHz) δ 9.43 (t, 1H), 8.69 (d, 1H), 8.51 (d, 1H), 8.23 (s, 1H), 8.16 (t, 2H), 8.07 (d, 1H), 7.97 (s, 1H), 7.84-7.76 (m, 4H), 7.71 (d, 1H), 7.57 (s, 1H), 7.43 (d, 1H), 6.86 (d, 1H), 6.80 (s, 2H), 4.63 (d, 2H), 4.42 (s, 2H).

Example 5: Preparation of N-((3-chloro-6-fluoro-1H-indol-5-yl)methyl)-2-((3-cyanoquinolin-6-yl)methyl)isonicotinamide

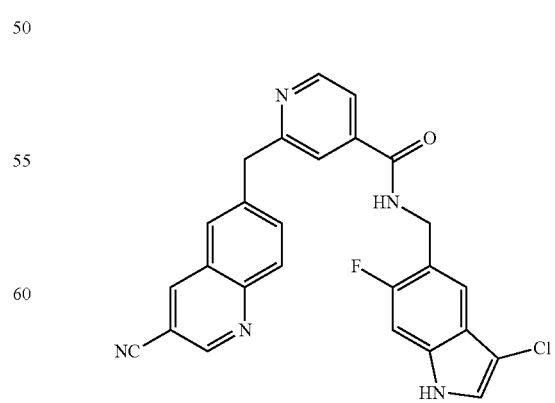

N-((3-chloro-6-fluoro-1H-indol-5-yl)methyl)-2-((3-cyanoquinolin-6-yl)methyl)isonicotinamide

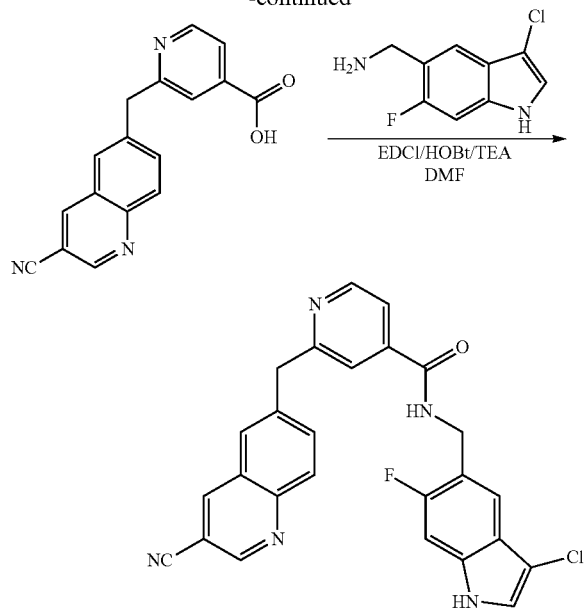

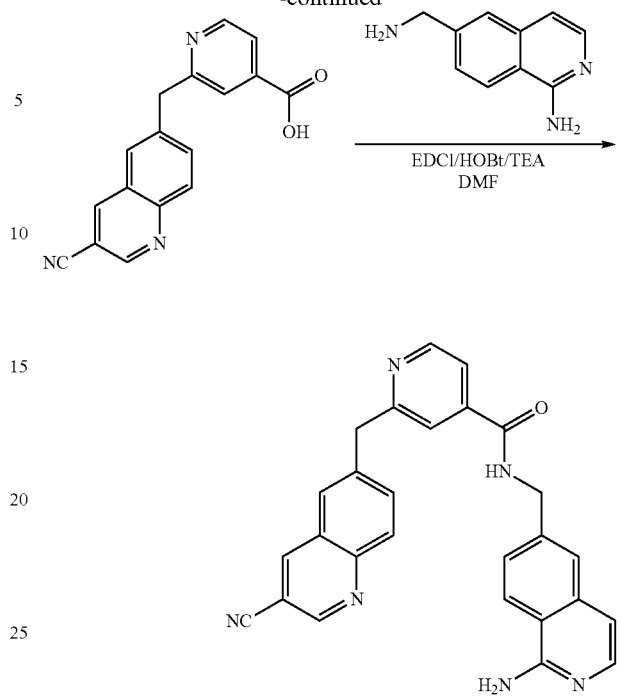

To a solution of 2-(3-isocyano-quinolin-6-ylmethyl)-isonicotinic acid (100 mg, 0.346 mmol, 1.0 eq) and C-(3-chloro-6-fluoro-1H-indol-5-yl)-methylamine (81 mg, 0.346 mmol, 1.0 eq) in DMF (8 mL) were added HOBT (70 mg, 0.519 mmol, 1.5 eq), EDCI (99.5 mg, 0.519 mmol, 1.5 eq) and Et$_3$N (140 mg, 1.384 mmol, 4 eq). The mixture was stirred at rt for 15 h and diluted with water. The organic layer was separated and the aqueous layer was extracted with DCM. The combined extracts were dried and concentrated. The residue was purified by prep-HPLC to give N-((3-chloro-6-fluoro-1H-indol-5-yl)methyl)-2-((3-cyanoquinolin-6-yl)methyl)isonicotinamide (15 mg, 9%) as an off-white solid. LRMS (M+H$^+$) m/z calculated 470.1, found 470.1.

$^1$H NMR (DMSO-d$_6$, 400 MHz) δ 11.37 (s, 1H), 9.23 (t, 1H), 9.07 (d, 1H), 8.99 (s, 1H), 8.61 (d, 1H), 8.02 (d, 1H), 7.93 (s, 1H), 7.88 (d, 1H), 7.77 (s, 1H), 7.62 (d, 1H), 7.47 (d, 1H), 7.40 (d, 1H), 7.18 (d, 1H), 4.54 (d, 2H), 4.37 (s, 2H).

Example 6: Preparation of N-((1-aminoisoquinolin-6-yl)methyl)-2-((3-cyanoquinolin-6-yl)methyl)isonicotinamide N-((1-aminoisoquinolin-6-yl)methyl)-2-((3-cyanoquinolin-6-yl)methyl)isonicotinamide (58 mg, 23.7%) was prepared as described for N-((3-chloro-6-fluoro-1H-indol-5-yl)methyl)-2-((3-cyanoquinolin-6-yl)methyl)isonicotinamide (Example 5) as an off-white solid. LRMS (M+H$^+$) m/z calculated 445.2, found 444.9.

$^1$H NMR (DMSO-d$_6$, 400 MHz) δ 13.20-13.12 (m, 1H), 9.51 (t, 1H), 9.12 (d, 1H), 9.06-8.99 (m, 2H), 8.69 (d, 1H), 8.50 (d, 1H), 8.07 (d, 1H), 7.99 (s, 1H), 7.93 (dd, 1H), 7.83 (s, 2H), 7.73-7.71 (m, 2H), 7.66 (d, 1H), 7.22 (d, 1H), 4.68 (d, 2H), 4.44 (s, 2H).

Example 7: Preparation of N-((6-amino-2,4-dimethylpyridin-3-yl)methyl)-2-((3-cyanoquinolin-6-yl)methyl)isonicotinamide

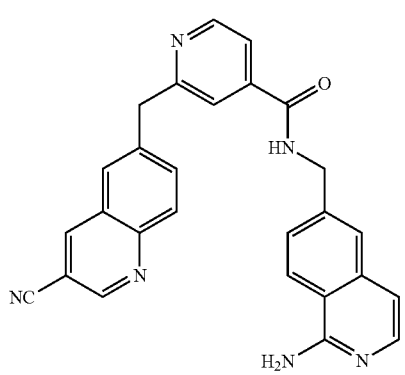

N-((1-aminoisoquinolin-6-yl)methyl)-2-((3-cyanoquinolin-6-yl)methyl)isonicotinamide

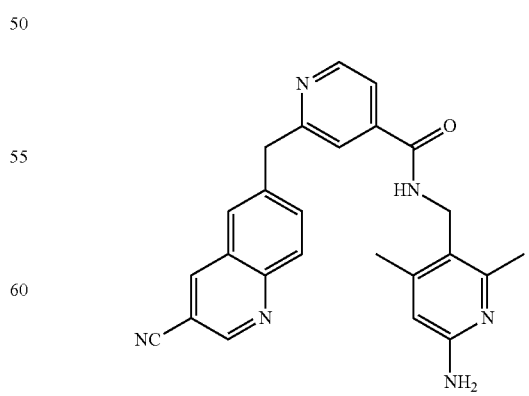

N-((6-amino-2,4-dimethylpyridin-3-yl)methyl)-2-((3-cyanoquinolin-6-yl)methyl)isonicotinamide 257
-continued

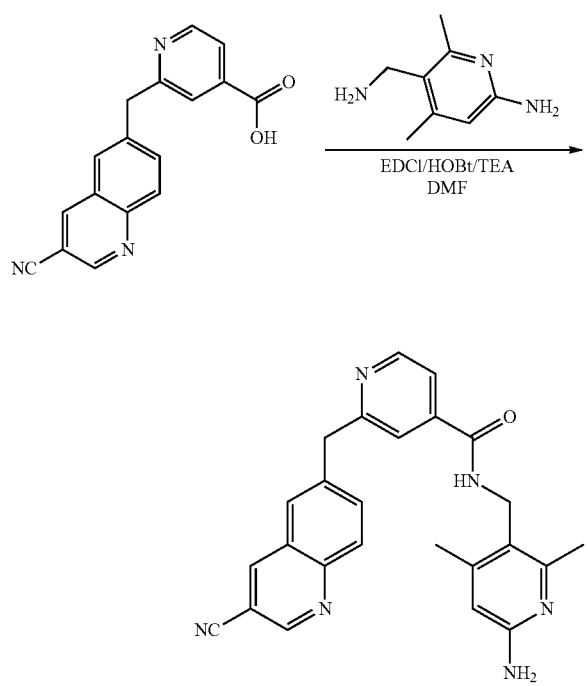

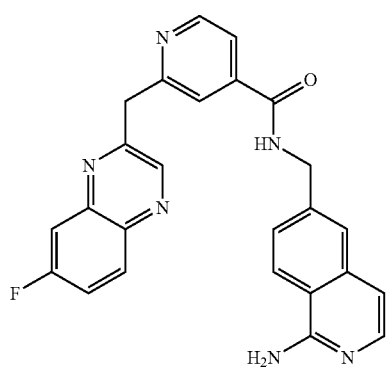

N-((6-amino-2,4-dimethylpyridin-3-yl)methyl)-2-((3-cyanoquinolin-6-yl)methyl)isonicotinamide (45 mg, 32.3%) was prepared as described for N-((3-chloro-6-fluoro-1H-indol-5-yl)methyl)-2-((3-cyanoquinolin-6-yl)methyl)isonicotinamide (Example 5) as a off white solid. LRMS (M+H$^+$) m/z calculated 423.2, found 422.9. $^1$H NMR (DMSO-d$_6$, 300 MHz) δ 9.12 (s, 1H), 9.03 (s, 1H), 8.69-8.65 (m, 1H), 8.61-8.59 (m, 1H), 8.05 (dd, 1H), 7.96-7.89 (m, 2H), 7.77 (s, 1H), 7.61-7.60 (m, 1H), 6.16 (d, 1H), 5.91-5.87 (m, 2H), 4.38-4.33 (m, 4H), 2.31 (s, 3H), 2.18 (s, 3H).

Example 8: Preparation of N-((1-aminoisoquinolin-6-yl)methyl)-2-((7-fluoroquinoxalin-2-yl)methyl)isonicotinamide N-((1-aminoisoquinolin-6-yl)methyl)-2-((7-fluoroquinoxalin-2-yl)methyl)isonicotinamide

258

Step 1: Preparation of 7-fluoro-3,4-dihydro-1H-quinoxalin-2-one

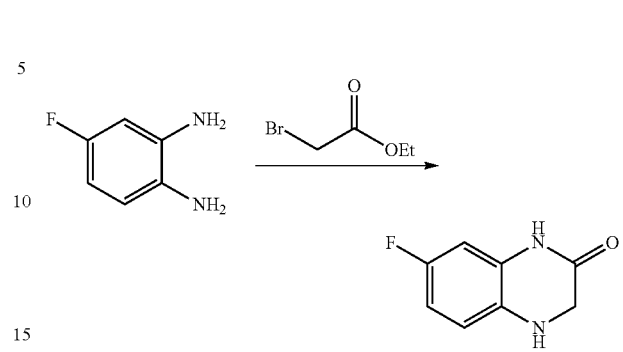

To a solution of 4-fluoro-benzene-1,2-diamine (20 g, 0.159 mol, 1 eq) in DMF (150 mL) was added Et$_3$N (44 mL, 0.318 mol, 2 eq), followed by ethyl 2-bromoacetate (29 g, 0.175 mol, 1.1 eq). The reaction mixture was stirred at rt for 16 h, then at 80° C. for 3 h. The DMF was evaporated by distillation. The reaction mixture was partitioned between H$_2$O and EtOAc. The organic layer was washed with sat. NaHCO$_3$, brine, and dried over Na$_2$SO$_4$. The solvent was evaporated under reduced pressure. The desired product was precipitated in a mixture of CH$_2$Cl$_2$ and hexane (1 to 1 ratio). Filtered and the filtrate was concentrated to dryness to afford 7-fluoro-3,4-dihydro-1H-quinoxalin-2-one (22 g, 83%).

Step 2: Preparation of 7-fluoro-quinoxalin-2-ol

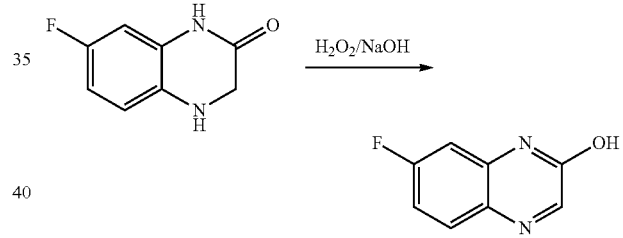

A mixture of 7-fluoro-3,4-dihydro-iH-quinoxalin-2-one (4.0 g, 24 mmol, 1.0 eq), sodium hydroxide (1.93 g, 48 mmol, 2.0 eq) and of 3 percent hydrogen peroxide solution (50 mL) was refluxed for 2 h, then it was acidified by slow addition of acetic acid. The resulting mixture is cooled to room temperature. The precipitated solid is collected by filtration, washed with ice-water, and dried in vacuum. The resulting residue was purified by column chromatography (DCM/MeOH=50:1, v/v) to afford 7-fluoro-quinoxalin-2-ol (2.60 g, 69%).

Step 3: Preparation of 2-chloro-7-fluoro-quinoxaline

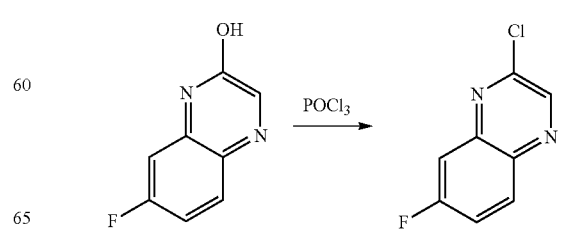

To the suspension of 7-fluoro-quinoxalin-2-ol (2 g, 12 mmol, 1 eq) in neat phosphorus oxychloride (10 mL) was added DMF (2 drops). The mixture was heated to 100° C. for 3 h. Then it was cooled to room temperature. Phosphorus oxychloride was removed in vacuum, and the residue was dissolved into EtOAc and dropped into ice water with stirring. The mixture was extracted with EtOAc for three times, the combined organic layers were washed with saturated NaHCO$_3$ solution. The organic layer was concentrated to afford 2-chloro-7-fluoro-quinoxaline (1.7 g, 77%).

Step 4: Preparation of 7-fluoro-2-(trimethylstannyl)quinoxaline

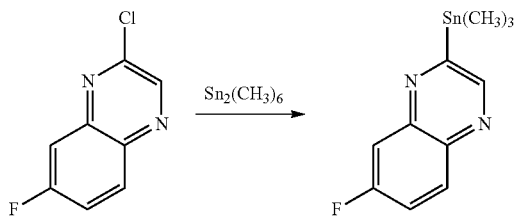

To a solution of 2-chloro-7-fluoro-quinoxaline (2.0 g, 11 mmol, 1 eq) in toluene (50 mL) was added hexamethylditin (7.2 g, 22 mmol, 2 eq) and Pd(PPh$_3$)$_4$ (635 mg, 0.55 mmol, 0.05 eq). The mixture was stirred at 90° C. for 12 h under nitrogen. The reaction mixture was concentrated, and the resulting residue was used in next step without further purification.

Step 5: Preparation of 2-(7-fluoro-quinoxalin-2-ylmethyl)-isonicotinic Acid Methyl Ester

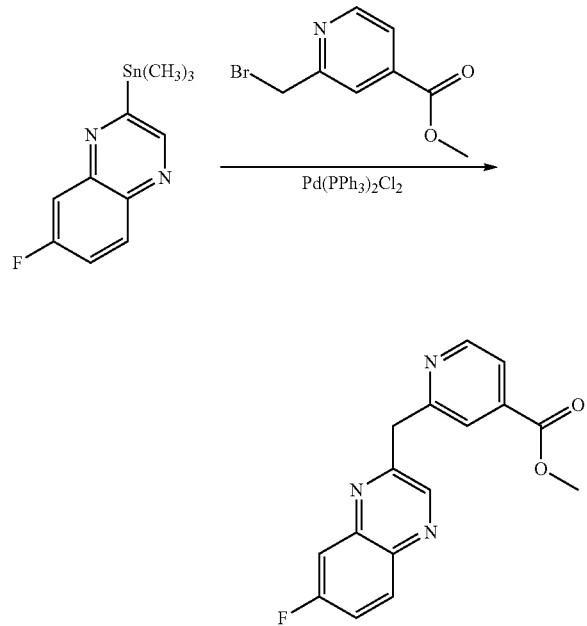

To a solution of 7-fluoro-2-trimethylstannanyl-quinoxaline (3.43 g, 11 mmol, 1.0 eq) in dioxane (60 mL) was added 2-bromomethyl-isonicotinic acid methyl ester (2.5 g, 11 mmol, 1.0 eq) and Pd(PPh$_3$)$_2$Cl$_2$ (386 mg, 0.55 mmol, 0.05 eq). The mixture was stirred at 90° C. for 3 h under nitrogen atmosphere, concentrated and purified by silica gel chromatography (PE/EA=3/1, v/v) to afford 2-(7-fluoro-quinoxalin-2-ylmethyl)-isonicotinic acid methyl ester (300 mg, 9% for 2 steps) as an off-white solid.

Step 6: Preparation of N-((1-aminoisoquinolin-6-yl)methyl)-2-((7-fluoroquinoxalin-2-yl) methyl) isonicotinamide

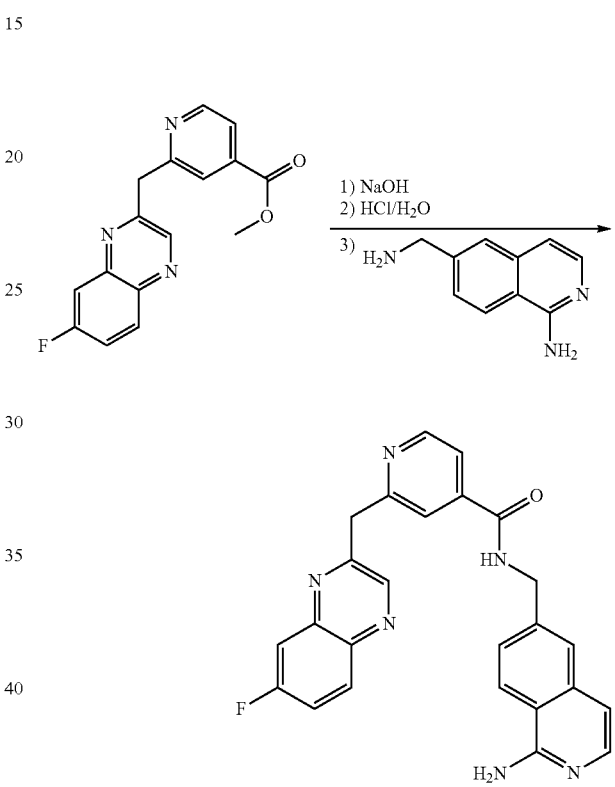

To a solution of 2-(7-fluoro-quinoxalin-2-ylmethyl)-isonicotinic acid methyl ester (70 mg, 0.235 mmol, 1.0 eq) in THF (10 mL)/H$_2$O (2 mL) was added NaOH (11.3 mg, 0.282 mmol, 1.2 eq). The mixture was stirred at 45° C. for 2 h and was acidified to pH 5-6 with 1 N HCl solution. The mixture was concentrated in vacuum, and the resulting residue was used in the next step without further purification. To a solution of this crude product and 6-aminomethyl-isoquinolin-1-ylamine (55.2 mg, 0.235 mmol, 1.0 eq) in DMF (8 mL) were added HOBT (47.6 mg, 0.352 mmol, 1.5 eq), EDCI (67.5 mg, 0.352 mmol, 1.5 eq) and Et$_3$N (95.1 mg, 0.940 mmol, 4 eq). The mixture was stirred at 45° C. for 15 h, and then concentrated. The resulting residue was purified by prep-HPLC to give N-((1-aminoisoquinolin-6-yl) methyl)-2-((7-fluoroquinoxalin-2-yl) methyl) isonicotinamide (15 mg, 14.6%) as a yellow solid. LRMS (M+H$^+$) m/z calculated 439.2, found 438.8. $^1$H NMR (CD$_3$OD, 400 MHz) δ 8.79 (s, 1H), 8.50 (d, 1H), 7.95-7.89 (m, 2H), 7.77 (s, 1H), 7.58-7.47 (m, 5H), 7.36 (d, 1H), 6.79 (d, 1H), 4.60 (s, 2H), 4.51 (s, 2H)

Example 9: Preparation of 2-[2-(acetylamino-methyl)-quinolin-6-ylmethyl]-N-(3-chloro-6-fluoro-1H-indol-5-ylmethyl)-isonicotinamide

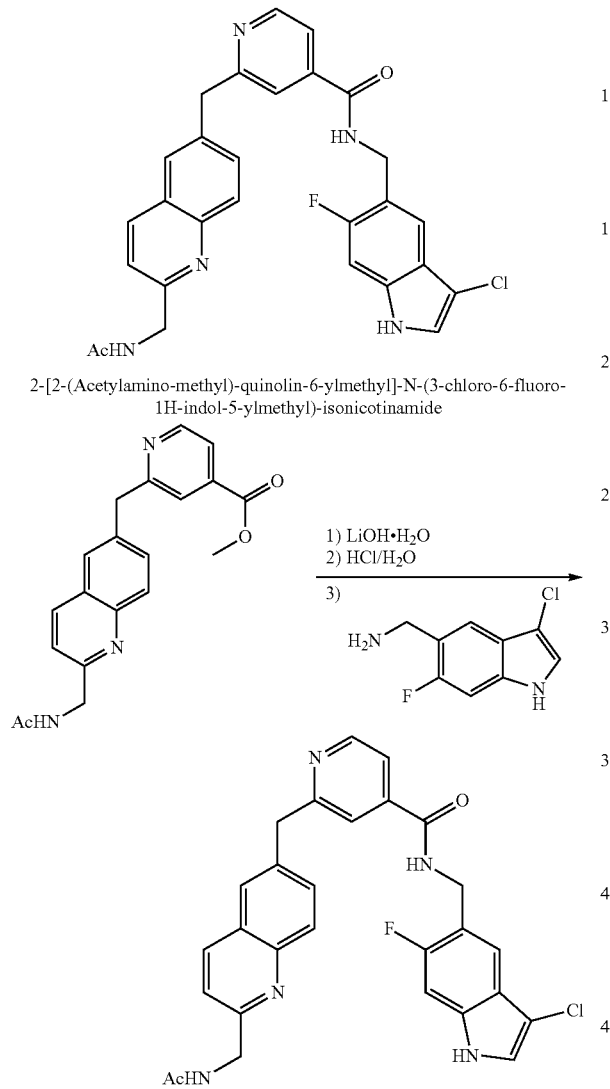

2-[2-(Acetylamino-methyl)-quinolin-6-ylmethyl]-N-(3-chloro-6-fluoro-1H-indol-5-ylmethyl)-isonicotinamide To a solution of 2-[2-(acetylamino-methyl)-quinolin-6-ylmethyl]-isonicotinic acid methyl ester (100 mg, 0.287 mmol, 1.0 eq) in THF (10 mL)/H$_2$O (2 mL) was added LiOH.H$_2$O (14.4 mg, 0.344 mmol, 1.2 eq). The mixture was stirred at 45° C. for 2 h, and was acidified to pH 5-6 with 1 N HCl solution. The mixture was concentrated in vacuum, and the residue was directly used without further purification. To a solution of this crude product and C-(3-chloro-6-fluoro-1H-indol-5-yl)-methylamine (67.3 mg, 0.287 mmol, 1.0 eq) in DMF (8 mL) were added HOBT (58 mg, 0.430 mmol, 1.5 eq), EDCI (82.4 mg, 0.430 mmol, 1.5 eq) and Et$_3$N (116 mg, 1.146 mmol, 4 eq). The mixture was stirred at 45° C. for 15 h then concentrated. The resulting residue was purified by prep-HPLC to give 2-[2-(acetylamino-methyl)-quinolin-6-ylmethyl]-N-(3-chloro-6-fluoro-1H-indol-5-ylmethyl)-isonicotinamide (15 mg, 10.2%) as a yellow solid. LRMS (M+H$^+$) m/z calculated 516.2, found 515.8. $^1$H NMR (DMSO-d$_6$, 400 MHz) δ 11.43 (s, 1H), 9.30 (t, 1H), 9.01 (s, 1H), 8.69-8.64 (m, 2H), 8.48 (d, 1H), 7.98 (d, 1H), 7.93 (s, 1H), 7.84-7.78 (m, 2H), 7.71 (d, 1H), 7.56-7.51 (m, 3H), 7.45 (d, 1H), 7.23 (d, 1H), 4.60-4.56 (m, 4H), 4.41 (s, 2H), 1.94 (s, 3H).

Example 10: Preparation of 2-[2-(acetylamino-methyl)-quinolin-6-ylmethyl]-N-(1-amino-isoquinolin-6-ylmethyl)-isonicotinamide

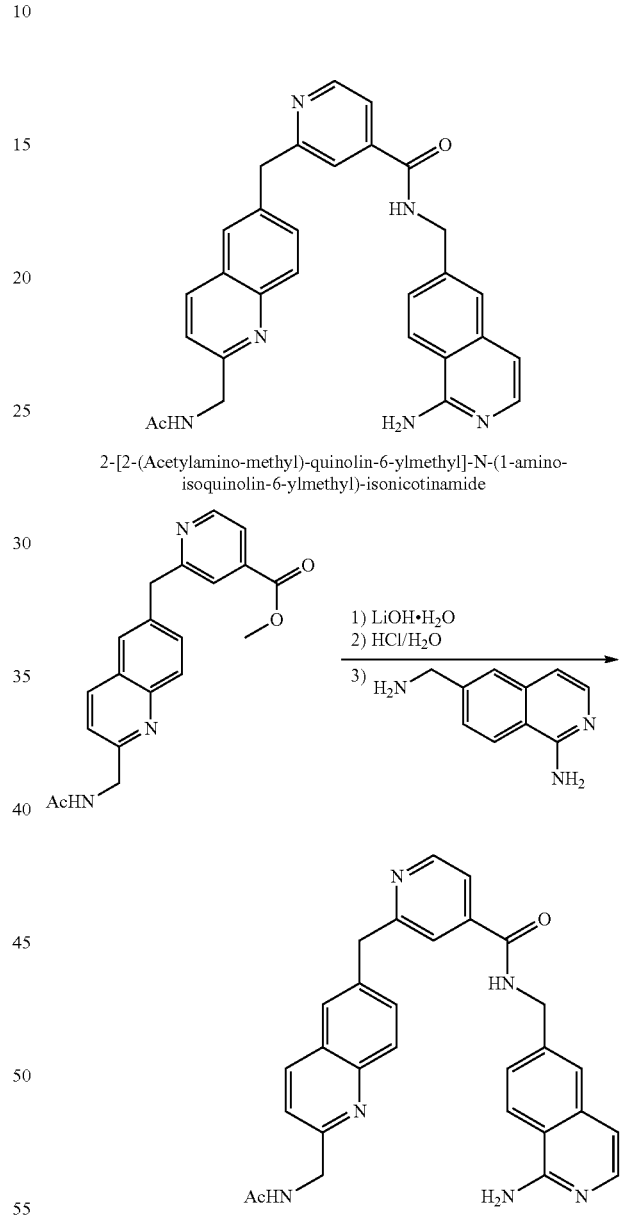

2-[2-(Acetylamino-methyl)-quinolin-6-ylmethyl]-N-(1-amino-isoquinolin-6-ylmethyl)-isonicotinamide 2-[2-(Acetylamino-methyl)-quinolin-6-ylmethyl]-N-(1-amino-isoquinolin-6-ylmethyl)-isonicotinamide (15 mg, 10.7%) was prepared as described for 2-[2-(acetylamino-methyl)-quinolin-6-ylmethyl]-N-(3-chloro-6-fluoro-1H-indol-5-ylmethyl)-isonicotinamide (Example 9) as an off white solid. LRMS (M+H$^+$) m/z calculated 491.2, found 490.9. $^1$H NMR (DMSO-d$_6$, 400 MHz) δ 8.97 (d, 1H), 8.76 (d, 1H), 8.41 (d, 1H), 8.24-8.20 (m, 2H), 8.08 (dd, 1H), 7.99 (s, 1H), 7.94-7.87 (m, 3H), 7.78 (dd, 1H), 7.57 (d, 1H), 7.21 (d, 1H), 4.88 (s, 2H), 4.82 (s, 2H), 4.63 (s, 2H), 2.13 (s, 3H).

Example 11: Preparation of 2-[2-(acetylamino-methyl)-quinolin-6-ylmethyl]-N-(6-amino-2,4-dimethyl-pyridin-3-ylmethyl)-isonicotinamide

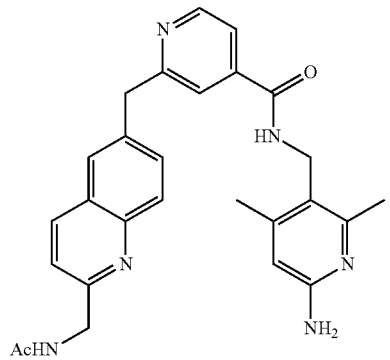

2-[2-(Acetylamino-methyl)-quinolin-6-ylmethyl]-N-(6-amino-2,4-dimethyl-pyridin-3-ylmethyl)-isonicotinamide

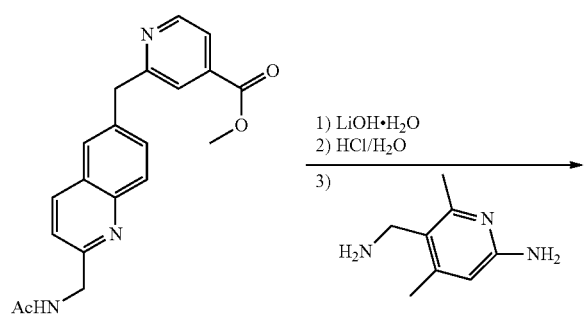

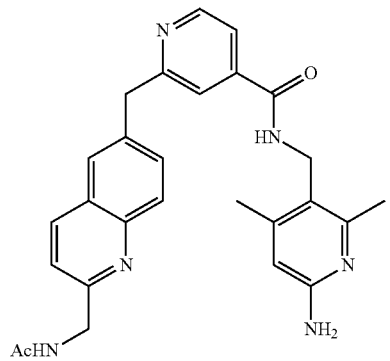

2-[2-(Acetylamino-methyl)-quinolin-6-ylmethyl]-N-(6-amino-2,4-dimethyl-pyridin-3-ylmethyl)-isonicotinamide (10 mg, 7.46%) was prepared as described for 2-[2-(acetylamino-methyl)-quinolin-6-ylmethyl]-N-(3-chloro-6-fluoro-1H-indol-5-ylmethyl)-isonicotinamide (Example 9) as a yellow solid. LRMS (M+H$^+$) m/z calculated 469.2, found 469.2.

$^1$H NMR (DMSO-d$_6$, 400 MHz) δ 8.48 (m, 1H), 8.13 (d, 1H), 7.82 (d, 1H), 7.66 (s, 1H), 7.59-7.54 (m, 2H), 7.48 (dd, 1H), 7.35 (d, 1H), 6.18 (s, 1H), 4.53 (s, 2H), 4.37 (s, 2H), 4.26 (s, 2H), 2.27 (s, 3H), 2.13 (s, 3H), 1.96 (s, 3H).

Example 12: Preparation of N-((3-chloro-6-fluoro-1H-indol-5-yl)methyl)-2-((6-(methylsulfonyl)quinolin-3-yl)methyl)isonicotinamide

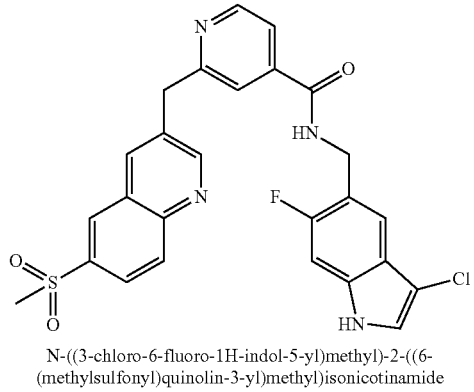 [SMILES: CS(=O)(=O)c1ccc2ncc(Cc3cc(C(=O)NCc4cc5c(Cl)c[nH]c5cc4F)ccn3)cc2c1]

N-((3-chloro-6-fluoro-1H-indol-5-yl)methyl)-2-((6-(methylsulfonyl)quinolin-3-yl)methyl)isonicotinamide

Step 1: Preparation of 6-methanesulfonyl-quinoline

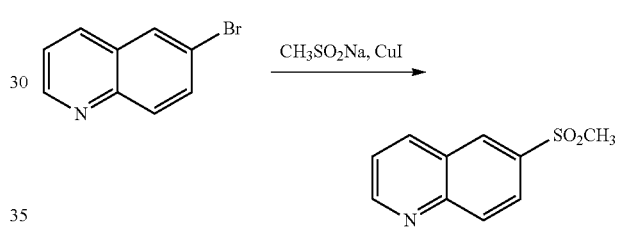

A mixture of 6-bromo-quinoline (20.7 g, 0.1 mol, 1 eq), sodium methanesulphinate (12.2 g, 0.12 mol, 1.2 eq), copper iodide (1.9 g, 0.01 mol, 0.1 eq), L-proline sodium salt (2.74 g, 0.02 mol, 0.2 eq) in 200 mL of DMSO was heated to 110° C. under nitrogen for 15 h. The cooled mixture was partitioned between ethyl acetate and water. The organic layer was separated, and the aqueous layer was extracted with ethyl acetate twice. The combined organic layers were washed with brine, dried over MgSO$_4$, and concentrated in vacuum. The resulting residue was purified by silica gel column (EA/PE=1/2, v/v) to give 6-methanesulfonyl-quinoline (13.5 g, 65%) as a yellow solid.

Step 2: Preparation of 3-bromo-6-methanesulfonyl-quinoline

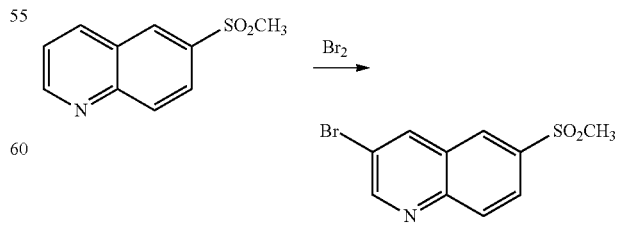

To a mixture of 6-methanesulfonyl-quinoline (6.0 g, 29.0 mmol, 1 eq) and pyridine (4.7 mL, 58.0 mmol, 2 eq) in CCl$_4$ (250 mL) was added Br$_2$ (0.9 mL, 34.8 mmol, 1.2 eq) drop wise. The mixture was heated to reflux for 2 h before being cooled to room temperature. The liquid in the flask was decanted and washed with saturated aqueous NaHCO₃ and water. The dark solid on the bottom of the flask was partitioned between aqueous NaHCO₃ and dichloromethane. The combined organic layers were washed with water again and dried before being evaporated to dryness in vacuum. The crude product was purified by silica gel column (EA/PE=1/10, v/v) to give 3-bromo-6-methanesulfonyl-quinoline (6.2 g, 75%) as a yellow solid.

Step 3: Preparation of 6-methanesulfonyl-3-vinyl-quinoline

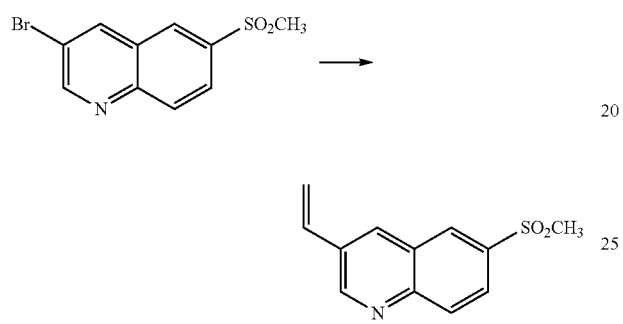

To a solution of 3-bromo-6-methanesulfonyl-quinoline (2.9 g, 10.2 mmol, 1 eq) and vinylboronic acid pinacol cyclic ester (2.1 g, 12.2 mmol, 1.2 eq) in dioxane (50 mL) and water (10 mL) was added Na₂CO₃ (3.24 g, 30.6 mmol, 3 eq) and Pd(dppf)Cl₂·CH₂Cl₂ (833 mg, 1.02 mmol, 0.1 eq). The mixture was stirred at 95° C. for 3 h. After cooling to rt, the solvent was removed in vacuum. The residue was purified by flash chromatography on a silica gel column (EA/PE=1/10, v/v) to afford 6-methanesulfonyl-3-vinyl-quinoline as a yellow solid (2.1 g, 88%).

Step 4: Preparation of 6-methanesulfonyl-quinoline-3-carbaldehyde

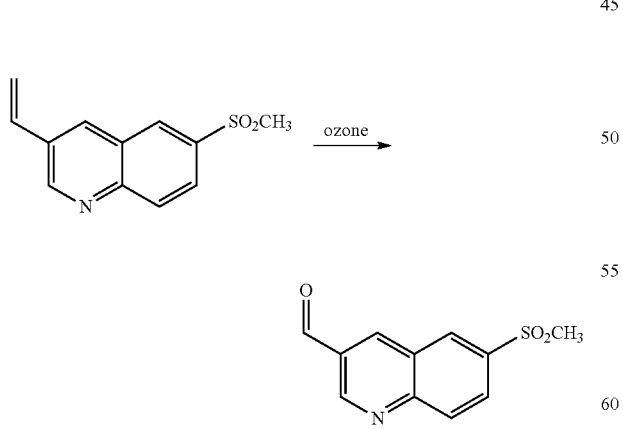

A 3-neck round-bottom flask was charged with 6-methanesulfonyl-3-vinyl-quinoline (2.1 g, 9.0 mmol, 1 eq) and dichloromethane (40 mL) and cooled to −78° C. Ozone was bubbled into the reaction mixture until blue color persisted (30 min). The reaction mixture was sparged with oxygen until blue color faded and quenched with methyl sulfide (6 mL). The mixture was stirred at rt for 1 h, then concentrated and purified by flash column chromatography (EA/PE=1/8, v/v) to give 6-methanesulfonyl-quinoline-3-carbaldehyde (1.0 g, 47%) as a white solid.

Step 5: Preparation of (6-methanesulfonyl-quinolin-3-yl)-methanol

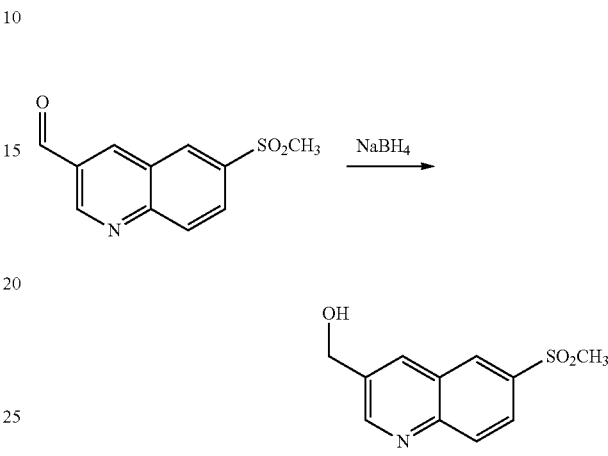

To a solution of 6-methanesulfonyl-quinoline-3-carbaldehyde (1.0 g, 4.25 mmol, 1 eq) in dry MeOH (20 mL) was added NaBH₄ (162 mg, 4.25 mmol, 1 eq) at 0° C. The mixture was stirred at the same temperature for 10 min. The reaction was quenched by the addition of water. The mixture was extracted with EA. The combined extracts were dried and concentrated. The residue was purified by chromatography on a silica gel column (EA/PE=1/2, v/v) to afford (6-methanesulfonyl-quinolin-3-yl)-methanol as a yellow solid (290 mg, 29%).

Step 6: Preparation of 3-chloromethyl-6-methanesulfonyl-quinoline

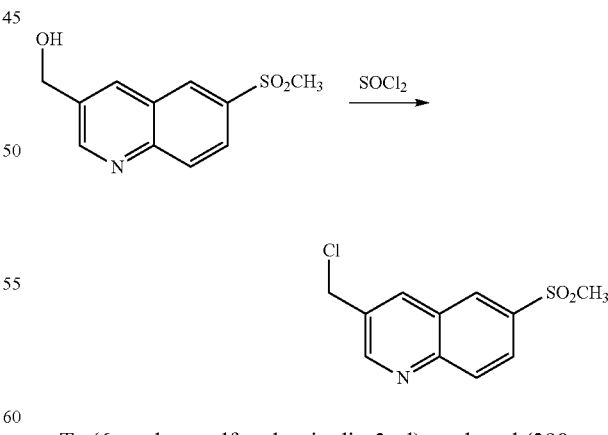

To (6-methanesulfonyl-quinolin-3-yl)-methanol (290 mg, 1.22 mmol, 1.0 eq) was added SOCl₂ (5 mL) and the mixture was stirred at rt for 2 h. The volatiles were then removed at 40° C. under vacuum, and the residue was dissolved in DCM. The mixture was washed with saturated aq. NaHCO₃, dried and concentrated to give 3-chloromethyl-6-methanesulfonyl-quinoline (310 mg, 99%) as a yellow solid.

Step 7: Preparation of 2-(6-methanesulfonyl-quinolin-3-ylmethyl)-isonicotinic Acid Methyl Ester

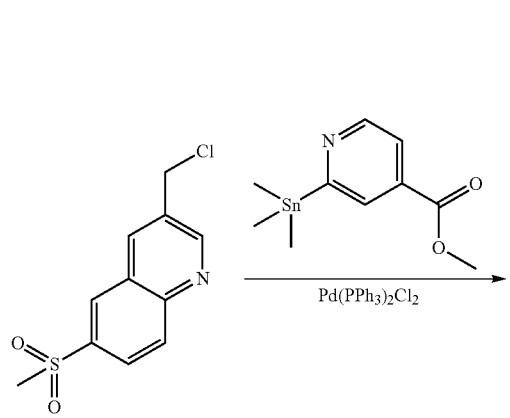

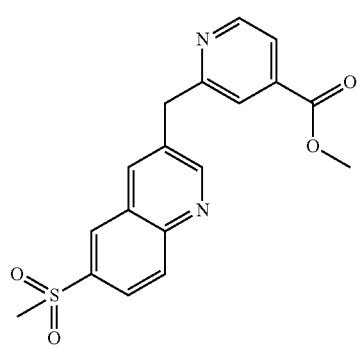

To a solution of 3-chloromethyl-6-methanesulfonyl-quinoline (310 mg, 2.61 mmol, 1.0 eq) in dioxane (20 mL) was added 2-trimethylstannanyl-isonicotinic acid methyl ester (864 mg, 2.87 mmol, 1.1 eq) and Pd(PPh$_3$)$_2$Cl$_2$ (183 mg, 0.26 mmol, 0.1 eq). The mixture was stirred at 90° C. for 3 h under nitrogen atmosphere, concentrated and purified by silica gel chromatography (DCM/MeOH=100/1, v/v) to afford 2-(6-methanesulfonyl-quinolin-3-ylmethyl)-isonicotinic acid methyl ester (290 mg, 67%) as a yellow solid.

Step 8: Preparation of N-((3-chloro-6-fluoro-1H-indol-5-yl)methyl)-2-((6-(methylsulfonyl)quinolin-3-yl)methyl)isonicotinamide

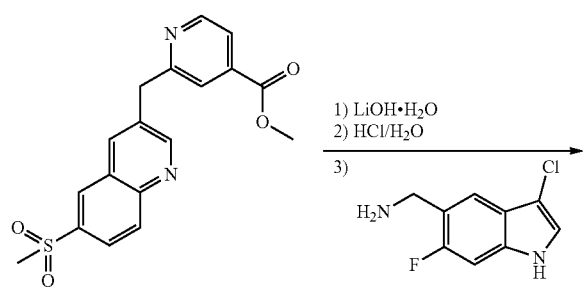

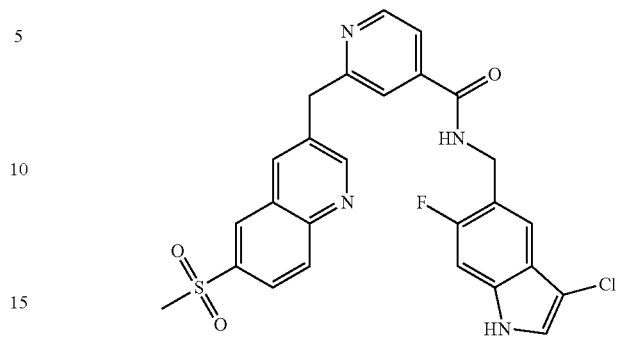

To a solution of 2-(6-methanesulfonyl-quinolin-3-ylmethyl)-isonicotinic Acid methyl ester (85 mg, 0.24 mmol, 1.0 eq) in THF (3 mL)/H$_2$O (2 mL) was added LiOH.H$_2$O (15 mg, 0.36 mmol, 1.5 eq). The mixture was stirred at 40° C. for 1 h and was acidified to pH 5 with 1 N HCl solution. The mixture was concentrated in vacuum and the residue was directly used without further purification. To a solution of the above crude product and C-(3-chloro-6-fluoro-1H-indol-5-yl)-methylamine hydrochloride (68 mg, 0.29 mmol, 1.2 eq) in DMF (5 mL) was added HATU (137 mg, 0.36 mmol, 1.5 eq) and Et$_3$N (97 mg, 0.96 mmol, 4 eq). The mixture was stirred at rt for 1 h and concentrated. The residue was purified by prep-HPLC to give N-((3-chloro-6-fluoro-1H-indol-5-yl)methyl)-2-((6-(methylsulfonyl)quinolin-3-yl)methyl)isonicotinamide (53 mg, 43% for 2 steps) as an off-white solid. LRMS (M+H$^+$) m/z calculated 523.1, found 522.8. $^1$H NMR (DMSO-d6, 400 MHz) δ 11.90 (s, 1H), 9.29 (s, 1H), 9.10 (s, 1H), 8.66 (d, 1H), 8.63 (s, 1H), 8.50 (s, 1H), 8.22 (d, 1H), 8.14 (d, 1H), 7.85 (s, 1H), 7.68 (d, 1H), 7.52 (s, 1H), 7.47 (d, 1H), 4.61 (d, 2H), 4.46 (s, 2H), 3.37 (s, 3H).

Example 13: Preparation of N-((1-aminoisoquinolin-6-yl)methyl)-2-((6-(methylsulfonyl)quinolin-3-yl)methyl)isonicotinamide

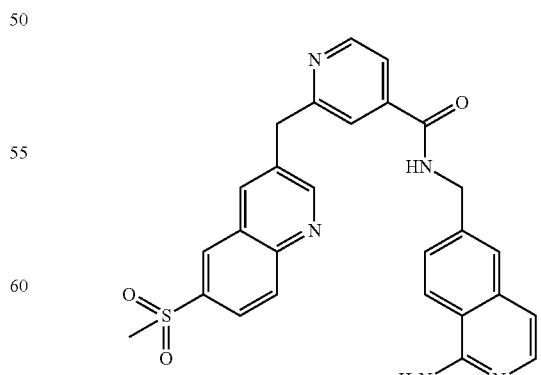

N-((1-aminoisoquinolin-6-yl)methyl)-2-((6-(methylsulfonyl)quinolin-3-yl)methyl)isonicotinamide

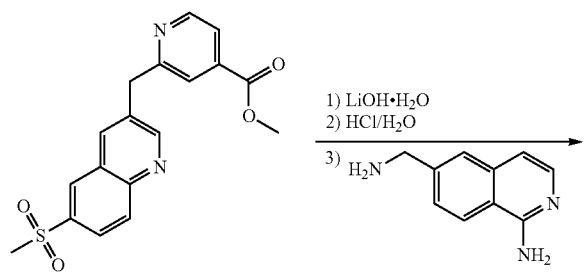

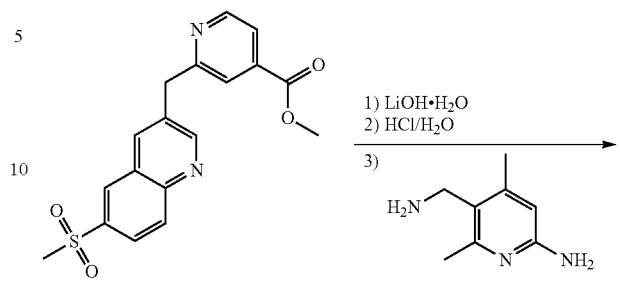

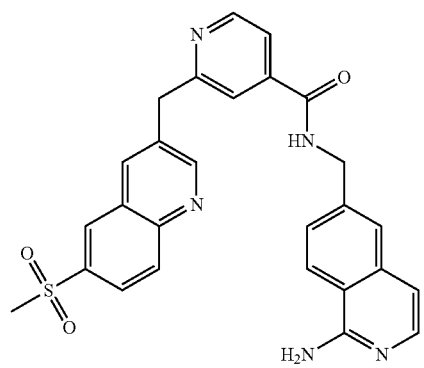

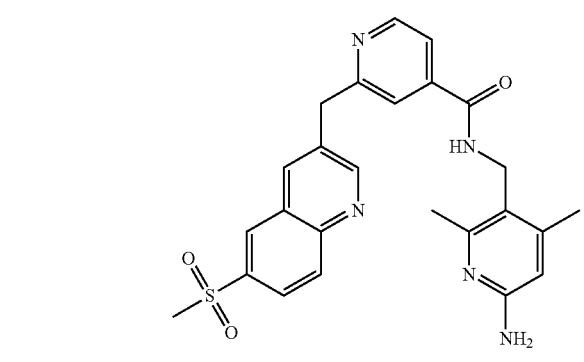

N-((1-aminoisoquinolin-6-yl)methyl)-2-((6-(methylsulfonyl)quinolin-3-yl)methyl)isonicotinamide (56 mg, 46% for 2 steps) was prepared as described for N-((3-chloro-6-fluoro-1H-indol-5-yl)methyl)-2-((6-(methylsulfonyl)quinolin-3-yl)methyl)isonicotinamide (Example 12) as an off-white solid. LRMS (M+H$^+$) m/z calculated 498.2, found 497.9.

$^1$H NMR (CD$_3$OD, 400 MHz) δ 8.85 (s, 1H), 8.51 (d, 1H), 8.37 (s, 1H), 8.21 (s, 1H), 7.99 (s, 1H), 7.89 (d, 1H), 7.71 (s, 1H), 7.55 (s, 1H), 7.53 (d, 1H), 7.45 (s, 1H), 7.32 (d, 1H), 6.74 (d, 1H), 4.56 (s, 2H), 4.32 (s, 2H), 3.07 (s, 3H).

Example 14: Preparation of N-((6-amino-2,4-dimethylpyridin-3-yl)methyl)-2-((6-(methylsulfonyl)quinolin-3-yl)methyl)isonicotinamide N-((6-amino-2,4-dimethylpyridin-3-yl)methyl)-2-((6-(methylsulfonyl)quinolin-3-yl)methyl)isonicotinamide (35 mg, 32% for 2 steps) was prepared as described for N-((3-chloro-6-fluoro-1H-indol-5-yl)methyl)-2-((6-(methylsulfonyl)quinolin-3-yl)methyl)isonicotinamide (Example 12) as an off-white solid. LRMS (M+H+) m/z calculated 476.2, found 476.0.

$^1$H NMR (CD$_3$OD, 400 MHz) δ 8.91 (d, 1H), 8.51 (d, 1H), 8.47 (s, 1H), 8.31 (s, 1H), 8.09 (d, 1H), 8.08 (d, 1H), 7.67 (s, 1H), 7.51 (d, 1H), 6.20 (s, 1H), 4.40 (s, 2H), 4.37 (s, 2H), 3.11 (s, 3H), 2.29 (s, 3H), 2.16 (s, 3H).

Example 15: Preparation of N-((6-amino-2,4-dimethylpyridin-3-yl)methyl)-2-((3-methyl-8-(methylsulfonyl)quinolin-6-yl)methyl)isonicotinamide

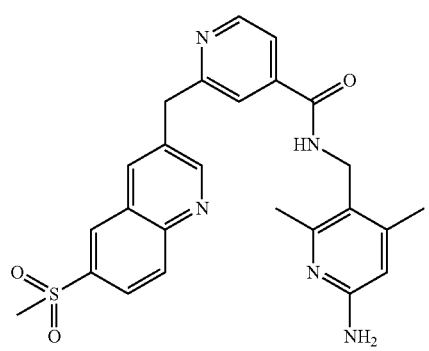

N-((6-amino-2,4-dimethylpyridin-3-yl)methyl)-2-((6-(methylsulfonyl)quinolin-3-yl)methyl)isonicotinamide

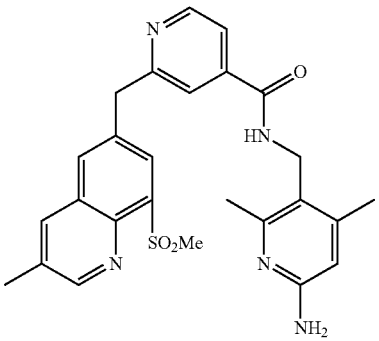

N-((6-amino-2,4-dimethylpyridin-3-yl)methyl)-2-((3-methyl-8-(methylsulfonyl)quinoliln-6-yl)methyl)isonicotinamide

Step 1: Preparation of 4-amino-3-iodo-benzoic Acid Methyl Ester

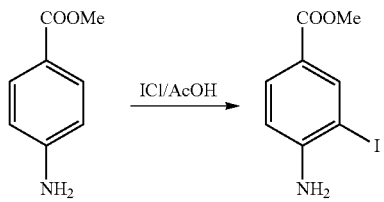 [SMILES: COC(=O)c1ccc(N)cc1 ; "ICl/AcOH" ; COC(=O)c1ccc(N)c(I)c1]

To a solution of 4-amino-benzoic acid methyl ester (20 g, 0.132 mol, 1 eq) in AcOH (500 mL) was added a solution of ICl (23.6 g, 0.146 mol, 1.1 eq) in AcOH (500 mL) at 0° C. The mixture was stirred at rt for 2 h. AcOH was evaporated under reduced pressure. The residue was diluted with DCM and washed with sat. NaHCO$_3$. The aqueous layer was extracted with DCM and the combined extracts were dried and concentrated. The residue was purified by chromatography on a silica gel column (EA/PE=1/15, v/v) to give 4-amino-3-iodo-benzoic acid methyl ester (27.4 g, 75%) as an off-white solid.

Step 2: Preparation of 8-iodo-3-methyl-quinoline-6-carboxylic Acid Methyl Ester

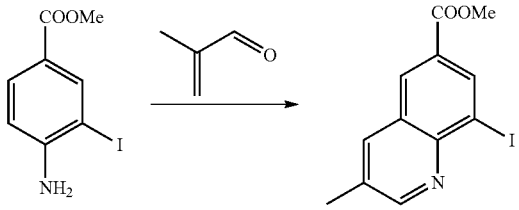

A mixture of 4-amino-3-iodo-benzoic acid methyl ester (26 g, 93.5 mmmol), 2-methyl-propenal (24.5 g, 0.28 mol, 3 eq) and 6 N HCl (95 mL) was heated to reflux for 24 h. Then the mixture was cooled and adjusted to pH ~5-6 using NaHCO$_3$ (aq). The mixture was extracted with DCM. The combined organic layers were washed with brine, dried over MgSO$_4$, filtered then concentrated and purified by column chromatography (EA/PE=1/20, v/v) to give 8-iodo-3-methyl-quinoline-6-carboxylic acid methyl ester (10.2 g, 33%) as a yellow solid.

Step 3: Preparation of (8-iodo-3-methyl-quinolin-6-yl)-methanol

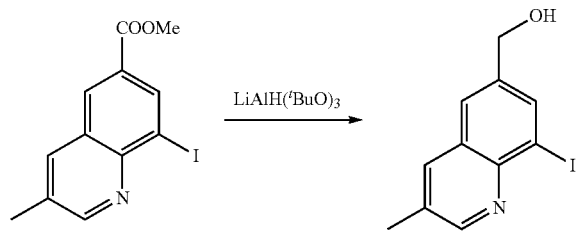 [SMILES: COC(=O)c1cc(I)c2ncc(C)cc2c1 ; Cc1cnc2c(I)cc(CO)cc2c1]

To a solution of 8-iodo-3-methyl-quinoline-6-carboxylic acid methyl ester (7.5 g, 22.9 mmol, 1 eq) was added LiAlH(t-BuO)$_3$ (14.6 g, 57.3 mmol, 2.5 eq). The resulting mixture was stirred at 40° C. for 12 h and then quenched by the addition of water. The mixture was extracted with EA. The combined extracts were dried and concentrated. The residue was purified by silica gel chromatography (PE/EA=2/1, v/v) to afford (8-iodo-3-methyl-quinolin-6-yl)-methanol (6.5 g, 95%) as a yellow solid.

Step 4: Preparation of (8-methanesulfonyl-3-methyl-quinolin-6-yl)-methanol

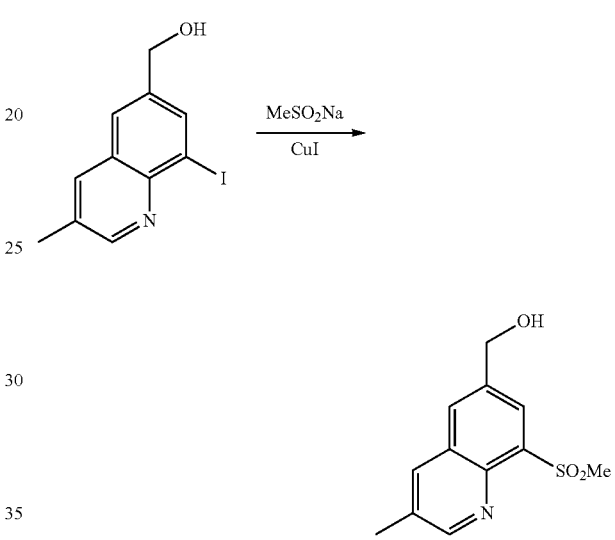

A mixture of (8-iodo-3-methyl-quinolin-6-yl)-methanol (6.5 g, 21.7 mmol, 1 eq), sodium methanesulphinate (2.66 g, 26.1 mmol, 1.2 eq), copper iodide (412 mg, 2.17 mol, 0.1 eq), L-proline sodium salt (594 mg, 4.34 mol, 0.2 eq) in 100 mL of DMSO was heated to 110° C. under nitrogen for 15 h. The cooled mixture was partitioned between ethyl acetate and water. The organic layer was separated, and the aqueous layer was extracted with ethyl acetate twice. The combined organic layers were washed with brine, dried over MgSO$_4$, and concentrated in vacuum. The residue was purified by silica gel column (EA/PE=1/2, v/v) to give (8-methanesulfonyl-3-methyl-quinolin-6-yl)-methanol (3.3 g, 60%) as a yellow solid.

Step 5: Preparation of 6-chloromethyl-8-methanesulfonyl-3-methyl-quinoline

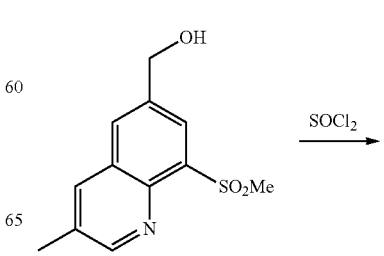

Step 7: Preparation of N-((6-amino-2,4-dimethyl-pyridin-3-yl)methyl)-2-((3-methyl-8-(methylsulfonyl)quinolin-6-yl)methyl)isonicotinamide

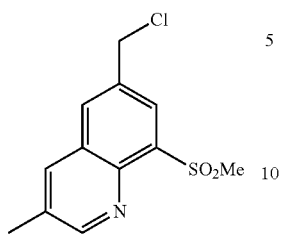

To (8-methanesulfonyl-3-methyl-quinolin-6-yl)-methanol (3.3 g, 13.1 mmol, 1.0 eq) was added SOCl$_2$ (50 mL) and the mixture was stirred at rt for 1 h. The volatiles were then removed under vacuum and the residue was dissolved in DCM. The mixture was washed with saturated aq. NaHCO$_3$, dried and concentrated to give 6-chloromethyl-8-methanesulfonyl-3-methyl-quinoline (3.4 g, 96%) as a yellow solid.

Step 6: Preparation of 2-(8-methanesulfonyl-3-methyl-quinolin-6-ylmethyl)-isonicotinic Acid Methyl Ester

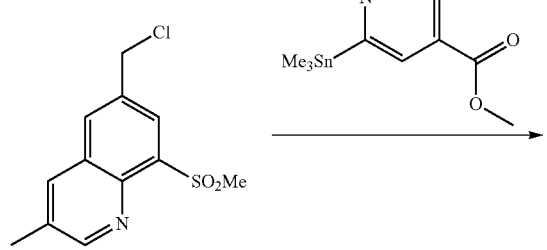

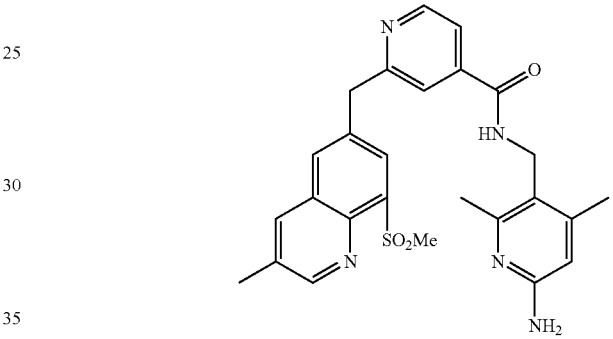

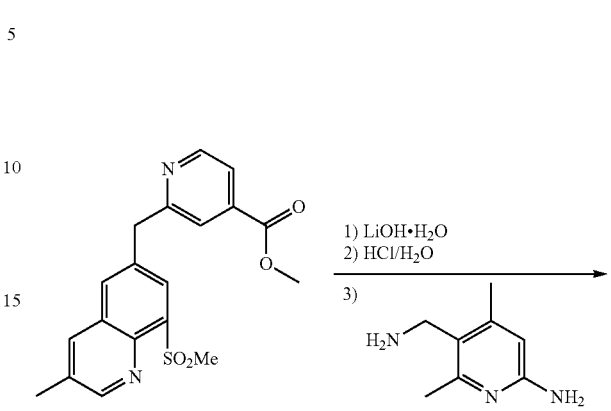

To a solution of 6-chloromethyl-8-methanesulfonyl-3-methyl-quinoline (3.0 g, 11.1 mmol, 1.0 eq) in dioxane (60 mL) was added 2-trimethylstannanyl-isonicotinic acid methyl ester (3.70 g, 12.3 mmol, 1.1 eq) and Pd(PPh$_3$)$_2$Cl$_2$ (779 mg, 1.11 mmol, 0.1 eq). The mixture was stirred at 90° C. for 3 h under nitrogen atmosphere, concentrated and purified by silica gel chromatography (DCM/MeOH=100/1, v/v) to afford 2-(8-methanesulfonyl-3-methyl-quinolin-6-ylmethyl)-isonicotinic acid methyl ester (2.26 g, 55%) as a yellow solid.

To a solution of 2-(8-methanesulfonyl-3-methyl-quinolin-6-ylmethyl)-isonicotinic acid methyl ester (120 mg, 0.32 mmol, 1.0 eq) in THF (3 mL)/H$_2$O (2 mL) was added LiOH.H$_2$O (26.88 mg, 0.64 mmol, 2.0 eq). The mixture was stirred at 40° C. for 1 h and was acidified to pH 5 with 1 N HCl solution. The mixture was concentrated in vacuo and the residue was directly used without further purification. To a solution of the above crude product and 5-aminomethyl-4,6-dimethyl-pyridin-2-ylamine (96.64 mg, 0.64 mmol, 2.0 eq) in DMF (5 mL) was added HOBT (64.8 mg, 0.48 mmol, 1.5 eq), EDCI (104.45 mg, 0.54 mmol, 1.7 eq) and Et$_3$N (0.17 mL, 1.28 mmol, 4 eq). The mixture was stirred at rt for overnight and diluted with water. The organic layer was separated and the aqueous layer was extracted with DCM. The combined extracts were dried and concentrated. The residue was purified by prep-HPLC to give N-((6-amino-2,4-dimethylpyridin-3-yl)methyl)-2-((3-methyl-8-(methylsulfonyl)quinolin-6-yl)methyl)isonicotinamide (30 mg, 18% for 2 steps) as an off-white solid. LRMS (M+H$^+$) m/z calculated 490.2, found 490.0. $^1$H NMR (DMSO-d$_6$, 400 MHz) δ: 8.93 (s, 1H), 8.67 (d, 2H), 8.27 (s, 2H), 8.16 (s, 1H), 7.82 (s, 1H), 7.63 (d, 1H), 6.13 (s, 1H), 5.70 (s, 2H), 4.44 (s, 2H), 4.35 (s, 2H), 3.58 (s, 3H), 2.52 (s, 3H), 2.31 (s, 3H), 2.17 (s, 3H).

Example 16: Preparation of N-((1-aminoisoquinolin-6-yl)methyl)-2-((3-methyl-8-(methylsulfonyl)quinolin-6-yl)methyl)isonicotinamide

Example 17: Preparation of N-((3-chloro-6-fluoro-1H-indol-5-yl)methyl)-2-((3-methyl-8-(methylsulfonyl)quinolin-6-yl)methyl)isonicotinamide

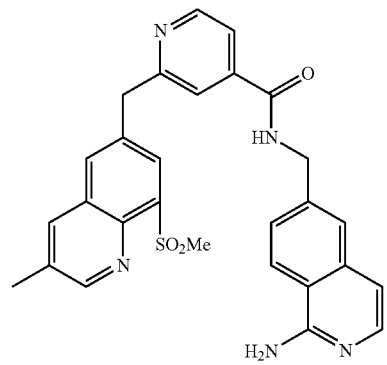

N-((1-aminoisoquinolin-6-yl)methyl)-2-((3-methyl-8-(methylsulfonyl)quinolin-6-yl)methyl)isonicotinamide

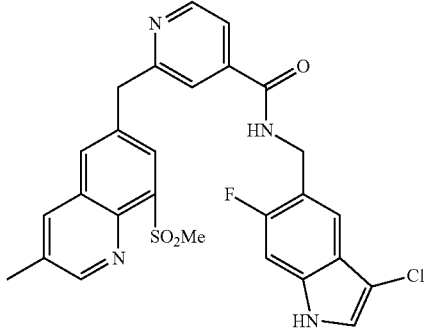

N-((3-chloro-6-fluoro-1H-indol-5-yl)methyl)-2-((3-methyl-8-(methylsulfonyl)quinolin-6-yl)methyl)isonicotinamide

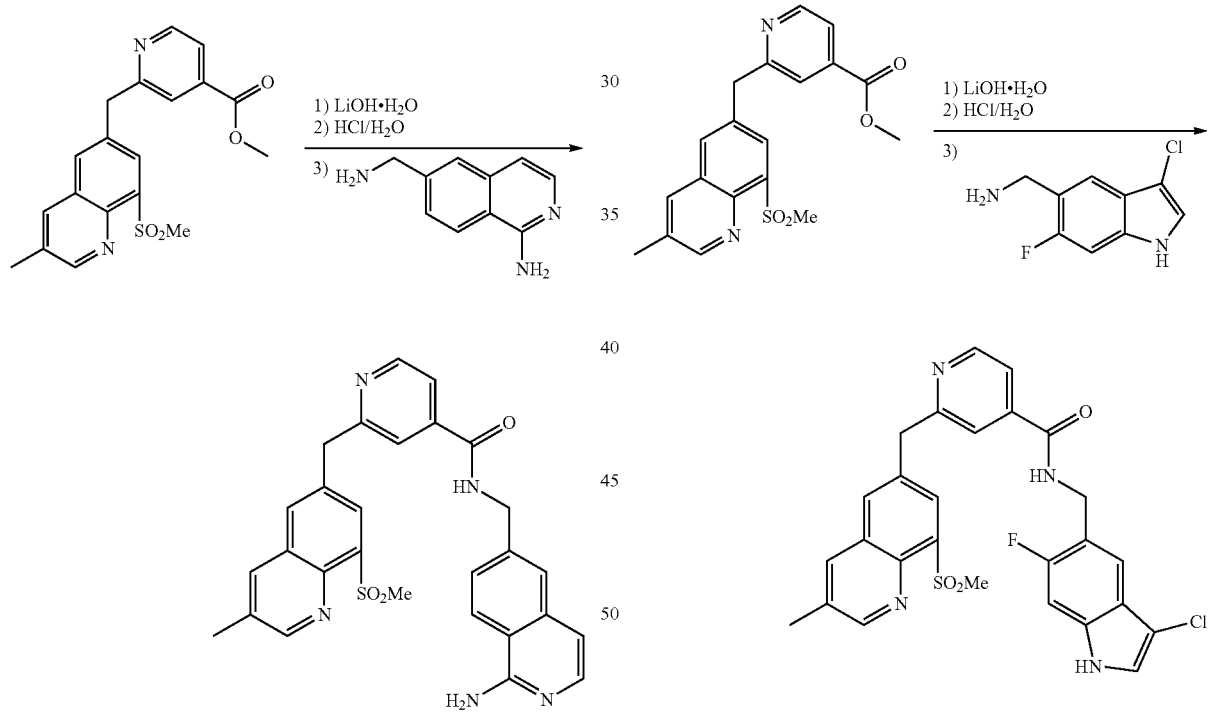

N-((1-aminoisoquinolin-6-yl)methyl)-2-((3-methyl-8-(methylsulfonyl)quinolin-6-yl)methyl)isonicotinamide (60 mg, 35% for 2 steps) was prepared as described for N-((6-amino-2,4-dimethylpyridin-3-yl)methyl)-2-((3-methyl-8-(methylsulfonyl)quinolin-6-yl)methyl)isonicotinamide (Example 15) as yellow solid. LRMS (M+H$^+$) m/z calculated 512.2, found 512.0.

$^1$H NMR (DMSO-d$_6$, 400 MHz) δ 8.85 (s, 1H), 8.64 (d, 1H), 8.31 (s, 1H), 8.11 (s, 1H), 8.05 (d, 2H), 7.81 (s, 1H), 7.69 (d, 2H), 7.60 (s, 1H), 7.47 (d, 1H), 6.91 (d, 1H), 4.69 (s, 2H), 4.45 (s, 2H), 3.52 (s, 3H), 2.52 (s, 3H).

N-((3-chloro-6-fluoro-1H-indol-5-yl)methyl)-2-((3-methyl-8-(methylsulfonyl)quinolin-6-yl)methyl)isonicotinamide (30 mg, 17% for 2 steps) was prepared as described for N-((6-amino-2,4-dimethylpyridin-3-yl)methyl)-2-((3-methyl-8-(methylsulfonyl)quinolin-6-yl)methyl)isonicotinamide (Example 15) as yellow solid. LRMS (M+H$^+$) m/z calculated 537.1, found 537.1.

$^1$H NMR (DMSO-d$_6$, 400 MHz) δ 11.40 (s, 1H), 9.26 (t, 1H), 8.93 (d, 1H), 8.67 (d, 1H), 8.28 (d, 2H), 8.16 (s, 1H), 7.86 (s, 1H), 7.68 (d, 1H), 7.51 (d, 1H), 7.46 (d, 1H), 7.24 (d, 1H), 4.60 (d, 2H), 4.45 (s, 2H), 3.57 (s, 3H), 2.50 (s, 3H).

Example 18: Preparation of N-((6-fluoro-1H-indol-5-yl)methyl)-2-((3-methyl-8-(methylsulfonyl)quinolin-6-yl)methyl)isonicotinamide

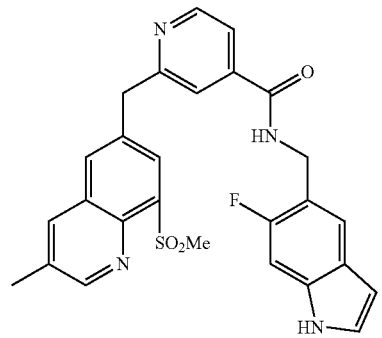

N-((6-fluoro-1H-indol-5-yl)methyl)-2-((3-methyl-8-(methylsulfonyl)quinolin-6-yl)methyl)isonicotinamide

Example 19: Preparation of N-((3-chloro-1H-pyrrolo[2,3-b]pyridin-5-yl)methyl)-2-((3-methyl-8-(methylsulfonyl)quinolin-6-yl)methyl)isonicotinamide

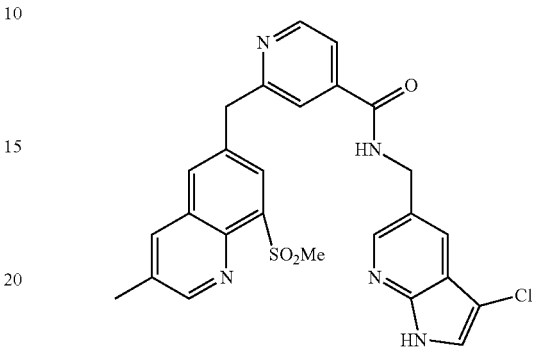

N-((3-chloro-1H-pyrrolo[2,3-b]pyridin-5-yl)methyl)-2-((3-methyl-8-(methylsulfonyl)quinolin-6-yl)methyl)isonicotinamide

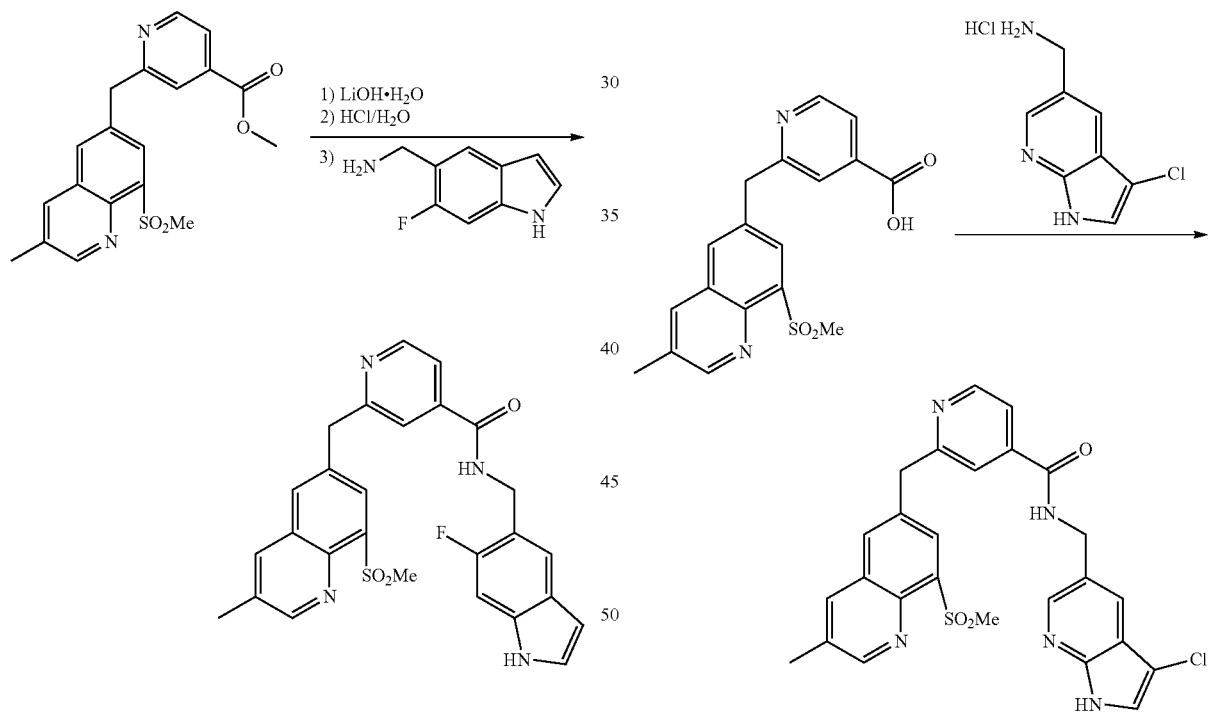

N-((6-fluoro-1H-indol-5-yl)methyl)-2-((3-methyl-8-(methylsulfonyl)quinolin-6-yl)methyl)isonicotinamide (40 mg, 28% for 2 steps) was prepared as described for N-((6-amino-2,4-dimethylpyridin-3-yl)methyl)-2-((3-methyl-8-(methylsulfonyl)quinolin-6-yl)methyl)isonicotinamide (Example 15) as an off-white solid. LRMS (M+H$^+$) m/z calculated 503.2, found 503.0. $^1$H NMR (DMSO-d$_6$, 400 MHz) δ 11.12 (s, 1H), 9.24 (t, 1H), 8.92 (d, 1H), 8.68 (d, 1H), 8.28 (d, 2H), 8.16 (s, 1H), 7.89 (s, 1H), 7.70 (d, 1H), 7.52 (d, 1H), 7.32 (s, 1H), 7.19 (d, 1H), 6.41 (d, 1H), 4.59 (d, 2H), 4.46 (s, 1H), 3.58 (s, 3H), 2.51 (s, 3H).

N-((3-chloro-1H-pyrrolo[2,3-b]pyridin-5-yl)methyl)-2-((3-methyl-8-(methylsulfonyl)quinolin-6-yl)methyl)isonicotinamide (55 mg, 38%) was prepared as described for N-((6-amino-2,4-dimethylpyridin-3-yl)methyl)-2-((3-methyl-8-(methylsulfonyl)quinolin-6-yl)methyl)isonicotinamide (Example 15) as a white solid. LRMS (M+H$^+$) m/z calculated 520.1, found 519.8.

$^1$H NMR (DMSO-d$_6$, 400 MHz) δ 9.35 (t, 1H), 8.92 (s, 1H), 8.66 (d, 1H), 8.26-8.32 (m, 3H), 8.16 (s, 1H), 7.88 (s, 1H), 7.85 (s, 1H), 7.65-7.68 (m, 2H), 4.59 (d, 2H), 4.45 (s, 2H), 3.56 (s, 3H), 2.51 (s, 3H).

Example 20: Preparation of N-((5-chloro-1H-indazol-3-yl)methyl)-2-((3-methyl-8-(methylsulfonyl)quinolin-6-yl)methyl)isonicotinamide

Example 21: Preparation of N-((3-chloro-4-fluoro-1H-indol-5-yl)methyl)-2-((3-methyl-8-(methylsulfonyl)quinolin-6-yl)methyl)isonicotinamide

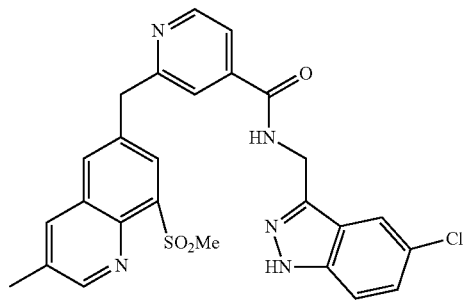

N-((5-chloro-1H-indazol-3-yl)methyl)-2-((3-methyl-8-(methylsulfonyl)quinolin-6-yl)methyl)isonicotinamide

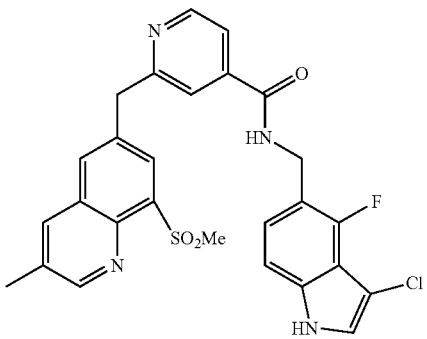

N-((3-chloro-4-fluoro-1H-indol-5-yl)methyl)-2-((3-methyl-8-(methylsulfonyl)quinolin-6-yl)methyl)isonicotinamide

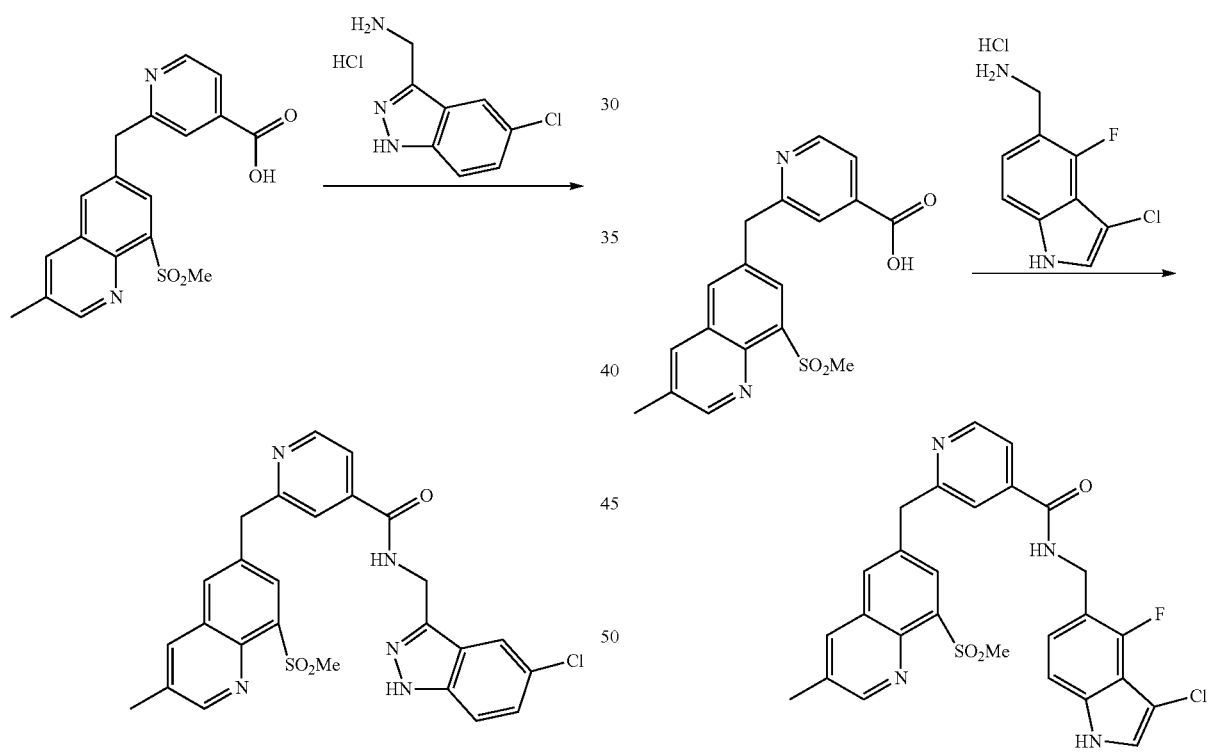

N-((5-chloro-1H-indazol-3-yl)methyl)-2-((3-methyl-8-(methylsulfonyl)quinolin-6-yl)methyl)isonicotinamide (30 mg, 21%) was prepared as described for N-((6-amino-2,4-dimethylpyridin-3-yl)methyl)-2-((3-methyl-8-(methylsulfonyl)quinolin-6-yl)methyl)isonicotinamide (Example 15) as a yellow solid. LRMS (M+H$^+$) m/z calculated 520.1, found 519.8. $^1$H NMR (DMSO-d$_6$, 400 MHz) δ 9.41 (t, 1H), 8.92 (s, 1H), 8.66 (d, 1H), 8.27 (d, 2H), 8.15 (s, 1H), 7.91 (s, 1H), 7.86 (s, 1H), 7.65 (d, 1H), 7.53 (d, 1H), 7.33 (d, 1H), 4.79 (d, 2H), 4.45 (s, 2H), 3.56 (s, 3H), 2.51 (s, 3H).

N-((3-chloro-4-fluoro-1H-indol-5-yl)methyl)-2-((3-methyl-8-(methylsulfonyl)quinolin-6-yl)methyl)isonicotinamide (40 mg, 27%) was prepared as described for N-((6-amino-2,4-dimethylpyridin-3-yl)methyl)-2-((3-methyl-8-(methylsulfonyl)quinolin-6-yl)methyl)isonicotinamide (Example 15) as a white solid. LRMS (M+H$^+$) m/z calculated 537.1, found 536.7.

$^1$H NMR (DMSO-d$_6$, 400 MHz) δ 11.60 (s, 1H), 9.26 (t, 1H), 8.92 (s, 1H), 8.66 (d, 1H), 8.27 (d, 2H), 8.16 (s, 1H), 7.85 (s, 1H), 7.65 (d, 1H), 7.52 (d, 1H), 7.12-7.21 (m, 2H), 4.58 (d, 2H), 4.45 (s, 2H), 3.57 (s, 3H), 2.51 (s, 3H).

Example 22: Preparation of N-(6-Amino-2,4-dimethyl-pyridin-3-ylmethyl)-2-(5-chloro-1-oxo-1H-isoquinolin-2-ylmethyl)-isonicotinamide

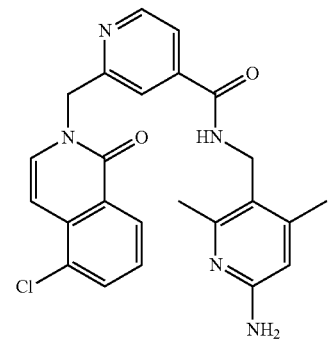

N-(6-Amino-2,4-dimethyl-pyridin-3-ylmethyl)-2-(5-chloro-1-oxo-1H-isoquinolin-2-ylmethyl)-isonicotinamide

Step 1: Preparation of methyl 2-chlorophenethylcarbamate

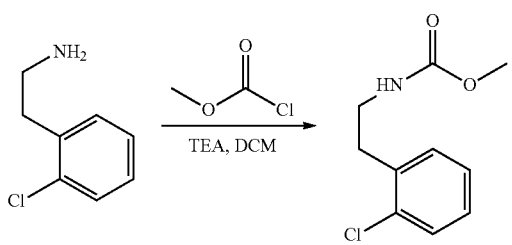

To a solution of 2-(2-chloro-phenyl)-ethylamine (10 g, 64 mmol, 1.0 eq) in DCM (150 mL) was added TEA (12.9 g, 128 mmol, 2.0 eq). The mixture was stirred at 0° C., and methyl chloroformate (9.07 g, 96 mmol, 1.5 eq) was added under nitrogen atmosphere. The mixture was allowed to warm to rt and stirred for 1 h, concentrated and purified by silica gel chromatography (PE/EA=5/1, v/v) to afford methyl 2-chlorophenethylcarbamate (9.0 g, 66%) as a colorless oil.

Step 2: Preparation of 5-chloro-3,4-dihydro-2H-isoquinolin-1-one

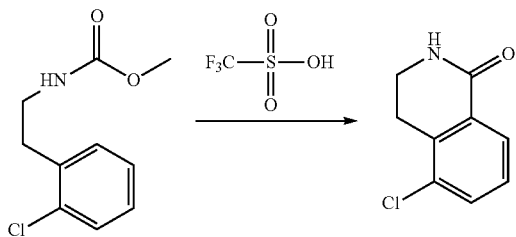

Trifluoromethanesulfonic acid (170 mL, 2.2 mol, 50 eq) was added to N-(6-amino-2,4-dimethyl-pyridin-3-ylmethyl)-2-(5-chloro-1-oxo-1H-isoquinolin-2-ylmethyl)-isonicotinamide (9.0 g, 44.2 mmol, 1.0 eq) at 0° C. The mixture was stirred at 70° C. for 24 h under nitrogen. Then the mixture was poured into ice-water to afford 5-chloro-3,4-dihydro-2H-isoquinolin-1-one (5.1 g, 67%) as a yellow oil.

Step 3: Preparation of 5-chloro-2H-isoquinolin-1-one

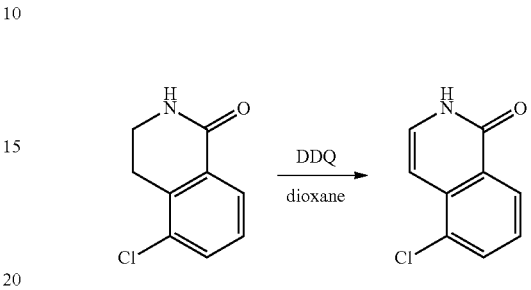

To a solution of 5-chloro-3,4-dihydro-2H-isoquinolin-1-one (5.1 g, 28 mmol, 1.0 eq) in dioxane (150 mL) was added DDQ (22 g, 70 mmol, 3.4 eq). The mixture was stirred at 100° C. for 72 h. The solvent was removed and EA was added. Then washed with 10% NaOH, the organic layer was concentrated, and purified by silica gel chromatography (PE/EA=3/1, v/v) to afford 5-chloro-2H-isoquinolin-1-one (1.3 g, 25%) as an orange oil.

Step 4: Preparation of 2-(5-chloro-1-oxo-1H-isoquinolin-2-ylmethyl)-isonicotinic Acid Methyl Ester

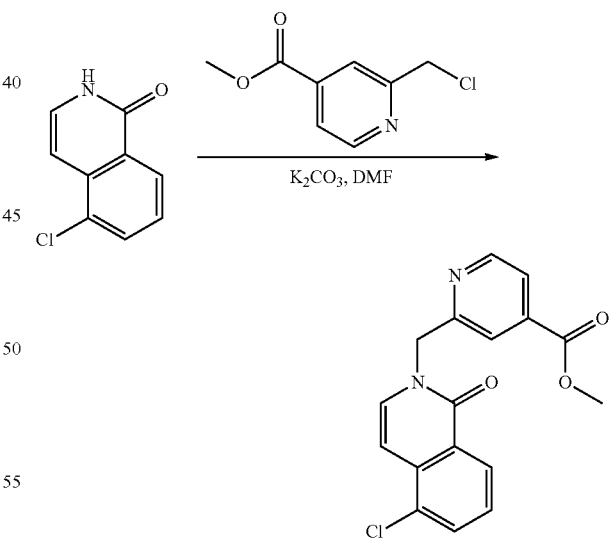

To a solution of 5-chloro-2H-isoquinolin-1-one (470 mg, 2.6 mmol, 1.0 eq) in DMF (10 mL) was added $K_2CO_3$ (723 mg, 5.2 mmol, 2.0 eq) and 2-chloromethyl-isonicotinic acid methyl ester (722 mg, 3.9 mmol, 1.5 eq). The mixture was stirred at 30° C. for 4 h. The solvent was removed and purified by silica gel chromatography (PE/EA=3/1, v/v) to afford 2-(5-chloro-1-oxo-1H-isoquinolin-2-ylmethyl)-isonicotinic acid methyl ester (710 mg, 83%) as a yellow solid.

Step 5: Preparation of N-(6-amino-2,4-dimethyl-pyridin-3-ylmethyl)-2-(5-chloro-1-oxo-1H-isoquinolin-2-ylmethyl)-isonicotinamide

Example 23: Preparation of N-((6-amino-2,4-dimethylpyridin-3-yl)methyl)-2-((6-chloro-1-oxoisoquinolin-2(1H)-yl)methyl)isonicotinamide

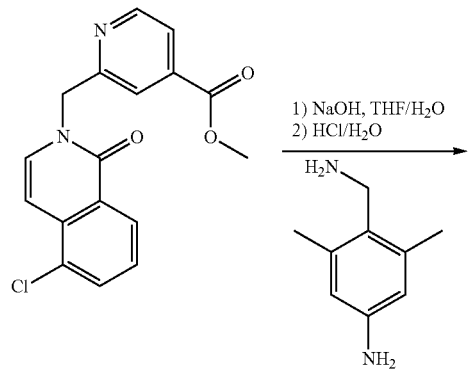

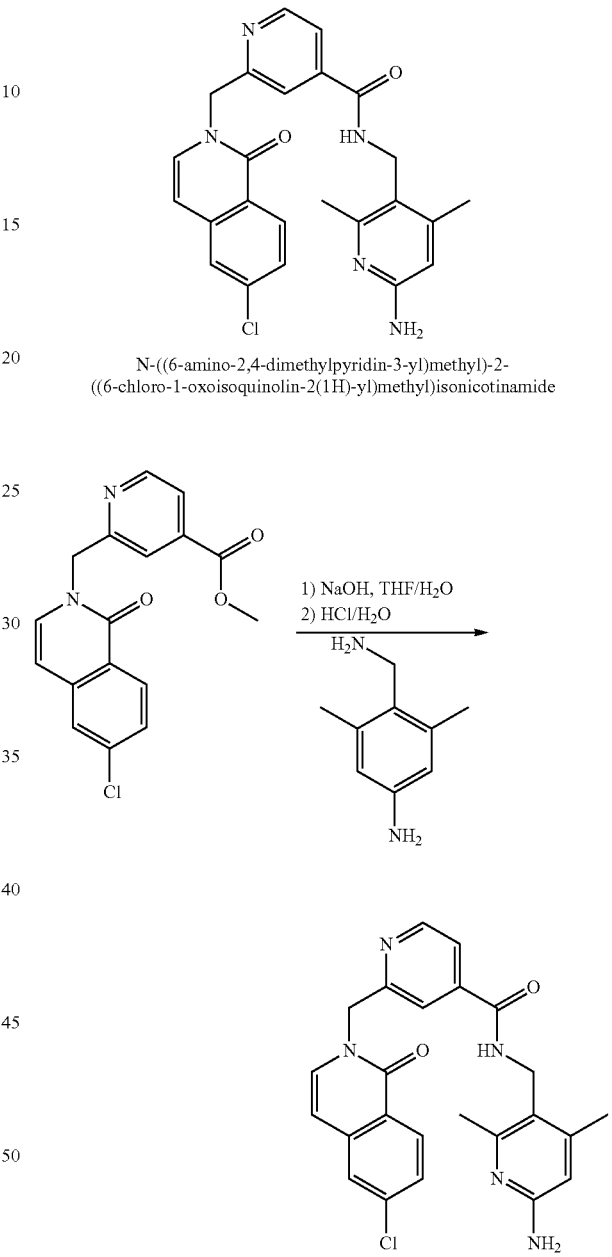

N-((6-amino-2,4-dimethylpyridin-3-yl)methyl)-2-((6-chloro-1-oxoisoquinolin-2(1H)-yl)methyl)isonicotinamide To a solution of 2-(5-chloro-1-oxo-1H-isoquinolin-2-ylmethyl)-isonicotinic acid methyl ester (210 mg, 0.54 mmol, 1.0 eq) in THF (5 mL)/H$_2$O (5 mL) was added NaOH (43 mg, 1.08 mmol, 2.0 eq). The mixture was stirred at 40° C. for 1 h and was acidified to pH 5 with 1 N HCl solution. The mixture was concentrated in vacuum and the residue was directly used without further purification. To a solution of the above crude product and 4-aminomethyl-3,5-dimethyl-phenylamine (122 mg, 0.81 mmol, 1.5 eq) in DMF (8 mL) was added HATU (230 mg, 0.6 mmol, 1.2 eq) and Et$_3$N (0.3 mL, 1.62 mmol, 3 eq). The mixture was stirred at rt for overnight, concentrated and purified by flash chromatography on a silica gel column (DCM/MeOH=10/1, v/v) to give N-(6-amino-2,4-dimethyl-pyridin-3-ylmethyl)-2-(5-chloro-1-oxo-1H-isoquinolin-2-ylmethyl)-isonicotinamide (31 mg, 13% for 2 steps) as a white solid. LRMS (M+H$^+$) m/z calculated 448.2, found 448.0. $^1$H NMR (DMSO-d$_6$, 400 MHz) δ 8.71 (m, 1H), 8.56-8.57 (d, 1H), 8.16-8.18 (d, 1H), 7.88-7.90 (d, 1H), 7.74-7.76 (d, 1H), 7.70 (s, 1H), 7.64-7.65 (d, 1H), 7.48-7.52 (t, 1H), 6.81-6.83 (d, 1H), 6.14 (s, 1H), 5.80 (m, 2H), 5.34 (s, 2H), 4.33-4.34 (d, 2H), 2.30 (s, 3H), 2.17 (s, 3H).

N-((6-amino-2,4-dimethylpyridin-3-yl)methyl)-2-((6-chloro-1-oxoisoquinolin-2(1H)-yl)methyl)isonicotinamide (45 mg, 33%) was prepared as described for N-(6-amino-2,4-dimethyl-pyridin-3-ylmethyl)-2-(5-chloro-1-oxo-1H-isoquinolin-2-ylmethyl)-isonicotinamide (Example 22) as a white solid. LRMS (M+H$^+$) m/z calculated 448.2, found 447.8.

$^1$H NMR (DMSO-d$_6$, 400 MHz) δ 8.71 (s, 1H), 8.58 (d, 1H), 8.17 (d, 1H), 7.83 (s, 1H), 7.68-7.65 (m, 3H), 7.54 (dd, 1H), 6.67 (d, 1H), 6.15 (s, 1H), 5.74 (br, 2H), 4.35 (d, 2H), 2.31 (s, 3H), 2.17 (s, 3H).

Example 24: Preparation of N-((6-amino-2,4-dimethylpyridin-3-yl)methyl)-2-((3-chloro-1H-indol-5-yl)methyl)isonicotinamide

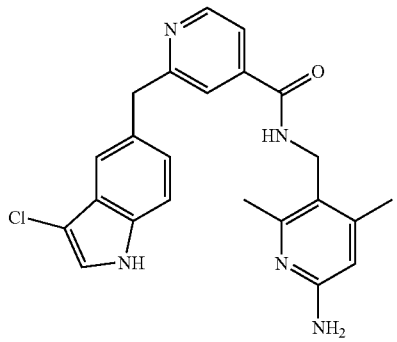

N-((6-amino-2,4-dimethylpyridin-3-yl)methyl)-
2-((3-chloro-1H-indol-5-
yl)methyl)isonicotinamide Step 1: Preparation of
3-chloro-1H-indole-5-carboxylic Acid Methyl Ester

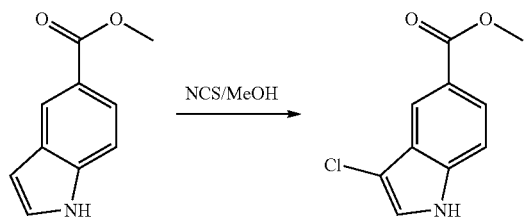

To a solution of 1H-indole-5-carboxylic acid methyl ester (10.0 g, 57.1 mmol, 1.0 eq) in MeOH was added NCS (8.4 g, 62.8 mmol, 1.1 eq). The mixture was stirred at rt for 3 h. MeOH was removed by evaporation and the residue was re-dissolved in EA. The mixture was washed with brine twice. The organic layer was dried and concentrated to give 3-chloro-1H-indole-5-carboxylic acid methyl ester (quant) as a yellow solid.

Step 2: Preparation of
3-chloro-indole-1,5-dicarboxylic Acid 1-tert-butyl Ester 5-methyl Ester

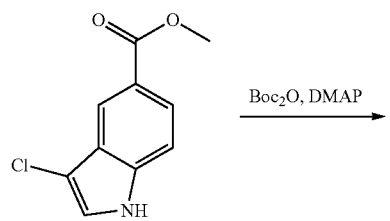

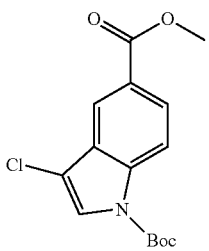

To a solution of 3-chloro-1H-indole-5-carboxylic acid methyl ester (11.9 g, 57.1 mmol, 1.0 eq) in MeOH was added Boc$_2$O (18.7 g, 86.7 mmol, 1.5 eq) and DMAP (348 mg, 2.86 mmol, 0.05 eq). The mixture was stirred at rt for 2 h. The mixture was concentrated and purified by chromatography on a silica gel column (EA/PE=1/10, v/v) to give 3-chloro-indole-1,5-dicarboxylic acid 1-tert-butyl ester 5-methyl ester (13.4 g, 76%) as an off-white solid.

Step 3: Preparation of
3-chloro-5-hydroxymethyl-indole-1-carboxylic Acid tert-butyl Ester

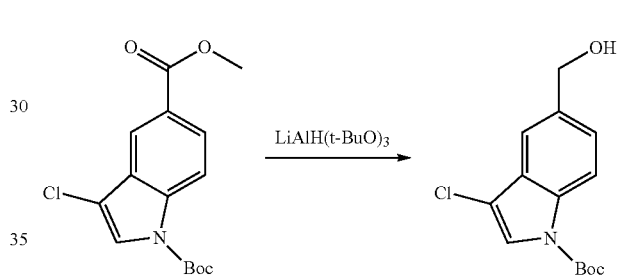

To a solution of 3-chloro-indole-1,5-dicarboxylic acid 1-tert-butyl ester 5-methyl ester (7.0 g, 22.6 mmol, 1 eq) in THF (100 mL) was added LiAlH(t-BuO)$_3$ (14.4 g, 56.6 mmol, 2.5 eq). The resulting mixture was stirred at 60° C. for 12 h and then quenched by the addition of water. The mixture was extracted with EA. The combined extracts were dried and concentrated. The residue was purified by silica gel chromatography (PE/EA=2/1, v/v) to afford 3-chloro-5-hydroxymethyl-indole-1-carboxylic acid tert-butyl ester (4.3 g, 68%) as a white solid.

Step 4: Preparation of
3-chloro-5-chloromethyl-indole-1-carboxylic Acid tert-butyl Ester

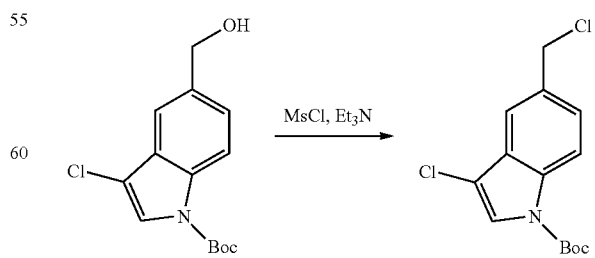

To a solution of 3-chloro-5-hydroxymethyl-indole-1-carboxylic acid tert-butyl ester (1.5 g, 5.34 mmol, 1 eq) in dry DCM (30 mL) was added Et₃N (1.5 mL, 10.68 mmol, 2 eq) and MsCl (0.62 mL, 8.01 mmol, 1.5 eq). The resulting mixture was stirred at rt for 24 h and then quenched by the addition of water. The mixture was extracted with DCM. The combined extracts were dried and concentrated. The residue was purified by silica gel chromatography (PE/EA=20/1, v/v) to afford 3-chloro-5-chloromethyl-indole-1-carboxylic acid tert-butyl ester (1.17 g, 73%) as a white solid.

Step 5: Preparation of 3-chloro-5-(4-methoxycarbonyl-pyridin-2-ylmethyl)-indole-1-carboxylic Acid tert-butyl Ester

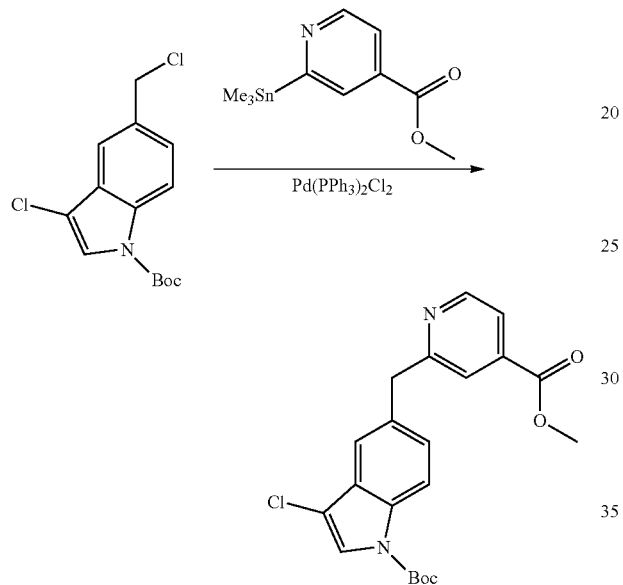

To a solution of 3-chloro-5-chloromethyl-indole-1-carboxylic acid tert-butyl ester (1.1 g, 3.68 mmol, 1.0 eq) in dioxane (20 mL) was added 2-trimethylstannanyl-isonicotinic acid methyl ester (1.22 g, 4.05 mmol, 1.1 eq) and Pd(PPh₃)₂Cl₂ (260 mg, 0.37 mmol, 0.1 eq). The mixture was stirred at 90° C. for 3 h under nitrogen atmosphere, concentrated and purified by silica gel chromatography (PE/EA=20/1, v/v) to afford 3-chloro-5-(4-methoxycarbonyl-pyridin-2-ylmethyl)-indole-1-carboxylic acid tert-butyl ester (690 mg, 47%) as an off-white solid.

Step 6: Preparation of 2-(3-chloro-1H-indol-5-ylmethyl)-isonicotinic Acid

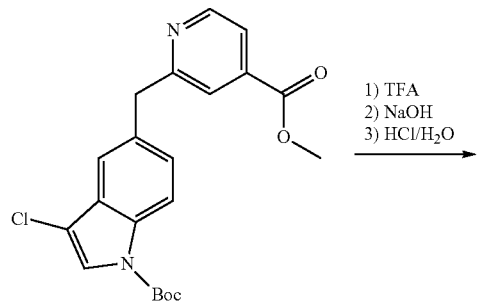

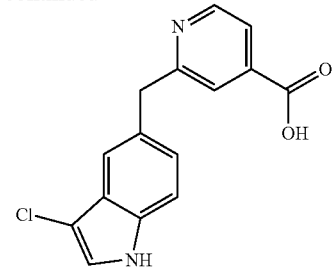

To a solution of 3-chloro-5-(4-methoxycarbonyl-pyridin-2-ylmethyl)-indole-1-carboxylic acid tert-butyl ester (690 mg, 1.72 mmol, 1.0 eq) in DCM (3 mL) was added TFA (5 mL). The mixture was stirred at rt for 2 h. Then the mixture was concentrated and the residue was re-dissolved in DCM and washed with sat.NaHCO₃ aq. The organic layer was concentrated. The residue was dissolved in THF/H₂O (5 mL, v/v=1:1). To the mixture was added NaOH. The mixture was stirred at rt for 0.5 h. Then the mixture was acidified to pH 5 with 1N HCl. The mixture was extracted with EA. The combined organic layers were dried and concentrated to give 2-(3-chloro-1H-indol-5-ylmethyl)-isonicotinic acid (220 mg, 45%) as a yellow solid.

Step 7: Preparation of N-((6-amino-2,4-dimethyl-pyridin-3-yl)methyl)-2-((3-chloro-1H-indol-5-yl)methyl)isonicotinamide

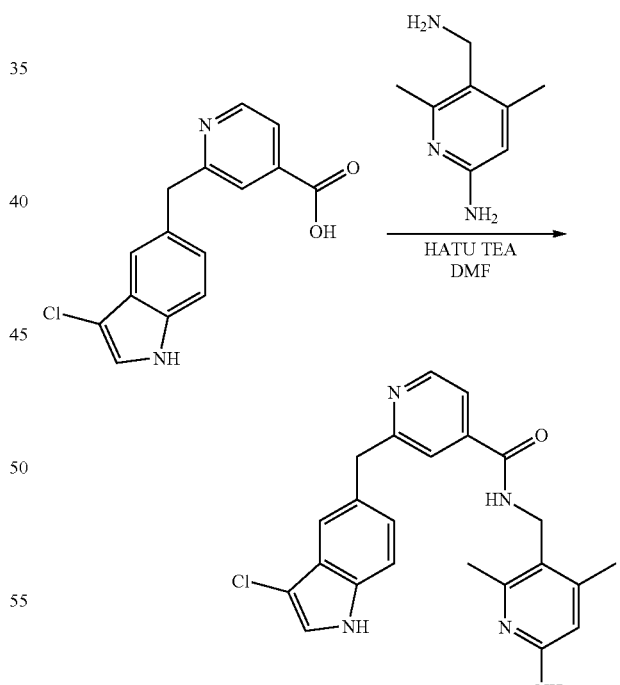

To a solution of 2-(3-chloro-1H-indol-5-ylmethyl)-isonicotinic acid (100 mg, 0.35 mmol, 1 eq) and 4-aminomethyl-3,5-dimethyl-phenylamine (117 mg, 0.52 mmol, 1.5 eq) in DMF (5 mL) was added HATU (160 mg, 0.42 mmol, 1.2 eq) and Et₃N (140 mg, 1.40 mmol, 4 eq). The mixture was stirred at rt for 1 h, concentrated and purified by prep-HPLC to give N-((6-amino-2,4-dimethylpyridin-3-yl)methyl)-2-

((3-chloro-1H-indol-5-yl)methyl)isonicotinamide (35 mg, 24%) as an off-white solid. LRMS (M+H⁺) m/z calculated 420.2, found 419.8.

¹H NMR (CD₃OD, 400 MHz) δ 8.54 (d, 1H), 7.61 (s, 1H), 7.54 (dd, 1H), 7.38 (s, 1H), 7.29 (d, 1H), 7.20 (s, 1H), 7.06 (dd, 1H), 6.28 (s, 1H), 4.45 (s, 2H), 4.25 (d, 2H), 2.36 (s, 3H), 2.22 (s, 3H).

Example 25: Preparation of N-((6-amino-2,4-dimethylpyridin-3-yl)methyl)-2-((3-methyl-1H-indol-5-yl)methyl)isonicotinamide

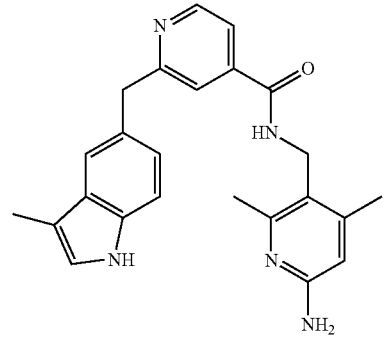

N-((6-amino-2,4-dimethylpyridin-3-yl)methyl)-2-((3-methyl-1H-indol-5-yl)methyl)isonicotinamide

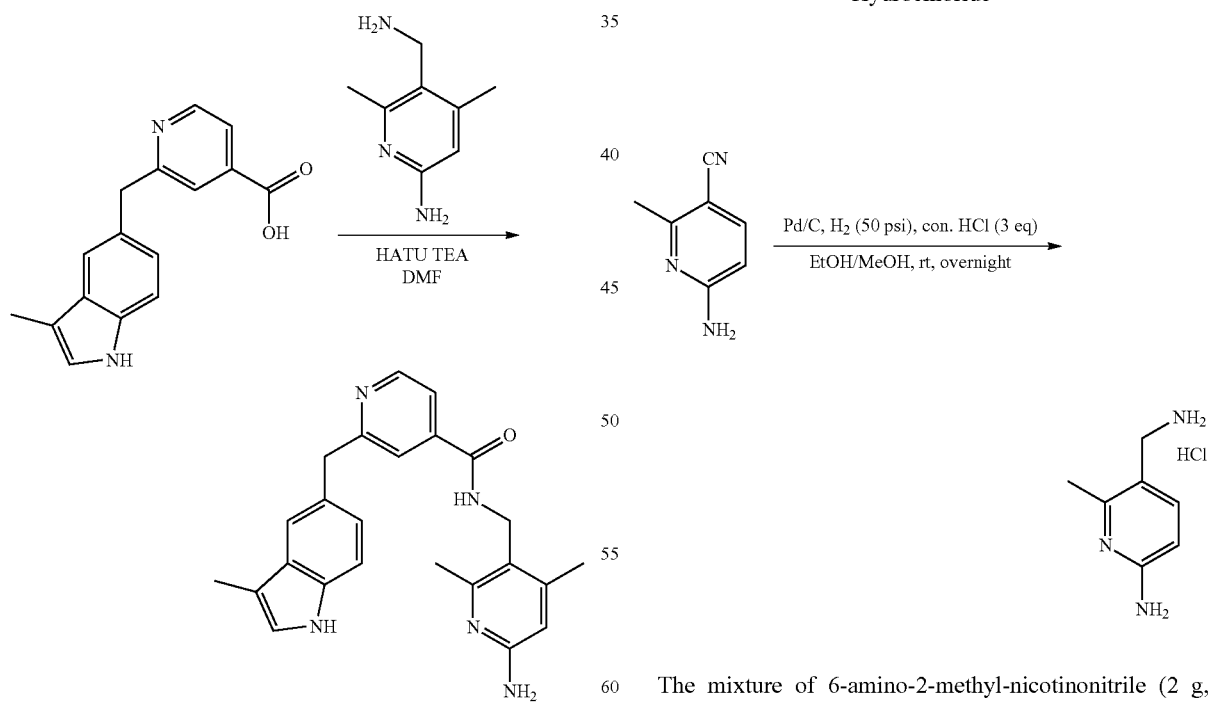

N-((6-amino-2,4-dimethylpyridin-3-yl)methyl)-2-((3-methyl-1H-indol-5-yl)methyl)isonicotinamide (25 mg, 16%) was prepared as described in Example 15, Steps 6 and 7 as a white solid. LRMS (M+H⁺) m/z calculated 400.2, found 399.9. ¹H NMR (CD₃OD, 400 MHz) δ 8.53 (d, 1H), 7.59 (s, 1H), 7.52 (d, 1H), 7.37 (s, 1H), 7.23 (d, 1H), 6.97 (d, 1H), 6.95 (s, 1H), 6.27 (s, 1H), 4.45 (s, 2H), 4.24 (d, 2H), 2.35 (s, 3H), 2.25 (s, 3H), 2.22 (s, 3H).

Example 26: Preparation of N-((6-amino-5-cyano-2-methylpyridin-3-yl)methyl)-2-((3-chloroquinolin-6-yl)methyl)isonicotinamide

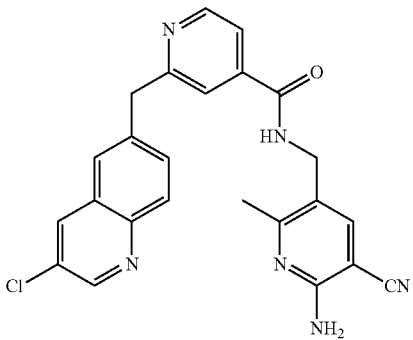

N-((6-amino-5-cyano-2-methylpyridin-3-yl)methyl)-2-((3-chloroquinolin-6-yl)methyl)isonicotinamide

Step 1: Preparation of 5-aminomethyl-6-methyl-pyridin-2-ylamine Hydrochloride The mixture of 6-amino-2-methyl-nicotinonitrile (2 g, 15.0 mmol, 1 eq), Pd/C (10%, 500 mg), and con.HCl (3 mL) in a solution of EtOH/MeOH (10 mL/10 mL) was stirred at rt under H₂ (50 psi) for overnight. The reaction mixture was filtered, and the filtrate was concentrated to give crude 5-aminomethyl-6-methyl-pyridin-2-ylamine hydrochloride (3.5 g) as a yellow solid. LRMS (M+H⁺) m/z calculated 138, found 138.

Step 2: Preparation of (6-amino-2-methyl-pyridin-3-ylmethyl)-carbamic Acid tert-butyl Ester

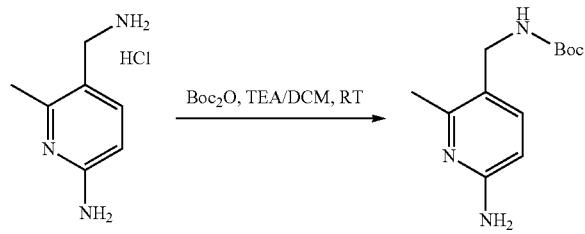

The mixture of 5-aminomethyl-6-methyl-pyridin-2-ylamine hydrochloride (3.5 g, crude) in DCM (50 mL) was added TEA (4.5 g, 45.0 mmol, 3 eq) followed by Boc₂O (4.9 g, 22.5 mmol, 1.5 eq). The reaction mixture was stirred at rt overnight. The reaction mixture was concentrated. The residue was purified by column chromatography on a silica gel (DCM/MeOH=20/1, v/v) to give (6-amino-2-methyl-pyridin-3-ylmethyl)-carbamic acid tert-butyl ester (3 g) as a white solid. LRMS (M+H⁺) m/z calculated 238, found 238.

Step 3: Preparation of (6-amino-5-bromo-2-methyl-pyridin-3-ylmethyl)-carbamic Acid tert-butyl Ester

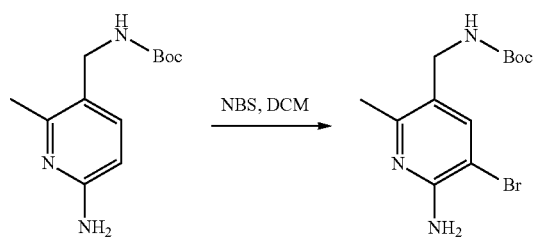 [SMILES: Cc1nc(N)ccc1CNC(=O)OC(C)(C)C ; Cc1nc(N)c(Br)cc1CNC(=O)OC(C)(C)C]

To the solution of (6-amino-2-methyl-pyridin-3-ylmethyl)-carbamic acid tert-butyl ester (3 g, 13.7 mmol, 1 eq) in DCM (30 mL) was added NBS (2.5 g, 13.9 mmol, 1.1 eq). The resultant mixture was concentrated. The residue was purified by column chromatography on a silica gel (PE/EA=10/1 to EA, v/v) to give (6-amino-5-bromo-2-methyl-pyridin-3-ylmethyl)-carbamic acid tert-butyl ester (2 g, 50%) as a white solid. LRMS (M+H⁺) m/z calculated 316, 318, found 316, 318.

Step 4: Preparation of (6-amino-5-cyano-2-methyl-pyridin-3-ylmethyl)-carbamic Acid tert-butyl Ester

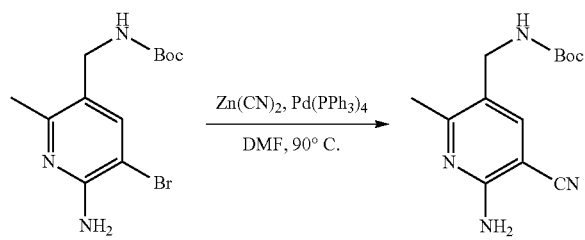 [SMILES: Cc1nc(N)c(Br)cc1CNC(=O)OC(C)(C)C ; Cc1nc(N)c(C#N)cc1CNC(=O)OC(C)(C)C]

The mixture of (6-amino-5-bromo-2-methyl-pyridin-3-ylmethyl)-carbamic acid tert-butyl ester (500 mg, 1.58 mmol, 1 eq), Zn(CN)₂ (185 mg, 1.58 mmol, 1.0 eq) and Pd(PPh₃)₄ (182 mg, 0.16 mmol, 0.1 eq) in DMF (20 mL) was heated to 95° C. and kept stirring for 3 h. Then it was cooled to rt, filtered, and the filtrate was concentrated. The residue was purified by column chromatography on a silica gel (PE/EA=2/1, v/v) to give (6-amino-5-cyano-2-methyl-pyridin-3-ylmethyl)-carbamic acid tert-butyl ester (300 mg, 72%) as a white solid. LRMS (M+H⁺) m/z calculated 263, found 263.

Step 5: Preparation of 2-amino-5-aminomethyl-6-methyl-nicotinonitrile Hydrochloride

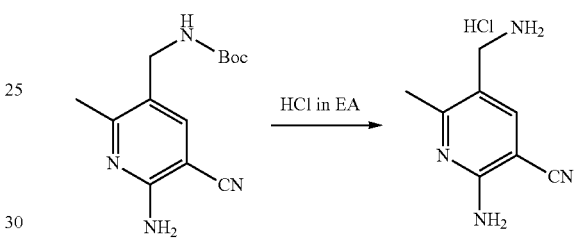

To the mixture of (6-amino-5-cyano-2-methyl-pyridin-3-ylmethyl)-carbamic acid tert-butyl ester (1.2 g, 4.6 mmol, 1 eq) in EA (10 mL) was added 10 mL of 6 N HCl in EA and kept stirring for 2 h. The reaction mixture was filtered, and the filter cake was washed with EA to give 2-amino-5-aminomethyl-6-methyl-nicotinonitrile hydrochloride (600 mg, 67%) as a white solid. LRMS (M+H⁺) m/z calculated 163, found 163.

Step 6: Preparation of N-((6-amino-5-cyano-2-methylpyridin-3-yl)methyl)-2-((3-chloroquinolin-6-yl)methyl)isonicotinamide

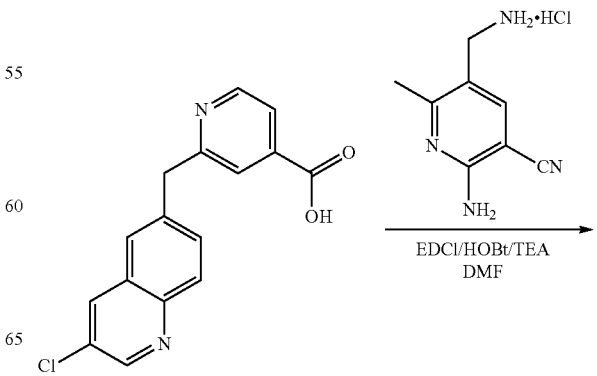

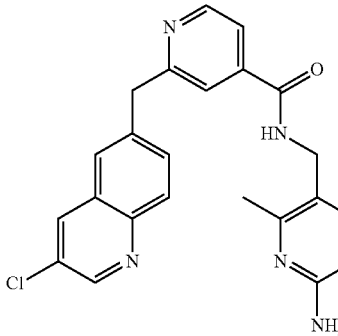

To a solution of 2-(3-chloro-quinolin-6-ylmethyl)-isonicotinic acid (80 mg, 0.27 mmol, 1 eq) in DMF (10 mL) was added 2-amino-5-aminomethyl-6-methyl-nicotinonitrile hydrochloride (54 mg, 0.27 mmol, 1 eq) followed by EDCI (78 mg, 0.41 mmol, 1.5 eq), HOBT (55 mg, 0.41 mmol, 1.5 eq) and TEA (82 mg, 0.81 mmol, 3.0 eq). The reaction mixture was heated to 45° C. kept stirring for overnight. Water was added, and the mixture was extracted with DCM. The organic layer was washed with water, dried over Na$_2$SO$_4$, filtered, and concentrated. The residue was purified by prep-HPLC to give N-((6-amino-5-cyano-2-methylpyridin-3-yl)methyl)-2-((3-chloroquinolin-6-yl)methyl)isonicotinamide (60 mg, 50%) as a white solid. LRMS (M+H$^+$) m/z calculated 443.1, found 442.8.

$^1$H NMR (DMSO-d$_6$, 400 MHz): δ 9.04 (t, 1H), 8.83 (d, 1H), 8.64 (d, 1H), 8.53 (s, 1H), 7.98 (d, 1H), 7.85 (s, 1H), 7.77 (s, 1H), 7.74 (d, 1H), 7.68 (s, 1H), 7.63 (s, 1H), 6.78 (s, 2H), 4.37 (s, 2H), 4.31 (d, 2H), 2.36 (s, 3H).

Example 27: Preparation of 2-amino-5-((2-((3-chloroquinolin-6-yl)methyl)isonicotinamido)methyl)-6-methylnicotinamide

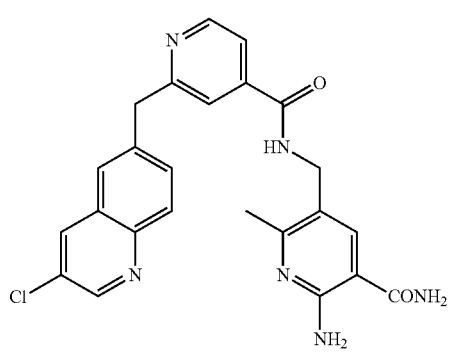

2-amino-5-((2-((3-chloroquinolin-6-yl)methyl)isonicotinamido)methyl)-6-methylnicotinamide

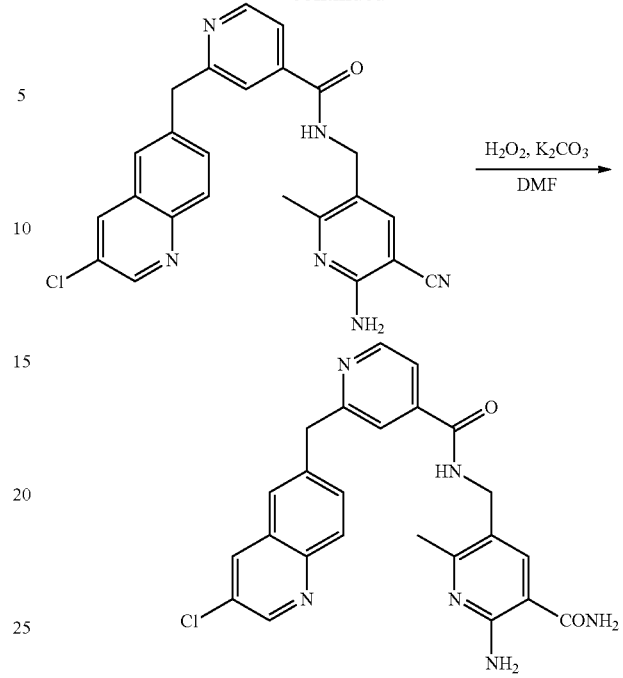

To a solution of N-((6-amino-5-cyano-2-methylpyridin-3-yl)methyl)-2-((3-chloroquinolin-6-yl)methyl)isonicotinamide (80 mg, 0.18 mmol, 1 eq) in DMF (5 mL) was added K$_2$CO$_3$ (50 mg, 0.36 mmol, 2.0 eq) followed by 30% of H$_2$O$_2$ (2 mL). The reaction mixture was heated to 50° C. kept stirring for 3 h. The reaction mixture was concentrated. The residue was purified by prep-HPLC to give 2-amino-5-((2-((3-chloroquinolin-6-yl)methyl)isonicotinamido) methyl)-6-methylnicotinamide (45 mg, 54%) as a white solid. LRMS (M+H$^+$) m/z calculated 461.1, found 461.1.

$^1$H NMR (DMSO-d$_6$, 400 MHz) δ 8.91 (t, 1H), 8.83 (d, 1H), 8.63 (d, 1H), 8.53 (d, 1H), 7.98 (d, 1H), 7.86 (s, 3H), 7.78 (s, 1H), 7.74 (d, 1H), 7.64 (d, 1H), 7.13-7.21 (m, 3H), 4.36 (s, 2H), 4.32 (d, 2H), 2.31 (s, 3H).

Example 28: Preparation of N-((6-amino-5-chloro-2-methylpyridin-3-yl)methyl)-2-((3-chloroquinolin-6-yl)methyl)isonicotinamide

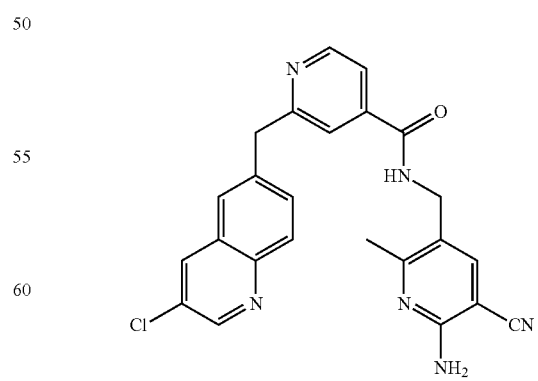

N-((6-amino-5-chloro-2-methylpyridin-3-yl)methyl)-2-((3-chloroquinolin-6-yl)methyl)isonicotinamide Step 1: Preparation of
6-amino-5-chloro-2-methyl-nicotinonitrile

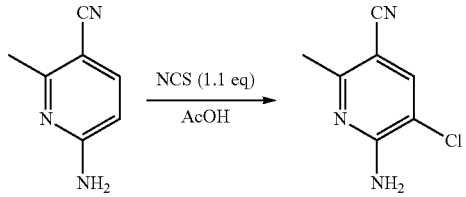

The mixture of 6-amino-2-methyl-nicotinonitrile (500 mg, 3.76 mmol, 1 eq) and NCS (1 g, 7.52 mmol, 2 eq) in AcOH (10 mL) was heated to 60° C. and kept stirring for 2 h. The reaction mixture was concentrated. The residue was purified by column chromatography on a silica gel (PE/EA=10/1 to EA, v/v) to give 6-amino-5-chloro-2-methyl-nicotinonitrile (400 mg, 64%) as a white solid. LRMS (M+H$^+$) m/z calculated 168, found 168.

Step 2: Preparation of
5-aminomethyl-3-chloro-6-methyl-pyridin-2-ylamine
Hydrochloride

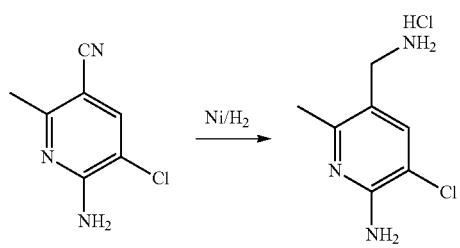

The mixture of 6-amino-5-chloro-2-methyl-nicotinonitrile (400 mg, 2.4 mmol, 1 eq), Rany Ni (400 mg) and conc. HCl (1 mL) in EtOH/MeOH (10 mL/10 mL) was stirred under H$_2$ (1 atm) at rt for overnight. The reaction mixture was filtered, and the filtrate was concentrated to give crude 5-aminomethyl-3-chloro-6-methyl-pyridin-2-ylamine hydrochloride (1 g) as a yellow solid. LRMS (M+H$^+$) m/z calculated 172, found 172.

Step 3: Preparation of N-((6-amino-5-cyano-2-methylpyridin-3-yl)methyl)-2-((3-chloroquinolin-6-yl)methyl)isonicotinamide

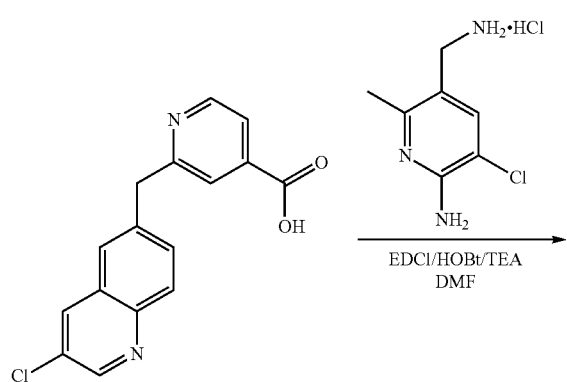

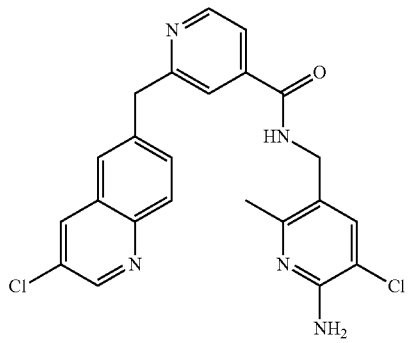

N-((6-amino-5-chloro-2-methylpyridin-3-yl)methyl)-2-((3-chloroquinolin-6-yl)methyl)isonicotinamide (15 mg, 12%) was prepared as described for N-((6-amino-5-cyano-2-methylpyridin-3-yl)methyl)-2-((3-chloroquinolin-6-yl)methyl)isonicotinamide (Example 26) as a white solid. LRMS (M+H$^+$) m/z calculated 452.1, found 451.8.

$^1$H NMR (DMSO-d$_6$, 400 MHz) δ 9.03 (t, 1H), 8.83 (d, 1H), 8.63 (d, 1H), 8.52 (d, 1H), 7.98 (d, 1H), 7.85 (s, 1H), 7.72-7.76 (m, 2H), 7.62 (d, 1H), 7.41 (s, 1H), 6.11 (s, 2H), 4.36 (s, 2H), 4.29 (d, 2H), 2.29 (s, 3H).

Example 29: Preparation of N-((6-amino-4-methyl-pyridin-3-yl)methyl)-2-((3-chloroquinolin-6-yl)methyl)isonicotinamide

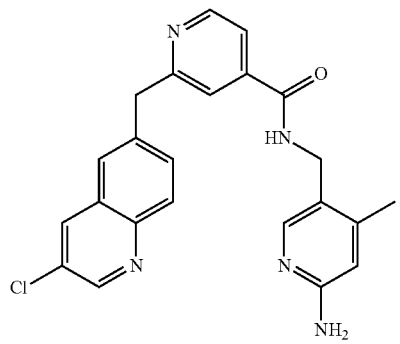

N-((6-amino-4-methylpyridin-3-yl)methyl)-2-((3-chloroquinolin-6-yl)methyl)isonicotinamide

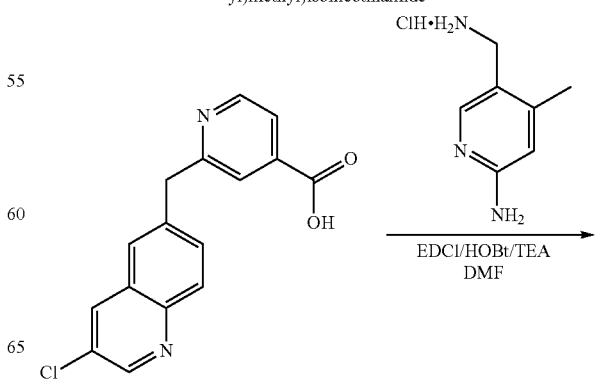

297

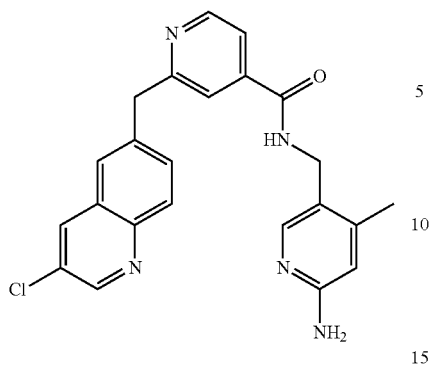

N-((6-amino-4-methylpyridin-3-yl)methyl)-2-((3-chloroquinolin-6-yl)methyl)isonicotinamide (25 mg, 22%) was prepared as described for N-((6-amino-5-cyano-2-methylpyridin-3-yl)methyl)-2-((3-chloroquinolin-6-yl)methyl)isonicotinamide (Example 26) as a white solid. LRMS (M+H$^+$) m/z calculated 418.1, found 417.8.

$^1$H NMR (DMSO-d$_6$, 300 MHz) δ 8.93 (t, 1H), 8.83 (d, 1H), 8.62 (d, 1H), 8.52 (d, 1H), 7.98 (d, 1H), 7.84 (s, 1H), 7.71-7.77 (m, 2H), 7.61 (d, 1H), 6.24 (s, 1H), 5.75 (s, 2H), 4.37 (s, 2H), 4.29 (d, 2H), 2.14 (s, 3H).

Example 30: Preparation of N-((6-amino-2-(trifluoromethyl)pyridin-3-yl)methyl)-2-((3-chloroquinolin-6-yl)methyl)isonicotinamide

298

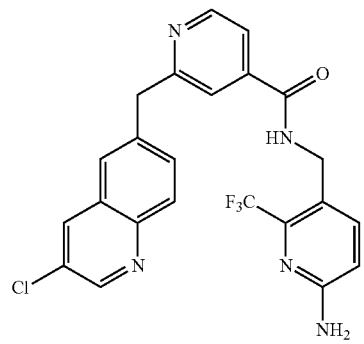

N-((6-amino-2-(trifluoromethyl)pyridin-3-yl)methyl)-2-((3-chloroquinolin-6-yl)methyl)isonicotinamide (45 mg, 35%) was prepared as described for N-((6-amino-5-cyano-2-methylpyridin-3-yl)methyl)-2-((3-chloroquinolin-6-yl)methyl)isonicotinamide (Example 26) as a white solid. LRMS (M+H$^+$) m/z calculated 472.1, found 471.8.

$^1$H NMR (DMSO-d$_6$, 400 MHz) δ 9.13 (t, 1H), 8.83 (d, 1H), 8.65 (d, 1H), 8.53 (d, 1H), 7.98 (d, 1H), 7.86 (s, 1H), 7.77 (s, 1H), 7.74 (d, 1H), 7.64 (d, 1H), 7.52 (d, 1H), 6.65 (d, 1H), 6.44 (s, 2H), 4.44 (d, 2H), 4.37 (s, 2H).

Example 31: Preparation of N-((1-aminoisoquinolin-6-yl)methyl)-2-((3-chloroquinolin-6-yl)methyl)isonicotinamide

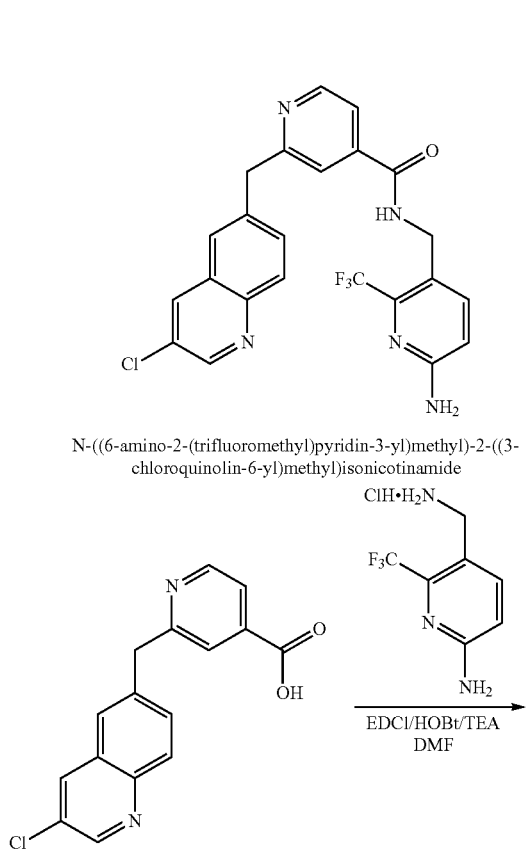

N-((6-amino-2-(trifluoromethyl)pyridin-3-yl)methyl)-2-((3-chloroquinolin-6-yl)methyl)isonicotinamide

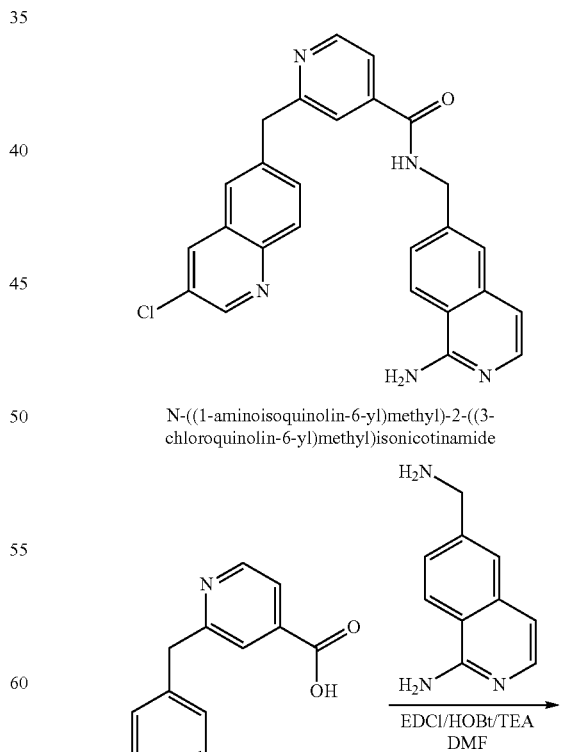

N-((1-aminoisoquinolin-6-yl)methyl)-2-((3-chloroquinolin-6-yl)methyl)isonicotinamide

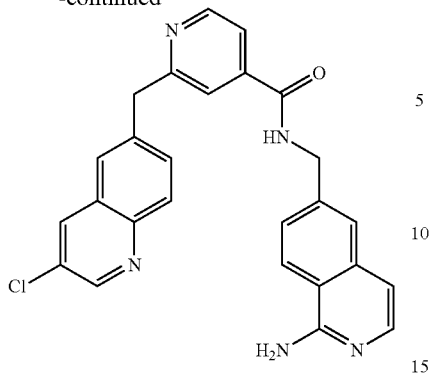

N-((1-aminoisoquinolin-6-yl)methyl)-2-((3-chloroquinolin-6-yl)methyl)isonicotinamide (65 mg, 45%) was prepared as described for N-((6-amino-5-cyano-2-methylpyridin-3-yl)methyl)-2-((3-chloroquinolin-6-yl)methyl)isonicotinamide (Example 26) as a white solid. LRMS (M+H$^+$) m/z calculated 454.1, found 453.9.

$^1$H NMR (DMSO-d$_6$, 400 MHz) δ 9.40 (t, 1H), 8.83 (d, 1H), 8.67 (d, 1H), 8.54 (s, 1H), 8.13 (d, 1H), 7.97 (d, 1H), 7.87 (s, 1H), 7.81 (s, 1H), 7.74-7.76 (m, 2H), 7.69 (d, 1H), 7.55 (s, 1H), 7.40 (d, 1H), 6.84 (d, 1H), 6.74 (s, 2H), 4.61 (d, 2H), 4.38 (s, 2H).

Example 32: Preparation of 2-(3-chloro-quinolin-6-ylmethyl)-N-(6-fluoro-1H-indazol-5-ylmethyl)-isonicotinamide

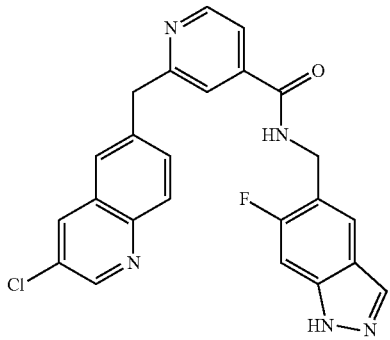

2-(3-Chloro-quinolin-6-ylmethyl)-N-(6-fluoro-1H-indazol-5-ylmethyl)-isonicotinamide Step 1: Preparation of 4-amino-2-fluoro-5-methyl-benzonitrile

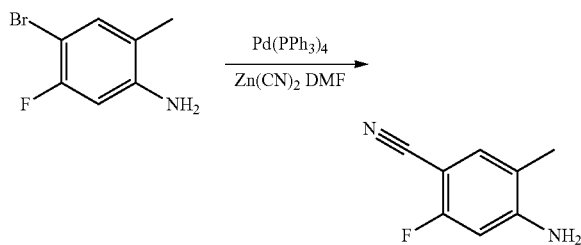

To a solution of 4-bromo-5-fluoro-2-methyl-phenylamine (20 g, 98.0 mmol, 1.0 eq) in DMF (100 mL) was added Zn(CN)$_2$ (28.7 g, 245 mmol, 2.5 eq), followed by addition of Pd(PPh$_3$)$_4$ under N$_2$ protection. The mixture was stirred at 90° C. for overnight. The mixture was concentrated in vacuo and the residue was dissolved in water, extracted with EA. The combined extracts were dried and concentrated. The residue was purified by column chromatography on a silica gel column (PE/EA=10/1, v/v) to afford 4-amino-2-fluoro-5-methyl-benzonitrile as a yellow solid (13.68 g, 92%).

Step 2: Preparation of 6-fluoro-1H-indazole-5-carbonitrile

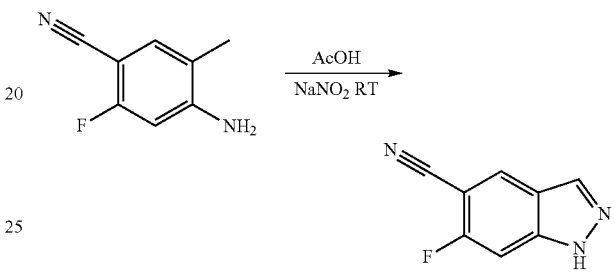

To a solution of 4-amino-2-fluoro-5-methyl-benzonitrile (13.68 g, 90.59 mmol, 1.0 eq) in AcOH (450 mL) was added NaNO$_2$ (7.5 g, 108.7 mmol, 1.2 eq). The mixture was stirred at rt for overnight. Upon completion, aqueous NaOH (50%) was added to the reaction mixture until pH 7-8. The mixture was extracted with EA. The organic layer was concentrated under pressure. The residue was purified by column chromatography on a silica gel column (PE/EA=15/1, v/v) to afford 6-fluoro-1H-indazole-5-carbonitrile as a white solid (5 g, 34%).

Step 3: Preparation of 6-fluoro-1-(tetrahydro-pyran-2-yl)-1H-indazole-5-carbonitrile

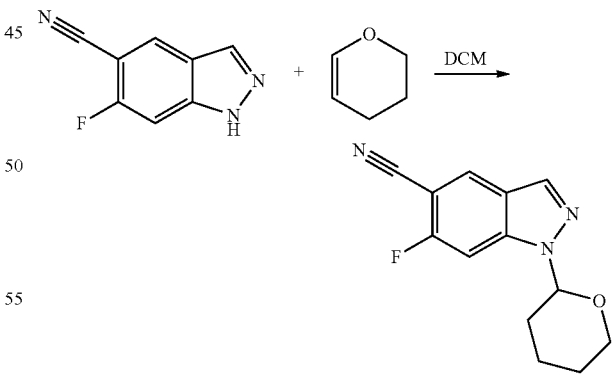

To a solution of 6-fluoro-1H-indazole-5-carbonitrile (5 g, 31.05 mmol, 1.0 eq) and 3,4-dihydro-2H-pyran (5.25 g, 62.1 mmol, 2 eq) in DCM (50 mL) was added PTSA (590 mg, 3.11 mmol, 0.1 eq) and the mixture was stirred at rt overnight. Solvent was removed in vacuo. The residue was dissolved in EA, washed with water, brine and dried over Na$_2$SO$_4$. The combined extracts were dried and concentrated. The residue was purified by chromatography on a silica gel column (PE/EA=15/1, v/v) to afford 6-fluoro-1-(tetrahydro-pyran-2-yl)-1H-indazole-5-carbonitrile as a brown solid (4.39 g, 57%).

Step 4: Preparation of (6-fluoro-1-(tetrahydro-2H-pyran-2-yl)-1H-indazol-5-yl)methanamine

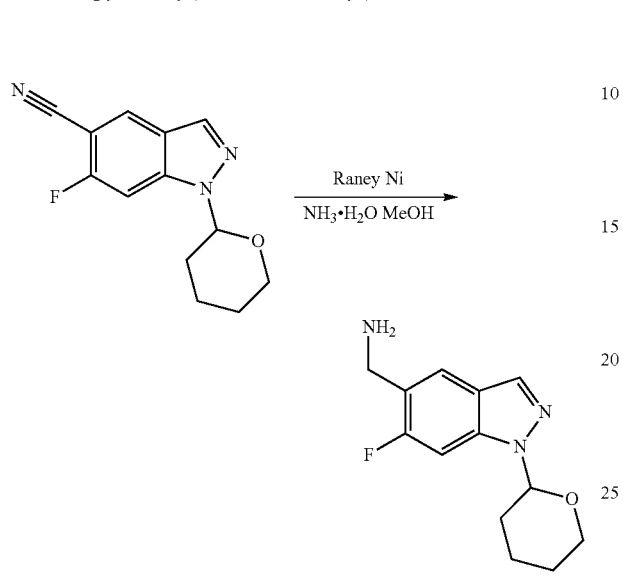

To a solution of 6-fluoro-1-(tetrahydro-pyran-2-yl)-1H-indazole-5-carbonitrile (4.39 g, 17.92 mmol, 1.0 eq) in MeOH (20 mL) was added Raney Ni (800 mg) under H2. The mixture was stirred at rt overnight. The reaction mixture was filtered and the filtrate was purified by chromatography on a silica gel column (PE/EA=15/1, v/v) to give (6-fluoro-1-(tetrahydro-2H-pyran-2-yl)-1H-indazol-5-yl)methanamine (3.8 g, 85%) as a white solid.

Step 5: Preparation of (6-fluoro-1H-indazol-5-yl)methanamine Hydrochloride

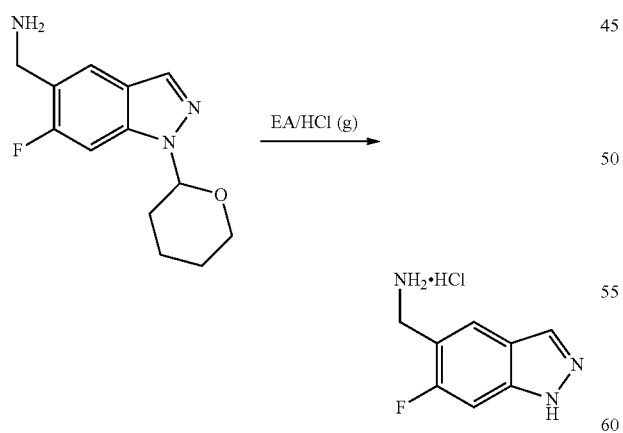

To a solution of C-[6-fluoro-1-(tetrahydro-pyran-2-yl)-1H-indazol-5-yl]-methylaminer (3.43 g, 15.26 mmol, 1 eq) in EA was added EA/HCl (10 M). The mixture was stirred at rt for 3 h. The reaction mixture was filtered and the filtrate was concentrated to give (6-fluoro-1H-indazol-5-yl)methanamine hydrochloride (3.43 mg, crude).

Step 6: Preparation of 2-(3-Chloro-quinolin-6-ylm-ethyl)-N-(6-fluoro-1H-indazol-5-ylmethyl)-isonicoti-namide

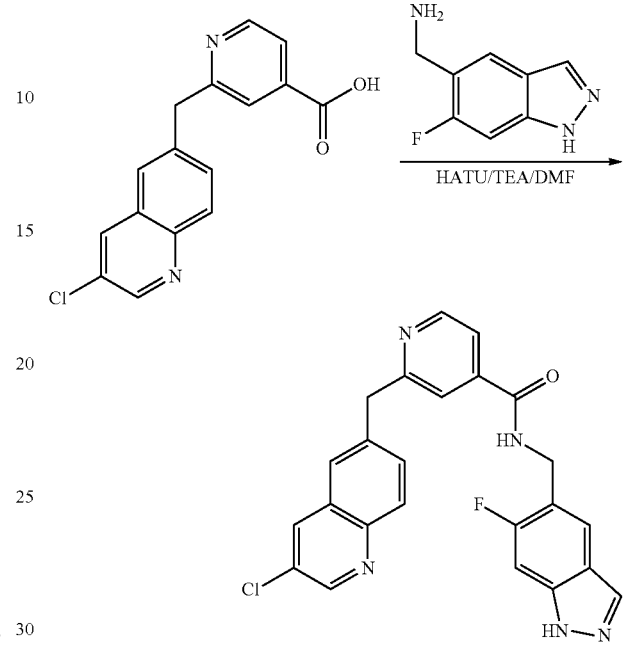

To a solution of C-(6-fluoro-1H-indazol-5-yl)-methylamine hydrochloride (80 mg, 0.4 mmol, 1.5 eq) in DMF (10 mL) was added 2-(3-chloro-quinolin-6-ylmethyl)-isonico-tinic acid (80 mg, 0.26 mmol, 1 eq), HATU (122 mg, 0.32 mmol/1.2 eq), and TEA (1 mL). The reaction mixture was stirred at rt for 3 h. Then it was quenched with water, extracted with DCM. The combined extracts were dried and concentrated, and the residue was purified by prep-HPLC to give 2-(3-Chloro-quinolin-6-ylmethyl)-N-(6-fluoro-1H-indazol-5-ylmethyl)-isonicotinamide (30 mg, 27%) as a white solid. LCMS (M+H⁺) m/z calculated 446.1, found 446.0.
$^1$H NMR (DMSO-d6, 400 MHz) δ 13.09 (s, 1H), 9.26-9.28 (t, 1H), 8.83-8.84 (d, 1H), 8.65-8.66 (d, 1H), 8.52-8.53 (d, 1H), 8.06 (s, 1H), 7.97-7.99 (d, 1H), 7.86 (s, 1H), 7.80 (s, 1H), 7.68-7.76 (m, 2H), 7.67-7.68 (d, 1H), 7.32-7.35 (d, 1H), 4.56-4.57 (d, 2H), 4.38 (s, 2H), 2.50 (s, 3H).

Example 33: Preparation of N-((3-chloro-6-fluoro-1H-indol-5-yl)methyl)-2-((3-chloroquinolin-6-yl)methyl)isonicotinamide

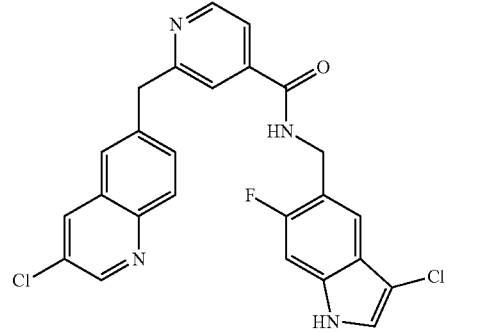

N-((3-chloro-6-fluoro-1H-indol-5-yl)methyl)-2-((3-chloroquinolin-6-yl)methyl)isonicotinamide

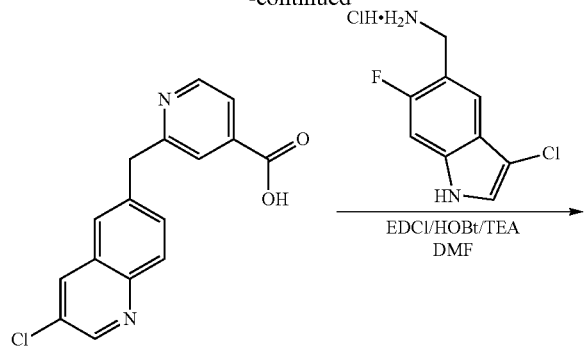

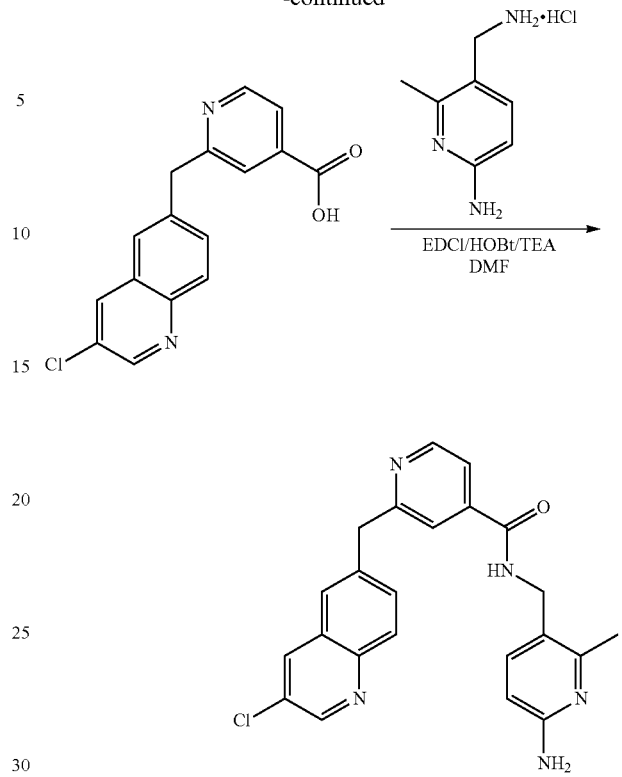

N-((3-chloro-6-fluoro-1H-indol-5-yl)methyl)-2-((3-chloroquinolin-6-yl)methyl)isonicotinamide (50 mg, 33%) was prepared as described for N-((6-amino-5-cyano-2-methylpyridin-3-yl)methyl)-2-((3-chloroquinolin-6-yl)methyl)isonicotinamide (Example 26) as a yellow solid. LRMS (M+H$^+$) m/z calculated 479.1, found 478.9.

$^1$H NMR (DMSO-d$_6$, 400 MHz): δ 11.42 (br, 1H), 9.25 (t, 1H), 8.83 (s, 1H), 8.65 (d, 1H), 8.53 (s, 1H), 7.98 (d, 1H), 7.85 (s, 1H), 7.79 (s, 1H), 7.74 (d, 1H), 7.66 (d, 1H), 7.51 (s, 1H), 7.44 (d, 1H), 7.22 (d, 1H), 4.58 (d, 2H), 4.37 (s, 2H).

N-((6-amino-2-methylpyridin-3-yl)methyl)-2-((3-chloroquinolin-6-yl)methyl)isonicotinamide (60 mg, 45%) was prepared as described for N-((6-amino-5-cyano-2-methylpyridin-3-yl)methyl)-2-((3-chloroquinolin-6-yl)methyl)isonicotinamide (Example 26) as a yellow solid. LRMS (M+H$^+$) m/z calculated 418.1, found 417.8.

$^1$H NMR (DMSO-d$_6$, 400 MHz) δ 9.00 (t, 1H), 8.83 (d, 1H), 8.63 (d, 1H), 8.53 (d, 1H), 7.98 (d, 1H), 7.85 (s, 1H), 7.73-7.76 (m, 2H), 7.62 (d, 1H), 7.77 (d, 1H), 6.26 (d, 1H), 5.85 (s, 2H), 4.36 (s, 2H), 4.28 (d, 2H), 2.28 (s, 3H).

Example 34: Preparation of N-((6-amino-2-methylpyridin-3-yl)methyl)-2-((3-chloroquinolin-6-yl)methyl)isonicotinamide Example 35: Preparation of N-((6-amino-2,4-dimethylpyridin-3-yl)methyl)-2-((3-chloroquinolin-6-yl)methyl)isonicotinamide

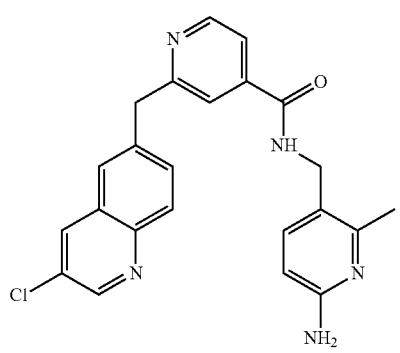

N-((6-amino-2-methylpyridin-3-yl)methyl)-2-((3-chloroquinolin-6-yl)methyl)isonicotinamide

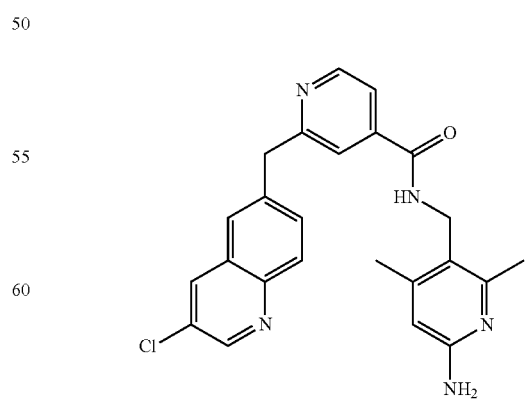

N-((6-amino-2,4-dimethylpyridin-3-yl)methyl)-2-((3-chloroquinolin-6-yl)methyl)isonicotinamide

305

-continued

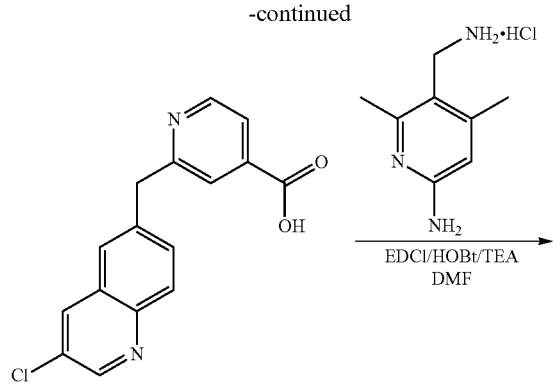

306

-continued

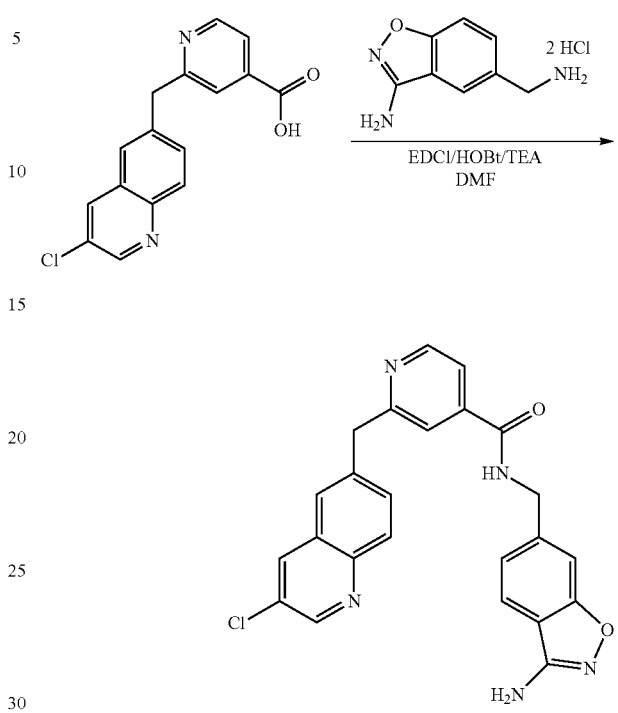

N-((6-amino-2,4-dimethylpyridin-3-yl)methyl)-2-((3-chloroquinolin-6-yl)methyl)isonicotinamide (40 mg, 29%) was prepared as described for N-((6-amino-5-cyano-2-methylpyridin-3-yl)methyl)-2-((3-chloroquinolin-6-yl)methyl)isonicotinamide (Example 26) as a yellow solid. LRMS (M+H$^+$) m/z calculated 432.2 found 432.0.

$^1$H NMR (DMSO-d$_6$, 400 MHz) δ 8.83 (d, 1H), 8.64 (t, 1H), 8.60 (d, 1H), 8.53 (s, 1H), 7.97 (d, 1H), 7.84 (s, 2H), 7.72-7.75 (m, 2H), 7.60 (d, 1H), 6.11 (s, 1H), 5.67 (s, 2H), 4.33-4.35 (m, 4H), 2.29 (s, 3H), 2.15 (s, 3H).

Example 36: Preparation of N-((3-aminobenzo[d]isoxazol-6-yl)methyl)-2-((3-chloroquinolin-6-yl)methyl)isonicotinamide N-((3-aminobenzo[d]isoxazol-6-yl)methyl)-2-((3-chloroquinolin-6-yl)methyl)isonicotinamide (65 mg, 46%) was prepared as described for N-((6-amino-5-cyano-2-methylpyridin-3-yl)methyl)-2-((3-chloroquinolin-6-yl)methyl)isonicotinamide (Example 26) as a yellow solid. LRMS (M+H$^+$) m/z calculated 444.1 found 443.9.

$^1$H NMR (DMSO-d$_6$, 400 MHz) δ 9.38 (t, 1H), 8.83 (d, 1H), 8.67 (s, 1H), 8.53 (d, 1H), 7.99 (d, 1H), 7.86 (s, 1H), 7.81 (s, 1H), 7.76 (d, 2H), 7.67 (d, 1H), 7.36 (s, 1H), 7.21 (d, 1H), 6.38 (s, 2H), 4.60 (d, 2H), 4.38 (s, 2H).

Example 37: Preparation of N-(5-Chloro-1H-indazol-3-ylmethyl)-2-(3-chloro-quinolin-6-ylmethyl)-isonicotinamide

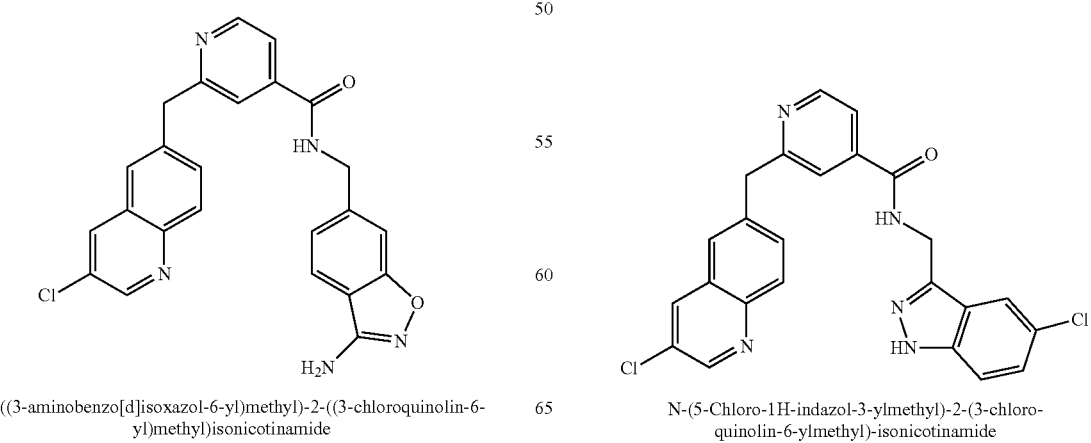

N-((3-aminobenzo[d]isoxazol-6-yl)methyl)-2-((3-chloroquinolin-6-yl)methyl)isonicotinamide N-(5-Chloro-1H-indazol-3-ylmethyl)-2-(3-chloro-quinolin-6-ylmethyl)-isonicotinamide

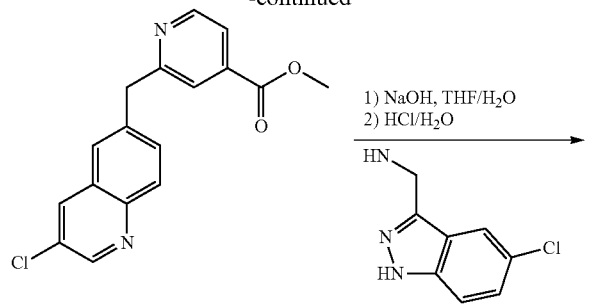
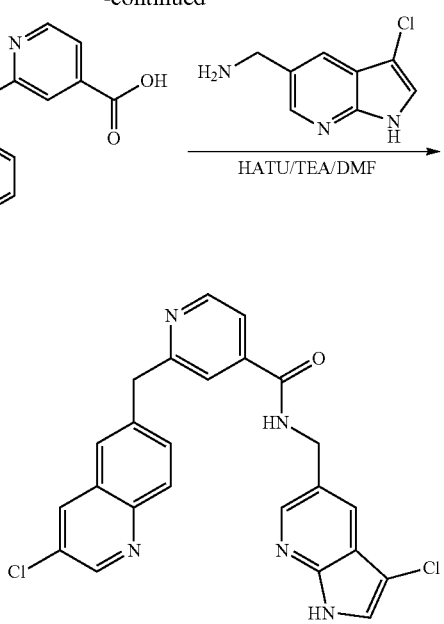

To a solution of 2-(3-chloro-quinolin-6-ylmethyl)-isonicotinic acid methyl ester (1.9 g, 6.1 mmol, 1.0 eq) in THF (15 mL)/H$_2$O (15 mL) was added NaOH (360 mg, 9.11 mmol, 1.5 eq). The mixture was stirred at 40° C. for 1 h and was acidified to pH 5 with 1 N HCl solution to get 0.8 g of product. To a solution of the above crude product (100 mg, 0.33 mmol, 1.0 eq) and C-(5-chloro-1H-indazol-3-yl)-methylamine (120 mg, 0.66 mmol, 2.0 eq) in DMF (8 mL) was added HATU (152 mg, 0.4 mmol, 1.2 eq) and Et$_3$N (0.15 mL, 0.99 mmol, 3 eq). The mixture was stirred at rt for overnight, concentrated and purified was purified by flash chromatography on a silica gel column (DCM/MeOH=10/1, v/v) to give N-(5-chloro-1H-indazol-3-ylmethyl)-2-(3-chloro-quinolin-6-ylmethyl)-isonicotinamide (46 mg, 30% for 2 steps) as a white solid.

LRMS (M+H$^+$) m/z calculated 462.1, found 461.9.

$^1$H NMR (DMSO-d$_6$, 400 MHz) δ 13.09 (s, 1H), 9.40 (m, 1H), 8.82-8.83 (d, 1H), 8.63-8.64 (d, 1H), 8.51-8.52 (d, 1H), 7.96-7.98 (d, 1H), 7.89 (s, 1H), 7.84 (s, 1H), 7.78 (s, 1H), 7.74 (d, 1H), 7.64 (d, 1H), 7.52-7.54 (d, 1H), 7.32-7.34 (dd, 1H), 4.77-4.78 (d, 2H), 4.36 (s, 2H).

Example 38: Preparation of N-(3-Chloro-1H-pyrrolo[2,3-b]pyridin-5-ylmethyl)-2-(3-chloro-quinolin-6-ylmethyl)-isonicotinamide To a solution of 2-(3-chloro-quinolin-6-ylmethyl)-isonicotinic acid (100 mg, 0.33 mmol, 1.0 eq) and C-(3-chloro-1H-pyrrolo[2,3-b]pyridin-5-yl)-methylamine (120 mg, 0.66 mmol, 2.0 eq) in DMF (8 mL) was added HATU (152 mg, 0.4 mmol, 1.2 eq) and Et$_3$N (0.15 mL, 0.99 mmol, 3 eq). The mixture was stirred at rt for overnight, concentrated and purified was purified by flash chromatography on a silica gel column (DCM/MeOH=10/1, v/v) to give N-(5-chloro-1H-indazol-3-ylmethyl)-2-(3-chloro-quinolin-6-ylmethyl)-isonicotinamide (13 mg, 8.5%) as a white solid. LRMS (M+H+) m/z calculated 462.1, found 461.9.

$^1$H NMR (DMSO-d$_6$, 400 MHz) δ 11.96 (s, 1H), 9.33 (m, 1H), 8.82 (d, 1H), 8.65 (d, 1H), 8.51-8.52 (d, 1H), 8.30 (d, 1H), 7.98 (d, 1H), 7.86 (m, 2H), 7.63-7.77 (m, 4H), 4.57-4.59 (d, 2H), 4.36 (s, 2H).

Example 39: Preparation of N-(6-Amino-2-methyl-pyridin-3-ylmethyl)-2-(3-chloro-quinolin-6-ylmethyl)-isonicotinamide

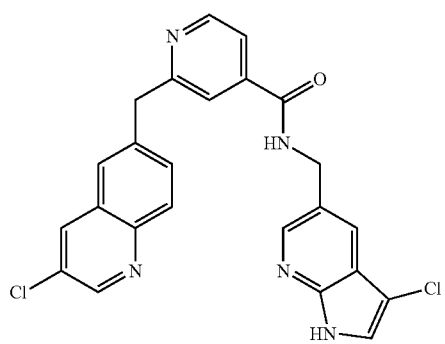

N-(3-Chloro-1H-pyrrolo[2,3-b]pyridin-5-ylmethyl)-2-(3-chloro-quinolin-6-ylmethyl)-isonicotinamide

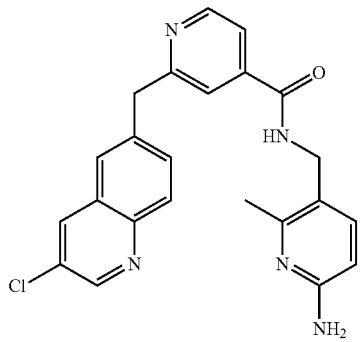

N-(6-Amino-2-methyl-pyridin-3-ylmethyl)-2-(3-chloro-quinolin-6-ylmethyl)-isonicotinamide

309

-continued

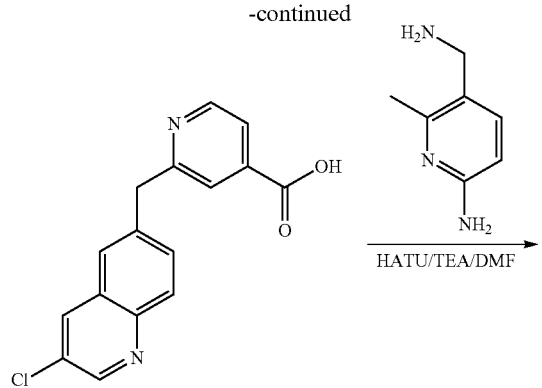

N-(6-amino-2-methyl-pyridin-3-ylmethyl)-2-(3-chloro-quinolin-6-ylmethyl)-isonicotinamide (41 mg, 30%) was prepared as described for N-(5-chloro-1H-indazol-3-ylmethyl)-2-(3-chloro-quinolin-6-ylmethyl)-isonicotinamide (Example 37) as a white solid.

LRMS (M+H$^+$) m/z calculated 418.1, found 418.0.

$^1$H NMR (DMSO-d$_6$, 400 MHz) δ 8.99 (m, 1H), 8.83 (d, 1H), 8.62-8.63 (d, 1H), 8.53 (d, 1H), 7.96-7.99 (d, 1H), 7.85 (s, 1H), 7.72-7.76 (m, 2H), 7.61-7.63 (d, 1H), 6.21-6.23 (d, 2H), 5.75 (s, 2H), 4.36 (s, 2H), 4.27 (d, 2H), 2.27 (s, 2H).

Example 40: Preparation of N-(3-Chloro-4-fluoro-1H-indol-5-ylmethyl)-2-(3-chloro-quinolin-6-ylmethyl)-isonicotinamide

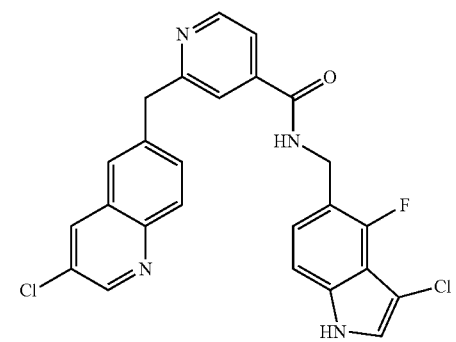

N-(3-Chloro-4-fluoro-1H-indol-5-ylmethyl)-2-(3-chloro-quinolin-6-ylmethyl)-isonicotinamide

310

-continued

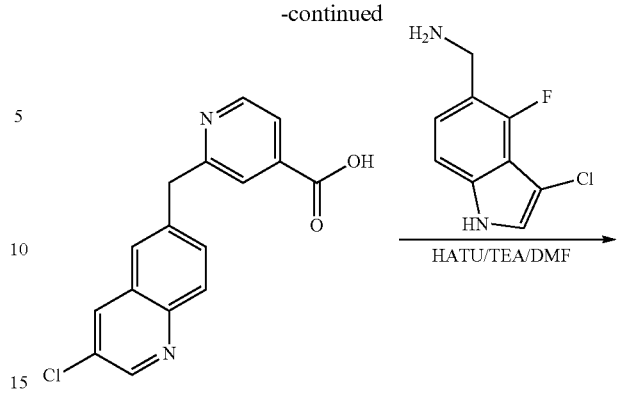

N-(3-chloro-4-fluoro-1H-indol-5-ylmethyl)-2-(3-chloro-quinolin-6-ylmethyl)-isonicotinamide (41 mg, 26%) was prepared as described for N-(5-chloro-1H-indazol-3-ylmethyl)-2-(3-chloro-quinolin-6-ylmethyl)-isonicotinamide (Example 37) as a white solid.

LRMS (M+H$^+$) m/z calculated 479.1, found 479.0.

$^1$H NMR (DMSO-d$_6$, 400 MHz) δ 11.59 (s, 1H), 9.23 (m, 1H), 8.82 (d, 1H), 8.63 (d, 1H), 8.52 (d, 1H), 7.98 (d, 1H), 7.84 (s, 1H), 7.78 (s, 1H), 7.72-7.74 (d, 1H), 7.63-7.64 (d, 1H), 7.50-7.51 (d, 1H), 7.12-7.19 (m, 2H), 4.55-4.57 (d, 2H), 4.36 (s, 2H).

Example 41: Preparation of 2-(3-chloro-quinolin-6-ylmethyl)-N-(6-fluoro-1H-indol-5-ylmethyl)-isonicotinamide

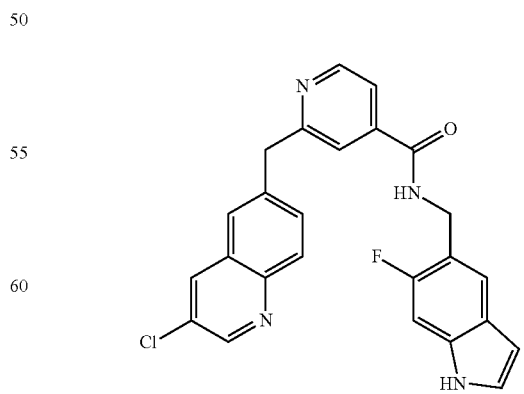

2-(3-Chloro-quinolin-6-ylmethyl)-N-(6-fluoro-1H-indol-5-ylmethyl)-isonicotinamide -continued

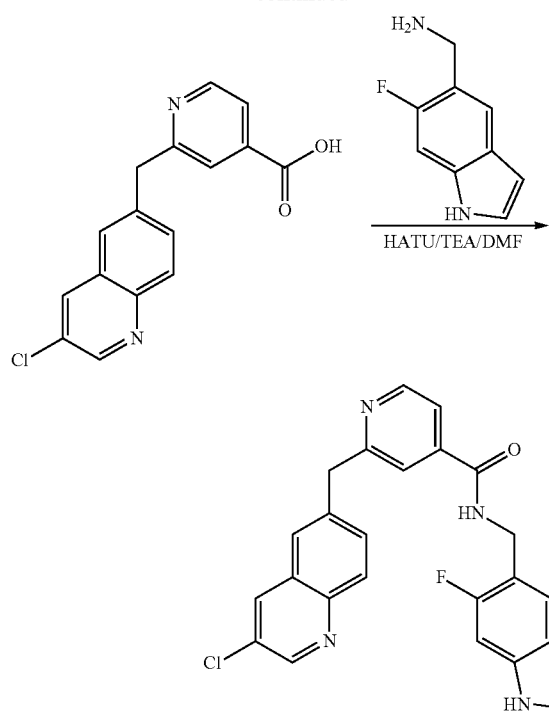

2-(3-Chloro-quinolin-6-ylmethyl)-N-(6-fluoro-1H-indol-5-ylmethyl)-isonicotinamide (71 mg, 48%) was prepared as described for N-(5-chloro-1H-indazol-3-ylmethyl)-2-(3-chloro-quinolin-6-ylmethyl)-isonicotinamide (Example 37) as a white solid. LRMS (M+H⁺) m/z calculated 445.1, found 445.0.

¹H NMR (DMSO-d₆, 400 MHz) δ 11.11 (s, 1H), 9.21 (m, 1H), 8.82 (d, 1H), 8.63 (d, 1H), 8.53 (d, 1H), 7.96 (d, 1H), 7.66-7.85 (m, 4H), 7.47 (d, 1H), 7.17-7.31 (m, 1H), 7.13 (d, 1H), 6.38 (d, 2H), 4.56 (d, 2H), 4.36 (s, 2H).

Example 42: Preparation of 2-((3-chloroquinolin-6-yl)methyl)-N-((2-methyl-6-(methylamino)pyridin-3-yl)methyl)isonicotinamide

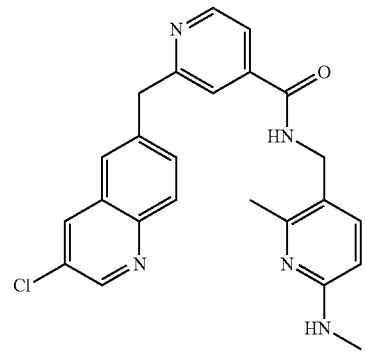

2-((3-chloroquinolin-6-yl)methyl)-N-((2-methyl-6-(methylamino)pyridin-3-yl)methyl)isonicotinamide -continued

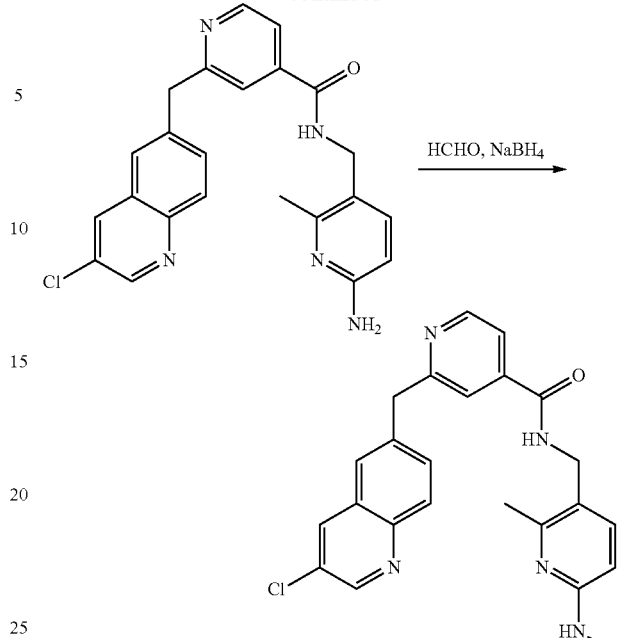

To a solution of sodium methoxide (33 mg, 0.6 mmol, 5.0 eq) in MeOH (20 mL), were added paraformaldehyde (36 mg, 1.2 mmol, 10.0 eq) and N-(6-amino-2-methyl-pyridin-3-ylmethyl)-2-(3-chloro-quinolin-6-ylmethyl)-isonicotinamide (50 mg, 0.12 mmol, 1.0 eq). The mixture was stirred at rt for 24 h until TLC indicated the SM was disappeared. Then sodium borohydride (14 mg, 0.36 mmol, 3.0 eq) was added, and the mixture was stirred at 40° C. for additional 3 h. The resulting mixture was concentrated and dissolved in EtOAc. The organic phase was washed with water and brine, dried and concentrated in vacuum. The residue was purified by prep-HPLC to give 2-((3-chloroquinolin-6-yl)methyl)-N-((2-methyl-6-(methylamino)pyridin-3-yl)methyl)isonicotinamide (13 mg, 25%). LRMS (M+H⁺) m/z calculated 432.2, found 431.8.

¹H NMR (DMSO-d6, 400 MHz) δ 8.98 (t, 1H), 8.82 (d, 1H), 8.63 (d, 1H), 8.52 (d, 1H), 7.98 (d, 1H), 7.85 (s, 1H), 7.74 (d, 1H), 7.72 (d, 1H), 7.62 (d, 1H), 7.26 (d, 1H), 6.23 (d, 1H), 6.19 (d, 1H), 4.36 (s, 2H), 4.29 (d, 2H), 2.72 (d, 3H), 2.31 (s, 3H).

Example 43: Preparation of N-((6-amino-2-cyclopropylpyridin-3-yl)methyl)-2-((3-chloroquinolin-6-yl)methyl)isonicotinamide

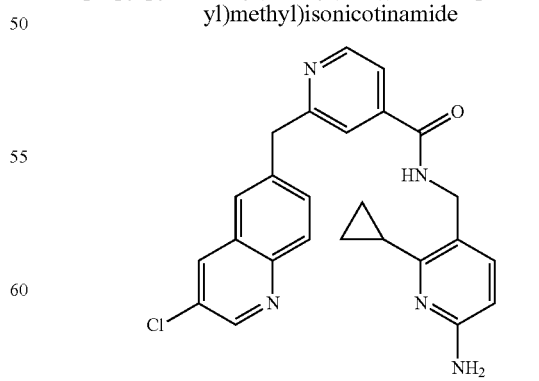

N-((6-amino-2-cyclopropylpyridin-3-yl)methyl)-2-((3-chloroquinolin-6-yl)methyl)isonicotinamide

Step 1: Preparation of 6-amino-2-chloro-nicotinonitrile

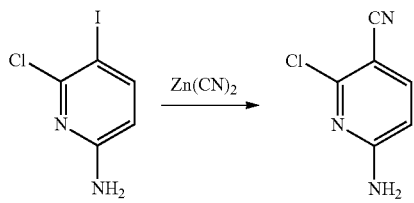

To a solution of 6-chloro-5-iodo-pyridin-2-ylamine (25.0 g, 98 mmol, 1.0 eq) in DMF (200 mL) was added Zn(CN)₂ (5.7 g, 49 mmol, 0.5 eq) and Pd(PPh₃)₄ (5.66 g, 4.9 mmol, 0.05 eq). The mixture was stirred at 65° C. overnight under N₂. Then EA and water was added. The organic layer was concentrated, and purified by silica gel chromatography (EA/PE=1/1, v/v) to afford 6-amino-2-chloro-nicotinonitrile (12.2 g, 81%) as a yellow solid.

Step 2: Preparation of 6-amino-2-cyclopropyl-nicotinonitrile

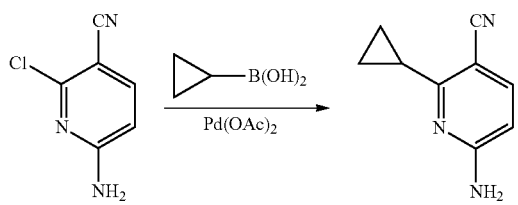

To a mixture of 6-amino-2-chloro-nicotinonitrile (3.0 g, 19.6 mmol, 1 eq), cyclopropylboronic acid (2.2 g, 25.5 mmol, 1.3 eq), K₃PO₄ (12.4 g, 58.8 mmol, 3 eq), tricyclohexylphosphine (550 mg, 1.96 mmol, 0.1 eq) in 200 mL of toluene and 10 mL of water was added Pd(OAc)₂ (220 mg, 0.98 mmol, 0.05 eq). The reaction mixture was stirred under reflux for 48 h. After cooling to rt, the solvent was removed by evaporation. The residue was diluted with water and extracted with EA. The combined organic layers were dried and concentrated. The residue was purified by chromatography on silica gel column (EA/PE=1/1, v/v) to give 6-amino-2-cyclopropyl-nicotinonitrile (1.6 g, 51%) as a yellow solid.

Step 3: Preparation of 5-(aminomethyl)-6-cyclopropylpyridin-2-amine Hydrochloride

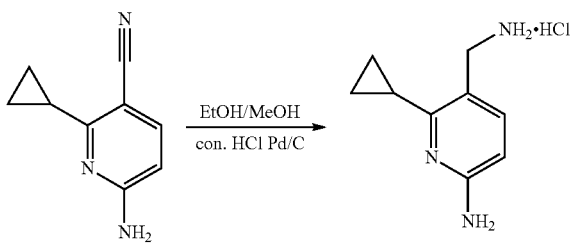

To a solution of 6-amino-2-cyclopropyl-nicotinonitrile (700 mg, 4.4 mmol, 1 eq) was added in MeOH (10 mL) and EtOH (10 mL), followed by addition of conc. HCl. Then Pd/C was added under N₂ and kept stirring at 40° C. overnight. After filtration and washed with MeOH, the organic phase was concentrated under reduce pressure to give the crude product (500 mg, 69%), which was used directly in the next reaction without further purification.

Step 4: Preparation of tert-butyl (6-amino-2-cyclopropylpyridin-3-yl)methylcarbamate

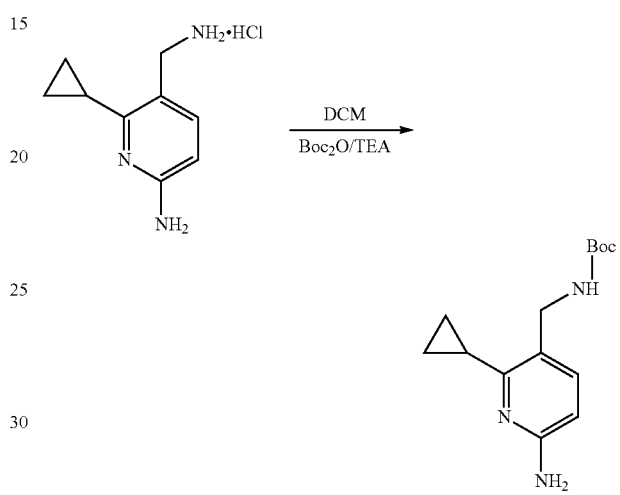

To a solution of 5-ainomethyl-6-cyclopropyl-pyridin-2-ylamine (500 mg, 3.06 mmol, 1 eq) and Boc₂O (920 mg, 3.68 mmol, 1.2 eq) in DCM was added TEA (1 mL) kept stirring at rt for 2 h. Then it was washed with water and extracted with EA. After concentration under reduce pressure, the residue was purified by chromatography on silica gel column (EA/PE=1/2, v/v) to give the target compound (300 mg, 37%).

Step 5: Preparation of 5-(aminomethyl)-6-cyclopropylpyridin-2-amine Hydrochloride

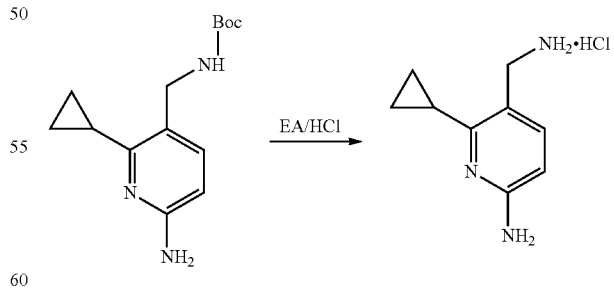

To a solution of aforementioned compound (6-amino-2-cyclopropyl-pyridin-3-ylmethyl)-carbamic acid tert-butyl ester in EA was added EA/HCl with stirring at rt for 2 h. After filtration and washed with EA, the product (120 mg, 53%) was obtained as white solid, which was used without purification.

Step 6: Preparation of N-((6-amino-2-cyclopropylpyridin-3-yl)methyl)-2-((3-chloroquinolin-6-yl)methyl)isonicotinamide

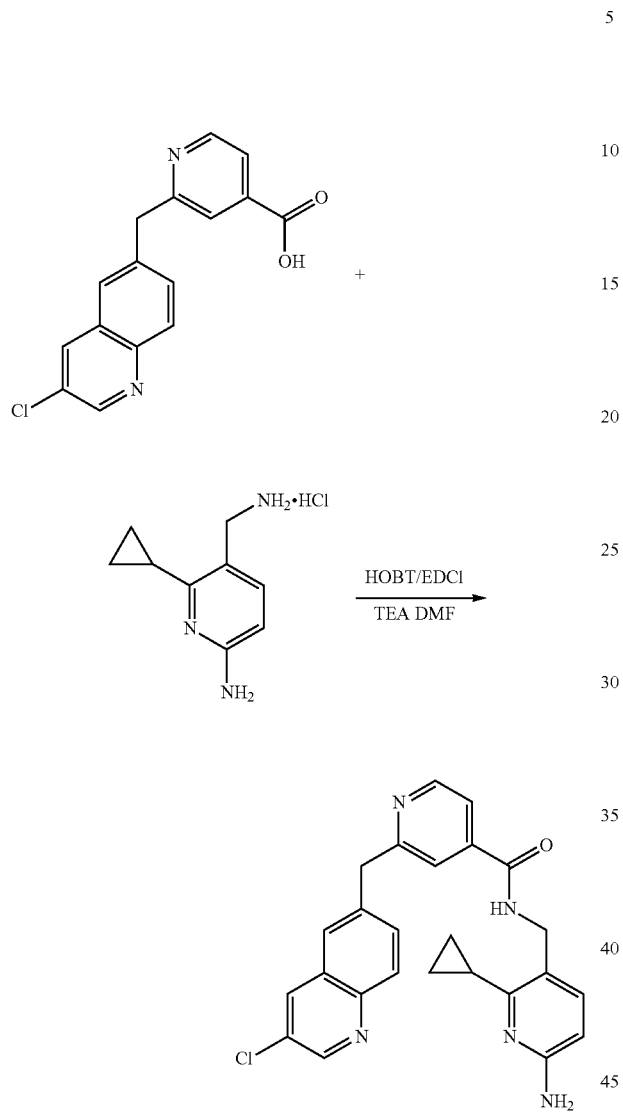

To a solution of 5-aminomethyl-6-cyclopropyl-pyridin-2-ylamine (46 mg, 0.2 mmol, 1.5 eq) in DMF (10 mL) was added 2-(3-chloro-quinolin-6-ylmethyl)-isonicotinic acid (40 mg, 0.13 mmol, 1 eq), HOBT (22 mg, 0.16 mmol, 1.2 eq), and EDCI (30 mg, 0.16 mmol, 1.2 eq). The reaction mixture was stirred at rt overnight. Then it was quenched with water, extracted with DCM. The combined extracts were dried and concentrated, and the residue was purified by prep-HPLC to give N-((6-amino-2-cyclopropylpyridin-3-yl)methyl)-2-((3-chloroquinolin-6-yl)methyl)isonicotinamide (7.7 mg, 13%) as a white solid. LRMS (M+H$^+$) m/z calculated 444.2, found 444.1.

$^1$H NMR (DMSO-d6, 400 MHz) δ 9.00 (t, 1H), 8.82 (d, 1H), 8.62 (d, 1H), 8.51 (d, 1H), 7.97 (d, 2H), 7.85 (s, 1H), 7.72 (d, 2H), 7.61 (d, 2H), 7.19 (d, 1H), 6.15 (d, 2H), 5.61 (s, 2H), 4.42 (d, 2H), 4.36 (s, 2H), 0.83 (s, 2H), 0.71-0.74 (m, 2H).

Example 44: Preparation of 2-((3-chloroquinolin-6-yl)methyl)-N-((6-(dimethylamino)-2-methylpyridin-3-yl)methyl)isonicotinamide

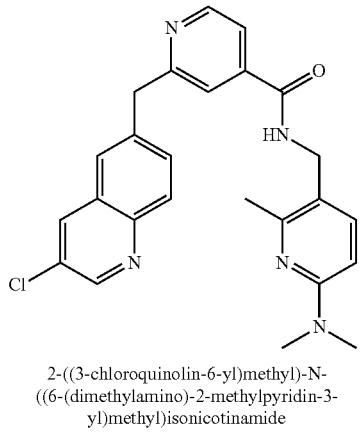 [SMILES: Cc1nc(N(C)C)ccc1CNC(=O)c1ccnc(Cc2ccc3ncc(Cl)cc3c2)c1]

2-((3-chloroquinolin-6-yl)methyl)-N-((6-(dimethylamino)-2-methylpyridin-3-yl)methyl)isonicotinamide

Step 1: Preparation of 6-(dimethylamino)-2-methylnicotinonitrile

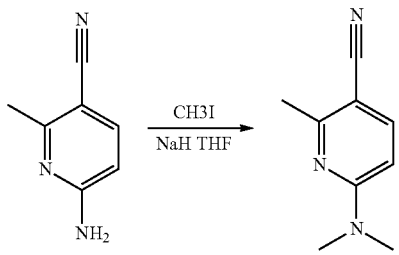

To a solution of 6-amino-2-methyl-nicotinonitrile (2 g, 15 mmol, 1.0 eq) and CH$_3$I (21 mg, 150 mmol, 10 eq) in THF (10 mL) was added NaH (1.8 mg, 75 mmol, 5.0 eq) under N$_2$. The mixture was stirred at rt overnight. The mixture was quenched with water, extracted with DCM. The combined extracts were dried and concentrated in vacuum to provide the compound (2.2 g, 91%), which was not further purified for next step.

Step 2: Preparation of 5-(aminomethyl)-N,N,6-trimethylpyridin-2-amine

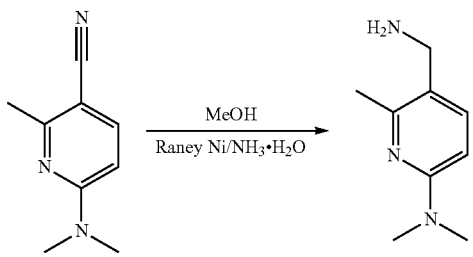

To a solution of 6-dimethylamino-2-methyl-nicotinonitrile (200 mg, 1.19 mmol, 1.0 eq) in MeOH (10 mL) was

317 added Raney Ni (400 mg) under H$_2$. The mixture was stirred at rt overnight. The reaction mixture was filtered and the filtrate was concentrated to provide the product (180 mg, 91%), which was directly used in next step without further purification.

Step 3: Preparation of 2-((3-chloroquinolin-6-yl)methyl)-N-((6-(dimethylamino)-2-methylpyridin-3-yl)methyl)isonicotinamide

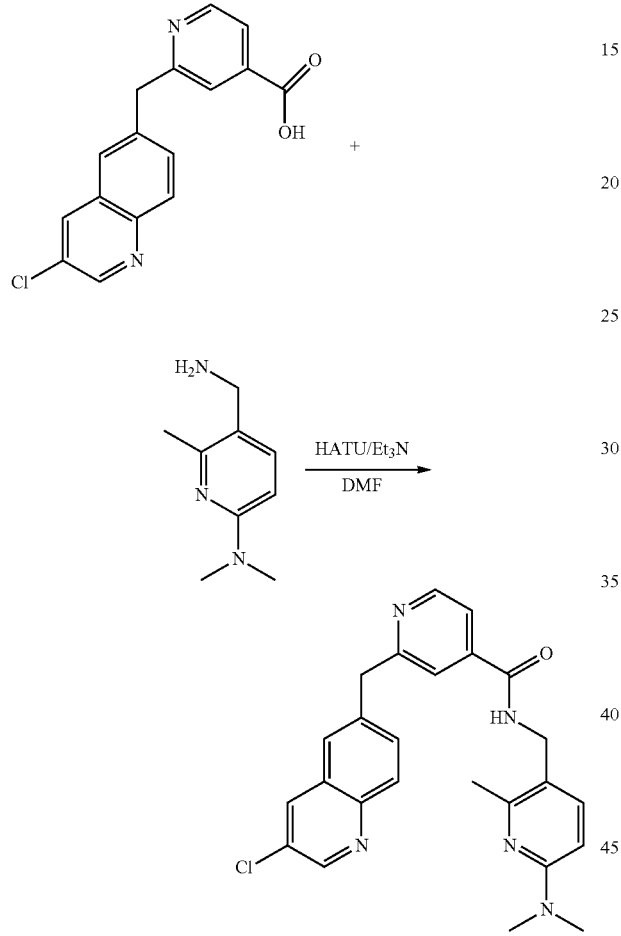

To a solution of 2-(3-chloro-quinolin-6-ylmethyl)-isonicotinic acid (326 mg, 1.09 mmol, 1 eq) in DMF (10 mL) was added (5-aminomethyl-6-methyl-pyridin-2-yl)-dimethylamine (180 mg, 1.09 mmol, 1 eq), HATU (497 mg, 1.3 mmol, 1.2 eq), and Et$_3$N (1 mL). The reaction mixture was stirred at rt for 3 h. Then it was quenched with water, extracted with DCM. The combined extracts were dried and concentrated. The residue was purified by prep-HPLC to give 2-((3-chloroquinolin-6-yl)methyl)-N-((6-(dimethylamino)-2-methylpyridin-3-yl)methyl)isonicotinamide (130 mg, 30%) as a gray solid. LRMS (M+H$^+$) m/z calculated 446.2, found 445.8.

$^1$H NMR (DMSO, 400 MHz) δ 9.00-9.02 (m, 1H), 8.82 (d, 1H), 8.62 (d, 1H), 8.51 (d, 1H), 7.96-7.98 (m, 1H), 7.84 (s, 1H), 7.72-7.75 (m, 2H), 7.61-7.62 (m, 1H), 7.34-7.37 (m, 1H), 6.40-6.41 (m, 1H), 4.31 (d, 4H), 2.96 (s, 6H), 2.35 (s, 3H).

318

Example 45: Preparation of 2-((2-(aminomethyl)quinolin-6-yl)methyl)-N-((3-chloro-6-fluoro-1H-indol-5-yl)methyl)isonicotinamide

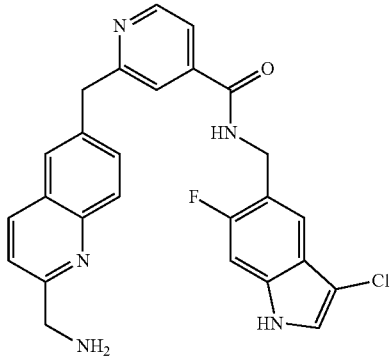 [SMILES: NCc1ccc2cc(Cc3cc(C(=O)NCc4cc5c(Cl)c[nH]c5cc4F)ccn3)ccc2n1]

2-((2-(Aminomethyl)quinolin-6-yl)methyl)-N-((3-chloro-6-fluoro-1H-indol-5-yl)methyl)isonicotinamide (60 mg, 79%) was prepared as described for Example 146. LRMS (M+H$^+$) m/z calculated 474.1, found 474.1. $^1$H NMR (DMSO-d$_6$, 400 MHz) δ 11.53 (s, 1H), 9.58 (s, 1H), 8.83 (d, 1H), 8.60 (br, 1H), 8.43 (d, 1H), 8.10 (d, 1H), 8.02-8.00 (m, 3H), 7.85 (d, 1H), 7.62 (d, 1H), 7.51 (s, 1H), 7.47 (d, 1H), 7.44 (d, 1H), 7.31 (s, 1H), 7.24 (d, 1H), 7.20 (d, 1H), 4.60 (d, 2H), 4.57 (s, 2H), 4.40 (q, 2H).

Example 46: Preparation of N-((6-amino-2,4-dimethylpyridin-3-yl)methyl)-2-((2-(aminomethyl)quinolin-6-yl)methyl)isonicotinamide

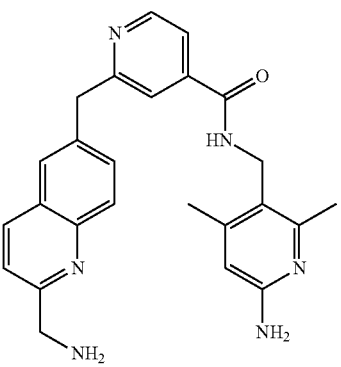 [SMILES: Cc1cc(N)nc(C)c1CNC(=O)c1ccnc(Cc2ccc3nc(CN)ccc3c2)c1]

N-((6-amino-2,4-dimethylpyridin-3-yl)methyl)-2-((2-(aminomethyl)quinolin-6-yl)methyl)isonicotinamide (35 mg, 53%) was prepared as described for Example 146. LRMS (M+H$^+$) m/z calculated 427.2, found 427.2. $^1$H NMR (CD$_3$OD, 400 MHz) δ 8.99 (d, 1H), 8.69 (d, 1H), 8.39 (s, 1H), 8.35 (d, 1H), 8.25 (d, 1H), 8.16 (s, 1H), 7.98 (d, 1H), 7.80 (d, 1H), 6.74 (s, 1H), 4.82 (s, 2H), 4.63 (s, 2H), 4.59 (s, 2H), 2.63 (s, 3H), 2.50 (s, 3H).

Example 47: Preparation of N-((3-aminobenzo[d]isoxazol-6-yl)methyl)-2-((3-methylquinolin-6-yl)methyl)isonicotinamide

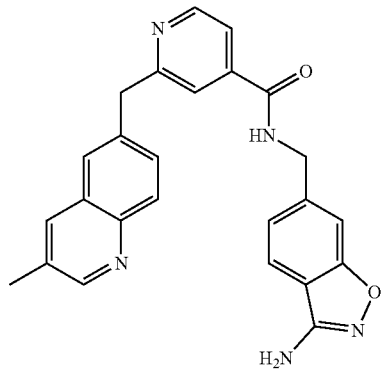

N-((3-aminobenzo[d]isoxazol-6-yl)methyl)-2-((3-methylquinolin-6-yl)methyl)isonicotinamide

Step 1: Preparation of tert-butyl {N-[(3-aminobenzo[d]isoxazol-6-yl)methyl](tert-butoxy)carbonylamino}formate

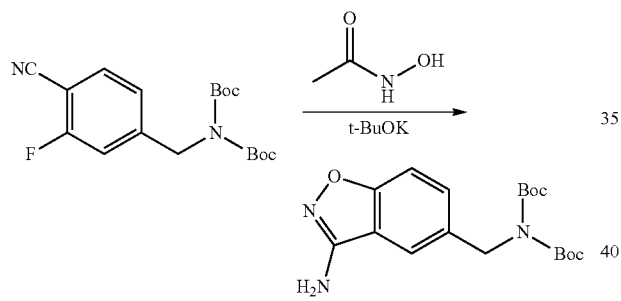

To a mixture of N-hydroxy-acetamide (964 mg, 12.86 mmol, 1.5 eq) in DMF (40 mL) was added t-BuOK (1.4 g, 12.86 mmol, 1.5 eq). After stirring for 30 min at rt, tert-butyl {(tert-butoxy)-N-[(4-cyano-3-fluorophenyl)methyl]carbonylamino}formate (3 g, 8.57 mmol, 1.0 eq) was added. The reaction mixture was stirred for 5 h at rt and then concentrated. The residue was purified by column chromatography on a silica gel (PE/EA=4/1 to 3/1, v/v) to give tert-butyl {N-[(3-aminobenzo[d]isoxazol-6-yl)methyl](tert-butoxy)carbonylamino}formate (2 g, 64%) as a white solid. LRMS (M+H$^+$) m/z calculated 364 found 364.

Step 2: Preparation of 5-aminomethyl-benzo[d]isoxazol-3-ylamine Dihydrochloride

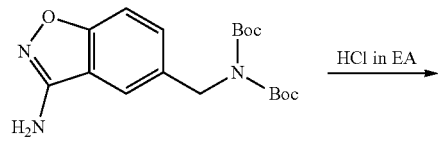

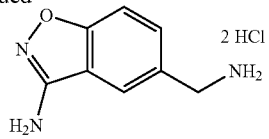

To a mixture of tert-butyl {N-[(3-aminobenzo[d]isoxazol-6-yl)methyl](tert-butoxy)carbonylamino}formate (2 g, 5.51 mmol, 1.0 eq) in MeOH (20 mL) was added 3 N of HCl in EA (5 mL). After stirring for 2 h at rt, the reaction mixture was filtered and the filter cake was washed with Et$_2$O to give the crude 5-aminomethyl-benzo[d]isoxazol-3-ylamine dihydrochloride (1.5 g) as a white solid. LRMS (M+H$^+$) m/z calculated 164 found 164.

Step 3: Preparation of N-((3-aminobenzo[d]isoxazol-6-yl)methyl)-2-((3-methylquinolin-6-yl)methyl)isonicotinamide

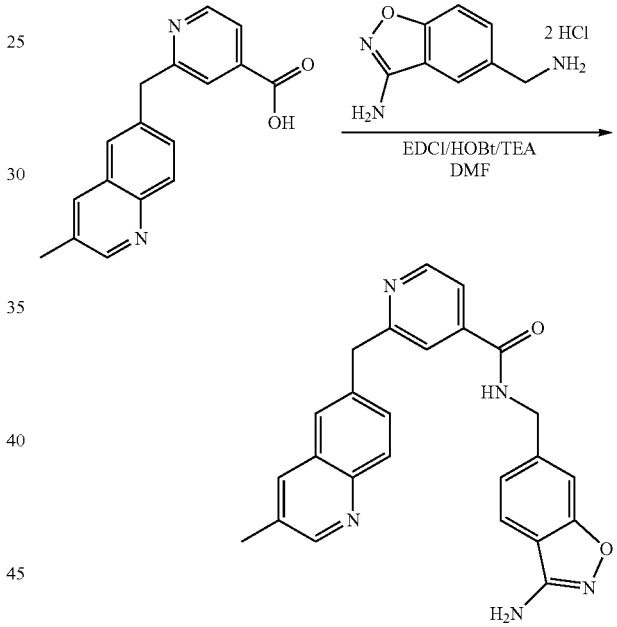

To a solution of 2-(3-methyl-quinolin-6-ylmethyl)-isonicotinic acid (150 mg, crude) in DMF (15 mL) was added 5-aminomethyl-benzo[d]isoxazol-3-ylamine dihydrochloride (80 mg, 0.34 mmol, 1.0 eq) followed by EDCI (98 mg, 0.51 mmol, 1.5 eq), HOBT (69 mg, 0.51 mmol, 1.5 eq) and TEA (103 mg, 1.02 mmol, 3.0 eq). The reaction mixture was heated to 45° C. kept stirring for overnight. Water was added, and the mixture was extracted with DCM. The organic layer was washed with water, dried over Na$_2$SO$_4$, filtered, and concentrated. The residue was purified by prep-HPLC to give N-((3-aminobenzo[d]isoxazol-6-yl)methyl)-2-((3-methylquinolin-6-yl)methyl)isonicotinamide (30 mg, 21%) as a yellow solid. LRMS (M+H$^+$) m/z calculated 424.2, found 424.0.

$^1$H NMR (DMSO-d$_6$, 400 MHz): δ 9.37 (t, 1H), 8.71 (s, 1H), 8.66 (d, 1H), 8.06 (s, 1H), 7.89 (d, 1H), 7.74-7.78 (m, 3H), 7.66 (d, 1H), 7.61 (d, 1H), 7.35 (s, 1H), 7.21 (d, 1H), 6.37 (s, 2H), 4.58 (d, 2H), 4.35 (s, 2H), 2.46 (s, 3H).

Example 48: Preparation of N-((3-aminobenzo[d]isoxazol-6-yl)methyl)-2-((6-methylquinolin-3-yl)methyl)isonicotinamide

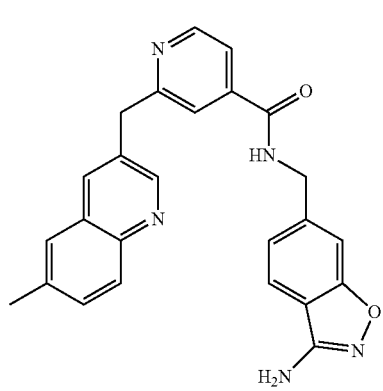

N-((3-aminobenzo[d]isoxazol-6-yl)methyl)-2-((6-methylquinolin-3-yl)methyl)isonicotinamide

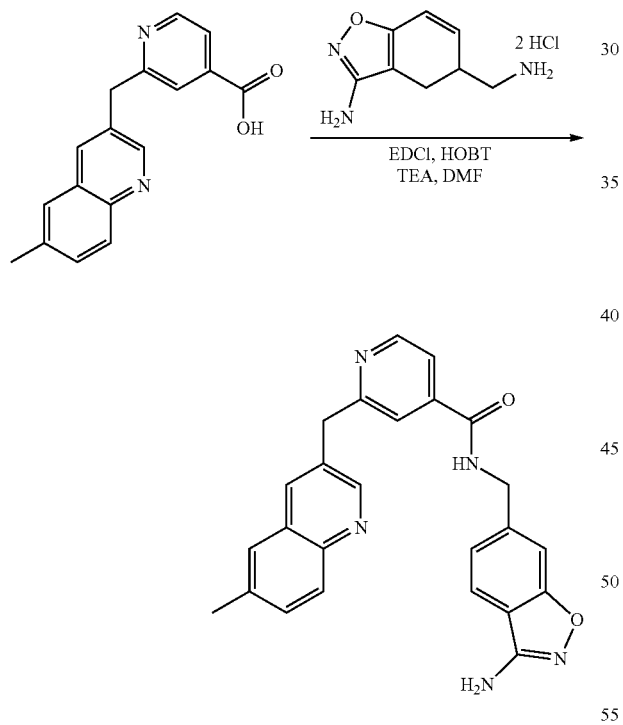

N-((3-aminobenzo[d]isoxazol-6-yl) methyl)-2-((6-methylquinolin-3-yl) methyl) isonicotinamide (30 mg, 21%) was prepared as described for N-((3-aminobenzo[d]isoxazol-6-yl)methyl)-2-((3-methylquinolin-6-yl)methyl)isonicotinamide (Example 47) as a yellow solid. LRMS (M+H⁺) m/z calculated 424.2, found 423.9. ¹H NMR (DMSO-d₆, 400 MHz) δ 9.40 (t, 1 H), 8.81 (s, 1H), 8.66 (d, 1H), 8.10 (s, 1H), 7.89 (d, 1H), 7.82 (s, 1H), 7.76 (d, 1H), 7.68 (t, 2H), 7.55 (d, 1H), 7.35 (s, 1H), 7.22 (d, 1H), 6.38 (s, 2H), 4.60 (d, 2H), 4.37 (s, 2H), 2.48 (s, 3H).

Example 49: Preparation of N-((3-chloro-6-fluoro-1H-indol-5-yl)methyl)-2-((3-chloro-8-cyanoquinolin-6-yl)methyl)isonicotinamide

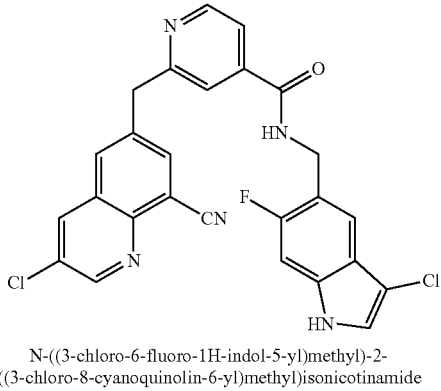 [SMILES: N#Cc1cc(Cc2cc(C(=O)NCc3cc4c(Cl)c[nH]c4cc3F)ccn2)cc2cc(Cl)cnc12]

N-((3-chloro-6-fluoro-1H-indol-5-yl)methyl)-2-((3-chloro-8-cyanoquinolin-6-yl)methyl)isonicotinamide

Step 1: Preparation of 3-chloro-8-iodo-quinoline-6-carboxylic Acid Methyl Ester

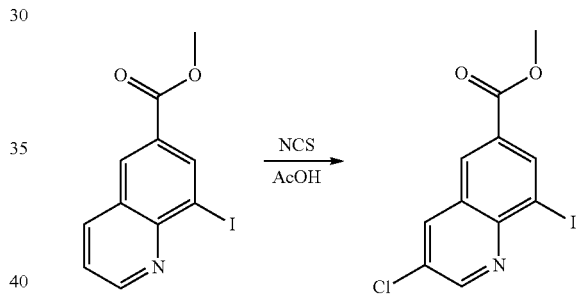

To a solution of 8-iodo-quinoline-6-carboxylic acid methyl ester (30 g, 96 mmol, 1.0 eq) in AcOH (1.0 L) was added NCS (38 g, 293 mmol, 3 eq). The mixture was stirred at 100° C. overnight, The mixture was concentrated in vacuo and the residue was purified by silica gel chromatography (PE/DCM=1/1, v/v) to afford 3-chloro-8-iodo-quinoline-6-carboxylic acid methyl ester (15 g, 49%) as yellow solid.

Step 2: Preparation of (3-chloro-8-iodo-quinolin-6-yl)-methanol

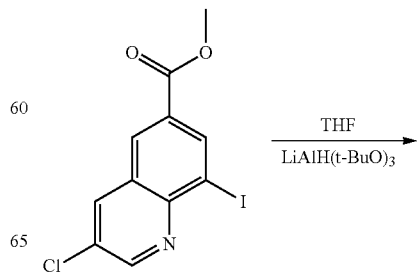

-continued

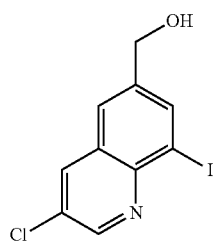

To a solution of 3-chloro-8-iodo-quinoline-6-carboxylic acid methyl ester (12 g, 34.5 mmol, 1.0 eq) in dry THF (200 mL) was added lithium tri-tert-butoxyaluminum hydride (22 g, 70 mmol, 3.4 eq) carefully. The mixture was stirred at 50° C. for 5 h under $N_2$ protected. Then EA and water was added. The organic layer was concentrated, and purified by silica gel chromatography (PE/DCM=1/1, v/v) to afford (3-chloro-8-iodo-quinolin-6-yl)-methanol (7.6 g, 69%) as white solid.

Step 3: Preparation of 3-chloro-6-hydroxymethyl-quinoline-8-carbonitrile

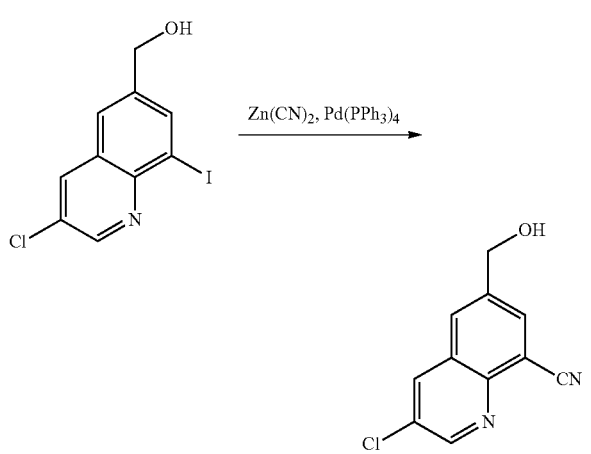

To a solution of (3-chloro-8-iodo-quinolin-6-yl)-methanol (7.6 g, 23.8 mmol, 1.0 eq) in DMF (100 mL) was added $Zn(CN)_2$ (2.79 g, 23.8 mmol, 1.0 eq) and $Pd(pph3)_4$ (2.75 g, 2.38 mmol, 0.1 eq) carefully. The mixture was stirred at 50° C. overnight under $N_2$ protected. Then EA and water was added. The organic layer was concentrated, and purified by silica gel chromatography (PE/DCM=1/2, v/v) to afford 3-chloro-6-hydroxymethyl-quinoline-8-carbonitrile (5.0 g, 96%) as yellow solid.

Step 4: Preparation of 3-chloro-6-chloromethyl-quinoline-8-carbonitrile

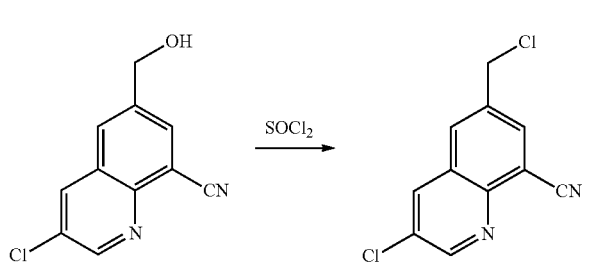 [SMILES: N#Cc1cc(CO)cc2cc(Cl)cnc12 ; "SOCl2" ; N#Cc1cc(CCl)cc2cc(Cl)cnc12]

A mixture of 3-chloro-6-hydroxymethyl-quinoline-8-carbonitrile (2.9 g, 13.3 mmol, 1.0 eq) in $SOCl_2$ (50 mL) was stirred at rt for 1 h and concentrated. The residue was dissolved in DCM and treated with sat.$NaHCO_3$ solution to give 3-chloro-6-chloromethyl-quinoline-8-carbonitrile (2.2 g, 70%) as a yellow solid.

Step 5: Preparation of 2-(3-chloro-8-cyano-quinolin-6-ylmethyl)-isonicotinic Acid Methyl Ester

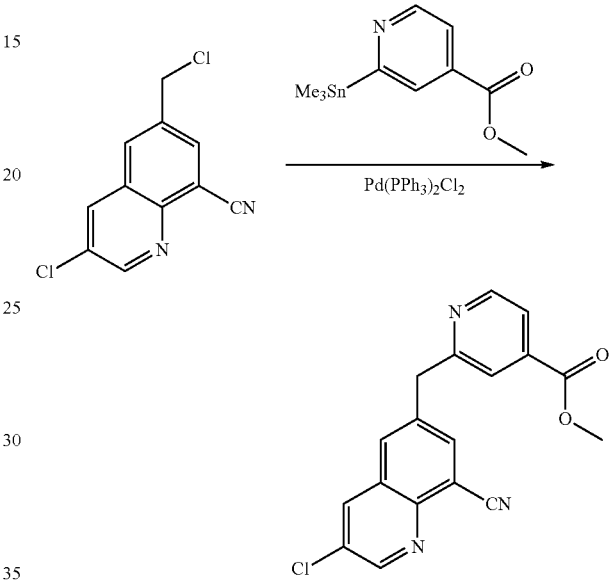

To a solution of 3-chloro-6-chloromethyl-quinoline-8-carbonitrile (2.0 g, 8.47 mmol, 1.0 eq) in dioxane (40 mL) was added 2-trimethylstannanyl-isonicotinic acid methyl ester (2.8 g, 9.32 mmol, 1.1 eq) and $Pd(PPh_3)_2Cl_2$ (597 mg, 0.85 mmol, 0.1 eq). The mixture was stirred at 90° C. for 3 h under nitrogen atmosphere, concentrated and purified by silica gel chromatography (DCM/MeOH=100/1, v/v) to afford 2-(3-chloro-8-cyano-quinolin-6-ylmethyl)-isonicotinic acid methyl ester (1.4 g, 49%) as a yellow solid.

Step 6: Preparation of 2-(3-chloro-8-cyano-quinolin-6-ylmethyl)-isonicotinic Acid

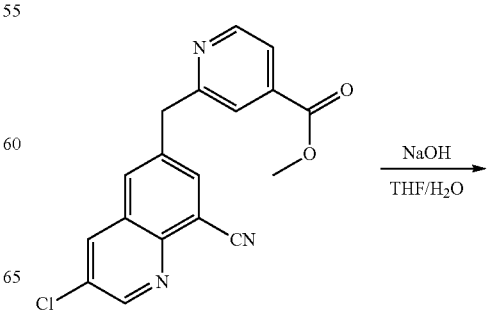

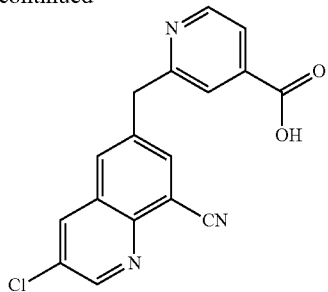

To a solution of 2-(3-chloro-8-cyano-quinolin-6-ylmethyl)-isonicotinic acid methyl ester (1.4 g, 4.2 mmol, 1.0 eq) in THF (5 mL) and H₂O (5 mL) was added NaOH (200 mg, 5 mmol, 1.2 eq). The mixture was stirred at rt for 2 h. Then it was acidified by 1 N HCl to PH=6 and extracted by EA. The organic layer was concentrated to afford 2-(3-chloro-8-cyano-quinolin-6-ylmethyl)-isonicotinic acid (1.1 g, 37%) as a white solid.

Step 7: Preparation of N-((3-chloro-6-fluoro-1H-indol-5-yl) methyl)-2-((3-chloro-8-cyanoquinolin-6-yl)methyl) isonicotinamide

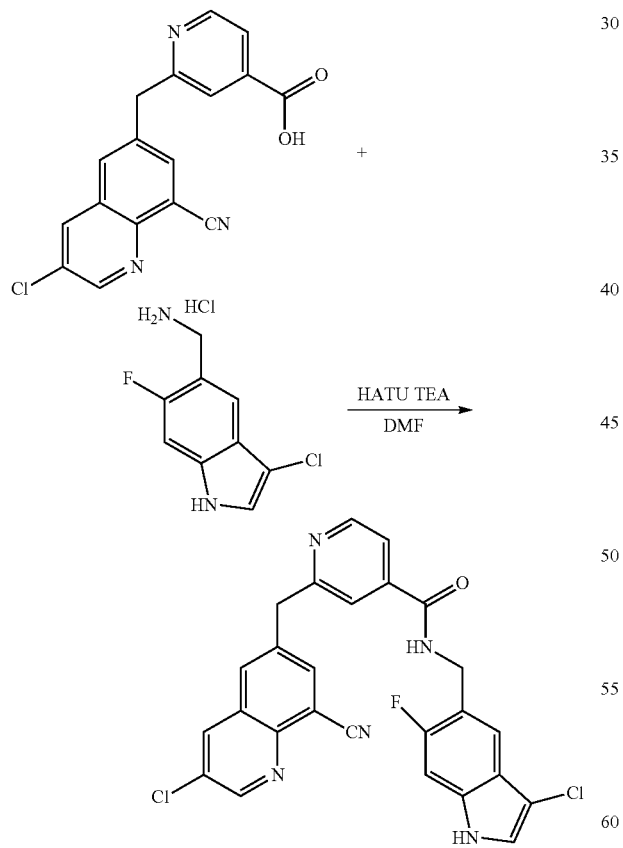

To a solution of 2-(3-chloro-quinolin-6-ylmethyl)-isonicotinic acid (120 mg, 0.37 mmol, 1.0 eq) and C-(3-chloro-6-fluoro-1H-indol-5-yl)-methylamine hydrochloride (200 mg, 0.73 mmol, 2.0 eq) in DMF (10 mL) was added HATU (170 mg, 4.4 mmol, 1.2 eq) and Et₃N (1.0 mL, 7.1 mmol, 19 eq). The mixture was stirred at rt overnight, Then EA and water was added. The organic layer was concentrated and the residue was purified by pre-HPLC to give N-((3-chloro-6-fluoro-1H-indol-5-yl) methyl)-2-((3-chloro-8-cyanoquinolin-6-yl)methyl) isonicotinamide (170 mg, 91%) as a yellow solid. LRMS (M+H⁺) m/z calculated 504.1, found 503.8.

1H NMR (DMSO-d6, 400 MHz) δ 11.39 (s, 1H), 9.24 (m, 1H), 9.03-9.04 (d, 1H), 8.71-8.72 (d, 1H), 8.64-8.66 (d, 1H), 8.40 (d, 1H), 8.19 (d, 1H), 7.84 (s, 1H), 7.66-7.68 (d, 1H), 7.44-7.51 (m, 2H), 7.21-7.24 (d, 1H), 4.59-4.60 (d, 2H), 4.43 (s, 2H).

Example 50: Preparation of N-((6-amino-2,4-dimethylpyridin-3-yl)methyl)-2-((3-chloro-8-cyanoquinolin-6-yl)methyl)isonicotinamide

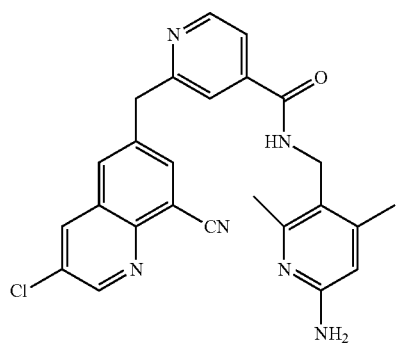

N-((-6-amino-2,4-dimethylpyridin-3-yl)methyl)-2-((3-chloro-8-cyano quinolin-6-yl)methyl)isonicotinamide

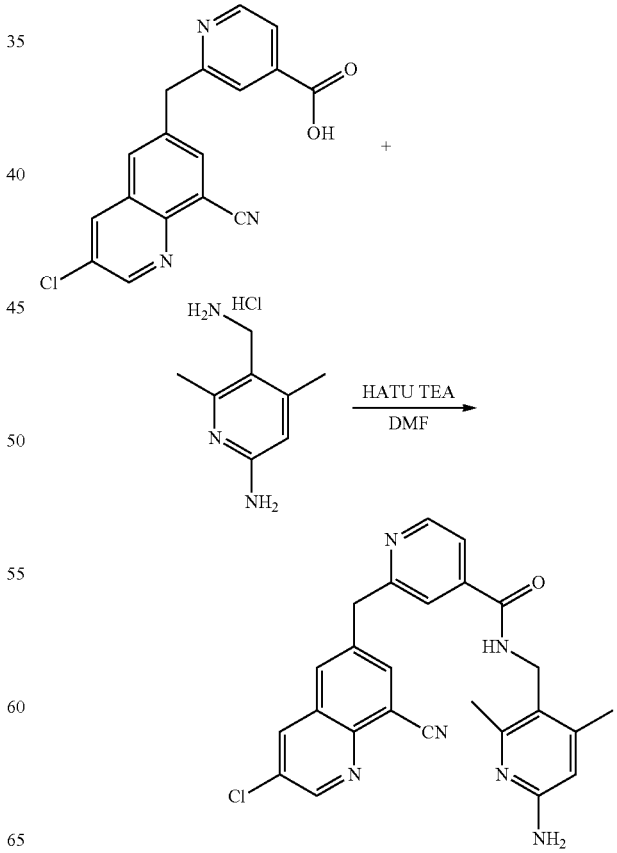

N-((6-amino-2,4-dimethylpyridin-3-yl)methyl)-2-((3-chloro-8-cyanoquinolin-6-yl)methyl)isonicotinamide (130 mg, 77%) was prepared as described for N-((3-chloro-6-fluoro-1H-indol-5-yl) methyl)-2-((3-chloro-8-cyanoquinolin-6-yl)methyl) isonicotinamide (Example 49) as white solid. LRMS (M+H$^+$) m/z calculated 456.2, found 456.8.

1H NMR (DMSO-d6, 400 MHz) δ 9.03-9.04 (d, 1H), 8.72-8.73 (d, 1H), 8.59-8.66 (m, 3H), 8.38-8.39 (d, 1H), 8.18-8.19 (d, 1H), 7.79 (s, 1H), 7.60-7.62 (dd, 1H), 6.15 (s, 1H), 5.77 (s, 1H), 4.41 (s, 2H), 4.34-4.35 (d, 2H), 2.31 (s, 3H), 2.18 (s, 3H).

Example 51: Preparation of N-((3-chloro-4-fluoro-1H-indol-5-yl)methyl)-2-((3-chloro-8-cyanoquinolin-6-yl)methyl)isonicotinamide mg, 43%) was prepared as described for N-((3-chloro-6-fluoro-1H-indol-5-yl) methyl)-2-((3-chloro-8-cyanoquinolin-6-yl)methyl) isonicotinamide (Example 49) as white solid. LRMS (M+H$^+$) m/z calculated 504.1, found 503.8.

$^1$H NMR (DMSO-d6, 400 MHz) δ 11.58 (s, 1H), 9.22 (m, 1H), 9.03-9.04 (d, 1H), 8.71-8.72 (d, 1H), 8.63-8.65 (d, 1H), 8.39-8.40 (d, 1H), 8.19 (s, 1H), 7.83 (s, 1H), 7.65-7.66 (m, 1H), 7.50-7.51 (d, 2H), 7.14-7.21 (m, 2H). 4.57-4.59 (d, 2H), 4.42 (s, 1H)

Example 52: Preparation of 2-((3-chloro-8-cyanoquinolin-6-yl)methyl)-N-((6-fluoro-1H-indol-5-yl)methyl)isonicotinamide

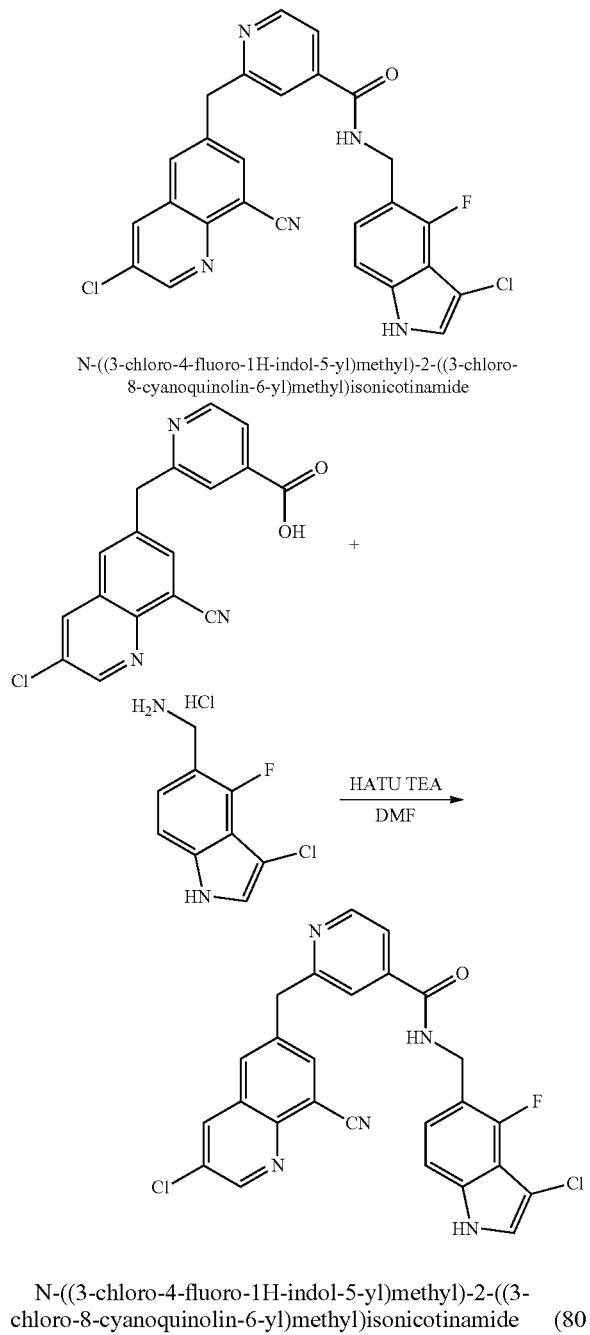

N-((3-chloro-4-fluoro-1H-indol-5-yl)methyl)-2-((3-chloro-8-cyanoquinolin-6-yl)methyl)isonicotinamide (80 mg,

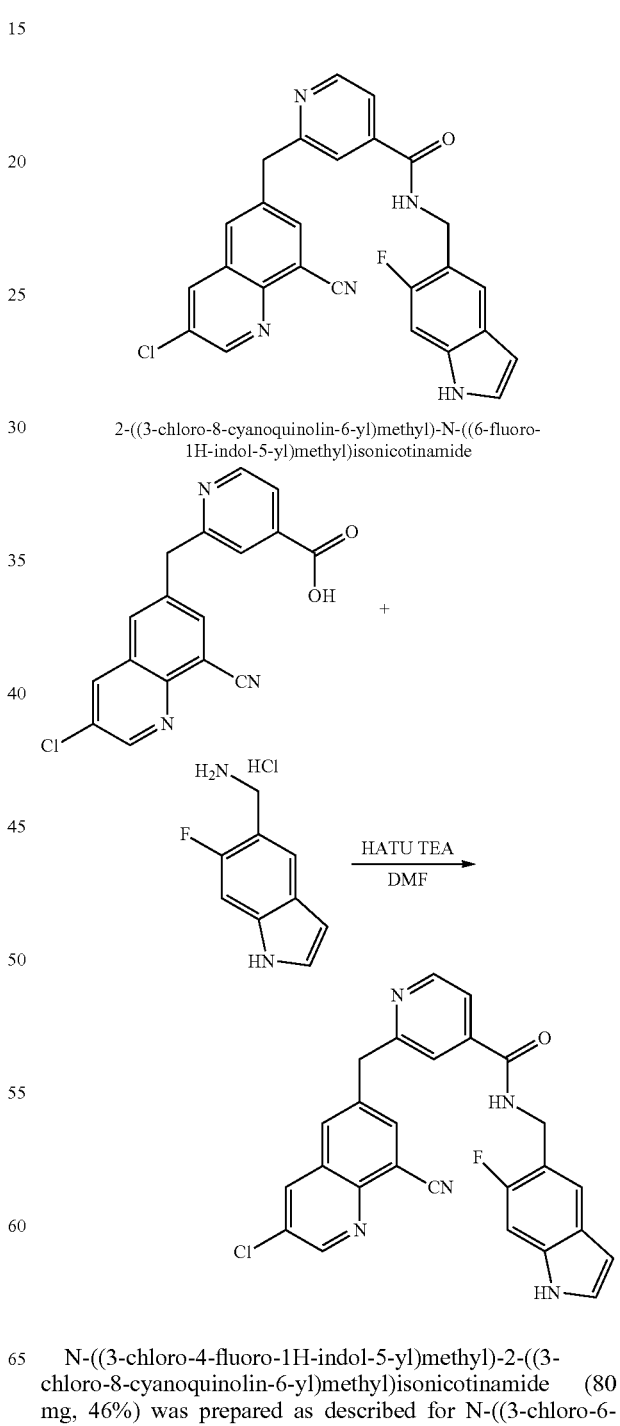

2-((3-chloro-8-cyanoquinolin-6-yl)methyl)-N-((6-fluoro-1H-indol-5-yl)methyl)isonicotinamide N-((3-chloro-4-fluoro-1H-indol-5-yl)methyl)-2-((3-chloro-8-cyanoquinolin-6-yl)methyl)isonicotinamide (80 mg, 46%) was prepared as described for N-((3-chloro-6- fluoro-1H-indol-5-yl) methyl)-2-((3-chloro-8-cyanoquino-lin-6-yl)methyl) isonicotinamide (Example 49) as white solid. LRMS (M+H$^+$) m/z calculated 469.7, found 469.7.

$^1$H NMR (DMSO-d6, 400 MHz) δ 11.09 (s, 1H), 9.19 (m, 1H), 9.03-9.04 (d, 1H), 8.72-8.73 (d, 1H), 8.64-8.65 (d, 1H), 8.39-8.40 (d, 1H), 8.19 (s, 1H), 7.84 (s, 1H), 7.67-7.69 (m, 1H), 7.49-7.50 (d, 2H), 7.31-7.32 (t, 1H) 7.14-7.18 (m, 2H), 6.39 (s, 1H), 4.56-4.58 (d, 2H), 4.42 (s, 1H).

Example 53: Preparation of N-((6-amino-4-methyl-pyridin-3-yl)methyl)-2-((3-chloro-8-cyanoquinolin-6-yl)methyl)isonicotinamide fluoro-1H-indol-5-yl)methyl)-2-((3-chloro-8-cyanoquino-lin-6-yl)methyl) isonicotinamide (Example 49) as yellow solid. LRMS (M+H+) m/z calculated 443.1, found 443.0.

$^1$H NMR (DMSO-d6, 400 MHz) δ 9.03-9.04 (d, 1H), 8.92-8.93 (t, 1H), 8.72-8.73 (d, 1H), 8.61-8.63 (m, 3H), 8.39-8.40 (d, 1H), 8.18-8.19 (d, 1H), 7.79 (s, 2H), 7.61-7.63 (dd, 1H), 6.27 (s, 1H), 5.77 (s, 1H), 4.41 (s, 2H), 4.29-4.32 (d, 2H), 2.15 (s, 3H).

Example 54: Preparation of 2-(3-chloro-8-cyano-quinolin-6-ylmethyl)-N-(5-chloro-1H-indazol-3-ylmethyl)-isonicotinamide

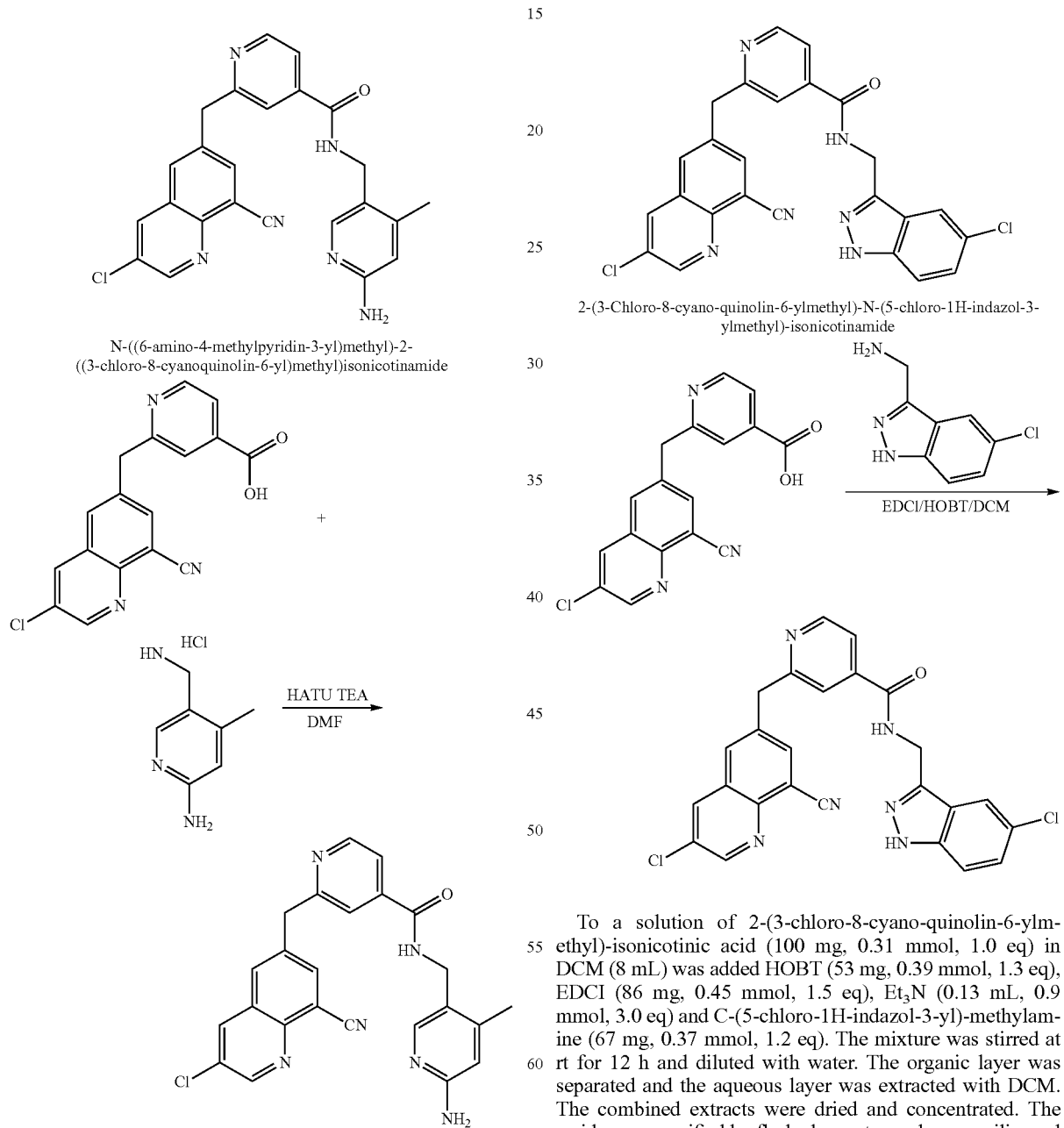

N-((6-amino-2,4-dimethylpyridin-3-yl)methyl)-2-((3-chloro-8-cyanoquinolin-6-yl)methyl)isonicotinamide (120 mg, 73%) was prepared as described for N-((3-chloro-6-

To a solution of 2-(3-chloro-8-cyano-quinolin-6-ylm-ethyl)-isonicotinic acid (100 mg, 0.31 mmol, 1.0 eq) in DCM (8 mL) was added HOBT (53 mg, 0.39 mmol, 1.3 eq), EDCI (86 mg, 0.45 mmol, 1.5 eq), Et$_3$N (0.13 mL, 0.9 mmol, 3.0 eq) and C-(5-chloro-1H-indazol-3-yl)-methylam-ine (67 mg, 0.37 mmol, 1.2 eq). The mixture was stirred at rt for 12 h and diluted with water. The organic layer was separated and the aqueous layer was extracted with DCM. The combined extracts were dried and concentrated. The residue was purified by flash chromatography on a silica gel column (DCM/MeOH=10/1, v/v) to give 2-(3-chloro-8-cyano-quinolin-6-ylmethyl)-N-(5-chloro-1H-indazol-3-yl-methyl)-isonicotinamide (50 mg, 34%) as a white solid. LRMS (M+H$^+$) m/z calculated 487.1, found 486.8.

¹H NMR (DMSO-d₆, 400 MHz) δ 13.07 (s, 1H), 9.36 (m, 1H), 9.04 (d, 1H), 8.70 (d, 1H), 8.63 (d, 1H), 8.38 (d, 1H), 8.18 (s, 1H), 7.89 (d, 1H), 7.82 (s, 1H), 7.64 (d, 1H), 7.53 (d, 1H), 7.31-7.34 (d, 1H), 4.78 (d, 2H), 4.42 (s, 2H).

Example 55: Preparation of 2-(3-chloro-8-cyano-quinolin-6-ylmethyl)-N-(3-chloro-1H-pyrrolo[2,3-b]pyridin-5-ylmethyl)-isonicotinamide

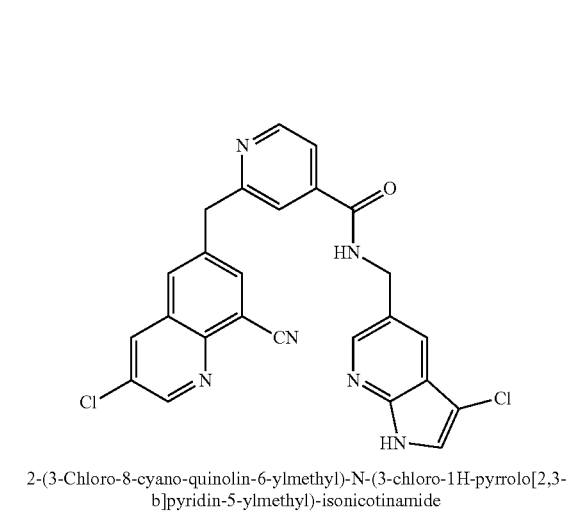

2-(3-Chloro-8-cyano-quinolin-6-ylmethyl)-N-(3-chloro-1H-pyrrolo[2,3-b]pyridin-5-ylmethyl)-isonicotinamide 2-(3-Chloro-8-cyano-quinolin-6-ylmethyl)-N-(3-chloro-1H-pyrrolo[2,3-b]pyridin-5-ylmethyl)-isonicotinamide (90 mg, 66%) was prepared as described for 2-(3-chloro-8-cyano-quinolin-6-ylmethyl)-N-(5-chloro-1H-indazol-3-yl-methyl)-isonicotinamide (Example 54) as a white solid. LRMS (M+H⁺) m/z calculated 487.1, found 486.8.

¹H NMR (DMSO-d₆, 400 MHz) δ 11.95 (s, 1H), 9.34 (m, 1H), 9.04 (d, 1H), 8.71 (d, 1H), 8.64 (d, 1H), 8.39 (d, 1H), 8.31 (s, 1H), 8.19 (s, 1H), 7.87 (s, 1H), 7.83 (d, 1H), 7.65-7.67 (m, 2H), 4.59-4.61 (d, 2H), 4.42 (s, 2H).

Example 56: Preparation of N-(6-amino-2-methyl-pyridin-3-ylmethyl)-2-(3-chloro-8-cyano-quinolin-6-ylmethyl)-isonicotinamide

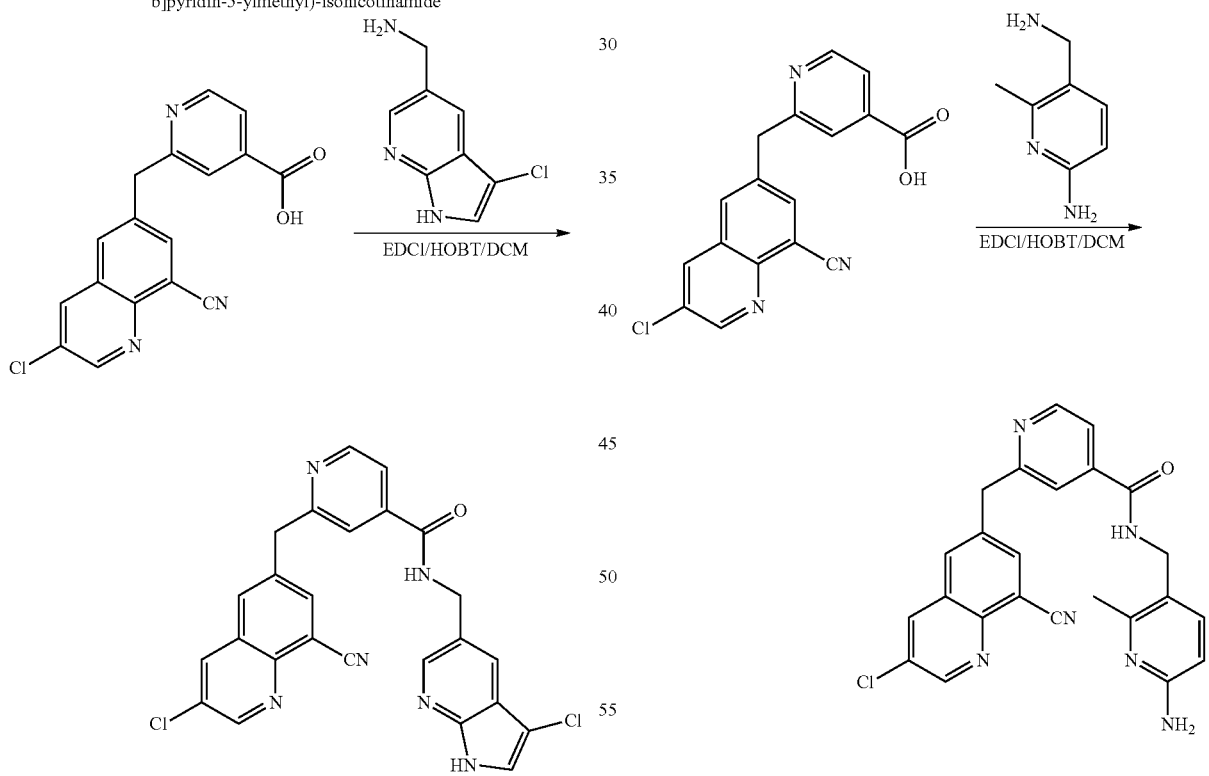

N-(6-Amino-2-methyl-pyridin-3-ylmethyl)-2-(3-chloro-8-cyano-quinolin-6-ylmethyl)isonicotinamide N-(6-amino-2-methyl-pyridin-3-ylmethyl)-2-(3-chloro-8-cyano-quinolin-6-ylmethyl)-isonicotinamide (50 mg, 38%) was prepared as described for 2-(3-chloro-8-cyano-quinolin-6-ylmethyl)-N-(5-chloro-1H-indazol-3-ylmethyl)-isonicotinamide (Example 54) as a white solid. LRMS (M+H⁺) m/z calculated 441.9, found 441.9.

¹H NMR (DMSO-d₆, 400 MHz) δ 9.04 (m, 2H), 8.72 (d, 1H), 8.64 (d, 1H), 8.39 (d, 1H), 8.19 (s, 1H), 7.80 (s, 1H), 7.63 (d, 1H), 7.38 (m, 1H), 6.38 (m, 1H), 6.25 (m, 1H), 4.42 (s, 2H), 4.30 (d, 2H).

Example 57: Preparation of N-(1-amino-isoquinolin-6-ylmethyl)-2-(3-chloro-8-cyano-quinolin-6-ylmethyl)-isonicotinamide

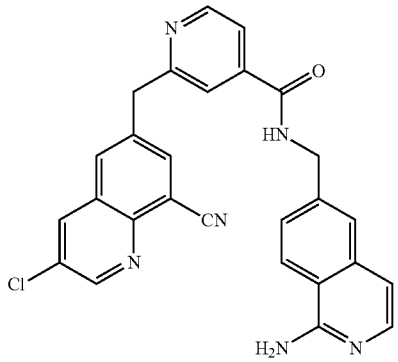

N-(1-Amino-isoquinolin-6-ylmethyl)-2-(3-chloro-8-cyano-quinolin-6-ylmethyl)-isonicotinamide

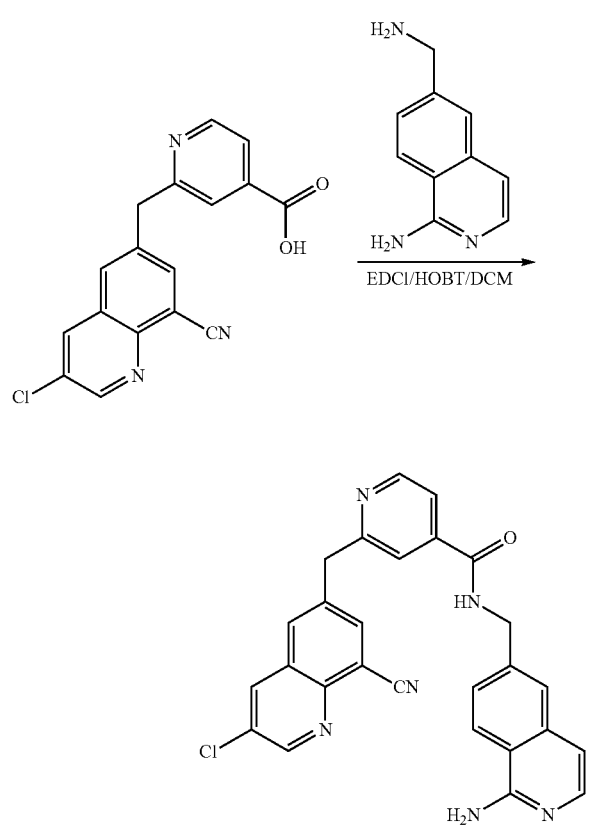

N-(1-amino-isoquinolin-6-ylmethyl)-2-(3-chloro-8-cyano-quinolin-6-ylmethyl)-isonicotinamide (100 mg, 73%) was prepared as described for 2-(3-chloro-8-cyano-quinolin-6-ylmethyl)-N-(5-chloro-1H-indazol-3-ylmethyl)-isonicotinamide (Example 54) as a white solid. LRMS (M+H+) m/z calculated 479.1, found 479.0.

$^1$H NMR (DMSO-d$_6$, 400 MHz) δ 9.39 (m, 2H), 9.04 (d, 1H), 8.72 (d, 1H), 8.66 (d, 1H), 8.40 (s, 1H), 8.20 (s, 1H), 8.12-8.15 (d, 1H), 7.86 (s, 1H), 7.75-7.76 (d, 1H), 7.69-7.70 (d, 1H), 7.56 (s, 1H), 7.39-7.41 (d, 1H), 6.84-6.85 (d, 1H), 6.72 (s, 1H), 4.62 (d, 2H), 4.44 (s, 2H).

Example 58: Preparation of 6-((4-(((6-amino-2,4-dimethylpyridin-3-yl)methyl)carbamoyl)pyridin-2-yl)methyl)-3-chloroquinoline-8-carboxamide

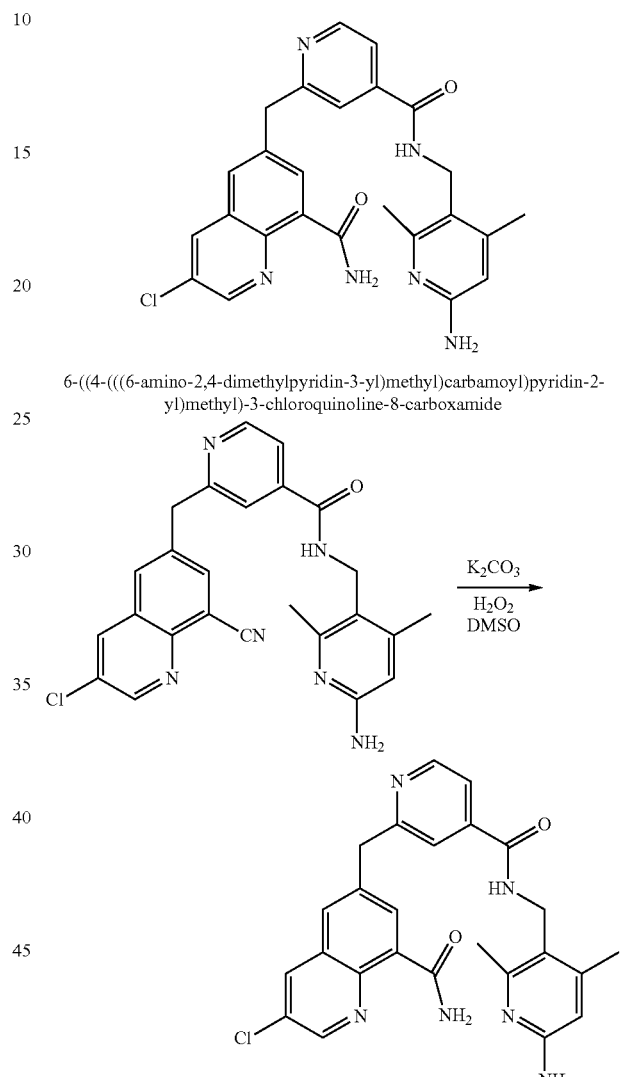

To a solution of N-((6-amino-2,4-dimethylpyridin-3-yl)methyl)-2-((3-chloro-8-cyanoquinolin-6-yl)methyl)isonicotinamide hydrochloride (100 mg, 0.22 mmol, 1.0 eq) and K$_2$CO$_3$ (215 mg, 1.56 mmol, 7.3 eq) in DMSO (10 mL) was added H$_2$O$_2$ (1 mL). The mixture was stirred at 50° C. for 3 h, Then EA and water was added, The organic layer was concentrated and purified by pre-HPLC to give 6-((4-(((6-amino-2,4-dimethylpyridin-3-yl)methyl)carbamoyl)pyridin-2-yl)methyl)-3-chloroquinoline-8-carboxamide (71 mg, 48%) as a white solid. LRMS (M+H+) m/z calculated 475.2, found 474.8.

$^1$H NMR (DMSO-d6, 400 MHz) δ 9.62 (d, 1H), 8.96-8.98 (d, 1H), 8.59-8.70 (m, 3H), 8.43-8.48 (d, 1H), 8.03-8.04 (d, 1H), 7.94 (s, 1H), 7.79 (s, 1H), 7.60-7.62 (dd, 1H), 6.11 (s, 1H), 5.66 (s, 1H), 4.40 (s, 2H), 4.33-4.35 (d, 2H), 2.30 (s, 3H), 2.16 (s, 3H).

Example 59: Preparation of 3-chloro-6-((4-(((3-chloro-6-fluoro-1H-indol-5-yl)methyl)carbamoyl)pyridin-2-yl)methyl)quinoline-8-carboxamide Example 60: Preparation of 3-chloro-6-((4-(((5-chloro-1H-indazol-3-yl)methyl)carbamoyl)pyridin-2-yl)methyl)quinoline-8-carboxamide

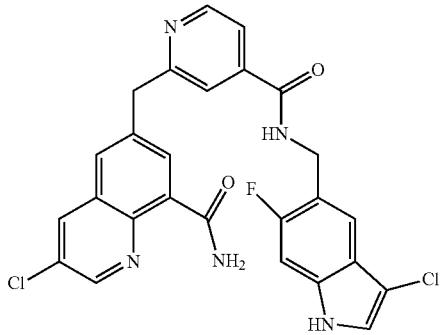

3-chloro-6-((4-(((3-chloro-6-fluoro-1H-indol-5-yl)methyl)carbamoyl)pyridin-2-yl)methyl)quinoline-8-carboxamide

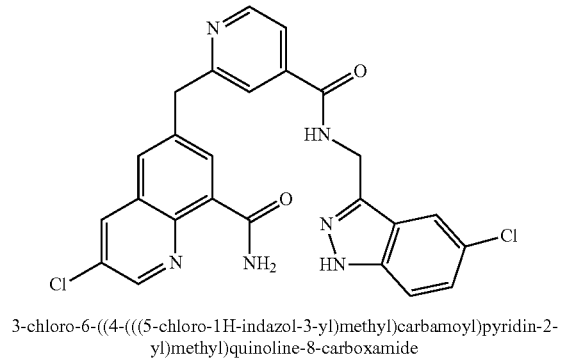

3-chloro-6-((4-(((5-chloro-1H-indazol-3-yl)methyl)carbamoyl)pyridin-2-yl)methyl)quinoline-8-carboxamide

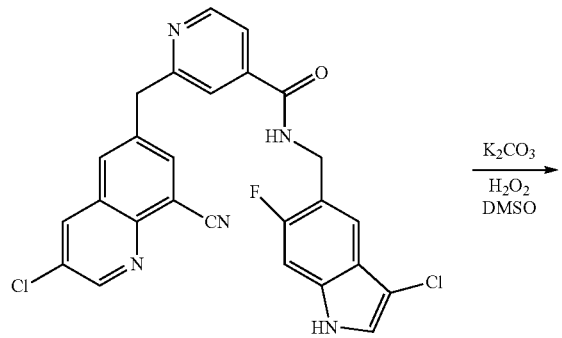

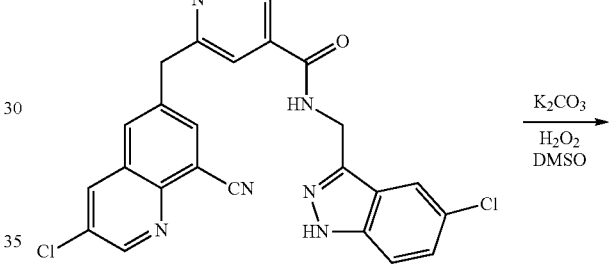

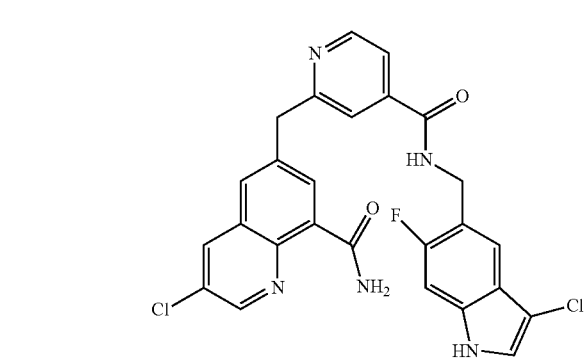

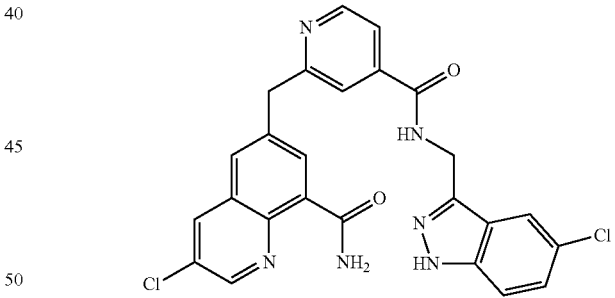

3-Chloro-6-((4-(((3-chloro-6-fluoro-1H-indol-5-yl)methyl)carbamoyl)pyridin-2-yl)methyl)quinoline-8-carboxamide (30 mg, 58%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 522.1, found 521.9.

$^1$H NMR (DMSO-d6, 400 MHz) δ 11.39 (s, 1H), 9.63 (s, 1H), 9.24-9.26 (t, 1H), 8.97-8.98 (d, 1H), 8.64-8.70 (dd, 2H), 8.44-8.45 (d, 1H), 8.04-8.05 (d, 1H), 7.95-7.96 (d, 1H), 7.66-7.68 (d, 1H), 7.43-7.50 (m, 1H), 7.20-7.24 (d, 1H), 4.57-4.59 (d, 2H), 4.42 (s, 2H).

3-Chloro-6-((4-(((5-chloro-1H-indazol-3-yl)methyl)carbamoyl)pyridin-2-yl)methyl)quinoline-8-carboxamide (20 mg, 66%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 505.1, found 504.9.

$^1$H NMR (DMSO-$d_6$, 400 MHz) δ 13.09 (s, 1H), 9.63 (s, 1H), 9.40-9.41 (t, 1H), 8.97-8.98 (d, 1H), 8.64-8.70 (dd, 2H), 8.43 (s, 1H), 7.84-8.02 (m, 3H), 7.64-7.65 (d, 1H), 7.51-7.54 (d, 1H), 7.31-7.32 (m, 1H), 4.77-4.79 (d, 2H), 4.41 (s, 2H).

Example 61: Preparation of 3-chloro-6-((4-(((3-chloro-1H-pyrrolo[2,3-b]pyridin-5-yl)methyl)carbamoyl)pyridin-2-yl)methyl)quinoline-8-carboxamide

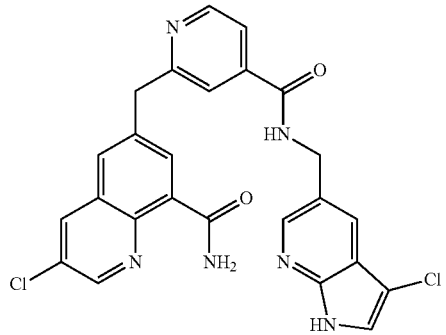

3-chloro-6-((4-(((3-chloro-1H-pyrrolo[2,3-b]pyridin-5-yl)methyl)carbamoyl)pyridin-2-yl)methyl)quinoline-8-carboxamide

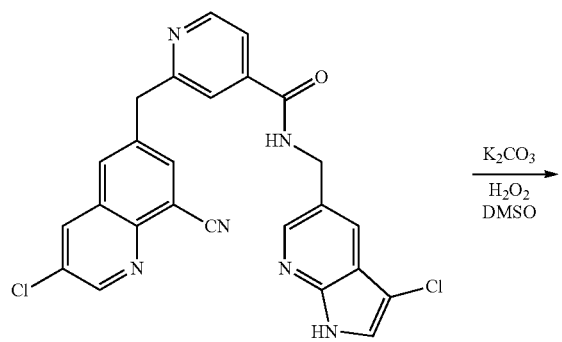 $\xrightarrow{\text{K}_2\text{CO}_3, \text{H}_2\text{O}_2, \text{DMSO}}$

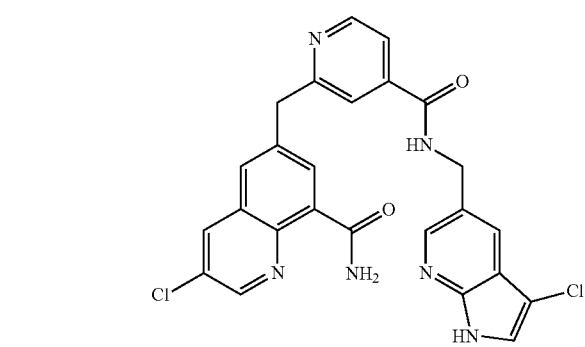

3-Chloro-6-((4-(((3-chloro-1H-pyrrolo[2,3-b]pyridin-5-yl)methyl)carbamoyl)pyridin-2-yl)methyl)quinoline-8-carboxamide (30 mg, 37%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 505.1, found 505.0.

$^1$H NMR (DMSO-d$_6$, 400 MHz) δ 9.63 (s, 1H), 9.34-9.35 (t, 1H), 8.96-8.97 (d, 1H), 8.69-8.70 (d, 1H), 8.64-8.66 (d, 1H), 8.44 (s, 1H), 8.31 (s, 1H), 8.04 (s, 1H), 7.95 (s, 1H), 7.87 (s, 1H), 7.82 (s, 1H), 7.65-7.67 (d, 2H), 4.58-4.60 (d, 2H), 4.42 (s, 2H).

Example 62: Preparation of 6-((4-(((6-amino-2-methylpyridin-3-yl)methyl)carbamoyl)pyridin-2-yl)methyl)-3-chloroquinoline-8-carboxamide

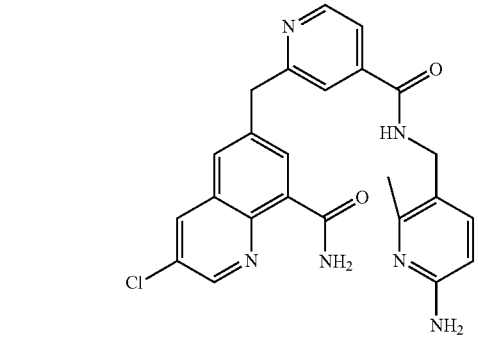

6-((4-(((6-amino-2-methylpyridin-3-yl)methyl)carbamoyl)pyridin-2-yl)methyl)-3-chloroquinoline-8-carboxamide

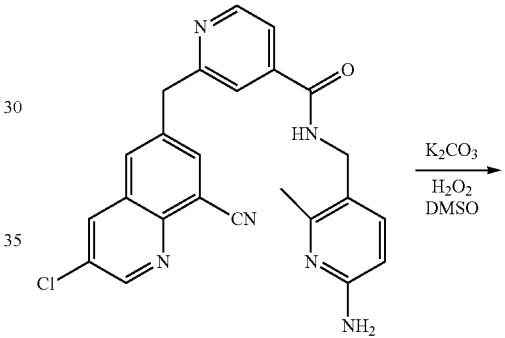 $\xrightarrow{\text{K}_2\text{CO}_3, \text{H}_2\text{O}_2, \text{DMSO}}$

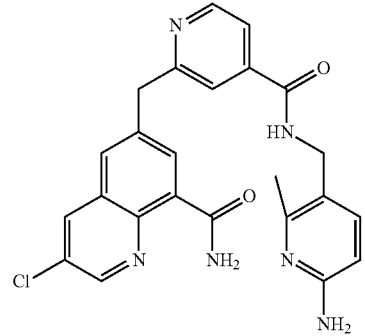

6-((4-(((6-Amino-2-methylpyridin-3-yl)methyl)carbamoyl)pyridin-2-yl)methyl)-3-chloroquinoline-8-carboxamide (28 mg, 44%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 461.1, found 461.1.

$^1$H NMR (DMSO-d$_6$, 400 MHz) δ 9.63 (s, 1H), 8.97-9.00 (m, 2H), 8.70-8.71 (d, 1H), 8.62-8.64 (d, 1H), 8.44-8.46 (d, 1H), 8.04 (s, 1H), 7.96 (s, 1H), 7.63-7.65 (dd, 1H), 7.23-7.25 (d, 1H), 6.22-6.25 (dd, 1H), 5.77 (s, 1H), 4.42 (s, 2H), 4.28-4.30 (d, 2H), 2.28 (s, 3H).

Example 63: Preparation of 6-((4-(((6-amino-4-methylpyridin-3-yl)methyl)carbamoyl)pyridin-2-yl)methyl)-3-chloroquinoline-8-carboxamide

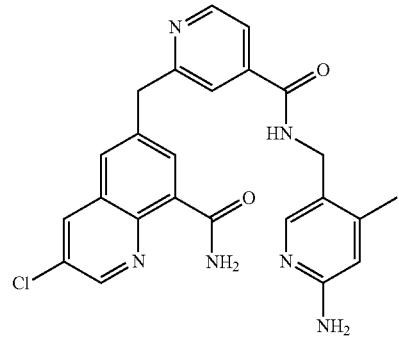

6-((4-(((6-amino-4-methylpyridin-3-yl)methyl)carbamoyl)pyridin-2-yl)methyl)-3-chloroquinoline-8-carboxamide

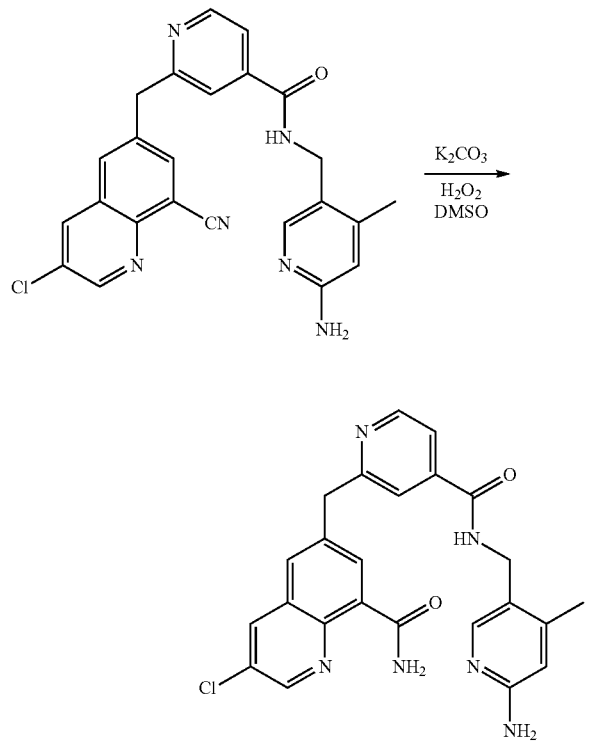

6-((4-(((6-Amino-4-methylpyridin-3-yl)methyl)carbamoyl)pyridin-2-yl)methyl)-3-chloroquinoline-8-carboxamide (70 mg, 69%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 461.1, found 461.1.

$^1$H NMR (DMSO-d$_6$, 400 MHz) δ 9.63 (s, 1H), 8.92-9.00 (m, 2H), 8.70-8.71 (d, 1H), 8.62-8.64 (d, 1H), 8.43-8.45 (d, 1H), 8.05 (s, 1H), 7.96 (s, 1H), 7.78-7.80 (dd, 1H), 7.61-7.63 (d, 1H), 6.26 (s, 1H), 5.81 (s, 1H), 4.41 (s, 2H), 4.29-4.31 (d, 2H), 2.15 (s, 3H).

Example 64: Preparation of 6-((4-(((1-aminoisoquinolin-6-yl)methyl)carbamoyl)pyridin-2-yl)methyl)-3-chloroquinoline-8-carboxamide

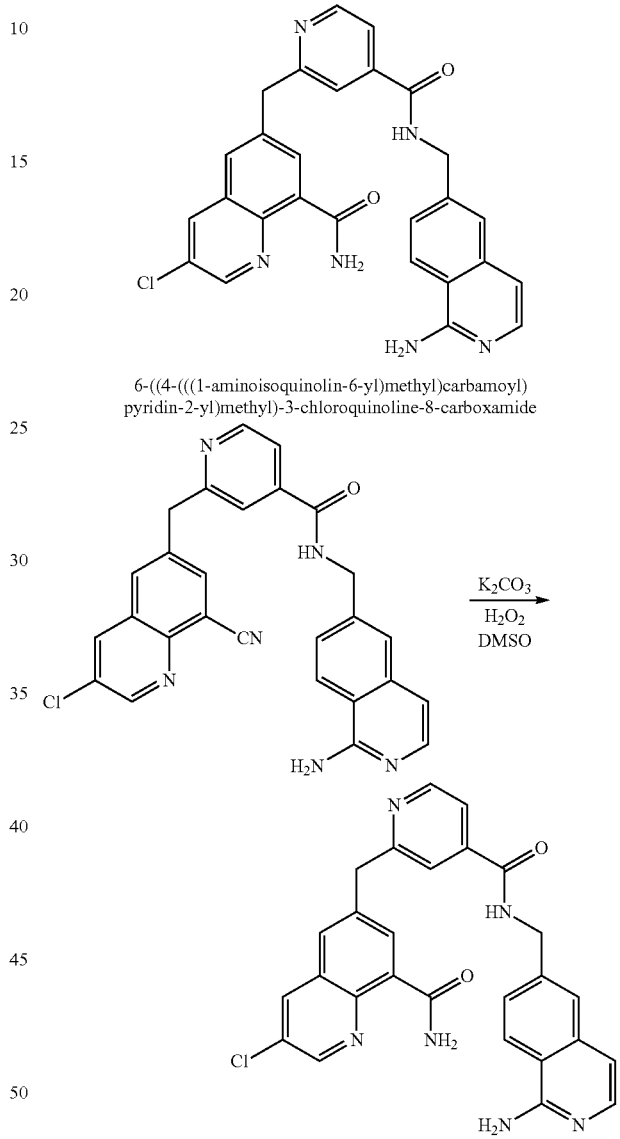

6-((4-(((1-aminoisoquinolin-6-yl)methyl)carbamoyl)pyridin-2-yl)methyl)-3-chloroquinoline-8-carboxamide 6-((4-(((1-Aminoisoquinolin-6-yl)methyl)carbamoyl)pyridin-2-yl)methyl)-3-chloroquinoline-8-carboxamide (25 mg, 16%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 497.1, found 497.0.

$^1$H NMR (DMSO-d$_6$, 400 MHz) δ 9.63 (s, 1H), 9.37-9.39 (t, 1H), 8.97-8.98 (m, 2H), 8.70-8.71 (d, 1H), 8.67-8.68 (d, 1H), 8.45-8.46 (d, 1H), 8.13-8.15 (d, 1H), 8.06 (s, 1H), 7.95 (s, 1H), 7.85 (s, 1H), 7.75-7.76 (d, 1H), 7.69-7.70 (dd, 1H), 7.54-7.56 (dd, 1H), 7.42 (s, 1H), 7.39-7.40 (d, 1H), 6.84-6.86 (d, 1H), 6.76 (s, 2H), 4.60-4.62 (d, 2H), 4.40 (s, 2H).

Example 65: Preparation of 3-chloro-6-((4-(((3-chloro-4-fluoro-1H-indol-5-yl)methyl)carbamoyl)pyridin-2-yl)methyl)quinoline-8-carboxamide Example 66: Preparation of 3-chloro-6-((4-(((6-fluoro-1H-indol-5-yl)methyl)carbamoyl)pyridin-2-yl)methyl)quinoline-8-carboxamide

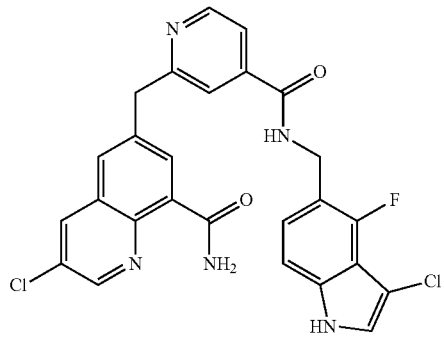

3-chloro-6-((4-(((3-chloro-4-fluoro-1H-indol-5-yl)methyl)carbamoyl)pyridin-2-yl)methyl)quinoline-8-carboxamide

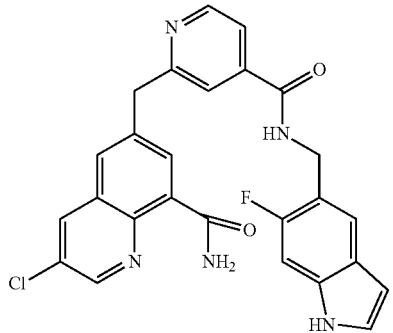

3-chloro-6-((4-(((6-fluoro-1H-indol-5-yl)methyl)carbamoyl)pyridin-2-yl)methyl)quinoline-8-carboxamide

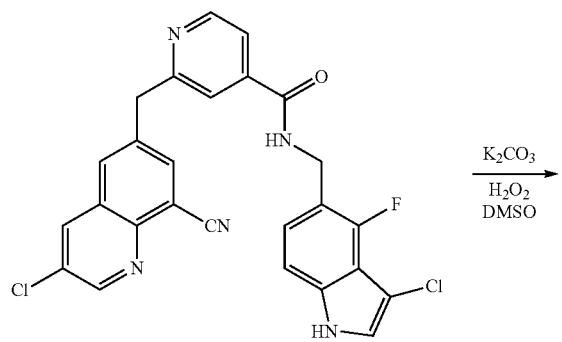

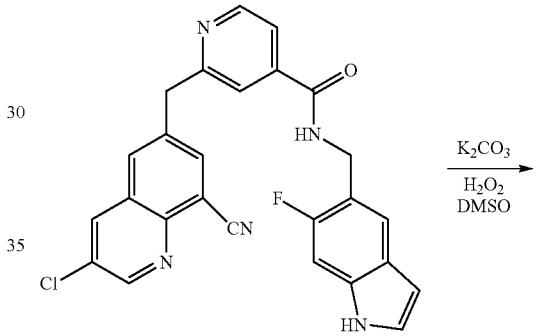

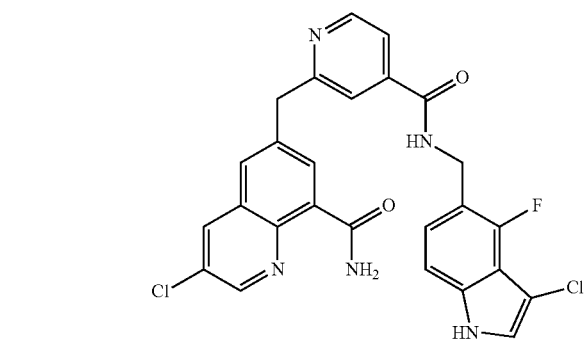

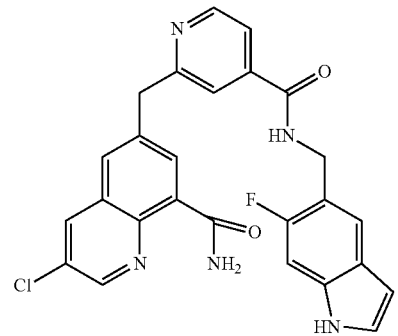

3-Chloro-6-((4-(((3-chloro-4-fluoro-1H-indol-5-yl)methyl)carbamoyl)pyridin-2-yl)methyl)quinoline-8-carboxamide (35 mg, 16%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 522.1, found 522.0.

$^1$H NMR (DMSO-$d_6$, 400 MHz) δ 11.58 (s, 1H), 9.62 (s, 1H), 9.22-9.25 (t, 1H), 8.97-8.98 (d, 2H), 8.69-8.70 (d, 1H), 8.63-8.65 (d, 1H), 8.43-8.44 (d, 1H), 8.04 (s, 1H), 7.94 (s, 1H), 7.82 (s, 1H), 7.65-7.66 (d, 1H), 7.51 (s, 1H), 7.14-7.20 (m, 2H), 4.56-4.57 (d, 2H), 4.41 (s, 2H).

3-Chloro-6-((4-(((6-fluoro-1H-indol-5-yl)methyl)carbamoyl)pyridin-2-yl)methyl)quinoline-8-carboxamide (35 mg, 42%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 488.1, found 488.0.

$^1$H NMR (DMSO-$d_6$, 400 MHz) δ 11.09 (s, 1H), 9.62 (s, 1H), 9.19-9.22 (t, 1H), 8.97-8.98 (d, 2H), 8.69-8.70 (d, 1H), 8.64-8.66 (d, 1H), 8.44-8.45 (d, 1H), 8.05 (s, 1H), 7.95 (s, 1H), 7.84 (s, 1H), 7.67-7.69 (d, 1H), 7.48-7.50 (s, 1H), 7.30-7.31 (t, 2H), 7.14-7.17 (1, 1H), 4.55-4.57 (d, 2H), 4.42 (s, 2H).

Example 67: Preparation of N-((6-amino-2,4-dimethylpyridin-3-yl)methyl)-2-((3-chloro-8-(methylsulfonyl)quinolin-6-yl)methyl)isonicotinamide

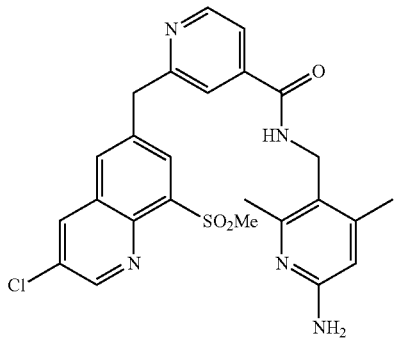

N-((6-amino-2,4-dimethylpyridin-3-yl)methyl)-2-((3-chloro-8-(methysulfonyl)quinolin-6-yl)methyl)isonicotinamide

Step 1: Preparation of (3-chloro-8-methanesulfonyl-quinolin-6-yl)-methanol

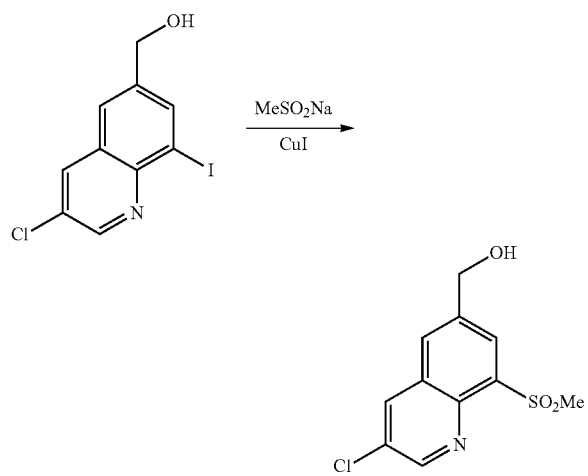

A mixture of (3-chloro-8-iodo-quinolin-6-yl)-methanol (7.6 g, 23.8 mmol, 1 eq), sodium methanesulphinate (2.92 g, 28.6 mmol, 1.2 eq), copper iodide (452 mg, 2.38 mol, 0.1 eq), L-proline sodium salt (652 mg, 4.76 mol, 0.2 eq) in 110 mL of DMSO was heated to 110° C. under nitrogen for 15 h. The cooled mixture was partitioned between ethyl acetate and water. The organic layer was separated, and the aqueous layer was extracted with ethyl acetate twice. The combined organic layers were washed with brine, dried over MgSO$_4$, and concentrated in vacuum. The residue was purified by silica gel column (EA/PE=1/2, v/v) to give (3-chloro-8-methanesulfonyl-quinolin-6-yl)-methanol (4.1 g, 64%) as a yellow solid.

Step 2: Preparation of 3-chloro-6-chloromethyl-8-methanesulfonyl-quinoline

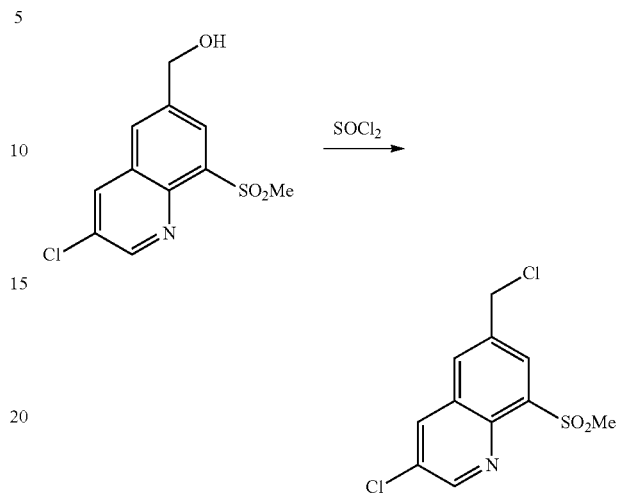

To (3-chloro-8-methanesulfonyl-quinolin-6-yl)-methanol (4.1 g, 15.1 mmol, 1.0 eq) was added SOCl$_2$ (50 mL) and the mixture was stirred at rt for 1 h. The volatiles were then removed under vacuum and the residue was dissolved in DCM. The mixture was washed with saturated aq. NaHCO$_3$, dried and concentrated to give 3-chloro-6-chloromethyl-8-methanesulfonyl-quinoline (4.3 g, 99%) as a yellow solid.

Step 3: Preparation of 2-(3-chloro-8-methanesulfonyl-quinolin-6-ylmethyl)-isonicotinic Acid Methyl Ester

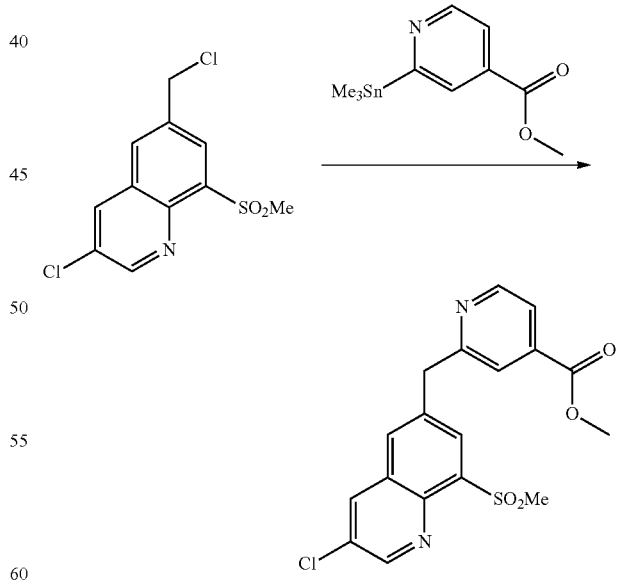

To a solution of 3-chloro-6-chloromethyl-8-methanesulfonyl-quinoline (4.3 g, 14.9 mmol, 1.0 eq) in dioxane (70 mL) was added 2-trimethylstannanyl-isonicotinic acid methyl ester (4.93 g, 16.4 mmol, 1.1 eq) and Pd(PPh$_3$)$_2$Cl$_2$ (1.04 g, 1.49 mmol, 0.1 eq). The mixture was stirred at 90° C. for 3 h under nitrogen atmosphere, concentrated and purified by silica gel chromatography (DCM/MeOH=50/1, v/v) to afford 2-(3-chloro-8-methanesulfonyl-quinolin-6-yl-methyl)-isonicotinic acid methyl ester (2.3 g, 40%) as a yellow solid.

Step 4: Preparation of N-((6-amino-2,4-dimethyl-pyridin-3-yl)methyl)-2-((3-chloro-8-(methylsulfonyl)quinolin-6-yl)methyl)isonicotinamide

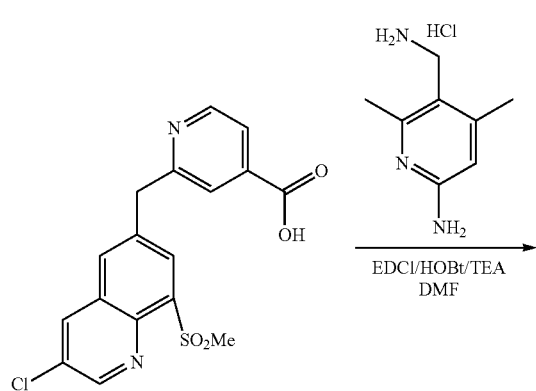

To a solution of 2-(3-chloro-8-methanesulfonyl-quinolin-6-ylmethyl)-isonicotinic acid (80 mg, 0.21 mmol, 1 eq) in DMF (10 mL) was added 5-aminomethyl-4,6-dimethyl-pyridin-2-ylamine hydrochloride (40 mg, 0.21 mmol, 1.0 eq) followed by EDCI (61 mg, 0.32 mmol, 1.5 eq), HOBT (43 mg, 0.32 mmol, 1.5 eq) and TEA (64 mg, 0.64 mmol, 3.0 eq). The reaction mixture was heated to 45° C. kept stirring for overnight. Water was added, and the mixture was extracted with DCM. The organic layer was washed with water, dried over $Na_2SO_4$, filtered, and concentrated. The residue was purified by prep-HPLC to give N-((6-amino-2,4-dimethylpyridin-3-yl)methyl)-2-((3-chloro-8-(methylsulfonyl)quinolin-6-yl)methyl)isonicotinamide (40 mg, 37%) as a yellow solid. LRMS (M+H$^+$) m/z calculated 510.1, found 509.8.

$^1$H NMR (DMSO-d$_6$, 400 MHz) δ 9.07 (d, 1H), 8.76 (d, 1H), 8.66 (t, 1H), 8.62 (d, 1H), 8.36 (d, 1H), 8.23 (s, 1H), 7.83 (s, 1H), 7.62 (d, 1H), 6.12 (s, 1H), 5.70 (s, 2H), 4.47 (s, 2H), 4.34 (d, 2H), 3.56 (s, 3H), 2.30 (s, 3H), 2.17 (s, 3H).

Example 68: Preparation of N-((3-chloro-6-fluoro-1H-indol-5-yl)methyl)-2-((3-chloro-8-(methylsulfonyl)quinolin-6-yl)methyl)isonicotinamide

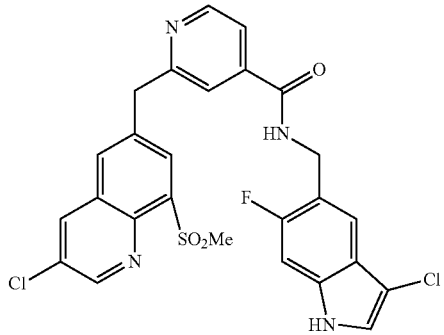

N-((3-chloro-6-fluoro-1H-indol-5-yl)methyl)-2-((3-chloro-8-(methylsulfonyl)quinolin-6-yl)methyl)isonicotinamide

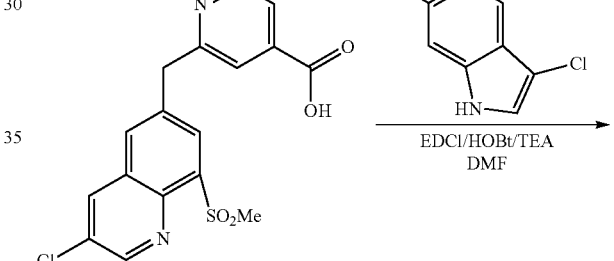

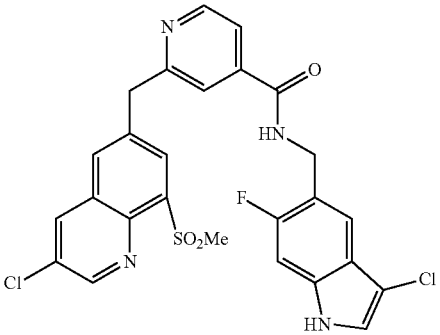

N-((3-chloro-6-fluoro-1H-indol-5-yl)methyl)-2-((3-chloro-8-(methylsulfonyl) quinolin-6-yl)methyl)isonicotinamide (40 mg, 34%) was prepared as described for N-((6-amino-2,4-dimethylpyridin-3-yl)methyl)-2-((3-chloro-8-(methylsulfonyl)quinolin-6-yl)methyl)isonicotinamide (Example 67) as a white solid. LRMS (M+H$^+$) m/z calculated 557.1, found 557.0.

$^1$H NMR (DMSO-d$_6$, 400 MHz) δ 11.41 (s, 1H), 9.27 (t, 1H), 9.07 (d, 1H), 8.76 (d, 1H), 8.67 (d, 1H), 8.37 (s, 1H), 8.23 (s, 1H), 7.88 (s, 1H), 7.68 (d, 1H), 7.51 (d, 2H), 7.46 (d, 1H), 7.23 (d, 2H), 4.59 (d, 2H), 4.49 (s, 2H), 3.56 (s, 3H).

Example 69: Preparation of N-((6-amino-2-methyl-pyridin-3-yl)methyl)-2-((3-chloro-8-(methylsulfonyl)quinolin-6-yl)methyl)isonicotinamide Example 70: Preparation of N-((6-amino-2,4-dimethylpyridin-3-yl)methyl)-2-((8-cyano-3-methylquinolin-6-yl)methyl)isonicotinamide

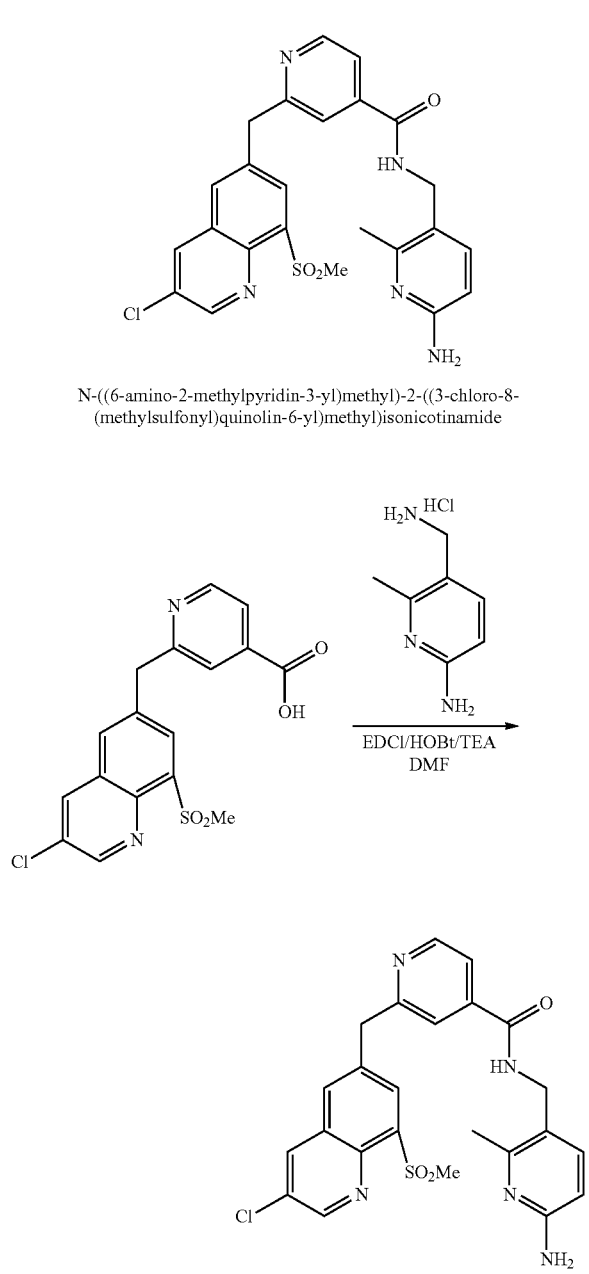

N-((6-amino-2-methylpyridin-3-yl)methyl)-2-((3-chloro-8-(methylsulfonyl)quinolin-6-yl)methyl)isonicotinamide

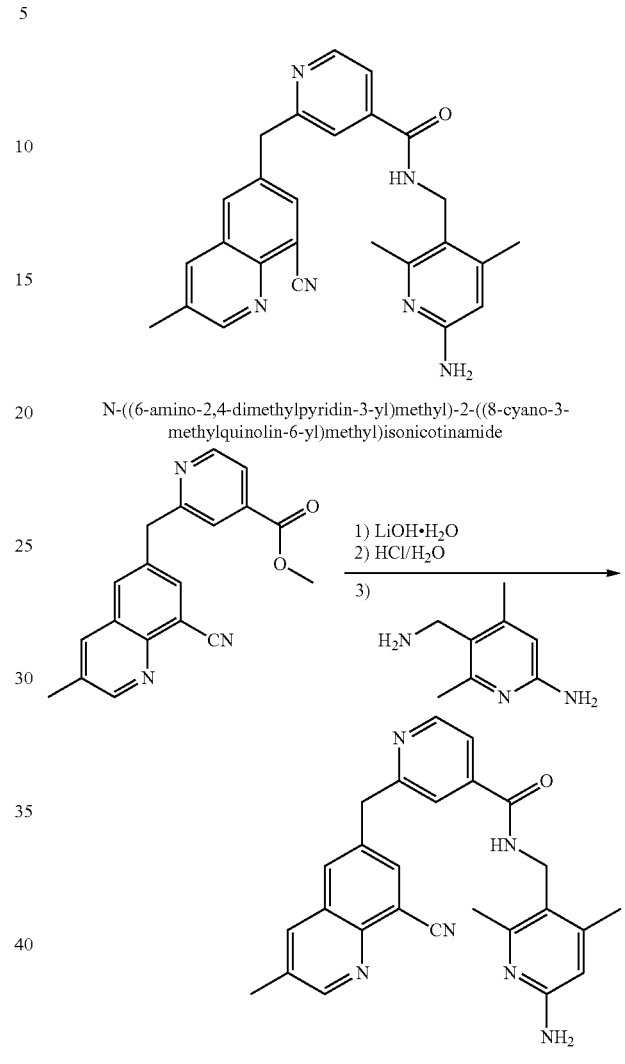

N-((6-amino-2,4-dimethylpyridin-3-yl)methyl)-2-((8-cyano-3-methylquinolin-6-yl)methyl)isonicotinamide N-((6-amino-2-methylpyridin-3-yl)methyl)-2-((3-chloro-8-(methylsulfonyl)quinolin-6-yl)methyl)isonicotinamide (40 mg, 34%) was prepared as described for N-((6-amino-2,4-dimethylpyridin-3-yl)methyl)-2-((3-chloro-8-(methylsulfonyl)quinolin-6-yl)methyl)isonicotinamide (Example 67) as a white solid. LRMS (M+H$^+$) m/z calculated 496.1, found 495.7.

$^1$H NMR (DMSO-d$_6$, 400 MHz) δ 9.07 (d, 1H), 9.01 (t, 1H), 8.76 (d, 1H), 8.64 (d, 1H), 8.36 (d, 1H), 8.23 (s, 1H), 7.85 (s, 1H), 7.65 (d, 1H), 7.24 (d, 1H), 6.23 (d, 1H), 5.75 (s, 2H), 4.48 (s, 2H), 4.30 (d, 2H), 3.56 (s, 3H), 2.28 (s, 3H).

To a solution of 2-(8-cyano-3-methyl-quinolin-6-ylmethyl)-isonicotinic acid methyl ester (300 mg, 0.95 mmol, 1.0 eq) in THF (16 mL)/H$_2$O (4 mL) was added LiOH.H$_2$O (79.49 mg, 1.89 mmol, 2.0 eq). The mixture was stirred at 40° C. for 1 h and was acidified to pH 5 with 1 N HCl solution. The mixture was concentrated in vacuo and the residue was directly used without further purification. To a solution of the above crude product and 5-aminomethyl-4,6-dimethyl-pyridin-2-ylamine (285 mg, 1.89 mmol, 2.0 eq) in DMF 10 mL) was added HOBT (192.37 mg, 1.43 mmol, 1.5 eq), EDCI (310.08 mg, 1.62 mmol, 1.7 eq) and Et$_3$N (0.53 mL, 3.8 mmol, 4 eq). The mixture was stirred at rt for overnight and diluted with water. The organic layer was separated and the aqueous layer was extracted with DCM. The combined extracts were dried and concentrated. The residue was purified by prep-HPLC to give N-((6-amino-2,4-dimethylpyridin-3-yl)methyl)-2-((8-cyano-3-methylquinolin-6-yl)methyl)isonicotinamide (90 mg, 21% for 2 steps) as an off-white solid. LRMS (M+H$^+$) m/z calculated 437.2, found 437.0.

$^1$H NMR (DMSO-d$_6$, 400 MHz) δ 8.89 (s, 1H), 8.61 (t, 2H), 8.23 (s, 2H), 8.10 (s, 1H), 7.78 (s, 1H), 7.61 (t, 1H), 6.12 (s, 1H), 5.67 (s, 2H), 4.37 (s, 2H), 4.35 (d, 2H), 2.50 (s, 3H), 2.30 (s, 3H), 2.16 (s, 3H).

Example 71: Preparation of N-((1-aminoisoquinolin-6-yl)methyl)-2-((8-cyano-3-methylquinolin-6-yl)methyl)isonicotinamide

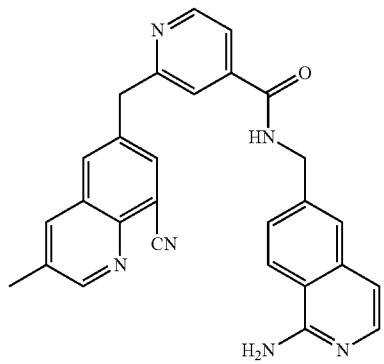

N-((1-aminoisoquinolin-6-yl)methyl)-2-((8-cyano-3-methylquinolin-6-yl)methyl)isonicotinamide 7.78 (d, 1H), 7.71 (d, 1H), 7.57 (s, 1H), 7.43 (d, 1H), 6.87 (d, 1H), 6.78 (s, 2H), 4.64 (d, 2H), 4.42 (s, 2H), 2.50 (s, 3H).

Example 72: Preparation of N-((3-chloro-6-fluoro-1H-indol-5-yl)methyl)-2-((8-cyano-3-methylquinolin-6-yl)methyl)isonicotinamide

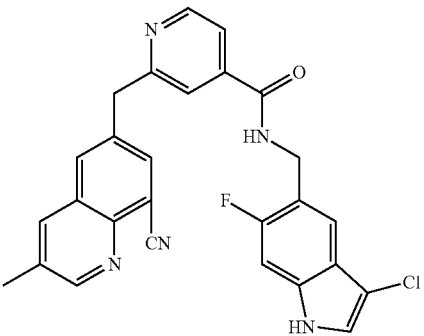

N-((3-chloro-6-fluoro-1H-indol-5-yl)methyl)-2-((8-cyano-3-methylquinolin-6-yl)methyl)isonicotinamide

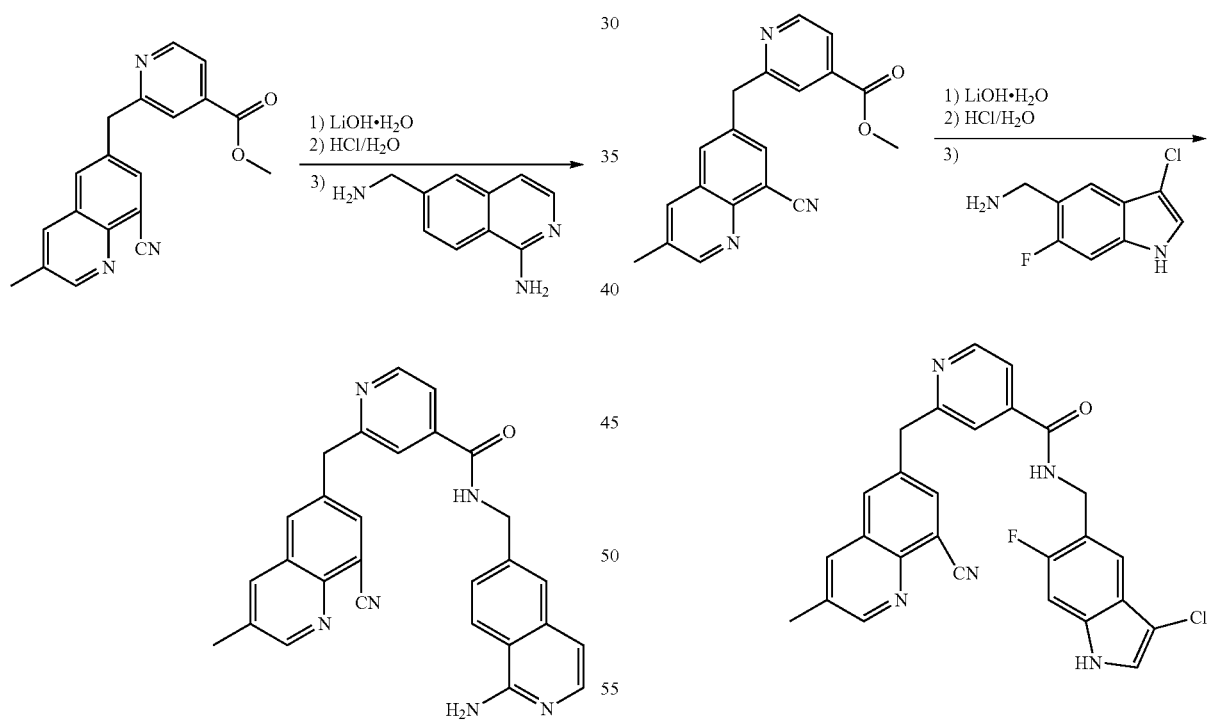

N-((1-aminoisoquinolin-6-yl)methyl)-2-((8-cyano-3-methylquinolin-6-yl)methyl)isonicotinamide (105 mg, 24% for 2 steps) was prepared as described for N-((6-amino-2,4-dimethylpyridin-3-yl)methyl)-2-((8-cyano-3-methylquinolin-6-yl)methyl)isonicotinamide (Example 70) as an off-white solid. LRMS (M+H$^+$) m/z calculated 459.2, found 459.0.

$^1$H NMR (DMSO-d$_6$, 400 MHz) δ 9.41 (t, 1H), 8.90 (s, 1H), 8.69 (d, 1H), 8.28 (d, 2H), 8.16 (d, 2H), 7.86 (s, 1H),

N-((3-chloro-6-fluoro-1H-indol-5-yl)methyl)-2-((8-cyano-3-methylquinolin-6-yl)methyl)isonicotinamide (100 mg, 21% for 2 steps) was prepared as described for N-((6-amino-2,4-dimethylpyridin-3-yl)methyl)-2-((8-cyano-3-methylquinolin-6-yl)methyl)isonicotinamide (Example 70) as an off-white solid. LRMS (M+H$^+$) m/z calculated 484.1, found 483.9.

$^1$H NMR (DMSO-d$_6$, 400 MHz) δ 11.32 (s, 1H), 8.90 (t, 1H), 8.67 (d, 1H), 8.62 (d, 1H), 8.27 (d, 2H), 8.12 (s, 1H), 7.83 (s, 1H), 7.68 (d, 1H), 7.52 (d, 1H), 7.46 (d, 1H), 7.25 (d, 1H), 4.61 (d, 2H), 4.41 (s, 2H), 2.50 (s, 3H).

Example 73: Preparation of N-((3-chloro-1H-pyrrolo[2,3-b]pyridin-5-yl)methyl)-2-((8-cyano-3-methylquinolin-6-yl)methyl)isonicotinamide

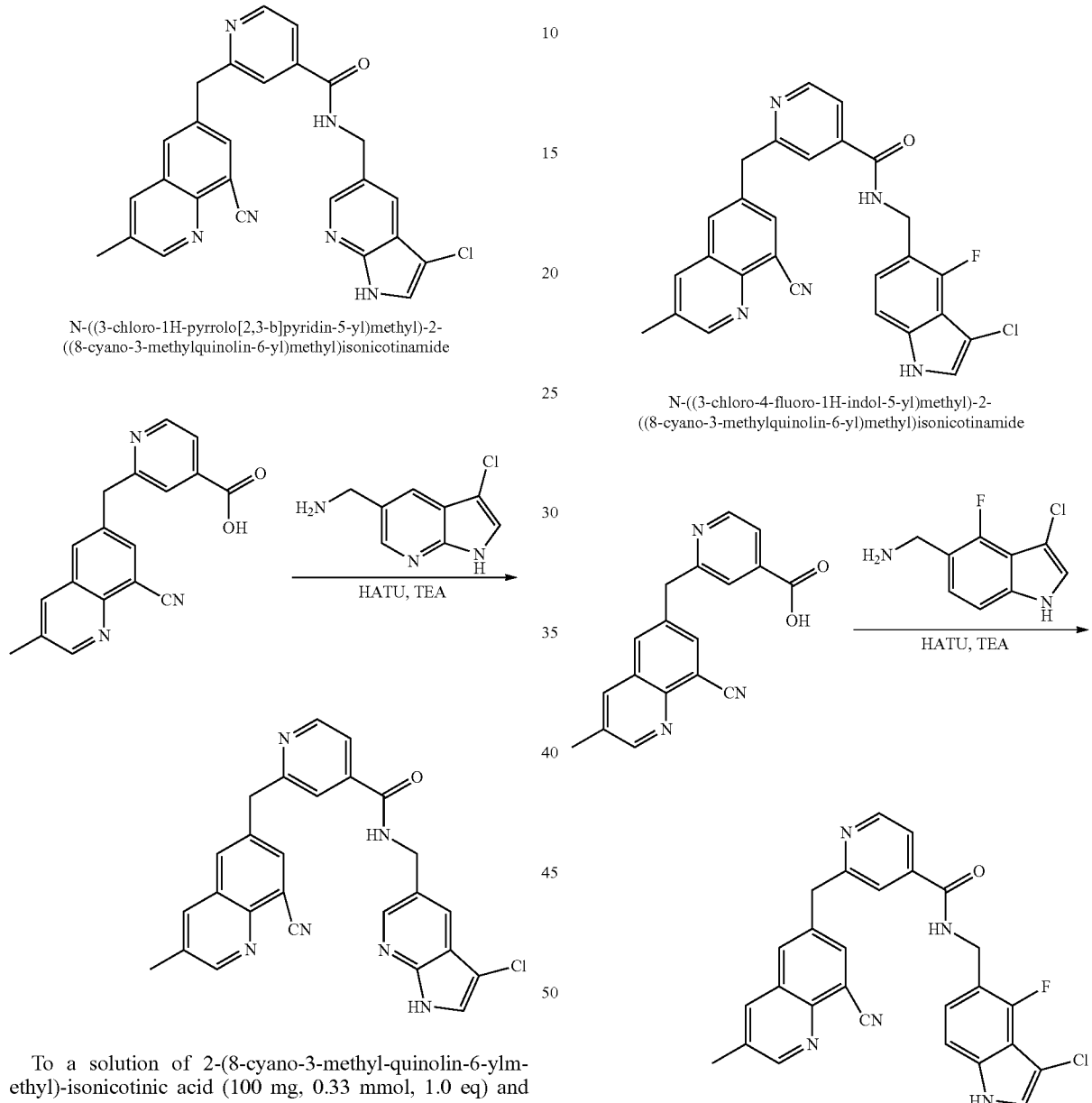

N-((3-chloro-1H-pyrrolo[2,3-b]pyridin-5-yl)methyl)-2-((8-cyano-3-methylquinolin-6-yl)methyl)isonicotinamide To a solution of 2-(8-cyano-3-methyl-quinolin-6-ylmethyl)-isonicotinic acid (100 mg, 0.33 mmol, 1.0 eq) and C-(3-chloro-1H-pyrrolo[2,3-b]pyridin-5-yl)-methylamine hydrochloride (144 mg, 0.66 mmol, 2.0 eq) in DMF (5 mL) was added HATU (188 mg, 0.50 mmol, 1.5 eq) and Et$_3$N (134 mg, 1.32 mmol, 4 eq). The mixture was stirred at rt for 2 h and diluted with water. The organic layer was separated and the aqueous layer was extracted with DCM. The combined extracts were dried and concentrated. The residue was purified by prep-HPLC to give N-((3-chloro-1H-pyrrolo[2,3-b]pyridin-5-yl)methyl)-2-((8-cyano-3-methylquinolin-6-yl)methyl)isonicotinamide (66 mg, 43%) as an off-white solid. LRMS (M+H$^+$) m/z calculated 467.1, found 466.8. $^1$H NMR (DMSO-d$_6$, 400 MHz) δ: 11.97 (s, 1H), 9.34 (t, 1H), 8.89 (s, 1H), 8.66 (d, 1H), 8.32 (s, 1H), 8.26 (s, 1H), 8.23 (s, 1H), 8.11 (s, 1H), 7.88 (s, 1H), 7.82 (s, 1H), 7.68 (d, 1H), 7.66 (d, 1H), 4.61 (d, 2H), 4.40 (s, 2H), 2.50 (s, 3H).

Example 74: Preparation of N-((3-chloro-4-fluoro-1H-indol-5-yl)methyl)-2-((8-cyano-3-methylquinolin-6-yl)methyl)isonicotinamide N-((3-chloro-4-fluoro-1H-indol-5-yl)methyl)-2-((8-cyano-3-methylquinolin-6-yl)methyl)isonicotinamide (70 mg, 44%) was prepared as described for N-((3-chloro-1H-pyrrolo[2,3-b]pyridin-5-yl)methyl)-2-((8-cyano-3-methylquinolin-6-yl)methyl)isonicotinamide (Example 73) as an off-white solid. LRMS (M+H$^+$) m/z calculated 484.1, found 483.8.
$^1$H NMR (DMSO-d$_6$, 400 MHz) δ 11.59 (s, 1H), 9.23 (t, 1H), 8.80 (d, 1H), 8.65 (d, 1H), 8.25 (s, 1H), 8.12 (s, 1H), 7.81 (s, 1H), 7.65 (d, 1H), 7.52 (d, 1H), 7.20 (d, 1H), 7.15 (d, 1H), 4.58 (d, 2H), 4.39 (s, 2H), 2.50 (s, 3H).

Example 75: Preparation of N-((5-chloro-1H-indazol-3-yl)methyl)-2-((8-cyano-3-methylquinolin-6-yl)methyl)isonicotinamide

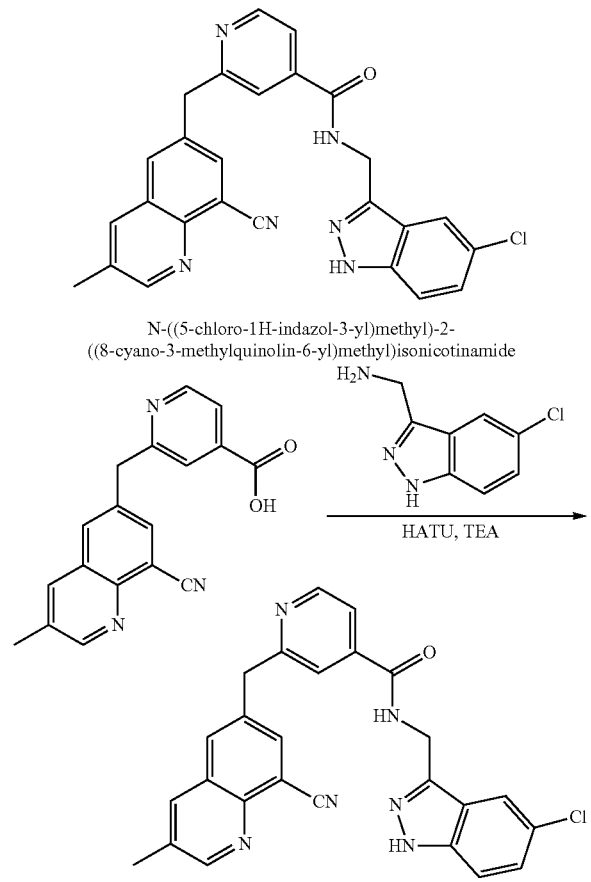

N-((5-chloro-1H-indazol-3-yl)methyl)-2-((8-cyano-3-methylquinolin-6-yl)methyl)isonicotinamide (74 mg, 48%) was prepared as described for N-((3-chloro-1H-pyrrolo[2,3-b]pyridin-5-yl)methyl)-2-((8-cyano-3-methylquinolin-6-yl)methyl)isonicotinamide (Example 73) as an off-white solid. LRMS (M+H⁺) m/z calculated 467.1, found 466.8.

¹H NMR (DMSO-d₆, 400 MHz) δ 13.09 (s, 1H), 9.38 (t, 1H), 8.90 (d, 1H), 8.65 (d, 1H), 8.25 (s, 2H), 8.12 (s, 1H), 7.89 (s, 1H), 7.81 (s, 1H), 7.64 (d, 1H), 7.53 (d, 1H), 7.34 (d, 1H), 7.32 (d, 1H), 4.79 (d, 2H), 4.39 (s, 2H), 2.50 (s, 3H).

Example 76: Preparation of 2-((8-cyano-3-methylquinolin-6-yl)methyl)-N-((6-fluoro-1H-indol-5-yl)methyl)isonicotinamide

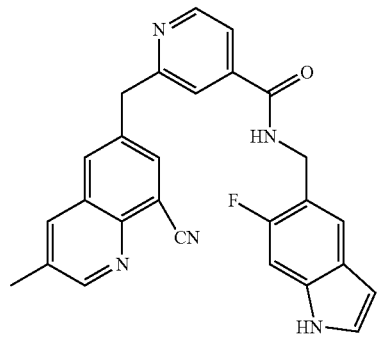

2-((8-cyano-3-methylquinolin-6-yl)methyl)-N-((6-fluoro-1H-indol-5-yl)methyl)isonicotinamide

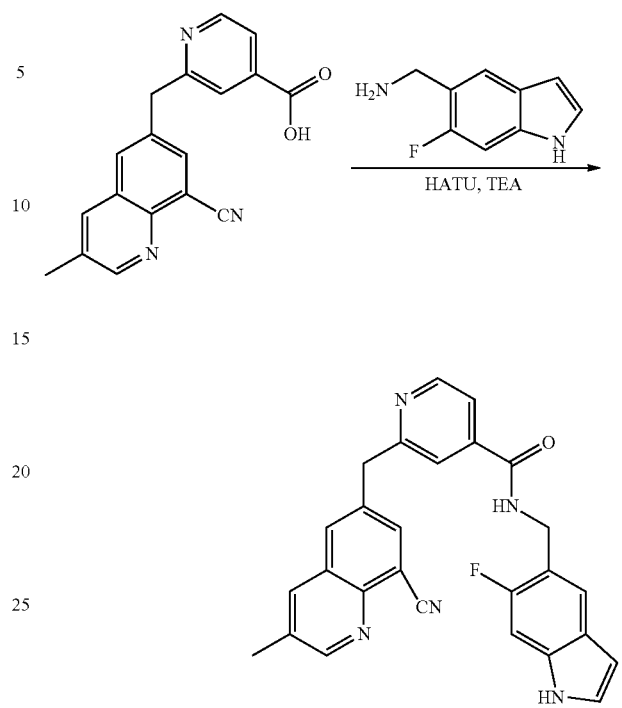

2-((8-Cyano-3-methylquinolin-6-yl)methyl)-N-((6-fluoro-1H-indol-5-yl)methyl)isonicotinamide (70 mg, 46%) was prepared as described for N-((3-chloro-1H-pyrrolo[2,3-b]pyridin-5-yl)methyl)-2-((8-cyano-3-methylquinolin-6-yl)methyl)isonicotinamide (Example 73) as an off-white solid. LRMS (M+H⁺) m/z calculated 450.2, found 449.8.

¹H NMR (DMSO-d₆, 400 MHz) δ 11.11 (s, 1H), 9.20 (t, 1H), 8.90 (d, 1H), 8.65 (d, 1H), 8.26 (t, 2H), 8.13 (s, 1H), 7.83 (s, 1H), 7.68 (d, 1H), 7.31 (d, 1H), 7.17 (d, 1H), 6.40 (s, 1H), 4.57 (d, 2H), 4.40 (s, 2H), 2.50 (s, 3H).

Example 77: Preparation of 6-((4-(((6-amino-2,4-dimethylpyridin-3-yl)methyl)carbamoyl)pyridin-2-yl)methyl)-3-methylquinoline-8-carboxamide

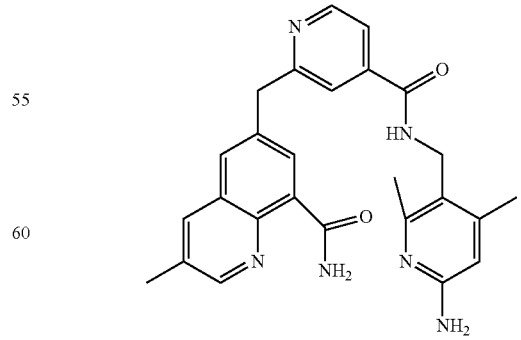

6-((4-(((6-amino-2,4-dimethylpyridin-3-yl)methyl)carbamoyl)pyridin-2-yl)methyl)-3-methylquinoline-8-carboxamide

355

-continued

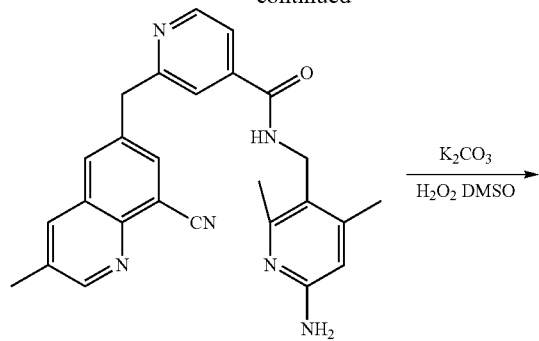

To a solution of N-(6-amino-2,4-dimethyl-pyridin-3-ylmethyl)-2-(8-cyano-3-methyl-quinolin-6-ylmethyl)-isonicotinamide (80 mg, 0.18 mmol, 1.0 eq) and K$_2$CO$_3$ (180.7 mg, 1.31 mmol, 7.3 eq) in DMSO (10 mL) was added H$_2$O$_2$ (1 mL). The mixture was stirred at 50° C. for 3 h, then EA and water was added, the organic layer was concentrated and purified by pre-HPLC to give 6-((4-(((6-amino-2,4-dimethylpyridin-3-yl)methyl)carbamoyl)pyridin-2-yl)methyl)-3-methylquinoline-8-carboxamide (4 mg, 4.8%) as a white solid. LRMS (M+H+) m/z calculated 455.2, found 454.9.

$^1$H NMR (DMSO-d$_6$, 400 MHz) δ 10.20 (s, 1H), 8.84 (s, 1H), 8.66 (s, 1H), 8.63 (s, 1H), 8.41 (s, 1H), 8.25 (s, 1H), 7.98 (s, 1H), 7.90 (s, 1H), 7.78 (s, 1H), 7.61 (s, 1H), 6.12 (s, 1H), 5.68 (s, 2H), 4.38 (d, 2H), 4.34 (s, 2H), 2.50 (s, 3H), 2.29 (s, 3H), 2.21 (s, 3H).

Example 78: Preparation of 6-((4-(((3-chloro-6-fluoro-1H-indol-5-yl)methyl)carbamoyl)pyridin-2-yl)methyl)-3-methylquinoline-8-carboxamide

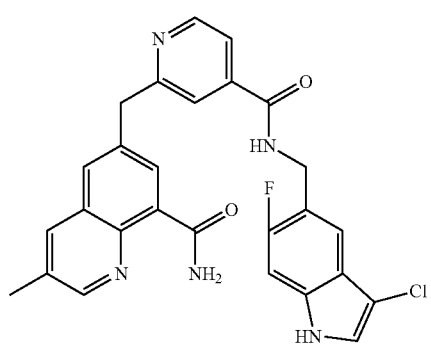

6-((4-(((3-chloro-6-fluoro-1H-indol-5-yl)methyl)cabamoyl)pyridin-2-yl)methyl)-3-methylquinoline-8-carboxamide

356

-continued

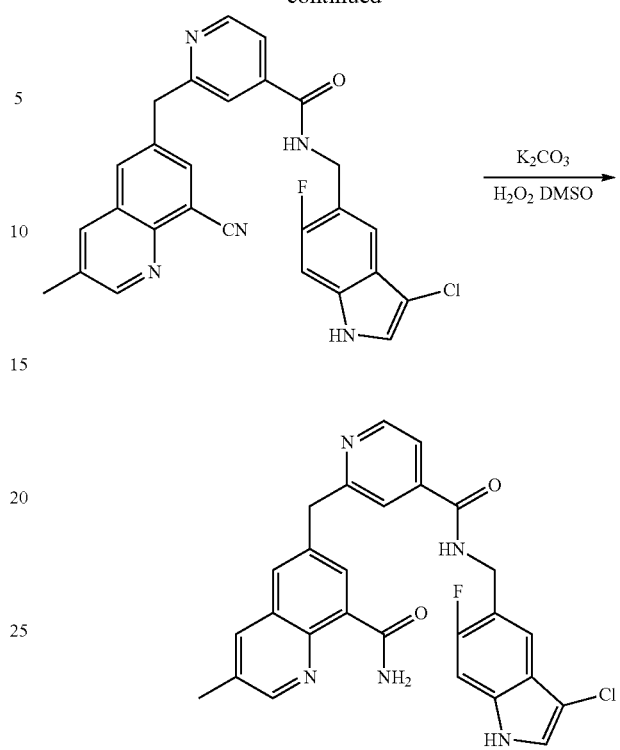

6-((4-(((3-chloro-6-fluoro-1H-indol-5-yl)methyl)carbamoyl)pyridin-2-yl)methyl)-3-methylquinoline-8-carboxamide (40 mg, 32%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a off-white solid. LRMS (M+H$^+$) m/z calculated 502.1, found 501.8. $^1$H NMR (DMSO-d$_6$, 400 MHz) δ 11.44 (s, 1H), 10.28 (d, 1H), 9.31 (t, 1H), 8.89 (s, 1H), 8.71 (d, 1H), 8.48 (s, 1H), 8.28 (s, 1H), 8.02 (s, 1H), 7.93 (s, 1H), 7.86 (s, 1H), 7.72 (d, 1H), 7.55 (d, 1H), 7.50 (d, 1H), 7.29 (d, 1H), 4.64 (d, 2H), 4.45 (s, 2H), 2.54 (s, 3H).

Example 79: Preparation of 6-((4-(((1-aminoisoquinolin-6-yl)methyl)carbamoyl)pyridin-2-yl)methyl)-3-methylquinoline-8-carboxamide

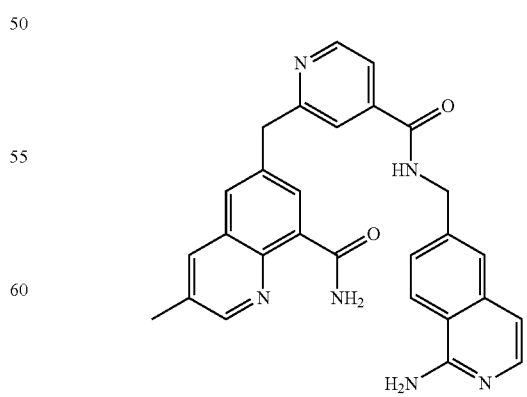

6-((4-(((1-aminoisoquinolin-6-yl)methyl)cabamoyl)pyridin-2-yl)methyl)-3-methylquinoline-8-carboxamide

357
-continued

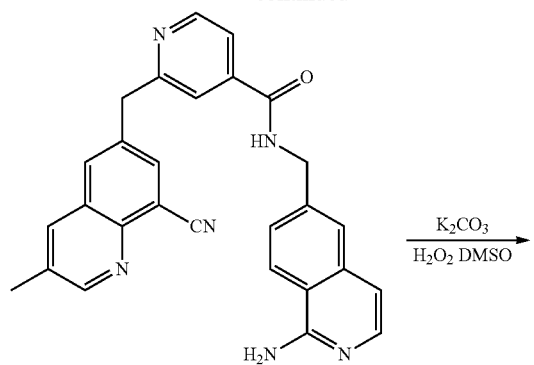

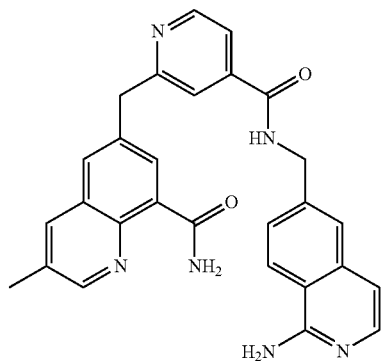

6-((4-(((1-Aminoisoquinolin-6-yl)methyl)carbamoyl) pyridin-2-yl)methyl)-3-methylquinoline-8-carboxamide (35 mg, 48%) was prepared as described for 6-((4-(((6-amino-2,4-dimethylpyridin-3-yl)methyl)carbamoyl)pyridin-2-yl) methyl)-3-methylquinoline-8-carboxamide (Example 77) as a white solid. LRMS (M+H⁺) m/z calculated 477.2, found 476.9.

$^1$H NMR (DMSO-d$_6$, 400 MHz) δ 10.22 (s, 1H), 9.40 (t, 1H), 8.85 (d, 1H), 8.68 (d, 1H), 8.43 (s, 1H), 8.26 (s, 1H), 8.15 (d, 1H), 8.00 (s, 1H), 7.89 (d, 1H), 7.76 (d, 1H), 7.70 (d, 1H), 7.56 (s, 1H), 7.42 (d, 2H), 6.86 (d, 1H), 6.76 (s, 2H), 4.62 (d, 2H), 4.42 (s, 2H), 2.50 (s, 3H).

Example 80: Preparation of 6-((4-(((3-chloro-1H-pyrrolo[2,3-b]pyridin-5-yl)methyl)carbamoyl)pyridin-2-yl)methyl)-3-methylquinoline-8-carboxamide

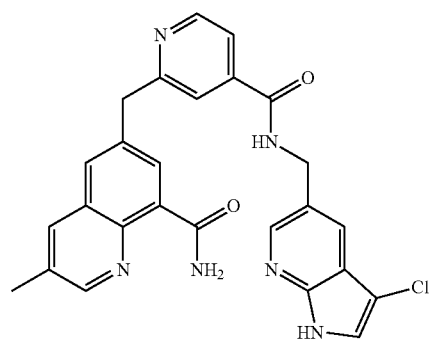

6-((4-(((3-chloro-1H-pyrrolo[2,3-b]pyridin-5-yl)methyl)carbamoyl) pyridin-2-yl)methyl)-3-methylquinoline-8-carboxamide

358
-continued

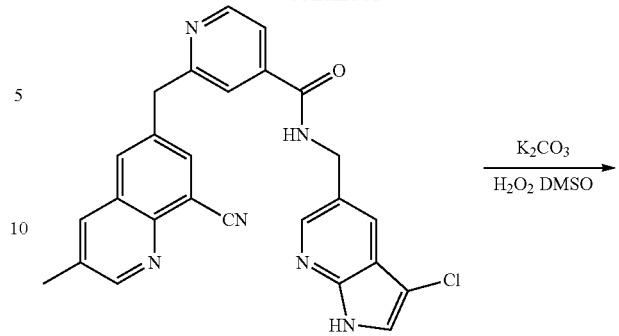

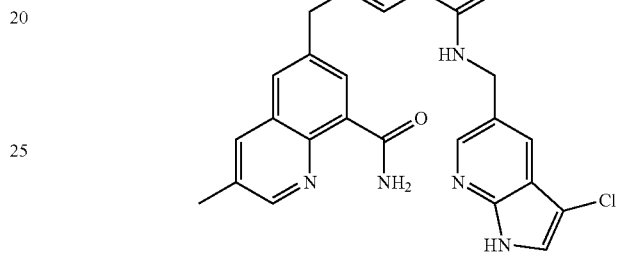

6-((4-(((3-Chloro-1H-pyrrolo[2,3-b]pyridin-5-yl)methyl) carbamoyl)pyridin-2-yl)methyl)-3-methylquinoline-8-carboxamide (20 mg, 38%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a white solid. LRMS (M+H⁺) m/z calculated 485.1, found 484.8.

$^1$H NMR (DMSO-d$_6$, 400 MHz) δ 10.23 (s, 1H), 9.36 (t, 1H), 8.84 (d, 1H), 8.66 (d, 1H), 8.43 (d, 1H), 8.31 (d, 1H), 8.24 (s, 1H), 7.98 (d, 1H), 7.88 (s, 2H), 7.80 (s, 1H), 7.67 (s, 1H), 7.66 (d, 1H), 4.60 (d, 2H), 4.40 (s, 2H), 2.51 (s, 3H).

Example 81: Preparation of 6-((4-(((3-chloro-4-fluoro-1H-indol-5-yl)methyl)carbamoyl)pyridin-2-yl)methyl)-3-methylquinoline-8-carboxamide

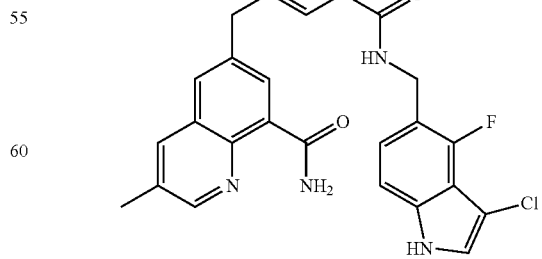

6-((4-(((3-chloro-4-fluoro-1H-indol-5-yl)methyl)carbamoyl) pyridin-2-yl)methyl)-3-methylquinoline-8-carboxamide

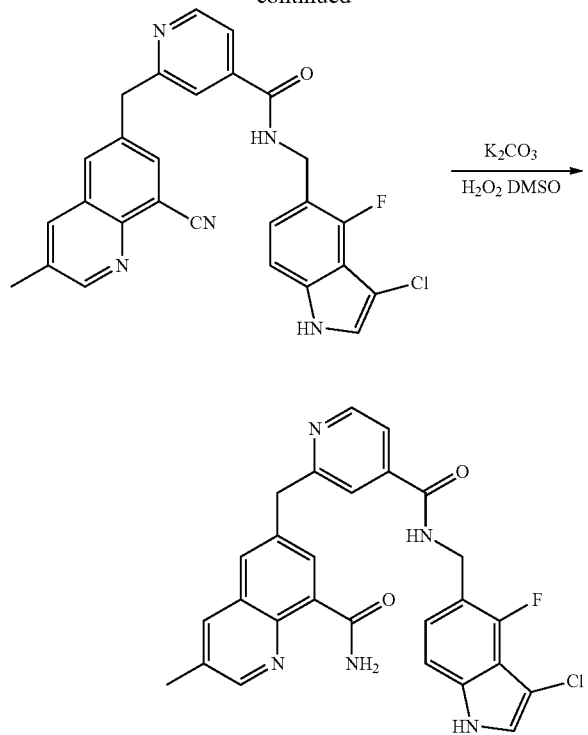

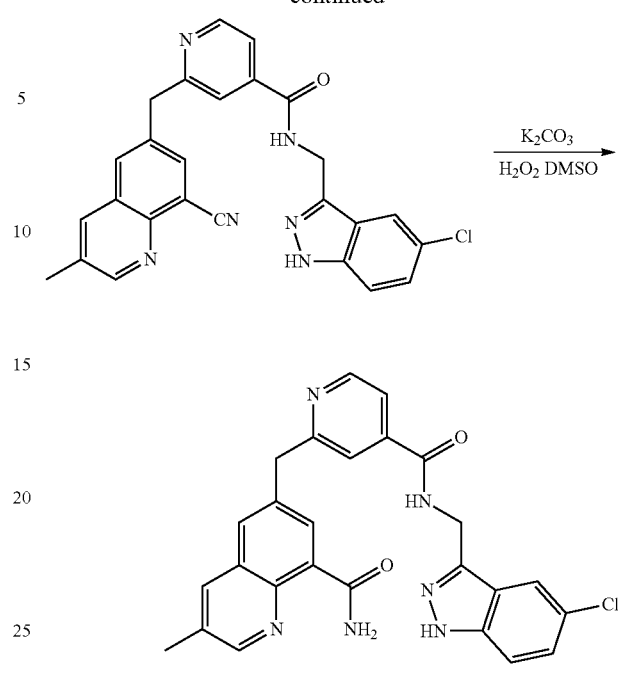

6-((4-(((3-Chloro-4-fluoro-1H-indol-5-yl)methyl)carbamoyl)pyridin-2-yl)methyl)-3-methylquinoline-8-carboxamide (30 mg, 41%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a white solid. LRMS (M+H+) m/z calculated 502.1, found 501.8.

$^1$H NMR (DMSO-d$_6$, 400 MHz) δ 11.59 (s, 1H), 10.23 (s, 1H), 9.26 (t, 1H), 8.85 (d, 1H), 8.65 (d, 1H), 8.42 (d, 1H), 8.25 (s, 1H), 7.98 (d, 1H), 7.88 (d, 1H), 7.80 (s, 1H), 7.66 (d, 1H), 7.51 (d, 1H), 7.21 (d, 1H), 7.16 (d, 1H), 4.58 (d, 2H), 4.40 (s, 2H), 2.51 (s, 3H).

Example 82: Preparation of 6-((4-(((5-chloro-1H-indazol-3-yl)methyl)carbamoyl)pyridin-2-yl)methyl)-3-methylquinoline-8-carboxamide 6-((4-(((5-Chloro-1H-indazol-3-yl)methyl)carbamoyl)pyridin-2-yl)methyl)-3-methylquinoline-8-carboxamide (20 mg, 48%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a white solid. LRMS (M+H+) m/z calculated 485.1, found 484.8.

$^1$H NMR (DMSO-d$_6$, 400 MHz) δ 13.08 (s, 1H), 10.21 (s, 1H), 9.39 (s, 1H), 8.84 (s, 1H), 8.65 (d, 1H), 8.42 (s, 1H), 8.25 (s, 1H), 7.97 (s, 1H), 7.89 (s, 2H), 7.80 (s, 1H), 7.64 (d, 1H), 7.53 (d, 1H), 7.34 (d, 1H), 4.78 (d, 2H), 4.39 (s, 2H), 2.50 (s, 3H).

Example 83: Preparation of 6-((4-(((6-fluoro-1H-indol-5-yl)methyl)carbamoyl)pyridin-2-yl)methyl)-3-methylquinoline-8-carboxamide

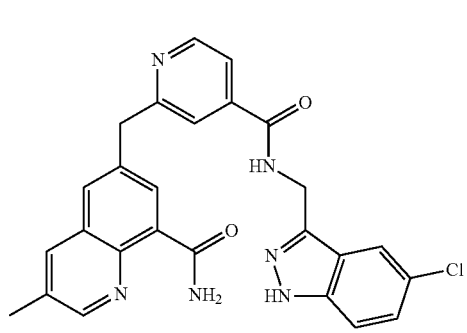

6-((4-(((5-chloro-1H-indazol-3-yl)methyl)carbamoyl)pyridin-2-yl)methyl)-3-methylquinoline-8-carboxamide

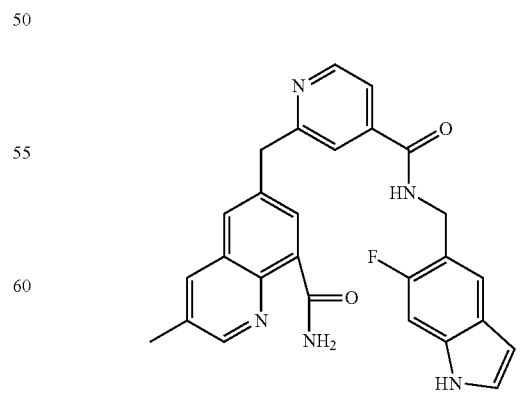

6-((4-(((6-fluoro-1H-indol-5-yl)methyl)carbamoyl)pyridin-2-yl)methyl)-3-methylquinoline-8-carboxamide 361
-continued

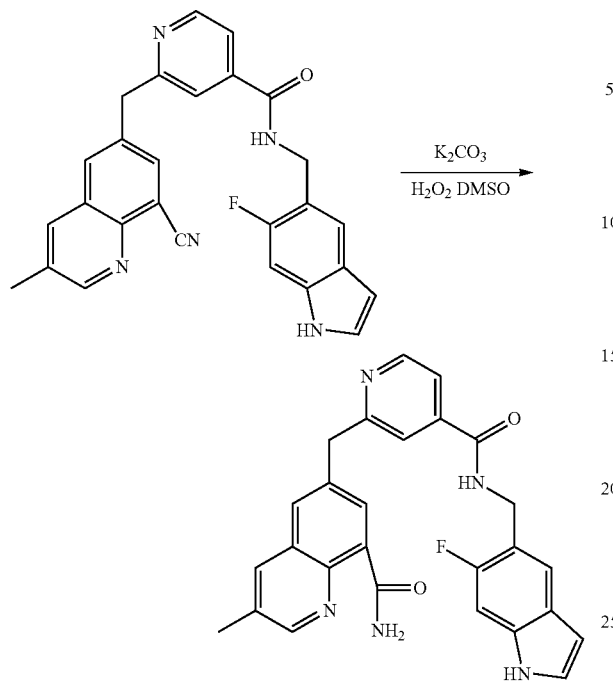

6-((4-((((6-fluoro-1H-indol-5-yl)methyl)carbamoyl)pyridin-2-yl)methyl)-3-methylquinoline-8-carboxamide (20 mg, 35%) was prepared as described for 6-((4-((((6-amino-2,4-dimethylpyridin-3-yl)methyl)carbamoyl)pyridin-2-yl)methyl)-3-methylquinoline-8-carboxamide (Example 77) as a white solid. LRMS (M+H+) m/z calculated 468.2, found 467.8.

$^1$H NMR (DMSO-d$_6$, 400 MHz) δ 11.11 (s, 1H), 10.23 (s, 1H), 9.23 (t, 1H), 8.84 (s, 1H), 8.66 (d, 1H), 8.44 (s, 1H), 8.26 (s, 1H), 7.99 (s, 1H), 7.90 (s, 1H), 7.83 (s, 1H), 7.69 (d, 1H), 7.51 (d, 1H), 7.18 (s, 1H), 7.18 (d, 1H), 6.40 (s, 1H), 4.57 (d, 2H), 4.41 (s, 2H), 2.51 (s, 3H).

Example 84: Preparation of 6-((4-((((6-amino-2,4-dimethylpyridin-3-yl)methyl)carbamoyl)pyridin-2-yl)methyl)-3-methylquinoline-8-carboxylic Acid 6-((4-(((6-amino-2,4-dimethylpyridin-3-yl)methyl)carbamoyl)pyridin-2-yl)methyl)-3-methylquinoline-8-carboxylic acid

362

Step 1: Preparation of 6-(4-methoxycarbonyl-pyridin-2-ylmethyl)-3-methyl-quinoline-8-carboxylic Acid Methyl Ester

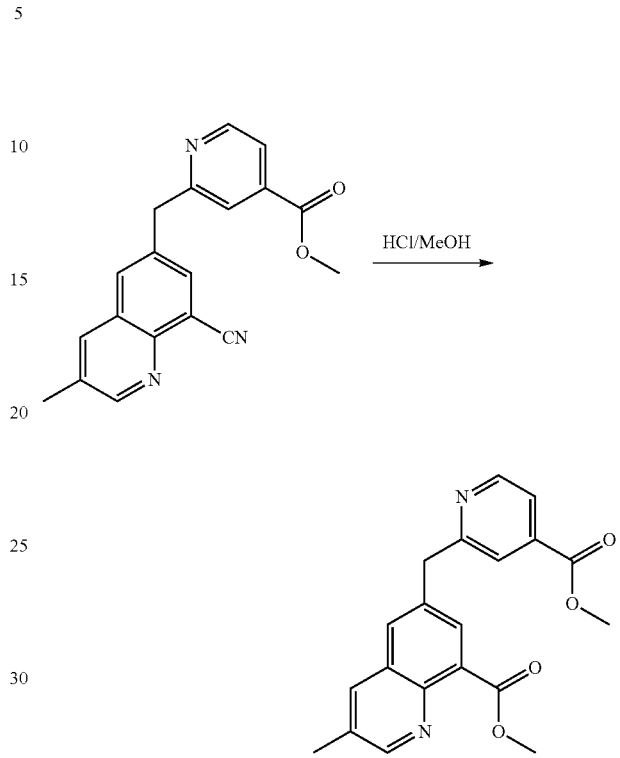

A mixture of 2-(8-cyano-3-methyl-quinolin-6-ylmethyl)-isonicotinic acid methyl ester (500 mg, 1.58 mmol, 1 eq) in HCl/MeOH (10 M, 25 mL) was heated under reflux for one week. After cooling to rt, solvent was removed by evaporation. The residue was diluted with DCM and washed with sat.NaHCO$_3$. The organic phase was separated, dried and concentrated. The residue was purified by chromatography on silica gel column (EA/PE=2/1, v/v) to give 6-(4-methoxycarbonyl-pyridin-2-ylmethyl)-3-methyl-quinoline-8-carboxylic acid methyl ester (100 mg, 18%) as a yellow solid.

Step 2: Preparation of 6-((4-((((6-amino-2,4-dimethylpyridin-3-yl)methyl)carbamoyl)pyridin-2-yl)methyl)-3-methylquinoline-8-carboxylic Acid

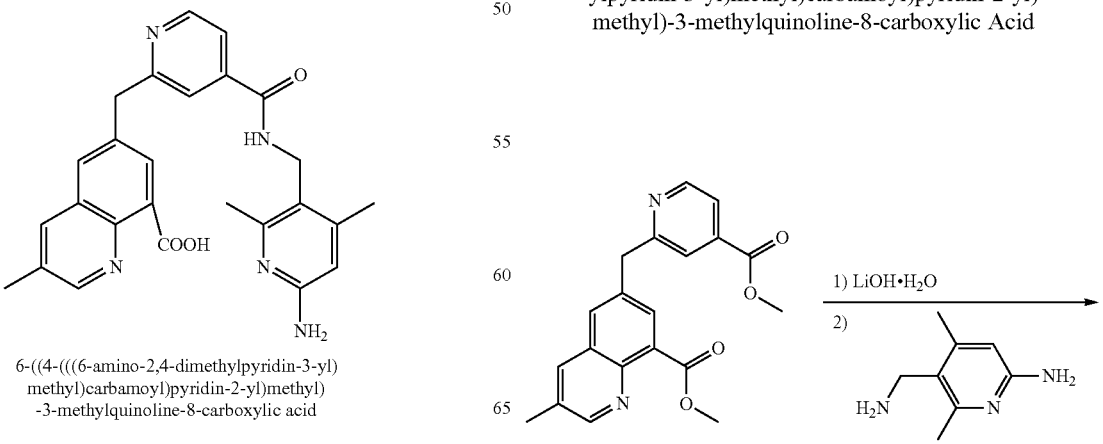

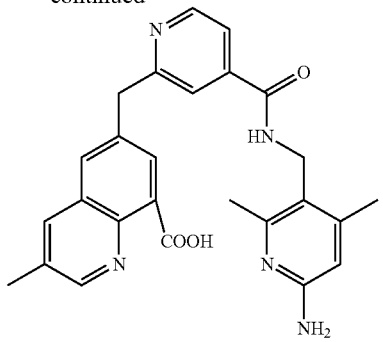

To a solution of 6-(4-methoxycarbonyl-pyridin-2-ylmethyl)-3-methyl-quinoline-8-carboxylic acid methyl ester (100 mg, 0.31 mmol, 1.0 eq) in THF/H₂O (5 mL, 1:1) was added LiOH.H₂O (39 mg, 0.93 mmol, 3 eq). The mixture was stirred at rt for 5 h and then concentrated. To a solution of the above crude product and 5-aminomethyl-4,6-dimethyl-pyridin-2-ylamine hydrochloride (88 mg, 0.47 mmol, 1.5 eq) in DMF (5 mL) was added HATU (188 mg, 0.50 mmol, 1.5 eq) and Et₃N (134 mg, 1.32 mmol, 4 eq). The mixture was stirred at rt for 2 h and diluted with water. The organic layer was separated and the aqueous layer was extracted with DCM, the combined extracts were dried and concentrated. The residue was purified by prep-HPLC to give 6-((4-(((6-amino-2,4-dimethylpyridin-3-yl)methyl)carbamoyl)pyridin-2-yl)methyl)-3-methylquinoline-8-carboxylic acid (2 mg, 1.4% for 2 steps) as an off-white solid. LRMS (M+H⁺) m/z calculated 456.2, found 455.9.

¹H NMR (CD₃OD, 400 MHz) δ 8.80 (s, 1H), 8.60 (d, 1H), 8.33 (s, 1H), 8.27 (s, 1H), 7.99 (s, 1H), 7.73 (s, 1H), 7.31 (d, 1H), 6.32 (s, 1H), 4.49 (s, 2H), 4.43 (s, 2H), 2.57 (s, 3H), 2.39 (s, 3H), 2.26 (s, 3H).

Example 85: Preparation of N-((6-amino-4-methylpyridin-3-yl)methyl)-2-((7-chloro-3-oxoisoquinolin-2(3H)-yl)methyl)isonicotinamide

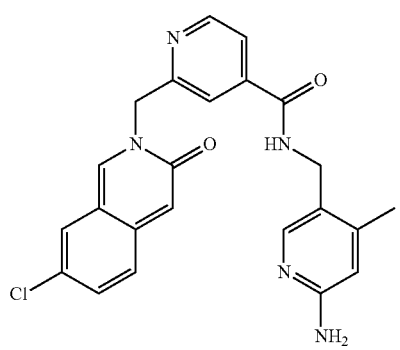

N-((6-amino-4-methylpyridin-3-yl)methyl)-2-((7-chloro-3-oxoisoquinolin-2(3H)-yl)methyl)isonicotinamide Step 1: Preparation of dimethoxy-acetic Acid

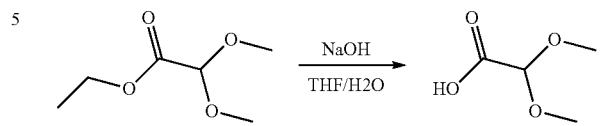

To a solution of dimethoxy-acetic acid ethyl ester (30 g, 170 mmol, 1.0 eq) in THF (100 mL) and H₂O (100 mL) was added NaOH (8.2 g, 205 mmol, 1.2 eq). The mixture was stirred at rt for 2 h. Then it was acidified by 1 N HCl to PH=6 and extracted by EA. The organic layer was concentrated to afford dimethoxy-acetic acid (15 g, 59%) as a yellow oil.

Step 2: Preparation of N-(3-chloro-benzyl)-2,2-dimethoxy-acetamide

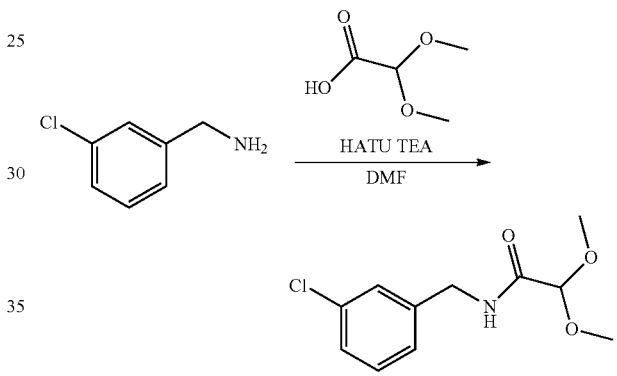

To a solution of dimethoxy-acetic acid (15 g, 100 mmol, 1.1 eq) and 3-chloro-benzylamine (13 g, 92 mmol, 1.0 eq) in DMF (200 mL) was added HATU (40 g, 100 mmol, 1.1 eq) and Et₃N (38 mL, 300 mmol, 3 eq). The mixture was stirred at rt overnight. Then EA and water was added, the organic layer was concentrated and the residue was purified by chromatography on a silica gel column (PE/EA=10/1-1/1, v/v) to give N-(3-chloro-benzyl)-2,2-dimethoxy-acetamide (13.5 g, 50%) as a yellow oil.

Step 3: Preparation of 2-(3-chloro-8-cyano-quinolin-6-ylmethyl)-isonicotinic Acid

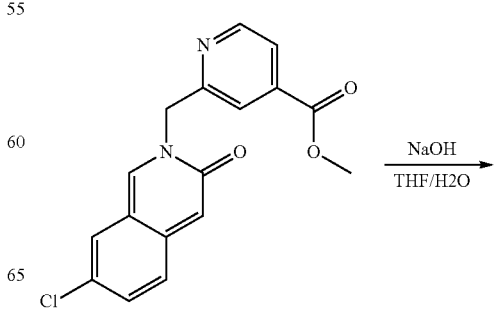

-continued

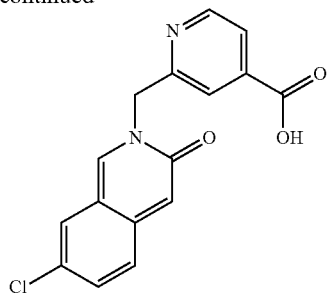

To a solution of 2-(7-chloro-3-oxo-3H-isoquinolin-2-yl-methyl)-isonicotinic acid methyl ester (350 mg, 1.1 mmol, 1.0 eq) in THF (5 mL) and H₂O (5 mL) was added NaOH (51 mg, 1.3 mmol, 1.2 eq). The mixture was stirred at rt for 2 h. Then it was acidified by 1 N HCl to PH=6 and extracted by EA. The organic layer was concentrated to afford 2-(3-chloro-8-cyano-quinolin-6-ylmethyl)-isonicotinic acid (320 mg, 91%) as a white solid.

Step 4: Preparation of N-((6-amino-4-methylpyridin-3-yl)methyl)-2-((7-chloro-3-oxoisoquinolin-2(3H)-yl)methyl)isonicotinamide

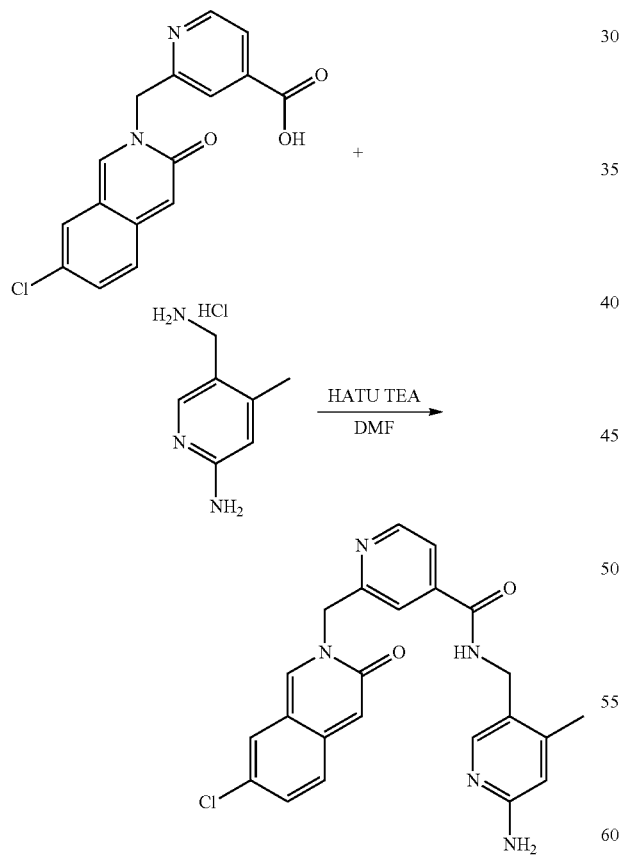

To a solution of 2-(7-chloro-3-oxo-3H-isoquinolin-2-yl-methyl)-isonicotinic acid (50 mg, 0.16 mmol, 1.0 eq) and 5-aminomethyl-4-methyl-pyridin-2-ylamine hydrochloride (57 mg, 0.33 mmol, 2.0 eq) in DMF (10 mL) was added HATU (73 mg, 0.19 mmol, 1.2 eq) and Et₃N (1.0 mL, 7.1 mmol, 44 eq). The mixture was stirred at rt for overnight, then EA and water was added. The organic layer was concentrated and the residue was purified by pre-HPLC to give N-((6-amino-4-methylpyridin-3-yl)methyl)-2-((7-chloro-3-oxoisoquinolin-2(3H)-yl)methyl)isonicotinamide (25 mg, 36%) as white solid. LRMS (M+H⁺) m/z calculated 434.1, found 434.0.

¹H NMR (DMSO-d₆, 400 MHz) δ 9.05 (s, 1H), 9.88-9.90 (t, 1H), 8.68-8.69 (d, 1H), 8.88-8.93 (m, 1H), 7.77 (s, 1H), 7.67-7.72 (m, 3H), 7.41 (d, 1H), 6.25 (s, 1H), 5.76 (s, 2H), 5.57 (s, 2H), 4.29-4.30 (d, 2H), 2.13 (s, 3H).

Example 86: Preparation of N-((6-amino-2-methylpyridin-3-yl)methyl)-2-((7-chloro-3-oxoisoquinolin-2(3H)-yl)methyl)isonicotinamide

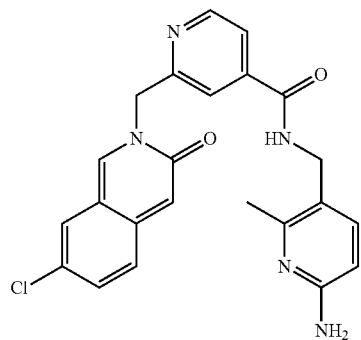

N-((6-amino-2-methylpyridin-3-yl)methyl-2-((7-chloro-3-oxoisoquinolin-2(3H)-yl)methyl)isonicotinamide

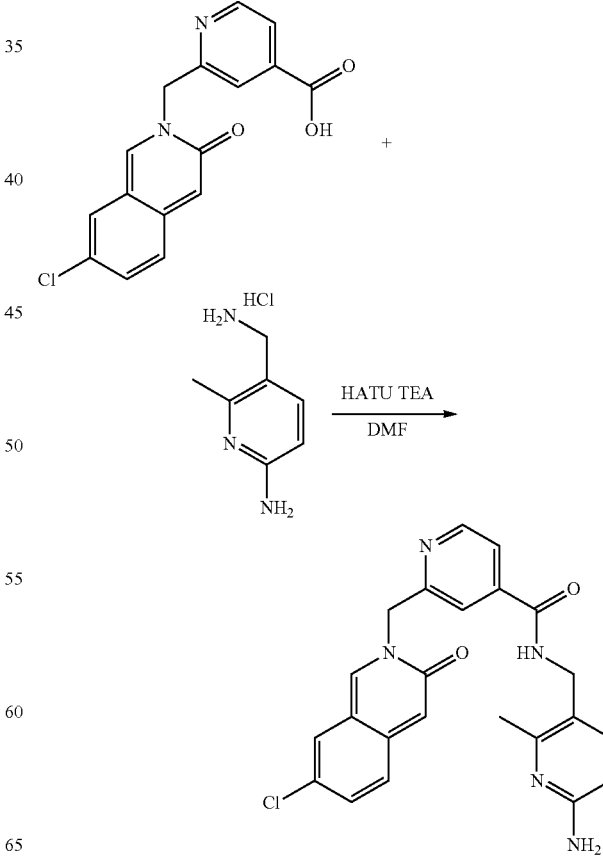

N-((6-amino-2-methylpyridin-3-yl)methyl)-2-((7-chloro-3-oxoisoquinolin-2(3H)-yl)methyl)isonicotinamide (27 mg, 37%) was prepared as described for N-((6-amino-4-methylpyridin-3-yl)methyl)-2-((7-chloro-3-oxoisoquinolin-2(3H)-yl)methyl)isonicotinamide (Example 85) as white solid. LRMS (M+H$^+$) m/z calculated 434.1, found 434.0.

$^1$H NMR (DMSO-d$_6$, 400 MHz) δ 9.05-9.07 (t, 1H), 9.04 (s, 1H), 8.69-8.70 (t, 1H), 8.17 (d, 1H), 7.90-7.92 (m, 1H), 7.67-7.63 (m, 2H), 7.41 (s, 3H), 7.23-7.26 (d, 1H), 6.22-6.24 (d, 1H), 5.76 (s, 1H), 5.57 (s, 2H), 4.28-4.30 (d, 2H), 2.27 (s, 3H).

Example 87: Preparation of N-((6-amino-2,4-dimethylpyridin-3-yl)methyl)-2-((7-chloro-3-oxoisoquinolin-2(3H)-yl)methyl)isonicotinamide N-((6-amino-2,4-dimethylpyridin-3-yl)methyl)-2-((7-chloro-3-oxoisoquinolin-2(3H)-yl)methyl)isonicotinamide (30 mg, 42%) was prepared as described for N-((6-amino-4-methylpyridin-3-yl)methyl)-2-((7-chloro-3-oxoisoquinolin-2(3H)-yl)methyl)isonicotinamide (Example 85) as white solid. LRMS (M+H$^+$) m/z calculated 448.1, found 448.0.

$^1$H NMR (DMSO-d$_6$, 400 MHz) δ 9.04 (s, 1H), 8.71-8.73 (t, 1H), 8.66-8.68 (d, 1H), 8.17-8.18 (d, 1H), 7.87-7.92 (m, 2H), 7.67-7.70 (m, 2H), 7.40 (s, 1H), 6.11 (s, 1H), 5.70 (s, 2H), 5.56 (s, 2H), 4.33-4.34 (d, 2H), 2.29 (s, 3H), 2.15 (s, 3H).

Example 88: Preparation of 2-((7-chloro-3-oxoisoquinolin-2(3H)-yl)methyl)-N-((3-chloro-6-fluoro-1H-indol-5-yl)methyl)isonicotinamide

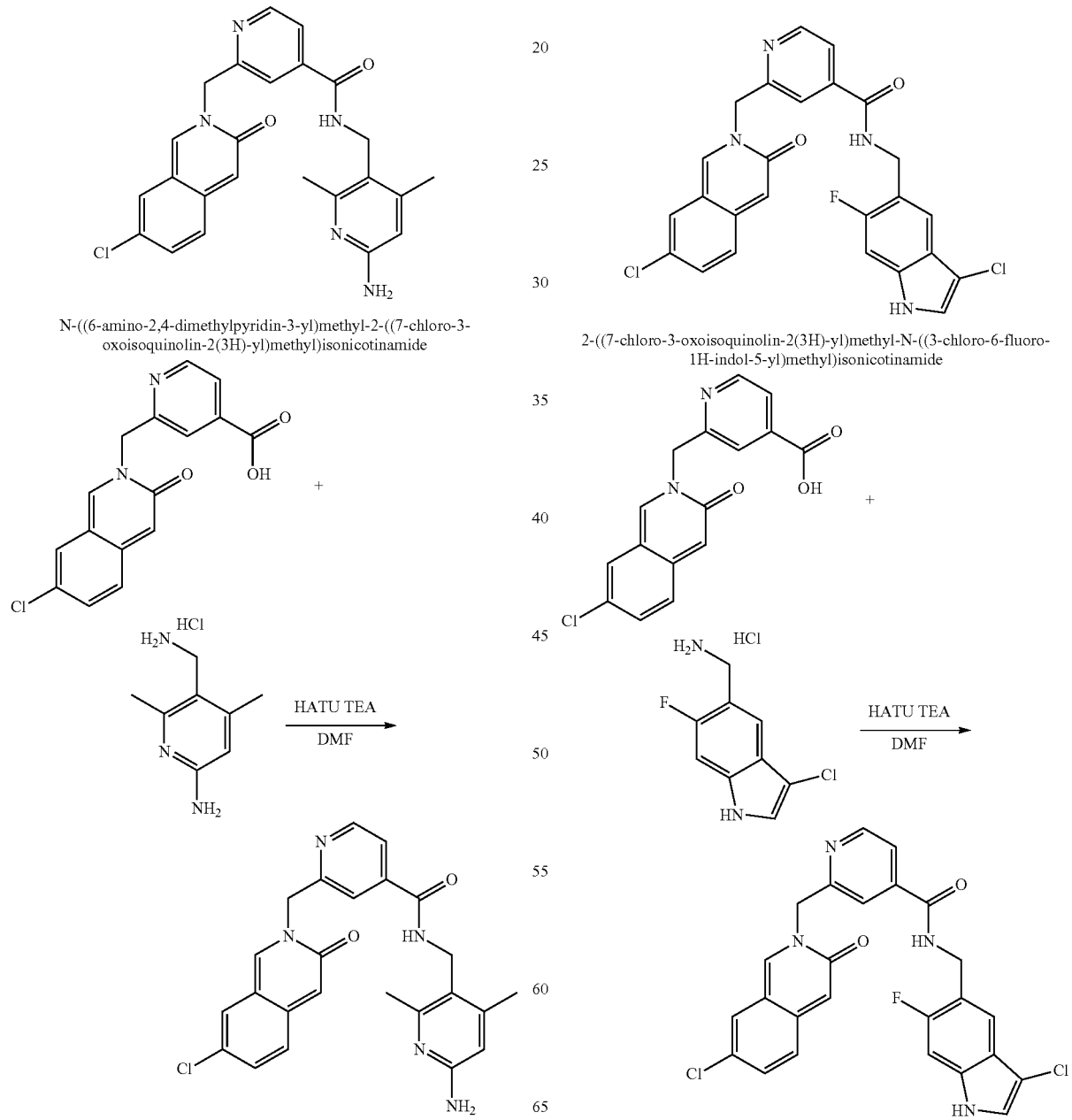

2-((7-Chloro-3-oxoisoquinolin-2(3H)-yl)methyl)-N-((3-chloro-6-fluoro-1H-indol-5-yl)methyl)isonicotinamide (55 mg, 70%) was prepared as described for N-((6-amino-4-methylpyridin-3-yl)methyl)-2-((7-chloro-3-oxoisoquinolin-2(3H)-yl)methyl)isonicotinamide (Example 85) as white solid. LRMS (M+H$^+$) m/z calculated 495.1, found 495.0.

$^1$H NMR (DMSO-d$_6$, 400 MHz) δ 11.40 (s, 1H), 9.33-9.35 (t, 1H), 9.04 (s, 1H), 8.72-8.73 (d, 1H), 8.17 (s, 1H), 8.89-8.94 (m, 2H), 7.69-7.70 (d, 1H), 7.66-7.67 (d, 1H), 7.50-7.51 (d, 1H), 7.24-7.45 (m, 2H), 7.21-7.24 (d, 1H), 5.59 (D, 2H), 4.58-4.60 (d, 2H).

Example 89: Preparation of N-(6-amino-2-methyl-pyridin-3-ylmethyl)-2-(3-chloro-quinolin-6-ylmethyl)-isonicotinamide

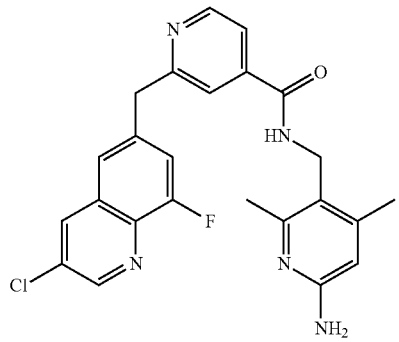

N-(6-Amino-2,4-dimethyl-pyridin-3-ylmethyl-2-(3-chloro-8-fluoro-quinolin-6-ylmethyl)-isonicotinamide Step 1: Preparation of 8-fluoro-quinoline-6-carboxylic Acid Methyl Ester

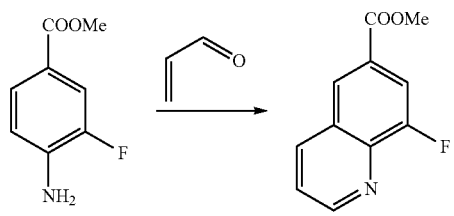

A mixture of 4-amino-3-fluoro-benzoic acid methyl ester (35 g, 0.207 mmol, 1 eq), acrolein (17.4 g, 0.311 mol, 1.5 eq) and 6 N HCl (600 mL) was stirred at 100° C. for 10 min. Then the mixture was cooled and adjusted to pH ~5-6 using NaHCO$_3$ (aq). The mixture was extracted with DCM. The combined organic layers were washed with brine, dried over MgSO$_4$, filtered then concentrated and purified by column chromatography (EA/PE=1/20, v/v) to give 8-fluoro-quinoline-6-carboxylic acid methyl ester (11 g, 21%) as a yellow solid.

Step 2: Preparation of 3-chloro-8-fluoro-quinoline-6-carboxylic Acid Methyl Ester

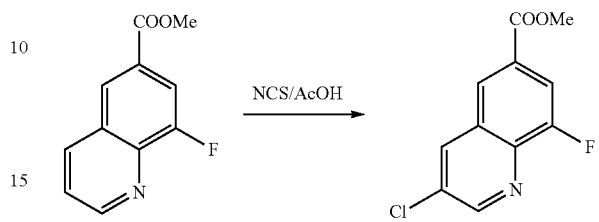

To a solution of 8-fluoro-quinoline-6-carboxylic acid methyl ester (11 g, 53.7 mmol, 1 eq) in DMF was added NCS (21.4 g, 0.161 mol, 3 eq). The reaction mixture was stirred at 120° C. overnight. The reaction mixture was allowed to cool to ambient temperature, treated with water, neutralized with solid NaHCO$_3$ and further stirred at rt for 30 min. Finally, powdered sodium thiosulfate was carefully added to remove excess of NCS. The mixture was extracted with EA. The organic layer was dried and concentrated under vacuum. The crude product was purified by flash-chromatography on silica gel to afford 3-chloro-8-fluoro-quinoline-6-carboxylic acid methyl ester (11.5 g, 90%) as a yellow solid.

Step 3: Preparation of (3-chloro-8-fluoro-quinolin-6-yl)-methanol

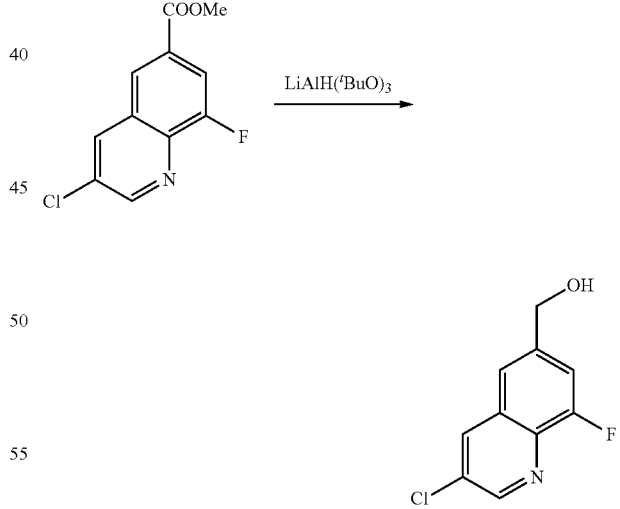

To a solution of 3-chloro-8-fluoro-quinoline-6-carboxylic acid methyl ester (4.5 g, 18.8 mmol, 1 eq) was added LiAlH(t-BuO)$_3$ (12.0 g, 47.1 mmol, 2.5 eq). The resulting mixture was stirred at 40° C. for 12 h and then quenched by the addition of water. The mixture was extracted with EA. The combined extracts were dried and concentrated. The residue was purified by silica gel chromatography (PE/EA=2/1, v/v) to afford (3-chloro-8-fluoro-quinolin-6-yl)-methanol (2.1 g, 53%) as a yellow solid.

Step 4: Preparation of 3-chloro-6-chloromethyl-8-fluoro-quinoline

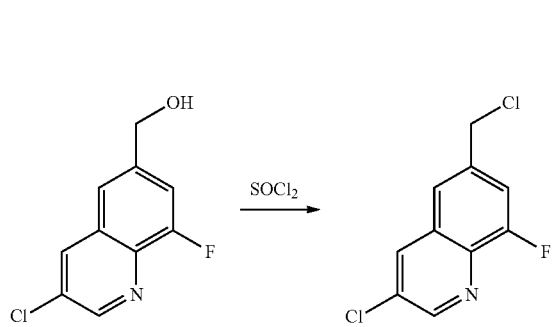 [SMILES: OCc1cc(F)c2ncc(Cl)cc2c1 ; "SOCl2" ; Fc1cc(CCl)cc2cc(Cl)cnc12]

A mixture of 3-chloro-8-fluoro-6-hydroxymethyl-quinoline (2.1 g, 9.95 mmol, 1.0 eq) in SOCl₂ (50 mL) was stirred at rt for 1 h and concentrated. The residue was dissolved in DCM and treated with sat.NaHCO₃ solution to give 3-chloro-6-chloromethyl-8-fluoro-quinoline (2.2 g, 96%) as a yellow solid.

Step 5: Preparation of 2-(3-chloro-8-fluoro-quinolin-6-ylmethyl)-isonicotinic Acid Methyl Ester

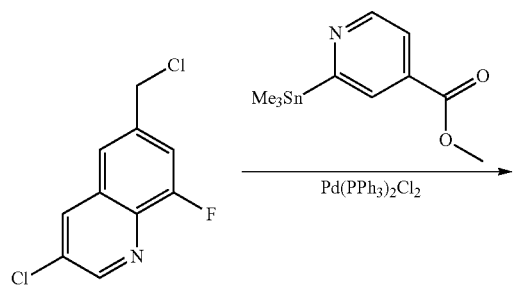

To a solution of 3-chloro-6-chloromethyl-8-fluoro-quinoline (2.2 g, 9.61 mmol, 1.0 eq) in dioxane (60 mL) was added 2-trimethylstannanyl-isonicotinic acid methyl ester (3.18 g, 10.6 mmol, 1.1 eq) and Pd(PPh₃)₂Cl₂ (674 mg, 0.96 mmol, 0.1 eq). The mixture was stirred at 90° C. for 3 h under nitrogen atmosphere, concentrated and purified by silica gel chromatography (DCM/MeOH=200/1, v/v) to afford 2-(3-chloro-8-fluoro-quinolin-6-ylmethyl)-isonicotinic acid methyl ester (1.6 g, 50%) as a yellow solid.

Step 6: Preparation of 2-((3-chloro-8-fluoroquinolin-6-yl)methyl)isonicotinic Acid

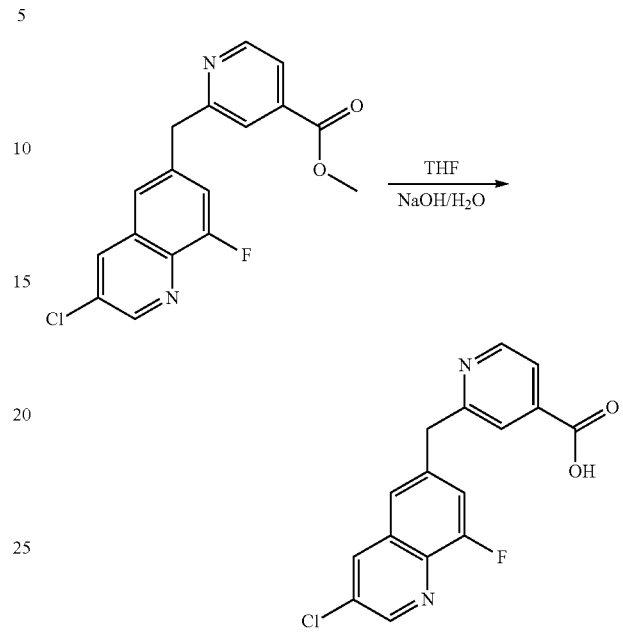

To a solution of 2-(3-chloro-8-fluoro-quinolin-6-ylmethyl)-isonicotinic acid methyl ester (800 mg, 2.4 mmol, 1 eq) in THF (20 ml)/water (10 ml) was added NaOH (116 mg, 0.29 mmol, 1.2 eq). The mixture was stirred at rt for 3 h. Then aqueous HCl (2 N) was added to the reaction mixture until pH 6-7. The mixture was extracted with EA, and the organic layer was concentrated under pressure. The gray compound was directly used in next step (500 mg, 76%).

Step 7: Preparation of N-(6-amino-2,4-dimethyl-pyridin-3-ylmethyl)-2-(3-chloro-8-fluoro-quinolin-6-ylmethyl)-isonicotinamide

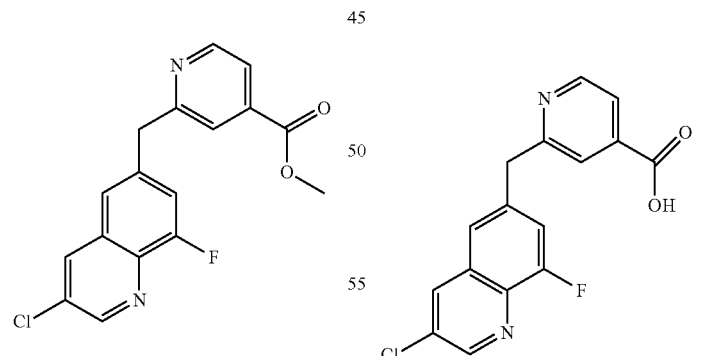
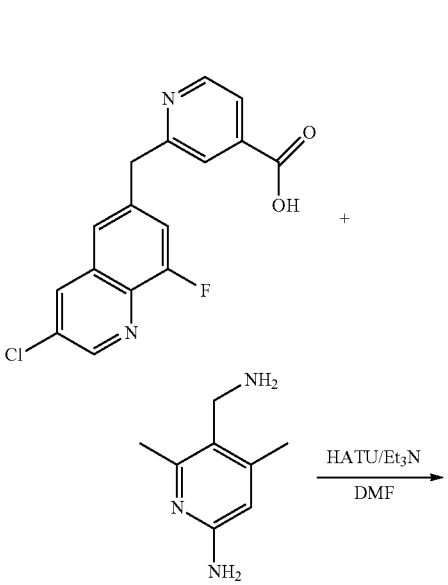

-continued

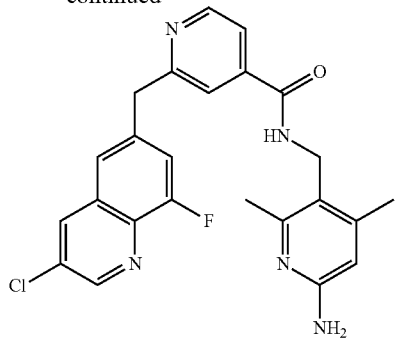

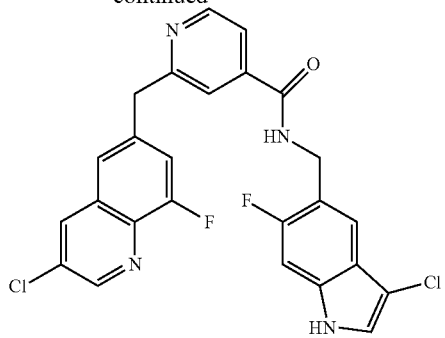

To a solution of 2-(3-chloro-quinolin-6-ylmethyl)-isonicotinic acid (100 mg, 0.3 mmol, 1 eq) in DMF (10 mL) was added 5-aminomethyl-4, 6-dimethyl-pyridin-2-ylamine (71 mg, 0.47 mmol, 1.5 eq), HATU (137 mg, 0.36 mmol, 1.2 eq) and Et$_3$N (1 mL). The mixture was stirred at rt for 3 h. Then it was quenched with water, extracted with DCM. The combined extracts were dried, concentrated, and the residue was purified by prep-HPLC to give N-(6-amino-2,4-dimethyl-pyridin-3-ylmethyl)-2-(3-chloro-8-fluoro-quinolin-6-ylmethyl)-isonicotinamide (39 mg, 29%) as a white solid. LRMS (M+H$^+$) m/z calculated 450.1, found 449.8.

$^1$H NMR (DMSO-d6, 400 MHz) δ: 8.88 (d, 1H), 8.60-8.62 (m, 3H), 7.75 (s, 1H), 7.68 (s, 1H), 7.58-7.61 (m, 2H), 6.13 (s, 1H), 5.71 (s, 2H), 4.33 (s, 4H), 2.30 (s, 3H), 2.16 (s, 3H).

Example 90: Preparation of N-(3-chloro-6-fluoro-1H-indol-5-ylmethyl)-2-(3-chloro-8-fluoro-quinolin-6-ylmethyl)-isonicotinamide N-(3-chloro-6-fluoro-1H-indol-5-ylmethyl)-2-(3-chloro-8-fluoro-quinolin-6-ylmethyl)-isonicotinamide (47 mg, 20%) was prepared as described for N-(6-amino-2,4-dimethyl-pyridin-3-ylmethyl)-2-(3-chloro-8-fluoro-quinolin-6-ylmethyl)-isonicotinamide (Example 89) as a white solid; LRMS (M+H$^+$) m/z calculated 497.1, found 497.7.

$^1$H NMR (DMSO-d6, 400 MHz) δ 11.38 (s, 1H), 9.23 (s, 1H), 8.88 (s, 1H), 8.61-8.66 (m, 2H), 7.80 (s, 1H), 7.59-7.69 (m, 3H), 7.43-7.50 (m, 2H), 7.20-7.23 (d, 1H), 4.57-4.59 (d, 2H), 4.36 (s, 2H).

Example 91: Preparation of N-(6-amino-2-methyl-pyridin-3-ylmethyl)-2-(3-chloro-8-fluoro-quinolin-6-ylmethyl)-isonicotinamide

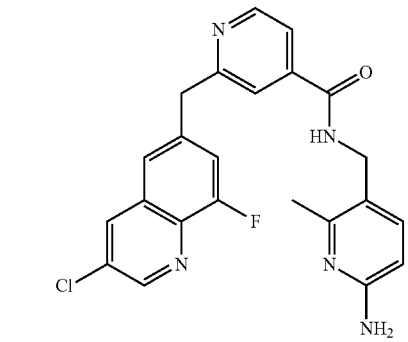

N-(6-Amino-2-methyl-pyridin-3-ylmethyl)-2-(3-chloro-8-fluoro-quinolin-6-ylmethyl)-isonicotinamide

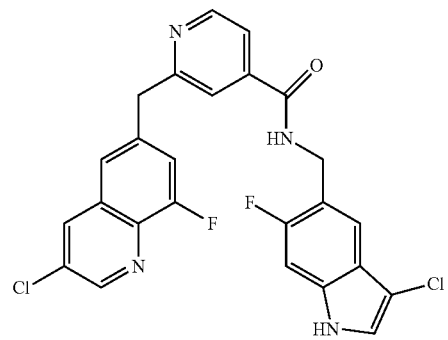

N-(3-Chloro-6-fluoro-1H-indol-5-ylmethyl)-2-(3-chloro-8-fluoro-quinolin-6-ylmethyl)-isonicotinamide

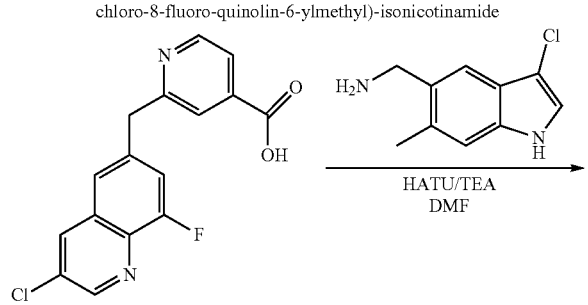

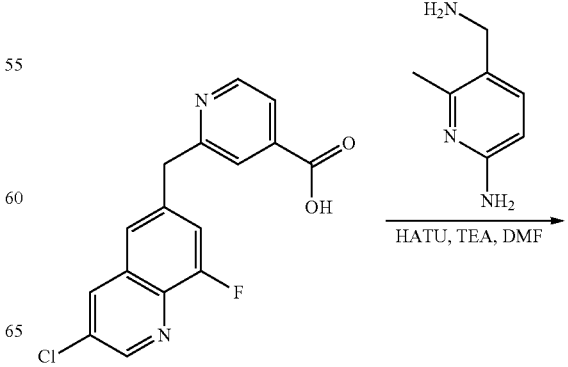

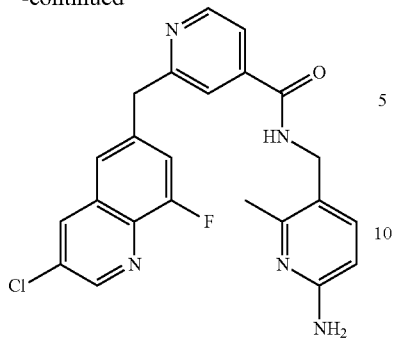

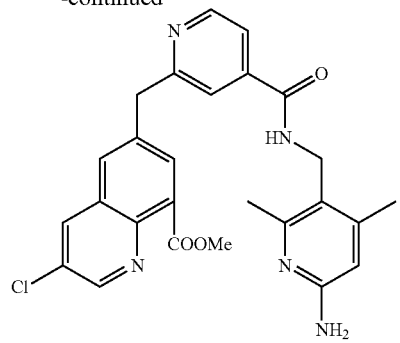

N-(6-amino-2-methyl-pyridin-3-ylmethyl)-2-(3-chloro-8-fluoro-quinolin-6-ylmethyl)-isonicotinamide (45 mg, 22%) was prepared as described for N-(6-amino-2,4-dimethyl-pyridin-3-ylmethyl)-2-(3-chloro-8-fluoro-quinolin-6-ylmethyl)-isonicotinamide (Example 89) as a white solid. LRMS (M+H$^+$) m/z calculated 436.1, found 436.0.

$^1$H NMR (DMSO-d6, 400 MHz) δ 8.97 (s, 1H), 8.88 (s, 1H), 8.6-8.64 (m, 2H), 7.77 (s, 1H), 7.68 (s, 1H), 7.59-7.63 (m, 2H), 7.42 (d, 1H), 6.26 (d, 1H), 5.80 (d, 2H), 4.35 (s, 2H), 4.29 (d, 2H).

Example 92: Preparation of methyl 6-((4-(((6-amino-2,4-dimethylpyridin-3-yl)methyl)carbamoyl)pyridin-2-yl)methyl)-3-chloroquinoline-8-carboxylate

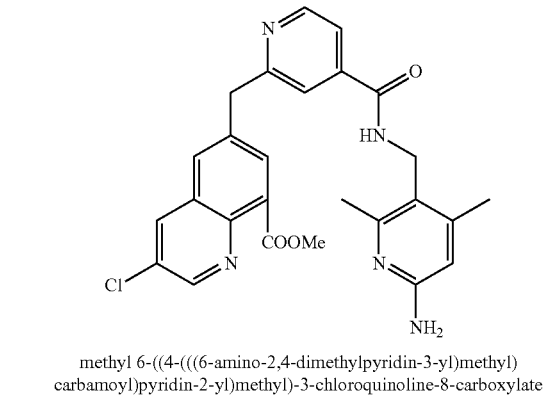

methyl 6-((4-(((6-amino-2,4-dimethylpyridin-3-yl)methyl)carbamoyl)pyridin-2-yl)methyl)-3-chloroquinoline-8-carboxylate To a solution of 5-aminomethyl-4,6-dimethyl-pyridin-2-ylamine (95 mg, 0.43 mmol, 1.7 eq) in DMF (10 mL) was added 6-(4-carboxy-pyridin-2-ylmethyl)-3-chloro-quinoline-8-carboxylic acid methyl ester (90 mg, 0.25 mmol, 1 eq), HATU (123 mg, 0.32 mmol, 1.3 eq), and Et$_3$N (0.5 mL). The mixture was stirred at rt overnight. Then it was quenched with water, extracted with DCM. The combined extracts were dried, concentrated, and the residue was purified by column chromatography (DCM/MeOH=20/1, v/v) to give methyl 6-((4-(((6-amino-2,4-dimethylpyridin-3-yl)methyl) carbamoyl)pyridin-2-yl)methyl)-3-chloroquinoline-8-carboxylate (100 mg, 81.9%) as a yellow solid. LRMS (M+H$^+$) m/z calculated 490.2, found 490.1.

$^1$H NMR (DMSO-d6, 400 MHz) δ 8.89-8.90 (m, 1H), 8.59-8.63 (m, 3H), 8.00 (s, 1H), 7.91-7.92 (m, 1H), 7.77 (s, 1H), 7.60 (d, 1H), 6.15 (s, 1H), 4.37 (s, 2H), 4.33-4.34 (d, 2H), 3.88 (s, 3H), 2.31 (s, 3H), 2.18 (s, 3H).

Example 93: Preparation of 6-((4-(((6-amino-2,4-dimethylpyridin-3-yl)methyl)carbamoyl)pyridin-2-yl)methyl)-3-chloroquinoline-8-carboxylic Acid

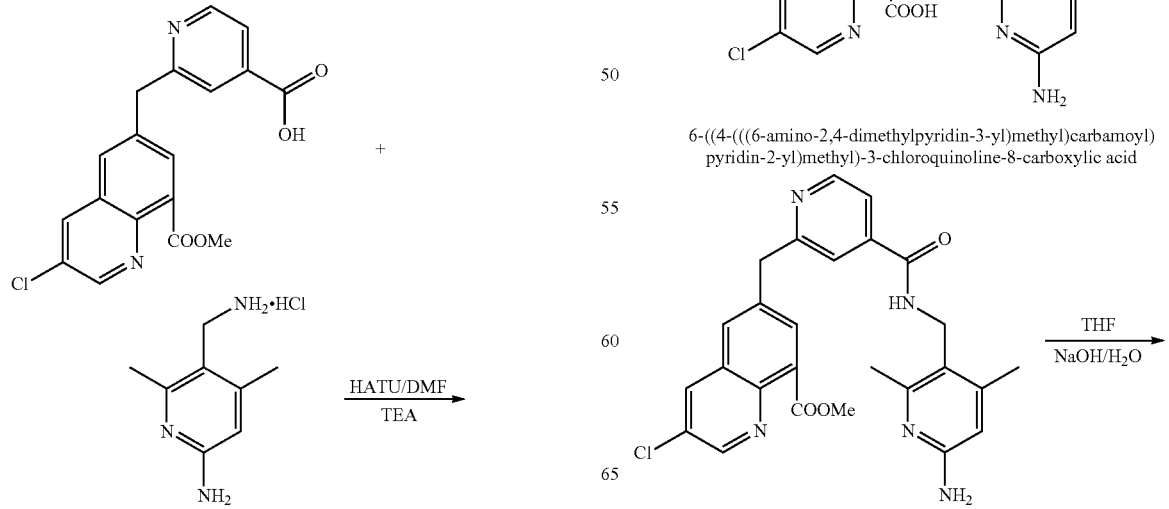

6-((4-(((6-amino-2,4-dimethylpyridin-3-yl)methyl)carbamoyl)pyridin-2-yl)methyl)-3-chloroquinoline-8-carboxylic acid

377

-continued

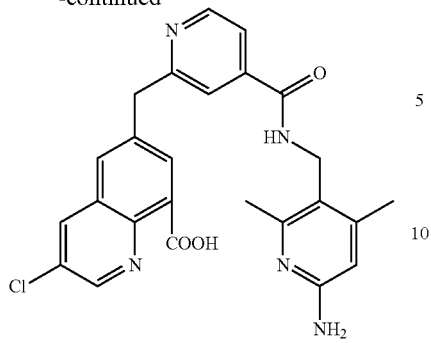

378

-continued

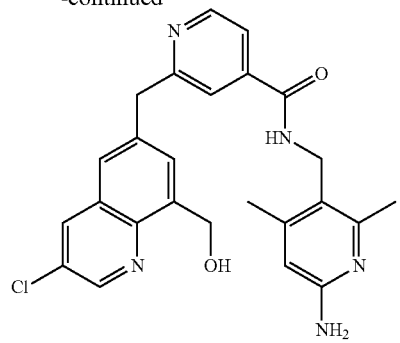

To a solution of 6-{4-[(6-amino-2,4-dimethyl-pyridin-3-ylmethyl)-carbamoyl]-pyridin-2-ylmethyl}-3-chloro-quinoline-8-carboxylic acid methyl ester (50 mg, 0.1 mmol, 1 eq) in THF (10 mL) was added a solution NaOH (4.9 mg, 0.12 mmol, 1.2 eq) in water (2 mL) and kept stirring at rt for 3 h. Then it was acidified to pH 5 with AcOH. The mixture was concentrated in vacuo and purified by a prep-HPLC to give 6-((4-(((6-amino-2,4-dimethylpyridin-3-yl)methyl)carbamoyl) pyridin-2-yl)methyl)-3-chloroquinoline-8-carboxylic acid (31.3 mg, 65.7%) as a gray solid. LRMS (M+H$^+$) m/z calculated 476.1, found 476.1.

$^1$H NMR (DMSO-d6, 400 MHz) δ 8.99 (s, 1H), 8.74 (s, 1H), 8.59-8.62 (m, 2H), 8.18 (s, 1H), 8.04 (s, 1H), 7.79 (s, 1H), 7.60 (d, 1H), 6.11 (s, 1H), 5.64 (s, 2H), 4.39 (s, 2H), 4.33 (d, 2H), 2.29 (s, 3H), 2.16 (s, 3H).

Example 94: Preparation of N-((6-amino-2,4-dimethylpyridin-3-yl)methyl)-2-((3-chloro-8-(hydroxymethyl)quinolin-6-yl)methyl)isonicotinamide To a solution of 6-{4-[(6-amino-2,4-dimethyl-pyridin-3-ylmethyl)-carbamoyl]-pyridin-2-ylmethyl}-3-chloro-quinoline-8-carboxylic acid methyl ester (100 mg, 0.2 mmol, 1 eq) in dry THF was added drop wise LiAlH$_4$ below −78° C. under N$_2$ over a period of 20 min. The reaction mixture was stirred for 5 h, and then it was quenched with potassium sodium tartrate and extracted with EA. The combine extracts were dried, concentrated and the residue was purified by prep-HPLC to give N-((6-amino-2,4-dimethylpyridin-3-yl) methyl)-2-((3-chloro-8-(hydroxymethyl)quinolin-6-yl) methyl)isonicotinamide (6.5 mg, 7%) as a white solid. LRMS (M+H$^+$) m/z calculated 462.2, found 462.1.

$^1$H NMR (DMSO-d6, 400 MHz) δ 8.81 (d, 1H), 8.59-8.63 (m, 2H), 8.50 (d, 1H), 7.77 (s, 1H), 7.72 (d, 2H), 7.59 (d, 1H), 6.13 (s, 1H), 5.72 (s, 2H), 5.26-5.28 (t, 1H), 5.07 (d, 1H), 4.32-4.33 (m, 4H), 2.30 (s, 3H), 2.16 (s, 3H).

Example 95: Preparation of methyl 6-((4-(((6-amino-2-methylpyridin-3-yl)methyl)carbamoyl)pyridin-2-yl)methyl)-3-chloroquinoline-8-carboxylate

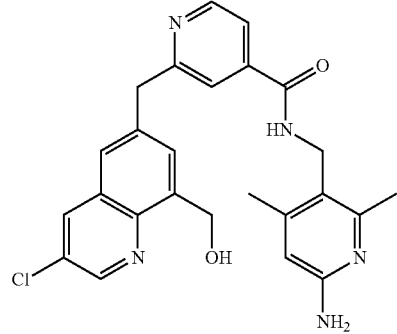

N-((6-amino-2,4-dimethylpyridin-3-yl)methyl)-2-((3-chloro-8-(hydroxymethyl)quinolin-6-yl)methyl)isonicotinamide

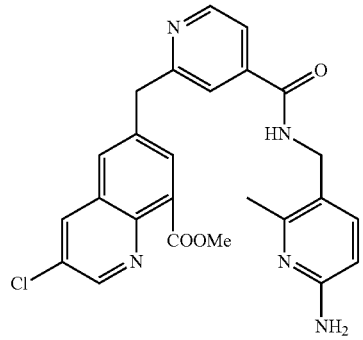

methyl 6-((4-(((6-amino-2-methylpyridin-3-yl)methyl)carbamoyl) pyridin-2-yl)methyl)-3-chloroquinoline-8-carboxylate

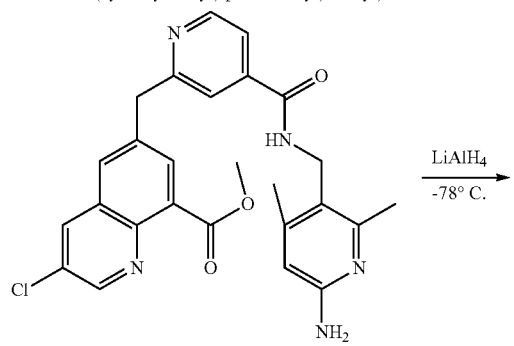

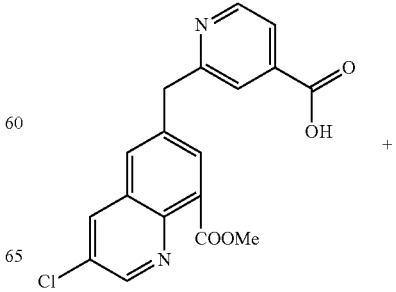

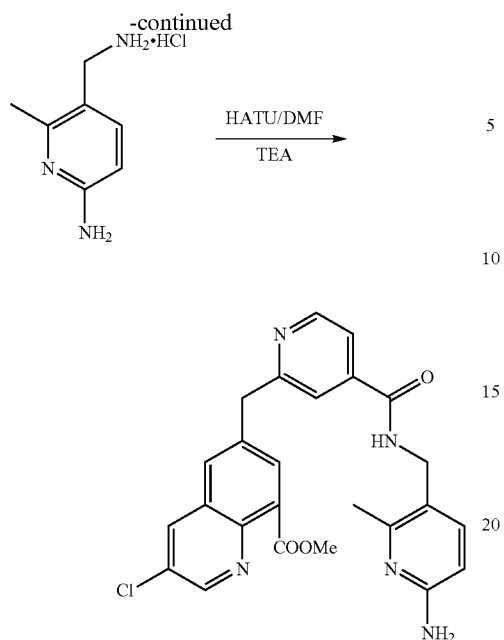

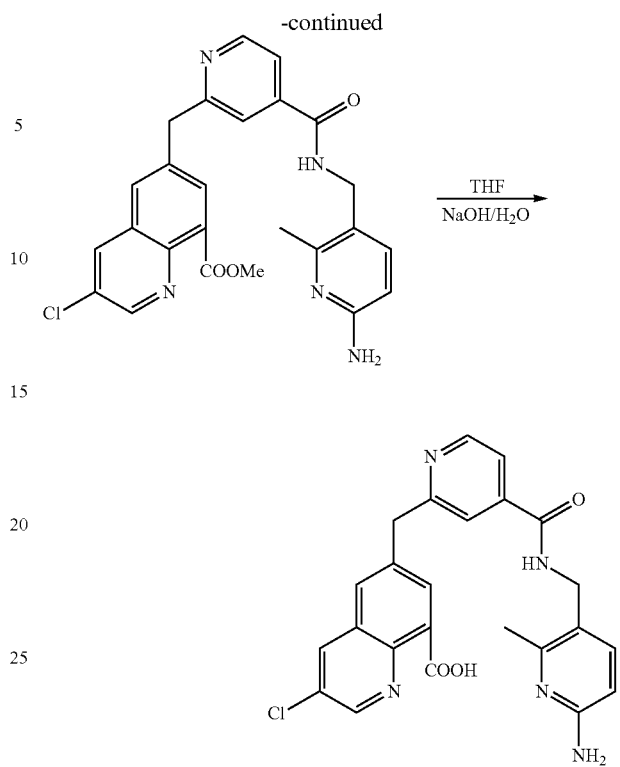

To a solution of 5-aminomethyl-6-methyl-pyridin-2-ylamine (89 mg, 0.43 mmol, 1.7 eq) in DMF (10 mL) was added 6-(4-carboxy-pyridin-2-ylmethyl)-3-chloro-quinoline-8-carboxylic acid methyl ester (90 mg, 0.25 mmol, 1 eq), HATU (123 mg, 0.32 mmol, 1.3 eq), and Et$_3$N (0.5 mL). The mixture was stirred at rt overnight. Then it was quenched with water, extracted with DCM. The combined extracts were dried and concentrated, the residue was purified on a silica gel column (DCM/MeOH=20/1, v/v) to give methyl 6-((4-(((6-amino-2-methylpyridin-3-yl)methyl)carbamoyl)pyridin-2-yl)methyl)-3-chloroquinoline-8-carboxylate (100 mg, 84.7%) as a yellow solid. LRMS (M+H$^+$) m/z calculated 476.1, found 476.1.

$^1$H NMR (DMSO-d6, 400 MHz) δ 8.98 (t, 1H), 8.90 (m, 1H), 8.61-8.63 (m, 2H), 8.00 (d, 1H), 7.92 (d, 1H), 7.79 (s, 1H), 7.62 (d, 1H), 7.25 (d, 1H), 6.25 (d, 1H), 5.81 (s, 2H), 4.38 (s, 2H), 4.28 (d, 2H), 3.89 (s, 3H), 2.28 (s, 3H).

Example 96: Preparation of 6-((4-(((6-amino-2-methylpyridin-3-yl)methyl)carbamoyl)pyridin-2-yl)methyl)-3-chloroquinoline-8-carboxylic Acid

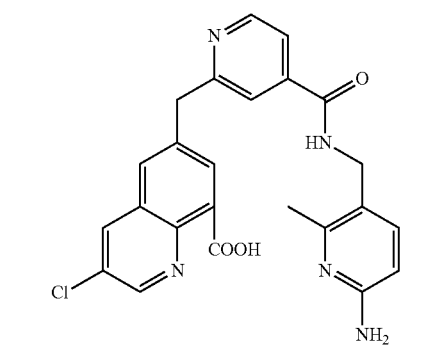

6-((4-(((6-amino-2-methylpyridin-3-yl)methyl)carbamoyl)pyridin-2-yl)methyl)-3-chloroquinoline-8-carboxylic acid 6-((4-(((6-Amino-2-methylpyridin-3-yl)methyl)carbamoyl)pyridin-2-yl)methyl)-3-chloroquinoline-8-carboxylic acid (54 mg, 83.59%) was prepared as described for 6-((4-(((6-amino-2,4-dimethylpyridin-3-yl)methyl)carbamoyl)pyridin-2-yl)methyl)-3-chloroquinoline-8-carboxylic acid (Example 93) as a white solid. LRMS (M+H$^+$) m/z calculated 462.1, found 462.1.

$^1$H NMR (DMSO-d6, 400 MHz) δ 9.07 (d, 1H), 8.99 (s, 1H), 8.83 (d, 1H), 8.62 (d, 1H), 8.41 (m, 1H), 8.17 (s, 1H), 7.82 (s, 1H), 7.62 (d, 1H), 7.24 (d, 2H), 6.21 (d, 1H), 5.72 (s, 1H), 4.45 (s, 2H), 4.28 (d, 2H), 2.27 (s, 3H).

Example 97: Preparation of N-((6-amino-2-methyl-pyridin-3-yl)methyl)-2-((3-chloro-8-(hydroxymethyl)quinolin-6-yl)methyl)isonicotinamide

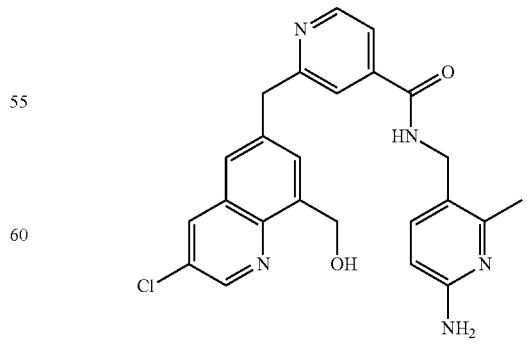

N-(6-Amino-2-methyl-pyridin-3-ylmethyl)-2-(3-chloro-8-hydroxymethyl-quinolin-6-ylmethyl)-isonicotinamide

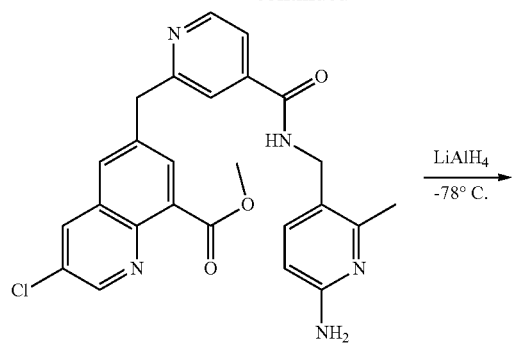

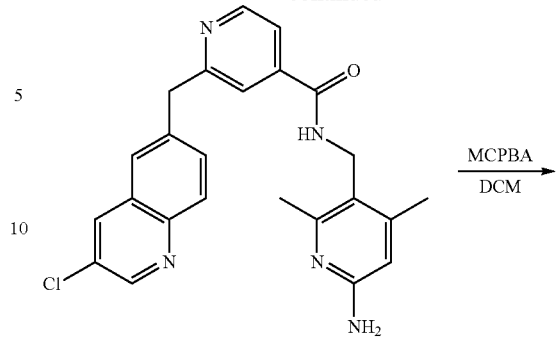

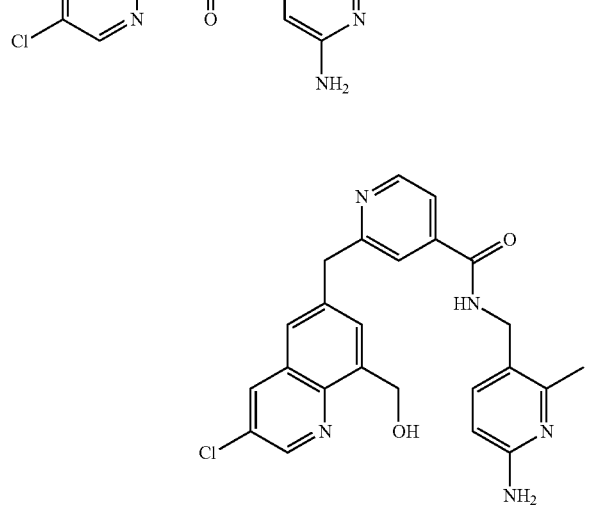

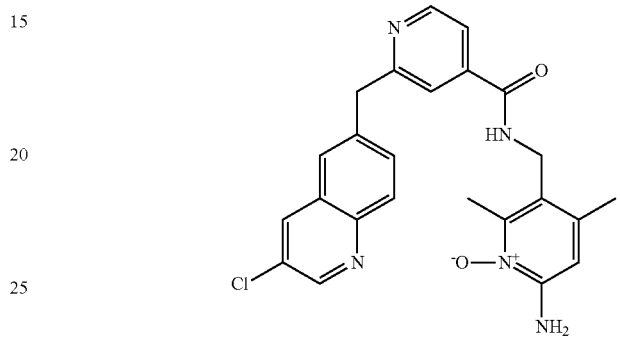

N-((6-amino-2-methylpyridin-3-yl)methyl)-2-((3-chloro-8-(hydroxymethyl)quinolin-6-yl)methyl)isonicotinamide (12.8 mg, 13.6%) was prepared as described for N-((6-amino-2,4-dimethylpyridin-3-yl)methyl)-2-((3-chloro-8-(hydroxymethyl)quinolin-6-yl)methyl)isonicotinamide (Example 94) as a white solid. LRMS (M+H⁺) m/z calculated 448.1, found 448.1.

¹H NMR (DMSO-d6, 400 MHz) δ 8.98 (m, 1H), 8.80 (d, 1H), 8.62 (d, 1H), 8.50 (d, 1H), 7.72 (t, 3H), 7.62 (d, 1H), 7.24 (d, 1H), 6.24 (d, 1H), 5.75 (s, 2H), 5.27 (m, 1H), 5.08 (d, 2H), 4.35 (s, 2H), 4.27 (d, 1H), 2.27 (s, 3H).

Example 98: Preparation of 6-amino-3-((2-((3-chloroquinolin-6-yl)methyl)isonicotinamido)methyl)-2,4-dimethylpyridine 1-oxide To a solution of N-((6-amino-2,4-dimethylpyridin-3-yl)methyl)-2-((3-chloroquinolin-6-yl)methyl) isonicotinamide (50 mg, 0.11 mmol, 1 eq) in dry DCM was added m-CPBA. The reaction mixture was stirred for 3 h. Then it was quenched with potassium sodium tartrate and extracted with DCM. The combine extracts were dried, concentrated and the residue was purified by prep-HPLC to give 6-amino-3-((2-((3-chloroquinolin-6-yl)methyl)isonicotinamido)methyl)-2,4-dimethylpyridine 1-oxide (12.8 mg, 13.6%) as a white solid. LRMS (M+H⁺) m/z calculated 448.1, found 448.1.

¹H NMR (DMSO-d6, 400 MHz) δ 8.82 (s, 1H), 8.73 (t, 1H), 8.60-8.61 (d, 1H), 8.51 (d, 1H), 7.96 (d, 1H), 7.84 (s, 1H), 7.70-7.73 (m, 2H), 7.57 (d, 1H), 6.70 (s, 2H), 6.53 (s, 1H), 4.34 (m, 4H), 2.41 (s, 3H), 2.23 (s, 3H).

Example 99: Preparation of 6-((4-(((6-amino-2,4-dimethylpyridin-3-yl)methyl)carbamoyl)pyridin-2-yl)methyl)-3-chloroquinoline 1-oxide

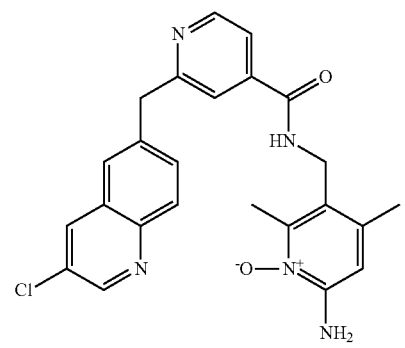

6-amino-3-((2-((3-chloroquinolin-6-yl)methyl)isonicotinamido)methyl)-2,4-dimethylpyridine 1-oxide

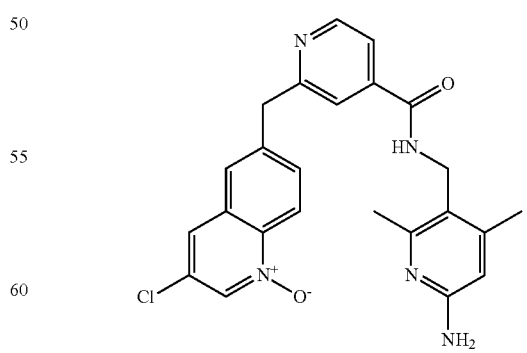

6-((4-(((6-amino-2,4-dimethylpyridin-3-yl)methyl)carbamoyl)pyridin-2-yl)methyl)-3-chloroquinoline 1-oxide

Step 1: Preparation of 3-chloro-6-chloromethyl-quinoline 1-oxide

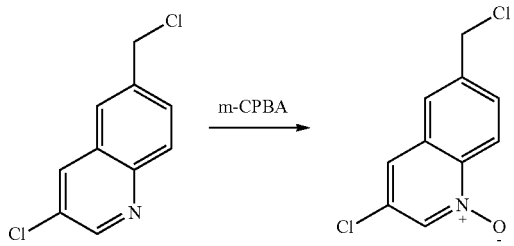

To a solution of 3-chloro-6-chloromethyl-quinoline (500 mg, 2.37 mmol, 1 eq) in dry DCM (20 mL) was added m-CPBA (1.23 g, 7.11 mmol, 3 eq). The mixture was stirred at 40° C. for 5 h. Then the reaction was quenched by sat. NaHCO$_3$ and extracted with DCM. The combined organic layers were dried and concentrated. The residue was purified by chromatography on a silica gel column (EA/PE=1/3, v/v) to give 3-chloro-6-chloromethyl-quinoline 1-oxide (400 mg, 74%) as a yellow solid.

Step 2: Preparation of 2-(3-chloro-1-oxy-quinolin-6-ylmethyl)-isonicotinic Acid Methyl Ester

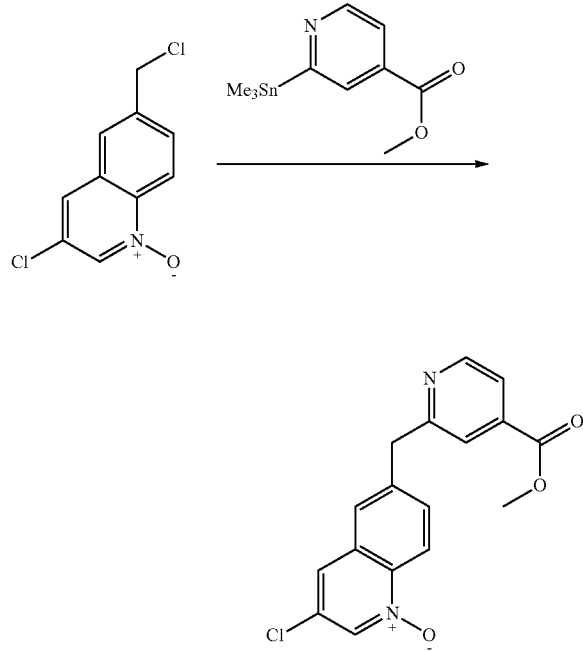

To a solution of 3-chloro-6-chloromethyl-quinoline 1-oxide (400 mg, 1.76 mmol, 1.0 eq) in dioxane (10 mL) was added 2-trimethylstannanyl-isonicotinic acid methyl ester (583 mg, 1.94 mmol, 1.1 eq) and Pd(PPh$_3$)$_2$Cl$_2$ (126 mg, 0.18 mmol, 0.1 eq). The mixture was stirred at 90° C. for 3 h under nitrogen atmosphere, then concentrated and purified by silica gel chromatography (DCM/MeOH=100/1, v/v) to afford 2-(3-chloro-1-oxy-quinolin-6-ylmethyl)-isonicotinic acid methyl ester (210 mg, 36%) as a yellow solid.

Step 3: Preparation of 6-((4-(((6-amino-2,4-dimethylpyridin-3-yl)methyl)carbamoyl)pyridin-2-yl)methyl)-3-chloroquinoline 1-oxide

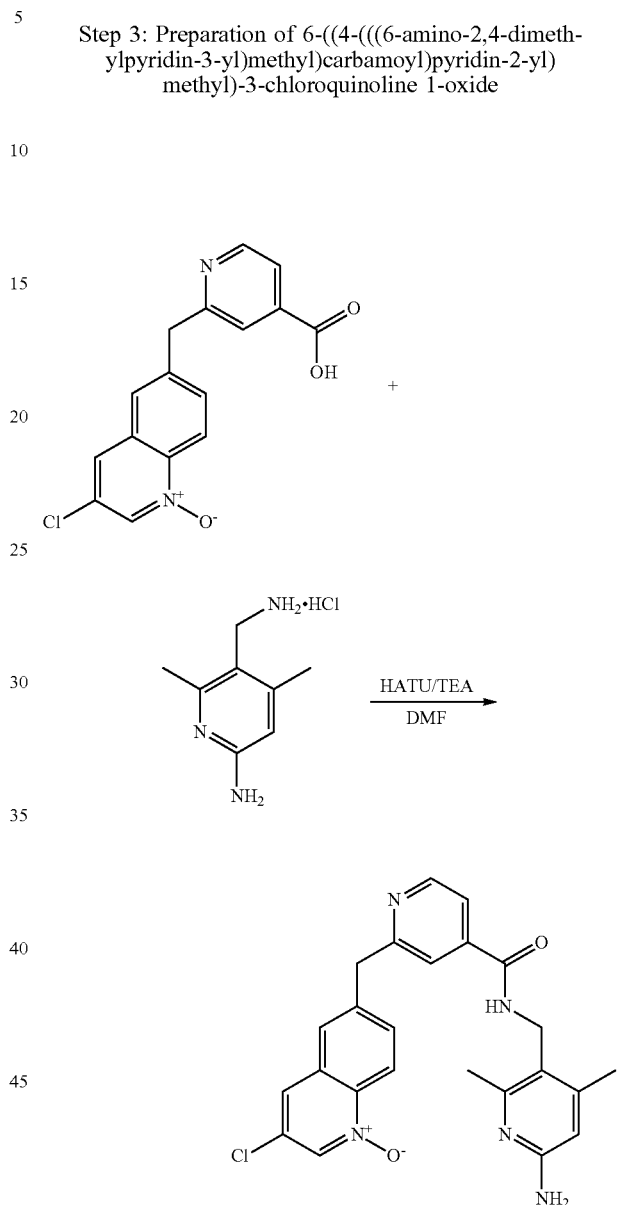

To a solution of 2-(3-chloro-1-oxy-quinolin-6-ylmethyl)-isonicotinic acid (100 mg, 0.32 mmol, 1 eq) in DMF (10 mL) was added 5-aminomethyl-4,6-dimethyl-pyridin-2-ylamin (106 mg, 0.48 mmol, 1.5 eq), HATU (182 mg, 0.48 mmol, 1.5 eq), and Et$_3$N (1 mL). The mixture was stirred at rt for 3 h. Then it was quenched with water, extracted with DCM. The combined extracts were dried, concentrated, and the residue was purified by prep-HPLC to give 6-((4-(((6-amino-2,4-dimethylpyridin-3-yl)methyl)carbamoyl)pyridin-2-yl)methyl)-3-chloroquinoline 1-oxide (30 mg, 21%) as a gray solid. LRMS (M+H$^+$) m/z calculated 448.1, found 447.8.

$^1$H NMR (DMSO-d6, 400 MHz) δ 8.74 (d, 1H), 8.59-8.63 (m, 2H), 8.38 (d, 1H), 8.10 (s, 1H), 7.91 (s, 1H), 7.73-7.75 (m, 2H), 7.59-7.61 (m, 1H), 6.13 (s, 1H), 5.71 (s, 2H), 4.33 (d, 4H), 2.30 (s, 3H), 2.16 (s, 3H).

Example 100: Preparation of N-((6-amino-2,4-dimethylpyridin-3-yl)methyl)-2-((3,8-dichloroquinolin-6-yl)methyl)isonicotinamide

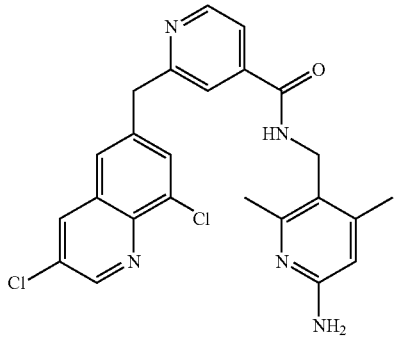

N-(6-amino-2,4-dimethylpyridin-3-yl)methyl)-2-
((3,8-dichloroquinolin-6-yl)methyl)
isonicotinamide

Step 1: Preparation of 2-((3,8-dichloroquinolin-6-yl)methyl)isonicotinic Acid

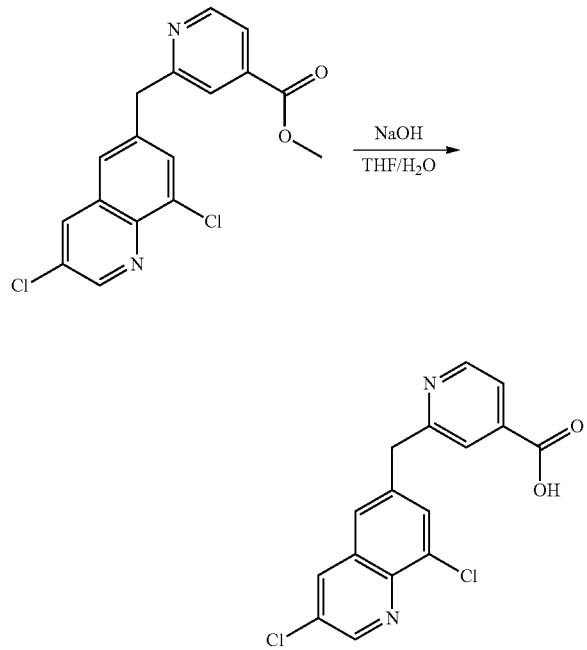 [SMILES: COC(=O)c1ccnc(Cc2cc(Cl)c3ncc(Cl)cc3c2)c1 ; "NaOH" ; "THF/H2O" ; O=C(O)c1ccnc(Cc2cc(Cl)c3ncc(Cl)cc3c2)c1]

To a solution of 2-(3,8-dichloro-quinolin-6-ylmethyl)-isonicotinic acid methyl ester (300 mg, 0.86 mmol, 1 eq) in THF (10 mL)/water (5 mL) was added NaOH (42 mg, 1.05 mmol, 1.2 eq). The mixture was stirred at rt for 3 h and then aqueous HCl (2 N) was added to adjust pH 4. The mixture was extracted with EA, and the organic layer was concentrated under pressure to provide the crude product (170 mg, 59%) without further purification.

Step 2: Preparation of N-((6-amino-2,4-dimethylpyridin-3-yl)methyl)-2-((3,8-dichloroquinolin-6-yl)methyl)isonicotinamide

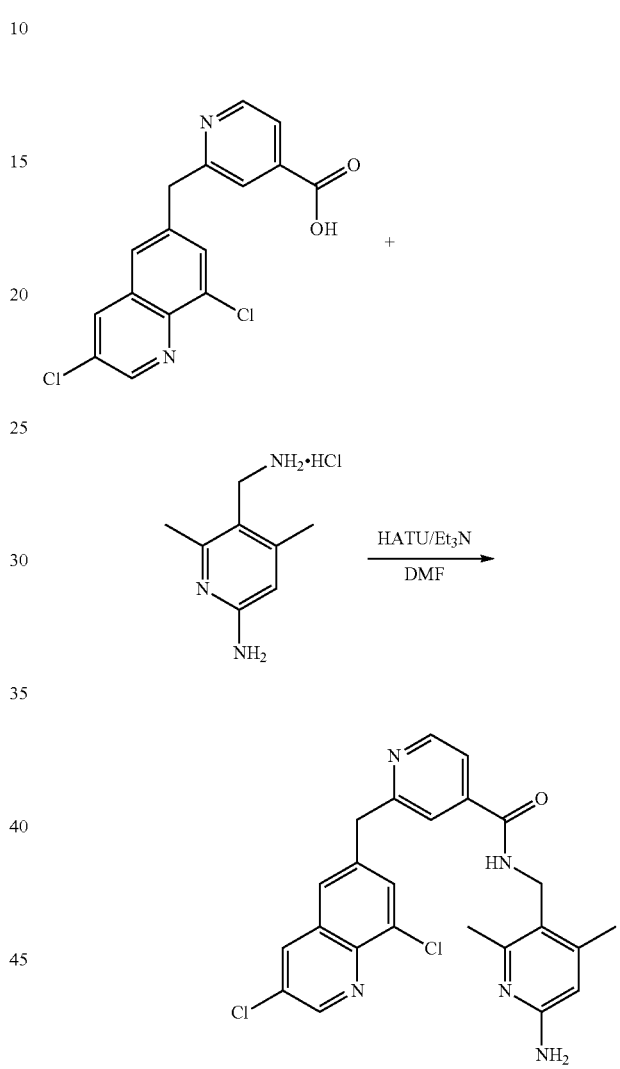

To a solution of 2-(3,8-dichloro-quinolin-6-ylmethyl)-isonicotinic acid (80 mg, 0.24 mmol, 1 eq) in DMF (10 mL) was added 5-aminomethyl-4, 6-dimethyl-pyridin-2-ylamine (83 mg, 0.36 mmol, 1.5 eq), HATU (110 mg, 0.29 mmol, 1.2 eq), and Et$_3$N (121.2 mg, 1.2 mmol, 5 eq). The mixture was stirred at rt for 3 h. Then it was quenched with water, extracted with DCM. The combined extracts were dried, concentrated, and the residue was purified by prep-HPLC to give N-((6-amino-2,4-dimethylpyridin-3-yl)methyl)-2-((3,8-dichloroquinolin-6-yl)methyl)isonicotinamide (16 mg, 14%) as a white solid. LRMS (M+H$^+$) m/z calculated 466.1, found 465.8.

$^1$H NMR (DMSO-d6, 400 MHz) δ 8.95 (s, 1H), 8.60-8.66 (m, 3H), 7.77-7.94 (m, 3H), 8.00 (s, 1H), 7.60 (d, 1H), 7.68-7.71 (m, 1H), 6.18 (s, 1H), 5.91 (s, 2H), 4.33-4.34 (m, 4H), 2.32 (s, 3H), 2.19 (s, 3H).

Example 101: Preparation of N-((6-amino-2-methylpyridin-3-yl)methyl)-2-((3,8-dichloroquinolin-6-yl)methyl)isonicotinamide

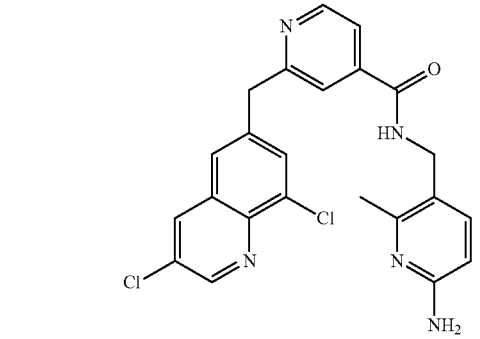

N-((6-amino-2-methylpyridin-3-yl)methyl)-2-((3,8-dichloroquinolin-6-yl)methyl)isonicotinamide

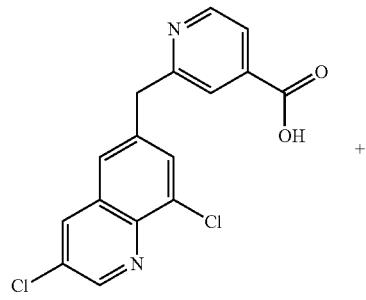

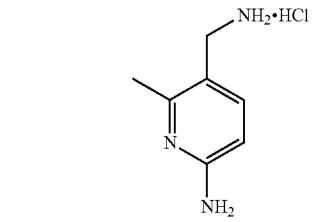

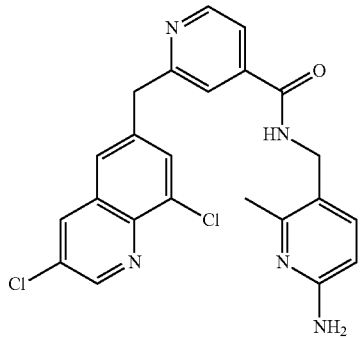

N-((6-amino-2-methylpyridin-3-yl)methyl)-2-((3,8-dichloroquinolin-6-yl)methyl)isonicotinamide (25 mg, 23%) was prepared as described for N-((6-amino-2,4-dimethylpyridin-3-yl)methyl)-2-((3,8-dichloroquinolin-6-yl)methyl)isonicotinamide (Example 100) as a white solid. LRMS (M+H$^+$) m/z calculated 452.1, found 451.8.

$^1$H NMR (DMSO-d6, 400 MHz) δ 8.94-8.98 (m, 2H), 8.63-8.64 (m, 2H), 7.95 (m, 1H), 7.84-7.88 (m, 2H), 7.62 (d, 1H), 6.24-6.26 (m, 1H), 6.80 (s, 2H), 4.28-4.36 (m, 4H), 2.28 (s, 3H)

Example 102: Preparation of N-((6-amino-2-methylpyridin-3-yl)methyl)-2-((3-chloro-5-fluoroquinolin-6-yl)methyl)isonicotinamide

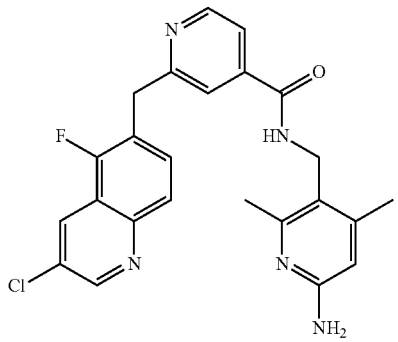

N-((6-amino-2,4-dimethylpyridin-3-yl)methyl)-2-((3-chloro-5-fluoroquinolin-6-yl)methyl)isonicotinamide

Step 1: Preparation of 5-fluoro-quinoline-6-carboxylic acid methyl ester and 7-fluoro-quinoline-6-carboxylic Acid Methyl Ester

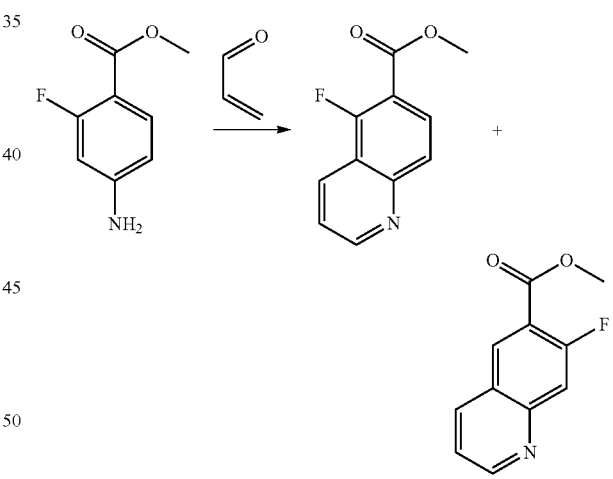

To a suspension of 4-amino-2-fluoro-benzoic acid methyl ester (20.0 g, 0.129 mol, 1 eq) and p-chloranil (35.0 g, 0.142 mol, 1.1 eq) in 500 mL of 6 N HCl solution was added acrolein (13.5 g, 0.194 mol, 1.5 eq, 80% purity). The mixture was stirred at 100° C. for 10 min. After cooling to rt, the mixture was basified to pH 3 with sat. NaHCO$_3$. The precipitate was removed by filtration. The filtrate was extracted with CHCl$_3$. The combined organic layers were dried and concentrated. The residue was purified by chromatography on silica gel column (EA/PE=1/10, v/v) to give 5-fluoro-quinoline-6-carboxylic acid methyl ester and 7-fluoro-quinoline-6-carboxylic acid methyl ester (3.0 g, 11%) as a yellow solid.

Step 2: Preparation of 3-chloro-5-fluoro-quinoline-6-carboxylic Acid Methyl Ester and 3-chloro-7-fluoro-quinoline-6-carboxylic Acid Methyl Ester

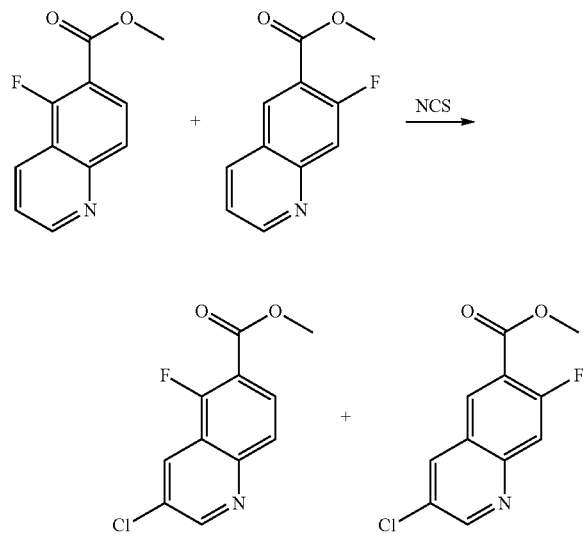

To a solution of mixture of 5-fluoro-quinoline-6-carboxylic acid methyl ester and 7-fluoro-quinoline-6-carboxylic acid methyl ester (3.7 g, 18.0 mmol, 1 eq) in DMF (90 mL) was added NCS (7.2 g, 54.0 mmol, 3 eq). The reaction mixture was stirred at 120° C. for 40 min under $N_2$. The reaction mixture was allowed to cool to ambient temperature, treated with water, neutralized with solid $NaHCO_3$ and stirred at rt for 30 min. Powdered sodium thiosulfate was carefully added to remove excess of NCS. The mixture was extracted with EA. The organic layer was dried and concentrated under vacuum. The crude product was purified by flash-chromatography on silica gel column to afford the mixture of 3-chloro-5-fluoro-quinoline-6-carboxylic acid methyl ester and 3-chloro-7-fluoro-quinoline-6-carboxylic acid methyl ester (2.1 g, 49%) as a yellow solid.

Step 3: Preparation of N-((6-amino-2,4-dimethyl-pyridin-3-yl)methyl)-2-((3-chloro-5-fluoroquinolin-6-yl)methyl)isonicotinamide

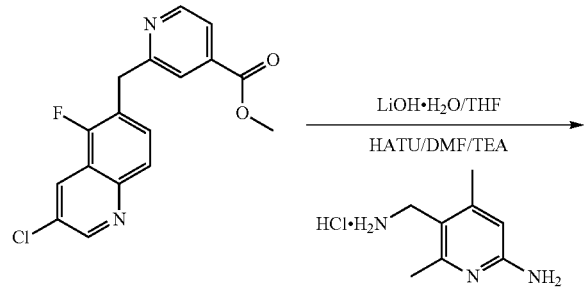

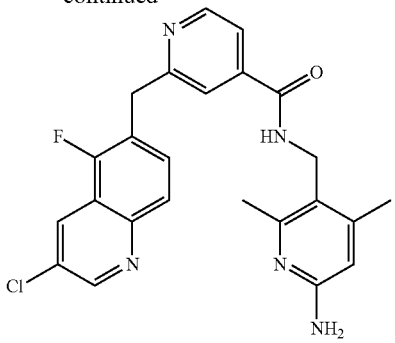

To a solution of 2-(3-chloro-5-fluoro-quinolin-6-ylmethyl)-isonicotinic acid methyl ester (104.4 mg, 0.32 mmol, 1.0 eq) in THF (5 mL)/$H_2O$ (5 mL) was added $LiOH \cdot H_2O$ (26.87 mg, 0.64 mmol, 2 eq). The mixture was stirred at 40° C. for 1 h and was acidified to pH 5 with 1 N HCl solution. The mixture was concentrated in vacuo and the residue was directly used without further purification. To a solution of the above crude product in DMF (10 mL) was added 5-aminomethyl-4,6-dimethyl-pyridin-2-ylamin (106 mg, 0.48 mmol, 1.5 eq), HATU (182 mg, 0.48 mmol, 1.5 eq), and $Et_3N$ (1 mL). The mixture was stirred at rt for 3 h. Then it was quenched with water, extracted with DCM. The combined extracts were dried, concentrated, and the residue was purified by prep-HPLC to give N-((6-amino-2,4-dimethyl-pyridin-3-yl)methyl)-2-((3-chloro-5-fluoroquinolin-6-yl)methyl)isonicotinamide (17 mg, 12.4%) as a white solid. LRMS (M+H$^+$) m/z calculated 450.1, found 450.1. $^1$H NMR (DMSO-d6, 400 MHz) δ 8.87 (d, 1H), 8.55-8.58 (m, 3H), 7.93 (d, 1H), 7.73-7.81 (m, 2H), 7.60 (d, 1H), 6.11 (s, 1H), 5.66 (s, 2H), 4.33-4.38 (m, 4H), 2.29 (s, 3H), 2.16 (s, 3H).

Example 103: Preparation of N-((6-amino-2-methylpyridin-3-yl)methyl)-2-((3-chloro-5-fluoroquinolin-6-yl)methyl)isonicotinamide

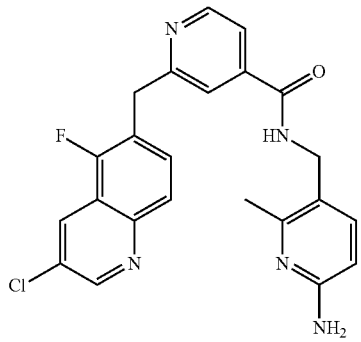

N-((6-amino-2-methylpyridin-3-yl)methyl)-2-((3-chloro-5-fluoroquinolin-6-yl)methyl)isonicotinamide

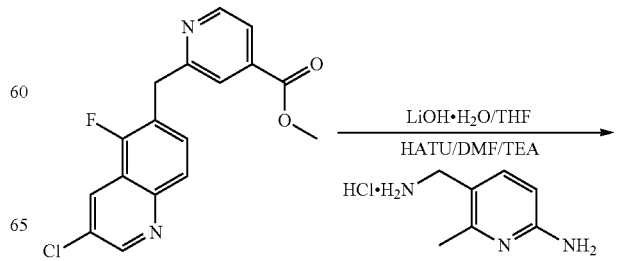

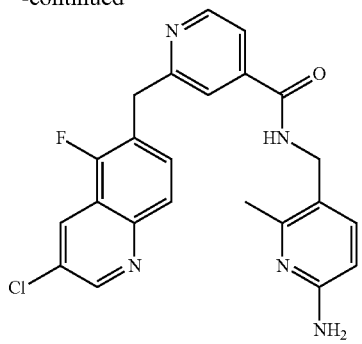

N-((6-amino-2-methylpyridin-3-yl)methyl)-2-((3-chloro-5-fluoroquinolin-6-yl)methyl)isonicotinamide (45 mg, 32%) was prepared as described for N-((6-amino-2,4-dimethylpyridin-3-yl)methyl)-2-((3-chloro-5-fluoroquinolin-6-yl)methyl)isonicotinamide (Example 102) as a white solid. LRMS (M+H⁺) m/z calculated 436.1, found 436.1. ¹H NMR (DMSO-d6, 400 MHz) δ 8.99 (m, 1H), 8.88 (s, 1H), 8.57 (d, 2H), 7.94 (d, 1H), 7.63-7.81 (m, 3H), 7.24 (s, 1H), 6.21 (d, 1H), 5.72 (s, 2H), 4.40 (s, 2H), 4.27 (d, 2H), 2.27 (s, 3H).

Example 104: Preparation of N-((6-amino-2-methylpyridin-3-yl)methyl)-2-((3-chloroquinolin-6-yl)methyl)isonicotinamide

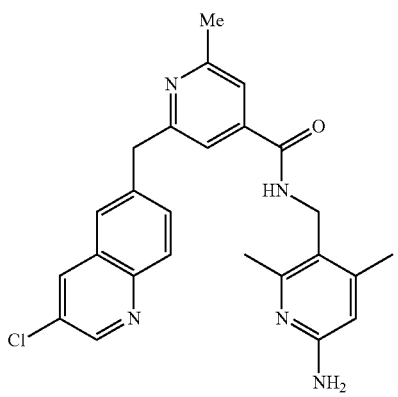

N-((6-amino-2,4-dimethylpyridin-3-yl)methyl)-2-((3-chloroquinolin-6-yl)methyl)-6-methylisonicotinamide Step 1: Preparation of methyl 3-chloroquinoline-6-carboxylate

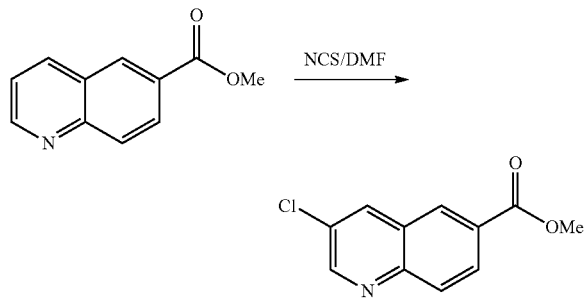

To a solution of methyl quinoline-6-carboxylate (15.0 g, 80.2 mmol, 1.0 eq) in DMF (200 ml) was added N-chlorosuccinimide (21.4 g, 0.16 mol, 2.0 eq) and the reaction mixture was stirred at 120° C. for 20 h. The reaction mixture was allowed to cool to rt, treated with brine and the mixture was extracted with EA. The organic layer was dried over Na₂SO₄, filtered and concentrated under vacuum. The crude product was purified by chromatography on silica gel (EA/PE=1/8, v/v) to afford methyl 3-chloroquinoline-6-carboxylate (9.1 g, 51%) as a yellow solid.

Step 2: Preparation of methyl (3-chloro-quinolin-6-yl)-methanol

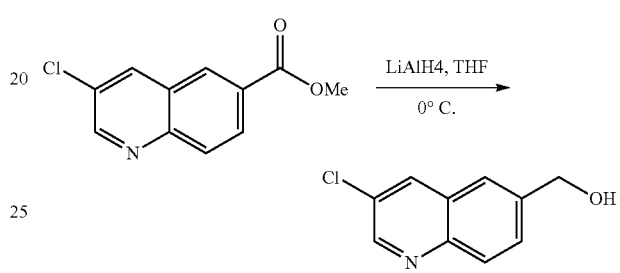

To a solution of methyl 3-chloroquinoline-6-carboxylate (8 g, 36.0 mmol, 1.0 eq) in dry THF was added LiAlH₄ (2.5M in THF, 5.8 mL, 0.4 eq). The resulting mixture was stirred at 0° C. for 1 h. After which period, additional LiAlH₄ (2.5M in THF, 2.8 mL, 0.2 eq) was added. The system was stirred for another 30 min at 0° C. and quenched by the slow addition of 1N aqueous NaOH. The resulting precipitate was filtered, and the filtrate was extracted with EA. The combined organic layers were dried and concentrated. The residue was purified by silica gel chromatography (PE/EA=20/1~5/1, v/v) to afford (3-chloro-quinolin-6-yl)-methanol (4.8 g, 69%) as a white solid.

Step 3: Preparation of 3-chloro-6-chloromethyl-quinoline

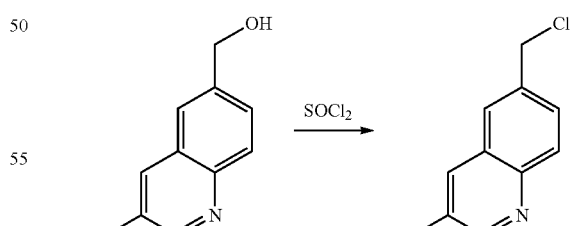

To (3-chloro-quinolin-6-yl)-methanol (3.3 g, 17.1 mmol, 1.0 eq) was added SOCl₂ (50 mL) and the mixture was stirred at rt for 1 h. The volatiles were then removed under vacuum and the residue was dissolved in DCM. The mixture was washed with saturated aq. NaHCO₃, dried and concentrated to give 3-chloro-6-chloromethyl-quinoline (3.4 g, 94%) as a yellow solid.

Step 4: Preparation of methyl 2-methyl-6-(trimethylstannyl)isonicotinate

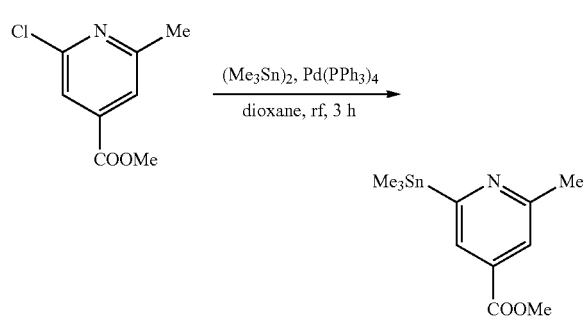

Hexamethyldistannane (0.21 mL, 334 mg, 1.02 mmol) and tetrakis(triphenylphosphine)palladium(0) (70 mg, 0.06 mmol) were added to a solution of methyl 2-chloro-6-methylisonicotinate (100 mg, 0.54 mmol) in dry dioxane (10 mL) and the resulting mixture was refluxed for 3 h under $N_2$. EtOAc (50 mL) and water (100 mL) were then added. The layers were separated and the organic layer was washed with water (5×100 mL), dried ($Na_2SO_4$), and the solvent removed by rotary evaporation to leave crude residue which was used in the next step without further purification.

Step 4: Preparation of methyl 2-((3-chloroquinolin-6-yl)methyl)-6-methylisonicotinate

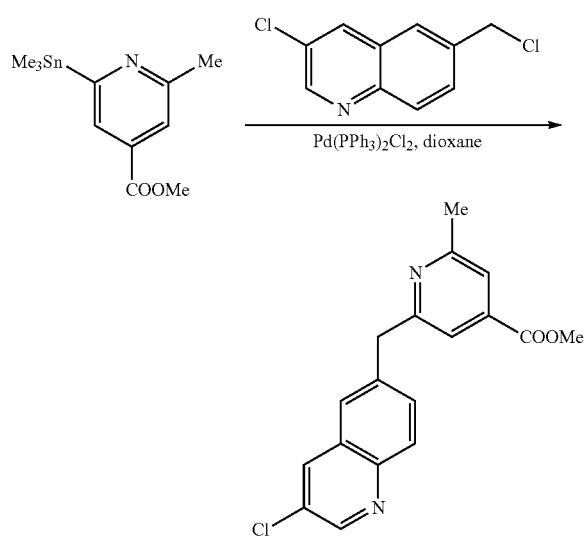

To a solution of 3-chloro-6-chloromethyl-quinoline (110 mg, 0.52 mmol, 1.0 eq) and crude methyl 2-methyl-6-(trimethylstannyl)isonicotinate in dioxane (10 mL) Pd(PPh$_3$)$_2$Cl$_2$ (36 mg, 0.05 mmol, 0.1 eq). The mixture was stirred at 90° C. for 3 h under nitrogen atmosphere, stripped of solvent and purified by silica gel chromatography (EA/PE=10/1~5:1, v/v) to afford methyl 2-((3-chloroquinolin-6-yl)methyl)-6-methylisonicotinate (70 mg, 40%) as a yellow solid.

$^1$H NMR (400 MHz, DMSO-d$_6$) δ 8.83 (d, 1H), 8.53 (d, 1H), 7.98 (d, 1H), 7.85 (d, 1H), 7.73 (dd, 1H), 7.58 (s, 1H), 7.57 (s, 1H), 4.36 (s, 2H), 3.85 (s, 3H), 2.53 (s, 3H).

Step 5: Preparation of 2-((3-chloroquinolin-6-yl)methyl)-6-methylisonicotinic Acid

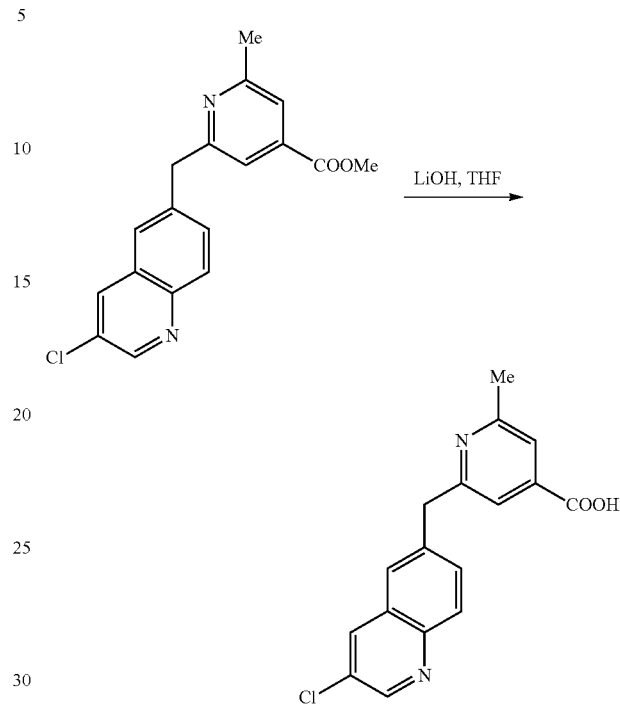

To a solution of 2-((3-chloroquinolin-6-yl)methyl)-6-methylisonicotinate (70 mg, 0.21 mmol, 1.0 eq.) in THF/H$_2$O (5 mL/1 mL) was added LiOH (71 mg, 2.1 mmol, 10 eq.). The resulting mixture was stirred for 1 h at room temperature; all starting material had been consumed (assessed by TLC). Volatile solvent was removed on rotavap, the aqueous residue was neutralized with 1M HCl and extracted with EtOAc (10 mL×3). The combined organic layers were washed with brine, dried over Na$_2$SO$_4$ and concentrated to furnish crude acid (50 mg, 75%), which was used directly in the next step without further purification.

Step 6: Preparation of N-((6-amino-2,4-dimethylpyridin-3-yl)methyl)-2-((3-chloroquinolin-6-yl)methyl)-6-methylisonicotinamide

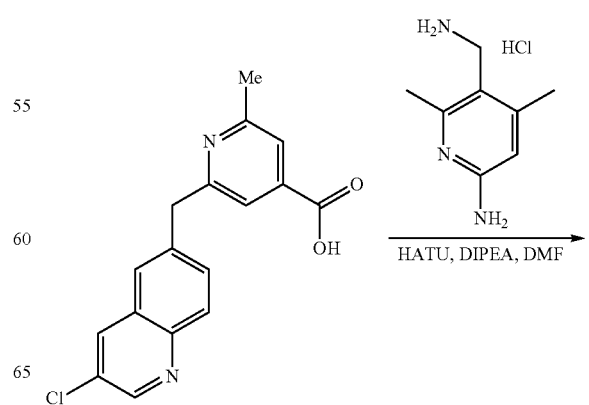

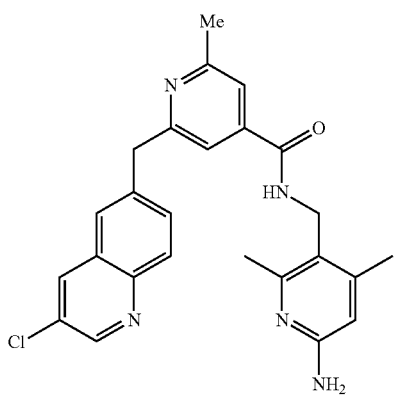

To a solution of 2-((3-chloroquinolin-6-yl)methyl)-6-methylisonicotinic acid (50 mg, 0.16 mmol, 1.0 eq.) in DMF (5 mL) was added 5-aminomethyl-6-methyl-pyridin-2-ylamine hydrochloride (33 mg, 0.0.19 mmol, 1.2 eq.) followed by HATU (91 mg, 0.24 mmol, 1.5 eq.) and DIPEA (0.08 mL, 0.48 mmol, 3.0 eq.) at 0° C. The reaction mixture was allowed to warm to room temperature and stirred for 2 h under $N_2$. Water (20 mL) was added, and the mixture was extracted with EtOAc (20 mL×3). The combined organic layers were washed with brine, dried over $Na_2SO_4$, filtered and concentrated. The residue was purified by prep-TLC (DCM:MeOH=15:1) to give N-((6-amino-2,4-dimethylpyridin-3-yl) methyl)-2-((3-chloroquinolin-6-yl)methyl)-6-methylisonicotinamide (24 mg, 34%) as a yellow solid. LRMS (M+H$^+$) m/z calculated 446.2, found 446.2. $^1$H NMR (DMSO-d$_6$, 400 MHz): δ 8.83 (d, 1H), 8.66 (s, 1H), 8.53 (d, 1H), 7.97 (d, 1H), 7.84 (d, 1H), 7.71 (dd, 1H), 7.50 (s, 1H), 7.47 (s, 1H), 6.32 (s, 2H), 4.32 (d, 2H), 4.29 (s, 2H), 2.48 (s, 3H), 2.37 (s, 3H), 2.23 (s, 3H).

Example 105: Preparation of N-((6-amino-2,4-dimethylpyridin-3-yl)methyl)-2-((5-chloro-1H-indazol-1-yl)methyl)isonicotinamide

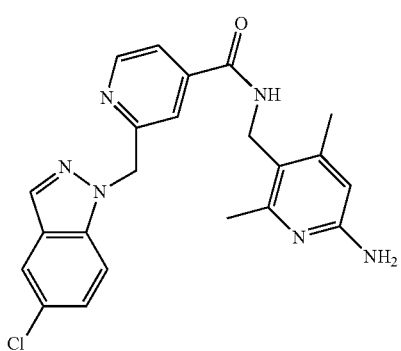

N-((6-amino-2,4-dimethylpyridin-3-yl)methyl)-2-((5-chloro-1H-indazol-1-yl)methyl)isonicotinamide

Step 1: Preparation of methyl 3-chloroquinoline-6-carboxylate

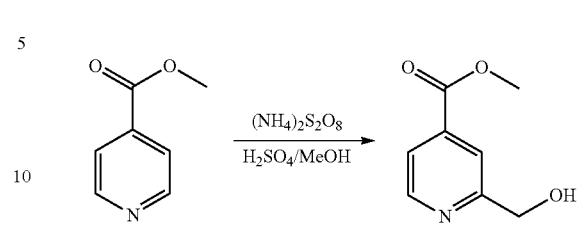

To a solution of methyl isonicotinate (5.0 g, 36.5 mmol, 1.0 eq) in MeOH (70 ml) was added conc.$H_2SO_4$ (300 mg, 3.1 mmol, 0.086 eq) dropwise at rt. The above mixture was heated at reflux, to which was added an aqueous solution of $(NH_4)_2S_2O_8$ (15.0 g, 65.7 mmol in 30 mL of water) dropwise. The reaction mixture was kept at reflux for additional 30 minutes, cooled to rt, treated with 4 M NaOH and aqueous $NaHCO_3$ to about pH 7. The aqueous mixture was concentrated under vacuum, and the residue was extracted with EtOAc (100 mL×2). The combined organic layers were washed with brine, dried over $Na_2SO_4$, filtered and concentrated under vacuum. The crude product was purified by chromatography on silica gel (PE/EA=1/3 to 1/1, v/v) to afford methyl 3-chloroquinoline-6-carboxylate (1.5 g, 25%) as a white solid. LCMS (M+H$^+$) m/z calculated 168, found 168.0. $^1$H NMR (CDCl$_3$, 400 MHz): δ 8.71 (d, J=4.8 Hz, 1H), 7.84 (d, J=0.8 Hz, 1H), 7.77 (dd, 1H), 4.84 (s, 2H), 3.96 (s, 3H).

Step 2: Preparation of methyl 2-(((methylsulfonyl)oxy)methyl)isonicotinate

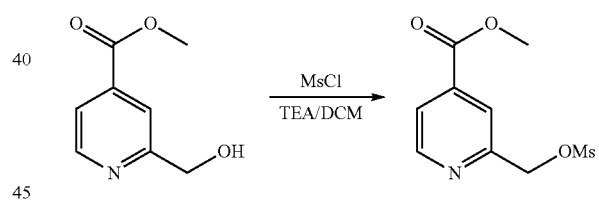

To a stirred solution of methyl 2-(hydroxymethyl)isonicotinate (1.0 g, 6.0 mmol, 1.0 eq) and TEA (1.2 g, 12.0 mmol, 2.0 eq) in DCM (15 mL) was added MsCl (755 g, 6.6 mmol, 1.1 eq) at 0° C. The resulting mixture was stirred at rt for a further 30 minutes, diluted with DCM (60 mL), washed with water (30 mL), brine (30 mL×2), dried and concentrated to afford methyl 2-(((methylsulfonyl)oxy) methyl)isonicotinate (1.2 g, 82%) as a dark brown oil.

Step 3: Preparation of methyl 2-((5-chloro-1H-indazol-1-yl)methyl)isonicotinate

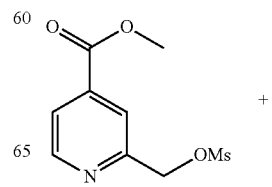

+

-continued

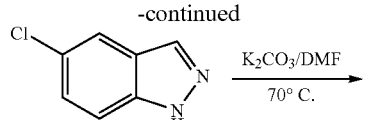

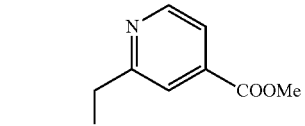

+

A mixture of methyl 2-(((methylsulfonyl)oxy)methyl)isonicotinate (300 mg, 1.22 mmol, 1.0 eq), 5-chloro-1H-indazole (280 mg, 1.84 mmol, 1.5 eq) and K₂CO₃ (337 mg, 2.44 mmol, 2 eq) in DMF (5 mL) was stirred at 70° C. for 2 hours. The mixture was cooled to rt, diluted with EtOAc (50 mL), washed with water (30 mL), brine (30 mL×2), dried and concentrated. The residue was purified by chromatography on silica gel (PE/EA=10/1~5/1 v/v) to afford methyl 2-((5-chloro-1H-indazol-1-yl)methyl)isonicotinate (120 mg, 33%) as a white solid. ¹H NMR (CDCl₃, 400 MHz): δ 8.68 (d, 1H), 8.00 (s, 1H), 7.73 (d, 1H), 7.69 (d, 1H), 7.48 (s, 1H), 7.34 (d, 1H), 7.28 (dd, 1H), 5.73 (s, 2H), 3.85 (s, 3H). Chromatography on silica gel (PE/EA=5/1 to 3/1, v/v) to afford methyl 2-((5-chloro-2H-indazol-2-yl)methyl)isonicotinate (70 mg, 19%) as a white solid. ¹H NMR (CDCl₃, 400 MHz): δ 8.73 (d, 1H), 8.05 (s, 1H), 7.79 (dd, 1H), 7.72 (s, 1H), 7.64-7.60 (m, 2H), 7.21 (dd, 1H), 5.75 (s, 2H), 3.90 (s, 3H).

Step 4: Preparation of 2-((5-chloro-1H-indazol-1-yl)methyl)isonicotinic Acid

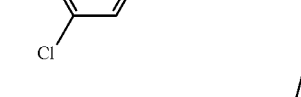

aq. LiOH
THF

-continued

To a solution of methyl 2-((5-chloro-1H-indazol-1-yl)methyl)isonicotinate (270 mg, 0.89 mmol, 1.0 eq) in THF (5 mL) was added LiOH H₂O (375 mg, 8.9 mmol, 10.0 eq) and water (5 mL). The mixture was stirred at rt for 2 hours, concentrated under vacuum to remove most THF. The aqueous mixture was adjusted with 1M HCl to about pH 7. The white suspension was filtered and the solid was washed with water (10 mL), evaporated under vacuum to dryness to afford 2-((5-chloro-1H-indazol-1-yl)methyl)isonicotinic acid (240 mg, 93%) as a white solid.

Step 5: Preparation of N-((6-amino-2,4-dimethyl-pyridin-3-yl)methyl)-2-((5-chloro-1H-indazol-1-yl)methyl)isonicotinamide

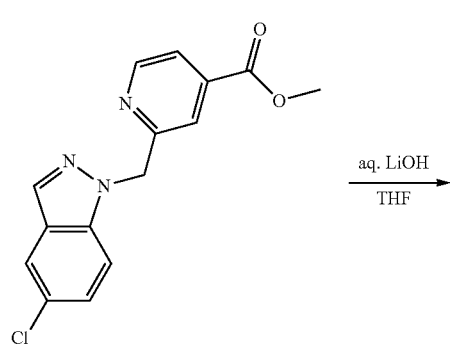

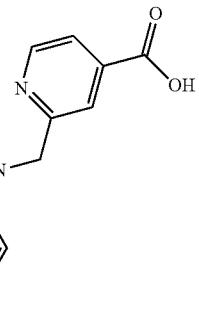

To a stirred mixture of 2-((5-chloro-1H-indazol-1-yl)methyl)isonicotinic acid (100 mg, 0.35 mmol, 1.0 eq), TEA (101 mg, 1.0 mmol, 3.0 eq) and 5-(aminomethyl)-4,6-dimethylpyridin-2-amine hydrochloride (65 mg, 0.35 mmol, 1.0 eq) in DMF (3 mL) was added HATU (264 mg, 0.7 mmol, 2.0 eq) at 0° C. The reaction mixture was stirred at rt for 16 h, and then diluted with EtOAc (50 mL). The new mixture was washed with water (30 mL), brine (30 mL×2), dried and concentrated. The residue was purified by chromatography on silica gel (DCM/MeOH=50/1 to 20/1, v/v) and then Prep-TLC (DCM/MeOH=20/1, v/v) to afford N-((6-amino-2,4-dimethylpyridin-3-yl)methyl)-2-((5-chloro-1H-indazol-1-yl)methyl)isonicotinamide (10 mg, 7%) as a white solid. LCMS (M+H⁺) m/z calculated 421, found 421.0.

¹H NMR (DMSO-d₆, 400 MHz): δ 8.68 (t, 1H), 8.57 (d, 1H), 8.10 (d, 1H), 7.88 (d, 1H), 7.75 (d, 1H), 7.65 (dd, 1H), 7.49 (s, 1H), 7.40 (dd, 1H), 6.14 (s, 1H), 5.82-5.73 (m, 4H), 4.30 (d, 2H), 2.28 (s, 3H), 2.15 (s, 3H). LRMS (M+H⁺) m/z calculated 421.2, found 421.0.

Example 106: Preparation of N-((6-amino-2,4-dimethylpyridin-3-yl)methyl)-2-((5-chloro-2H-indazol-2-yl)methyl)isonicotinamide

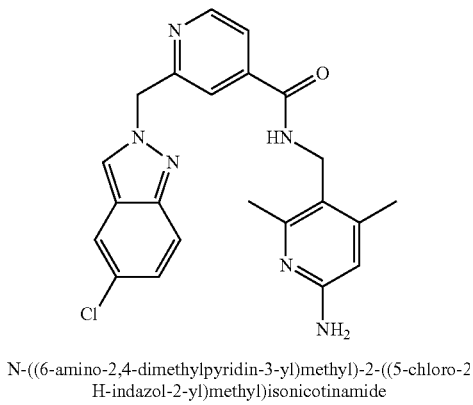 [SMILES: Cc1cc(N)nc(C)c1CNC(=O)c1ccnc(Cn2cc3cc(Cl)ccc3n2)c1]

N-((6-amino-2,4-dimethylpyridin-3-yl)methyl)-2-((5-chloro-2H-indazol-2-yl)methyl)isonicotinamide Step 1: Preparation of 2-((5-chloro-2H-indazol-2-yl)methyl)isonicotinic Acid

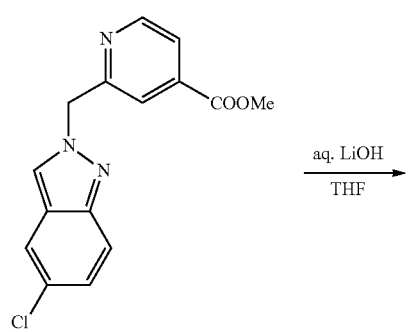

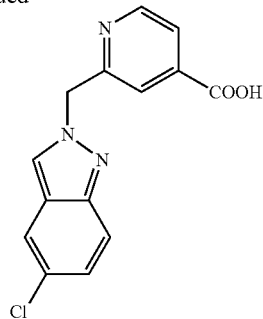

To a solution of methyl 2-((5-chloro-2H-indazol-2-yl)methyl)isonicotinate (150 mg, 0.50 mmol, 1.0 eq) in THF (5 mL) was added LiOH H₂O (208 mg, 5.0 mmol, 10.0 eq) and water (5 mL). The mixture was stirred at rt for 2 hours, concentrated under vacuum to remove most THF. The aqueous mixture was adjusted with 1M HCl to pH ~7. The white suspension was filtered and the solid was washed with water (10 mL), concentrated to afford 2-((5-chloro-2H-indazol-2-yl)methyl)isonicotinic acid (110 mg, 77%) as a white solid.

Step 2: Preparation of N-((6-amino-2,4-dimethylpyridin-3-yl)methyl)-2-((5-chloro-2H-indazol-2-yl)methyl)isonicotinamide

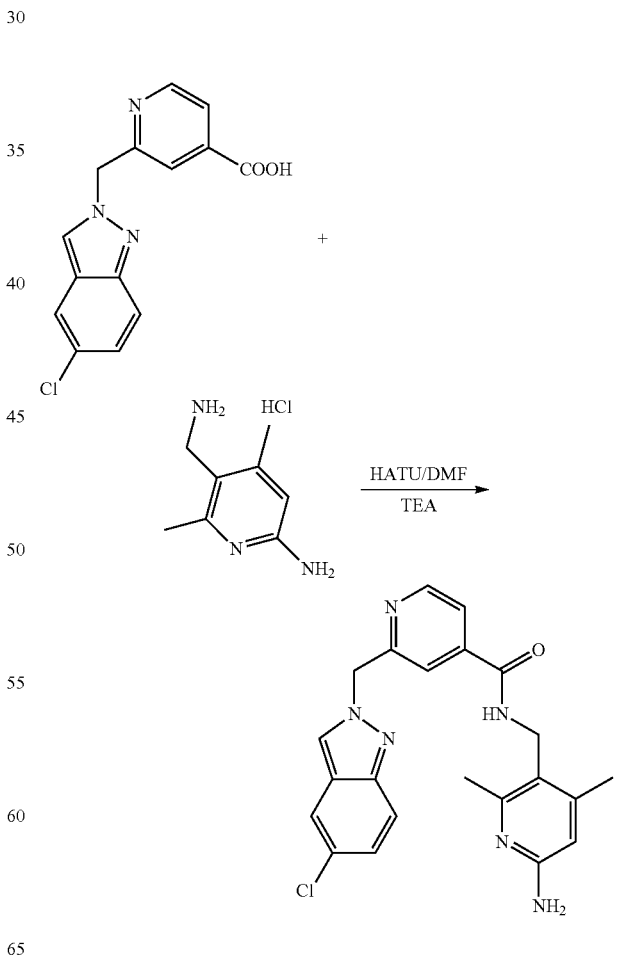

To a stirred mixture of 2-((5-chloro-2H-indazol-2-yl)methyl)isonicotinic acid (110 mg, 0.38 mmol, 1.0 eq), TEA (105 mg, 1.0 mmol, 3.0 eq) and 5-(aminomethyl)-4,6-dimethylpyridin-2-amine hydrochloride (71 mg, 0.38 mmol, 1.0 eq) in DMF (3 mL) was added HATU (290 mg, 0.76 mmol, 2.0 eq) at 0° C. The reaction mixture was stirred at rt for 16 h, and then diluted with EtOAc (50 mL). The new mixture was washed with water (30 mL), brine (30 mL×2), dried and concentrated. The residue was purified by chromatography on silica gel (DCM/MeOH=50/1 to 10/1, v/v) and then Prep-TLC (DCM/MeOH=10/1, v/v) to afford N-((6-amino-2,4-dimethylpyridin-3-yl)methyl)-2-((5-chloro-2H-indazol-2-yl)methyl)isonicotinamide (30 mg, 19%) as a white solid. LCMS (M+H⁺) m/z calculated 421.2, found 421.0.

¹H NMR (DMSO-d₆, 400 MHz): δ 8.84 (s, 1H), 8.65 (d, 1H), 8.55 (d, 1H), 7.85 (dd, 1H), 7.69 (dd, 1H), 7.60-7.63 (m, 2H), 7.23 (dd, 1H), 6.38 (s, 1H), 5.81 (s, 2H), 4.33 (d, 2H), 2.41 (s, 3H), 2.27 (s, 3H).

Example 107: Preparation of N-((6-amino-2,4-dimethylpyridin-3-yl)methyl)-2-((5-methyl-2H-indazol-2-yl)methyl)isonicotinamide

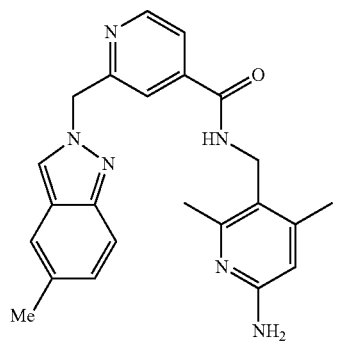

N-((6-amino-2,4-dimethylpyridin-3-yl)methyl)-2-((5-methyl-2-((5-methyl-2H-indazol-2-yl)methyl)isonicotinamide Step 1: Preparation of methyl 2-((5-chloro-2H-indazol-2-yl)methyl)isonicotinate

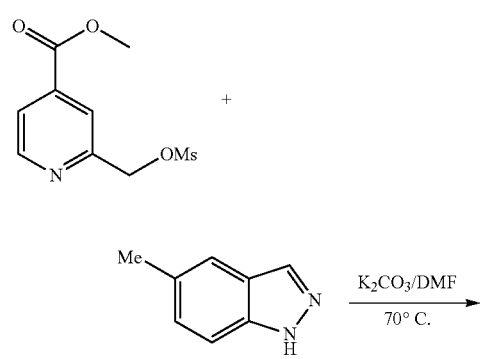

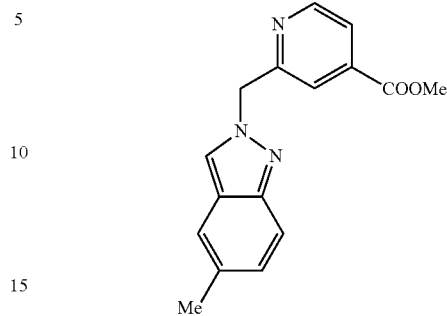

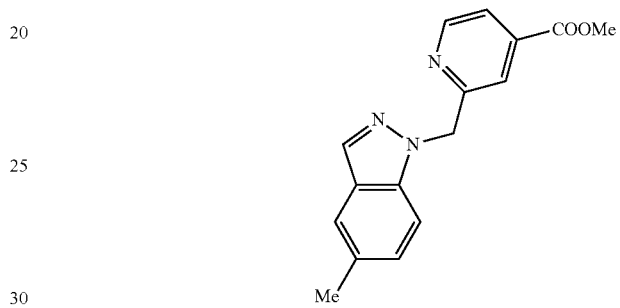

Methyl 2-((5-methyl-2H-indazol-2-yl)methyl)isonicotinate and methyl 2-((5-methyl-1H-indazol-1-yl)methyl)isonicotinate were prepared as described for methyl 2-((5-chloro-2H-indazol-2-yl)methyl)isonicotinate.

¹H NMR (CDCl₃, 400 MHz): δ 8.72 (d, 1H), 7.98 (s, 1H), 7.77 (dd, 1H), 7.67 (s, 1H), 7.61 (d, 1H), 7.39 (s, 1H), 7.12 (dd, 1H), 5.75 (s, 2H), 3.88 (s, 3H), 2.40 (s, 3H).

Methyl 2-((5-methyl-1H-indazol-1-yl)methyl)isonicotinate: 1H NMR (CDCl₃, 400 MHz): δ 8.72 (d, 1H), 8.00 (s, 1H), 7.72 (d, 1H), 7.51 (s, 1H), 7.47 (s, 1H), 7.29 (d, 1H), 7.18 (d, 1H), 5.76 (s, 2H), 3.84 (s, 3H), 2.43 (s, 3H).

Step 2: Preparation of N-((6-amino-2,4-dimethylpyridin-3-yl)methyl)-2-((5-chloro-2H-indazol-2-yl)methyl)isonicotinamide

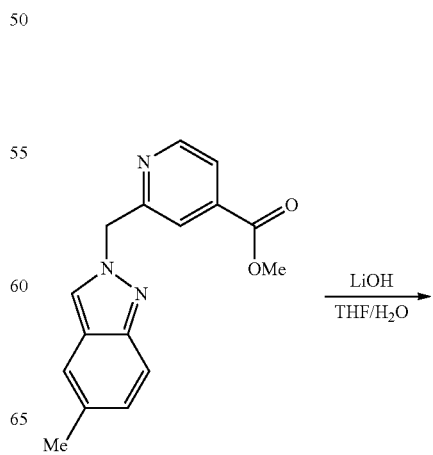

403
-continued

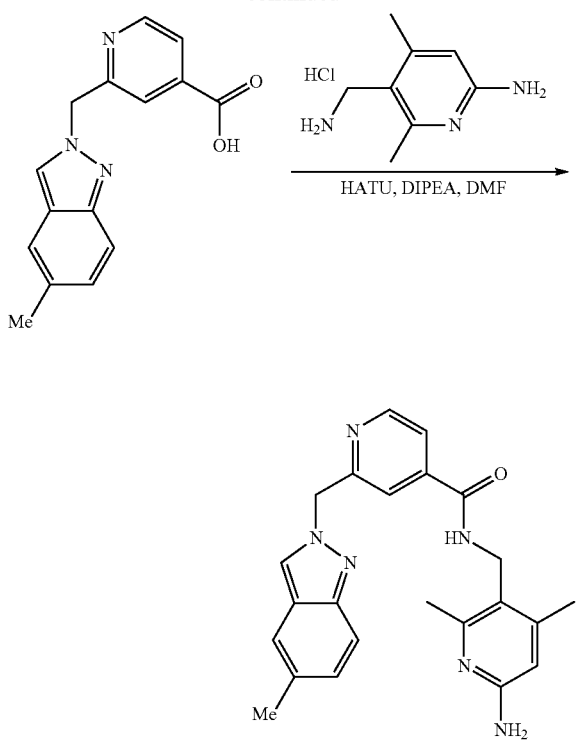

N-((6-amino-2,4-dimethylpyridin-3-yl)methyl)-2-((5-methyl-2H-indazol-2-yl)methyl)isonicotinamide was prepared as described for N-((6-amino-2,4-dimethylpyridin-3-yl)methyl)-2-((5-chloro-2H-indazol-2-yl)methyl) isonicotinamide. LCMS (M+H+) m/z calculated 401.2, found 401.0. 1H NMR (DMSO-d6, 400 MHz): δ 8.78 (s, 1H), 8.63 (d, 1H), 8.38 (s, 1H), 7.75-7.64 (m, 1H), 7.54 (s, 1H), 7.47 (d, 1H), 7.46 (s, 1H), 7.07 (dd, 1H), 6.29 (s, 2H), 5.75 (s, 2H), 4.32 (d, 2H), 2.35 (s, 6H), 2.22 (s, 3H).

Example 108: Preparation of N-((6-amino-2,4-dimethylpyridin-3-yl)methyl)-2-((5-methyl-3a,7a-dihydro-1H-indazol-1-yl)methyl)isonicotinamide

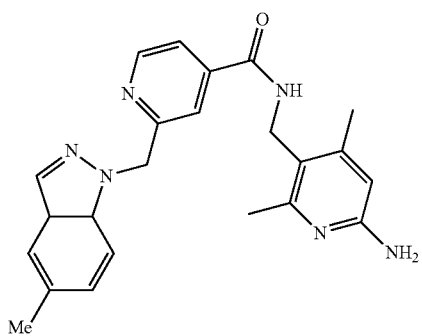

N-((6-amino-2,4-dimethylpyridin-3-yl)methyl)-2-((5-methyl-3a,7a-dihydro-1H-indazol-1-yl)methyl)isonicotinamide

404
-continued

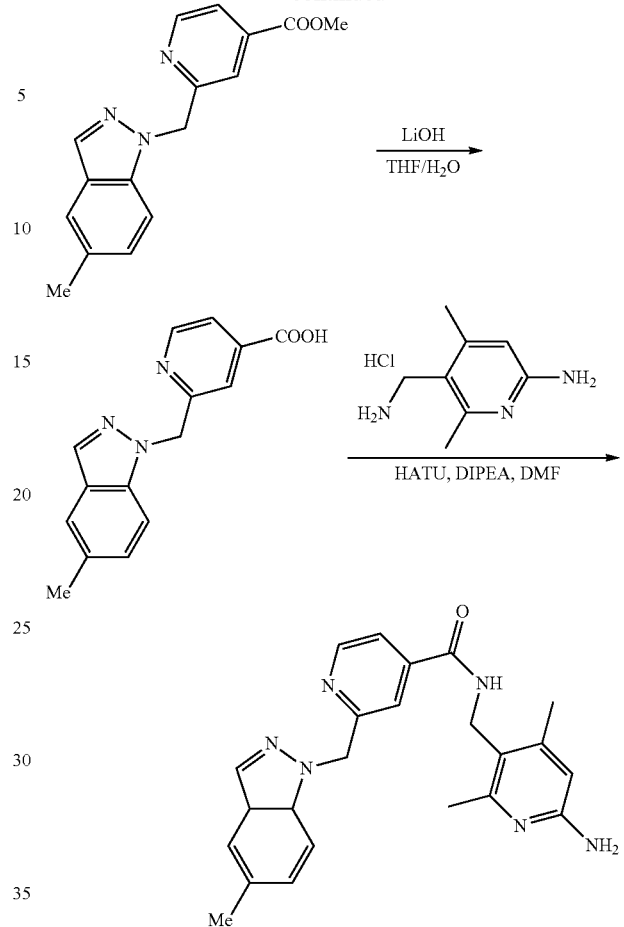

N-((6-amino-2,4-dimethylpyridin-3-yl)methyl)-2-((5-methyl-3a, 7a-dihydro-1H-indazol-1-yl)methyl)isonicotinamide was prepared as described for N-((6-amino-2,4-dimethylpyridin-3-yl)methyl)-2-((5-chloro-1H-indazol-1-yl)methyl)isonicotinamide (Example 105). LCMS (M+H$^+$) m/z calculated 401.2, found 401.0. $^1$H NMR (DMSO-d$_6$, 400 MHz): δ 8.68 (t, 1H), 8.59 (d, 1H), 8.01 (d, 1H), 7.63 (dd, 1H), 7.54 (d, 1H), 7.53 (s, 1H), 7.38 (s, 1H), 7.26-7.13 (m, 1H), 6.16 (s, 1H), 5.87 (s, 2H), 5.75 (s, 2H), 4.29 (d, 2H), 2.40 (s, 3H), 2.29 (s, 3H), 2.15 (s, 3H).

Example 109: Preparation of N-((3-chloro-6-fluoro-1H-indol-5-yl)methyl)-2-((6-methyl-2-(methylsulfonyl)quinolin-3-yl)methyl)isonicotinamide

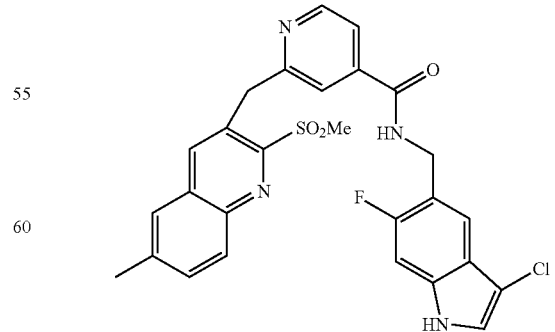

N-((3-chloro-6-fluoro-1H-indol-5-yl)methyl)-2-((6-methyl-2-(methylsulfonyl)quinolin-3-yl)methyl)isonicotinamide (19 mg, 13% yields for 2 steps) was prepared as described for N-((6-amino-2,4-dimethylpyridin-3-yl)methyl)-2-((3-methyl-8-(methylsulfonyl)quinolin-6-yl)methyl)isonicotinamide (Example 15) as purple solid. LRMS (M+H⁺) m/z calculated 537.1, found 537.1. ¹H NMR (DMSO-d₆, 400 MHz) δ 11.40 (s, 1H), 9.27-9.24 (t, 1H), 8.63-8.62 (d, 1H), 8.31 (s, 1H), 8.02-8.00 (d, 1H), 7.82 (s, 1H), 7.75-7.45 (m, 5H), 7.24-7.21 (d, 1H), 4.78 (s, 2H), 4.60-4.58 (d, 2H), 3.52 (s, 3H), 2.52-2.51 (t, 3H).

Example 110: Preparation of N-((3-chloro-6-fluoro-1H-indol-5-yl)methyl)-2-((2-methylquinolin-6-yl)methyl)isonicotinamide

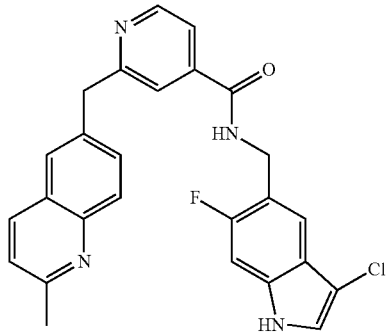 [SMILES: Cc1ccc2cc(Cc3cc(C(=O)NCc4cc5c(Cl)c[nH]c5cc4F)ccn3)ccc2n1]

N-((3-chloro-6-fluoro-1H-indol-5-yl)methyl)-2-((2-methylquinolin-6-yl)methyl)isonicotinamide (16 mg, 15% yields for 2 steps) was prepared as described in Example 15, Steps 6 and 7 as a yellow solid. LRMS (M+H⁺) m/z calculated 459.1, found 459.1. ¹H NMR (DMSO-d₆, 300 MHz) δ 11.39 (s, 1H), 9.24 (t, 1H), 8.66-8.64 (d, 1H), 8.18-8.16 (d, 1H), 7.85-7.78 (m, 3H), 7.65-7.62 (m, 2H), 7.50-7.36 (m, 3H), 7.24-7.20 (d, 1H), 4.59-4.57 (d, 2H), 4.33 (s, 2H), 2.62 (s, 3H).

Example 111: Preparation of N-((1-aminoisoquinolin-6-yl)methyl)-2-((2-methylquinolin-6-yl)methyl)isonicotinamide

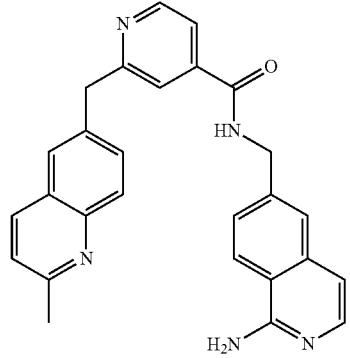 [SMILES: Cc1ccc2cc(Cc3cc(C(=O)NCc4ccc5c(N)nccc5c4)ccn3)ccc2n1]

N-((1-aminoisoquinolin-6-yl)methyl)-2-((2-methylquinolin-6-yl)methyl)isonicotinamide (30 mg, 20% yields for 2 steps) was prepared as described for N-((1-aminoisoquinolin-6-yl)methyl)-2-((3-methylquinolin-6-yl)methyl)isonicotinamide (Example 142). LRMS (M+H⁺) m/z calculated 434.2, found 434.2. ¹H NMR (CD₃OD, 300 MHz) δ 8.64 (d, 1H), 8.14 (d, 1H), 8.06 (d, 1H), 7.88 (d, 1H), 7.77-7.59 (m, 6H), 7.47 (d, 1H), 7.37 (d, 1H), 6.90 (d, 1H), 4.69 (s, 2H), 4.38 (s, 2H), 2.68 (s, 3H).

Example 112: Preparation of N-((6-amino-2-methylpyridin-3-yl)methyl)-2-((2-methylquinolin-6-yl)methyl)isonicotinamide

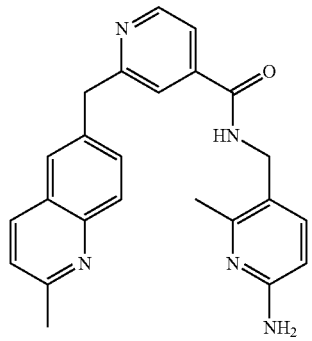 [SMILES: Cc1ccc2cc(Cc3cc(C(=O)NCc4ccc(N)nc4C)ccn3)ccc2n1]

N-((6-amino-2-methylpyridin-3-yl)methyl)-2-((2-methylquinolin-6-yl)methyl)isonicotinamide (29 mg, 14% yields for 2 steps) was prepared as described in Example 15, Steps 6 and 7 as a yellow solid. LRMS (M+H⁺) m/z calculated 398.1, found 398.1. ¹H NMR (DMSO-d₆, 400 MHz) δ 9.02 (t, 1H), 8.65-8.63 (d, 1H), 8.18-8.16 (d, 1H), 7.86-7.63 (m, 5H), 7.38-7.36 (d, 2H), 7.26-7.24 (d, 1H), 6.25-6.23 (d, 1H), 5.77-5.76 (d, 2H), 4.33-4.29 (m, 4H), 2.63 (s, 3H), 2.23 (s, 3H).

Example 113: Preparation of N-((6-amino-2,4-dimethylpyridin-3-yl)methyl)-2-((2-methylquinolin-6-yl)methyl)isonicotinamide

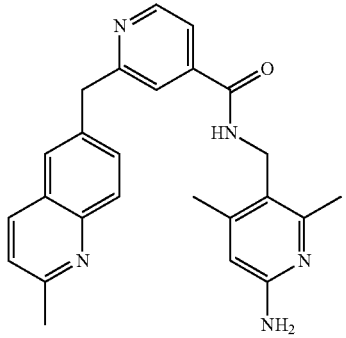

N-((6-amino-2,4-dimethylpyridin-3-yl)methyl)-2-((2-methylquinolin-6-yl)methyl)isonicotinamide (45 mg, 16%) was prepared as described in Example 15, Steps 6 and 7. LRMS (M+H+) m/z calculated 411.9, found 411.9. ¹H NMR (DMSO-d₆, 300 MHz) δ 8.59-8.65 (m, 2H), 8.17 (d, 1H), 7.83 (d, 1H), 7.75 (d, 2H), 7.58-7.64 (m, 2H), 7.37 (d, 1H), 6.11 (s, 1H), 5.67 (s, 2H), 4.30-4.34 (m, 3H), 2.61 (d, 3H), 2.29 (s, 3H), 2.15 (s, 3H).

Example 114: Preparation of N-((6-amino-2,4-dimethylpyridin-3-yl)methyl)-2-((6-methylquinolin-3-yl)methyl)isonicotinamide

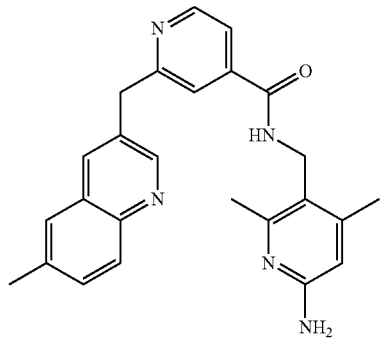

N-((6-amino-2,4-dimethylpyridin-3-yl)methyl)-2-((6-methylquinolin-3-yl)methyl)isonicotinamide (29 mg, 21% yield for 2 steps) was prepared as described in Example 15, Steps 6 and 7 as a yellow solid. LRMS (M+H$^+$) m/z calculated 412.1, found 412.1. $^1$H NMR (DMSO-d$_6$, 400 MHz) δ 8.72 (s, 1H), 8.57-8.52 (d, 2H), 8.00 (s, 1H), 7.80-7.58 (m, 2H), 7.53-7.44 (m, 3H), 6.05 (s, 1H), 5.62 (s, 2H), 4.26 (s, 4H), 2.42-2.39 (m, 3H), 2.22 (s, 3H), 2.07 (s, 3H).

Example 115: Preparation of N-((1-aminoisoquinolin-6-yl)methyl)-2-((6-methylquinolin-3-yl)methyl)isonicotinamide

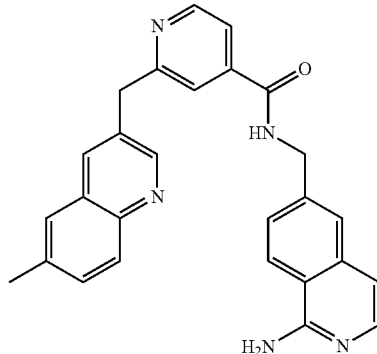

N-((1-aminoisoquinolin-6-yl)methyl)-2-((6-methylquinolin-3-yl)methyl)isonicotinamide (27 mg, 18% yields for 2 steps) was prepared as described for N-((1-aminoisoquinolin-6-yl)methyl)-2-((3-methylquinolin-6-yl)methyl)isonicotinamide (Example 142). LRMS (M+H$^+$) m/z calculated 434.2, found 434.2. $^1$H NMR (CD$_3$OD, 400 MHz) δ 8.74 (d, 1H), 8.66 (d, 1H), 8.11 (s, 1H), 8.07 (d, 1H), 7.88 (d, 1H), 7.83 (s, 1H), 7.72 (d, 1H), 7.69 (d, 1H), 7.61 (s, 2H), 7.51 (d, 1H), 7.49 (d, 1H), 6.92 (d, 1H), 4.71 (s, 2H), 4.41 (s, 2H), 2.51 (s, 3H).

Example 116: Preparation of N-((3-chloro-6-fluoro-1H-indol-5-yl)methyl)-2-((6-methylquinolin-3-yl)methyl) isonicotinamide

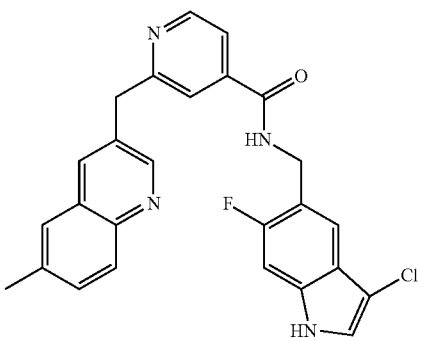 [SMILES: Cc1ccc2ncc(Cc3cc(C(=O)NCc4cc5c(Cl)c[nH]c5cc4F)ccn3)cc2c1]

N-((3-chloro-6-fluoro-1H-indol-5-yl)methyl)-2-((6-methyl quinolin-3-yl) methyl)isonicotinamide (62 mg, 40%) was prepared as described in Example 15, Steps 6 and 7 as an off-white solid. LRMS (M+H+) m/z calculated 459, found 459. $^1$H NMR (DMSO-d$_6$, 400 MHz) δ 11.39 (s, 1H), 9.24 (t, 1H), 8.80 (s, 1H), 8.64 (d, 1H), 8.09 (s, 1H), 7.87 (d, 1H), 7.81 (s, 1H), 7.65-7.67 (m, 2H), 7.50-7.55 (m, 2H), 7.45 (d, 1H), 7.23 (d, 1H), 4.59 (d, 2H), 4.37 (s, 2H), 2.48 (s, 3H).

Example 117: Preparation of N-((6-amino-2-methylpyridin-3-yl)methyl)-2-((6-methylquinolin-3-yl)methyl)isonicotinamide

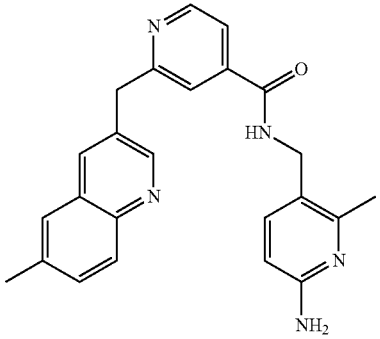

N-((6-amino-2-methylpyridin-3-yl)methyl)-2-((6-methylquinolin-3-yl)methyl)isonicotinamide was prepared as described in Example 15, Steps 6 and 7.

Example 118: Preparation of N-((1-aminoisoquinolin-6-yl)methyl)-2-((6-fluoroquinolin-3-yl)methyl)isonicotinamide

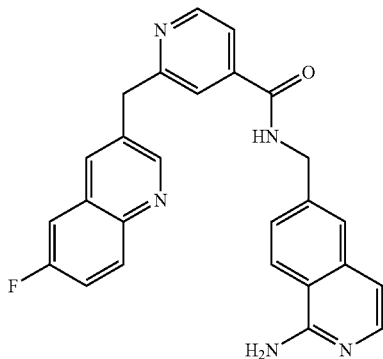

N-((1-aminoisoquinolin-6-yl)methyl)-2-((6-fluoroquinolin-3-yl)methyl)isonicotinamide (30 mg, 20% yields for 2 steps) was prepared as described for N-((1-aminoisoquinolin-6-yl)methyl)-2-((3-methylquinolin-6-yl)methyl)isonicotinamide (Example 142). LRMS (M+H$^+$) m/z calculated 438.2, found 438.2. $^1$H NMR (CD$_3$OD, 300 MHz) δ 8.81 (d, 1H), 8.66 (d, 1H), 8.20 (d, 1H), 8.08 (d, 1H), 8.05 (dd, 1H), 7.83 (s, 1H), 7.71 (d, 1H), 7.70 (d, 1H), 7.62 (s, 1H), 7.57-7.47 (m, 3H), 6.93 (d, 1H), 4.72 (s, 2H), 4.44 (s, 2H).

Example 119: Preparation of N-((6-amino-2,4-dimethylpyridin-3-yl)methyl)-2-((6-fluoroquinolin-3-yl)methyl)isonicotinamide

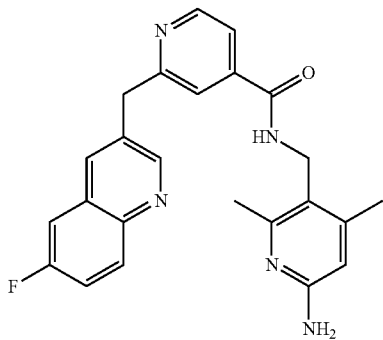 [SMILES: Cc1cc(N)nc(C)c1CNC(=O)c1ccnc(Cc2cnc3ccc(F)cc3c2)c1]

N-((6-amino-2,4-dimethylpyridin-3-yl)methyl)-2-((6-fluoroquinolin-3-yl)methyl)isonicotinamide (35 mg, 25% yield for 2 steps) was prepared as described in Example 15, Steps 6 and 7 as an off-white solid. LRMS (M+H$^+$) m/z calculated 416.1, found 416.1. $^1$H NMR (DMSO-d$_6$, 300 MHz) δ 8.87-8.86 (d, 1H), 8.66-8.58 (m, 2H), 8.18 (d, 1H), 8.06-8.02 (m, 1H), 7.78-7.72 (m, 2H), 7.64-7.58 (m, 2H), 6.11 (s, 2H), 5.68 (s, 2H), 4.36-4.33 (m, 4H), 2.30 (s, 3H), 2.16 (s, 3H).

Example 120: Preparation of N-((3-chloro-6-fluoro-1H-indol-5-yl)methyl)-2-((6-fluoroquinolin-3-yl)methyl)isonicotinamide

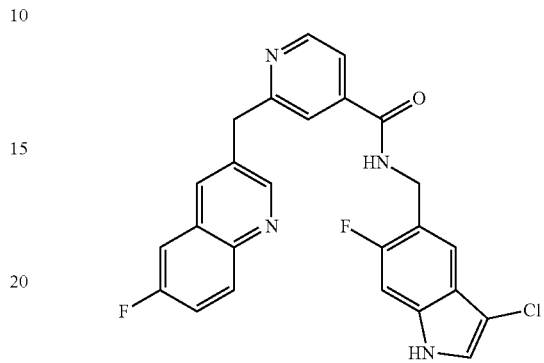

N-((3-chloro-6-fluoro-1H-indol-5-yl)methyl)-2-((6-fluoroquinolin-3-yl)methyl)isonicotinamide (42 mg, 26.8%) was prepared as described in Example 15, Steps 6 and 7. LRMS (M+H$^+$) m/z calculated 463.1, found 463.1. $^1$H NMR (DMSO-d$_6$, 300 MHz) δ 11.41 (s, 1H), 9.26 (t, 1H), 8.88 (d, 1H), 8.65 (d, 1H), 8.10 (s, 1H), 8.02-8.07 (m, 1H), 7.82 (s, 1H), 7.74 (dd, 1H), 7.61-7.67 (m, 2H), 7.51 (s, 1H), 7.45 (d, 1H), 7.22 (d, 1H), 4.59 (d, 2H), 4.39 (s, 2H).

Example 121: Preparation of N-((6-amino-2-methylpyridin-3-yl)methyl)-2-((6-fluoroquinolin-3-yl)methyl)isonicotinamide

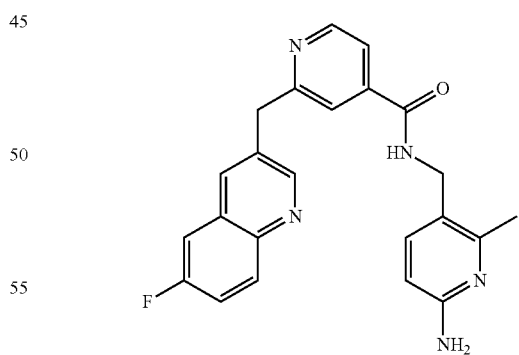

N-((6-amino-2-methylpyridin-3-yl)methyl)-2-((6-fluoroquinolin-3-yl)methyl)isonicotinamide (18 mg, 13.2%) was prepared as described in Example 15, Steps 6 and 7. LRMS (M+H$^+$) m/z calculated 401.9, found 401.9. $^1$H NMR (CD$_3$OD, 300 MHz) δ 8.80 (d, 1H), 8.63 (d, 1H), 8.20 (s, 1H), 8.01-8.04 (m, 1H), 7.78 (s, 1H), 7.63-7.64 (m, 1H), 7.52-7.58 (m, 3H), 7.40 (d, 1H), 4.43 (d, 4H), 2.38 (s, 3H).

Example 122: Preparation of N-((6-amino-2,4-dimethylpyridin-3-yl)methyl)-2-((7-fluoroquinolin-3-yl)methyl)isonicotinamide

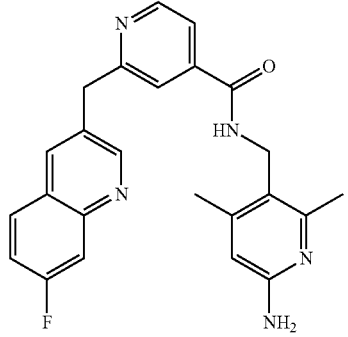 [SMILES: Cc1cc(N)nc(C)c1CNC(=O)c1ccnc(Cc2cnc3cc(F)ccc3c2)c1]

N-((6-amino-2,4-dimethylpyridin-3-yl)methyl)-2-((7-fluoroquinolin-3-yl)methyl)isonicotinamide (35 mg, 25%) was prepared as described in Example 15, Steps 6 and 7. LRMS (M+H⁺) m/z calculated 415.9, found 415.9. ¹H NMR (DMSO-d₆, 300 MHz) δ 8.92 (d, 1H), 8.65 (t, 1H), 8.60 (d, 1H), 8.26 (s, 1H), 8.04 (dd, 1H), 7.79 (s, 1H), 7.73 (dd, 1H), 7.61 (d, 1H), 7.51-7.55 (m, 1H), 6.13 (s, 1H), 5.68 (s, 2H), 4.35-4.37 (m, 4H), 2.31 (s, 3H), 2.17 (s, 3H).

Example 123: Preparation of N-((3-chloro-6-fluoro-1H-indol-5-yl)methyl)-2-((7-fluoroquinolin-3-yl)methyl)isonicotinamide

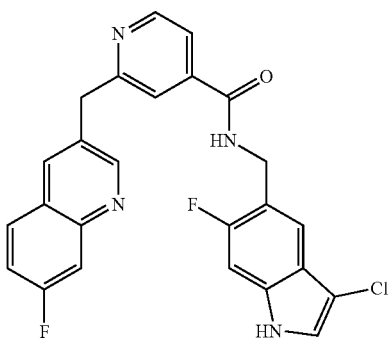 [SMILES: O=C(NCc1cc2c(Cl)c[nH]c2cc1F)c1ccnc(Cc2cnc3cc(F)ccc3c2)c1]

N-((3-chloro-6-fluoro-1H-indol-5-yl)methyl)-2-((7-fluoroquinolin-3-yl)methyl)isonicotinamide (45 mg, 28.7%) was prepared as described in Example 15, Steps 6 and 7. LRMS (M+H⁺) m/z calculated 462.8, found 462.8. ¹H NMR (DMSO-d₆, 300 MHz) δ 11.39-11.42 (m, 1H), 9.26 (t, 1H), 8.92 (s, 1H), 8.64 (d, 1H), 8.27 (s, 1H), 8.04 (dd, 1H), 7.82 (s, 1H), 7.65-7.74 (m, 2H), 7.43-7.55 (m, 3H), 7.22 (d, 1H), 4.59 (d, 2H), 4.38 (s, 2H).

Example 124: Preparation of N-((1-aminoisoquinolin-6-yl)methyl)-2-((7-fluoroquinolin-3-yl)methyl)isonicotinamide

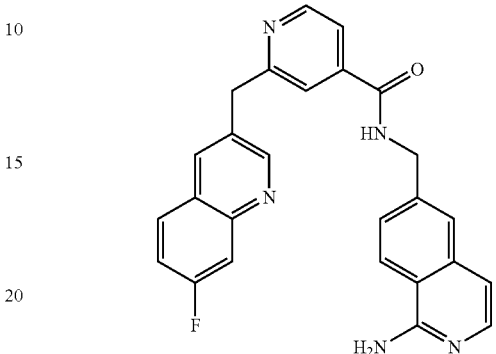

N-((1-aminoisoquinolin-6-yl)methyl)-2-((7-fluoroquinolin-3-yl)methyl)isonicotinamide (16 mg, 10.8%) was prepared as described for N-((1-aminoisoquinolin-6-yl)methyl)-2-((3-methylquinolin-6-yl)methyl)isonicotinamide (Example 142). LRMS (M+H⁺) m/z calculated 437.8, found 437.8. ¹H NMR (CD₃OD, 400 MHz) δ 8.72 (d, 1H), 8.52 (d, 1H), 8.09 (s, 1H), 7.93 (d, 1H), 7.77-7.80 (m, 1H), 7.70 (s, 1H), 7.56-7.58 (m, 2H), 7.47-7.50 (m, 2H), 7.35 (d, 2H), 7.26-7.31 (m, 1H), 6.78 (d, 1H), 4.58 (s, 2H), 4.29 (s, 2H).

Example 125: Preparation of N-((3-chloro-6-fluoro-1H-indol-5-yl)methyl)-2-(quinolin-3-ylmethyl)isonicotinamide

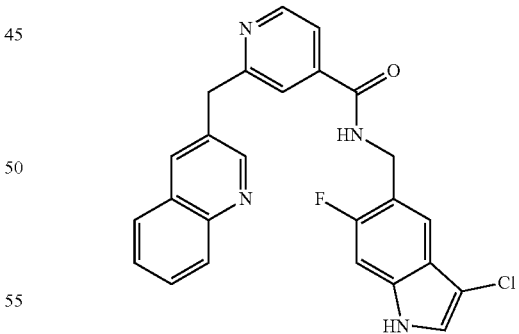

N-((3-chloro-6-fluoro-1H-indol-5-yl)methyl)-2-(quinolin-3-ylmethyl)isonicotinamide (24 mg, 17% yields for 2 steps) was prepared as described in Example 15, Steps 6 and 7 as a yellow solid. LRMS (M+H⁺) m/z calculated 445.1, found 445.1. ¹H NMR (DMSO-d₆, 400 MHz) δ 11.40 (s, 1H), 9.26 (t, 1H), 9.01 (s, 1H), 8.66-8.65 (d, 1H), 8.40 (s, 1H), 8.05-8.00 (t, 2H), 7.85 (s, 1H), 7.80 (t, 1H), 7.69-7.66 (m, 2H), 7.51-7.44 (m, 2H), 7.24-7.21 (d, 1H), 4.60-4.59 (d, 2H), 4.44 (s, 2H).

Example 126: Preparation of N-((3-chloro-6-fluoro-1H-indol-5-yl)methyl)-2-((6-chloroquinolin-3-yl)methyl)isonicotinamide

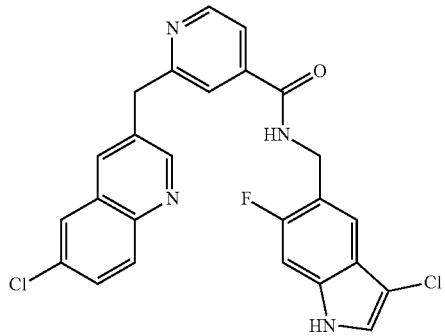 [SMILES: O=C(NCc1cc2c(Cl)c[nH]c2cc1F)c1ccnc(Cc2cnc3ccc(Cl)cc3c2)c1]

N-((3-chloro-6-fluoro-1H-indol-5-yl)methyl)-2-((6-chloro quinolin-3-yl)methyl) isonicotinamide (12 mg, 15%) was prepared as described in Example 15, Steps 6 and 7 as an off-white solid. LRMS (M+H$^+$) m/z calculated 479, found 479. $^1$H NMR (DMSO-d$_6$, 400 MHz) δ 11.39 (s, 1H), 9.25 (t, 1H), 8.92 (d, 1H), 8.64 (d, 1H), 8.20 (s, 1H), 8.08 (d, 1H), 8.00 (d, 1H), 7.82 (s, 1H), 7.71 (d, 1H), 7.66 (d, 2H), 7.50 (d, 2H), 7.45 (d, 1H), 7.22 (d, 1H), 4.59 (d, 2H), 4.40 (s, 2H).

Example 127: Preparation of N-((1-aminoisoquinolin-6-yl)methyl)-2-((2-methylquinolin-7-yl)methyl)isonicotinamide

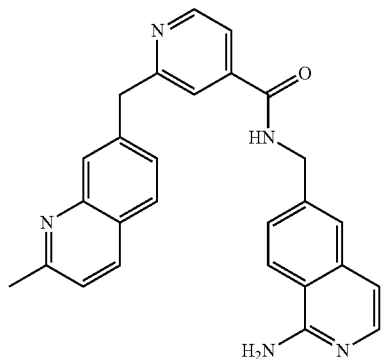

N-((1-aminoisoquinolin-6-yl)methyl)-2-((2-methylquinolin-7-yl)methyl)isonicotinamide (35 mg, 22%) was prepared as described for N-((1-aminoisoquinolin-6-yl)methyl)-2-((3-methylquinolin-6-yl)methyl)isonicotinamide (Example 142). LRMS (M+H$^+$) m/z calculated 434, found 434. $^1$H NMR (DMSO-d$_6$, 400 MHz) δ 9.39 (t, 1H), 8.67 (d, 1H), 8.18 (d, 1H), 8.13 (d, 1H), 7.80-7.85 (m, 3H), 7.75 (d, 1H), 7.68 (d, 1H), 7.54 (s, 1H), 7.47 (d, 1H), 7.35-7.40 (m, 2H), 6.84 (d, 1H), 6.72 (s, 2H), 4.60 (d, 2H), 4.37 (s, 2H), 2.62 (s, 3H).

Example 128: Preparation of N-((3-chloro-6-fluoro-1H-indol-5-yl)methyl)-2-((2-methylquinolin-7-yl)methyl)isonicotinamide

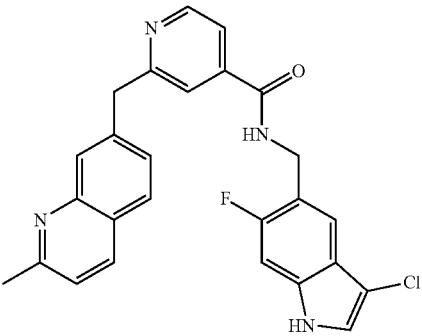 [SMILES: Cc1ccc2ccc(Cc3cc(C(=O)NCc4cc5c(Cl)c[nH]c5cc4F)ccn3)cc2n1]

N-((3-chloro-6-fluoro-1H-indol-5-yl)methyl)-2-((2-methylquinolin-7-yl)methyl)isonicotinamide (25 mg, 15%) was prepared as described in Example 15, Steps 6 and 7. LRMS (M+H+) m/z calculated 459, found 459. $^1$H NMR (DMSO-d$_6$, 300 MHz) δ 11.40 (br, 1H), 9.26 (t, 1H), 8.65 (d, 1H), 8.17 (d, 1H), 7.79-7.84 (m, 3H), 7.65 (d, 1H), 7.42-7.50 (m, 3H), 7.35 (d, 1H), 7.22 (d, 2H), 4.57 (d, 2H), 4.35 (s, 2H), 2.62 (s, 3H).

Example 129: Preparation of N-((6-amino-2,4-dimethylpyridin-3-yl)methyl)-2-((2-methylquinolin-7-yl)methyl)isonicotinamide

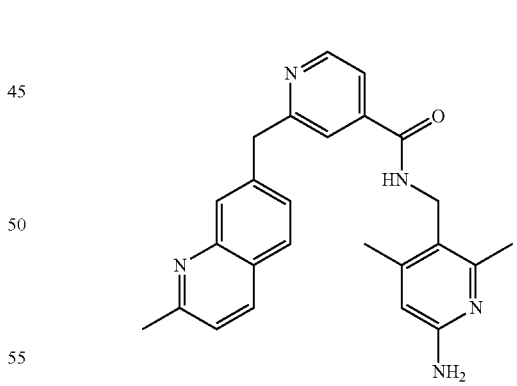

N-((6-amino-2,4-dimethylpyridin-3-yl)methyl)-2-((2-methylquinolin-7-yl)methyl)isonicotinamide (10 mg, 7%) was prepared as described in Example 15, Steps 6 and 7. LRMS (M+H$^+$) m/z calculated 412, found 412. $^1$H NMR (DMSO-d$_6$, 300 MHz) δ 8.59-8.64 (m, 2H), 8.17 (d, 1H), 7.82 (d, 1H), 7.76 (d, 2H), 7.60 (d, 1H), 7.45 (d, 1H), 7.35 (d, 1H), 6.10 (s, 1H), 5.67 (s, 2H), 4.33 (s, 4H), 2.62 (s, 3H), 2.29 (s, 3H), 2.15 (s, 3H).

Example 130: Preparation of N-(3-chloro-6-fluoro-1H-indol-5-ylmethyl)-2-(2-cyano-quinolin-6-ylmethyl)-isonicotinamide

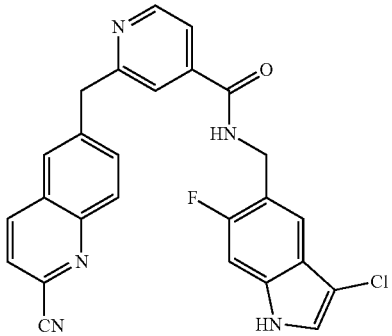 [SMILES: N#Cc1ccc2cc(Cc3cc(C(=O)NCc4cc5c(Cl)c[nH]c5cc4F)ccn3)ccc2n1]

N-(3-chloro-6-fluoro-1H-indol-5-ylmethyl)-2-(2-cyano-quinolin-6-ylmethyl)-isonicotinamide (90 mg, 22% yields for 2 steps) was prepared as described in Example 15, Steps 6 and 7. LRMS (M+H⁺) m/z calculated 570.1, found 570.1. ¹H NMR (DMSO-d₆, 400 MHz) δ 11.41 (s, 1H), 9.26 (t, 1H), 8.60-8.65 (m, 2H), 8.00-8.08 (m, 3H), 7.87-7.89 (dd, 1H), 7.81 (s, 1H), 7.66-7.67 (dd, 1H), 7.50-7.51 (d, 1H), 7.43-7.45 (d, 1H), 7.21-7.24 (d, 1H), 4.58-4.59 (d, 2H), 4.42 (s, 2H).

Example 131: Preparation of N-(6-amino-2,4-dimethyl-pyridin-3-ylmethyl)-2-(2-cyano-quinolin-6-ylmethyl)-isonicotinamide

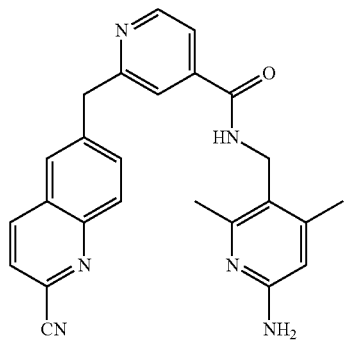 [SMILES: Cc1cc(N)nc(C)c1CNC(=O)c1ccnc(Cc2ccc3nc(C#N)ccc3c2)c1]

N-(6-amino-2,4-dimethyl-pyridin-3-ylmethyl)-2-(2-cyano-quinolin-6-ylmethyl)-isonicotinamide (90 mg, 26% yields for 2 steps) was prepared as described in Example 15, Steps 6 and 7. LRMS (M+H⁺) m/z calculated 423.1, found 423.1. ¹H NMR (DMSO-d₆, 400 MHz) δ 8.60-8.64 (m, 3H), 8.00-8.07 (m, 3H), 7.86-7.88 (m, 1H), 7.78 (s, 1H), 7.61-7.62 (d, 1H), 6.12 (s, 1H), 5.68 (s, 2H), 4.33-4.40 (m, 4H), 2.30 (s, 3H), 2.16 (s, 3H).

Example 132: Preparation of N-((1-aminoisoquinolin-6-yl)methyl)-2-((3-methylisoquinolin-6-yl)methyl)isonicotinamide

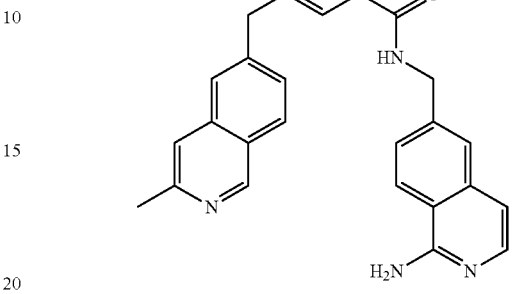

Step 1: Preparation of 6-bromo-3-methyl-isoquinoline

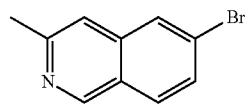

To a solution of 4-bromo-benzylamine (10.0 g, 54 mmol, 1.0 eq) in DCE (100 mL) was added 1,1-dimethoxy-propan-2-one (7.0 g, 59 mmol, 1.1 eq) and MgSO₄ (20 g). The mixture was stirred at 40° C. overnight. Then to the mixture was added NaBH₃CN (4.08 g, 64.8 mmol, 1.2 eq). After stirring at rt for 5 h the mixture was filtered. The filtrate was concentrated to give a yellow oil. Chlorosulfonic acid (30 mL) was cooled to −10° C. and the above crude product was added dropwise. The reaction mixture was heated to 100° C. for 10 min, then cooled and poured into ice. The mixture was neutralized with 2M NaOH and extracted with EA. The combined extracts were dried and concentrated. The residue was purified by silica gel chromatography (PE/EA=2/1, v/v) to afford 6-bromo-3-methyl-isoquinoline (4.0 g, 34% yield for 3 steps) as a yellow solid.

Step 2: Preparation of 3-methyl-isoquinoline-6-carboxylic Acid Methyl Ester

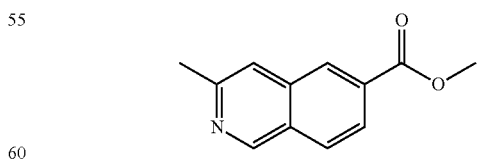

An autoclave vessel was charged with 6-bromo-3-methyl-isoquinoline (4.0 g, 18 mmol), Pd(dppf)Cl₂ (735 mg, 0.9 mmol, 0.05 eq) and triethylamine (5.0 mL, 36 mmol, 2 eq) in 40 mL of methanol. The vessel was purged with nitrogen three times and carbon monoxide three times. The vessel was pressurized to 3 MPa with carbon monoxide and heated to 100° C. The reaction was thus stirred overnight, then allowed to cool to room temperature. The resulting solution was concentrated and purified by flash chromatography on silica gel (PE/EA=1/1, v/v) to afford 3-methyl-isoquinoline-6-carboxylic acid methyl ester (3.4 g, 94%) as a white solid.

Step 3: Preparation of (3-methyl-isoquinolin-6-yl)-methanol

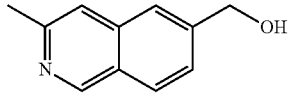

To a solution of 3-methyl-isoquinoline-6-carboxylic acid methyl ester (3.3 g, 16.42 mmol, 1 eq) in dry THF (100 mL) was added LiAlH(t-BuO)$_3$ (12.5 g, 45.25 mmol, 3 eq). The resulting mixture was stirred at 60° C. for 5 h and then quenched by the addition of water. The mixture was extracted with EA. The combined extracts were dried and concentrated. The residue was purified by silica gel chromatography (PE/EA=1/1, v/v) to afford (3-methyl-isoquinolin-6-yl)-methanol (2.5 g, 89%) as a white solid.

Step 4: Preparation of 6-chloromethyl-3-methyl-isoquinoline

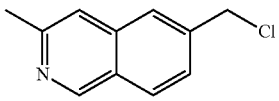

To (3-methyl-isoquinolin-6-yl)-methanol (1.5 g, 8.67 mmol, 1 eq) was added SOCl$_2$ (9 mL) and the mixture was stirred at rt for 3 h. The volatiles were then removed at 40° C. under vacuum and the residue was dissolved in DCM. The mixture was washed with saturated aq. NaHCO$_3$, dried and concentrated to give 6-chloromethyl-3-methyl-isoquinoline (1.4 g, 85%) as a white solid.

Step 5: Preparation of 2-(3-Methyl-isoquinolin-6-ylmethyl)-isonicotinic Acid Methyl Ester

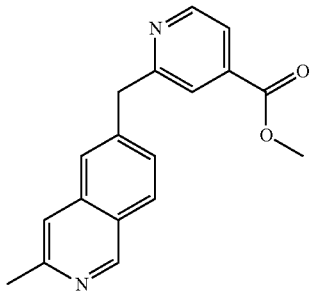

2-(3-Methyl-isoquinolin-6-ylmethyl)-isonicotinic acid methyl ester (1.0 g, 47%) was prepared as described for Example 24, Step 5.

Step 6: Preparation of N-((1-aminoisoquinolin-6-yl)methyl)-2-((3-methylisoquinolin-6-yl)methyl)isonicotinamide

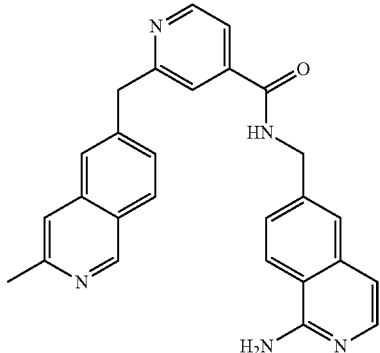

N-((1-aminoisoquinolin-6-yl)methyl)-2-((3-methylisoquinolin-6-yl)methyl)isonicotinamide (20 mg, 14% yields for 2 steps) was prepared as described for N-((1-aminoisoquinolin-6-yl)methyl)-2-((3-methylquinolin-6-yl)methyl)isonicotinamide (Example 142). LRMS (M+H$^+$) m/z calculated 434.2, found 434.2. $^1$H NMR (CD$_3$OD, 400 MHz) δ 9.06 (s, 1H), 8.66 (d, 1H), 8.08 (d, 1H), 7.97 (d, 1H), 7.80 (s, 1H), 7.71 (s, 2H), 7.70 (s, 1H), 7.62 (s, 1H), 7.56 (s, 1H), 7.50 (d, 1H), 7.47 (d, 1H), 6.92 (d, 1H), 4.71 (s, 2H), 4.11 (s, 2H), 2.64 (s, 3H).

Example 133: Preparation of N-((3-chloro-6-fluoro-1H-indol-5-yl)methyl)-2-((3-methylisoquinolin-6-yl)methyl)isonicotinamide

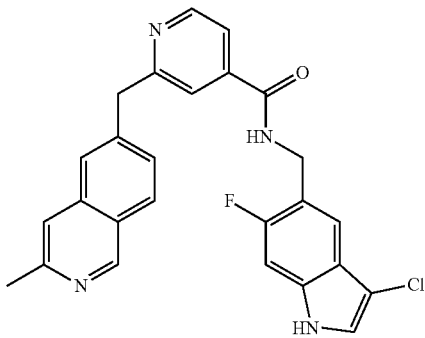 [SMILES: Cc1cc2cc(Cc3cc(C(=O)NCc4cc5c(Cl)c[nH]c5cc4F)ccn3)ccc2cn1]

N-((3-chloro-6-fluoro-1H-indol-5-yl)methyl)-2-((3-methylisoquinolin-6-yl)methyl)isonicotinamide (43 mg, 28% yields for 2 steps) was prepared as described for Example 132. LRMS (M+H+) m/z calculated 459.1, found 459.1. $^1$H NMR (DMSO-d$_6$, 400 MHz) δ 11.42 (s, 1H), 9.26 (t, 1H), 9.15 (s, 1H), 8.67 (d, 1H), 8.00 (dd, 1H), 7.79 (s, 1H), 7.72 (s, 1H), 7.67 (d, 1H), 7.58 (s, 1H), 7.53 (d, 1H), 7.52 (s, 1H), 7.46 (d, 1H), 7.24 (d, 1H), 4.60 (d, 2H), 4.36 (s, 2H), 2.59 (s, 3H).

Example 134: Preparation of N-((1-aminoisoquinolin-6-yl)methyl)-2-((2-(methylsulfonyl)quinolin-6-yl)methyl)isonicotinamide

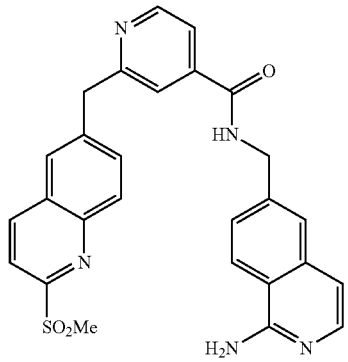 [SMILES: CS(=O)(=O)c1ccc2cc(Cc3cc(C(=O)NCc4ccc5c(N)nccc5c4)ccn3)ccc2n1]

N-((1-aminoisoquinolin-6-yl)methyl)-2-((2-(methylsulfonyl)quinolin-6-yl)methyl)isonicotinamide (34 mg, 34% yields for 2 steps) was prepared as described for N-((1-aminoisoquinolin-6-yl)methyl)-2-((3-methylquinolin-6-yl)methyl)isonicotinamide (Example 142). LRMS (M+H+) m/z calculated 498.2, found 498.2. $^1$H NMR (CD$_3$OD, 400 MHz) δ 8.66 (d, 1H), 8.49 (d, 1H), 8.06 (d, 1H), 8.03 (d, 1H), 8.02 (s, 1H), 7.88 (s, 1H), 7.81 (s, 1H), 7.78 (d, 1H), 7.69 (d, 1H), 7.67 (d, 1H), 7.59 (s, 1H), 7.46 (d, 1H), 6.88 (d, 1H), 4.69 (s, 2H), 4.43 (s, 2H), 3.37 (s, 3H).

Example 135: Preparation of N-((3-chloro-6-fluoro-1H-indol-5-yl)methyl)-2-((2-(methylsulfonyl)quinolin-6-yl)methyl)isonicotinamide

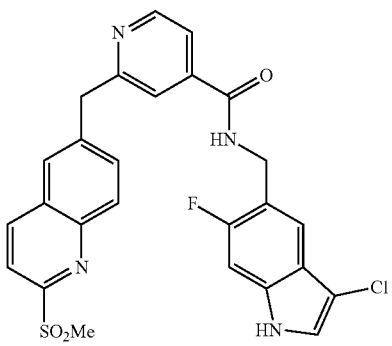 [SMILES: CS(=O)(=O)c1ccc2cc(Cc3cc(C(=O)NCc4cc5c(Cl)c[nH]c5cc4F)ccn3)ccc2n1]

N-((3-chloro-6-fluoro-1H-indol-5-yl)methyl)-2-((2-(methylsulfonyl)quinolin-6-yl)methyl)isonicotinamide (24 mg, 23% yields for 2 steps) was prepared as described in Example 15, Steps 6 and 7. LRMS (M+H+) m/z calculated 523.1, found 523.1. $^1$H NMR (CD$_3$OD, 400 MHz) δ 8.53 (d, 1H), 8.47 (d, 1H), 8.02 (d, 1H), 7.99 (d, 1H), 7.84 (s, 1H), 7.75 (d, 1H), 7.68 (s, 1H), 7.56 (d, 1H), 7.40 (d, 1H), 7.13 (s, 1H), 7.02 (s, 1H), 4.58 (s, 2H), 4.36 (s, 2H), 3.25 (s, 3H).

Example 136: Preparation of N-((1-aminoisoquinolin-6-yl)methyl)-2-((4-cyanoquinolin-6-yl)methyl)isonicotinamide

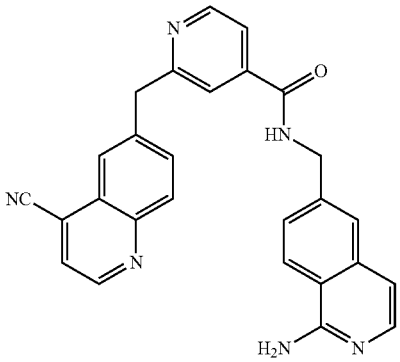 [SMILES: N#Cc1ccnc2ccc(Cc3cc(C(=O)NCc4ccc5c(N)nccc5c4)ccn3)cc12]

N-((1-aminoisoquinolin-6-yl)methyl)-2-((4-cyanoquinolin-6-yl)methyl)isonicotinamide (43 mg, 29% yields for 2 steps) was prepared as described for N-((1-aminoisoquinolin-6-yl)methyl)-2-((3-methylquinolin-6-yl)methyl)isonicotinamide (Example 142). LRMS (M+H+) m/z calculated 445.2, found 445.2. $^1$H NMR (CD$_3$OD, 300 MHz) δ 9.40 (t, 1H), 9.06 (d, 1H), 8.69 (d, 1H), 8.15-8.11 (m, 3H), 8.06 (s, 1H), 7.92 (d, 1H), 7.87 (s, 1H), 7.77 (d, 1H), 7.71 (d, 1H), 7.56 (s, 1H), 7.41 (d, 1H), 6.85 (d, 1H), 6.73 (s, 2H), 4.62 (d, 2H), 4.50 (s, 2H).

Example 137: Preparation of N-((3-chloro-6-fluoro-1H-indol-5-yl)methyl)-2-((4-cyanoquinolin-6-yl)methyl)isonicotinamide

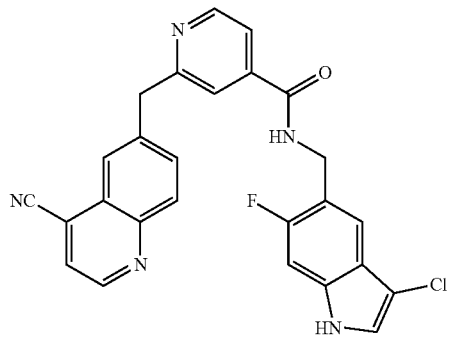 [SMILES: N#Cc1ccnc2ccc(Cc3cc(C(=O)NCc4cc5c(Cl)c[nH]c5cc4F)ccn3)cc12]

N-((3-chloro-6-fluoro-1H-indol-5-yl)methyl)-2-((4-cyanoquinolin-6-yl)methyl)isonicotinamide (45 mg, 29% yields for 2 steps) was prepared as described in Example 15, Steps 6 and 7 as a yellow solid. LRMS (M+H+) m/z calculated 470.1, found 470.1. $^1$H NMR (DMSO, 400 MHz) δ 11.42 (s, 1H), 9.28 (t, 1H), 9.07 (d, 1H), 8.68 (d, 1H), 8.14 (d, 1H), 8.12 (s, 1H), 8.06 (s, 1H), 7.91 (d, 1H), 7.86 (s, 1H), 7.68 (d, 1H), 7.51 (d, 1H), 7.46 (d, 1H), 7.24 (d, 1H), 4.60 (d, 1H), 4.49 (s, 2H).

Example 138: Preparation of N-((6-amino-2,4-dimethylpyridin-3-yl)methyl)-2-((4-cyanoquinolin-6-yl)methyl)isonicotinamide

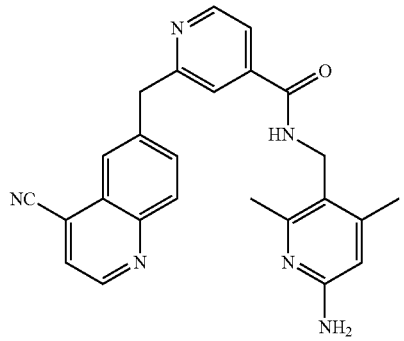 [SMILES: Cc1cc(N)nc(C)c1CNC(=O)c1ccnc(Cc2ccc3nccc(C#N)c3c2)c1]

N-((6-amino-2,4-dimethylpyridin-3-yl)methyl)-2-((4-cyanoquinolin-6-yl)methyl)isonicotinamide (23 mg, 17% yields for 2 steps) was prepared as described in Example 15, Steps 6 and 7 as a yellow solid. LRMS (M+H$^+$) m/z calculated 423.2, found 423.2. $^1$H NMR (CD$_3$OD, 300 MHz) δ 8.98 (d, 1H), 8.63 (d, 1H), 8.10 (d, 1H), 8.07 (s, 1H), 7.93 (d, 1H), 7.86 (dd, 1H), 7.77 (s, 1H), 7.63 (dd, 1H), 6.29 (s, 1H), 4.50 (s, 2H), 4.49 (s, 2H), 2.38 (s, 3H), 2.26 (s, 3H).

Example 139: Preparation of N-((1-aminoisoquinolin-6-yl)methyl)-2-((7-chloroquinolin-3-yl)methyl)isonicotinamide

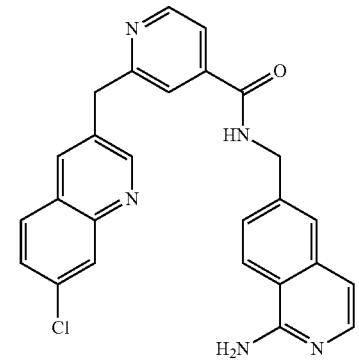

N-((1-aminoisoquinolin-6-yl)methyl)-2-((7-chloroquinolin-3-yl)methyl)isonicotinamide (34 mg, 23% yields for 2 steps) was prepared as described for N-((1-aminoisoquinolin-6-yl)methyl)-2-((3-methylquinolin-6-yl)methyl) isonicotinamide (Example 142). LRMS (M+H$^+$) m/z calculated 454.1, found 454.1. $^1$H NMR (DMSO-d$_6$, 400 MHz) δ 9.42 (d, 1H), 8.96 (s, 1H), 8.68 (d, 1H), 8.20 (s, 1H), 8.15 (d, 1H), 8.05 (s, 1H), 8.02 (d, 1H), 7.86 (s, 1H), 7.78 (d, 1H), 7.70 (d, 1H), 7.63 (dd, 1H), 7.56 (s, 1H), 7.42 (d, 1H), 6.86 (d, 1H), 4.63 (d, 2H), 4.42 (s, 2H).

Example 140: Preparation of N-((3-chloro-6-fluoro-1H-indol-5-yl)methyl)-2-((7-chloroquinolin-3-yl)methyl)isonicotinamide

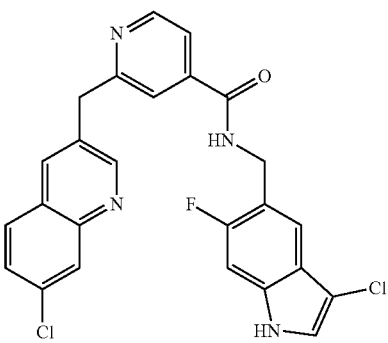 [SMILES: O=C(NCc1cc2c(Cl)c[nH]c2cc1F)c1ccnc(Cc2cnc3cc(Cl)ccc3c2)c1]

N-((3-chloro-6-fluoro-1H-indol-5-yl)methyl)-2-((7-chloroquinolin-3-yl)methyl)isonicotinamide (35 mg, 23% yields for 2 steps) was prepared as described in Example 15, Steps 6 and 7 as a white solid. LRMS (M+H$^+$) m/z calculated 479.1, found 479.1. $^1$H NMR (DMSO-d$_6$, 400 MHz) δ 11.42 (s, 1H), 9.27 (t, 1H), 8.95 (d, 1H), 8.66 (d, 1H), 8.27 (s, 1H), 8.04 (d, 1H), 8.01 (d, 1H), 7.83 (s, 1H), 7.67 (d, 1H), 7.62 (dd, 1H), 7.52 (d, 1H), 7.46 (d, 1H), 7.25 (d, 1H), 4.60 (d, 2H), 4.40 (s, 2H).

Example 141: Preparation of N-((6-amino-2,4-dimethylpyridin-3-yl)methyl)-2-((7-chloroquinolin-3-yl)methyl)isonicotinamide

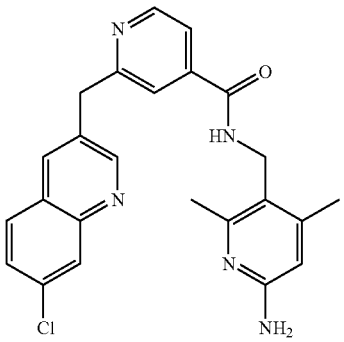

N-((6-amino-2,4-dimethylpyridin-3-yl)methyl)-2-((7-chloroquinolin-3-yl)methyl)isonicotinamide (10 mg, 7% yields for 2 steps) was prepared as described in Example 15, Steps 6 and 7 as a white solid. LRMS (M+H$^+$) m/z calculated 432.2, found 432.2. $^1$H NMR (CD$_3$OD, 400 MHz) δ 8.87 (d, 1H), 8.63 (d, 1H), 8.25 (s, 1H), 8.00 (s, 1H), 7.91 (d, 1H), 7.78 (s, 1H), 7.63 (d, 1H), 7.60 (dd, 1H), 6.32 (s, 1H), 4.53 (d, 2H), 4.44 (s, 2H), 2.41 (s, 3H), 2.29 (s, 3H).

Example 142: Preparation of N-((1-aminoisoquinolin-6-yl)methyl)-2-((3-methylquinolin-6-yl)methyl)isonicotinamide

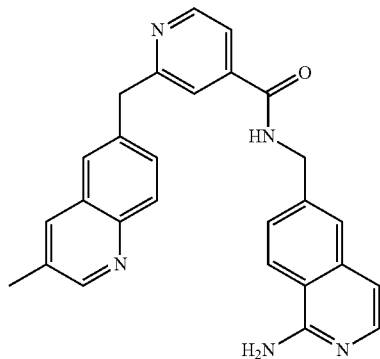

To a solution of 2-(3-methyl-quinolin-6-ylmethyl)-isonicotinic acid (150 mg, crude) in DMF (15 mL) was added 6-aminomethyl-isoquinolin-1-ylamine (62 mg, 0.36 mmol, 1.0 eq) followed by EDCI (104 mg, 0.54 mmol, 1.5 eq), HOBT (73 mg, 0.54 mmol, 1.5 eq) and TEA (109 mg, 1.08 mmol, 3.0 eq). The reaction mixture was heated to 40° C. kept stirring for overnight. Water was added, and the mixture was extracted with DCM. The organic layer was washed with water, dried over $Na_2SO_4$, filtered, and concentrated. The residue was purified by prep-HPLC to give N-((1-aminoisoquinolin-6-yl)methyl)-2-((3-methylquinolin-6-yl)methyl) isonicotinamide (30 mg, 19%) as a white solid. LRMS (M+H$^+$) m/z calculated 434, found 434.

$^1$H NMR (DMSO-$d_6$, 400 MHz) δ 9.40 (t, 1H), 8.71 (s, 1H), 8.67 (d, 1H), 8.13 (d, 1H), 8.07 (s, 1H), 7.90 (d, 1H), 7.75-7.80 (m, 3H), 7.68 (d, 1H), 7.62 (d, 1H), 7.54 (s, 1H), 7.49 (d, 1H), 6.84 (d, 1H), 6.77 (s, 2H), 4.60 (d, 2H), 4.35 (s, 2H), 2.46 (s, 3H).

Example 143: Preparation of N-((3-chloro-6-fluoro-1H-indol-5-yl)methyl)-2-((3-methylquinolin-6-yl)methyl)isonicotinamide

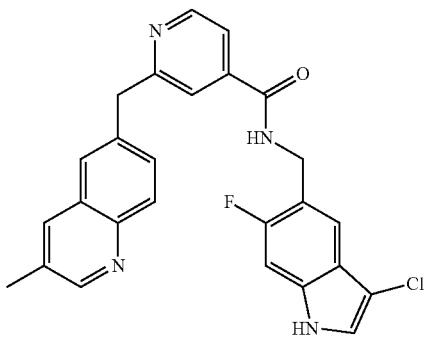 [SMILES: Cc1cnc2ccc(Cc3cc(C(=O)NCc4cc5c(Cl)c[nH]c5cc4F)ccn3)cc2c1]

N-((3-chloro-6-fluoro-1H-indol-5-yl)methyl)-2-((3-methylquinolin-6-yl)methyl)isonicotinamide (30 mg, 18%) was prepared as described for Example 15, Steps 6 and 7 as a yellow solid. LRMS (M+H+) m/z calculated 459, found 459. 1H NMR (DMSO-$d_6$, 300 MHz) δ 11.42 (br, 1H), 9.25 (t, 1H), 8.71 (s, 1H), 8.65 (d, 1H), 8.05 (s, 1H), 7.89 (d, 1H), 7.76 (d, 2H), 7.60-7.66 (m, 2H), 7.51 (d, 1H), 7.43 (d, 1H), 7.22 (d, 2H), 4.58 (d, 2H), 4.34 (s, 2H), 2.46 (s, 3H).

Example 144: Preparation of N-((6-amino-2,4-dimethylpyridin-3-yl)methyl)-2-((3-methylquinolin-6-yl)methyl)isonicotinamide

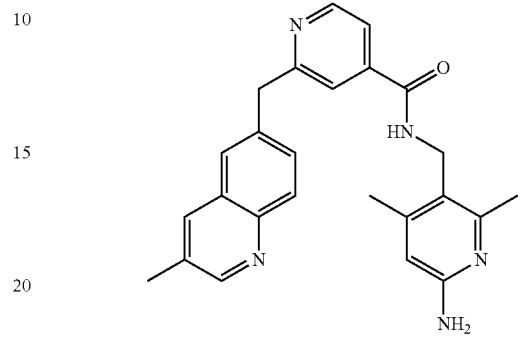

To a solution of 2-(3-methyl-quinolin-6-ylmethyl)-isonicotinic acid (150 mg, crude) in DMF (15 mL) was added 5-aminomethyl-4,6-dimethyl-pyridin-2-ylamine dihydrochloride (400 mg, crude) followed by EDCI (104 mg, 0.54 mmol, 1.5 eq), HOBT (73 mg, 0.54 mmol, 1.5 eq) and TEA (109 mg, 1.08 mmol, 3.0 eq). The reaction mixture was heated to 40° C. kept stirring for overnight. Water was added, and the mixture was extracted with DCM. The organic layer was washed with water, dried over $Na_2SO_4$, filtered, and concentrated. The residue was purified by prep-HPLC to give N-((6-amino-2,4-dimethylpyridin-3-yl)methyl)-2-((3-methylquinolin-6-yl)methyl)isonicotinamide (25 mg, 17%) as a yellow solid. LRMS (M+H$^+$)m/z calculated 412, found 412. $^1$H NMR (DMSO-$d_6$, 300 MHz) δ 8.71 (s, 1H), 8.65 (t, 1H), 8.60 (d, 1H), 8.06 (s, 1H), 7.89 (d, 1H), 7.74 (d, 2H), 7.60 (d, 2H), 6.10 (s, 1H), 5.70 (s, 2H), 4.32 (s, 4H), 2.46 (s, 3H), 2.29 (s, 3H), 2.15 (s, 3H).

Example 145: Preparation of N-((6-amino-2,4-dimethylpyridin-3-yl)methyl)-2-((3-methylisoquinolin-6-yl)methyl)isonicotinamide

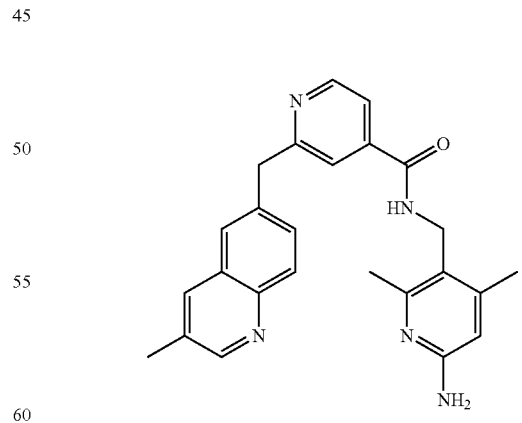

N-((6-amino-2,4-dimethylpyridin-3-yl)methyl)-2-((3-methylisoquinolin-6-yl)methyl)isonicotinamide (29 mg, 21% yields for 2 steps) was prepared as described for Example 15, Steps 6 and 7. LRMS (M+H$^+$) m/z calculated 412.2, found 412.2. $^1$H NMR (CD$_3$OD, 400 MHz) δ 9.05 (s, 1H), 8.61 (d, 1H), 7.96 (s, 1H), 7.73 (s, 1H), 7.69 (s, 1H), 7.62 (dd, 1H), 7.55 (s, 1H), 7.52 (d, 1H), 6.30 (s, 1H), 4.49 (s, 2H), 4.38 (s, 2H), 2.64 (s, 3H), 2.39 (s, 3H), 2.26 (s, 3H).

Example 146: Preparation of N-((1-aminoisoquinolin-6-yl)methyl)-2-((2-(aminomethyl)quinolin-6-yl)methyl)isonicotinamide

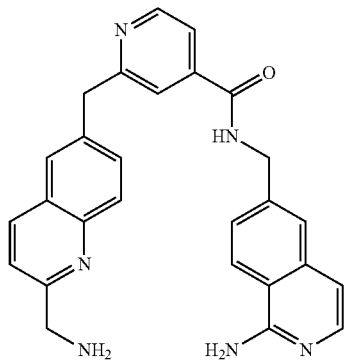 [SMILES: NCc1ccc2cc(Cc3cc(C(=O)NCc4ccc5c(N)nccc5c4)ccn3)ccc2n1]

Step 1: Preparation of (6-{4-[(1-Amino-isoquinolin-6-ylmethyl)-carbamoyl]-pyridin-2-ylmethyl}-quinolin-2-ylmethyl)-carbamic Acid tert-butyl Ester

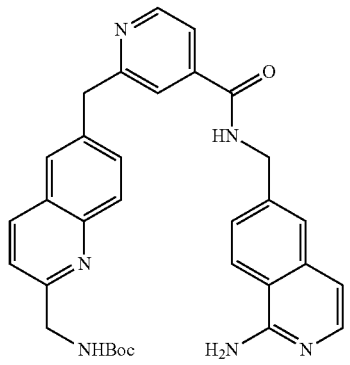 [SMILES: CC(C)(C)OC(=O)NCc1ccc2cc(Cc3cc(C(=O)NCc4ccc5c(N)nccc5c4)ccn3)ccc2n1]

(6-{4-[(1-Amino-isoquinolin-6-ylmethyl)-carbamoyl]-pyridin-2-ylmethyl}-quinolin-2-ylmethyl)-carbamic acid tert-butyl ester (70 mg, 35%) was prepared as described for Example 15, Steps 6 and 7.

Step 2: Preparation of N-((1-aminoisoquinolin-6-yl)methyl)-2-((2-(aminomethyl)quinolin-6-yl)methyl)isonicotinamide

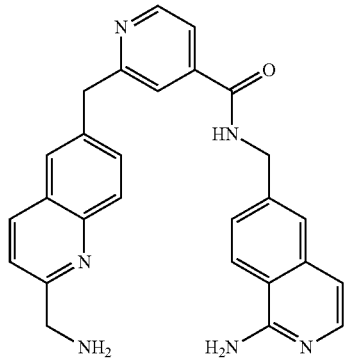 [SMILES: NCc1ccc2cc(Cc3cc(C(=O)NCc4ccc5c(N)nccc5c4)ccn3)ccc2n1]

To a solution of (6-{4-[(1-amino-isoquinolin-6-ylmethyl)-carbamoyl]-pyridin-2-ylmethyl}-quinolin-2-ylmethyl)-carbamic acid tert-butyl ester (80 mg, 0.13 mmol) in EA (1 mL) was added HCl/EA solution. The mixture was stirred at rt for 1 h. The precipitate was collected by filtration to give N-((1-aminoisoquinolin-6-yl)methyl)-2-((2-(aminomethyl)quinolin-6-yl)methyl) isonicotinamide (50 mg, 66%) as an off-white solid. LRMS (M+H$^+$) m/z calculated 449.2, found 449.2. $^1$H NMR (DMSO-d$_6$, 400 MHz) δ 13.51 (s, 1H), 10.05 (s, 1H), 9.25 (br, 1H), 8.88 (d, 1H), 8.63-8.62 (m, 4H), 8.45 (d, 1H), 8.19 (s, 1H), 8.09-8.01 (m, 3H), 7.89 (d, 1H), 7.85 (s, 1H), 7.73-7.64 (m, 4H), 7.20 (d, 1H), 4.69 (d, 2H), 4.59 (s, 2H), 4.39 (t, 2H).

Example 147: Preparation of N-((6-amino-2,4-dimethylpyridin-3-yl)methyl)-2-((5-chloro-1H-indol-2-yl)methyl)isonicotinamide

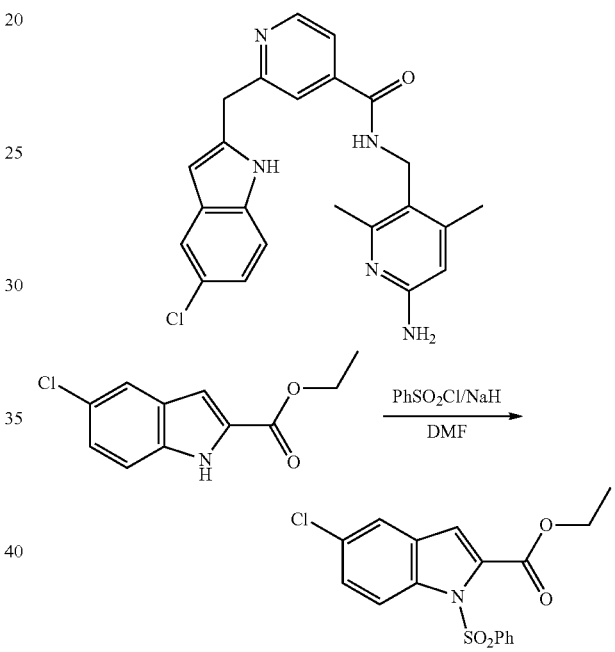

To a solution of ethyl 5-chloro-1H-indole-2-carboxylate (300.0 mg, 1.3 mmol, 1.0 eq) in DMF (2.0 mL) was added NaH (80.0 mg, 2.0 mol, 60% in mineral oil, 1.5 eq) and the reaction mixture was stirred at 0° C. for 30 min, then was added PhSO$_2$Cl (473 mg, 2.68 mmol, 2.0 eq) drop-wise. The mixture was stirred at rt for 2 h, then diluted with brine and extracted with EtOA (2.0 mL×3). The combined organic layers were dried over Na$_2$SO$_4$, filtered and concentrated. The resulting residue was purified by chromatography on silica gel (EA/PE=1/20, v/v) to afford ethyl 5-chloro-1-(phenylsulfonyl)-1H-indole-2-carboxylate (400.0 mg, 80%) as a yellow solid.

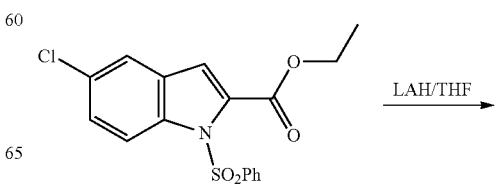

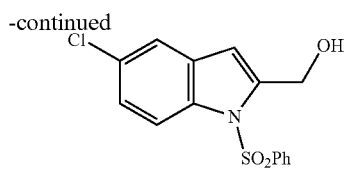

To a suspension of LAH (62.0 mg, 1.7 mmol, 2.0 eq) in THF (20.0 mL) was added ethyl 5-chloro-1-(phenylsulfonyl)-1H-indole-2-carboxylate (300.0 mg, 0.8 mmol, 1.0 eq) at 0° C. under $N_2$. The resulting mixture was stirred at 0° C. for 30 min, then quenched by the addition of EA (20.0 mL), then water (20.0 mL). The mixture was extracted with EA (20 mL×3). The combined organic layers were dried over anhydrous $Na_2SO_4$ and concentrated to afford (5-chloro-1-(phenylsulfonyl)-1H-indol-2-yl)methanol (250.0 mg, 95%).

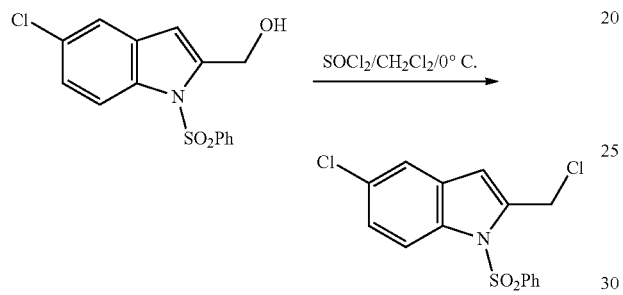

To a solution of (5-chloro-1-(phenylsulfonyl)-1H-indol-2-yl)methanol (500.0 mg, 1.6 mmol, 1.0 eq) in $CH_2Cl_2$ (10.0 mL) was added $SOCl_2$ (1.2 mL, 15.5 mmol, 10.0 e.q) at 0° C. and the mixture was stirred 0° C. for 2 h. The mixture was quenched by addition of ice-water (20 mL) and extracted with $CH_2Cl_2$ (20 mL×3). The combined organic layers were dried, concentrated. The resulting residue was purified by chromatography on silica gel (EA/PE=1/30, v/v) to provide 5-chloro-2-(chloromethyl)-1-(phenylsulfonyl)-1H-indole (300.0 mg, 56%).

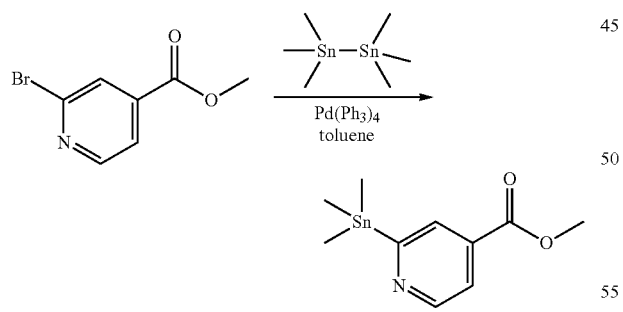

To a solution of methyl 2-bromoisonicotinate (0.864 g, 4.0 mmol, 1.0 eq) in toluene (40.0 mL) were added 1,1,1,2,2,2-hexamethyldistannane (1.96 g, 6.0 mmol, 1.5 eq) and $Pd(PPh_3)_4$ (0.262 g, 0.2 mmol, 0.05 eq). The mixture was stirred at 80° C. for 16 h under $N_2$, then cooled and filtered. The filtrate was concentrated. Toluene (20 mL) was added to the residue and the mixture was concentrated to give methyl 2-(trimethylstannyl)isonicotinate (2.0 g, ca. 100%) as a yellow oil, which was used in the next step without further purification.

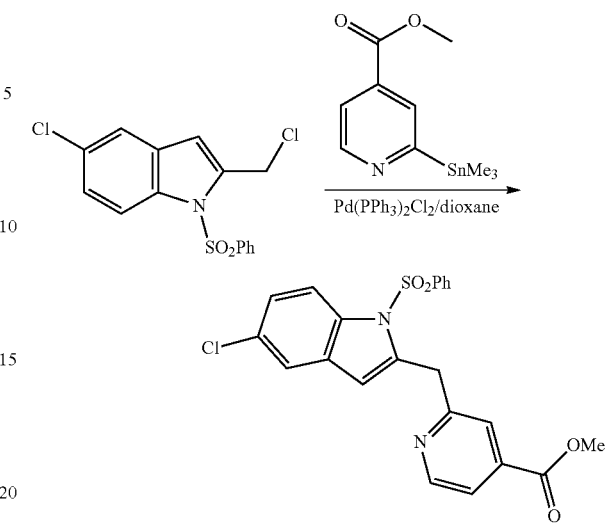

To a solution of 5-chloro-2-(chloromethyl)-1-(phenylsulfonyl)-1H-indole (300.0 mg, 0.9 mmol, 1.0 eq) in dioxane (2.00 mL) was added 2-trimethylstannanyl-isonicotinic acid methyl ester (292.0 mg, 0.97 mmol, 1.1 eq) and $Pd(PPh_3)_2Cl_2$ (31 mg, 0.05 mmol, 0.05 eq). The mixture was stirred at 120° C. for 18 h under nitrogen atmosphere, cooled and concentrated. The resulting residue was purified by chromatography on silica gel (DCM/MeOH=10/1, v/v) to afford methyl 2-((5-chloro-1-(phenylsulfonyl)-1H-indol-2-yl)methyl)isonicotinate (200 mg, 50%).

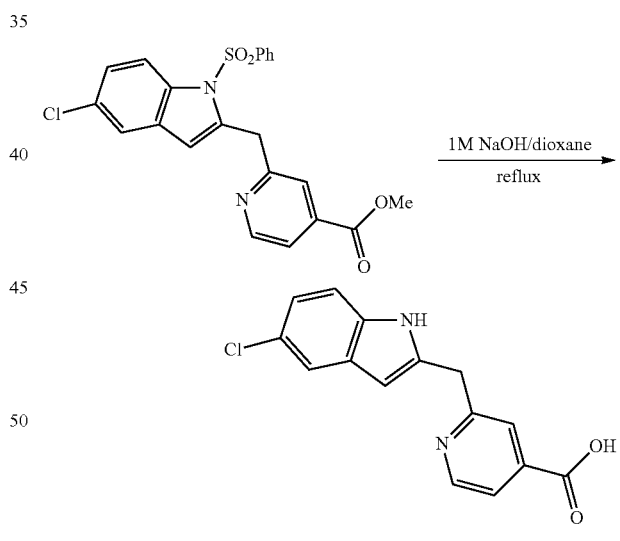

To a mixture of methyl 2-((5-chloro-1-(phenylsulfonyl)-1H-indol-2-yl) methyl)isonicotinate (200 mg, crude) in dioxane (6.0 mL) was added 1 N NaOH aqueous solution (3 mL). The reaction mixture was stirred at 100° C. for 20 hrs, then cooled and concentrated. The residue was diluted with EtOAc (10 mL) and Water (10 mL), then neutralized with 1 M HCl to pH 2 and extracted with EtOAc (10 mL×3). The combined organic layers were dried over $Na_2SO_4$, filtered and concentrated. The resulting residue was purified on Prep-TLC to provide 2-((5-chloro-1H-indol-2-yl)methyl) isonicotinic acid (36.0 mg, 30%).

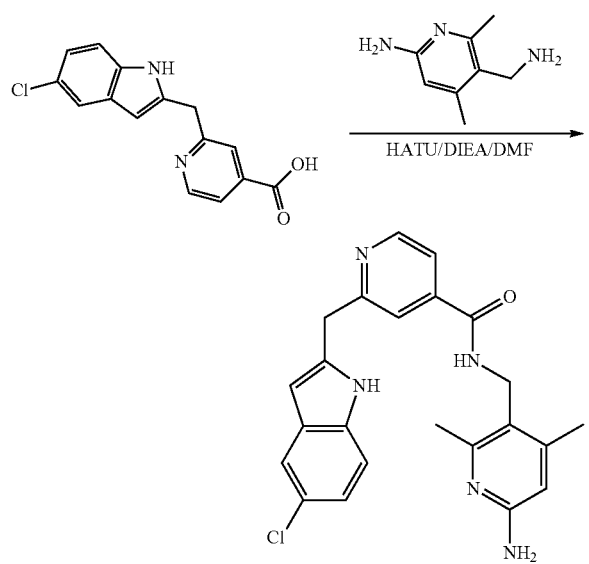

To a mixture of 2-((5-chloro-1H-indol-2-yl)methyl)isonicotinic acid (36.0 mg, crude, 0.13 mmol, 1.0 eq), 5-(aminomethyl)-4,6-dimethylpyridin-2-amine (23.0 mg, 0.15 mmol, 1.2 eq) and HATU (76 mg, 0.2 mmol, 1.5 eq) in DMF (1.0 mL) was added DIEA (34.0 mg, 0.3 mmol, 2.0 eq). The mixture was stirred at rt for 2 h under N$_2$, then water (10.0 mL) was added, and extracted with EtOAc (10.0 mL×3). The combined organic layers were washed with water 5 times, dried over Na$_2$SO$_4$, filtered and concentrated. The resulting residue was purified on Prep-TLC to give N-((6-amino-2,4-dimethylpyridin-3-yl)methyl)-2-((5-chloro-1H-indol-2-yl)methyl)isonicotinamide (14.0 mg, 30%) as a yellow solid. $^1$H NMR (CD$_3$OD, 400 MHz): δ 8.60 (d, 1H), 7.65 (s, 1H), 7.59 (t, 1H), 7.39 (d, 1H), 7.23 (s, 1H), 7.00 (d, 1H), 6.43 (s, 1H), 6.17 (s, 1H), 4.48 (s, 2H), 4.31 (s, 2H), 2.44 (s, 2H), 2.31 (s, 2H). LRMS (M+H$^+$) m/z calculated 420.2 found 420.4.

Example 148: Preparation of N-((6-amino-2,4-dimethylpyridin-3-yl)methyl)-2-((3-chloro-1,7-naphthyridin-6-yl)methyl)isonicotinamide

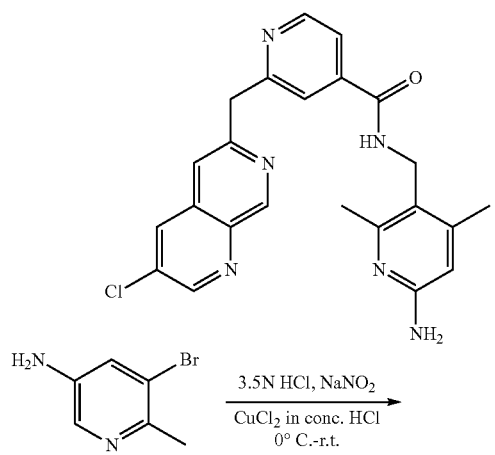

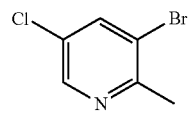

To a solution of 5-bromo-6-methylpyridin-3-amine (7.0 g, 37.5 mmol, 1.0 eq) in 3.5 N HCl (42.0 mL) cooled to −10° C. was added a solution of NaNO$_2$ (2.6 g, 37.5 mmol, 1.0 eq) in H$_2$O (14.0 mL) dropwise. When the addition was completed, the reaction mixture was stirred at 0-5° C. for 2 h, then was added to a solution of CuCl$_2$·2H$_2$O (19.2 g, 112.4 mmol, 3.0 eq) in conc. HCl (42.0 mL). The reaction mixture was stirred at rt for 2 h and extracted with CH$_2$Cl$_2$ (50 mL×2). The combined organic layers were dried over Na$_2$SO$_4$, filtered and concentrated under vacuum to afford 3-bromo-5-chloro-2-methylpyridine (5.8 g, 75%).

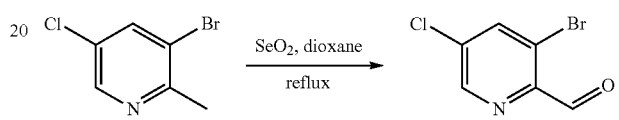

A mixture of 3-bromo-5-chloro-2-methylpyridine (5.8 g, 28.1 mmol, 1.0 eq) and selenium dioxide (7.5 g, 67.5 mmol, 2.4 eq) in 1,4-dioxane (100.0 mL) was stirred under reflux for 48 h, then concentrated in vacuum. The resulting residue was purified by chromatography on silica gel (PE/EA=40/1-20/1, v/v) to afford 3-bromo-5-chloropicolinaldehyde (611.0 mg, 10%) as a white solid.

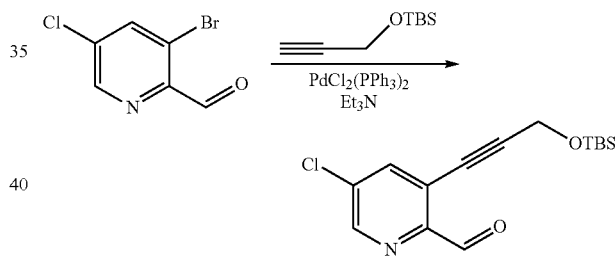

A mixture of 3-bromo-5-chloropicolinaldehyde (492.0 mg, 2.2 mmol, 1.0 eq), tert-butyldimethyl(prop-2-yn-1-yloxy)silane (766.0 mg, 4.5 mmol, 2.0 eq), PdCl$_2$(PPh$_3$)$_2$ (67.0 mg, 0.1 mmol, 0.04 eq), CuI (34.0 mg, 0.18 mmol, 0.08 eq), and Et$_3$N (336.0 mg, 3.3 mmol, 1.5 eq) in DMF (12 ml) was stirred at rt for 16 h, then concentrated under vacuum. The resulting residue was purified by chromatography on silica gel (PE/EA=50/1-20/1, v/v) to afford 3-(3-((tert-butyldimethylsilyl)oxy)prop-1-yn-1-yl)-5-chloropicolinaldehyde (500.0 mg, 72%).

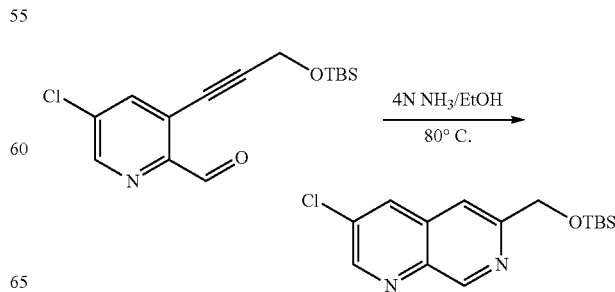

A solution of 3-(3-((tert-butyldimethylsilyl)oxy)prop-1-yn-1-yl)-5-chloropicolinaldehyde (672.0 mg, 2.2 mmol, 1.0 eq) in 4N NH₃ ethanol solution (8.0 mL) was stirred at 80° C. for 2 h, then concentrated. The resulting residue was purified by chromatography on silica gel (PE/EA=50/1-20/1, v/v) to afford 6-(((tert-butyldimethylsilyl)oxy)methyl)-3-chloro-1,7-naphthyridine (410.0 mg, 61%) as a yellow liquid.

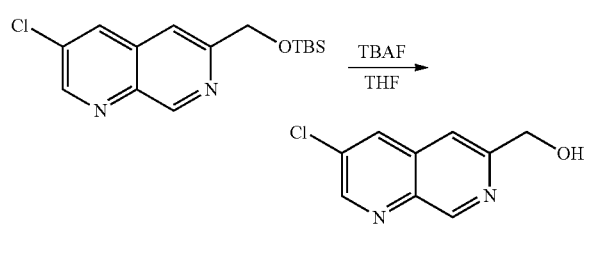

To a mixture of 6-(((tert-butyldimethylsilyl)oxy)methyl)-3-chloro-1,7-naphthyridine (300.0 mg, 0.97 mmol, 1.0 eq) in THF (10.0 mL) was added TBAF solution (1N in THF) (1.6 mL, 1.6 mmol, 1.6 eq). The mixture was stirred at rt for 2 h, then concentrated. The resulting residue was purified by chromatography on silica gel (PE/EA=3/1-1/1, v/v) to afford (3-chloro-1,7-naphthyridin-6-yl)methanol (130.0 mg, 69%) as a white solid.

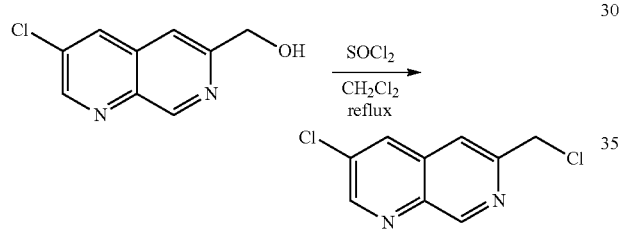

To a solution of (3-chloro-1,7-naphthyridin-6-yl)methanol (130.0 mg, 0.7 mmol, 1.0 eq) in CH₂Cl₂ (4.0 mL) was added SOCl₂ (2.0 mL). The mixture was stirred at rt for 1 h, then concentrated. The residue was dissolved in DCM (10.0 mL), washed with saturated aq. NaHCO₃, dried and concentrated to give 3-chloro-6-(chloromethyl)-1,7-naphthyridine (140.0 mg, 99%).

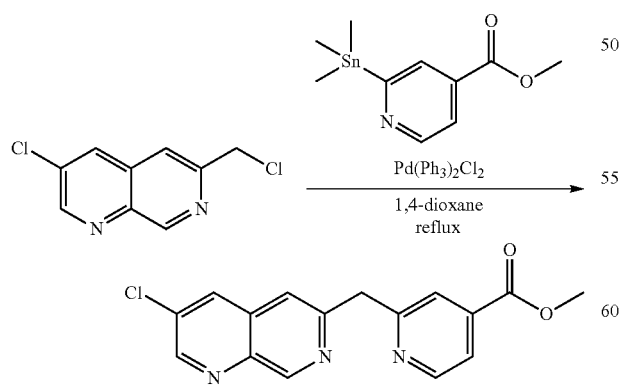

To a solution of 3-chloro-6-(chloromethyl)-1,7-naphthyridine (160.0 mg, 0.75 mmol, 1.0 eq) in dioxane (10.0 mL) was added methyl 2-(trimethylstannyl)isonicotinate (270 mg, crude, 0.90 mmol, 1.2 eq) and Pd(PPh₃)₂Cl₂ (25.0 mg, 0.04 mmol, 0.05 eq). The mixture was stirred at 90° C. for 16 h under nitrogen atmosphere, then cooled and concentrated. The resulting residue was purified by chromatography on silica gel (EA/PE=1/4-1/1, v/v) to afford methyl 2-((3-chloro-1,7-naphthyridin-6-yl)methyl)isonicotinate (130.0 mg, 55%) as a yellow solid.

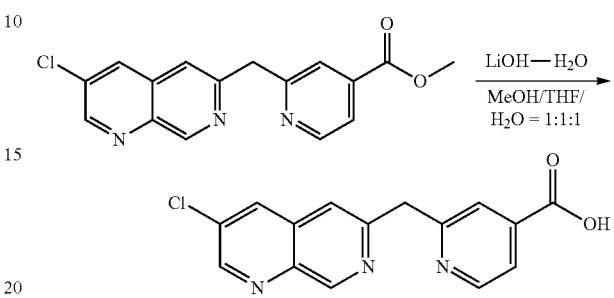

To a solution of methyl 2-((3-chloro-1,7-naphthyridin-6-yl)methyl)isonicotinate (130 mg, 0.41 mmol, 1.0 eq) in a mixed solution of methanol (2.0 mL), THF (2.0 mL) and H₂O (2 mL) was added LiOH—H₂O (34.8 mg, 0.83 mmol, 2.0 eq). The mixture was stirred at rt for 3 h, then concentrated and acidified topPH=3-4. The resulting precipitate was collected by filtration and dried to provide 2-((3-chloro-1,7-naphthyridin-6-yl)methyl)isonicotinic acid (75.0 mg, 60%).

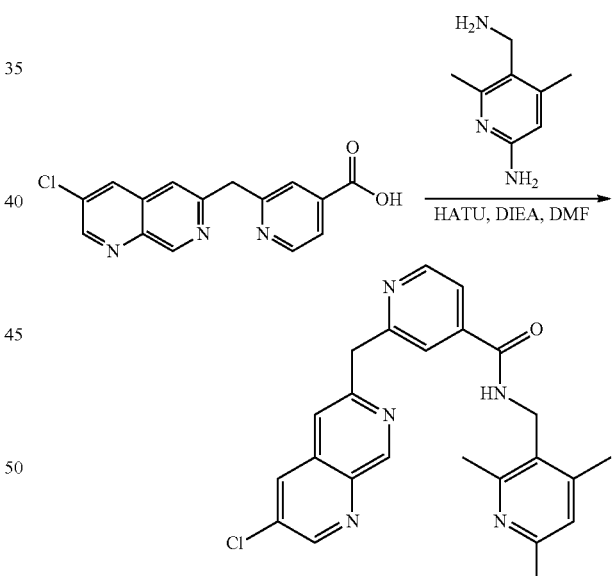

To a solution of 2-((3-chloro-1,7-naphthyridin-6-yl)methyl)isonicotinic acid (25.0 mg, crude) in DMF (2.0 mL) was added HATU (70.0 mg, 0.18 mmol, 2.2 eq), followed by 5-aminomethyl-6-methyl-pyridin-2-ylamine (27.6 mg, 0.18 mmol, 2.2 eq), DIEA (43.0 mg, 0.33 mmol, 4.0 eq). The mixture was stirring at rt for 1 h, then was added brine (20.0 mL) and extracted with EA (20.0 mL×3). The combined organic layer was washed with brine, dried over Na₂SO₄ and concentrated. The resulting residue was purified on Prep-TLC (methanol/DCM=1/10, v/v) to give N-((6-amino-2,4-dimethylpyridin-3-yl)methyl)-2-((3-chloro-1,7-naphthyridin-6-yl)methyl)isonicotinamide (14.5 mg, 40%). ¹H NMR (CD₃OD, 400 MHz): δ 9.29 (s, 1H), 8.93 (d, 1H), 8.59 (d, 1H), 8.42 (d, 1H), 7.78 (d, 2H), 7.59-7.61 (m, 2H), 6.52 (s, 1H), 4.54 (d, 2H), 4.50 (s, 2H), 2.50 (s, 3H), 2.38 (s, 3H). LRMS (M+H⁺) m/z calculated 433.1, found 433.4.

Example 149: Preparation of N-((6-amino-2-methylpyridin-3-yl)methyl)-2-((3-chloro-1,7-naphthyridin-6-yl)methyl)isonicotinamide

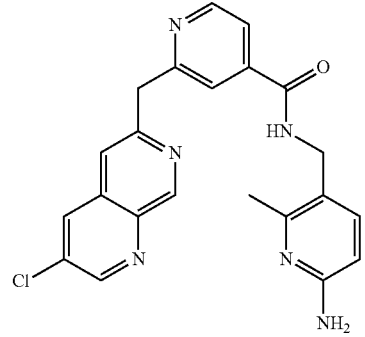 [SMILES: Cc1nc(N)ccc1CNC(=O)c1ccnc(Cc2cc3cc(Cl)cnc3cn2)c1]

N-((6-amino-2-methylpyridin-3-yl)methyl)-2-((3-chloro-1,7-naphthyridin-6-yl)methyl)isonicotinamide (15.5 mg) was prepared as described for N-((6-amino-2,4-dimethylpyridin-3-yl)methyl)-2-((3-chloro-1,7-naphthyridin-6-yl)methyl)isonicotinamide. ¹H NMR (CD₃OD, 400 MHz): δ 9.30 (s, 1H), 8.93 (d, 1H), 8.61 (d, 1H), 8.43 (d, 1H), 7.78 (s, 2H), 7.63 (t, 1H), 7.54 (d, 1H), 6.52 (d, 1H), 4.57 (d, 2H), 4.43 (s, 2H), 2.42 (s, 3H). LRMS (M+H⁺) m/z calculated 419.1, found 419.4.

Example 150: Preparation of N-((6-amino-2,4-dimethylpyridin-3-yl)methyl)-2-((2-chloro-1H-pyrrolo[2,3-b]pyridin-5-yl)methyl)isonicotinamide

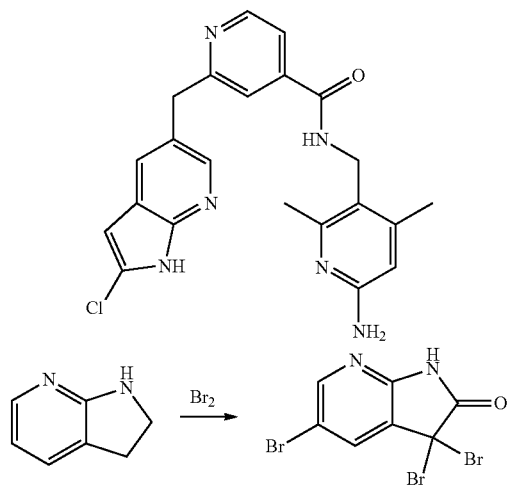

To a solution of 7-azaindole (5.0 g, 42 mmol, 1.0 eq) in a mixture of water (330.0 mL) and t-butanol (330.0 mL) was added bromine (27.0 mL, 0.5 mol, 12.6 eq) drop-wise at rt. The mixture was stirred for 16 h and concentrated under reduced pressure. The aqueous phase was treated with basified by saturated aqueous NaHCO₃ to pH 9. The precipitate was collected by filtration and dried to provide tribrominatedoxindole (13.4 g, 85%).

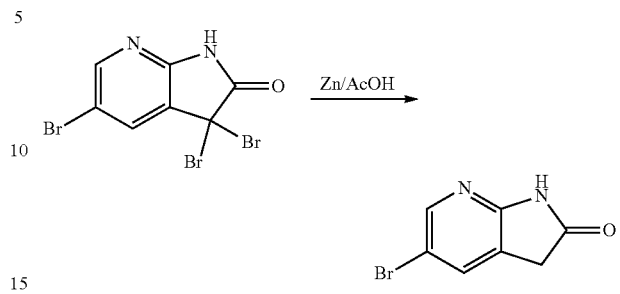

To a solution of 3,3,5-tribromo-1H-pyrrolo[2,3-b]pyridin-2(3H)-one (2.5 g, 6.8 mmol, 1.0 eq) in acetic acid (50.0 mL) was added zinc (4.4 g, 67.5 mmol, 10.0 eq) under N₂ at rt. The mixture was stirred for 5 h, then concentrated. The residue was diluted with water and extracted with EA (50.0 mL×3). The combined organic layers were dried over anhydrous Na₂SO₄ and concentrated. The resulting residue was purified by chromatography on silica gel (DCM/methanol=95/5, v/v) to provide 5-bromo-1H-pyrrolo[2,3-b]pyridin-2(3H)-one (1.36 g, 95%).

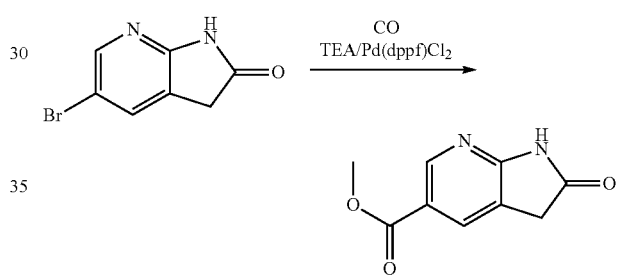

To a solution of 5-bromo-1H-pyrrolo[2,3-b]pyridin-2(3H)-one (500.0 mg, 2.4 mmol, 1.0 eq) in DMF (10 mL)/methanol (30 mL) were added Pd(dppf)Cl₂ (86.0 mg, 0.12 mmol, 0.05 eq) and triethylamine (716.0 mg, 7.1 mmol, 3.0 eq). The mixture was stirred under CO (25 atm) at 100° C. for 16 h, then cooled, filtered and concentrated. The residue was diluted with water (10.0 mL) and extracted with diethyl ether (10.0 mL×3). The combined organic layers were dried over anhydrous Na₂SO₄, concentrated under vacuum. The resulting residue was purified by chromatography on silica gel (EA/PE=1/1, v/v) to provide methyl 2-oxo-2,3-dihydro-1H-pyrrolo[2,3-b]pyridine-5-carboxylate (250 mg, 55%).

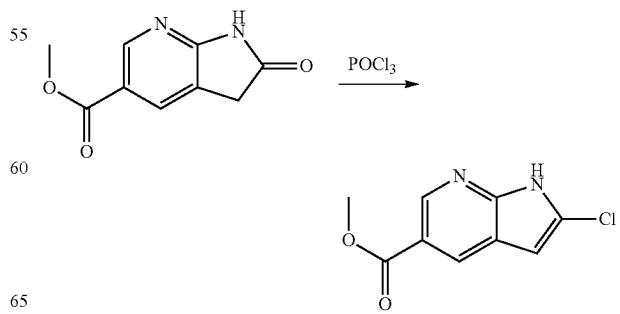

To a solution of methyl 2-oxo-2,3-dihydro-1H-pyrrolo[2,3-b]pyridine-5-carboxylate (140.0 mg, 0.73 mmol, 1.0 eq) in POCl₃ (5.0 mL) was added N,N-dimethylaniline (88.0 mg, 0.73 mmol, 1.0 eq). The mixture was stirred at 90° C. for 16 h, the cooled and concentrated. The resulting residue was purified by chromatography on silica gel (EA/PE=1/2, v/v) to provide methyl 2-chloro-1H-pyrrolo[2,3-b]pyridine-5-carboxylate (100.0 mg, 65%).

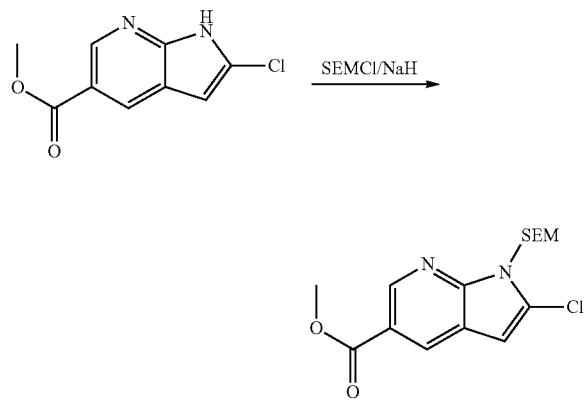 [SMILES: COC(=O)c1cnc2[nH]c(Cl)cc2c1 ; "SEMCl/NaH" ; COC(=O)c1cnc2c(c1)cc(Cl)n2COCC[Si](C)(C)C]

To a solution of methyl 2-chloro-1H-pyrrolo[2,3-b]pyridine-5-carboxylate (100.0 mg, 0.5 mmol, 1.0 eq) in THF (4 mL) was added sodium hydride (21.0 mg, 0.5 mmol, 1.1 eq), followed by 2-(trimethylsilyl)ethoxymethyl chloride (80.0 mg, 0.5 mmol, 1.0 eq). The reaction mixture was stirred at rt for 2 h, then was added water (4 mL) and extracted with DCM (4 mL×3). The combined organic layers were dried over Na₂SO₄, filtered and concentrated to provide crude methyl 2-chloro-1-((2-(trimethylsilyl)ethoxy)methyl)-1H-pyrrolo[2,3-b]pyridine-5-carboxylate (137.0 mg, 83%), which was used in the next step without further purification.

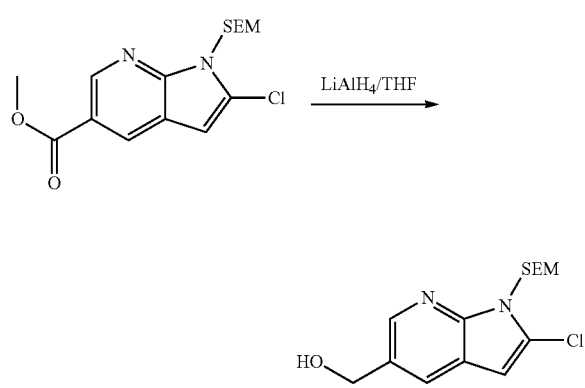

To a solution of methyl 2-chloro-1-((2-(trimethylsilyl)ethoxy)methyl)-1H-pyrrolo[2,3-b]pyridine-5-carboxylate (137.0 mg, 0.4 mmol, 1.0 eq) in THF (4.0 mL) was added lithium aluminium hydride (31.0 mg, 0.8 mmol, 2.0 eq) at 0° C. The reaction mixture was stirred at rt for 2 h, was added water (4.0 mL) drop-wise and extracted with EtOAc (10.0 mL×3). The combined organic layers were dried over Na₂SO₄, filtered and concentrated. The resulting residue was purified by chromatography on silica gel (DCM/EtOAc=1/1, v/v) to provide (2-chloro-1-((2-(trimethylsilyl)ethoxy)methyl)-1H-pyrrolo[2,3-b]pyridin-5-yl)methanol (46 mg, 38%).

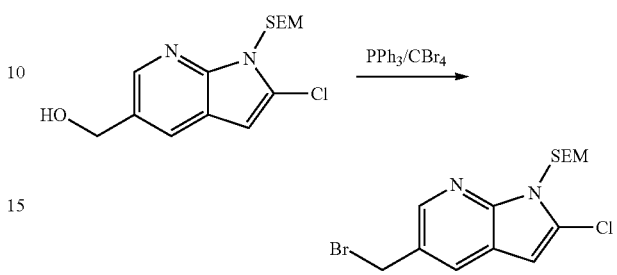

To a solution of (2-chloro-1-((2-(trimethylsilyl)ethoxy)methyl)-1H-pyrrolo[2,3-b]pyridin-5-yl)methanol (46.0 mg, 0.14 mmol, 1.0 eq) in CH₂Cl₂ (2.0 mL), were added triphenylphosphine (38.0 mg, 0.22 mmol, 1.5 eq) and carbon tetrabromide (48.0 mg, 0.22 mmol, 1.5 eq). The reaction mixture was stirred at rt for 2 h, then concentrated. The resulting residue was purified by chromatography on silica gel (EtOAc/PE=1/2, v/v) to provide 5-(bromomethyl)-2-chloro-1-((2-(trimethylsilyl)ethoxy)methyl)-1H-pyrrolo[2,3-b] pyridine (45.0 mg, 80%).

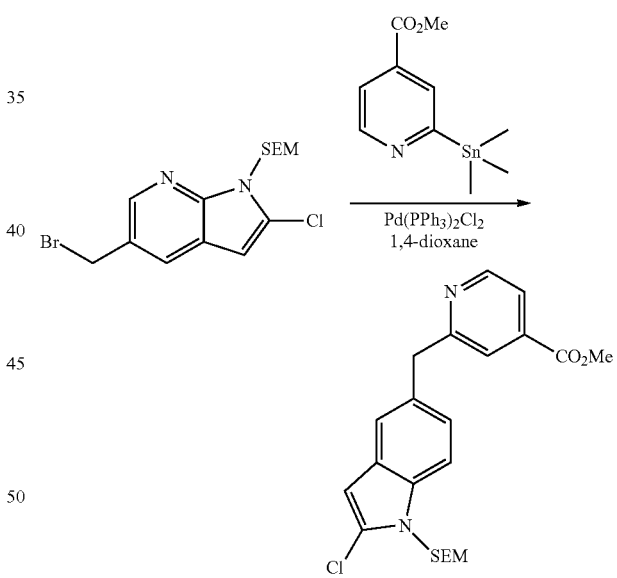

To a solution of 5-(bromomethyl)-2-chloro-1-((2-(trimethylsilyl)ethoxy)methyl)-1H-pyrrolo[2,3-b]pyridine (45.0 mg, 0.12 mmol, 1.0 eq) in dioxane (5.0 mL) were added 2-trimethylstannanyl-isonicotinic acid methyl ester (72.0 mg, 0.24 mmol, 0.24 eq) and Pd(PPh₃)₂Cl₂ (8.0 mg, 0.05 mmol, 0.05 eq). The mixture was stirred at 90° C. for 3 h under nitrogen atmosphere, the cooled, filtered and concentrated. The resulting residue was purified by chromatography on silica gel (EtOAc/PE=1/1, v/v) to provide methyl 2-((2-chloro-1-((2-(trimethylsilyl) ethoxy)methyl)-1H-indol-5-yl)methyl)isonicotinate (35 mg, 68%) as a light yellow solid.

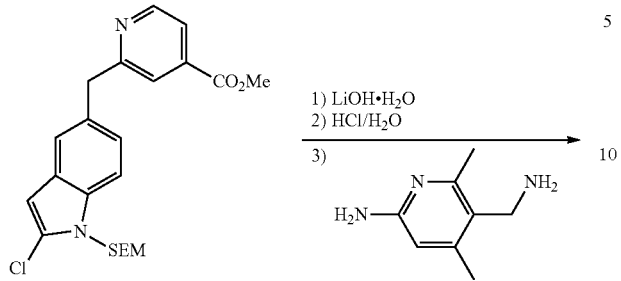

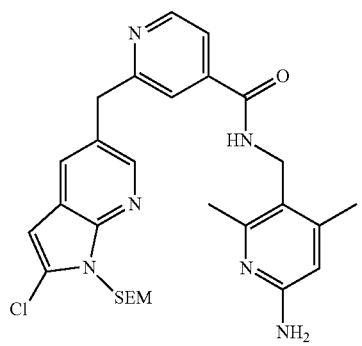

To a solution of methyl 2-((2-chloro-1-((2-(trimethylsilyl)ethoxy)methyl)-1H-indol-5-yl)methyl)isonicotinate (35.0 mg, 0.08 mmol, 1.0 eq) in THF (1 mL)/H₂O (1 mL) was added LiOH.H₂O (4 mg, 0.097 mmol, 1.2 eq). The mixture was stirred at rt for 2 h and acidified to pH=5-6 with 1 N HCl solution, then concentrated in vacuum and the residue was directly used without further purification. To a solution of this crude product (13 mg, 0.097 mmol, 1.2 eq) in DMF (2.0 mL) were added HATU (37.0 mg, 0.097 mmol, 1.2 eq) and Et₃N (24.0 mg, 0.243 mmol, 3.0 eq). The mixture was stirred at rt for 2 h, then concentrated. The residue was purified by chromatography on silica gel (DCM/MeOH=10/1, v/v) to provide N-((6-amino-2,4-dimethylpyridin-3-yl)methyl)-2-((2-chloro-1-((2-(trimethylsilyl)ethoxy) methyl)-1H-pyrrolo[2,3-b]pyridin-5-yl)methyl)isonicotinamide (26.0 mg, 58.3%).

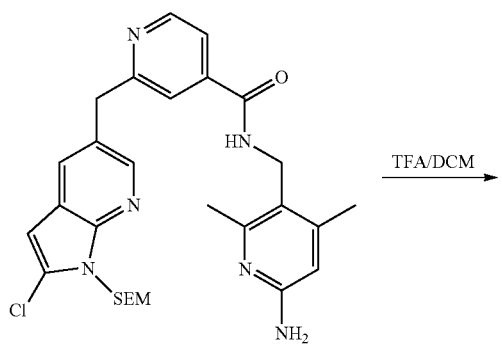

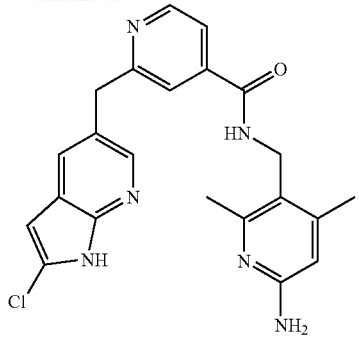

To a solution of N-((6-amino-2,4-dimethylpyridin-3-yl)methyl)-2-((2-chloro-1-((2-(trimethylsilyl)ethoxy)methyl)-1H-pyrrolo[2,3-b]pyridin-5-yl)methyl)isonicotinamide (26.0 mg, 0.047 mmol, 1.0 eq) in DCM (0.2 mL) was added TFA (0.1 mL). The mixture was stirred at rt for 2 h and adjusted to pH=8-9 with saturated NaHCO₃ solution. The mixture was concentrated and the residue was purified on f silica gel chromatography (DCM/MeOH=8/1, v/v) to provide N-((6-amino-2,4-dimethylpyridin-3-yl) methyl)-2-((2-chloro-1H-pyrrolo[2,3-b]pyridin-5-yl)methyl)isonicotinamide (14.0 mg, 70%).

¹H NMR (CD₃OD, 400 MHz): δ 8.59 (d, 1H), 8.13 (d, 1H), 7.80 (d, 1H), 7.19 (s, 1H), 7.63 (t, 1H), 6.58 (s, 1H), 6.35 (s, 1H), 4.51 (s, 2H), 4.28 (s, 2H), 2.52 (s, 3H), 2.38 (s, 3H). LRMS (M+H⁺) m/z calculated 421.1, found 421.4.

Example 151: Preparation of N-((6-amino-2,4-dimethylpyridin-3-yl)methyl)-2-((5-(trifluoromethyl)-1H-indol-2-yl)methyl)isonicotinamide

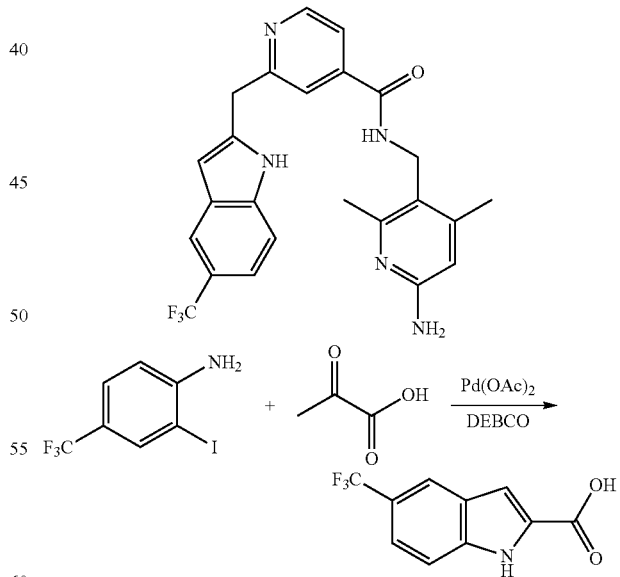

A mixture of 2-iodo-4-(trifluoromethyl)aniline (6.0 g, 20.9 mmol, 1.0 eq), 2-oxopropanoic acid (3.7 g, 41.8 mmol, 2.0 eq), 1,4-diaza-bicyclo[2.2.2]octane (4.7 g, 41.8 mmol, 2.0 eq) and Pd(OAc)₂ (10.0 mg, 0.05 eq) in DMF (25 mL) was heated at 105° C. under N₂ for 10 h, then cooled to rt. EtOAc (200.0 mL) and water (200.0 mL) were added. The organic layer was separated and washed with brine, dried over Na₂SO₄ and concentrated under vacuum. The resulting residue was purified by chromatography on silica gel (PE/EtOAc=10/1, v/v) to provide crude 5-(trifluoromethyl)-1H-indole-2-carboxylic acid (5.0 g).

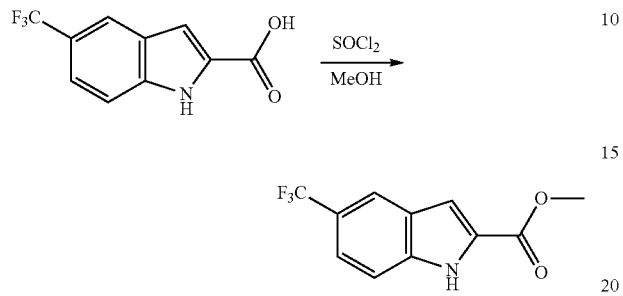

To a solution of 5-(trifluoromethyl)-1H-indole-2-carboxylic acid (5.0 g crude) in MeOH (50.0 mL) was added SOCl₂ (5.0 mL). The reaction was stirred under eflux for 4 h, then concentrated. The resulting residue was purified by chromatography on silica gel (PE/EtOAc=10/1, v/v) to provide methyl 5-(trifluoromethyl)-1H-indole-2-carboxylate (1.88 g, 37% in 2 steps).

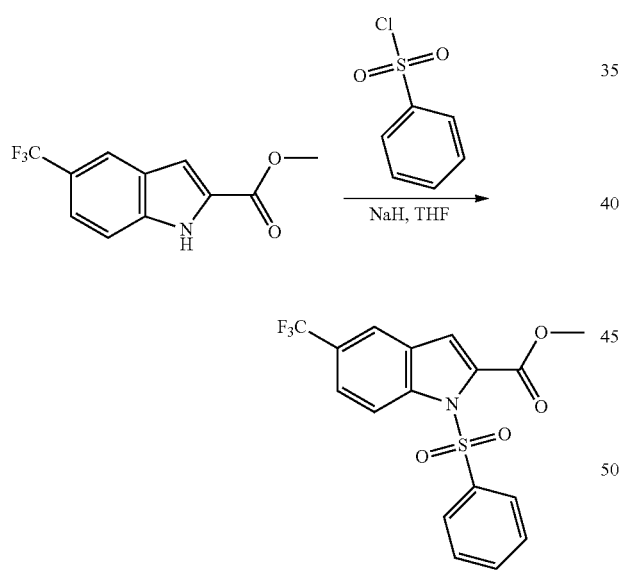

To a solution of methyl 5-(trifluoromethyl)-1H-indole-2-carboxylate (1.0 g, 4.1 mmol, 1.0 eq) in dry THF (25.0 mL) was added NaH (180.0 mg, 60%, 4.52 mmol, 1.1 eq). 5 mins later, PhSO₂Cl (0.87 g, 4.93 mmol, 1.2 eq) was added. After the addition, the reaction mixture was stirred at rt for 16 h, then quenched with NH₄Cl aqueous (15%, 30 mL) and extracted with EtOAc (30 mL×3). The combined organic layers were dried over anhydrous Na₂SO₄ and concentrated. The resulting residue was purified by chromatography on silica gel (PE/EtOAc=10/1, v/v) to afford methyl 1-(phenylsulfonyl)-5-(trifluoromethyl)-1H-indole-2-carboxylate (1.1 g, 70%).

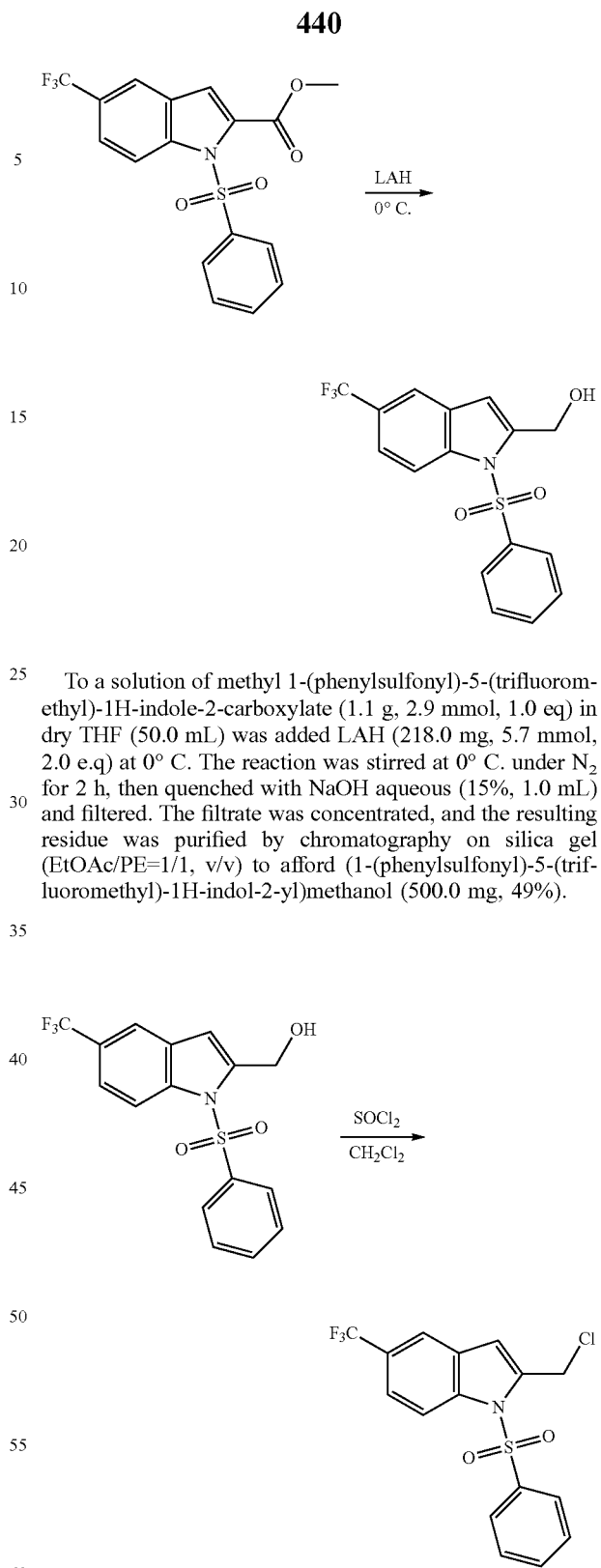

To a solution of methyl 1-(phenylsulfonyl)-5-(trifluoromethyl)-1H-indole-2-carboxylate (1.1 g, 2.9 mmol, 1.0 eq) in dry THF (50.0 mL) was added LAH (218.0 mg, 5.7 mmol, 2.0 e.q) at 0° C. The reaction was stirred at 0° C. under N₂ for 2 h, then quenched with NaOH aqueous (15%, 1.0 mL) and filtered. The filtrate was concentrated, and the resulting residue was purified by chromatography on silica gel (EtOAc/PE=1/1, v/v) to afford (1-(phenylsulfonyl)-5-(trifluoromethyl)-1H-indol-2-yl)methanol (500.0 mg, 49%).

To a solution of (1-(phenylsulfonyl)-5-(trifluoromethyl)-1H-indol-2-yl) methanol (500.0 mg, 1.41 mmol, 1.0 eq) in DCM (30.0 mL) was added SOCl₂ (837.0 mg, 7.0 mmol, 5.0 eq). The mixture was stirred at rt for 2 h, then concentrated to provide 2-(chloromethyl)-1-(phenylsulfonyl)-5-(trifluoromethyl)-1H-indole (300.0 mg, 57%).

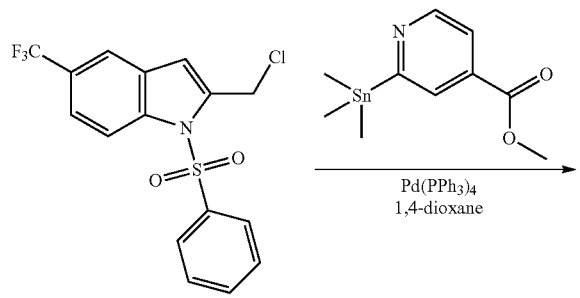

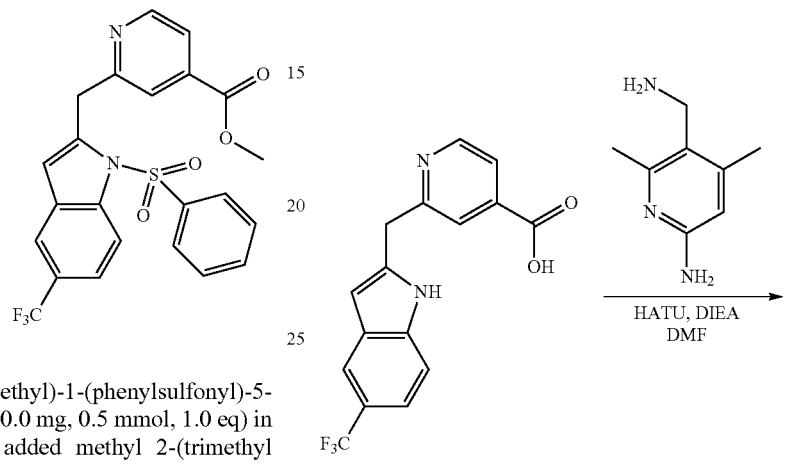

To a solution of 2-(chloromethyl)-1-(phenylsulfonyl)-5-(trifluoromethyl)-1H-indole (200.0 mg, 0.5 mmol, 1.0 eq) in 1,4-dioxane (10.0 mL) were added methyl 2-(trimethylstannyl)isonicotinate (89.0 mg, 0.6 mmol, 1.2 eq) and Pd(PPh₃)₄ (31.0 mg, 0.027 mmol, 0.05 eq). The reaction was stirred at 100° C. under N₂ for 16 h, then cooled and concentrated under vacuum. The resulting residue was purified on Prep-TLC (EtOAc/PE=1/1, v/v) to provide methyl 2-((1-(phenylsulfonyl)-5-(trifluoromethyl)-1H-indol-2-yl)methyl)isonicotinate (170.0 mg, 66%).

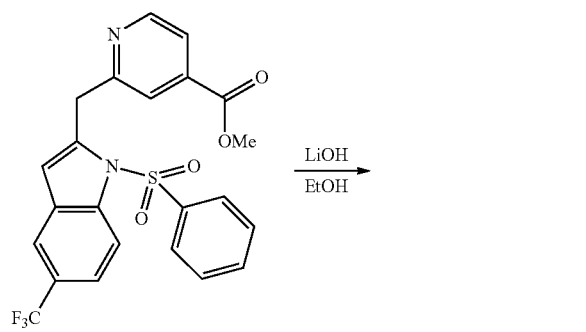

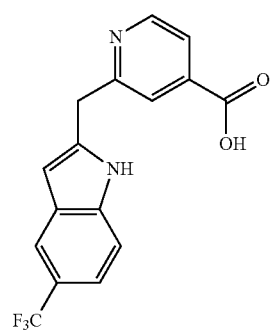

To a solution of methyl 2-((1-(phenylsulfonyl)-5-(trifluoromethyl)-1H-indol-2-yl)methyl)isonicotinate (170.0 mg, 0.36 mmol, 1.0 eq) in MeOH (20.0 mL) was added LiOH.H₂O (75.0 mg, 1.8 mmol, 5.0 eq). The mixture was stirred at rt for 16 h, then acidified to pH=3 with 4 N HCl and concentrated. EtOAc (50.0 mL) and water (50.0 mL) were added. The organic layer was separated and concentrated to provide 2-((5-(trifluoromethyl)-1H-indol-2-yl)methyl)isonicotinic acid (110.0 mg, 95%).

To a solution of 2-((5-(trifluoromethyl)-1H-indol-2-yl)methyl)isonicotinic acid (55.0 mg, 0.17 mmol, 1.0 eq) and 5-(aminomethyl)-4,6-dimethylpyridin-2-amine (31.0 mg, 0.17 mmol, 1.0 eq) in DMF (5 mL) were added HATU (98 mg, 0.26 mmol, 1.5 e.q) and DIEA (88.0 mg, 0.68 mmol, 4.0 eq). The mixture was stirred at rt for 16 h, then EtOAc (50.0 mL) and water (50.0 mL) were added. The organic layer was separated, dried over anhydrous Na₂SO₄ and concentrated. The resulting residue was purified on Prep-TLC (DCM/MeOH=10/1, v/v) to provide N-((6-amino-2,4-dimethylpyridin-3-yl)methyl)-2-((5-(trifluoromethyl)-1H-indol-2-yl)methyl)isonicotinamide (36.0 mg, 47%). ¹H NMR (CDCl₃, 400 MHz): δ 9.20 (s, 1H), 8.71 (d, 1H), 7.81 (s, 1H), 7.57 (s, 1H), 7.46 (m, 1H), 7.35 (m, 2H), 6.45 (s, 1H), 6.23 (s, 1H), 5.94 (s, 1H), 4.55 (d, 2H), 4.49 (d, 2H), 4.32 (s, 2H), 2.43 (s, 3H), 2.25 (s, 3H). LCMS (M+H⁺) m/z calculated 454.2, found 454.5.

Example 152: Preparation of N-((6-amino-2,4-dimethylpyridin-3-yl)methyl)-2-((2-(trifluoromethyl)-1H-pyrrolo[2,3-b]pyridin-5-yl)methyl)isonicotinamide

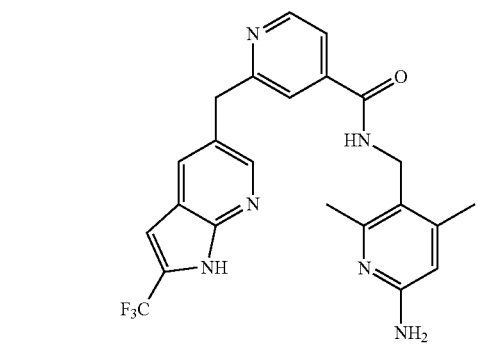

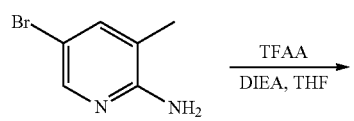

To a solution of 5-bromo-3-methylpyridin-2-amine (5.0 g, 26.7 mmol, 1.0 e.q) and DIEA (10.4 g, 80.2 mmol, 3.0 eq) in THF (20 mL) was added TFAA (12.4 g, 58.8 mmol, 2.2 eq) at 0° C. The reaction mixture was stirred at rt for 16 h, then concentrated under vacuum. EtOAc (200 mL) was added the residue and the mixture was washed with NaHCO₃ (10%, 200 mL) and concentrated. The resulting residue was purified by chromatography on silica gel (EtOAc/PE=1/5, v/v) to afford N-(5-bromo-3-methylpyridin-2-yl)-2,2,2-trifluoroacetamide (4.7 g, 61%).

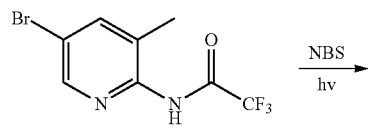

To a solution of N-(5-bromo-3-methylpyridin-2-yl)-2,2,2-trifluoroacetamide (4.7 g, 16.4 mmol, 1.0 eq) in CCl₄ (60.0 mL) were added NBS (2.9 g, 16.4 mmol, 1.0 eq) and BPO (0.2 g, 8.2 mmol, 0.05 eq). The reaction was stirred at 70° C. under UV light irradiation under N₂ for 16 h, then concentrated under vacuum, partitioned between EtOAc (50.0 mL) and water (50.0 mL). The organic layer was separated, dried over anhydrous Na₂SO₄ and concentrated to provide crude N-(5-bromo-3-(bromomethyl) pyridine-2-yl)-2,2,2-trifluoroacetamide (5.0 g).

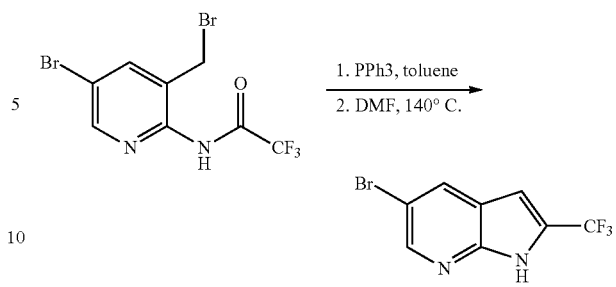

To a solution of N-(5-bromo-3-(bromomethyl)pyridin-2-yl)-2,2,2-trifluoroacetamide (5.0 g, crude) in toluene (50 mL) was added PPh₃ (5.0 g). The reaction mixture was stirred at 60° C. for 6 h, then concentrated under vacuum and was added Et₂O (50.0 mL). The mixture was filtered. The filter cake was added to DMF (15 mL) which was stirred at 140° C. for 16 h, then cooled and added DCM (100.0 mL). The solution was washed with NaHCO₃ (10%, 100 mL) and concentrated. The resulting residue was purified by chromatography on silica gel (EtOAc/PE=1/3, v/v) to afford 5-bromo-2-(trifluoromethyl)-1H-pyrrolo[2,3-b]pyridine (250 mg, 6% in 2 steps).

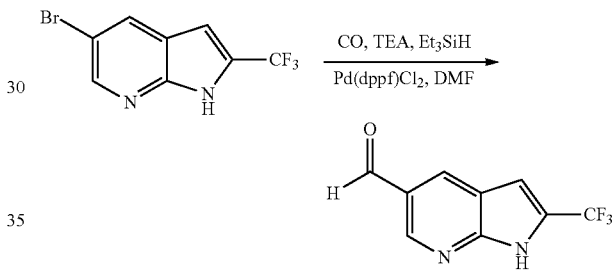

To a solution of 5-bromo-2-(trifluoromethyl)-1H-pyrrolo[2,3-b]pyridine (250.0 mg, 0.9 mmol, 1.0 eq) in DMF (5.0 mL) were added Et₃N (477.0 mg, 4.7 mmol, 5.0 eq), Et₃SiH (453 mg, 3.77 mmol, 4.0 eq) and Pd(dppf)Cl₂ (39 mg, 0.047 mmol, 0.05 eq). The mixture was stirred under CO atmosphere at 90° C. for 16 h, then cooled and added EtOAc (50.0 mL) and water (50.0 mL). The organic layer was separated and concentrated. The resulting residue was purified by chromatography on silica gel (EtOAc/PE=1/3, v/v) to provide 2-(trifluoromethyl)-1H-pyrrolo[2,3-b]pyridine-5-carbaldehyde (95.0 mg, 47%).

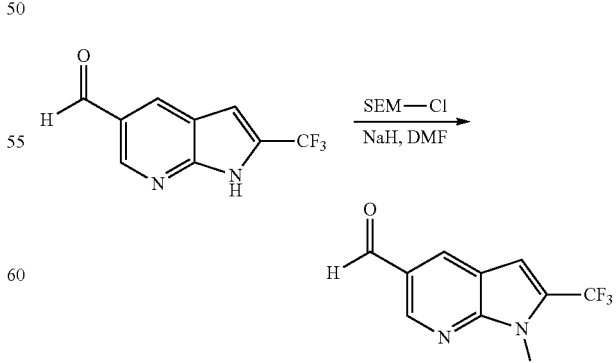

To a suspension of NaH (35.0 mg, 60%, 0.89 mmol, 2.0 eq) in DMF (3.0 mL) was added a solution of 2-(trifluoromethyl)-1H-pyrrolo[2,3-b]pyridine-5-carbaldehyde (95.0 mg, 0.4 mmol, 1.0 eq) in DMF (2.0 mL). 15 mins later, SEM-Cl (148.0 mg, 0.9 mmol, 2.0 eq) was added. The mixture was stirred at rt for 2 h, then quenched with NH₄Cl (15%, 50 mL) and extracted with EtOAc (50 mL×3). The combined organic layers were concentrated to provide 2-(trifluoromethyl)-1-((2-(trimethylsilyl) ethoxy)methyl)-1H-pyrrolo[2,3-b]pyridine-5-carbaldehyde (200 mg).

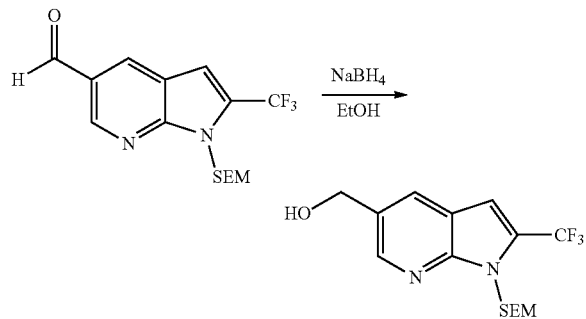

To a solution of 2-(trifluoromethyl)-1-((2-(trimethylsilyl) ethoxy)methyl)-1H-pyrrolo[2,3-b]pyridine-5-carbaldehyde (200 mg crude, 0.4 mmol, 1.0 eq) in EtOH (10.0 mL) was added NaBH₄ (84 mg, 2.20 mmol, 5.0 eq). The reaction was stirred at rt for 30 min, then partitioned between EtOAc (50.0 mL) and water (50.0 mL). The organic layer was separated and concentrated. The resulting residue was purified on Prep-TLC (EtOAc/PE=1/1, v/v) to PROVIDE (2-(trifluoromethyl)-1-((2-(trimethylsilyl)ethoxy)methyl)-1H-pyrrolo[2,3-b] pyridin-5-yl)methanol (90 mg, 59% in 2 steps).

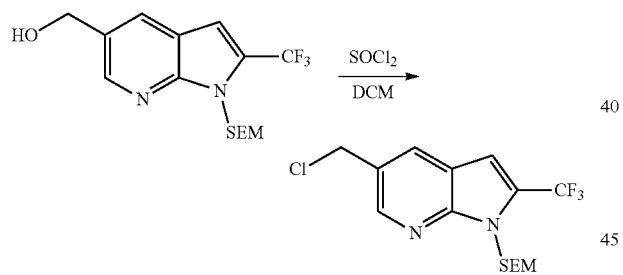

To a solution of (2-(trifluoromethyl)-1-((2-(trimethylsilyl) ethoxy)methyl)-1H-pyrrolo[2,3-b]pyridin-5-yl)methanol (90.0 mg, 0.26 mmol, 1.0 eq) in DCM (20 mL) was added SOCl₂ (155.0 mg, 1.3 mmol, 5.0 eq). The reaction was stirred under reflux for 2 h, then cooled and concentrated to afford 5-(chloromethyl)-2-(trifluoromethyl)-1-((2-(trimethylsilyl) ethoxy)methyl)-1H-pyrrolo[2,3-b]pyridine (90 mg).

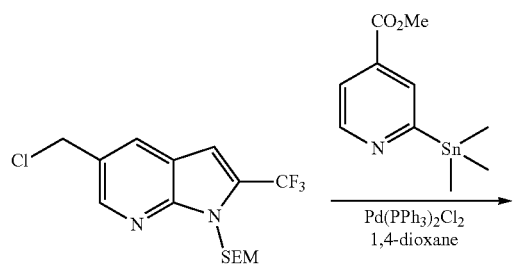

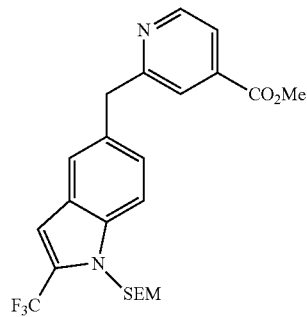

To a solution of 5-(chloromethyl)-2-(trifluoromethyl)-1-((2-(trimethylsilyl) ethoxy)methyl)-1H-pyrrolo[2,3-b]pyridine (90 mg, crude, 0.25 mmol, 1.0 eq) in 1,4-dioxane (10.0 mL) were added methyl 2-(trimethylstannyl)isonicotinate (89.0 mg, 0.3 mmol, 1.2 eq) and Pd(PPh₃)₂Cl₂ (9.0 mg, 0.012 mmol, 0.05 eq). The mixture was stirred at 100° C. under N₂ for 16 h, then cooled and concentrated under vacuum. The resulting residue was purified on Prep-TLC (EtOAc/PE=1/1, v/v) to afford methyl 2-((2-(trifluoromethyl)-1-((2-(trimethylsilyl) ethoxy)methyl)-1H-indol-5-yl) methyl)isonicotinate (40 mg, 33% in 2 steps).

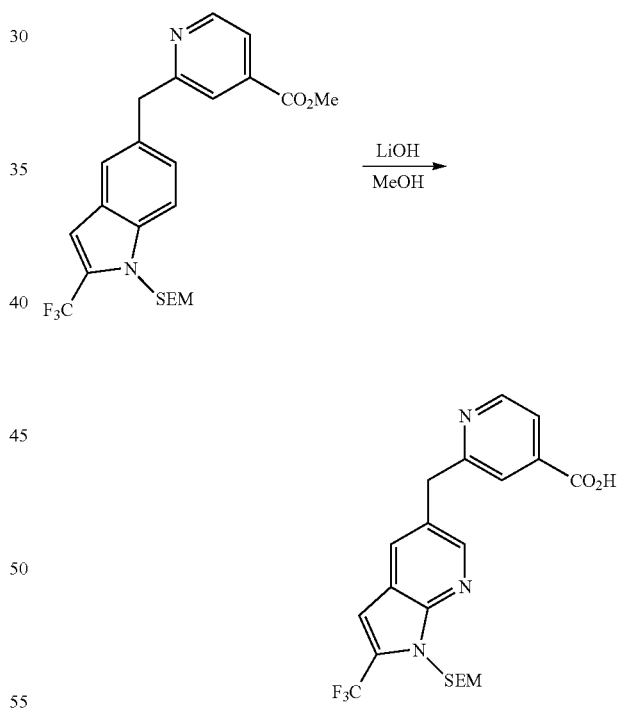

To a solution of methyl 2-((2-(trifluoromethyl)-1-((2-(trimethylsilyl)ethoxy) methyl)-1H-indol-5-yl)methyl) isonicotinate (40.0 mg, 0.086 mmol, 1.0 eq) in MeOH (10.0 mL) was added LiOH.H₂O (18.0 mg, 0.4 mmol, 5.0 eq) and water (1 mL). The MIXTURE was stirred at rt for 2 h, then acidified to pH=3 with 4 N HCl. EtOAc (50.0 mL) and water (50.0 mL) were added and the organic layer was separated and concentrated to provide 2-((2-(trifluoromethyl)-1-((2-(trimethylsilyl)ethoxy) methyl)-1H-pyrrolo[2,3-b] pyridin-5-yl)methyl)isonicotinic acid isonicotinate (30.0 mg, 77%).

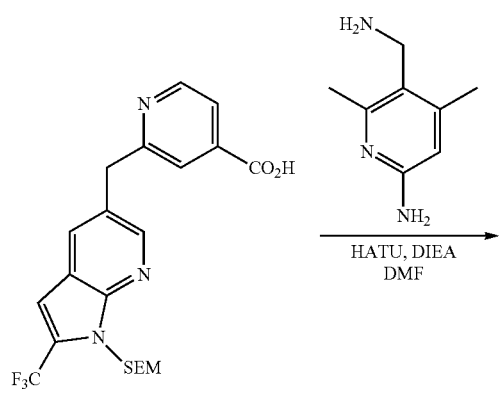

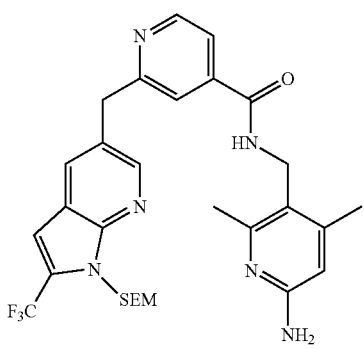

To a solution of 2-((2-(trifluoromethyl)-1-((2-(trimethylsilyl)ethoxy)methyl)-1H-pyrrolo[2,3-b]pyridin-5-yl)methyl)isonicotinic acid isonicotinate (30.0 mg, 0.066 mmol, 1.0 eq) and 5-(aminomethyl)-4,6-dimethylpyridin-2-amine (11.0 mg, 0.073 mmol, 1.1 eq) in DMF (2.5 mL) were added HATU (38.0 mg, 0.1 mmol, 1.5 eq) and DIEA (34.0 mg, 0.27 mmol, 4.0 eq). The reaction was stirred at rt for 16 h, then EtOAc (50.0 mL) and water (50.0 mL) were added. The organic layer was separated and concentrated. The resulting residue was purified on Prep-TLC (DCM/MeOH=10/1, v/v) to provide N-((6-amino-2,4-dimethylpyridin-3-yl)methyl)-2-((2-(trifluoromethyl)-1-((2-(trimethylsilyl)ethoxy)methyl)-1H-pyrrolo[2,3-b]pyridin-5-yl)methyl)isonicotinamide isonicotinate (34.0 mg, 88%).

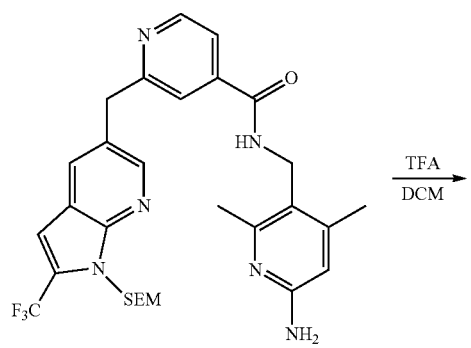

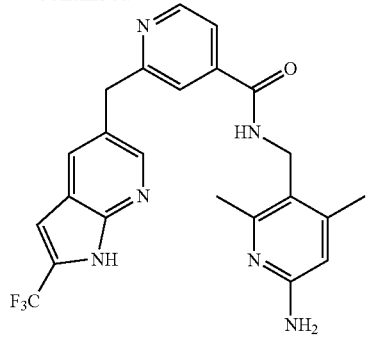

To a solution of N-((6-amino-2,4-dimethylpyridin-3-yl)methyl)-2-((2-(trifluoromethyl)-1-((2-(trimethylsilyl)ethoxy)methyl)-1H-pyrrolo[2,3-b]pyridin-5-yl)methyl)isonicotinamide isonicotinate (34.0 mg, 0.058 mmol, 1.0 eq) in DCM (1.0 mL) was added TFA (5.0 mL). The mixture was stirred at rt for 2 h, then basified to pH=8 with saturated NaHCO₃ solution. The aqueous phase was extracted with EtOAc (30.0 mL×3). The combined organic layers were concentrated and residue was purified on Prep-TLC (DCM/MeOH=5/1, v/v) to provide N-((6-amino-2,4-dimethylpyridin-3-yl)methyl)-2-((2-(trifluoromethyl)-1H-pyrrolo[2,3-b]pyridin-5-yl)methyl)isonicotinamide (10.0 mg, 38%) as a yellow solid. $^1$H NMR (CDCl$_3$+DMSO-d$_6$, 400 MHz): δ 8.59 (d, 1H), 8.37 (s, 1H), 8.07 (d, 1H), 7.88 (s, 1H), 7.70 (s, 1H), 6.74 (s, 1H), 6.24 (s, 1H), 4.74 (s, 2H), 4.48 (d, 2H), 4.27 (s, 2H), 2.41 (s, 3H), 2.25 (s, 3H). LCMS (M+H$^+$) m/z calculated 455.2, found 455.5.

Example 153: Preparation of N-((6-amino-2,4-dimethylpyridin-3-yl)methyl)-2-((6-chloropyrrolo[1,2-c]pyrimidin-3-yl)methyl)isonicotinamide

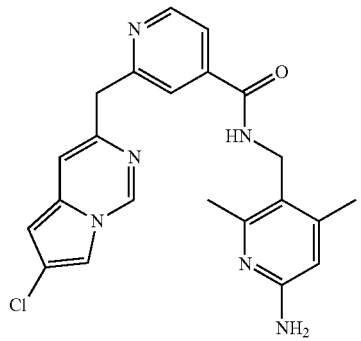

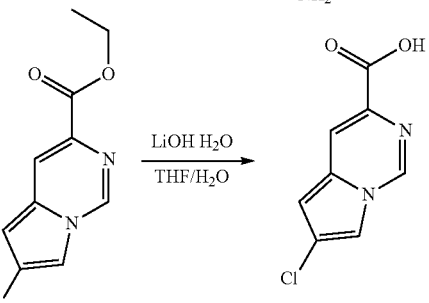

To a solution of ethyl 6-chloropyrrolo[1,2-c]pyrimidine-3-carboxylate (1.7 g, 7.4 mmol, 1.0 eq) in THF (4.5 mL)/

H₂O (4.5 mL) was added LiOH.H₂O (450.0 mg, 0.097 mmol, 1.5 eq). The mixture was stirred at rt for 2 h and acidified to pH 5-6 with 1N HCl, then concentrated to afford 6-chloropyrrolo[1,2-c]pyrimidine-3-carboxylic acid (1.5 g crude) which is used in the next step directly without further purification.

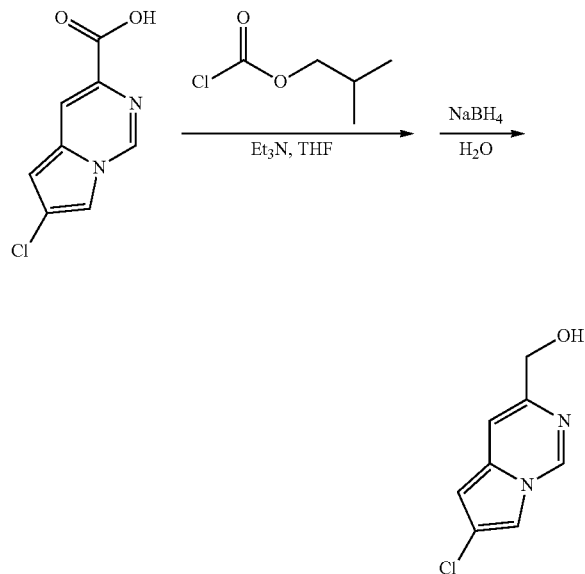

To a solution of 6-chloropyrrolo[1,2-c]pyrimidine-3-carboxylic acid (2.9 g, 14.8 mmol, 1.0 eq) in THF (15 mL) was added Et₃N (3.2 g, 32.0 mmol, 2.2 eq). The mixture was allowed to cool to 0° C., then was added isobutyl carbonochloridate (2.4 g, 17.0 mmol, 1.2 eq) drop-wise and the mixture was stirred at 0° C. for 2 h. Sodium borohydride (2.4 g, 17.0 mmol, 1.2 eq) was added to the reaction mixture in portion. The mixture was stirred for 2 h. Water (25 mL) was added to quench the mixture, which was then extracted with EtOAc (25 mL×2). The combined organic layers were dried over anhydrous Na₂SO₄ and concentrated. The resulting residue was purified by chromatography on silica gel on (PE/EA=1/1, v/v) to provide (6-chloropyrrolo[1,2-c]pyrimidin-3-yl)methanol (980 mg, 36% two steps).

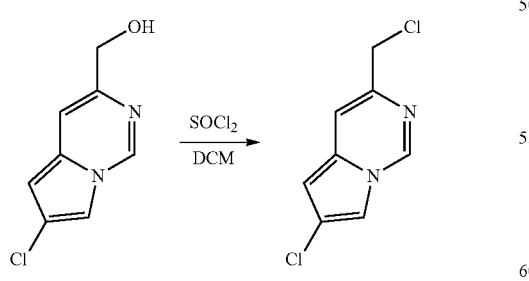

To a solution of (6-chloropyrrolo[1,2-c]pyrimidin-3-yl)methanol (800.0 mg, 4.4 mmol, 1.0 eq) in DCM (20 mL) was added SOCl₂ (1.57 g, 13.2 mmol, 3.0 eq). The mixture was stirred under reflux for 2 h, then cooled and concentrated to afford 6-chloro-3-(chloromethyl)pyrrolo[1,2-c]pyrimidine (637 mg, crude).

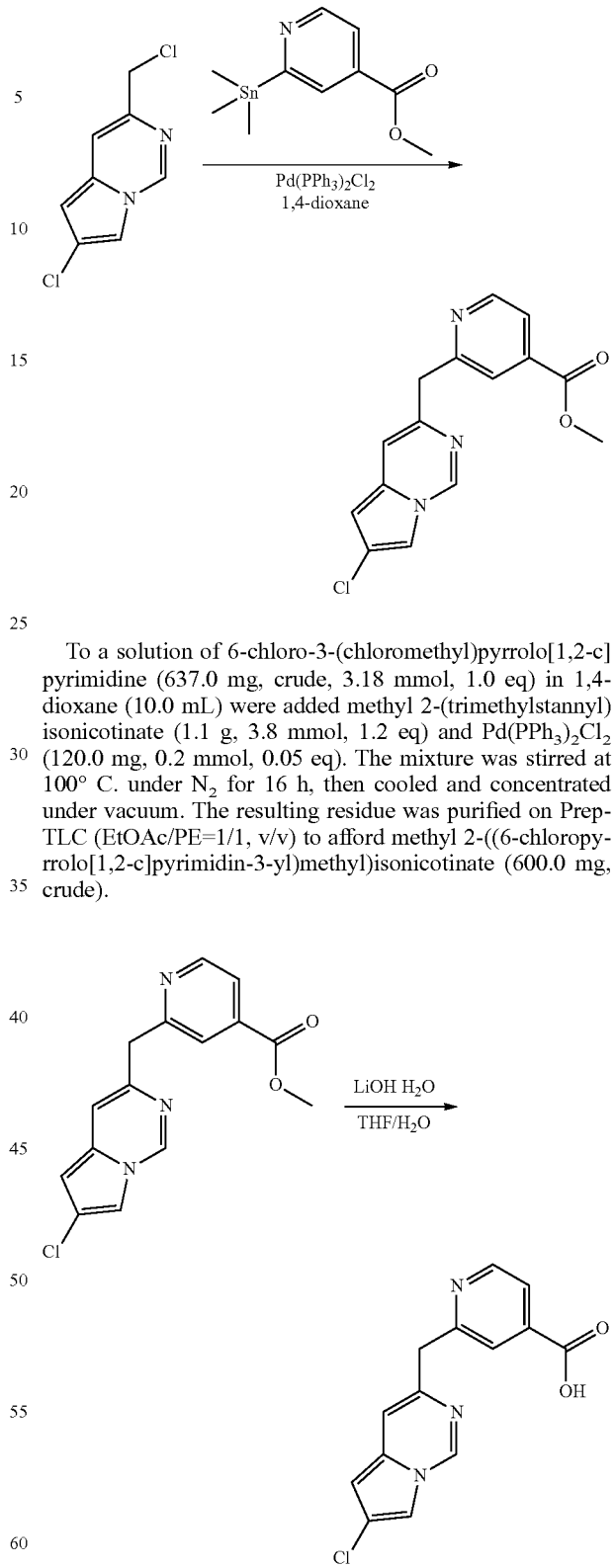

To a solution of 6-chloro-3-(chloromethyl)pyrrolo[1,2-c]pyrimidine (637.0 mg, crude, 3.18 mmol, 1.0 eq) in 1,4-dioxane (10.0 mL) were added methyl 2-(trimethylstannyl)isonicotinate (1.1 g, 3.8 mmol, 1.2 eq) and Pd(PPh₃)₂Cl₂ (120.0 mg, 0.2 mmol, 0.05 eq). The mixture was stirred at 100° C. under N₂ for 16 h, then cooled and concentrated under vacuum. The resulting residue was purified on Prep-TLC (EtOAc/PE=1/1, v/v) to afford methyl 2-((6-chloropyrrolo[1,2-c]pyrimidin-3-yl)methyl)isonicotinate (600.0 mg, crude).

To a solution of methyl 2-((6-chloropyrrolo[1,2-c]pyrimidin-3-yl) methyl)isonicotinate (600.0 mg, 2 mmol, 1.0 eq) in THF (5.0 mL) was added LiOH.H₂O (160.0 mg, 4.0 mmol, 5.0 eq) and water (3 mL). The mixture was stirred at rt for 2 h, then acidified to pH=3 with 4 N HCl. EtOAc (50.0 mL)

and water (50.0 mL) were added and the organic layer was separated and concentrated to provide 2-((6-chloropyrrolo[1,2-c]pyrimidin-3-yl)methyl)isonicotinic acid (225.0 mg, 17% for 3 steps).

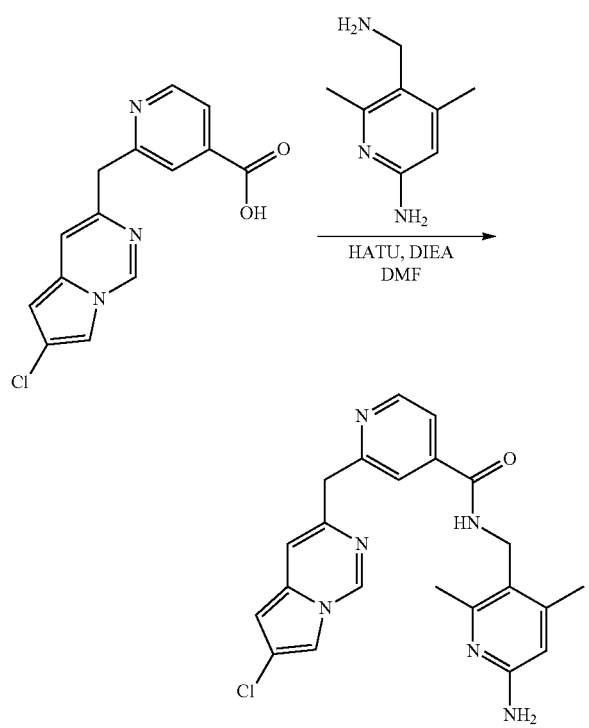

To a solution of 2-((6-chloropyrrolo[1,2-c]pyrimidin-3-yl)methyl)isonicotinic acid (520.0 mg, 1.8 mmol, 1.0 eq) and 5-(aminomethyl)-4,6-dimethylpyridin-2-amine (300.0 mg, 2.0 mmol, 1.1 eq) in DMF (2.5 mL) were added HATU (1.0 g, 2.7 mmol, 1.5 eq) and DIEA (940.0 mg, 7.2 mmol, 4.0 eq). The mixture was stirred at rt for 16 h, then EtOAc (50.0 mL) and water (50.0 mL) were added. The organic layer was separated and concentrated. The resulting residue was purified on Prep-HPLC (basic) to provide N-((6-amino-2,4-dimethylpyridin-3-yl)methyl)-2-((6-chloropyrrolo[1,2-c]pyrimidin-3-yl)methyl)isonicotinamide (222.0 mg, 30%) as white solid.

Example 154: Preparation of N-((6-chloro-[1,2,4]triazolo[4,3-a]pyridin-3-yl)methyl)-2-((3-chloroquinolin-6-yl)methyl)isonicotinamide

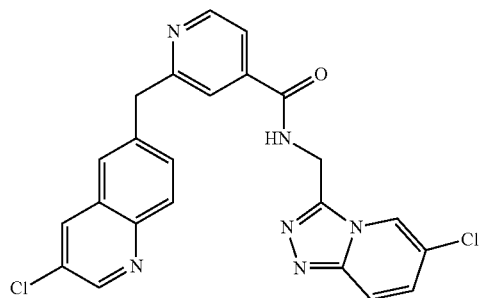

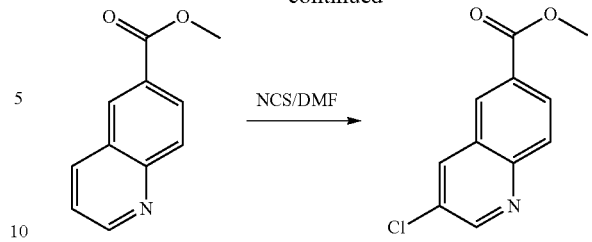

To a solution of methyl quinoline-6-carboxylate (15.0 g, 80.2 mmol, 1.0 eq) in DMF (200 ml) was added N-chlorosuccinimide (21.4 g, 0.16 mol, 2.0 eq) and the reaction mixture was stirred at 120° C. for 20 h. The reaction mixture was allowed to cool to ambient temperature, treated with brine and the mixture was extracted with EA. The organic layer was dried over Na$_2$SO$_4$, filtered and concentrated under vacuum. The crude product was purified on chromatography on silica gel (EA/PE=1/8, v/v) to afford methyl 3-chloroquinoline-6-carboxylate (9.1 g, 51%) as a yellow solid.

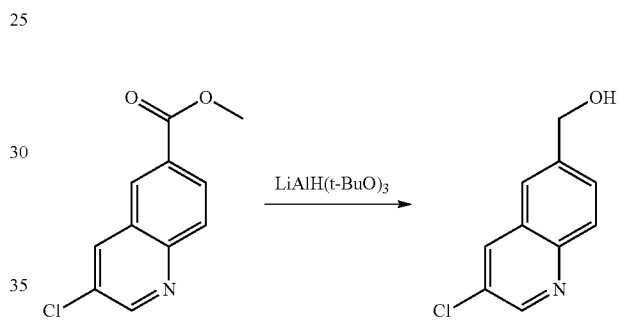

To a solution of methyl 3-chloroquinoline-6-carboxylate (9.0 g, 40.7 mmol, 1.0 eq) was added LiAlH(t-BuO)$_3$ (31.0 g, 0.122 mol, 3.0 eq). The resulting mixture was stirred at 40° C. for 12 h, and then quenched by the addition of water, extracted with EA, the combined extracts were dried and concentrated. The resulting residue was purified by chromatography on silica gel (PE/EA=2/1, v/v) to afford (3-chloroquinolin-6-yl)-methanol (5.9 g, 75%) as a white solid.

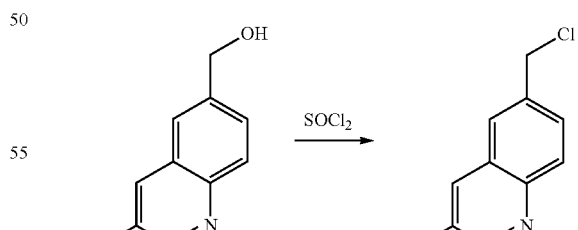

To (3-chloro-quinolin-6-yl)-methanol (3.3 g, 17.1 mmol, 1.0 eq) was added SOCl$_2$ (50 mL) and the mixture was stirred at rt for 1 h. The volatiles were then removed under vacuum and the residue was dissolved in DCM. The mixture was washed with saturated aq. NaHCO$_3$, dried and concentrated to provide 3-chloro-6-chloromethyl-quinoline (3.4 g, 94%) as a yellow solid.

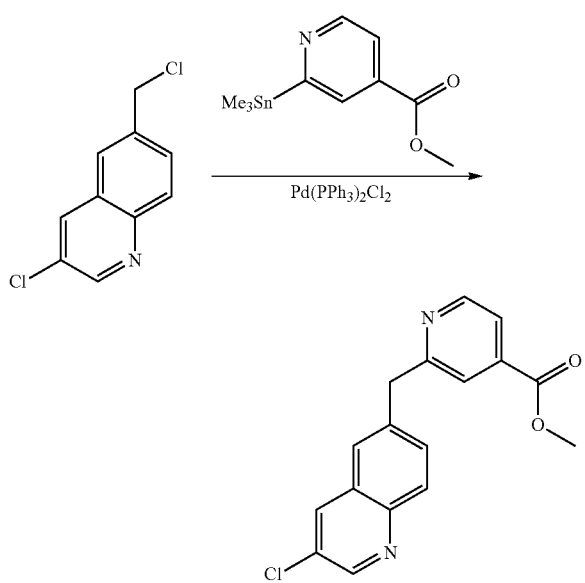

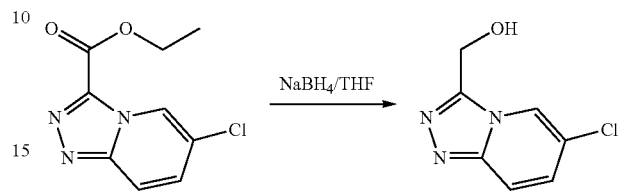

To a solution of 3-chloro-6-chloromethyl-quinoline (3.4 g, 16.1 mmol, 1.0 eq) in dioxane (80 mL) was added 2-trimethylstannanyl-isonicotinic acid methyl ester (5.34 g, 17.7 mmol, 1.1 eq) and Pd(PPh$_3$)$_2$Cl$_2$ (1.13 g, 1.61 mmol, 0.1 eq). The mixture was stirred at 90° C. for 3 h under N$_2$, concentrated and purified by chromatography on silica gel (EA/PE=1/1, v/v) to afford 2-(3-chloro-quinolin-6-ylmethyl)-isonicotinic acid methyl ester (1.72 g, 34%) as a yellow solid.

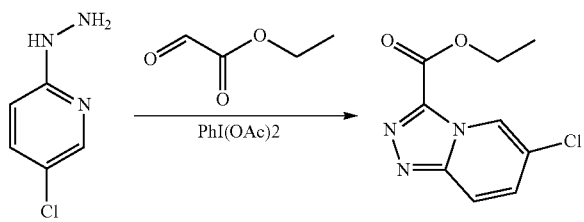

A mixture of 2,5-dichloropyridine (7.4 g, 50.0 mmol, 1.0 eq) in NH$_2$NH$_2$·H$_2$O (58.8 g, 85%, 1000 mmol, 20.0 eq) was stirred under reflux for 8 h, then cooled and extracted with DCM (100 m×3). The combined organic layers were concentrated to afford 5-chloro-2-hydrazinylpyridine (6.00 g, 83%) as a white solid.

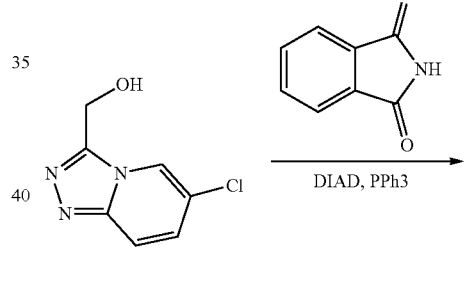

To a solution of 5-chloro-2-hydrazinylpyridine (3.6 g, 24.9 mmol, 1.0 eq) in MeOH (100.0 mL) was added ethyl 2-oxoacetate (5.1 g, 50% in toluene, 24.9 mmol, 1.0 eq). The mixture was heated at 80° C. under reflux for 1 h, then cooled and concentrated. The residue was dissolved in DCM (100.0 mL) and was added PhI(OAc)$_2$ (8.0 g, 24.9 mmol, 1.0 eq). The reaction mixture was stirred at rt for 8 h, then partitioned between DCM (100.0 mL) and water (100.0 mL). The organic layer was concentrated and purified by chromatography on silica gel (EA/PE=1/1, v/v) to afford ethyl 6-chloro-[1,2,4]triazolo[4,3-a] pyridine-3-carboxylate (5.0 g, 89%).

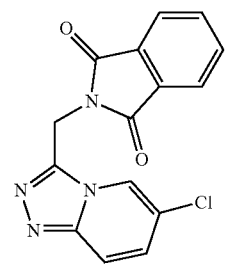

To a solution of ethyl 6-chloro-[1,2,4]triazolo[4,3-a]pyridine-3-carboxylate (1.9 g, 10.0 mmol, 1.0 eq) in THF (100.0 mL) was added NaBH$_4$ (756.0 mg, 20.0 mmol, 2.0 eq) portion-wise. LiCl (1.3 g, 30.0 mmol, 3.0 eq) in MeOH (20.0 mL) was then added to the mixture drop-wise at 0° C. The mixture was stirred at 50° C. for 30 min under N2, then quenched with 1 M HCl and neutralized with Na$_2$CO$_3$ to pH 9. The mixture was extracted with EtOAc (100.0 mL×3). The combined organic layers were washed with brine, dried and concentrated to afford (6-chloro-[1,2,4]triazolo[4,3-a]pyridin-3-yl)methanol (1.0 g, 60%).

To a solution of (6-chloro-[1,2,4]triazolo[4,3-a]pyridin-3-yl)methanol (459.0 mg, 2.5 mmol, 1.0 eq) in THF (20.0 mL) were added PPh$_3$ (984.0 mg, 3.8 mmol, 1.5 eq) and DIAD (758.0 mg, 3.8 mmol, 1.5 eq) at 0° C. The mixture was stirred at 0° C. for 30 min under N$_2$, then isoindoline-1,3-dione (551.0 mg, 3.8 mmol, 1.5 eq) was added. The mixture was stirred overnight, then partitioned between EtOAc (20.0 mL) and water (20.0 mL). The organic layer was concentrated and purified by chromatography on silica gel (MeOH/DCM=1/50, v/v) to afford 2-((6-chloro-[1,2,4]triazolo[4,3-a]pyridin-3-yl)methyl)isoindoline-1,3-dione (190.0 mg, 24%).

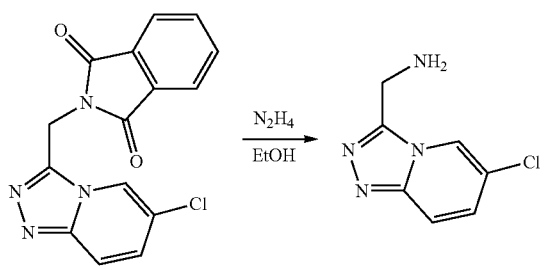 [SMILES: "EtOH" ; O=C1c2ccccc2C(=O)N1Cc1nnc2ccc(Cl)cn12 ; "N2H4" ; NCc1nnc2ccc(Cl)cn12]

To a solution of 2-((6-chloro-[1,2,4]triazolo[4,3-a]pyridin-3-yl)methyl) isoindoline-1,3-dione (190.0 mg, 0.6 mmol, 1.0 eq) in EtOH (20.0 mL) was added NH$_2$NH$_2$.H$_2$O (300.0 mg, 85%, 6.0 mmol, 10.0 eq). The mixture was stirred under reflux for 5 h under N$_2$, then cooled and concentrated. The residue was partitioned between DCM (20.0 mL) and water (20.0 mL). The organic layer was separated and concentrated to afford (6-chloro-[1,2,4]triazolo[4,3-a] pyridin-3-yl)methanamine (80.0 mg, 37%) which was used in the next step without further purification.

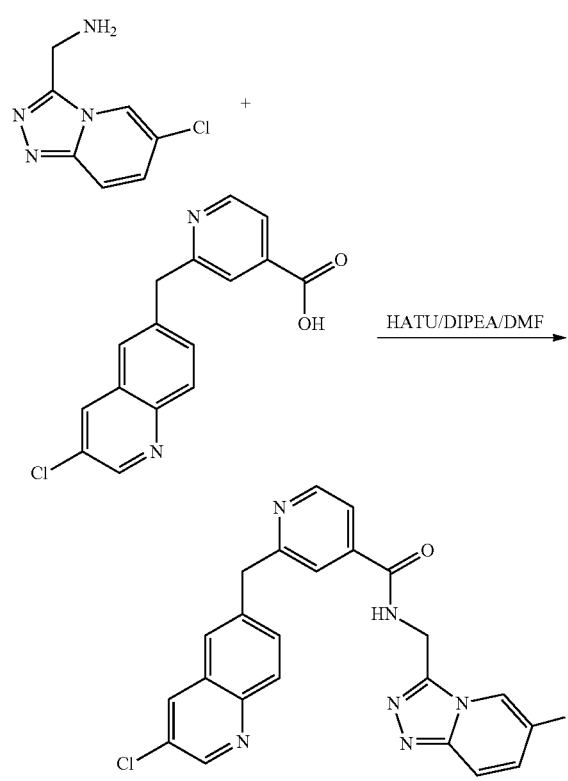

To a solution of (6-chloro-[1,2,4]triazolo[4,3-a]pyridin-3-yl)methanamine (80.0 mg, 0.4 mmol, 1.0 eq) and 2-((3-chloroquinolin-6-yl)methyl)isonicotinic acid (132.0 mg, 0.44 mmol, 1.0 eq) in DMF (10.0 mL) were added HATU (201.0 mg, 0.53 mmol, 1.2 eq) and DIEA (0.19 mL, 1.32 mmol, 3.0 eq). The mixture was stirred at rt overnight, then EA (20.0 mL) and water (20.0 mL) were added. The organic layer was washed with water 5 times, dried, and concentrated. The resulting residue was purified on Prep-TLC to provide N-((6-chloro-[1,2,4]triazolo[4,3-a] pyridin-3-yl)methyl)-2-((3-chloroquinolin-6-yl)methyl)isonicotinamide (90.0 mg, 50%). $^1$H NMR (DMSO-d$_6$, 400 MHz): δ 9.53 (s, 1H), 8.87 (s, 1H), 8.82 (s, 1H), 8.65 (d, 1H), 8.51 (s, 1H), 7.96 (d, 1H), 7.84 (t, 2H), 7.77 (s, 1H), 7.73 (d, 1H), 7.63 (d, 1H), 7.45 (d, 1H), 5.0 (d, 2H), 4.37 (s, 2H). LRMS (M+H$^+$) m/z calculated 463.1, found 463.4.

Example 155: Preparation of 2-((3-chloroquinolin-6-yl)methyl)-N-((5-methyl-[1,2,3]triazolo[1,5-a]pyridin-3-yl)methyl)isonicotinamide

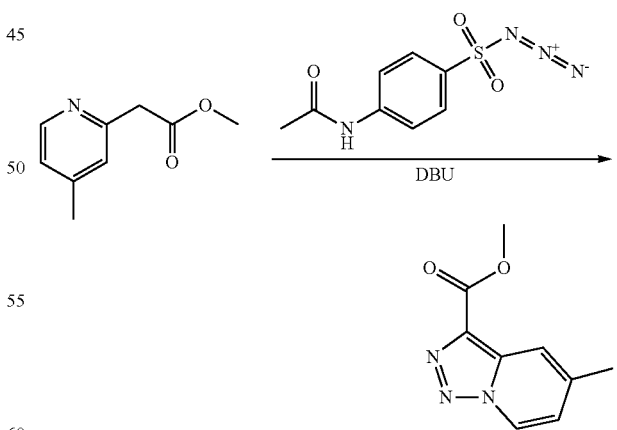

A hexane solution of n-BuLi (1.5 M, 50 mL, 75.0 mmol) was added to a solution of 2,4-dimethylpyridine (6.8 g, 63.0 mmol) in dry THF (100.0 mL) at −78° C. with stirring under N$_2$ atmosphere. A solution of dimethyl carbonate (5.7 g, 63.0 mmol) in dry THF (40.0 mL) was added to the mixture at −78° C. The reaction mixture was slowly warmed to rt, then acidified with 3N HCl to pH 6-7 and concentrated. The residual was extracted with DCM (100 mL×3) and the combined organic layers were concentrated. The resulting residue was purified by chromatography on silica gel (PE:EA=20:1, v/v) to afford methyl 2-(4-methylpyridin-2-yl)acetate (3.3 g, 32%).

To a solution of methyl 2-(4-methylpyridin-2-yl)acetate (1.0 g, 6.1 mmol) and DBU (0.96 ml, 6.7 mmol) in dry acetonitrile (20 mL), was added p-ABSA (1.5 g, 6.4 mmol) at rt in small portions. The resulting solution was stirred overnight and concentrated. The residue was dissolved into 50 mL of DCM, washed with water and brine, dried and concentrated. The resulting residue was purified by chromatography on silica gel (PE:EA=3:1, v/v) to provide methyl 5-methyl-[1,2,3]triazolo[1,5-a]pyridine-3-carboxylate (1.16 g, 91%).

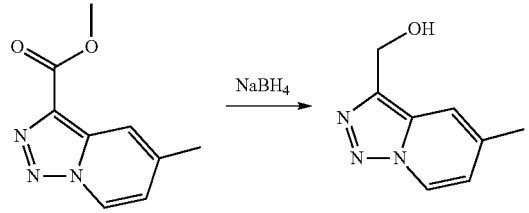

To a solution of methyl 5-methyl-[1,2,3]triazolo[1,5-a]pyridine-3-carboxylate (1.16 g, 6.1 mmol, 1.0 eq) in THF (120.0 mL) was added NaBH$_4$ (2.3 g, 60.7 mmol, 10.0 eq) in portions. LiCl (2.6 g, 60.7 mmol, 10.0 eq) in MeOH (20 mL) was added to the mixture dropwise at 0° C. The reaction mixture was stirred at 50° C. for 30 min under N$_2$, then quenched with 1 M HCl and neutralized with Na$_2$CO$_3$ to pH 9. The mixture was extracted with EtOAc (100 mL×3). The combined organic layers were washed with brine, dried and concentrated to afford (5-methyl-[1,2,3]triazolo[1,5-a]pyridin-3-yl)methanol (600.0 mg, 61%).

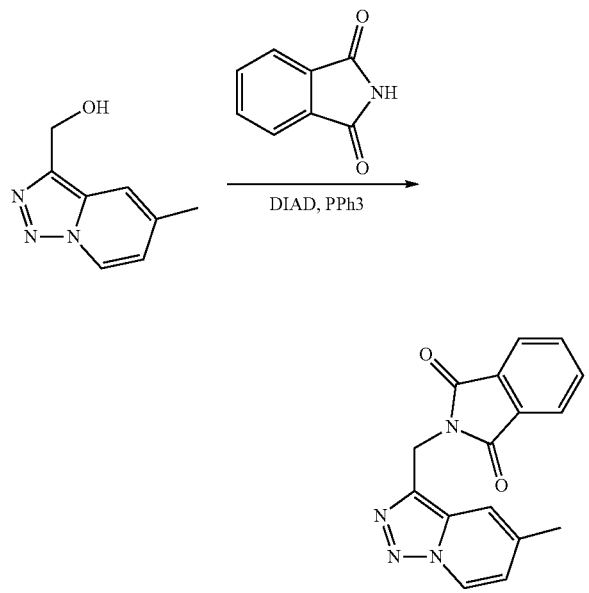

To a solution of (5-methyl-[1,2,3]triazolo[1,5-a]pyridin-3-yl)methanol (160.0 mg, 1.0 mmol, 1.0 eq) in THF (4.0 mL) were added PPh$_3$ (393.0 mg, 1.5 mmol, 1.5 eq) and DIAD (303.0 mg, 1.5 mmol, 1.5 eq), followed by isoindoline-1,3-dione (221.0 mg, 1.5 mmol, 1.5 eq). The mixture was stirred at 100° C. under microwave irradiation for 100 min, and then partitioned between EtOAc (100 mL) and water (100 mL). The organic layer was separated and concentrated. The resulting residue was purified by chromatography on silica gel (MeOH/DCM=1/50, v/v) to afford 2-(5-methyl-[1,2,3]triazolo[1,5-a]pyridin-3-yl)isoindoline-1,3-dione (25.0 mg, 9%).

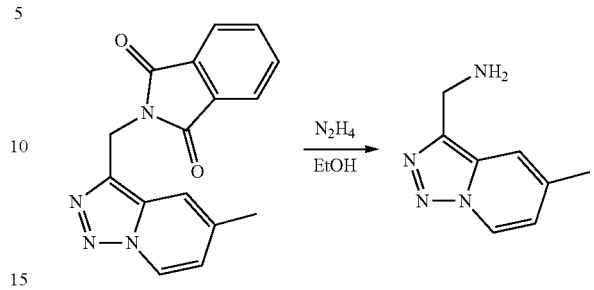

To a solution of 2-(5-methyl-[1,2,3]triazolo[1,5-a]pyridine-3-yl)isoindoline-1,3-dione (25.0 mg, 0.086 mmol, 1.0 eq) in EtOH (2.0 mL) was added NH$_2$NH$_2$.H$_2$O (43.0 mg, 85%, 0.86 mmol, 10.0 eq). The mixture was stirred under reflux for 5 h, then cooled and concentrated. The resulting residue was partitioned between DCM (100 mL) and water (100 mL). The organic layer was separated and concentrated to afford 5-methyl-[1,2,3]triazolo[1,5-a]pyridin-3-amine (10.0 mg, 79%) which was used into the next step without further purification.

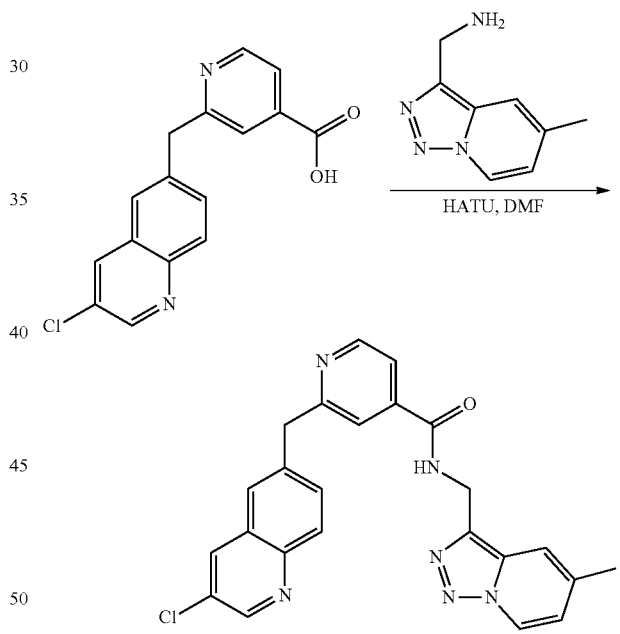

To a solution of 5-methyl-[1,2,3]triazolo[1,5-a]pyridin-3-amine (12.0 mg, 0.074 mmol, 1.0 eq) and 2-((3-chloroquinolin-6-yl)methyl)isonicotinic acid (12.0 mg, 0.037 mmol, 0.5 eq) in DMF (4.0 mL) were added HATU (42.0 mg, 0.1 mmol, 1.5 eq) and DIEA (22.0 mg, 0.2 mmol, 3.0 eq). The mixture was stirred at rt overnight, and then EA (20.0 mL) and water (20.0 mL) were added. The organic layer was separated, dried and concentrated. The resulting residue was purified on Prep-TLC to provide 2-((3-chloroquinolin-6-yl)methyl)-N-((5-methyl-[1,2,3]triazolo[1,5-a]pyridin-3-yl)methyl) isonicotinamide (9.0 mg, 50%) as a white solid. 1H NMR (400 MHz, DMSO-d6) δ 9.39 (s, 1H), 8.91 (d, J=7.0 Hz, 1H), 8.83 (d, J=2.4 Hz, 1H), 8.63 (d, J=5.0 Hz, 1H), 8.51 (d, J=2.4 Hz, 1H), 7.97 (d, J=8.7 Hz, 1H), 7.84 (s, 1H), 7.77 (s, 1H), 7.72 (dd, J=8.7, 2.0 Hz, 2H), 7.66-7.59 (m, 1H), 7.00

(dd, J=7.2, 1.6 Hz, 1H), 4.79 (d, J=5.6 Hz, 2H), 4.36 (s, 2H), 2.37 (s, 3H). LRMS (M+H⁺) m/z calculated 443.1, found 443.4.

Example 156: Preparation of 2-((3-chloroquinolin-6-yl)methyl)-N-((7-methylimidazo [1,5-a]pyridin-1-yl)methyl)isonicotinamide

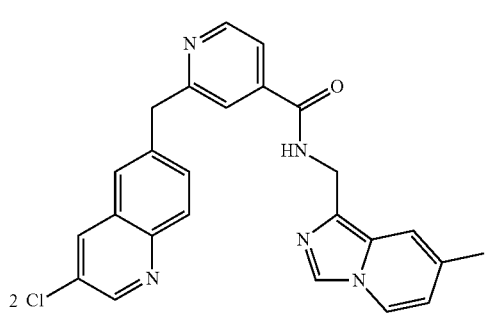 [SMILES: Cc1ccn2cnc(CNC(=O)c3ccnc(Cc4ccc5ncc(Cl)cc5c4)c3)c2c1]

2-((3-chloroquinolin-6-yl)methyl)-N-((7-methylimidazo [1,5-a]pyridin-1-yl) methyl)isonicotinamide (5.0 mg) was prepared as described for 2-((3-chloroquinolin-6-yl) methyl)-N-((5-methyl-[1,2,3] triazolo[1,5-a]pyridin-3-yl) methyl)isonicotinamide. ¹H NMR (CDCl₃, 400 MHz) δ 8.75 (d, 1H), 8.67 (d, 1H), 8.52 (s, 1H), 8.10 (d, 1H), 7.99 (d, 1H), 7.93 (d, 1H), 7.80 (s, 1H), 7.68 (s, 2H), 7.65 (d, 1H), 7.59 (s, 1H), 6.77 (d, 1H), 4.97 (d, 2H), 4.38 (s, 2H), 2.39 (s, 3H). LRMS (M+H⁺) m/z calculated 442.1, found 442.4.

Example 157: Preparation of N-((6-chloroimidazo [1,2-a]pyridin-3-yl)methyl)-2-((3-chloroquinolin-6-yl)methyl)isonicotinamide

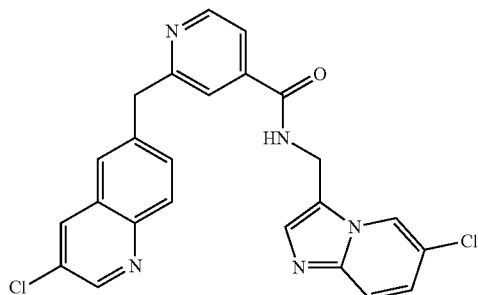

N-((6-chloroimidazo[1,2-a]pyridin-3-yl)methyl)-2-((3-chloroquinolin-6-yl) methyl)isonicotinamide (1.8 mg) was prepared as described for 2-((3-chloroquinolin-6-yl) methyl)-N-((5-methyl-[1,2,3] triazolo[1,5-a]pyridin-3-yl) methyl)isonicotinamide. ¹H NMR 1H NMR (400 MHz, CD₃OD): δ 8.65 (d, 1H), 8.67 (s, 1H), 8.52 (d, 1H), 8.24 (d, 1H), 7.86 (d, 1H), 7.68 (s, 1H), 7.61 (d, 2H), 7.59 (d, 1H), 7.52 (d, 2H), 7.46 (d, 1H), 7.24 (d, 1H), 4.31 (s, 2H), 3.07 (s, 2H). LRMS (M+H⁺) m/z calculated 462.1, found 462.4.

Example 158: Preparation of 2-((3-chloroquinolin-6-yl)methyl)-N-((3,7-dimethylimidazo [1,5-a]pyridin-1-yl)methyl)isonicotinamide

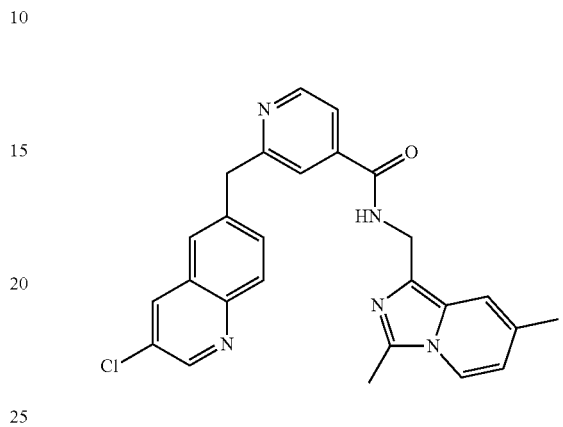

2-((3-chloroquinolin-6-yl)methyl)-N-((3,7-dimethylimidazo [1,5-a]pyridin-1-yl)methyl)isonicotinamide (10.2 mg) was prepared as described for 2-((3-chloroquinolin-6-yl) methyl)-N-((5-methyl-[1,2,3] triazolo[1,5-a]pyridin-3-yl) methyl)isonicotinamide. ¹H NMR (MeOD, 400 MHz) δ=8.24 (d, 1H), 8.57-8.61 (m, 1H), 8.16 (s, 1H), 7.81 (d, 1H), 7.58-7.70 (m, 5H), 7.23 (s, 1H), 6.53 (d, 1H), 4.65 (s, 2H), 4.33 (s, 2H), 2.45 (s, 3H), 2.19 (s, 3H). LCMS (M+H⁺) m/z calculated 456.2, found 456.5.

Example 159: Preparation of N-((3,7-dimethylimidazo[1,5-a]pyridin-1-yl)methyl)-2-((3-(trifluoromethyl)quinolin-6-yl)methyl)isonicotinamide

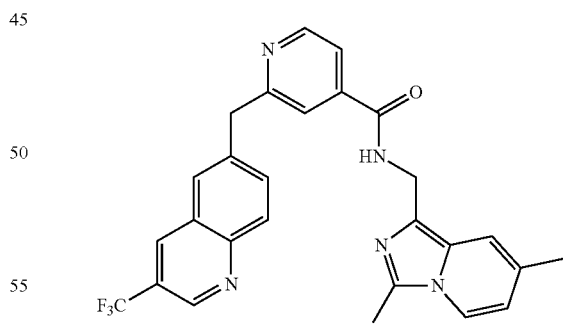

2-((3-chloroquinolin-6-yl)methyl)-N-((3,7-dimethylimidazo [1,5-a]pyridin-1-yl)methyl)isonicotinamide (14.5 mg) was prepared as described for 2-((3-chloroquinolin-6-yl) methyl)-N-((5-methyl-[1,2,3] triazolo[1,5-a]pyridin-3-yl) methyl)isonicotinamide. ¹H NMR (MeOD, 400 MHz) δ=8.97 (s, 1H), 8.58-8.62 (m, 2H), 8.00 (d, 1H), 7.92 (s, 1H), 7.80 (d, 1H), 7.92-7.73 (m, 2H), 7.62 (d, 1H), 7.28 (s, 1H), 6.46 (d, 1H), 4.68 (s, 2H), 4.40 (s, 2H), 2.50 (s, 3H), 2.22 (s, 3H). LCMS (M+H+) m/z calculated 490.2, found 490.7.

Example 160: Preparation of 2-((3-chloroquinolin-6-yl)methyl)-N-((7-methyl-3-(trifluoromethyl)imidazo[1,5-a]pyridin-1-yl)methyl)isonicotinamide

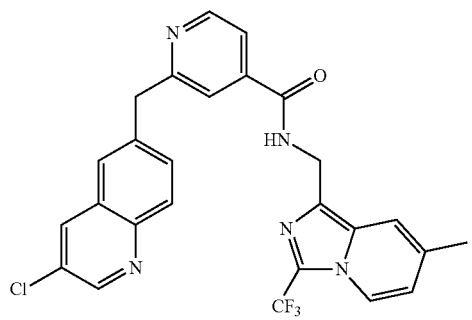 [SMILES: Cc1ccn2c(C(F)(F)F)nc(CNC(=O)c3ccnc(Cc4ccc5ncc(Cl)cc5c4)c3)c2c1]

2-((3-chloroquinolin-6-yl)methyl)-N-((7-methyl-3-(trifluoromethyl)imidazo [1,5-a]pyridin-1-yl)methyl)isonicotinamide (6.9 mg) was prepared as described for 2-((3-chloroquinolin-6-yl) methyl)-N-((5-methyl-[1,2,3] triazolo [1,5-a]pyridin-3-yl)methyl) isonicotinamide. $^1$H NMR (MeOD, 400 MHz) δ=8.96 (s, 1H), 8.88 (d, 1H), 8.58 (s, 1H), 8.17-8.22 (m, 3H), 8.07 (d, 1H), 7.94 (s, 1H), 7.83 (d, 1H), 7.63 (s, 1H), 6.83 (d, 1H), 4.80 (s, 2H), 4.69 (s, 2H), 2.36 (s, 3H). LCMS (M+H$^+$) m/z calculated 510.1, found 510.5.

Example 161: Preparation of 2-((3-chloroquinolin-6-yl)methyl)-N-((6-methyl-2,3-dihydro-1H-pyrrolo[2,3-b]pyridin-5-yl)methyl)isonicotinamide

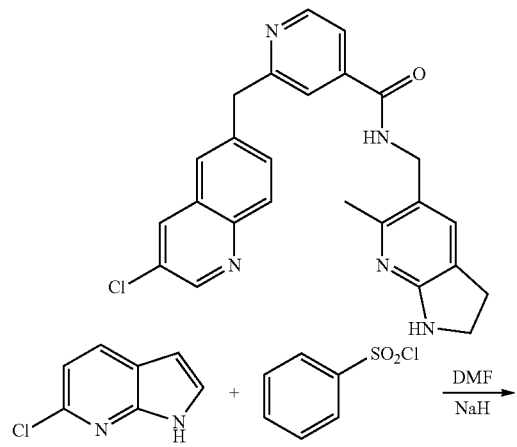

To a solution of 6-chloro-1H-pyrrolo[2,3-b]pyridine (1.5 g, 10 mmol) in DMF (20 mL) was added NaH (600.0 mg, 15 mmol, 60 percent dispersion in mineral oil) at 0° C. and the reaction mixture was stirred at 0° C. for 30 min. Then benzenesulfonyl chloride (1.9 g, 11 mmol,) was added drop-wise. The mixture was stirred at rt for 2 h, then diluted EtOAc (50.0 mL) washed with brine (30 mL×3), dried over Na$_2$SO$_4$, and filtered. The filtrate was concentrated under vacuum and the residue was purified by chromatography on silica gel (petroleum ether/EtOAc=50/1, v/v) to afford 6-chloro-1-(phenylsulfonyl)-1H-pyrrolo[2,3-b] pyridine (2.55 g, 87% yield).

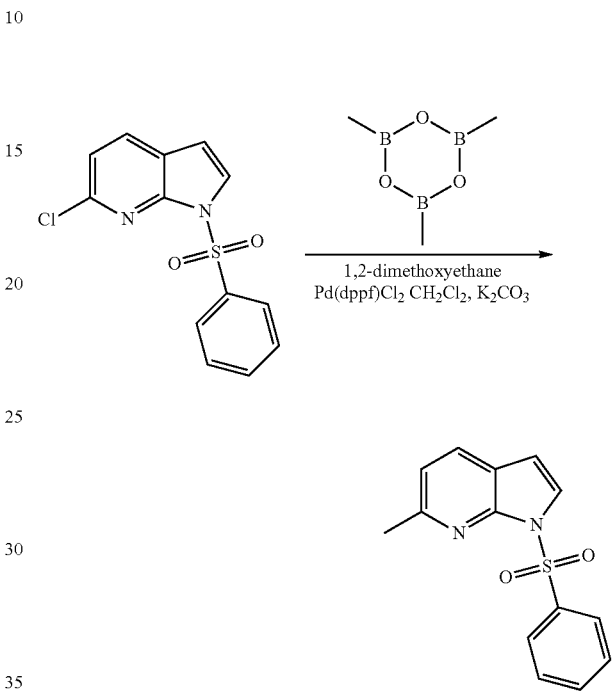

The mixture of 6-chloro-1-(phenylsulfonyl)-1H-pyrrolo[2,3-b]pyridine (1.2 g, 4.1 mmol), 2,4,6-trimethyl-1,3,5,2,4,6-trioxatriborinane (619.0 mg, 4.9 mmol), K$_2$CO$_3$ (1.7 g, 12.3 mmol), [1,1'-Bis(diphenylphosphino)ferrocene]-dichloropalladium (II) complex with dichloromethane (171.0 mg, 0.21 mmol) and 1,2-dimethoxyethane (10.0 mL) was stirred at 120° C. for 2 h under microwave irradiation under N$_2$, then cooled and diluted with EtOAc (30 mL), washed with brine (8 mL×3), dried over anhydrous Na$_2$SO$_4$ and concentrated under reduced pressure. The resulting residue was purified by chromatography on silica gel (petroleum ether/EtOAc=50/1, v/v) to provide 6-methyl-1-(phenylsulfonyl)-1H-pyrrolo[2,3-b]pyridine (1.1 g, 95% yield). $^1$H NMR (400 MHz, CDCl$_3$): δ 8.24 (s, 1H), 8.23 (s, 1H), 7.69-7.45 (m, 5H), 7.01 (d, J=8.0 Hz, 1H), 6.52 (d, J=3.6 Hz, 1H), 2.62 (s, 3H).

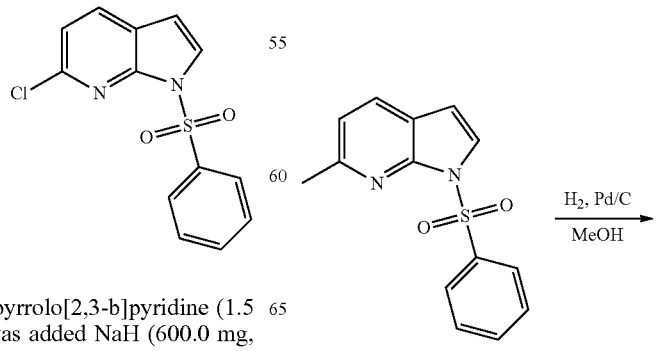

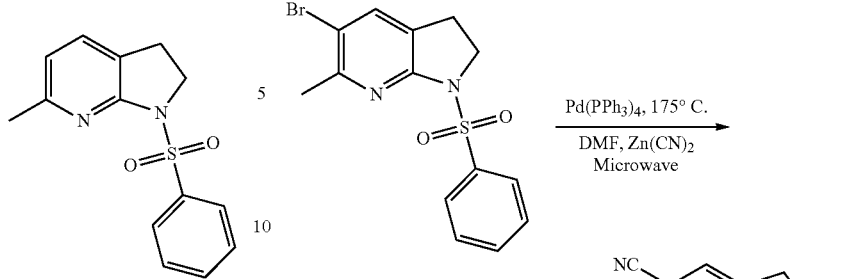

To a solution of 6-methyl-1-(phenylsulfonyl)-1H-pyrrolo[2,3-b]pyridine (1.1 g, 3.9 mmol) in MeOH (15.0 mL) was added Pd/C (150.0 mg). The mixture was degassed with H₂ twice and stirred at rt overnight under H₂ atmosphere overnight, then filtered through a pad of celite. The filtrate was concentrated to afford 6-methyl-1-(phenylsulfonyl)-2,3-dihydro-1H-pyrrolo[2,3-b]pyridine (820.0 mg, 77% yield). $^1$H NMR (400 MHz, CDCl$_3$): δ 8.15 (s, 1H), 8.13 (d, 1H), 7.55-7.44 (m, 3H), 7.21 (d, 1H), 6.65 (d, J=7.2 Hz, 1H), 4.04 (t, 2H), 2.97 (t, 2H), 2.46 (s, 3H).

To a solution of 6-methyl-1-(phenylsulfonyl)-2,3-dihydro-1H-pyrrolo[2,3-b]pyridine (820.0 mg, 3.0 mmol) in CH₂Cl₂ (10.0 mL) was added N-bromosuccinimide (532.0 mg, 3.0 mmol). The mixture was stirred at rt overnight, then concentrated under reduced pressure. The resulting residue was purified by chromatography on silica gel (petroleum ether/EtOAc=40/1, v/v) to provide 5-bromo-6-methyl-1-(phenylsulfonyl)-2,3-dihydro-1H-pyrrolo[2,3-b]pyridine (900.0 mg, 85%). $^1$H NMR (400 MHz, CDCl$_3$): δ 8.11 (d, 2H), 7.57 (t, 1H), 7.48 (t, 2H), 7.43 (s, 1H), 4.08 (t, 2H), 3.00 (t, 2H), 2.55 (s, 3H).

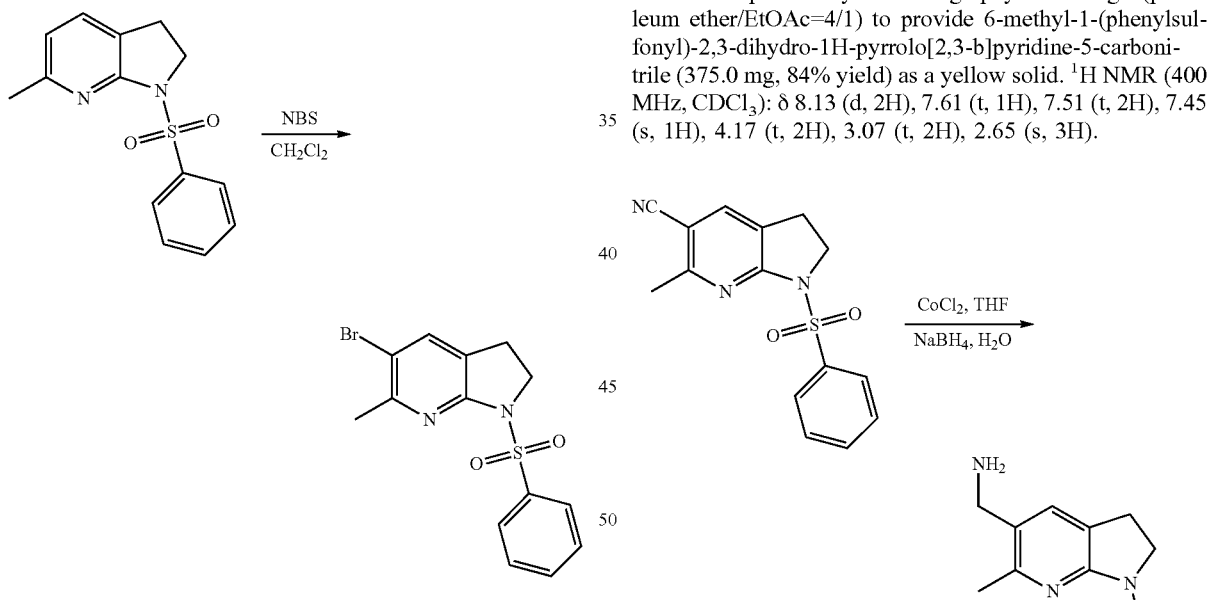

A mixture of 5-bromo-6-methyl-1-(phenylsulfonyl)-2,3-dihydro-1H-pyrrolo[2,3-b]pyridine (529.0 mg, 1.5 mmol), Zn(CN)₂ (258.0 mg, 2.2 mmol), Pd(PPh₃)₄ (347.0 mg, 0.3 mmol) in DMF (4.0 mL) was stirred at 175° C. under microwave irradiation for 30 min, then cooled to rt, diluted with EtOAc (20.0 mL), washed with brine (12 mL×3), dried over anhydrous Na₂SO₄ and concentrated. The resulting residue was purified by chromatography on silica gel (petroleum ether/EtOAc=4/1) to provide 6-methyl-1-(phenylsulfonyl)-2,3-dihydro-1H-pyrrolo[2,3-b]pyridine-5-carbonitrile (375.0 mg, 84% yield) as a yellow solid. $^1$H NMR (400 MHz, CDCl$_3$): δ 8.13 (d, 2H), 7.61 (t, 1H), 7.51 (t, 2H), 7.45 (s, 1H), 4.17 (t, 2H), 3.07 (t, 2H), 2.65 (s, 3H).

To a solution of 6-methyl-1-(phenylsulfonyl)-2,3-dihydro-1H-pyrrolo[2,3-b]pyridine-5-carbonitrile (360.0 mg, 1.2 mmol) in THF (4.0 mL) and H₂O (2.0 mL) were added NaBH₄ (137.0 mg, 3.6 mmol) and CoCl₂ (313 mg, 2.41 mmol). The mixture was stirred at rt for 2 h, then diluted with EtOAc (30.0 mL), washed with brine (15 mL×3), dried over anhydrous Na₂SO₄ and concentrated under reduced pressure to provide (6-methyl-1-(phenylsulfonyl)-2,3-dihydro-1H-pyrrolo[2,3-b]pyridin-5-yl)methanamine (290 mg, 80%).

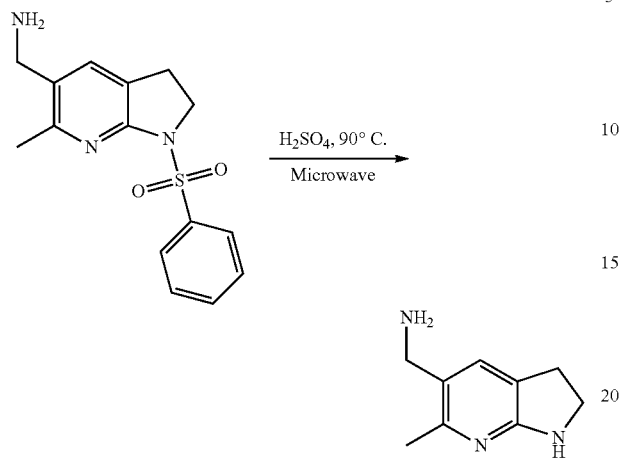

In a microwave tube with a magnetic stirrer was placed (6-methyl-1-(phenylsulfonyl)-2,3-dihydro-1H-pyrrolo[2,3-b]pyridin-5-yl)methanamine (270.0 mg, 0.9 mmol) and H₂SO₄ (3.0 mL). The mixture was stirred at 90° C. for 10 min under microwave irradiation. After cooling to rt, the mixture was diluted with ice-water (16.0 mL), washed with diethyl ether (10 mL×2), basified with NaOH and extracted with EtOAc (15 mL×3). The combined organic layers were dried over anhydrous Na₂SO₄ and concentrated under reduced pressure to provide (6-methyl-2,3-dihydro-1H-pyrrolo[2,3-b] pyridin-5-yl)methanamine (120.0 mg, 83%).

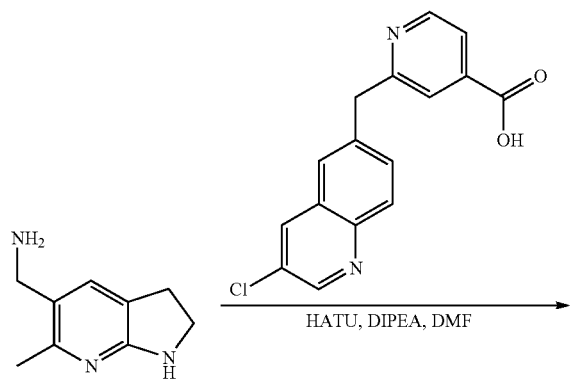

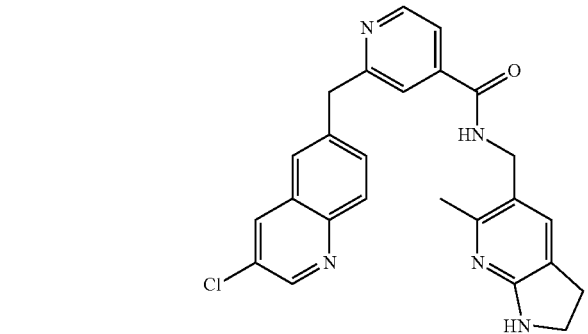

To a solution of 2-((3-chloroquinolin-6-yl)methyl)isonicotinic acid (36.0 mg, 0.1 mmol) in DMF (2.0 mL) was added HATU (91.0 mg, 0.24 mmol), followed by (6-methyl-2,3-dihydro-1H-pyrrolo[2,3-b]pyridin-5-yl)methanamine (20.0 mg, 0.12 mmol) and DIPEA (31 mg, 0.24 mmol). The reaction mixture was stirred at rt for 3 h, then diluted with EtOAc (15 mL), washed with brine (8 mL×3), dried over anhydrous Na₂SO₄ and concentrated under reduced pressure. The resulting residue was purified on Prep-HPLC to provide 2-((3-chloroquinolin-6-yl)methyl)-N-((6-methyl-2,3-dihydro-1H-pyrrolo[2,3-b] pyridin-5-yl)methyl)isonicotinamide (27.0 mg, 40% yield). $^1$H NMR (CD₃OD, 400 MHz): δ 8.76 (s, 1H), 8.69 (s, 1H), 8.35 (s, 1H), 7.97 (d, J=8.8 Hz, 1H), 7.82-7.69 (m, 4H), 7.55 (s, 1H), 4.46 (s, 2H), 4.38 (s, 2H), 3.85 (t, J=8.4 Hz, 2H), 3.13 (t, J=8.4 Hz, 2H), 2.46 (s, 3H). LRMS (M+H⁺) m/z calculated 444.2, found 444.4.

Example 162: Preparation of N-((6-methyl-2,3-dihydro-1H-pyrrolo[2,3-b]pyridin-5-yl)methyl)-2-((3-(trifluoromethyl)quinolin-6-yl)methyl)isonicotinamide

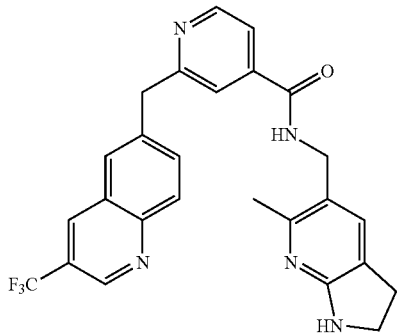 [SMILES: Cc1nc2c(cc1CNC(=O)c1ccnc(Cc3ccc4ncc(C(F)(F)F)cc4c3)c1)CCN2]

N-((6-methyl-2,3-dihydro-1H-pyrrolo[2,3-b]pyridin-5-yl)methyl)-2-((3-(trifluoromethyl)quinolin-6-yl)methyl)isonicotinamide (36.2 mg) was prepared as described for 2-((3-chloroquinolin-6-yl)methyl)-N-((6-methyl-2,3-dihydro-1H-pyrrolo[2,3-b] pyridin-5-yl)methyl)isonicotinamide. $^1$H NMR (CDCl₃, 400 MHz): δ 9.04 (d, 1H), 8.68 (d, 1H), 8.37 (s, 1H), 8.10 (d, 1H), 7.78 (s, 1H), 7.75 (d, 1H), 7.57 (s, 1H), 7.42 (dd, 5.2 Hz, 1H), 7.15 (s, 1H), 6.18 (s, 1H), 4.46 (d, 2H), 4.41 (s, 2H), 3.61 (t, 2H), 3.00 (t, 2H), 2.36 (s, 3H). LRMS (M+H⁺) m/z calculated 478.2, found 478.5.

Example 163: Preparation of 2-((3-chloroquinolin-6-yl)methyl)-N-((2-methyl-6,7-dihydro-5H-pyrrolo[3,4-b]pyridin-3-yl)methyl)isonicotinamide

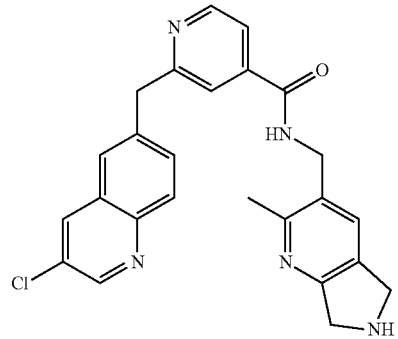 [SMILES: Cc1nc2c(cc1CNC(=O)c1ccnc(Cc3ccc4ncc(Cl)cc4c3)c1)CNC2]

2-((3-chloroquinolin-6-yl)methyl)-N-((2-methyl-6,7-dihydro-5H-pyrrolo[3,4-b]pyridin-3-yl)methyl)isonicotinamide (4.0 mg) was prepared as described for 2-((3-chloroquinolin-6-yl)methyl)-N-((6-methyl-2,3-dihydro-1H-pyrrolo[2,3-b] pyridin-5-yl)methyl)isonicotinamide. 1H NMR (CD3OD, 400 MHz): δ 8.76 (d, 1H), 8.63 (d, 1H), 8.36 (d, 1H), 7.96 (d, 1H), 7.61-7.80 (5H), 4.70 (d, 2H), 4.56 (d, 2H), 4.16 (s, 2H), 4.10 (s, 2H), 2.53 (d, 3H). LRMS (M+H$^+$) m/z calculated 443.2, found 443.6.

Example 164: Preparation of N-((2-methyl-6,7-dihydro-5H-pyrrolo[3,4-b]pyridin-3-yl) methyl)-2-((3-(trifluoromethyl)quinolin-6-yl)methyl)isonicotinamide

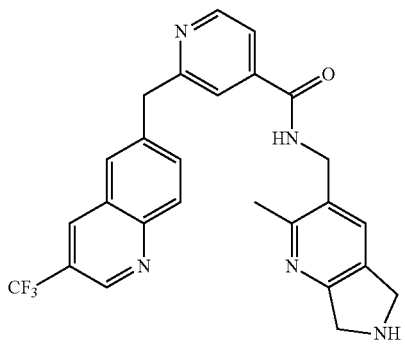 [SMILES: Cc1nc2c(cc1CNC(=O)c1ccnc(Cc3ccc4ncc(C(F)(F)F)cc4c3)c1)CNC2]

N-((2-methyl-6,7-dihydro-5H-pyrrolo[3,4-b]pyridin-3-yl) methyl)-2-((3-(trifluoromethyl)quinolin-6-yl)methyl) isonicotinamide (4.0 mg) was prepared as described for 2-((3-chloroquinolin-6-yl)methyl)-N-((6-methyl-2,3-dihydro-1H-pyrrolo[2,3-b]pyridin-5-yl)methyl)isonicotinamide. 1H NMR (CD3OD, 400 MHz): δ 9.04 (s, 1H), 8.72 (s, 1H), 8.65 (d, 1H), 8.07 (d, 1H), 8.02 (s, 1H), 7.87 (d, 1H), 7.80 (s, 1H), 7.74 (s, 1H), 7.68 (d, 2H), 4.60 (s, 4H), 4.48 (d, 4H), 2.60 (s, 3H). LRMS (M+H$^+$) m/z calculated 478.1, found 478.3.

Example 165: Preparation of N-((6-amino-2-methyl-4-(trifluoromethyl) pyridin-3-yl)methyl)-2-((3-chloroquinolin-6-yl)methyl)isonicotinamide

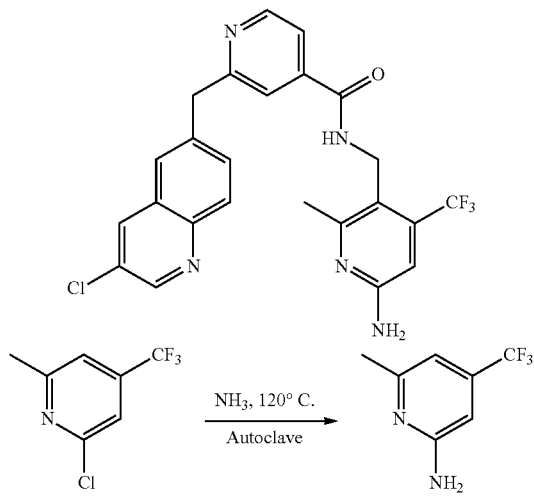

A mixture of 2-chloro-6-methyl-4-(trifluoromethyl)pyridine (5.0 g, 25.5 mmol) and ammonia hydroxide (80 mL) was heated in an autoclave at 120° C. for 3 days, then cooled and concentrated. The resulting residue was purified by chromatography on silica gel (EA/PE=1:3, v/v) to provide 6-methyl-4-(trifluoromethyl)pyridin-2-amine (0.87 g, 19.4%)

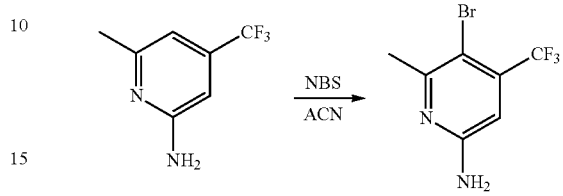

To a solution of 6-methyl-4-(trifluoromethyl)pyridin-2-amine (0.87 g, 5.0 mmol) in 25 mL of acetonitrile was added N-bromosuccinimide (900.0 mg, 5.5 mmol). The reaction mixture was stirred at rt under argon atmosphere for 5 h, then concentrated. The resulting residue was purified by chromatography on silica gel (EA:PE=1:10) to provide 5-bromo-6-methyl-4-(trifluoromethyl)pyridin-2-amine (1.03 g, 80.8%).

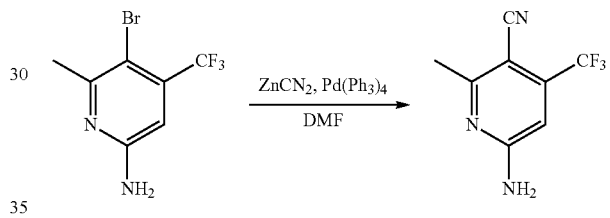

In a microwave tube with a magnetic stirrer were placed 5-bromo-6-methyl-4-(trifluoromethyl)pyridin-2-amine (870.0 mg, 3.4 mmol), CuCN (1.3 g mg, 15.4 mmol), Pd$_2$(dpa)$_3$ (320.0 mg, 0.34 mmol), dppf (380.0 mg, 0.7 mmol) and DMF (10 mL). The tube was stirred at 180° C. for 30 min under microwave irradiation. After cooling to rt, the mixture was diluted with EtOAc (50.0 mL), washed with brine (50.0 mL×3), dried over anhydrous Na$_2$SO$_4$ and concentrated under reduced pressure. The resulting residue was purified by chromatography on silica gel (PE:EA=1:5) to provide 6-amino-2-methyl-4-(trifluoromethyl) nicotinonitrile (600.0 mg, 87.4%)

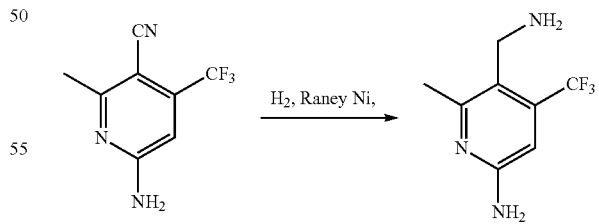

A mixture of 6-amino-2-methyl-4-(trifluoromethyl) nicotinonitrile (25.0 mg, 0.12 mmol) and Raney Ni (20.0 mg) in MeOH (5.0 ml) was stirred at rt under H$_2$ (1 atm) overnight, then filtered. The filtrate was concentrated under vacuum and the residue was purified by chromatography on silica gel (DCM/MeOH=10/1, v/v) to provide 5-(aminomethyl)-6-methyl-4-(trifluoromethyl)pyridin-2-amine (15.0 mg, 59.1%).

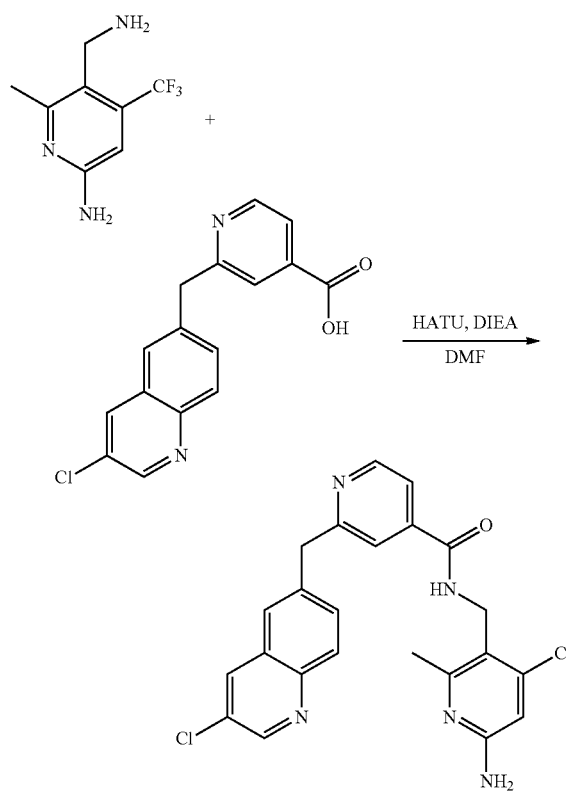

To a solution of 5-(aminomethyl)-6-methyl-4-(trifluoromethyl)pyridin-2-amine (22.0 mg, crude) in DMF (2 mL) was added HATU (35.0 mg, 0.9 mmol), followed by 2-((3-chloroquinolin-6-yl)methyl)isonicotinic acid (15.0 mg, 0.07 mmol) and DIEA (20 mg, 0.17 mmol). The reaction mixture was stirred at rt for 1 h, then brine (20 mL) was added. The mixture was extracted with EA (20 mL×3). The combined organic layers were washed with brine, dried over $Na_2SO_4$, filtered and concentrated. The resulting residue was purified on Prep-TLC (DCM:MeOH=10:1) to provide N-((6-amino-2-methyl-4-(trifluoromethyl) pyridin-3-yl) methyl)-2-((3-chloroquinolin-6-yl)methyl)isonicotinamide (17.0 mg, 47.5%). $^1$H NMR (DMSO-d6, 400 MHz): δ 8.83 (s, 1H), 8.61 (d, 1H), 8.53 (s, 1H), 7.96 (d, 1H), 7.85 (s, 1H), 7.72 (s, 2H), 7.61 (s 1H), 7.34 (s 1H), 7.24 (s, 1H), 7.20 (s, 1H), 6.65 (s, 1H), 6.5 (br, 1H), 4.40 (s, 2H), 4.34 (s, 2H), 2.32 (s, 3H). LRMS (M+H$^+$) m/z calculated 486.1, found 486.4.

Example 166: Preparation of N-((6-amino-4-methoxy-2-methylpyridin-3-yl)methyl)-2-((3-chloroquinolin-6-yl)methyl)isonicotinamide

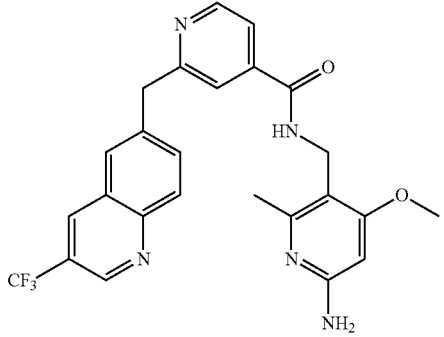 [SMILES: COc1cc(N)nc(C)c1CNC(=O)c1ccnc(Cc2ccc3ncc(C(F)(F)F)cc3c2)c1]

N-((6-amino-4-methoxy-2-methylpyridin-3-yl)methyl)-2-((3-chloroquinolin-6-yl)methyl)isonicotinamide (9.2 mg) was prepared as described for N-((6-amino-2-methyl-4-(trifluoromethyl) pyridin-3-yl) methyl)-2-((3-chloroquinolin-6-yl)methyl)isonicotinamide. $^1$H NMR (CD$_3$OD, 400 MHz): δ 8.72 (s, 1H), 8.61 (d, 1H), 8.31 (s, 1H), 7.93 (d, 1H), 7.69 (s, 1H), 7.68 (dd, 2H), 7.59 (d, 1H), 6.13 (s, 1H), 4.48 (s, 2H), 4.40 (s, 2H), 3.85 (s, 3H), 2.44 (s, 3H). LRMS (M+H$^+$) m/z calculated 448.1, found 448.5.

Example 167: Preparation of N-((6-amino-4-cyano-2-methylpyridin-3-yl)methyl)-2-((3-chloroquinolin-6-yl)methyl)isonicotinamide

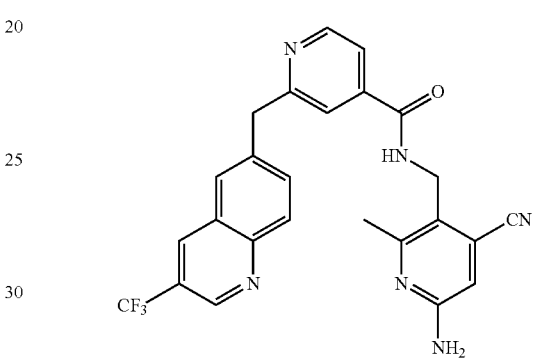

N-((6-amino-4-cyano-2-methylpyridin-3-yl)methyl)-2-((3-chloroquinolin-6-yl) methyl)isonicotinamide (1.0 mg) was prepared as described for N-((6-amino-2-methyl-4-(trifluoromethyl) pyridin-3-yl) methyl)-2-((3-chloroquinolin-6-yl)methyl)isonicotinamide. $^1$H NMR (CDCl$_3$, 400 MHz): δ 9.04 (d, 1H), 8.68 (d, 1H), 8.37 (s, 1H), 8.10 (d, 1H), 7.78 (s, 1H), 7.75 (d, 1H), 7.57 (s, 1H), 7.42 (dd, 5.2 Hz, 1H), 7.15 (s, 1H), 6.18 (s, 1H), 4.46 (d, 2H), 4.41 (s, 2H), 3.61 (t, 2H), 3.00 (t, 2H), 2.36 (s, 3H). LRMS (M+H$^+$) m/z calculated 443.2, found 443.5.

Example 168: Preparation of N-(4-(aminomethyl)benzyl)-2-((3-chloroquinolin-6-yl) methyl)isonicotinamide

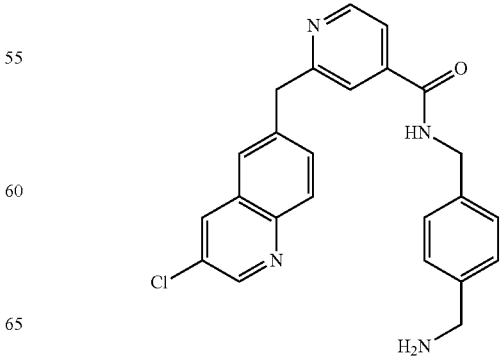

-continued

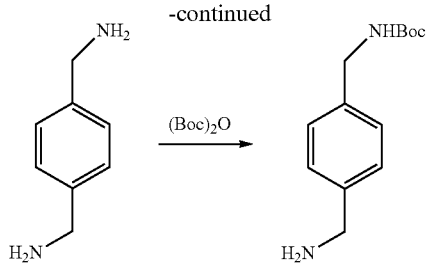

To a solution of 1,4-phenylenedimethanamine (1.4 g, 10.0 mmoL, 1.0 eq) in THF (10.0 mL) was added aq. NaOH (10.0 mL, 1 M, 1.0 eq.) and (Boc)$_2$O (1.1 g, 5.0 mmoL, 0.5 eq) at 10° C. for 4.0 h, then s extracted with EA (20.0 mL×3). The combined organic layers were dried over Na$_2$SO$_4$, filtered and concentrated under vacuum. The resulting residue was purified by chromatography on silica gel (MeOH/DCM=1/10, v/v) to afford tert-butyl 4-(aminomethyl) benzylcarbamate (826.0 mg, 35%).

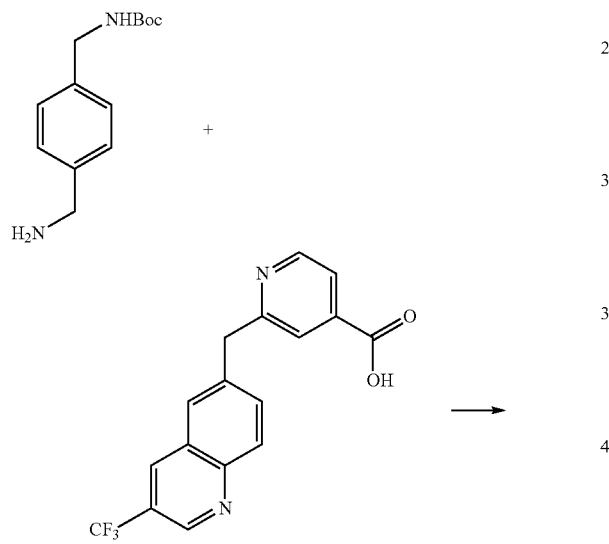

To a solution of 2-((3-chloroquinolin-6-yl)methyl)isonicotinic acid (29.0 mg, 1.0 mmoL, 1.0 eq)) in DMF (2.0 mL) was added tert-butyl 4-(aminomethyl)benzylcarbamate (24 mg, 1.0 mmol, 1.0 eq), followed by HATU (39 mg, 1.0 mmol, 1.0 eq), and DIEA (26 mg, 2.0 mmol, 2.0 eq). The reaction mixture was stirred at 20° C. for 4 h, and water (10.0 mL) was added. The mixture was extracted with DCM (10.0 mL×3). The combined organic layers were washed with water, dried over Na$_2$SO$_4$ and concentrated. The resulting residue was purified Prep-TLC to provide tert-butyl 4-((2-((3-chloroquinolin-6-yl)methyl)isonicotinamido) methyl) benzylcarbamate (45.0 mg, 88%).

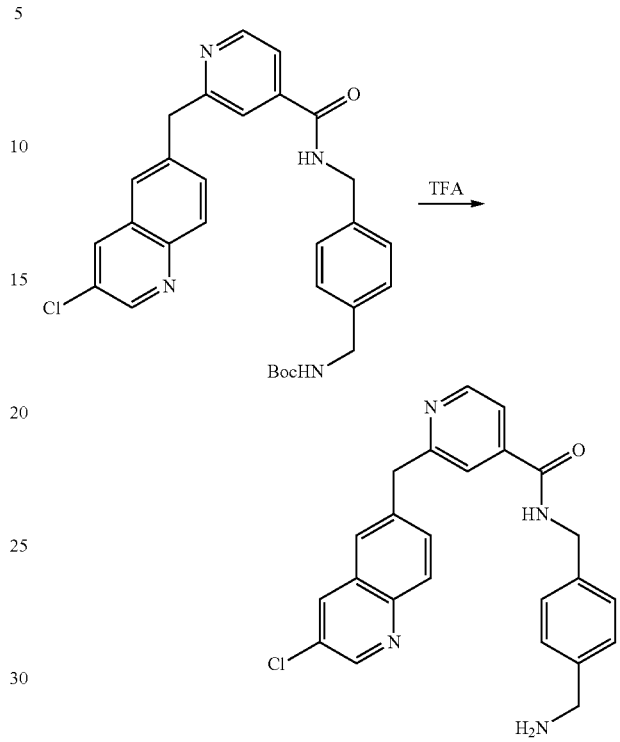

To a solution of (3-chloro-quinolin-6-yl)-methanol (45.0 mg, 0.9 mmoL, 1.0 eq) in DCM (5.0 mL) was added TFA (2.0 mL). The mixture was stirred at rt for 4 h, then concentrated under vacuum. The resulting residue was purified on Prep-HPLC to provide N-((6-amino-2-methylpyridin-3-yl)methyl)-2-((3-chloroquinolin-6-yl)methyl)isonicotinamide (31.0 mg, 86%).

$^1$H NMR (CD$_3$OD, 400 MHz): δ 8.79 (s, 1H), 8.75 (d, 1H), 8.39 (s, 1H), 8.00 (dd, 1H), 7.93 (s, 1H), 7.84-7.88 (m, 2H), 7.73 (d, 1H), 4.53-4.57 (m, 4H), 4.08 (s, 2H). LCMS (M+H$^+$) m/z calculated 417.1, found 417.7.

Example 169: Preparation of N-((6-(aminomethyl) pyridin-3-yl)methyl)-2-((3-chloroquinolin-6-yl) methyl)isonicotinamide

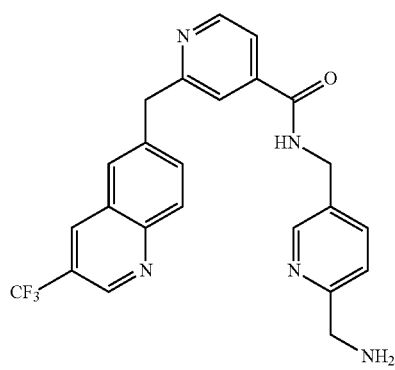 [SMILES: NCc1ccc(CNC(=O)c2ccnc(Cc3ccc4ncc(C(F)(F)F)cc4c3)c2)cn1]

N-((6-(aminomethyl)pyridin-3-yl)methyl)-2-((3-chloroquinolin-6-yl) methyl)isonicotinamide (20.7 mg) was prepared as described for N-(4-(aminomethyl) benzyl)-2-((3-chloroquinolin-6-yl) methyl)isonicotinamide. $^1$H NMR (CD$_3$OD, 400 MHz): δ 8.80 (s, 1H), 8.79 (d, 1H), 8.53 (d, 1H), 8.39 (s, 1H), 7.98-8.01 (m, 2H), 7.92 (d, 1H), 7.81-7.85 (m, 2H), 7.74 (d, 1H), 7.36 (d, 1H), 4.59 (s, 2H), 4.55 (s, 2H), 4.48 (s, 2H). LCMS (M+H+) m/z calculated 418.1, found 418.5.

Example 170: Preparation of N-((5-(aminomethyl)pyridin-2-yl)methyl)-2-((3-chloroquinolin-6-yl)methyl)isonicotinamide

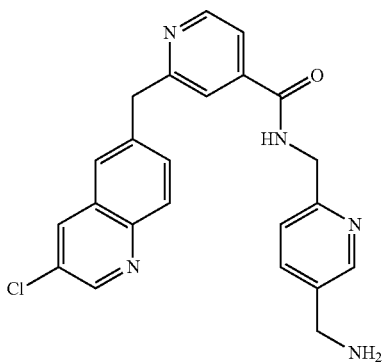 [SMILES: NCc1ccc(CNC(=O)c2ccnc(Cc3ccc4ncc(Cl)cc4c3)c2)nc1]

N-((5-(aminomethyl)pyridin-2-yl)methyl)-2-((3-chloroquinolin-6-yl) methyl)isonicotinamide (24.4 mg) was prepared as described for N-(4-(aminomethyl) benzyl)-2-((3-chloroquinolin-6-yl) methyl)isonicotinamide. $^1$H NMR (CD$_3$OD, 400 MHz): δ 8.81 (s, 1H), 8.79 (d, 1H), 8.63 (d, 1H), 8.41 (s, 1H), 8.02-8.06 (m, 3H), 7.93 (d, 1H), 7.86 (s, 1H), 7.74 (d, 1H), 7.53 (d, 1H), 4.78 (s, 2H), 4.54 (s, 2H), 4.45 (s, 2H). LCMS (M+H+) m/z calculated 418.1, found 418.5.

Example 171: Preparation of N-((6-(aminomethyl)-2,4-dimethylpyridin-3-yl)methyl)-2-((3-chloroquinolin-6-yl)methyl)isonicotinamide

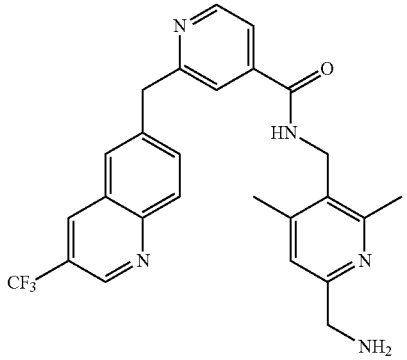 [SMILES: Cc1cc(CN)nc(C)c1CNC(=O)c1ccnc(Cc2ccc3ncc(C(F)(F)F)cc3c2)c1]

N-((6-(aminomethyl)-2,4-dimethylpyridin-3-yl)methyl)-2-((3-chloroquinolin-6-yl)methyl)isonicotinamide (7.0 mg) was prepared as described for N-(4-(aminomethyl) benzyl)-2-((3-chloroquinolin-6-yl) methyl)isonicotinamide. $^1$H NMR (CDCl$_3$, 400 MHz): δ 8.80 (s, 1H), 8.70 (s, 1H), 8.39 (s, 1H), 8.00 (d, 1H), 7.82 (d, 1H), 7.75 (d, 1H), 7.71 (d, 1H), 7.23 (s, 1H), 4.66 (s, 2H), 4.48 (s, 2H), 4.19 (s, 2H), 3.97 (s, 2H), 2.69 (s, 3H), 2.50 (s, 3H). LRMS (M+H$^+$) m/z calculated 446.2, found 446.5.

Example 172: Preparation of N-((6-(aminomethyl)-2,4-dimethylpyridin-3-yl)methyl)-2-((3-(trifluoromethyl)quinolin-6-yl)methyl)isonicotinamide

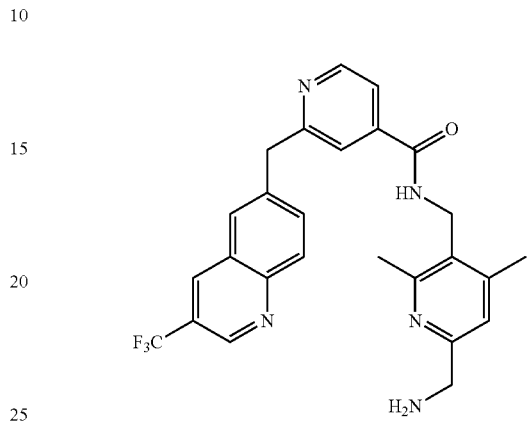

N-((6-(aminomethyl)-2,4-dimethylpyridin-3-yl)methyl)-2-((3-(trifluoromethyl)quinolin-6-yl)methyl)isonicotinamide (28.0 mg) was prepared as described for N-(4-(aminomethyl) benzyl)-2-((3-chloroquinolin-6-yl) methyl)isonicotinamide. $^1$H NMR (CDCl$_3$, 400 MHz): δ 9.06 (s, 1H), 8.72 (d, 1H), 8.09 (d, 1H), 8.0 (s, 1H), 7.88-7.91 (m, 3H), 4.68 (s, 2H), 4.55 (s, 2H), 4.26 (s, 2H), 2.74 (s, 3H), 2.55 (s, 3H). LRMS (M+H$^+$) m/z calculated 480.2, found 480.5.

Example 173: Preparation of N-((6-(1-aminoethyl)-2,4-dimethylpyridin-3-yl)methyl)-2-((3-chloroquinolin-6-yl)methyl)isonicotinamide

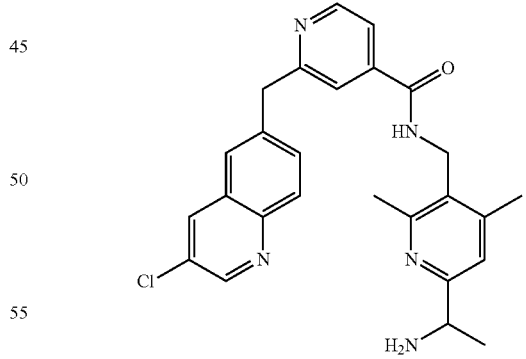

N-((6-(1-aminoethyl)-2,4-dimethylpyridin-3-yl)methyl)-2-((3-chloroquinolin-6-yl)methyl)isonicotinamide (1.2 mg) was prepared as described for N-(4-(aminomethyl) benzyl)-2-((3-chloroquinolin-6-yl) methyl)isonicotinamide. $^1$H NMR (CDCl$_3$, 400 MHz): δ 8.78 (s, 1H), 8.63 (s, 1H), 8.37 (s, 1H), 7.99 (s, 1H), 7.80 (s, 1H), 7.74 (s, 1H), 7.70 (s, 1H), 7.65 (s, 1H), 4.64 (s, 2H), 4.45 (s, 3H), 2.65 (s, 3H), 2.45 (s, 3H), 1.56 (s, 3H). LRMS (M+H$^+$) m/z calculated 460.2, found 460.6.

Example 174: Preparation of N-((6-(2-hydroxypropan-2-yl)-2,4-dimethylpyridin-3-yl) methyl)-2-((3-(trifluoromethyl)quinolin-6-yl)methyl)isonicotinamide

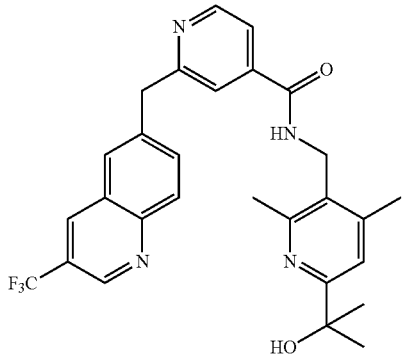 [SMILES: Cc1cc(C(C)(C)O)nc(C)c1CNC(=O)c1ccnc(Cc2ccc3ncc(C(F)(F)F)cc3c2)c1]

N-((6-(2-hydroxypropan-2-yl)-2,4-dimethylpyridin-3-yl) methyl)-2-((3-(trifluoromethyl)quinolin-6-yl)methyl)isonicotinamide (2.0 mg) was prepared as described for N-(4-(aminomethyl) benzyl)-2-((3-chloroquinolin-6-yl) methyl) isonicotinamide. $^1$H NMR (CDCl$_3$, 400 MHz): δ 9.13 (s, 1H), 8.88 (s, 1H), 8.86 (s, 1H), 8.63 (s, 1H), 8.04-8.07 (m, 2H), 7.95 (s, 1H), 7.74 (d, 1H), 7.59 (s, 1H), 5.52 (t, 1H), 4.74 (d, 2H), 4.51 (d, 2H), 4.39 (s, 2H), 2.67 (s, 3H), 2.62 (s, 3H), 1.23 (s, 6H). LRMS (M+H+) m/z calculated 509.2, found 509.6.

Example 175: Preparation of 2-((3-chloroquinolin-6-yl)methyl)-N-((4,6-dimethyl-2,3-dihydro-1H-pyrrolo[2,3-b]pyridin-5-yl)methyl)isonicotinamide

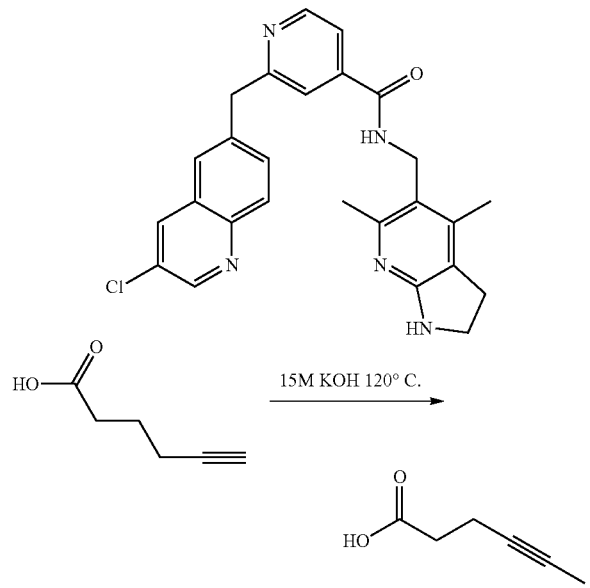

To a solution of KOH in H$_2$O (15 M, 10.0 mL) was added hex-5-ynoic acid (4.0 g, 35.7 mmol) dropwise under ice-bath and the reaction mixture was stirred under reflux under nitrogen for 4 h, then neutralized with 12 M HCl to pH 2, extracted with EtOAc (50.0 mL×3). The combined organic layers were dried over Na$_2$SO$_4$ and concentrated to afford 5-carboxypent-2-yn-1-ylium (3.2 g, 80%) as a white solid.

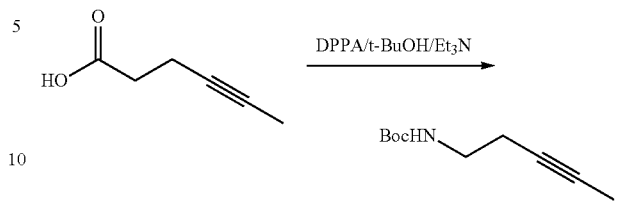

To a solution of 5-carboxypent-2-yn-1-ylium (3.8 g, 33.9 mmol) in t-BuOH (50.0 mL) were added diphenylphosphoryl azide (10.3 g, 37.3 mmol) and Et3N (4.88 mL, 33.9 mmol). The reaction mixture was heated under reflux for 10 h, then cooled and concentrated. The residue was dissolved in EtOAc (50.0 mL) and extracted with 1 N HCl, water, saturated aq. NaHCO$_3$ and brine. The organic layer was dried over MgSO$_4$ and concentrated to afford crude tert-butyl pent-3-yn-1-ylcarbamate (4.0 g, 80%), which was used in the next step without further purification.

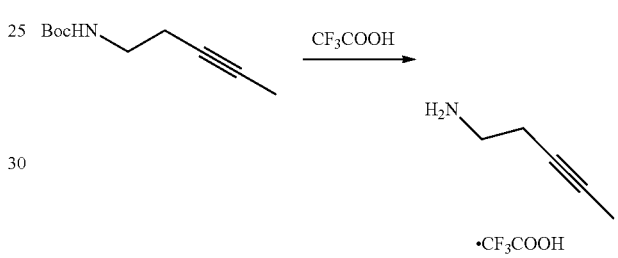

TFA (5.0 mL) was added to a solution of tert-butyl pent-3-yn-1-ylcarbamate (1.4 g, 7.5 mmol) in DCM (50 mL). The solution was stirred at rt for 3 h, during which a precipitate was formed. The precipitate was collected by filtration and dried to afford pent-3-yn-1-amine 2,2,2-trifluoroacetate (0.66 g, 40%)

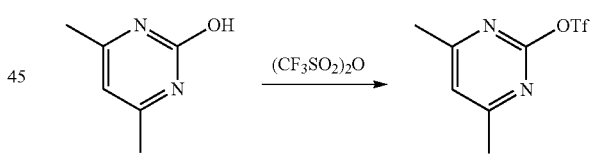

To a mixture of 4,6-dimethylpyrimidin-2-ol (6.0 g, 33.1 mmol, 1.0 eq) and Et3N (7.0 mL, 49.7 mmol) in CH$_2$Cl$_2$ (100.0 mL) was added Tf$_2$O (5.8 mL, 34.77 mmol, 1.1 eq) at 0° C. The suspension was stirred at rt for 2 h under N$_2$, then filtered. The filtrate was concentrated and the residue was purified by chromatography on silica gel (petroleum ether/EtOAc=5/1, v/v) to provide 4,6-dimethylpyrimidin-2-yl trifluoromethanesulfonate (5.0 g, 50%).

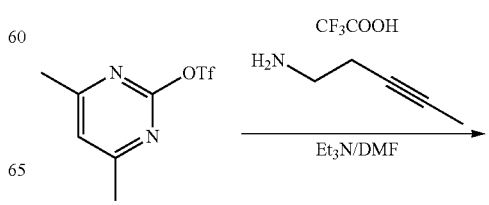

-continued

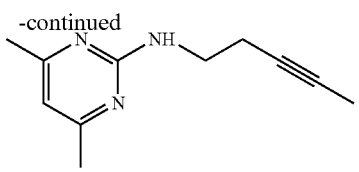

A mixture of 4,6-dimethylpyrimidin-2-yl trifluoromethanesulfonate (1.0 g, 4.0 mmol), pent-3-yn-1-amine 2,2,2-trifluoroacetate (0.66 g, 3.4 mmol) and Et3N (1.9 mL, 13.4 mmol) in DMF (5.0 mL) was stirred at rt for 1 day, then was quenched by the addition of water (5.0 mL) and extracted with ether (50.0 mL×3). The combined organic layers were dried over MgSO₄ concentrated under vacuum to afford 4,6-dimethyl-N-(pent-3-yn-1-yl) pyrimidin-2-amine (0.7 g, 57%).

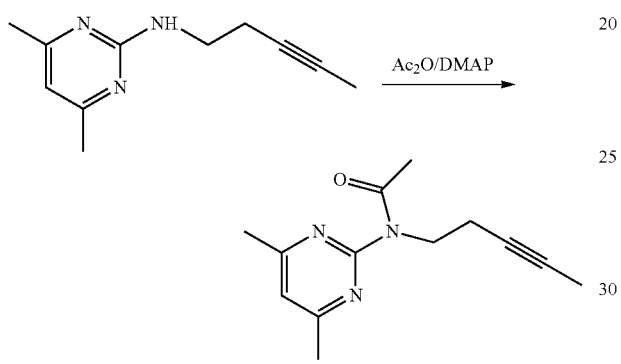

A mixture of 4,6-dimethyl-N-(pent-3-yn-1-yl) pyrimidin-2-amine (630.0 mg, 3.3 mmol) and DMAP (81.0 mg, 3.2 mmol) in Ac2O (10.0 mL) was heated at 100° C. overnight, then cooled and concentrated. The residue was dissolved in EtOAc (40.0 mL) and washed with saturated aq NaHCO₃ solution and brine, dried over MgSO₄, concentrated to provide N-(4,6-dimethylpyrimidin-2-yl)-N-(pent-3-yn-1-yl) acetamide (680.0 mg, 90%).

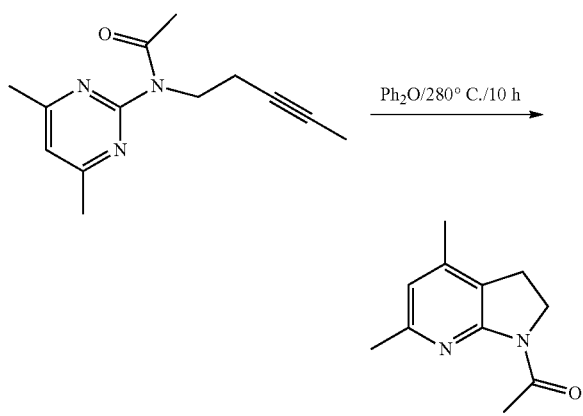

A solution of N-(4,6-dimethylpyrimidin-2-yl)-N-(pent-3-yn-1-yl)acetamide (660.0 mg, 2.9 mmol) in diphenyl ether (10.0 mL) was heated under reflux for 10 h, then cooled and was added ether (25 mL). The resulting solution was extracted with 1 N HCl (25 mL×3). The aqueous layer was neutralized with solid NaHCO₃ until the pH=7-8. The suspension was extracted with CH₂Cl₂ (25 mL×3). The combined organic layers were dried over MgSO₄ and concentrated under reduced pressure to afford 1-(4,6-dimethyl-2,3-dihydro-1H-pyrrolo[2,3-b]pyridin-1-yl)ethanone (460.0 mg, 82%)

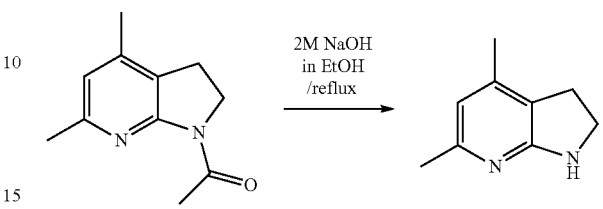

A mixture of 1-(4,6-dimethyl-2,3-dihydro-1H-pyrrolo[2,3-b] pyridin-1-yl) ethanone (450.0 mg, 2.4 mmol) in NaOH/EtOH (2 M, 25 mL) was heated under reflux for 2 h. NH₄Cl was added to neutralize the solution and concentrated. The resulting mixture was extracted with CH₂Cl₂ (25 mL×3). The combined organic layers were concentrated to provide 4,6-dimethyl-2,3-dihydro-1H-pyrrolo[2,3-b]pyridine (400.0 mg, 92%).

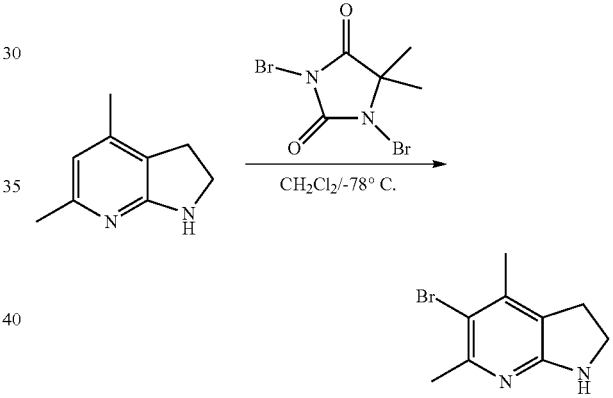

To a solution of 4,6-dimethyl-2,3-dihydro-1H-pyrrolo[2,3-b]pyridine (300.0 mg, 2.0 mmol) in DCM (30.0 mL) was added 1,3-dibromo-5,5-dimethylhydantoin (580.0 mg, 2.0 mmol) at −78° C. under N₂ for 3 h. The cooling bath was removed and saturated aq Na₂S₂O₃ (5 mL) was immediately added, and the contents of the flask was swirled thoroughly to destroy the remaining 1,3-dibromo-5,5-dimethylhydantoin. After the solution was warmed to rt while stirring, water and excess solid KOH were added. The CH₂Cl₂ was removed under reduced pressure and the basic suspension was filtered. The precipitate was washed with water and dried to provide 5-bromo-4,6-dimethyl-2,3-dihydro-1H-pyrrolo[2,3-b]pyridine (380.0 mg, 90%).

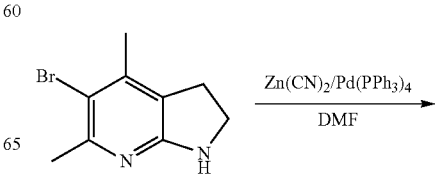

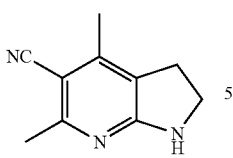

To a solution of 5-bromo-4,6-dimethyl-2,3-dihydro-1H-pyrrolo[2,3-b]pyridine e (300.0 mg, 1.3 mmol) in DMF (2.0 mL) were added $Zn(CN)_2$ (240.0 mg, 2.0 mmol) and $Pd(PPh_3)_4$ (150.0 mg, 0.13 mmol) under $N_2$. The mixture was irradiated under microwave at 170° C. for 45 min, then cooled and diluted with EtOAc (20.0 mL), washed with water, dried with anhydrous $Na_2SO_4$ and concentrated. The resulting residue was purified by chromatography on silica gel (DCM/MeOH=10/1, v/v) to afford 4,6-dimethyl-2,3-dihydro-1H-pyrrolo[2,3-b]pyridine-5-carbonitrile (300.0 mg, 80%).

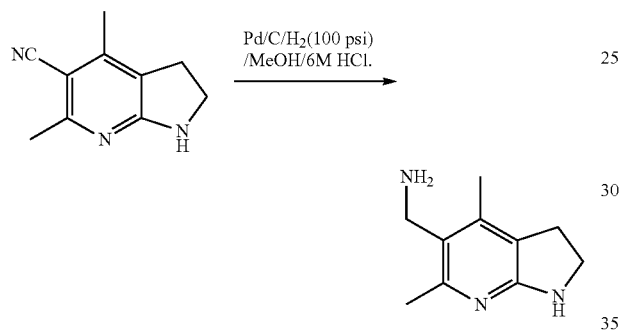

To a mixture of 4,6-dimethyl-2,3-dihydro-1H-pyrrolo[2,3-b]pyridine-5-carbonitrile (120.0 mg, 0.7 mmol) in MeOH (40.0 mL) was added Pd/C (10%, 200.0 mg) and 6 N HCl (1 mL). The mixture was stirred under $H_2$ (100 psi) at rt for 16 h, then filtered off through Celite. The filtrate was concentrated and the residue was purified by chromatography on silica gel (DCM/MeOH=10/1, v/v) to afford (4,6-dimethyl-2,3-dihydro-1H-pyrrolo[2,3-b] pyridin-5-yl)methanamine (120 mg, 98%).

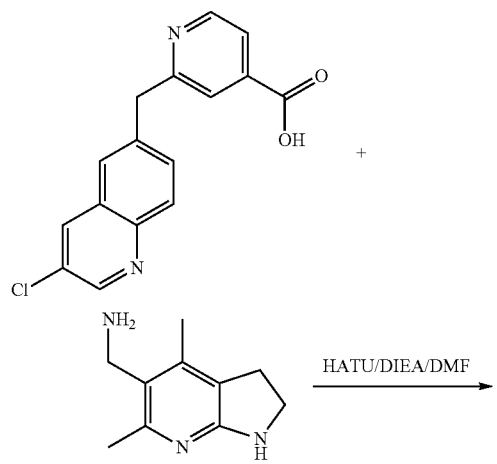

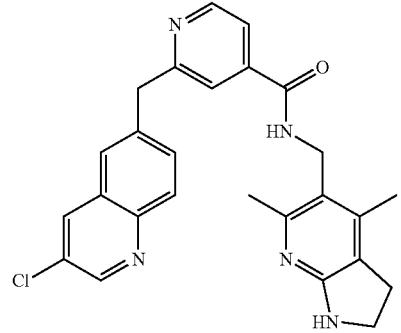

To a mixture of (4,6-dimethyl-2,3-dihydro-1H-pyrrolo[2,3-b]pyridin-5-yl) methanamine (21.0 mg, 0.12 mmol, 1.0 eq), 2-((3-chloroquinolin-6-yl)methyl)isonicotinic acid (30.0 mg, 0.10 mmol, 0.8 eq) and HATU (76.0 mg, 0.2 mmol, 1.5 eq) in DMF (2 mL) was added DIEA (39.0 mg, 0.30 mmol, 3.0 eq). The reaction mixture was stirred at rt for 2 h under $N_2$. Water (10.0 mL) was added and the mixture was extracted with EtOAc (10 mL×3). The combined organic layers were washed with water, dried over $Na_2SO_4$ and concentrated. The resulting residue was purified on Prep-TLC to provide 2-((3-chloroquinolin-6-yl)methyl)-N-((4,6-dimethyl-2,3-dihydro-1H-pyrrolo[2,3-b]pyridin-5-yl)methyl)isonicotinamide (16.0 mg, 30%).

$^1$H NMR (CD$_3$OD, 400 MHz): δ 8.67 (d, 1H), 8.60 (d, 1H), 8.25 (s, 1H), 7.86 (d, 1H), 7.73 (s, 2H), 7.61~7.66 (m, 2H), 4.44 (s, 2H), 4.38 (s, 2H), 3.66 (t, 2H), 2.97 (t, 2H), 2.38 (s, 3H), 2.18 (s, 3H). LRMS (M+H$^+$) m/z calculated 458.2 found 458.5.

Example 176: Preparation of N-((4,6-dimethyl-2,3-dihydro-1H-pyrrolo[2,3-b]pyridin-5-yl)methyl)-2-((3-(trifluoromethyl)quinolin-6-yl)methyl)isonicotinamide

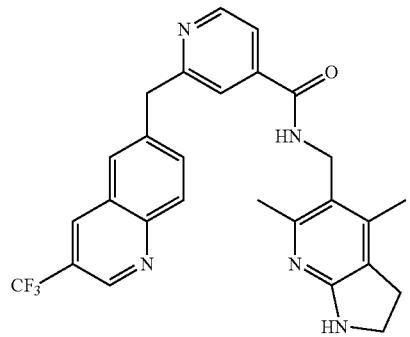 [SMILES: Cc1nc2c(c(C)c1CNC(=O)c1ccnc(Cc3ccc4ncc(C(F)(F)F)cc4c3)c1)CCN2]

N-((4,6-dimethyl-2,3-dihydro-1H-pyrrolo[2,3-b]pyridin-5-yl)methyl)-2-((3-(trifluoromethyl)quinolin-6-yl)methyl) isonicotinamide (13.0 mg) was prepared as described for 2-((3-chloroquinolin-6-yl)methyl)-N-((4,6-dimethyl-2,3-dihydro-1H-pyrrolo[2,3-b]pyridin-5-yl)methyl)isonicotinamide. 1H NMR (CD3OD, 400 MHz): δ 9.02 (s, 1H), 8.69 (s, 1H), 8.60 (d, 1H), 8.04 (d, 1H), 7.98 (s, 1H), 7.84 (d, 1H), 7.73 (s, 1H), 7.60 (d, 1H), 4.48 (s, 2H), 4.44 (s, 2H), 3.59~3.64 (t, 2H), 2.96~3.00 (t, 2H), 2.38 (s, 3H), 2.20 (s, 3H).

LRMS (M+H$^+$) m/z calculated 492.1, found 492.4.

Example 177: Preparation of N-((1-amino-5-methylisoquinolin-6-yl)methyl)-2-((3-chloroquinolin-6-yl)methyl)isonicotinamide

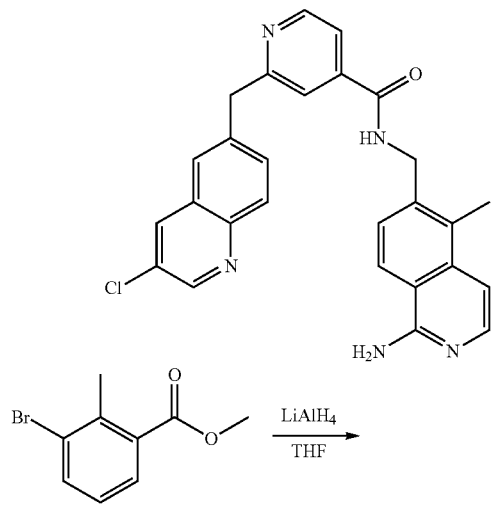

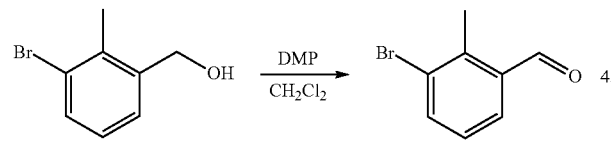

To a solution of methyl 3-bromo-2-methylbenzoate (5.0 g, 21.8 mmol, 1.0 eq), in anhydrous THF (50 mL) was added LiAlH$_4$ (1.2 g, 32.7 mmol) slowly at 0° C. under N$_2$ protection. The reaction mixture was stirred at 10° C. for 1 h, then quenched by the slow addition of H$_2$O (1.2 g), 15% NaOH (1.2 g), and H$_2$O (3.6 g). The mixture was stirred for 30 min, then filtered and the filter was concentrated to afford 3-bromo-2-methylphenyl)methanol (5.2 g, ca. 100%).

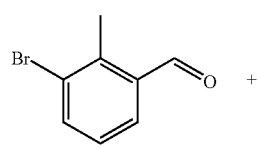

To a solution of 3-bromo-2-methylphenyl)methanol (5.2 g, 24.6 mmol) in CH$_2$Cl$_2$ (200.0 mL) was added DMP (11.5 g, 27.1 mmol) and the reaction mixture was stirred at rt for 1 h, then quenched by a solution of Na$_2$SO$_3$ (3.4 g, 27.1 mmol) in 100 mL of H$_2$O. The mixture was adjusted to pH 8-9 by the addition of aq. NaHCO$_3$ solution, and extracted by CH$_2$Cl$_2$ (100.0 mL×3). The combined organic phase was washed NaHCO$_3$ solution, brine, dried by Na$_2$SO$_4$ and concentrated to afford 3-bromo-2-methylbenzaldehyde (5.2 g, ca. 100%).

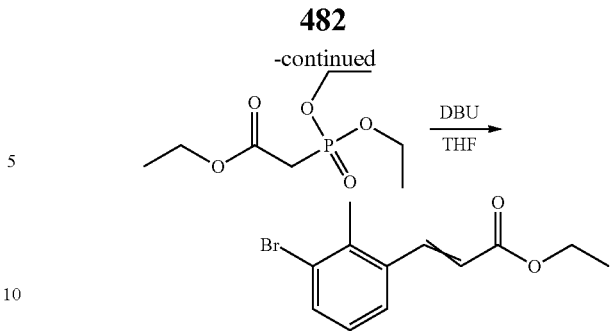

A mixture of 3-bromo-2-methylbenzaldehyde (5.7 g, 27.3 mmol, 1.0 eq) and ethyl 2-(diethoxyphosphoryl)acetate (7.3 g, 32.7 mmol) in anhydrous THF (100.0 mL) was stirred at 0° C. under N$_2$ protection, then was added a solution of DBU (5.0 g, 32.7 mmol) in anhydrous THF (50.0 mL) dropwise. The reaction mixture was stirred at 0° C. over night, then diluted by EA (200.0 mL), quenched by 1N HCl (100.0 mL), extracted by EA (100.0 mL×2). The combined organic layers were washed brine, dried by Na$_2$SO$_4$ and concentrated to afford ethyl 3-(3-bromo-2-methylphenyl)acrylate (7.7 g, ca. 100%).

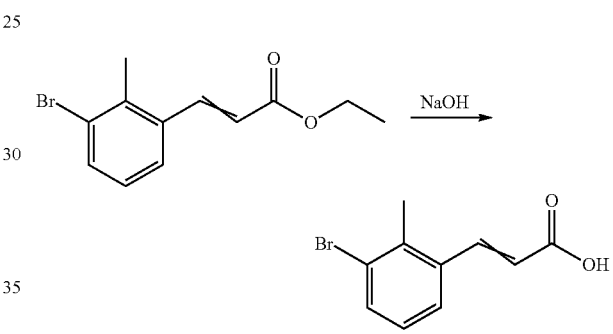

To a solution of ethyl 3-(3-bromo-2-methylphenyl)acrylate (8.4 g, 31.2 mmol, 1.0 eq) in THF (100.0 mL) and MeOH (50.0 mL) was added a solution of NaOH (3.7 g, 93.6 mmol) in H$_2$O (100.0 mL). The reaction mixture was stirred at rt over night, then acidified to pH1-2 by 1N HCl. The mixture was concentrated to remove THF and MeOH, then filtered to afford 3-(3-bromo-2-methylphenyl)acrylic acid (6.1 g, 81%).

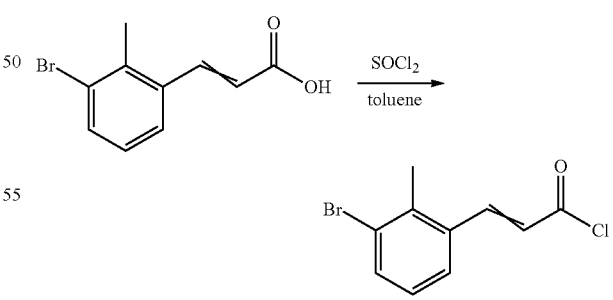

To a solution of 3-(3-bromo-2-methylphenyl)acrylic acid (6.1 g, 25.3 mmol, 1.0 eq) in toluene (120.0 mL) was added SOCl$_2$ (6.0 g, 50.6 mmol). The reaction mixture was heated under 110° C. overnight, then cooled and concentrated to afford 3-(3-bromo-2-methylphenyl)acryloyl chloride (6.0 g, 92%) which was used to next step without further purification.

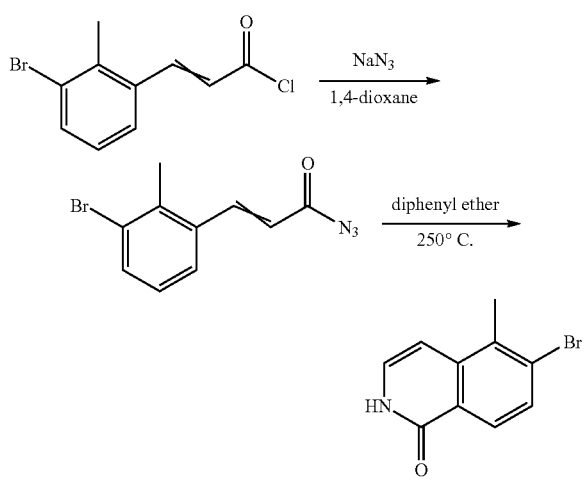

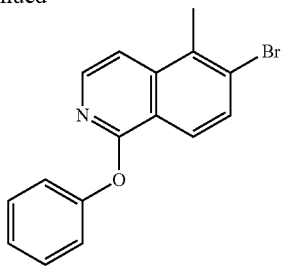

A mixture of phenol (11.0 g, 117.0 mmol) and KOH (1.5 g, 27.3 mmol) was stirred at 50° C. for 1 h, then 6-bromo-1-chloro-5-methylisoquinoline (4.0 g, 15.6 mmol) was added to the above reaction mixture. The reaction mixture was heated at 160° C. for 2 h, then cooled and poured into ice-water which was adjusted to pH=14 by 10N aq. NaOH, extracted by CH$_2$Cl$_2$ (100.0 mL×3). The combined organic layers were washed by brine, dried by Na$_2$SO$_4$ and concentrated to afford 6-bromo-5-methyl-1-phenoxyisoquinoline (4.6 g, 94%).

A solution of 3-(3-bromo-2-methylphenyl)acryloyl chloride (6.0 g, 23.1 mmol, 1.0 eq) in 1,4-dioxane (120.0 mL) was added dropwise to a solution of NaN$_3$ (1.7 g, 25.4 mmol, 1.1 eq) in 1,4-dioxane/H$_2$O (1:1, 120.0 mL) at 0° C. and the reaction was stirred at 0° C. for 1 h. LC-MS confirmed that the reaction finished, the reaction mixture was diluted by EA (100.0 mL), washed by aq. NaHCO$_3$ solution, brine, dried by Na$_2$SO$_4$ and filtered. To the filtrate was added diphenyl ether (90.0 mL) and concentrated to remove EA. The solution of 3-(3-bromo-2-methylphenyl)acryloyl azide was stirred at 250° C. for 5 h, then cooled to 25° C., diluted by PE (800.0 mL) and filtered to afford 6-bromo-5-methylisoquinolin-1(2H)-one (3.9 g, 71%).

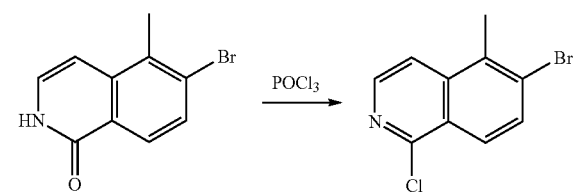

6-bromo-5-methylisoquinolin-1(2H)-one (3.9 g, 16.4 mmol, 1.0 eq) was dissolved in POCl$_3$ (60.0 mL) which was then heated at 110° C. over night, then cooled and concentrated. The residue was diluted by CH$_2$Cl$_2$ (100.0 mL), adjusted to pH 7-8 by aq. NaHCO$_3$ solution, then extracted by CH$_2$Cl$_2$ (150 mL×3). The combined organic layers were washed by brine (100.0 mL), dried by Na$_2$SO$_4$ and concentrated to afford 6-bromo-1-chloro-5-methylisoquinoline (4.0 g, ca. 00%).

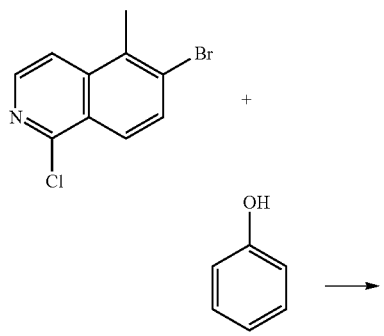

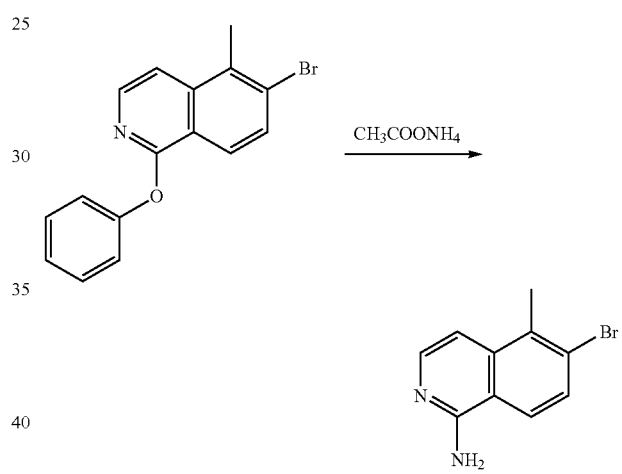

A mixture of 6-bromo-5-methyl-1-phenoxyisoquinoline (3.0 g, 9.6 mmol) and CH$_3$COONH$_4$ (22.2 g, 288.0 mmol) was stirred at 160° C. for 16 h, then cooled poured into ice-water (300.0 mL) which was adjusted to pH 14 by aq. NaOH solution and filtered to afford 6-bromo-5-methylisoquinolin-1-amine (650.0 mg, 30%).

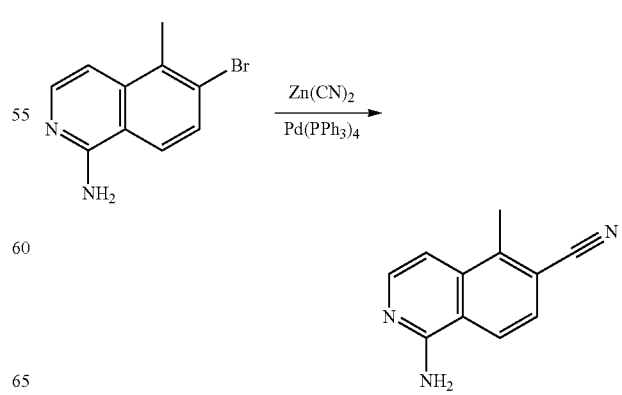

A mixture of 6-bromo-5-methylisoquinolin-1-amine (250.0 mg, 1.05 mmol), Zn(CN)₂ (369.0 mg, 3.2 mmol), Pd(PPh₃)₄ (122.0 mg, 0.11 mmol) in DMF (3.0 mL) was stirred at 180° C. under microwave for 2 h, then cooled and diluted by EA (100.0 mL) and filtered. The filtrate was washed by brine (50.0 mL), dried by Na₂SO₄ and concentrated. The resulting residue was purified on silica gel column (PE:EA=5:1-PE:EA=2:1) to afford 1-amino-5-methylisoquinoline-6-carbonitrile (150.0 mg, 78%).

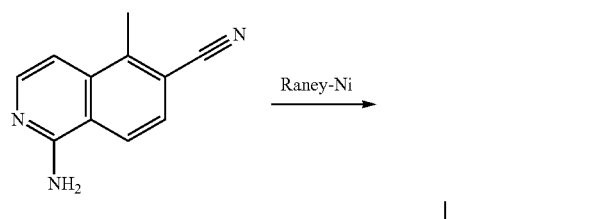

A mixture of 1-amino-5-methylisoquinoline-6-carbonitrile (200.0 mg, 1.1 mmol), Raney-Ni (200.0 mg), NH₃·H₂O (10.0 mL) in CH₃OH (20.0 mL) was stirred at H₂ atmosphere overnight, then filtered. The filtrate was concentrated and the residue was purified on silica gel column (DCM/MeOH=1:1, v/v) to afford 6-(aminomethyl)-5-methylisoquinolin-1-amine (101.0 mg, 49%).

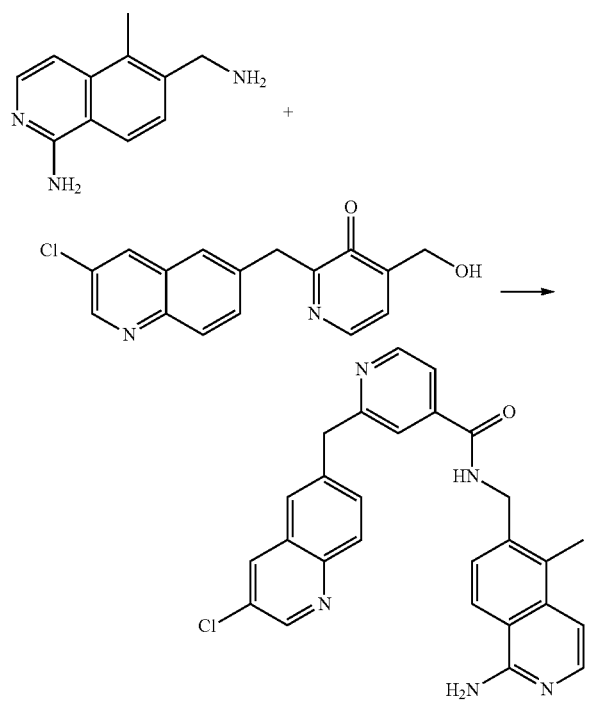

A mixture of 6-(aminomethyl)-5-methylisoquinolin-1-amine (100.0 mg, 0.5 mmol, 1.0 eq), 2-((3-chloroquinolin-6-yl)methyl)isonicotinic acid (158.3 mg, 0.5 mmol, 1.0 eq), HATU (202.0 mg, 0.5 mmol, 1.0 eq) in DMF (3.0 mL) was stirred at rt for 10 min, then was added DIEA (205.0 mg, 1.6 mmo, 3.0 eq). The reaction mixture was stirred at r.t over night, then purified on Prep-LCMS to afford N-((1-amino-5-methylisoquinolin-6-yl)methyl)-2-((3-chloroquinolin-6-yl)methyl)isonicotinamide (50.0 mg, 20%). ¹H NMR. (DMSO-d6, 400 MHz) δ 9.25 (s, 1H), 8.83 (s, 1H), 8.65 (d, 1H), 8.53 (s, 1H), 8.02-7.97 (m, 2H), 7.86-7.66 (m, 5H), 7.38 (d, 1H), 7.04 (d, 1H), 6.81 (s, 2H), 4.64 (d, 2H), 4.37 (s, 2H), 2.50 (s, 3H). LRMS (M+H⁺) m/z calculated 468.2, found 468.5.

Example 178: Preparation of N-((1-amino-5-fluoroisoquinolin-6-yl)methyl)-2-((3-chloroquinolin-6-yl)methyl)isonicotinamide

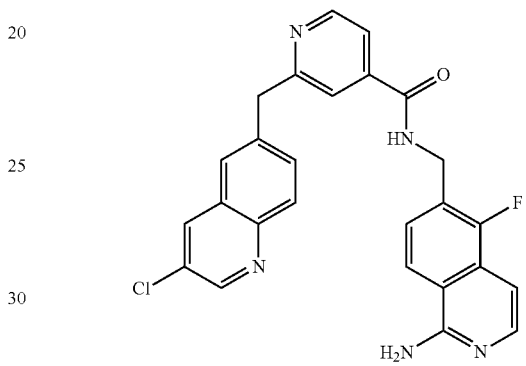

N-((1-amino-5-fluoroisoquinolin-6-yl)methyl)-2-((3-chloroquinolin-6-yl)methyl) isonicotinamide (9.0 mg) was prepared as described for N-((1-amino-5-methylisoquinolin-6-yl)methyl)-2-((3-chloroquinolin-6-yl)methyl)isonicotinamide. ¹H NMR (CD3OD, 400 MHz): δ 8.72 (s, 1H), 8.63 (d, 1H), 8.20 (s, 1H), 7.97 (d, 1H), 7.82-7.66 (m, 6H), 7.52 (t, 1H), 7.17 (d, 1H), 4.47 (s, 2H), 4.38 (d, 2H). LRMS (M+H+) m/z calculated 472.1, found 472.6.

Example 179: Preparation of N-((1-aminoisoquinolin-6-yl)methyl)-2-((3-chloroquinolin-6-yl)methyl) isonicotinamide

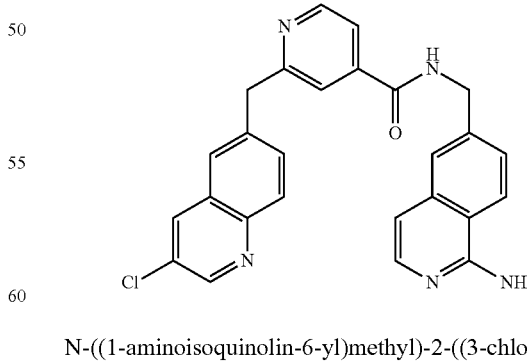

N-((1-aminoisoquinolin-6-yl)methyl)-2-((3-chloroquinolin-6-yl)methyl) isonicotinamide (28.0 mg) was prepared as described for N-((1-amino-5-methylisoquinolin-6-yl)methyl)-2-((3-chloroquinolin-6-yl)methyl)isonicotinamide. ¹H NMR (CD₃OD, 400 MHz): δ 8.85 (s, 1H), 8.76 (s, 1H), 8.35 (d, 1H), 8.27 (d, 1H), 8.16 (s, 1H), 7.97 (d, 1H), 7.85

(s, 1H), 7.76 (s, 1H), 7.69 (d, 1H), 7.45 (d, 1H), 7.08 (d, 1H), 4.76 (s, 2H), 4.64 (s, 2H), 3.00 (t, 2H), 2.36 (s, 3H). LRMS (M+H⁺) m/z calculated 454.1, found 454.4.

Example 180: Preparation of N-((1-amino-7-fluoroisoquinolin-6-yl)methyl)-2-((3-chloroquinolin-6-yl)methyl)isonicotinamide

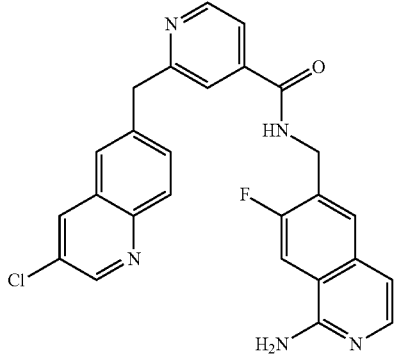

N-((1-amino-7-fluoroisoquinolin-6-yl)methyl)-2-((3-chloroquinolin-6-yl) methyl)isonicotinamide (2.5 mg) was prepared as described for N-((1-amino-5-methyl isoquinoli-6-yl)methyl)-2-((3-chloroquinolin-6-yl)methyl)isonicotinamide. ¹H NMR (CD₃OD, 400 MHz) δ 8.75 (s, 1H), 8.66 (d, 1H), 8.35 (d, 1H), 7.98 (s, 1H), 7.96 (d, 1H), 7.81-7.69 (m, 5H), 7.63 (d, 1H), 7.01 (d, 1H), 4.76 (s, 2H), 4.44 (s, 2H). LRMS (M+H⁺) m/z calculated 472.1, found 472.5.

Example 181: Preparation of N-((1-amino-7-methylisoquinolin-6-yl)methyl)-2-((3-chloroquinolin-6-yl)methyl)isonicotinamide

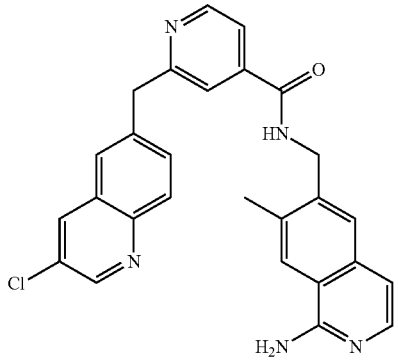

N-((1-amino-7-methylisoquinolin-6-yl)methyl)-2-((3-chloroquinolin-6-yl) methyl)isonicotinamide (13.0 mg) was prepared as described for N-((1-amino-5-methyl isoquinoli-6-yl)methyl)-2-((3-chloroquinolin-6-yl)methyl)isonicotinamide. ¹H NMR (CD₃OD, 400 MHz): δ 8.78-8.81 (m, 2H), 8.38 (s, 1H), 8.21 (s, 1H), 8.03 (s, 1H), 8.00 (d, 1H), 7.85 (s, 1H), 7.75 (s, 2H), 7.47 (d, 1H), 7.08 (s, 1H), 4.75 (s, 2H), 4.56 (s, 2H), 2.57 (s, 2H). LCMS (M+H⁺) m/z calculated 468.2, found 468.4.

Example 182: Preparation of N-((1-amino-7-fluoroisoquinolin-6-yl)methyl)-2-((3-(trifluoromethyl)quinolin-6-yl)methyl)isonicotinamide

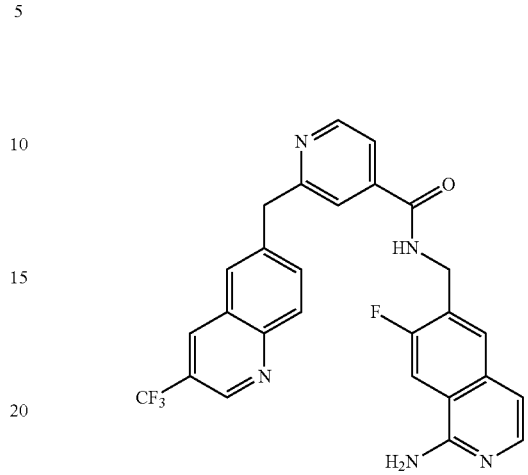

N-((1-amino-7-fluoroisoquinolin-6-yl)methyl)-2-((3-(trifluoromethyl) quinolin-6-yl)methyl)isonicotinamide (3.0 mg) was prepared as described for N-((1-amino-5-methyl isoquinoli-6-yl)methyl)-2-((3-chloroquinolin-6-yl) methyl)isonicotinamide. ¹H NMR (CD₃OD, 400 MHz) δ 9.03 (s, 1H), 8.71 (s, 1H), 8.66 (d, 1H), 8.08 (d, 1H), 8.01 (s, 1H), 7.95-7.88 (m, 2H), 7.82 (s, 1H), 7.74 (d, 1H), 7.70 (d, 1H), 7.64 (d, 1H), 6.99 (d, 1H), 4.76 (s, 2H), 4.48 (s, 2H). LRMS (M+H⁺) m/z calculated 506.2, found 506.5.

Example 183: Preparation of N-((1-amino-7-methylisoquinolin-6-yl)methyl)-2-((3-(trifluoromethyl)quinolin-6-yl)methyl)isonicotinamide

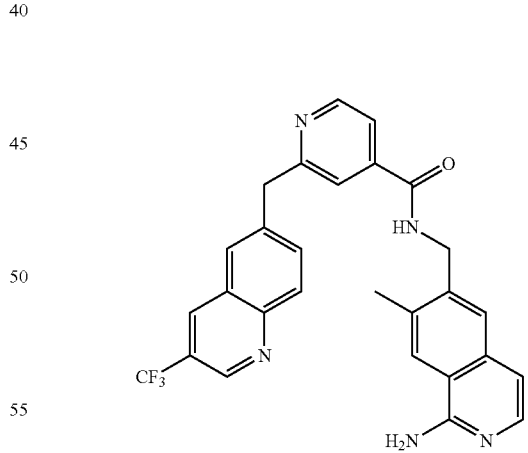

N-((1-amino-7-methylisoquinolin-6-yl)methyl)-2-((3-(trifluoromethyl)quinolin-6-yl)methyl)isonicotinamide (11.0 mg) was prepared as described for N-((1-amino-5-methyl isoquinoli-6-yl)methyl)-2-((3-chloroquinolin-6-yl) methyl) isonicotinamide. ¹H NMR (CD₃OD, 400 MHz): δ 9.04 (s, 1H), 8.68 (s, 2H), 8.23 (s, 1H), 8.08 (d, 1H), 7.88 (d, 1H), 7.75 (d, 2H), 7.45 (d, 1H), 7.11 (d, 1H), 7.15 (s, 1H), 4.75 (s, 2H), 4.50 (s, 2H), 2.58 (s, 3H). LCMS (M+H⁺) m/z calculated 501.5, found 502.5.

Example 184: Preparation of N-((1-amino-5-methylisoquinolin-6-yl)methyl)-2-((3-(trifluoromethyl)quinolin-6-yl)methyl)isonicotinamide

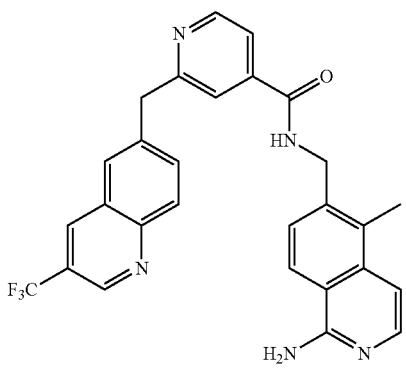 [SMILES: Cc1c(CNC(=O)c2ccnc(Cc3ccc4ncc(C(F)(F)F)cc4c3)c2)ccc2c(N)nccc12]

N-((1-amino-5-methylisoquinolin-6-yl)methyl)-2-((3-(trifluoromethyl) quinolin-6-yl)methyl)isonicotinamide (9.8 mg) was prepared as described for N-((1-amino-5-methyl isoquinoli-6-yl)methyl)-2-((3-chloroquinolin-6-yl) methyl) isonicotinamide. $^1$H NMR. (DMSO-d6, 400 MHz) δ 9.33 (t, 1H), 9.14 (s, 1H), 8.90 (s, 1H), 8.67 (d, 1H), 8.19-8.07 (m, 3H), 7.93-7.68 (m, 6H), 7.52 (d, 1H), 7.21 (d, 1H), 4.66 (d, 2H), 4.43 (s, 2H), 2.50 (s, 3H). LRMS (M+H$^+$) m/z calculated 502.2, found 502.6.

Example 185: Preparation of 2-((3-chloroquinolin-6-yl)methyl)-N-((3-(trifluoromethyl) imidazo[1,5-a]pyridin-6-yl)methyl)isonicotinamide

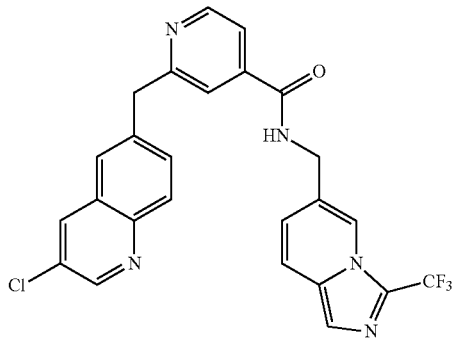 [SMILES: O=C(NCc1ccc2cnc(C(F)(F)F)n2c1)c1ccnc(Cc2ccc3ncc(Cl)cc3c2)c1]

A solution of 5-bromopicolinonitrile (10.0 g, 54.6 mmol) in BH$_3$/THF (300.0 mL, 300.0 mmol, 1.0 M) was heated under reflux for 2 h under N$_2$, then cooled and MeOH (30.0 mL) was added slowly, followed by 1N HCl (80.0 mL). The mixture was then refluxed for an additional 7 h. After being cooled the mixture was poured into aq. K$_2$CO$_3$ (10%, 600.0 mL) which was extracted with DCM (300.0 mL×3). The combined organic layers were dried over Na$_2$SO$_4$, filtered and concentrated under vacuum. The resulting residue was purified by chromatography on silica gel (DCM/MeOH=20/1, v/v) to afford (5-bromopyridin-2-yl)methanamine (3.7 g, 36.2%).

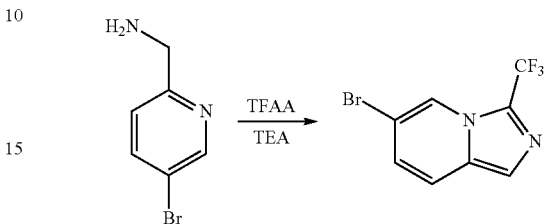

To a solution of 5-bromo-2-aminomethylpyridine (1.3 g, 6.8 mmol, 1.0 eq.) in CH$_2$Cl$_2$ (50.0 mL) were added TEA (2.5 mL) and trifluoroacetic anhydride (3.4 g, 16.3 mmol, 2.4 eq.) at rt. The mixture was stirred at rt for 18 h and concentrated. The residue was dissolved in EA (100.0 mL), washed with aqueous sat. NaHCO$_3$ solution (50.0 mL) and brine (50.0 mL), dried over Na$_2$SO$_4$ and concentrated. The resulting residue was purified on a silica gel column chromatography (EA/PE=1:5, v/v) to provide 6-bromo-3-(trifluoromethyl)imidazo[1,5-a]pyridine (1.3 g, 71.0%).

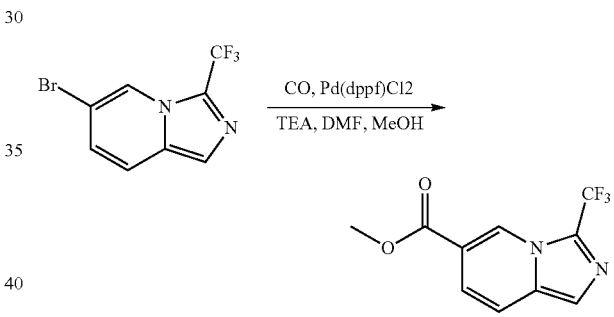

To a solution of 6-bromo-3-(trifluoromethyl)imidazo[1,5-a]pyridine (0.7 g, 2.6 mmol, 1.0 eq.) in DMF/MeOH (10.0 mL/10.0 mL) were added Et$_3$N (1.1 mL, 7.8 mmol, 3.0 eq.) and Pd(dppf)Cl$_2$ (320.0 mg, 0.4 mmol, 0.15 eq). The mixture was stirred under CO atmosphere at 90° C. for 16 h, then cooled and EtOAc (50.0 mL) and water (50.0 mL) were added. The organic layer was separated and concentrated. The resulting residue was purified by chromatography on silica gel (EA/PE=1/5, v/v) to provide methyl 3-(trifluoromethyl)imidazo[1,5-a] pyridine-6-carboxylate (600.0 mg, 94.5%).

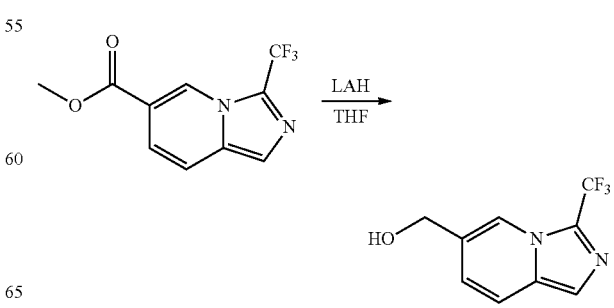

To a solution of methyl 3-(trifluoromethyl)imidazo[1,5-a]pyridine-6-carboxylate (0.6 g, 2.5 mmol, 1.0 eq) in THF (30.0 mL) was added lithium aluminium hydride (280.0 mg, 7.3 mmol, 3.0 eq) at −78° C. The reaction mixture was warmed to rt and stirred for 2 h. Water (30.0 mL) was added and the mixture was extracted with EtOAc (30.0 mL×3). The combined organic layer was washed with water, dried over Na₂SO₄, filtered and concentrated. The resulting residue was purified by chromatography on silica gel (PE/EtOAc=5/1, v/v) to afford (3-(trifluoromethyl) imidazo[1,5-a]pyridin-6-yl)methanol (370.0 mg, 70.0%).

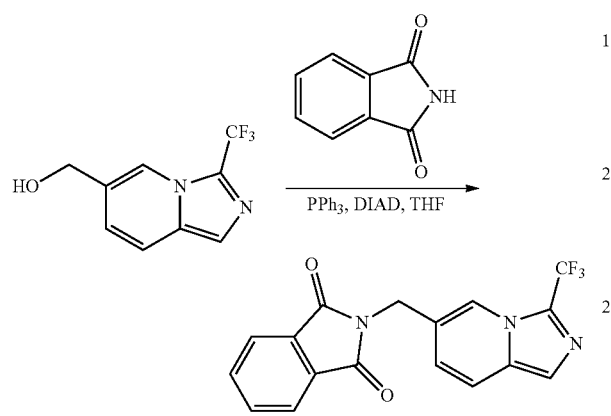

To a solution of (3-(trifluoromethyl)imidazo[1,5-a]pyridin-6-yl)methanol (450.0 mg, 2.1 mmol, 1.0 eq) in THF (30.0 mL) were added PPh₃ (1.1 g, 4.2 mmol, 2.0 eq) and DIAD (0.9 mL, 4.2 mmol, 2.0 eq), followed by isoindoline-1,3-dione (370.0 mg, 2.5 mmol, 1.2 eq). The mixture was stirred at rt for 12 h, then partitioned between EtOAc (30.0 mL) and water (30.0 mL). The organic layer was separated and concentrated. The resulting residue was purified by chromatography on silica gel (PE/EtOAc=5/1, v/v) to afford 2-((3-(trifluoromethyl)imidazo[1,5-a] pyridin-6-yl)methyl) isoindoline-1,3-dione (1.0 g, Ca. 100.0%).

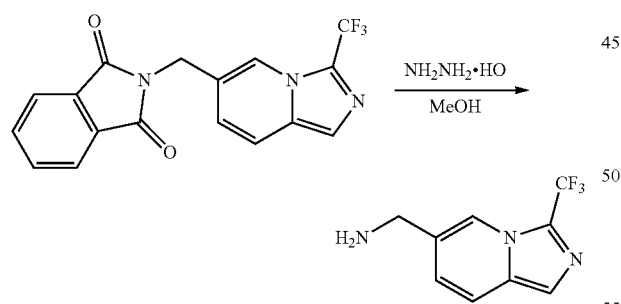

To a solution of 2-((3-(trifluoromethyl)imidazo[1,5-a] pyridin-6-yl) methyl)isoindoline-1,3-dione (1.0 g, 2.1 mmol, 1.0 eq) in MeOH (30.0 mL) was added NH₂NH₂·H₂O (2.0 mL, 85%, 21.0 mmol, 10.0 eq). The mixture was stirred under reflux for 5 h, then cooled and concentrated. The residue was partitioned between DCM (30.0 mL) and water (30.0 mL). The organic layer was separated and concentrated. The resulting residue was purified by chromatography on silica gel (DCM/MeOH=20/1, v/v) to afford (3-(trifluoromethyl)imidazo [1,5-a]pyridin-6-yl)methanamine (420.0 mg, 93.0%).

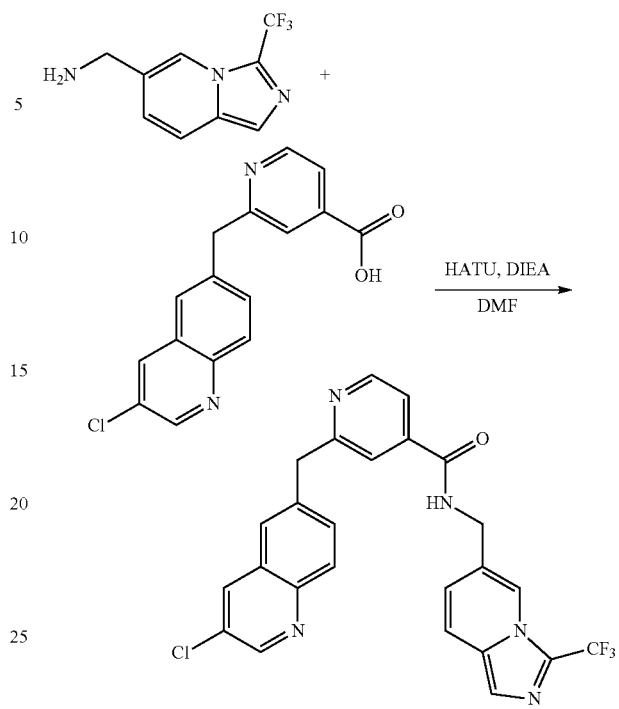

To a solution of (3-(trifluoromethyl)imidazo[1,5-a]pyridin-6-yl)methanamine (10.0 mg, 0.05 mmol, 1.0 eq) and 2-((3-chloroquinolin-6-yl)methyl)isonicotinic acid (15.0 mg, 0.05 mmol, 1.0 eq) in DMF (2.0 mL) were added HATU (28.0 mg, 0.08 mmol, 1.5 eq) and DIEA (20.0 mg, 0.15 mmol, 3.0 eq). The mixture was stirred at rt for 2 h, then partitioned between EA (30.0 mL) and water (30.0 mL). The organic layer was separated, washed with brine and concentrated. The resulting residue was purified on Prep-HPLC to provide 2-((3-chloroquinolin-6-yl) methyl)-N-((3-(trifluoromethyl) imidazo[1,5-a]pyridin-6-yl)methyl) isonicotinamide (8.9 mg, 36.0%). ¹H NMR (400 MHz, CD3OD): δ 8.74-8.62 (m, 2H), 7.97 (s, 2H), 7.85 (d, 1H), 7.58-7.42 (m, 4H), 7.42 (s, 1H), 7.13 (s, 1H), 6.92 (d, 1H), 4.57 (d, 2H), 4.37 (s, 2H). LRMS (M+H⁺) m/z calculated 496.1, found 496.6.

Example 186: Preparation of N-((1-amino-3-(trifluoromethyl)imidazo[1,5-a] pyridin-6-yl)methyl)-2-((3-chloroquinolin-6-yl)methyl)isonicotinamide

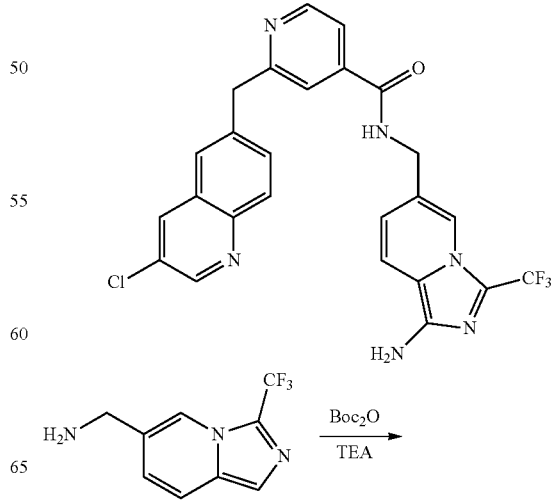

-continued

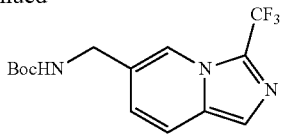

To a solution of (3-(trifluoromethyl)imidazo[1,5-a]pyridin-6-yl)methanamine (420.0 mg, 2.0 mmol, 1.0 eq) in CH$_2$Cl$_2$ (30.0 mL) were added TEA (0.6 mL, 3.9 mmol, 2.0 eq) and Boc$_2$O (0.53 g, 2.34 mmol, 1.2 equiv.) at rt. The mixture was stirred at rt for 3 h, then concentrated. The residue was dissolved in EA (100.0 mL), washed with water (50.0 mL), brine (50.0 mL), dried over Na$_2$SO$_4$ and concentrated. The residue was purified by chromatography on silica gel (EA/PE=1:5, v/v) to provide tert-butyl ((3-(trifluoromethyl)imidazo[1,5-a]pyridin-6-yl)methyl)carbamate (500.0 mg, 81.4%).

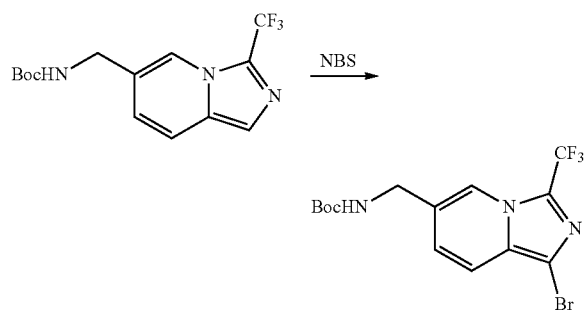

To a solution of tert-butyl ((3-(trifluoromethyl)imidazo[1,5-a]pyridin-6-yl) methyl)carbamate (0.5 g, 1.58 mmol) in acetonitrile (30.0 mL) was added N-bromosuccinimide (300.0 mg, 1.9 mmol, 1.2 eq). The reaction mixture was stirred at rt under argon atmosphere for 5 h, then concentrated. The resulting residue was purified by chromatography on silica gel (EA:PE=1:5) to provide tert-butyl ((1-bromo-3-(trifluoromethyl)imidazo[1,5-a]pyridin-6-yl)methyl)carbamate (480.0 mg, 77.4%).

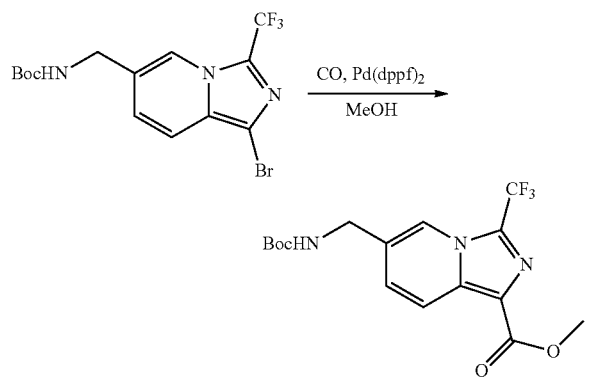

To a solution of tert-butyl ((1-bromo-3-(trifluoromethyl) imidazo[1,5-a] pyridin-6-yl)methyl)carbamate (100.0 mg, 0.3 mmol, 1.0 eq) in DMF/MeOH (3.0 mL/3.0 mL) were added Et$_3$N (0.11 mL, 7.5 mmol, 3.0 eq) and Pd(dppf)Cl$_2$ (30.0 mg, 0.38 mmol, 0.15 eq). The mixture was stirred under CO atmosphere at 90° C. for 16 h, then cooled and added EtOAc (50.0 mL) and water (50.0 mL). The organic layer was separated and concentrated. The resulting residue was purified by chromatography on silica gel (EA/PE=1/5, v/v) to provide methyl 6-(((tert-butoxycarbonyl)amino) methyl)-3-(trifluoromethyl)imidazo[1,5-a]pyridine-1-carboxylate (80.0 mg, 85.6%).

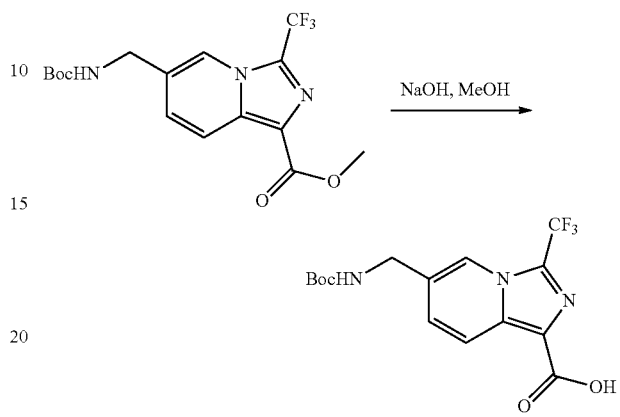

To a solution of methyl 6-(((tert-butoxycarbonyl)amino) methyl)-3-(trifluoromethyl)imidazo[1,5-a]pyridine-1-carboxylate (80.0 mg, 0.2 mmol) in MeOH (5.0 mL) was added 2N NaOH (0.2 mL, 0.42 mmol, 2.0 eq). The reaction mixture was stirred at 50° C. for 2 h, cooled, acidified to pH 4 with 1N HCl, extracted with EA, dried over Na$_2$SO$_4$ and concentrated to provide 6-(((tert-butoxycarbonyl)amino) methyl)-3-(trifluoromethyl) imidazo[1,5-a]pyridine-1-carboxylic acid (66.0 mg, 87.5%).

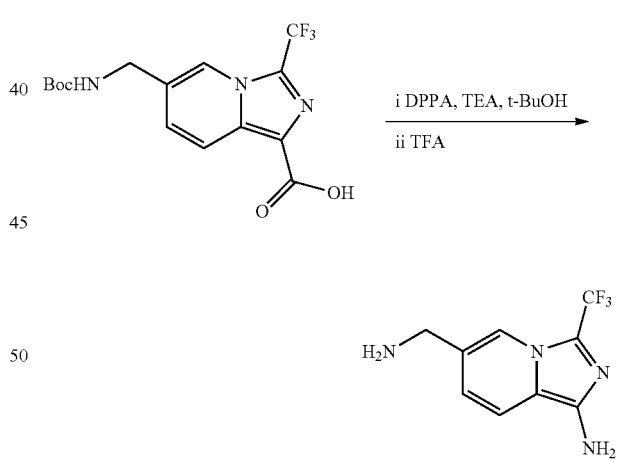

To a solution of 6-(((tert-butoxycarbonyl)amino)methyl)-3-(trifluoromethyl) imidazo[1,5-a]pyridine-1-carboxylic acid (66.0 mg, 0.17 mmol, 1.0 eq) in t-BuOH (5.0 mL) was added DPPA (72.0 mg, 0.3 mmol, 1.5 eq) and TEA (26 mg, 0.26 mmol, 1.5 eq). The reaction mixture was stirred at 90° C. for 12 h, then concentrated. The resulting residue was purified by chromatography on silica gel (EA:PE=1:5) to provide the intermediate 41.0 mg which was dissolved in DCM (2.0 mL), TFA (0.5 mL). The mixture was stirred for 1 h, then concentrated to provide 6-(aminomethyl)-3-(trifluoromethyl)imidazo[1,5-a]pyridin-1-amine.

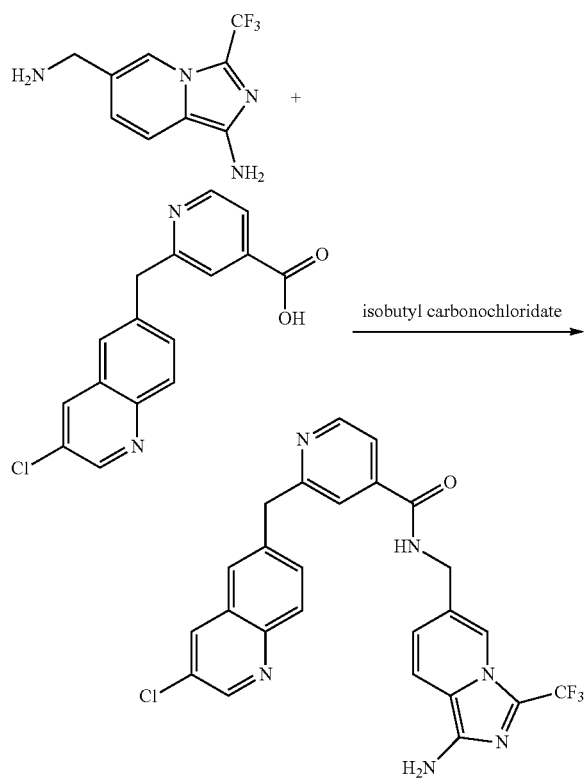

A solution of 2-((3-chloroquinolin-6-yl)methyl)isonicotinic acid (28.0 mg, 0.1 mmol, 1.0 eq) in dry DMF (2.0 mL) was cooled to 0° C. TEA (11.0 mg, 0.1 mmol, 1.2 eq) and isobutyl carbonochloridate (19.0 mg, 0.14 mmol, 1.5 eq) were added to the above mixture and the resulting mixture was stirred at 0° C. for 3 h. 6-(aminomethyl)-3-(trifluoromethyl)imidazo[1,5-a]pyridin-1-amine (21.0, 0.1 mmol) and TEA (11.0 mg, 0.1 mmol) were added to the above solution and the resulting mixture was stirred at rt for 14 h, then concentrated. The resulting residue was purified on Prep-HPLC to provide N-((1-amino-3-(trifluoromethyl)imidazo[1,5-a]pyridin-6-yl)methyl)-2-((3-chloroquinolin-6-yl)methyl)isonicotinamide (10.0 mg, 21.0% yield). $^1$H NMR (CDCl3, 400 MHz) δ 8.70-8.65 (m, 2H), 7.96 (s, 1H), 7.84 (d, 1H), 7.69 (s, 1H), 7.59-7.51 (m, 5H), 7.22-7.20 (m, 2H), 6.55 (d, 1H), 5.48 (s, 2H), 4.47 (d, 2H), 4.36 (s, 3H). LRMS (M+H$^+$) m/z calculated 511.1, found 511.6.

Example 187: Preparation of N-((3-aminoimidazo[1,5-a]pyridin-7-yl)methyl)-2-((3-chloroquinolin-6-yl)methyl)isonicotinamide

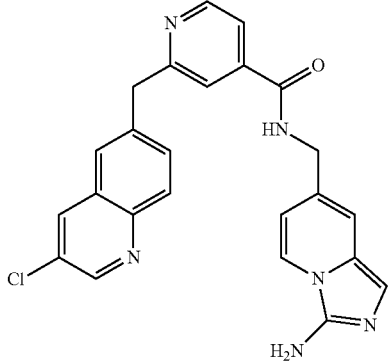 [SMILES: Nc1ncc2cc(CNC(=O)c3ccnc(Cc4ccc5ncc(Cl)cc5c4)c3)ccn12]

N-((3-aminoimidazo[1,5-a]pyridin-7-yl)methyl)-2-((3-chloroquinolin-6-yl)methyl)isonicotinamide (5.0 mg) was prepared as described for N-((1-amino-3-(trifluoromethyl)imidazo[1,5-a] pyridin-6-yl)methyl)-2-((3-chloroquinolin-6-yl)methyl)isonicotinamide. $^1$H NMR (CD$_3$OD, 400 MHz): δ 8.75 (s, 1H), 8.64 (s, 1H), 8.35 (s, 1H), 7.96 (d, 1H), 7.70 (d, 2H), 7.17 (s, 1H), 6.99 (s, 1H), 4.41 (d, 4H). LRMS (M+H+) m/z calculated 443.2, found 443.6.

Example 188: Preparation of 2-((3-chloroquinolin-6-yl)methyl)-N-((7-methylimidazo [1,5-a]pyridin-6-yl)methyl)isonicotinamide

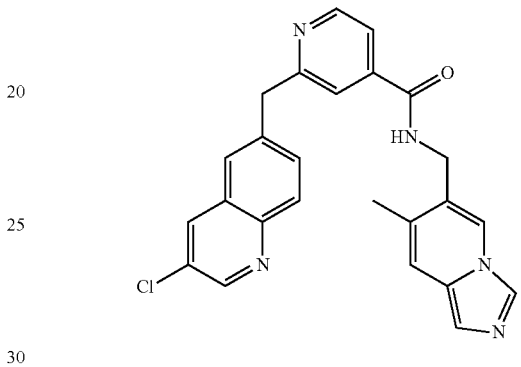

2-((3-chloroquinolin-6-yl)methyl)-N-((7-methylimidazo [1,5-a]pyridin-6-yl) methyl) isonicotinamide (1.8 mg) was prepared as described for 2-((3-chloroquinolin-6-yl)methyl)-N-((3-(trifluoromethyl) imidazo[1,5-a]pyridin-6-yl)methyl)isonicotinamide. $^1$H NMR. (CD$_3$OD, 400 MHz) δ 8.76 (d, 1H), 8.65 (d, 1H), 8.57 (s, 1H), 8.36 (s, 1H), 8.23 (s, 1H), 7.97 (d, 1H), 7.79 (d, 2H), 7.70-7.73 (m, 2H), 7.41 (s, 2H), 4.54 (s, 2H), 4.43 (s, 2H), 3.34 (s, 1H), 2.34 (s, 3H). LRMS (M+H$^+$) m/z calculated 442.1, found 442.0.

Example 189: Preparation of N-((3-chloro-4-methyl-1H-pyrrolo[2,3-b]pyridin-5-yl) methyl)-2-((3-chloroquinolin-6-yl)methyl)isonicotinamide

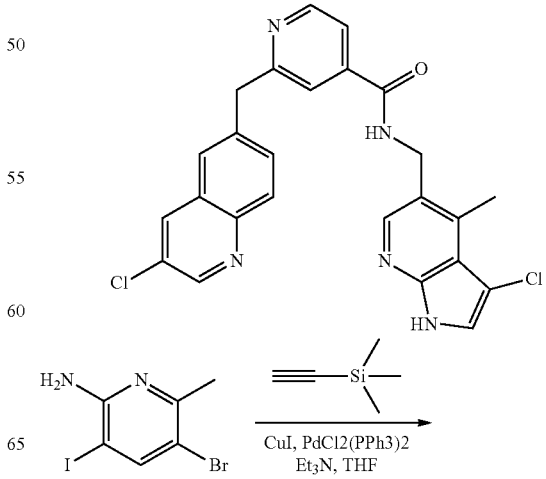

-continued

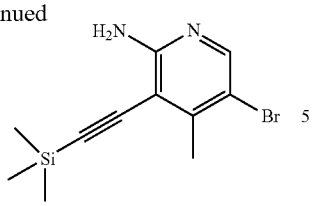

A mixture of 5-bromo-3-iodo-6-methylpyridin-2-amine (1.4 g, 4.6 mmol, 1.0 eq), ethynyltrimethylsilane (405 mg, 4.81 mmol, 1.05 eq), PdCl$_2$(PPh$_3$)$_2$ (71.5 mg, 0.05 eq), CuI (48.6 mg, 0.03 eq) and Et$_3$N (556 mg, 5.5 mmol, 1.2 eq) in THF (20 mL) was stirred under reflux for 16 h, then concentrated in vacuum. The resulting residue was purified by chromatography on silica gel (Petroether/EtOAc=10/1, v/v) to afford 5-bromo-4-methyl-3-((trimethylsilyl)ethynyl) pyridin-2-amine (1.3 g, 97%).

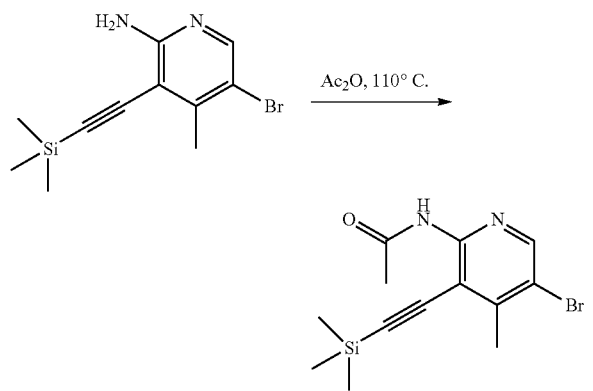

To a solution of 5-bromo-4-methyl-3-((trimethylsilyl) ethynyl)pyridin-2-amine (1.2 g, 4.2 mmol) in Ac$_2$O (20.0 mL) was stirred at 110° C. for 30 min, then cooled and poured into ice-water (20.0 mL) and adjusted pH=7-8 by 1N NaOH. The mixture was extracted with EtOAc (20 mL×3). The combined organic layers were washed with brine (20.0 mL), dried over anhydrous Na$_2$SO$_4$ and concentrated. The resulting residue was purified by chromatography on silica gel (Petroether/EtOAc=10/1, v/v) to afford N-(5-bromo-4-methyl-3-((trimethylsilyl)ethynyl) pyridin-2-yl)acetamide (620.0 mg, 45%).

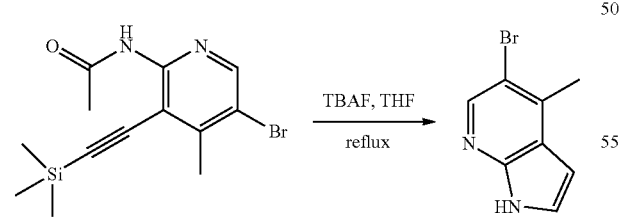

To a solution of N-(5-bromo-4-methyl-3-((trimethylsilyl) ethynyl)pyridin-2-yl)acetamide (620.0 mg, 1.9 mmol, 1.0 eq) in THF (10.0 mL) was added TBAF (3.8 mL, 3.8 mmol, 2.0 eq) (1 M/L in THF) dropwise at rt. The reaction mixture was stirred at rt for 16 h, then concentrated. The resulting residue was purified by chromatography on silica gel (Petroether/EtOAc=10/1, v/v) to afford 5-bromo-4-methyl-1H-pyrrolo[2,3-b]pyridine (345.0 mg, 86%) as a white solid.

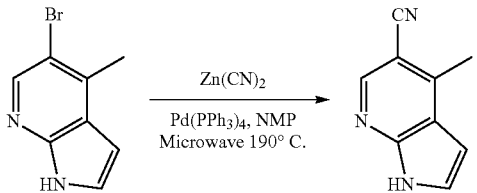

To a solution of 5-bromo-4-methyl-1H-pyrrolo[2,3-b] pyridine (220.0 mg, 0.9 mmol, 1.0 eq) in NMP (4.0 mL) were added Zn(CN)$_2$ (287.5 mg, 2.5 mmol, 1.5 eq) and Pd(PPh$_3$)$_4$ (57.5 mg, 10%). The reaction was stirred at 190° C. under microwave irradiation for 2 h, then cooled and purified on Prep-HPLC to afford 4-methyl-1H-pyrrolo[2,3-b]pyridine-5-carbonitrile (200.0 mg, 78%).

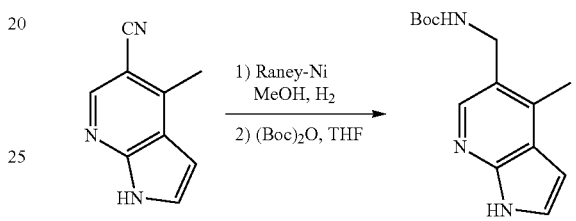

To a solution of 4-methyl-1H-pyrrolo[2,3-b]pyridine-5-carbonitrile (150.0 mg, 1.0 mmol, 1.0 eq) in MeOH (20.0 mL) was added Raney Ni (50.0 mg). The reaction was stirred at rt under H$_2$ (1 atm) for 16 h, then filtered. The filtrate was concentrated, and the resulting residue was dissolved in THF (20.0 mL), and (Boc)$_2$O (207.0 mg, 1.0 mmol, 1.0 eq) was added. The reaction mixture was stirred for 2 h, and then concentrated. The resulting residue was purified by chromatography on silica gel (Petroether/ EtOAc=1/1, v/v) to afford tert-butyl ((4-methyl-1H-pyrrolo [2,3-b]pyridin-5-yl)methyl)carbamate (52.0 mg, 18%).

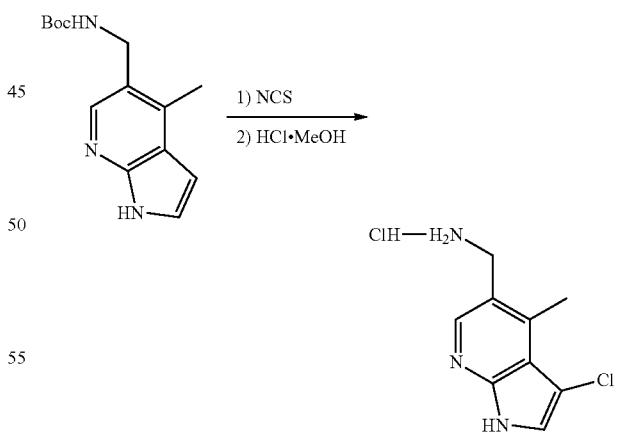

To a solution of tert-butyl ((4-methyl-1H-pyrrolo[2,3-b] pyridin-5-yl) methyl)carbamate (52.0 mg, 0.2 mmol, 1.0 eq) in CH$_3$CN (4.0 mL) was added NCS (26.6 mg, 0.2 mmol, 1.0 eq). The reaction mixture was stirred at 70° C. under N$_2$ for 2.5 h, then cooled and poured into brine (50.0 mL). The mixture was extracted with EtOAc (20 mL×2). The combined organic layers were dried over anhydrous Na$_2$SO$_4$ and concentrated in vacuum. The resulting residue was purified by chromatography on silica gel (CH$_2$Cl$_2$/MeOH=30/1, v/v) to afford tert-butyl ((3-chloro-4-methyl-1H-pyrrolo[2,3-b]pyridin-5-yl)methyl)carbamate, which was dissolved in 4 N HCL/MeOH (4.0 mL) and stirred at rt for 2 h, then concentrated in vacuum to afford (3-chloro-4-methyl-1H-pyrrolo[2,3-b]pyridin-5-yl) methanamine hydrochloride (37.0 mg, quant.).

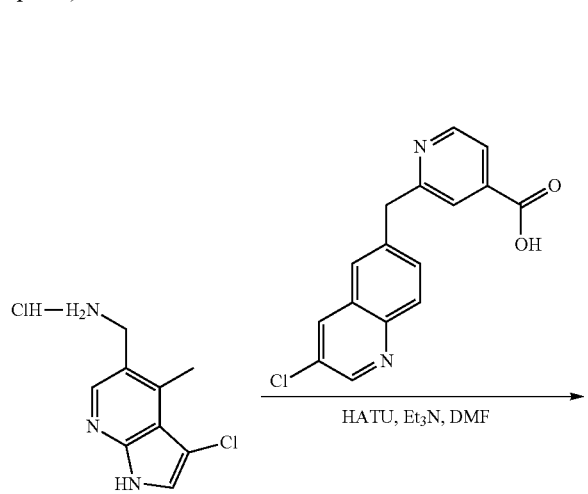

To a solution of 2-((3-chloroquinolin-6-yl)methyl)isonicotinic acid (56.7 mg, 0.2 mmol, 1.0 eq) in DMF (5.0 mL) were added HATU (143.6 mg, 0.4 mmol, 2.0 eq), (3-chloro-4-methyl-1H-pyrrolo[2,3-b]pyridin-5-yl) methanamine hydrochloride (37.0 mg, 0.2 mmol, 1.0 eq) and Et$_3$N (114.8 mg, 1.1 mmol, 6.0 eq). The reaction mixture was stirred at rt for 2 h, then partitioned between EtOAc (50.0 mL) and water (50.0 mL). The organic layer was separated and concentrated. The resulting residue was purified on Prep-TLC (DCM/MeOH=10/1, v/v) to afford N-((3-chloro-4-methyl-1H-pyrrolo[2,3-b]pyridin-5-yl) methyl)-2-((3-chloroquinolin-6-yl)methyl)isonicotinamide (9.8 mg, 11%). $^1$H NMR (DMSO-d6, 400 MHz): δ 11.94 (s, 1H), 9.14 (s, 1H), 8.90 (s, 1H), 8.70 (d, 1H), 8.59 (s, 1H), 8.28 (s, 1H), 8.06 (d, 1H), 7.92 (s, 1H), 7.83-7.79 (m, 2H), 7.70-7.66 (m, 2H), 4.65 (d, 2H), 4.43 (s, 2H), 2.80 (s, 3H). LCMS (M+H$^+$) m/z calculated 476.1, found 476.4.

Example 190: Preparation of N-((3-chloro-6-methyl-1H-indol-5-yl)methyl)-2-((3-chloroquinolin-6-yl)methyl)isonicotinamide

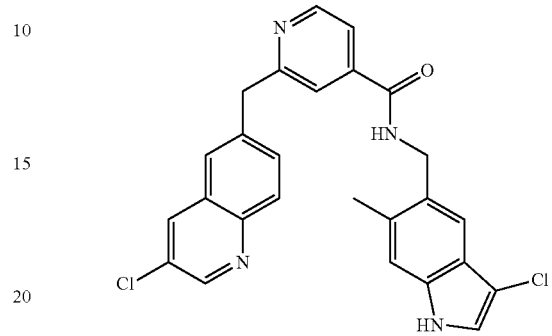

N-((3-chloro-6-methyl-1H-indol-5-yl)methyl)-2-((3-chloroquinolin-6-yl)methyl) isonicotinamide (8.1 mg) was prepared as described for N-((3-chloro-4-methyl-1H-pyrrolo[2,3-b]pyridin-5-yl) methyl)-2-((3-chloroquinolin-6-yl)methyl)isonicotinamide. $^1$H NMR. (DMSO-d6, 400 MHz): δ 11.2 (s, 1H), 9.15 (s, 1H), 8.83 (s, 1H), 8.66 (s, 1H), 8.52 (s, 1H), 7.99-7.69 (m, 4H), 7.37 (d, 2H), 7.22 (s, 1H), 4.55 (s, 2H), 4.38 (s, 2H), 2.38 (s, 3H). LRMS (M+H$^+$)m/z calculated 475.1, found 475.5.

Example 191: Preparation of N-((3-chloro-6-methyl-1H-pyrrolo[2,3-b]pyridin-5-yl) methyl)-2-((3-chloroquinolin-6-yl)methyl)isonicotinamide

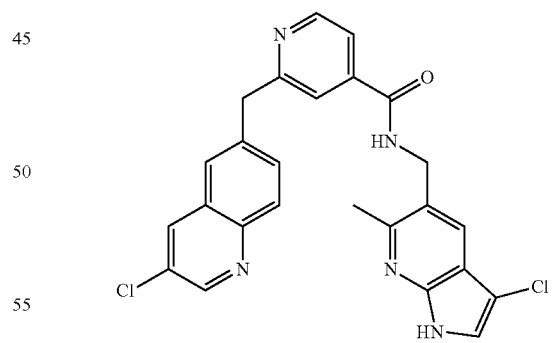

N-((3-chloro-6-methyl-1H-pyrrolo[2,3-b]pyridin-5-yl) methyl)-2-((3-chloroquinolin-6-yl)methyl)isonicotinamide (7.2 mg) was prepared as described for N-((3-chloro-4-methyl-1H-pyrrolo[2,3-b]pyridin-5-yl) methyl)-2-((3-chloroquinolin-6-yl)methyl)isonicotinamide. $^1$H NMR (DMSO-d6, 400 MHz): δ 9.20 (s, 1H), 8.83 (s, 1H), 8.65 (s, 1H), 8.52 (d, 1H), 7.98-7.54 (m, 8H), 4.58 (s, 2H), 4.37 (s, 2H), 2.68 (s, 3H). LRMS (M+H$^+$) m/z calculated 476.1, found 476.4.

Example 192: Preparation of N-((3-chloro-4,6-dimethyl-1H-pyrrolo[2,3-b]pyridin-5-yl)methyl)-2-((3-chloroquinolin-6-yl)methyl)isonicotinamide

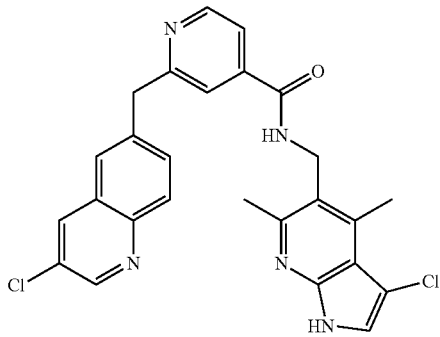 [SMILES: Cc1nc2[nH]cc(Cl)c2c(C)c1CNC(=O)c1ccnc(Cc2ccc3ncc(Cl)cc3c2)c1]

N-((3-chloro-4,6-dimethyl-1H-pyrrolo[2,3-b]pyridin-5-yl)methyl)-2-((3-chloroquinolin-6-yl)methyl)isonicotinamide (24.7 mg) was prepared as described for N-((3-chloro-4-methyl-1H-pyrrolo[2,3-b]pyridin-5-yl) methyl)-2-((3-chloroquinolin-6-yl) methyl)isonicotinamide. $^1$H NMR. (CD$_3$OD, 400 MHz) δ 8.79 (d, 1H), 8.70 (d, 1H), 8.36 (s, 1H), 7.97 (d, 1H), 7.80 (s, 1H), 7.78-7.80 (m, 2H), 7.70 (d, 1H), 7.54 (s, 1H), 4.77 (s, 2H), 4.48 (s, 2H), 3.00 (s, 3H), 2.84 (s, 3H). LRMS (M+H$^+$) m/z calculated 490.1, found 490.4.

Example 193: Preparation of N-((6-acetamido-2,4-dimethylpyridin-3-yl)methyl)-2-((3-chloroquinolin-6-yl)methyl)isonicotinamide

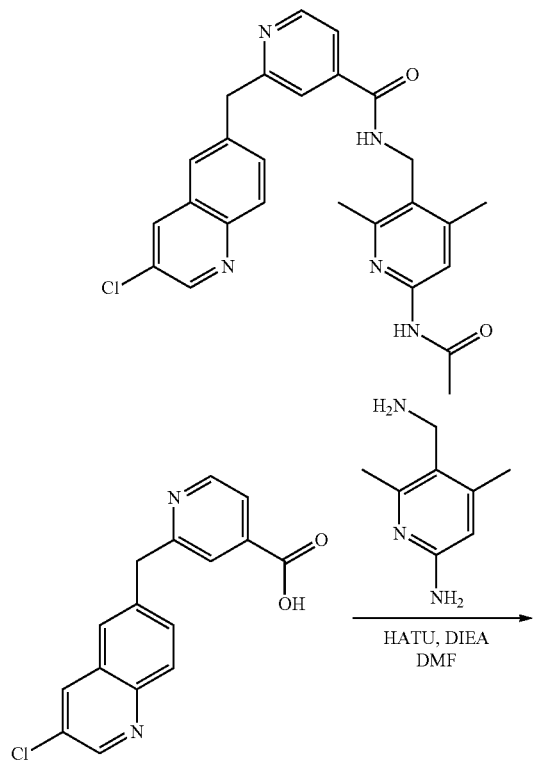

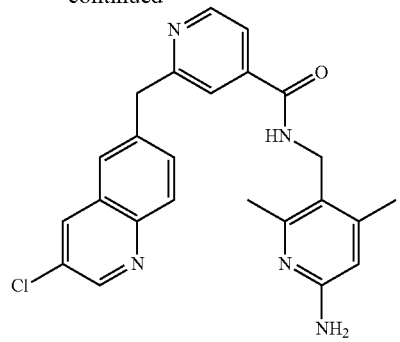

To a solution of 2-((3-chloroquinolin-6-yl)methyl)isonicotinic acid (30.0 mg, 0.1 mmol, 1.0 eq) and 5-(aminomethyl)-4,6-dimethylpyridin-2-amine (15.0 mg, 0.1 mmol, 1.0 eq) in DMF (1.5 mL) were added HATU (76.0 mg, 0.2 mmol, 2.0 eq) and DIEA (52.0 mg, 0.4 mmol, 4.0 eq). The mixture was stirred at rt for 2 h, and partitioned between EtOAc (40.0 mL) and water (40.0 mL). The organic layer was separated, dried and concentrated to afford N-((6-amino-2,4-dimethylpyridin-3-yl)methyl)-2-((3-chloroquinolin-6-yl)methyl) isonicotinamide (100 mg, crude).

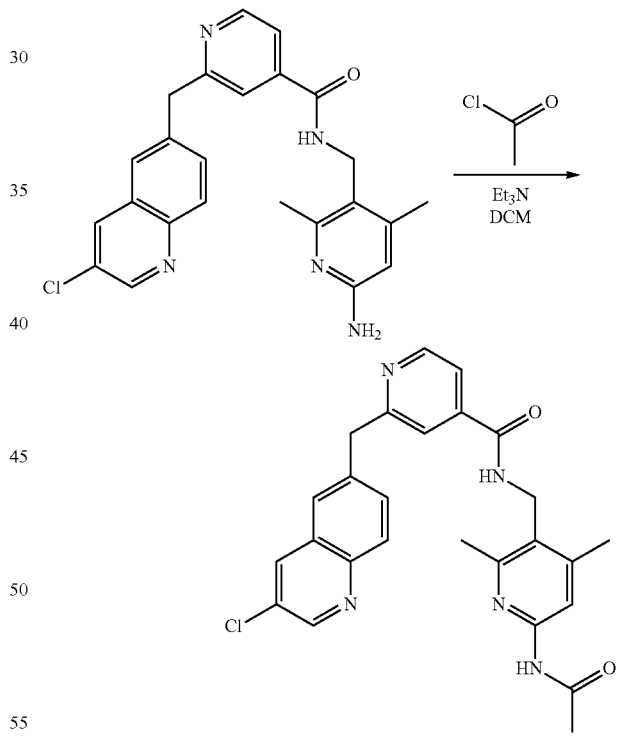

To a solution of N-((6-amino-2,4-dimethylpyridin-3-yl) methyl)-2-((3-chloro quinolin-6-yl)methyl)isonicotinamide (100 mg crude, 0.1 mmol, 1.0 eq) and Et$_3$N (30 mg, 0.3 mmol, 3.0 eq) in DCM (15.0 mL) was added acetyl chloride (24.0 mg, 0.3 mmol, 3.0 eq). The mixture was stirred at rt for 16 h, then concentrated. The resulting residue was purified on Prep-TLC (DCM/MeOH=10/1, v/v) to afford N-((6-acetamido-2,4-dimethylpyridin-3-yl)methyl)-2-((3-chloroquinolin-6-yl)methyl)isonicotinamide (14.0 mg, 30% in 2 steps). $^1$H NMR (CDCl$_3$, 400 MHz): δ 8.71-8.67 (m, 2H), 8.01 (s, 1H), 7.93 (d, 1H), 7.80-7.76 (m, 2H), 7.57 (s, 3H), 7.42 (d, 1H), 6.20 (s, 1H), 4.61 (d, 2H), 4.37 (d, 2H), 4.27 (s, 2H), 2.45 (s, 3H), 2.34 (s, 3H), 2.16 (s, 3H). LCMS (M+H⁺) m/z calculated 474.2, found 474.4.

Example 194: Preparation of 2-((3-chloroquinolin-6-yl)methyl)-N-((2,4,6-trimethyl Pyridin-3-yl)methyl)isonicotinamide

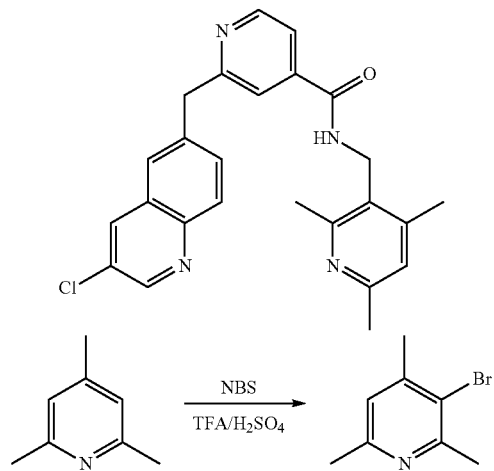

To a solution of 2,4,6-trimethylpyridine (1.2 g, 9.9 mmol, 1.0 eq) in TFA (2.0 mL) were added H₂SO₄ (98%, 2.7 mL) and NBS (1.76 g, 9.9 mmol, 1.0 eq). The mixture was stirred at rt for 40 h, then poured into ice-water (100.0 mL) and adjusted to pH 9 with NaHCO₃. The aqueous phase was extracted with EtOAc (100 mL×3). The combined organic layers were dried and concentrated. The resulting residue was purified by chromatography on silica gel (EtOAc/PE=1/10, v/v) to afford 3-bromo-2,4,6-trimethylpyridine (1.3 g, 65%).

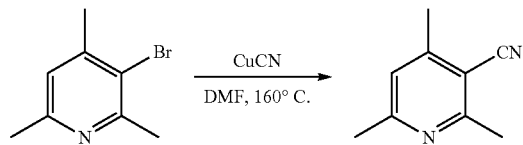

To a solution of 3-bromo-2,4,6-trimethylpyridine (670.0 mg, 3.4 mmol, 1.0 eq) in DMF (15.0 mL) was added CuCN (300.0 mg, 3.4 mmol, 1.0 eq). The mixture was stirred at 160° C. for 16 h, then cooled and partitioned between EtOAc (150.0 mL) and water (150.0 mL). The organic layer was separated and concentrated. The resulting residue was purified by chromatography on silica gel (EtOAc/PE=1/3, v/v) to afford 2,4,6-trimethylnicotinonitrile (220.0 mg, 45%).

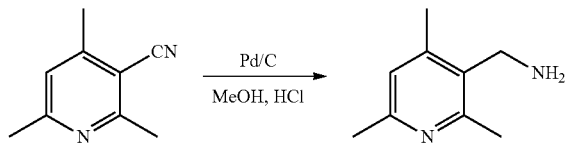

To a solution of 2,4,6-trimethylnicotinonitrile (105.0 mg, 0.7 mmol, 1.0 eq) in MeOH (15.0 mL) was added Pd/C (5%, 10.0 mg) and HCl (12 N, 2 drops). The mixture was stirred at rt under H₂ (1 atm) for 16 h, then filtered. The filtrate was concentrated, and the resulting residue was purified by chromatography on silica gel (EtOAc/MeOH=1/1, v/v) to afford (2,4,6-tri methylpyridin-3-yl)methanamine (35.0 mg, 32%).

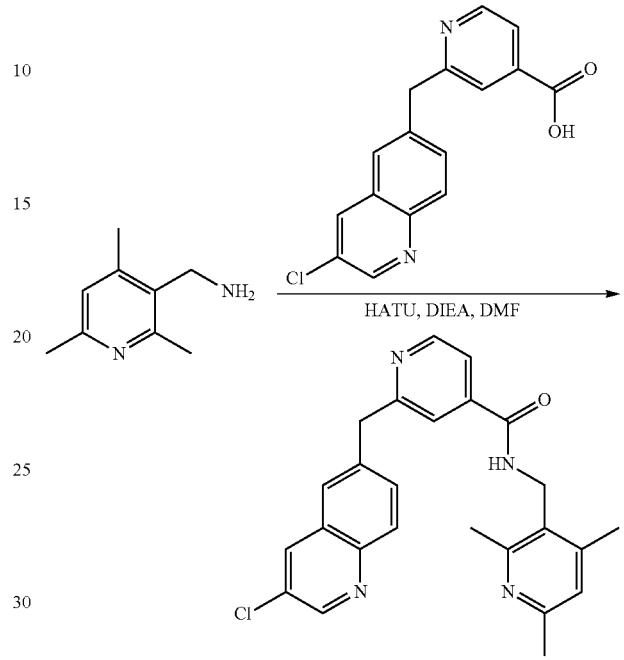

To a solution of 2-((3-chloroquinolin-6-yl)methyl)isonicotinic acid (47.0 mg, 0.16 mmol, 1.0 eq) and (2,4,6-trimethylpyridin-3-yl)methanamine (35.0 mg, 0.24 mmol, 1.5 eq) in DMF (2.5 mL) were added HATU (90.0 mg, 0.24 mmol, 1.5 eq) and DIEA (81.0 mg, 0.63 mmol, 4.0 eq). The mixture was stirred at rt for 16 h, then partitioned between EtOAc (40.0 mL) and water (40.0 mL). The organic layer was separated and concentrated. The resulting residue was purified on Prep-TLC (DCM/MeOH=10/1, v/v) to afford 2-((3-chloroquinolin-6-yl)methyl)-N-((2,4,6-trimethylpyridin-3-yl)methyl) isonicotinamide (46.0 mg, 68%). ¹H NMR (CDCl₃, 400 MHz): δ 8.74 (d, 1H), 8.67 (d, 1H), 8.03 (d, 1H), 7.97 (d, 1H), 7.60 (d, 2H), 7.56 (s, 1H), 7.42 (d, 1H), 6.89 (s, 1H), 6.19 (t, 1H), 4.64 (d, 2H), 4.37 (s, 2H), 2.55 (s, 3H), 2.47 (s, 3H), 2.34 (s, 3H). LCMS (M+H⁺) m/z calculated 431.2, found 431.5.

Example 195: Preparation of 2-((3-chloroquinolin-6-yl)methyl)-N-((2,4-dimethyl-5,6,7,8-tetrahydro-1,8-naphthyridin-3-yl)methyl)isonicotinamide

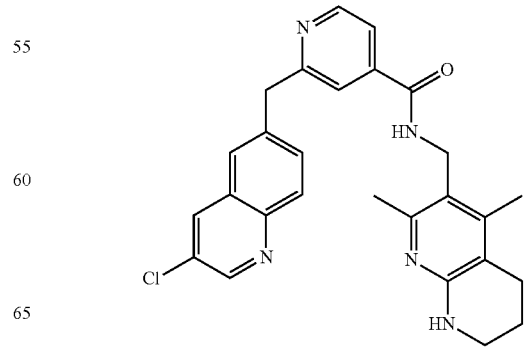

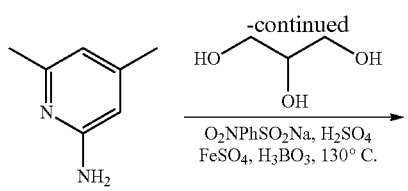

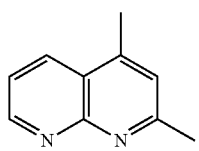

To a solution of sodium 3-nitrobenzenesulfinate (4.5 g, 20.0 mmol, 2.0 eq) in H$_2$SO$_4$ (98%, 6 mL) were added FeSO$_4$·7H$_2$O (2.8 g, 10.0 mmol, 1.0 eq) and H$_3$BO$_3$ (0.6 g, 10.0 mmol, 1.0 eq), followed by glycerol (2.8 g, 30.0 mmol, 3.0 eq) and 4,6-dimethylpyridin-2-amine (1.2 g, 10.0 mmol, 1.0 eq). The mixture was heated at 130° C. for 1 h, then cooled and poured into ice-water (150.0 mL) and adjusted to pH 9 with NaOH. The aqueous phase was extracted with EtOAc (100 mL×5). The combined organic layers were dried and concentrated. The resulting residue was purified by chromatography on silica gel (DCM/MeOH=10/1, v/v) to afford 2,4-dimethyl-1,8-naphthyridine (770.0 mg, 49%).

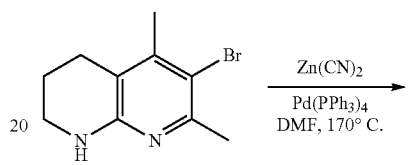

To a solution of 2,4-dimethyl-1,8-naphthyridine (500.0 mg, 3.2 mmol, 1.0 eq) in MeOH (20.0 mL) was added Pd/C (5%, 50 mg). The mixture was stirred at rt under H$_2$ (1 atm) for 60 h, then filtered. The filtrate was concentrated and the residue was purified by chromatography on silica gel (DCM/MeOH=20/1, v/v) to afford 5,7-dimethyl-1,2,3,4-tetrahydro-1,8-naphthyridine (170.0 mg, 33%).

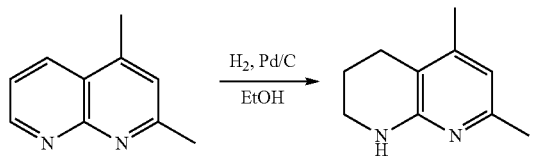

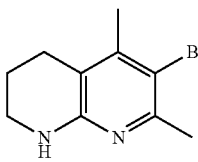

To a solution of 5,7-dimethyl-1,2,3,4-tetrahydro-1,8-naphthyridine (170.0 mg, 1.1 mmol, 1.0 eq) in DCM (25 mL) was added a solution of a solution of 1,3-dibromo-5,5-dimethylimidazolidine-2,4-dione (150 mg, 0.52 mmol, 0.5 eq) in DCM (5 mL) dropwise at −78° C. under N$_2$. After the addition, the mixture was stirred at −78° C. for 15 min, then quenched with saturated Na$_2$S$_2$O$_3$ aqueous (30.0 mL), and aqueous KOH (10%, 20.0 mL) was added. The aqueous layer was extracted with DCM (50.0 mL×2). The combined organic layers were dried and concentrated to afford 6-bromo-5,7-dimethyl-1,2,3,4-tetrahydro-1,8-naphthyridine (220.0 mg, 87%).

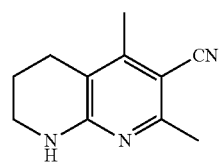

To a solution of 6-bromo-5,7-dimethyl-1,2,3,4-tetrahydro-1,8-naphthyridine (220.0 mg, 0.9 mmol, 1.0 eq) in DMF (7.5 mL) were added Zn(CN)$_2$ (160.0 mg, 1.4 mmol, 1.5 eq) and Pd(PPh$_3$)$_4$ (105.0 mg, 0.091 mmol, 0.1 eq). The mixture was stirred at 170° C. under microwave irradiation for 50 min, then cooled and partitioned between EtOAc (50.0 mL) and water (50.0 mL). The organic layer was separated and concentrated and the residue was purified by chromatography on silica gel (EtOAc/PE=1/3, v/v) to afford 2,4-dimethyl-5,6,7,8-tetrahydro-1,8-naphthyridine-3-carbonitrile (142.0 mg, 82%).

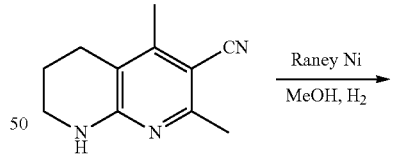

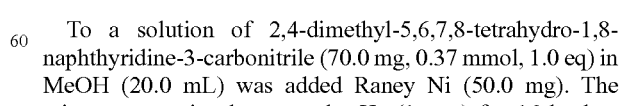

To a solution of 2,4-dimethyl-5,6,7,8-tetrahydro-1,8-naphthyridine-3-carbonitrile (70.0 mg, 0.37 mmol, 1.0 eq) in MeOH (20.0 mL) was added Raney Ni (50.0 mg). The mixture was stirred at rt under H$_2$ (1 atm) for 16 h, then filtered. The filtrate was concentrated, and the resulting residue was purified on Prep-TLC (DCM/MeOH=10/1, v/v) to afford (2,4-dimethyl-5,6,7,8-tetrahydro-1,8-naphthyridin-3-yl)methanamine (31.0 mg, 43%).

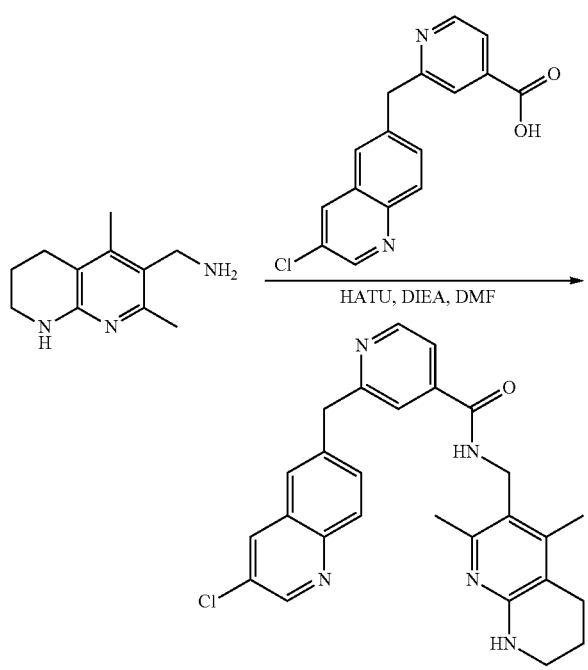

To a solution of 2-((3-chloroquinolin-6-yl)methyl)isonicotinic acid (48.0 mg, 0.16 mmol, 1.0 eq) and (2,4-dimethyl-5,6,7,8-tetrahydro-1,8-naphthyridin-3-yl)methanamine (31.0 mg, 0.16 mmol, 1.0 eq) in DMF (5.0 mL) were added HATU (92.0 mg, 0.24 mmol, 1.5 eq) and DIEA (84 mg, 0.65 mmol, 4.0 eq). The mixture was stirred at rt for 16 h, then partitioned between EtOAc (50.0 mL) and water (50.0 mL). The organic layer was separated and concentrated. The resulting residue was purified on Prep-TLC (DCM/MeOH=10/1, v/v) to afford 2-((3-chloroquinolin-6-yl)methyl)-N-((2,4-dimethyl-5,6,7,8-tetrahydro-1,8-naphthyridin-3-yl)methyl)isonicotinamide (26.0 mg, 34%). $^1$H NMR (CDCl$_3$, 400 MHz): δ 8.70 (s, 1H), 8.66 (d, 1H), 8.01 (s, 1H), 7.93 (d, 1H), 7.60-7.59 (m, 3H), 7.47 (d, 1H), 6.33 (s, 1H), 5.45 (s, 1H), 4.52 (d, 2H), 4.36 (s, 2H), 3.34 (m, 2H), 2.60 (t, 2H), 2.35 (s, 3H), 2.14 (s, 3H), 1.94 (m, 2H). LCMS (M+H$^+$) m/z calculated 472.2, found 472.4.

Example 196: Preparation of N-((6-amino-2,4-dimethylpyridin-3-yl)methyl)-2-((3-chloro quinolin-6-yl)methyl)-6-(5-oxo-4,5-dihydro-1H-1,2,4-triazol-3-yl)isonicotinamide

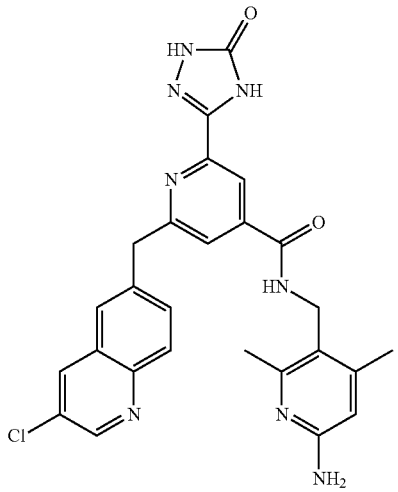

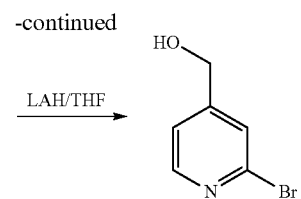

To a suspension of LAH (7.2 g, 190.0 mmol, 2.0 eq) in THF (150.0 mL) was added ethyl 5-chloro-1-(phenylsulfonyl)-1H-indole-2-carboxylate (20.5 g, 95.0 mmol, 1.0 eq.) at 0° C. under N$_2$. The resulting mixture was stirred at 0° C. for 30 min, then quenched by the addition of EtOAc (100.0 mL), followed by water (50.0 mL). The mixture was extracted with EA (100 mL×3). The combined organic layers were dried over anhydrous Na$_2$SO$_4$ and concentrated to afford (2-bromopyridin-4-yl)methanol (13.5 g, 35%).

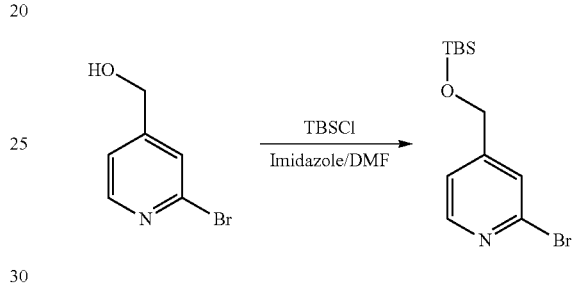

To a solution of (2-bromopyridin-4-yl)methanol (13.5 g, 72.0 mmol, 1.0 eq.) and imidazole (13.5 g, 144.0 mmol, 2.0 eq.) in DMF (50.0 mL) was added TBSCl (12.9 g, 86.0 mmol, 1.2 e.q) at 0° C. and the mixture was stirred at 25° C. for 16 h, then quenched by the addition of ice-water (50.0 mL) and extracted with EOAc (100 mL×3). The combined organic layers were dried and concentrated. The resulting residue was purified by chromatography on silica gel (EA/PE=1/3, v/v) to provide 2-bromo-4-(((tert-butyldimethylsilyl)oxy)methyl)pyridine (16.4 g, 75%).

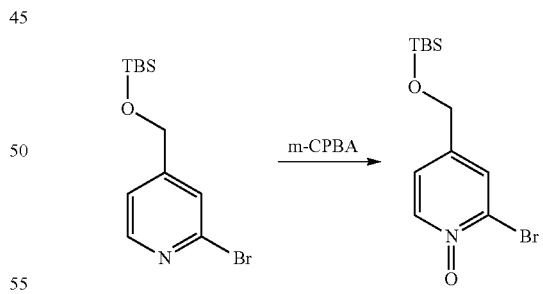

To a solution of 2-bromo-4-(((tert-butyldimethylsilyl)oxy)methyl)pyridine (16.4 g, 54 mmol) in DCM (150.0 mL) was added m-CPBA (11.3 g, 65.0 mmol, 1.2 e.q) at 0° C. The mixture was stirred at 25° C. for 16 h, then quenched by the addition of ice-water (50.0 mL) and extracted with EOAc (100.0 mL×3). The combined organic layers were dried and concentrated. The resulting residue was purified by chromatography on silica gel (EA/PE=2/1, v/v) to provide 2-bromo-4-(((tert-butyldimethylsilyl)oxy)methyl)pyridine 1-oxide (9.3 g, 53%).

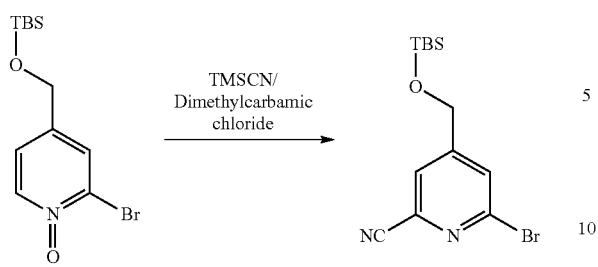

To a solution of 2-bromo-4-(((tert-butyldimethylsilyl)oxy)methyl)pyridine 1-oxide (9.3 g, 29.0 mmol, 1.0 eq.) and TMSCN (4.5 g, 45.0 mmol, 1.5 eq.) in DCM (150.0 mL) at 0° C. was added dimethylcarbamic chloride (4.8 g, 45.0 mmol, 1.5 e.q) and the mixture was stirred at 25° C. for 16 h, then quenched by the addition of ice-water (50.0 mL) and extracted with EOAc (120 mL×2). The combined organic layers were dried and concentrated. The resulting residue was purified by chromatography on silica gel (EA/PE=2/1, v/v) to provide 6-bromo-4-(((tert-butyldimethylsilyl)oxy)methyl)picolinonitrile (6.4 g, 65%).

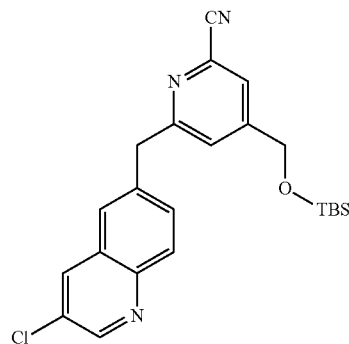

To a solution of 6-bromo-4-(((tert-butyldimethylsilyl)oxy)methyl) picolinonitrile (1.4 g, 4.0 mmol, 1.0 eq.) in toluene (40.0 mL) were added 1,1,1,2,2,2-hexamethyldistannane (2.0 g, 6.0 mmol, 1.5 eq.) and Pd(PPh$_3$)$_4$ (0.3 g, 0.2 mmol, 0.05 eq.). The mixture was stirred at 80° C. for 16 h under N$_2$, then cooled and filtered. The filtrate was concentrated in vacuo. Toluene (20 mL) was added to the residue and the mixture was concentrated to provide 4-(((tert-butyldimethylsilyl)oxy)methyl)-6-(trimethylstannyl) picolinonitrile (1.6 g, quant.) as a yellow oil which was used in the next step without further purification.

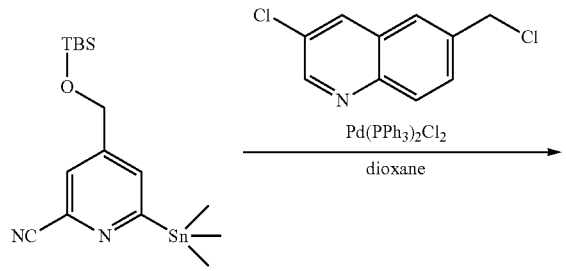

To a solution of 4-(((tert-butyldimethylsilyl)oxy)methyl)-6-(trimethylstannyl)-picolinonitrile (370.0 mg, 0.9 mmol, 1.0 eq.) in dioxane (4.0 mL) were added 2-trimethylstannanyl-isonicotinic acid methyl ester (290.0 mg, 0.95 mmol, 1.1 eq.) and Pd(PPh$_3$)$_2$Cl$_2$ (31.0 mg, 0.05 mmol, 0.05 eq). The mixture was stirred at 110° C. for 16 h under nitrogen atmosphere, cooled and concentrated. The resulting residue was purified by chromatography on silica gel (DCM/MeOH=20/1, v/v) to afford 4-(((tert-butyldimethylsilyl)oxymethyl)-6-((3-chloroquinolin-6-yl)methyl)picolinonitrile (230 mg).

To a solution of 4-(((tert-butyldimethylsilyl) oxy)methyl)-6-((3-chloroquinolin-6-yl) methyl)picolinonitrile (230.0 mg, 0.5 mmol, 1.0 eq.) in THF (4.0 mL) was added TBAF in THF (1.1 mL, 1.1 mmol, 2.0 eq.). The mixture was stirred at 25° C. for 16 h under nitrogen atmosphere, cooled and concentrated. The resulting residue was purified on Prep-TLC (DCM/MeOH=10/1, v/v) to afford 6-((3-chloroquinolin-6-yl)methyl)-4-(hydroxymethyl)picolinonitrile (150.0 mg, 90%).

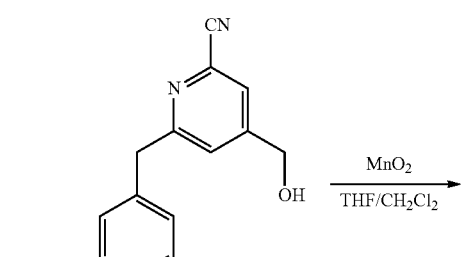

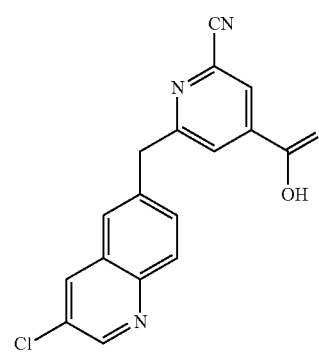

To a solution of 4-(((tert-butyldimethylsilyl)oxy)methyl)-6-((3-chloroquinolin-6-yl)methyl)picolinonitrile (150.0 mg, 0.5 mmol, 1.0 eq.) in THF (4.0 mL) and DCM (4.0 mL) was added MnO$_2$ (420.0 mg, 4.8 mmol, 10.0 eq.). The mixture was stirred at 25° C. for 16 h under nitrogen atmosphere, filtered and concentrated to afford 2-((3-chloroquinolin-6-yl)methyl)-6-cyanoisonicotinic acid (145.0 mg, 90%).

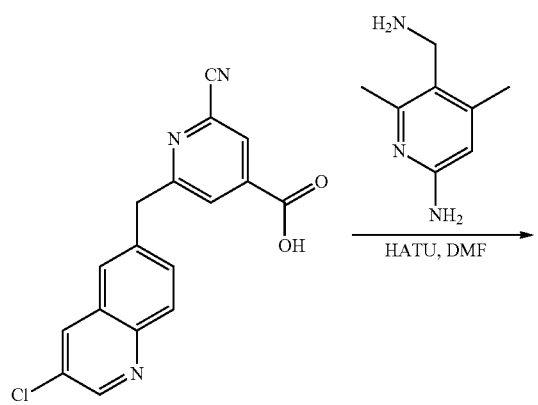

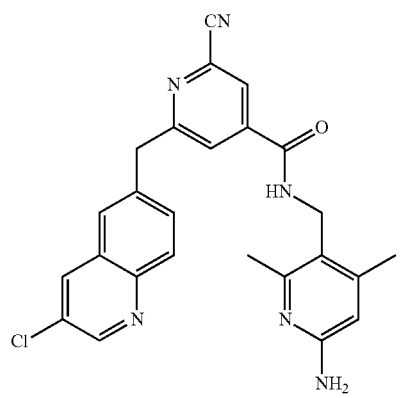

To a solution of 2-((3-chloroquinolin-6-yl)methyl)-6-cyanoisonicotinic acid (80.0 mg, 0.3 mmol, 1.0 eq.) and 5-(aminomethyl)-4,6-dimethylpyridin-2-amine (44.0 mg, 0.3 mmol, 1.0 eq.) in DMF (2.5 mL) were added HATU (132.0 mg, 0.4 mmol, 1.5 eq.) and DIEA (136.0 mg, 1.2 mmol, 4.0 eq.). The reaction was stirred at rt for 16 h, then partitioned between EtOAc (25.0 mL) and water (25.0 mL). The organic layer was separated and concentrated. The resulting residue was purified on Prep-TLC (DCM/MeOH=10/1, v/v) to provide N-((6-amino-2,4-dimethylpyridin-3-yl)methyl)-2-((3-chloroquinolin-6-yl)methyl)-6-cyanoisonicotinamide (50.0 mg, 44%).

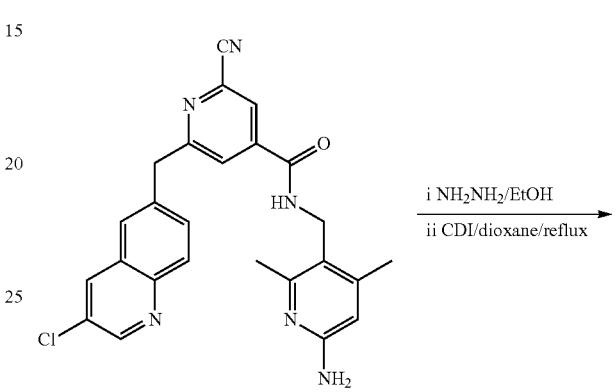

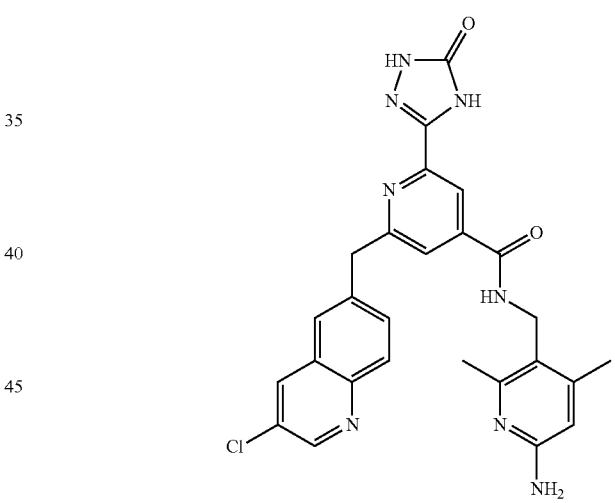

A mixture of N-((6-amino-2,4-dimethylpyridin-3-yl)methyl)-2-((3-chloroquinolin-6-yl)methyl)-6-cyanoisonicotinamide (40.0 mg 0.1 mmol, 1.0 eq.) in EtOH (4.0 mL) was added hydrazine hydrate (14.5 mg, 0.3 mmol, 3.0 eq.). The mixture was stirred at 25° C. for 1 h, then was added CDI (47.0 mg, 0.3 mmol, 3.0 eq.) in dioxane (2 mL). The mixture was stirred under nitrogen atmosphere for 8 h, cooled, concentrated and purified by Prep-HPLC to provide N-((6-amino-2,4-dimethylpyridin-3-yl)methyl)-2-((3-chloroquinolin-6-yl)methyl)-6-(5-oxo-4,5-dihydro-1H-1,2,4-triazol-3-yl)isonicotinamide (4.0 mg, 8%). $^1$H NMR (CD3OD, 400 MHz): δ 8.76 (s, 1H), 8.36 (s, 1H), 8.18 (s, 1H), 7.96 (d, 1H), 7.87 (s, 1H), 7.80 (d, 1H), 7.68 (s, 1H), 4.46 (d, 2H), 4.43 (d, 2H), 2.56 (s, 3H), 2.44 (s, 3H). LCMS (M+H$^+$) m/z calculated 515.2, found 515.5.

Example 197: Preparation of N-((6-amino-2-methylpyridin-3-yl)methyl)-2-((3-chloroquinolin-6-yl)methyl)isonicotinamide

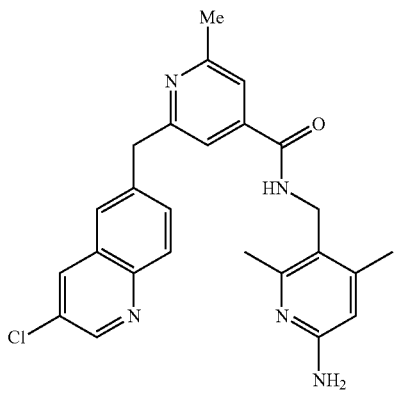

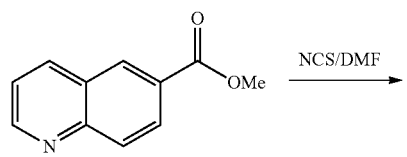

To a solution of methyl quinoline-6-carboxylate (15.0 g, 80.2 mmol, 1.0 eq) in DMF (200 mL) was added N-chlorosuccinimide (21.4 g, 0.16 mol, 2.0 eq) and the reaction mixture was stirred at 120° C. for 20 h, then cooled to rt, and washed with brine. The mixture was extracted with EA. The combined organic layers were dried over Na₂SO₄, filtered and concentrated. The resulting residue was purified by chromatography on silica gel (EA/PE=1/8) to afford methyl 3-chloroquinoline-6-carboxylate (9.1 g, 51%) as a yellow solid.

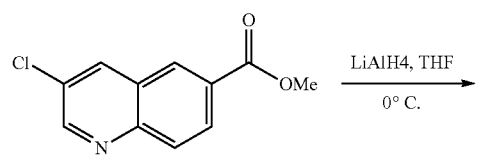

To a solution of methyl 3-chloroquinoline-6-carboxylate (8 g, 36.0 mmol, 1.0 eq) in dry THF was added LiAlH₄ (2.5M in THF, 5.8 mL, 0.4 eq). The resulting mixture was stirred at 0° C. for 1 h. After which period, additional LiAlH₄ (2.5 M in THF, 2.8 mL, 0.2.0 eq) was added. The system was stirred for another 30 min at 0° C. and quenched by the slow addition of 1N aqueous NaOH. The resulting precipitate was filtered, the filtrate was extracted with EA. The combined organic layer was dried and concentrated. The resulting residue was purified by chromatography on silica gel (PE/EA=20/1~5/1) to afford (3-chloro-quinolin-6-yl)-methanol (4.8 g, 69%) as a white solid.

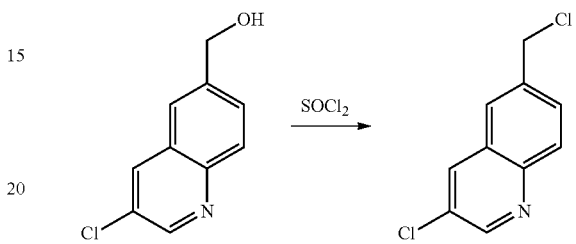

To (3-chloro-quinolin-6-yl)-methanol (3.3 g, 17.1 mmol, 1.0 eq) was added SOCl₂ (50 mL) and the mixture was stirred at rt for 1 h. The volatiles were then concentrated under vacuum and the residue was dissolved in DCM. The mixture was washed with saturated aq. NaHCO₃, dried and concentrated to give 3-chloro-6-chloromethyl-quinoline (3.4 g, 94%) as a yellow solid.

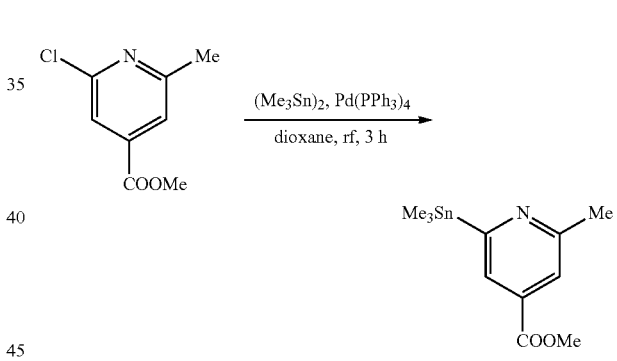

Hexamethyldistannane (0.21 mL, 334 mg, 1.0 mmol) and tetrakis(triphenylphosphine)palladium(0) (70 mg, 0.1 mmol) were added to a solution of methyl 2-chloro-6-methylisonicotinate (100 mg, 0.5 mmol) in dry dioxane (10 mL) and the resulting mixture was refluxed for 3 h under N₂. AcOEt (50 mL) and water (100 mL) were then added. The layers were separated and the organic layer was washed with water (5×100 mL), dried (Na₂SO₄), and concentrated. The resulting residue was used in the next step without further purification.

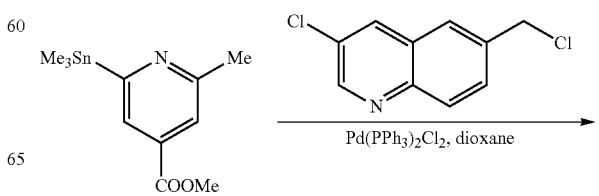

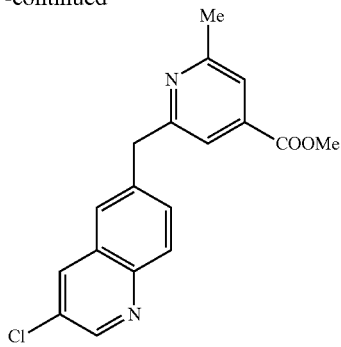

To a solution of 3-chloro-6-chloromethyl-quinoline (110 mg, 0.5 mmol, 1.0 eq) and crude methyl 2-methyl-6-(trimethylstannyl)isonicotinate from the above step in dioxane (10 mL) was added Pd(PPh$_3$)$_2$Cl$_2$ (36 mg, 0.05 mmol, 0.1.0 eq). The mixture was stirred at 90° C. for 3 h under nitrogen atmosphere, then concentrated under vacuum. The resulting residue was purified by chromatography on silica gel (EA/PE=10/1~5:1) to afford methyl 2-((3-chloroquinolin-6-yl)methyl)-6-methylisonicotinate (70 mg, 40%) as a yellow solid. $^1$H NMR (400 MHz, DMSO-d$_6$): δ 8.83 (d, 1H), 8.53 (d, 1H), 7.98 (d, 1H), 7.85 (d, 1H), 7.73 (dd, 1H), 7.58 (s, 1H), 7.57 (s, 1H), 4.36 (s, 2H), 3.85 (s, 3H), 2.53 (s, 3H).

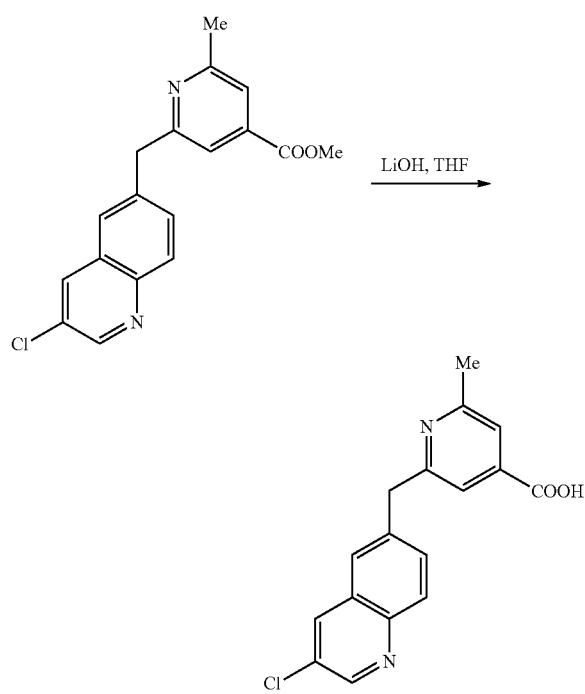

To the solution of 2-((3-chloroquinolin-6-yl)methyl)-6-methylisonicotinate (70 mg, 0.2 mmol, 1.0 eq) in THF/H$_2$O (5 mL/1 mL) was added LiOH (71 mg, 2.1 mmol, 10 eq). The resulting system was stirred for 1 h at room temperature until all starting material had been consumed (assessed by TLC), then concentrated under vacuum and the aqueous reside was neutralized with 1M HCl and extracted with EtOAc (10 mL×3). The combined organic layers were washed with brine, dried over Na$_2$SO$_4$ and concentrated to provide crude acid (50 mg, 75%), which was used in the next step without further purification.

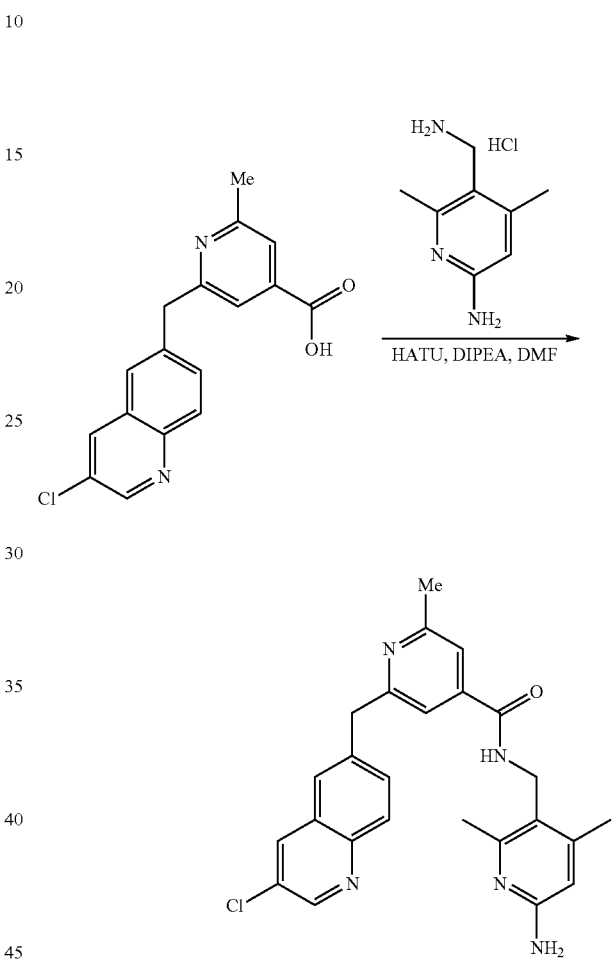

To a solution of 2-((3-chloroquinolin-6-yl)methyl)-6-methylisonicotinic acid (50 mg, 0.2 mmol, 1.0 eq) in DMF (5 mL) was added 5-aminomethyl-6-methyl-pyridin-2-ylamine hydrochloride (33 mg, 0.2 mmol, 1.2.0 eqeq), followed by HATU (91 mg, 0.2 mmol, 1.5 eq) and DIPEA (0.1 mL, 0.5 mmol, 3.0 eq) at 0° C. The reaction mixture was allowed to warm to room temperature and stirred for 2 h under N$_2$. Water (20 mL) was added, and the mixture was extracted with EtOAc (20 mL×3). The combined organic layers were washed with brine, dried over Na$_2$SO$_4$, filtered and concentrated. The residue was purified by prep-TLC (DCM:MeOH=15:1) to give N-((6-amino-2,4-dimethyl pyridin-3-yl)methyl)-2-((3-chloroquinolin-6-yl)methyl)-6-methylisonicotinamide (24 mg, 34%) as a yellow solid.

$^1$H NMR (DMSO-d$_6$, 400 MHz): δ 8.83 (d, 1H), 8.66 (brs, 1H), 8.53 (d, 1H), 7.97 (d, 1H), 7.84 (d, 1H), 7.71 (dd, 1H), 7.50 (s, 1H), 7.47 (s, 1H), 6.32 (brs, 2H), 4.32 (d, 2H), 4.29 (s, 2H), 2.48 (s, 3H), 2.37 (s, 3H), 2.23 (s, 3H). LRMS (M+H$^+$) m/z calculated 446.2, found 446, 448.

Example 198: Preparation of N-((6-amino-2,4-dimethylpyridin-3-yl)methyl)-2-((5-chloro-1H-indazol-1-yl) methyl)isonicotinamide

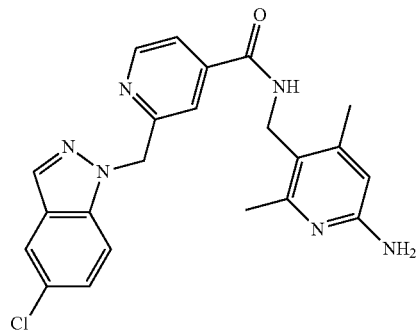

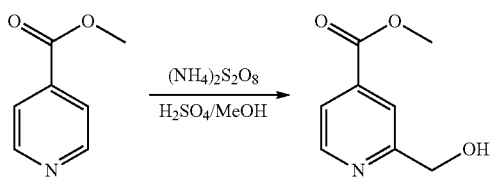

To a solution of methyl isonicotinate (5.0 g, 36.5 mmol, 1.0 eq) in MeOH (70 mL) was added conc. H₂SO₄ (300 mg, 3.1 mmol, 0.086 eq) dropwise at rt. The above mixture was heated at reflux, to which was added an aqueous solution of (NH₄)₂S₂O₈ (15.0 g, 65.7 mmol in 30 mL of water) dropwise. The reaction mixture was kept at reflux for 30 minutes, cooled to rt, treated with 4 M NaOH and aqueous NaHCO₃ to pH 7. The aqueous mixture was concentrated under vacuum to remove most MeOH, and the residue was extracted with EtOAc (100 mL×2). The combined organic layers were washed with brine, dried over Na₂SO₄, filtered and concentrated under vacuum. The residue was purified by chromatography on silica gel (PE/EA=1/3 to 1/1) to afford methyl 3-chloroquinoline-6-carboxylate (1.5 g, 25%) as a white solid. ¹H NMR (CDCl₃, 400 MHz): δ 8.71 (d, 1H), 7.84 (d, 1H), 7.77 (dd, 1H), 4.84 (s, 2H), 3.96 (s, 3H). LRMS (M+H⁺) m/z calculated 168.1, found 168.0.

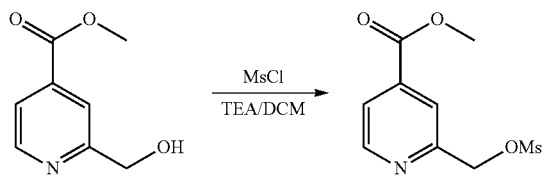 [SMILES: "MsCl" ; COC(=O)c1ccnc(CO)c1 ; "TEA/DCM" ; COC(=O)c1ccnc(COS(C)(=O)=O)c1]

To a stirred solution of methyl 2-(hydroxymethyl)isonicotinate (1.0 g, 6.0 mmol, 1.0 eq) and TEA (1.2 g, 12.0 mmol, 2.0 eq) in DCM (15 mL) was added MsCl (755 mg, 6.6 mmol, 1.1.0 eq) at 0° C. The resulting mixture was stirred at rt for 30 minutes, and then diluted with DCM (60 mL), washed with water (30 mL), brine (30 mL×2), dried and concentrated to afford methyl 2-(((methylsulfonyl)oxy)methyl)isonicotinate (1.2 g, 82%).

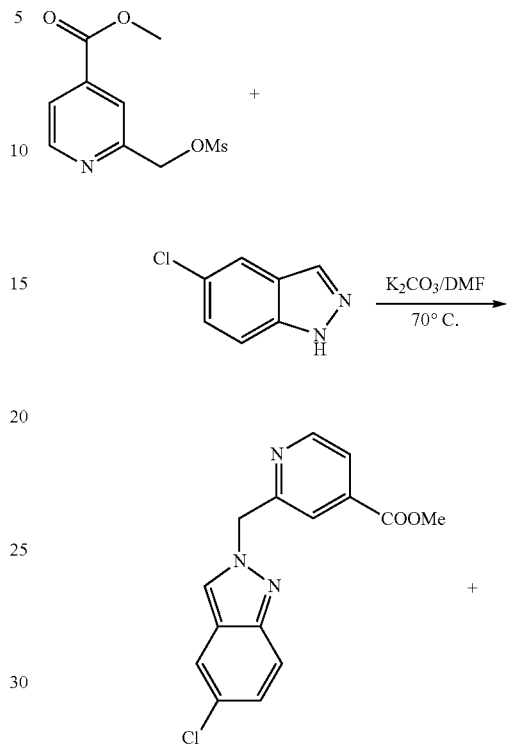

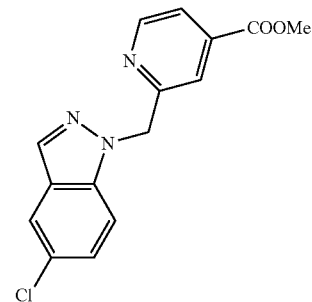

A mixture of methyl 2-(((methylsulfonyl)oxy)methyl) isonicotinate (300 mg, 1.22 mmol, 1.0 eq), 5-chloro-1H-indazole (280 mg, 1.84 mmol, 1.5 eq) and K₂CO₃ (337 mg, 2.44 mmol, 2.0 eq) in DMF (5 mL) was stirred at 70° C. for 2 h, then cooled to rt, diluted with EtOAc (50 mL), washed with water (30 mL), brine (30 mL×2), dried and concentrated. The resulting residue was purified by chromatography on silica gel (PE/EA=10/1~5/1) to afford methyl 2-((5-chloro-1H-indazol-1-yl)methyl)isonicotinate (120 mg, 33%) as a white solid. ¹H NMR (CDCl₃, 400 MHz): δ 8.68 (d, 1H), 8.00 (s, 1H), 7.73 (d, 1H), 7.69 (d, 1H), 7.48 (s, 1H), 7.34 (d, 1H), 7.28 (dd, 1H), 5.73 (s, 2H), 3.85 (s, 3H). Chromatography on silica gel (PE/EA=5/1 to 3/1) to afford methyl 2-((5-chloro-2H-indazol-2-yl)methyl)isonicotinate (70 mg, 19%) as a white solid.

¹H NMR (CDCl₃, 400 MHz): δ 8.73 (d, 1H), 8.05 (s, 1H), 7.79 (dd, 1H), 7.72 (s, 1H), 7.64-7.60 (m, 2H), 7.21 (dd, 1H), 5.75 (s, 2H), 3.90 (s, 3H).

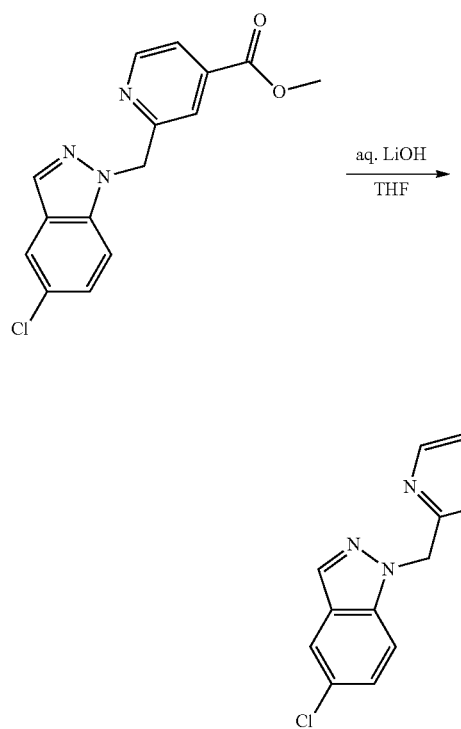

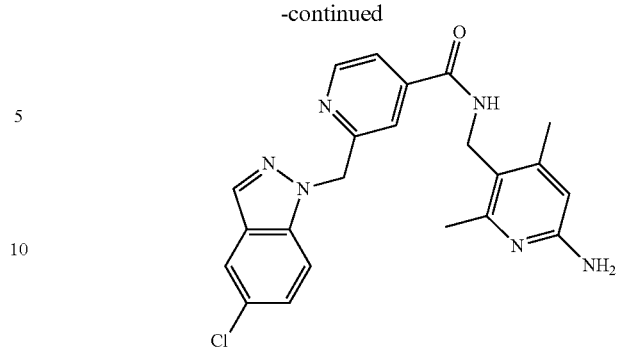

To a solution of methyl 2-((5-chloro-1H-indazol-1-yl)methyl)isonicotinate (270 mg, 0.89 mmol, 1.0 eq) in THF (5 mL) was added LiOH·H$_2$O (375 mg, 8.9 mmol, 10.0 eq) and water (5 mL). The mixture was stirred at rt for 2 h, then concentrated under vacuum to remove most THF. The aqueous mixture was adjusted with 1M HCl to about pH=7. The white suspension was filtered, and the solid was washed with water (10 mL), and dried to afford 2-((5-chloro-1H-indazol-1-yl)methyl)isonicotinic acid (240 mg, 93%) as a white solid.

To a stirred mixture of 2-((5-chloro-1H-indazol-1-yl)methyl)isonicotinic acid (100 mg, 0.35 mmol, 1.0 eq), TEA (101 mg, 1.0 mmol, 3.0 eq) and 5-(aminomethyl)-4,6-dimethylpyridin-2-amine hydrochloride (65 mg, 0.35 mmol, 1.0 eq) in DMF (3 mL) was added HATU (264 mg, 0.7 mmol, 2.0 eq) at 0° C. The reaction mixture was stirred at rt for 16 h, then diluted with EtOAc (50 mL). The resulting mixture was washed with water (30 mL), brine (30 mL×2), dried and concentrated. The resulting residue was purified by chromatography on silica gel (DCM/MeOH=50/1 to 20/1) and prep-TLC (DCM/MeOH=20/1) to afford N-((6-amino-2,4-dimethylpyridin-3-yl)methyl)-2-((5-chloro-1H-indazol-1-yl)methyl)isonicotinamide (10 mg, 7%) as a white solid.

$^1$H NMR (DMSO-d$_6$, 400 MHz): δ 8.68 (brt, 1H), 8.57 (d, 1H), 8.10 (d, 1H), 7.88 (d, 1H), 7.75 (d, 1H), 7.65 (dd, 1H), 7.49 (s, 1H), 7.40 (dd, 1H), 6.14 (s, 1H), 5.82-5.73 (m, 4H), 4.30 (d, 2H), 2.28 (s, 3H), 2.15 (s, 3H). LRMS (M+H+) m/z calculated 421.1, found 421.0.

Example 199: Preparation of N-((6-amino-2,4-dimethylpyridin-3-yl)methyl)-2-((5-chloro-2H-indazol-2-yl)methyl)isonicotinamide

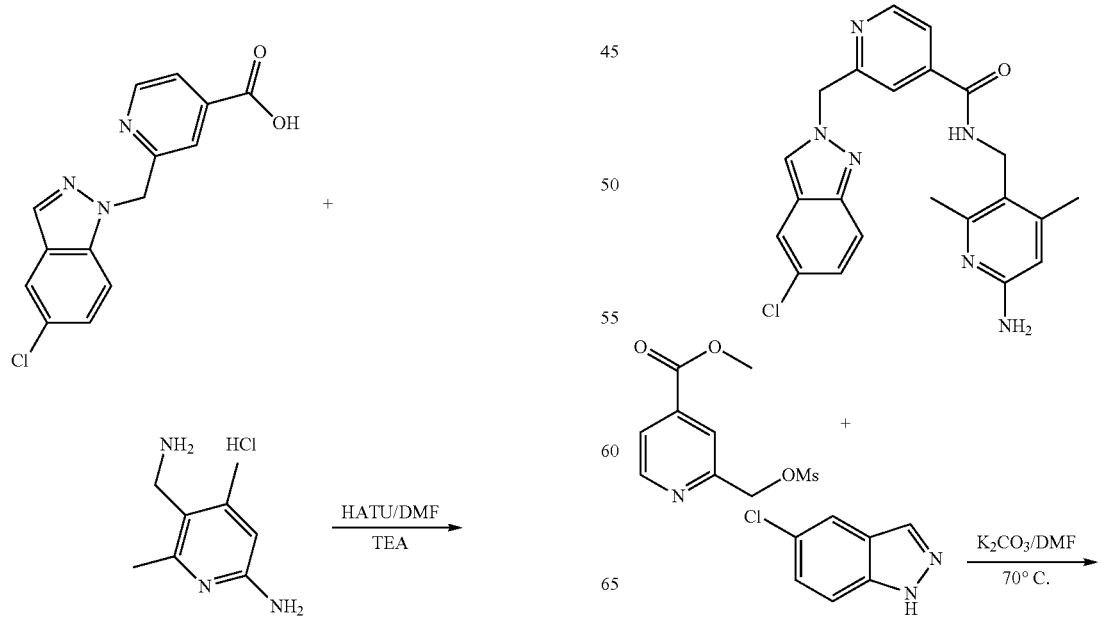

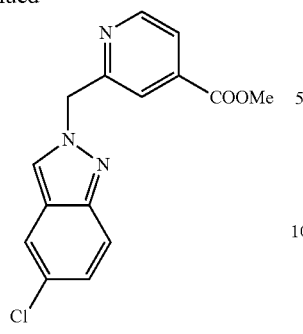

A mixture of methyl 2-(((methylsulfonyl)oxy)methyl)isonicotinate (300 mg, 1.22 mmol, 1.0 eq), 5-chloro-1H-indazole (280 mg, 1.84 mmol, 1.5 eq) and K$_2$CO$_3$ (337 mg, 2.44 mmol, 2 eq) in DMF (5 mL) was stirred at 70° C. for 2 h, then cooled to rt, diluted with EtOAc (50 mL), washed with water (30 mL), brine (30 mL×2), dried and concentrated. The residue was purified by chromatography on silica gel (EA/PE=1/5 to 1/3) to afford methyl 2-((5-chloro-2H-indazol-2-yl)methyl)isonicotinate (70 mg, 19%) as a white solid. $^1$H NMR (CDCl$_3$, 400 MHz): δ 8.73 (d, 1H), 8.05 (s, 1H), 7.79 (dd, 1H), 7.72 (s, 1H), 7.64-7.60 (m, 2H), 7.21 (dd, 1H), 5.75 (s, 2H), 3.90 (s, 3H).

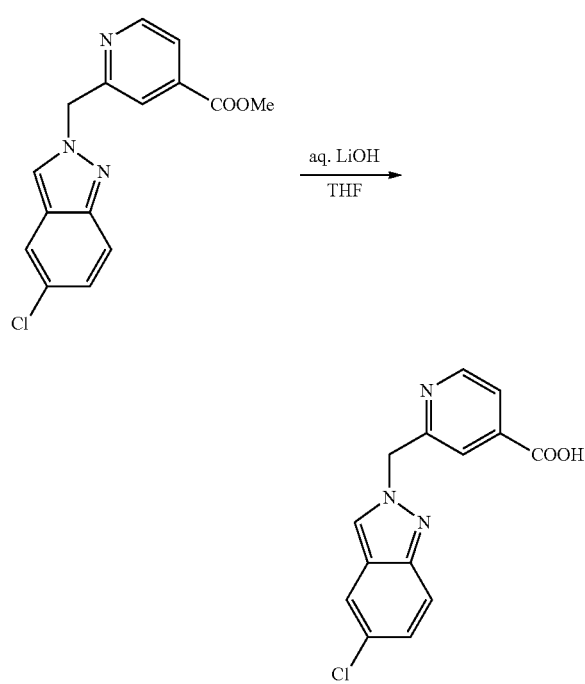

To a solution of methyl 2-((5-chloro-2H-indazol-2-yl)methyl)isonicotinate (150 mg, 0.50 mmol, 1.0 eq) in THF (5 mL) were added LiOH.H$_2$O (208 mg, 5.0 mmol, 10.0 eq) and water (5 mL). The mixture was stirred at rt for 2 h, concentrated under vacuum to remove most THF. The aqueous mixture was adjusted with 1M HCl to about pH=7. The white suspension was filtered and the solid was washed with water (10 mL), dried to afford 2-((5-chloro-2H-indazol-2-yl)methyl)isonicotinic acid (110 mg, 77%) as a white solid.

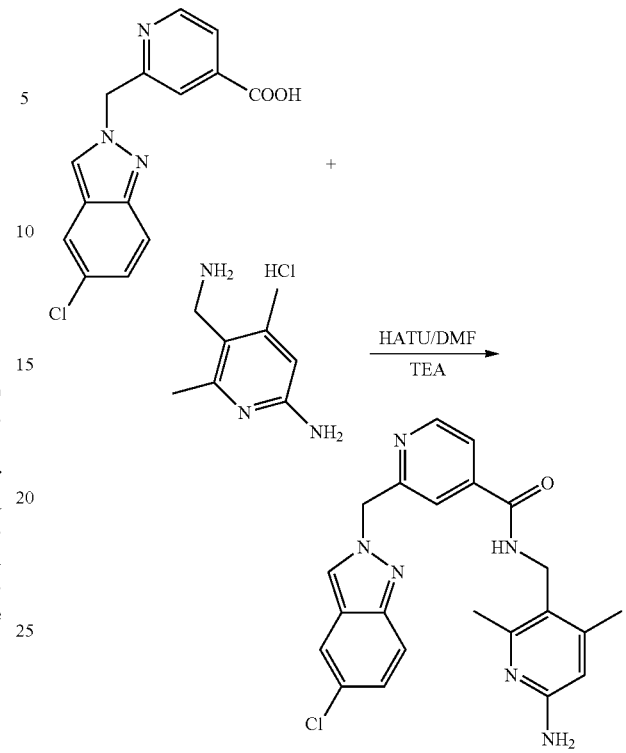

To a stirred mixture of 2-((5-chloro-2H-indazol-2-yl)methyl)isonicotinic acid (110 mg, 0.38 mmol, 1.0 eq), TEA (105 mg, 1.0 mmol, 3.0 eq) and 5-(aminomethyl)-4,6-dimethylpyridin-2-amine hydrochloride (71 mg, 0.38 mmol, 1.0 eq) in DMF (3 mL) was added HATU (290 mg, 0.76 mmol, 2.0 eq) at 0° C. The reaction mixture was stirred at rt for further 16 h, then diluted with EtOAc (50 mL). The resulting mixture was washed with water (30 mL), brine (30 mL×2), dried and concentrated. The residue was purified by chromatography on silica gel (DCM/MeOH=50/1 to 10/1) and prep-TLC (DCM/MeOH=10/1) to afford N-((6-amino-2,4-dimethylpyridin-3-yl)methyl)-2-((5-chloro-2H-indazol-2-yl)methyl)isonicotinamide (30 mg, 19%) as a white solid. $^1$H NMR (400, DMSO-d$_6$): δ 8.84 (br, 1H), 8.65 (d, 1H), 8.55 (d, 1H), 7.85 (dd, 1H), 7.69 (dd, 1H), 7.60-7.63 (m, 2H), 7.23 (dd, 1H), 6.38 (s, 1H), 5.81 (s, 2H), 4.33 (d, 2H), 2.41 (s, 3H), 2.27 (s, 3H). LRMS (M+H$^+$) m/z calculated 421.1, found 421.0.

Example 200: Preparation of N-((6-amino-2,4-dimethylpyridin-3-yl)methyl)-2-((5-methyl-2H-indazol-2-yl)methyl)isonicotinamide

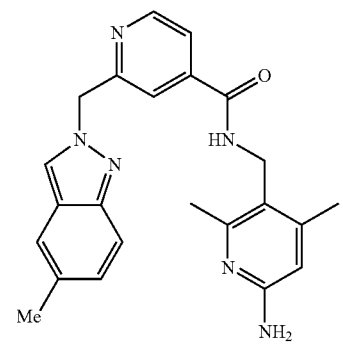 [SMILES: Cc1ccc2nn(Cc3cc(C(=O)NCc4c(C)cc(N)nc4C)ccn3)cc2c1]

N-((6-amino-2,4-dimethylpyridin-3-yl)methyl)-2-((5-methyl-2H-indazol-2-yl)methyl)isonicotinamide was prepared as described for N-((6-amino-2,4-dimethylpyridin-3-yl)methyl)-2-((5-chloro-2H-indazol-2-yl)methyl)isonicotinamide. $^1$H NMR (DMSO-d$_6$, 400 MHz): δ 8.78 (s, 1H), 8.63 (d, 1H), 8.38 (s, 1H), 7.75-7.64 (m, 1H), 7.54 (s, 1H), 7.47 (d1H), 7.46 (s, 1H), 7.07 (dd 1H), 6.29 (s, 2H), 5.75 (s, 2H), 4.32 (d2H), 2.35 (s, 6H), 2.22 (s, 3H).

Example 201: Preparation of N-((6-amino-2,4-dimethylpyridin-3-yl)methyl)-2-((5-methyl-3a,7a-dihydro-1H-indazol-1-yl)methyl)isonicotinamide

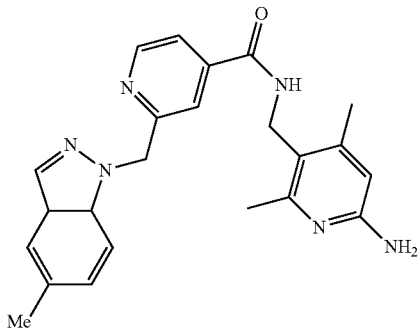 [SMILES: CC1=CC2C=NN(Cc3cc(C(=O)NCc4c(C)cc(N)nc4C)ccn3)C2C=C1]

N-((6-amino-2,4-dimethylpyridin-3-yl)methyl)-2-((5-methyl-3a,7a-dihydro-1H-indazol-1-yl)methyl)isonicotinamide was prepared as described for N-((6-amino-2,4-dimethylpyridin-3-yl)methyl)-2-((5-chloro-2H-indazol-2-yl)methyl)isonicotinamide. $^1$H NMR (DMSO-d$_6$, 400 MHz): δ 8.68 (t, 1H), 8.59 (d, 1H), 8.01 (d, 1H), 7.63 (dd, 1H), 7.54 (d, 1H), 7.53 (s, 1H), 7.38 (s, 1H), 7.26-7.13 (m, 1H), 6.16 (s, 1H), 5.87 (brs, 2H), 5.75 (s, 2H), 4.29 (d2H), 2.40 (s, 3H), 2.29 (s, 3H), 2.15 (s, 3H).

Example 202: Preparation of N-((6-amino-2,4-dimethylpyridin-3-yl)methyl)-2-((5-chloro-1H-pyrazolo[3,4-b]pyridin-1-yl)methyl)isonicotinamide

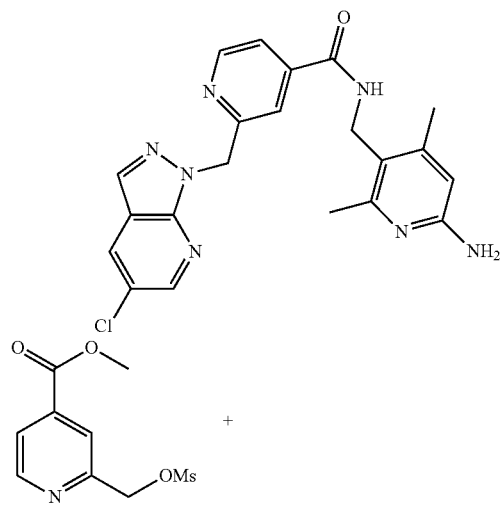

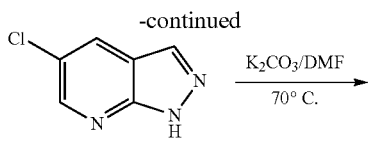

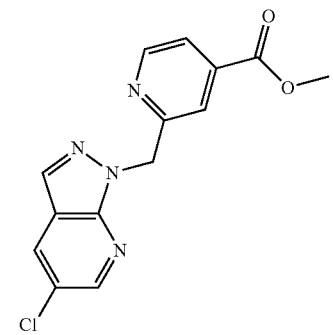

A mixture of methyl 2-(((methylsulfonyl)oxy)methyl)isonicotinate (1.28 g, 5.8 mmol, 2.0 eq), 5-chloro-1H-pyrazolo[3,4-b]pyridine (400 mg, 2.6 mmol, 1.0 eq) and K$_2$CO$_3$ (1.08 g, 7.8 mmol, 3.0 eq) in DMF (10 mL) was stirred at 70° C. for 2 h, then cooled to rt, diluted with EtOAc (60 mL), washed with water (30 mL), brine (30 mL×2), dried and concentrated. The residue was purified by chromatography on silica gel (EA/PE=1/10 to 1/4) to afford methyl 2-((5-chloro-1H-pyrazolo[3,4-b]pyridin-1-yl)methyl)isonicotinate (460 mg, 58%) as a brown solid. $^1$H NMR (400 MHz, CDCl$_3$): δ 8.73 (d, 1H), 8.50 (d, 1H), 8.07 (d, 1H), 8.06 (s, 1H), 7.77 (dd, 1H), 7.62 (s, 1H), 5.94 (s, 2H), 3.90 (s, 3H).

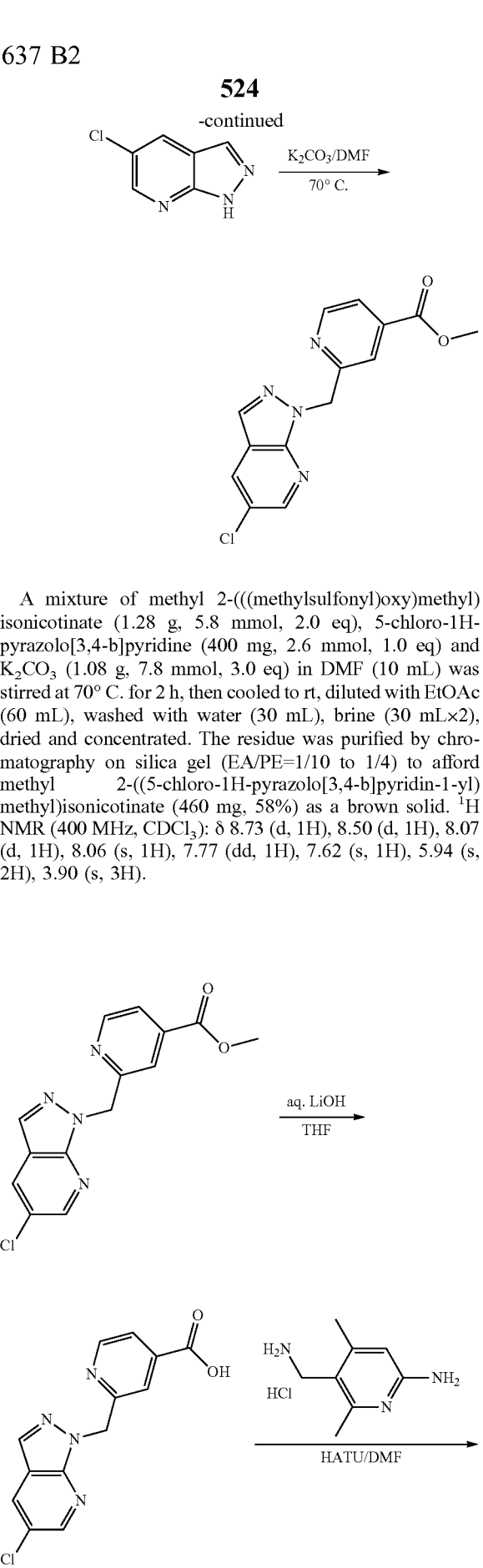

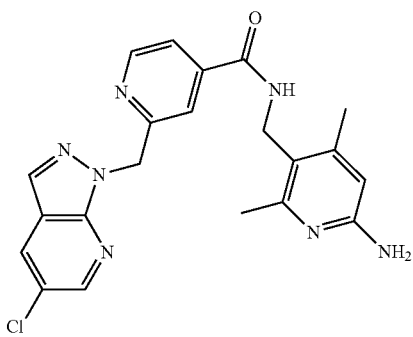

To a solution of methyl 2-((5-chloro-1H-pyrazolo[3,4-b]pyridin-1-yl)methyl)isonicotinate (460 mg, 1.52 mmol, 1.0 eq) in THF (5 mL) were added LiOH.H$_2$O (640 mg, 15.2 mmol, 10.0 eq) and water (5 mL). The mixture was stirred at rt for 2 h, then concentrated under vacuum to remove most THF. The aqueous mixture was adjusted with 1M HCl to about pH=7. The white suspension was filtered and the solid was washed with water (30 mL), concentrated under vacuum to afford 2-((5-chloro-1H-pyrazolo[3,4-b]pyridin-1-yl)methyl)isonicotinic acid (400 mg, 91%) as a white solid.

To a stirred mixture of 2-((5-chloro-1H-indazol-1-yl)methyl)isonicotinic acid (100 mg, 0.35 mmol, 1.0 eq), TEA (101 mg, 1.0 mmol, 3.0 eq) and 5-(aminomethyl)-4,6-dimethylpyridin-2-amine hydrochloride (65 mg, 0.35 mmol, 1.0 eq) in DMF (3 mL) was added HATU (264 mg, 0.7 mmol, 2.0 eq) at 0° C. The reaction mixture was stirred at rt for a further 16 h, then diluted with EtOAc (50 mL). The resulting mixture was washed with water (30 mL), brine (30 mL×2), dried and concentrated. The residue was purified by chromatography on silica gel (DCM/MeOH=50/1 to 20/1) and prep-TLC (DCM/MeOH=20/1) to afford N-((6-amino-2,4-dimethylpyridin-3-yl)methyl)-2-((5-chloro-1H-indazol-1-yl)methyl)isonicotinamide (10 mg, 7%) as a white solid.

$^1$H NMR (400 MHz, DMSO-d$_6$): δ 8.68 (brt, 1H), 8.57 (d, 1H), 8.10 (d, 1H), 7.88 (d, 1H), 7.75 (d, 1H), 7.65 (dd, 1H), 7.49 (s, 1H), 7.40 (dd, 1H), 6.14 (s, 1H), 5.82-5.73 (m, 4H), 4.30 (d, 2H), 2.28 (s, 3H), 2.15 (s, 3H). LRMS (M+H$^+$) m/z calculated 422.1, found 422.0.

Example 203: Preparation of N-((6-amino-2,4-dimethylpyridin-3-yl)methyl)-2-((5-chloro-2H-pyrazolo[3,4-b]pyridin-2-yl)methyl)isonicotinamide

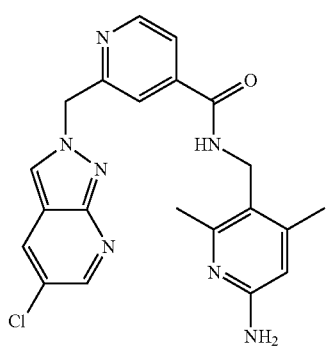

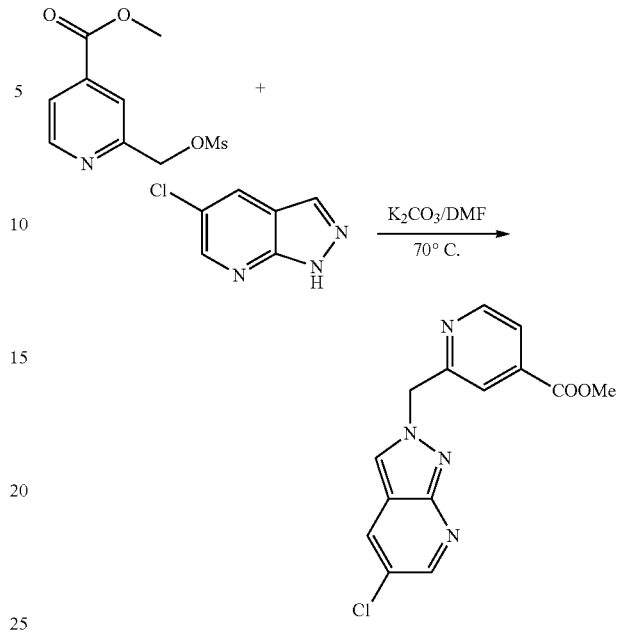

A mixture of methyl 2-(((methylsulfonyl)oxy)methyl)isonicotinate (1.28 g, 5.8 mmol, 2.0 eq), 5-chloro-1H-pyrazolo[3,4-b]pyridine (400 mg, 2.6 mmol, 1.0 eq) and K$_2$CO$_3$ (1.08 g, 7.8 mmol, 3.0 eq) in DMF (10 mL) was stirred at 70° C. for 2 h. The mixture was cooled to rt, diluted with EtOAc (60 mL), washed with water (30 mL), brine (30 mL×2), dried and concentrated. The residue was purified by chromatography on silica gel (EA/PE=1/4 to 1/1) to afford methyl 2-((5-chloro-2H-pyrazolo[3,4-b]pyridin-2-yl)methyl)isonicotinate (210 mg, 27%) as a brown solid. $^1$H NMR (CDCl$_3$, 400 MHz): δ 8.74 (d, J=4.8 Hz, 1H), 8.60 (d, J=2.4 Hz, 1H), 8.18 (1H, s), 8.02 (d, 1H), 7.95 (s, 1H), 7.87 (dd, 1H), 5.84 (s, 2H), 3.94 (s, 3H).

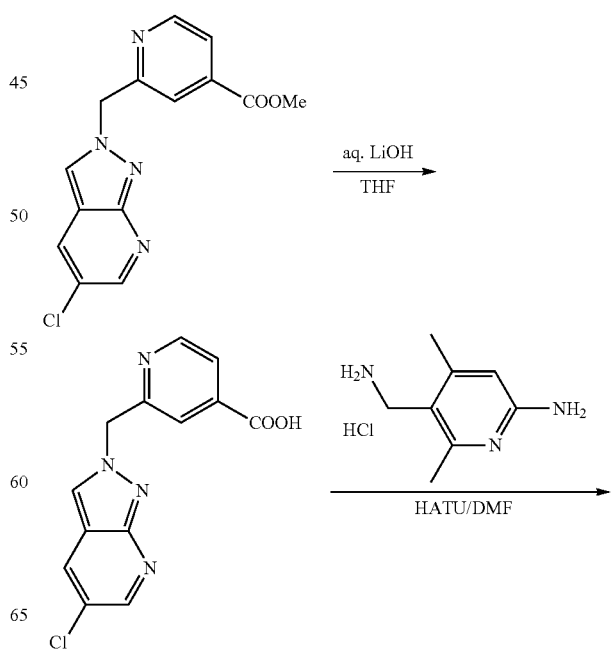

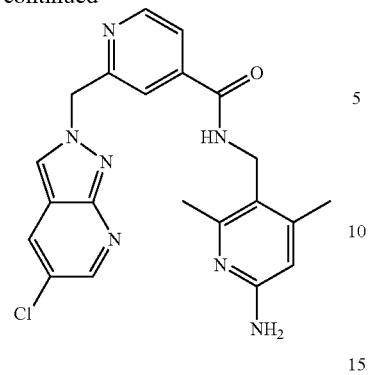

To a solution of methyl methyl 2-((5-chloro-2H-pyrazolo[3,4-b]pyridin-2-yl)methyl)isonicotinate (210 mg, 0.70 mmol, 1.0 eq) in THF (5 mL) were added LiOH.H$_2$O (292 mg, 7.0 mmol, 10.0 eq) and water (5 mL). The mixture was stirred at rt for 2 h, then concentrated under vacuum to remove most THF. The aqueous mixture was adjusted with 1M HCl to about pH=7. The white suspension was filtered and the solid was washed with water (30 mL), dried under vacuum to dryness to afford 2-((5-chloro-2H-pyrazolo[3,4-b]pyridin-2-yl)methyl)isonicotinic acid (130 mg, 65%) as a white solid.

To a stirred mixture of 2-((5-chloro-2H-pyrazolo[3,4-b]pyridin-2-yl)methyl)isonicotinic acid (60 mg, 0.21 mmol, 1.0 eq), DIEA (81 mg, 0.63 mmol, 3.0 eq) and 5-(aminomethyl)-4,6-dimethylpyridin-2-amine hydrochloride (58 mg, 0.31 mmol, 1.5 eq) in DMF (5 mL) was added HATU (160 mg, 0.42 mmol, 2.0 eq) at 0° C. The reaction mixture was stirred at rt for a further 16 h, then diluted with EtOAc (80 mL). The resulting mixture was washed with water (30 mL), brine (30 mL×2), dried and concentrated. The residue was purified by prep-TLC (DCM/MeOH=20/1, 80 mL, 2 mL of 7 M NH$_3$/MeOH as additive) to afford N-((6-amino-2,4-dimethylpyridin-3-yl)methyl)-2-((5-chloro-2H-pyrazolo[3,4-b]pyridin-2-yl)methyl)isonicotinamide (20 mg, 23%) as a white solid. LRMS (M+H$^+$) m/z calculated 422.1, found 422.0.

$^1$H NMR (400 MHz, DMSO-d$_6$): δ 8.71 (br, 1H), 8.65-8.60 (m, 2H), 8.56 (d, 1H), 8.41 (d, 1H), 7.73-7.68 (m, 2H), 6.11 (s, 1H), 5.85 (s, 2H), 5.68 (s, 2H), 4.33 (d, 2H), 2.28 (s, 3H), 2.15 (s, 3H,).

Example 204: Preparation of N-((6-amino-2,4-dimethylpyridin-3-yl)methyl)-2-((6-chloro-1,8-naphthyridin-3-yl)methyl)isonicotinamide

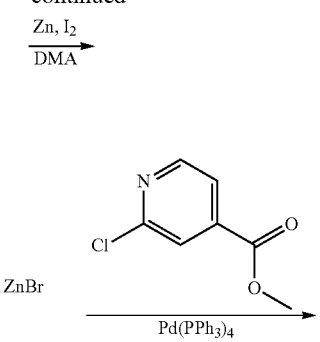

A Schlenk flask was charged with a PTFE-coated stir-bar, flame dried, and charged with zinc powder (2.56 g, 40 mmol, 2.0 equiv). The flask was heated in a 70° C. oil bath under high vacuum for 40 minute. The flask was then refilled with argon and allowed to cool to room temperature. Iodine (254 mg, 1 mmol, 0.05 equiv) and DMA (50 mL, 0.40 mol/L alkyl halide) were added. The mixture was stirred at room temperature until the red-yellow color disappeared (typically 30 seconds). Alkyl bromide (3.6 g, 20 mmol, 1.0 eq) was added and the mixture stirred at 70° C. under argon for 12 h, then cooled to rt.

To the above suspension were added methyl 2-chloroisonicotinate (3.41 g, 20 mmol, 1.0 eq) and Pd(PPh$_3$)$_4$ (1154 mg, 1 mmol, 0.05 eq). The mixture was stirred at 80° C. for 4 h Until TLC showed the SM was disappeared (PE:EA=5:1) and cooled to rt. The mixture was filtered and poured into water and extracted with EA for 3 times. The organic layer was washed with brine, dried over Na$_2$SO$_4$, filtered, concentrated and purified by chromatography on silica gel (PE:EA=5:1) to afford methyl 2-(2-(1,3-dioxolan-2-yl)ethyl)isonicotinate (2.37 g, 50%) as yellow oil.

$^1$H NMR (400 MHz, CDCl$_3$): δ 8.70-8.68 (m, 1H), 7.76 (s, 1H), 7.68-7.66 (m, 1H), 4.97 (t, 1H), 4.02-3.99 (m, 2H), 3.96 (s, 3H), 3.90-3.87 (m, 2H), 3.04-3.00 (m, 2H), 2.18-2.13 (m, 2H).

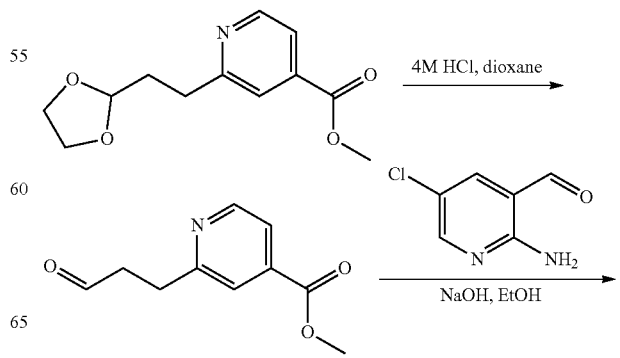

-continued

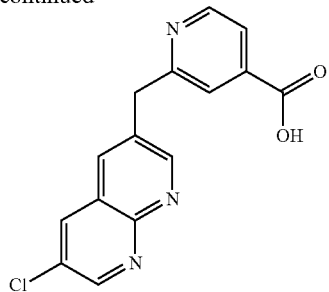

To a solution of methyl 2-(2-(1,3-dioxolan-2-yl)ethyl)isonicotinate (1.0 g, 4.22 mmol, 1.0 eq) in dioxane was added 4M HCl (3 mL, 3.0 eq). The mixture was stirred at 100° C. for 2 h and concentrated to afford methyl 2-(3-oxopropyl)isonicotinate (1 g, crude) as a white solid, which was used for the next step directly.

To a mixture of methyl 2-(3-oxopropyl)isonicotinate (1.0 g, crude, 1.0 eq) and 2-amino-5-chloronicotinaldehyde (0.78 g, 5 mmol, 1.0 eq) in EtOH (10 mL), was added NaOH (0.6 g, 15 mmol, 3 eq). The mixture was stirred under reflux for 30 min. The dark mixture was concentrated and acidified to pH=4-5. The formed solid was collected and triturated with MeOH to afford 2-((6-chloro-1,8-naphthyridin-3-yl)methyl)isonicotinic acid (0.9 g, 60%) as an off-white solid.

$^1$H NMR (400 MHz, DMSO-d$_6$): δ 9.11 (s, 1H), 9.02 (s, 1H), 8.66-8.64 (m, 2H), 8.30 (s, 1H), 7.85 (s, 1H), 7.65 (d, 1H), 4.46 (s, 2H).

The mixture of 2-((6-chloro-1,8-naphthyridin-3-yl)methyl)isonicotinic acid (60 mg, 0.2 mmol, 1.0 eq), amine (30 mg, 0.2 mmol, 1.0 eq), HATU (114 mg, 0.3 mmol, 1.5 eq) and DIEA (52 mg, 0.4 mmol, 2.0 eq) in DMF was stirred at rt for 30 min. Then poured into water and extracted with EA for 4 times. The EA layer was washed with brine, dried over Na$_2$SO$_4$, filtered, concentrated and purified by prep-HPLC to afford N-((6-amino-2,4-dimethylpyridin-3-yl)methyl)-2-((6-chloro-1,8-naphthyridin-3-yl)methyl)isonicotinamide (30 mg, 35%) as a white solid.

$^1$H NMR (400 MHz, DMSO-d$_6$): δ 9.08 (s, 1H), 9.00 (s, 1H), 8.75 (s, 1H), 8.64-8.59 (m, 2H), 8.28 (s, 1H), 7.81 (s, 1H), 7.62 (d, 1H), 6.30 (br, 2H), 4.41 (s, 2H), 4.33 (d, 1H), 2.37 (s, 3H), 2.23 (s, 3H).

Example 205: Preparation of N-((6-amino-2-methylpyridin-3-yl)methyl)-2-((6-chloro-1,8-naphthyridin-3-yl)methyl)isonicotinamide

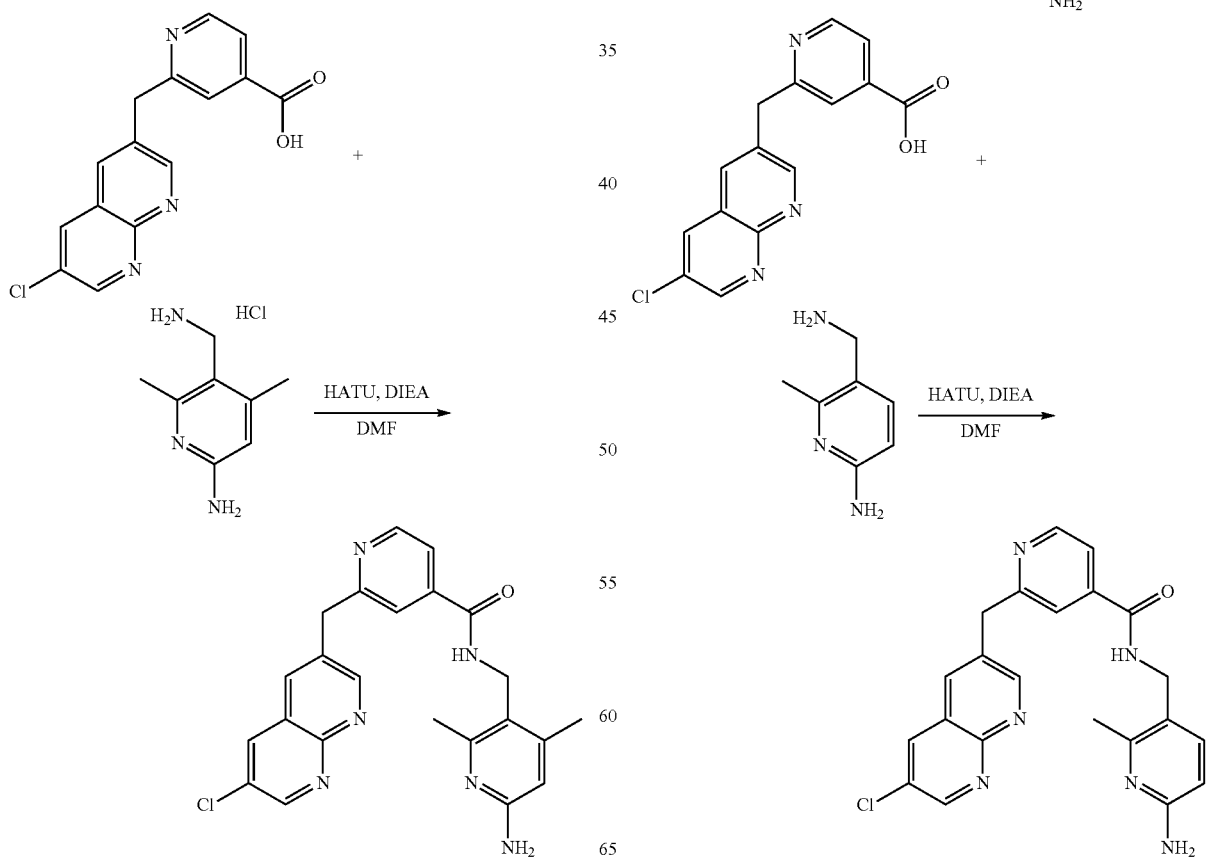

A mixture of 2-(6-Chloro-[1,8]naphthyridin-3-ylmethyl)-isonicotinic acid (60 mg, 0.2 mmol), 5-Aminomethyl-6-methyl-pyridin-2-ylamine (28 mg, 0.2 mmol), HATU (114 mg, 0.3 mmol), DIPEA (78 mg, 0.6 mmol) in DMF (1 mL) was stirred at rt for 0.5 h. Then washed with water (4 mL) and extracted with EtOAc (50×4 mL), the organic layer was combined and dried over Na$_2$SO$_4$. Then the organic layer was concentrated under reduced pressure. The residue was purified by flash column chromatography eluting 10% MeOH in DCM to afford N-((6-amino-2-methylpyridin-3-yl)methyl)-2-((6-chloro-1,8-naphthyridin-3-yl)methyl)isonicotinamide (20 mg, 25%) as a white solid.

$^1$H NMR (400 MHz, DMSO-d$_6$): δ 9.11 (d, J=2.4 Hz, 1H), 9.03-9.00 (m, 2H), 8.66-8.63 (m, 2H), 8.29 d, J=2.4 Hz, 1H), 7.82 (s, 1H), 7.64 (dd, J$_1$=5.2 Hz, J$_2$=1.6 Hz, 1H), 7.26 (d, J=8.4 Hz, 1H), 6.24 (d, J=8.4 Hz 1H), 5.77 (s, 2H), 4.44 (s, 2H), 4.30 (d, J=5.2 Hz, 2H), 2.29 (s, 3H). LRMS (M+H): m/z calculated 419.1, found 419.0.

Example 206: Preparation of N-((3-chloropyrrolo[1,2-a]pyrimidin-6-yl)methyl)-2-((3-chloroquinolin-6-yl)methyl)isonicotinamide

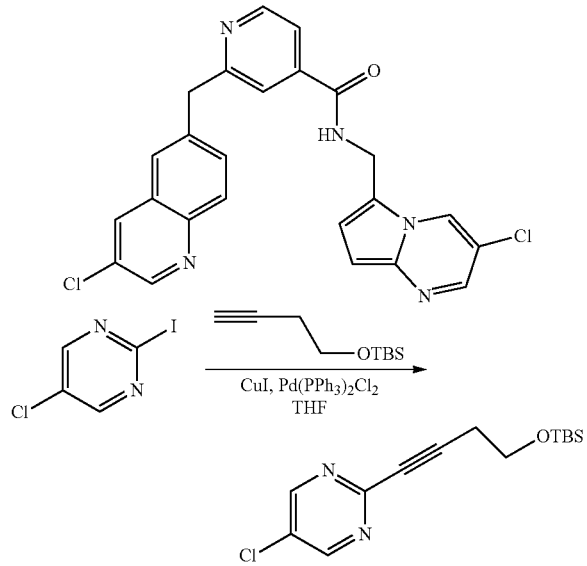

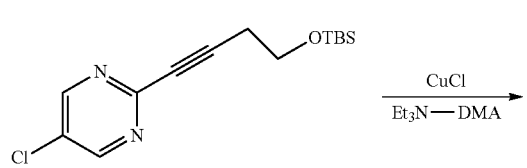

The mixture of 5-chloro-2-iodopyrimidine (5.0 g, 20.8 mmol), alkyne (4.2 g, 22.9 mmol), CuI (399 mg, 2.1 mmol), Pd(PPh$_3$)Cl$_2$ (702 mg, 1.0 mmol) and Et$_3$N (3.2 g, 31.2 mmol) in THF (50 mL) was stirred at rt under N$_2$ atmosphere for 2 hs and concentrated. The residue was purified by chromatography on silica gel (PE:EA=50:1) to afford 2-(4-((tert-butyldimethylsilyl)oxy)but-1-yn-1-yl)-5-chloropyrimidine (4.0 g, 65%) as yellow oil.

$^1$H NMR (400 MHz, CDCl$_3$): δ 8.66 (s, 2H), 3.89 (t, 2H), 2.71 (t, 2H), 0.92 (s, 9H), 0.11 (s, 6H).

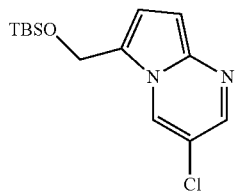

To a solution of 2-(4-(tert-butyldimethylsilyloxy)but-1-ynyl)-5-chloropyrimidine (4.0 g, 13.5 mmol) in DMA (40 mL) and Et$_3$N (6 mL) was added CuCl (660 mg, 6.7 mmol). The mixture was stirred at 125° C. under N$_2$ atmosphere for 5 h, then poured into water (150 mL) and extracted with EA (50 mL×3). The combined organic layers were washed with brine, dried over Na$_2$SO$_4$, filtered, concentrated and purified by chromatography on silica gel (PE:EA=50:1) to afford 6-(((tert-butyldimethylsilyl)oxy)methyl)-3-chloropyrrolo[1,2-a]pyrimidine (2.0 g, 50%) as yellow oil.

$^1$H NMR (400 MHz, CDCl$_3$): δ 8.43 (s, 1H), 8.06 (s, 1H), 6.86 (d, 1H), 6.63 (d, 1H), 4.97 (s, 2H), 0.90 (s, 9H), 0.04 (s, 6H).

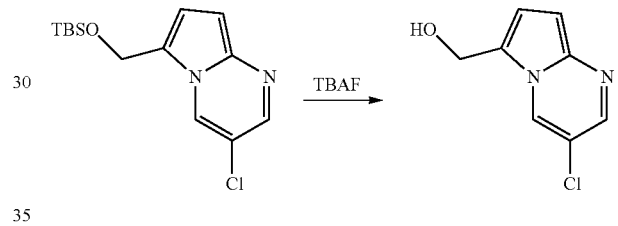

To a solution of 6-(((tert-butyldimethylsilyl)oxy)methyl)-3-chloropyrrolo[1,2-a]pyrimidine (1.0 g, 3.4 mmol) in THF (10 mL) was added TBAF (5 mL, 1 M, 5 mmol) at 0° C. dropwise. The mixture was stirred at 0° C. for 1 h and poured into ice-water (20 mL). The mixture was extracted with EA (10 mL×3). The combined organic layers were washed with brine, dried over Na$_2$SO$_4$, filtered, concentrated and purified by chromatography on silica gel eluting with PE:EA=5:1-1:1 to afford (3-chloropyrrolo[1,2-a]pyrimidin-6-yl)methanol (500 mg, 81%) as a yellow solid.

$^1$H NMR (400 MHz, DMSO-d$_6$): δ 8.77 (s, 1H), 8.10 (s, 1H), 6.97 (d, 1H), 6.56 (d, 1H), 5.23 (t, 1H), 4.77 (d, 2H).

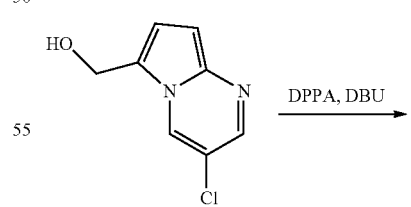

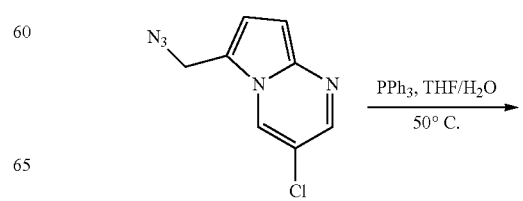

533

-continued

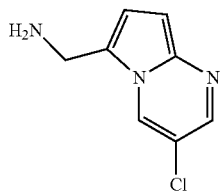

To a solution of (3-chloropyrrolo[1,2-a]pyrimidin-6-yl)methanol (200 mg, 1.1 mmol) in THF (20 mL) were added DPPA (452 mg, 1.6 mmol) and DBU (250 mg, 1.6 mmol) in sequence at 0° C. The mixture was stirred at rt for 24 h and poured into water (150 mL) and extracted with EA (10 mL×3). The combined organic layers were washed with brine, dried over $Na_2SO_4$, filtered, concentrated and purified by chromatography on silica gel eluting with PE:EA=10:1-5:1 to afford 6-(azidomethyl)-3-chloropyrrolo[1,2-a]pyrimidine (210 mg, 92%) as a yellow solid, which was used for next step directly.

The mixture of 6-(azidomethyl)-3-chloropyrrolo[1,2-a]pyrimidine (210 mg, 1 mmol) and $PPh_3$ (393 mg, 1.5 mmol) in THF (8 mL) and $H_2O$ (2 mL) was stirred at 50° C. overnight. The mixture was dried over $Na_2SO_4$, filtered, concentrated and purified by prep-TLC (DCM:MeOH=10:1) to afford (3-chloropyrrolo[1,2-a]pyrimidin-6-yl)methanamine (100 mg, 57%) as a yellow solid.

$^1$H NMR (400 MHz, DMSO-$d_6$): δ 8.96 (s, 1H), 8.07 (s, 1H), 6.98 (d, 1H), 6.57 (d, 1H), 4.13-4.12 (br, 2H), 4.12 (s, 2H).

534 by prep-TLC (PE:EA=5:1) to afford methyl 2-((3-chloroquinolin-6-yl)methyl)isonicotinate (50 mg, 34%) as a white solid.

$^1$H NMR (400 MHz, DMSO-$d_6$): δ 8.84 (d, 1H), 8.74-8.73 (m, 1H), 8.54 (d, 1H), 7.99 (d, 1H), 7.88-7.84 (m, 2H), 7.76-7.74 (m, 1H), 7.71-7.69 (m, 1H), 4.43 (s, 2H), 3.88 (s, 3H).

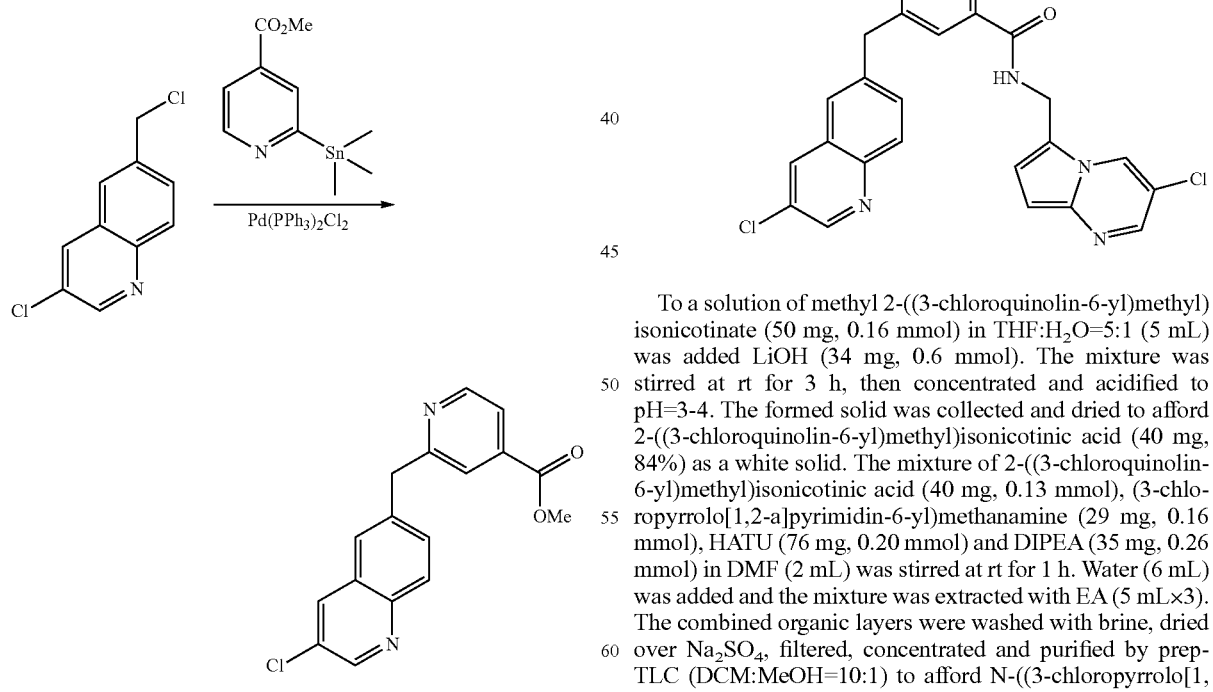

To a solution of methyl 2-((3-chloroquinolin-6-yl)methyl)isonicotinate (50 mg, 0.16 mmol) in THF:$H_2O$=5:1 (5 mL) was added LiOH (34 mg, 0.6 mmol). The mixture was stirred at rt for 3 h, then concentrated and acidified to pH=3-4. The formed solid was collected and dried to afford 2-((3-chloroquinolin-6-yl)methyl)isonicotinic acid (40 mg, 84%) as a white solid. The mixture of 2-((3-chloroquinolin-6-yl)methyl)isonicotinic acid (40 mg, 0.13 mmol), (3-chloropyrrolo[1,2-a]pyrimidin-6-yl)methanamine (29 mg, 0.16 mmol), HATU (76 mg, 0.20 mmol) and DIPEA (35 mg, 0.26 mmol) in DMF (2 mL) was stirred at rt for 1 h. Water (6 mL) was added and the mixture was extracted with EA (5 mL×3). The combined organic layers were washed with brine, dried over $Na_2SO_4$, filtered, concentrated and purified by prep-TLC (DCM:MeOH=10:1) to afford N-((3-chloropyrrolo[1,2-a]pyrimidin-6-yl)methyl)-2-((3-chloroquinolin-6-yl)methyl)isonicotinamide (33 mg, 53%) as a yellow solid.

$^1$H NMR (400 MHz, DMSO-$d_6$): δ 9.29 (br, 1H), 8.96 (s, 1H), 8.83 (s, 1H), 8.64 (d, 1H), 8.52 (d, 1H), 8.09 (s, 1H), 7.97 (d, 1H), 7.84 (s, 1H), 7.75-7.72 (m, 2H), 7.62-7.60 (m, 1H), 7.01 (d, 1H), 6.59 (d, 1H), 4.78 (d, 2H), 4.37 (s, 2H).

The mixture of 3-chloro-6-(chloromethyl)quinoline (100 mg, 0.47 mmol), methyl 2-(trimethylstannyl)isonicotinate (141 mg, 0.47 mmol) and Pd(PPh$_3$)$_2$Cl$_2$ (33 mg, 0.047 mmol) in dioxane (5 mL) was stirred at 110° C. for 3 h, then cooled to rt and filtered. The filtrate was concentrated and purified Example 207: Preparation of N-((6-amino-2,4-dimethylpyridin-3-yl)methyl)-2-((3-chloroquinolin-6-yl)methyl)-6-cyanoisonicotinamide

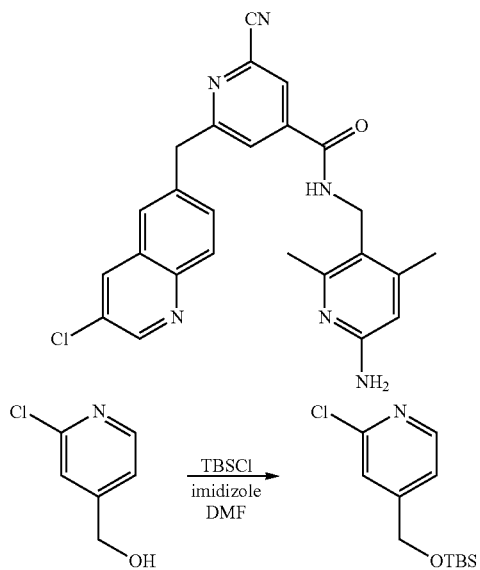

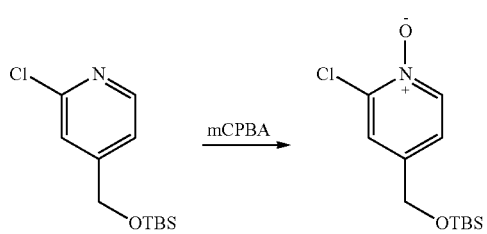

To a solution of (2-chloropyridin-4-yl)methanol (2.72 g, 19 mmol, 1.05 eq) in DMF (20 mL) was added TBSCl (2.99 g, 19.9 mmol, 1.05 eq), then cooled to 0° C., imidizole (2.71 g, 39.9 mmol, 2.1.0 eq) was added in portions. The reaction mixture was stirred at rt for 3 h, then diluted with ethyl acetate and cold water. The organic layer was separated, washed with brine twice, dried over Na$_2$SO$_4$ and concentrated under vacuum. The residue was purified by Combi-flash (PE/EA=10/1, silica gel) to afford 4-((tert-butyldimethylsilyloxy)methyl)-2-chloropyridine (5.3 g, 96%) as a white solid. MS LRMS (M+H$^+$) m/z calculated 258.1, found 257.9.

To a solution of 4-((tert-butyldimethylsilyloxy)methyl)-2-chloropyridine (2.0 g, 7.78 mmol, 1.0 eq) in DCM (20 mL) was added mCPBA (2.99 g, 17.5 mol, 2.2.0 eq) at 0° C. and the reaction mixture was stirred at rt for 18 h, then quenched by NaHSO$_3$ aqueous (20 mL), extracted with EA (15 mL), then the organic layers were washed by NaHCO$_3$ aqueous, water and brine, dried over Na$_2$SO$_4$, filtered and concentrated under vacuum. The residue was purified by chromatography on silica gel (EA/PE=1/1) to afford 4-((tert-butyldimethylsilyloxy)methyl)-2-chloropyridine 1-oxide (1.6 g, 75%) as a white solid.

LRMS (M+H$^+$) m/z calculated 274.1, found 274.1.

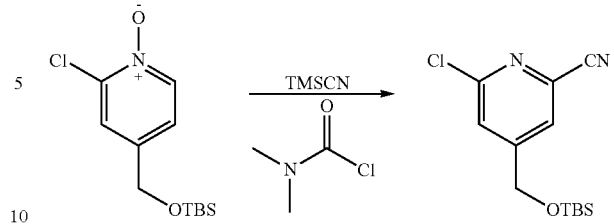

To a solution of 4-((tert-butyldimethylsilyloxy)methyl)-2-chloropyridine 1-oxide (1.6 g, 5.86 mmol, 1.0 eq) in CHCl3 (20 mL) were added trimethylsilanecarbonitrile (2.66 g, 26.9 mmol, 4.6 eq) and dimethylcarbamic chloride (2.6 g, 25 mmol, 4.27 eq), then the reaction mixture was heated at 50° C. for 18 h, then concentrated under reduced pressure. The residue was purified with Flash chromatography (PE/EA=10/1, silica gel, uv) to afford 4-((tert-butyldimethylsilyloxy)methyl)-6-chloropicolinonitrile (1.3 g, 78%) as a white solid. $^1$H NMR (CDCl$_3$) d: 7.56-7.66 (m, 1H), 7.47-7.56 (m, 1H), 0.93-1.05 (m, 10H), 0.07-0.21 (m, 7H). LRMS (M+H$^+$) m/z calculated 283.1, found 282.8.

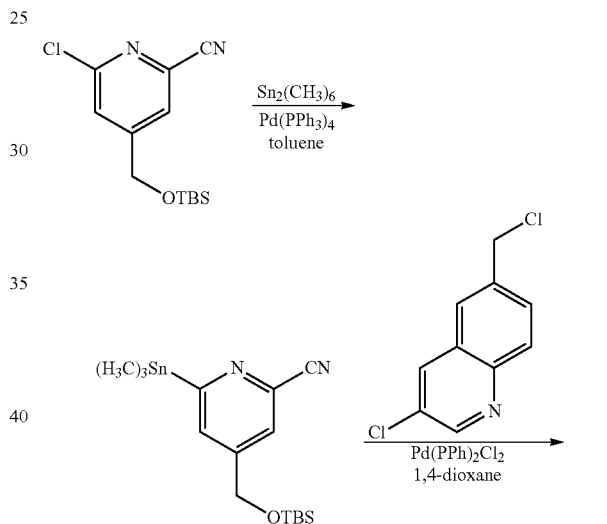

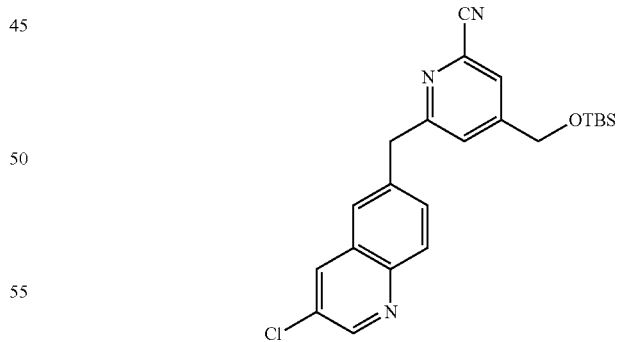

The mixture of 4-((tert-butyldimethylsilyloxy)methyl)-6-chloropicolinonitrile (300 mg, 1.06 mmol, 1.0 eq), hexamethyldistannane (695 mg, 2.12 mmol, 2.0 eq) and Pd(PPh$_3$)$_4$ (122 mg, 0.106 mmol, 0.1.0 eq) in dry toluene (15 mL) was heated at 110° C. for 6 h, then cooled to rt, quenched by water (20 mL), extracted with EA (10 mL×3). The combined organic layers were washed by water, brine, dried over Na$_2$SO$_4$, filtered, and concentrated to get the residue which was used to the next step without further purification.

To a mixture of 3-chloro-6-(chloromethyl)quinoline (120 mg, 0.566 mmol, 1.0 eq) and Pd(PPh$_3$)$_2$Cl$_2$ (39 mg, 0.0566 mmol, 0.1.0 eq 1.0 eq) in 1,4-dioxane (10 mL) was added the tin reagent form last step, then the reaction mixture was heated at 100° C. for 18 h, then concentrated under reduced pressure. The residue was purified with Flash chromatography (PE/EA=10/1~5/1,) to afford 4-((tert-butyldimethylsilyloxy)methyl)-6-((3-chloroquinolin-6-yl)methyl)picolinonitrile (85 mg, 23% in two steps).

LRMS (M+H$^+$) m/z calculated 424.2.1, found 424.2.

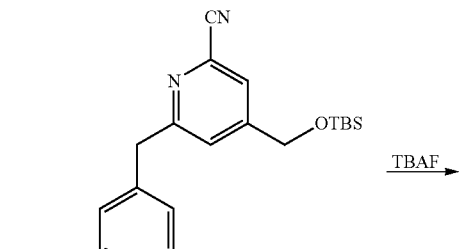

TBAF

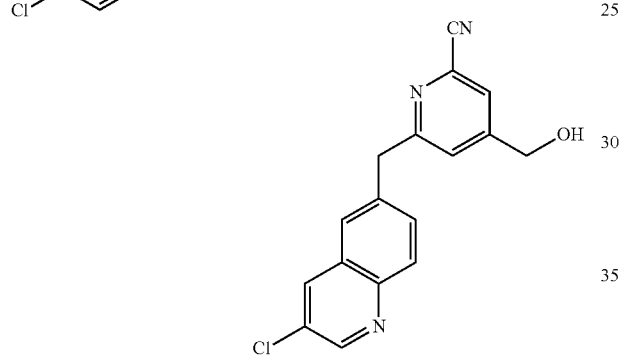

To a solution of 4-((tert-butyldimethylsilyloxy)methyl)-6-((3-chloroquinolin-6-yl)methyl)picolinonitrile (85 mg, 0.2 mmol, 1.0 eq) in THF (5 mL) was added 1N TBAF in THF (0.4 mL, 0.4 mmol, 2.0 eq) dropwise at 0° C., then the reaction mixture was stirred at rt for 2 h, then quenched by water (10 mL), extracted with EA (10 mL×3), the combined organic layer was washed by brine, dried over Na$_2$SO$_4$, filtered and concentrated. The residue was purified with Prep-TLC (PE/EA=1/1, silica gel, uv) to afford 6-((3-chloroquinolin-6-yl)methyl)-4-(hydroxymethyl)picolinonitrile (65 mg, 95%) as a white solid.

LRMS (M+H$^+$) m/z calculated 309.1, found 309.7.

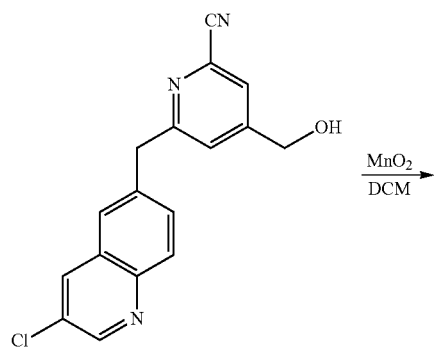

MnO$_2$ / DCM

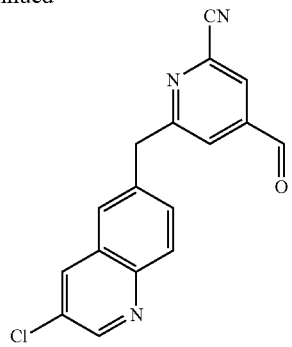

To a solution of 6-((3-chloroquinolin-6-yl)methyl)-4-(hydroxymethyl)picolinonitrile (60 mg, 0.194 mmol, 1.0 eq) in DCM (30 mL) was added MnO$_2$ (84 mg, 0.97 mmol, 5.0 eq), then the mixture was stirred at rt overnight. The mixture was filtered and the filtrate was concentrated to get the residue which was purified with Prep-TLC (PE/EA=2/1, silica gel, uv) to afford 6-((3-chloroquinolin-6-yl)methyl)-4-formylpicolinonitrile (20 mg, 32%) as a white solid. LRMS (M+H$^+$) m/z calculated 308.1, found 307.7.

NaClO$_2$
NaH$_2$PO$_4$
2-methyl-2-ene
t-BuOH

To a suspension of 6-((3-chloroquinolin-6-yl)methyl)-4-formylpicolinonitrile (20 mg, 0.065 mmol, 1.0 eq) in t-BuOH (5 mL) were added sat. NaH$_2$PO$_4$ (39 mg, 0.325 mmol, 5.0 eq) and 2-methylbut-2-ene (27.3 mg, 0.39 mmol, 6.0 eq), followed by NaClO$_2$ (19 mg, 0.26 mmol, 4.0 eq). The mixture was stirred overnight at rt, the solvent was removed under reduced pressure, the residue was dissolved into water (2 mL), then was adjusted to pH=5 with 1N HCl, the precipate was filtered and the filter cake was dried under reduced pressure to get 2-((3-chloroquinolin-6-yl)methyl)-6-cyanoisonicotinic acid (10 mg, 50%) as a white solid. LRMS (M+H$^+$) m/z calculated 324.1, found 323.7.

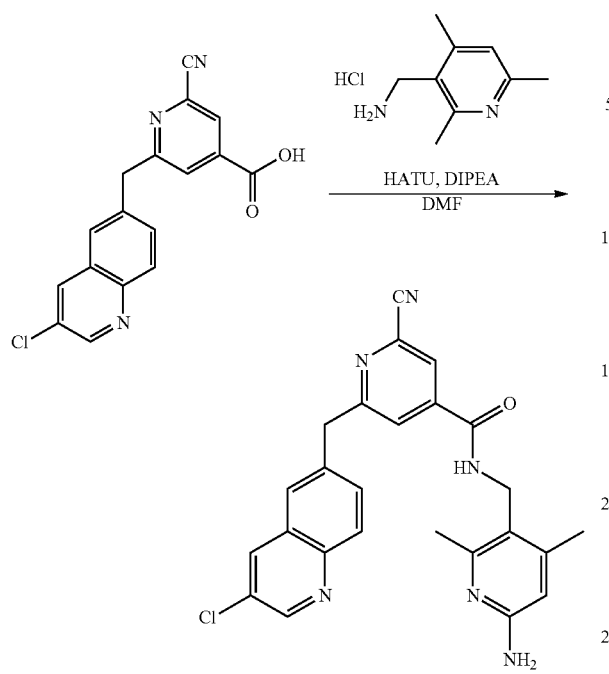

The mixture of 2-((3-chloroquinolin-6-yl)methyl)-6-cyanoisonicotinic acid (10 mg, 0.0325 mmol, 1.0 eq), HATU (18 mg, 0.048 mmol, 1.5 eq), 5-(aminomethyl)-4,6-dimethylpyridin-2-amine hydrochloride (5.6 mg, 0.0325 mmol, 1.0 eq) and DIPEA (25 mg, 0.097 mmol, 3.0 eq) in DMF (2 mL) was stirred at rt for 2 h. The reaction mixture was poured into water (10 mL), extracted with EA (10 mL×3), the combined organic layers were washed by brine, dried over Na₂SO₄, filtered and concentrated to get residue which was purified with Prep-TLC (DCM/Methanol=10/1) to obtain N-((6-amino-2,4-dimethylpyridin-3-yl)methyl)-2-((3-chloroquinolin-6-yl)methyl)-6-cyanoisonicotinamide (5 mg, 35%) as a white solid.

¹H NMR (400 MHz, CD3OD) d: 8.78 (d, 1H), 8.39 (d, 1H), 8.07 (d, 1H), 7.94-8.03 (m, 2H), 7.83-7.87 (m, 1H), 7.75 (dd, 1H), 6.41 (s, 1H), 4.51 (s, 2H), 4.47 (s, 2H), 2.44 (s, 3H), 2.31 (s, 3H). LRMS (M+H⁺) m/z calculated 457.1, found 456.9.

Example 208: Preparation of N⁴-((6-amino-2,4-dimethylpyridin-3-yl)methyl)-6-((3-chloroquinolin-6-yl)methyl)pyridine-2,4-dicarboxamide

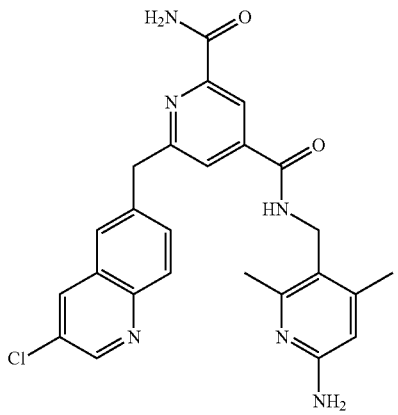

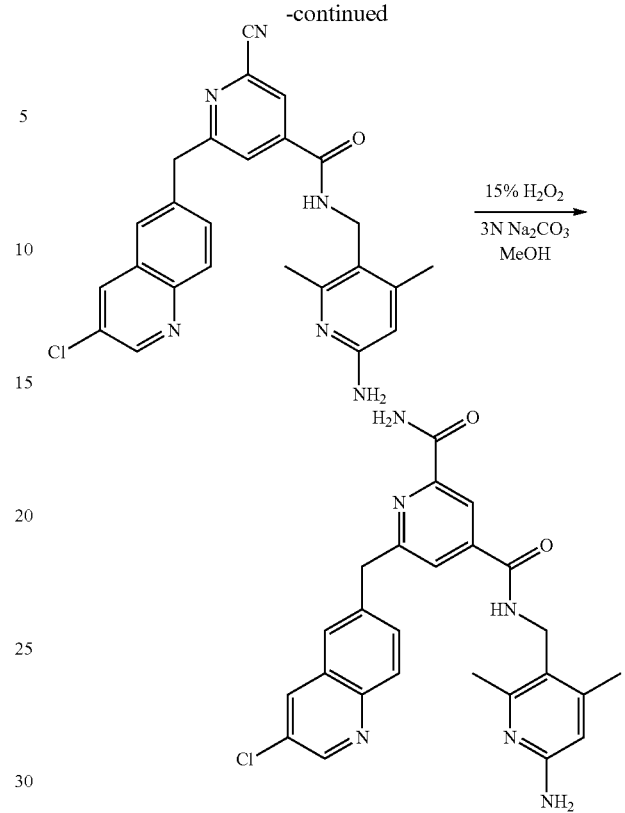

To a solution of N-((6-amino-2,4-dimethylpyridin-3-yl)methyl)-2-((3-chloroquinolin-6-yl)methyl)-6-cyanoisonicotinamide (20 mg, 0.044 mmol, 1.0 eq) in methanol (3 mL) was added 3N aqueous Na₂CO₃ solution (5 mL) and 15% H₂O₂ (5 mL), the mixture was stirred at rt overnight. Then the reaction was quenched by aqueous NaHSO₃ solution (5 mL), extracted with EA (10 mL×3), the combined organic layers were washed by brine, dried over Na₂SO₄, filtered and concentrated to get residue which was purified with Prep-TLC (DCM/Methanol=8/1) to obtain N-((6-amino-2,4-dimethylpyridin-3-yl)methyl)-2-((3-chloroquinolin-6-yl)methyl)-6-cyanoisonicotinamide (8 mg, 40%) as a white solid. ¹H NMR (CD₃OD) d: 8.78 (d, 1H), 8.39 (d, 1H), 8.29 (d, 1H), 8.01 (d, 1H), 7.87-7.82 (m, 3H), 6.48 (s, 1H), 4.52 (s, ₂H), 4.50 (s, 2H), 2.48 (s, 3H), 2.36 (s, 3H). LRMS (M+H⁺) m/z calculated 475.2, found 474.9.

Example 209: Preparation of 4-((6-amino-2,4-dimethylpyridin-3-yl)methylcarbamoyl)-6-((3-chloroquinolin-6-yl)methyl)picolinic Acid

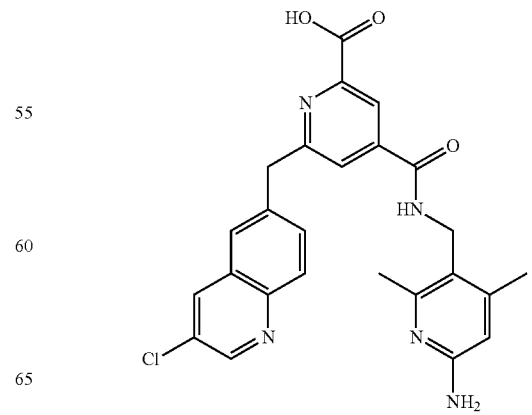

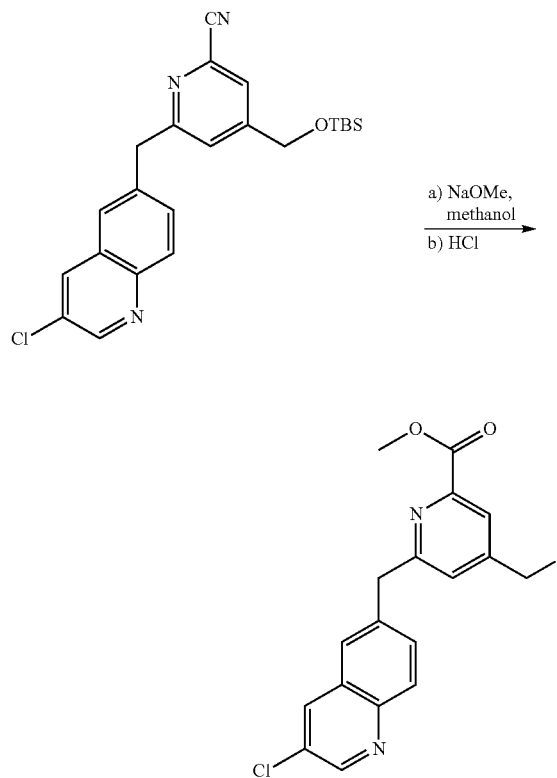

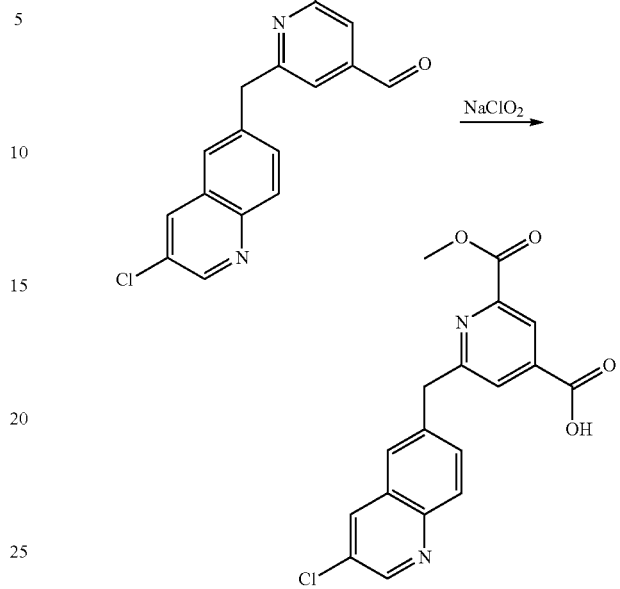

To a solution of 4-((tert-butyldimethylsilyloxy)methyl)-6-((3-chloroquinolin-6-yl)methyl)picolinonitrile (600 mg, 1.42 mmol, 1.0 eq) in methanol (15 mL) was added 0.5N NaOMe, the mixture was heated at 65° C. for 3 h, then cooled to rt, then 1N HCl (1.7 mL, 7.1 mmol, 5 eq) was added at rt and the mixture was stirred for 2 h. The mixture was basified by the addition of sat. NaHCO$_3$ solution and extracted with EA (10 mL×3), the combined organic layers were washed by brine, dried over Na$_2$SO$_4$, filtered and concentrated to get residue which was purified with Flash chromatography (PE/EA=3/2,) to obtain methyl 6-((3-chloroquinolin-6-yl)methyl)-4-(hydroxymethyl)picolinate (410 mg, 84%) as a white solid. LRMS (M+H$^+$) m/z calculated 443.1, found 342.9.

2-((3-chloroquinolin-6-yl)methyl)-6-cyanoisonicotinic acid (175 mg, 70%) was synthesized as described for 2-((3-chloroquinolin-6-yl)methyl)-6-cyanoisonicotinic acid (10 mg, 50%) as a white solid. $^1$H NMR (DMSO-d$_6$) δ: 8.84 (d, J=2.4 Hz, 1H), 8.53 (d, J=2.4 Hz, 1H), 8.27 (d, J=1.2 Hz, 1H), 7.95-8.03 (m, 2H), 7.85 (s, 1H), 7.75 (dd, J=8.9, 1.8 Hz, 1H), 4.50 (s, 2H), 3.91 (s, 3H). LRMS (M+H$^+$) m/z calculated 357.1, found 356.9.

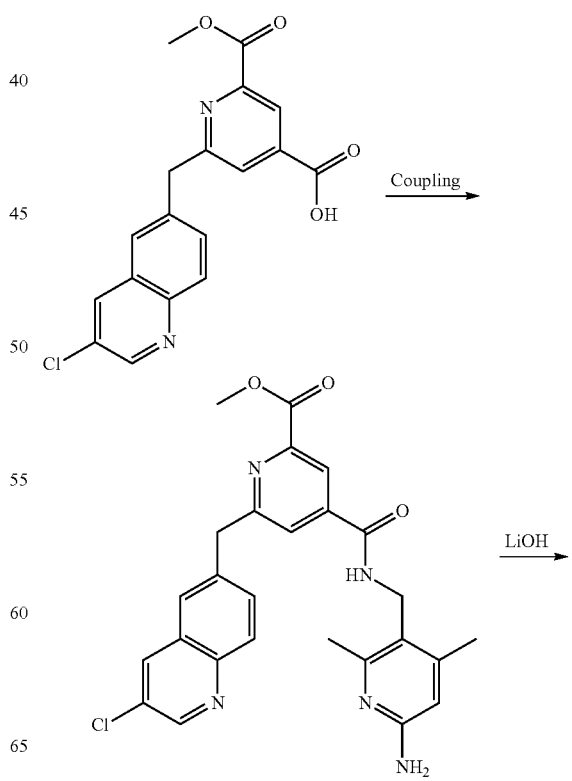

543
-continued

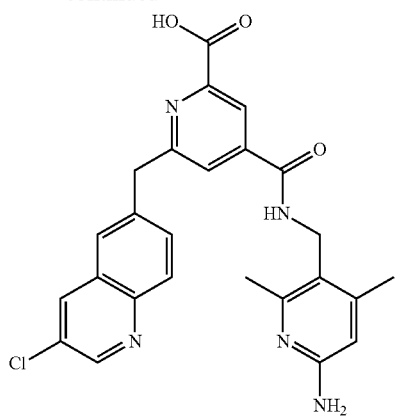

The amide was prepared similarly as previous described. To the resulting mixture of 4-((6-amino-2,4-dimethylpyridin-3-yl)methylcarbamoyl)-6-((3-chloroquinolin-6-yl)methyl)picolinate (70 mg, 0.143 mmol, 1.0 eq) in methanol (10 mL) and water (3 mL) was added LiOH.H$_2$O (28 mg, 0.715 mmol, 5.0 eq), then the mixture was stirred at rt for 1 h, the methanol was removed under reduced pressure to get the residue, water (10 mL) was added, then was adjusted to pH=6 with 1N HCl, the precipitated was filtered and the filter cake was washed by water and methanol to get 4-((6-amino-2,4-dimethylpyridin-3-yl)methylcarbamoyl)-6-((3-chloroquinolin-6-yl)methyl)picolinic acid (40 mg, 59%) as a white solid. MS (LC/MS): 475.9 (M+H)+.

$^1$H NMR (DMSO-d$_6$) δ: 8.84 (d, 2H), 8.53 (d, 1H), 8.29 (s, 1H), 8.00 (d, 1H), 7.91 (s, 1H), 7.84 (s, 1H), 7.76 (dd, 1H), 6.13 (s, 1H), 5.74 (br. s., 2H), 4.44 (s, 2H), 4.35 (d, J=4.6 Hz, 2H), 2.30 (s, 3H), 2.16 (s, 3H).

Example 210: Preparation of N-((6-amino-2,4-dimethylpyridin-3-yl)methyl)-2-((3-chloroquinolin-6-yl)methyl)-6-(2-hydroxypropan-2-yl)isonicotinamide

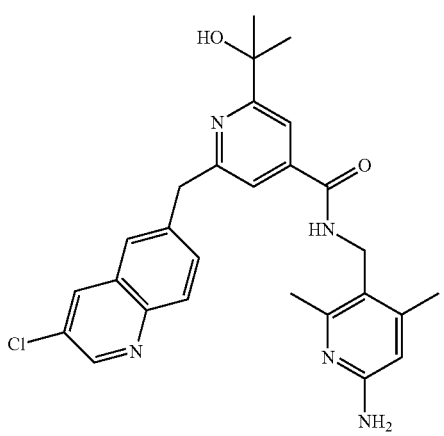

544
-continued

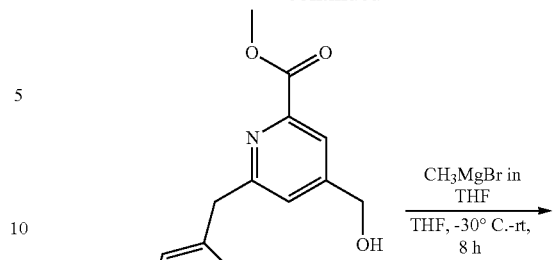

A solution of methyl 6-((3-chloroquinolin-6-yl)methyl)-4-(hydroxymethyl)picolinate (150 mg, 0.44 mmol, 1.0 eq) in 20 mL of tetrahydrofuran was cooled to −30° C. under an atmosphere of nitrogen. A 1M solution of methylmagnesium bromide in tetrahydrofuran (1 ML, 2.27 mmol, 2.3 eq) was added dropwise to this solution at the temperature between −30° C. and −20° C. The resulting mixture was stirred at 0° C. for 8 h, and EA (100 mL) and an aqueous solution of ammonium chloride (100 mL) were added to it. The EA layer was separated and dried over Na$_2$SO$_4$ and concentrated in vacuo. The resulting residue was purified by Pre-TLC (DCM:MeOH=20:1) to give 2-(6-((3-chloroquinolin-6-yl)methyl)-4-(hydroxymethyl)pyridin-2-yl)propan-2-ol (85 mg, 57%) as a yellow solid.

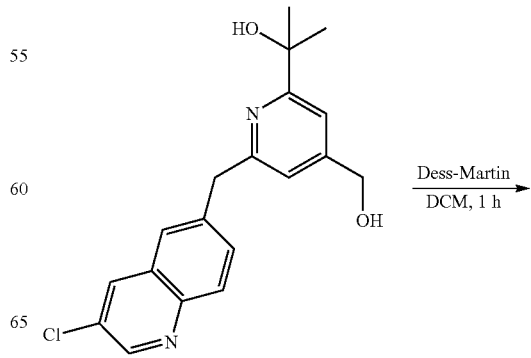

-continued

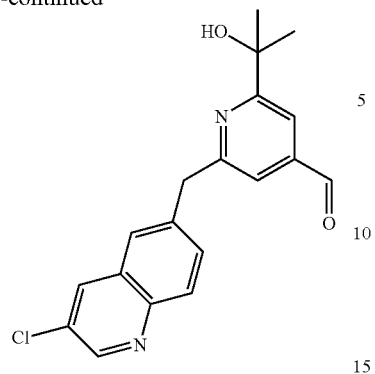

A solution of 2-(6-((3-chloroquinolin-6-yl)methyl)-4-(hydroxymethyl)pyridin-2-yl)propan-2-ol (85 mg, 0.23 mmol, 1.0 eq) in DCM (10 mL) was treated with Dess-Martin periodinane (195 mg, 0.46 mmol, 2.0 eq) and stirred at rt for 2 h. The reaction mixture was quenched with sat. aq. sodium hydrogen-carbonate solution and sat. aq. sodium thiosulfate solution (1:1). The resulting mixture was stirred at rt for 30 min, then extracted with dichloromethane three times and the combined organic layers were dried over magnesium sulfate and concentrated. Purification by Pre-TLC (DCM:MEOH=20:1) afforded 2-((3-chloroquinolin-6-yl)methyl)-6-(2-hydroxypropan-2-yl)isonicotinaldehyde (72 mg, 85%) as a white solid.

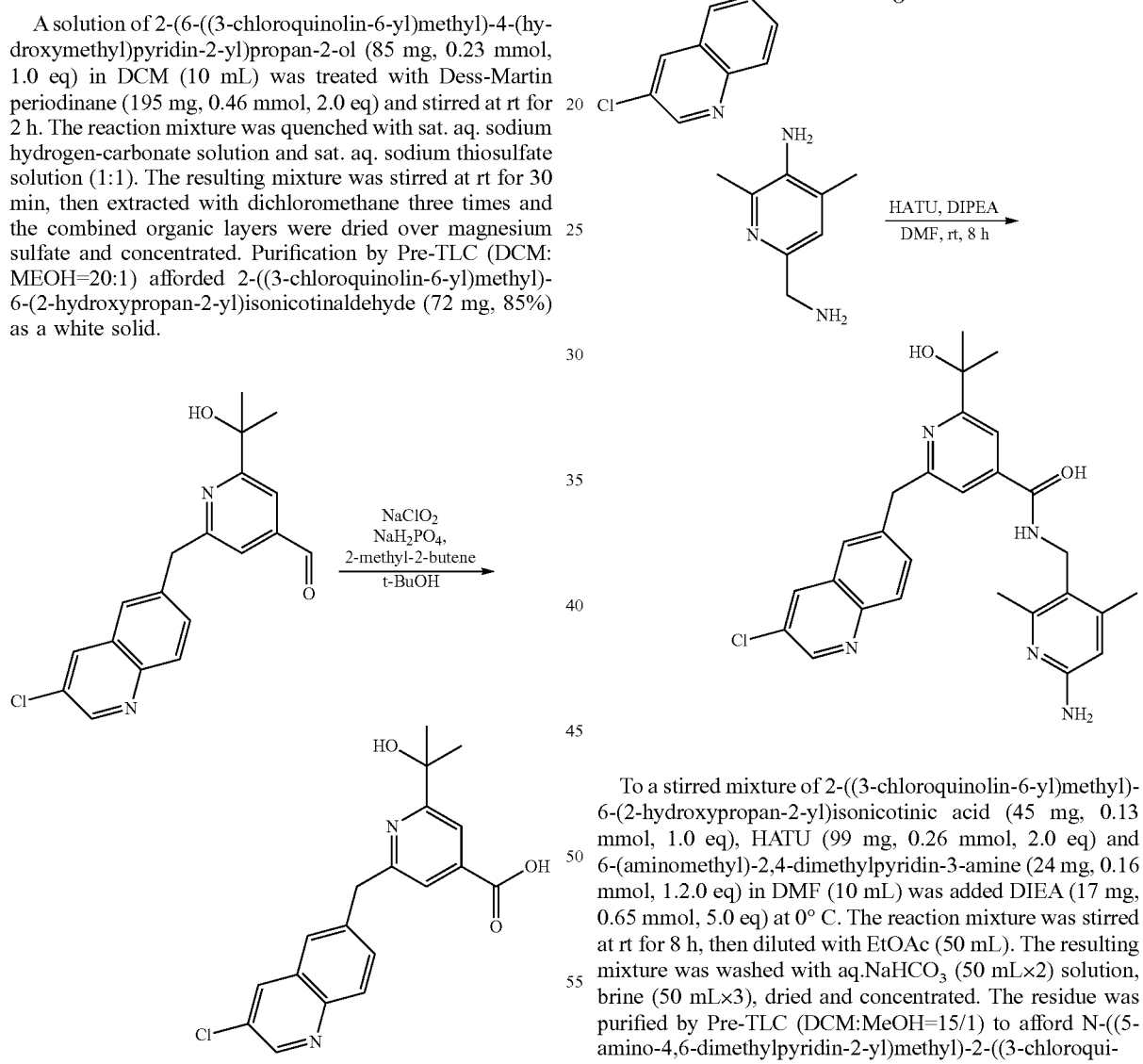

To a mixture of 2-((3-chloroquinolin-6-yl)methyl)-6-(2-hydroxypropan-2-yl)isonicotinaldehyde (72 mg, 0.21 mmol, 1.0 eq) in n-BuOH (5 mL) was added NaH$_2$PO$_4$ (126 mg, 1.05 mmol, 5.0 eq) and 2-methyl-2-butene (88 mg, 1.26 mmol, 6.0 eq) at rt. Then NaClO$_2$ (76 mg, 0.84 mmol, 4 eq) was added into the above solution and stirred at rt for 8 h. The mixture was diluted with DCM (100 mL) and water (100 mL). The organic layer was washed with brine (50 mL×3), dried over Na$_2$SO$_4$, filtered and concentrated under vacuum. The residue was purified by Pre-TLC (DCM:MeOH=20:1) to afford 2-((3-chloroquinolin-6-yl)methyl)-6-(2-hydroxypropan-2-yl)isonicotinic acid (45 mg, 60%) as a yellow solid.

To a stirred mixture of 2-((3-chloroquinolin-6-yl)methyl)-6-(2-hydroxypropan-2-yl)isonicotinic acid (45 mg, 0.13 mmol, 1.0 eq), HATU (99 mg, 0.26 mmol, 2.0 eq) and 6-(aminomethyl)-2,4-dimethylpyridin-3-amine (24 mg, 0.16 mmol, 1.2.0 eq) in DMF (10 mL) was added DIEA (17 mg, 0.65 mmol, 5.0 eq) at 0° C. The reaction mixture was stirred at rt for 8 h, then diluted with EtOAc (50 mL). The resulting mixture was washed with aq.NaHCO$_3$ (50 mL×2) solution, brine (50 mL×3), dried and concentrated. The residue was purified by Pre-TLC (DCM:MeOH=15/1) to afford N-((5-amino-4,6-dimethylpyridin-2-yl)methyl)-2-((3-chloroquinolin-6-yl)methyl)-6-(2-hydroxypropan-2-yl)isonicotinamide (12 mg, 19%) as a yellow solid.

$^1$H NMR (DMSO-d$_6$): 8.83 (d, J=2.4 Hz, 1H), 8.71 (t, J=4.4 Hz, 1H), 8.52 (d, J=2.4 Hz, 1H), 7.98 (d, J=8.6 Hz, 1H), 7.82-7.90 (m, 2H), 7.77 (dd, J=8.6, 1.9 Hz, 1H), 7.54 (d, J=1.3 Hz, 1H), 6.26 (s, 1H), 6.16 (s, 1H), 5.28 (s, 1H), 4.26-4.39 (m, 4H), 4.12 (d, J=5.4 Hz, 1H), 3.18 (d, J=4.8 Hz, 2H), 2.35 (s, 3H), 2.22 (s, 3H), 1.38-1.49 (m, 6H). LRMS (M+H$^+$) m/z calculated 490.2, found 491.

Example 211: Preparation of N-((6-amino-2,4-dimethylpyridin-3-yl)methyl)-2-(aminomethyl)-6-((3-chloroquinolin-6-yl)methyl)isonicotinamide

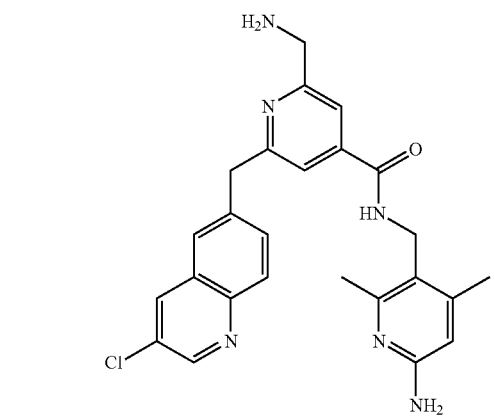

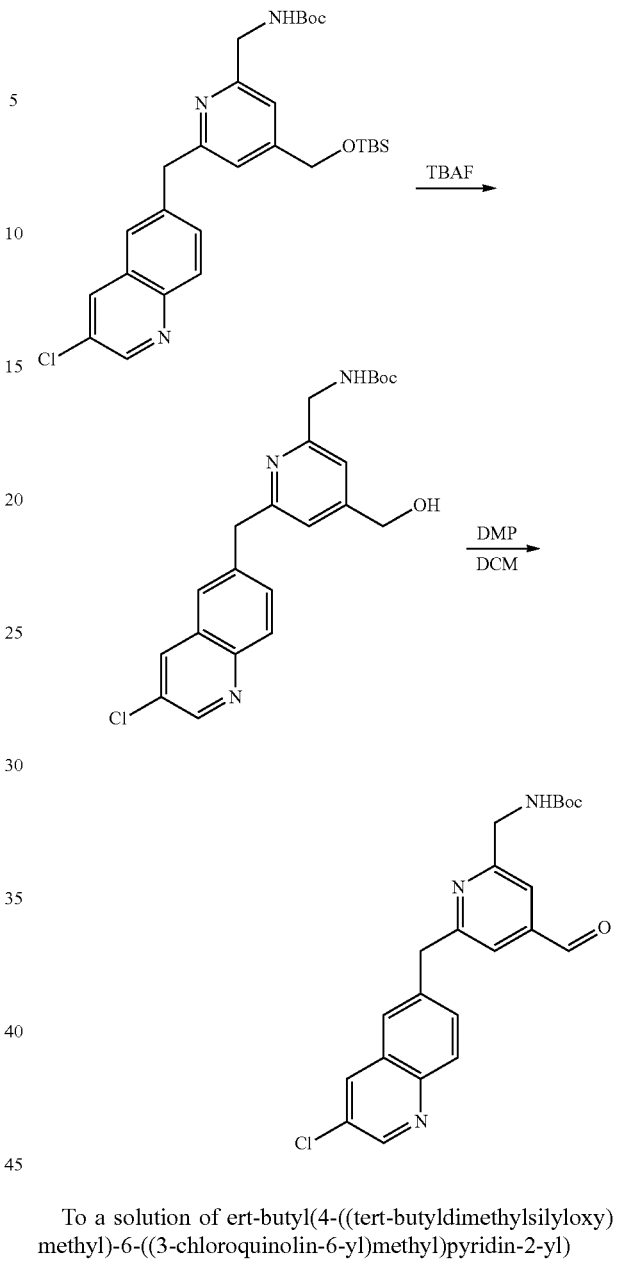

To a solution of 4-((((tert-butyldimethylsilyl)oxy)methyl)-6-((3-chloroquinolin-6-yl)methyl)picolinonitrile (400 mg, 0.94 mmol, 1.0 eq) and NiCl$_2$.6H$_2$O (112 mg, 0.48 mmol, 0.5 eq) in MeOH (10 mL) was added NaBH$_4$ (200 mg) at 0° C. The resulting system was stirred for additional 20 min and filtered. The filtrate was concentrated to give crude amine as yellow solid (260 mg, 0.6 mmol).

The crude amine, TEA (180 mg, 1.8 mmol, 3.0 eq) and (Boc)$_2$O (160 mg, 0.74 mmol, 1.2 eq) were dissolved in MeOH and the resulting solution was stirred at room temperature for 16 h, then concentrated. The residue was purified by column on silica gel (PE:EA=3:1) to give tert-butyl ((4-((((tert-butyldimethylsilyl)oxy)methyl)-6-((3-chloroquinolin-6-yl)methyl)pyridin-2-yl)methyl)carbamate (240 mg). LRMS (M+H$^+$) m/z calculated 528.2, found 528.2.

To a solution of ert-butyl(4-(((tert-butyldimethylsilyloxy)methyl)-6-((3-chloroquinolin-6-yl)methyl)pyridin-2-yl)methylcarbamate (240 mg, 0.45 mmol, 1.0 eq) in THF (10 mL) was added 1N TBAF in THF (0.9 mL, 0.9 mmol, 2.0 eq) dropwise at 0° C., then the reaction mixture was stirred at rt for 2 h, then quenched by water (10 mL), then extracted with EA (10 mL×3), the combined organic layers were washed by brine, dried over Na$_2$SO$_4$, filtered and concentrated to get crude alcohol, which was used to next step directly.

A solution of alcohol (180 mg, 0.44 mmol, 1.0 eq) in DCM (10 mL) was treated with Dess-Martin periodinane (380 mg, 0.88 mmol, 2.0 eq) and stirred at rt for 2 h. The reaction mixture was quenched with sat. aq. NaHCO$_3$ solution and sat. aq. sodium thiosulfate solution (1:1) and stirred at rt for 30 min. The aqueous layer was extracted with dichloromethane three times and the combined organic layers were dried over magnesium sulfate and concentrated. Purification by Pre-TLC (DCM:MEOH=20:1) afforded titled compound (150 mg) as a white solid.

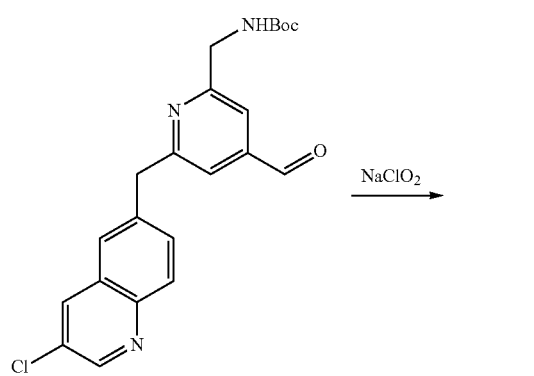

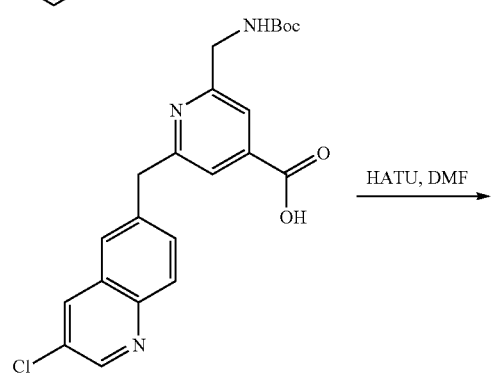

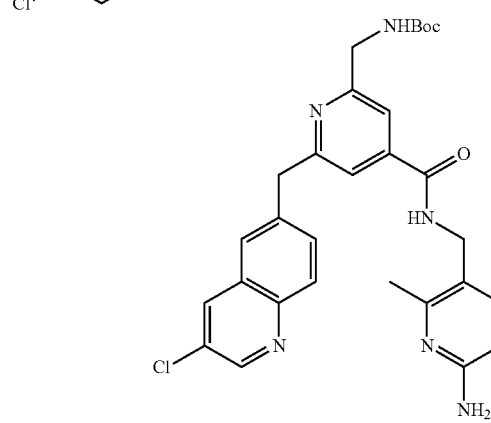

The titled compound was prepared by NaClO₂ oxidation and amide coupling similarly to previously described method.

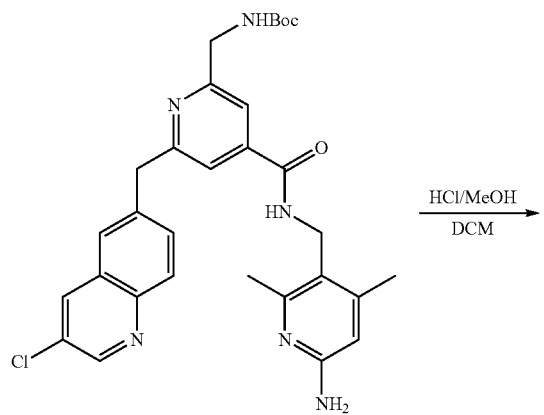

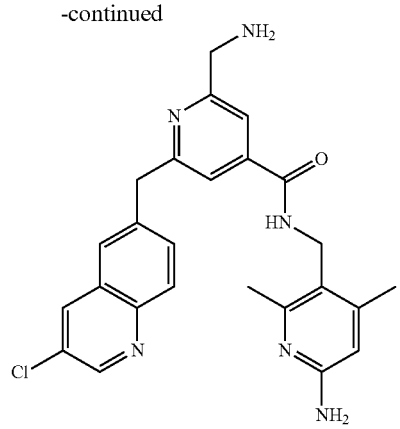

To the solution of tert-butyl (4-((6-amino-2,4-dimethyl-pyridin-3-yl)methylcarbamoyl)-6-((3-chloroquinolin-6-yl)methyl)pyridin-2-yl)methylcarbamate (50 mg) in DCM (5 mL) was added HCl/MeOH (0.5 mL). The mixture was stirred at room temperature for 2 h. The precipitate was filtered and washed with DCM/MeOH (20:1) three times to afford N-((6-amino-2,4-dimethylpyridin-3-yl)methyl)-2-(aminomethyl)-6-((3-chloroquinolin-6-yl)methyl)isonicotinamide as white solid (5 mg).

¹H NMR (400 MHz, CD₃OD): 8.78 (d, 1H), 8.39 (d, 1H), 7.99 (d, 1H), 7.88 (s, 1H), 7.81 (dd, 1H), 7.69 (s, 1H), 7.72 (s, 1H), 6.71 (s, 1H), 4.50 (d, 4H), 4.36 (s, 2H), 2.60 (s, 3H), 2.47 (s, 3H). LRMS (M+H⁺) m/z calculated 461.2, found 461.2.

Example 212: Preparation of N-((6-amino-2,4-dimethylpyridin-3-yl)methyl)-2-((3-chloroquinolin-6-yl)methyl)-6-(hydroxymethyl)isonicotinamide

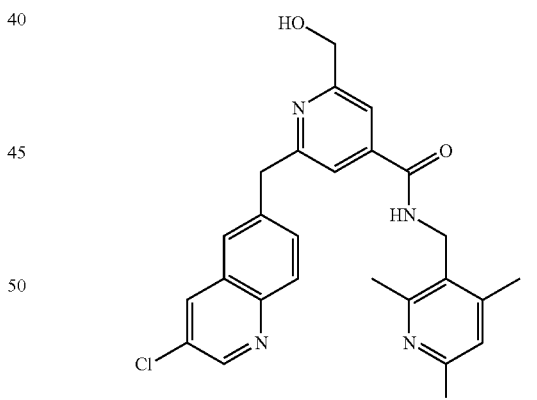

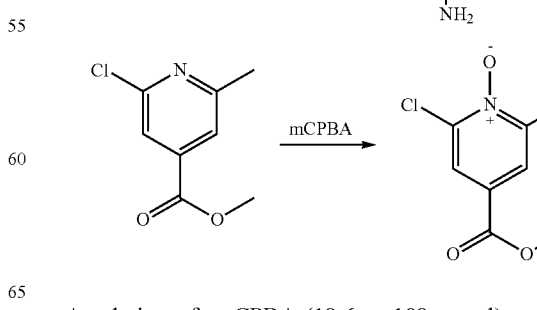

A solution of m-CPBA (18.6 g, 108 mmol) was added portion-wise to a solution of methyl 2-chloro-6-methylpyridine-4-carboxylate (10 g, 54 mmol) in 100 mL of CH$_2$Cl$_2$ at rt. The reaction mixture is stirred for 2 h, and concentrated to dryness. Sat. NaHCO$_3$ (20 mL) and EtOAc (30 mL) were added. The layers are separated and the aqueous layer is extracted twice with EtOAc (30 mL each). The combined organic layer was dried (Na$_2$SO$_4$), filtered, and concentrated in vacuo to give an off-white solid which was used to next run directly.

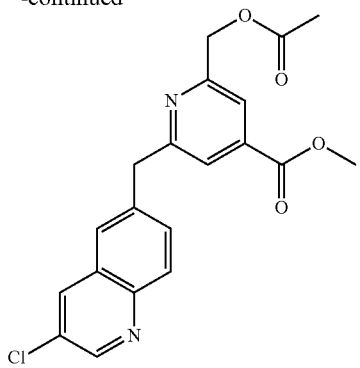

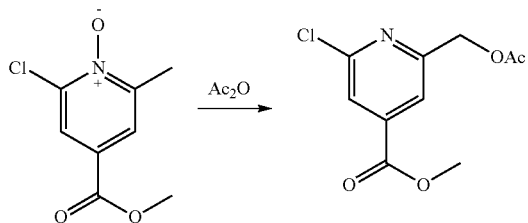

2-Chloro-6-methyl-1-oxy-isonicotinic acid ester (6.0 g, 30 mmol, 1.0 eq) is dissolved in acetic acid anhydride (30 mL) and the reaction mixture was stirred at 100° C. for 2 h, then cooled and concentrated. The residue was dissolved with EtOAc and adjusted with NaHCO$_3$ to pH=7-8. The separated organic phase was dried over Na$_2$SO$_4$. After removal of solvent, the residue was purified on silica gel column (PE:EA=5:1) to afford methyl 2-(acetoxymethyl)-6-chloroisonicotinate as yellow solid (4.2 g)

Hexamethyldistannane (0.26 mL, 418 mg, 1.28 mmol) and tetrakis(triphenylphosphine)palladium (122 mg, 0.106 mmol) were added to a solution of methyl 2-(acetoxymethyl)-6-chloroisonicotinate (260 mg, 1.06 mmol) in dry dioxane (10 mL) and the resulting mixture was heated under refluxed for 3 h under N$_2$. AcOEt (50 mL) and water (100 mL) were then added. The layers were separated and the organic layer was washed with water (5×100 mL), dried (Na$_2$SO$_4$) and the solvent was removed by rotary evaporation to leave crude residue which was used in the next step without further purification.

To a solution of 3-chloro-6-chloromethyl-quinoline (225 mg, 1.06 mmol, 1.0 eq) and crude methyl 2-(acetoxymethyl)-6-(trimethylstannyl)isonicotinate from the above step in dioxane (10 mL) was added Pd(PPh$_3$)$_2$Cl$_2$ (74 m g, 0.106 mmol, 0.1.0 eq). The mixture was stirred at 110° C. for 3 h under nitrogen atmosphere, concentrated and finally purified by silica gel chromatography (EA/PE=10/1~5:1) to afford methyl 2-(acetoxymethyl)-6-((3-chloroquinolin-6-yl)methyl)isonicotinate (215 mg, 40%) as yellow oil.

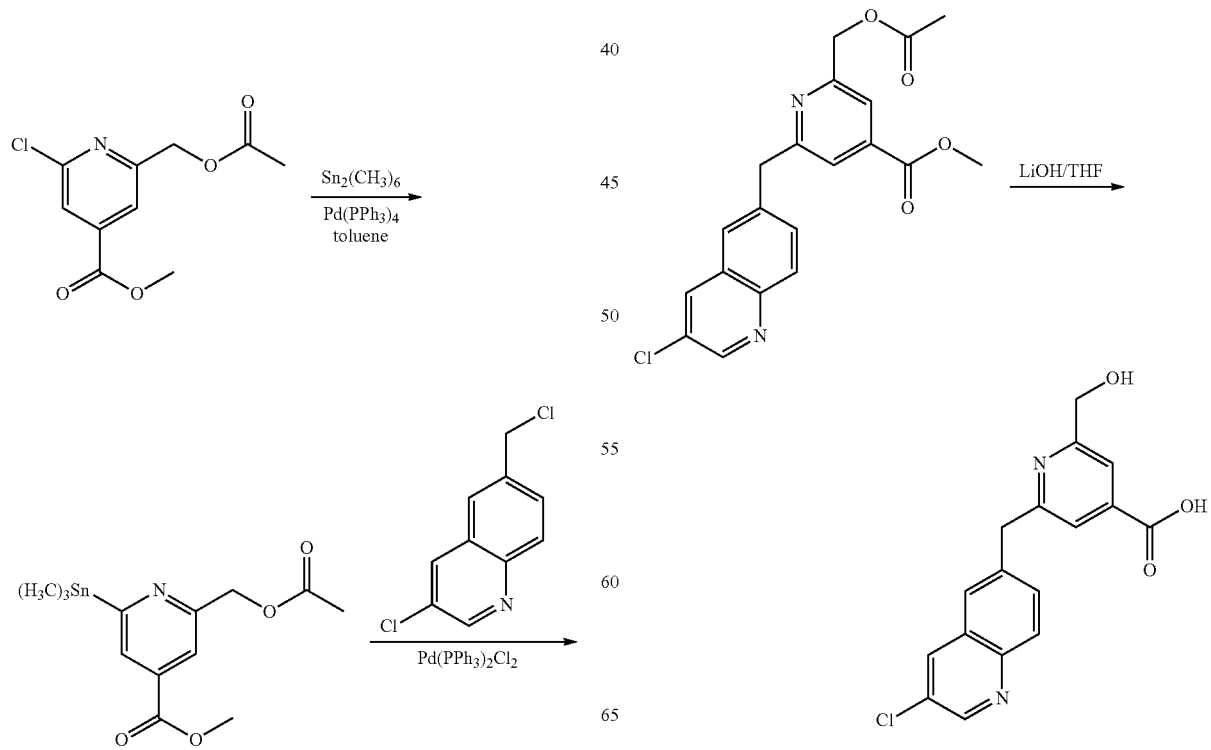

To the solution of methyl 2-(acetoxymethyl)-6-((3-chloroquinolin-6-yl)methyl)isonicotinate (215 mg, 0.56 mmol, 1.0 eq) in THF/H$_2$O (5 mL/1 mL) was added LiOH (234 mg, 5.58 mmol, 10 eq). The resulting system was stirred for 1 h at rt until all starting material had been consumed (assessed by TLC), concentrated and the aqueous reside was neutralized with 1M HCl and extracted with EtOAc (10 mL×3). The combined organic layers were washed with brine, dried over Na$_2$SO$_4$ and concentrated to afford crude acid (79 mg) which was used directly to next run.

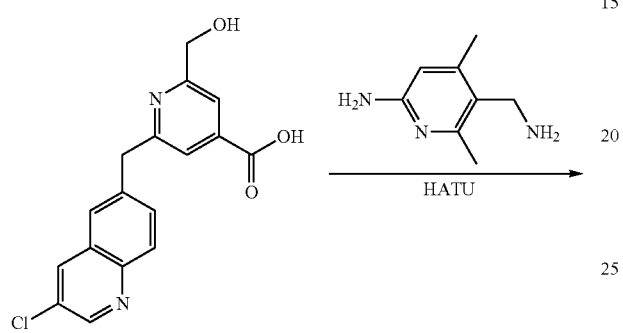

To a solution of 2-((3-chloroquinolin-6-yl)methyl)-6-(hydroxymethyl)isonicotinic acid (79 mg, 0.24 mmol, 1.0 eq) in DMF (5 mL) was added 5-aminomethyl-6-methyl-pyridin-2-ylamine hydrochloride (65 mg, 0.29 mmol, 1.2.0 eqeq) followed by HATU (137 mg, 0.36 mmol, 1.5 eq) and DIPEA (0.15 mL, 0.72 mmol, 3.0 eq) at 0° C. The reaction mixture was allowed to warm to rt and stirred for 2 h under N$_2$. Water (20 mL) was added and the mixture was extracted with EtOAc (20 mL×3). The combined organic layers were washed with brine, dried over Na$_2$SO$_4$, filtered and concentrated. The residue was purified by prep-TLC (DCM:MeOH=15:1) to give N-(4-amino-2,6-dimethylbenzyl)-2-((3-chloroquinolin-6-yl)methyl)-6-(hydroxymethyl) isonicotinamide (77 mg) as a yellow solid.

$^1$H NMR (400 MHz, CD$_3$OD) δ 8.73 (d, 1H), 8.33 (d, 1H), 7.94 (d, 1H), 7.79 (d, 1H), 7.74 (s, 1H), 7.71 (dd, 1H), 7.56 (s, 1H), 6.67 (s, 1H), 4.73 (s, 3H), 4.48 (s, 2H), 4.38 (s, 2H), 2.57 (s, 3H), 2.43 (s, 3H). LRMS (M+H$^+$) m/z calculated 462.2, found 462.2.

Example 213: Preparation of N-((6-amino-2,4-dimethylpyridin-3-yl)methyl)-2-((3-chloroquinolin-6-yl)methyl)-6-(cyanomethyl)isonicotinamide

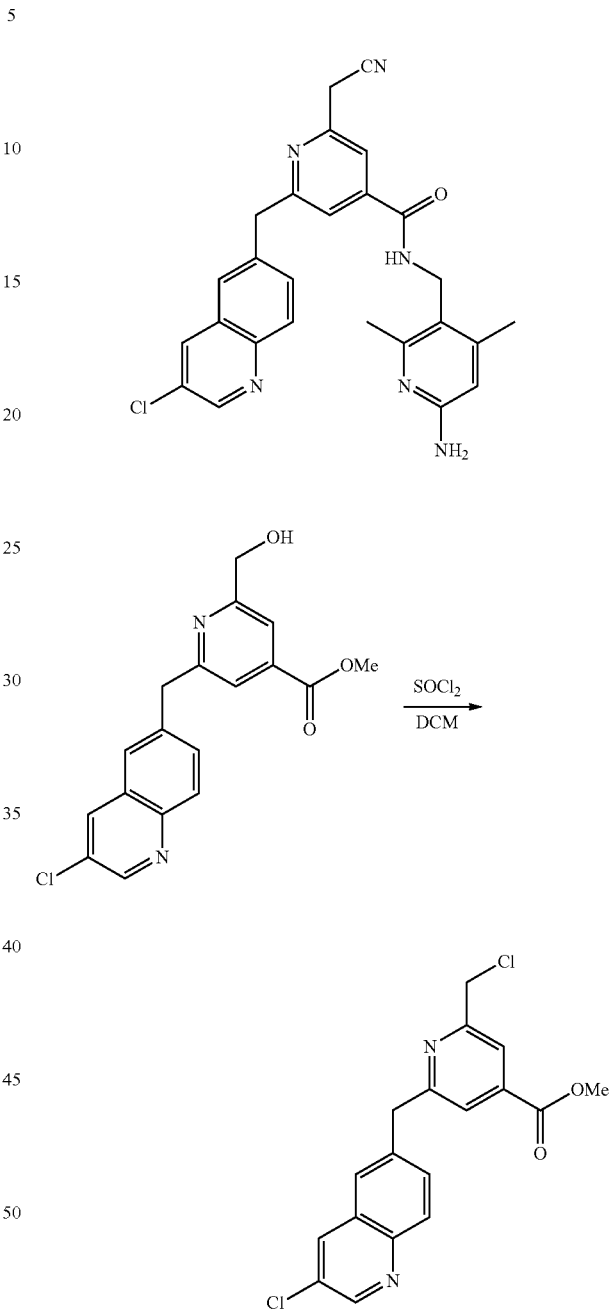

To a solution of methyl 2-((3-chloroquinolin-6-yl)methyl)-6-(hydroxymethyl)isonicotinate (375 mg, 1.09 mmol, 1.0 eq) in 20 mL of DCM was added SOCl$_2$ (386 mg, 3.27 mmol, 3 eq) slowly at 0° C., then stirred at 0° C. for 30 min. The mixture was stirred at rt for 3 h, then concentrated and adjusted with Sat. NaHCO$_3$ to pH=7~8 slowly, extracted with EA (50 mL×2). The EA layer was separated and dried over Na$_2$SO$_4$, filtered and concentrated under vacuum. The residue was purified by chromatography on silica gel (EtOAc/PE=1/20 to 1/8) to afford methyl 2-(chloromethyl)-6-((3-chloroquinolin-6-yl)methyl)isonicotinate (310 mg, 78%) as a white solid.

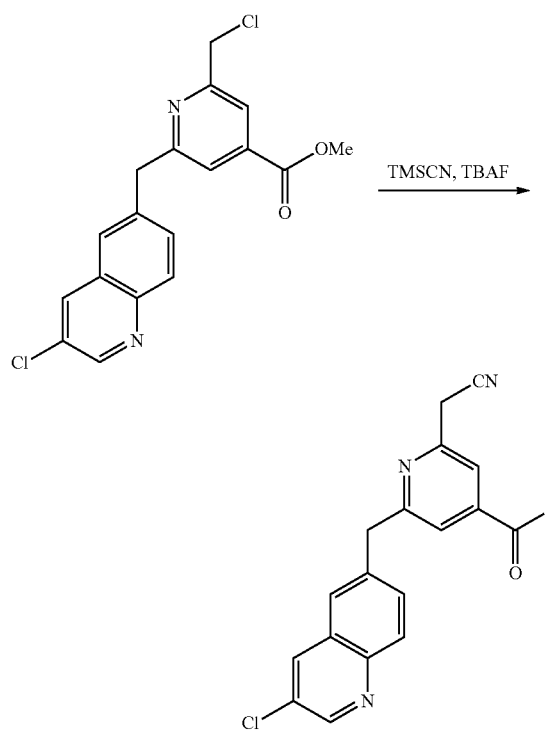

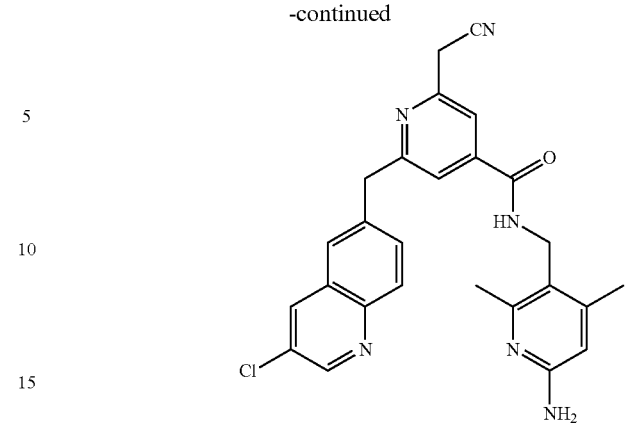

To a solution of methyl 2-(chloromethyl)-6-((3-chloroquinolin-6-yl)methyl)isonicotinate (310 mg, 0.86 mmol, 1.0 eq) in 15 mL of acetonitrile were added TMSCN (128 mg, 1.29 mmol, 1.5 eq) and TBAF in THF (1M, 1.29 mL, 1.29 mmol, 1.5 eq) and stirred at rt for 24 h. The mixture was concentrated to remove most acetonitrile. The residue was extracted with EA (100 mL) and washed with water (100 mL). The organic layer was dried over Na$_2$SO$_4$, filtered and concentrated under vacuum. The residue was purified by chromatography on silica gel (EtOAc/PE=1/20 to 1/8) to afford methyl 2-((3-chloroquinolin-6-yl)methyl)-6-(cyanomethyl)isonicotinate (233 mg, 77%) as a white solid.

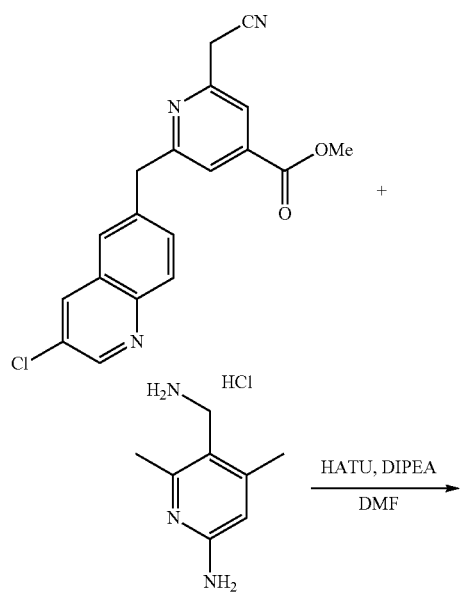

To a solution of methyl 2-((3-chloroquinolin-6-yl)methyl)-6-(cyanomethyl)isonicotinate (233 mg, 0.66 mmol, 1.0 eq) in THF (15 mL) was dropwised LiOH.H$_2$O (33 mg, 0.79 mmol, 1.2.0 eq) in H$_2$O (15 mL) at 0° C. and stirred at 0° C. for 30 min, then adjusted with 1M HCl to pH=3~4 and extracted with EA (50 mL×2), washed with water (50 mL×2) and brine (50 mL). The organic layer was dried over Na$_2$SO$_4$, filtered and concentrated to obtain 2-((3-chloroquinolin-6-yl)methyl)-6-(cyanomethyl)isonicotinic acid (205 mg, 92%) as a yellow solid which was used to next step without purification.

To a stirred mixture of 2-((3-chloroquinolin-6-yl)methyl)-6-(cyanomethyl)isonicotinic acid (205 mg, 0.61 mmol, 1.0 eq), HATU (464 mg, 1.22 mmol, 2.0 eq) and 6-(aminomethyl)-2,4-dimethylpyridin-3-amine (227 mg, 0.98 mmol, 1.2.0 eq) in DMF (20 mL) was added DIPEA (393 mg, 3.05 mmol, 5.0 eq) at 0° C. The reaction mixture was stirred at rt for 8 h, then diluted with EtOAc (100 mL). The resulting mixture was washed with aq.NaHCO$_3$ (100 mL×2), brine (100 mL×3), dried and concentrated. The residue was purified by chromatography on silica gel (DCM/MeOH=30/1 to 20/1) to afford tert-butyl 5-((2-((3-chloroquinolin-6-yl)methyl)-6-(cyanomethyl)isonicotinamido)methyl)-4,6-dimethylpyridin-2-ylcarbamate (120 mg, 34%) as a yellow solid. 1H NMR (400 MHz, DMSO-d6) 8.93 (s, 1H), 8.85 (d, 1H), 8.52 (d, 1H), 7.99 (d, 1H), 7.89 (s, 1H), 7.76 (d, 1H), 7.71 (s, 1H), 7.65 (s, 1H), 6.53 (s, 1H), 4.33-4.41 (m, 4H), 4.26 (s, 2H), 2.48 (s, 3H), 2.33 (s, 3H)

Example 214: Preparation of N-((6-amino-2,4-dimethylpyridin-3-yl)methyl)-2-(2-amino-2-oxoethyl)-6-((3-chloroquinolin-6-yl)methyl)isonicotinamide

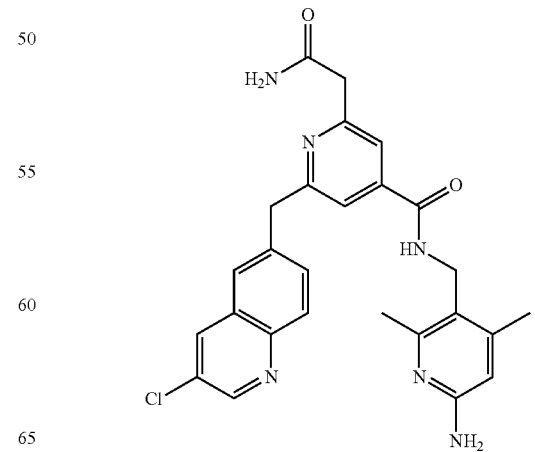

The mixture of tert-butyl 5-((2-((3-chloroquinolin-6-yl)methyl)-6-(cyanomethyl)isonicotinamido)methyl)-4,6-dimethylpyridin-2-ylcarbamate (100 mg, 0.17 mmol, 1.0 eq) in 3 mL of con.H₂SO₄ was stirred at rt for 8 h, then basified with saturated aqueous sodium bicarbonate and extracted with 10 percent methanol in DCM (100 mL). The organic layer was concentrated, and the resulting residue was purified by Pre-TLC (DCM:MEOH=10:1) to afford N-((6-amino-2,4-dimethylpyridin-3-yl)methyl)-2-(2-amino-2-oxoethyl)-6-((3-chloroquinolin-6-yl)methyl)isonicotinamide (15 mg, 15%) as a yellow solid.

¹H NMR (400 MHz, DMSO-d6): 8.84 (d, J=2.4 Hz, 1H), 8.61 (t, J=4.4 Hz, 1H), 8.51 (d, J=2.1 Hz, 1H), 7.98 (d, J=8.9 Hz, 1H), 7.85 (s, 1H), 7.74 (dd, J=8.6, 1.9 Hz, 1H), 7.59 (s, 2H), 7.50 (s, 1H), 7.00 (s, 1H), 6.16 (s, 1H), 5.78 (s, 2H), 4.27-4.40 (m, 4H), 3.61 (s, 2H), 2.31 (s, 3H), 2.17 (s, 3H). LRMS (M+H⁺) m/z calculated 489.2, found 489.2.

Example 215: Preparation of N-((6-amino-2,4-dimethylpyridin-3-yl)methyl)-2-((5-(trifluoromethyl)-1H-pyrrolo[2,3-b]pyridin-2-yl)methyl)isonicotinamide

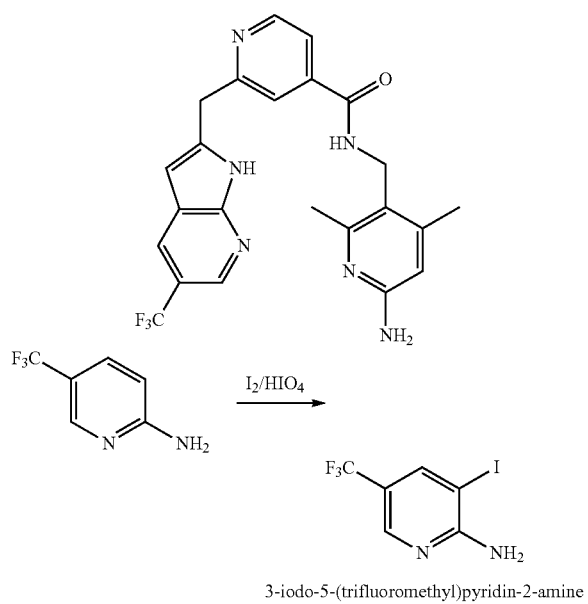

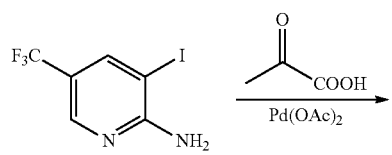
3-iodo-5-(trifluoromethyl)pyridin-2-amine

To a stirred solution of 5-(trifluoromethyl)pyridin-2-amine (5.0 g, 30.8 mmol) in a mixture of AcOH/H₂O/con.H₂SO₄ (100 mL/3.5 mL/0.5 mL) were added periodic acid (1.33 g, 5.8 mmol) and I₂ (3.12 g, 12.3 mmol). Then the resulting mixture was flushed with Ar₂ and stirred at 85° C. overnight until complete of reaction then concentrated and basified with 15% aqueous NaOH to pH=10~14. The formed solid was filtered, washed with water and dried to afford 3-iodo-5-(trifluoromethyl)pyridin-2-amine as a yellowish solid (8.2 g, 90%). ¹H NMR (400 MHz, CDCl₃): δ 8.30 (s, 1H), 8.09 (d, 1H), 5.48 (s, 2H).

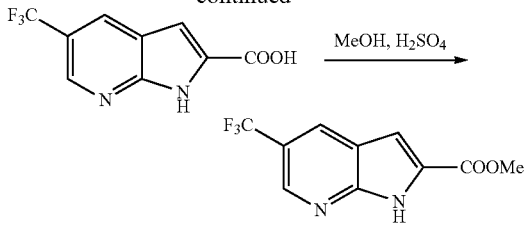

To a stirred solution of 3-iodo-5-(trifluoromethyl)pyridin-2-amine (2.0 g, 6.94 mmol) in dry DMF (20 mL) were added pyruvic acid (1.8 g, 20.83 mmol), DABCO (2.41 g, 20.83 mmol). The resulting mixture was flushed with Ar₂ and Pd(OAc)₂ (0.78 g, 3.47 mmol) was added and purged with Ar₂ for 10 minute. The resulting mixture was stirred at 110° C. in a sealed tube for 3 h, then concentrated and the residue was diluted with MeOH (30 mL). At rt con.H₂SO₄ (6 mL) was added dropwise and the resulting mixture was stirred under reflux overnight. The reaction mixture was concentrated and basified with 15% aqueous NaOH to pH 10~14. Then the mixture was extracted with EA three times, and the combined organic layers were washed with brine, dried over Na₂SO₄, filtered and concentrated. The resulting residue was purified by flash column chromatography to give methyl 5-(trifluoromethyl)-1H-pyrrolo[2,3-b]pyridine-2-carboxylate as a white solid (320 mg, yield: 35%). LRMS (M+H⁺) m/z 245.

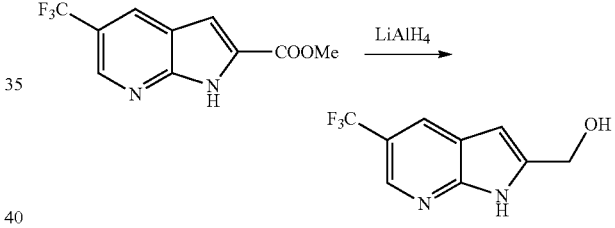

To a stirred solution of methyl 5-(trifluoromethyl)-1H-pyrrolo[2,3-b]pyridine-2-carboxylate (320 mg, 1.311 mmol) in dry THF (10 mL) was added LiAlH₄ dropwise (1.0 M in THF, 2.6 mL, 2.623 mmol) at 0° C. and the resulting mixture was stirred at rt for 3 h. The reaction mixture was quenched with 0.2 mL of H₂O, 0.2 mL of 15% aqueous NaOH and 0.6 mL of H₂O at 0° C. The resulting mixture was stirred at rt for 15 minutes and MgSO₄ (1.0 g) was added and stirred at rt for 15 minutes. The resulting mixture was filtered and concentrated to give (5-(trifluoromethyl)-1H-pyrrolo[2,3-b]pyridin-2-yl)methanol as a white solid (255 mg, yield: 90%). LRMS (M+H⁺) m/z 217.

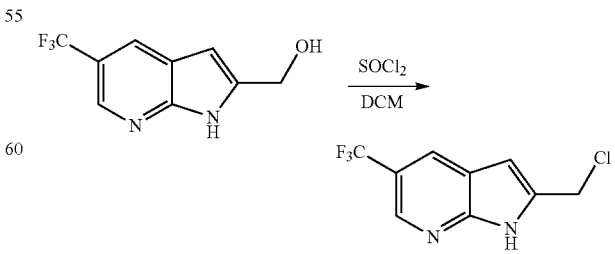

To a stirred solution of primary alcohol (552 mg, 2.554 mmol) in dry DCM (10 mL) was at 0° C. was added SOCl₂

(0.9 mL, 12.768 mmol) dropwise, and the resulting mixture was stirred at 0° C. for 1 h. The reaction mixture was quenched with sat.NaHCO₃ aq. to PH=8~9 at 0° C. The resulting mixture was extracted with EA three times and the EA layer was washed with brine, dried over Na₂SO₄, filtered and concentrated to give crude 2-(chloromethyl)-5-(trifluoromethyl)-1H-pyrrolo[2,3-b]pyridine as a yellowish solid (550 mg, 83%). LRMS (M+H⁺) m/z 235.

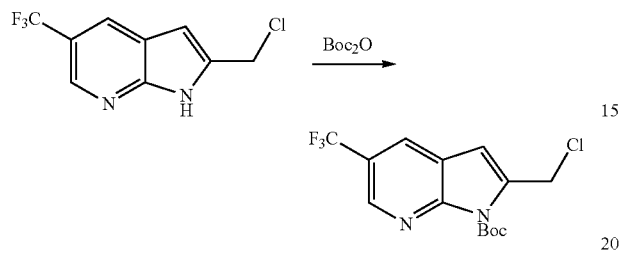

To a stirred solution of 2-(chloromethyl)-5-(trifluoromethyl)-1H-pyrrolo[2,3-b]pyridine (100 mg, 0.427 mmol) in dry THF (5 mL) at 0° C. was added (Boc)₂O (140 mg, 0.641 mmol) dropwise and a solution of DMAP (21 mg, 0.171 mmol) in dry THF (1 mL). The reaction mixture was stirred at rt for 1.5 h. The reaction mixture was concentrated and purified by Prep-TLC to give tert-butyl 2-(chloromethyl)-5-(trifluoromethyl)-1H-pyrrolo[2,3-b]pyridine-1-carboxylate (100 mg, 70%). LRMS (M+H⁺) m/z 278.

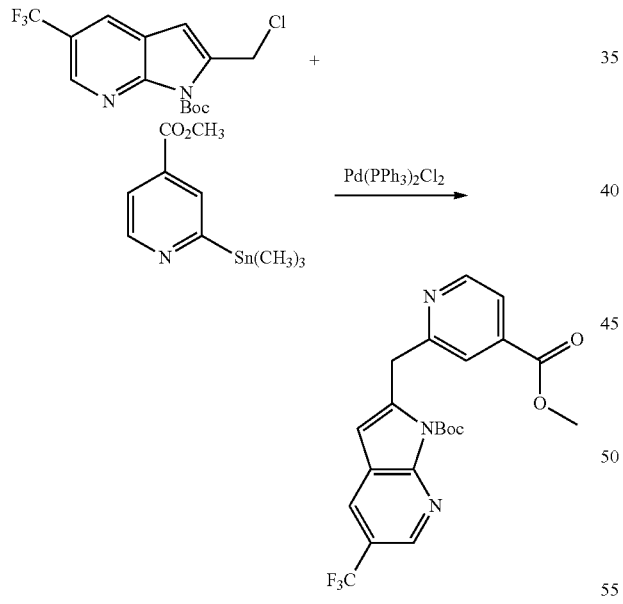

To a stirred solution of methyl 2-chloroisonicotinate (2.0 g, 11.7 mmol) in dry 1,4-dioxane (20 mL) were added Sn₂(CH₃)₆ (4.8 mL, 23.3 mmol) and Pd(PPh₃)₄ (1.35 g, 1.17 mmol). The reaction mixture was flushed with Ar₂ three times and stirred at 110° C. The reaction mixture was concentrated and purified by column chromatography on Al₂O₃ to give pure product methyl 2-(trimethylstannyl)isonicotinate (1.5 g, 42%). ¹H NMR (400 MHz, CDCl₃) δ 8.93 (dd, 1H), 7.99 (dd, 1H), 7.69 (dd, 1H), 3.97 (s, 3H), 0.39 (s, 9H).

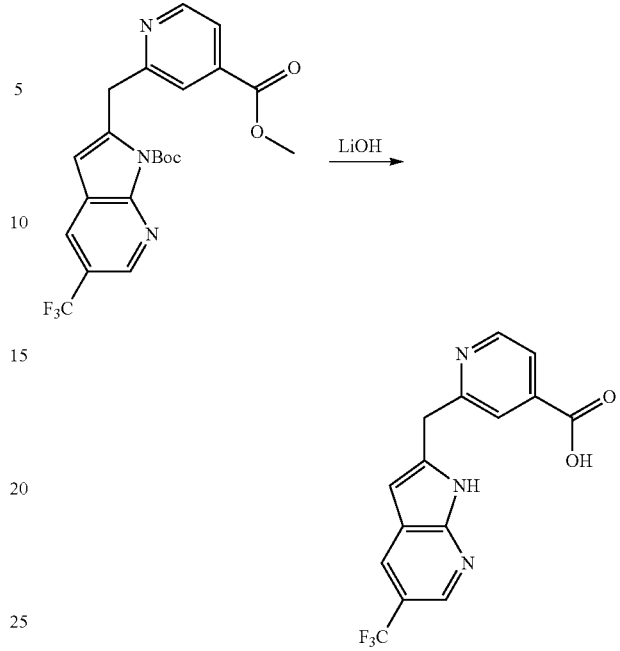

To a stirred solution of tert-butyl 2-((4-(methoxycarbonyl)pyridin-2-yl)methyl)-5-(trifluoromethyl)-1H-pyrrolo[2,3-b]pyridine-1-carboxylate (120 mg, 0.276 mmol) in a mixture of THF/MeOH/H₂O (2 mL/2 mL/1 mL) was added LiOH.H₂O (60 mg, 1.379 mmol). The reaction mixture was stirred at rt for 1.5 h. The reaction mixture was added aqueous 1N HCl dropwise to pH 4-5, and the solid was collected to afford 2-((5-(trifluoromethyl)-1H-pyrrolo[2,3-b]pyridin-2-yl)methyl)isonicotinic acid (52 mg, 60%). LRMS (M+H⁺) m/z 322. ¹H NMR (400 MHz, DMSO-d₆): δ 13.69 (s, 1H), 12.23 (s, 1H), 8.71 (d, 1H), 8.48 (d, 1H), 8.26 (s, 1H), 7.79 (s, 1H), 7.70 (dd, 1H), 6.39 (d, 1H), 4.40 (s, 2H).

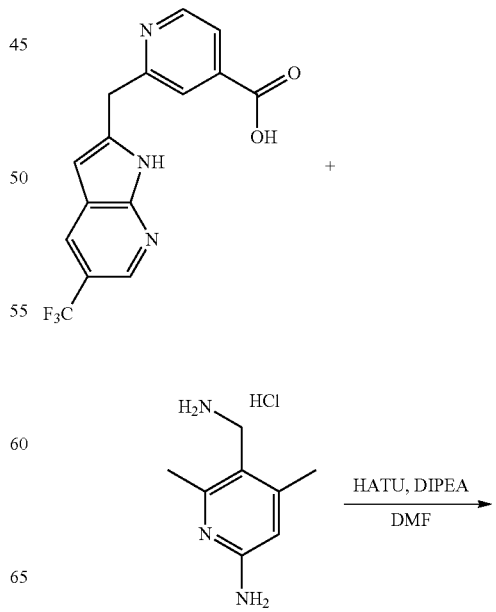

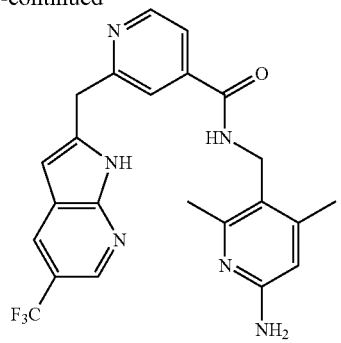

To a stirred solution of (50 mg, 0.156 mmol) in dry DMF (2 mL) at 0° C. were added 5-(aminomethyl)-4,6-dimethylpyridin-2-amine 2 HCl (35 mg, 0.156 mmol), DIPEA (81 mg, 0.624 mmol) and HATU (65 mg, 0.172 mmol). Then the resulting mixture was flushed with $Ar_2$ three times and stirred at rt for 2 h. The reaction mixture was diluted with water and extracted with EA three times. The EA layer was washed with brine, dried over $Na_2SO_4$, filtered and concentrated. The residue was purified by Pre-TLC to give N-((6-amino-2,4-dimethylpyridin-3-yl)methyl)-2-((5-(trifluoromethyl)-1H-pyrrolo[2,3-b]pyridin-2-yl)methyl) isonicotinamide as a yellowish solid (23 mg, 30%). LRMS (M+H$^+$) m/z 455. HPLC 95%. $^1$H NMR (400 MHz, DMSO-d$_6$) δ 12.19 (s, 1H), 8.66 (t, 1H), 8.62 (d, 1H), 8.47 (d, 1H), 8.24 (d, 1H), 7.75 (s, 1H), 7.64 (dd, 1H), 6.34 (d, 1H), 6.15 (s, 1H), 5.77 (s, 2H), 4.34 (s, 4H), 2.31 (s, 3H), 2.18 (s, 3H).

Example 216: Preparation of N-((6-amino-2-methylpyridin-3-yl)methyl)-2-((6-chloro-1,8-naphthyridin-3-yl)methyl)-5-cyanoisonicotinamide

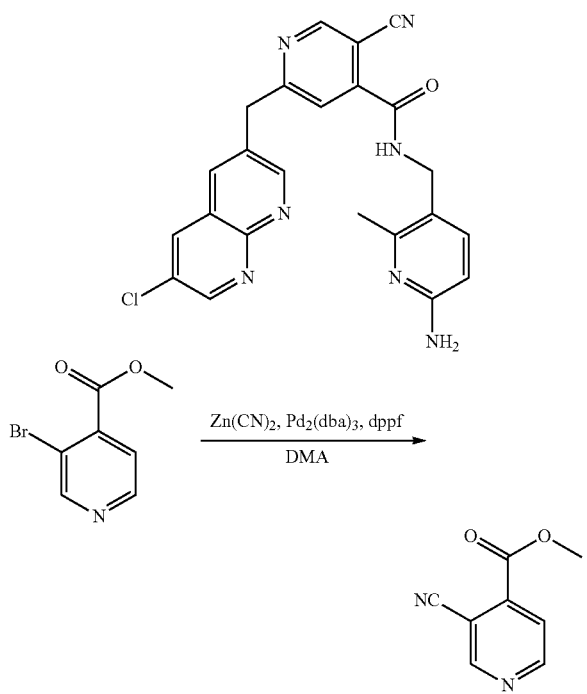

A mixture of methyl 3-bromoisonicotinate (37.0 g, 171.3 mmol, 1.0 eq), Zn(CN)$_2$ (20.0 g, 171.3 mmol, 1.0 eq), Pd$_2$(dba)$_3$ (4.7 g, 5.12 mmol, 0.03 eq) and dppf (5.7 g, 10.24 mmol, 0.06 eq) in DMA (200 mL) was stirred at 110° C. overnight, cooled to rt, poured into water and extracted with EA (200 mL×2), washed with water (200 mL) and brine (200 mL×2), dried and concentrated. The residue was purified by chromatography on silica gel (PE to PE/EA=20:1) to afford methyl 3-cyanoisonicotinate (14.5 g, 50.4%) as a white solid.

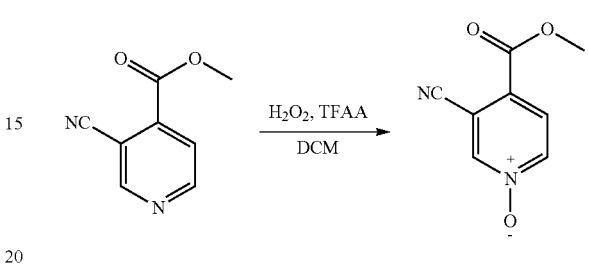

A mixture of methyl 3-cyanoisonicotinate (14.5 g, 90.0 mmol, 1.0 eq), H$_2$O$_2$ (40.8 g, 360 mmol, 4.0 eq) in DCM (400 mL) was cooled to 0° C. and TFAA (75.6 g, 360 mmol, 4.0 eq) was added dropwise. The reaction mixture was stirred at 40° C. overnight. Saturated aqueous Na$_2$SO$_3$ was added and the solution was poured into a separatory funnel containing 1M HCl. The layers were separated and the organic layer was washed with saturated aqueous sodium bicarbonate, dried over Na$_2$SO$_4$, filtered and concentrated to afford 3-cyano-4-(methoxycarbonyl)pyridine 1-oxide (13.5 g, 84.3%) as a white solid.

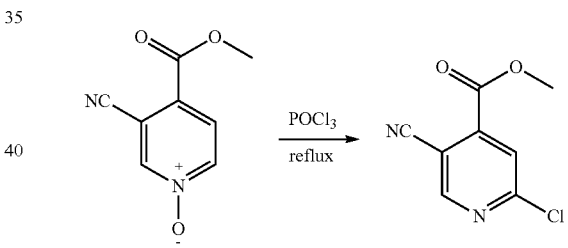

A mixture of 3-cyano-4-(methoxycarbonyl)pyridine 1-oxide (13.0 g, 73.0 mmol, 1.0 eq) in POCl$_3$ (80 mL) was heated at 110° C. under N$_2$ for 3 h, cooled to rt, concentrated to remove most POCl$_3$. The residue was diluted with DCM (200 mL) and ice water (100 mL), basified with aq.NaHCO$_3$ to pH=7-8. The organic layer was washed with brine (50 mL×3), dried over Na$_2$SO$_4$, filtered and concentrated under vacuum. The resulting residue was purified by chromatography on silica gel (EtOAc/PE=1/20 to 1/8) to afford methyl 2-chloro-5-cyanoisonicotinate (3.0 g, 21%) as a white solid $^1$H NMR (400 MHz, CDCl$_3$): δ 8.83 (d, 1

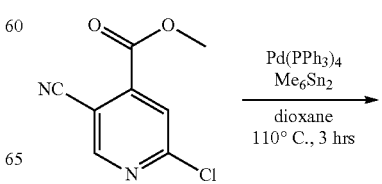

-continued

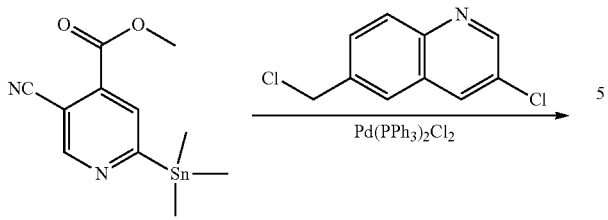

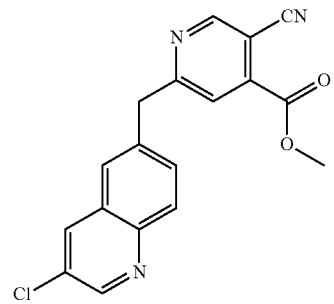

A mixture of methyl 2-chloro-5-cyanoisonicotinate (3.0 g, 15.3 mmol, 1.0 eq), Me$_6$Sn$_2$ (6.0 g, 18.4 mmol, 1.2.0 eq) and Pd(PPh$_3$)$_4$ (707 mg, 0.61 mmol, 0.04 eq) in anhydrous dioxane (50 mL) was heated at 110° C. under N$_2$ for 3 h, cooled to rt, diluted with EtOAc (80 mL), washed with water (50 mL), brine (50 mL×3), dried and concentrated to afford crude methyl 5-cyano-2-(trimethylstannyl)isonicotinate (4.6 g, 92%), which was used in the next step without further purification.

A mixture of crude methyl 5-cyano-2-(trimethylstannyl) isonicotinate (4.6 g, 14.2 mmol, 1.0 eq), 3-chloro-6-(chloromethyl)quinoline (3.0 g, 14.2 mmol, 1.0 eq) and Pd(PPh$_3$)$_2$Cl$_2$ (397 mg, 0.57 mmol, 0.04 eq) in dioxane (60 mL) was stirred at 90° C. for 16 h under N$_2$, cooled to rt, concentrated to remove most solvent. The residue was diluted with EtOAc (80 mL) and water (50 mL), then filtered. The organic layer was washed with brine (30 mL×3), dried and concentrated. The residue was purified by chromatography on silica gel (EA/PE=1/10 to 1/3) to afford methyl 2-((3-chloroquinolin-6-yl)methyl)-5-cyanoisonicotinate (1.1 mg, 23%) as a white solid. $^1$H NMR (400 MHz, CDCl$_3$): δ 8.99 (s, 1H), 8.81 (d, 1H), 8.13 (d, 1H), 8.10 (d, 1H), 7.84 (s, 1H), 7.66 (s, 1H), 7.63 (dd, 1H), 4.46 (s, 2H), 4.01 (s, 3H).

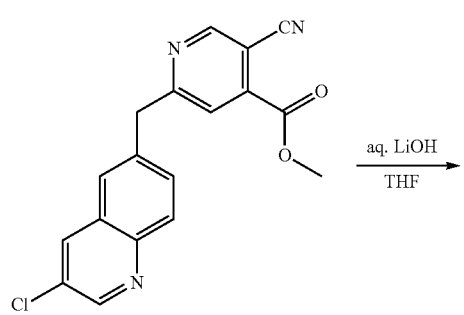

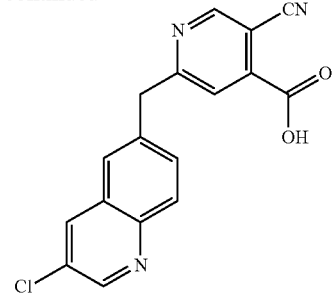

To a solution of methyl 2-((3-chloroquinolin-6-yl) methyl)-5-cyanoisonicotinate (500 mg, 1.48 mmol, 1.0 eq) in THF (15 mL) was added LiOH.H2O (374 mg, 8.9 mmol, 6.0 eq) and water (5 mL). The mixture was stirred at rt for 1 h, then concentrated under vacuum. The aqueous mixture was adjusted with 1M HCl to pH 6-7. The white suspension was filtered and the solid was washed with water (10 mL), concentrated to afford 2-((3-chloroquinolin-6-yl)methyl)-5-cyanoisonicotinic acid (478 mg, 99%) as a white solid. $^1$H NMR (400 MHz, DMSO-d$_6$): δ 9.07 (s, 1H), 8.84 (d, 1H), 8.52 (d, 1H), 8.01-7.97 (m, 2H), 7.86 (d, 1H), 7.74 (dd, 1H), 4.49 (s, 2H).

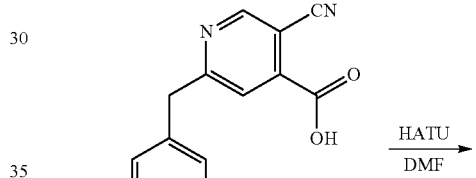

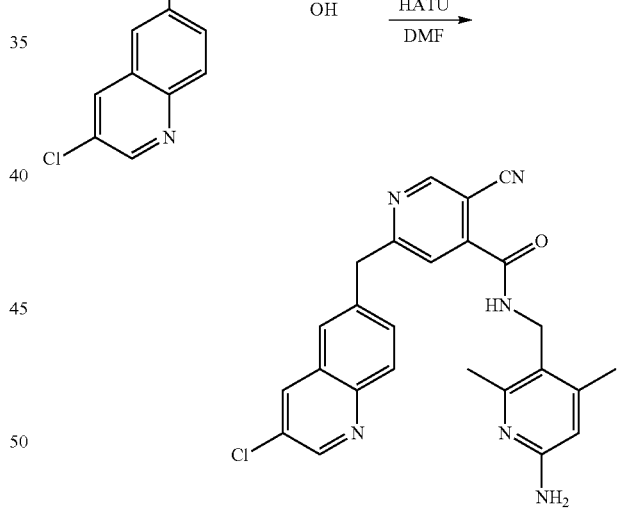

To a stirred mixture of 2-((3-chloroquinolin-6-yl)methyl)-5-cyanoisonicotinic acid (400 mg, 1.23 mmol, 1.0 eq), DIEA (793 mg, 6.2 mmol, 5.0 eq) and 5-(aminomethyl)-4,6-dimethylpyridin-2-amine hydrochloride (332 mg, 1.48 mmol, 1.2.0 eq) in DMF (10 mL) was added HATU (935 mg, 2.46 mmol, 2.0 eq) at 0° C. The reaction mixture was stirred at rt for 16 h, then diluted with EtOAc (150 mL). The resulting mixture was washed with aq.NaHCO$_3$ (50 mL×2), brine (50 mL×3), dried and concentrated. The resulting residue was purified by chromatography on silica gel (DCM/MeOH=50/1 to 20/1) to afford N-((6-amino-2,4-dimethylpyridin-3-yl)methyl)-2-((3-chloroquinolin-6-yl)methyl)-5-cyanoisonicotinamide (200 mg, 99%) as a brown solid and 40 mg of which was purified by prep-TLC (DCM/MeOH=20/1) to afford N-((6-amino-2,4-dimethylpyridin-3-yl)methyl)-2-((3-chloroquinolin-6-yl)methyl)-5-cyanoisonicotinamide (10 mg, 7%) as a white solid. LRMS (M+H⁺) m/z calculated 457.1, found 457.0.

$^1$H NMR (DMSO-d$_6$, 400 MHz): δ 8.68 (brt, 1H), 8.57 (d, 1H), 8.10 (d, 1H), 7.88 (d, 1H), 7.75 (d, 1H), 7.65 (dd, 1H), 7.49 (s, 1H), 7.40 (dd, 1H), 6.14 (s, 1H), 5.82-5.73 (m, 4H), 4.30 (d, 2H), 2.28 (s, 3H), 2.15 (s, 3H).

Example 217: Preparation of N-((6-amino-2,4-dimethylpyridin-3-yl)methyl)-2-((8-amino-3-chloroquinolin-6-yl)methyl)isonicotinamide

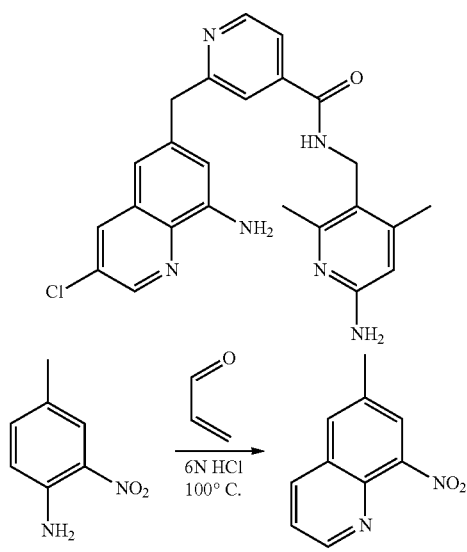

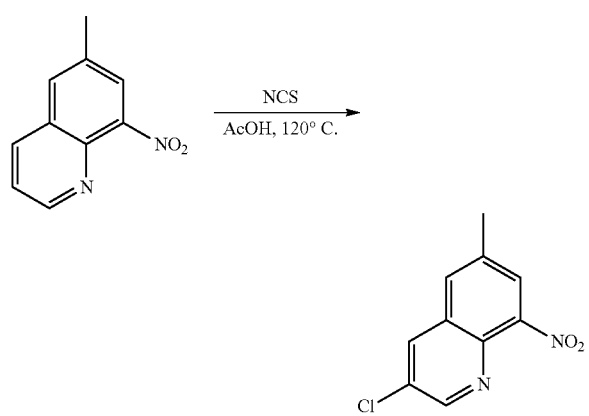

To a solution of 4-methyl-2-nitro-phenylamine (10.0 g, 65.79 mmol, 1.0 eq) in 6 N HCl (300 mL) was added acrylaldehyde (7.39 g, 131.58 mmol, 2.0 eq). The mixture was stirred at 100° C. for 3 h. The mixture was neutralized with NaHCO$_3$ solid and extracted with DCM. The combined organic phase was dried and concentrated. The resulting residue was purified by chromatography on a silica gel column (PE/EA=5/1, v/v) to give 6-methyl-8-nitro-quinoline (6.0 g, 49%) as a yellow solid.

To a solution of 6-methyl-8-nitro-quinoline (6.0 g, 31.91 mmol, 1.0 eq) in AcOH (60 mL) was added NCS (8.49 g, 63.83 mmol, 2.0 eq). The mixture was stirred at 120° C. overnight. After cooling to rt, the mixture was concentrated and the resulting residue was purified by chromatography on a silica gel column (PE/EA=4/1, v/v) to give 3-chloro-6-methyl-8-nitro-quinoline (4.5 g, 63%) as a yellow solid.

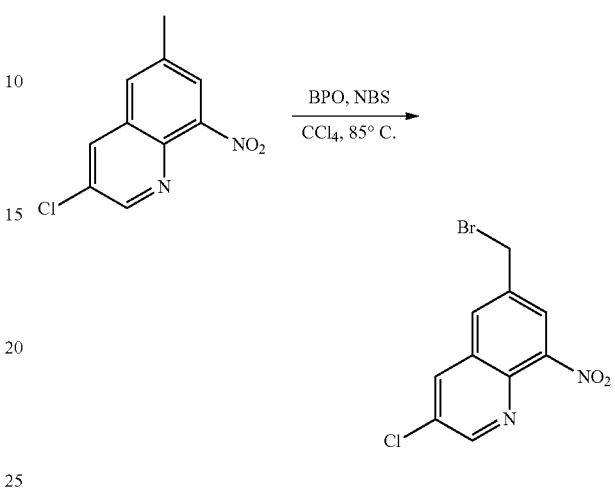

To a solution of 3-chloro-6-methyl-8-nitro-quinoline (1.0 g, 4.49 mmol, 1.0 eq) in CCl$_4$ (20 mL) was added NBS (880 mg, 4.94 mmol, 1.1 eq) and BPO (544 mg, 2.25 mmol, 0.5 eq). The mixture was stirred at 85° C. overnight. The mixture was concentrated and the resulting residue was purified by chromatography on a silica gel column (PE/EA=10/1, v/v) to give 6-bromomethyl-3-chloro-8-nitro-quinoline (400 mg, 30%) as a yellow solid.

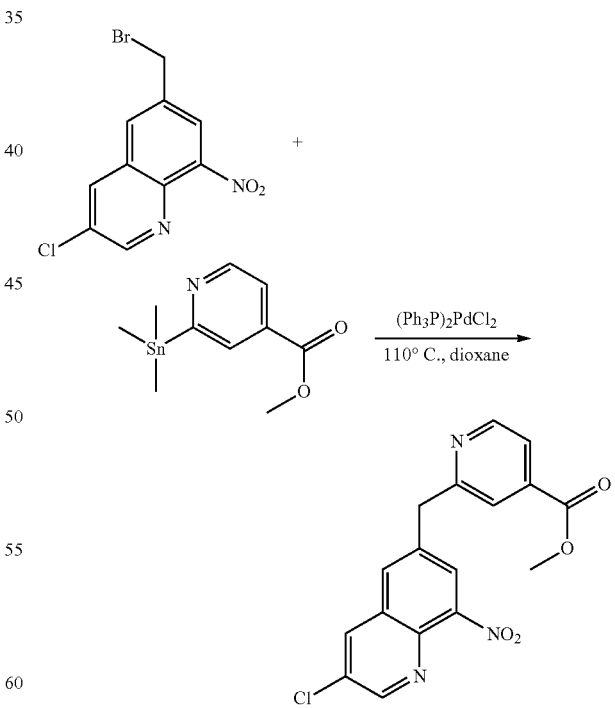

A mixture of 6-bromomethyl-3-chloro-8-nitro-quinoline (400 mg, 1.33 mmol, 1.0 eq), 2-trimethylstannanyl-isonicotinic acid methyl ester (440 mg, 1.46 mmol, 1.1 eq) and (Ph$_3$P)$_2$PdCl$_2$ (93 mg, 0.13 mmol, 0.1 eq) in dioxane (15 mL) was stirred at 110° C. overnight under N$_2$. The mixture was concentrated and the resulting residue was purified by chromatography on a silica gel column (PE/EA=2/1, v/v) to give 2-(3-chloro-8-nitro-quinolin-6-ylmethyl)-isonicotinic acid methyl ester (400 mg, 84%) as a brown solid.

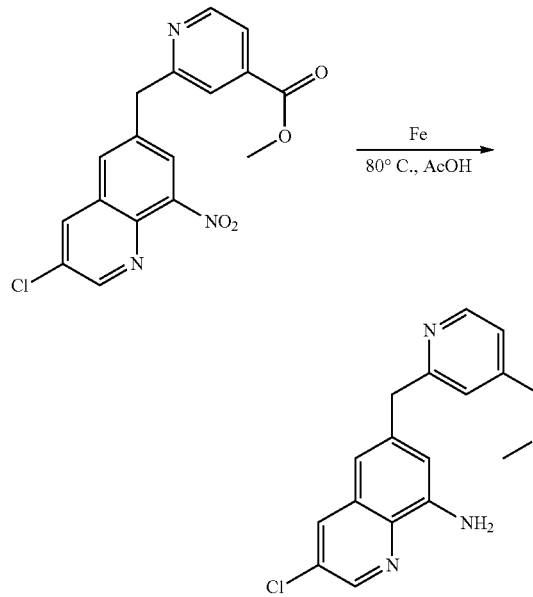

To a solution of 2-(3-chloro-8-nitro-quinolin-6-ylmethyl)-isonicotinic acid methyl ester (400 mg, 1.12 mmol, 1.0 eq) in AcOH (15 mL) was added Fe (1.1 g, 5.59 mmol, 5.0 eq) at rt. The mixture was stirred at 75° C. for 2 h. Then it was filtered and the filtrate was concentrated. The resulting residue was purified by chromatography on a silica gel (PE/EA=3/1, v/v) to give 2-(8-amino-3-chloro-quinolin-6-ylmethyl)-isonicotinic acid methyl ester (186 mg, 51%) as a yellow solid.

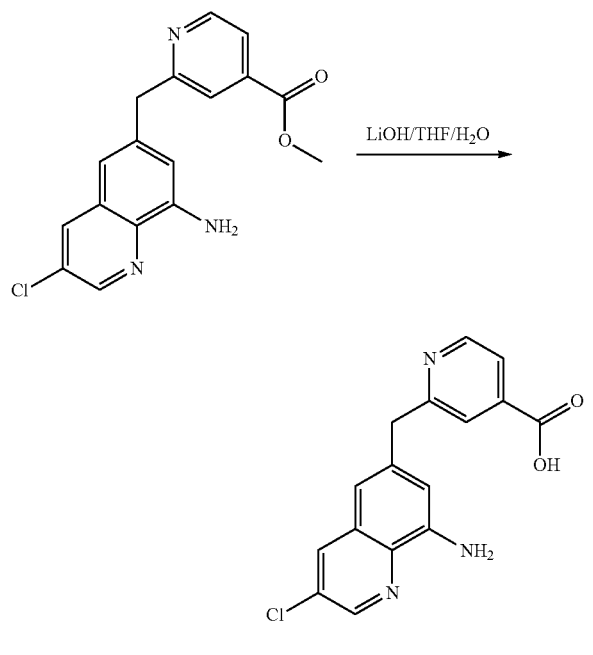

A mixture of 2-(8-amino-3-chloro-quinolin-6-ylmethyl)-isonicotinic acid methyl ester (240 mg, 0.74 mmol, 1.0 eq) and LiOH (17.6 mg, 0.88 mmol, 1.2 eq) in THF/H$_2$O (5/1, 20 mL) was stirred at rt for 3 h. The mixture was acidified with 1 N aq. HCl to pH 3, extracted with EA (30 mL×3). The combined organic layers were dried over anhydrous Na$_2$SO$_4$, and concentrated to give 2-(8-amino-3-chloro-quinolin-6-ylmethyl)-isonicotinic acid (200 mg, 86%) as a white solid.

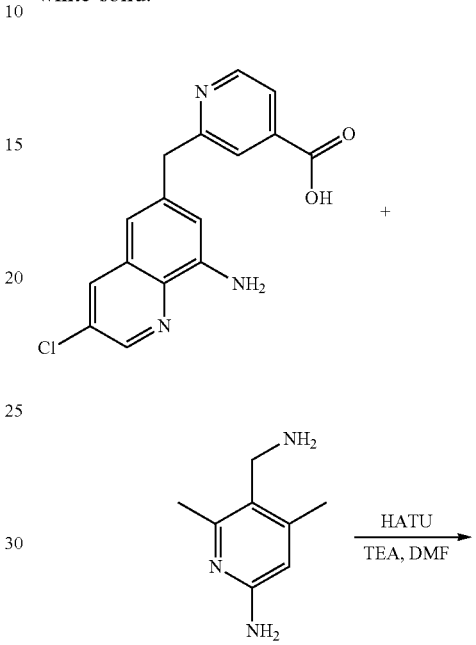

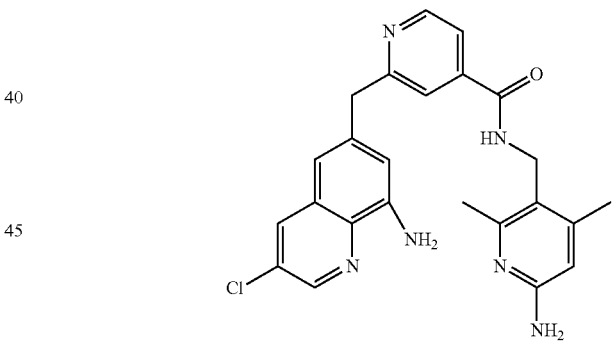

A mixture of 2-(8-amino-3-chloro-quinolin-6-ylmethyl)-isonicotinic acid (100 mg, 0.32 mmol, 1.0 eq), 5-aminomethyl-4,6-dimethyl-pyridin-2-ylamine (91 mg, 0.48 mmol, 1.5 eq), HATU (146 mg, 0.38 mmol, 1.2 eq), and TEA (97 mg, 0.96 mmol, 3.0 eq) in DMF (5 mL) was stirred at rt for 8 h. The mixture was concentrated and the resulting residue was purified by Prep-HPLC to give N-((6-amino-2,4-dimethylpyridin-3-yl)methyl)-2-((8-amino-3-chloroquinolin-6-yl)methyl)isonicotinamide (15 mg, 10.5%) as a white solid.

LRMS (M+H$^+$) m/z calculated 447.2, found 447.1. 1H NMR (DMSO-d6, 400 MHz): δ 8.62-8.58 (m, 3H), 8.29 (d, 1H), 7.69 (s, 1H), 7.60 (dd, 1H), 6.93 (d, 1H), 6.77 (d, 1H), 6.12 (s, 1H), 5.97 (s, 2H), 5.68 (s, 2H), 4.32 (d, 2H), 4.15 (s, 2H), 2.29 (s, 3H), 2.16 (s, 3H).

Example 218: Preparation of N-((6-amino-2-methylpyridin-3-yl)methyl)-2-((8-amino-3-chloroquinolin-6-yl)methyl)isonicotinamide

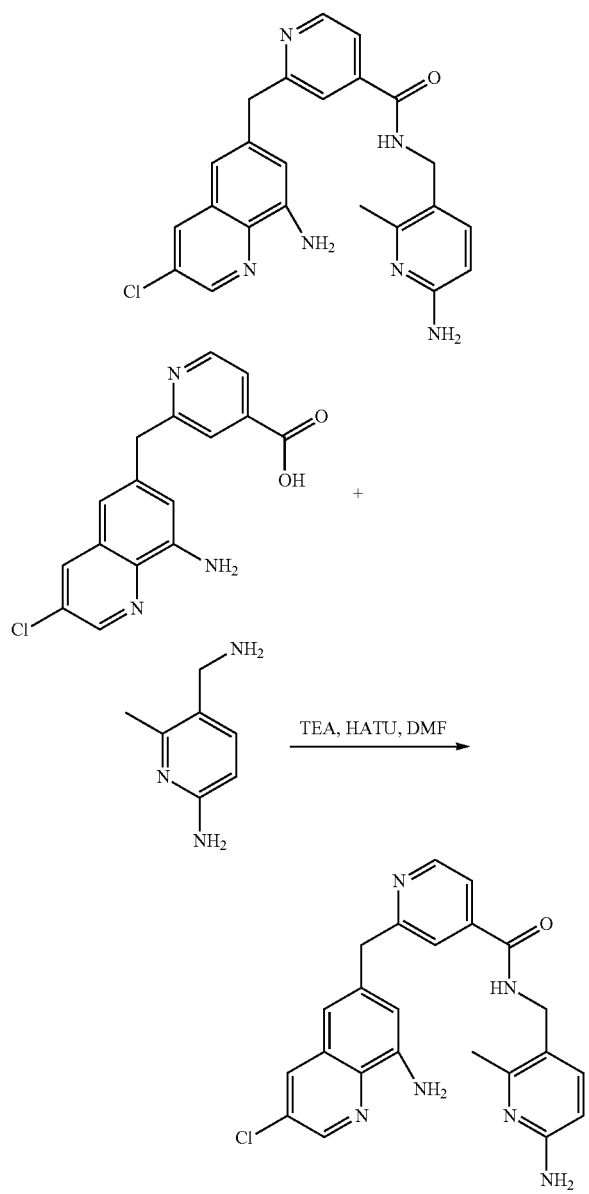

A mixture of 2-(8-amino-3-chloro-quinolin-6-ylmethyl)-isonicotinic acid (100 mg, 0.32 mmol, 1.0 eq), 5-aminomethyl-6-methyl-pyridin-2-ylamine (84 mg, 0.48 mmol, 1.5 eq), HATU (146 mg, 0.38 mmol, 1.2 eq), and TEA (97 mg, 0.96 mmol, 3.0 eq) in DMF (5 mL) was stirred at rt for 8 h. The mixture was concentrated and the resulting residue was purified by Prep-HPLC to give N-((6-amino-2-methylpyridin-3-yl)methyl)-2-((8-amino-3-chloroquinolin-6-yl)methyl)isonicotinamide (78 mg, 56.5%) as a white solid.

LRMS (M+H+) m/z calculated 433.1, found 433.1. $^1$H NMR (DMSO-d6, 400 MHz): δ 8.97 (t, 1H), 8.62 (d, 7OH), 8.61 (s, 1H), 8.30 (s, 1H), 7.70 (s, 1H), 7.61 (d, 1H), 7.24 (d, 1H), 6.94 (s, 1H), 6.78 (s, 1H), 6.23 (d, 1H), 5.97 (s, 2H), 5.75 (s, 2H), 4.27 (d, 2H), 4.16 (s, 2H), 2.27 (s, 3H).

Example 219: Preparation of N-((6-amino-2,4-dimethylpyridin-3-yl)methyl)-2-((3-chloro-8-(2-hydroxypropan-2-yl)quinolin-6-yl)methyl)isonicotinamide

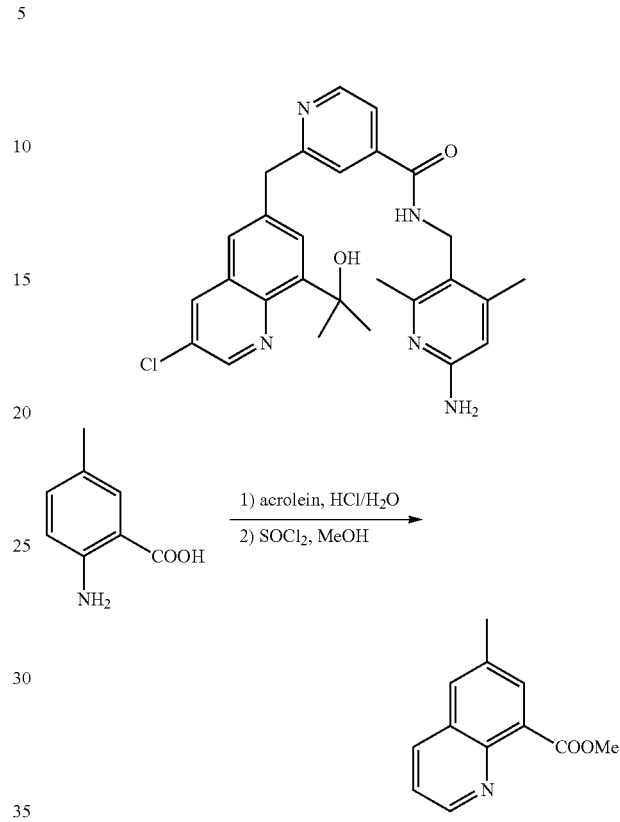

To a mixture of 2-amino-5-methyl-benzoic acid (28.0 g, 0.185 mmol, 1 eq) and p-chloranil (50.0 g, 0.204 mol, 1.1 eq) in 6 N aq. HCl (740 mL) was added acrolein (19.5 g, 80% purity, 0.278 mol, 1.5 eq) dropwise. The mixture was stirred at 100° C. for 10 min, and then the mixture was cooled to rt and adjusted to pH 4 using aq. NaHCO$_3$. The precipitate was removed by filtration. The filtrate was extracted with DCM. The combined organic layers were washed with brine, dried over MgSO$_4$, filtered and concentrated. The resulting residue was dissolved in dry MeOH (300 mL) and SOCl$_2$ (44 g, 0.37 mol, 2 eq) was added. The mixture was stirred under reflux for 20 h. After cooling to rt, the mixture was concentrated and the resulting residue was basified to pH 9 with saturated NaHCO$_3$ aqueous solution and brine. The mixture was extracted with DCM, dried over MgSO$_4$, filtered and concentrated. The resulting residue was purified by chromatography on a silica gel column (EA/PE=1/10, v/v) to give 6-methyl-quinoline-8-carboxylic acid methyl ester (22.0 g, 59% for 2 steps) as a yellow oil.

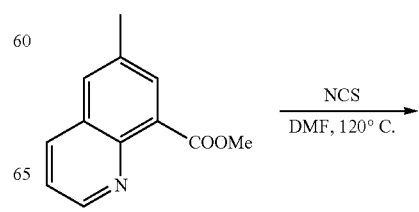

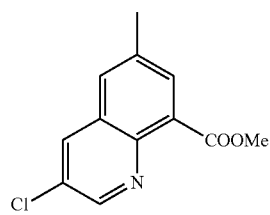

A mixture of 6-methyl-quinoline-8-carboxylic acid methyl ester (3.2 g, 15.84 mmol, 1 eq), and NCS (6.3 g, 47.52 mmol, 3 eq) in DMF (50 mL) was stirred at 120° C. for 1 h. After cooling to rt, DMF was removed by evaporation. The resulting residue was diluted with DCM and washed with brine. The organic layer was concentrated and the resulting residue was purified by chromatography on a silica gel column (EA/PE=1/15, v/v) to give 3-chloro-6-methyl-quinoline-8-carboxylic acid methyl ester (2.6 g, 69%) as an off-white solid. $^1$H NMR (DMSO-d6, 400 MHz) δ 8.88 (d, 1H), 8.53 (d, 1H), 7.88 (s, 1H), 7.84 (s, 1H), 3.92 (s, 3H), 3.52 (s, 3H).

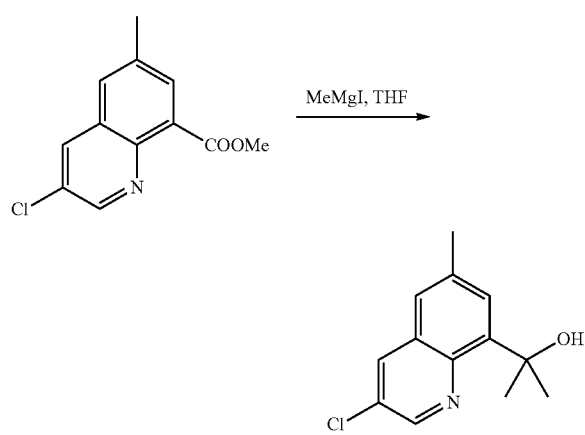

To a solution of 3-chloro-6-methyl-quinoline-8-carboxylic acid methyl ester (4.4 g, 18.72 mmol, 1 eq) in dry THF (150 mL) was added dropwise MeMgI (37.4 mL, 112.34 mmol, 3M in Et$_2$O, 6.0 eq). The mixture was stirred at rt overnight. Then the mixture was cooled to 0° C. and quenched by the addition of sat aq. NH$_4$Cl. The mixture was extracted with EA. The combined organic layers were washed with brine, dried over MgSO$_4$, filtered and concentrated in vacuum. The resulting residue was purified by chromatography on a silica gel column (EA/PE=1/10, v/v) to give 2-(3-chloro-6-methyl-quinolin-8-yl)-propan-2-ol (2.9 g, 66%) as a yellow solid.

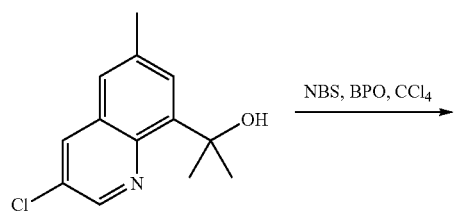

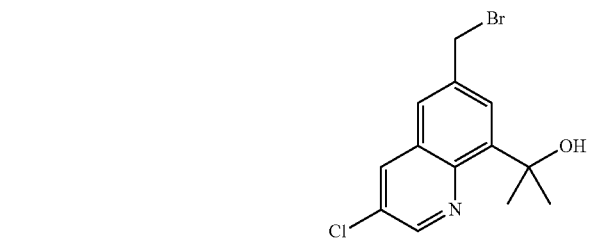

To a solution of 2-(3-chloro-6-methyl-quinolin-8-yl)-propan-2-ol (3.0 g, 12.77 mmol, 1 eq) in CCl$_4$ (100 mL) were added NBS (2.5 g, 14.04 mmol, 1.1 eq) and BPO (310 mg, 1.28 mmol, 0.1 eq). The mixture was stirred at 90° C. for 2 h. It was cooled to rt, and concentrated. The resulting residue was purified by chromatography on a silica gel column (EA/PE=1/10, v/v) to give 2-(6-bromomethyl-3-chloro-quinolin-8-yl)-propan-2-ol (1.1 g, 28%) as a yellow solid. $^1$H NMR (DMSO-d6, 400 MHz) δ 8.92 (d, 1H), 8.58 (d, 1H), 8.06 (s, 1H), 7.93 (s, 1H), 4.89 (s, 2H), 3.36 (br, 1H), 1.75 (s, 6H).

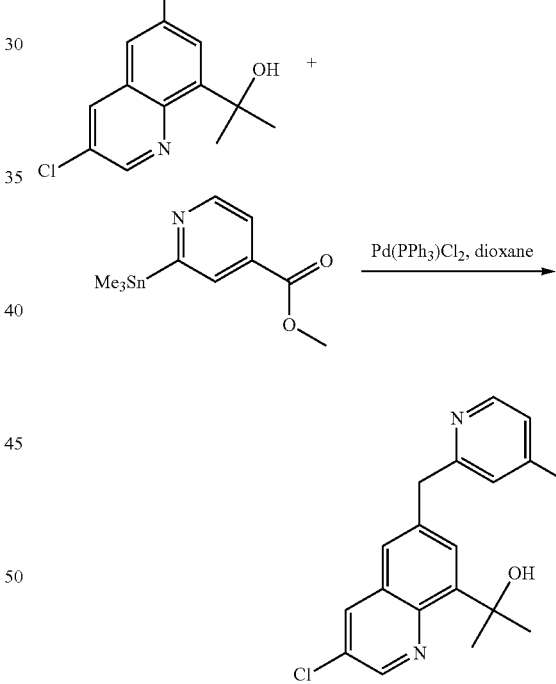

To a solution of 2-(6-bromomethyl-3-chloro-quinolin-8-yl)-propan-2-ol (1.1 g, 3.51 mmol, 1.0 eq) in dioxane (30 mL) were added 2-trimethylstannanyl-isonicotinic acid methyl ester (1.16 g, 3.86 mmol, 1.1 eq) and Pd(PPh$_3$)$_2$Cl$_2$ (245 mg, 0.35 mmol, 0.1 eq). The mixture was stirred at 90° C. for 3 h under nitrogen atmosphere, and then stripped of solvent. The resulting residue was purified by chromatography on a silica gel column (DCM/MeOH=80/1, v/v) to afford 2-[3-chloro-8-(1-hydroxy-1-methyl-ethyl)-quinolin-6-ylmethyl]-isonicotinic acid methyl ester (520 mg, 40%) as a yellow solid.

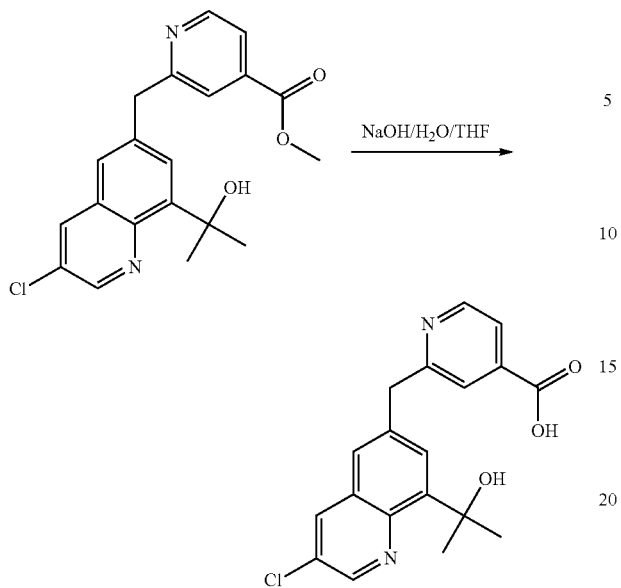

To a solution of 2-[3-chloro-8-(1-hydroxy-1-methyl-ethyl)-quinolin-6-ylmethyl]-isonicotinic acid methyl ester (0.63 g, 1.7 mmol, 1.0 eq) in THF (5 mL) and H₂O (1 mL) was added NaOH (0.136 g, 3.4 mmol, 2.0 eq) and the reaction mixture was stirred at rt for 3 h. The reaction mixture was neutralized with 1 N aq. HCl to pH 3, extracted with EA and concentrated to afford 2-[3-chloro-8-(1-hydroxy-1-methyl-ethyl)-quinolin-6-ylmethyl]-isonicotinic acid (0.4 g, 66%) as a white solid.

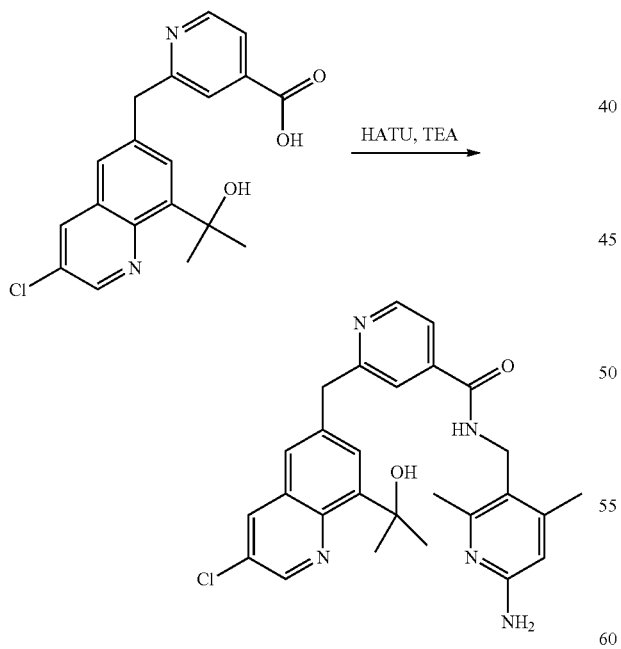

To a solution of 2-[3-chloro-8-(1-hydroxy-1-methyl-ethyl)-quinolin-6-ylmethyl]-isonicotinic acid (200 mg, crude) in DMF (10 mL) was added 5-aminomethyl-4,6-dimethyl-pyridin-2-ylamine hydrochloride (149 mg, 0.67 mmol, 1.2 eq), followed by HATU (255 mg, 0.67 mmol, 1.2 eq) and TEA (169 mg, 1.68 mmol, 3.0 eq). The reaction mixture was heated at 35° C. overnight. Water was added, and the mixture was extracted with DCM. The organic layer was washed with water, dried over Na₂SO₄, filtered and concentrated. The resulting residue was purified by Prep-HPLC to give N-((6-amino-2,4-dimethylpyridin-3-yl)methyl)-2-((3-chloro-8-(2-hydroxypropan-2-yl)quinolin-6-yl)methyl)isonicotinamide (71 mg, 25.9%) as a white solid.

LRMS (M+H+) m/z calculated 490.2, found 490.8. 1H NMR (CDCl₃, 400 MHz): δ 8.71 (d, 1H), 8.67 (d, 1H), 8.09 (d, 1H), 7.58 (s, 2H), 7.50 (s, 1H), 7.45-7.44 (m, 1H), 7.31 (s, 1H), 6.24 (s, 1H), 4.54-4.52 (m, 4H), 4.35 (s, 2H), 3.31 (d, 1H), 2.39 (s, 3H), 2.25 (s, 3H), 1.71-1.65 (m, 6H).

Example 220: Preparation of N-((6-amino-2-methylpyridin-3-yl)methyl)-2-((3-chloro-8-(2-hydroxypropan-2-yl)quinolin-6-yl)methyl)isonicotinamide

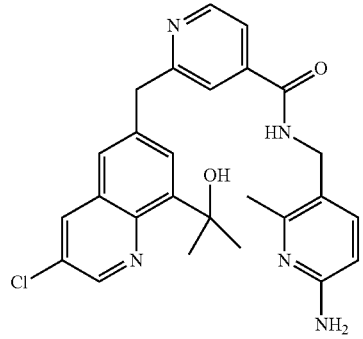 [SMILES: Cc1nc(N)ccc1CNC(=O)c1ccnc(Cc2cc(C(C)(C)O)c3ncc(Cl)cc3c2)c1]

To a solution of 2-[3-chloro-8-(1-hydroxy-1-methyl-ethyl)-quinolin-6-ylmethyl]-isonicotinic acid (200 mg, crude) in DMF (10 mL) was added 5-aminomethyl-6-methyl-pyridin-2-ylamine (140 mg, 0.67 mmol, 1.2 eq) followed by HATU (255 mg, 0.67 mmol, 1.2 eq) and TEA (169 mg, 1.68 mmol, 3.0 eq). The reaction mixture was heated to 35° C., and kept stirring for overnight. Water was added, and the mixture was extracted with DCM. The organic layer was washed with water, dried over Na₂SO₄, filtered and concentrated. The resulting residue was purified by Prep-HPLC to give N-((6-amino-2-methylpyridin-3-yl)methyl)-2-((3-chloro-8-(2-hydroxypropan-2-yl)quinolin-6-yl)methyl)isonicotinamide (92 mg, 34.6%) as a white solid.

LRMS (M+H+) m/z calculated 476.2, found 476.8. ¹H NMR (CDCl₃, 400 MHz): δ 8.71 (d, 1H), 8.67 (d, 1H), 8.10 (d, 1H), 7.58 (s, 1H), 7.51 (s, 1H), 7.49 (m, 1H), 7.42-7.40 (m, 1H), 6.32-6.30 (m, 1H), 6.21 (s, 1H), 4.49-4.48 (d, 2H), 4.39-4.35 (m, 4H), 2.39 (s, 3H), 2.20 (s, 1H), 1.72 (s, 6H).

Example 221: Preparation of N-((3-chloro-6-fluoro-1H-indol-5-yl)methyl)-2-((3-chloro-8-(2-hydroxypropan-2-yl)quinolin-6-yl)methyl)isonicotinamide

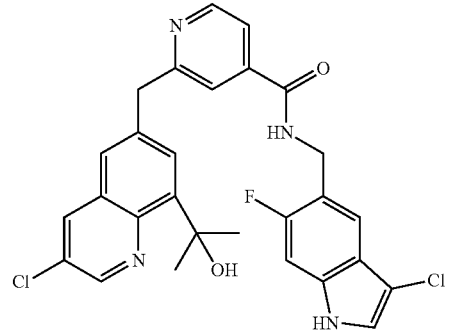 [SMILES: CC(C)(O)c1cc(Cc2cc(C(=O)NCc3cc4c(Cl)c[nH]c4cc3F)ccn2)cc2cc(Cl)cnc12]

To a solution of 2-[3-chloro-8-(1-hydroxy-1-methylethyl)-quinolin-6-ylmethyl]-isonicotinic acid (100 mg, 0.28 mmol, 1 eq) in DMF (5 mL) was added (3-chloro-6-fluoro-1H-indol-5-yl)methanamine (79 mg, 0.34 mmol, 1.2 eq), followed by HOBT (57 mg, 0.42 mmol, 1.5 eq), EDCI (81 mg, 0.42 mmol, 1.5 eq) and TEA (84 mg, 0.84 mmol, 3.0 eq). The reaction mixture was heated to 35° C. and stirred overnight. Water was added, and the mixture was extracted with DCM. The organic layer was washed with water, dried over Na$_2$SO$_4$, filtered and concentrated. The resulting residue was purified by Prep-HPLC to give N-((3-chloro-6-fluoro-1H-indol-5-yl)methyl)-2-((3-chloro-8-(2-hydroxypropan-2-yl)quinolin-6-yl)methyl)isonicotinamide (8 mg, 5.3%) as a white solid.

LRMS (M+H+) m/z calculated 537.1, found 537.1. $^1$H NMR (DMSO-d6, 400 MHz): δ 11.41 (s, 1H), 9.27 (t, 1H), 8.86 (d, 1H), 8.66 (d, 1H), 8.52 (d, 1H), 7.94 (d, 1H), 7.79 (s, 1H), 7.70 (s, 1H), 7.67 (dd, 1H), 7.51 (d, 1H), 7.44 (d, 1H), 7.22 (d, 1H), 5.85 (s, 1H), 4.59 (d, 2H), 4.36 (s, 2H), 1.70 (s, 6H).

Example 222: Preparation of N-((3-chloro-4-fluoro-1H-indol-5-yl)methyl)-2-((3-chloro-8-(2-hydroxypropan-2-yl)quinolin-6-yl)methyl)isonicotinamide

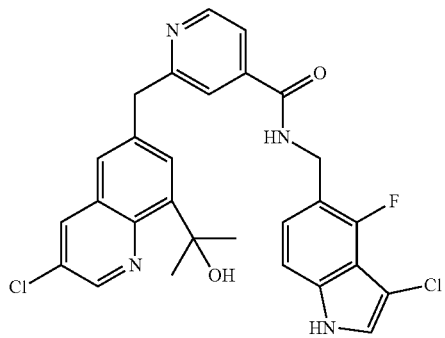 [SMILES: CC(C)(O)c1cc(Cc2cc(C(=O)NCc3ccc4[nH]cc(Cl)c4c3F)ccn2)cc2cc(Cl)cnc12]

To a solution of 2-[3-chloro-8-(1-hydroxy-1-methylethyl)-quinolin-6-ylmethyl]-isonicotinic acid (100 mg, 0.28 mmol, 1 eq) in DMF (5 mL) was added (3-chloro-4-fluoro-1H-indol-5-yl)methanamine (79 mg, 0.34 mmol, 1.2 eq) followed by HOBT (57 mg, 0.42 mmol, 1.5 eq), EDCI (81 mg, 0.42 mmol, 1.5 eq) and TEA (84 mg, 0.84 mmol, 3.0 eq). The reaction mixture was heated to 35° C. and stirred overnight. Water was added, and the mixture was extracted with DCM. The organic layer was washed with water, dried over Na$_2$SO$_4$, filtered and concentrated. The residue was purified by Prep-HPLC to give N-((3-chloro-4-fluoro-1H-indol-5-yl)methyl)-2-((3-chloro-8-(2-hydroxypropan-2-yl)quinolin-6-yl)methyl)isonicotinamide (34 mg, 22.6%) as a white solid.

LRMS (M+H$^+$) m/z calculated 537.1, found 537.1. 1H NMR (DMSO-d6, 400 MHz): δ 11.60 (s, 1H), 9.25 (t, 1H), 8.85 (d, 1H), 8.65 (d, 1H), 8.52 (d, 1H), 7.94 (d, 1H), 7.78 (s, 1H), 7.70 (s, 1H), 7.66 (dd, 1H), 7.51 (d, 1H), 7.20-7.12 (m, 2H), 5.85 (s, 1H), 4.58 (d, 2H), 4.35 (s, 2H), 1.70 (s, 6H).

Example 223: Preparation of N-((3-chloro-1H-pyrrolo[2,3-b]pyridin-5-yl)methyl)-2-((3-chloro-8-(2-hydroxypropan-2-yl)quinolin-6-yl)methyl)isonicotinamide

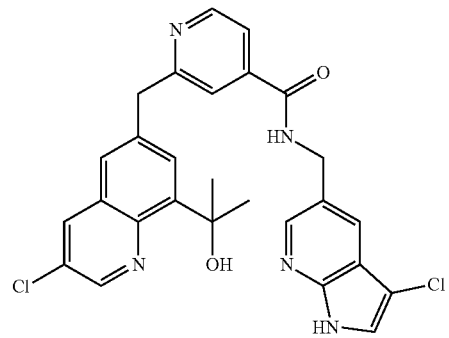 [SMILES: CC(C)(O)c1cc(Cc2cc(C(=O)NCc3cnc4[nH]cc(Cl)c4c3)ccn2)cc2cc(Cl)cnc12]

To a solution of 2-[3-chloro-8-(1-hydroxy-1-methylethyl)-quinolin-6-ylmethyl]-isonicotinic acid (100 mg, 0.28 mmol, 1 eq) in DMF (5 mL) was added (3-chloro-1H-pyrrolo[2,3-b]pyridin-5-yl)methanamine (74 mg, 0.34 mmol, 1.2 eq) followed by HOBT (57 mg, 0.42 mmol, 1.5 eq), EDCI (81 mg, 0.42 mmol, 1.5 eq) and TEA (84 mg, 0.84 mmol, 3.0 eq). The reaction mixture was heated to 35° C. and stirred overnight. Water was added, and the mixture was extracted with DCM. The organic layer was washed with water, dried over Na$_2$SO$_4$, filtered and concentrated. The resulting residue was purified by Prep-HPLC to give N-((3-chloro-1H-pyrrolo[2,3-b]pyridin-5-yl)methyl)-2-((3-chloro-8-(2-hydroxypropan-2-yl)quinolin-6-yl)methyl)isonicotinamide (24 mg, 16.6%) as a white solid.

LRMS (M+H+) m/z calculated 520.1, found 520.1. 1H NMR (DMSO-d6, 400 MHz): δ 9.35 (t, 1H), 8.85 (d, 1H), 8.65 (d, 1H), 8.52 (d, 1H), 8.31 (d, 1H), 7.94 (d, 1H), 7.78 (d, 1H), 7.70-7.65 (m, 3H), 5.84 (s, 1H), 4.59 (d, 2H), 4.35 (s, 2H), 1.70 (s, 6H).

Example 224: Preparation of N-((1-aminoisoquinolin-6-yl)methyl)-2-((3-chloro-8-(2-hydroxypropan-2-yl)quinolin-6-yl)methyl)isonicotinamide

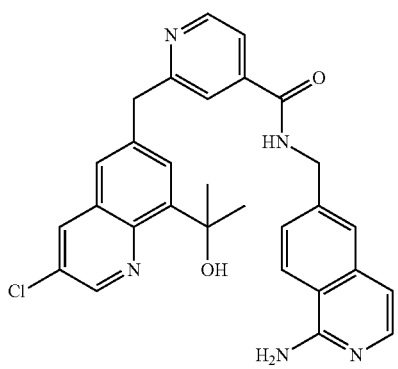 [SMILES: CC(C)(O)c1cc(Cc2cc(C(=O)NCc3ccc4c(N)nccc4c3)ccn2)cc2cc(Cl)cnc12]

To a solution of 2-[3-chloro-8-(1-hydroxy-1-methylethyl)-quinolin-6-ylmethyl]-isonicotinic acid (100 mg, 0.28 mmol, 1 eq) in DMF (5 mL) was added 6-aminomethyl-isoquinolin-1-ylamine (59 mg, 0.34 mmol, 1.2 eq) followed by HOBT (57 mg, 0.42 mmol, 1.5 eq), EDCI (81 mg, 0.42 mmol, 1.5 eq) and TEA (84 mg, 0.84 mmol, 3.0 eq). The reaction mixture was heated to 35° C. and stirred overnight. Water was added, and the mixture was extracted with DCM. The organic layer was washed with water, dried over Na₂SO₄, filtered and concentrated. The resulting residue was purified by Prep-HPLC to give N-((1-aminoisoquinolin-6-yl)methyl)-2-((3-chloro-8-(2-hydroxypropan-2-yl)quinolin-6-yl)methyl)isonicotinamide (2.4 mg, 1.7%) as a white solid.

LRMS (M+H+) m/z calculated 512.2, found 512.2. ¹H NMR (DMSO-d6, 400 MHz): δ 9.41 (t, 1H), 8.85 (d, 1H), 8.68 (d, 1H), 8.53 (d, 1H), 8.14 (d, 1H), 7.95 (d, 1H), 7.81 (s, 1H), 7.74 (d, 1H), 7.71 (d, 1H), 7.70 (d, 1H), 7.56 (s, 1H), 7.40 (d, 1H), 6.85 (d, 1H), 5.85 (s, 1H), 4.61 (d, 2H), 4.37 (s, 2H), 1.71 (s, 6H).

Example 225: Preparation of N-((5-chloro-1H-indazol-3-yl)methyl)-2-((3-chloro-8-(2-hydroxypropan-2-yl)quinolin-6-yl)methyl)isonicotinamide

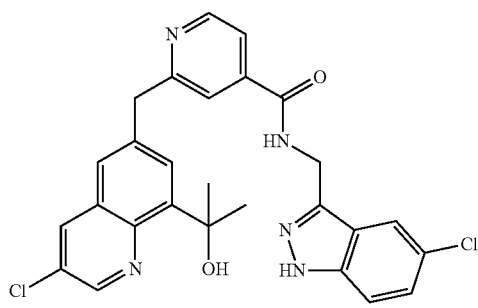 [SMILES: CC(C)(O)c1cc(Cc2cc(C(=O)NCc3n[nH]c4ccc(Cl)cc34)ccn2)cc2cc(Cl)cnc12]

To a solution of 2-[3-chloro-8-(1-hydroxy-1-methyl-ethyl)-quinolin-6-ylmethyl]-isonicotinic acid (100 mg, 0.28 mmol, 1 eq) in DMF (5 mL) was added (5-chloro-1H-indazol-3-yl)methanamine (74 mg, 0.34 mmol, 1.2 eq) followed by HOBT (57 mg, 0.42 mmol, 1.5 eq), EDCI (81 mg, 0.42 mmol, 1.5 eq) and TEA (84 mg, 0.84 mmol, 3.0 eq). The reaction mixture was heated to 35° C. and stirred overnight. Water was added, and the mixture was extracted with DCM. The organic layer was washed with water, dried over Na₂SO₄, filtered and concentrated. The resulting residue was purified by Prep-HPLC to give N-((5-chloro-1H-indazol-3-yl)methyl)-2-((3-chloro-8-(2-hydroxypropan-2-yl)quinolin-6-yl)methyl)isonicotinamide (2.4 mg, 1.6%) as a white solid.

LRMS (M+H+) m/z calculated 520.1, found 520.1. ¹H NMR (DMSO-d6, 400 MHz): δ 13.10 (s, 1H), 9.40 (t, 1H), 8.85 (d, 1H), 8.65 (d, 1H), 8.51 (d, 1H), 7.93 (d, 1H), 7.89 (d, 1H), 7.78 (s, 1H), 7.69 (d, 1H), 7.65 (dd, 1H), 7.52 (d, 1H), 7.32 (dd, 1H), 5.84 (s, 1H), 4.78 (d, 2H), 4.35 (s, 2H), 1.69 (s, 6H).

Example 226: Preparation of N-((6-amino-2,4-dimethylpyridin-3-yl)methyl)-2-((6-chloro-7-fluoroquinolin-3-yl)methyl)isonicotinamide

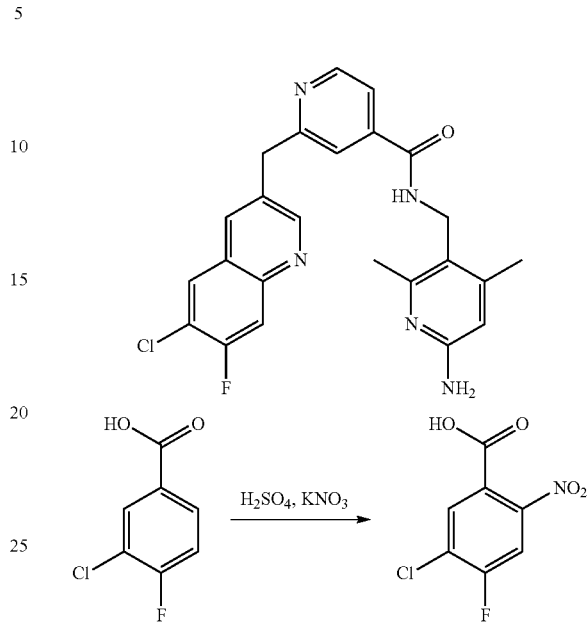

A mixture of 3-chloro-4-fluoro-benzoic acid (20.0 g, 115.6 mmol) in sulphuric acid (150 mL) was cooled to 0° C. Then 60% nitric acid (8.7 g) was added slowly at 0° C. The mixture was stirred at rt overnight and then diluted with water. The precipitated solid was filtered to give 5-chloro-4-fluoro-2-nitrobenzoic acid (20.2 g, 80.2%).

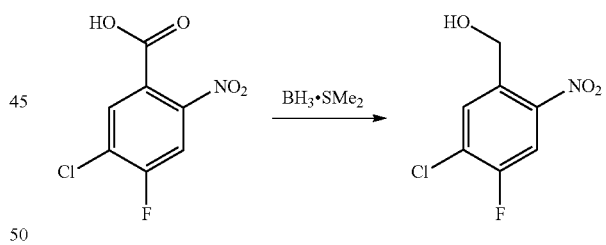

To a solution of 5-chloro-4-fluoro-2-nitro-benzoic acid (20.0 g, 91.1 mmol, 1 eq) in dry THF (300 mL) was added BH₃.DMS (27.3 mL, 10M, 273 mmol, 3 eq) dropwise at 0~–5° C. over period of 30 min. Then the mixture was heated at 70° C. for 4 h. TLC analysis showed that the start material was consumed completely. The mixture was diluted with aqueous potassium sodium tartrate and extracted with EtOAc. The combined organic layers were washed with brine, dried over Na₂SO₄, filtered and concentrated. The resulting residue was purified by chromatography on a silica gel column (PE/EA=10/1 to 5/2, v/v) to give (5-chloro-4-fluoro-2-nitro-phenyl)-methanol (16.0 g, 85.6%) as a yellow solid.

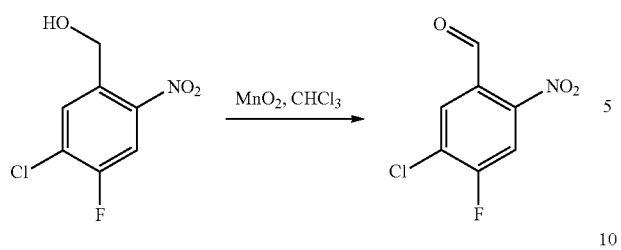

A mixture of (5-chloro-4-fluoro-2-nitro-phenyl)-methanol (16 g, 78 mmol, 1 eq) and MnO₂ (34 g, 0.39 mol, 5 eq) in CHCl₃ (320 mL) was stirred at 45° C. overnight. The mixture was filtered and the filtrate was concentrated to give 5-chloro-4-fluoro-2-nitro-benzaldehyde (9.54 g, 60%) as a yellow solid.

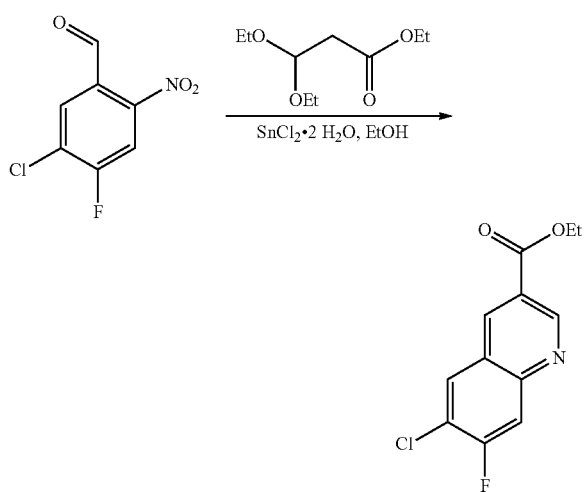

To a solution of 5-chloro-4-fluoro-2-nitro-benzaldehyde (9.5 g, 46.7 mmol, 1 eq) in ethanol (200 mL) was added tin(II) chloride dihydrate (42.2 g, 0.187 mol) and 3,3-diethoxypropionic acid ethyl ester (22.2 g, 117 mmol, 2.5 eq). The reaction was heated to reflux for 4 h. After cooling to rt, the mixture was concentrated and the resulting residue was diluted with EtOAc and washed with sat.NaHCO₃ aqueous solution. The resulting emulsion was filtered through Celite, rinsing with ethyl acetate. The organic layers were separated and the aqueous was extracted with ethyl acetate. The combined organics were washed with brine, dried over magnesium sulfate, filtered, and concentrated. The resulting residue was purified by chromatography on a silica gel column (PE/EA=100-30/1, v/v) to give 6-chloro-7-fluoro-quinoline-3-carboxylic acid ethyl ester (9.0 g, 76.3%) as a yellow solid.

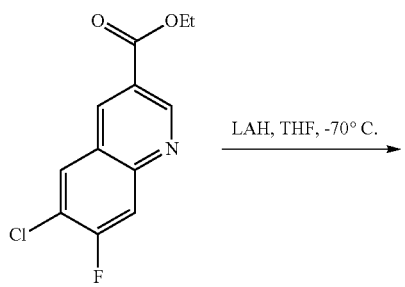

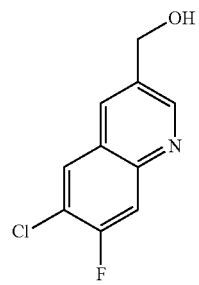

To a solution of 6-chloro-7-fluoro-quinoline-3-carboxylic acid ethyl ester (9.0 g, 35.6 mmol, 1 eq) in dry THF (180 mL) was added LAH (53.4 mL, 1M, 53.4 mmol, 1.5 eq) dropwise at −70° C. The mixture was stirred at this temperature for 1.5 h and quenched by the addition of 3 N aq. HCl solution. The mixture was extracted with EA, and the combined organic layers were dried and concentrated. The resulting residue was purified by chromatography on a silica gel column (PE/EA=5/1, v/v) to give (6-chloro-7-fluoro-quinolin-3-yl)-methanol (3.4 g, 45.3%) as a yellow solid.

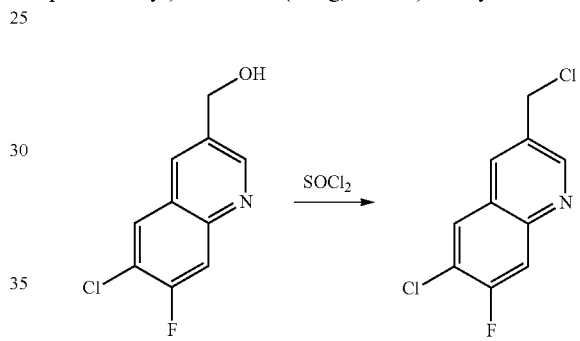

A mixture of (6-chloro-7-fluoro-quinolin-3-yl)-methanol (3.4 g, 16.1 mmol) in SOCl₂ (80 mL) was stirred at rt for 2 h and then concentrated. The resulting residue was diluted with EtOAc and washed with NaHCO₃ aqueous solution. The organic layer was concentrated to give 6-chloro-3-chloromethyl-7-fluoro-quinoline (3.6 g, 97.3%)

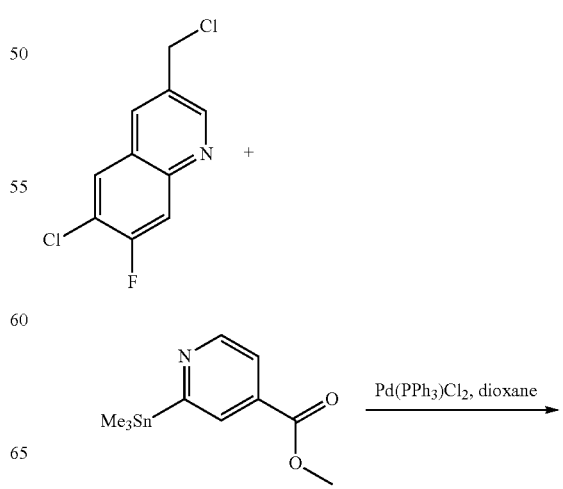

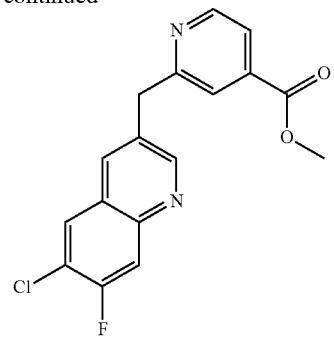

To a solution of 6-chloro-3-chloromethyl-7-fluoro-quinoline (3.6 g, 15.7 mmol, 1.0 eq) in dioxane (100 mL) was added 2-trimethylstannanyl-isonicotinic acid methyl ester (1.74 g, 17.2 mmol, 1.1 eq) and Pd(PPh₃)₂Cl₂ (1.1 g, 1.57 mmol, 0.1 eq). The mixture was stirred at 90° C. for 6 h under nitrogen atmosphere, and stripped of solvent. The resulting residue was purified by chromatography on a silica gel column (DCM/MeOH=100/1, v/v) to afford 2-(6-chloro-7-fluoro-quinolin-3-ylmethyl)-isonicotinic acid methyl ester (1.5 g, 35%) as a yellow solid.

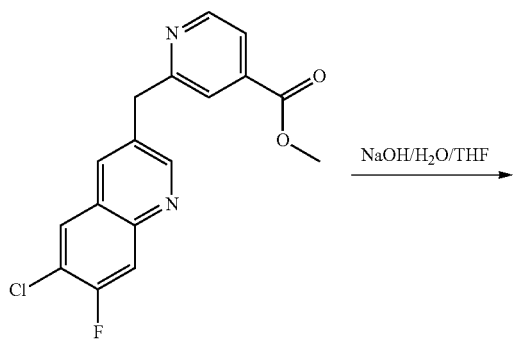

A mixture of 2-(6-chloro-7-fluoro-quinolin-3-ylmethyl)-isonicotinic acid methyl ester (2.7 g, 8.16 mmol, 1 eq) and NaOH (40.8 mmol, 2 N, 20 mL, 5 eq) in THF (80 mL) was stirred at rt for 2 h. Then THF was removed by evaporation. The aqueous layer was acidified to pH 2 with 3 N HCl solution. The precipitate was filtered to give 2-(6-chloro-7-fluoro-quinolin-3-ylmethyl)-isonicotinic acid (1.5 g, 58.1%).

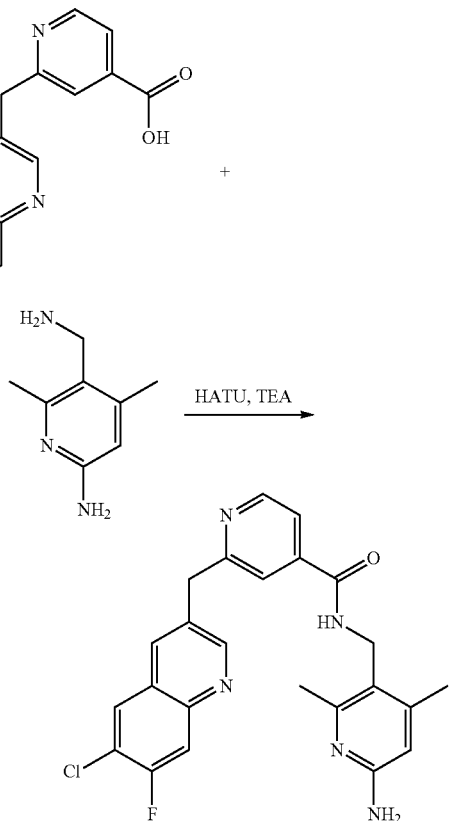

To a solution of 2-(6-chloro-7-fluoro-quinolin-3-ylmethyl)-isonicotinic acid (800 mg, 2.53 mmol, 1 eq) in DMF (16 mL) was added 5-aminomethyl-4,6-dimethyl-pyridin-2-ylamine (624 mg, 2.78 mmol, 1.1 eq) followed by HATU (1.15 g, 3.04 mmol, 1.2 eq) and TEA (1.76 mL, 12.7 mmol, 5.0 eq). The reaction mixture was stirred at rt for 4 h and concentrated. The resulting residue was purified by chromatography on a silica gel column (DCM/MeOH=20/1, v/v) to give N-((6-amino-2,4-dimethylpyridin-3-yl)methyl)-2-((6-chloro-7-fluoroquinolin-3-yl)methyl)isonicotinamide (400 mg, 35.1%) as a white solid.

LRMS (M+H+) m/z calculated 450.1, found 449.8. ¹H NMR (DMSO-d6, 400 MHz): δ 8.93 (d, 1H), 8.63 (t, 1H), 8.60 (d, 1H), 8.30 (d, 1H), 8.22 (d, 1H), 7.96 (d, 1H), 7.78 (s, 1H), 7.60 (dd, 1H), 6.13 (s, 1H), 5.71 (s, 2H), 4.37 (s, 2H), 4.35 (d, 2H), 2.31 (s, 3H), 2.17 (s, 3H).

Example 227: Preparation of N-((6-amino-2-methylpyridin-3-yl)methyl)-2-((6-chloro-7-fluoroquinolin-3-yl)methyl)isonicotinamide

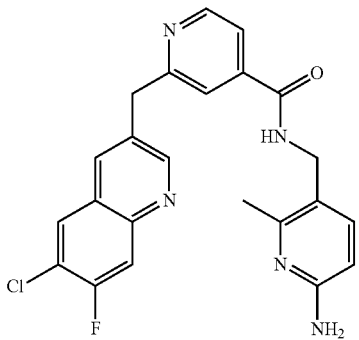

To a solution of 2-(6-chloro-7-fluoro-quinolin-3-ylmethyl)-isonicotinic acid (221 mg, 0.7 mmol, 1 eq) in DMF (8 mL) was added 5-aminomethyl-6-methyl-pyridin-2-ylamine (147 mg, 0.7 mmol, 1 eq) followed by HATU (319 mg, 0.84 mmol, 1.2 eq) and TEA (0.49 mL, 3.5 mmol, 5.0 eq). The reaction mixture was stirred at rt for 4 h and concentrated. The resulting residue was purified by chromatography on a silica gel column (DCM/MeOH=20/1, v/v) to give N-((6-amino-2,4-dimethylpyridin-3-yl)methyl)-2-((6-chloro-7-fluoroquinolin-3-yl)methyl)isonicotinamide (400 mg, 35.1%) as a white solid.

LRMS (M+H+) m/z calculated 436.1, found 435.8. $^1$H NMR (DMSO-d6, 400 MHz): δ 8.97 (t, 1H), 8.94 (d, 1H), 8.61 (d, 1H), 8.30 (d, 1H), 8.23 (d, 1H), 7.96 (d, 1H), 7.79 (s, 1H), 7.62 (dd, 1H), 7.24 (d, 1H), 6.23 (s, 1H), 5.74 (s, 2H), 4.38 (s, 2H), 4.29 (d, 2H), 2.28 (s, 3H).

Example 228: Preparation of N-((6-amino-2,4-dimethylpyridin-3-yl)methyl)-2-((3-(trifluoromethyl)quinolin-6-yl)methyl)isonicotinamide

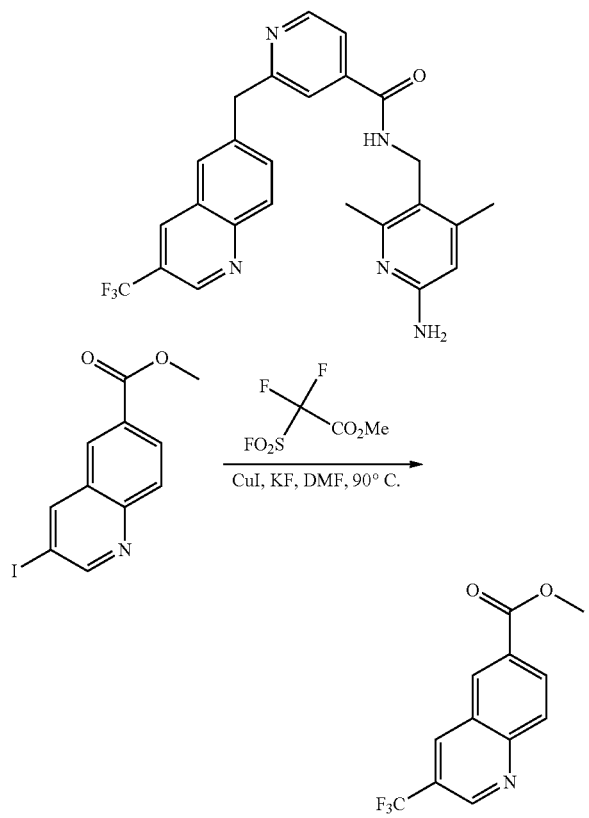

was purified by chromatography on a silica gel column (PE/EA=10/1 to 7/1, v/v) to give 3-trifluoromethyl-quinoline-6-carboxylic acid methyl ester as a pale-yellow solid (2 g, 68.9% yield). LRMS (M+H$^+$) m/z calculated 256.1, found 256.

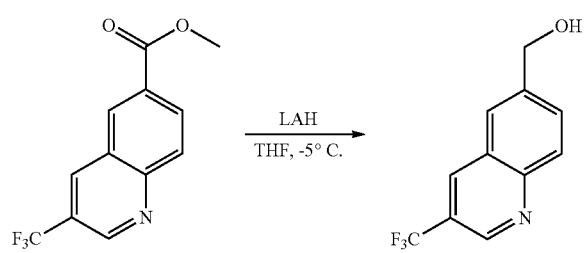 [SMILES: COC(=O)c1ccc2ncc(C(F)(F)F)cc2c1 ; "LAH" ; "THF, -5° C." ; OCc1ccc2ncc(C(F)(F)F)cc2c1]

LAH (1M in THF, 3 mL, 2.98 mmol, 1 eq) was added into a solution of 3-trifluoromethyl-quinoline-6-carboxylic acid methyl ester (760 mg, 2.98 mmol, 1 eq) in anhydrous THF (10 mL). The resulting suspension was stirred at −5° C. under nitrogen gas for 2 h. LC-MS showed that the reaction was complete. The reaction was quenched with potassium sodium tartrate (15 mL) and then extracted with DCM (10 mL×3). The combined extracts were dried over anhydrous Na$_2$SO$_4$ and concentrated in vacuo. The crude product was purified by chromatography on a silica gel column (PE/EA=7/1 to 3/1, v/v) to give (3-trifluoromethyl-quinolin-6-yl)-methanol as a yellow solid (500 mg, 73.9% yield).

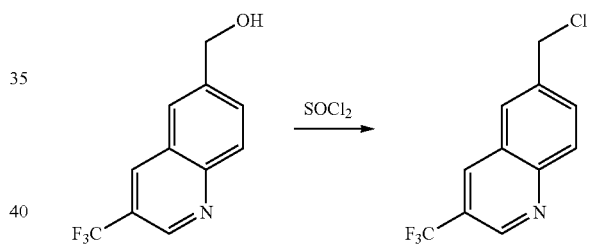

The large excess of SOCl$_2$ (200 mL) was added into a solid of (3-trifluoromethyl-quinolin-6-yl)-methanol (690 mg, 3.04 mmol). The resulting heterogeneous mixture was stirred at ambient temperature for 2 h. After 2 h, LC-MS showed that the reaction was completed. The excess of SOCl$_2$ was evaporated via rotatory evaporator. The residue was neutralized with NaHCO$_3$ until pH 7.5. The basic reaction mixture was extracted with DCM (10 mL×3). The combined extracts were dried over anhydrous Na$_2$SO$_4$ and concentrated in vacuum to provide 6-chloromethyl-3-trifluoromethyl-quinoline as a yellow oil. (710 mg, 95.1% yield).

A three-necked bottom flask was charged with 3-iodo-quinoline-6-carboxylic acid methyl ester (3.6 g, 11.5 mmol, 1 eq), difluoro-fluorosulfonyl-acetic acid methyl ester (4.4 g, 23 mmol, 2 eq) and CuI (4.4 g, 23 mmol, 2 eq) and DMF (100 mL). The resulting bright-yellow-colored heterogeneous mixture was stirred at 90° C. under N$_2$ for 2 h. LC-MS indicated that the reaction was complete. The solvent of the reaction mixture was removed under reduced pressure. The resulting residue was partitioned between DCM (20 mL×3) and water (10 mL). The combined organic extracts were washed with saturated Na$_2$S$_2$O$_3$ (10 mL), dried over anhydrous Na$_2$SO$_4$ and concentrated in vacuo. The crude product

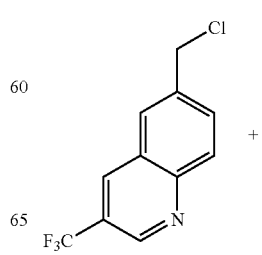

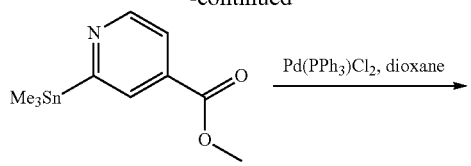

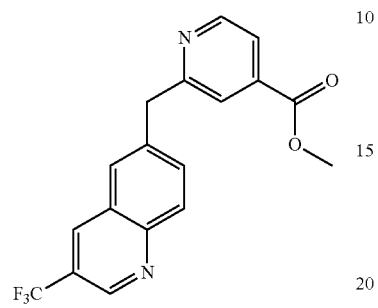

To a solution of 6-chloromethyl-3-trifluoromethyl-quinoline (960 mg, 3.90 mmol, 1.0 eq) in dioxane (30 mL) were added 2-trimethylstannanyl-isonicotinic acid methyl ester (435 mg, 4.31 mmol, 1.1 eq) and Pd(PPh$_3$)$_2$Cl$_2$ (274 mg, 0.39 mmol, 0.1 eq). The mixture was stirred at 90° C. for 3 h under nitrogen atmosphere and stripped of solvent. The resulting residue was purified by chromatography on a silica gel column (DCM/MeOH=100/1, v/v) to afford 2-(3-trifluoromethyl-quinolin-6-ylmethyl)-isonicotinic acid methyl ester (380 mg, 28%) as a yellow solid.

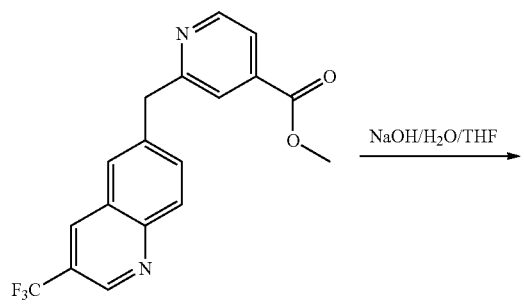

To a solution of 2-(3-trifluoromethyl-quinolin-6-ylmethyl)-isonicotinic acid methyl ester (0.4 g, 1.15 mmol, 1.0 eq) in THF (5 mL) and H$_2$O (1 mL) was added NaOH (0.138 g, 3.45 mol, 3.0 eq) and the reaction mixture was stirred at rt for 3 h. The reaction mixture was then neutralized with 1 N aq. HCl to pH 3, extracted with EA and concentrated to afford 2-(3-trifluoromethyl-quinolin-6-ylmethyl)-isonicotinic acid (0.3 g, 78.9%) as a white solid.

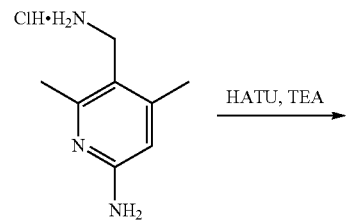

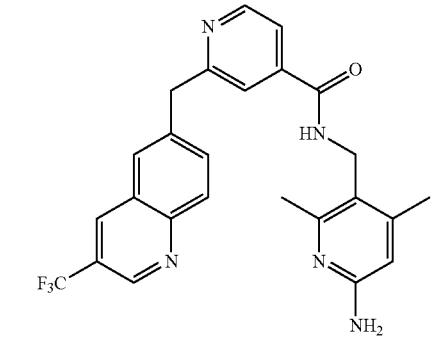

To a solution of 2-(3-trifluoromethyl-quinolin-6-ylmethyl)-isonicotinic acid (150 mg, 0.45 mmol, 1.0 eq) in DMF (10 mL) was added 5-aminomethyl-4,6-dimethyl-pyridin-2-ylamine dihydrochloride (120 mg, 0.54 mmol, 1.2 eq) followed by HATU (220 mg, 0.586 mmol, 1.3 eq) and TEA (139 mg, 1.35 mmol, 3.0 eq). The reaction mixture was heated at 35° C. overnight. Water was added, and the mixture was extracted with DCM. The organic layer was washed with water, dried over Na$_2$SO$_4$, filtered and concentrated. The resulting residue was purified by Prep-HPLC to give N-((6-amino-2,4-dimethylpyridin-3-yl)methyl)-2-((3-(trifluoromethyl)quinolin-6-yl)methyl)isonicotinamide (31 mg, 14.8%) as a white solid.

LRMS (M+H+) m/z calculated 466.2, found 465.8. $^1$H NMR (CDCl$_3$, 400 MHz): δ 9.03 (d, 1H), 8.69 (d, 1H), 8.36 (d, 1H), 8.09 (d, 1H), 7.78-7.75 (d, 2H), 7.60 (s, 1H), 7.45-7.42 (m, 1H), 6.18 (s, 1H), 6.08 (s, 1H), 4.55-4.53 (d, 2H), 4.42 (s, 2H), 4.33 (s, 2H), 2.39 (s, 3H), 2.24 (s, 3H).

Example 229: Preparation of N-((6-amino-2-methylpyridin-3-yl)methyl)-2-((3-(trifluoromethyl)quinolin-6-yl)methyl)isonicotinamide

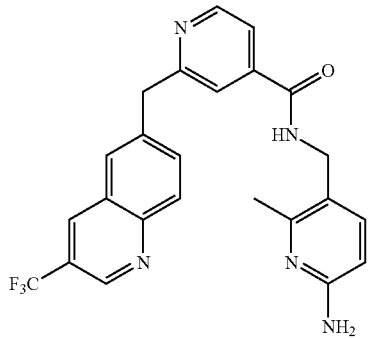 [SMILES: Cc1nc(N)ccc1CNC(=O)c1ccnc(Cc2ccc3ncc(C(F)(F)F)cc3c2)c1]

To a solution of 2-(3-trifluoromethyl-quinolin-6-ylmethyl)-isonicotinic acid (150 mg, 0.45 mmol, 1.0 eq) in DMF (10 mL) was added 5-aminomethyl-6-methyl-pyridin-2-ylamine (112 mg, 0.54 mmol, 1.2 eq) followed by HATU (220 mg, 0.586 mmol, 1.3 eq) and TEA (136 mg, 1.35 mmol, 3.0 eq). The reaction mixture was heated at 35° C. overnight. Water was added, and the mixture was extracted with DCM. The organic layer was washed with water, dried over Na$_2$SO$_4$, filtered and concentrated. The resulting residue was purified by Prep-HPLC to give N-(6-Amino-2-methyl-pyridin-3-ylmethyl)-2-(3-trifluoromethyl-quinolin-6-ylmethyl)-isonicotinamide (36 mg, 17.6%) as a white solid.

LRMS (M+H+) m/z calculated 452.2, found 451.8. $^1$H NMR (CDCl$_3$, 400 MHz): δ 9.04 (d, 1H), 8.70 (d, 1H), 8.37 (s, 1H), 8.11-8.08 (d, 1H), 7.78-7.75 (d, 2H), 7.59 (s, 1H), 7.45-7.43 (m, 1H), 7.32-7.27 (m, 1H), 6.32-6.29 (d, 2H), 4.51-4.49 (d, 2H), 4.42-4.41 (m, 4H), 2.39 (s, 3H).

Example 230: Preparation of N-((3-chloro-6-fluoro-1H-indol-5-yl)methyl)-2-((3-(trifluoromethyl)quinolin-6-yl)methyl)isonicotinamide

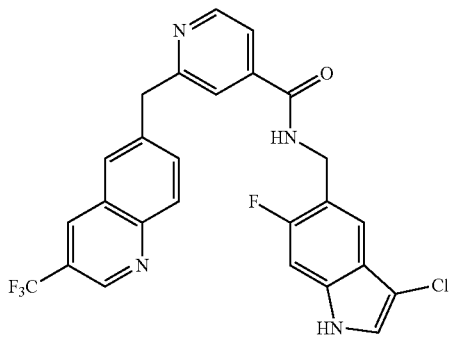 [SMILES: O=C(NCc1cc2c(Cl)c[nH]c2cc1F)c1ccnc(Cc2ccc3ncc(C(F)(F)F)cc3c2)c1]

To a solution of 2-(3-trifluoromethyl-quinolin-6-ylmethyl)-isonicotinic acid (80 mg, 0.24 mmol, 1.0 eq) in DMF (5 mL) were added (3-chloro-6-fluoro-1H-indol-5-yl)methanamine (85 mg, 0.31 mmol, 1.3 eq) followed by HOBt (42 mg, 0.31 mmol, 1.3 eq), EDCI (59.8 mg, 0.31 mmol, 1.3 eq) and TEA (73 mg, 0.72 mmol, 3.0 eq). The reaction mixture was heated to 35° C. and stirred overnight. Water was added, and the mixture was extracted with DCM. The organic layer was washed with water, dried over Na$_2$SO$_4$, filtered and concentrated. The resulting residue was purified by Prep-HPLC to give N-((3-chloro-6-fluoro-1H-indol-5-yl)methyl)-2-((3-(trifluoromethyl)quinolin-6-yl)methyl)isonicotinamide (91.3 mg, 74%) as a white solid.

LRMS (M+H+) m/z calculated 513.1 found 513.1. $^1$H NMR (DMSO-d6, 400 MHz): δ 11.38 (s, 1H), 9.25 (d, 1H), 9.13 (s, 1H), 8.88 (s, 1H), 8.66 (d, 1H), 8.10-8.06 (m, 2H), 7.92 (d, 1H), 7.81 (s, 1H), 7.67 (d, 1H), 7.50 (s, 1H), 7.45 (d, 1H), 7.22 (d, 1H), 4.59 (d, 2H), 4.42 (s, 2H).

Example 231: Preparation of N-((3-chloro-1H-pyrrolo[2,3-b]pyridin-5-yl)methyl)-2-((3-(trifluoromethyl)quinolin-6-yl)methyl)isonicotinamide

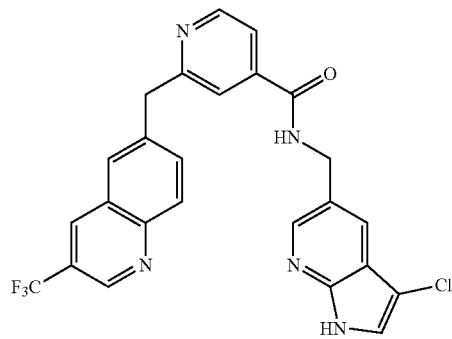 [SMILES: O=C(NCc1cnc2[nH]cc(Cl)c2c1)c1ccnc(Cc2ccc3ncc(C(F)(F)F)cc3c2)c1]

To a solution of 2-(3-trifluoromethyl-quinolin-6-ylmethyl)-isonicotinic acid (80 mg, 0.24 mmol, 1.0 eq) in DMF (5 mL) was added (3-chloro-1H-pyrrolo[2,3-b]pyridin-5-yl)methanamine (79.6 mg, 0.31 mmol, 1.3 eq) followed by HOBT (42 mg, 0.31 mmol, 1.3 eq), EDCI (59.8 mg, 0.31 mmol, 1.3 eq) and TEA (73 mg, 0.72 mmol, 3.0 eq). The reaction mixture was heated to 35° C. kept stirring for overnight. Water was added, and the mixture was extracted with DCM. The organic layer was washed with water, dried over Na$_2$SO$_4$, filtered and concentrated. The resulting residue was purified by Prep-HPLC to give N-((3-chloro-1H-pyrrolo[2,3-b]pyridin-5-yl)methyl)-2-((3-(trifluoromethyl)quinolin-6-yl)methyl)isonicotinamide (31.2 mg, 26.1%) as a white solid.

LRMS (M+H+) m/z calculated 496.1, found 496.1. $^1$H NMR (DMSO-d6, 400 MHz): δ 11.95 (s, 1H), 9.33 (d, 1H), 9.13 (s, 1H), 8.88 (s, 1H), 8.66 (d, 1H), 8.31 (s, 1H), 8.09-8.05 (m, 2H), 7.92-7.86 (m, 2H), 7.79 (s, 1H), 7.67-7.64 (m, 2H), 4.59 (d, 2H), 4.41 (s, 2H).

Example 232: Preparation of N-((1-aminoisoquinolin-6-yl)methyl)-2-((3-(trifluoromethyl)quinolin-6-yl)methyl)isonicotinamide

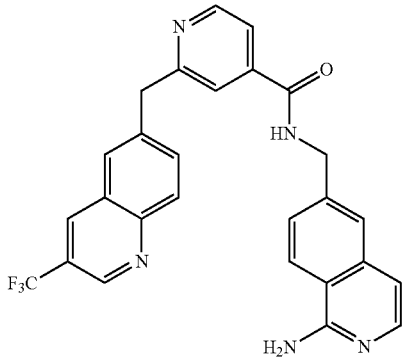 [SMILES: Nc1nccc2cc(CNC(=O)c3ccnc(Cc4ccc5ncc(C(F)(F)F)cc5c4)c3)ccc12]

To a solution of 2-(3-trifluoromethyl-quinolin-6-ylmethyl)-isonicotinic acid (80 mg, 0.24 mmol, 1.0 eq) in DMF (5 mL) was added 6-aminomethyl-isoquinolin-1-ylamine (79.6 mg, 0.31 mmol, 1.3 eq) followed by HOBt (42 mg, 0.31 mmol, 1.3 eq), EDCI (59.8 mg, 0.31 mmol, 1.3 eq) and TEA (73 mg, 0.72 mmol, 3.0 eq). The reaction mixture was heated to 35° C. and stirred overnight. Water was added, and the mixture was extracted with DCM. The organic layer was washed with water, dried over $Na_2SO_4$, filtered and concentrated. The resulting residue was purified by Prep-HPLC to give N-((1-aminoisoquinolin-6-yl)methyl)-2-((3-(trifluoromethyl)quinolin-6-yl)methyl)isonicotinamide (65.4 mg, 55.9%) as a white solid.

LRMS (M+H+) m/z calculated 488.2 found 488.2. $^1$H NMR (DMSO-d6, 400 MHz): δ 9.38 (t, 1H), 9.13 (s, 1H), 8.89 (s, 1H), 8.68 (d, 1H), 8.15-8.07 (m, 3H), 7.94 (d, 1H), 7.83 (s, 1H), 7.76 (d, 1H), 7.70 (d, 1H), 7.56 (s, 1H), 7.41 (d, 1H), 6.85 (d, 2H), 6.75 (s, 2H), 4.62 (d, 2H), 4.43 (s, 2H).

Example 233: Preparation of N-((5-chloro-1H-indazol-3-yl)methyl)-2-((3-(trifluoromethyl)quinolin-6-yl)methyl)isonicotinamide

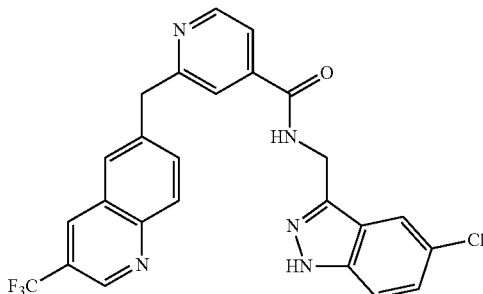

To a solution of 2-(3-trifluoromethyl-quinolin-6-ylmethyl)-isonicotinic acid (80 mg, 0.24 mmol, 1.0 eq) in DMF (5 mL) was added (5-chloro-1H-indazol-3-yl)methanamine (79.6 mg, 0.31 mmol, 1.3 eq) followed by HOBT (42 mg, 0.31 mmol, 1.3 eq), EDCI (59.8 mg, 0.31 mmol, 1.3 eq) and TEA (73 mg, 0.72 mmol, 3.0 eq). The reaction mixture was heated to 35° C. and stirred overnight. Water was added, and the mixture was extracted with DCM. The organic layer was washed with water, dried over $Na_2SO_4$, filtered and concentrated. The resulting residue was purified by Prep-HPLC to give N-(5-Chloro-1H-indazol-3-ylmethyl)-2-(3-trifluoromethyl-quinolin-6-ylmethyl)-isonicotinamide (52.7 mg, 44.2%) as a white solid.

LRMS (M+H+) m/z calculated 496.1 found 496.1. $^1$H NMR (DMSO-d6, 400 MHz): δ 9.37 (m, 1H), 9.13 (s, 1H), 8.87 (s, 1H), 8.64 (d, 1H), 8.09-8.05 (m, 2H), 7.91-7.88 (m, 2H), 7.79 (s, 1H), 7.65 (d, 1H), 7.53 (d, 1H), 7.34 (d, 1H), 4.78 (d, 2H), 4.40 (s, 2H).

Example 234: Preparation of N-((3-chloro-4-fluoro-1H-indol-5-yl)methyl)-2-((3-(trifluoromethyl)quinolin-6-yl)methyl)isonicotinamide

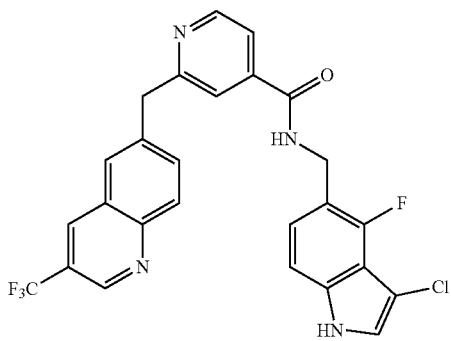 [SMILES: O=C(NCc1ccc2[nH]cc(Cl)c2c1F)c1ccnc(Cc2ccc3ncc(C(F)(F)F)cc3c2)c1]

To a solution of 2-(3-trifluoromethyl-quinolin-6-ylmethyl)-isonicotinic acid (80 mg, 0.24 mmol, 1.0 eq) in DMF (5 mL) was added (3-chloro-4-fluoro-1H-indol-5-yl)methanamine (85 mg, 0.31 mmol, 1.3 eq) followed by HOBT (42 mg, 0.31 mmol, 1.3 eq), EDCI (59.8 mg, 0.31 mmol, 1.3 eq) and TEA (73 mg, 0.72 mmol, 3.0 eq). The reaction mixture was heated to 35° C. and stirred overnight. Water was added, and the mixture was extracted with DCM. The organic layer was washed with water, dried over $Na_2SO_4$, filtered and concentrated. The resulting residue was purified by Prep-HPLC to give N-((3-chloro-4-fluoro-1H-indol-5-yl)methyl)-2-((3-(trifluoromethyl)quinolin-6-yl)methyl)isonicotinamide (70 mg, 56.5%) as a white solid.

LRMS (M+H+) m/z calculated 513.1 found 513.1. $^1$H NMR (DMSO-d6, 400 MHz): δ 11.56 (s, 1H), 9.20 (m, 1H), 9.10 (s, 1H), 8.86 (s, 1H), 8.62 (d, 1H), 8.08-8.03 (m, 2H), 7.89 (d, 1H), 7.71 (s, 1H), 7.63 (d, 1H), 7.49 (d, 1H), 7.17-7.11 (m, 2H), 4.55 (d, 2H), 4.38 (s, 2H).

Example 235: Preparation of N-((6-amino-2,4-dimethylpyridin-3-yl)methyl)-2-((3-chloro-8-sulfamoylquinolin-6-yl)methyl)isonicotinamide

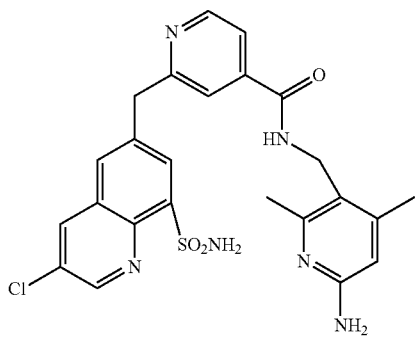

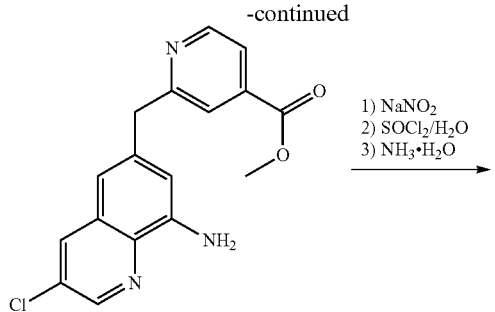

1) NaNO₂
2) SOCl₂/H₂O
3) NH₃·H₂O

To a solution of 2-(8-amino-3-chloro-quinolin-6-ylmethyl)-isonicotinic acid methyl ester (180 mg, 0.549 mmol, 1.0 eq) in conc.HCl (5 mL) was added a solution of NaNO₂ (37.89 mg, 0.549 mmol, 1.0 eq) in H₂O (1 mL) at 0° C. The reaction mixture was stirred at 0° C. for 2 h. To H₂O (4 mL) in another flask was added dropwise SOCl₂ (327 mg, 2.746 mmol, 5.0 eq) at 0° C. The mixture was stirred at 0° C. for 10 min. After that, CuCl (5.435 mg, 0.055 mmol, 0.1 eq) and the first step's solution were added at 0° C. The mixture was stirred at 0° C. for 2 h and then concentrated. The resulting residue was dissolved in dioxane (15 mL). To this solution was added NH₃·H₂O (1 mL) at 0° C. The mixture was stirred at rt for 2 h and concentrated. The resulting residue was purified by chromatography on a silica gel column (PE/EA=1/1, v/v) to give 2-(3-chloro-8-sulfamoyl-quinolin-6-ylmethyl)-isonicotinic acid methyl ester (60 mg, 28%) as a yellow solid.

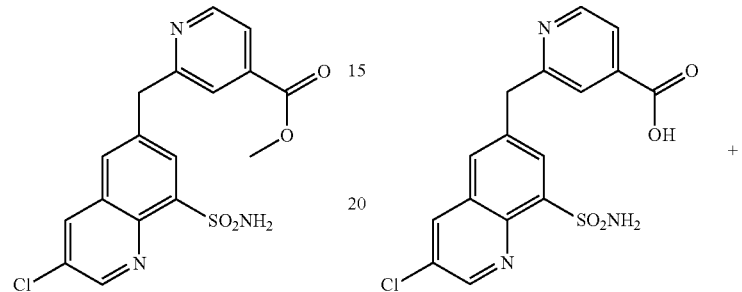

NaOH/THF/H₂O

To a solution of 2-(3-chloro-8-sulfamoyl-quinolin-6-ylmethyl)-isonicotinic acid methyl ester (60 mg, 0.15 mmol, 1.0 eq) in THF (10 mL) and water (5 mL) was added NaOH (12 mg, 0.31 mmol, 2.0 eq). The mixture was stirred at rt for 1 h. The reaction solution was neutralized with 2 N aq. HCl to pH 3 and then concentrated to give 2-((3-chloro-8-sulfamoylquinolin-6-yl)methyl)isonicotinic acid (47 mg, 81%).

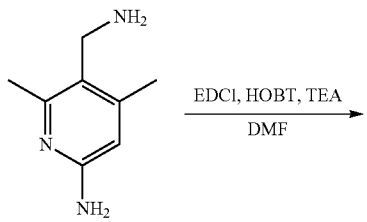

EDCl, HOBT, TEA
DMF

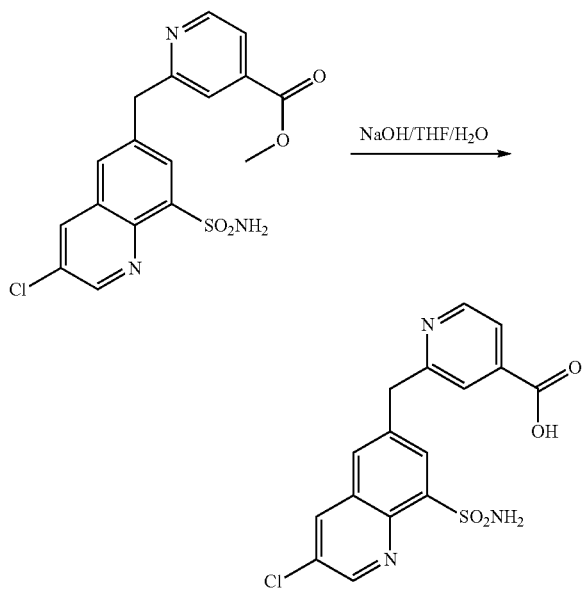

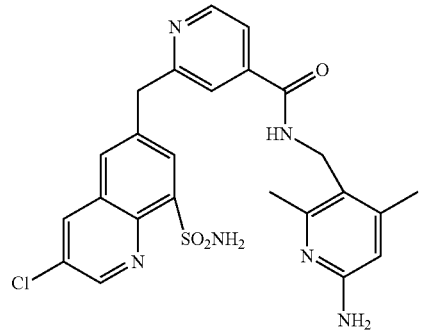

A mixture of 2-(3-chloro-8-sulfamoyl-quinolin-6-ylmethyl)-isonicotinic acid (80 mg, 0.21 mmol, 1.0 eq), 5-aminomethyl-4,6-dimethyl-pyridin-2-ylamine (38 mg, 0.25 mmol, 1.2 eq), HOBT (43 mg, 0.32 mmol, 1.5 eq), EDCI (61 mg, 0.32 mmol, 1.5 eq), and TEA (64 mg, 0.63 mmol, 3.0 eq) in DMF (10 mL) was stirred at rt overnight. The mixture was concentrated and the resulting residue was purified by Prep-HPLC to get N-((6-amino-2,4-dimethylpyridin-3-yl)methyl)-2-((3-chloro-8-sulfamoylquinolin-6-yl)methyl)isonicotinamide (15 mg, 14%) as a white solid.

LRMS (M+H⁺) m/z calculated 511.1, found 510.7. $^1$H NMR (DMSO-d₆, 400 MHz): δ 8.96 (d, 1H), 8.71 (d, 1H), 8.59-8.61 (m, 2H), 8.245 (d, 1H), 8.12 (s, 1H), 7.81 (s, 2H), 7.62 (d, 1H), 7.25 (s, 1H), 6.12 (s, 1H), 5.65 (s, 2H), 4.42 (s, 2H), 4.34 (d, 2H), 2.29 (s, 3H), 2.16 (s, 3H).

Example 236: Preparation of N-(1-(6-amino-2-methylpyridin-3-yl)ethyl)-2-((3-chloroquinolin-6-yl)methyl)isonicotinamide

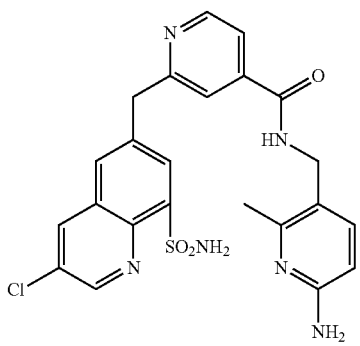

A mixture of 2-(3-chloro-8-sulfamoyl-quinolin-6-ylmethyl)-isonicotinic acid (80 mg, 0.21 mmol, 1.0 eq), 5-aminomethyl-6-methyl-pyridin-2-ylamine (34 mg, 0.25 mmol, 1.2 eq), HOBT (43 mg, 0.32 mmol, 1.5 eq), EDCI (61 mg, 0.32 mmol, 1.5 eq), and TEA (64 mg, 0.63 mmol, 3.0 eq) in DMF (10 mL) was stirred at rt overnight. The mixture was concentrated and the resulting residue was purified by Prep-HPLC to get N-(1-(6-amino-2-methylpyridin-3-yl)ethyl)-2-((3-chloroquinolin-6-yl)methyl)isonicotinamide (21 mg, 20%) as a white solid.

LRMS (M+H$^+$) m/z calculated 497.1, found 496.7. $^1$H NMR (DMSO-d$_6$, 400 MHz): δ 8.97 (d, 1H), 8.71 (d, 1H), 8.62 (d, 1H), 8.24 (d, 1H), 8.12 (s, 1H), 7.83 (s, 2H), 7.62 (d, 1H), 7.25 (s, 2H), 6.23 (d, 1H), 5.72 (s, 2H), 4.44 (s, 2H), 4.29 (d, 2H), 2.28 (s, 3H)

Example 237: Preparation of N-(1-(6-amino-2-methylpyridin-3-yl)ethyl)-2-((3-chloroquinolin-6-yl)methyl)isonicotinamide

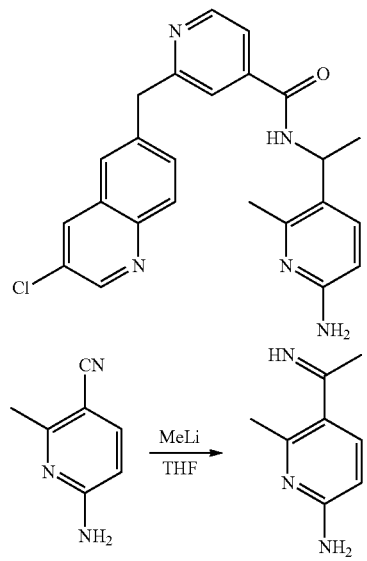

To a solution of 6-amino-2-methyl-nicotinonitrile (2 g, 15 mmol, 1 eq) in 30 mL of anhydrous tetrahydrofuran at 0° C. was added dropwise a solution of 1.94 mL of methyl lithium (18 mL, 1.6M in hexane, 30 mmol) under argon. The reaction mixture was stirred at 0° C. for 30 mins, then heated to 40° C. for 2 h. Methanol was added at 0° C. and the solvent was concentrated to get 5-(1-imino-ethyl)-6-methyl-pyridin-2-ylamine (2 g, crude), which was directly used in the next step without further purification.

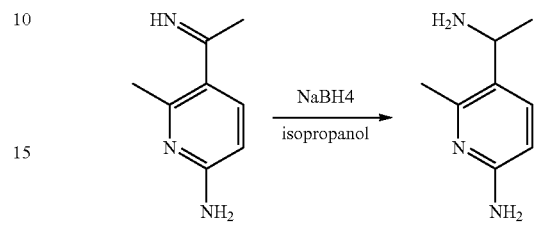

To a solution of 5-(1-imino-ethyl)-6-methyl-pyridin-2-ylamine (2 g, crude) in isopropanol (50 mL) was added NaBH$_4$ (1.5 g) at 0° C., then the mixture was stirred at rt for 12 h. Water was added and the mixture was stirred for 30 min, and the reaction was extracted with diethyl ether. The organic layer was dried over anhydrous Na$_2$SO$_4$, filtered and concentrated in vacuo to get 5-(1-aminoethyl)-6-methylpyridin-2-amine (2 g, crude) as a yellow solid.

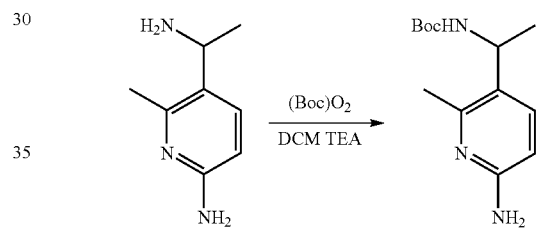

To a solution of 5-(1-aminoethyl)-6-methylpyridin-2-amine (2 g, crude) in DCM (30 mL) were added (Boc)$_2$O (4.3 g) and TEA (2 mL). The reaction mixture was stirred at rt overnight. The mixture was concentrated and the resulting residue was purified by chromatography on a silica gel column (PE/EA=1/1, v/v) to get tert-butyl (1-(6-amino-2-methylpyridin-3-yl)ethyl)carbamate (620 mg) as a yellow solid.

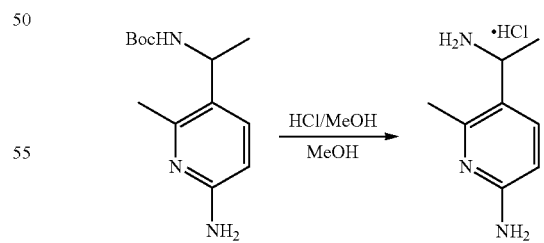

To a solution of [1-(6-amino-2-methyl-pyridin-3-yl)-ethyl]-carbamic acid tert-butyl ester (620 mg, 2.5 mmol, 1.0 eq) in anhydrous MeOH (10 mL) was added 20 mL of 2 N HCl in MeOH at 0° C. under N$_2$. The mixture is brought back to rt and stirred for 2 h. The reaction mixture was evaporated to dryness to provide 5-(1-aminoethyl)-6-methylpyridin-2-amine hydrochloride (430 mg, 92%).

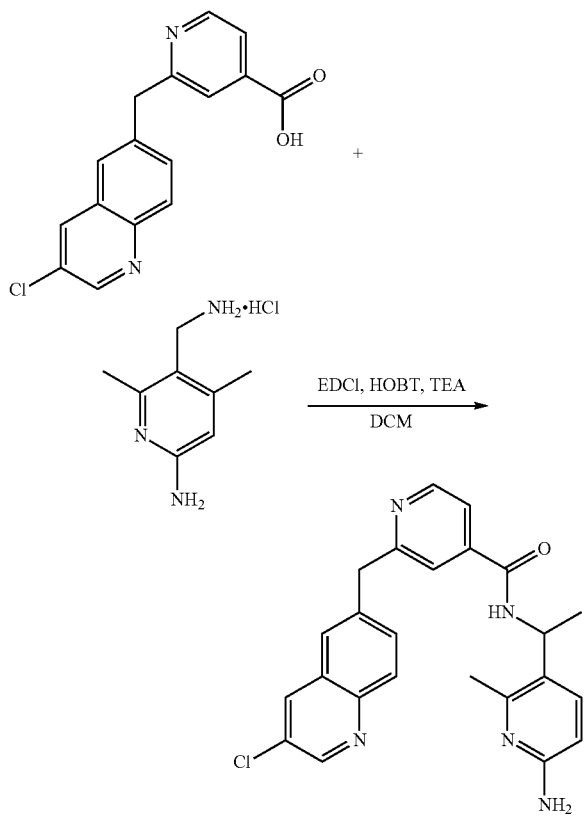

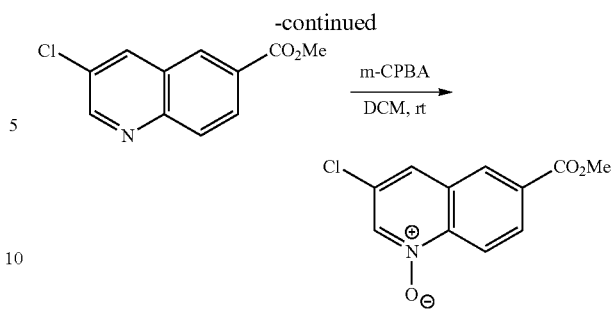

To a round-bottomed flask were added 3-chloro-quinoline-6-carboxylic acid methyl ester (5 g, 22.5 mmol, 1.0 eq), m-CPBA (12 g, 67.5 mmol, 3 eq) and DCM (80 mL). The resulting brown-colored suspensions were stirred at ambient temperature overnight. LC-MS indicated that the reaction was complete. Saturated $Na_2S_2O_3$ (100 mL) was added and the mixture was extracted with DCM (100 mL×3). The combined organic layers were dried over anhydrous $Na_2SO_4$ and concentrated in vacuum. The resulting residue was purified by chromatography on a silica gel column (PE/EA=5/1 to 1/1, v/v) to provide 3-chloro-1-oxy-quinoline-6-carboxylic acid methyl ester as a brown solid (4.2 g, 78.5% yield). LRMS (M+H$^+$) m/z calculated 237.6, found 238.

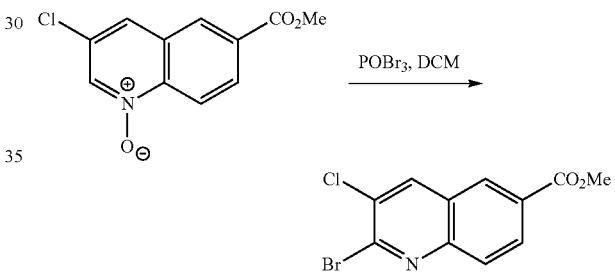

A mixture of 2-(3-chloro-quinolin-6-ylmethyl)-isonicotinic acid (100 mg, 0.34 mmol, 1.0 eq), 5-(1-amino-ethyl)-6-methyl-pyridin-2-ylamine hydrochloride (38 mg, 0.41 mmol, 1.2 eq), HOBT (69 mg, 0.51 mmol, 1.5 eq), EDCI (97 mg, 0.51 mmol, 1.5 eq), and TEA (103 mg, 1.02 mmol, 3.0 eq) in DMF (10 mL) was stirred at rt overnight. The mixture was concentrated and the resulting residue was purified by Prep-HPLC to get N-(1-(6-amino-2-methylpyridin-3-yl)ethyl)-2-((3-chloroquinolin-6-yl)methyl)isonicotinamide (35 mg, 24%) as a white solid. LRMS (M+H$^+$) m/z calculated 432.2, found 431.8. $^1$H NMR (DMSO-d$_6$, 400 MHz): δ 8.87 (d, 1H), 8.82 (d, 1H), 8.62 (d, 1H), 8.51 (d, 1H), 7.98 (d, 1H), 7.84 (s, 1H), 7.71-7.74 (m, 2H), 7.61-7.63 (m, 1H), 7.40 (d, 1H), 6.27 (d, 1H), 5.10 (s, 2H), 5.15 (m, 1H), 4.35 (s, 2H), 2.30 (s, 3H).

POBr$_3$ (7.24 g, 25.2 mmol, 2 eq) was added into a solution of 3-chloro-1-oxy-quinoline-6-carboxylic acid methyl ester (3 g, 12.6 mmol, 1 eq) in DCM (50 mL). The resulting suspensions were stirred at ambient temperature overnight. LC-MS indicated that the reaction was complete. The excess of POBr$_3$ was hydrolyzed by the addition of crashed ice. The acidic mixture was neutralized with saturated aq. NaHCO$_3$ until pH 7. The neutralized mixture was extracted with DCM (30 mL×3). The combined organic layers were dried over anhydrous Na$_2$SO$_4$ and concentrated under reduced pressure. The resulting residue was purified by chromatography on a silica gel column (PE/EA=15/1 to 5/1, v/v) to afford 2-bromo-3-chloro-quinoline-6-carboxylic acid methyl ester (2.5 g, 86% yield) as a brownish-yellow solid.

Example 238: Preparation of N-((6-amino-2,4-dimethylpyridin-3-yl)methyl)-2-((3-chloro-2-methylquinolin-6-yl)methyl)isonicotinamide

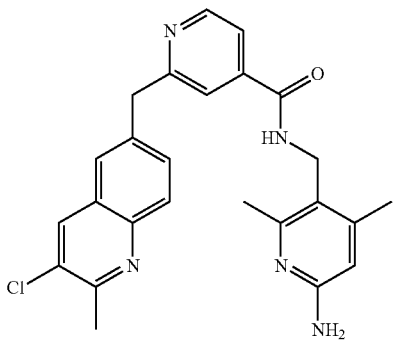

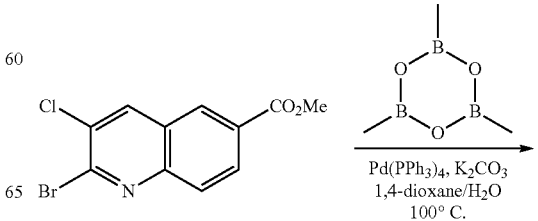

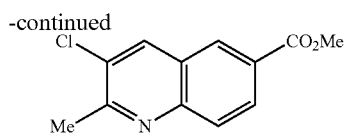

To a three-necked bottom flask was charged with 2-bromo-3-chloro-quinoline-6-carboxylic acid methyl ester (2.7 g, 8.9 mmol, 1 eq), 2,4,6-trimethyl-cyclotriboroxane (10 g, 80 mmol, 9 eq), Pd(PPh$_3$)$_4$ (1.03 g, 0.89 mmol, 0.1 eq), K$_2$CO$_3$ (3.68 g, 26.7 mmol, 3 eq), 1,4-dioxane (100 mL) and H$_2$O (20 mL). The resulting pale-yellow suspensions were stirred at 100° C. under nitrogen overnight. LC-MS indicated that the reaction was complete. The solvent of the reaction mixture was removed under reduced pressure. The resulting residue was partitioned between DCM (15 mL×3) and H$_2$O (10 mL). The combined organic phases were dried over anhydrous Na$_2$SO$_4$ and concentrated in vacuo. The resulting residue was purified by chromatography on a silica gel column (PE/EA=8/1 to 6/1, v/v) to afford 3-chloro-2-methyl-quinoline-6-carboxylic acid methyl ester (1 g, 47.8%) as a white solid.

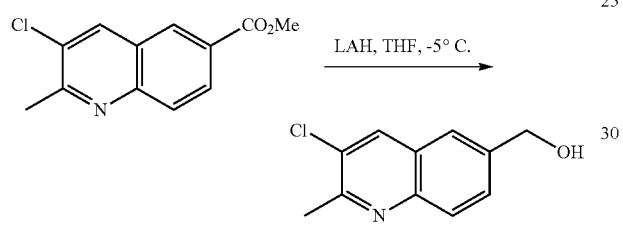

LAH (1M in THF, 1.9 mL, 1.89 mmol, 1.5 eq) was added into a solution of 3-chloro-2-methyl-quinoline-6-carboxylic acid methyl ester (300 mg, 1.26 mmol, 1.0 eq) in anhydrous THF (10 mL). The resulting mixture was stirred at −5° C. under nitrogen gas for 3 h. LC-MS indicated that the reaction was complete. The reaction was quenched by the addition of potassium sodium tartrate aqueous solution (15 mL) and extracted with DCM (5 mL×3). The combined layers were dried over anhydrous Na$_2$SO$_4$ and concentrated in vacuo. The resulting residue was purified by chromatography on a silica gel column (PE/EA=6/1 to 3/1, v/v) to give (3-chloro-2-methyl-quinolin-6-yl)-methanol as a yellow solid (209 mg, 79.8%).

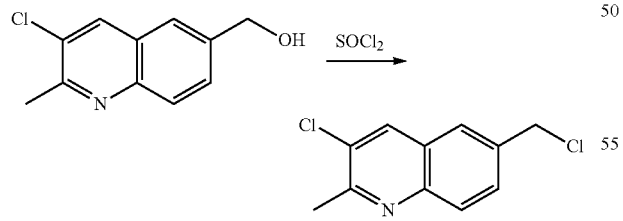

A large excess of SOCl$_2$ (30 mL) was added into a solid of (3-chloro-2-methyl-quinolin-6-yl)-methanol (250 mg, 1.2 mmol, 1 eq). The resulting homogeneous mixture was stirred at ambient temperature for 2.5 h. LC-MS demonstrated that the reaction was complete. The excess of SOCl$_2$ was removed via rotatory evaporator. The resulting residue was neutralized with aq. NaHCO$_3$ until pH 7.5 and then extracted with DCM (10 mL×3). The combined extracts were dried over anhydrous Na$_2$SO$_4$ and concentrated under reduced pressure to provide 3-chloro-6-chloromethyl-2-methyl-quinoline as a pale-yellow solid. (270 mg, 99.6%).

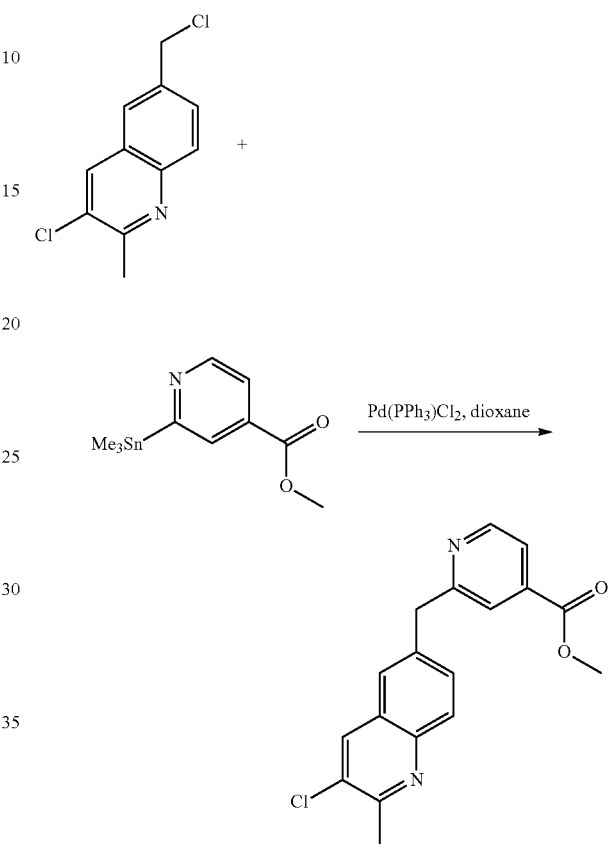

To a solution of 3-chloro-6-chloromethyl-2-methyl-quinoline (400 mg, 1.78 mmol, 1.0 eq) in dioxane (30 mL) were added 2-trimethylstannanyl-isonicotinic acid methyl ester (591 mg, 1.96 mmol, 1.1 eq) and Pd(PPh$_3$)$_2$Cl$_2$ (126 mg, 0.18 mmol, 0.1 eq). The mixture was stirred at 90° C. for 3 h under nitrogen atmosphere, and stripped of solvent. The resulting residue was purified by chromatography on a silica gel column (DCM/MeOH=100/1, v/v) to afford 2-(3-chloro-2-methyl-quinolin-6-ylmethyl)-isonicotinic acid methyl ester (380 mg, 29%) as a yellow solid.

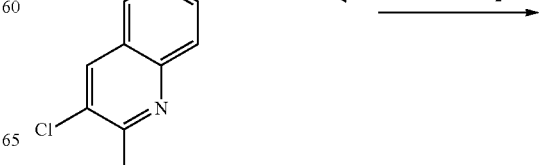

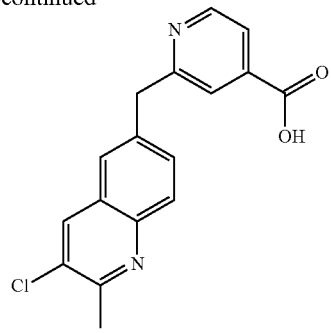

To a solution of 2-(3-chloro-2-methyl-quinolin-6-ylmethyl)-isonicotinic acid methyl ester (0.14 g, 0.4 mmol, 1.0 eq) in THF (5 mL) and H₂O (1 mL) was added NaOH (0.034 g, 0.8 mol, 2.0 eq) and the reaction mixture was stirred at rt for 3 h. 1N HCl was added to this mixture until pH<7, and then extracted with EA. The organic layer was concentrated in vacuum to afford 2-(3-chloro-2-methyl-quinolin-6-ylmethyl)-isonicotinic acid (0.12 g, 92.3%) as a white solid.

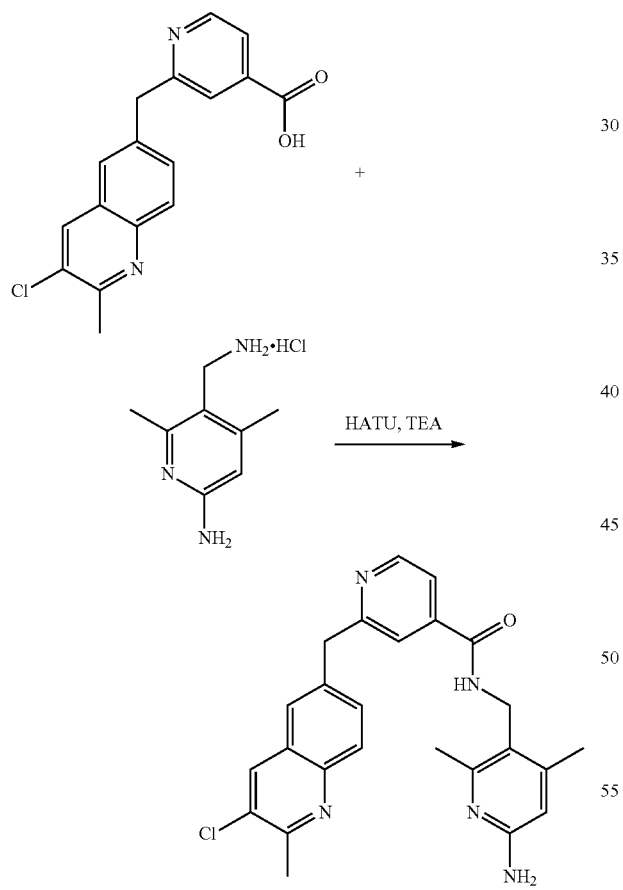

To a solution of 2-(3-chloro-2-methyl-quinolin-6-ylmethyl)-isonicotinic acid (60 mg, 0.45 mmol, 1.0 eq) in DMF (10 mL) was added 5-aminomethyl-4,6-dimethyl-pyridin-2-ylamine dihydrochloride (51 mg, 0.23 mmol, 1.2 eq) followed by HATU (95 mg, 0.25 mmol, 1.3 eq) and TEA (58 mg, 0.58 mmol, 3.0 eq). The reaction mixture was heated to 35° C. kept stirring for overnight. Water was added, and the mixture was extracted with DCM. The organic layer was washed with water, dried over Na₂SO₄, filtered and concentrated. The resulting residue was purified by Prep-HPLC to give N-(6-Amino-2,4-dimethyl-pyridin-3-ylmethyl)-2-(3-chloro-2-methyl-quinolin-6-ylmethyl)-isonicotinamide (23 mg, 27%) as a white solid.

LRMS (M+H+) m/z calculated 446.2, found 445.8. ¹H NMR (CDCl₃, 400 MHz): δ 9.03 (d, 1H), 8.69 (d, 1H), 8.36 (d, 1H), 8.09 (d, 1H), 7.78-7.75 (d, 2H), 7.60 (s, 1H), 7.45-7.42 (m, 1H), 6.18 (s, 1H), 6.08 (s, 1H), 4.55-4.53 (d, 2H), 4.42 (s, 2H), 4.33 (s, 2H), 2.39 (s, 3H), 2.24 (s, 3H).

Example 239: Preparation of N-((6-amino-2-methylpyridin-3-yl)methyl)-2-((3-chloro-2-methylquinolin-6-yl)methyl)isonicotinamide

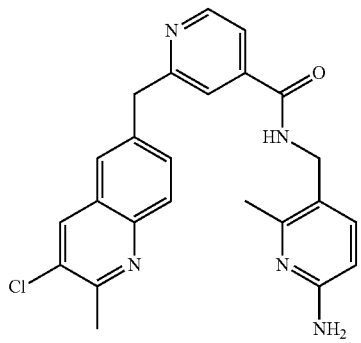

To a solution of 2-(3-chloro-2-methyl-quinolin-6-ylmethyl)-isonicotinic acid (60 mg, 0.45 mmol, 1.0 eq) in DMF (10 mL) was added 5-aminomethyl-6-methyl-pyridin-2-ylamine (51 mg, 0.23 mmol, 1.2 eq) followed by HATU (95 mg, 0.25 mmol, 1.3 eq) and TEA (58 mg, 0.58 mmol, 3.0 eq). The reaction mixture was heated at 35° C. and stirred overnight. Water was added, and the mixture was extracted with DCM. The organic layer was dried over Na₂SO₄, filtered and concentrated. The resulting residue was purified by Prep-HPLC to give N-((6-amino-2-methylpyridin-3-yl)methyl)-2-((3-chloro-2-methylquinolin-6-yl)methyl)isonicotinamide (31 mg, 37%) as a white solid.

LRMS (M+H+) m/z calculated 432.2, found 431.8. ¹H NMR (CDCl₃, 400 MHz): δ 8.68 (d, 1H), 8.00 (s, 1H), 7.89 (d, 1H), 7.56-7.54 (m, 3H), 7.45 (d, 1H), 7.29-7.27 (m, 1H), 6.29-6.27 (m, 2H), 4.48-4.46 (d, 2H), 4.39 (s, 2H), 4.35 (s, 2H), 2.76 (s, 3H), 2.36 (s, 3H).

Example 240: Preparation of N-((6-amino-2,4-dimethylpyridin-3-yl)methyl)-2-(3-(5-oxo-4,5-dihydro-1,2,4-oxadiazol-3-yl)benzyl)isonicotinamide

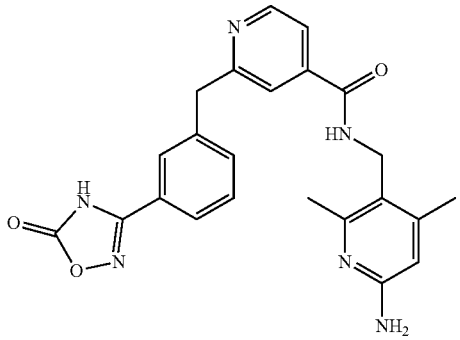

601

-continued

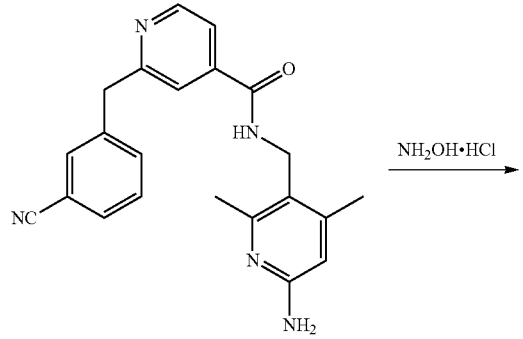

To a solution of N-(6-amino-2,4-dimethyl-pyridin-3-ylmethyl)-2-(3-cyano-benzyl)-isonicotinamide (50 mg, 0.135 mmol, 1.0 eq) in EtOH (10 mL) was added NaHCO$_3$ (0.034 g, 0.4 mmol, 3 eq). Then NH$_2$OH.HCl (0.056 g, 0.8 mmol, 6 eq) in water (5 mL) was added, and the mixture was heated at 100° C. for 2 h. Most of the ethanol was removed in vacuo and the resulting residue was dissolved with DCM and washed with water. The organic phase was separated, dried and concentrated to give N-(6-amino-2,4-dimethyl-pyridin-3-ylmethyl)-2-[3-(N-hydroxycarbamimidoyl)-benzyl]-isonicotinamide (500 mg, 99%) as a yellow solid.

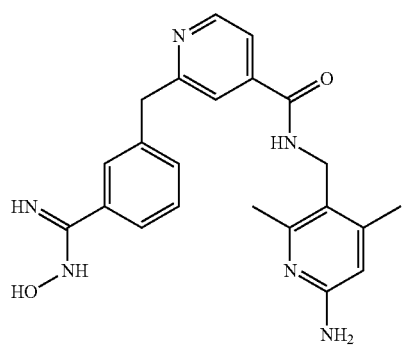

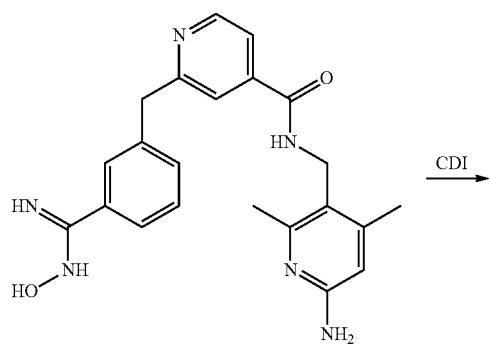

602

-continued

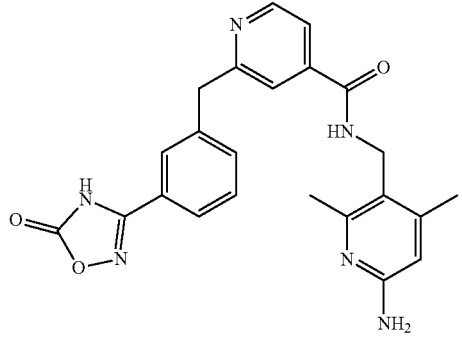

To a solution of N-(6-amino-2,4-dimethyl-pyridin-3-ylmethyl)-2-[3-(N-hydroxycarbamimidoyl)-benzyl]-isonicotinamide (100 mg, 0.25 mmol, 1 eq) in THF (10 mL) was added CDI (52 mg, 0.32 mmol, 1.3 eq). The reaction mixture was stirred at rt for 1 h, then heated to 80° C. for 3 h. After cooling to rt, the mixture was concentrated, and the resulting residue was purified by Prep-HPLC give N-((6-amino-2,4-dimethylpyridin-3-yl)methyl)-2-(3-(5-oxo-4,5-dihydro-1,2,4-oxadiazol-3-yl)benzyl)isonicotinamide (42 mg, 39.6%) as a white solid. LRMS (M+H+) m/z calculated 430 found 430. $^1$H NMR (DMSO-d6, 400 MHz): δ 8.66 (m, 1H), 8.60 (d, 1H), 7.71 (d, 2H), 7.64-7.58 (m, 2H), 7.49-7.46 (m, 2H), 6.19 (s, 1H), 5.93 (s, 2H), 4.35 (d, 2H), 4.20 (s, 2H), 2.33 (s, 3H), 2.19 (s, 3H).

Example 241: Preparation of N-((6-amino-2,4-dimethylpyridin-3-yl)methyl)-2-((8-(aminomethyl)-3-chloroquinolin-6-yl)methyl)isonicotinamide

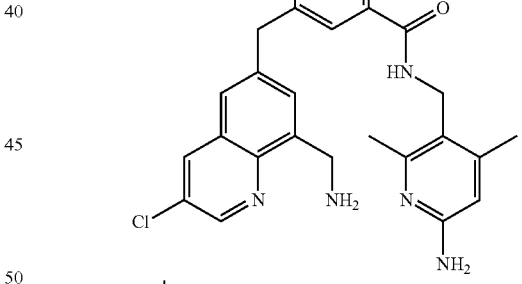

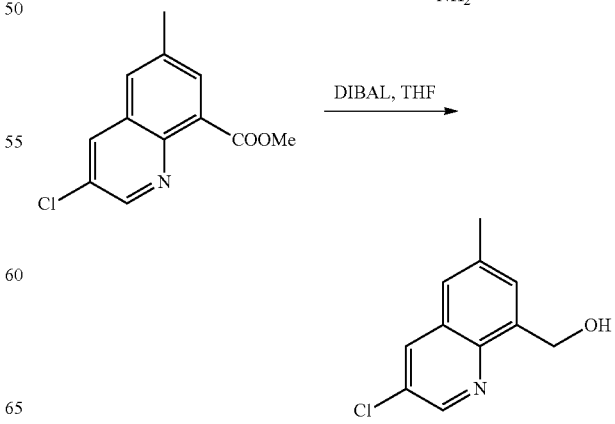

To a solution of 3-chloro-6-methyl-quinoline-8-carboxylic acid methyl ester (6.0 g, 25.5 mmol, 1 eq) in dry THF (250 mL) was added DIBAL-H (56.0 mL, 56.0 mmol, 1M in toluene, 2.2 eq) dropwise at −78° C. The mixture was stirred at the same temperature for 30 min. Then the mixture was quenched by the addition of water. The mixture was extracted with EA. The combined organic layers were washed with brine, dried over MgSO$_4$, filtered and concentrated. The resulting residue was purified by chromatography on a silica gel column (EA/PE=1/5, v/v) to give (3-chloro-6-methyl-quinolin-8-yl)-methanol (5.1 g, 96%) as a white solid. $^1$H NMR (DMSO-d6, 400 MHz) δ 8.79 (d, 1H), 8.44 (d, 1H), 7.70 (s, 1H), 7.61 (s, 1H), 5.11 (s, 2H), 5.21 (br, 1H), 2.50 (s, 3H).

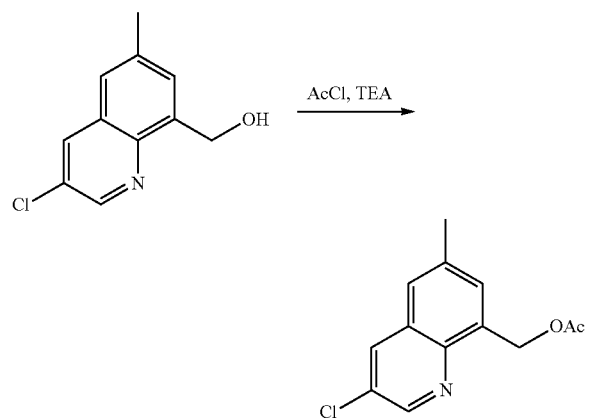

To a solution of (3-chloro-6-methyl-quinolin-8-yl)-methanol (3.2 g, 15.5 mmol, 1 eq) in dry DCM (50 mL) were added TEA (2.0 g, 20.2 mmol, 1.3 eq) and AcCl (1.45 g, 18.6 mmol, 1.2 eq) at 0° C. The mixture was stirred at rt for 30 min. Then the mixture was quenched by the addition of water. The mixture was extracted with DCM. The combined organic layers were washed with brine, dried over MgSO$_4$, filtered and concentrated. The resulting residue was purified by chromatography on a silica gel column (EA/PE=1/5, v/v) to give acetic acid 3-chloro-6-methyl-quinolin-8-ylmethyl ester (3.1 g, 82%) as an off-white solid.

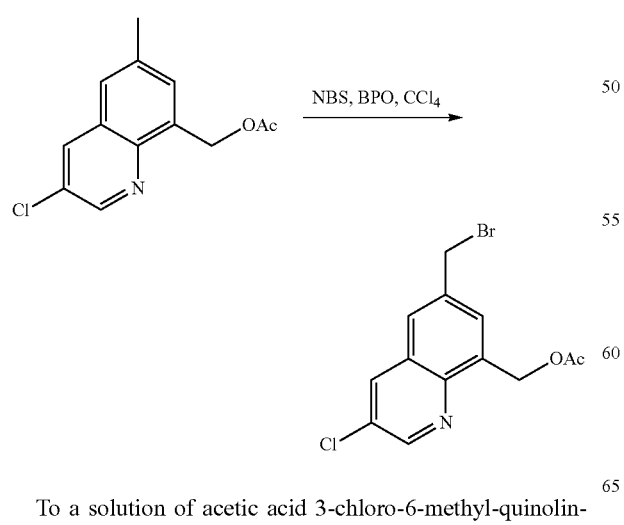

To a solution of acetic acid 3-chloro-6-methyl-quinolin-8-ylmethyl ester (3.4 g, 13.6 mmol, 1 eq) in CCl$_4$ (130 mL) were added NBS (2.66 g, 15.0 mmol, 1.1 eq) and BPO (330 mg, 0.14 mmol, 0.1 eq). The mixture was stirred at 90° C. for 4 h. After the mixture was cooled to rt, the mixture was concentrated. The resulting residue was purified by chromatography on a silica gel column (EA/PE=1/10, v/v) to give acetic acid 6-bromomethyl-3-chloro-quinolin-8-ylmethyl ester (1.1 g, 24.7%) as a yellow solid.

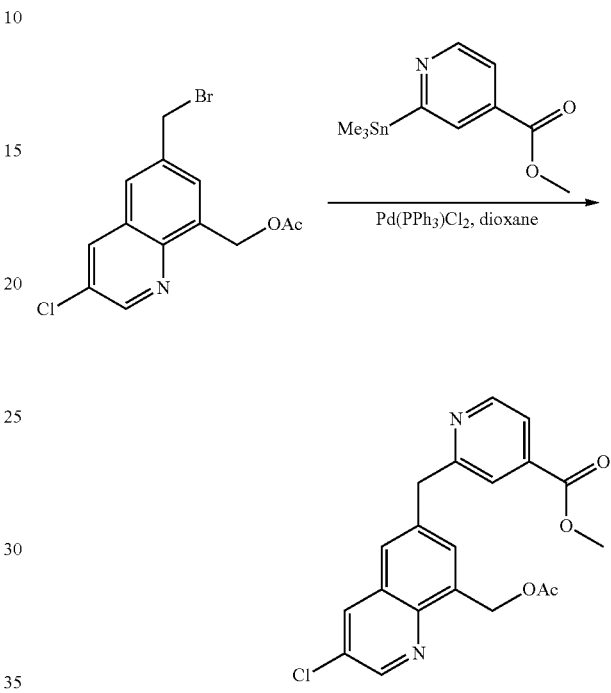

To a solution of acetic acid 6-bromomethyl-3-chloro-quinolin-8-ylmethyl ester (1.1 g, 3.50 mmol, 1.0 eq) in dioxane (30 mL) were added 2-trimethylstannanyl-isonicotinic acid methyl ester (1.16 g, 3.86 mmol, 1.1 eq) and Pd(PPh$_3$)$_2$Cl$_2$ (245 mg, 0.35 mmol, 0.1 eq). The mixture was stirred at 90° C. for 3 h under nitrogen atmosphere, and stripped of solvent. The resulting residue was purified by chromatography on a silica gel column (DCM/MeOH=80/1, v/v) to afford 2-(8-acetoxymethyl-3-chloro-quinolin-6-ylmethyl)-isonicotinic acid methyl ester (310 mg, 23%) as a yellow solid. $^1$H NMR (CDCl$_3$, 400 MHz) δ 8.79 (d, 1H), 8.74 (d, 1H), 8.07 (d, 1H), 7.76 (s, 1H), 7.73 (d, 1H), 7.67 (s, 1H), 7.59 (s, 1H), 5.75 (s, 2H), 4.40 (s, 2H), 3.93 (s, 3H), 2.13 (s, 3H).

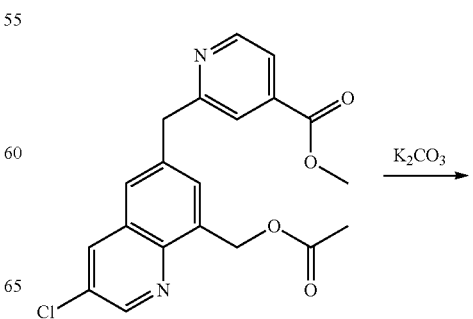

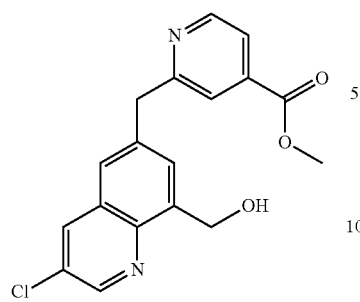

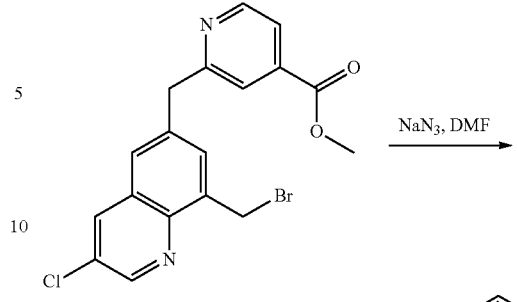

To a solution of 2-(8-acetoxymethyl-3-chloro-quinolin-6-ylmethyl)-isonicotinic acid methyl ester (200 mg, 0.519 mmol, 1 eq) in CH$_3$OH (50 mL) was added K$_2$CO$_3$ (36 mg, 0.26 mmol, 0.5 eq). The reaction mixture was stirred at rt for 1 h and concentrated. The resulting residue was purified by chromatography on a silica gel column (PE/EA=2/1, v/v) to give 2-(3-chloro-8-hydroxymethyl-quinolin-6-ylmethyl)-isonicotinic acid methyl ester (132 mg, 74.2%) as a yellow solid.

To a solution of 2-(8-bromomethyl-3-chloro-quinolin-6-ylmethyl)-isonicotinic acid methyl ester (156 mg, 0.386 mmol, 1 eq) in DMF (50 mL) was added NaN$_3$ (75 mg, 1.15 mmol, 3 eq). The reaction mixture was stirred at 80° C. for 2 h. After cooling to rt, the mixture was diluted with water and extracted with EA. The organic layer was dried and concentrated to get give 2-(8-azidomethyl-3-chloro-quinolin-6-ylmethyl)-isonicotinic acid methyl ester (130 mg, 92.9%) without further purification.

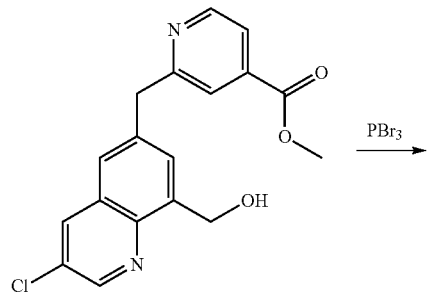

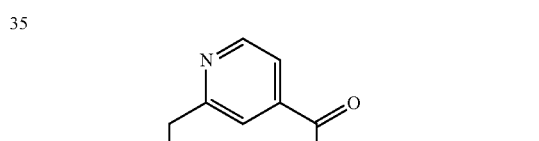

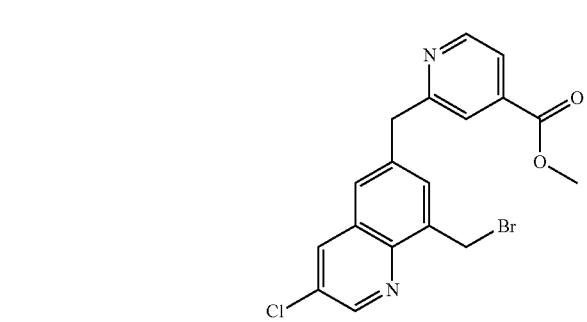

To a solution of 2-(3-chloro-8-hydroxymethyl-quinolin-6-ylmethyl)-isonicotinic acid methyl ester (132 mg, 0.386 mmol, 1.0 eq) in DCM (50 mL) was added PBr$_3$ (0.07 mL, 0.772 mmol, 2 eq). The reaction mixture was stirred at rt overnight and concentrated. The residue was diluted with DCM and washed with NaHCO$_3$ aqueous solution. The organic layer was dried and concentrated. The resulting residue was purified by chromatography on a silica gel column (PE/EA=4/1, v/v) to give 2-(8-bromomethyl-3-chloro-quinolin-6-ylmethyl)-isonicotinic acid methyl ester (150 mg, 99%) as a yellow solid.

To a solution of 2-(8-azidomethyl-3-chloro-quinolin-6-ylmethyl)-isonicotinic acid methyl ester (0.13 g, 0.354 mmol, 1.0 eq) in THF (5 mL) and H$_2$O (1 mL) was added NaOH (0.043 g, 1.06 mol, 3.0 eq) and the reaction mixture was stirred at rt for 3 h. The reaction mixture was acidified to pH 3 with 3 N HCl, then extracted with EA, and concentrated under reduced pressure to afford 2-(8-azidomethyl-3-chloro-quinolin-6-ylmethyl)-isonicotinic acid (0.1 g, 80%) as a white solid.

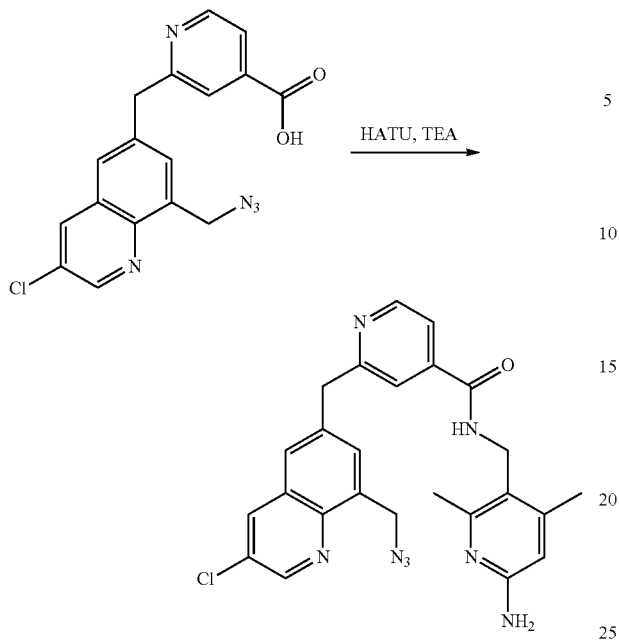

To a solution of 2-(8-azidomethyl-3-chloro-quinolin-6-ylmethyl)-isonicotinic acid (110 mg, 0.312 mmol, 1.0 eq) in DMF (10 mL) were added 5-aminomethyl-6-methyl-pyridin-2-ylamine (104 mg, 0.467 mmol, 1.5 eq) followed by HATU (237 mg, 0.623 mmol, 2.0 eq) and TEA (94 mg, 0.935 mmol, 3.0 eq). The reaction mixture was stirred at rt overnight. Water was added, and the mixture was extracted with DCM. The organic layer was washed with water, dried over $Na_2SO_4$, filtered and concentrated to give N-(6-amino-2,4-dimethyl-pyridin-3-ylmethyl)-2-(8-azidomethyl-3-chloro-quinolin-6-ylmethyl)-isonicotinamide (120 mg, 79.5%) without purification.

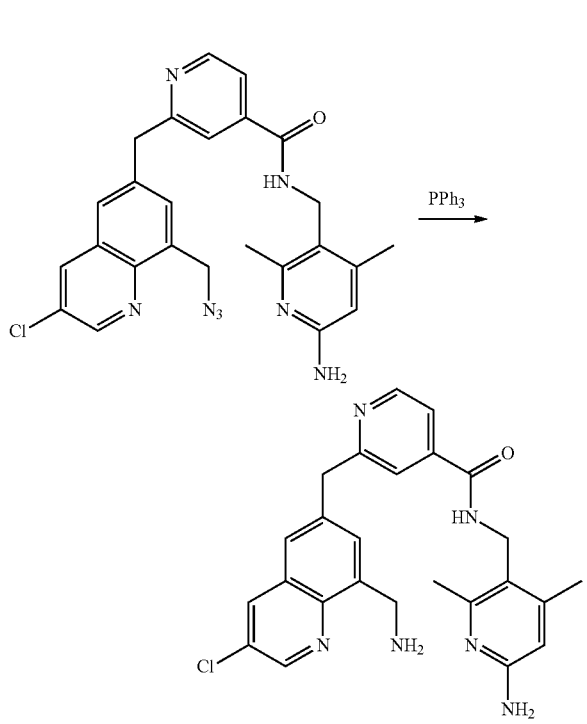

To a solution of N-(6-amino-2,4-dimethyl-pyridin-3-ylmethyl)-2-(8-azidomethyl-3-chloro-quinolin-6-ylmethyl)-isonicotinamide (0.05 g, 0.103 mmol, 1.0 eq) in THF (5 mL) was added $PPh_3$ (0.03 g, 0.113 mmol, 1.1 eq) and the reaction mixture was stirred at rt for 12 h. 0.2 mL of $NH_3.H_2O$ was added and the reaction mixture was stirred at rt for 3 h. After concentration, the resulting residue was purified by Prep-HPLC to give N-((6-amino-2,4-dimethyl-pyridin-3-yl)methyl)-2-((8-(aminomethyl)-3-chloroquinolin-6-yl)methyl)isonicotinamide (21 mg, 44.7%) as a white solid. LRMS (M+H+) m/z calculated 461.2, found 460.8. $^1$H NMR ($CDCl_3$, 400 MHz): δ 8.75 (d, 1H), 8.66 (d, 1H), 8.04 (d, 1H), 7.55-7.53 (m, 3H), 7.51 (d, 1H), 6.19 (s, 2H), 4.53 (d, 2H), 4.34-4.31 (m, 6H), 2.37 (s, 3H), 2.23 (s, 3H).

Example 242: Preparation of 2-((3-chloroquinolin-6-yl)methyl)-N-((6-((2-methoxyethyl)amino)-2-methylpyridin-3-yl)methyl)isonicotinamide

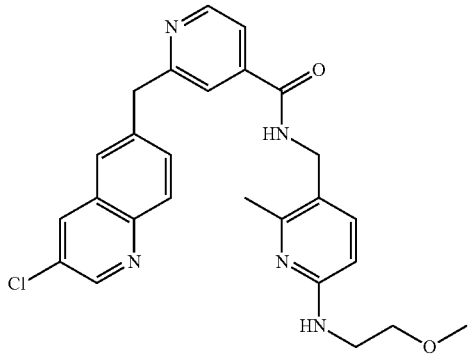

To a solution of 6-amino-nicotinonitrile (3.0 g, 22.56 mmol, 1.0 eq) in DMF (150 mL) was added NaH (60%) (1.35 g, 33.84 mmol, 1.5 eq) at 0° C. The mixture was stirred at 0° C. for 1 h. After that, 1-bromo-2-methoxy-ethane (3.1 g, 22.56 mmol, 1.0 eq) was added. The reaction mixture was stirred at rt overnight. The mixture was quenched with $NH_4Cl$ aq. and extracted with EA (200 mL×3). The combined organic layers were dried over $Na_2SO_4$, filtered and concentrated. The resulting residue was purified by chromatography on a silica gel column (PE/EA=10/1, v/v) to get 6-(2-methoxy-ethylamino)-2-methyl-nicotinonitrile (500 mg, 12%) as a white solid.

$^1$H NMR ($CDCl_3$, 400 MHz): δ 7.49 (d, 1H), 6.23 (d, 1H), 5.29 (br., 1H), 3.54-3.59 (m, 4H), 3.38 (s, 3H), 2.54 (s, 3H).

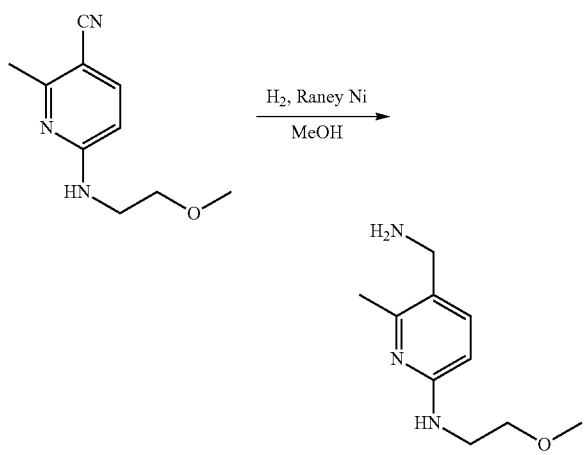

A mixture of 6-(2-methoxy-ethylamino)-2-methyl-nicotinonitrile (500 mg, 2.61 mmol, 1.0 eq) and Raney Ni (100 mg, 30% wt) in MeOH (20 mL) was stirred at rt overnight under hydrogen. Then it was filtered and the filtrate was concentrated. The resulting residue was purified by chromatography on a silica gel column (DCM/MeOH=10/1, v/v) to give (5-aminomethyl-6-methyl-pyridin-2-yl)-(2-methoxy-ethyl)-amine (200 mg, 39%) as a yellow solid.

A mixture of 2-(3-chloro-quinolin-6-ylmethyl)-isonicotinic acid (127 mg, 0.43 mmol, 1.0 eq), (5-aminomethyl-6-methyl-pyridin-2-yl)-(2-methoxy-ethyl)-amine (100 mg, 0.51 mmol, 1.2 eq), HOBt (87 mg, 0.65 mmol, 1.5 eq), EDCI (124 mg, 0.65 mmol, 1.5 eq), and TEA (130 mg, 1.29 mmol, 3.0 eq) in DCM (10 mL) was stirred at rt overnight. The mixture was concentrated and the resulting residue was purified by Prep-HPLC to get 2-((3-chloroquinolin-6-yl)methyl)-N-((6-((2-methoxyethyl)amino)-2-methylpyridin-3-yl)methyl)isonicotinamide (25 mg, 12%) as a white solid.

LRMS (M+H$^+$) m/z calculated 476.2, found 475.8. $^1$H NMR (DMSO-d$_6$, 400 MHz): δ 8.97 (t, 1H), 8.82 (d, 1H), 8.62 (d, 1H), 8.52 (d, 1H), 7.97 (d, 1H), 7.84 (d, 1H), 7.76-7.72 (m, 2H), 7.63-7.61 (m, 1H), 7.24 (d, 1H), 6.29 (d, 2H), 4.36 (s, 2H), 4.29 (d, 2H), 3.45-3.35 (m, 4H), 3.25 (s, 3H), 2.31 (s, 3H).

Example 243: Preparation of N-((6-amino-2,4-dimethylpyridin-3-yl)methyl)-2-((3-cyclopropylquinolin-6-yl)methyl)isonicotinamide

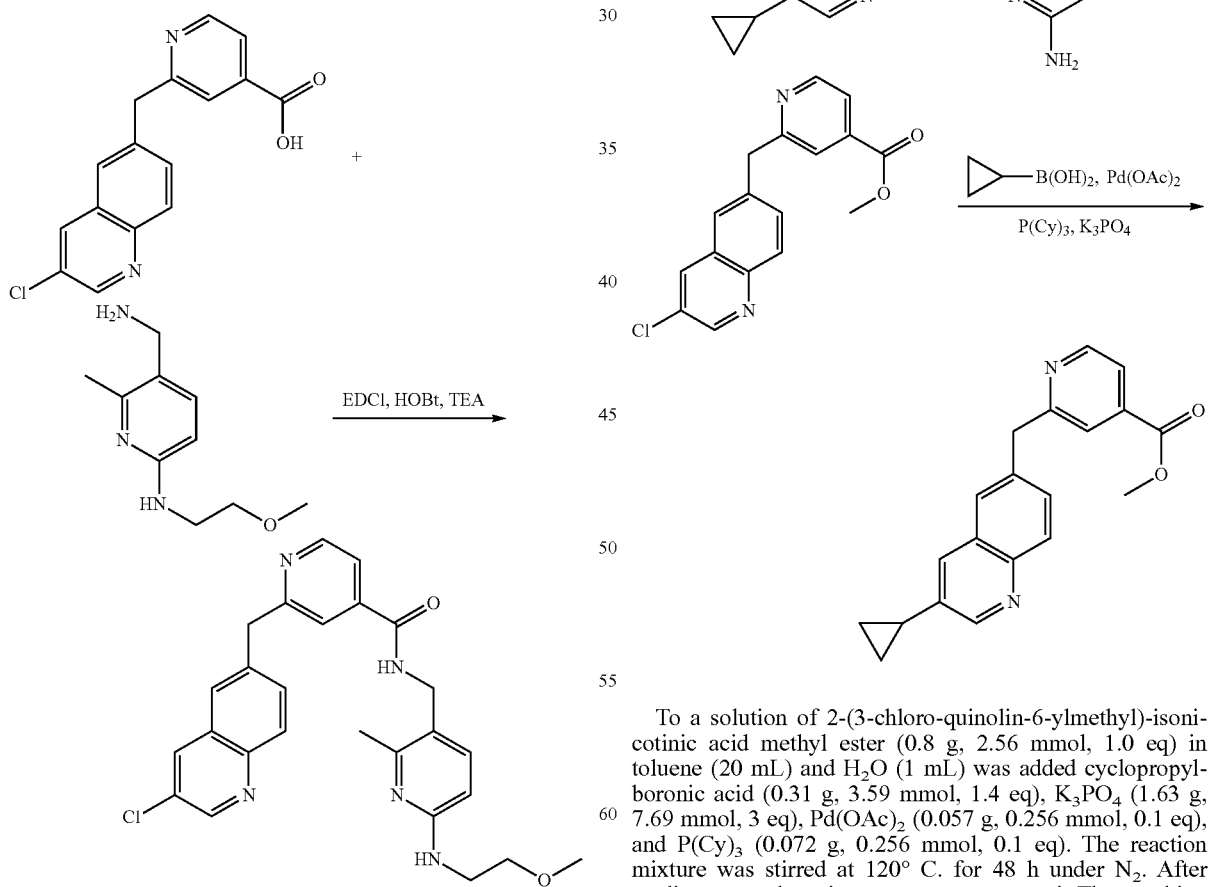

To a solution of 2-(3-chloro-quinolin-6-ylmethyl)-isonicotinic acid methyl ester (0.8 g, 2.56 mmol, 1.0 eq) in toluene (20 mL) and H$_2$O (1 mL) was added cyclopropylboronic acid (0.31 g, 3.59 mmol, 1.4 eq), K$_3$PO$_4$ (1.63 g, 7.69 mmol, 3 eq), Pd(OAc)$_2$ (0.057 g, 0.256 mmol, 0.1 eq), and P(Cy)$_3$ (0.072 g, 0.256 mmol, 0.1 eq). The reaction mixture was stirred at 120° C. for 48 h under N$_2$. After cooling to rt, the mixture was concentrated. The resulting residue was purified by chromatography on a silica gel column (PE/EA=5/1, v/v) to afford 2-(3-cyclopropyl-quinolin-6-ylmethyl)-isonicotinic acid methyl ester (0.31 g, 38%) as a white.

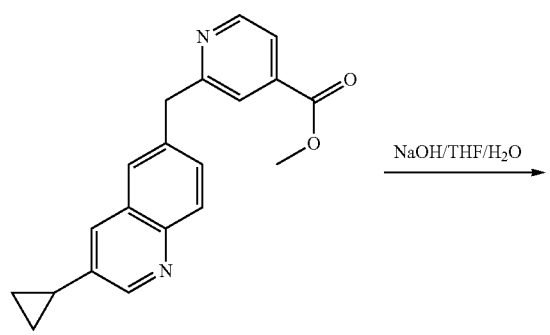

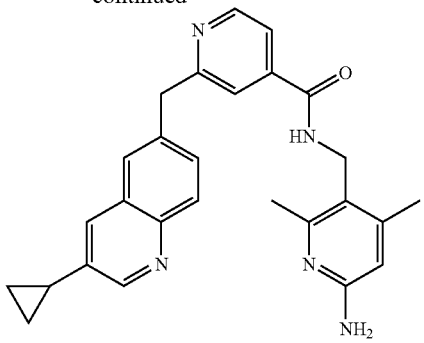

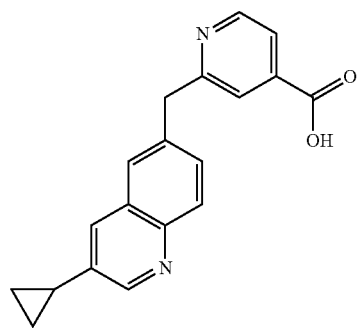

To a solution of 2-(3-Cyclopropyl-quinolin-6-ylmethyl)-isonicotinic acid methyl ester (0.31 g, 0.975 mmol, 1.0 eq) in THF (10 mL) and H₂O (1 mL) was added NaOH (0.078 g, 1.95 mmol, 2.0 eq) and the reaction mixture was stirred at rt for 3 h. The reaction mixture was acidified to pH 3 with 3 N HCl, then extracted with EA, and concentrated under reduced pressure to afford 2-(3-cyclopropyl-quinolin-6-yl-methyl)-isonicotinic acid (0.22 g, 74.3%) as a white solid.

To a solution of 2-(3-cyclopropyl-quinolin-6-ylmethyl)-isonicotinic acid (0.11 g, 0.362 mmol, 1 eq) in DMF (5 mL) was added 5-aminomethyl-4,6-dimethyl-pyridin-2-ylamine dihydrochloride (0.098 g, 0.47 mmol, 1.3 eq) followed by HATU (0.179 g, 0.47 mmol, 1.3 eq) and TEA (0.98 g, 1.08 mmol, 3.0 eq). The reaction mixture was stirred at rt overnight. Water was added, and the mixture was extracted with DCM. The organic layer was washed with water, dried over Na₂SO₄, filtered and concentrated. The resulting residue was purified by Prep-HPLC to give N-((6-amino-2,4-dimethylpyridin-3-yl)methyl)-2-((3-cyclopropylquinolin-6-yl)methyl)isonicotinamide (73 mg, 46%) as a white solid. LRMS (M+H+) m/z calculated 438.2, found 437.9. ¹H NMR (DMSO-d6, 400 MHz): δ 8.66 (t, 2H), 7.91-7.88 (d, 1H), 7.59 (d, 1H), 7.55 (d, 2H), 7.48 (d, 1H), 7.42 (d, 1H), 6.20 (s, 1H), 6.15 (s, 1H), 4.52 (d, 2H), 4.34 (s, 2H), 4.28 (s, 2H), 2.35 (s, 3H), 2.20 (s, 3H), 2.06-2.00 (m, 1H), 1.11-1.06 (m, 2H), 0.83-0.79 (m, 2H).

Example 244: Preparation of N-((6-amino-2-methylpyridin-3-yl)methyl)-2-((3-cyclopropylquinolin-6-yl)methyl)isonicotinamide

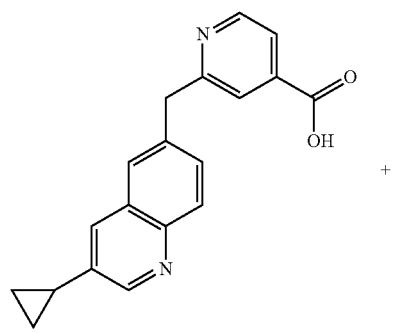

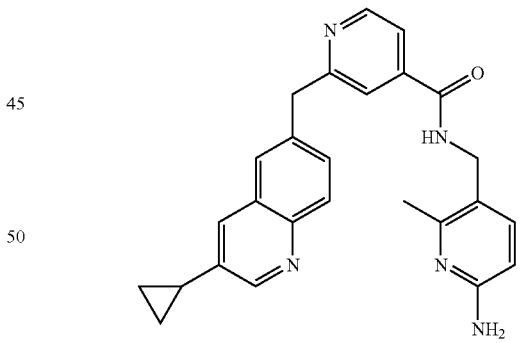

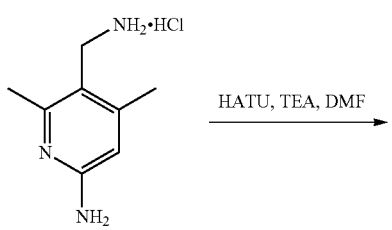

To a solution of 2-(3-cyclopropyl-quinolin-6-ylmethyl)-isonicotinic acid (0.11 g, 0.362 mmol, 1 eq) in DMF (5 mL) was added 5-aminomethyl-6-methyl-pyridin-2-ylamine (0.098 g, 0.47 mmol, 1.3 eq) followed by HATU (0.179 g, 0.47 mmol, 1.3 eq) and TEA (0.98 g, 1.08 mmol, 3.0 eq). The reaction mixture was heated at 35° C. and stirred overnight. Water was added, and the mixture was extracted with DCM. The organic layer was washed with water, dried over Na₂SO₄, filtered and concentrated. The resulting residue was purified by Prep-HPLC to give N-((6-amino-2-methylpyridin-3-yl)methyl)-2-((3-cyclopropylquinolin-6-yl)methyl)isonicotinamide (0.081 g, 52.9%) as a white solid.

LRMS (M+H+) m/z calculated 437.2 found 437.5. ¹H NMR (DMSO-d6, 400 MHz): δ 8.66 (t, 2H), 7.90-7.88 (d, 1H), 7.59 (d, 1H), 7.53 (d, 2H), 7.47 (d, 2H), 7.24 (s, 1H), 6.54 (s, 1H), 6.26 (d, 1H), 4.45 (d, 2H), 4.37-4.33 (d, 4H), 2.33 (s, 3H), 2.06-2.01 (m, 1H), 1.11-1.06 (m, 2H), 0.83-0.79 (m, 2H).

Example 245: Preparation of N-((3-chloro-6-fluoro-1H-indol-5-yl)methyl)-2-((3-cyclopropylquinolin-6-yl)methyl)isonicotinamide

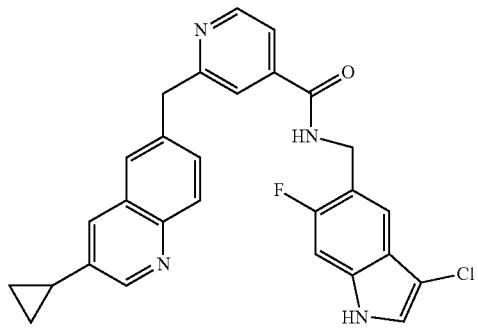 [SMILES: O=C(NCc1cc2c(Cl)c[nH]c2cc1F)c1ccnc(Cc2ccc3ncc(C4CC4)cc3c2)c1]

To a solution of 2-(3-cyclopropyl-quinolin-6-ylmethyl)-isonicotinic acid (80 mg, 0.24 mmol, 1 eq) in DMF (5 mL) was added (3-chloro-6-fluoro-1H-indol-5-yl)methanamine (95 mg, 0.34 mmol, 1.3 eq) followed by HOBT (58 mg, 0.34 mmol, 1.3 eq), EDCI (82 mg, 0.34 mmol, 1.3 eq) and TEA (80 mg, 0.79 mmol, 3.0 eq). The reaction mixture was heated at 35° C. and stirred overnight. Water was added, and the mixture was extracted with DCM. The organic layer was washed with water, dried over Na₂SO₄, filtered and concentrated. The resulting residue was purified by Prep-HPLC to give N-((3-chloro-6-fluoro-1H-indol-5-yl)methyl)-2-((3-cyclopropylquinolin-6-yl)methyl)isonicotinamide (63.8 mg, 50.1%) as a white solid.

LRMS (M+H+) m/z calculated 485.2 found 485.1. ¹H NMR (DMSO-d6, 400 MHz): δ 11.38 (s, 1H), 9.22 (d, 1H), 8.70-8.64 (m, 2H), 7.89-7.86 (m, 2H), 7.76 (s, 1H), 7.71 (s, 1H), 7.65 (d, 1H), 7.60 (d, 1H), 7.50 (d, 1H), 7.44 (d, 1H), 7.23 (d, 1H), 4.58 (d, 2H), 4.32 (s, 2H), 2.13-2.08 (m, 1H), 1.08-1.03 (m, 2H), 0.87-0.83 (m, 2H).

Example 246: Preparation of N-((3-chloro-1H-pyrrolo[2,3-b]pyridin-5-yl)methyl)-2-((3-cyclopropylquinolin-6-yl)methyl)isonicotinamide

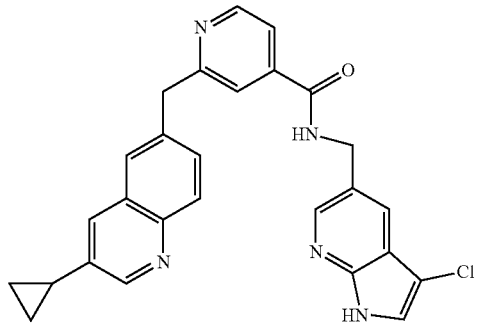 [SMILES: O=C(NCc1cnc2[nH]cc(Cl)c2c1)c1ccnc(Cc2ccc3ncc(C4CC4)cc3c2)c1]

To a solution of 2-(3-cyclopropyl-quinolin-6-ylmethyl)-isonicotinic acid (80 mg, 0.24 mmol, 1.0 eq) in DMF (5 mL) was added (3-chloro-1H-pyrrolo[2,3-b]pyridin-5-yl)methanamine (89 mg, 0.31 mmol, 1.3 eq) followed by HOBT (58 mg, 0.34 mmol, 1.3 eq), EDCI (82 mg, 0.34 mmol, 1.3 eq) and TEA (80 mg, 0.78 mmol, 3.0 eq). The reaction mixture was heated at 35° C. and stirred overnight. Water was added, and the mixture was extracted with DCM. The organic layer was washed with water, dried over Na₂SO₄, filtered and concentrated. The resulting residue was purified by Prep-HPLC to give N-((3-chloro-1H-pyrrolo[2,3-b]pyridin-5-yl)methyl)-2-((3-cyclopropylquinolin-6-yl)methyl)isonicotinamide (80.8 mg, 65.6%) as a white solid. LRMS (M+H+) m/z calculated 468.2, found 468.1. ¹H NMR (DMSO-d6, 400 MHz): δ 11.95 (s, 1H), 9.33 (d, 1H), 8.69 (s, 1H), 8.63 (s, 1H), 8.31 (s, 1H), 7.88-7.86 (m, 3H), 7.75-7.56 (m, 5H), 4.59 (d, 2H), 4.32 (s, 2H), 2.11-2.07 (m, 2H), 1.08-1.04 (m, 2H), 0.87-0.83 (m, 2H).

Example 247: Preparation of N-((1-aminoisoquinolin-6-yl)methyl)-2-((3-cyclopropylquinolin-6-yl)methyl)isonicotinamide

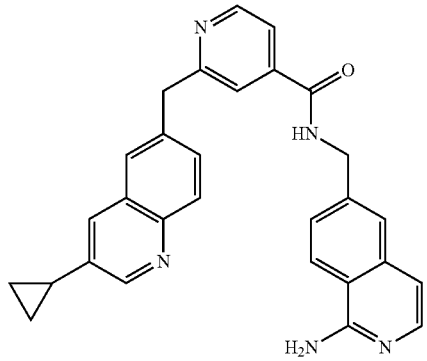 [SMILES: Nc1nccc2cc(CNC(=O)c3ccnc(Cc4ccc5ncc(C6CC6)cc5c4)c3)ccc12]

To a solution of 2-(3-cyclopropyl-quinolin-6-ylmethyl)-isonicotinic acid (80 mg, 0.26 mmol, 1.0 eq) in DMF (5 mL) was added 6-aminomethyl-isoquinolin-1-ylamine (86 mg, 0.34 mmol, 1.3 eq) followed by HOBt (58 mg, 0.34 mmol, 1.3 eq), EDCI (82 mg, 0.34 mmol, 1.3 eq) and TEA (80 mg, 0.78 mmol, 3.0 eq). The reaction mixture was heated at 35° C. and stirred overnight. Water was added, and the mixture was extracted with DCM. The organic layer was washed with water, dried over Na₂SO₄, filtered and concentrated. The resulting residue was purified by Prep-HPLC to give N-((1-aminoisoquinolin-6-yl)methyl)-2-((3-cyclopropylquinolin-6-yl)methyl)isonicotinamide (71 mg, 58.9%) as a white solid.

LRMS (M+H+) m/z calculated 460.2 found 460.2. ¹H NMR (DMSO-d6, 400 MHz): δ 9.36 (t, 1H), 8.70 (s, 1H), 8.65 (d, 1H), 8.13 (d, 1H), 7.89 (d, 1H), 7.87 (s, 1H), 7.78-7.74 (m, 3H), 7.72 (d, 1H), 7.65 (d, 1H), 7.54 (d, 1H), 7.40 (d, 1H), 6.84 (d, 1H), 6.71 (s, 2H), 4.61 (d, 2H), 4.34 (s, 2H), 2.12 (m, 1H), 1.07-1.03 (m, 2H), 0.87-0.84 (m, 2H).

Example 248: Preparation of N-((3-chloro-4-fluoro-1H-indol-5-yl)methyl)-2-((3-cyclopropylquinolin-6-yl)methyl)isonicotinamide

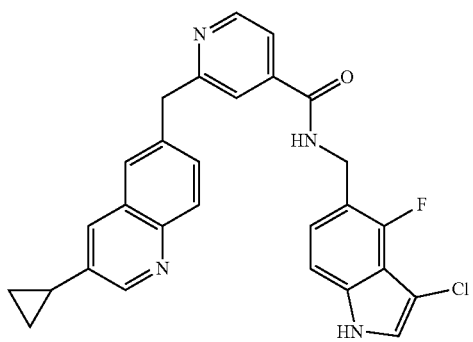 [SMILES: O=C(NCc1ccc2[nH]cc(Cl)c2c1F)c1ccnc(Cc2ccc3ncc(C4CC4)cc3c2)c1]

To a solution of 2-(3-cyclopropyl-quinolin-6-ylmethyl)-isonicotinic acid (80 mg, 0.26 mmol, 1.0 eq) in DMF (5 mL) was added (3-chloro-4-fluoro-1H-indol-5-yl)methanamine (95 mg, 0.34 mmol, 1.3 eq) followed by HOBT (58 mg, 0.34 mmol, 1.3 eq), EDCI (82 mg, 0.34 mmol, 1.3 eq) and TEA (80 mg, 0.79 mmol, 3.0 eq). The reaction mixture was heated at 35° C. and stirred overnight. Water was added, and the mixture was extracted with DCM. The organic layer was washed with water, dried over Na$_2$SO$_4$, filtered and concentrated. The resulting residue was purified by Prep-HPLC to give N-((3-chloro-4-fluoro-1H-indol-5-yl)methyl)-2-((3-cyclopropylquinolin-6-yl)methyl)isonicotinamide (76.5 mg, 60%) as a white solid.

LRMS (M+H+) m/z calculated 485.2 found 485.1. $^1$H NMR (DMSO-d6, 400 MHz): δ 11.56 (s, 1H), 9.20 (d, 1H), 8.69 (s, 1H), 8.62 (s, 1H), 7.88 (s, 1H), 7.86 (s, 1H), 7.75 (s, 1H), 7.70 (s, 1H), 7.63 (d, 1H), 7.59 (d, 1H), 7.50 (d, 1H), 7.18 (d, 1H), 7.10 (d, 1H), 4.57 (d, 2H), 4.38 (s, 2H), 2.11 (m, 1H), 1.07-1.03 (m, 2H), 0.87-0.84 (m, 2H).

Example 249: Preparation of N-((5-chloro-1H-indazol-3-yl)methyl)-2-((3-cyclopropylquinolin-6-yl)methyl)isonicotinamide

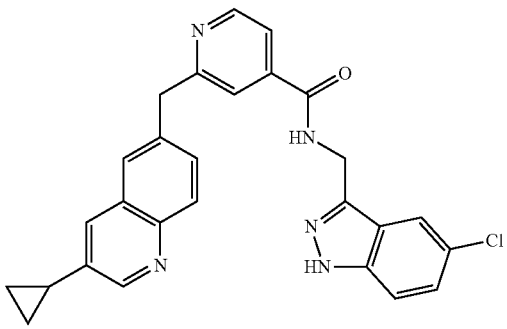 [SMILES: O=C(NCc1n[nH]c2ccc(Cl)cc12)c1ccnc(Cc2ccc3ncc(C4CC4)cc3c2)c1]

To a solution of 2-(3-cyclopropyl-quinolin-6-ylmethyl)-isonicotinic acid (80 mg, 0.24 mmol, 1.0 eq) in DMF (5 mL) was added (5-chloro-1H-indazol-3-yl)methanamine (89 mg, 0.34 mmol, 1.3 eq) followed by HOBT (58 mg, 0.34 mmol, 1.3 eq), EDCI (82 mg, 0.34 mmol, 1.3 eq) and TEA (780 mg, 0.79 mmol, 3.0 eq). The reaction mixture was heated at 35° C. and stirred overnight. Water was added, and the mixture was extracted with DCM. The organic layer was washed with water, dried over Na$_2$SO$_4$, filtered and concentrated. The resulting residue was purified by Prep-HPLC to give N-((5-chloro-H-indazol-3-yl)methyl)-2-((3-cyclopropylquinolin-6-yl)methyl)isonicotinamide (70.9 mg, 57.7%) as a white solid.

LRMS (M+H+) m/z calculated 468.2 found 468.1. $^1$H NMR (DMSO-d6, 400 MHz): δ 9.37 (t, 1H), 9.13 (s, 1H), 8.87 (s, 1H), 7.88-7.85 (m, 3H), 7.76 (s, 1H), 7.70 (s, 1H), 7.63-7.51 (m, 3H), 7.34 (d, 1H), 7.31 (s, 1H), 4.78 (d, 2H), 4.32 (s, 2H), 1.07-1.03 (m, 2H), 0.87-0.84 (m, 2H).

Example 250: Preparation of 6-((4-(((6-amino-2,4-dimethylpyridin-3-yl)methyl)carbamoyl)pyridin-2-yl)methyl)quinoline-3-carboxamide

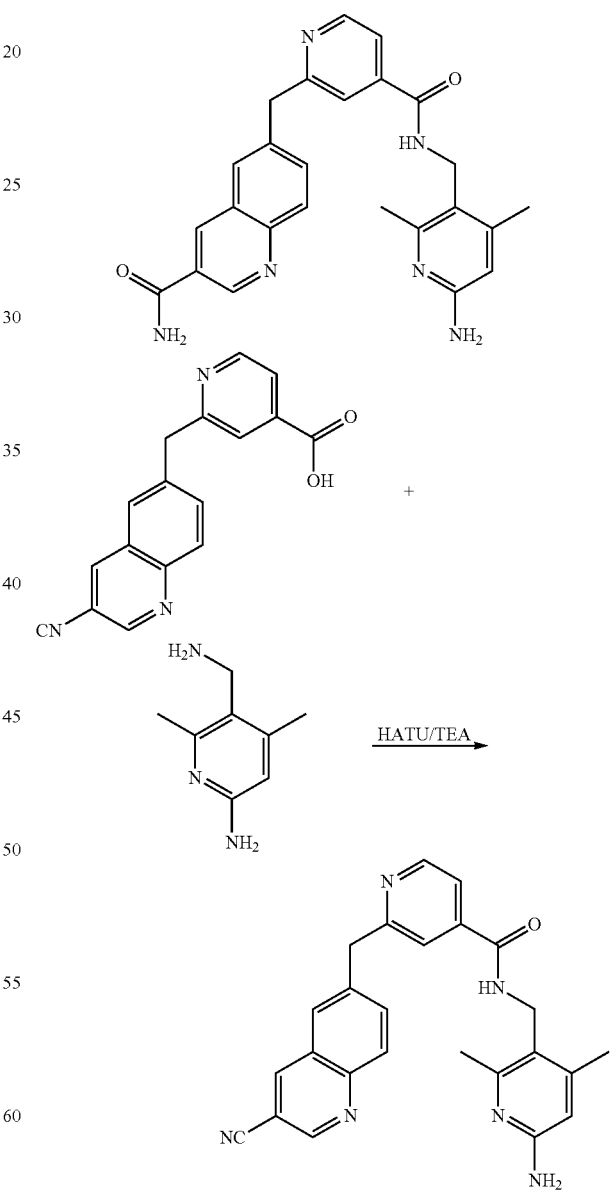

To a solution of 2-(3-isocyano-quinolin-6-ylmethyl)-isonicotinic acid (0.1 g, 0.35 mmol, 1.0 eq) in DMF (5 mL) was added 5-aminomethyl-4,6-dimethyl-pyridin-2-ylamine dihydrochloride (0.099 g, 0.45 mmol, 1.3 eq) followed by HATU (0.171 g, 0.45 mmol, 1.3 eq) and TEA (0.105 g, 1.04 mmol, 3.0 eq). The reaction mixture was stirred at rt overnight. Water was added, and the mixture was extracted with DCM. The organic layer was washed with water, dried over Na$_2$SO$_4$, filtered and concentrated to give N-(6-amino-2,4-dimethyl-pyridin-3-ylmethyl)-2-(3-cyano-quinolin-6-ylmethyl)-isonicotinamide (0.14 g, 99%) as a white solid without further purification.

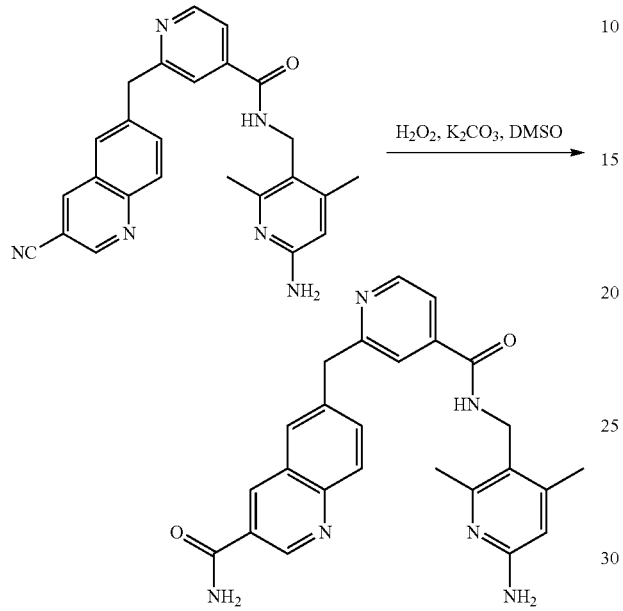

To a solution of N-(6-amino-2,4-dimethyl-pyridin-3-ylmethyl)-2-(3-cyano-quinolin-6-ylmethyl)-isonicotinamide (0.15 g, 0.355 mmol, 1 eq) in DMSO (5 mL) was added K$_2$CO$_3$ (0.074 g, 0.533 mmol, 1.5 eq) and H$_2$O$_2$. The reaction mixture was heated to 50° C. and stirred for 3 h. Water was added, and the mixture was extracted with DCM. The organic layer was washed with water, dried over Na$_2$SO$_4$, filtered and concentrated. The resulting residue was purified by Prep-HPLC to give 6-((4-(((6-amino-2,4-dimethylpyridin-3-yl)methyl)carbamoyl)pyridin-2-yl)methyl)quinoline-3-carboxamide (62 mg, 39.7%) as a white solid.

LRMS (M+H+) m/z calculated 441.2 found 440.8. $^1$H NMR (DMSO-d6, 400 MHz): δ 9.23 (s, 1H), 8.75 (d, 1H), 8.63-8.60 (m, 2H), 8.25 (s, 1H), 8.01-7.98 (d, 1H), 7.90 (s, 1H), 7.79-7.75 (m, 2H), 7.65 (s, 1H), 7.61 (t, 1H), 6.12 (s, 1H), 5.68 (s, 2H), 4.37-4.33 (m, 4H), 2.29 (s, 3H), 2.16 (s, 3H).

Example 251: Preparation of 6-((4-(((6-amino-2-methylpyridin-3-yl)methyl)carbamoyl)pyridin-2-yl)methyl)quinoline-3-carboxamide

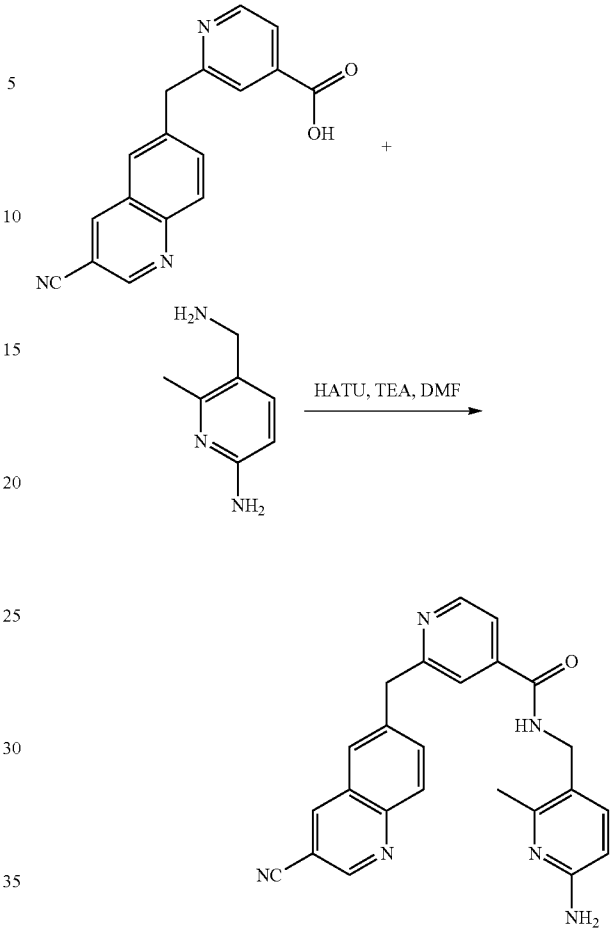

To a solution of 2-(3-isocyano-quinolin-6-ylmethyl)-isonicotinic acid (0.1 g, 0.35 mmol, 1.0 eq) in DMF (5 mL) was added 5-aminomethyl-6-methyl-pyridin-2-ylamine (0.107 g, 0.52 mmol, 1.5 eq) followed by HATU (0.171 g, 0.45 mmol, 1.3 eq) and TEA (0.105 g, 1.04 mmol, 3.0 eq). The reaction mixture was stirred at rt overnight. Water was added, and the mixture was extracted with DCM. The organic layer was washed with water, dried over Na$_2$SO$_4$, filtered and concentrated to give N-(6-amino-2-methyl-pyridin-3-ylmethyl)-2-(3-cyano-quinolin-6-ylmethyl)-isonicotinamide (0.14 g, 99%) as a white solid without purification.

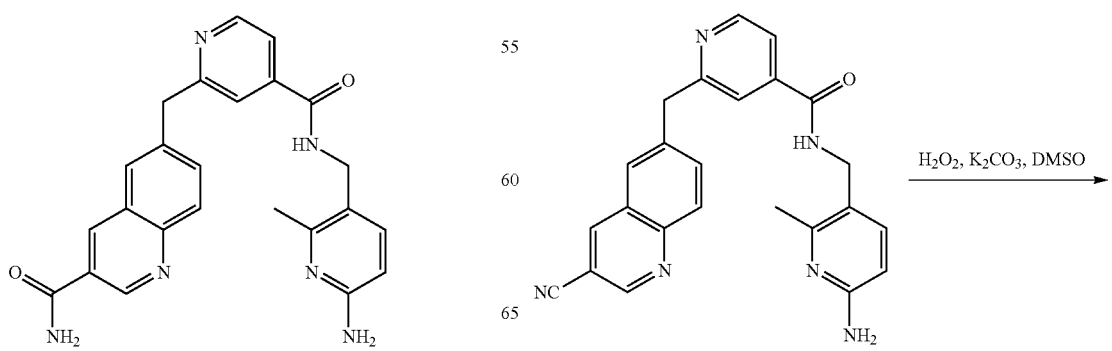

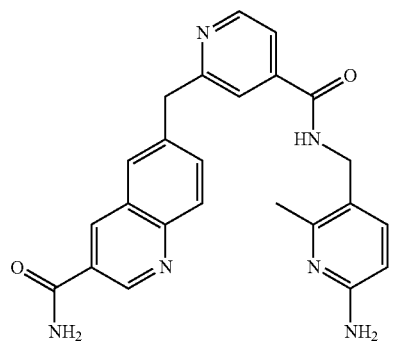

To a solution of N-(6-Amino-2-methyl-pyridin-3-ylmethyl)-2-(3-cyano-quinolin-6-ylmethyl)-isonicotinamide (0.15 g, 0.355 mmol, 1 eq) in DMSO (5 mL) were added K₂CO₃ (0.074 g, 0.533 mmol, 1.5 eq) and H₂O₂. The reaction mixture was heated to 50° C. kept stirring for 3 h. Water was added, and the mixture was extracted with DCM. The organic layer was washed with water, dried over Na₂SO₄, filtered and concentrated. The resulting residue was purified by Prep-HPLC to give 6-((4-(((6-amino-2,4-dimethylpyridin-3-yl)methyl)carbamoyl)pyridin-2-yl)methyl)quinoline-3-carboxamide (0.082 g, 52.4%) as a white solid.

LRMS (M+H+) m/z calculated 426.2 found 426.5. ¹H NMR (DMSO-d6, 400 MHz): δ 9.23 (s, 1H), 8.98-8.96 (m, 1H), 8.76 (d, 1H), 8.63 (d, 1H), 8.26 (s, 1H), 8.01-7.99 (d, 1H), 7.91 (s, 1H), 7.80-7.77 (m, 2H), 7.65-7.61 (m, 2H), 7.26-7.23 (d, 1H), 6.25-6.23 (m, 1H), 5.75 (s, 2H), 4.38 (s, 2H), 4.29-4.27 (d, 2H), 2.27 (s, 3H).

Example 252: Preparation of 2-((3-chloroquinolin-6-yl)methyl)-N-((6-((2-hydroxyethyl)amino)-2-methylpyridin-3-yl)methyl)isonicotinamide

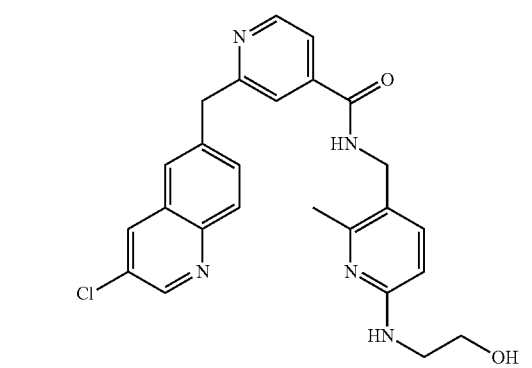

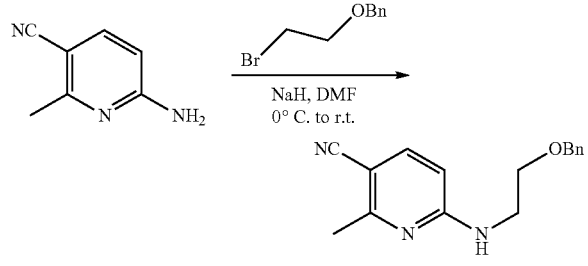

A three-necked bottom flask was charged with 6-amino-2-methyl-nicotinonitrile (5 g, 37.6 mmol), NaH (4.5 g, 112.8 mmol) and anhydrous DMF (300 mL). The resulting mixture was stirred at 0° C. under N₂ for 30 min. After 30 min, (2-bromo-ethoxymethyl)-benzene (5 g, 23.2 mmol) was added very slowly into the above mixture, then the reaction mixture was allowed to warm to ambient temperature and stirred under N₂ for 3.5 h. After 2 h, the reaction mixture was turned from homogeneous pale-yellow solution to brownish-red suspension. After 3.5 h, LC-MS indicated that the reaction was completed. Then it was quenched with methanol (100 mL) and the solvent was removed under reduced pressure. The residue was partitioned between DCM (200 mL×3) and water (30 mL). The combined organic extracts were dried over anhydrous Na₂SO₄ and concentrated in vacuo. The resulting residue was purified by chromatography on a silica gel column (PE/EA=6/1 to 2/1, v/v) to give 6-(2-benzyloxy-ethylamino)-2-methyl-nicotinonitrile as a bright-yellow liquid (3.76 g, 37.4%).

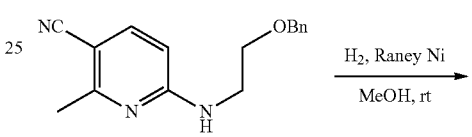

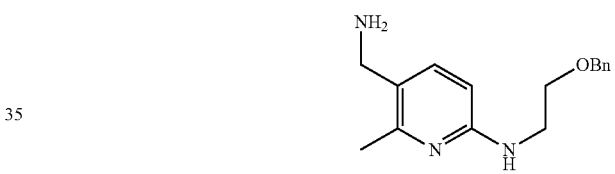

A three-necked bottom flask was charged with 6-(2-benzyloxy-ethylamino)-2-methyl-nicotinonitrile (1.5 g, 5.61 mmol) and Raney nickel (9 g) in methanol (100 mL), then replaced with H₂ six times. The resulting black-colored suspension was stirred at ambient temperature under H₂ (15 psi) for 40 min. LC-MS revealed that the reaction was complete. The reaction mixture was filtered by a pad of celite and washed with methanol. The combined organic phase was evaporated under reduced pressure to afford (5-aminomethyl-6-methyl-pyridin-2-yl)-(2-benzyloxyethyl)-amine as an off-white liquid (950 mg, 62.5% yield).

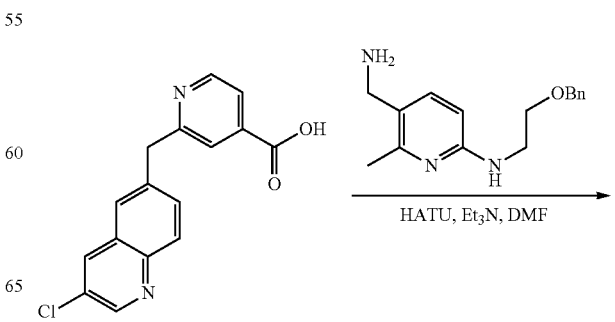

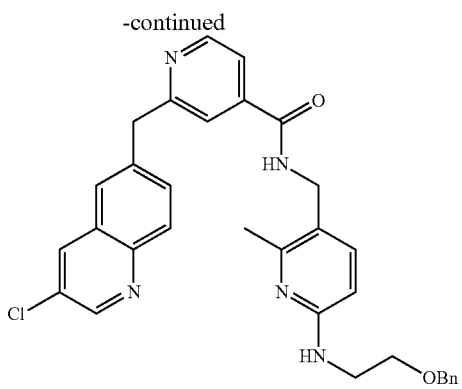

A round-bottomed flask was charged with 2-(3-chloro-quinolin-6-ylmethyl)-isonicotinic acid (300 mg, 1 mmol), (5-aminomethyl-6-methyl-pyridin-2-yl)-(2-benzyloxy-ethyl)-amine (407 mg, 1.5 mmol), HATU (418 mg, 1.1 mmol), Et$_3$N (152 mg, 1.5 mmol) and DMF (15 mL). The resulting dark-yellow-colored homogeneous mixture was stirred at ambient temperature for 25 min. LC-MS indicated that the reaction was complete. The reaction mixture was extracted with DCM (50 mL×3). The combined organic phase was dried over anhydrous Na$_2$SO$_4$ and concentrated to dryness under reduced pressure. The resulting residue was purified by chromatography on a silica gel column (PE/EA=1/1, v/v to MeOH/DCM=10/1, v/v) to provide N-[6-(2-benzyloxy-ethylamino)-2-methyl-pyridin-3-ylmethyl]-2-(3-chloro-quinolin-6-ylmethyl)-isonicotinamide as a yellow oil (400 mg, 72.4%).

TiCl$_4$ (1.1 mL, 9.78 mmol) was added into a solution of N-[6-(2-benzyloxy-ethylamino)-2-methyl-pyridin-3-ylmethyl]-2-(3-chloro-quinolin-6-ylmethyl)-isonicotinamide (180 mg, 0.326 mmol) in anhydrous DCM (25 mL) at −78° C. under N$_2$, then the reaction mixture was allowed to warm to −10° C. and stirred under N$_2$ for 2 h. LC-MS indicated that the reaction was complete. The excess of TiCl$_4$ was coordinated by the addition of potassium sodium tartrate (30 mL). The resulting white-colored suspension was extracted with DCM/MeOH (10/1, v/v) (40 mL×10). The combined organic layers were dried over anhydrous Na$_2$SO$_4$ and concentrated under reduced pressure. The resulting residue was purified by Prep-HPLC to afford 2-((3-chloroquinolin-6-yl)methyl)-N-((6-((2-hydroxyethyl)amino)-2-methylpyridin-3-yl)methyl)isonicotinamide (32 mg, 21%) as a yellow solid.

LRMS (M+H$^+$) m/z calculated 462.2, found 462.1. $^1$H NMR (DMSO-d$_6$, 400 MHz): δ 8.98 (t, 1H), 8.82 (d, 1H), 8.62 (d, 1H), 8.52 (d, 1H), 7.97 (s, 1H), 7.76 (s, 1H), 7.72 (dd, 1H), 7.62 (d, 1H), 6.28 (d, 1H), 6.26 (s, 1H), 4.36 (s, 2H), 4.28 (d, 2H), 3.50 (t, 2H), 3.26 (t, 2H), 2.51 (s, 3H).

Example 253: Preparation of N-((6-amino-2-methylpyridin-3-yl)methyl)-2-((8-(aminomethyl)-3-chloroquinolin-6-yl)methyl)isonicotinamide

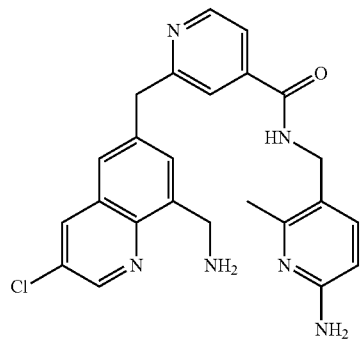

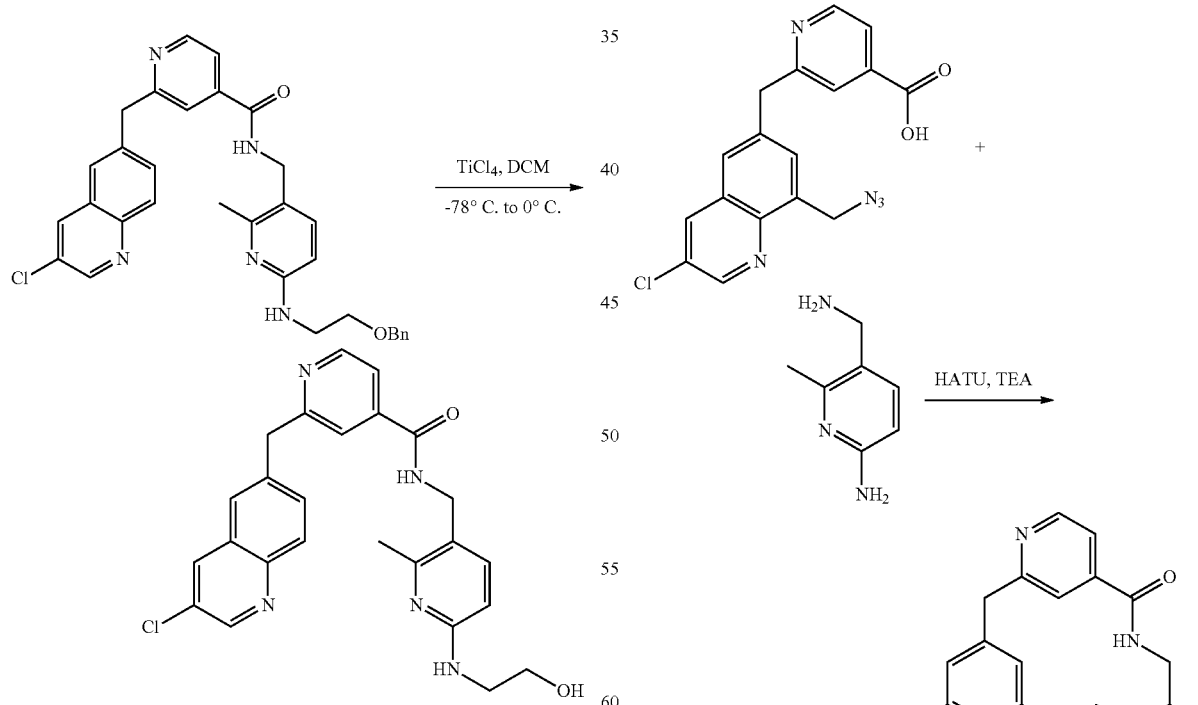

To a solution of 2-(8-azidomethyl-3-chloro-quinolin-6-ylmethyl)-isonicotinic acid (220 mg, 0.623 mmol, 1.0 eq) in DMF (10 mL) was added 5-aminomethyl-6-methyl-pyridin-2-ylamine (169 mg, 0.81 mmol, 1.3 eq) followed by HATU (310 mg, 0.81 mmol, 1.3 eq) and TEA (189 mg, 1.87 mmol, 3.0 eq). The reaction mixture was stirred at rt overnight. Water was added, and the mixture was extracted with DCM. The organic layer was washed with water, dried over Na$_2$SO$_4$, filtered and concentrated to give N-((6-amino-2-methylpyridin-3-yl)methyl)-2-((8-(aminomethyl)-3-chloro-quinolin-6-yl)methyl)isonicotinamide (290 mg, 99%) without further purification.

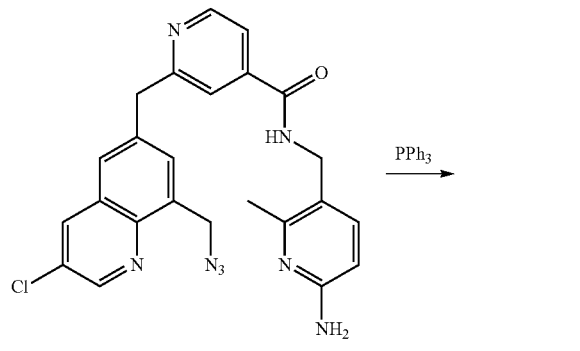

To a solution of N-(6-amino-2-methyl-pyridin-3-ylmethyl)-2-(8-azidomethyl-3-chloro-quinolin-6-ylmethyl)-isonicotinamide (295 mg, 0.62 mmol, 1.0 eq) in THF (5 mL) was added PPh$_3$ (197 mg, 0.75 mmol, 1.2 eq) and the reaction mixture was stirred at rt for 12 h. Then 0.5 mL NH$_3$.H$_2$O was added with stirring at rt for 3 h. after concentration to remove the solvent, The resulting residue was purified by Prep-HPLC to give N-(6-amino-2,4-dimethyl-pyridin-3-ylmethyl)-2-(8-aminomethyl-3-chloro-quinolin-6-ylmethyl)-isonicotinamide (80 mg, 28.8%) as a white solid.

LRMS (M+H+) m/z calculated 447.2, found 447.2. $^1$H NMR (DMSO-d$_6$, 400 MHz): δ 8.97 (t, 1H), 8.84 (d, 1H), 8.63 (d, 1H), 8.50 (s, 1H), 7.75 (s, 2H), 7.70 (s, 1H), 7.62 (dd, 1H), 7.23 (d, 1H), 6.22 (d, 1H), 5.71 (s, 2H), 4.33 (s, 2H), 4.28 (d, 2H), 4.23 (s, 2H), 2.27 (s, 3H).

Example 254: Preparation of N-((6-amino-2,4-dimethylpyridin-3-yl)methyl)-2-((3-isopropylquinolin-6-yl)methyl)isonicotinamide

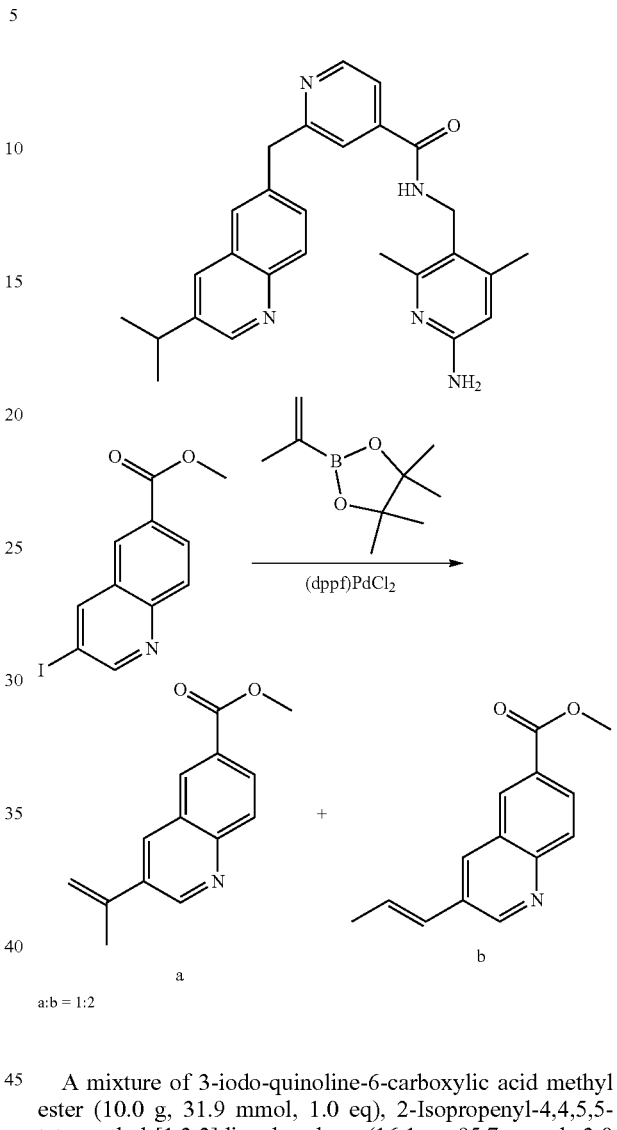

a:b = 1:2

A mixture of 3-iodo-quinoline-6-carboxylic acid methyl ester (10.0 g, 31.9 mmol, 1.0 eq), 2-Isopropenyl-4,4,5,5-tetramethyl-[1,3,2]dioxaborolane (16.1 g, 95.7 mmol, 3.0 eq), Pd(dppf)Cl$_2$ (2.6 g, 3.19 mmol, 1.5 eq) and K$_2$CO$_3$ (13.2 g, 95.7 mmol, 3.0 eq) in dioxane (100 mL) and H$_2$O (20 mL) was stirred at 100° C. overnight under nitrogen. The mixture was concentrated and the resulting residue was purified by chromatography on a silica gel column (PE/EA=3/1, v/v) to give 3-isopropenyl-quinoline-6-carboxylic acid methyl ester and 3-propenyl-quinoline-6-carboxylic acid methyl ester (5.5 g, 76%), which were hard to separate from each other.

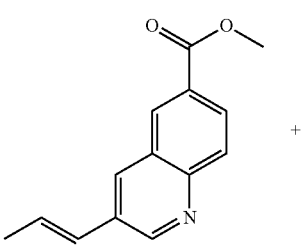

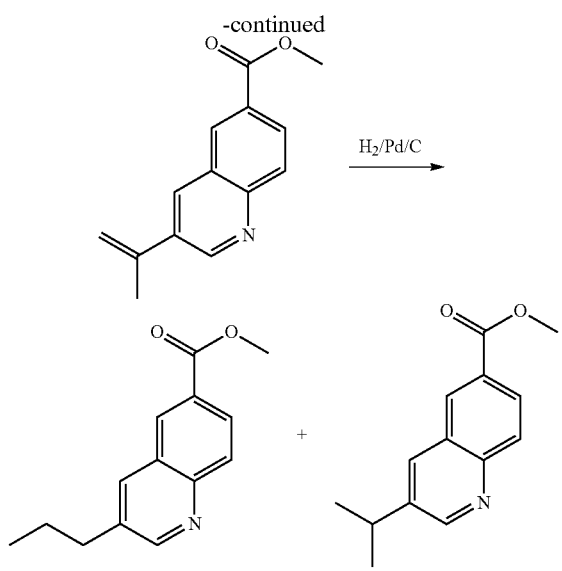

To a solution of 3-isopropenyl-quinoline-6-carboxylic acid methyl ester and 3-propenyl-quinoline-6-carboxylic acid methyl ester (5.5 g, 24.20 mmol, 1.0 eq) in MeOH (60 mL) was added Pd/C (550 mg, 10% wt) at rt. The mixture was stirred at rt overnight under hydrogen. The mixture was filtered and the filtrate was concentrated to afford 3-propyl-quinoline-6-carboxylic acid methyl ester and 3-isopropyl-quinoline-6-carboxylic acid methyl ester (5.0 g, crude) as a yellow oil without further purification. LRMS (M+H⁺) m/z calculated 229.1, found 229.0.

To a solution of 3-propyl-quinoline-6-carboxylic acid methyl ester and 3-isopropyl-quinoline-6-carboxylic acid methyl ester (5.0 g, 21.8 mmol, 1.0 eq) in THF (100 mL) was added (t-BuO)₃AlLiH (16.6 g, 65.4 mmol, 3.0 eq) at rt. The mixture was stirred at 60° C. overnight. The mixture was concentrated and the resulting residue was purified by chromatography on a silica gel column (PE/EA=3/1, v/v to EA) to give (3-propyl-quinolin-6-yl)-methanol and (3-isopropyl-quinolin-6-yl)-methanol (1.5 g, 34%) as a yellow oil.

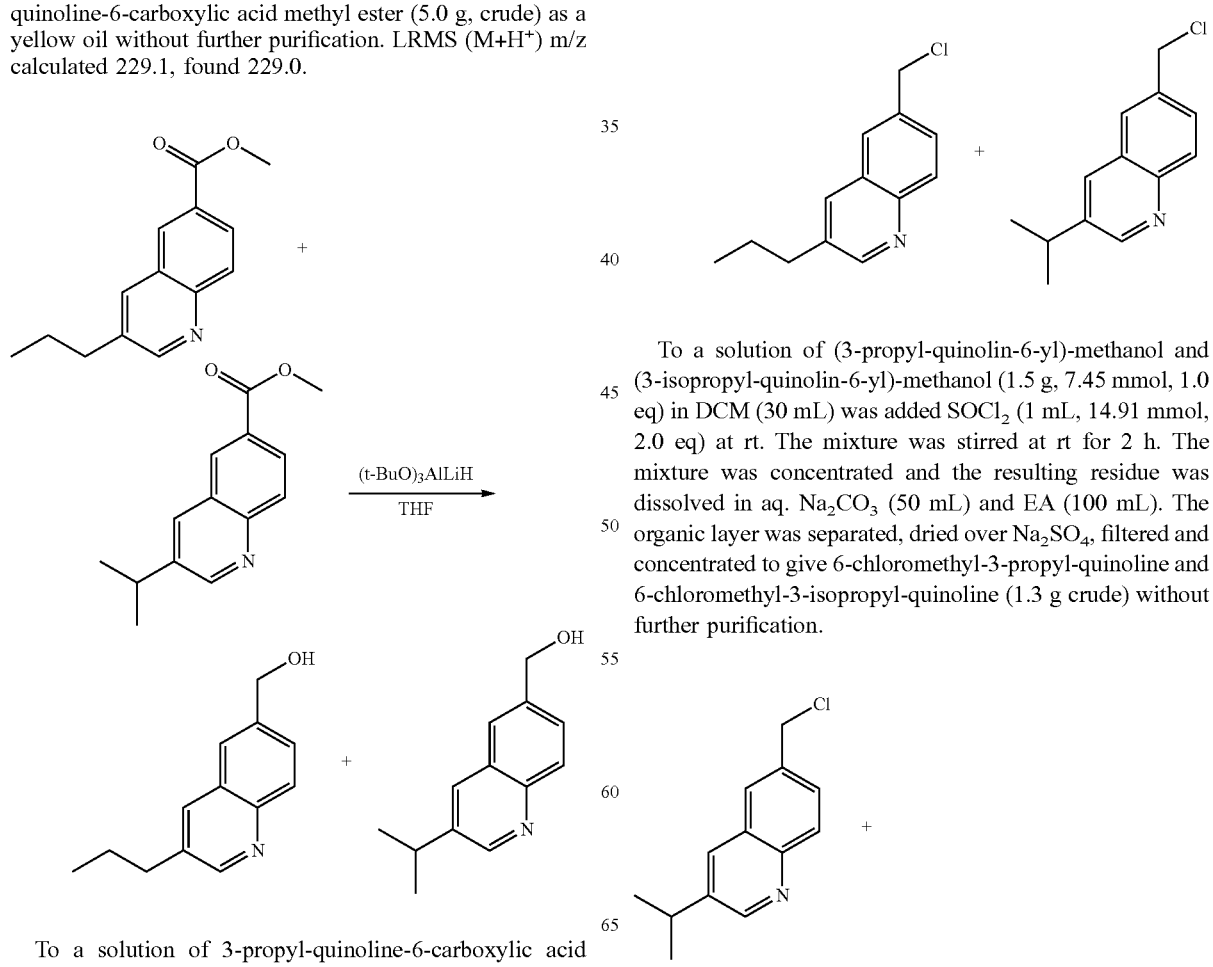

To a solution of (3-propyl-quinolin-6-yl)-methanol and (3-isopropyl-quinolin-6-yl)-methanol (1.5 g, 7.45 mmol, 1.0 eq) in DCM (30 mL) was added SOCl₂ (1 mL, 14.91 mmol, 2.0 eq) at rt. The mixture was stirred at rt for 2 h. The mixture was concentrated and the resulting residue was dissolved in aq. Na₂CO₃ (50 mL) and EA (100 mL). The organic layer was separated, dried over Na₂SO₄, filtered and concentrated to give 6-chloromethyl-3-propyl-quinoline and 6-chloromethyl-3-isopropyl-quinoline (1.3 g crude) without further purification.

627
-continued

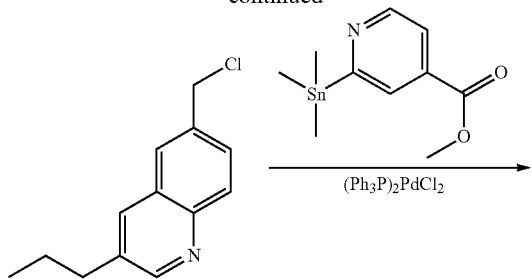 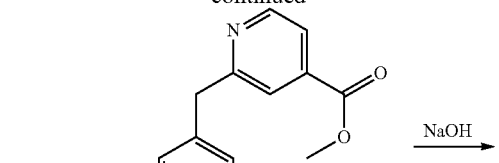

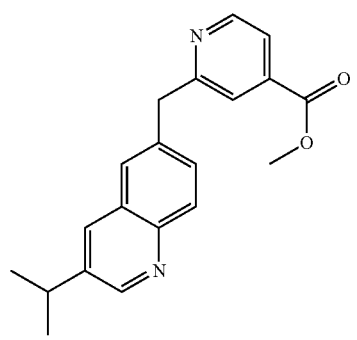  +

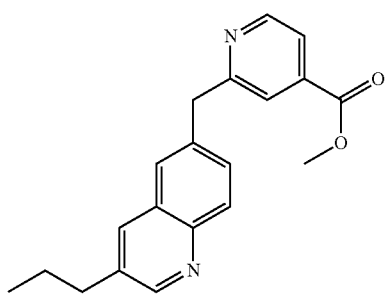

A mixture of 6-chloromethyl-3-propyl-quinoline and 6-chloromethyl-3-isopropyl-quinoline (1.3 g, 5.9 mmol, 1.0 eq), 2-trimethylstannanyl-isonicotinic acid methyl ester (1.8 g, 5.9 mmol, 1.0 eq) and Pd(Ph₃P)₂Cl₂ (414 mg, 0.59 mmol, 0.1 eq) in dioxane (50 mL) was stirred at 90° C. overnight under nitrogen. The mixture was concentrated and the resulting residue was purified by chromatography on a silica gel column (PE/EA=3/1, v/v) to give 2-(3-isopropyl-quinolin-6-ylmethyl)-isonicotinic acid methyl ester and 2-(3-propyl-quinolin-6-ylmethyl)-isonicotinic acid methyl ester (1.0 g, 53%) as a yellow oil.

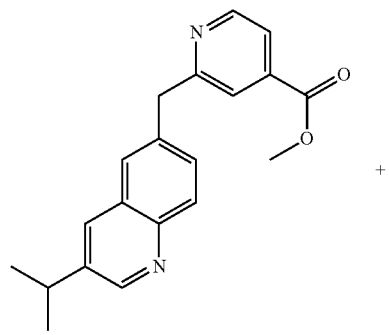  +

628
-continued

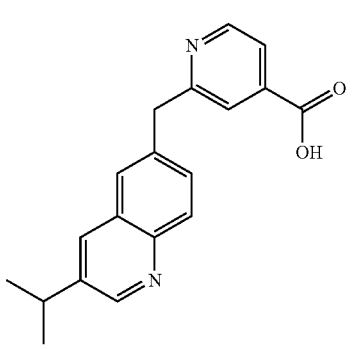

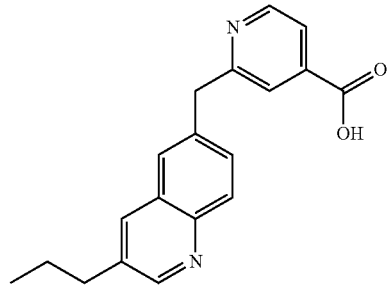  +

To a solution of 2-(3-isopropyl-quinolin-6-ylmethyl)-isonicotinic acid methyl ester and 2-(3-propyl-quinolin-6-ylmethyl)-isonicotinic acid methyl ester (1.0 g, 3.12 mmol, 1.0 eq) in THF (30 mL) was added a solution of NaOH (250 mg, 6.24 mmol, 2.0 eq) at rt. The mixture was stirred at rt for 1 h and then neutralized with 1N HCl. After concentration, the resulting residue was purified by Prep-HPLC to give 2-(3-isopropyl-quinolin-6-ylmethyl)-isonicotinic acid (300 mg, 31%) and 2-(3-propyl-quinolin-6-ylmethyl)-isonicotinic acid (542 mg, 56%).

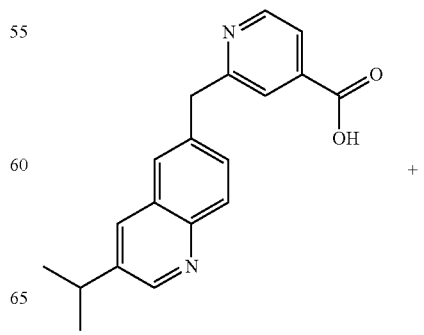  +

-continued

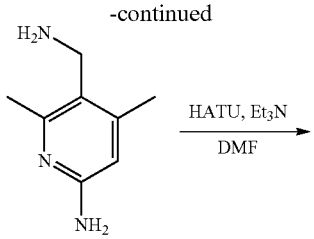

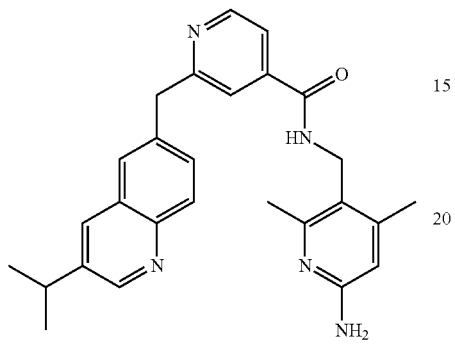

To a solution of 2-(3-isopropyl-quinolin-6-ylmethyl)-isonicotinic acid (270 mg, 0.88 mmol, 1.0 eq), 5-aminomethyl-4,6-dimethyl-pyridin-2-ylamine (200 mg, 1.32 mmol, 1.5 eq) and Et$_3$N (267 mg, 2.64 mmol, 3.0 eq) in DMF (10 mL) was added HATU (462 mg, 1.32 mmol, 1.5 eq). The mixture was stirred at rt for 2 h. The mixture was concentrated and the resulting residue was purified by Prep-HPLC to obtain N-((6-amino-2,4-dimethylpyridin-3-yl)methyl)-2-((3-isopropylquinolin-6-yl)methyl)isonicotinamide (55 mg, 14%) as a white solid.

LRMS (M+H$^+$) m/z calculated 440.2, found 440.2. $^1$H NMR (DMSO-d$_6$, 300 MHz): δ 8.77 (s, 1H), 8.62-8.57 (m, 2H), 8.06 (s, 1H), 7.87 (d, 1H), 7.75 (s, 1H), 7.70 (s, 1H), 7.60-7.58 (m, 2H), 6.09 (s, 1H), 5.67 (s, 2H), 4.31-4.30 (m, 4H), 3.11-3.06 (m, 1H), 2.27 (s, 3H), 2.13 (s, 3H), 1.30 (d, 6H).

Example 255: Preparation of N-((6-amino-2,4-dimethylpyridin-3-yl)methyl)-2-((3-propylquinolin-6-yl)methyl)isonicotinamide

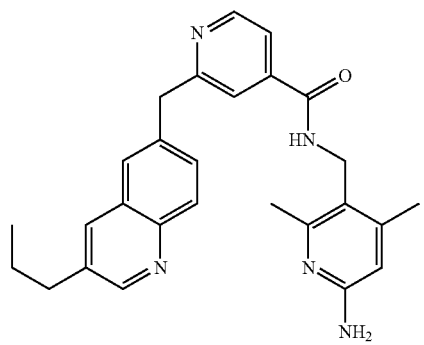

-continued

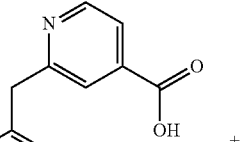

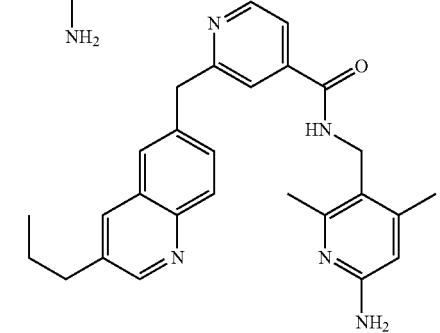

To a solution of 2-(3-propyl-quinolin-6-ylmethyl)-isonicotinic acid (50 mg, 0.16 mmol, 1.0 eq), 5-aminomethyl-4,6-dimethyl-pyridin-2-ylamine (37 mg, 0.24 mmol, 1.5 eq) and Et$_3$N (49 mg, 0.49 mmol, 3.0 eq) in DMF (10 mL) was added HATU (86 mg, 0.24 mmol, 1.5 eq). The mixture was stirred at rt for 2 h. The mixture was concentrated and the resulting residue was purified by Prep-HPLC to obtain N-((6-amino-2,4-dimethylpyridin-3-yl)methyl)-2-((3-propylquinolin-6-yl)methyl)isonicotinamide (9.5 mg, 13%) as a white solid.

LRMS (M+H$^+$) m/z calculated 440.2, found 440.2. $^1$H NMR (DMSO-d$_6$, 400 MHz): δ 8.72 (d, 1H), 8.61 (t, 1H), 8.59 (d, 1H), 8.05 (s, 1H), 7.89 (d, 1H), 7.76 (s, 1H), 7.73 (s, 1H), 7.61 (s, 1H), 7.59 (d, 1H), 6.12 (s, 1H), 5.66 (s, 2H), 4.33 (s, 2H), 4.32 (d, 2H), 2.74 (t, 2H), 2.29 (s, 3H), 2.16 (s, 3H), 1.70-1.67 (m, 2H), 0.92 (t, 3H).

Example 256: Preparation of N-((6-chloroimidazo[1,2-a]pyrimidin-3-yl)methyl)-2-((3-chloroquinolin-6-yl)methyl)isonicotinamide

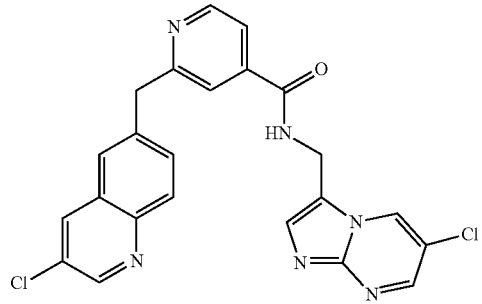

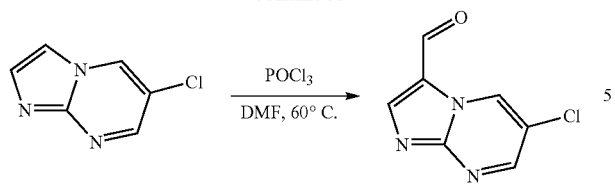

To a solution of 6-chloro-imidazo[1,2-a]pyrimidine (11.0 g, 71.6 mmol, 1.0 eq) in DMF (150 mL) was added POCl₃ (38.0 g, 250.7 mmol, 3.5 eq) at 0° C. The mixture was warmed to rt, and then heated to 60° C. for 24 h. The mixture was concentrated and the residue was purified by chromatography on a silica gel column (PE/EA=1/1, v/v) to give 6-chloro-imidazo[1,2-a]pyrimidine-3-carbaldehyde (4.0 g, 33%) as a yellow solid.

¹H NMR (DMSO-d₆, 400 MHz): δ 9.99 (s, 1H), 9.70 (d, 1H), 8.95 (d, 1H), 8.72 (d, 1H).

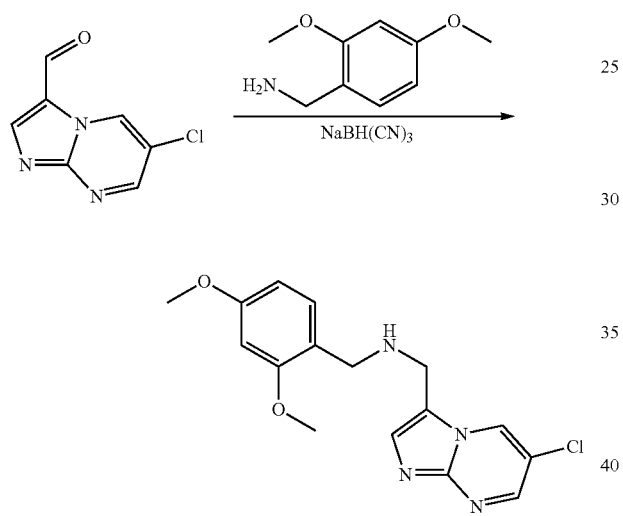

To a solution of 6-chloro-imidazo[1,2-a]pyrimidine-3-carbaldehyde (700 mg, 3.86 mmol, 1.0 eq) in DCM (20 mL) was added 2,4-dimethoxy-benzylamine (967 mg, 5.78 mmol, 1.5 eq). The mixture was stirred at rt for 30 min, and then NaBH₃CN (363 mg, 5.78 mmol, 1.5 mmol) and MeOH (2 mL) was added. The mixture was stirred at rt overnight. The mixture was concentrated and the resulting residue was purified by chromatography on a silica gel column (EA) to give (6-chloro-imidazo[1,2-a]pyrimidin-3-ylmethyl)-(2,4-dimethoxy-benzyl)-amine (300 mg, 23%) as a yellow solid.

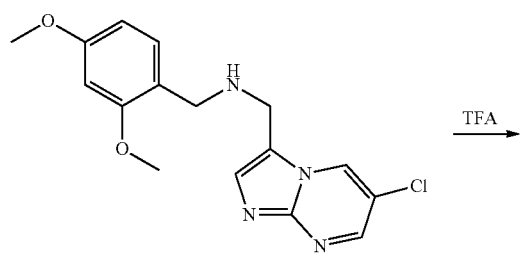

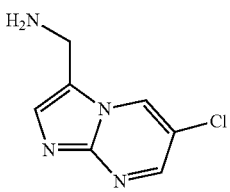

A mixture of (6-chloro-imidazo[1,2-a]pyrimidin-3-ylmethyl)-(2,4-dimethoxy-benzyl)-amine (300 mg, 0.90 mmol, 1.0 eq) in TFA (8 mL) was stirred at 60° C. for 3 h. The mixture was concentrated and the resulting residue was purified by chromatography on a silica gel column (DCM/MeOH=10/1, v/v) to give (6-chloroimidazo[1,2-a]pyrimidin-3-yl)methanamine (100 mg, 61%) as a yellow oil.

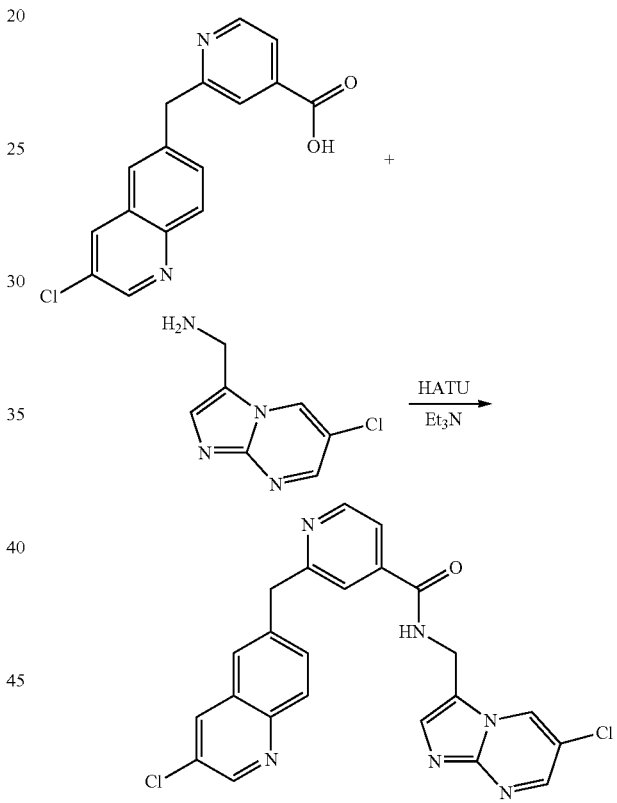

To a solution of 2-(3-chloro-quinolin-6-ylmethyl)-isonicotinic acid (100 mg, 0.33 mmol, 1.0 eq), (6-chloroimidazo[1,2-a]pyrimidin-3-yl)methanamine (74.0 mg, 0.5 mmol, 1.5 eq) and Et₃N (101 mg, 1.0 mmol) in DMF (4 mL) was added HATU (175 mg, 0.50 mmol, 1.5 eq). The mixture was stirred at rt for 2 h. The mixture was concentrated and the resulting residue was purified by Prep-HPLC to obtain N-((6-chloroimidazo[1,2-a]pyrimidin-3-yl)methyl)-2-((3-chloroquinolin-6-yl)methyl)isonicotinamide (45 mg, 30%) as a white solid.

LRMS (M+H⁺) m/z calculated 463.2, found 463.1. ¹H NMR (DMSO-d₆, 300 MHz): δ 9.24 (d, 2H), 8.80 (d, 1H), 8.61 (d, 1H), 8.56 (d, 1H), 8.48 (d, 1H), 7.94 (d, 1H), 7.81 (d, 1H), 7.75-7.68 (m, 3H), 7.58-7.56 (m, 1H), 4.78 (d, 2H), 4.34 (s, 2H).

Example 257: Preparation of N-((6-amino-2,4-dimethylpyridin-3-yl)methyl)-2-((3-(hydroxymethyl)quinolin-6-yl)methyl)isonicotinamide

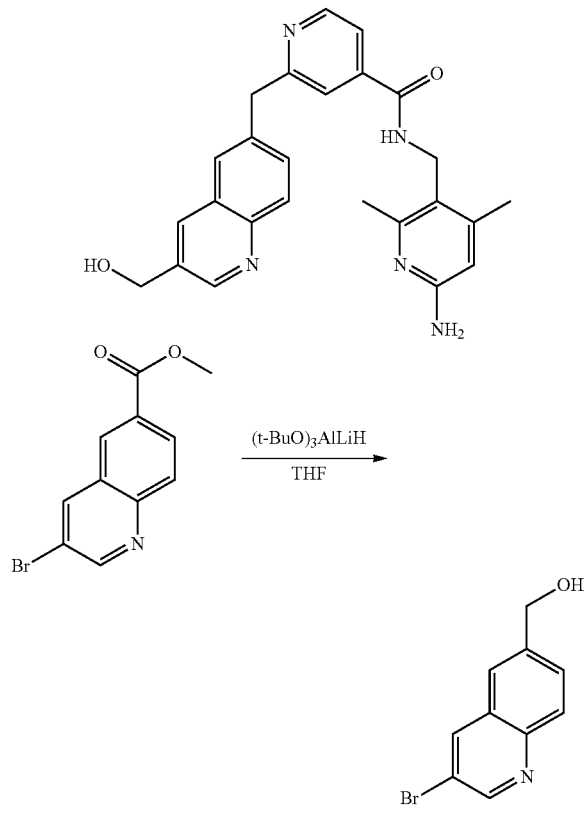

To a solution of 3-bromo-quinoline-6-carboxylic acid methyl ester (5.0 g, 18.8 mmol, 1.0 eq) in THF (50 mL) was added (t-BuO)₃AlLiH (14.3 g, 56.4 mmol, 3.0 eq) at rt. The mixture was stirred at 60° C. for 20 h. After concentration, the resulting residue was purified by chromatography on a silica gel column (PE/EA=1/1, v/v) to give (3-bromo-quinolin-6-yl)-methanol (3.0 g, 67%) as a white solid.

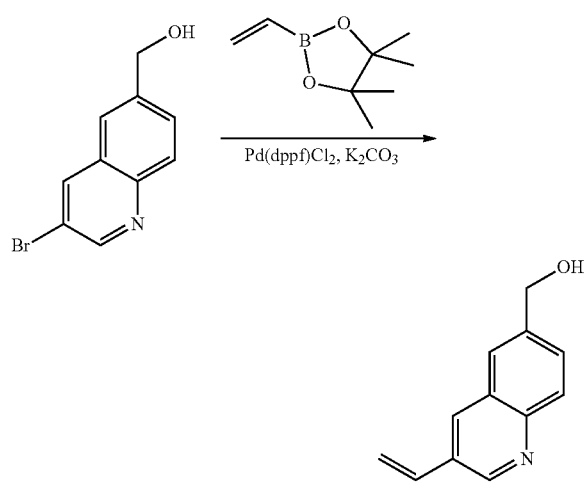

A mixture of (3-bromo-quinolin-6-yl)-methanol (12.0 g, 50.4 mmol, 1.0 eq), 4,4,5,5-tetramethyl-2-vinyl-[1,3,2]dioxaborolane (38.8 g, 252.01 mmol, 5.0 eq), Pd(dppf)Cl₂ (4.1 g, 5.04 mmol, 0.1 eq) and K₂CO₃ (20.9 g, 151.2 mmol, 3.0 eq) in dioxane (100 mL) and water (10 mL) was stirred at 100° C. under nitrogen overnight. The mixture was concentrated and the resulting residue was purified by chromatography on a silica gel column (PE/EA=1/1) to give (3-vinyl-quinolin-6-yl)-methanol (6.0 g, 64%) as a yellow solid.

¹H NMR (DMSO-d₆, 300 MHz): δ 9.04 (d, 1H), 8.33 (d, 1H), 7.99-7.87 (m, 2H), 7.73-7.66 (m, 1H), 6.99-6.89 (m, 1H), 6.15 (d, 1H), 5.51-5.40 (m, 2H), 4.71 (d, 2H).

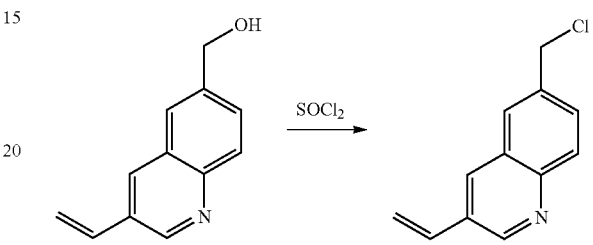

To a solution of (3-vinyl-quinolin-6-yl)-methanol (6.0 g, 32.4 mmol, 1.0 eq) in DCM (20 mL) was added SOCl₂ (19.2 g, 161.9 mmol) at 0° C. The mixture was stirred at room temperature for 4 h. The mixture was concentrated, and then EA (200 mL) was added. The organic solution was washed with aq. Na₂CO₃ (20 mL×3), dried over Na₂SO₄, filtered and concentrated. The resulting residue was purified by chromatography on a silica gel column (PE/EA=3/1, v/v) to give 6-chloromethyl-3-vinyl-quinoline (4.0 g, 61%) as a yellow solid.

¹H NMR (CDCl₃, 300 MHz): δ 8.96 (d, 1H), 8.74 (d, 1H), 8.03-8.00 (m, 2H), 7.76 (d, 1H), 6.90-6.81 (m, 1H), 6.00 (d, 1H), 5.45 (d, 1H), 4.40 (s, 2H).

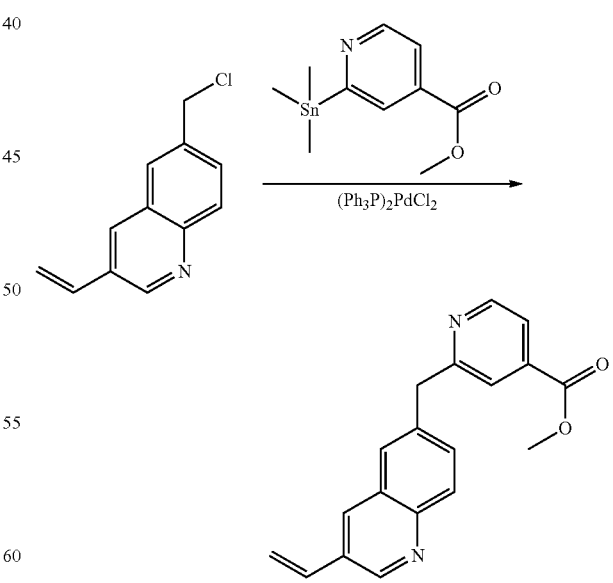

A mixture of 6-chloromethyl-3-vinyl-quinoline (4.0 g, 19.6 mmol, 1.0 eq), 2-trimethylstannanyl-isonicotinic acid methyl ester (5.9 g, 19.6 mmol, 1.0 eq), (PPh₃)₂PdCl₂ (1.4 g, 1.96 mmol, 0.1 eq) and K₂CO₃ (8.1 g, 58.9 mmol, 3.0 eq) in DMF (30 mL) was stirred at 90° C. under nitrogen for 5 h. The mixture was concentrated and the residue was purified by chromatography on a silica gel column (PE/EA=3/1, v/v) to give 2-(3-vinyl-quinolin-6-ylmethyl)-isonicotinic acid methyl ester (2.0 g, 34%) as a yellow solid.

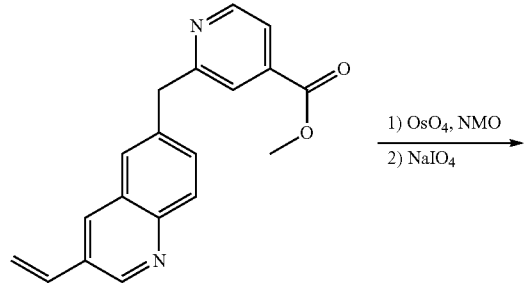

To a solution of 2-(3-vinyl-quinolin-6-ylmethyl)-isonicotinic acid methyl ester (2.0 g, 6.57 mmol, 1.0 eq) in acetone (20 mL) was added OsO₄ (83 mg, 0.33 mmol, 0.05 eq) and NMO (1.5 g, 13.14 mmol, 2.0 eq). The mixture was stirred at room temperature overnight. The reaction mixture was concentrated and aq.Na₂CO₃ (20 mL) was added, extracted with DCM/MeOH (10/1, 50 mL×3). The organic layers were combined and dried over Na₂SO₄, filtered and concentrated. The resulting residue was used in next step without further purification. To an acetone (20 mL) solution of the above product was added NaIO₄ (2.8 g, 13.1 mmol, 2.0 eq) and water (5 mL). The mixture was stirred at rt for 2 h. It was concentrated and the resulting residue was purified by chromatography on a silica gel column (PE/EA=2/1, v/v) to give 2-(3-formyl-quinolin-6-ylmethyl)-isonicotinic acid methyl ester (500 mg, 24%) as a yellow solid.

¹H NMR (DMSO-d₆, 300 MHz): δ 10.21 (s, 1H), 9.21 (d, 1H), 8.89 (d, 1H), 8.71 (d, 1H), 8.08-8.03 (m, 2H), 7.89-7.84 (m, 2H), 7.66-7.70 (m, 1H), 4.44 (s, 2H), 3.85 (s, 3H).

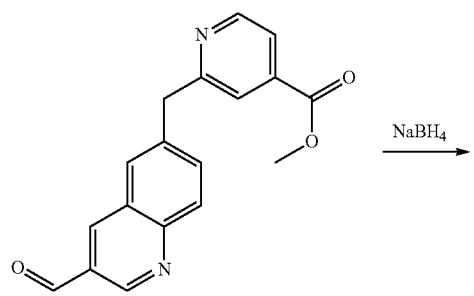

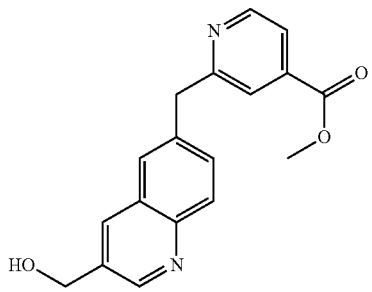

To a solution of 2-(3-formyl-quinolin-6-ylmethyl)-isonicotinic acid methyl ester (200 mg, 0.65 mmol, 1.0 eq) in MeOH was added NaBH₄ (25 mg, 0.65 mmol, 1.0 eq) at 0° C. The mixture was stirred at 0° C. for 2 h. The mixture was concentrated and the resulting residue was purified by chromatography on a silica gel column (DCM/MeOH=10/1, v/v) to give 2-(3-hydroxymethyl-quinolin-6-ylmethyl)-isonicotinic acid methyl ester (150 mg, 75%) as a yellow solid.

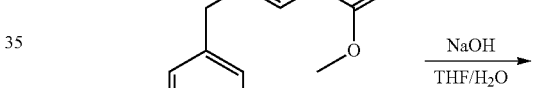

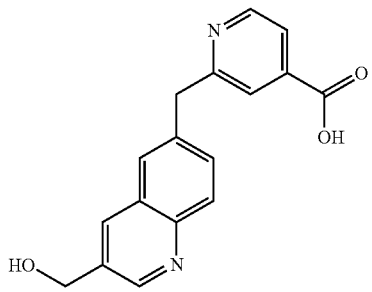

To a solution of 2-(3-hydroxymethyl-quinolin-6-ylmethyl)-isonicotinic acid methyl ester (150 mg, 0.49 mmol, 1.0 eq) in THF (4 mL) and water (1 mL) was added NaOH (39 mg, 0.97 mmol, 2.0 eq). The mixture was stirred at room temperature for 2 h. 2 N aq. HCl was added to adjust pH 3, extracted with DCM. The organic layer was separated, dried over Na₂SO₄, filtered and concentrated to give 2-(3-hydroxymethyl-quinolin-6-ylmethyl)-isonicotinic acid (150 mg, crude) without further purification.

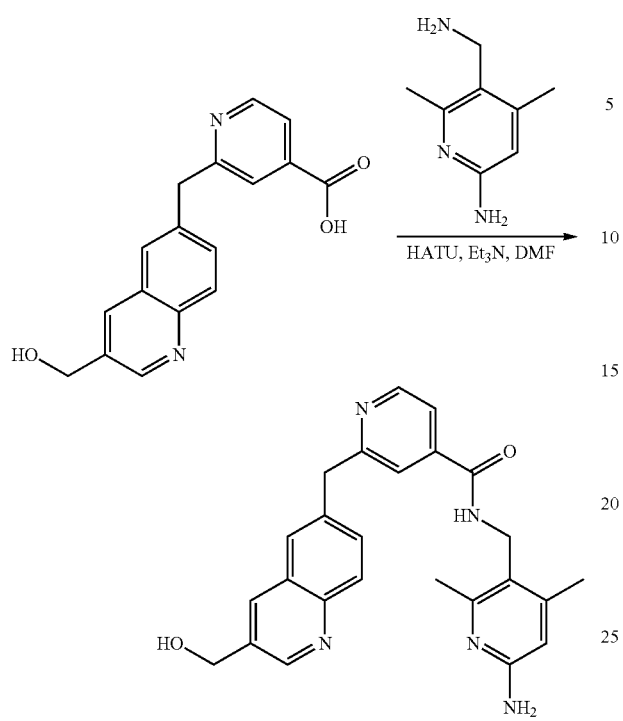

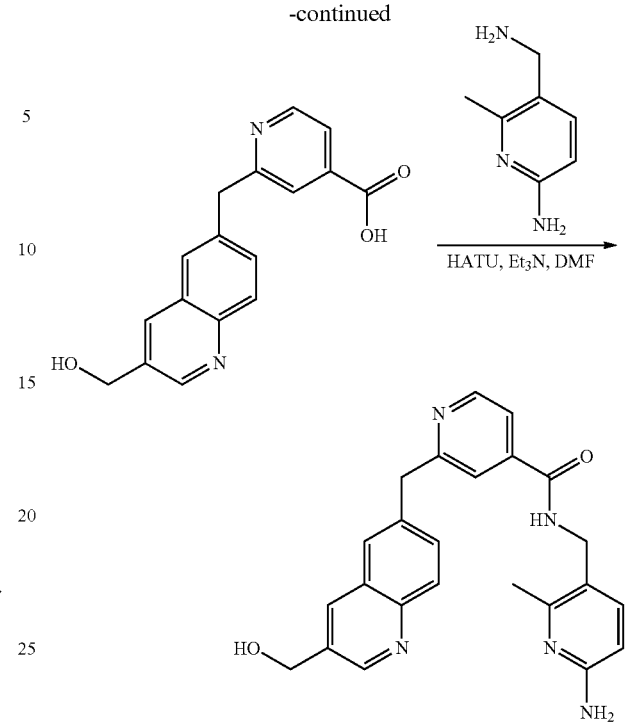

To a solution of 2-(3-hydroxymethyl-quinolin-6-ylmethyl)-isonicotinic acid (60 mg, 0.2 mmol, 1.0 eq), 5-aminomethyl-4,6-dimethyl-pyridin-2-ylamine (46.0 mg, 0.3 mmol, 1.5 eq) and Et₃N (61 mg, 0.6 mmol) in DMF (3 mL) was added HATU (105 mg, 0.3 mmol, 1.5 eq). The mixture was stirred at rt for 2 h. The mixture was concentrated and the resulting residue was purified by Prep-HPLC to provide N-((6-amino-2,4-dimethylpyridin-3-yl)methyl)-2-((3-(hydroxymethyl)quinolin-6-yl)methyl)isonicotinamide (8.0 mg, 11%) as a white solid.

LRMS (M+H⁺) m/z calculated 428.2, found 428.2. ¹H NMR (DMSO-d₆, 300 MHz): δ 8.78 (s, 1H), 8.60-8.57 (m, 2H), 8.13 (s, 1H), 7.89 (d, 1H), 7.80 (d, 1H), 7.71 (s, 1H), 7.62-7.56 (m, 2H), 6.11 (s, 1H), 5.71 (br, 2H), 5.40 (t, 1H), 4.68 (d, 2H), 4.31 (s, 4H), 2.28 (s, 3H), 2.15 (s, 3H).

Example 258: Preparation of N-((6-amino-2-methylpyridin-3-yl)methyl)-2-((3-(hydroxymethyl)quinolin-6-yl)methyl)isonicotinamide To a solution of 2-(3-hydroxymethyl-quinolin-6-ylmethyl)-isonicotinic acid (60 mg, 0.2 mmol, 1.0 eq), 5-aminomethyl-6-methyl-pyridin-2-ylamine (41.0 mg, 0.3 mmol, 1.5 eq) and Et₃N (61 mg, 0.6 mmol) in DMF (3 mL) was added HATU (105 mg, 0.3 mmol, 1.5 eq). The mixture was stirred at rt for 2 h. The mixture was concentrated and the resulting residue was purified by Prep-HPLC to afford N-((6-amino-2-methylpyridin-3-yl)methyl)-2-((3-(hydroxymethyl)quinolin-6-yl)methyl)isonicotinamide (6.0 mg, 11%) as a white solid.

LRMS (M+H⁺) m/z calculated 414.2, found 414.2. ¹H NMR (DMSO-d₆, 300 MHz): δ 8.94-8.92 (m, 1H), 8.78 (d, 1H), 8.60 (d, 1H), 8.13 (s, 1H), 7.90 (d, 1H), 7.81 (s, 1H), 7.72 (s, 1H), 7.63-7.59 (m, 2H), 7.20 (d, 1H), 6.20 (d, 1H), 5.67 (d, 2H), 5.40 (t, 1H), 4.67 (d, 2H), 4.32 (s, 2H), 4.25 (d, 2H), 2.25 (s, 3H).

Example 259: Preparation of 2-((3-chloroquinolin-6-yl)methyl)-N-((6-fluoro-1H-indol-5-yl)methyl)isonicotinamide

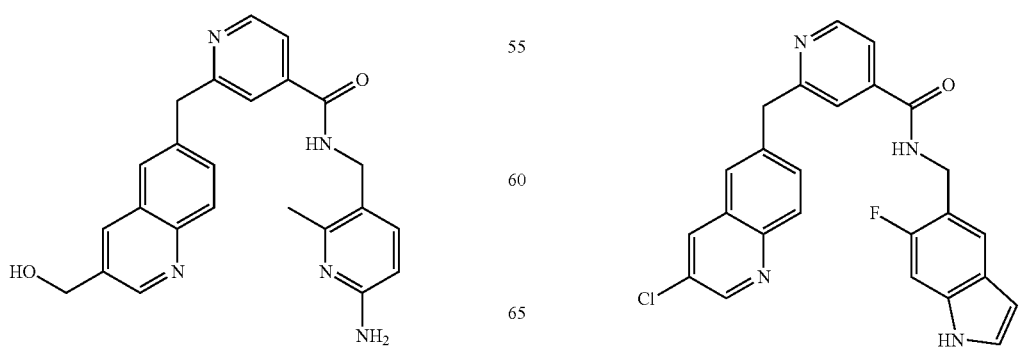

639

-continued

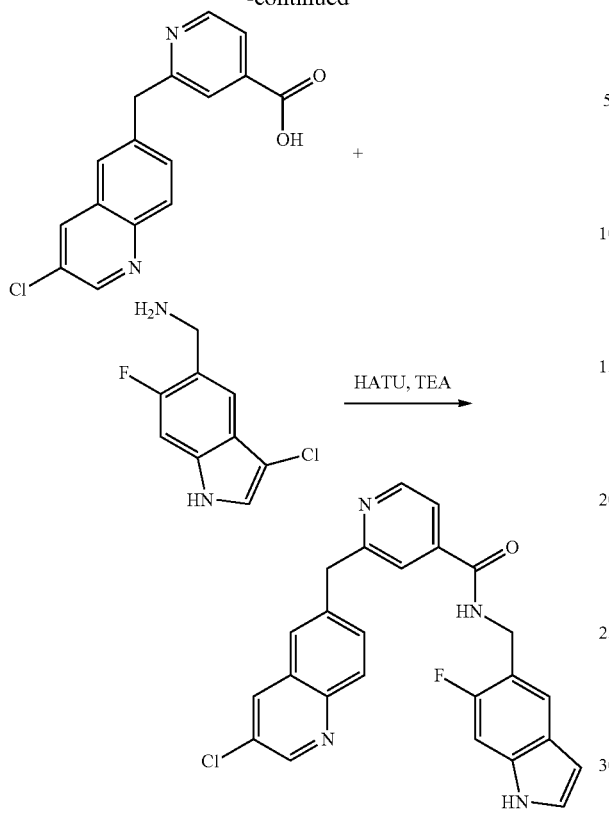

HATU, TEA

To a solution of 2-(3-hydroxymethyl-quinolin-6-ylmethyl)-isonicotinic acid (100 mg, 0.33 mmol, 1.0 eq), (3-chloro-6-fluoro-1H-indol-5-yl)methanamine (66 mg, 0.40 mmol, 1.2 eq) and Et$_3$N (100 mg, 1.0 mmol, 3 eq) in DMF (3 mL) was added HATU (140 mg, 0.37 mmol, 1.1 eq). The mixture was stirred at rt for 2 h. The mixture was concentrated and the resulting residue was purified by Prep-HPLC to give 2-((3-chloroquinolin-6-yl)methyl)-N-((6-fluoro-1H-indol-5-yl)methyl)isonicotinamide (39 mg, 26%) as an off white solid.

LRMS (M+H$^+$) m/z calculated 445.1, found 445.1. $^1$H NMR (DMSO-d$_6$, 400 MHz): δ 11.09 (s, 1H), 9.19 (t, 1H), 8.83 (d, 1H), 8.65 (d, 1H), 8.52 (d, 1H), 7.99 (d, 1H), 7.85 (s, 1H), 7.81 (s, 1H), 7.73 (d, 1H), 7.68 (d, 1H), 7.49 (d, a H), 7.30 (d, 1H), 7.15 (d, 1H), 6.39 (s, 1H), 4.56 (d, 2H), 4.38 (d, 2H).

Example 260: Preparation of 2-((3-chloroquinolin-6-yl)methyl)-N-((6-fluoro-1H-indazol-5-yl)methyl)isonicotinamide

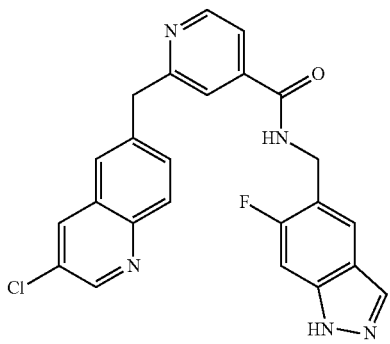

640

-continued

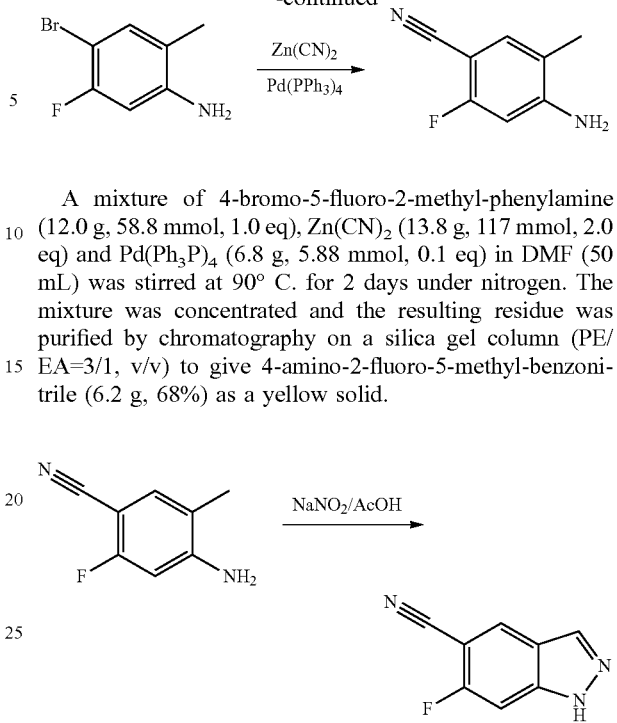

A mixture of 4-bromo-5-fluoro-2-methyl-phenylamine (12.0 g, 58.8 mmol, 1.0 eq), Zn(CN)$_2$ (13.8 g, 117 mmol, 2.0 eq) and Pd(Ph$_3$P)$_4$ (6.8 g, 5.88 mmol, 0.1 eq) in DMF (50 mL) was stirred at 90° C. for 2 days under nitrogen. The mixture was concentrated and the resulting residue was purified by chromatography on a silica gel column (PE/EA=3/1, v/v) to give 4-amino-2-fluoro-5-methyl-benzonitrile (6.2 g, 68%) as a yellow solid.

To a solution of 4-amino-2-fluoro-5-methyl-benzonitrile (6.2 g, 41.3 mmol, 1.0 eq) in AcOH (30 mL) was added NaNO$_2$ (5.6 g, 82.6 mmol, 2.0 eq) at 0° C. The mixture was stirred at rt overnight. The mixture was concentrated and the resulting residue was purified by chromatography on a silica gel column (PE/EA=3/1, v/v) to give 6-fluoro-1H-indazole-5-carbonitrile (2.0 g, purity 80%) as a yellow solid.

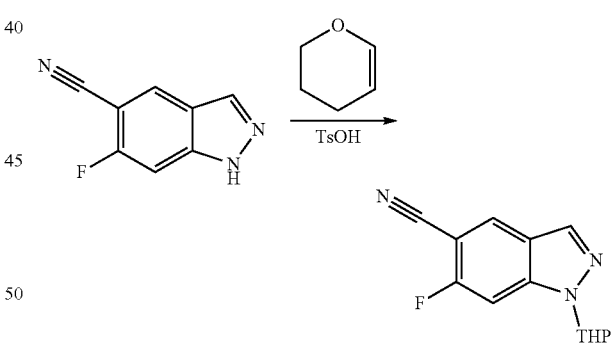

To a solution of 6-fluoro-1H-indazole-5-carbonitrile (1.0 g, 6.2 mmol, 1.0 eq) and 3,4-dihydro-2H-pyran (1.0 g, 12.4 mmol, 2.0 eq) in DCM (15 mL) was added TsOH (106 mg, 0.62 mmol, 0.1 eq). The mixture was stirred at room temperature overnight. The mixture was concentrated and the resulting residue was purified by chromatography on a silica gel column (PE/EA=3/1, v/v) to give 6-fluoro-1-(tetrahydro-pyran-2-yl)-1H-indazole-5-carbonitrile (1.0 g, 67%) as a yellow solid.

$^1$H NMR (CDCl$_3$, 300 MHz): δ 8.07-8.04 (m, 2H), 7.41 (d, 1H), 5.69-5.65 (m, 1H), 4.01-3.97 (m, 1H), 3.78-3.71 (m, 1H), 2.47-2.42 (m, 1H), 2.12-2.09 (m, 1H), 1.81-1.67 (m, 4H).

641

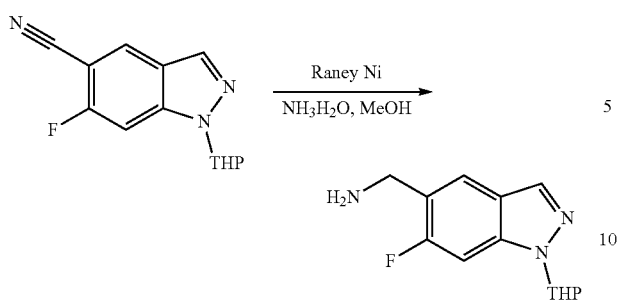

To a solution of 6-fluoro-1-(tetrahydro-pyran-2-yl)-1H-indazole-5-carbonitrile (400 mg, 1.63 mmol, 1.0 eq) in MeOH (10 mL) and NH$_3$.H$_2$O (1 mL) was added Raney Ni (40 mg, 10% wt) at rt. The mixture was stirred at rt for 4 h under hydrogen. The reaction solution was filtered and the filtrate was concentrated to give (6-fluoro-1-(tetrahydro-2H-pyran-2-yl)-1H-indazol-5-yl)methanamine (400 mg, crude) as a yellow solid without further purification.

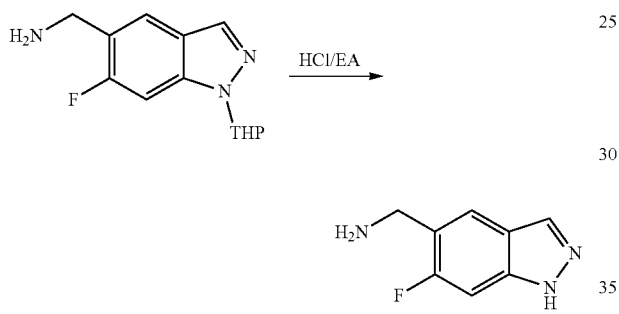

To a solution of (6-fluoro-1-(tetrahydro-2H-pyran-2-yl)-1H-indazol-5-yl)methanamine (400 mg, 1.61 mmol, 1.0 eq) in EA (10 mL) was added HCl/EA (10 mL). The mixture was stirred at room temperature for overnight. The mixture was concentrated to give (6-fluoro-1H-indazol-5-yl)methanamine (300 mg, crude) as a white solid without further purification.

642

-continued

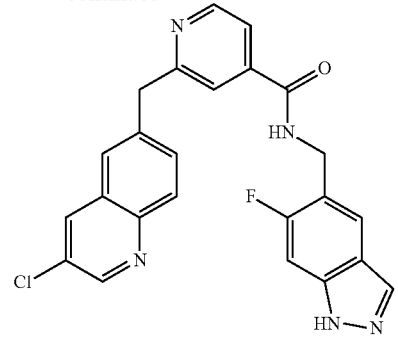

To a solution of 2-(3-chloro-quinolin-6-ylmethyl)-isonicotinic acid (70 mg, 0.23 mmol, 1.0 eq), (6-fluoro-1H-indazol-5-yl)methanamine (58.0 mg, 0.35 mmol, 1.5 eq) and Et$_3$N (70 mg, 0.370 mmol) in DMF (4 mL) was added HATU (122 mg, 0.35 mmol, 1.5 eq). The mixture was stirred at rt for 2 h. The mixture was concentrated and the resulting residue was purified by Prep-HPLC to obtain 2-((3-chloro-quinolin-6-yl)methyl)-N-((6-fluoro-1H-indazol-5-yl)methyl)isonicotinamide (38 mg, 37%) as a white solid.

LRMS (M+H$^+$) m/z calculated 446.1, found 446.1. $^1$H NMR (DMSO-d$_6$, 300 MHz): δ 13.07 (br., 1H), 9.28-9.24 (m, 1H), 8.83 (d, 1H), 8.65 (d, 1H), 8.52 (d, 1H), 8.05 (s, 1H), 7.98 (d, 1H), 7.85 (s, 1H), 7.80 (s, 1H), 7.76-7.67 (m, 3H), 7.33 (d, 1H), 4.56 (d, 2H), 4.37 (s, 2H).

Example 261: Preparation of 2-((3-chloroquinolin-6-yl)methyl)-N-((3-methyl-1H-indazol-5-yl)methyl)isonicotinamide

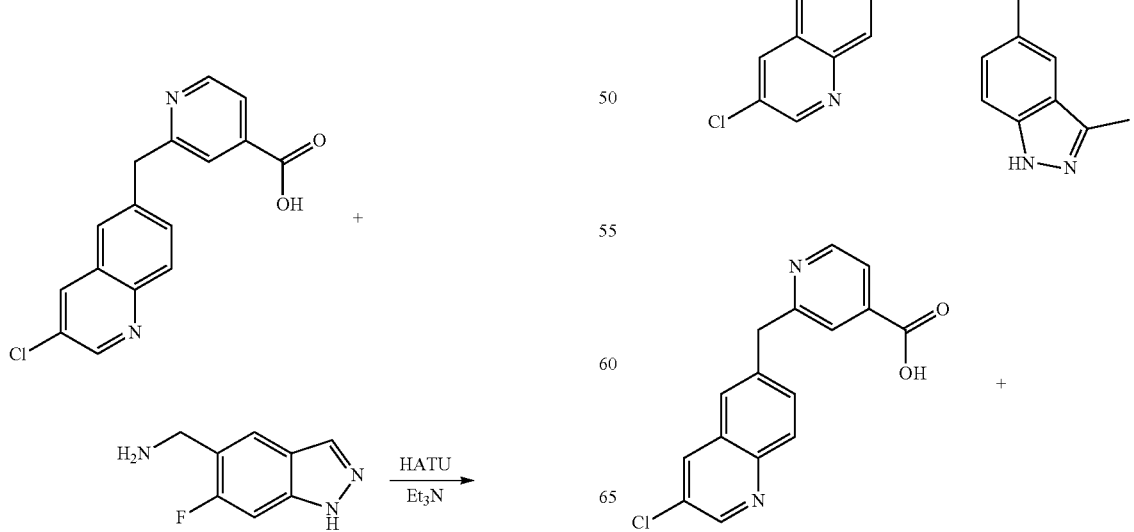

643

-continued

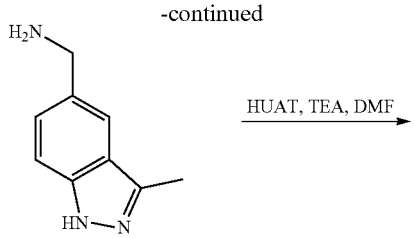

HUAT, TEA, DMF →

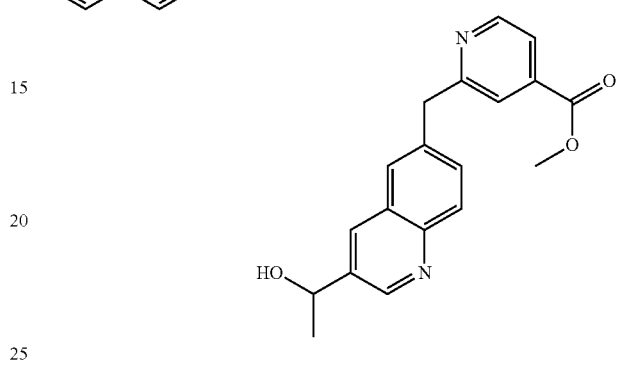

To a solution of 2-(3-chloro-quinolin-6-ylmethyl)-isonicotinic acid (50 mg, 0.17 mmol, 1.0 eq), (3-methyl-1H-indazol-5-yl)methanamine (33 mg, 0.20 mmol, 1.2 eq) and Et₃N (69 mg, 0.68 mmol, 4 eq) in DMF (4 mL) was added HATU (71 mg, 0.19 mmol, 1.1 eq). The mixture was stirred at rt for 2 h. The mixture was concentrated and the resulting residue was purified by Prep-HPLC to provide 2-((3-chloroquinolin-6-yl)methyl)-N-((3-methyl-1H-indazol-5-yl)methyl)isonicotinamide (23 mg, 31%) as a white solid.

LRMS (M+H⁺) m/z calculated 446.1, found 446.1. ¹H NMR (DMSO-d₆, 300 MHz): δ 12.57 (s., 1H), 9.27 (t, 1H), 8.82 (d, 1H), 8.64 (d, 1H), 8.51 (d, 1H), 7.97 (d, 1H), 7.85 (s, 1H), 7.78 (s, 1H), 7.73 (dd, 1H), 7.66 (dd, 1H), 7.60 (s, 1H), 7.40 (d, 1H), 7.29 (d, 1H), 4.56 (d, 2H), 4.37 (s, 2H), 2.45 (s, 3H).

Example 262: Preparation of N-((6-amino-2,4-dimethylpyridin-3-yl)methyl)-2-((3-(1-hydroxyethyl)quinolin-6-yl)methyl)isonicotinamide

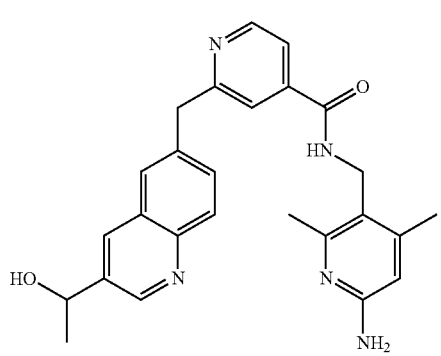

644

-continued

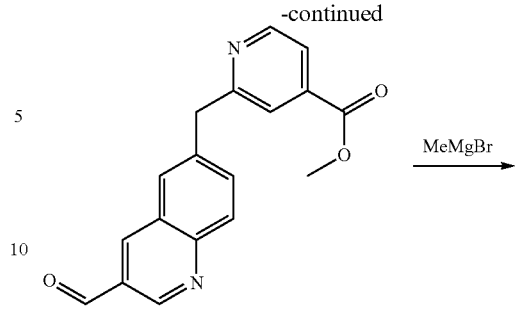

MeMgBr →

To a solution of 2-(3-formyl-quinolin-6-ylmethyl)-isonicotinic acid methyl ester (1.0 g, 3.17 mmol, 1.0 eq) in THF (10 mL) was added MeMgBr (1.6 mL, 3 M, 4.9 mmol, 1.5 eq) at −78° C. The mixture was stirred at the same temperature for 5 h and quenched with aq. NH₄Cl and extracted with EA (30 mL×3). The organic layers were dried over Na₂SO₄, filtered and concentrated. The resulting residue was purified by chromatography on a silica gel column (EA) to give 2-[3-(1-hydroxy-ethyl)-quinolin-6-ylmethyl]-isonicotinic acid methyl ester (100 mg, 10%) as a yellow oil. ¹H NMR (DMSO-d₆, 300 MHz): δ 8.87 (d, 1H), 8.72 (d, 1H), 8.06-8.02 (m, 2H), 7.74-7.59 (m, 4H), 5.34 (d, 1H), 5.16-5.10 (m, 1H), 4.40 (s, 2H), 3.91 (s, 3H), 1.68 (d, 3H).

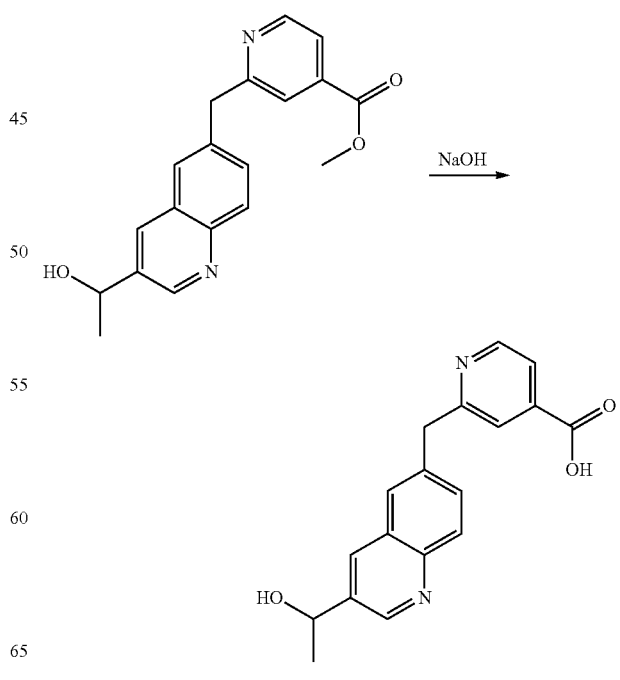

NaOH →

To a solution of 2-[3-(1-Hydroxy-ethyl)-quinolin-6-ylmethyl]-isonicotinic acid methyl ester (100 mg, 0.31 mmol, 1.0 eq) in THF (4 mL) and water (1 mL) was added NaOH (25 mg, 0.62 mmol, 2.0 eq). The mixture was stirred at rt for 2 h. 2 N HCl was added to adjust to pH 3, and then extracted with DCM. The organic layer was concentrated to give 2-[3-(1-hydroxy-ethyl)-quinolin-6-ylmethyl]-isonicotinic acid (80 mg, crude) without further purification.

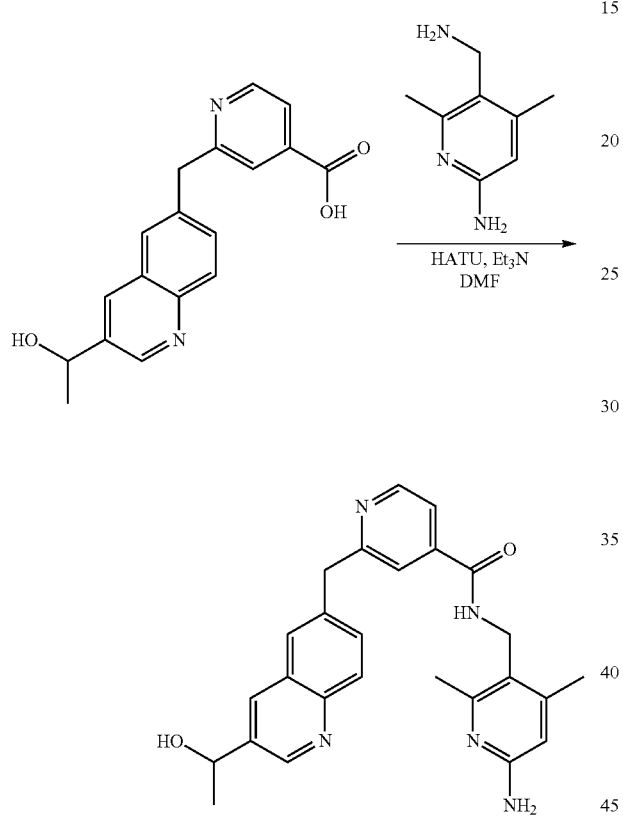

To a solution of 2-[3-(1-hydroxy-ethyl)-quinolin-6-ylmethyl]-isonicotinic acid (40 mg, 0.13 mmol, 1.0 eq), 5-aminomethyl-4,6-dimethyl-pyridin-2-ylamine (29 mg, 0.19 mmol, 1.5 eq) and Et$_3$N (38 mg, 0.38 mmol) in DMF (4 mL) was added HATU (66 mg, 0.19 mmol, 1.5 eq). The mixture was stirred at rt for 2 h. The mixture was concentrated and the resulting residue was purified by Prep-HPLC to afford N-((6-amino-2,4-dimethylpyridin-3-yl)methyl)-2-((3-(1-hydroxyethyl)quinolin-6-yl)methyl)isonicotinamide (6.0 mg, 11%) as a white solid.

LRMS (M+H$^+$) m/z calculated 442.2, found 442.2. $^1$H NMR (DMSO-d$_6$, 400 MHz): δ 8.85 (d, 1H), 8.62-8.59 (m, 2H), 8.15 (d, 1H), 7.90 (d, 1H), 7.82 (d, 1H), 7.72 (s, 1H), 7.64-7.58 (m, 2H), 6.11 (s, 1H), 5.64 (s, 2H), 5.44 (br/s, 1H), 4.97-4.92 (m, 1H), 4.33 (d, 2H), 4.32 (s, 2H), 2.29 (s, 3H), 2.15 (s, 3H), 1.43 (d, 3H).

Example 263: Preparation of N-((6-amino-2-methylpyridin-3-yl)methyl)-2-((3-(1-hydroxyethyl)quinolin-6-yl)methyl)isonicotinamide

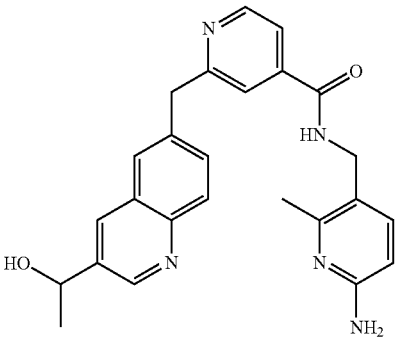 [SMILES: Cc1nc(N)ccc1CNC(=O)c1ccnc(Cc2ccc3ncc(C(C)O)cc3c2)c1]

To a solution of 2-[3-(1-hydroxy-ethyl)-quinolin-6-ylmethyl]-isonicotinic acid (40 mg, 0.13 mmol, 1.0 eq), 5-aminomethyl-6-methyl-pyridin-2-ylamine (26 mg, 0.19 mmol, 1.5 eq) and Et$_3$N (38 mg, 0.38 mmol) in DMF (4 mL) was added HATU (66 mg, 0.19 mmol, 1.5 eq). The mixture was stirred at rt for 2 h. The mixture was concentrated and the resulting residue was purified by Prep-HPLC to obtain N-((6-amino-2-methylpyridin-3-yl)methyl)-2-((3-(1-hydroxyethyl)quinolin-6-yl)methyl)isonicotinamide (7.0 mg, 11%) as a white solid.

LRMS (M+H$^+$) m/z calculated 428.2, found 428.2. $^1$H NMR (DMSO-d$_6$, 300 MHz): δ 8.96-8.94 (m, 1H), 8.83 (d, 1H), 8.60 (d, 1H), 8.14 (s, 1H), 7.90 (d, 1H), 7.80 (s, 1H), 7.71 (s, 1H), 7.63-7.58 (m, 2H), 7.20 (d, 1H), 6.20 (d, 1H), 5.69 (s, 1H), 5.41 (d, 1H), 4.94-4.91 (m, 1H), 4.31 (s, 2H), 4.27 (d, 2H), 2.25 (s, 3H), 1.41 (d, 3H).

Example 264: Preparation of N-((6-amino-2,4-dimethylpyridin-3-yl)methyl)-2-((3-methoxyquinolin-6-yl)methyl)isonicotinamide

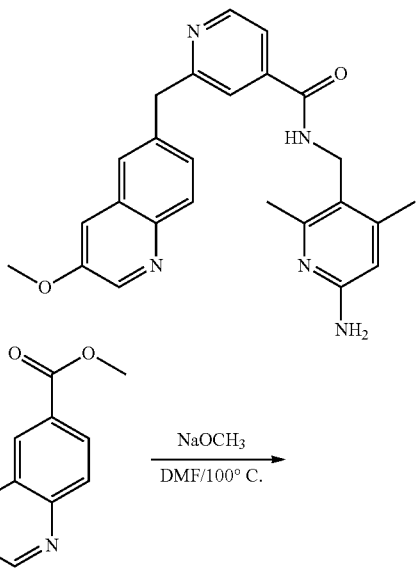

-continued

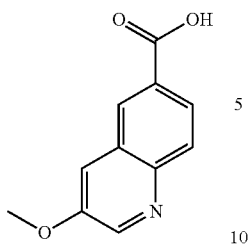

-continued

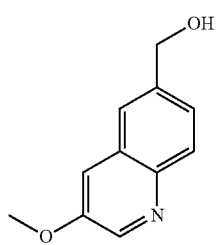

To a solution of 3-bromo-quinoline-6-carboxylic acid methyl ester (5.0 g, 18.8 mmol, 1.0 eq) in DMF (120 mL) was added CH₃ONa (4.05 g, 75 mmol, 4 eq). The mixture was heated at 100° C. with stirring for 3 h. Then it was evaporated to dryness in vacuo and the resulting residue was purified by chromatography on a silica gel column (PE/EA=10/1, v/v) to get 3-methoxy-quinoline-6-carboxylic acid (1.2 g, 31%) as a yellow solid.

LRMS (M+H⁺) m/z calculated 204.06, found 204.1. ¹H NMR (DMSO-d6, 300 MHz): δ 8.61 (d, 1H), 8.46 (s, 1H), 8.13 (d, 1H), 7.86 (d, 1H), 7.77 (s, 1H), 3.89 (s, 3H).

To a solution of 3-methoxy-quinoline-6-carboxylic acid methyl ester (700 mg, 3.23 mmol, 1.0 eq) in THF (20 mL) was added LiAlH(Ot-Bu)₃ (2.44 g, 9.69 mmol, 3.0 eq). The mixture was heated at 60° C. with stirring overnight. The sergnette salt was added and extracted with EA. The organic phase were dried over Na₂SO₄, filtrated and concentrated in vacuo. The resulting residue was purified by chromatography on a silica gel column (PE/EA=10/1, v/v) to get (3-methoxy-quinolin-6-yl)-methanol (310 mg, 51%) as a white solid.

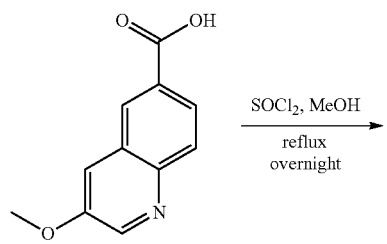

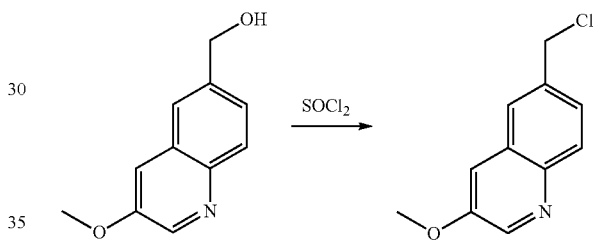

A mixture of (3-methoxy-quinolin-6-yl)-methanol (600, 6.74 mmol) in 20 mL SOCl₂ (20 mL) was stirred at rt for 2 h. Then the SOCl₂ was removed in vacuo, saturated aqueous NaHCO₃ was added and the mixture was extracted with DCM. The combined organic layers were dried over MgSO₄, filtrated and concentrated to get 6-chloromethyl-3-methoxy-quinoline (560 mg, 85%) as a yellow solid.

To a solution of 3-methoxy-quinoline-6-carboxylic acid (1.0 g, 5 mmol, 1.0 eq) in MeOH (50 mL) was added SOCl₂ (1.1 mL, 15 mmol, 3.0 eq). The mixture was heated at 80° C. overnight. The mixture was evaporated to dryness in vacuo to get 3-methoxy-quinoline-6-carboxylic acid methyl ester (1 g, 93.6%) as a yellow solid.

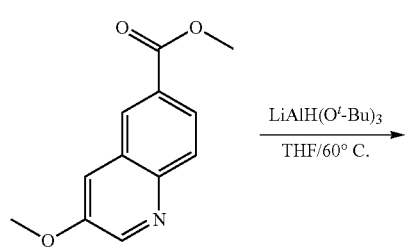

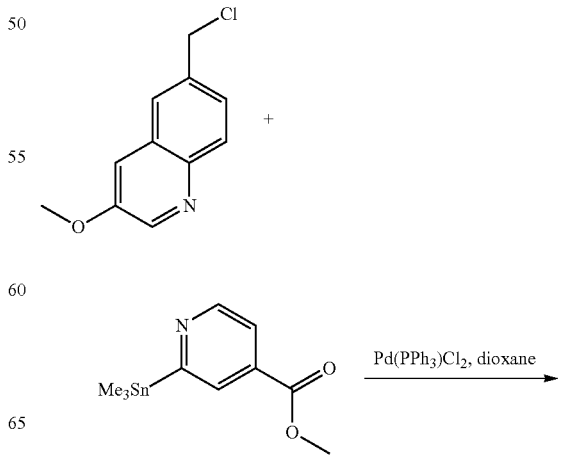

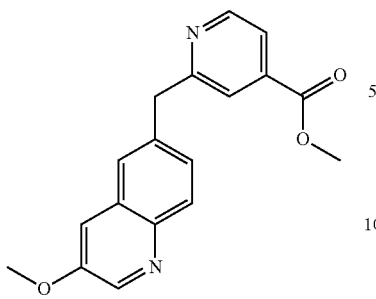

To a solution of 6-chloromethyl-3-methoxy-quinoline (305 mg, 1.47 mmol, 1.0 eq) in dioxane (30 mL) was added 2-trimethylstannanyl-isonicotinic acid methyl ester (486 mg, 1.61 mmol, 1.1 eq) and Pd(PPh₃)₂Cl₂ (109 mg, 0.15 mmol, 0.1 eq). The mixture was stirred at 90° C. for 3 h under nitrogen atmosphere, stripped of solvent and finally purified by chromatography on a silica gel column (DCM/MeOH=100/1, v/v) to afford 2-(3-methoxy-quinolin-6-ylmethyl)-isonicotinic acid methyl ester (205 mg, 45%) as a yellow solid.

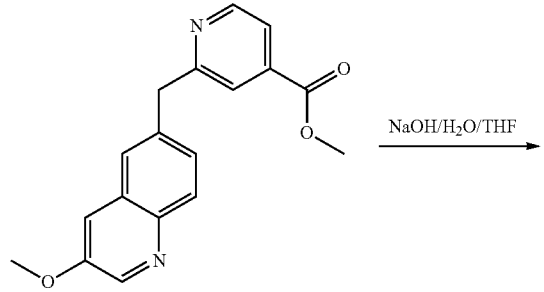

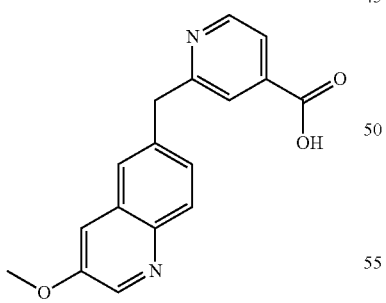

To a solution of 2-(3-methoxy-quinolin-6-ylmethyl)-isonicotinic acid methyl ester (205 mg, 0.67 mmol, 1.0 eq) in THF (5 mL) and H₂O (5 mL) was added NaOH (80 mg, 2.0 mmol, 3.0 eq) and the reaction mixture was stirred at rt for 3 h. The reaction mixture was neutralized with 1 N HCl to pH 3, extracted with EA and concentrated to afford 2-(3-methoxy-quinolin-6-ylmethyl)-isonicotinic acid (166 mg, 85%) as a white solid.

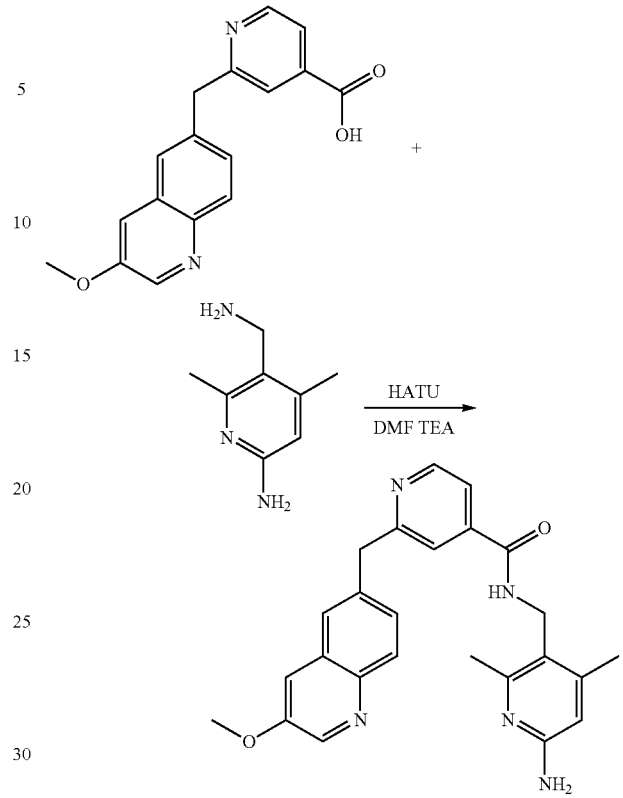

A mixture of 2-(3-Methoxy-quinolin-6-ylmethyl)-isonicotinic acid (200 mg, 0.68 mmol, 1.0 eq), 5-aminomethyl-4,6-dimethyl-pyridin-2-ylamine (123 mg, 0.82 mmol, 1.2 eq), HATU (388 mg, 1.02 mmol, 1.5 eq), and TEA (206 mg, 2.04 mmol, 3.0 eq) in DMF (30 mL) was stirred at rt overnight. The mixture was concentrated and the resulting residue was purified by Prep-HPLC to get N-((6-amino-2,4-dimethylpyridin-3-yl)methyl)-2-((3-methoxyquinolin-6-yl)methyl)isonicotinamide (110 mg, 38%) as a white solid.

LCMS (M+H⁺) m/z calculated 428.2, found 428.2. ¹H NMR (DMSO-d₆, 300 MHz): δ 8.54-8.60 (m, 3H), 7.83 (d, 1H), 7.66-7.71 (m, 3H), 7.49 (d, 1H), 7.46 (d, 1H), 6.10 (s, 1H), 5.65 (s, 2H), 4.28-4.32 (m, 4H), 3.88 (s, 3H), 2.27 (s, 3H), 2.14 (s, 3H).

Example 265: Preparation of N-(6-amino-2-methyl-pyridin-3-ylmethyl)-2-(3-methoxy-quinolin-6-ylmethyl)-isonicotinamide

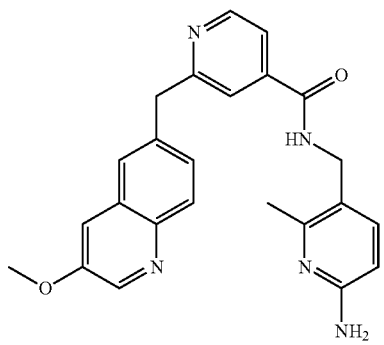

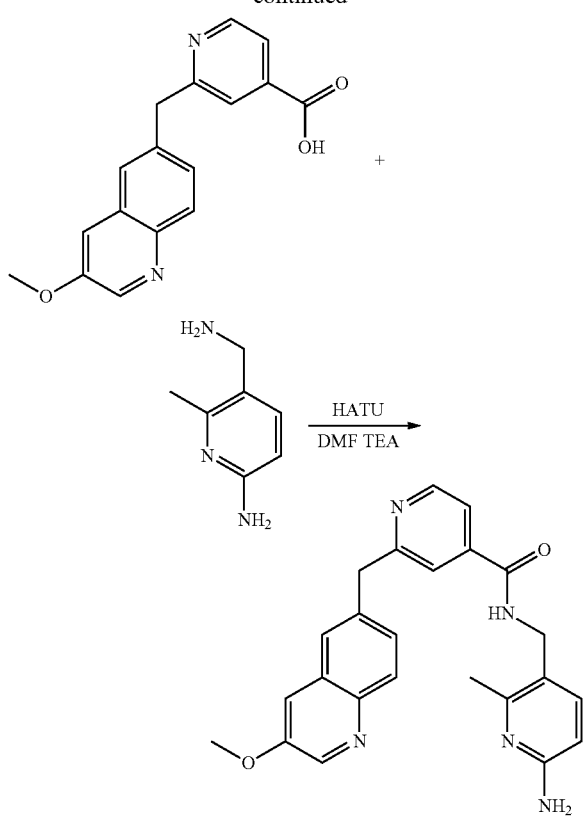

A mixture of 2-(3-methoxy-quinolin-6-ylmethyl)-isonicotinic acid (200 mg, 0.68 mmol, 1.0 eq), 5-aminomethyl-6-methyl-pyridin-2-ylamine (112 mg, 0.82 mmol, 1.2 eq), HATU (388 mg, 1.02 mmol, 1.5 eq), and TEA (206 mg, 2.04 mmol, 3.0 eq) in DMF (30 mL) was stirred at rt overnight. The mixture was concentrated and the resulting residue was purified by Prep-HPLC to get N-((6-amino-2-methylpyridin-3-yl)methyl)-2-((3-methoxyquinolin-6-yl)methyl)isonicotinamide (95 mg, 34%) as a white solid.

LCMS (M+H$^+$) m/z calculated 414.2, found 414.2. $^1$H NMR (DMSO-d$_6$, 300 MHz): δ 8.93-8.96 (m, 1H), 8.61 (d, 1H), 8.55 (d, 1H), 7.84 (d, 1H), 7.59-7.72 (m, 4H), 7.47 (d, 1H), 7.20 (d, 1H), 6.20 (d, 1H), 5.70 (s, 2H), 4.25-4.30 (m, 4H), 3.88 (s, 3H), 2.25 (s, 3H).

Example 266: Preparation of 2-((3-chloroquinolin-6-yl)methyl)-N-((3-methyl-1H-pyrazolo[3,4-b]pyridin-5-yl)methyl)isonicotinamide

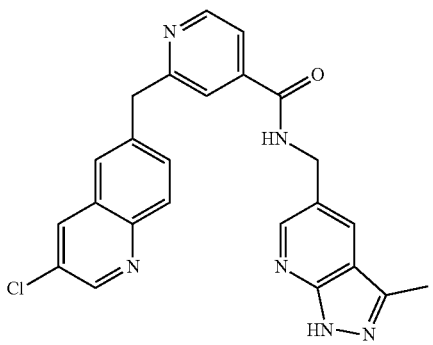

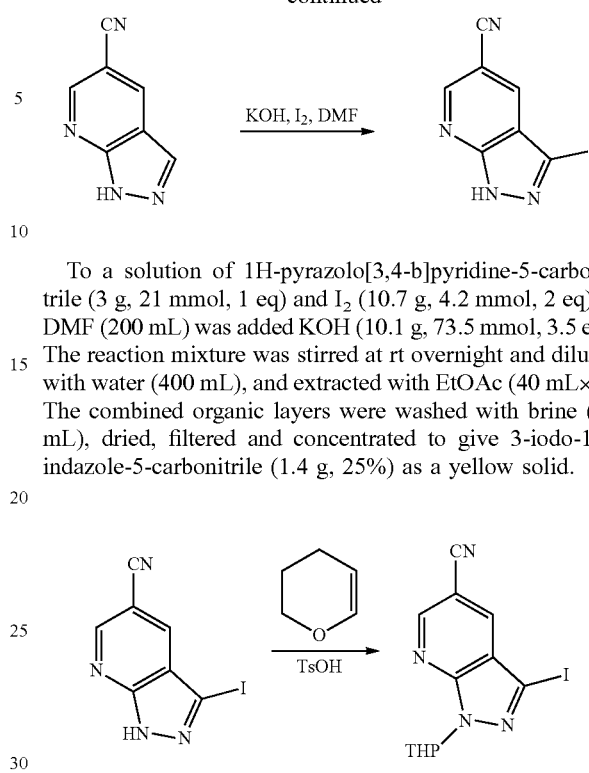

To a solution of 1H-pyrazolo[3,4-b]pyridine-5-carbonitrile (3 g, 21 mmol, 1 eq) and I$_2$ (10.7 g, 4.2 mmol, 2 eq) in DMF (200 mL) was added KOH (10.1 g, 73.5 mmol, 3.5 eq). The reaction mixture was stirred at rt overnight and diluted with water (400 mL), and extracted with EtOAc (40 mL×3). The combined organic layers were washed with brine (40 mL), dried, filtered and concentrated to give 3-iodo-1H-indazole-5-carbonitrile (1.4 g, 25%) as a yellow solid.

To a solution of 3-iodo-1H-pyrazolo[3,4-b]pyridine-5-carbonitrile (1.4 g, 5.2 mmol, 1.0 eq) and 3,4-dihydro-2H-pyran (874 mg, 10.4 mmol, 2.0 eq) in DCM (30 mL) was added TsOH (89 mg, 0.52 mmol, 0.1 eq). The mixture was stirred at rt overnight. The mixture was washed with sat. NaHCO$_3$ aqueous solution and the organic layer was dried and concentrated to give 3-iodo-1-(tetrahydro-pyran-2-yl)-1H-pyrazolo[3,4-b]pyridine-5-carbonitrile (1.56 g, 85%) as a yellow solid.

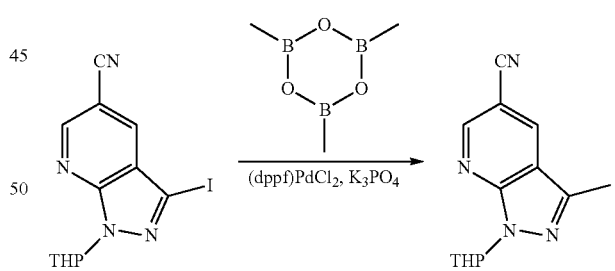

A mixture of 3-iodo-1-(tetrahydro-pyran-2-yl)-1H-pyrazolo[3,4-b]pyridine-5-carbonitrile (1.56 g, 4.4 mmol), K$_3$PO$_4$ (1.87 g, 8.8 mmol, 2.0 eq), Pd(dppf)Cl$_2$ (322 mg, 0.44 mmol, 0.1 eq), and trimethylboroxine (2.2 g, 50% in THF, 8.8 mmol, 2.0 eq) in dioxane (30 mL) under nitrogen was heated at 120° C. for 2 d. The reaction mixture was filtered and the filtrate was diluted with H$_2$O and extracted with EtOAc. The combined extracts were dried and concentrated. The resulting residue was purified by chromatography on a silica gel column (EA/PE=1/2, v/v) to give 3-methyl-1-(tetrahydro-pyran-2-yl)-1H-pyrazolo[3,4-b]pyridine-5-carbonitrile (223 mg, 21%) as white solid.

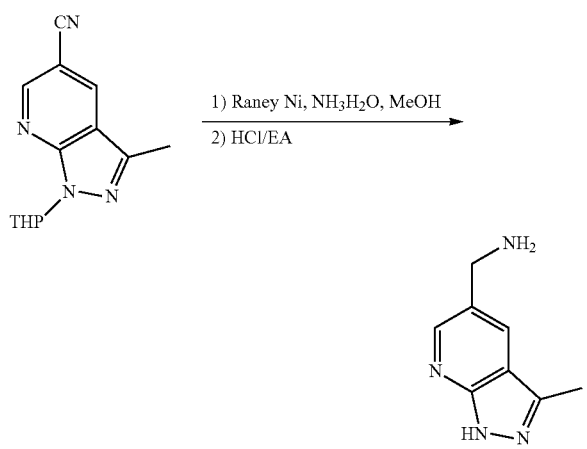

To a solution of 3-methyl-1-(tetrahydro-pyran-2-yl)-1H-pyrazolo[3,4-b]pyridine-5-carbonitrile (223 mg, 0.92 mmol, 1.0 eq) in MeOH (10 mL) and NH$_3$.H$_2$O (3 mL) was added Raney Ni (40 mg, 10% wt) at rt. The mixture was stirred at rt for 4 h under hydrogen. The reaction solution was filtered and the filtrate was concentrated. The resulting residue was dissolved in EA (5 mL) and 20 mL of HCl solution in EA was added. The mixture was stirred at rt for 3 h. The resulting precipitate was collected and dried to give (3-methyl-1H-pyrazolo[3,4-b]pyridin-5-yl)methanamine hydrochloride (140 mg, 76% for 2 steps) as a white solid.

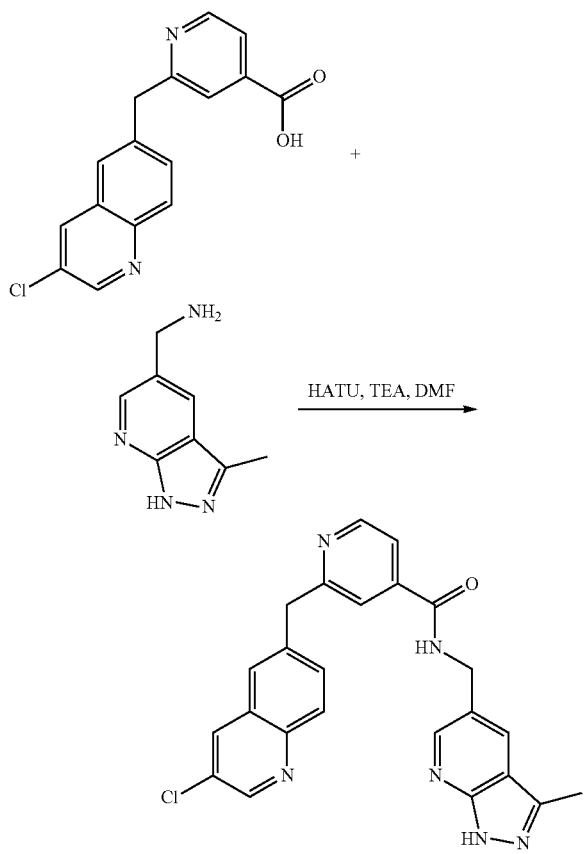

To a solution of 2-(3-chloro-quinolin-6-ylmethyl)-isonicotinic acid (100 mg, 0.33 mmol, 1.0 eq) in DMF (5 mL) was added (3-methyl-1H-pyrazolo[3,4-b]pyridin-5-yl)methanamine hydrochloride (80 g, 0.40 mmol, 1.2 eq) followed by HATU (138 mg, 0.36 mmol, 1.1 eq) and TEA (100 mg, 1.0 mmol, 3.0 eq). The reaction mixture was stirred at rt overnight. Water was added, and the mixture was extracted with DCM. The organic layer was washed with water, dried over Na$_2$SO$_4$, filtered and concentrated. The resulting residue was purified by Prep-HPLC to give 2-((3-chloroquinolin-6-yl)methyl)-N-((3-methyl-1H-pyrazolo[3,4-b]pyridin-5-yl)methyl)isonicotinamide (20 mg, 14%) as a white solid.

LRMS (M+H$^+$) m/z calculated 443.1, found 443.1. $^1$H NMR (DMSO-d6, 400 MHz): δ 13.16 (s, 1H), 9.31 (t, 1H), 8.82 (d, 1H), 8.65 (d, 1H), 8.50 (dd, 1H), 8.10 (s, 1H), 7.96 (d, 1H), 7.85 (s, 1H), 7.78 (s, 1H), 7.72 (d, 1H), 7.64 (d, 1H), 4.60 (d, 2H), 4.37 (s, 2H), 2.47 (s, 3H).

Example 267: Preparation of 2-((3-chloroquinolin-6-yl)methyl)-N-((3-(trifluoromethyl)-1H-indazol-5-yl)methyl)isonicotinamide

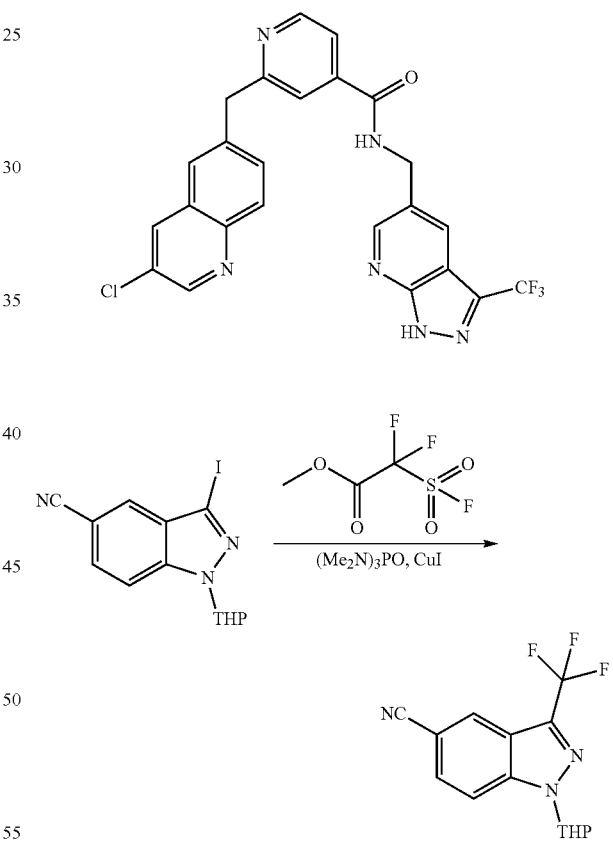

A mixture of 3-iodo-1-(tetrahydro-pyran-2-yl)-1H-indazole-5-carbonitrile (600 mg, 1.71 mmol, 1.0 eq), (Me$_2$N)$_3$PO (1.2 g, 6.81 mmol, 4.0 eq), CuI (162 mg, 0.855 mmol, 0.5 eq), and difluoro-fluorosulfonyl-acetic acid methyl ester (489 mg, 2.55 mmol, 1.5 eq) in 20 mL of DMF was heated at 80° C. overnight. After completion, DMF was evaporated in vacuo, and the resulting residue was purified by Prep-HPLC to give 1-(tetrahydro-pyran-2-yl)-3-trifluoromethyl-1H-indazole-5-carbonitrile (350 mg, 67%) as a yellow solid.

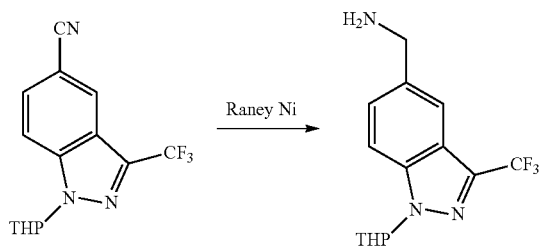

To a solution of 1-(tetrahydro-pyran-2-yl)-3-trifluoromethyl-1H-indazole-5-carbonitrile (200 mg, 0.68 mmol, 1.0 eq) in MeOH (10 mL) and NH₃.H₂O (2 mL) was added Raney Ni (20 mg, 10% wt) at rt. The mixture was stirred at rt for 4 h under hydrogen. The mixture was filtered and the filtrate was concentrated to obtain (1-(tetrahydro-2H-pyran-2-yl)-3-(trifluoromethyl)-1H-indazol-5-yl)methanamine (210 mg, crude) as a yellow oil.

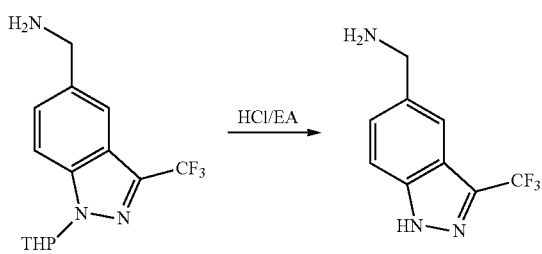

To a solution of (1-(tetrahydro-2H-pyran-2-yl)-3-(trifluoromethyl)-1H-indazol-5-yl)methanamine (210 mg, 0.68 mmol, 1.0 eq) in EA (10 mL) was added HCl/EA (10 mL) at rt. The mixture was stirred at 35° C. for 2 d. The mixture was concentrated to obtain (3-(trifluoromethyl)-1H-indazol-5-yl)methanamine (200 mg, crude) as a yellow solid.

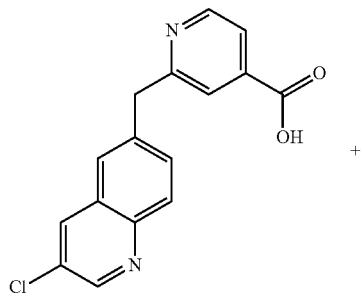

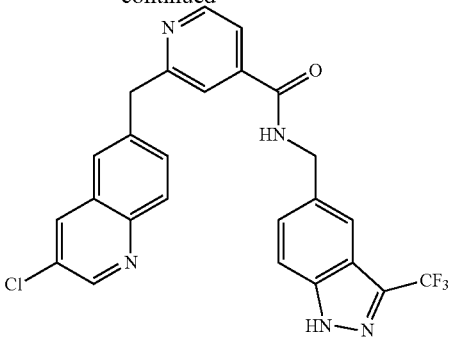

To a solution of 2-(3-chloro-quinolin-6-ylmethyl)-isonicotinic acid (100 mg, 0.33 mmol, 1.0 eq), (3-(trifluoromethyl)-1H-indazol-5-yl)methanamine (108 mg, 0.50 mmol, 1.5 eq) and Et₃N (151 mg, 1.50 mmol, 3.0 eq) in DMF (4 mL) was added HATU (190 mg, 0.50 mmol, 1.5 eq). The mixture was stirred at rt for 2 h. The mixture was concentrated and the resulting residue was purified by Prep-HPLC to obtain 2-((3-chloroquinolin-6-yl)methyl)-N-((3-(trifluoromethyl)-1H-indazol-5-yl)methyl)isonicotinamide (22 mg, 13%) as a white solid.

LRMS (M+H⁺) m/z calculated 496.1, found 496.1. ¹H NMR (DMSO-d₆, 300 MHz): δ 9.37-9.33 (m, 1H), 8.81 (d, 1H), 8.63 (d, 1H), 8.50 (d, 1H), 7.95 (d, 1H), 7.83 (s, 1H), 7.75-7.62 (m, 5H), 7.47 (d, 1H), 4.59 (d, 2H), 4.35 (s, 2H).

Example 268: Preparation of N-((5-chloro-1H-indol-3-yl)methyl)-2-((3-chloroquinolin-6-yl)methyl)isonicotinamide

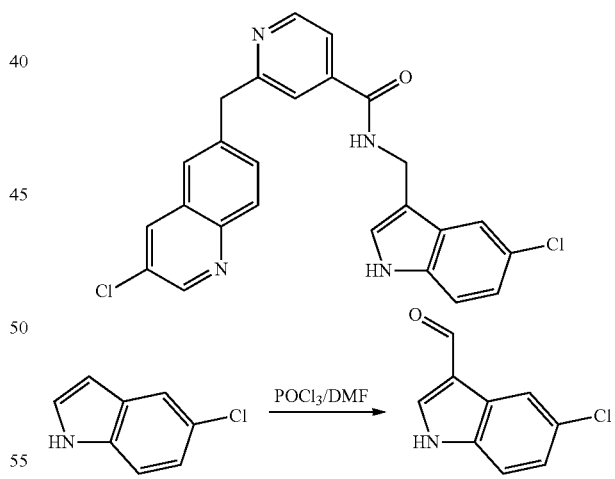

To a solution of 5-chloro-1H-indole (5.0 g, 33.11 mmol, 1.0 eq) in DMF (50 mL) was added POCl₃ (10.0 g, 66.22 mmol, 2.0 eq) at 0° C. The mixture was stirred at 80° C. overnight. The mixture was concentrated and the resulting residue was diluted with EA (200 mL). The mixture was washed with aq. Na₂CO₃ (200 mL) and the organic layer was dried over Na₂SO₄, filtered and concentrated. The resulting residue was purified by chromatography on a silica gel column (PE/EA=3/1 to 1/1, v/v) to give 5-chloro-1H-indole-3-carbaldehyde (5.5 g, 85%) as a yellow solid.

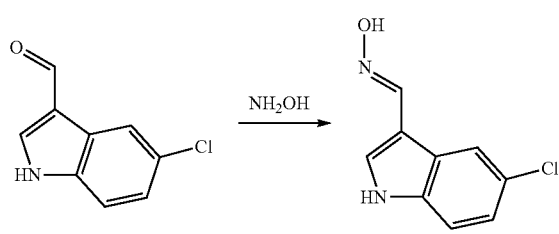 [SMILES: O=Cc1c[nH]c2ccc(Cl)cc12 ; "NH2OH" ; O/N=C/c1c[nH]c2ccc(Cl)cc12]

To a solution of 5-chloro-1H-indole-3-carbaldehyde (2.0 g, 11.13 mmol, 1.0 eq) and NH₂OH.HCl (1.1 g, 16.69 mmol, 1.5 eq) in EtOH (20 mL) was added Na₂CO₃ (2.4 g, 22.26 mmol, 2.0 eq) at rt. The mixture was stirred at rt overnight. EA (150 mL) was added and the mixture was washed with water (10 mL×3). The organic layers were dried over Na₂SO₄, filtered and concentrated to give 5-chloro-1H-indole-3-carbaldehyde oxime (1.8 g, 83%) as a white solid.

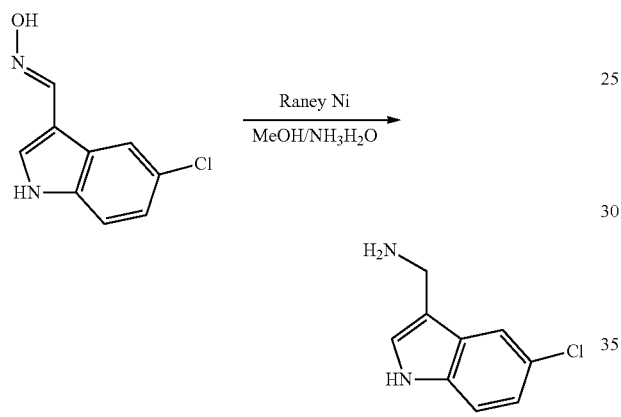

To a solution of 5-chloro-1H-indole-3-carbaldehyde oxime (300 mg, 1.54 mmol, 1.0 eq) in MeOH (12 mL) and NH₃.H₂O (3 mL) was added Raney Ni (30 mg, 10% wt) at rt. The mixture was stirred at rt for 4 h under hydrogen. The mixture was filtered and the filtrate was concentrated to obtain C-(5-chloro-1H-indol-3-yl)-methylamine (300 mg, crude) as a yellow oil.

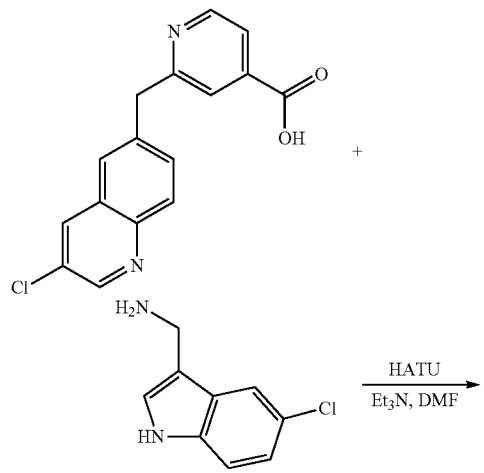

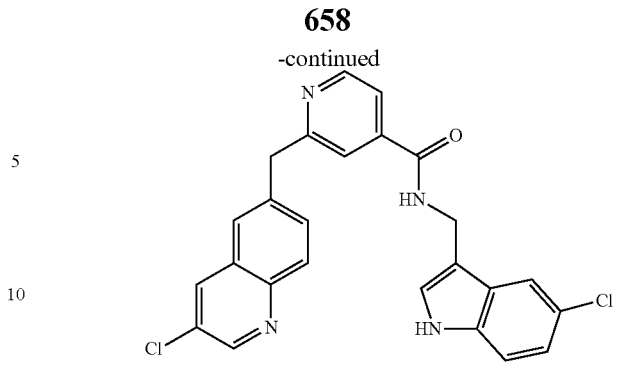

To a solution of 2-(3-chloro-quinolin-6-ylmethyl)-isonicotinic acid (70 mg, 0.23 mmol, 1.0 eq), C-(5-chloro-1H-indol-3-yl)-methylamine (63.0 mg, 0.35 mmol, 1.5 eq) and Et₃N (70 mg, 0.7 mmol) in DMF (4 mL) was added HATU (122 mg, 0.35 mmol, 1.5 eq). The mixture was stirred at rt for 2 h. It was concentrated and the resulting residue was purified by Prep-HPLC to obtain N-((5-chloro-1H-indol-3-yl)methyl)-2-((3-chloroquinolin-6-yl)methyl)isonicotinamide (23.0 mg, 22%) as a white solid.

LRMS (M+H⁺) m/z calculated 461.1, found 461.1. ¹H NMR (DMSO-d₆, 300 MHz): δ 11.13 (d, 1H), 9.11-9.07 (m, 1H), 8.81 (d, 1H), 8.60 (d, 1H), 8.49 (s, 1H), 7.94 (d, 1H), 7.82 (s, 1H), 7.74-7.65 (m, 3H), 7.59 (d, 1H), 7.36-7.33 (m, 2H), 7.05-7.02 (m, 1H), 4.54 (d, 2H), 4.33 (s, 2H).

Example 269: Preparation of N-((5-chloro-1H-pyrrolo[2,3-b]pyridin-3-yl)methyl)-2-((3-chloroquinolin-6-yl)methyl)isonicotinamide

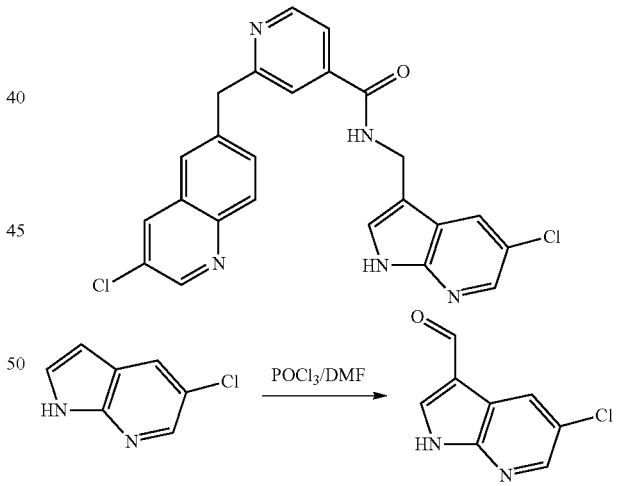

To a solution of 5-chloro-1H-pyrrolo[2,3-b]pyridine (5.0 g, 32.77 mmol, 1.0 eq) in DMF (50 mL) was added POCl₃ (10.0 g, 65.54 mmol, 2.0 eq) at 0° C. The mixture was stirred at 80° C. overnight. The mixture was concentrated and the resulting residue was diluted with EA (200 mL). The mixture was washed with aq.Na₂CO₃ (200 mL). The organic layer was dried over Na₂SO₄, filtered and concentrated. The resulting residue was purified by chromatography on a silica gel column (PE/EA=3/1 to 1/1, v/v) to give 5-chloro-1H-pyrrolo[2,3-b]pyridine-3-carbaldehyde (3.8 g, 64%) as a yellow solid.

659

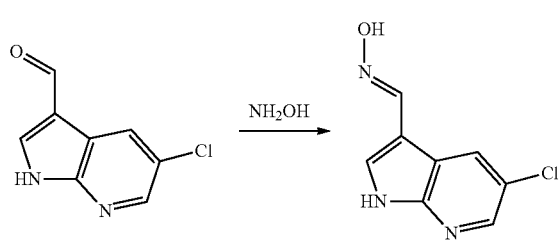 [SMILES: O=Cc1c[nH]c2ncc(Cl)cc12 ; "NH2OH" ; O/N=C/c1c[nH]c2ncc(Cl)cc12]

To a solution of 5-chloro-1H-pyrrolo[2,3-b]pyridine-3-carbaldehyde (2.0 g, 11.07 mmol, 1.0 eq) and NH₂OH.HCl (1.1 g, 16.61 mmol, 1.5 eq) in EtOH (20 mL) was added Na₂CO₃ (2.3 g, 22.14 mmol, 2.0 eq) at rt. The mixture was stirred at rt overnight. EA (150 mL) was added and washed with water (10 mL×3). The organic layer was dried over Na₂SO₄, filtered and concentrated to give 5-chloro-1H-pyrrolo[2,3-b]pyridine-3-carbaldehyde oxime (1.9 g, 88%) as a white solid.

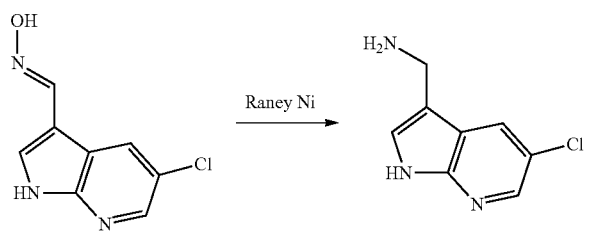 [SMILES: O/N=C/c1c[nH]c2ncc(Cl)cc12 ; NCc1c[nH]c2ncc(Cl)cc12]

To a solution of 5-chloro-1H-pyrrolo[2,3-b]pyridine-3-carbaldehyde oxime (500 mg, 2.56 mmol, 1.0 eq) in MeOH (25 mL) and NH₃.H₂O (5 mL) was added Raney Ni (50 mg, 10% wt) at rt. The mixture was stirred at rt for 4 h under hydrogen. The mixture was filtered and the filtrate was concentrated to obtain (5-chloro-1H-pyrrolo[2,3-b]pyridin-3-yl)methanamine (100 mg, crude) as a yellow oil.

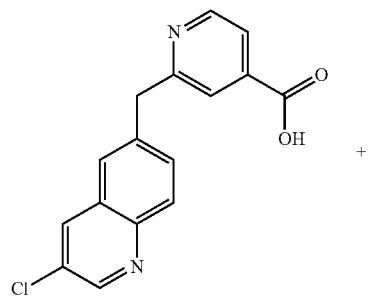

+

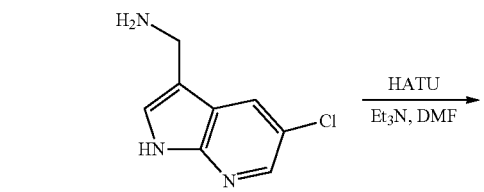

660

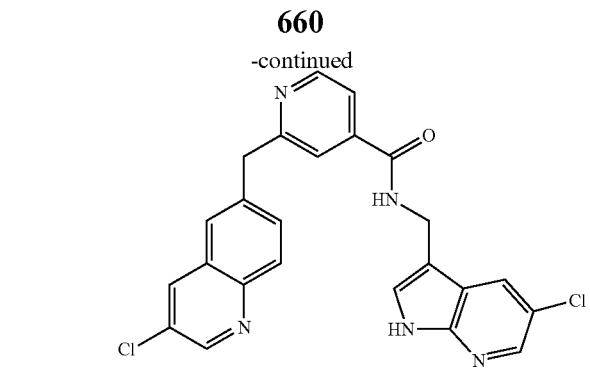

To a solution of 2-(3-chloro-quinolin-6-ylmethyl)-isonicotinic acid (70 mg, 0.23 mmol, 1.0 eq), (5-chloro-1H-pyrrolo[2,3-b]pyridin-3-yl)methanamine (63.0 mg, 0.35 mmol, 1.5 eq) and Et₃N (70 mg, 0.7 mmol) in DMF (4 mL) was added HATU (122 mg, 0.35 mmol, 1.5 eq). The mixture was stirred at rt for 2 h. The mixture was concentrated and the resulting residue was purified by Prep-HPLC to obtain N-((5-chloro-1H-pyrrolo[2,3-b]pyridin-3-yl)methyl)-2-((3-chloroquinolin-6-yl)methyl)isonicotinamide (25.0 mg, 24%) as a white solid.

LRMS (M+H⁺) m/z calculated 462.1, found 462.1. ¹H NMR (DMSO-d₆, 300 MHz): δ 9.21-9.17 (m, 1H), 8.82 (d, 1H), 8.61 (d, 1H), 8.51 (d, 1H), 8.18-8.14 (m, 2H), 7.98 (d, 1H), 7.84 (s, 1H), 7.75-7.71 (m, 2H), 7.62-7.60 (m, 1H), 7.53 (s, 1H), 4.56 (d, 2H), 4.35 (s, 2H).

Example 270: Preparation of N-((5-chloro-2-methyl-1H-indol-3-yl)methyl)-2-((3-chloroquinolin-6-yl)methyl)isonicotinamide

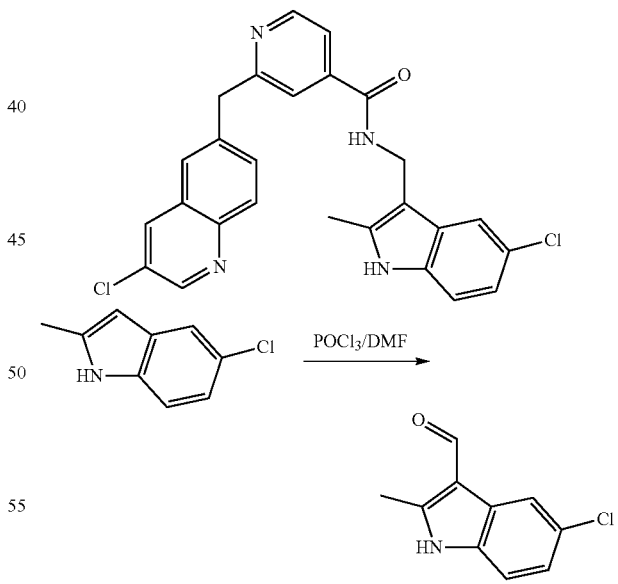

To a solution of 5-chloro-2-methyl-1H-indole (5.0 g, 30.19 mmol, 1.0 eq) in DMF (50 mL) was added POCl₃ (9.2 g, 60.38 mmol, 2.0 eq) at 0° C. The mixture was stirred at 80° C. overnight. The mixture was concentrated and the residue was diluted EA (200 mL). The mixture was washed with aq. Na₂CO₃ (200 mL). The organic layers were dried over Na₂SO₄, filtered and concentrated. The resulting residue was purified by chromatography on a silica gel column (PE/EA=3/1 to 1/1, v/v) to give 5-chloro-2-methyl-1H-indole-3-carbaldehyde (4.2 g, 72%) as a yellow solid.

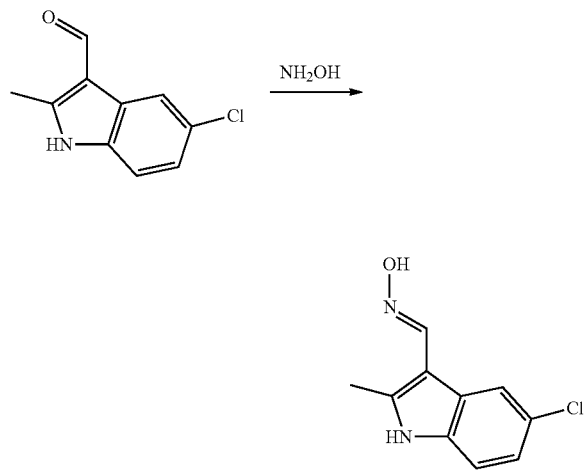

To a solution of 5-chloro-2-methyl-1H-indole-3-carbaldehyde (4.2 g, 21.69 mmol, 1.0 eq) and NH$_2$OH.HCl (2.2 g, 32.54 mmol, 1.5 eq) in EtOH (40 mL) was added Na$_2$CO$_3$ (4.6 g, 43.38 mmol, 2.0 eq) at rt. The mixture was stirred at rt overnight. EA (300 mL) was added and the mixture was washed with water (20 mL×3). The organic layer was dried over Na$_2$SO$_4$, filtered and concentrated to give 5-chloro-2-methyl-1H-indole-3-carbaldehyde oxime (3.2 g, 71%) as a white solid.

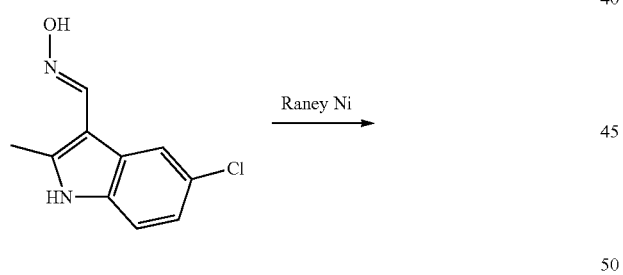

To a solution of 5-chloro-2-methyl-1H-indole-3-carbaldehyde oxime (500 mg, 2.40 mmol, 1.0 eq) in MeOH (25 mL) and NH$_3$.H$_2$O (5 mL) was added Raney Ni (50 mg, 10% wt) at rt. The mixture was stirred at rt for 4 h under hydrogen. The mixture was filtered and the filtrate was concentrated to obtain (5-chloro-2-methyl-1H-indol-3-yl)methanamine (200 mg, crude) as a yellow oil.

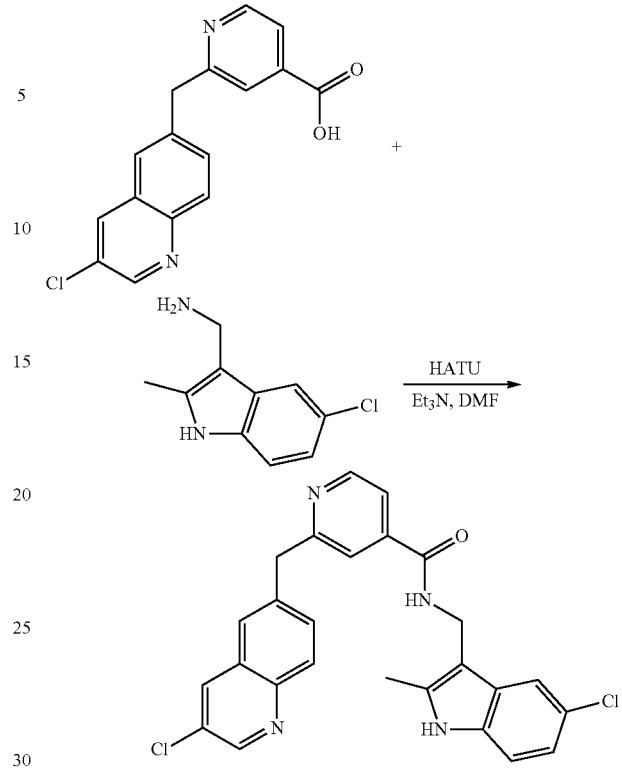

To a solution of 2-(3-chloro-quinolin-6-ylmethyl)-isonicotinic acid (70 mg, 0.23 mmol, 1.0 eq), (5-chloro-2-methyl-1H-indol-3-yl)methanamine (68.0 mg, 0.35 mmol, 1.5 eq) and Et$_3$N (70 mg, 0.7 mmol) in DMF (4 mL) was added HATU (122 mg, 0.35 mmol, 1.5 eq). The mixture was stirred at rt for 2 h. The mixture was concentrated and the resulting residue was purified by Prep-HPLC to obtain N-((5-chloro-2-methyl-1H-indol-3-yl)methyl)-2-((3-chloroquinolin-6-yl)methyl)isonicotinamide (43.0 mg, 39%) as a white solid.

LRMS (M+H$^+$) m/z calculated 475.1, found 475.1. $^1$H NMR (DMSO-d$_6$, 300 MHz): δ 11.05 (s, 1H), 9.03-9.01 (m, 1H), 8.80 (d, 1H), 8.58 (d, 1H), 8.48 (d, 1H), 7.95 (d, 1H), 7.80 (d, 1H), 7.71-7.67 (m, 2H), 7.23 (d, 1H), 6.96-6.93 (m, 1H), 4.47 (d, 2H), 4.32 (s, 2H), 2.40 (s, 3H).

Example 271: Preparation of 2-((3-chloroquinolin-6-yl)methyl)-N-((3-(trifluoromethyl)-1H-pyrazolo[3,4-b]pyridin-5-yl)methyl)isonicotinamide

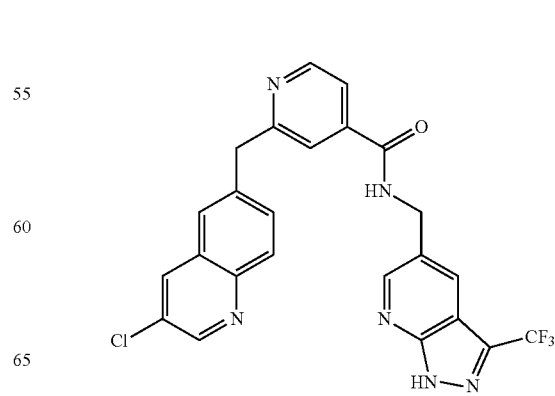

663
-continued

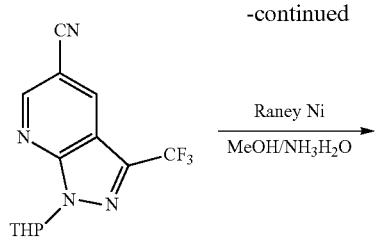

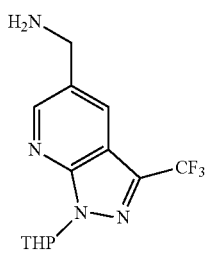

To a solution of 1-(tetrahydro-pyran-2-yl)-3-trifluoromethyl-1H-pyrazolo[3,4-b]pyridine-5-carbonitrile (140 mg, 0.47 mmol, 1.0 eq) in MeOH (10 mL) and NH₃H₂O (2 mL) was added Raney Ni (14 mg, 10% wt) at rt. The mixture was stirred at rt for 4 h under hydrogen. The mixture was filtered and the filtrate was concentrated to obtain (1-(tetrahydro-2H-pyran-2-yl)-3-(trifluoromethyl)-1H-pyrazolo[3,4-b]pyridin-5-yl)methanamine (150 mg, crude) as a yellow oil.

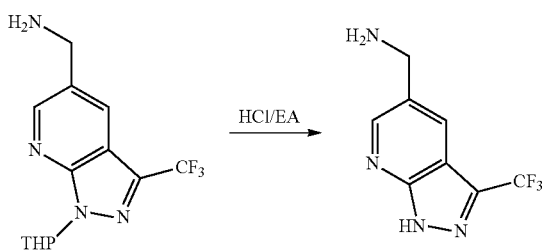

To a solution of (1-(tetrahydro-2H-pyran-2-yl)-3-(trifluoromethyl)-1H-pyrazolo[3,4-b]pyridin-5-yl)methanamine (150 mg, 0.50 mmol, 1.0 eq) in EA (10 mL) was added HCl/EA (10 mL) at rt. The mixture was stirred at 35° C. for 2 d. The mixture was concentrated to obtain (3-(trifluoromethyl)-1H-pyrazolo[3,4-b]pyridin-5-yl)methanamine (170 mg, crude) as a yellow solid.

664
-continued

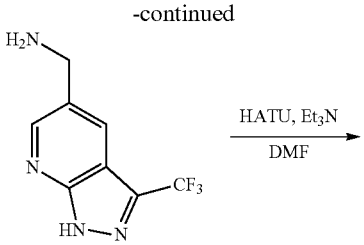

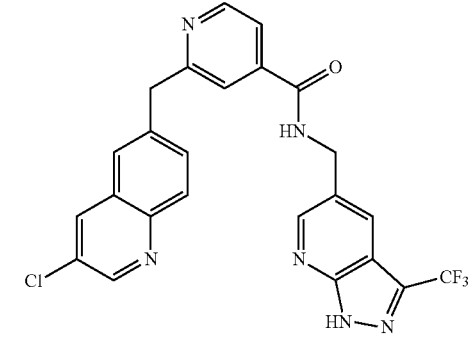

To a solution of 2-(3-chloro-quinolin-6-ylmethyl)-isonicotinic acid (50 mg, 0.17 mmol, 1.0 eq), (3-(trifluoromethyl)-1H-pyrazolo[3,4-b]pyridin-5-yl)methanamine (54.0 mg, 0.25 mmol, 1.5 eq) and Et₃N (51 mg, 0.51 mmol) in DMF (4 mL) was added HATU (87 mg, 0.25 mmol, 1.5 eq). The mixture was stirred at rt for 2 h. The mixture was concentrated and the resulting residue was purified by Prep-HPLC to obtain 2-((3-chloroquinolin-6-yl)methyl)-N-((3-(trifluoromethyl)-1H-pyrazolo[3,4-b]pyridin-5-yl)methyl)isonicotinamide (4.0 mg, 5%) as a white solid.

LRMS (M+H⁺) m/z calculated 496.1, found 496.1. ¹H NMR (DMSO-d₆, 400 MHz): δ 14.6 (s, 1H), 9.41-9.39 (m, 1H), 8.83 (d, 1H), 8.72 (d, 1H), 8.67 (d, 1H), 8.51 (d, 1H), 8.23 (s, 1H), 7.97 (d, 1H), 7.85 (s, 1H), 7.78 (s, 1H), 7.74 (d, 1H), 7.66-7.65 (d, 1H), 4.65 (d, 2H), 4.38 (s, 2H).

Example 272: Preparation of N-((6-amino-2,4-dimethylpyridin-3-yl)methyl)-2-((3-chloro-8-(1H-tetrazol-5-yl)quinolin-6-yl)methyl)isonicotinamide

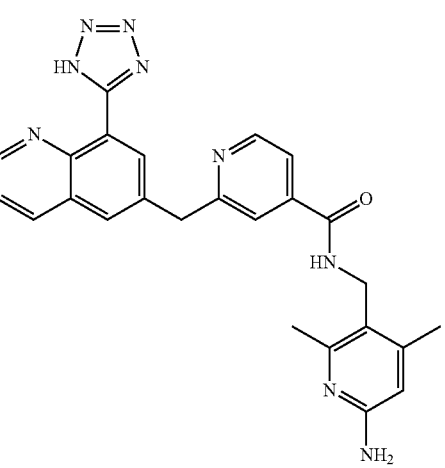

-continued

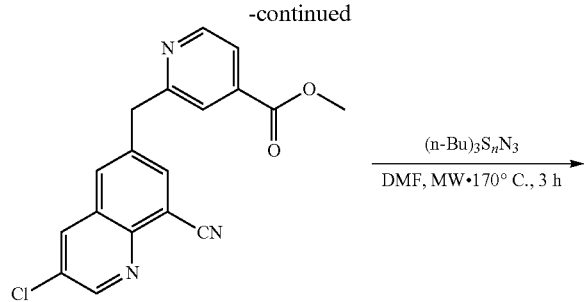

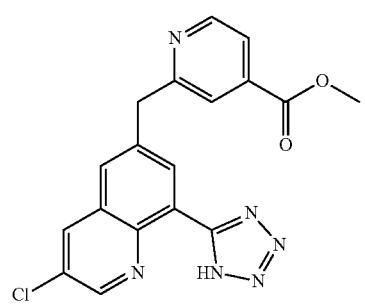

A mixture of 2-(3-chloro-8-cyano-quinolin-6-ylmethyl)-isonicotinic acid methyl ester (332 mg, 1 mmol, 1.0 eq) and (n-Bu)₃S$_n$N₃ (1.64 g, 5 mmol, 5.0 eq) in 16 mL of DMF was heated to 170° C. under MW for 3 h. After cooling to rt, the mixture was concentrated, and the resulting residue was purified by pre-HPLC to get 2-[3-chloro-8-(1H-tetrazol-5-yl)-quinolin-6-ylmethyl]-isonicotinic acid methyl ester (150 mg, 40%) as a white solid.

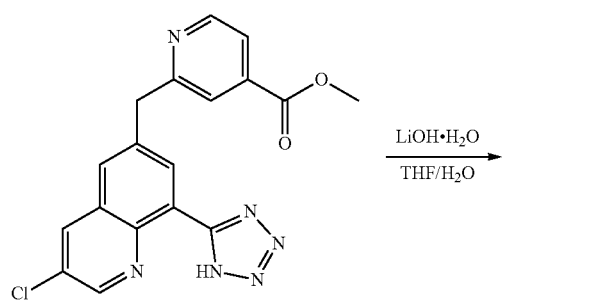

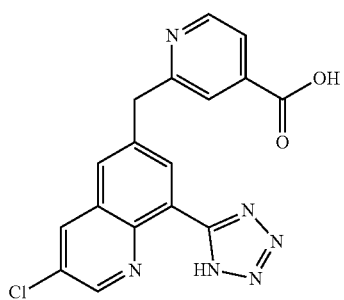

A mixture of 2-[3-chloro-8-(1H-tetrazol-5-yl)-quinolin-6-ylmethyl]-isonicotinic acid methyl ester (150 mg, 0.4 mmol, 1.0 eq) and LiOH.H₂O (50 mg, 1.2 mmol, 3.0 eq) in 10 mL of H₂O/THF (v/v, 1/1) was stirred at rt overnight. 1 N HCl was added and the resulting precipitate was filtered to give 2-[3-chloro-8-(1H-tetrazol-5-yl)-quinolin-6-ylmethyl]-isonicotinic acid (110 mg, 75%) as a white solid.

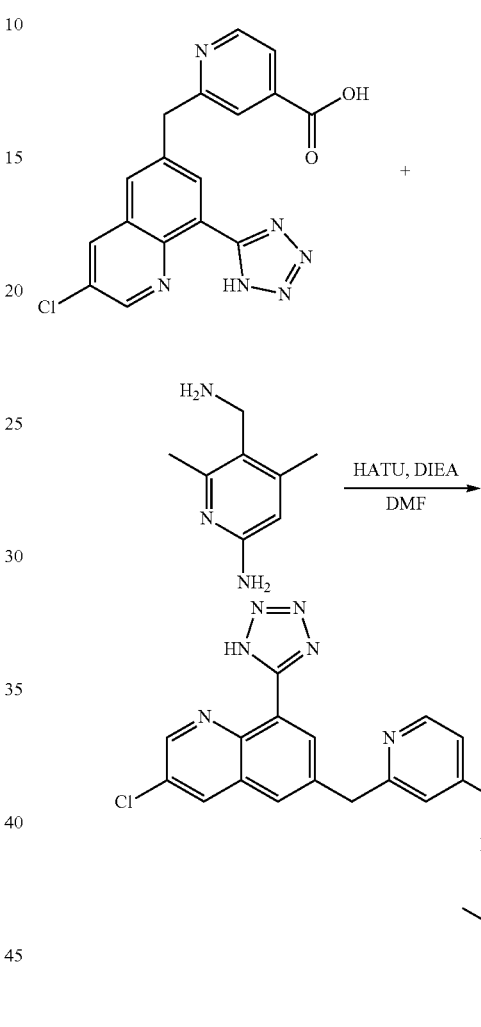

To a solution of 2-[3-chloro-8-(1H-tetrazol-5-yl)-quinolin-6-ylmethyl]-isonicotinic acid (50 mg, 0.137 mmol, 1 eq) in DMF (4 mL) were added 5-aminomethyl-4,6-dimethyl-pyridin-2-ylamine (30 mg, 0.164 mmol, 1.2 eq), HATU (57 mg, 0.15 mmol, 1.1 eq) and DIEA (53 mg, 0.41 mmol, 3 eq). The mixture was stirred at rt overnight. The mixture was evaporated to dryness in vacuo and the resulting residue was purified by pre-HPLC to get N-((6-amino-2,4-dimethylpyridin-3-yl)methyl)-2-((3-chloro-8-(1H-tetrazol-5-yl)quinolin-6-yl)methyl)isonicotinamide (23.8 mg, 35%) as a white solid.

LRMS (M+H⁺) m/z calculated 500.2, found 500.1. ¹H NMR (DMSO-d6, 300 MHz): δ 8.93 (d, 1H), 8.71 (d, 1H), 8.60 (d, 1H), 8.46 (d, 1H), 8.08 (d, 1H), 7.82 (s, 1H), 7.62 (s, 1H), 6.13 (s, 1H), 5.75 (s, 2H), 4.45 (s, 2H), 4.33 (d, 2H), 2.30 (s, 3H), 2.17 (s, 3H).

Example 273: Preparation of N-((6-amino-2-methylpyridin-3-yl)methyl)-2-((3-chloro-8-(1H-tetrazol-5-yl)quinolin-6-yl)methyl)isonicotinamide

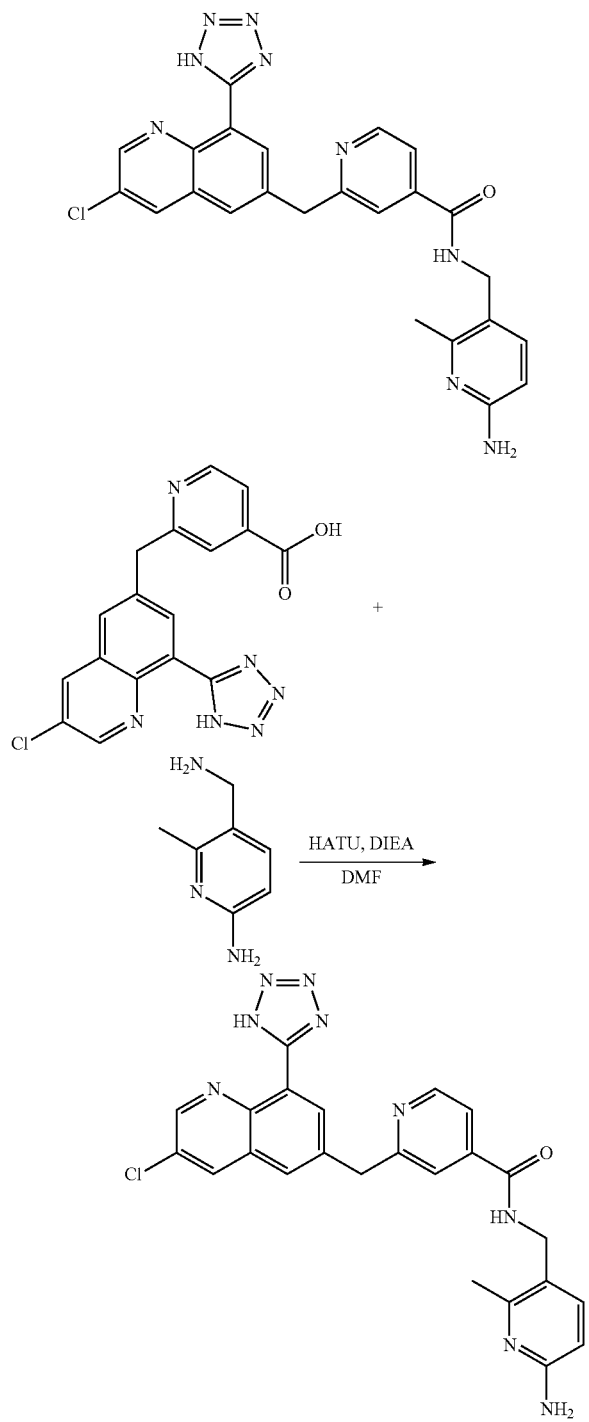

To a solution of 2-[3-chloro-8-(1H-tetrazol-5-yl)-quinolin-6-ylmethyl]-isonicotinic acid (50 mg, 0.137 mmol, 1 eq) in DMF (4 mL) were added 5-aminomethyl-6-methyl-pyridin-2-ylamine (28.5 mg, 0.164 mmol, 1.2 eq), HATU (57 mg, 0.151 mmol, 1.1 eq) and DIEA (53 mg, 0.41 mmol, 3.0 eq). The mixture was stirred at rt overnight. After that, the mixture was evaporated to dryness in vacuo and the resulting residue was purified by pre-HPLC to get N-((6-amino-2-methylpyridin-3-yl)methyl)-2-((3-chloro-8-(1H-tetrazol-5-yl)quinolin-6-yl)methyl)isonicotinamide (8.5 mg, 13%) as a white solid.

LRMS (M+H$^+$) m/z calculated 486.2, found 486.1. $^1$H NMR (DMSO-d6, 300 MHz): δ 9.00 (s, 1H), 8.93 (d, 1H), 8.73 (s, 1H), 8.61 (d, 1H), 8.51 (s, 1H), 7.83 (s, 1H), 7.62 (d, 1H), 7.24 (t, 1H), 6.22 (d, 1H), 5.82 (t, 2H), 4.46 (s, 2H), 4.26 (d, 2H), 2.25 (d, 3H).

Example 274: Preparation of N-((6-amino-2,4-dimethylpyridin-3-yl)methyl)-2-(3-chloroquinoline-6-carbonyl)isonicotinamide

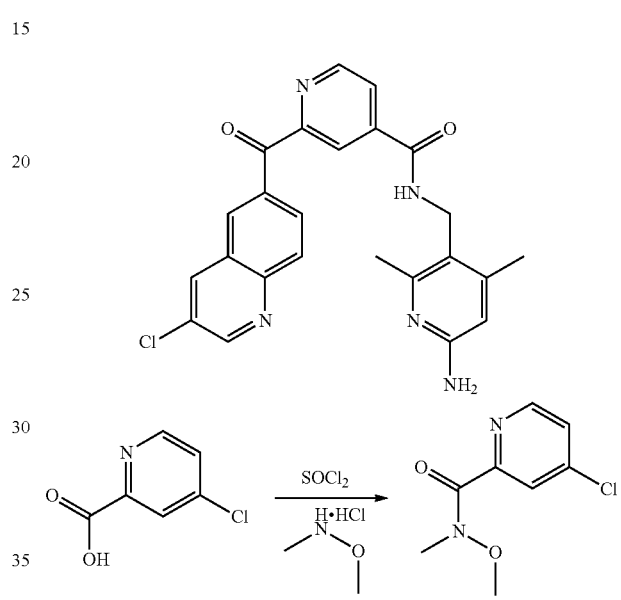

Thionyl chloride (1 L) was charged in 2 L three-neck vase at 0° C., and 4-chloro-pyridine-2-carboxylic acid (200 g, 1.27 mmol) was added in parts below 5° C. The mixture was kept below 5° C. for 1 h, then heated to reflux for 3 h. The reaction was concentrated to remove thionyl chloride. The resulting residue was dissolved in dry DCM (2.5 L). TEA (482 mL, 3.81 mmol) was added drop wise below 10° C., and then methoxymethylamine hydrochloride (186 g, 1.9 mmol) was added in parts. The reaction was allowed to warm to rt for 3 h and the reaction was quenched with the addition of 3 L water. The water layer was extracted with DCM three times and the combined organic layers were washed with brine, dried over sodium sulfate, and concentrated. The resulting residue was purified by chromatography on a silica gel column (PE/EA=5/1, v/v) to give 4-chloro-pyridine-2-carboxylic acid methoxy-methyl-amide (120 g, 47.5%) as a yellow solid.

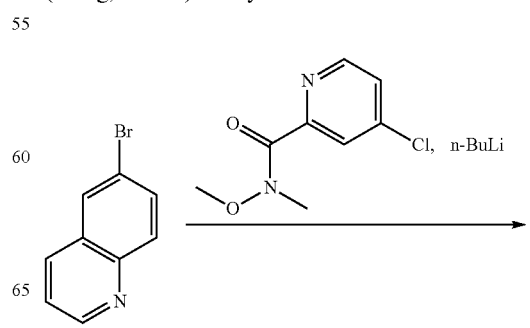

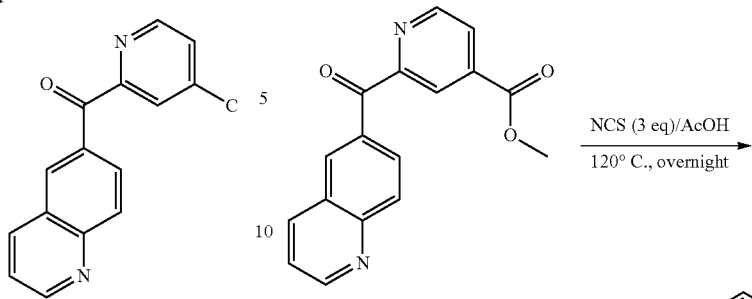

To a solution of 6-bromoquinoline (55 g, 264 mmol, 1.0 eq) in THF (270 mL) was added n-BuLi (106 mL, 2.5 M, 0.264 mol, 1.0 eq) at −78° C. under N₂. After stirring for 0.5 h, 4-chloro-pyridine-2-carboxylic acid methoxy-methyl-amide (42.2 g, 211 mmol, 0.8 eq) in THF (200 mL) was added slowly. The reaction mixture was maintained at this temperature with stirring for 1 h, and then added saturate aq. NH₄Cl, extracted with ethyl acetate (100 mL×2), dried over Na₂SO₄, filtered and concentrated. The resulting residue was purified by chromatography on a silica gel column (PE/EA=4/1, v/v) to give (4-chloro-pyridin-2-yl)-quinolin-6-yl-methanone (11 g, 15.5%) as a yellow solid.

A mixture of 2-(quinoline-6-carbonyl)-isonicotinic acid methyl ester (75 g, 256.8 mmol, 1.0 eq) and NCS (102.5 g, 770.5 mmol, 3.0 eq) in AcOH (2.57 L) was heated at 120° C. for 18 h under nitrogen atmosphere, stripped of solvent and the resulting black residue was purified by chromatography on a silica gel column (EA/PE=1/1, v/v) to afford 2-(3-chloro-quinoline-6-carbonyl)-isonicotinic acid methyl ester (34 g, 41%) as an off-white solid. Moreover, 18 g of the start material 2-(quinoline-6-carbonyl)-isonicotinic acid methyl ester was recovered.

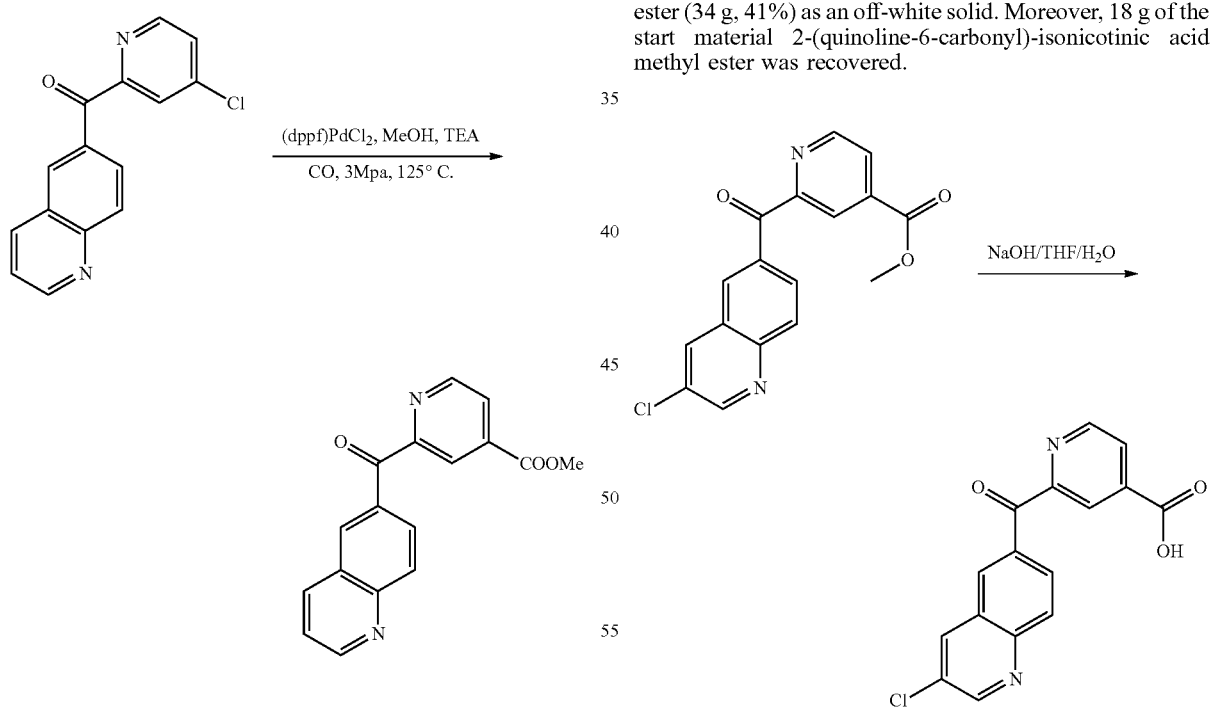

A solution of (4-chloro-pyridin-2-yl)-quinolin-6-yl-methanone (200 g, 746 mmol, 1.0 eq) and Pd(dppf)Cl₂ (60.8 g, 74.6 mmol, 0.1 eq) was added to autoclave. Then MeOH (7 L) and TEA (320 mL) was added. The mixture was stirred at 125° C. under CO atmosphere (3 Mpa) overnight. The mixture was concentrated and resulting residue was purified by chromatography on a silica gel column (DCM/EA=10/1, v/v) to give 2-(quinoline-6-carbonyl)-isonicotinic acid methyl ester (160 g, 73%) as a white solid.

A mixture of 2-(3-chloro-quinoline-6-carbonyl)-isonicotinic acid methyl ester (5.0 g, 15.3 mmol, 1 eq) and NaOH (1.22 g, 30.6 mmol, 2 eq) in THF (40 mL) and H₂O (40 mL) was stirred at rt for 2 h. Then THF was removed by evaporation. The aqueous layer was acidified to pH 2 with 3 N aq. HCl solution. The precipitate was filtered to give 2-(3-chloro-quinoline-6-carbonyl)-isonicotinic acid methyl ester (3.58 g, 75%) as a white solid.

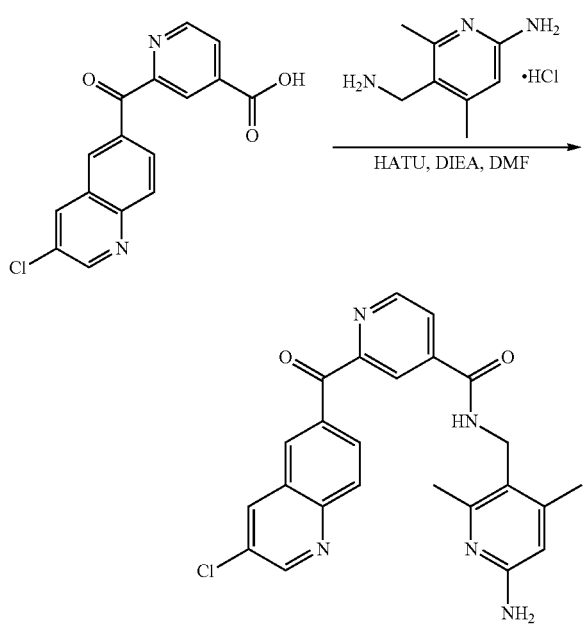

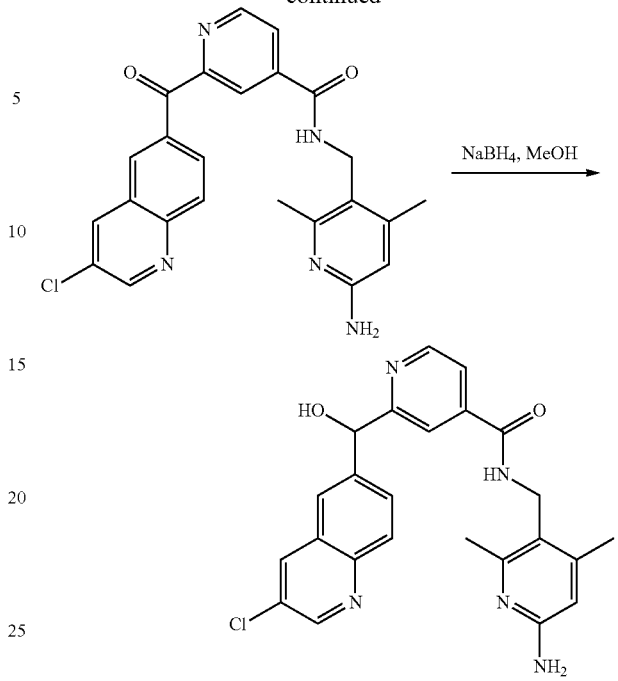

To a solution of 2-(3-chloro-quinoline-6-carbonyl)-isonicotinic acid (100 mg, 0.32 mmol, 1.0 eq.) and 5-aminomethyl-4,6-dimethyl-pyridin-2-ylamine hydrochloride (120 mg, 0.64 mmol, 2 eq) in DMF (5 mL) were added HATU (146 mg, 0.384 mmol, 1.2 eq) and DIEA (123 mg, 0.96 mmol, 3 eq). The mixture was stirred at rt for 1 h and diluted with water. The organic layer was separated and the aqueous layer was extracted with EA. The combined extracts were dried and concentrated. The resulting residue was purified by chromatography on a silica gel column (EA/MeOH=5/1, v/v) to give N-(6-amino-2,4-dimethyl-pyridin-3-ylmethyl)-2-(3-chloro-quinoline-6-carbonyl)-isonicotinamide as a white solid (60 mg, 42%).

LRMS (M+H⁺) m/z calculated 446.1, found 446.1. ¹H NMR (DMSO-d₆, 400 MHz): δ 9.04 (s, 1H), 8.94 (t, 1H), 8.88 (d, 1H), 8.67 (s, 1H), 8.48 (s, 1H), 8.2 (dd, 1H), 8.08 (d, 1H), 6.15 (s, 1H), 5.74 (br s, 2H), 4.41 (d, 2H), 2.34 (s, 3H), 2.20 (s, 3H).

Example 275: Preparation of N-((6-amino-2,4-dimethylpyridin-3-yl)methyl)-2-((3-chloroquinolin-6-yl)(hydroxy)methyl)isonicotinamide A mixture of N-(6-amino-2,4-dimethyl-pyridin-3-ylmethyl)-2-(3-chloro-quinoline-6-carbonyl)-isonicotinamide (200 mg, 0.45 mmol, 1.0 eq) and sodium borohydride (26 mg, 0.67 mmol, 1.5 eq) in MeOH (10 mL) was stirred at rt for 2 h. After removal of the solvent, the residue was diluted with water (20 mL) and extracted with EA. The combined organic layers were washed with brine (20 mL), dried over anhydrous sodium sulfate, filtered, concentrated. The resulting residue was purified by Prep-HPLC to give N-((6-amino-2,4-dimethylpyridin-3-yl)methyl)-2-((3-chloroquinolin-6-yl)(hydroxy)methyl)isonicotinamide (55 mg, 27%) as a white solid.

LRMS (M+H⁺) m/z calculated 448.1, found 448.2. ¹H NMR (DMSO-d₆, 400 MHz): δ 8.84 (s, 1H), 8.73 (t, 1H), 8.88 (d, 1H), 8.67 (s, 1H), 8.60 (d, 1H), 8.56 (d, 1H), 8.04 (d, 2H), 7.90 (dd, 2H), 7.61 (d, 1H), 6.49 (d, 1H), 6.12 (s, 1H), 5.96 (s, 1H), 5.68 (s, 2H), 4.35 (d, 2H), 2.34 (s, 3H), 2.20 (s, 3H).

Example 276: Preparation of 2-[Amino-(3-chloro-quinolin-6-yl)-methyl]-N-(6-amino-2,4-dimethyl-pyridin-3-ylmethyl)-isonicotinamide

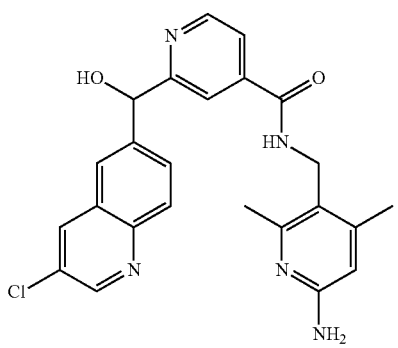

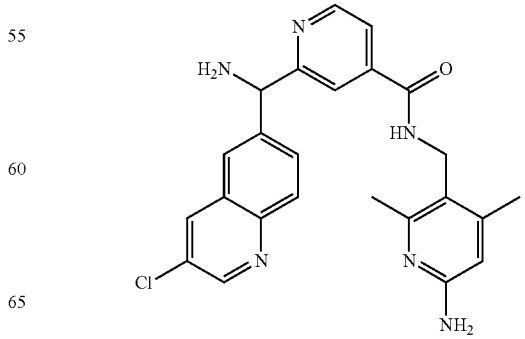

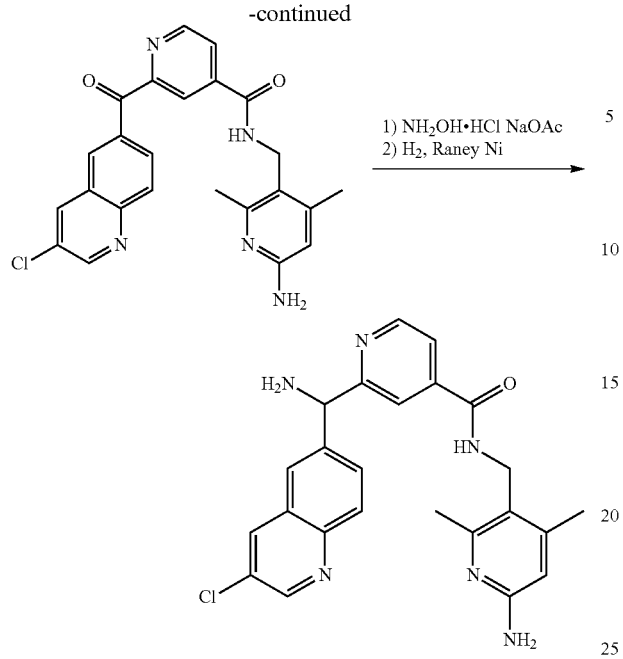

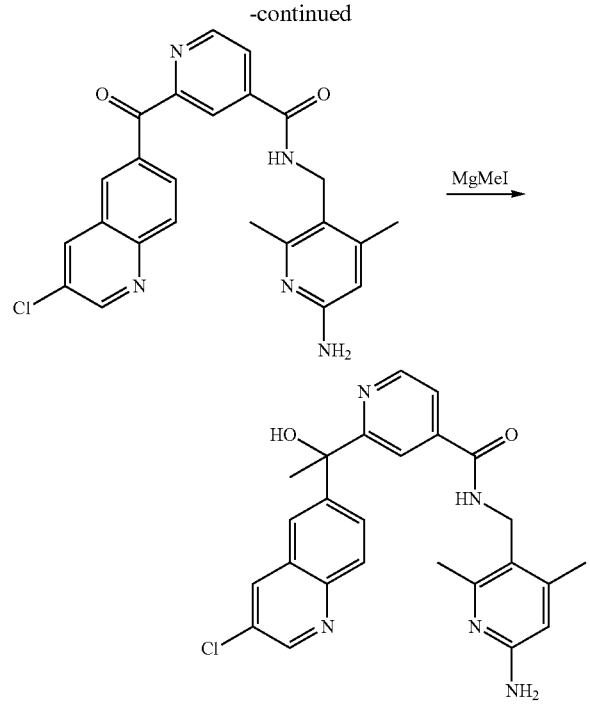

A mixture of N-(6-amino-2,4-dimethyl-pyridin-3-ylmethyl)-2-(3-chloro-quinoline-6-carbonyl)-isonicotinamide (200 mg, 0.45 mmol, 1.0 eq.), hydroxylamine hydrochloride (37.5 mg, 0.54 mmol, 1.2 eq.) and sodium acetate (73 mg, 0.54 mmol, 1.2 equiv.) in ethanol (5 mL) was refluxed for 12 h under $N_2$ atmosphere. Water was added to the mixture and the reaction mixture was extracted with ethyl acetate. The combined organic phases were washed with brine and dried over $Na_2SO_4$. The solvent was evaporated and the residue was hydrogenated at 40° C. overnight under a pressure of 50 psi with 40 mg of Raney Ni. The catalyst was filtered off, and the filtrate was concentrated in vacuo. The resulting residue was purified by Prep-HPLC to give 2-[amino-(3-chloro-quinolin-6-yl)-methyl]-N-(6-amino-2,4-dimethyl-pyridin-3-ylmethyl)-isonicotinamide (60 mg, 30%) as a white solid.

LRMS (M+H$^+$) m/z calculated 447.2, found 447.2. $^1$H NMR (DMSO-d$_6$, 400 MHz): δ 8.83 (s, 1H), 8.59-8.56 (m, 3H), 8.01-7.95 (m, 3H), 7.84 (d, 1H), 7.61 (d, 1H), 6.12 (s, 1H), 5.69 (s, 2H), 5.41 (s, 1H), 4.35 (d, 2H), 3.17 (br s, 2H), 2.34 (s, 3H), 2.20 (s, 3H).

Example 277: Preparation of N-((6-amino-2,4-dimethylpyridin-3-yl)methyl)-2-(1-(3-chloroquinolin-6-yl)-1-hydroxyethyl)isonicotinamide To a mixture of N-(6-amino-2,4-dimethyl-pyridin-3-ylmethyl)-2-(3-chloro-quinoline-6-carbonyl)-isonicotinamide (100 mg, 0.22 mmol, 1.0 eq) in dry THF (10 mL) was added MgMeI (0.37 mL, 3 M in Et$_2$O, 1.12 mmol, 3 eq) at 0° C. The mixture was stirred at rt overnight and then quenched by the addition of sat. NH$_4$Cl aq. The mixture was extracted with EA and the combined organic layers were concentrated. The resulting residue was purified by Prep-HPLC to give N-((6-amino-2,4-dimethylpyridin-3-yl)methyl)-2-(1-(3-chloroquinolin-6-yl)-1-hydroxyethyl)isonicotinamide (10 mg, 9.7%) as an off white solid.

LRMS (M$^+$+1) m/z calculated 462.2, found 462.2. $^1$H NMR (CD$_3$OD, 400 MHz): δ 8.73 (d, 1H), 8.57 (dd, 1H), 8.38 (d, 1H), 8.11 (d, 1H), 8.09 (d, 1H), 7.88 (d, 1H), 7.86 (d, 1H), 7.55 (dd, 1H), 6.32 (s, 1H), 4.49 (s, 2H), 2.40 (s, 3H), 2.27 (s, 3H), 1.92 (s, 3H).

Example 278: Preparation of N-((6-amino-2,4-dimethylpyridin-3-yl)methyl)-2-((3-(2,2-difluoroethyl)quinolin-6-yl)methyl)isonicotinamide

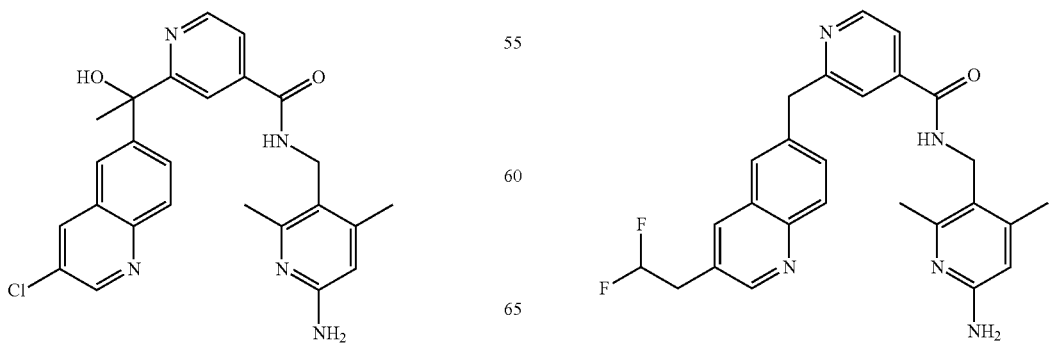

-continued

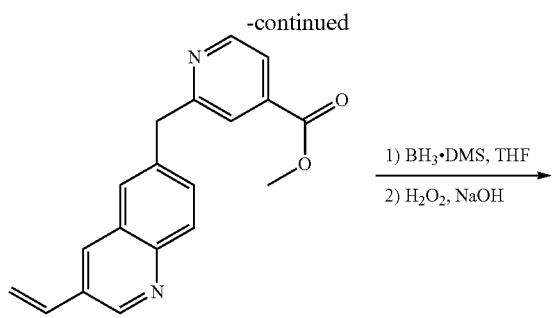

To a solution of 2-(3-vinyl-quinolin-6-ylmethyl)-isonicotinic acid methyl ester (800 mg, 2.6 mmol, 1.0 eq) in THF (30 mL) was added BH₃.DMS (10 M, 2.6 mL, 26 mmol, 10.0 eq) at 0° C. The mixture was stirred at rt overnight. After that, the mixture was cooled to 0° C. and 3 N NaOH (13 mL, 39 mmol, 15.0 eq), and H₂O₂ (30%, 6.0 mL, 52 mmol, 20.0 eq) were added slowly. The mixture was warmed to rt and stirred for 4 h. The mixture was extracted with EA (30 mL×3). The organic layers were dried over Na₂SO₄, filtered and concentrated. The resulting residue was purified by chromatography on a silica gel column (EA) to give 2-[3-(2-hydroxy-ethyl)-quinolin-6-ylmethyl]-isonicotinic acid methyl ester (450 mg, 54%) as a yellow oil.

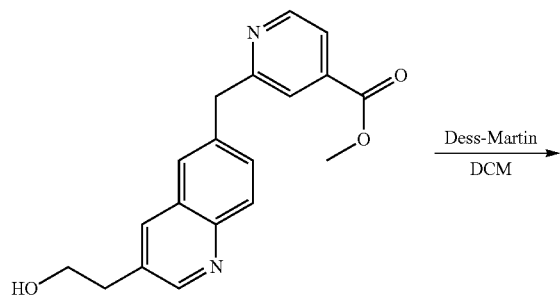

To a solution of 2-[3-(2-hydroxy-ethyl)-quinolin-6-ylmethyl]-isonicotinic acid methyl ester (260 mg, 0.81 mmol, 1.0 eq) in DCM (10 mL) was added Dess-Martin reagent (513 mg, 1.21 mmol, 1.5 eq) at 0° C. The mixture was stirred at rt for 1 h. After that, Na₂CO₃ aq. (20 mL) was added and extracted with EA (30 mL×3). The organic layers were dried over Na₂SO₄, filtered and concentrated. The resulting residue was purified by chromatography on a silica gel column (PE/EA=1/1, v/v) to give 2-[3-(2-oxo-ethyl)-quinolin-6-ylmethyl]-isonicotinic acid methyl ester (80 mg, 30%) as a yellow oil.

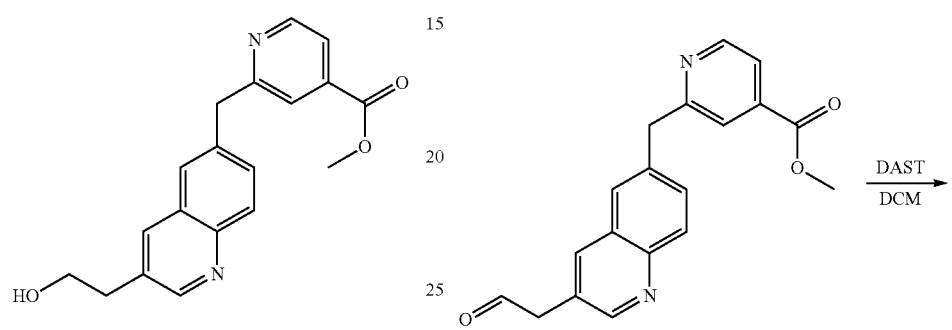

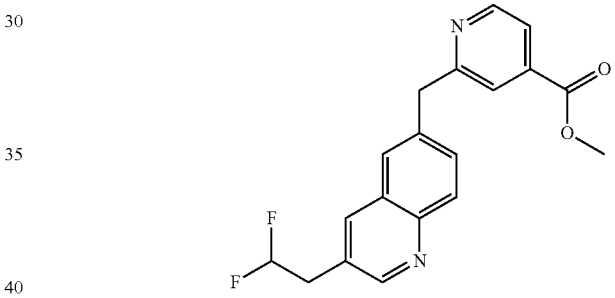

To a solution of 2-[3-(2-oxo-ethyl)-quinolin-6-ylmethyl]-isonicotinic acid methyl ester (80 mg, 0.25 mmol, 1.0 eq) in DCM (10 mL) was added DAST (402 mg, 2.5 mmol, 10.0 eq) at 0° C. The mixture was stirred at rt overnight. After that, Na₂CO₃ aq. (20 mL) was added and extracted with EA (20 mL×3). The organic layers were dried over Na₂SO₄, filtered and concentrated. The resulting residue was purified by Prep-TLC (PE/EA=3/1, v/v) to give 2-[3-(2,2-difluoro-ethyl)-quinolin-6-ylmethyl]-isonicotinic acid methyl ester (20 mg, 23%) as a yellow oil.

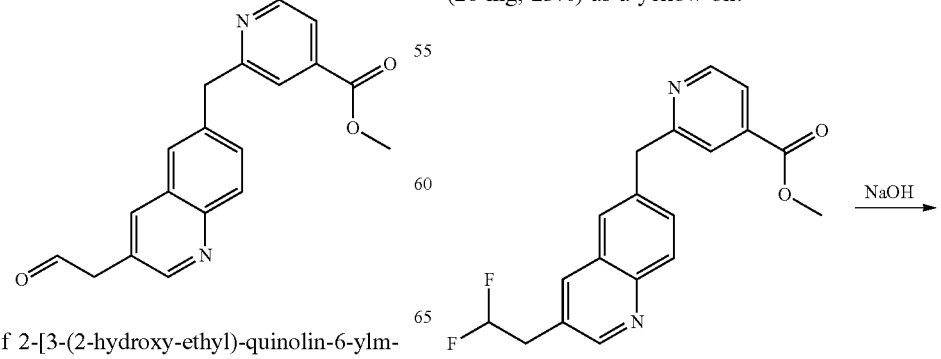

-continued

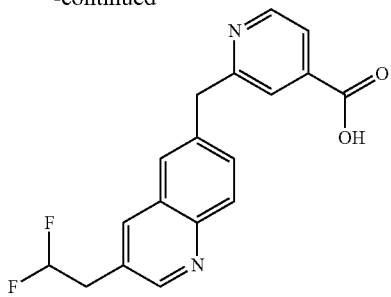

To a solution of 2-[3-(2,2-difluoro-ethyl)-quinolin-6-yl-methyl]-isonicotinic acid methyl ester (20 mg, 0.058 mmol, 1.0 eq) in THF (10 mL) was added a solution of NaOH (4.7 mg, 0.11 mmol, 2.0 eq) at rt. The mixture was stirred at rt for 1 h. The mixture was neutralized with 1 N HCl to pH 3 and extracted with DCM. The organic phase was concentrated to give 2-[3-(2,2-difluoro-ethyl)-quinolin-6-ylmethyl]-isonicotinic acid (27 mg, crude) as a yellow solid without further purification.

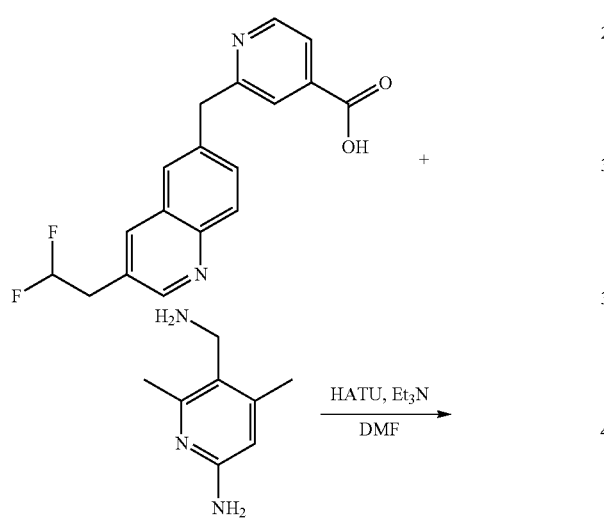

To a solution of 2-[3-(2,2-difluoro-ethyl)-quinolin-6-yl-methyl]-isonicotinic acid (20.0 mg, 0.061 mmol, 1.0 eq), 5-aminomethyl-4,6-dimethyl-pyridin-2-ylamine (14.0 mg, 0.091 mmol, 1.5 eq) and Et$_3$N (18 mg, 0.18 mmol, 3.0 eq) in DMF (2 mL) was added HATU (32 mg, 0.091 mmol, 1.5 eq). The mixture was stirred at rt for 2 h. The mixture was concentrated and the resulting residue was purified by Prep-HPLC to obtain N-((6-amino-2,4-dimethylpyridin-3-yl)methyl)-2-((3-(2,2-difluoroethyl)quinolin-6-yl)methyl)isonicotinamide (5.0 mg, 18%) as a white solid.

LRMS (M+H$^+$) m/z calculated 461.2, found 461.2. $^1$H NMR (DMSO-d$_6$, 300 MHz): δ 9.02 (d, 1H), 8.63-8.54 (m, 3H), 8.01-7.94 (m, 2H), 7.79-7.73 (m, 2H), 7.59-7.57 (m, 1H), 6.07 (s, 1H), 5.65 (s, 2H), 4.34-4.30 (m, 4H), 2.67 (s, 3H), 2.15-2.03 (m, 6H).

Example 279: Preparation of N-((6-amino-2-methylpyridin-3-yl)methyl)-2-((3-(2,2-difluoroethyl)quinolin-6-yl)methyl)isonicotinamide

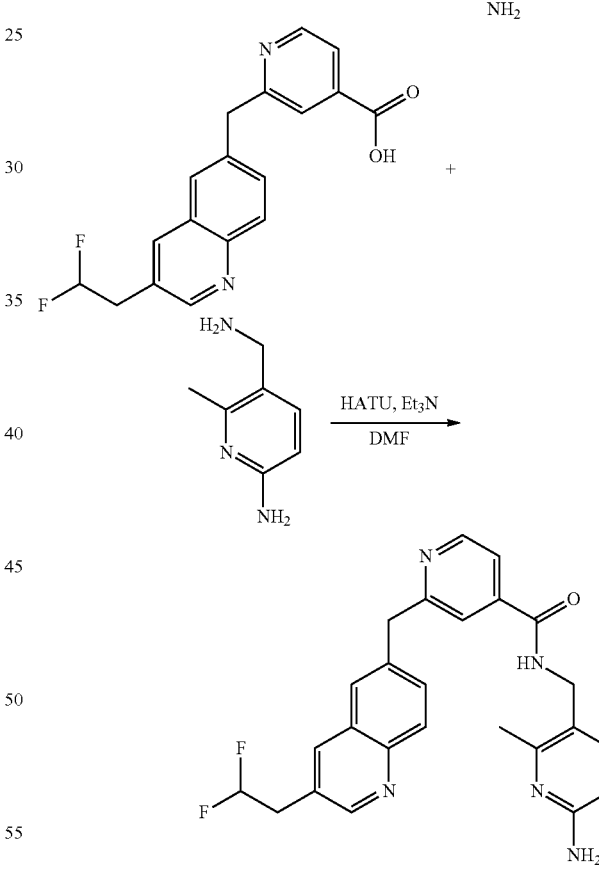

To a solution of 2-[3-(2,2-difluoro-ethyl)-quinolin-6-yl-methyl]-isonicotinic acid (20.0 mg, 0.061 mmol, 1.0 eq), 5-aminomethyl-6-methyl-pyridin-2-ylamine (12.0 mg, 0.091 mmol, 1.5 eq) and Et$_3$N (18 mg, 0.18 mmol, 3.0 eq) in DMF (2 mL) was added HATU (32 mg, 0.091 mmol, 1.5 eq). The mixture was stirred at rt for 2 h. The mixture was concentrated and the resulting residue was purified by Prep-HPLC to obtain N-((6-amino-2-methylpyridin-3-yl)methyl)-2-((3-(2,2-difluoroethyl)quinolin-6-yl)methyl)isonicotinamide (6.5 mg, 24%) as a white solid.

LRMS (M+H⁺) m/z calculated 448.2, found 448.2. ¹H NMR (DMSO-d₆, 300 MHz): δ 9.00-9.96 (m, 2H), 8.62-8.55 (m, 2H), 8.01-7.94 (m, 2H), 7.79-7.74 (m, 2H), 7.61-7.59 (m, 1H), 7.22-7.20 (m, 1H), 6.21 (d, 1H), 5.73 (s, 2H), 4.36 (s, 2H), 4.25 (d, 2H), 2.25 (s, 3H), 2.09 (t, 3H).

Example 280: Preparation of N-((3-chloro-6-fluoro-1H-indol-5-yl)methyl)-2-((3-ethylquinolin-6-yl)methyl)isonicotinamide

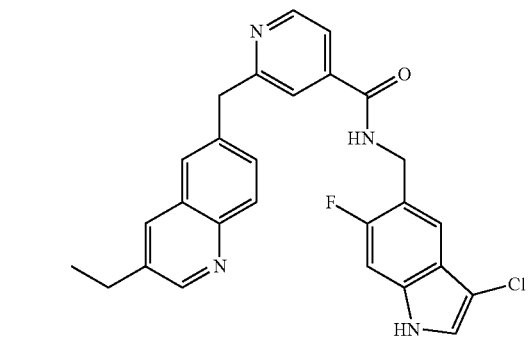

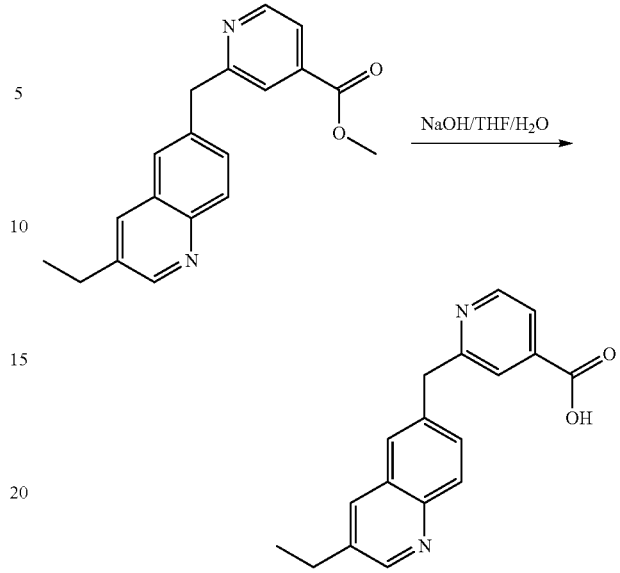

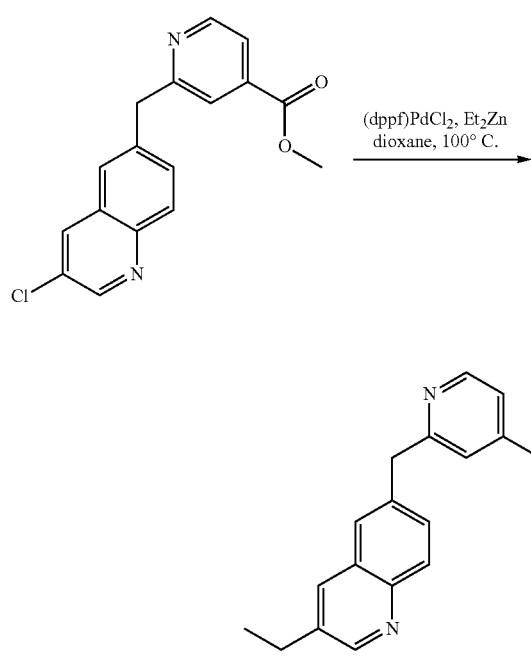

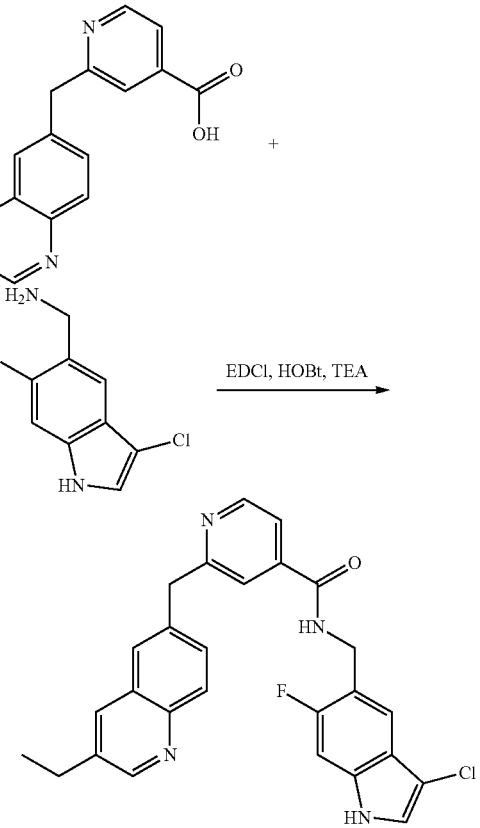

To a solution of 2-(3-chloro-quinolin-6-ylmethyl)-isonicotinic acid methyl ester (3.0 g, 9.61 mmol, 1 eq) in dioxane (60 ml), Pd(dppf)Cl₂ (703 mg, 0.96 mmol, 0.1 eq) was added under N₂. To this mixture was added dropwise diethyl zinc (13.1 mL, 14.42 mmol, 1.1 M solution in toluene, 1.5 eq). The mixture was stirred at 90° C. for 24 h and then was cooled to rt and carefully quenched with water. The mixture was filtered over celite and the filtrate was extracted twice with EA. The combined organic extracts were dried over MgSO₄, filtered and concentrated. The resulting residue was purified by chromatography on a silica gel column (EA/PE=1/1, v/v) to give 2-(3-ethyl-quinolin-6-ylmethyl)-isonicotinic acid methyl ester (1.0 g, 34%) as a pale yellow solid.

To a solution of 2-(3-ethyl-quinolin-6-ylmethyl)-isonicotinic acid methyl ester (1.0 g, 3.27 mmol, 1.0 eq) in THF (10 mL), H₂O (10 mL) was added NaOH (261 mg, 6.54 mmol, 2.0 eq) and the reaction mixture was stirred at rt for 3 h. The reaction mixture was acidified to pH 3 with 3 N HCl, then extracted with EA, concentrated under reduced pressure to afford 2-(3-ethyl-quinolin-6-ylmethyl)-isonicotinic acid (850 mg, 89%) as a yellow solid.

To a solution of 2-(3-ethyl-quinolin-6-ylmethyl)-isonicotinic acid (50 mg, 0.17 mmol, 1 eq) in DMF (5 mL) was added C-(3-chloro-6-fluoro-1H-indol-5-yl)-methylamine (52 mg, 0.22 mmol, 1.3 eq) followed by HOBT (30 mg, 0.22 mmol, 1.3 eq), EDCI (42 mg, 0.22 mmol, 1.3 eq) and TEA (52 mg, 0.51 mmol, 3.0 eq). The reaction mixture was heated at 35° C. and stirred overnight. Water was added, and the mixture was extracted with DCM. The organic layer was dried over Na$_2$SO$_4$, filtered and concentrated. The resulting residue was purified by Prep-HPLC to give N-((3-chloro-6-fluoro-1H-indol-5-yl)methyl)-2-((3-ethylquinolin-6-yl)methyl)isonicotinamide (6 mg, 7%) as an off white solid.

LRMS (M+H$^+$) m/z calculated 473.1, found 473.1. $^1$H NMR (DMSO-d6, 300 MHz): δ 11.39 (s, 1H), 9.25 (t, 1H), 8.72 (s, 1H), 8.62 (s, 1H), 8.05 (d, 1H), 7.86 (s, 1H), 7.75 (s, 2H), 7.63 (d, 1H), 7.58 (d, 1H), 7.48 (s, 1H), 7.41 (d, 1H), 7.21 (d, 1H), 4.55 (d, 2H), 4.32 (s, 1H), 2.77 (q, 2H), 1.25 (t, 3H).

Example 281: Preparation of N-((3-chloro-1H-pyrrolo[2,3-b]pyridin-5-yl)methyl)-2-((3-ethylquinolin-6-yl)methyl)isonicotinamide

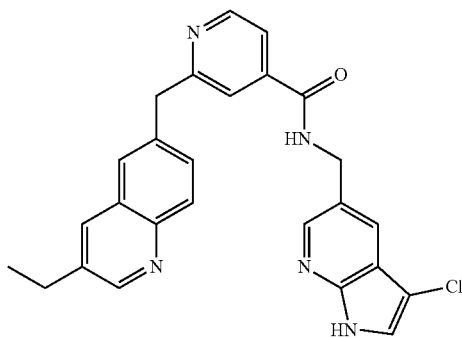 [SMILES: CCc1cnc2ccc(Cc3cc(C(=O)NCc4cnc5[nH]cc(Cl)c5c4)ccn3)cc2c1]

To a solution of 2-(3-ethyl-quinolin-6-ylmethyl)-isonicotinic acid (50 mg, 0.17 mmol, 1.0 eq) in DMF (5 mL) was added (3-chloro-1H-pyrrolo[2,3-b]pyridin-5-yl)methanamine (48 mg, 0.22 mmol, 1.3 eq) followed by HOBT (30 mg, 0.22 mmol, 1.3 eq), EDCI (42 mg, 0.22 mmol, 1.3 eq) and TEA (52 mg, 0.51 mmol, 3.0 eq). The reaction mixture was heated at 35° C. and stirred overnight. Water was added, and the mixture was extracted with DCM. The organic layer was dried over Na$_2$SO$_4$, filtered and concentrated. The resulting residue was purified by Prep-HPLC to give N-((3-chloro-1H-pyrrolo[2,3-b]pyridin-5-yl)methyl)-2-((3-ethylquinolin-6-yl)methyl)isonicotinamide (6 mg, 7%) as an off white solid.

LRMS (M+H+) m/z calculated 456.2, found 455.8. $^1$H NMR (DMSO-d6, 400 MHz): δ 11.96 (s, 1H), 9.35 (t, 1H), 8.74 (s, 1H), 8.64 (d, 1H), 8.30 (d, 1H), 8.07 (s, 1H), 7.90 (d, 1H), 7.86 (d, 1H), 7.77 (s, 1H), 7.75 (s, 1H), 7.67 (s, 1H), 7.63 (s, 1H), 7.61 (d, 1H), 4.58 (d, 1H), 4.34 (s, 2H), 2.78 (q, 2H), 1.25 (t, 3H).

Example 282: Preparation of N-((3-chloro-4-fluoro-1H-indol-5-yl)methyl)-2-((3-ethylquinolin-6-yl)methyl)isonicotinamide

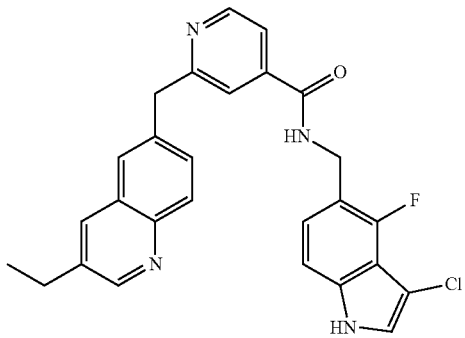 [SMILES: CCc1cnc2ccc(Cc3cc(C(=O)NCc4ccc5[nH]cc(Cl)c5c4F)ccn3)cc2c1]

To a solution of 2-(3-ethyl-quinolin-6-ylmethyl)-isonicotinic acid (50 mg, 0.17 mmol, 1.0 eq) in DMF (5 mL) was added (3-chloro-4-fluoro-1H-indol-5-yl)methanamine (51 mg, 0.22 mmol, 1.3 eq) followed by HOBT (30 mg, 0.22 mmol, 1.3 eq), EDCI (42 mg, 0.22 mmol, 1.3 eq) and TEA (52 mg, 0.51 mmol, 3.0 eq). The reaction mixture was heated at 35° C. and stirred overnight. Water was added, and the mixture was extracted with DCM. The organic layer was dried over Na$_2$SO$_4$, filtered and concentrated. The resulting residue was purified by Prep-HPLC to give N-((3-chloro-4-fluoro-1H-indol-5-yl)methyl)-2-((3-ethylquinolin-6-yl)methyl)isonicotinamide (9 mg, 11%) as a white solid.

LRMS (M+H$^+$) m/z calculated 473.1, found 473.1. $^1$H NMR (DMSO-d6, 300 MHz): δ 11.58 (s, 1H), 9.23 (t, 1H), 8.72 (s, 1H), 8.61 (d, 1H), 8.05 (d, 1H), 7.88 (d, 1H), 7.74 (s, 2H), 7.61 (d, 1H), 7.57 (d, 1H), 7.49 (s, 1H), 7.18-7.11 (m, 2H), 4.54 (d, 1H), 4.31 (s, 2H), 2.78 (q, 2H), 1.25 (t, 3H).

Example 283: Preparation of N-((1-aminoisoquinolin-6-yl)methyl)-2-((3-ethylquinolin-6-yl)methyl)isonicotinamide

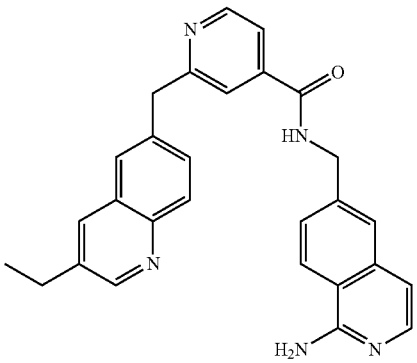 [SMILES: CCc1cnc2ccc(Cc3cc(C(=O)NCc4ccc5c(N)nccc5c4)ccn3)cc2c1]

To a solution of 2-(3-ethyl-quinolin-6-ylmethyl)-isonicotinic acid (50 mg, 0.17 mmol, 1.0 eq) in DMF (5 mL) was added 6-aminomethyl-isoquinolin-1-ylamine (38 mg, 0.22 mmol, 1.3 eq) followed by HOBT (30 mg, 0.22 mmol, 1.3 eq), EDCI (42 mg, 0.22 mmol, 1.3 eq) and TEA (52 mg, 0.51 mmol, 3.0 eq). The reaction mixture was heated at 35° C. and stirred overnight. Water was added, and the mixture was extracted with DCM. The organic layer was dried over Na₂SO₄, filtered and concentrated. The resulting residue was purified by Prep-HPLC to give N-((1-aminoisoquinolin-6-yl)methyl)-2-((3-ethylquinolin-6-yl)methyl)isonicotinamide (6 mg, 8%) as an off white solid.

LRMS (M+H⁺) m/z calculated 448.2, found 448.2. ¹H NMR (DMSO-d6, 300 MHz): δ 9.37 (t, 1H), 8.72 (s, 1H), 8.65 (d, 1H), 8.11 (d, 1H), 8.06 (s, 1H), 7.88 (d, 1H), 7.77 (s, 2H), 7.72 (d, 1 H), 7.65 (d, 1H), 7.61 (d, 1H), 7.52 (s, 1H), 7.37 (d, 1H), 6.81 (d, 1H), 6.71 (s, 2H), 4.58 (d, 1H), 4.33 (s, 2H), 2.75 (q, 2H), 1.25 (t, 3H).

Example 284: Preparation of N-((5-chloro-1H-indazol-3-yl)methyl)-2-((3-ethylquinolin-6-yl)methyl)isonicotinamide

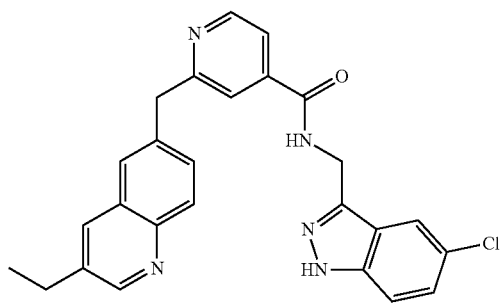 [SMILES: CCc1cnc2ccc(Cc3cc(C(=O)NCc4n[nH]c5ccc(Cl)cc45)ccn3)cc2c1]

To a solution of 2-(3-ethyl-quinolin-6-ylmethyl)-isonicotinic acid (50 mg, 0.17 mmol, 1.0 eq) in DMF (5 mL) was added (5-chloro-1H-indazol-3-yl)methanamine (48 mg, 0.22 mmol, 1.3 eq) followed by HOBT (30 mg, 0.22 mmol, 1.3 eq), EDCI (42 mg, 0.22 mmol, 1.3 eq) and TEA (52 mg, 0.51 mmol, 3.0 eq). The reaction mixture was heated at 35° C. and stirred overnight. Water was added, and the mixture was extracted with DCM. The organic layer was dried over Na₂SO₄, filtered and concentrated. The resulting residue was purified by Prep-HPLC to give N-((5-chloro-1H-indazol-3-yl)methyl)-2-((3-ethylquinolin-6-yl)methyl)isonicotinamide (6 mg, 7%) as a white solid.

LRMS (M+H⁺) m/z calculated 456.2, found 456.1. ¹H NMR (DMSO-d6, 300 MHz): δ 13.10 (s, 1H), 9.36 (t, 1H), 8.71 (d, 1H), 8.61 (d, 1H), 8.04 (s, 1H), 7.88 (s, 1H), 7.86 (d, 1H), 7.74 (s, 2H), 7.60 (s, 1H), 7.58 (d, 1H), 7.49 (d, 1H), 7.30 (d, 1H), 4.75 (d, 1H), 4.31 (s, 2H), 2.76 (q, 2H), 1.25 (t, 3H).

Example 285: Preparation of N-((6-amino-2-methylpyridin-3-yl)methyl)-2-((3-ethylquinolin-6-yl)methyl)isonicotinamide

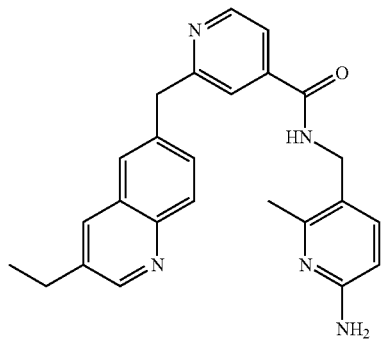

To a solution of 2-(3-ethyl-quinolin-6-ylmethyl)-isonicotinic acid (60 mg, 0.205 mmol, 1.0 eq) and 5-aminomethyl-6-methyl-pyridin-2-ylamine hydrochloride (54 mg, 0.308 mmol, 1.5 eq) in DMF (5 mL) was added HATU (94 mg, 0.246 mmol, 1.2 eq) and DIEA (80 mg, 0.615 mmol, 3 eq). The mixture was stirred at rt for 1 h and diluted with water. It was extracted with EA, and the combined extracts were dried and concentrated. The resulting residue was purified by flash chromatography on a silica gel column (EA/MeOH=5/1, v/v) to give N-((6-amino-2-methylpyridin-3-yl)methyl)-2-((3-ethylquinolin-6-yl)methyl)isonicotinamide as a white solid (17 mg, 33%).

LRMS (M+H⁺) m/z calculated 412.2, found 412.1 ¹H NMR (CDCl₃, 400 MHz) δ 8.70-8.65 (m, 2H), 7.84 (d, 1H), 7.83 (s, 1H), 7.62 (s, 1H), 7.53-7.42 (m, 3H), 7.03 (br s, 1H), 6.45 (d, 1H), 5.34 (br s, 2H), 4.44 (d, 2H), 4.36 (d, 2H), 2.79 (dd, 2H), 2.39 (s, 3H), 1.33 (s, 3H).

Example 286: Preparation of N-((6-amino-2,4-dimethylpyridin-3-yl)methyl)-2-((3-ethylquinolin-6-yl)methyl)isonicotinamide

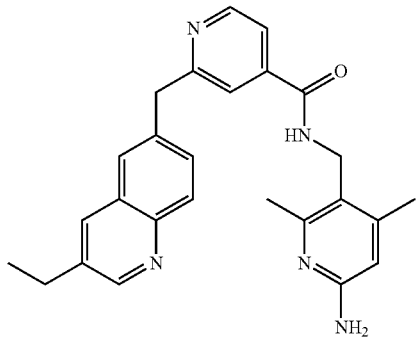 [SMILES: CCc1cnc2ccc(Cc3cc(C(=O)NCc4c(C)cc(N)nc4C)ccn3)cc2c1]

To a solution of 2-(3-ethyl-quinolin-6-ylmethyl)-isonicotinic acid (100 mg, 0.342 mmol, 1.0 eq) and 5-aminomethyl-4,6-dimethyl-pyridin-2-ylamine hydrochloride (128 mg, 0.685 mmol, 2 eq) in DMF (5 mL) were added HATU (156 mg, 0.410 mmol, 1.2 eq) and DIEA (129 mg, 1 mmol, 3 eq). The mixture was stirred at rt for 1 h and diluted with water. It was extracted with EA. The combined extracts were dried and concentrated. The resulting residue was purified by Prep-HPLC to give N-(6-amino-2,4-dimethyl-pyridin-3-yl-methyl)-2-(3-ethyl-quinolin-6-ylmethyl)-isonicotinamide as a white solid (16 mg, 33%).

LRMS (M+H⁺) m/z calculated 426.2, found 426.2 ¹H NMR (CDCl₃, 400 MHz) δ 8.70-8.65 (m, 2H), 7.94 (d, 1H), 7.83 (s, 1H), 7.60 (s, 1H), 7.41-7.40 (m, 2H), 6.17 (s, 1H), 6.09 (br s, 1H), 4.52 (d, 2H), 4.35 (d, 2H), 4.30 (d, 2H), 2.81 (dd, 2H), 2.37 (s, 3H), 2.22 (s, 3H), 1.33 (s, 3H).

Example 287: Preparation of N-((3-chloro-6-fluoro-1H-indol-5-yl)methyl)-2-((3-methyl-8-sulfamoylquinolin-6-yl)methyl)isonicotinamide

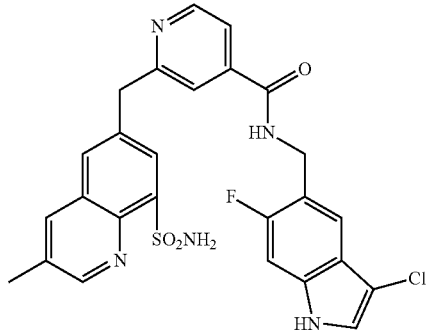

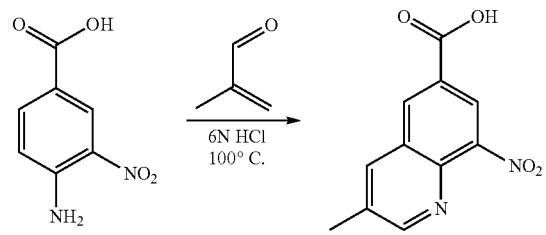

To a solution of 4-amino-3-nitro-benzoic acid (20.0 g, 109.8 mmol, 1.0 eq) in 6 N HCl (1000 mL) was added 2-methyl-propenal (15.4 g, 219.6 mmol, 2.0 eq) at 100° C. The mixture was stirred at 100° C. overnight. The mixture was neutralized with NaHCO₃ solid. The resulting precipitate was collected by filtration and the yellow solid was dried in vacuo to give 3-methyl-8-nitro-quinoline-6-carboxylic acid (17.0 g, crude) without further purification.

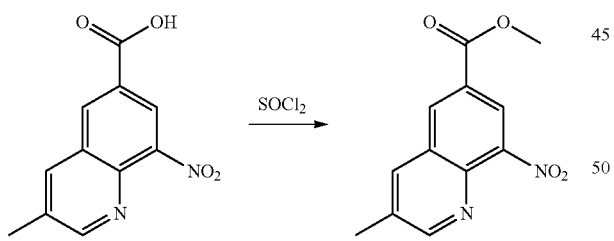

To a solution of 3-methyl-8-nitro-quinoline-6-carboxylic acid (17.0 g, crude, 73.0 mmol, 1.0 eq) in MeOH (300 mL) was added SOCl₂ (17.0 g, 146 mmol, 2.0 eq) at 0° C. The mixture was stirred under reflux overnight. The mixture was concentrated and the resulting residue was diluted with Na₂CO₃ aq. (80 mL), extracted with DCM (200 mL×3). The organic layers were dried over Na₂SO₄, filtered and concentrated. The resulting residue was purified by chromatography on a silica gel column (PE/EA=3/1, v/v) to give 3-methyl-8-nitro-quinoline-6-carboxylic acid methyl ester (10.0 g, 37% for 2 steps) as a yellow solid.

¹H NMR (DMSO-d₆, 300 MHz): δ 9.01 (d, 1H), 8.84 (s, 1H), 8.54 (d, 2H), 3.96 (s, 3H), 2.55 (s, 3H).

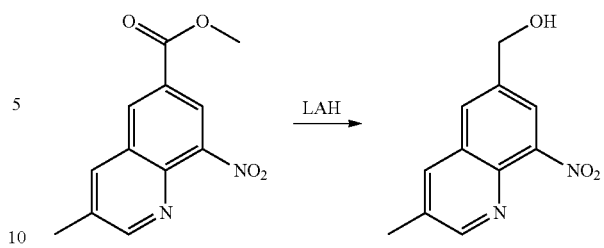

To a solution of 3-methyl-8-nitro-quinoline-6-carboxylic acid methyl ester (8.0 g, 32.49 mmol, 1.0 eq) in THF (400 mL) was added AlLiH₄ (1M, 32 mL, 32.49 mmol) at −78° C. The mixture was warmed to rt and stirred at rt overnight. The mixture was quenched with aq. NH₄Cl (200 mL) and extracted with EA (200 mL×3). The combined organic layers were dried over Na₂SO₄, filtered and concentrated. The resulting residue was purified by chromatography on a silica gel column (PE/EA=3/1, v/v) to give (3-methyl-8-nitro-quinolin-6-yl)-methanol (2.5 g, 35%) as a yellow solid.

¹H NMR (DMSO-d₆, 300 MHz): δ 8.87 (d, 1H), 8.31 (s, 1H), 8.01 (s, 2H), 5.57 (t, 1H), 4.74 (d, 2H), 2.53 (s, 3H).

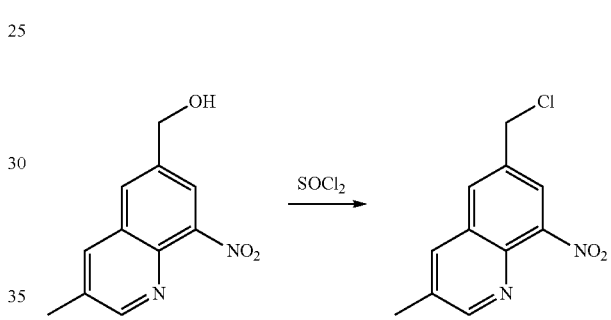

A mixture of (3-methyl-8-nitro-quinolin-6-yl)-methanol (2.5 g, 11.46 mmol, 1.0 eq) in SOCl₂ (20 mL) was stirred at rt for 1 h. The mixture was concentrated and the resulting residue was dissolved in aq. Na₂CO₃ (40 mL), extracted with EA (50 mL×3). The combined organic layers were dried over Na₂SO₄, filtered and concentrated to give 6-chloromethyl-3-methyl-8-nitro-quinoline (2.5 g, 92.6%) as a yellow solid.

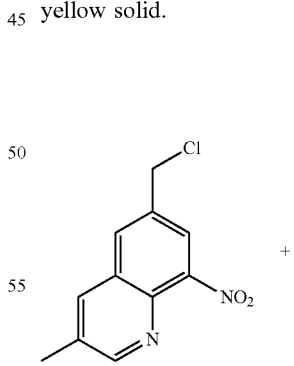

+

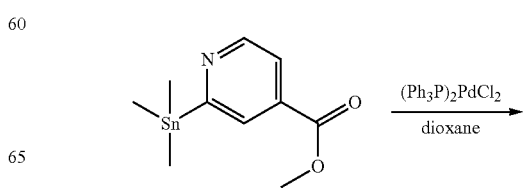

-continued

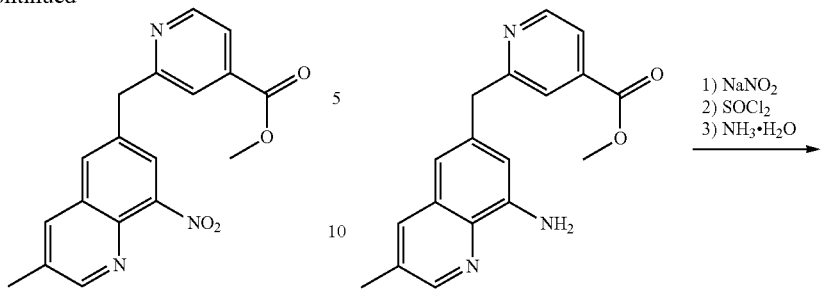

A mixture of 6-chloromethyl-3-methyl-8-nitro-quinoline (2.5 g, 10.56 mmol, 1.0 eq), 2-trimethylstannanyl-isonicotinic acid methyl ester (3.2 g, 10.56 mmol, 1.0 eq) and (Ph$_3$P)$_2$PdCl$_2$ (741 mg, 1.06 mmol, 0.1 eq) in dioxane (40 mL) was stirred at 90° C. overnight. The mixture was concentrated and the resulting residue was purified by chromatography on a silica gel column (PE/EA=3/1, v/v) to give 2-(3-methyl-8-nitro-quinolin-6-ylmethyl)-isonicotinic acid methyl ester (1.3 g, 36%) as a yellow solid.

LRMS (M+H$^+$) m/z calculated 338.1, found 338.1. $^1$H NMR (DMSO-d$_6$, 300 MHz): δ 8.86 (s, 1H), 8.73 (d, 1H), 8.28 (s, 1H), 8.17 (s, 1H), 8.09 (s, 1H), 7.92 (s, 1H), 7.71 (d, 1H), 4.47 (s, 2H), 3.89 (s, 3H), 2.51 (s, 3H).

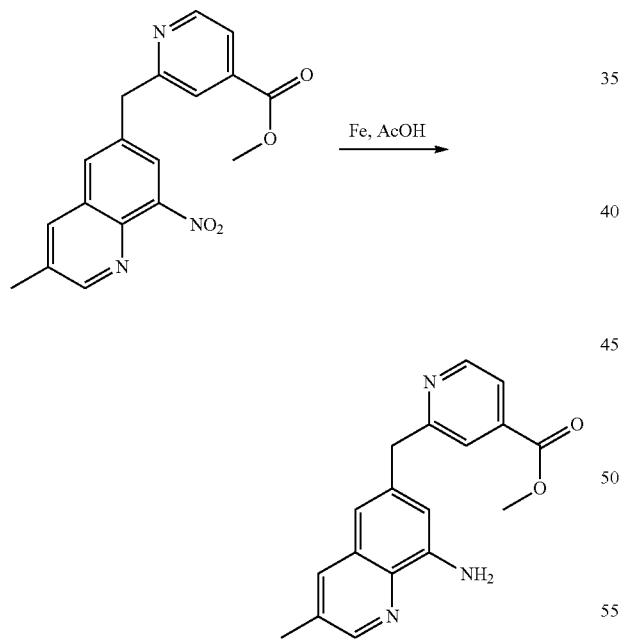

To a solution of 2-(3-methyl-8-nitro-quinolin-6-ylmethyl)-isonicotinic acid methyl ester (1.3 g, 3.85 mmol, 1.0 eq) in AcOH (10 mL) was added Fe (1.1 g, 19.25 mmol, 5.0 eq) at rt. The mixture was stirred at 80° C. for 2 h. The mixture was filtered and the filtrate was concentrated. The resulting residue was purified by chromatography on a silica gel column (PE/EA=1/1, v/v) to give 2-(8-amino-3-methyl-quinolin-6-ylmethyl)-isonicotinic acid methyl ester (900 mg, 76%) as a yellow solid.

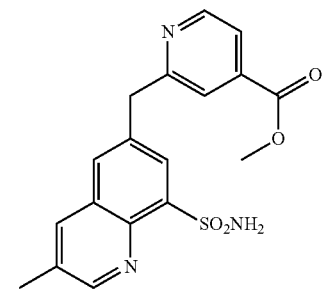

To a solution of 2-(8-amino-3-methyl-quinolin-6-ylmethyl)-isonicotinic acid methyl ester (600 mg, 1.95 mmol, 1.0 eq) in conc.HCl (4 mL) was added a solution of NaNO$_2$ (135 mg, 1.95 mmol, 1.0 eq) in H$_2$O (1 mL) at 0° C. The mixture was stirred at 0° C. for 2 h. To another flask was added H$_2$O (4 mL) and dropwise SOCl$_2$ (1.2 g, 9.75 mmol, 5.0 eq) at 0° C. The mixture was stirred at 0° C. for 10 min. After that, CuCl (19.0 mg, 0.19 mmol, 0.1 eq) and the first step's solution was added at 0° C. The mixture was stirred at 0° C. for 2 h and concentrated. The resulting residue was dissolved in dioxane (20 mL). To this mixture was added NH$_3$.H$_2$O (1 mL) at 0° C. and the mixture was stirred at rt for 2 h. The reaction solution was concentrated and the resulting residue was purified by chromatography on silica gel column (PE/EA=3/1) to give 2-(3-methyl-8-sulfamoyl-quinolin-6-ylmethyl)-isonicotinic acid methyl ester (380 mg, 52%) as a yellow solid.

LRMS (M+H$^+$) m/z calculated 372.1, found 372.1. $^1$H NMR (DMSO-d$_6$, 300 MHz): δ 8.87 (s, 1H), 8.72 (d, 1H), 8.26 (s, 1H), 8.16 (s, 1H), 8.09 (s, 1H), 7.92 (s, 1H), 7.69 (d, 1H), 7.21 (s, 2H), 4.47 (s, 2H), 3.87 (s, 3H), 2.51 (s, 3H).

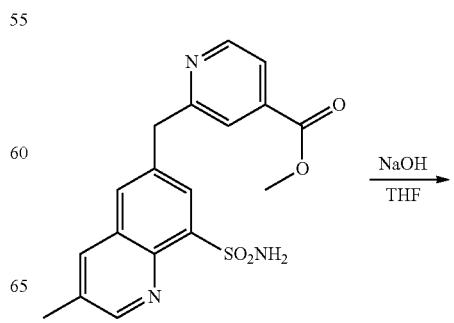

689
-continued

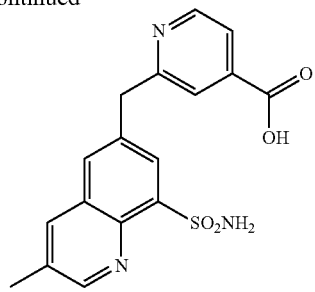

To a solution of 2-(3-methyl-8-sulfamoyl-quinolin-6-yl-methyl)-isonicotinic acid methyl ester (500 mg, 1.35 mmol, 1.0 eq) in THF (10 mL) and water (5 mL) was added NaOH (81 mg, 2.02 mmol, 1.5 eq). The mixture was stirred at rt for 2 h. The reaction solution was neutralized with 2N HCl to pH 3 and extract with DCM. The organic phase was concentrated to give 2-(3-methyl-8-sulfamoyl-quinolin-6-ylmethyl)-isonicotinic acid (550 mg, crude) without further purification.

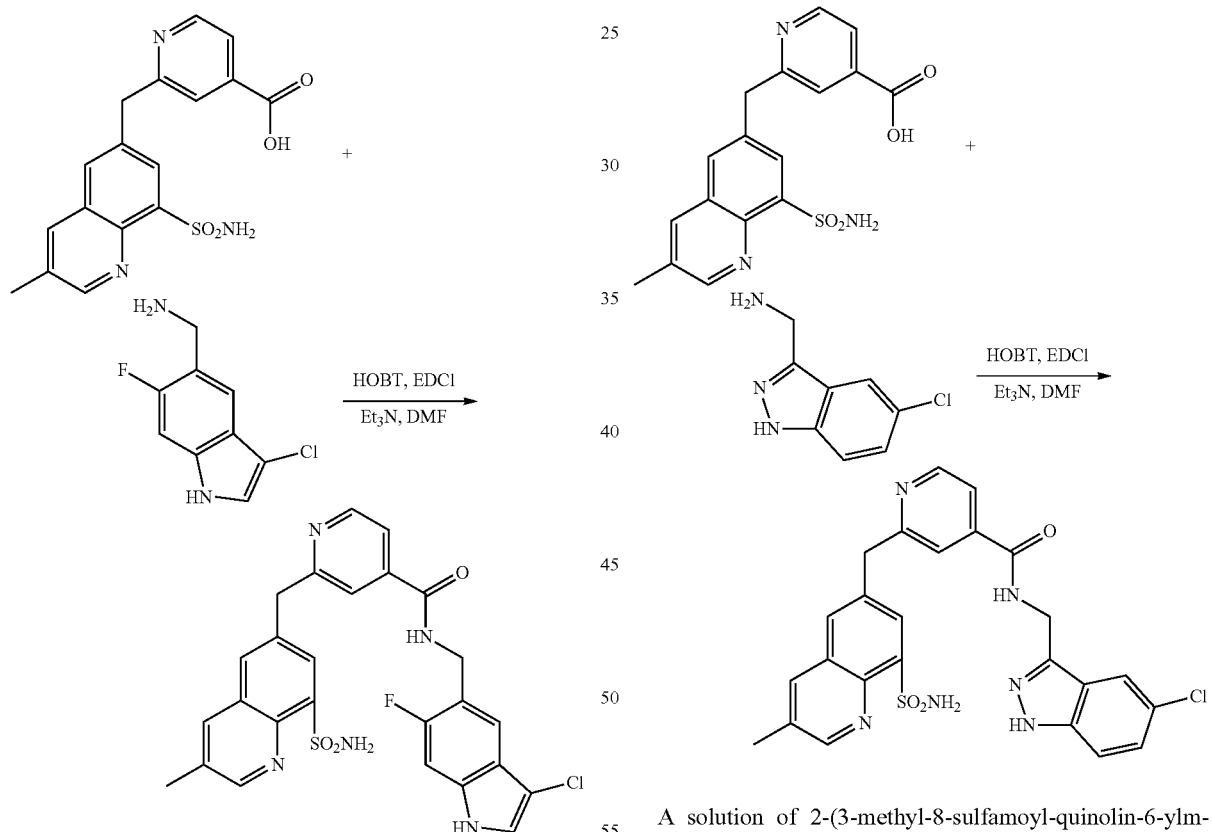

A solution of 2-(3-methyl-8-sulfamoyl-quinolin-6-ylmethyl)-isonicotinic acid (100 mg, 0.28 mmol, 1.0 eq), (3-chloro-6-fluoro-1H-indol-5-yl)methanamine (83.0 mg, 0.42 mmol, 1.5 eq), HOBT (57 mg, 0.42 mmol, 1.5 eq), EDCI (80 mg, 0.42 mmol, 1.5 eq) and Et₃N (85 mg, 0.84 mmol, 3.0 eq) in DMF (2 mL) was stirred at 30° C. overnight. The mixture was concentrated and the resulting residue was purified by Prep-HPLC to obtain N-((3-chloro-6-fluoro-1H-indol-5-yl)methyl)-2-((3-methyl-8-sulfamoylquinolin-6-yl)methyl)isonicotinamide (62.0 mg, 41%) as a white solid.

690

LRMS (M+H⁺) m/z calculated 538.1, found 538.1. ¹H NMR (DMSO-d₆, 400 MHz): δ 9.28-9.25 (m, 1H), 8.87 (d, 1H), 8.66 (d, 1H), 8.26 (s, 1H), 8.15 (d, 1H), 8.06 (d, 1H), 7.85 (s, 1H), 7.67-7.66 (m, 1H), 7.51 (s, 1H), 7.45 (d, 1H), 7.21 (d, 1H), 4.58 (d, 2H), 4.42 (s, 2H), 2.51 (s, 3H).

Example 288: Preparation of N-((5-chloro-1H-indazol-3-yl)methyl)-2-((3-methyl-8-sulfamoylquinolin-6-yl)methyl)isonicotinamide

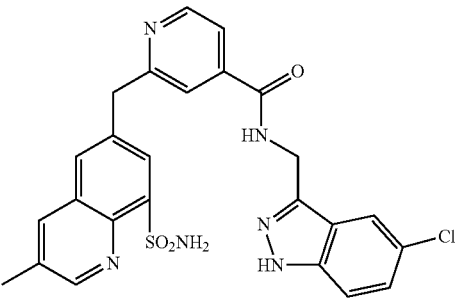

A solution of 2-(3-methyl-8-sulfamoyl-quinolin-6-ylmethyl)-isonicotinic acid (100 mg, 0.28 mmol, 1.0 eq), (5-chloro-1H-indazol-3-yl)methanamine (76.0 mg, 0.42 mmol, 1.5 eq), HOBT (57 mg, 0.42 mmol, 1.5 eq), EDCI (80 mg, 0.42 mmol, 1.5 eq) and Et₃N (85 mg, 0.84 mmol, 3.0 eq) in DMF (2 mL) was stirred at 30° C. overnight. The mixture was concentrated and the resulting residue was purified by Prep-HPLC to obtain N-((5-chloro-1H-indazol-3-yl)methyl)-2-((3-methyl-8-sulfamoylquinolin-6-yl)methyl) isonicotinamide (28.0 mg, 19%) as a white solid.

LRMS (M+H⁺) m/z calculated 521.1, found 521.1. ¹H NMR (DMSO-d₆, 400 MHz): δ 9.43-9.38 (m, 1H), 8.87 (d, 1H), 8.64 (d, 1H), 8.25 (d, 1H), 8.14 (d, 1H), 8.06 (d, 1H), 7.90 (d, 1H), 7.85 (s, 1H), 7.65 (d, 1H), 7.54 (d, 1H), 7.34 (d, 1H), 4.78 (d, 2H), 4.41 (s, 2H), 2.51 (s, 3H).

Example 289: Preparation of N-((1-aminoisoquinolin-6-yl)methyl)-2-((3-methyl-8-sulfamoylquinolin-6-yl)methyl)isonicotinamide

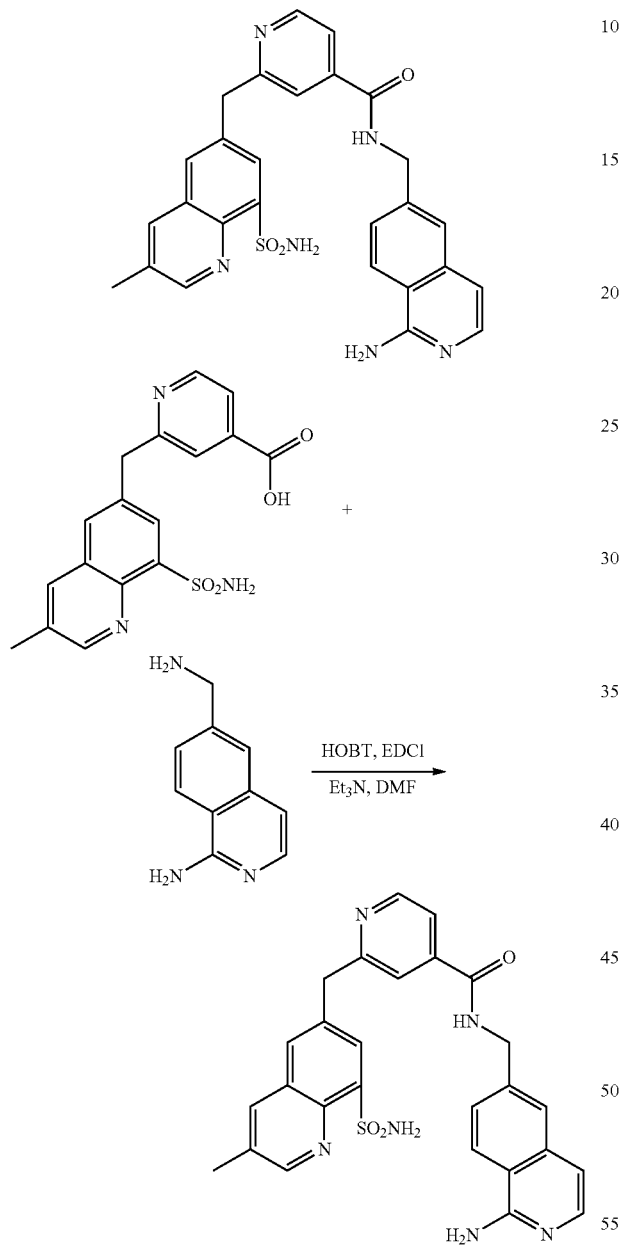

A solution of 2-(3-methyl-8-sulfamoyl-quinolin-6-ylmethyl)-isonicotinic acid (100 mg, 0.28 mmol, 1.0 eq), 6-aminomethyl-isoquinolin-1-ylamine (73.0 mg, 0.42 mmol, 1.5 eq), HOBT (57 mg, 0.42 mmol, 1.5 eq), EDCI (80 mg, 0.42 mmol, 1.5 eq) and Et$_3$N (85 mg, 0.84 mmol, 3.0 eq) in DMF (2 mL) was stirred at 30° C. overnight. The mixture was concentrated and the resulting residue was purified by Prep-HPLC to obtain N-((1-aminoisoquinolin-6-yl)methyl)-2-((3-methyl-8-sulfamoylquinolin-6-yl)methyl)isonicotinamide (14.0 mg, 11%) as a white solid. LRMS (M+H$^+$) m/z calculated 513.2, found 513.1. $^1$H NMR (DMSO-d$_6$, 400 MHz): δ 9.42-9.39 (m, 1H), 8.87 (d, 1H), 8.68 (d, 1H), 8.26 (s, 1H), 8.17-8.15 (m, 2H), 8.08 (s, 1H), 7.87 (s, 1H), 7.75 (d, 1H), 7.70 (d, 1H), 7.58 (s, 1H), 7.44-7.41 (m, 1H), 7.20 (s, 2H), 6.89-6.87 (m, 3H), 4.61 (d, 2H), 4.43 (s, 2H), 2.52 (s, 3H).

Example 290: Preparation of N-((3-chloro-4-fluoro-1H-indol-5-yl)methyl)-2-((3-methyl-8-sulfamoylquinolin-6-yl)methyl)isonicotinamide

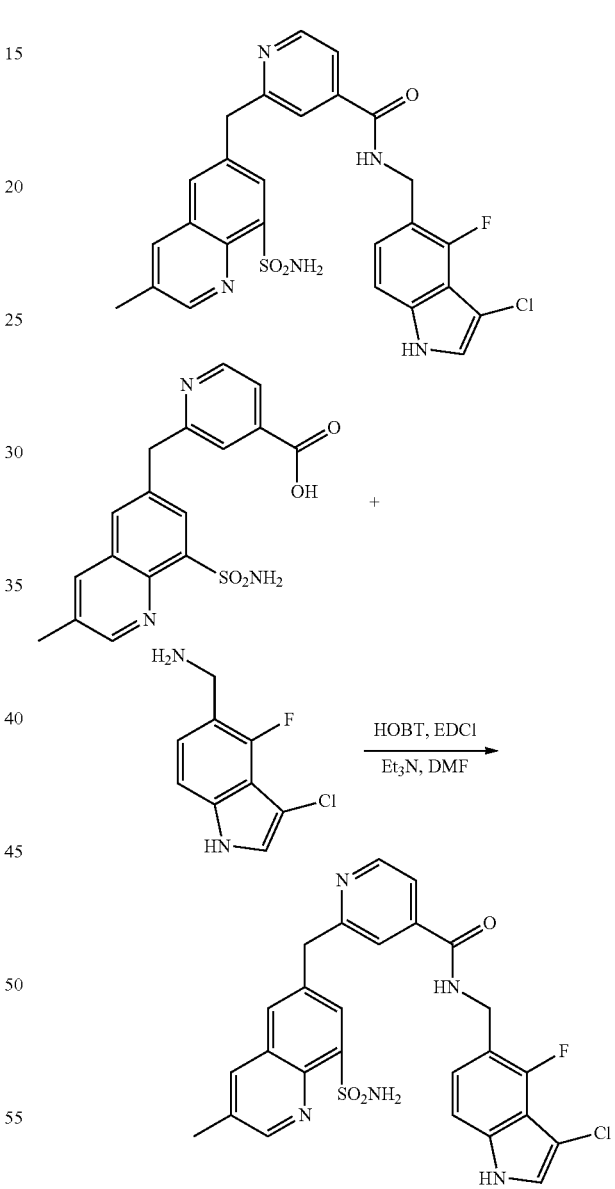

A solution of 2-(3-methyl-8-sulfamoyl-quinolin-6-ylmethyl)-isonicotinic acid (100 mg, 0.28 mmol, 1.0 eq), (3-chloro-4-fluoro-1H-indol-5-yl)methanamine (83.0 mg, 0.42 mmol, 1.5 eq), HOBT (57 mg, 0.42 mmol, 1.5 eq), EDCI (80 mg, 0.42 mmol, 1.5 eq) and Et$_3$N (85 mg, 0.84 mmol, 3.0 eq) in DMF (2 mL) was stirred at 30° C. overnight. The mixture was concentrated and the resulting residue was purified by Prep-HPLC to obtain N-((3-chloro- 4-fluoro-1H-indol-5-yl)methyl)-2-((3-methyl-8-sulfamoylquinolin-6-yl)methyl)isonicotinamide (29.0 mg, 19%) as a white solid.

LRMS (M+H$^+$) m/z calculated 538.1, found 538.1. $^1$H NMR (DMSO-d$_6$, 400 MHz): δ 9.28-9.26 (m, 1H), 8.87 (d, 1H), 8.64 (d, 1H), 8.26 (s, 1H), 8.14 (d, 1H), 8.07 (s, 1H), 7.84 (s, 1H), 7.65 (d, 1H), 7.52 (s, 1H), 7.20 (d, 1H), 7.13 (d, 1H), 0.4.58 (d, 2H), 4.41 (s, 2H), 2.51 (s, 3H).

Example 291: Preparation of N-((3-chloro-1H-pyrrolo[2,3-b]pyridin-5-yl)methyl)-2-((3-methyl-8-sulfamoylquinolin-6-yl)methyl)isonicotinamide

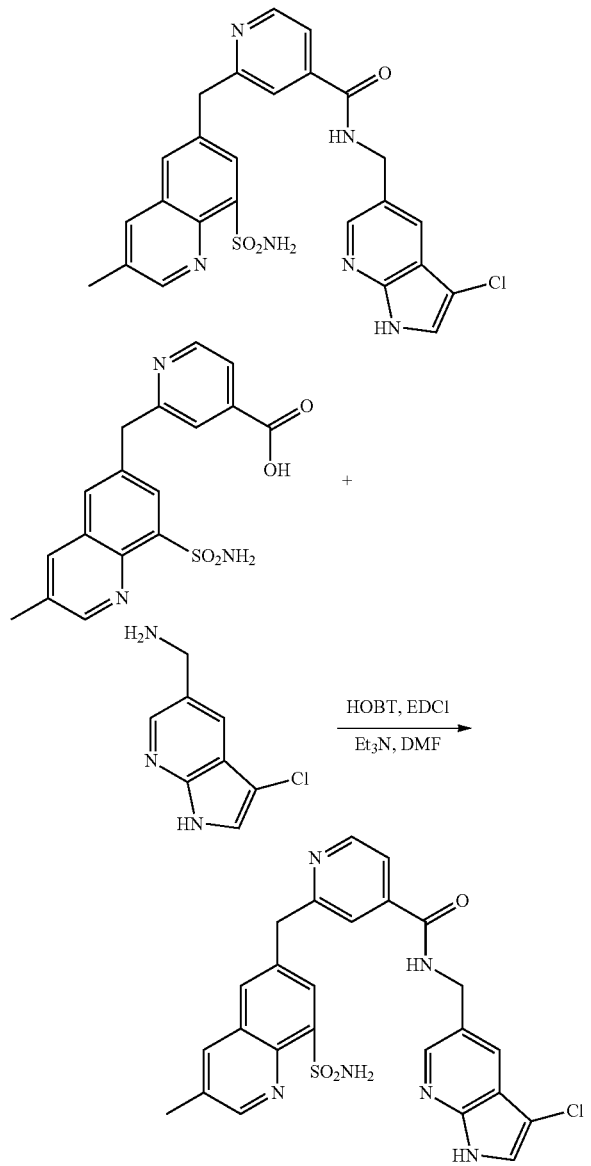

A solution of 2-(3-methyl-8-sulfamoyl-quinolin-6-ylmethyl)-isonicotinic acid (100 mg, 0.28 mmol, 1.0 eq), (3-chloro-1H-pyrrolo[2,3-b]pyridin-5-yl)methanamine (76.0 mg, 0.42 LRMS (M+H$^+$) m/z calculated 521.1, found 521.1. $^1$H NMR (DMSO-d$_6$, 400 MHz): δ 9.37-9.34 (m, 1H), 8.87 (d, 1H), 8.66 (d, 1H), 8.31 (s, 1H), 8.14 (s, 1H), 8.06 (s, 1H), 7.87 (s, 1H), 7.83 (s, 1H), 7.68-7.64 (m, 2H), 4.60 (d, 2H), 4.42 (s, 2H), 2.50 (s, 3H).

Example 292: Preparation of N-((3-chloro-6-fluoro-1H-indol-5-yl)methyl)-2-((3-morpholinoquinolin-6-yl)methyl)isonicotinamide

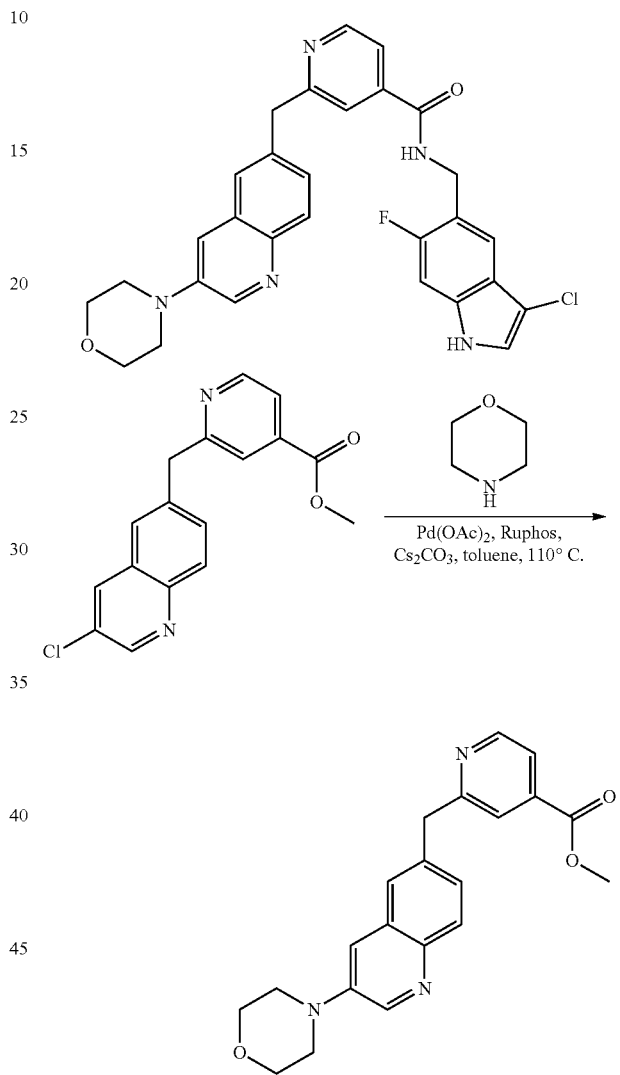

A flame-dried three-necked round-bottomed flask was charged with 2-(3-chloro-quinolin-6-ylmethyl)-isonicotinic acid methyl ester (500 mg, 1.6 mmol, 1 eq), morpholine (0.15 mL, 1.68 mmol, 1.05 eq), Pd(OAc)$_2$ (5.5 mg, 0.016 mmol, 0.01 eq), RuPhos (14.9 mg, 0.032 mmol, 0.02 eq), Cs$_2$CO$_3$ (1.1 g, 3.2 mmol, 2 eq) and anhydrous toluene (10 mL). The mixture was stirred at 110° C. under N$_2$ overnight. After cooling to ambient temperature, the mixture was concentrated and the resulting residue was diluted with DCM and washed with brine. The combined organic portions were dried over anhydrous Na$_2$SO$_4$ and concentrated to dryness under reduced pressure. Purification was carried out by chromatography on a silica gel column (PE/EA=1/1, v/v) to give 2-(3-morpholin-4-yl-quinolin-6-ylmethyl)-isonicotinic acid methyl ester as a yellow oil (285 mg, 49%).

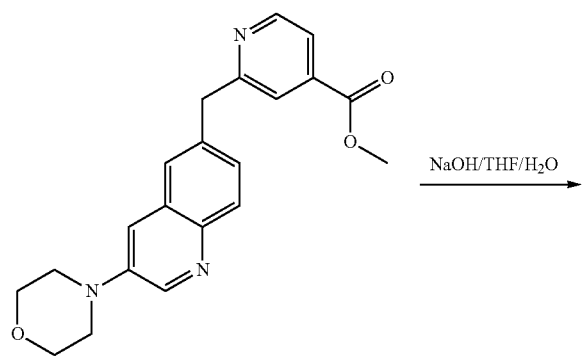

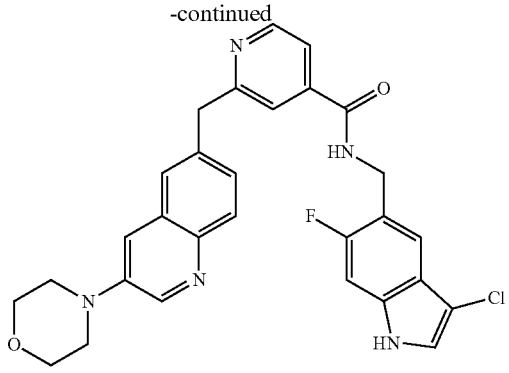

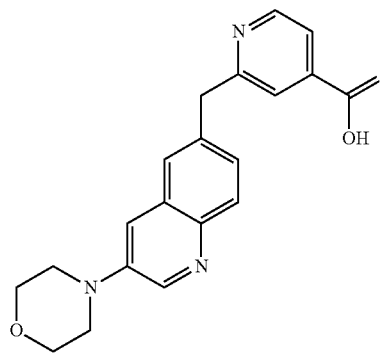

To a solution of 2-(3-morpholin-4-yl-quinolin-6-ylmethyl)-isonicotinic acid methyl ester (285 mg, 0.78 mmol, 1.0 eq) in THF (5 mL), H₂O (5 mL) was added NaOH (63 mg, 1.57 mmol, 2.0 eq) and the reaction mixture was stirred at rt for 3 h. The reaction mixture was acidified to pH 3 with 3 N HCl, then extracted with EA, and concentrated under reduced pressure to afford 2-(3-ethyl-quinolin-6-ylmethyl)-isonicotinic acid (247 mg, 90%) as a yellow solid.

To a solution of 2-(3-morpholin-4-yl-quinolin-6-ylmethyl)-isonicotinic acid (100 mg, 0.29 mmol, 1 eq) in DMF (5 mL) was added (3-chloro-6-fluoro-1H-indol-5-yl)methanamine (87 mg, 0.37 mmol, 1.3 eq) followed by HOBT (50 mg, 0.37 mmol, 1.3 eq), EDCI (71 mg, 0.37 mmol, 1.3 eq) and TEA (88 mg, 0.87 mmol, 3.0 eq). The reaction mixture was heated at 35° C. and stirred overnight. Water was added, and the mixture was extracted with DCM. The organic layer was dried over Na₂SO₄, filtered and concentrated. The resulting residue was purified by Prep-HPLC to give N-((3-chloro-6-fluoro-1H-indol-5-yl)methyl)-2-((3-morpholinoquinolin-6-yl)methyl)isonicotinamide (55 mg, 36.2%) as a white solid.

LRMS (M+H⁺) m/z calculated 530.2, found 530.2. ¹H NMR (DMSO-d6, 400 MHz): δ 11.42 (s, 1H), 9.29 (t, 1H), 9.00 (s, 1H), 8.68 (d, 1H), 7.96 (s, 1H), 7.92 (d, 1H), 7.82 (s, 1H), 7.80 (s, 1H), 7.72 (d, 1H), 7.62 (d, 1H), 7.51 (d, 1H), 7.46 (d, 1H), 7.23 (d, 2H), 4.59 (d, 1H), 4.38 (s, 2H), 3.81 (t, 4H), 3.34 (t, 4H).

Example 293: Preparation of N-((1-aminoisoquinolin-6-yl)methyl)-2-((3-morpholinoquinolin-6-yl)methyl)isonicotinamide

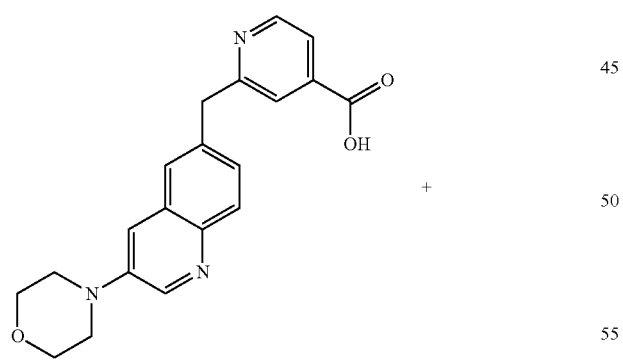

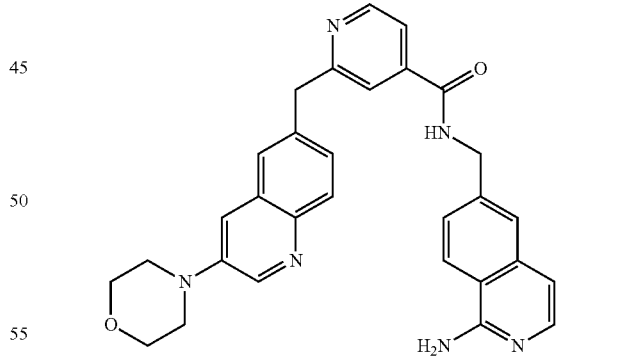

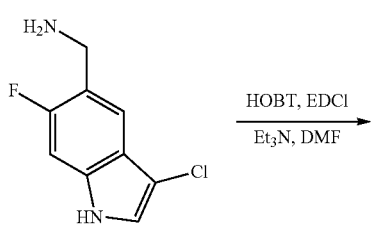

To a solution of 2-(3-morpholin-4-yl-quinolin-6-ylmethyl)-isonicotinic acid (100 mg, 0.29 mmol, 1 eq) in DMF (5 mL) was added 6-aminomethyl-isoquinolin-1-ylamine (64 mg, 0.37 mmol, 1.3 eq) followed by HOBT (50 mg, 0.37 mmol, 1.3 eq), EDCI (71 mg, 0.37 mmol, 1.3 eq) and TEA (88 mg, 0.87 mmol, 3.0 eq). The reaction mixture was heated at 35° C. and stirred overnight. Water was added, and the mixture was extracted with DCM. The organic layer was dried over Na₂SO₄, filtered and concentrated. The resulting residue was purified by Prep-HPLC to give N-((1-aminoisoquinolin-6-yl)methyl)-2-((3-morpholinoquinolin-6-yl)methyl)isonicotinamide (21 mg, 14.6%) as a white solid.

LRMS (M+H⁺) m/z calculated 505.2, found 505.2. ¹H NMR (DMSO-d6, 400 MHz): δ 9.39 (t, 1H), 8.81 (d, 1H), 8.67 (d, 1H), 8.14 (d, 1H), 7.84-7.74 (m, 3H), 7.68 (d, 1H), 7.65 (s, 1H), 7.55 (s, 1H), 7.48 (d, 1H), 7.45-7.39 (m, 2H), 6.85 (d, 1H), 6.80 (s, 2H), 4.60 (d, 1H), 4.31 (s, 2H), 3.79 (t, 4H), 3.26 (t, 4H).

Example 294: Preparation of N-((3-chloro-1H-pyrrolo[2,3-b]pyridin-5-yl)methyl)-2-((3-morpholinoquinolin-6-yl)methyl)isonicotinamide

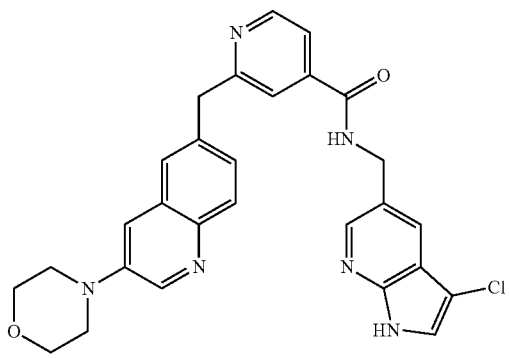 [SMILES: O=C(NCc1cnc2[nH]cc(Cl)c2c1)c1ccnc(Cc2ccc3ncc(N4CCOCC4)cc3c2)c1]

To a solution of 2-(3-morpholin-4-yl-quinolin-6-ylmethyl)-isonicotinic acid (100 mg, 0.29 mmol, 1 eq) in DMF (5 mL) was added (3-chloro-1H-pyrrolo[2,3-b]pyridin-5-yl)methanamine (81 mg, 0.37 mmol, 1.3 eq) followed by HOBT (50 mg, 0.37 mmol, 1.3 eq), EDCI (71 mg, 0.37 mmol, 1.3 eq) and TEA (88 mg, 0.87 mmol, 3.0 eq). The reaction mixture was heated at 35° C. and stirred overnight. Water was added, and the mixture was extracted with DCM. The organic layer was dried over Na₂SO₄, filtered and concentrated. The resulting residue was purified by Prep-HPLC to give N-((3-chloro-1H-pyrrolo[2,3-b]pyridin-5-yl)methyl)-2-((3-morpholinoquinolin-6-yl)methyl)isonicotinamide (8.1 mg, 5.6%) as a white solid.

LRMS (M+H⁺) m/z calculated 513.2, found 513.2. ¹H NMR (DMSO-d6, 400 MHz): δ 9.33 (t, 1H), 8.81 (s, 1H), 8.64 (d, 1H), 8.30 (s, 1H), 7.86 (s, 1H), 7.79 (d, 1H), 7.74 (s, 1H), 7.67 (s, 1 H), 7.63 (s, 2H), 7.47 (d, 1H), 7.42 (d, 1H), 4.59 (d, 1H), 4.30 (s, 2H), 3.79 (t, 4H), 3.25 (t, 4H).

Example 295: Preparation of N-((5-chloro-1H-indazol-3-yl)methyl)-2-((3-morpholinoquinolin-6-yl)methyl)isonicotinamide

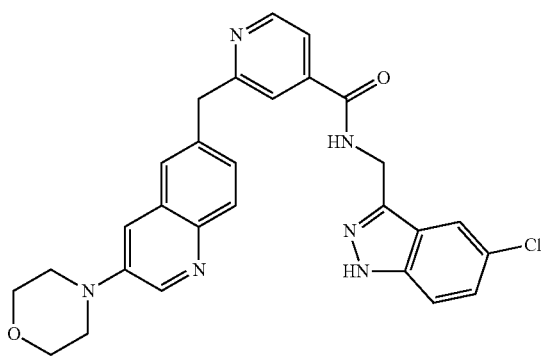 [SMILES: O=C(NCc1n[nH]c2ccc(Cl)cc12)c1ccnc(Cc2ccc3ncc(N4CCOCC4)cc3c2)c1]

To a solution of 2-(3-morpholin-4-yl-quinolin-6-ylmethyl)-isonicotinic acid (100 mg, 0.29 mmol, 1 eq) in DMF (5 mL) was added (5-chloro-1H-indazol-3-yl)methanamine (81 mg, 0.37 mmol, 1.3 eq) followed by HOBT (50 mg, 0.37 mmol, 1.3 eq), EDCI (71 mg, 0.37 mmol, 1.3 eq) and TEA (88 mg, 0.87 mmol, 3.0 eq). The reaction mixture was heated at 35° C. and stirred overnight. Water was added, and the mixture was extracted with DCM. The organic layer was dried over Na₂SO₄, filtered and concentrated. The resulting residue was purified by Prep-HPLC to give N-((5-chloro-1H-indazol-3-yl)methyl)-2-((3-morpholinoquinolin-6-yl)methyl)isonicotinamide (11 mg, 7.5%) as a white solid.

LRMS (M+H⁺) m/z calculated 513.2, found 513.2. ¹H NMR (DMSO-d6, 400 MHz): δ 9.39 (t, 1H), 8.81 (s, 1H), 8.64 (d, 1H), 7.89 (s, 1H), 7.77 (d, 1H), 7.75 (s, 1H), 7.63 (s, 2H), 7.53 (d, 1H), 7.46 (s, 1H), 7.42 (d, 1H), 7.33 (d, 1H), 4.78 (d, 1H), 4.29 (s, 2H), 3.79 (t, 4H), 3.25 (t, 4H).

Example 296: Preparation of N-((6-amino-2,4-dimethylpyridin-3-yl)methyl)-2-((3-chloroquinolin-6-yl)(methoxy)methyl)isonicotinamide

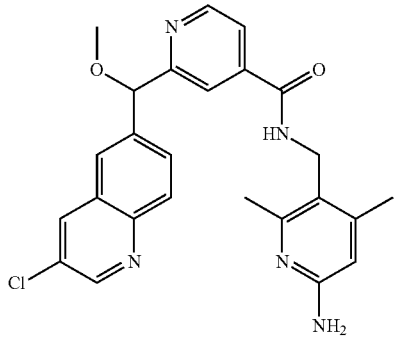

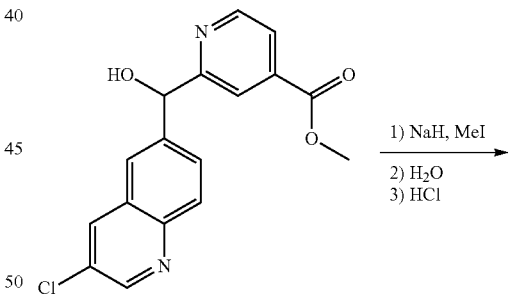

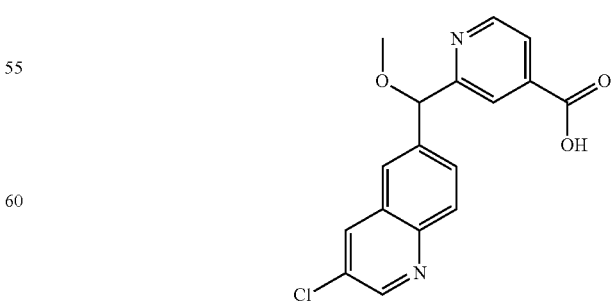

To a solution of 2-[(3-chloro-quinolin-6-yl)-hydroxymethyl]-isonicotinic acid methyl ester (500 mg, 1.52 mmol, 1 eq) in dry THF (10 mL) was added NaH (304 mg, 60% purity, 7.60 mmol, 5 eq) at 0° C. The mixture was stirred at this temperature for 1 h, and then MeI (2.14 g, 15.2 mmol, 10 eq) was added. The mixture was stirred at rt for 48 h and then quenched by the addition of water. After stirring for 1 h, the mixture was acidified to pH 3 with 1 N HCl solution. The mixture was extracted with DCM and the combined organic layers were dried and concentrated to give 2-[(3-chloro-quinolin-6-yl)-methoxy-methyl]-isonicotinic acid (423 mg, 85%) as a brown solid, which was directly used in next step without further purification.

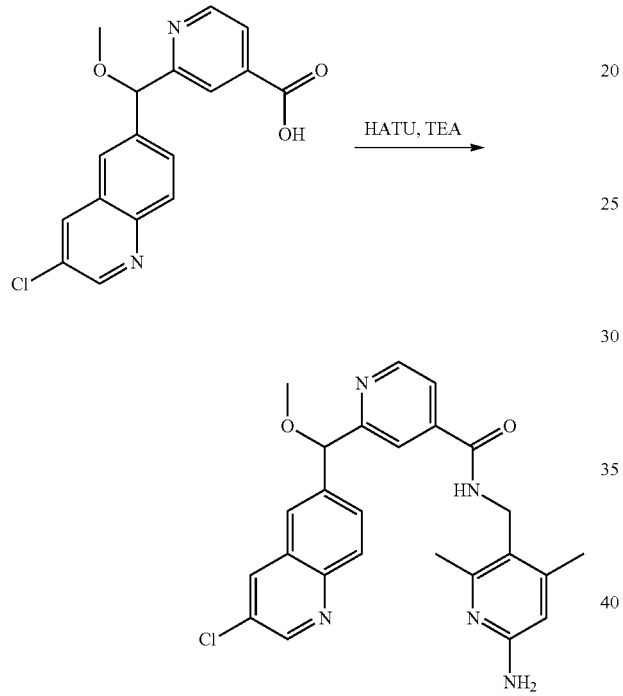

To a solution of 2-[(3-chloro-quinolin-6-yl)-methoxy-methyl]-isonicotinic acid (100 mg, 0.30 mmol, 1 eq) in DMF (5 mL) was added 5-aminomethyl-4,6-dimethyl-pyridin-2-ylamine (88 mg, 0.40 mmol, 1.3 eq) followed by HATU (152 mg, 0.40 mmol, 1.3 eq) and TEA (91 mg, 0.9 mmol, 3.0 eq). The reaction mixture was stirred at rt overnight. Water was added, and the mixture was extracted with DCM. The organic layer was dried over Na$_2$SO$_4$, filtered and concentrated. The resulting residue was purified by Prep-HPLC to give N-((6-amino-2,4-dimethylpyridin-3-yl)methyl)-2-((3-chloroquinolin-6-yl)(methoxy)methyl)isonicotinamide (35 mg, 25%).

LRMS (M+H$^+$) m/z calculated 462.2, found 462.2. $^1$H NMR (DMSO-d6, 400 MHz): δ 8.86 (d, 1H), 8.76 (t, 1H), 8.62 (d, 1H), 8.58 (d, 1H), 8.04 (s, 1H), 8.01 (d, 1H), 7.99 (d, 1H), 7.77 (d, 1H), 7.65 (dd, 1H), 6.13 (s, 1H), 5.71 (s, 2H), 5.66 (s, 1H), 4.36 (d, 1H), 3.39 (s, 3H), 2.31 (s, 3H), 2.18 (s, 3H).

Example 297: Preparation of 2-((3-aminoquinolin-6-yl)methyl)-N-((3-chloro-6-fluoro-1H-indol-5-yl)methyl)isonicotinamide

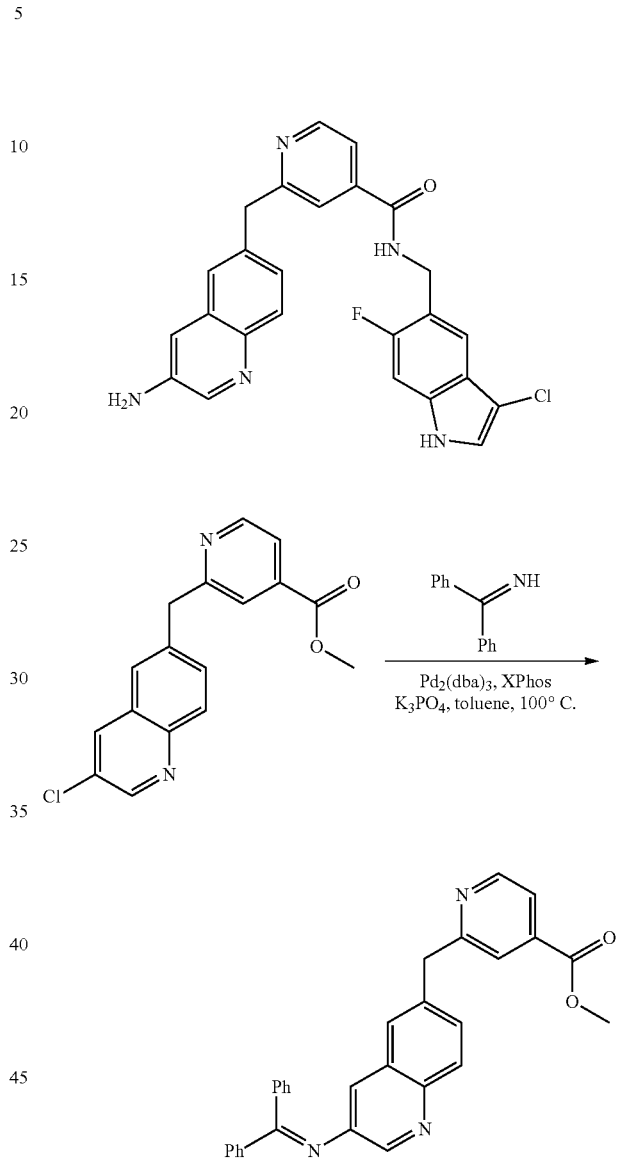

A flame-dried three-necked round-bottomed flask was charged with 2-(3-chloro-quinolin-6-ylmethyl)-isonicotinic acid methyl ester (500 mg, 1.6 mmol), benzhydrylideneamine (0.3 mL, 1.9 mmol), Pd$_2$(dba)$_3$ (147 mg, 0.16 mmol), XPhos (76.2 mg, 0.16 mmol), K$_3$PO$_4$ (8.66 g, 40.8 mmol) and anhydrous toluene (18 mL). The mixture was stirred at stirred at 100° C. under N$_2$ overnight. After cooling to ambient temperature, the mixture was concentrated. The resulting residue was diluted with DCM and washed with brine. The combined organic layers were dried over anhydrous Na$_2$SO$_4$ and concentrated in vacuo. The resulting residue was purified by chromatography on a silica gel column (PE/EA=6/1 to 3/1, v/v) to afford 2-[3-(benzhydrylidene-amino)-quinolin-6-ylmethyl]-isonicotinic acid methyl ester as a yellow oil (359 mg, 49% yield).

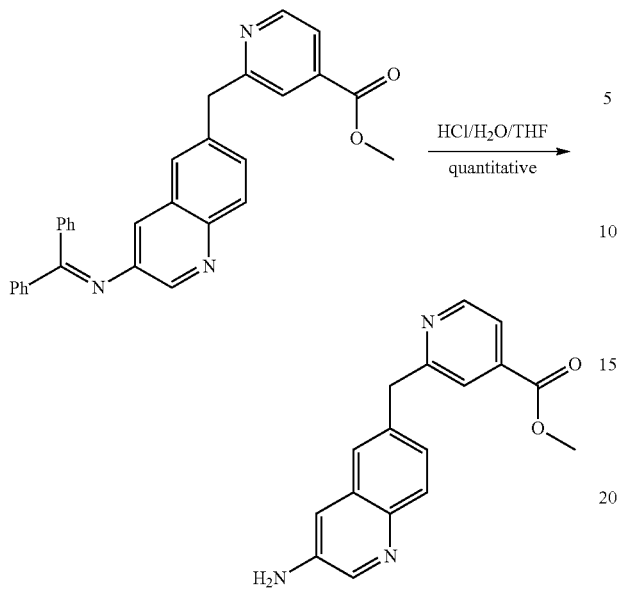

To a stirred solution of 2-[3-(benzhydrylidene-amino)-quinolin-6-ylmethyl]-isonicotinic acid methyl ester (700 mg, 1.53 mmol, 1 eq) in THF (5 mL) was added 2 N HCl solution (5 mL). The mixture was stirred at rt for 0.5 h and then basified to pH 9 with sat. NaHCO$_3$ solution. The mixture was extracted with EA and the combined organic layers were dried and concentrated to give 2-(3-amino-quinolin-6-ylmethyl)-isonicotinic acid methyl ester (450 mg, crude).

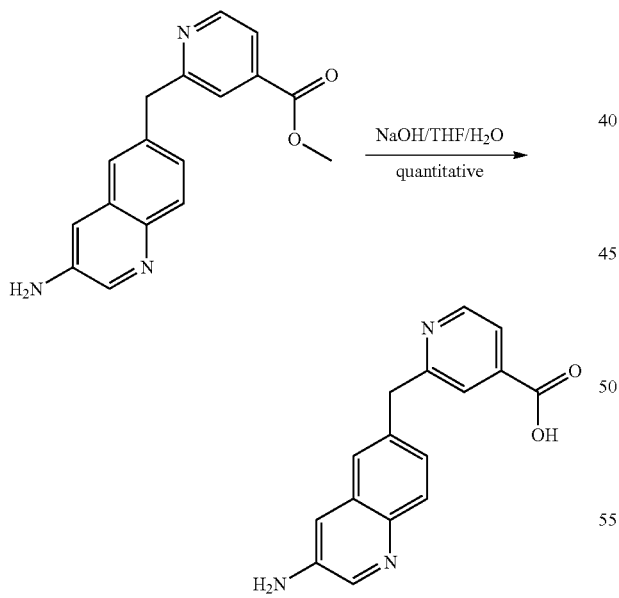

To a solution of 2-(3-amino-quinolin-6-ylmethyl)-isonicotinic acid methyl ester (450 mg, 1.14 mmol, 1.0 eq) in THF (5 mL) and H$_2$O (5 mL) was added NaOH (92 mg, 2.29 mmol, 2.0 eq) and the reaction mixture was stirred at rt for 2 h. The reaction mixture was acidified to pH 3 with 3 N HCl, then extracted with EA, and concentrated under reduced pressure to afford 2-(3-amino-quinolin-6-ylmethyl)-isonicotinic acid (430 mg, crude) as a yellow solid.

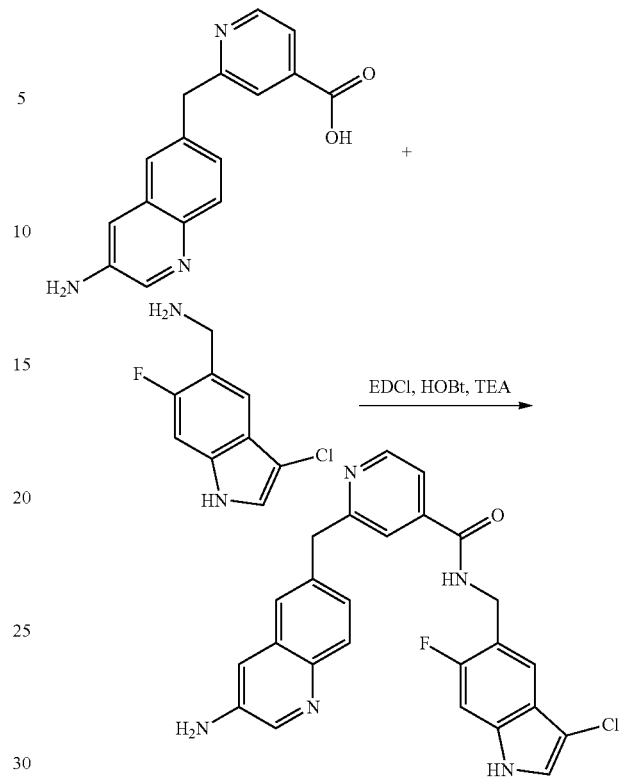

To a solution of 2-(3-amino-quinolin-6-ylmethyl)-isonicotinic acid (80 mg, 0.29 mmol, 1 eq) in DMF (5 mL) was added (3-chloro-6-fluoro-1H-indol-5-yl)methanamine (81 mg, 0.34 mmol, 1.2 eq) followed by HOBT (51 mg, 0.38 mmol, 1.3 eq), EDCI (73 mg, 0.38 mmol, 1.3 eq) and TEA (88 mg, 0.87 mmol, 3.0 eq). The reaction mixture was heated at 35° C. and stirred overnight. Water was added, and the mixture was extracted with DCM. The organic layer was dried over Na$_2$SO$_4$, filtered and concentrated. The resulting residue was purified by Prep-HPLC to give 2-((3-aminoquinolin-6-yl)methyl)-N-((3-chloro-6-fluoro-1H-indol-5-yl)methyl)isonicotinamide (35 mg, 26.5%) as a white solid.

LRMS (M+H$^+$) m/z calculated 460.1, found 460.1. $^1$H NMR (DMSO-d6, 400 MHz): δ 11.41 (s, 1H), 9.25 (t, 1H), 8.64 (d, 1H), 8.36 (d, 1H), 7.75 (s, 1H), 7.65 (d, 1H), 7.63 (s, 1H), 7.51 (s, 1H), 7.50 (s, 1H), 7.43 (d, 1H), 7.24 (s, 1H), 7.21 (s, 1H), 7.06 (s, 1H), 5.64 (s, 2H), 4.59 (d, 2H), 4.24 (s, 2H).

Example 298: Preparation of N-((1-aminoisoquinolin-6-yl)methyl)-2-((3-aminoquinolin-6-yl)methyl)isonicotinamide

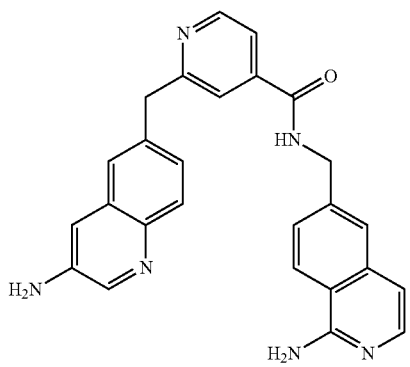 [SMILES: Nc1cnc2ccc(Cc3cc(C(=O)NCc4ccc5c(N)nccc5c4)ccn3)cc2c1]

To a solution of 2-(3-amino-quinolin-6-ylmethyl)-isonicotinic acid (80 mg, 0.29 mmol, 1 eq) in DMF (5 mL) was added C-(3-chloro-6-fluoro-1H-indol-5-yl)-methylamine (59 mg, 0.34 mmol, 1.2 eq) followed by HOBT (51 mg, 0.38 mmol, 1.3 eq), EDCI (73 mg, 0.38 mmol, 1.3 eq) and TEA (88 mg, 0.87 mmol, 3.0 eq). The reaction mixture was heated at 35° C. and stirred overnight. Water was added, and the mixture was extracted with DCM. The organic layer was dried over $Na_2SO_4$, filtered and concentrated. The resulting residue was purified by Prep-HPLC to give N-((1-aminoisoquinolin-6-yl)methyl)-2-((3-aminoquinolin-6-yl)methyl)isonicotinamide (32 mg, 25.8%) as a white solid.

LRMS (M+H$^+$) m/z calculated 435.2, found 435.2. $^1$H NMR (DMSO-d6, 400 MHz): δ 9.39 (t, 1H), 8.65 (d, 1H), 8.37 (d, 1H), 8.14 (d, 1H), 7.76 (s, 1H), 7.75 (d, 1H), 7.67 (d, 1H), 7.66 (d, 1H), 7.55 (s, 1H), 7.50 (s, 1H), 7.39 (dd, 1H), 7.24 (dd, 1H), 7.06 (d, 1H), 6.85 (d, 1H), 6.78 (s, 2H), 5.65 (s, 2H), 4.60 (d, 2H), 4.26 (s, 2H).

Example 299: Preparation of 2-((3-aminoquinolin-6-yl)methyl)-N-((5-chloro-1H-indazol-3-yl)methyl)isonicotinamide

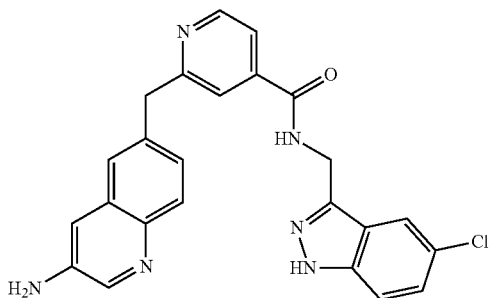

To a solution of 2-(3-amino-quinolin-6-ylmethyl)-isonicotinic acid (80 mg, 0.29 mmol, 1 eq) in DMF (5 mL) was added (5-chloro-1H-indazol-3-yl)methanamine (74 mg, 0.34 mmol, 1.2 eq) followed by HOBT (51 mg, 0.38 mmol, 1.3 eq), EDCI (73 mg, 0.38 mmol, 1.3 eq) and TEA (88 mg, 0.87 mmol, 3.0 eq). The reaction mixture was heated at 35° C. and stirred overnight. Water was added, and the mixture was extracted with DCM. The organic layer was dried over $Na_2SO_4$, filtered and concentrated. The resulting residue was purified by Prep-HPLC to give 2-((3-aminoquinolin-6-yl)methyl)-N-((5-chloro-1H-indazol-3-yl)methyl)isonicotinamide (44.6 mg, 35.2%) as a white solid.

LRMS (M+H$^+$) m/z calculated 443.1, found 443.1. $^1$H NMR (DMSO-d6, 400 MHz): δ 9.38 (t, 1H), 8.62 (d, 1H), 8.36 (d, 1H), 7.89 (d, 1H), 7.74 (s, 1H), 7.65 (d, 1H), 7.61 (d, 1H), 7.52 (d, 1H), 7.48 (s, 1H), 7.33 (dd, 1H), 7.21 (dd, 1H), 7.06 (s, 1H), 5.63 (s, 2H), 4.77 (d, 2H), 4.23 (s, 2H).

Example 300: Preparation of 2-((3-aminoquinolin-6-yl)methyl)-N-((3-chloro-1H-pyrrolo[2,3-b]pyridin-5-yl)methyl)isonicotinamide

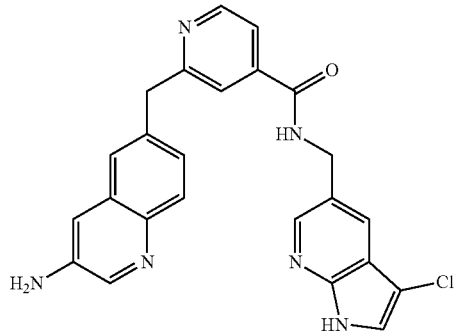 [SMILES: Nc1cnc2ccc(Cc3cc(C(=O)NCc4cnc5[nH]cc(Cl)c5c4)ccn3)cc2c1]

To a solution of 2-(3-amino-quinolin-6-ylmethyl)-isonicotinic acid (80 mg, 0.29 mmol, 1 eq) in DMF (5 mL) was added (3-chloro-1H-pyrrolo[2,3-b]pyridin-5-yl)methanamine (74 mg, 0.34 mmol, 1.2 eq) followed by HOBT (51 mg, 0.38 mmol, 1.3 eq), EDCI (73 mg, 0.38 mmol, 1.3 eq) and TEA (88 mg, 0.87 mmol, 3.0 eq). The reaction mixture was heated at 35° C. and stirred overnight. Water was added, and the mixture was extracted with DCM. The organic layer was dried over $Na_2SO_4$, filtered and concentrated. The resulting residue was purified by Prep-HPLC to give 2-((3-aminoquinolin-6-yl)methyl)-N-((3-chloro-1H-pyrrolo[2,3-b]pyridin-5-yl)methyl)isonicotinamide (22.7 mg, 17.9%) as a white solid.

LRMS (M+H+) m/z calculated 435.2, found 435.2. $^1$H NMR (DMSO-d6, 400 MHz): δ 11.97 (s, 1H), 9.32 (t, 1H), 8.63 (d, 1H), 8.36 (d, 1H), 8.30 (d, 1H), 7.90 (s, 1H), 7.72 (s, 1H), 7.68-7.61 (m, 3H), 7.48 (s, 1H), 7.21 (dd, 1H), 7.07 (d, 1H), 5.65 (s, 2H), 4.59 (d, 2H), 4.24 (s, 2H).

Example 301: Preparation of 2-((3-aminoquinolin-6-yl)methyl)-N-((3-chloro-4-fluoro-1H-indol-5-yl)methyl)isonicotinamide

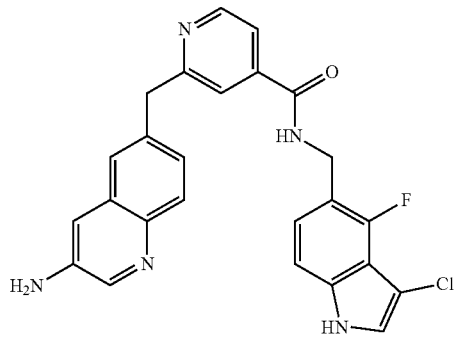 [SMILES: Nc1cnc2ccc(Cc3cc(C(=O)NCc4ccc5[nH]cc(Cl)c5c4F)ccn3)cc2c1]

To a solution of 2-(3-amino-quinolin-6-ylmethyl)-isonicotinic acid (80 mg, 0.29 mmol, 1 eq) in DMF (5 mL) was added (3-chloro-4-fluoro-1H-indol-5-yl)methanamine (81 mg, 0.34 mmol, 1.2 eq) followed by HOBT (51 mg, 0.38 mmol, 1.3 eq), EDCI (73 mg, 0.38 mmol, 1.3 eq) and TEA (88 mg, 0.87 mmol, 3.0 eq). The reaction mixture was heated at 35° C. and stirred overnight. Water was added, and the mixture was extracted with DCM. The organic layer was dried over Na$_2$SO$_4$, filtered and concentrated. The resulting residue was purified by Prep-HPLC to give 2-((3-aminoquinolin-6-yl)methyl)-N-((3-chloro-4-fluoro-1H-indol-5-yl)methyl)isonicotinamide (54.6 mg, 41.1%) as a white solid.

LRMS (M+H$^+$) m/z calculated 460.1, found 460.1. $^1$H NMR (DMSO-d6, 400 MHz): δ 9.23 (t, 1H), 8.62 (d, 1H), 8.37 (d, 1H), 7.74 (s, 1H), 7.66 (d, 1H), 7.62 (dd, 1H), 7.51 (s, 1H), 7.50 (s, 1H), 7.48 (d, 1H), 7.23 (d, 1H), 7.21 (d, 1H), 7.13 (d, 1H), 7.06 (s, 1H), 5.63 (s, 2H), 4.56 (d, 2H), 4.24 (s, 2H).

Example 302: Preparation of N-((3-chloro-6-fluoro-1H-indol-5-yl)methyl)-2-((3-(piperidin-1-yl)quinolin-6-yl)methyl)isonicotinamide

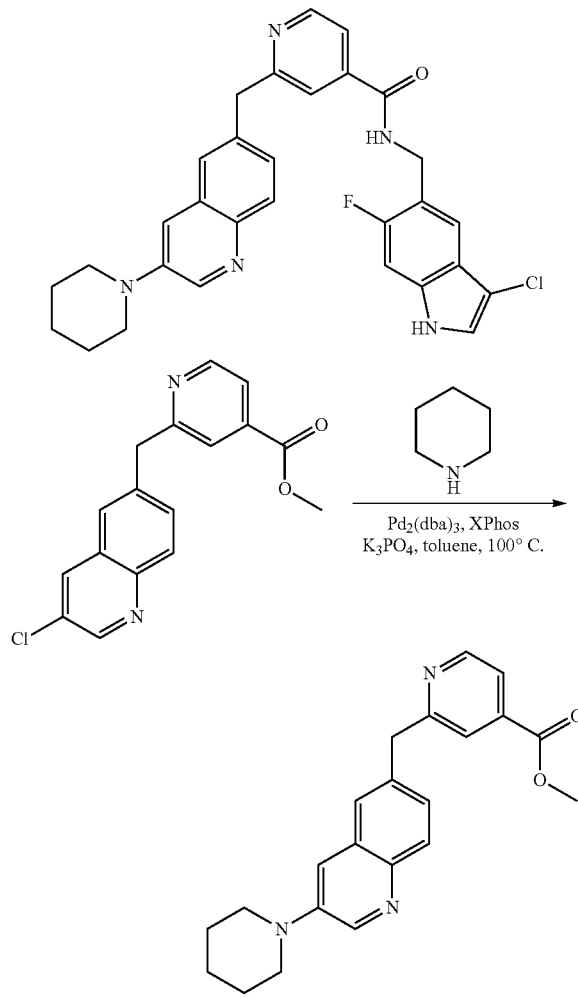

A flame-dried three-necked round-bottomed flask was charged with 2-(3-chloro-quinolin-6-ylmethyl)-isonicotinic acid methyl ester (700 mg, 2.2 mmol), piperidine (0.3 mL, 2.5 mmol), Pd$_2$(dba)$_3$ (202 mg, 0.22 mmol), XPhos (105 mg, 0.22 mmol), K$_3$PO$_4$ (11.9 g, 56.1 mmol) and anhydrous toluene (130 mL). The mixture was stirred at stirred at 100° C. under N$_2$ overnight. After cooling to ambient temperature, the mixture was concentrated. The resulting residue was diluted with DCM was washed with brine. The combined organic portions were dried over anhydrous Na$_2$SO$_4$ and concentrated to dryness by rotatory evaporator. The resulting residue was purified by chromatography on a silica gel column (PE/EA=1/1, v/v) to provide 2-(3-piperidin-1-yl-quinolin-6-ylmethyl)-isonicotinic acid methyl ester as a yellow oil (249.3 mg, 54%).

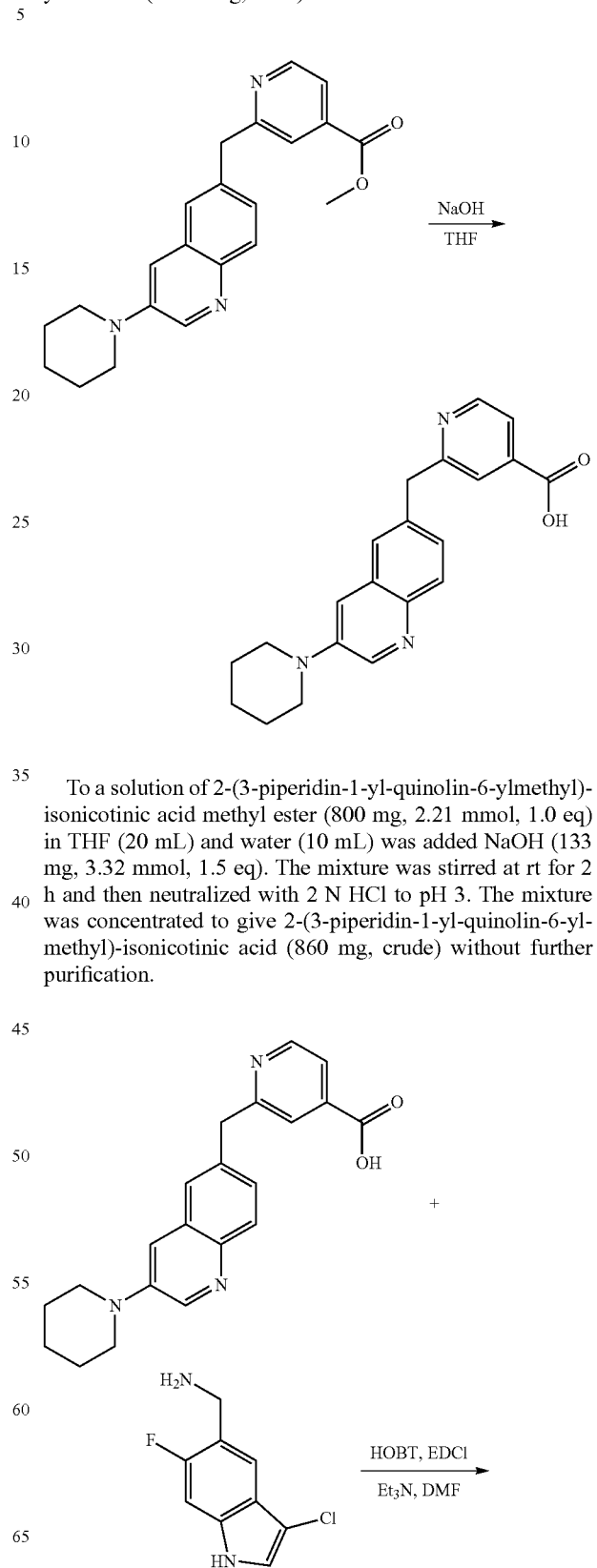

To a solution of 2-(3-piperidin-1-yl-quinolin-6-ylmethyl)-isonicotinic acid methyl ester (800 mg, 2.21 mmol, 1.0 eq) in THF (20 mL) and water (10 mL) was added NaOH (133 mg, 3.32 mmol, 1.5 eq). The mixture was stirred at rt for 2 h and then neutralized with 2 N HCl to pH 3. The mixture was concentrated to give 2-(3-piperidin-1-yl-quinolin-6-yl-methyl)-isonicotinic acid (860 mg, crude) without further purification.

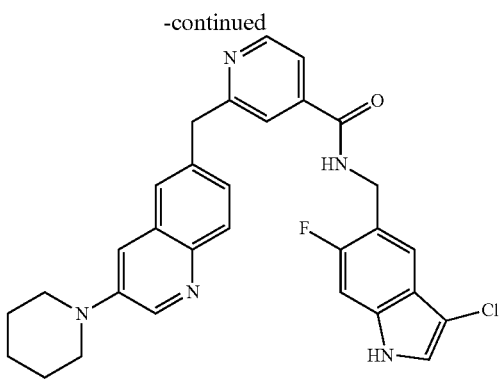

A solution of 2-(3-piperidin-1-yl-quinolin-6-ylmethyl)-isonicotinic acid (100 mg, 0.29 mmol, 1.0 eq), (3-chloro-6-fluoro-1H-indol-5-yl)methanamine (85.0 mg, 0.43 mmol, 1.5 eq), HOBT (58 mg, 0.43 mmol, 1.5 eq), EDCI (82 mg, 0.43 mmol, 1.5 eq) and Et$_3$N (87 mg, 0.86 mmol, 3.0 eq) in DMF (2 mL) was stirred at 30° C. overnight. The mixture was concentrated and the resulting residue was purified by Prep-HPLC to obtain N-((3-chloro-6-fluoro-1H-indol-5-yl)methyl)-2-((3-(piperidin-1-yl)quinolin-6-yl)methyl)isonicotinamide (24.0 mg, 16%) as a white solid.

LRMS (M+H$^+$) m/z calculated 528.2, found 528.2. $^1$H NMR (DMSO-d$_6$, 400 MHz): δ 11.40 (s, 1H), 9.26-9.24 (m, 1H), 8.77 (d, 1H), 8.65 (d, 1H), 7.77-7.75 (m, 2H), 7.66-7.64 (m, 1H), 7.61 (d, 1H), 7.51 (d, 1H), 7.44-7.37 (m, 3H), 7.21 (d, 1H), 4.58 (d, 2H), 4.29 (s, 2H), 3.28-3.24 (m, 4H), 1.66-1.57 (m, 6H).

Example 303: Preparation of N-((1-aminoisoquinolin-6-yl)methyl)-2-((3-(piperidin-1-yl)quinolin-6-yl)methyl)isonicotinamide

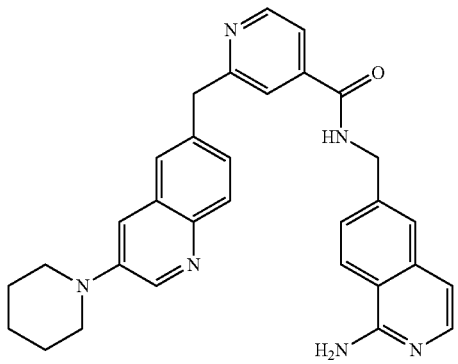 [SMILES: Nc1nccc2cc(CNC(=O)c3ccnc(Cc4ccc5ncc(N6CCCCC6)cc5c4)c3)ccc12]

A solution of 2-(3-piperidin-1-yl-quinolin-6-ylmethyl)-isonicotinic acid (100 mg, 0.29 mmol, 1.0 eq), 6-aminomethyl-isoquinolin-1-ylamine (75.0 mg, 0.43 mmol, 1.5 eq), HOBT (58 mg, 0.43 mmol, 1.5 eq), EDCI (82 mg, 0.43 mmol, 1.5 eq) and Et$_3$N (87 mg, 0.86 mmol, 3.0 eq) in DMF (2 mL) was stirred at 30° C. overnight. The mixture was concentrated and the resulting residue was purified by Prep-HPLC to obtain N-((1-aminoisoquinolin-6-yl)methyl)-2-((3-(piperidin-1-yl)quinolin-6-yl)methyl)isonicotinamide (29.0 mg, 20%) as a white solid.

LRCMS (M+H$^+$) m/z calculated 503.2, found 503.2. $^1$H NMR (DMSO-d$_6$, 400 MHz): δ 9.40-9.37 (m, 1H), 8.77 (d, 1H), 8.67 (d, 1H), 8.15 (d, 1H), 7.77-7.74 (m, 3H), 7.68-7.66 (m, 1H), 7.63 (d, 1H), 7.56 (s, 1H), 7.44-7.38 (m, 3H), 6.86-6.85 (m, 3H), 4.60 (d, 2H), 4.30 (s, 2H), 3.28-3.25 (m, 4H), 1.69-1.57 (m, 6H).

Example 304: Preparation of N-((5-chloro-1H-indazol-3-yl)methyl)-2-((3-(piperidin-1-yl)quinolin-6-yl)methyl)isonicotinamide

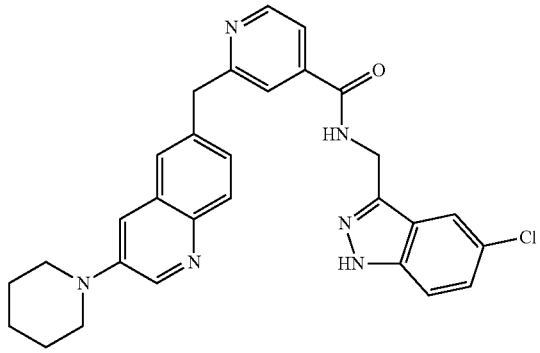 [SMILES: O=C(NCc1n[nH]c2ccc(Cl)cc12)c1ccnc(Cc2ccc3ncc(N4CCCCC4)cc3c2)c1]

A solution of 2-(3-piperidin-1-yl-quinolin-6-ylmethyl)-isonicotinic acid (100 mg, 0.29 mmol, 1.0 eq), (5-chloro-1H-indazol-3-yl)methanamine (78.0 mg, 0.43 mmol, 1.5 eq), HOBT (58 mg, 0.43 mmol, 1.5 eq), EDCI (82 mg, 0.43 mmol, 1.5 eq) and Et$_3$N (87 mg, 0.86 mmol, 3.0 eq) in DMF (2 mL) was stirred at 30° C. overnight. The mixture was concentrated and the resulting residue was purified by Prep-HPLC to obtain the target compound (29.0 mg, 20%) as a white solid.

LRMS (M+H$^+$) m/z calculated 511.2, found 511.2. $^1$H NMR (DMSO-d$_6$, 400 MHz): δ 13.07 (s, 1H), 9.39-9.36 (m, 1H), 8.76 (d, 1H), 8.64-8.62 (m, 1H), 7.88 (d, 1H), 7.76-7.74 (m, 2H), 7.63-7.60 (m, 2H), 7.54 (d, 1H), 7.42-7.31 (m, 3H), 4.78-4.77 (m, 2H), 4.28 (s, 2H), 3.31-3.25 (m, 4H), 1.66-1.57 (m, 6H).

Example 305: Preparation of N-((3-chloro-4-fluoro-1H-indol-5-yl)methyl)-2-((3-(piperidin-1-yl)quinolin-6-yl)methyl)isonicotinamide

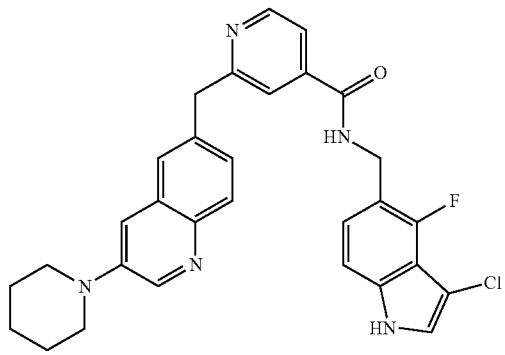 [SMILES: O=C(NCc1ccc2[nH]cc(Cl)c2c1F)c1ccnc(Cc2ccc3ncc(N4CCCCC4)cc3c2)c1]

A solution of 2-(3-piperidin-1-yl-quinolin-6-ylmethyl)-isonicotinic acid (100 mg, 0.29 mmol, 1.0 eq), (3-chloro-4-fluoro-1H-indol-5-yl)methanamine (85.0 mg, 0.43 mmol, 1.5 eq), HOBT (58 mg, 0.43 mmol, 1.5 eq), EDCI (82 mg, 0.43 mmol, 1.5 eq) and Et$_3$N (87 mg, 0.86 mmol, 3.0 eq) in DMF (2 mL) was stirred at 30° C. overnight. The mixture was concentrated and the resulting residue was purified by Prep-HPLC to obtain N-((3-chloro-4-fluoro-1H-indol-5-yl)methyl)-2-((3-(piperidin-1-yl)quinolin-6-yl)methyl)isonicotinamide (36.0 mg, 24%) as a white solid.

LRMS (M+H⁺) m/z calculated 528.2, found 528.2. $^1$H NMR (DMSO-d$_6$, 400 MHz): δ 11.62 (s, 1H), 9.29-9.27 (m, 1H), 9.02 (s, 1H), 8.66 (d, 1H), 8.02 (s, 1H), 7.90 (d, 1H), 7.80 (s, 2H), 7.69 (d, 1H), 7.60 (d, 1H), 7.53 (d, 1H), 7.20-7.12 (m, 2H), 4.57 (d, 2H), 4.35 (s, 2H), 3.38-3.37 (m, 4H), 1.67-1.60 (m, 6H).

Example 306: Preparation of N-((3-chloro-1H-pyrrolo[2,3-b]pyridin-5-yl)methyl)-2-((3-(piperidin-1-yl)quinolin-6-yl)methyl)isonicotinamide

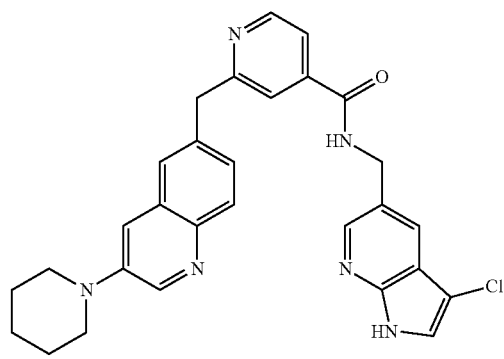 [SMILES: O=C(NCc1cnc2[nH]cc(Cl)c2c1)c1ccnc(Cc2ccc3ncc(N4CCCCC4)cc3c2)c1]

A solution of 2-(3-piperidin-1-yl-quinolin-6-ylmethyl)-isonicotinic acid (100 mg, 0.29 mmol, 1.0 eq), (3-chloro-1H-pyrrolo[2,3-b]pyridin-5-yl)methanamine (78.0 mg, 0.43 mmol, 1.5 eq), HOBT (58 mg, 0.43 mmol, 1.5 eq), EDCI (82 mg, 0.43 mmol, 1.5 eq) and Et$_3$N (87 mg, 0.86 mmol, 3.0 eq) in DMF (5 mL) was stirred at 30° C. overnight. The mixture was concentrated and the resulting residue was purified by Prep-HPLC to obtain N-((3-chloro-1H-pyrrolo[2,3-b]pyridin-5-yl)methyl)-2-((3-(piperidin-1-yl)quinolin-6-yl)methyl)isonicotinamide (12 mg, 8%) as a white solid.

LRMS (M+H⁺) m/z calculated 511.2, found 511.2. $^1$H NMR (DMSO-d$_6$, 400 MHz): δ 11.96 (s, 1H), 9.34-9.31 (m, 1H), 8.77 (d, 1H), 8.64 (d, 1H), 8.30 (s, 1H), 7.86 (s, 1H), 7.76-7.74 (m, 2H), 7.67 (d, 1H), 7.63-7.61 (m, 2H), 7.43-7.37 (m, 2H), 4.58 (d, 2H), 4.28 (s, 2H), 3.27-3.25 (m, 4H), 1.66-1.57 (m, 6H).

Example 307: Preparation of N-((3-chloro-6-fluoro-1H-indol-5-yl)methyl)-2-((3-(pyrrolidin-1-yl)quinolin-6-yl)methyl)isonicotinamide

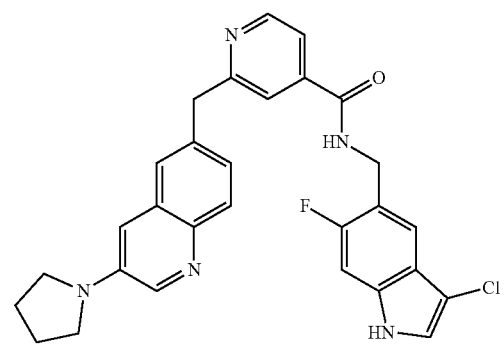

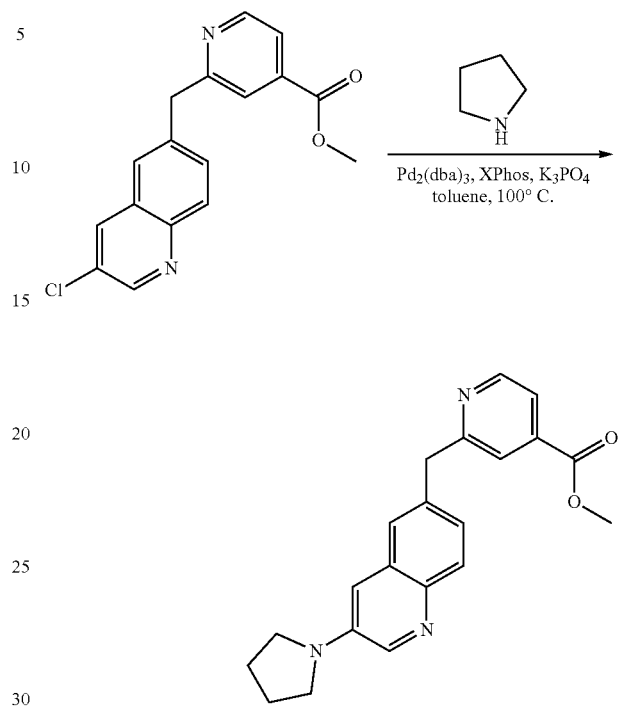

A flame-dried three-necked round-bottomed flask was charged with 2-(3-chloro-quinolin-6-ylmethyl)-isonicotinic acid methyl ester (875 mg, 2.2 mmol), pyrrolidine (0.2 mL, 2.7 mmol), Pd$_2$(dba)$_3$ (202 mg, 0.22 mmol), XPhos (105 mg, 0.22 mmol), K$_3$PO$_4$ (12 g, 56.1 mmol) and anhydrous toluene (150 mL). The resulting bright-yellow-colored suspensions were stirred at stirred at 100° C. under N$_2$ for 2.5 h. After cooling to ambient temperature, the mixture was extracted with EtOAc (30 mL×3). The combined organic layers were dried over anhydrous Na$_2$SO$_4$, filtered and concentrated in vacuo. The resulting residue was purified by chromatography on a silica gel column (PE/EA=1/1 to DCM/MeOH=15/1, v/v) to afford 2-(3-pyrrolidin-1-yl-quinolin-6-ylmethyl)-isonicotinic acid methyl ester as a yellow oil (493.7 mg, 64.6%).

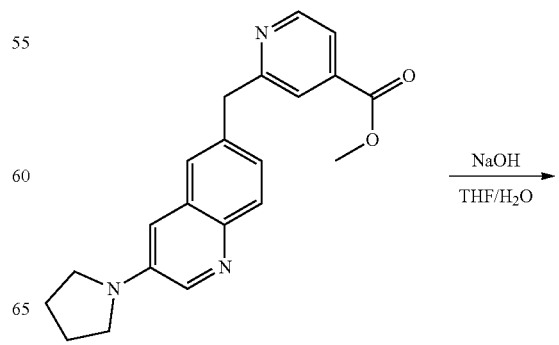

-continued

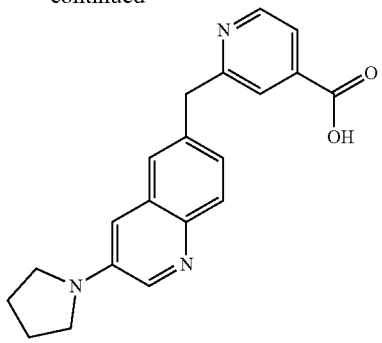

To a solution of 2-(3-pyrrolidin-1-yl-quinolin-6-ylmethyl)-isonicotinic acid methyl ester (493.7 mg, 1.42 mmol, 1.0 eq) in THF (20 mL) and water (10 mL) was added NaOH (85.4 mg, 2.13 mmol, 1.5 eq). The mixture was stirred at rt for 2 h. The reaction solution was neutralized with 2 N HCl to pH 3. The mixture was concentrated to give 2-(3-pyrrolidin-1-yl-quinolin-6-ylmethyl)-isonicotinic acid (610 mg, crude) without further purification.

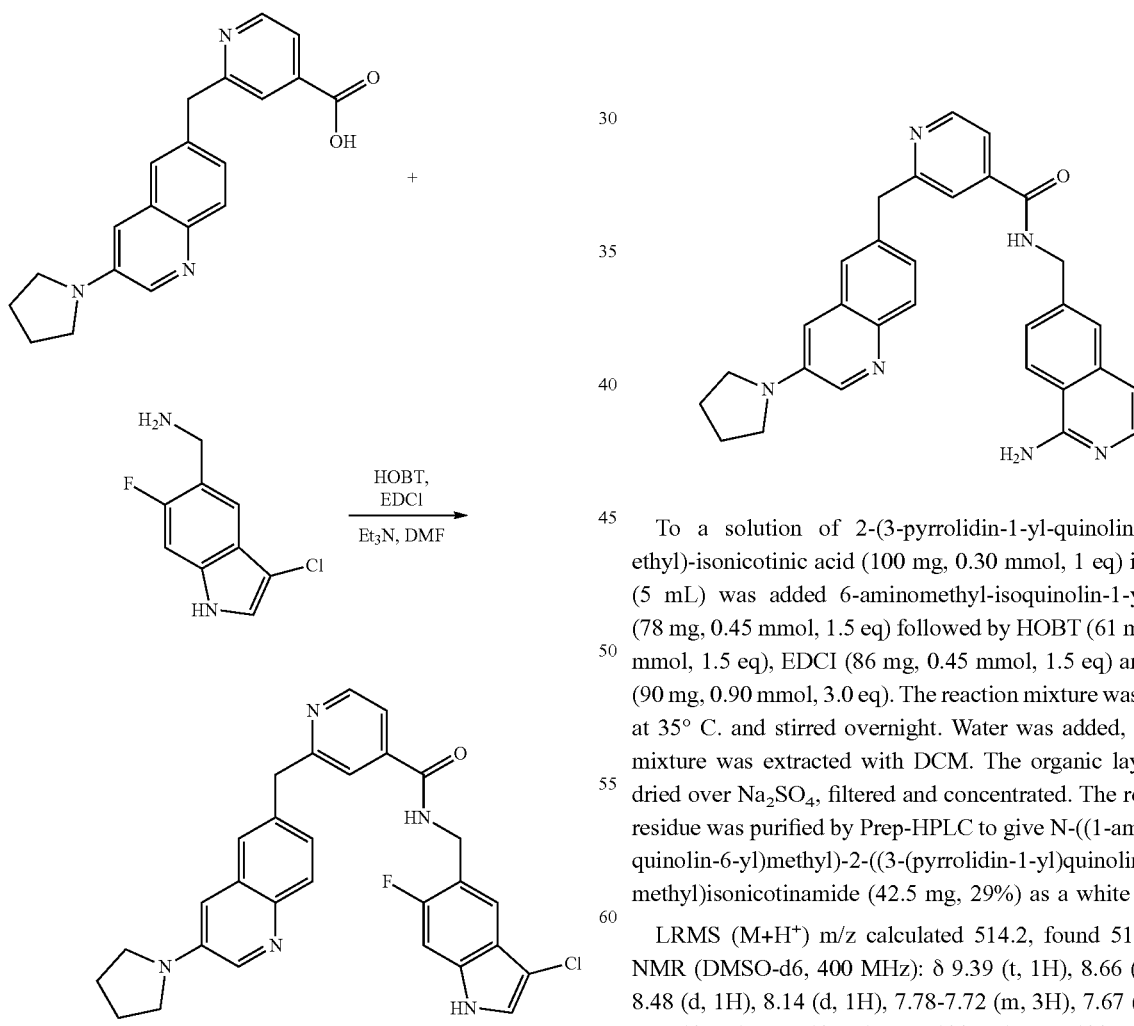

To a solution of 2-(3-pyrrolidin-1-yl-quinolin-6-ylmethyl)-isonicotinic acid (100 mg, 0.30 mmol, 1 eq) in DMF (5 mL) was added (3-chloro-6-fluoro-1H-indol-5-yl)methanamine (105 mg, 0.45 mmol, 1.5 eq) followed by HOBT (61 mg, 0.45 mmol, 1.5 eq), EDCI (86 mg, 0.45 mmol, 1.5 eq) and TEA (90 mg, 0.90 mmol, 3.0 eq). The reaction mixture was heated at 35° C. and stirred overnight. Water was added, and the mixture was extracted with DCM. The organic layer was dried over $Na_2SO_4$, filtered and concentrated. The resulting residue was purified by Prep-HPLC to give N-((3-chloro-6-fluoro-1H-indol-5-yl)methyl)-2-((3-(pyrrolidin-1-yl)quinolin-6-yl)methyl)isonicotinamide (38.6 mg, 25.1%) as a white solid.

LRMS (M+H$^+$) m/z calculated 514.2, found 514.2. $^1$H NMR (DMSO-d6, 400 MHz): δ 11.40 (s, 1H), 9.25 (t, 1H), 8.64 (d, 1H), 8.48 (d, 1H), 7.76 (s, 1H), 7.71 (d, 1H), 7.65 (s, 1H), 7.54 (s, 1H), 7.50 (s, 1H), 7.43 (d, 1H), 7.27 (d, 1H), 7.25 (d, 1H), 7.01 (s, 1H), 4.57 (d, 1H), 4.26 (s, 2H), 3.37 (t, 4H), 1.99 (t, 4H).

Example 308: Preparation of N-((1-aminoisoquinolin-6-yl)methyl)-2-((3-(pyrrolidin-1-yl)quinolin-6-yl)methyl)isonicotinamide To a solution of 2-(3-pyrrolidin-1-yl-quinolin-6-ylmethyl)-isonicotinic acid (100 mg, 0.30 mmol, 1 eq) in DMF (5 mL) was added 6-aminomethyl-isoquinolin-1-ylamine (78 mg, 0.45 mmol, 1.5 eq) followed by HOBT (61 mg, 0.45 mmol, 1.5 eq), EDCI (86 mg, 0.45 mmol, 1.5 eq) and TEA (90 mg, 0.90 mmol, 3.0 eq). The reaction mixture was heated at 35° C. and stirred overnight. Water was added, and the mixture was extracted with DCM. The organic layer was dried over $Na_2SO_4$, filtered and concentrated. The resulting residue was purified by Prep-HPLC to give N-((1-aminoisoquinolin-6-yl)methyl)-2-((3-(pyrrolidin-1-yl)quinolin-6-yl)methyl)isonicotinamide (42.5 mg, 29%) as a white solid.

LRMS (M+H$^+$) m/z calculated 514.2, found 514.2. $^1$H NMR (DMSO-d6, 400 MHz): δ 9.39 (t, 1H), 8.66 (d, 1H), 8.48 (d, 1H), 8.14 (d, 1H), 7.78-7.72 (m, 3H), 7.67 (d, 1H), 7.56 (d, 1H), 7.55 (d, 1H), 7.39 (dd, 1H), 7.27 (dd, 1H), 7.02 (d, 1H), 6.84 (d, 1H), 6.77 (s, 2H), 4.60 (d, 1H), 4.28 (s, 2H), 3.37 (t, 4H), 1.99 (t, 4H).

Example 309: Preparation of N-((5-chloro-1H-indazol-3-yl)methyl)-2-((3-(pyrrolidin-1-yl)quinolin-6-yl)methyl)isonicotinamide

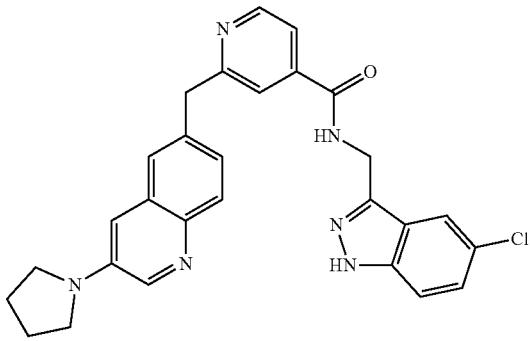 [SMILES: O=C(NCc1n[nH]c2ccc(Cl)cc12)c1ccnc(Cc2ccc3ncc(N4CCCC4)cc3c2)c1]

To a solution of 2-(3-pyrrolidin-1-yl-quinolin-6-ylmethyl)-isonicotinic acid (100 mg, 0.30 mmol, 1 eq) in DMF (5 mL) was added (5-chloro-1H-indazol-3-yl)methanamine (98 mg, 0.45 mmol, 1.5 eq) followed by HOBT (61 mg, 0.45 mmol, 1.5 eq), EDCI (86 mg, 0.45 mmol, 1.5 eq) and TEA (90 mg, 0.90 mmol, 3.0 eq). The reaction mixture was heated at 35° C. and stirred overnight. Water was added, and the mixture was extracted with DCM. The organic layer was dried over $Na_2SO_4$, filtered and concentrated. The resulting residue was purified by Prep-HPLC to give N-((5-chloro-1H-indazol-3-yl)methyl)-2-((3-(pyrrolidin-1-yl)quinolin-6-yl)methyl)isonicotinamide (20.5 mg, 13.8%) as a white solid.

LRMS (M+H+) m/z calculated 514.2, found 514.2. $^1$H NMR (DMSO-d6, 400 MHz): δ 13.08 (s, 1H), 9.39 (t, 1H), 8.63 (d, 1H), 8.47 (d, 1H), 7.89 (d, 1H), 7.75 (s, 1H), 7.71 (d, 1H), 7.61 (dd, 1H), 7.54 (s, 1H), 7.52 (d, 1H), 7.32 (dd, 1H), 7.25 (dd, 1H), 7.01 (d, 1H), 4.78 (d, 1H), 4.25 (s, 2H), 3.37 (t, 4H), 1.99 (t, 4H).

Example 310: Preparation of N-((3-chloro-1H-pyrrolo[2,3-b]pyridin-5-yl)methyl)-2-((3-(pyrrolidin-1-yl)quinolin-6-yl)methyl)isonicotinamide

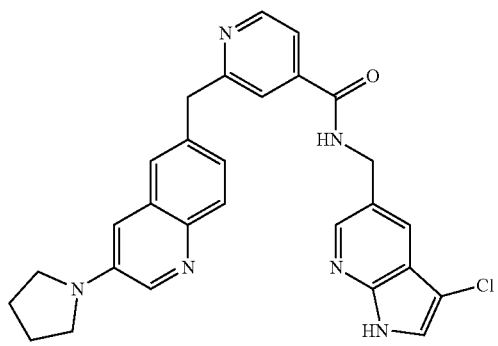 [SMILES: O=C(NCc1cnc2[nH]cc(Cl)c2c1)c1ccnc(Cc2ccc3ncc(N4CCCC4)cc3c2)c1]

To a solution of 2-(3-pyrrolidin-1-yl-quinolin-6-ylmethyl)-isonicotinic acid (100 mg, 0.30 mmol, 1 eq) in DMF (5 mL) was added (3-chloro-1H-pyrrolo[2,3-b]pyridin-5-yl)methanamine (98 mg, 0.45 mmol, 1.5 eq) followed by HOBT (61 mg, 0.45 mmol, 1.5 eq), EDCI (86 mg, 0.45 mmol, 1.5 eq) and TEA (90 mg, 0.90 mmol, 3.0 eq). The reaction mixture was heated at 35° C. and stirred overnight. Water was added, and the mixture was extracted with DCM. The organic layer was dried over $Na_2SO_4$, filtered and concentrated. The resulting residue was purified by Prep-HPLC to give N-((3-chloro-1H-pyrrolo[2,3-b]pyridin-5-yl)methyl)-2-((3-(pyrrolidin-1-yl)quinolin-6-yl)methyl)isonicotinamide (52.7 mg, 35.4%) as a white solid.

LRMS (M+H+) m/z calculated 497.2, found 497.2. $^1$H NMR (DMSO-d6, 400 MHz): δ 11.98 (s, 1H), 9.34 (t, 1H), 8.64 (d, 1H), 8.48 (d, 1H), 8.31 (s, 1H), 7.87 (s, 1H), 7.75-7.68 (m, 3H), 7.63 (d, 1H), 7.54 (s, 1H), 7.26 (d, 1H), 7.01 (d, 1H), 4.59 (d, 1H), 4.26 (s, 2H), 3.36 (t, 4H), 1.99 (t, 4H).

Example 311: Preparation of N-((3-chloro-4-fluoro-1H-indol-5-yl)methyl)-2-((3-(pyrrolidin-1-yl)quinolin-6-yl)methyl)isonicotinamide

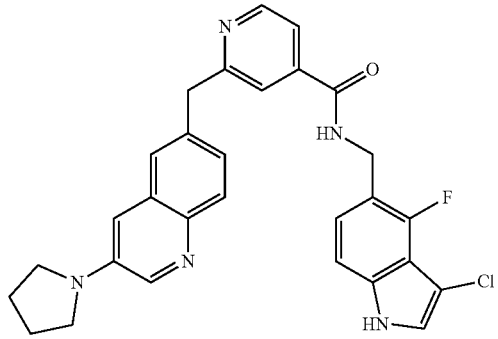 [SMILES: O=C(NCc1ccc2[nH]cc(Cl)c2c1F)c1ccnc(Cc2ccc3ncc(N4CCCC4)cc3c2)c1]

To a solution of 2-(3-pyrrolidin-1-yl-quinolin-6-ylmethyl)-isonicotinic acid (100 mg, 0.30 mmol, 1 eq) in DMF (5 mL) was added (3-chloro-4-fluoro-1H-indol-5-yl)methanamine (105 mg, 0.45 mmol, 1.5 eq) followed by HOBT (61 mg, 0.45 mmol, 1.5 eq), EDCI (86 mg, 0.45 mmol, 1.5 eq) and TEA (90 mg, 0.90 mmol, 3.0 eq). The reaction mixture was heated at 35° C. and stirred overnight. Water was added, and the mixture was extracted with DCM. The organic layer was dried over $Na_2SO_4$, filtered and concentrated. The resulting residue was purified by Prep-HPLC to give N-((3-chloro-4-fluoro-1H-indol-5-yl)methyl)-2-((3-(pyrrolidin-1-yl)quinolin-6-yl)methyl)isonicotinamide (21.5 mg, 13.9%) as a white solid.

LRMS (M+H+) m/z calculated 514.2, found 514.2. $^1$H NMR (DMSO-d6, 400 MHz): δ 11.60 (s, 1H), 9.24 (t, 1H), 8.63 (d, 1H), 8.48 (d, 1H), 7.75 (s, 1H), 7.71 (d, 1H), 7.63 (s, 1H), 7.54 (s, 1H), 7.52 (s, 1H), 7.26 (d, 1H), 7.19 (d, 1H), 7.13 (d, 1H), 7.02 (s, 1H), 4.56 (d, 1H), 4.26 (s, 2H), 3.37 (t, 4H), 1.99 (t, 4H).

Example 312: Preparation of N-((5-chloro-1H-indazol-3-yl)methyl)-2-((3-(piperazin-1-yl)quinolin-6-yl)methyl)isonicotinamide

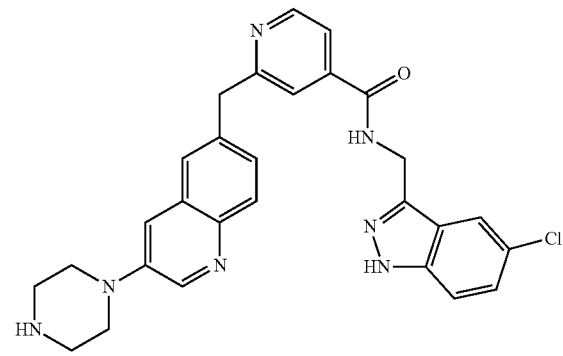

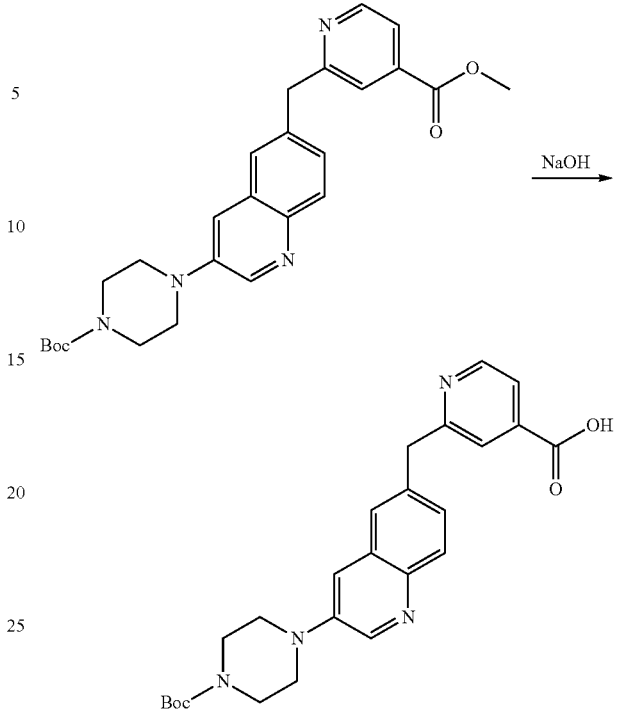

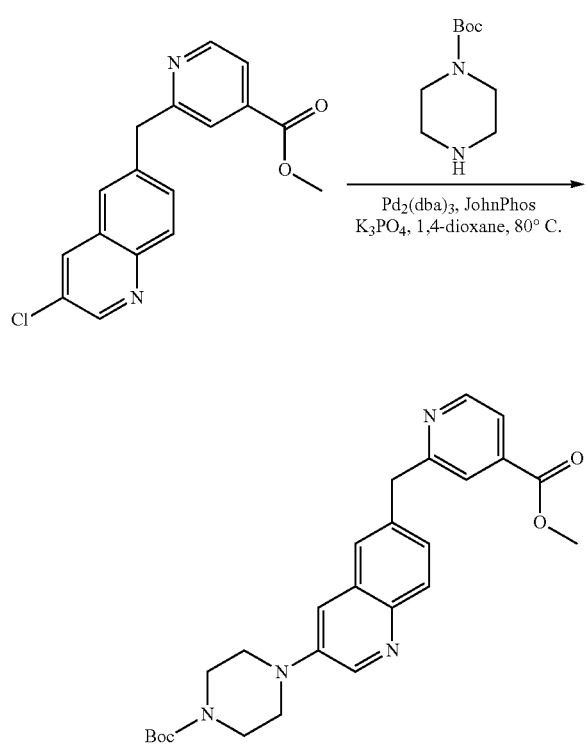

A flame-dried three-necked round-bottomed flask was charged with 2-(3-chloro-quinolin-6-ylmethyl)-isonicotinic acid methyl ester (500 mg, 1.6 mmol), piperazine-1-carboxylic acid tert-butyl ester (358 mg, 1.92 mmol), Pd$_2$(dba)$_3$ (293 mg, 0.32 mmol), JohnPhos (191 mg, 0.64 mmol), K$_3$PO$_4$ (8.67 g, 40.8 mmol) and anhydrous toluene (110 mL). The resulting brown-colored suspensions were stirred at 80° C. under N$_2$ overnight. After cooling to rt, the reaction mixture was concentrated. The resulting residue was diluted with DCM and washed with brine. The organic layer was dried over anhydrous Na$_2$SO$_4$ and concentrated to dryness by rotatory evaporator. The resulting residue was purified bu chromatography on a silica gel column (PE/EA=1/1, v/v to DCM/MeOH=10/1, v/v) to provide 2-(3-piperidin-1-yl-quinolin-6-ylmethyl)-isonicotinic acid methyl ester as a yellow oil (500 mg, 67%).

A round-bottomed flask was charged with 4-[6-(4-methoxycarbonyl-pyridin-2-ylmethyl)-quinolin-3-yl]-piperazine-1-carboxylic acid tert-butyl ester (900 mg, 1.95 mmol), NaOH (93 mg, 2.33 mmol), THF (3 mL) and distilled water (3 mL). The mixture was stirred at rt for 2 h and then neutralized with 1 N HCl to pH 3. The neutralized mixture was extracted with EtOAc (20 mL×10). The combined organic portions were washed with brine and then concentrated in vacuo to provide 4-[6-(4-carboxy-pyridin-2-ylmethyl)-quinolin-3-yl]-piperazine-1-carboxylic acid tert-butyl ester as an orange-brown solid (839.5 mg, 96%).

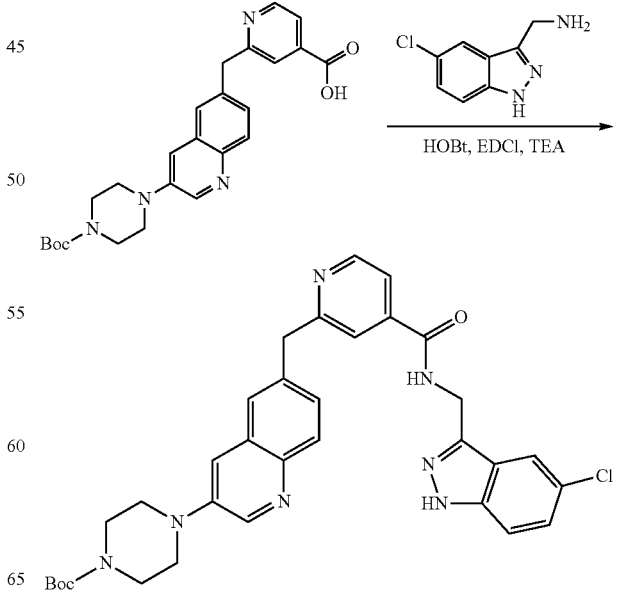

A round-bottomed flask was charged with 4-[6-(4-carboxy-pyridin-2-ylmethyl)-quinolin-3-yl]-piperazine-1-carboxylic acid tert-butyl ester (80 mg, 0.178 mmol), (5-chloro-1H-indazol-3-yl)methanamine (38.9 mg, 0.356 mmol), EDCI (51.1 mg, 0.267 mmol), HOBt (36.1 mg, 0.267 mmol), Et₃N (0.074 mL, 0.534 mmol), and anhydrous DMF (3 mL). The mixture was stirred at 45° C. overnight. LC-MS showed that the reaction was complete. The reaction mixture was filtered by a pad of celite and washed with MeOH. The combined organic phases were concentrated to dryness under reduced pressure. The resulting residue was purified by Prep-HPLC to provide 4-(6-{4-[(5-chloro-1H-indazol-3-ylmethyl)-carbamoyl]-pyridin-2-ylmethyl})-quinolin-3-yl)-piperazine-1-carboxylic acid tert-butyl ester as a white solid (81.6 mg, 75%).

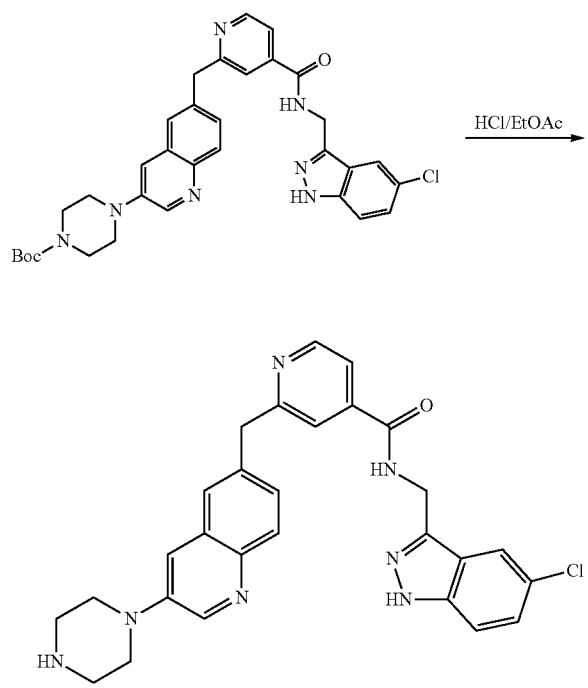

To a solution of 4-(6-{4-[(5-chloro-1H-indazol-3-ylmethyl)-carbamoyl]-pyridin-2-ylmethyl}-quinolin-3-yl)-piperazine-1-carboxylic acid tert-butyl ester (81.6 mg, 0.13 mmol) in EA (3 mL) was added a solution of HCl in EA (3 mL). The mixture was stirred at ambient temperature for 30 min. The resulting precipitate was filtered and washed with EtOAc and dried to afford N-(5-chloro-1H-indazol-3-ylmethyl)-2-(3-piperazin-1-yl-quinolin-6-ylmethyl)-isonicotinamide as a bright-yellow solid (60 mg, 88%).

LRMS (M+H⁺) m/z calculated 512.2, found 512.2. ¹H NMR (DMSO-d6, 400 MHz): δ 13.10 (s, 1H), 9.67 (t, 1H), 9.57 (s, 2H), 9.17 (d, 1H), 8.77 (d, 1H), 8.30 (s, 1H), 8.17 (d, 1H), 8.00 (s, 1H), 7.93-7.90 (m, 3H), 7.81 (d, 1H), 7.53 (d, 1H), 7.33 (dd, 1H), 4.79 (d, 1H), 4.52 (s, 2H), 3.71 (t, 4H), 3.26 (t, 4H).

Example 313: Preparation of N-((3-chloro-6-fluoro-1H-indol-5-yl)methyl)-2-((3-(piperazin-1-yl)quinolin-6-yl)methyl)isonicotinamide

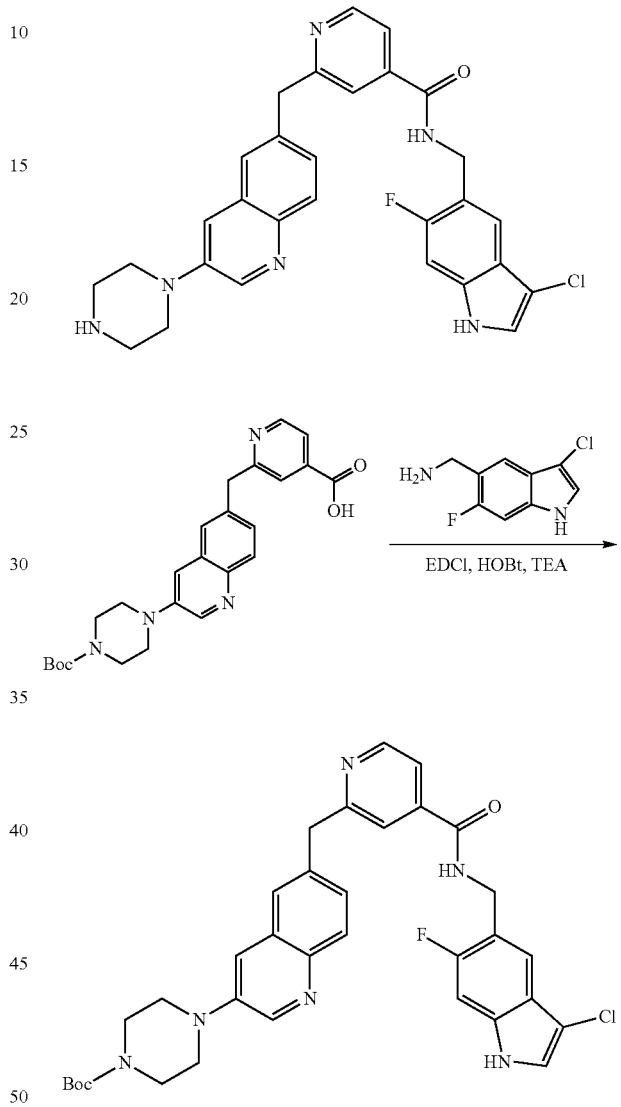

A round-bottomed flask was charged with 4-[6-(4-carboxy-pyridin-2-ylmethyl)-quinolin-3-yl]-piperazine-1-carboxylic acid tert-butyl ester (80 mg, 0.178 mmol), (3-chloro-6-fluoro-1H-indol-5-yl)methanamine (96.7 mg, 0.356 mmol), EDCI (51.1 mg, 0.267 mmol), HOBt (36.1 mg, 0.267 mmol), Et₃N (0.074 mL, 0.534 mmol), and anhydrous DMF (3 mL). The mixture was stirred at 45° C. for 2 h. After 2 h, LC-MS showed that the reaction was complete. The reaction mixture was filtered by a pad of celite and washed with MeOH. The combined organic phase was concentrated to dryness under reduced pressure. The resulting residue was purified by Prep-HPLC to provide 4-(6-{4-[(3-chloro-6-fluoro-1H-indol-5-ylmethyl)-carbamoyl]-pyridin-2-ylmethyl}-quinolin-3-yl)-piperazine-1-carboxylic acid tert-butyl ester as a yellow solid (52 mg, 46.5%).

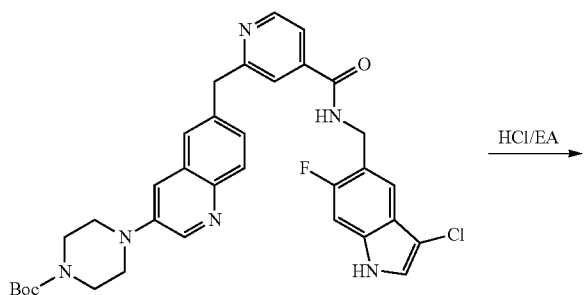

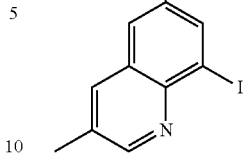

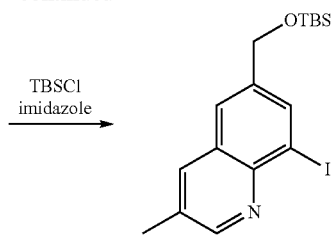

A mixture of (8-iodo-3-methyl-quinolin-6-yl)-methanol (10 g, 33.4 mmol, 1 eq), TBDS-Cl (6.0 g, 40 mmol, 1.2 eq) and imidazole (4.5 g, 66.8 mmol, 2 eq) in DCM (500 mL) was stirred at rt for 2 h. Then the mixture was washed with water and brine, dried over $Na_2SO_4$ and concentrated to give 6-(tert-butyl-dimethyl-silanyloxymethyl)-8-iodo-3-methyl-quinoline (10 g, 72%) as a white solid.

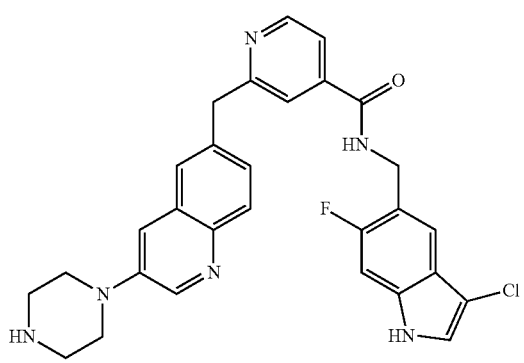

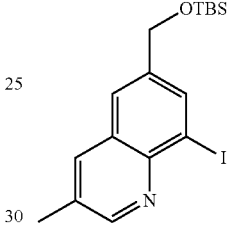

To a solution of 4-(6-{4-[(3-chloro-6-fluoro-1H-indol-5-ylmethyl)-carbamoyl]-pyridin-2-ylmethyl}-quinolin-3-yl)-piperazine-1-carboxylic acid tert-butyl ester (52 mg, 0.083 mmol) in EA (3 mL) was added a solution of HCl in EA (3 mL). The mixture was stirred at ambient temperature overnight. Then the resulting precipitate was filtered and the filter cake was washed with EtOAc and dried under reduced pressure to give N-(3-chloro-6-fluoro-1H-indol-5-ylmethyl)-2-(3-piperazin-1-yl-quinolin-6-ylmethyl)-isonicotinamide as a yellow solid (20 mg, 45.6% yield).

LRMS (M+H$^+$) m/z calculated 529.2, found 529.2. $^1$H NMR (DMSO-d6, 400 MHz): δ 11.48 (s, 1H), 9.45 (s, 2H), 9.43 (s, 1H), 9.13 (d, 1H), 9.74 (d, 1H), 8.20-8.05 (m, 2H), 7.98-7.85 (m, 4H), 7.51 (d, 1H), 7.46 (d, 1H), 7.23 (d, 1H), 4.59 (d, 1H), 4.46 (s, 2H), 3.67 (t, 4H), 3.27 (t, 4H).

Example 314: Preparation of N-((3-chloro-6-fluoro-1H-indol-5-yl)methyl)-2-((8-(2-hydroxypropan-2-yl)-3-methylquinolin-6-yl)methyl)isonicotinamide

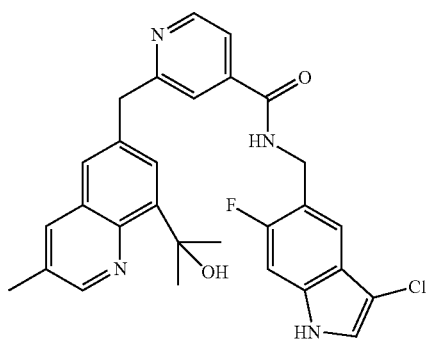

To a solution of 6-(tert-butyl-dimethyl-silanyloxymethyl)-8-iodo-3-methyl-quinoline (10 g, 24.2 mmol, 1 eq) in dioxane (200 mL) were added Pd(dppf)Cl$_2$ (1.7 g, 2.4 mmol, 0.1 eq), tributyl-(1-ethoxyvinyl)tin (10.4 g, 29 mmol, 1.2 eq), and CsF (7.3 g, 48 mmol, 2 eq). The reaction mixture was degassed with N$_2$ three times, and then heated at 80° C. overnight. The reaction was quenched with a solution of KF, and extracted with EA three times. The combined organic layers were washed with brine, dried over sodium sulfate, and concentrated. The resulting residue was purified by chromatography on a silica gel column (EA/PE=1/10, v/v) to give 6-(tert-butyl-dimethyl-silanyloxymethyl)-8-(1-ethoxy-vinyl)-3-methyl-quinoline (7.7 g, 89%) as a yellow oil.

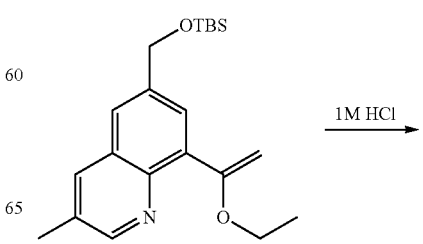

-continued

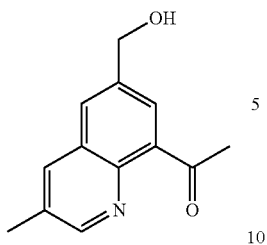

To a solution of 6-(tert-butyl-dimethyl-silanyloxymethyl)-8-(1-ethoxy-vinyl)-3-methyl-quinoline (300 mg, 0.84 mmol, 1 eq) in 10 mL of THF was added 2 mL of HCl (1 N). The reaction was stirred at rt for 3 h and diluted with 10 mL of water. The mixture was extracted with EA and the organic layer was dried with sodium sulfate, filtered and concentrated. The resulting residue was purified by chromatography on a silica gel column (PE/EA=2/1, v/v) to give 1-(6-hydroxymethyl-3-methyl-quinolin-8-yl)-ethanone (170 mg, 94%) as a yellow solid.

To a solution of 1-(6-hydroxymethyl-3-methyl-quinolin-8-yl)-ethanone (170 mg, 0.79 mmol, 1 eq) in dry THF was added methylmagnesium iodide (1.8 mL, 2 eq) under $N_2$ below 0° C. The reaction was stirred at rt for 2 h, and then quenched with water. The solution was extracted with EA, dried, concentrated, and the resulting residue was purified by chromatography on a silica gel column (EA/PE=1/2, v/v) to afford 2-(6-hydroxymethyl-3-methyl-quinolin-8-yl)-propan-2-ol (70 mg, 38%).

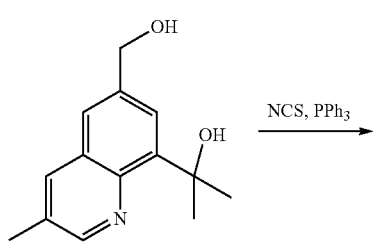

-continued

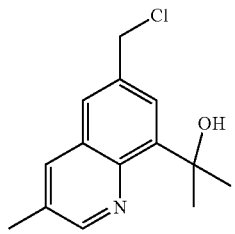

To the solution of 2-(6-hydroxymethyl-3-methyl-quinolin-8-yl)-propan-2-ol (190 mg, 0.82 mmol, 1 eq) in dry DCM (20 mL) was added PPh$_3$ (0.9 g, 3.4 mmol, 4 eq). The reaction mixture was cooled to −20° C., and then pyridine (0.55 mL, 5.7 mmol, 7 eq) and NCS (210 mg, 1.6 mmol, 2 eq) were added. The mixture was allowed to warm to rt and stirred overnight. The mixture was concentrated and the resulting residue was purified by chromatography on a silica gel column (EA/PE=1/4, v/v) to afford 2-(6-chloromethyl-3-methyl-quinolin-8-yl)-propan-2-ol (89 mg, 43%) as a yellow solid.

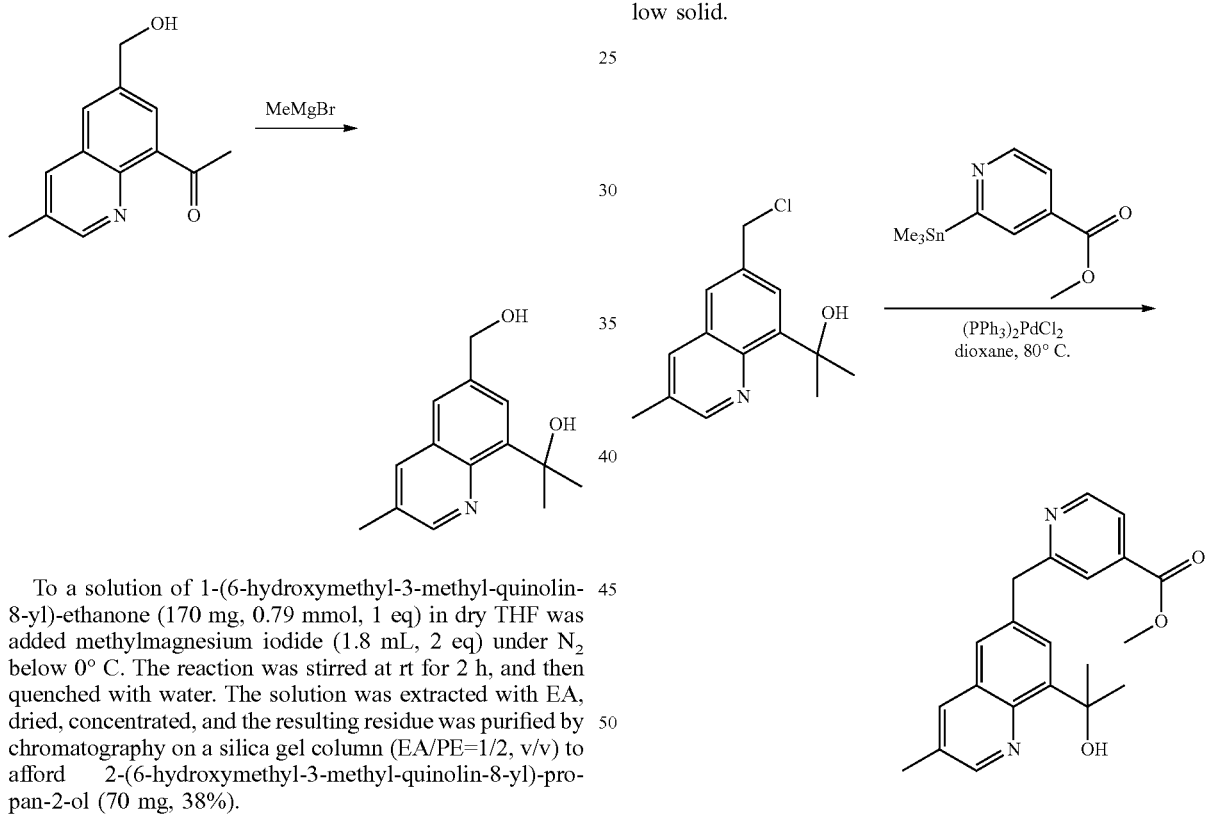

To a mixture 2-(6-chloromethyl-3-methyl-quinolin-8-yl)-propan-2-ol (89 mg, 0.35 mmol, 1 eq) and 2-trimethylstannanyl-isonicotinic acid methyl ester (150 mg, 0.35 mmol, 1 eq) in dioxane (5 mL) was added Pd(PPh$_3$)$_2$Cl$_2$. The reaction solution was degassed with N$_2$ three times, and heated at 80° C. overnight. The solution was poured into 20 mL of water, extracted with EA. The combined organic layers were washed with brine, dried over sodium sulfate, filtered and concentrated. The resulting residue was purified by chromatography on a silica gel column (DCM/MeOH=40/1, v/v) to afford 2-[8-(1-hydroxy-1-methyl-ethyl)-3-methyl-quinolin-6-ylmethyl]-isonicotinic acid methyl ester (60 mg, 28.6%) as a yellow solid.

723

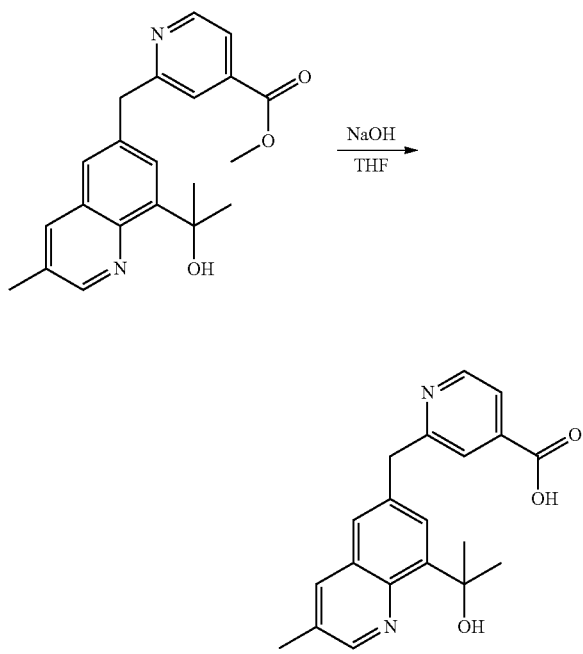

To a solution of 2-[8-(1-hydroxy-1-methyl-ethyl)-3-methyl-quinolin-6-ylmethyl]-isonicotinic acid methyl ester (1.0 g, 1.35 mmol, 1.0 eq) in THF (20 mL) was added a solution of NaOH (171 mg, 4.28 mmol, 1.5 eq) in water (10 mL) at rt. The mixture was stirred at rt for 3 h. The reaction solution was neutralized with 1 N HCl to pH 3. The mixture was concentrated to give 2-[8-(1-hydroxy-1-methyl-ethyl)-3-methyl-quinolin-6-ylmethyl]-isonicotinic acid (1.0 g, crude) without further purification.

724

-continued

A mixture of 2-[8-(1-hydroxy-1-methyl-ethyl)-3-methyl-quinolin-6-ylmethyl]-isonicotinic acid (150 mg, 0.45 mmol, 1.0 eq), (3-chloro-6-fluoro-1H-indol-5-yl)methanamine (132 mg, 0.67 mmol, 1.5 eq), HOBT (90 mg, 0.67 mmol, 1.5 eq), EDCI (128 mg, 0.67 mmol, 1.5 eq) and Et$_3$N (136 mg, 1.35 mmol, 3.0 eq) in DMF (2 mL) was stirred at 30° C. overnight. After that, water (10 mL) was added, and the resulting precipitate was filtered, which was further purified by Prep-HPLC to give N-((3-chloro-6-fluoro-1H-indol-5-yl)methyl)-2-((8-(2-hydroxypropan-2-yl)-3-methylquinolin-6-yl)methyl)isonicotinamide (35 mg, 15%) as a white solid.

LRMS (M+H$^+$) m/z calculated 517.2, found 517.1. $^1$H NMR (DMSO-d$_6$, 400 MHz): δ 11.40 (s, 1H), 9.26-9.23 (m, 1H), 8.73 (d, 1H), 8.67-8.65 (m, 1H), 8.11 (s, 1H), 7.78-7.74 (m, 2H), 7.67-7.66 (m, 1H), 7.61 (d, 1H), 7.51 (d, 1H), 7.43 (d, 1H), 7.21 (d, 1H), 4.58 (d, 2H), 4.33 (s, 2H), 2.46 (s, 3H), 1.67 (s, 6H).

Example 315: Preparation of N-((3-chloro-4-fluoro-1H-indol-5-yl)methyl)-2-((8-(2-hydroxypropan-2-yl)-3-methylquinolin-6-yl)methyl)isonicotinamide

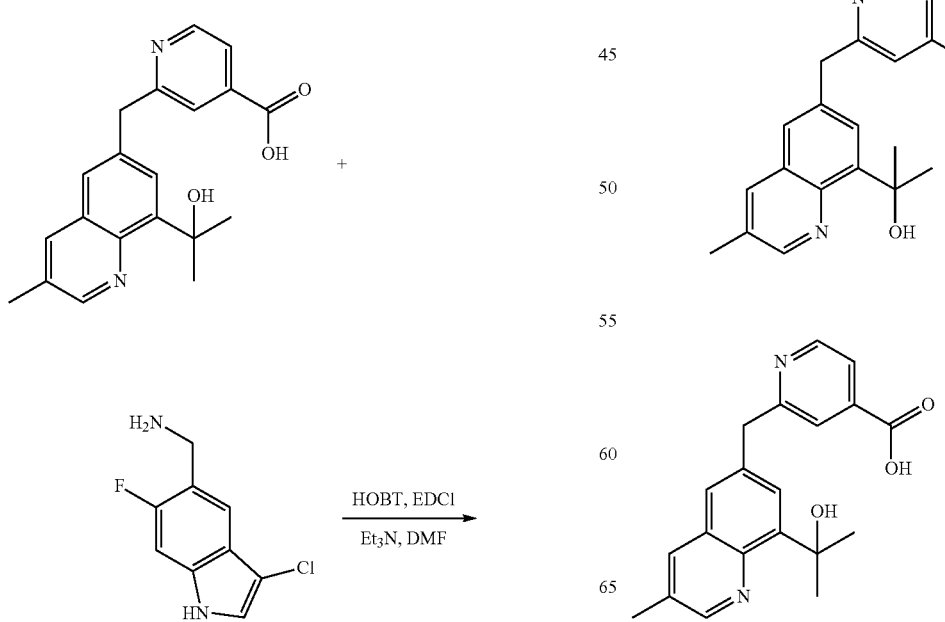

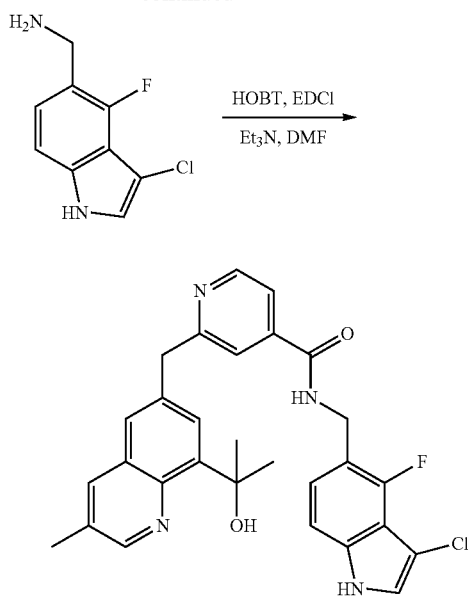

A mixture of 2-[8-(1-hydroxy-1-methyl-ethyl)-3-methyl-quinolin-6-ylmethyl]-isonicotinic acid (150 mg, 0.45 mmol, 1.0 eq), (3-chloro-4-fluoro-1H-indol-5-yl)methanamine (132 mg, 0.67 mmol, 1.5 eq), HOBT (90 mg, 0.67 mmol, 1.5 eq), EDCI (128 mg, 0.67 mmol, 1.5 eq) and Et₃N (136 mg, 1.35 mmol, 3.0 eq) in DMF (2 mL) was stirred at 30° C. overnight. After that, water (10 mL) was added, and the resulting precipitate was filtered. The solid was further purified by Prep-HPLC to give N-((3-chloro-4-fluoro-1H-indol-5-yl)methyl)-2-((8-(2-hydroxypropan-2-yl)-3-methylquinolin-6-yl)methyl)isonicotinamide (71.0 mg, 31%) as a white solid.

LRCMS (M+H⁺) m/z calculated 517.2, found 517.2. ¹H NMR (DMSO-d₆, 400 MHz): δ 11.59 (s, 1H), 9.26-9.23 (m, 1H), 8.71 (d, 1H), 8.64 (d, 1H), 8.09 (s, 1H), 7.76-7.73 (m, 2H), 7.65-7.64 (m, 1H), 7.60 (d, 1H), 7.51 (d, 1H), 7.19-7.12 (m, 2H), 6.57 (s, 1H), 4.56 (d, 2H), 4.32 (s, 2H), 2.45 (s, 3H), 1.66 (s, 6H).

Example 316: Preparation of N-((3-chloro-1H-pyrrolo[2,3-b]pyridin-5-yl)methyl)-2-((8-(2-hydroxypropan-2-yl)-3-methylquinolin-6-yl)methyl)isonicotinamide

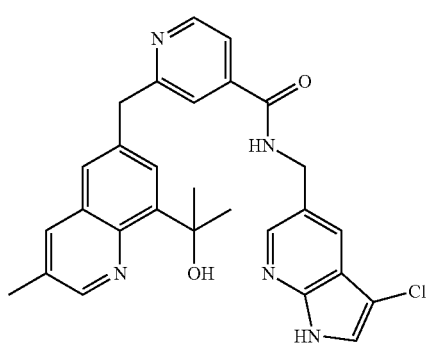

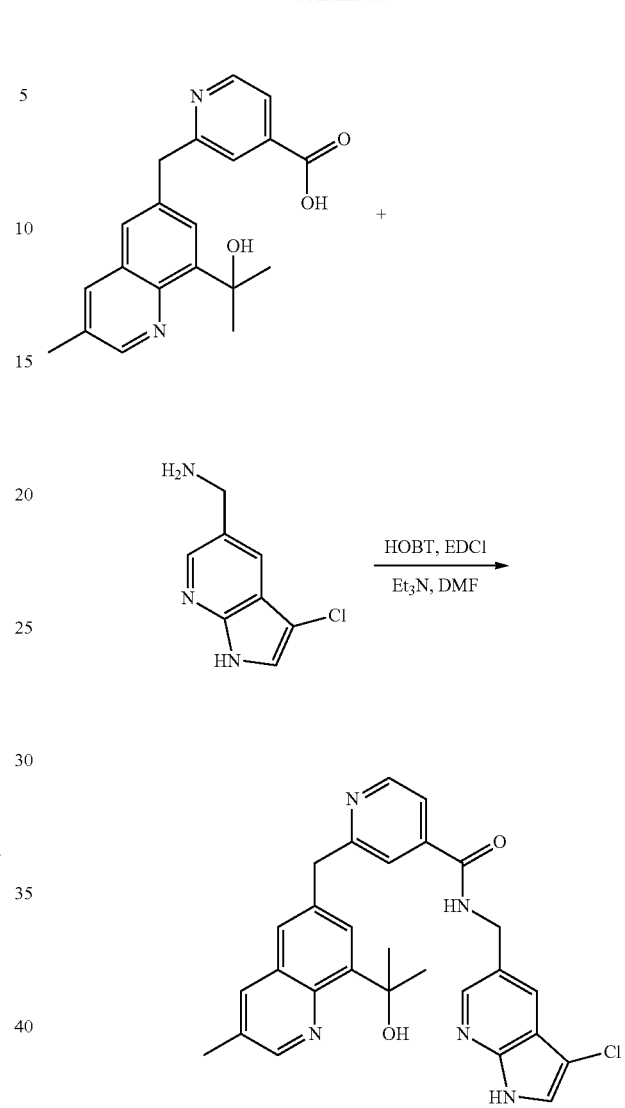

A solution of 2-[8-(1-hydroxy-1-methyl-ethyl)-3-methyl-quinolin-6-ylmethyl]-isonicotinic acid (150 mg, 0.45 mmol, 1.0 eq), (3-chloro-1H-pyrrolo[2,3-b]pyridin-5-yl)methanamine (121 mg, 0.67 mmol, 1.5 eq), HOBT (90 mg, 0.67 mmol, 1.5 eq), EDCI (128 mg, 0.67 mmol, 1.5 eq) and Et₃N (136 mg, 1.35 mmol, 3.0 eq) in DMF (2 mL) was stirred at 30° C. overnight. After that, water (10 mL) was added, and the resulting precipitate was filtered. The solid was further purified by Prep-HPLC to give N-((3-chloro-1H-pyrrolo[2,3-b]pyridin-5-yl)methyl)-2-((8-(2-hydroxypropan-2-yl)-3-methylquinolin-6-yl)methyl)isonicotinamide (46.0 mg, 20%) as a white solid.

LRMS (M+H⁺) m/z calculated 500.2, found 500.1. ¹H NMR (DMSO-d₆, 400 MHz): δ 11.97 (s, 1H), 9.35-9.33 (m, 1H), 8.72 (d, 1H), 8.65 (d, 1H), 8.31 (d, 1H), 8.09 (s, 1H), 7.86 (d, 1H), 7.77-7.74 (m, 2H), 7.68-7.60 (m, 3H), 6.59 (br.s., 1H), 4.58 (d, 2H), 4.33 (s, 2H), 2.45 (s, 3H), 1.67 (s, 6H).

Example 317: Preparation of N-((5-chloro-1H-indazol-3-yl)methyl)-2-((8-(2-hydroxypropan-2-yl)-3-methylquinolin-6-yl)methyl)isonicotinamide

Example 318: Preparation of N-((6-amino-2,4-dimethylpyridin-3-yl)methyl)-2-((8-(2-hydroxypropan-2-yl)-3-methylquinolin-6-yl)methyl)isonicotinamide

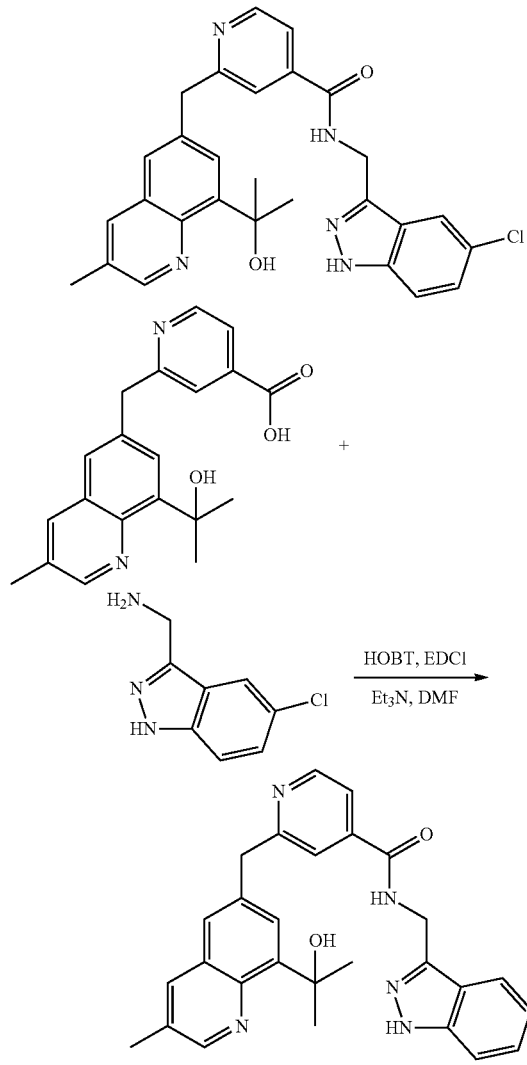

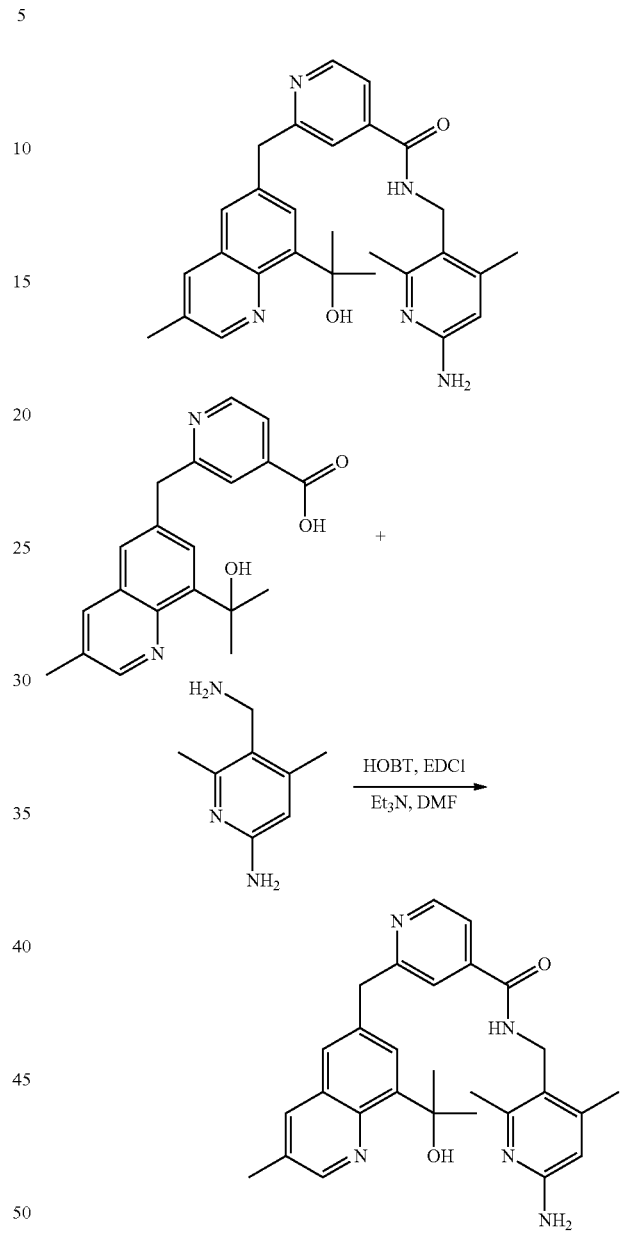

A mixture of 2-[8-(1-hydroxy-1-methyl-ethyl)-3-methyl-quinolin-6-ylmethyl]-isonicotinic acid (150 mg, 0.45 mmol, 1.0 eq), (5-chloro-1H-indazol-3-yl)methanamine (121 mg, 0.67 mmol, 1.5 eq), HOBT (90 mg, 0.67 mmol, 1.5 eq), EDCI (128 mg, 0.67 mmol, 1.5 eq) and Et$_3$N (136 mg, 1.35 mmol, 3.0 eq) in DMF (2 mL) was stirred at 30° C. overnight. After that water (10 mL) was added, and the resulting precipitate was filtered and the solid was further purified by Prep-HPLC to give N-((5-chloro-1H-indazol-3-yl)methyl)-2-((8-(2-hydroxypropan-2-yl)-3-methylquinolin-6-yl)methyl)isonicotinamide (29.0 mg, 13%) as a white solid.

LRMS (M+H$^+$) m/z calculated 500.2, found 500.2. $^1$H NMR (DMSO-d$_6$, 400 MHz): δ 13.08 (s, 1H), 9.39-9.37 (m, 1H), 8.72 (d, 1H), 8.64 (d, 1H), 8.08 (s, 1H), 7.88 (d, 1H), 7.71-7.72 (m, 2H), 7.65-7.51 (m, 3H), 7.34-7.31 (m, 1H), 6.58 (d, 1H), 4.78 (d, 2H), 4.32 (s, 2H), 2.45 (s, 3H), 1.66 (s, 6H).

A solution of 2-[8-(1-hydroxy-1-methyl-ethyl)-3-methyl-quinolin-6-ylmethyl]-isonicotinic acid (150 mg, 0.45 mmol, 1.0 eq), 5-aminomethyl-4,6-dimethyl-pyridin-2-ylamine (101 mg, 0.67 mmol, 1.5 eq), HOBT (90 mg, 0.67 mmol, 1.5 eq), EDCI (128 mg, 0.67 mmol, 1.5 eq) and Et$_3$N (136 mg, 1.35 mmol, 3.0 eq) in DMF (2 mL). The mixture was stirred at 30° C. overnight. After that, water (10 mL) was added and extracted with DCM/MeOH (10/1, v/v). The organic layers were dried over Na$_2$SO$_4$, filtered and concentrated. The resulting residue was purified by Prep-HPLC to give N-((6-amino-2,4-dimethylpyridin-3-yl)methyl)-2-((8-(2-hydroxypropan-2-yl)-3-methylquinolin-6-yl)methyl)isonicotinamide (39.0 mg, 18%) as a white solid.

LRMS (M+H$^+$) m/z calculated 470.2, found 470.2. $^1$H NMR (DMSO-d$_6$, 400 MHz): δ 8.72 (d, 1H), 8.67-8.64 (m, 1H), 8.09 (d, 1H), 7.73 (d, 2H), 7.61-7.59 (m, 2H), 6.58 (s, 1H), 6.16 (s, 1H), 5.85 (br.s., 2H), 4.33-4.30 (m, 4H), 2.46 (s, 3H), 2.31 (s, 3H), 2.17 (s, 3H), 1.67 (s, 6H).

Example 319: Preparation of N-((1-aminoisoquinolin-6-yl)methyl)-2-((8-(2-hydroxypropan-2-yl)-3-methylquinolin-6-yl)methyl)isonicotinamide

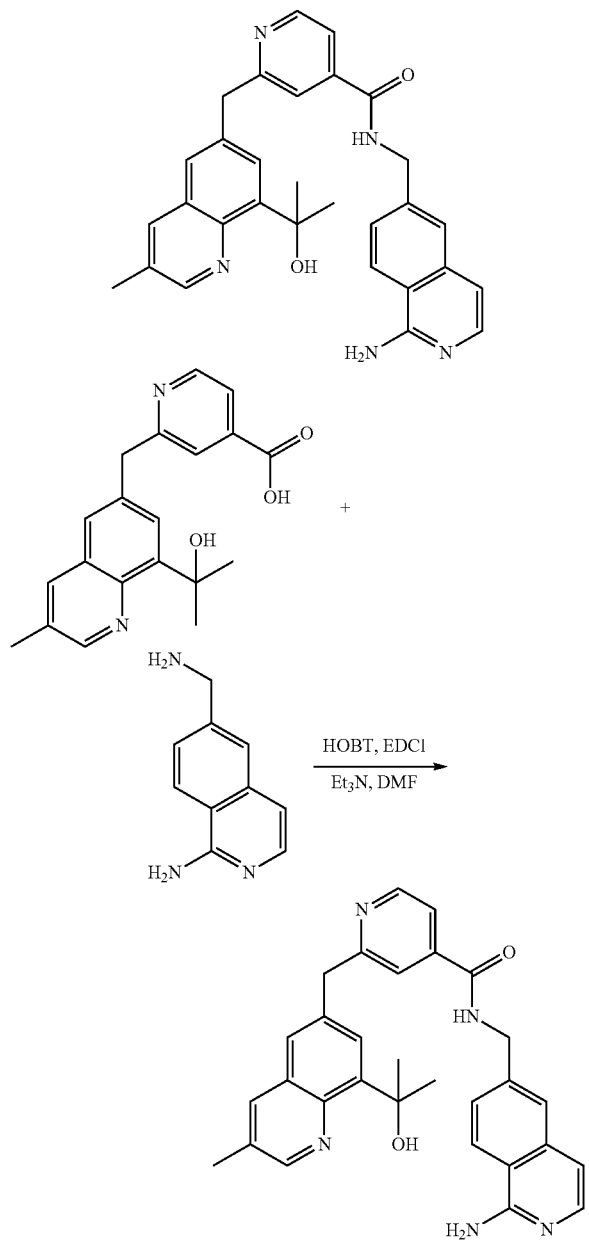

A solution of 2-[8-(1-hydroxy-1-methyl-ethyl)-3-methyl-quinolin-6-ylmethyl]-isonicotinic acid (150 mg, 0.45 mmol, 1.0 eq), 6-aminomethyl-isoquinolin-1-ylamine (116 mg, 0.67 mmol, 1.5 eq), HOBT (90 mg, 0.67 mmol, 1.5 eq), EDCI (128 mg, 0.67 mmol, 1.5 eq) and Et$_3$N (136 mg, 1.35 mmol, 3.0 eq) in DMF (2 mL) was stirred at 30° C. overnight. After that, water (10 mL) was added and the reaction mixture was extracted with DCM/MeOH (10/1, v/v). The organic layers were dried over Na$_2$SO$_4$, filtered and concentrated. The resulting residue was purified by Prep-HPLC to give N-((1-aminoisoquinolin-6-yl)methyl)-2-((8-(2-hydroxypropan-2-yl)-3-methylquinolin-6-yl)methyl)isonicotinamide (99.0 mg, 45%) as a white solid.

LRMS (M+H$^+$) m/z calculated 492.2, found 492.2. $^1$H NMR (DMSO-d$_6$, 400 MHz): δ 9.41-9.37 (m, 1H), 8.73 (d, 1H), 8.68 (d, 1H), 8.14-8.10 (m, 2H), 7.79 (s, 1H), 7.76-7.74 (m, 2H), 7.70-7.68 (m, 1H), 7.62 (d, 1H), 7.55 (s, 1H), 7.41-7.38 (m, 1H), 6.85 (d, 1H), 6.76 (s, 2H), 6.58 (s, 1H), 4.60 (d, 2H), 4.34 (s, 2H), 2.46 (s, 3H), 1.67 (s, 6H).

Example 320: Preparation of 2-((3-(azetidin-1-yl)quinolin-6-yl)methyl)-N-((3-chloro-6-fluoro-1H-indol-5-yl)methyl)isonicotinamide

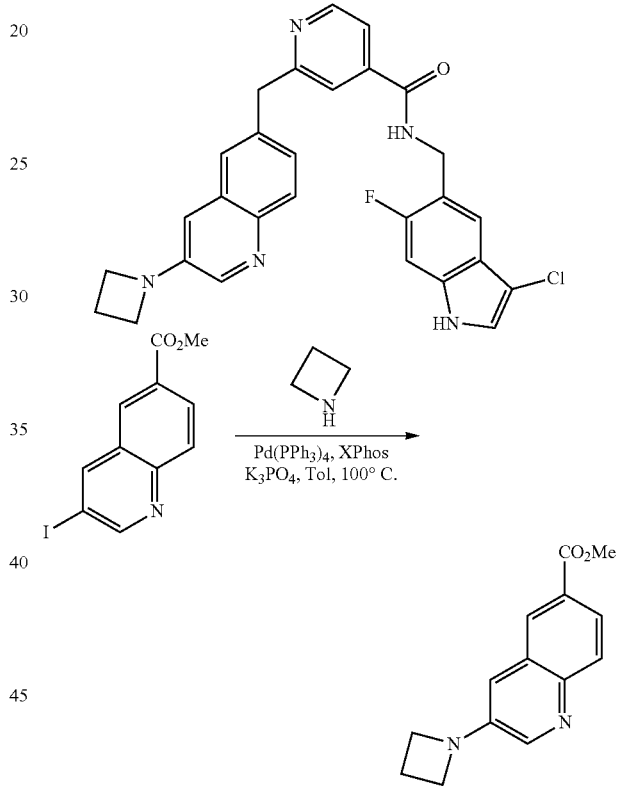

A flame-dried three-necked round-bottomed flask was charged with 3-iodo-quinoline-6-carboxylic acid methyl ester (300 mg, 0.96 mmol), azetidine (3 mL, 47.9 mmol), Pd(PPh$_3$)$_4$ (107 mg, 0.096 mmol), XPhos (45 mg, 0.096 mmol), K$_3$PO$_4$ (5.2 g, 24.5 mmol) and anhydrous toluene (100 mL). The resulting off-white-colored heterogeneous mixture was stirred at 100° C. under N$_2$ for overnight. LC-MS showed that the reaction was complete. The reaction mixture was partitioned between EtOAc (30 mL×3) and water (6 mL). The combined organic portions were dried over anhydrous Na$_2$SO$_4$ and concentrated in vacuo. The resulting residue was purified by chromatography on a silica gel column (PE/EA=6/1 to 2/1, v/v) to give 3-azetidin-1-yl-quinoline-6-carboxylic acid methyl ester as a yellow solid (155 mg, 66% yield).

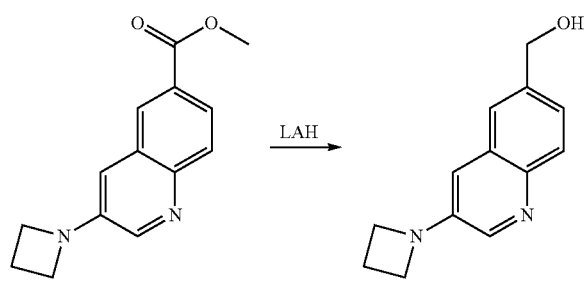 [SMILES: COC(=O)c1ccc2ncc(N3CCC3)cc2c1 ; "LAH" ; OCc1ccc2ncc(N3CCC3)cc2c1]

LAH (1M in THF, 9.1 mL, 9.09 mmol, 1 eq) was added into a solution of 3-azetidin-1-yl-quinoline-6-carboxylic acid methyl ester (2.2 g, 9.09 mmol, 1 eq) in anhydrous THF (100 mL). The resulting suspension was stirred at −5° C. under nitrogen gas for 2 h. After 2 h, LC-MS showed that the reaction was complete. The reaction mixture was quenched with potassium sodium tartrate (15 mL). After quenching the reaction, the mixture was extracted with DCM (10 mL×3). The combined extracts were dried over anhydrous $Na_2SO_4$ and concentrated in vacuo. The resulting residue was purified by chromatography on a silica gel column (PE/EA=6/1 to 3/1, v/v) to give (3-azetidin-1-yl-quinolin-6-yl)-methanol (600 mg, 31%) as a yellow solid.

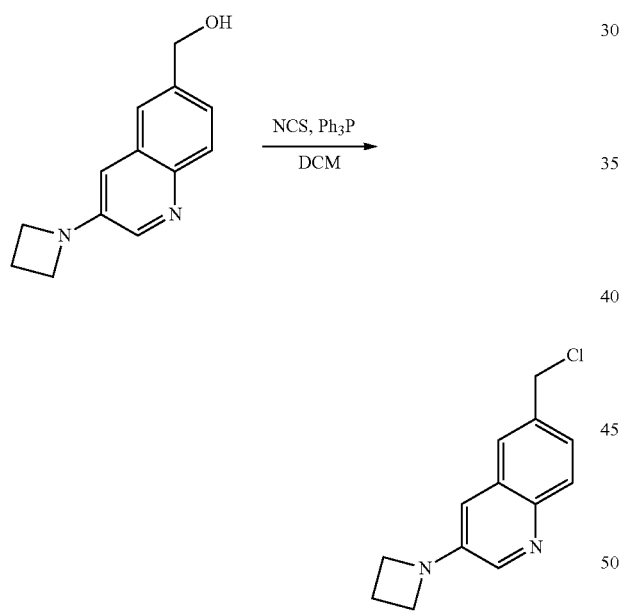

To a solution of (3-azetidin-1-yl-quinolin-6-yl)-methanol (1.1 g, 5.13 mmol, 1.0 eq) in DCM (50 mL) was added $Ph_3P$ (1.6 g, 6.16 mmol, 1.2 eq) and NCS (823 mg, 6.16 mmol, 1.2 eq) at 0° C. The mixture was stirred at rt for 1 h. The mixture was concentrated and the resulting residue was purified by chromatography on a silica gel column (PE/EA=5/1, v/v) to give 3-azetidin-1-yl-6-chloromethyl-quinoline (740 mg, 62%) as a yellow solid.

LRMS (M+H⁺) m/z calculated 233.1, found 233.1. ¹H NMR (DMSO-d₆, 300 MHz): δ 8.34 (d, 1H), 7.83 (d, 1H), 7.76 (d, 1H), 7.45-7.41 (m, 1H), 7.03 (d, 1H), 4.89 (s, 2H), 4.02-3.97 (m, 4H), 2.44-2.35 (m, 2H).

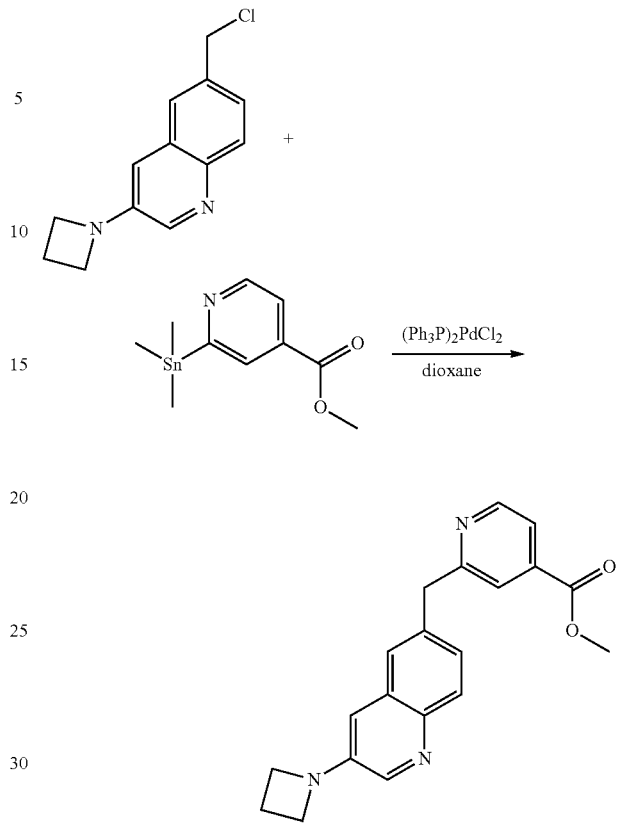

A mixture of 3-azetidin-1-yl-6-chloromethyl-quinoline (740 mg, 3.18 mmol, 1.0 eq), 2-trimethylstannanyl-isonicotinic acid methyl ester (957 mg, 3.18 mmol, 1.0 eq) and $(Ph_3P)_2PdCl_2$ (224 mg, 0.32 mmol, 0.1 eq) in dioxane (40 mL) was stirred at 90° C. overnight. The mixture was concentrated and the resulting residue was purified by chromatography on a silica gel column (PE/EA=3/1 to 1/1, v/v) to give 2-(3-azetidin-1-yl-quinolin-6-ylmethyl)-isonicotinic acid methyl ester (400 mg, 38%) as a yellow oil.

LRMS (M+H⁺) m/z calculated 334.1, found 334.1. ¹H NMR (DMSO-d₆, 300 MHz): δ 8.72 (d, 1H), 8.27 (d, 1H), 7.76 (d, 2H), 7.68-7.67 (m, 1H), 7.63-7.57 (m, 1H), 7.34-7.31 (m, 1H), 6.98 (d, 1H), 4.32 (s, 2H), 4.04-3.95 (m, 4H), 3.86 (s, 3H), 2.40-2.36 (m, 2H).

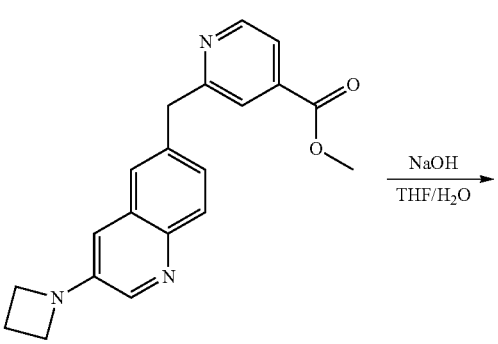

733

-continued

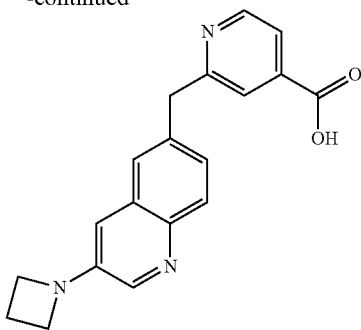

To a solution of 2-(3-azetidin-1-yl-quinolin-6-ylmethyl)-isonicotinic acid methyl ester (400 mg, 1.20 mmol, 1.0 eq) in THF (10 mL) was added a solution of NaOH (72 mg, 1.80 mmol, 1.5 eq) in water (10 mL) at rt. The mixture was stirred at rt for 30 min. Then the solution was neutralized with 1N HCl to pH 3. The mixture was concentrated to give 2-(3-azetidin-1-yl-quinolin-6-ylmethyl)-isonicotinic acid (300 mg, crude) as a yellow solid without further purification.

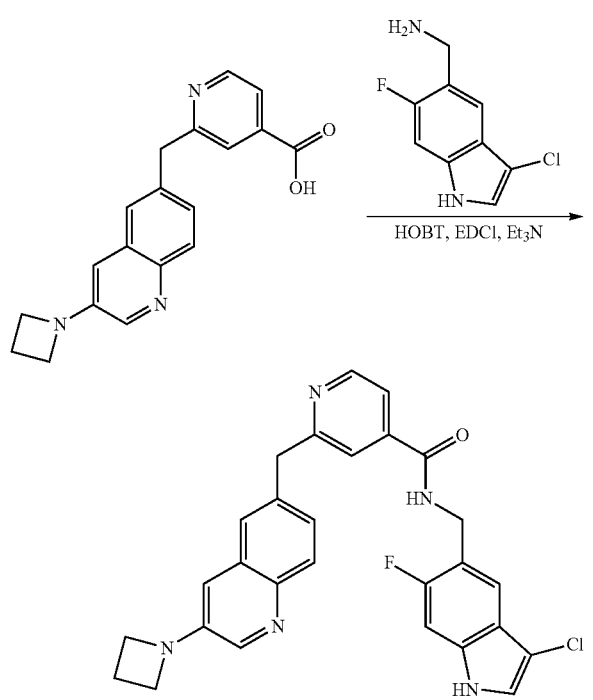

A mixture of 2-(3-azetidin-1-yl-quinolin-6-ylmethyl)-isonicotinic acid (50 mg, 0.16 mmol, 1.0 eq), (3-chloro-6-fluoro-1H-indol-5-yl)methanamine (47 mg, 0.23 mmol, 1.5 eq), HOBT (31 mg, 0.23 mmol, 1.5 eq), EDCI (44 mg, 0.23 mmol, 1.5 eq) and Et₃N (48 mg, 0.48 mmol, 3.0 eq) in DMF (2 mL) was stirred at 30° C. overnight. The mixture was concentrated and the resulting residue was purified by Prep-HPLC to give 2-((3-(azetidin-1-yl)quinolin-6-yl) methyl)-N-((3-chloro-6-fluoro-1H-indol-5-yl)methyl)isonicotinamide (9.0 mg, 11%) as a white solid.

LRMS (M+H⁺) m/z calculated 500.2, found 500.1. ¹H NMR (DMSO-d₆, 400 MHz): δ 11.41 (s, 1H), 9.26-9.24 (m, 1H), 8.64 (d, 1H), 8.28 (d, 1H), 7.77-7.75 (m, 2H), 7.65-7.64 (m, 1H), 7.56 (d, 1H), 7.51 (d, 1H), 7.43 (d, 1H), 7.35-7.32 (m, 1H), 7.23 (d, 1H), 6.99 (d, 1H), 4.57 (d, 2H), 4.27 (s, 2H), 3.99-3.95 (m, 4H), 2.42-2.34 (m, 2H).

Example 321: Preparation of 2-((3-(azetidin-1-yl) quinolin-6-yl)methyl)-N-((3-chloro-4-fluoro-1H-indol-5-yl)methyl)isonicotinamide

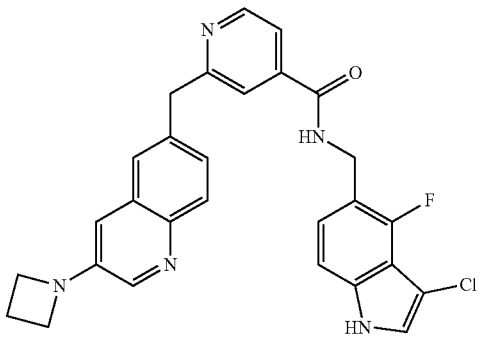 [SMILES: O=C(NCc1ccc2[nH]cc(Cl)c2c1F)c1ccnc(Cc2ccc3ncc(N4CCC4)cc3c2)c1]

A mixture of 2-(3-azetidin-1-yl-quinolin-6-ylmethyl)-isonicotinic acid (50 mg, 0.16 mmol, 1.0 eq), (3-chloro-4-fluoro-1H-indol-5-yl)methanamine (47 mg, 0.23 mmol, 1.5 eq), HOBT (31 mg, 0.23 mmol, 1.5 eq), EDCI (44 mg, 0.23 mmol, 1.5 eq) and Et₃N (48 mg, 0.48 mmol, 3.0 eq) in DMF (2 mL) was stirred at 30° C. overnight. The mixture was concentrated and the resulting residue was purified by Prep-HPLC to give 2-((3-(azetidin-1-yl)quinolin-6-yl) methyl)-N-((3-chloro-4-fluoro-1H-indol-5-yl)methyl)isonicotinamide (21.2 mg, 26%) as a white solid.

LRMS (M+H⁺) m/z calculated 500.2, found 500.1. ¹H NMR (DMSO-d₆, 400 MHz): δ 11.59 (s, 1H), 9.24-9.21 (m, 1H), 8.63 (d, 1H), 8.27 (d, 1H), 7.76-7.74 (m, 2H), 7.63 (d, 1H), 7.55-7.51 (m, 2H), 7.33 (d, 1H), 7.19-7.13 (m, 2H), 6.97 (d, 1H), 4.55 (d, 2H), 4.26 (s, 2H), 3.98-3.95 (m, 4H), 2.45-2.33 (m, 2H).

Example 322: Preparation of 2-((3-(azetidin-1-yl) quinolin-6-yl)methyl)-N-((3-chloro-1H-pyrrolo[2,3-b]pyridin-5-yl)methyl)isonicotinamide

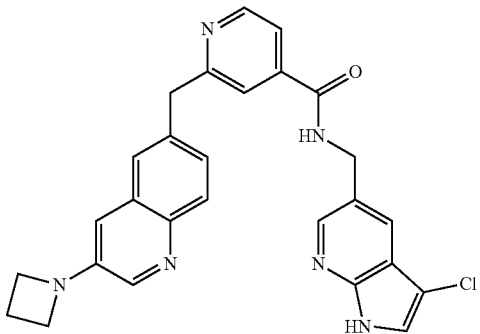 [SMILES: O=C(NCc1cnc2[nH]cc(Cl)c2c1)c1ccnc(Cc2ccc3ncc(N4CCC4)cc3c2)c1]

A mixture of 2-(3-azetidin-1-yl-quinolin-6-ylmethyl)-isonicotinic acid (50 mg, 0.16 mmol, 1.0 eq), (3-chloro-1H-pyrrolo[2,3-b]pyridin-5-yl)methanamine (42 mg, 0.23 mmol, 1.5 eq), HOBT (31 mg, 0.23 mmol, 1.5 eq), EDCI (44 mg, 0.23 mmol, 1.5 eq) and Et₃N (48 mg, 0.48 mmol, 3.0 eq) in DMF (2 mL) was stirred at 30° C. overnight. The mixture was concentrated and the resulting residue was purified by Prep-HPLC to give 2-((3-(azetidin-1-yl)quinolin-6-yl)methyl)-N-((3-chloro-1H-pyrrolo[2,3-b]pyridin-5-yl)methyl)isonicotinamide (26 mg, 34%) as a white solid.

LRMS (M+H⁺) m/z calculated 483.2, found 483.1. ¹H NMR (DMSO-d$_6$, 400 MHz): δ 11.96 (s, 1H), 9.34-9.31 (m, 1H), 8.64 (d, 1H), 8.30 (d, 1H), 8.27 (d, 1H), 7.86 (d, 1H), 7.76-7.74 (m, 2H), 7.68 (d, 1H), 7.63-7.62 (m, 1H), 7.55 (d, 1H), 7.33-7.31 (m, 1H), 6.97 (d, 1H), 4.59 (d, 2H), 4.27 (s, 2H), 3.98-3.95 (m, 4H), 2.42-2.36 (m, 2H).

Example 323: Preparation of N-((1-aminoisoquinolin-6-yl)methyl)-2-((3-(azetidin-1-yl)quinolin-6-yl)methyl)isonicotinamide

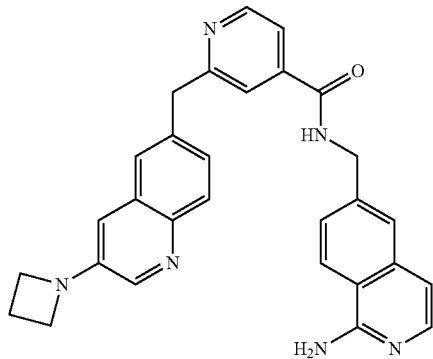 [SMILES: Nc1nccc2cc(CNC(=O)c3ccnc(Cc4ccc5ncc(N6CCC6)cc5c4)c3)ccc12]

A mixture of 2-(3-azetidin-1-yl-quinolin-6-ylmethyl)-isonicotinic acid (50 mg, 0.16 mmol, 1.0 eq), 6-aminomethyl-isoquinolin-1-ylamine (42 mg, 0.23 mmol, 1.5 eq), HOBT (31 mg, 0.23 mmol, 1.5 eq), EDCI (44 mg, 0.23 mmol, 1.5 eq) and Et₃N (48 mg, 0.48 mmol, 3.0 eq) in DMF (2 mL) was stirred at 30° C. overnight. The mixture was concentrated and the resulting residue was purified by Prep-HPLC to give N-((1-aminoisoquinolin-6-yl)methyl)-2-((3-(azetidin-1-yl)quinolin-6-yl)methyl)isonicotinamide (8 mg, 11%) as a white solid.

LRMS (M+H+) m/z calculated 475.2, found 475.2. ¹H NMR (DMSO-d$_6$, 400 MHz): δ 9.39-9.36 (m, 1H), 8.65 (d, 1H), 8.27 (d, 1H), 8.12 (d, 1H), 7.77-7.75 (m, 3H), 7.68-7.66 (m, 1H), 7.55 (d, 2H), 7.39-7.32 (m, 2H), 6.97 (d, 1H), 6.84 (d, 1H), 6.72 (s, 2H), 4.59 (d, 2H), 4.28 (s, 2H), 3.98-3.95 (m, 4H), 2.43-2.36 (m, 2H).

Example 324: Preparation of 2-((3-(azetidin-1-yl)quinolin-6-yl)methyl)-N-((5-chloro-1H-indazol-3-yl)methyl)isonicotinamide

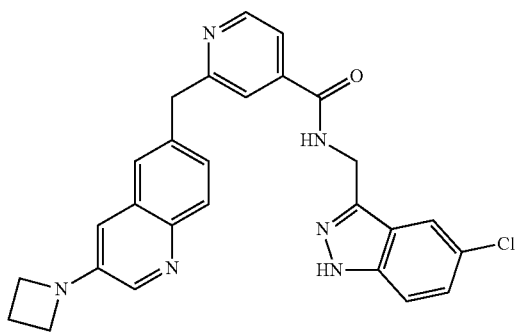 [SMILES: O=C(NCc1n[nH]c2ccc(Cl)cc12)c1ccnc(Cc2ccc3ncc(N4CCC4)cc3c2)c1]

A mixture of 2-(3-azetidin-1-yl-quinolin-6-ylmethyl)-isonicotinic acid (50 mg, 0.16 mmol, 1.0 eq), (5-chloro-1H-indazol-3-yl)methanamine (42 mg, 0.23 mmol, 1.5 eq), HOBT (31 mg, 0.23 mmol, 1.5 eq), EDCI (44 mg, 0.23 mmol, 1.5 eq) and Et₃N (48 mg, 0.48 mmol, 3.0 eq) in DMF (2 mL) was stirred at 30° C. overnight. The mixture was concentrated and the resulting residue was purified by Prep-HPLC to give 2-((3-(azetidin-1-yl)quinolin-6-yl)methyl)-N-((5-chloro-1H-indazol-3-yl)methyl)isonicotinamide (8 mg, 11%) as a white solid.

LRMS (M+H⁺) m/z calculated 492.2, found 492.2. ¹H NMR (DMSO-d$_6$, 400 MHz): δ 13.08 (s, 1H), 9.39-9.37 (m, 1H), 8.62 (d, 1H), 8.27 (d, 1H), 7.89 (d, 1H), 7.76-7.73 (m, 2H), 7.63-7.61 (m, 1H), 7.55-7.52 (m, 2H), 7.35-7.31 (m, 2H), 6.96 (d, 1H), 6.77 (d, 2H), 4.26 (s, 2H), 3.96-3.95 (m, 4H), 2.39-2.36 (m, 2H).

II. Biological Evaluation

Example 1: In Vitro Enzyme Inhibition

The ability of the compounds disclosed herein to inhibit human plasma kallikrein activity was quantified according to the procedures below.

A 10 mM solution of the test compound was made in DMSO. This solution was serially diluted 1:5 in DMSO to yield 2000, 400, 80, 16, 3.2, 0.64, 0.128, 0.0256 and 0.00512 μM compound test solutions. A control tube containing only DMSO is included. 16 μL of each compound test solution was combined with 384 μL of assay buffer (50 mM Tris-HCl pH 7.5, 150 mM NaCl, 0.01% Triton X-100) to yield a "4× test compound buffer stock".

Separately, a 40 nM solution of human Plasma Kallikrein (Abcam) and a 93.6 μM solution Pro-Phe-Arg-AMC (Bachem) were made using assay buffer. These solutions are hereby referred to as 4×hPK and 2×PFR-AMC, respectively.

60 μL of each 4× test compound buffer stock was combined with 60 μL of 4×hPK to yield 120 μL of "2× test compound buffer stock/2×hPK". 50 μL was removed from this mixture and placed into duplicate wells on a Microfluor 1Black U-bottom microtiter plate (Thermo Scientific). This plate was incubated for 5 minutes at 37° C. To each well, 50 L of pre-warmed 2×PFR-AMC was added to start the enzymatic reaction. Cleavage of PFR-AMC was monitored in a Biotek Synergy H4 reader set at 37° C. Readings are taken every 43 seconds for 1 hour. The highest mean velocity over 20 reads (~15 minutes) is used to calculate the IC$_{50}$. The IC$_{50}$ is calculated using the Gen5 (Biotek Instruments).

The ability of the compounds in Table 3 to inhibit human plasma kallikrein activity was determined.

TABLE 3

| Chemical Synthesis Example | Name | hPK IC$_{50}$ |
|---|---|---|
| 1 | 6-((4-(((3-chloro-6-fluoro-1H-indol-5-yl)methyl)carbamoyl)pyridin-2-yl)methyl)quinoline-2-carboxamide | B |
| 2 | 6-((4-(((6-amino-2,4-dimethylpyridin-3-yl)methyl)carbamoyl)pyridin-2-yl)methyl)quinoline-2-carboxamide | B |
| 3 | N-((1-aminoisoquinolin-6-yl)methyl)-2-((2-cyanoquinolin-6-yl)methyl)isonicotinamide | A |
| 4 | 6-((4-(((1-aminoisoquinolin-6-yl)methyl)carbamoyl)pyridin-2-yl)methyl)quinoline-2-carboxamide | B |
| 5 | N-((3-chloro-6-fluoro-1H-indol-5-yl)methyl)-2-((3-cyanoquinolin-6-yl)methyl)isonicotinamide | A |
| 6 | N-((1-aminoisoquinolin-6-yl)methyl)-2-((3-cyanoquinolin-6-yl)methyl)isonicotinamide | A |
| 7 | N-((6-amino-2,4-dimethylpyridin-3-yl)methyl)-2-((3-cyanoquinolin-6-yl)methyl)isonicotinamide | A |
| 8 | N-((1-aminoisoquinolin-6-yl)methyl)-2-((7-fluoroquinoxalin-2-yl)methyl)isonicotinamide | B |
| 9 | 2-((2-(acetamidomethyl)quinolin-6-yl)methyl)-N-((3-chloro-6-fluoro-1H-indol-5-yl)methyl)isonicotinamide | B |
| 10 | 2-((2-(acetamidomethyl)quinolin-6-yl)methyl)-N-((1-aminoisoquinolin-6-yl)methyl)isonicotinamide | B |
| 11 | 2-((2-(acetamidomethyl)quinolin-6-yl)methyl)-N-((6-amino-2,4-dimethylpyridin-3-yl)methyl)isonicotinamide | B |
| 12 | N-((3-chloro-6-fluoro-1H-indol-5-yl)methyl)-2-((6-(methylsulfonyl)quinolin-3-yl)methyl)isonicotinamide | A |
| 13 | N-((1-aminoisoquinolin-6-yl)methyl)-2-((6-(methylsulfonyl)quinolin-3-yl)methyl)isonicotinamide | B |
| 14 | N-((6-amino-2,4-dimethylpyridin-3-yl)methyl)-2-((6-(methylsulfonyl)quinolin-3-yl)methyl)isonicotinamide | B |
| 15 | N-((6-amino-2,4-dimethylpyridin-3-yl)methyl)-2-((3-methyl-8-(methylsulfonyl)quinolin-6-yl)methyl)isonicotinamide | A |
| 16 | N-((1-aminoisoquinolin-6-yl)methyl)-2-((3-methyl-8-(methylsulfonyl)quinolin-6-yl)methyl)isonicotinamide | A |
| 17 | N-((3-chloro-6-fluoro-1H-indol-5-yl)methyl)-2-((3-methyl-8-(methylsulfonyl)quinolin-6-yl)methyl)isonicotinamide | A |
| 18 | N-((6-fluoro-1H-indol-5-yl)methyl)-2-((3-methyl-8-(methylsulfonyl)quinolin-6-yl)methyl)isonicotinamide | A |
| 19 | N-((3-chloro-1H-pyrrolo[2,3-b]pyridin-5-yl)methyl)-2-((3-methyl-8-(methylsulfonyl)quinolin-6-yl)methyl)isonicotinamide | A |
| 20 | N-((5-chloro-1H-indazol-3-yl)methyl)-2-((3-methyl-8-(methylsulfonyl)quinolin-6-yl)methyl)isonicotinamide | A |
| 21 | N-((3-chloro-4-fluoro-1H-indol-5-yl)methyl)-2-((3-methyl-8-(methylsulfonyl)quinolin-6-yl)methyl)isonicotinamide | A |
| 22 | N-((6-amino-2,4-dimethylpyridin-3-yl)methyl)-2-((5-chloro-1-oxoisoquinolin-2(1H)-yl)methyl)isonicotinamide | B |
| 23 | N-((6-amino-2,4-dimethylpyridin-3-yl)methyl)-2-((6-chloro-1-oxoisoquinolin-2(1H)-yl)methyl)isonicotinamide | C |
| 24 | N-((6-amino-2,4-dimethylpyridin-3-yl)methyl)-2-((3-chloro-1H-indol-5-yl)methyl)isonicotinamide | B |
| 25 | N-((6-amino-2,4-dimethylpyridin-3-yl)methyl)-2-((3-methyl-1H-indol-5-yl)methyl)isonicotinamide | B |
| 26 | N-((6-amino-5-cyano-2-methylpyridin-3-yl)methyl)-2-((3-chloroquinolin-6-yl)methyl)isonicotinamide | C |
| 27 | 2-amino-5-((2-((3-chloroquinolin-6-yl)methyl)isonicotinamido)methyl)-6-methylnicotinamide | D |
| 28 | N-((6-amino-5-chloro-2-methylpyridin-3-yl)methyl)-2-((3-chloroquinolin-6-yl)methyl)isonicotinamide | C |
| 29 | N-((6-amino-4-methylpyridin-3-yl)methyl)-2-((3-chloroquinolin-6-yl)methyl)isonicotinamide | A |
| 30 | N-((6-amino-2-(trifluoromethyl)pyridin-3-yl)methyl)-2-((3-chloroquinolin-6-yl)methyl)isonicotinamide | D |
| 31 | N-((1-aminoisoquinolin-6-yl)methyl)-2-((3-chloroquinolin-6-yl)methyl)isonicotinamide | A |
| 32 | 2-((3-chloroquinolin-6-yl)methyl)-N-((6-fluoro-1H-indazol-5-yl)methyl)isonicotinamide | C |
| 33 | N-((3-chloro-6-fluoro-1H-indol-5-yl)methyl)-2-((3-chloroquinolin-6-yl)methyl)isonicotinamide | A |
| 34 | N-((6-amino-2-methylpyridin-3-yl)methyl)-2-((3-chloroquinolin-6-yl)methyl)isonicotinamide | A |
| 35 | N-((6-amino-2,4-dimethylpyridin-3-yl)methyl)-2-((3-chloroquinolin-6-yl)methyl)isonicotinamide | A |
| 36 | N-((3-aminobenzo[d]isoxazol-6-yl)methyl)-2-((3-chloroquinolin-6-yl)methyl)isonicotinamide | C |
| 37 | N-((5-chloro-1H-indazol-3-yl)methyl)-2-((3-chloroquinolin-6-yl)methyl)isonicotinamide | A |
| 38 | N-((3-chloro-1H-pyrrolo[2,3-b]pyridin-5-yl)methyl)-2-((3-chloroquinolin-6-yl)methyl)isonicotinamide | A |

TABLE 3-continued

| Chemical Synthesis Example | Name | hPK IC$_{50}$ |
|---|---|---|
| 39 | N-((6-amino-2-methylpyridin-3-yl)methyl)-2-((3-chloroquinolin-6-yl)methyl)isonicotinamide | A |
| 40 | N-((3-chloro-4-fluoro-1H-indol-5-yl)methyl)-2-((3-chloroquinolin-6-yl)methyl)isonicotinamide | A |
| 41 | 2-((3-chloroquinolin-6-yl)methyl)-N-((6-fluoro-1H-indol-5-yl)methyl)isonicotinamide | A |
| 42 | 2-((3-chloroquinolin-6-yl)methyl)-N-((2-methyl-6-(methylamino)pyridin-3-yl)methyl)isonicotinamide | B |
| 43 | N-((6-amino-2-cyclopropylpyridin-3-yl)methyl)-2-((3-chloroquinolin-6-yl)methyl)isonicotinamide | B |
| 44 | 2-((3-chloroquinolin-6-yl)methyl)-N-((6-(dimethylamino)-2-methylpyridin-3-yl)methyl)isonicotinamide | D |
| 45 | 2-((2-(aminomethyl)quinolin-6-yl)methyl)-N-((3-chloro-6-fluoro-1H-indol-5-yl)methyl)isonicotinamide | B |
| 46 | N-((6-amino-2,4-dimethylpyridin-3-yl)methyl)-2-((2-(aminomethyl)quinolin-6-yl)methyl)isonicotinamide | A |
| 47 | N-((3-aminobenzo[d]isoxazol-6-yl)methyl)-2-((3-methylquinolin-6-yl)methyl)isonicotinamide | C |
| 48 | N-((3-aminobenzo[d]isoxazol-6-yl)methyl)-2-((6-methylquinolin-3-yl)methyl)isonicotinamide | D |
| 49 | N-((3-chloro-6-fluoro-1H-indol-5-yl)methyl)-2-((3-chloro-8-cyanoquinolin-6-yl)methyl)isonicotinamide | A |
| 50 | N-((6-amino-2,4-dimethylpyridin-3-yl)methyl)-2-((3-chloro-8-cyanoquinolin-6-yl)methyl)isonicotinamide | A |
| 51 | N-((3-chloro-4-fluoro-1H-indol-5-yl)methyl)-2-((3-chloro-8-cyanoquinolin-6-yl)methyl)isonicotinamide | A |
| 52 | 2-((3-chloro-8-cyanoquinolin-6-yl)methyl)-N-((6-fluoro-1H-indol-5-yl)methyl)isonicotinamide | A |
| 53 | N-((6-amino-4-methylpyridin-3-yl)methyl)-2-((3-chloro-8-cyanoquinolin-6-yl)methyl)isonicotinamide | B |
| 54 | N-((5-chloro-1H-indazol-3-yl)methyl)-2-((3-chloro-8-cyanoquinolin-6-yl)methyl)isonicotinamide | A |
| 55 | N-((3-chloro-1H-pyrrolo[2,3-b]pyridin-5-yl)methyl)-2-((3-chloro-8-cyanoquinolin-6-yl)methyl)isonicotinamide | A |
| 56 | N-((6-amino-2-methylpyridin-3-yl)methyl)-2-((3-chloro-8-cyanoquinolin-6-yl)methyl)isonicotinamide | A |
| 57 | N-((1-aminoisoquinolin-6-yl)methyl)-2-((3-chloro-8-cyanoquinolin-6-yl)methyl)isonicotinamide | A |
| 58 | 6-((4-(((6-amino-2,4-dimethylpyridin-3-yl)methyl)carbamoyl)pyridin-2-yl)methyl)-3-chloroquinoline-8-carboxamide | A |
| 59 | 3-chloro-6-((4-(((3-chloro-6-fluoro-1H-indol-5-yl)methyl)carbamoyl)pyridin-2-yl)methyl)quinoline-8-carboxamide | A |
| 60 | 3-chloro-6-((4-(((5-chloro-1H-indazol-3-yl)methyl)carbamoyl)pyridin-2-yl)methyl)quinoline-8-carboxamide | A |
| 61 | 3-chloro-6-((4-(((3-chloro-1H-pyrrolo[2,3-b]pyridin-5-yl)methyl)carbamoyl)pyridin-2-yl)methyl)quinoline-8-carboxamide | A |
| 62 | 6-((4-(((6-amino-2-methylpyridin-3-yl)methyl)carbamoyl)pyridin-2-yl)methyl)-3-chloroquinoline-8-carboxamide | A |
| 63 | 6-((4-(((6-amino-4-methylpyridin-3-yl)methyl)carbamoyl)pyridin-2-yl)methyl)-3-chloroquinoline-8-carboxamide | A |
| 64 | 6-((4-(((1-aminoisoquinolin-6-yl)methyl)carbamoyl)pyridin-2-yl)methyl)-3-chloroquinoline-8-carboxamide | A |
| 65 | 3-chloro-6-((4-(((3-chloro-4-fluoro-1H-indol-5-yl)methyl)carbamoyl)pyridin-2-yl)methyl)quinoline-8-carboxamide | A |
| 66 | 3-chloro-6-((4-(((6-fluoro-1H-indol-5-yl)methyl)carbamoyl)pyridin-2-yl)methyl)quinoline-8-carboxamide | A |
| 67 | N-((6-amino-2,4-dimethylpyridin-3-yl)methyl)-2-((3-chloro-8-(methylsulfonyl)quinolin-6-yl)methyl)isonicotinamide | A |
| 68 | N-((3-chloro-6-fluoro-1H-indol-5-yl)methyl)-2-((3-chloro-8-(methylsulfonyl)quinolin-6-yl)methyl)isonicotinamide | A |
| 69 | N-((6-amino-2-methylpyridin-3-yl)methyl)-2-((3-chloro-8-(methylsulfonyl)quinolin-6-yl)methyl)isonicotinamide | A |
| 70 | N-((6-amino-2,4-dimethylpyridin-3-yl)methyl)-2-((8-cyano-3-methylquinolin-6-yl)methyl)isonicotinamide | A |
| 71 | N-((1-aminoisoquinolin-6-yl)methyl)-2-((8-cyano-3-methylquinolin-6-yl)methyl)isonicotinamide | A |
| 72 | N-((3-chloro-6-fluoro-1H-indol-5-yl)methyl)-2-((8-cyano-3-methylquinolin-6-yl)methyl)isonicotinamide | A |
| 73 | N-((3-chloro-1H-pyrrolo[2,3-b]pyridin-5-yl)methyl)-2-((8-cyano-3-methylquinolin-6-yl)methyl)isonicotinamide | A |
| 74 | N-((3-chloro-4-fluoro-1H-indol-5-yl)methyl)-2-((8-cyano-3-methylquinolin-6-yl)methyl)isonicotinamide | A |
| 75 | N-((5-chloro-1H-indazol-3-yl)methyl)-2-((8-cyano-3-methylquinolin-6-yl)methyl)isonicotinamide | A |
| 76 | 2-((8-cyano-3-methylquinolin-6-yl)methyl)-N-((6-fluoro-1H-indol-5-yl)methyl)isonicotinamide | A |

TABLE 3-continued

| Chemical Synthesis Example | Name | hPK IC$_{50}$ |
|---|---|---|
| 77 | 6-((4-(((6-amino-2,4-dimethylpyridin-3-yl)methyl)carbamoyl)pyridin-2-yl)methyl)-3-methylquinoline-8-carboxamide | A |
| 78 | 6-((4-(((3-chloro-6-fluoro-1H-indol-5-yl)methyl)carbamoyl)pyridin-2-yl)methyl)-3-methylquinoline-8-carboxamide | A |
| 79 | 6-((4-(((1-aminoisoquinolin-6-yl)methyl)carbamoyl)pyridin-2-yl)methyl)-3-methylquinoline-8-carboxamide | A |
| 80 | 6-((4-(((3-chloro-1H-pyrrolo[2,3-b]pyridin-5-yl)methyl)carbamoyl)pyridin-2-yl)methyl)-3-methylquinoline-8-carboxamide | A |
| 81 | 6-((4-(((3-chloro-4-fluoro-1H-indol-5-yl)methyl)carbamoyl)pyridin-2-yl)methyl)-3-methylquinoline-8-carboxamide | A |
| 82 | 6-((4-(((5-chloro-1H-indazol-3-yl)methyl)carbamoyl)pyridin-2-yl)methyl)-3-methylquinoline-8-carboxamide | A |
| 83 | 6-((4-(((6-fluoro-1H-indol-5-yl)methyl)carbamoyl)pyridin-2-yl)methyl)-3-methylquinoline-8-carboxamide | A |
| 84 | 6-((4-(((6-amino-2,4-dimethylpyridin-3-yl)methyl)carbamoyl)pyridin-2-yl)methyl)-3-methylquinoline-8-carboxylic acid | A |
| 85 | N-((6-amino-4-methylpyridin-3-yl)methyl)-2-((7-chloro-3-oxoisoquinolin-2(3H)-yl)methyl)isonicotinamide | B |
| 86 | N-((6-amino-2-methylpyridin-3-yl)methyl)-2-((7-chloro-3-oxoisoquinolin-2(3H)-yl)methyl)isonicotinamide | B |
| 87 | N-((6-amino-2,4-dimethylpyridin-3-yl)methyl)-2-((7-chloro-3-oxoisoquinolin-2(3H)-yl)methyl)isonicotinamide | B |
| 88 | 2-((7-chloro-3-oxoisoquinolin-2(3H)-yl)methyl)-N-((3-chloro-6-fluoro-1H-indol-5-yl)methyl)isonicotinamide | B |
| 89 | N-((6-amino-2,4-dimethylpyridin-3-yl)methyl)-2-((3-chloro-8-fluoroquinolin-6-yl)methyl)isonicotinamide | A |
| 90 | N-((3-chloro-6-fluoro-1H-indol-5-yl)methyl)-2-((3-chloro-8-fluoroquinolin-6-yl)methyl)isonicotinamide | A |
| 91 | N-((6-amino-2-methylpyridin-3-yl)methyl)-2-((3-chloro-8-fluoroquinolin-6-yl)methyl)isonicotinamide | A |
| 92 | methyl 6-((4-(((6-amino-2,4-dimethylpyridin-3-yl)methyl)carbamoyl)pyridin-2-yl)methyl)-3-chloroquinoline-8-carboxylate | A |
| 93 | 6-((4-(((6-amino-2,4-dimethylpyridin-3-yl)methyl)carbamoyl)pyridin-2-yl)methyl)-3-chloroquinoline-8-carboxylic acid | A |
| 94 | N-((6-amino-2,4-dimethylpyridin-3-yl)methyl)-2-((3-chloro-8-(hydroxymethyl)quinolin-6-yl)methyl)isonicotinamide | A |
| 95 | methyl 6-((4-(((6-amino-2-methylpyridin-3-yl)methyl)carbamoyl)pyridin-2-yl)methyl)-3-chloroquinoline-8-carboxylate | A |
| 96 | 6-((4-(((6-amino-2-methylpyridin-3-yl)methyl)carbamoyl)pyridin-2-yl)methyl)-3-chloroquinoline-8-carboxylic acid | B |
| 97 | N-((6-amino-2-methylpyridin-3-yl)methyl)-2-((3-chloro-8-(hydroxymethyl)quinolin-6-yl)methyl)isonicotinamide | A |
| 98 | 6-amino-3-((2-((3-chloroquinolin-6-yl)methyl)isonicotinamido)methyl)-2,4-dimethylpyridine 1-oxide | B |
| 99 | 6-((4-(((6-amino-2,4-dimethylpyridin-3-yl)methyl)carbamoyl)pyridin-2-yl)methyl)-3-chloroquinoline 1-oxide | A |
| 100 | N-((6-amino-2,4-dimethylpyridin-3-yl)methyl)-2-((3,8-dichloroquinolin-6-yl)methyl)isonicotinamide | A |
| 101 | N-((6-amino-2-methylpyridin-3-yl)methyl)-2-((3,8-dichloroquinolin-6-yl)methyl)isonicotinamide | A |
| 102 | N-((6-amino-2,4-dimethylpyridin-3-yl)methyl)-2-((3-chloro-5-fluoroquinolin-6-yl)methyl)isonicotinamide | A |
| 103 | N-((6-amino-2-methylpyridin-3-yl)methyl)-2-((3-chloro-5-fluoroquinolin-6-yl)methyl)isonicotinamide | A |
| 104 | N-((6-amino-2,4-dimethylpyridin-3-yl)methyl)-2-((3-chloroquinolin-6-yl)methyl)-6-methylisonicotinamide | A |
| 105 | N-((6-amino-2,4-dimethylpyridin-3-yl)methyl)-2-((5-chloro-1H-indazol-1-yl)methyl)isonicotinamide | A |
| 106 | N-((6-amino-2,4-dimethylpyridin-3-yl)methyl)-2-((5-chloro-2H-indazol-2-yl)methyl)isonicotinamide | A |
| 107 | N-((6-amino-2,4-dimethylpyridin-3-yl)methyl)-2-((5-methyl-2H-indazol-2-yl)methyl)isonicotinamide | B |
| 108 | N-((6-amino-2,4-dimethylpyridin-3-yl)methyl)-2-((5-methyl-1H-indazol-1-yl)methyl)isonicotinamide | A |
| 109 | N-((3-chloro-6-fluoro-1H-indol-5-yl)methyl)-2-((6-methyl-2-(methylsulfonyl)quinolin-3-yl)methyl)isonicotinamide | B |
| 110 | N-((3-chloro-6-fluoro-1H-indol-5-yl)methyl)-2-((2-methylquinolin-6-yl)methyl)isonicotinamide | A |
| 111 | N-((1-aminoisoquinolin-6-yl)methyl)-2-((2-methylquinolin-6-yl)methyl)isonicotinamide | A |
| 112 | N-((6-amino-2-methylpyridin-3-yl)methyl)-2-((2-methylquinolin-6-yl)methyl)isonicotinamide | A |

TABLE 3-continued

| Chemical Synthesis Example | Name | hPK IC$_{50}$ |
|---|---|---|
| 113 | N-((6-amino-2,4-dimethylpyridin-3-yl)methyl)-2-((2-methylquinolin-6-yl)methyl)isonicotinamide | A |
| 114 | N-((6-amino-2,4-dimethylpyridin-3-yl)methyl)-2-((6-methylquinolin-3-yl)methyl)isonicotinamide | A |
| 115 | N-((1-aminoisoquinolin-6-yl)methyl)-2-((6-methylquinolin-3-yl)methyl)isonicotinamide | A |
| 116 | N-((3-chloro-6-fluoro-1H-indol-5-yl)methyl)-2-((6-methylquinolin-3-yl)methyl)isonicotinamide | A |
| 117 | N-((6-amino-2-methylpyridin-3-yl)methyl)-2-((6-methylquinolin-3-yl)methyl)isonicotinamide | A |
| 118 | N-((1-aminoisoquinolin-6-yl)methyl)-2-((6-fluoroquinolin-3-yl)methyl)isonicotinamide | A |
| 119 | N-((6-amino-2,4-dimethylpyridin-3-yl)methyl)-2-((6-fluoroquinolin-3-yl)methyl)isonicotinamide | A |
| 120 | N-((3-chloro-6-fluoro-1H-indol-5-yl)methyl)-2-((6-fluoroquinolin-3-yl)methyl)isonicotinamide | A |
| 121 | N-((6-amino-2-methylpyridin-3-yl)methyl)-2-((6-fluoroquinolin-3-yl)methyl)isonicotinamide | A |
| 122 | N-((6-amino-2,4-dimethylpyridin-3-yl)methyl)-2-((7-fluoroquinolin-3-yl)methyl)isonicotinamide | A |
| 123 | N-((3-chloro-6-fluoro-1H-indol-5-yl)methyl)-2-((7-fluoroquinolin-3-yl)methyl)isonicotinamide | A |
| 124 | N-((1-aminoisoquinolin-6-yl)methyl)-2-((7-fluoroquinolin-3-yl)methyl)isonicotinamide | A |
| 125 | N-((3-chloro-6-fluoro-1H-indol-5-yl)methyl)-2-(quinolin-3-ylmethyl)isonicotinamide | A |
| 126 | N-((3-chloro-6-fluoro-1H-indol-5-yl)methyl)-2-((6-chloroquinolin-3-yl)methyl)isonicotinamide | A |
| 127 | N-((1-aminoisoquinolin-6-yl)methyl)-2-((2-methylquinolin-7-yl)methyl)isonicotinamide | A |
| 128 | N-((3-chloro-6-fluoro-1H-indol-5-yl)methyl)-2-((2-methylquinolin-7-yl)methyl)isonicotinamide | A |
| 129 | N-((6-amino-2,4-dimethylpyridin-3-yl)methyl)-2-((2-methylquinolin-7-yl)methyl)isonicotinamide | B |
| 130 | N-((3-chloro-6-fluoro-1H-indol-5-yl)methyl)-2-((2-isocyanoquinolin-6-yl)methyl)isonicotinamide | A |
| 131 | N-((6-amino-2,4-dimethylpyridin-3-yl)methyl)-2-((2-isocyanoquinolin-6-yl)methyl)isonicotinamide | A |
| 132 | N-((1-aminoisoquinolin-6-yl)methyl)-2-((3-methylisoquinolin-6-yl)methyl)isonicotinamide | A |
| 133 | N-((3-chloro-6-fluoro-1H-indol-5-yl)methyl)-2-((3-methylisoquinolin-6-yl)methyl)isonicotinamide | A |
| 134 | N-((1-aminoisoquinolin-6-yl)methyl)-2-((2-(methylsulfonyl)quinolin-6-yl)methyl)isonicotinamide | B |
| 135 | N-((3-chloro-6-fluoro-1H-indol-5-yl)methyl)-2-((2-(methylsulfonyl)quinolin-6-yl)methyl)isonicotinamide | B |
| 136 | N-((1-aminoisoquinolin-6-yl)methyl)-2-((4-cyanoquinolin-6-yl)methyl)isonicotinamide | A |
| 137 | N-((3-chloro-6-fluoro-1H-indol-5-yl)methyl)-2-((4-cyanoquinolin-6-yl)methyl)isonicotinamide | B |
| 138 | N-((6-amino-2,4-dimethylpyridin-3-yl)methyl)-2-((4-cyanoquinolin-6-yl)methyl)isonicotinamide | A |
| 139 | N-((1-aminoisoquinolin-6-yl)methyl)-2-((7-chloroquinolin-3-yl)methyl)isonicotinamide | A |
| 140 | N-((3-chloro-6-fluoro-1H-indol-5-yl)methyl)-2-((7-chloroquinolin-3-yl)methyl)isonicotinamide | A |
| 141 | N-((6-amino-2,4-dimethylpyridin-3-yl)methyl)-2-((7-chloroquinolin-3-yl)methyl)isonicotinamide | A |
| 142 | N-((1-aminoisoquinolin-6-yl)methyl)-2-((3-methylquinolin-6-yl)methyl)isonicotinamide | A |
| 143 | N-((3-chloro-6-fluoro-1H-indol-5-yl)methyl)-2-((3-methylquinolin-6-yl)methyl)isonicotinamide | A |
| 144 | N-((6-amino-2,4-dimethylpyridin-3-yl)methyl)-2-((3-methylquinolin-6-yl)methyl)isonicotinamide | A |
| 145 | N-((6-amino-2,4-dimethylpyridin-3-yl)methyl)-2-((3-methylisoquinolin-6-yl)methyl)isonicotinamide | A |
| 146 | N-((1-aminoisoquinolin-6-yl)methyl)-2-((2-(aminomethyl)quinolin-6-yl)methyl)isonicotinamide | B |
| 147 | N-((6-amino-2,4-dimethylpyridin-3-yl)methyl)-2-((5-chloro-1H-indol-2-yl)methyl)isonicotinamide | A |
| 148 | N-((6-amino-2,4-dimethylpyridin-3-yl)methyl)-2-((3-chloro-1,7-naphthyridin-6-yl)methyl)isonicotinamide | A |
| 149 | N-((6-amino-2-methylpyridin-3-yl)methyl)-2-((3-chloro-1,7-naphthyridin-6-yl)methyl)isonicotinamide | A |
| 150 | N-((6-amino-2,4-dimethylpyridin-3-yl)methyl)-2-((2-chloro-1H-pyrrolo[2,3-b]pyridin-5-yl)methyl)isonicotinamide | B |

TABLE 3-continued

| Chemical Synthesis Example | Name | hPK IC$_{50}$ |
|---|---|---|
| 151 | N-((6-amino-2,4-dimethylpyridin-3-yl)methyl)-2-((5-(trifluoromethyl)-1H-indol-2-yl)methyl)isonicotinamide | B |
| 152 | N-((6-amino-2,4-dimethylpyridin-3-yl)methyl)-2-((2-(trifluoromethyl)-1H-pyrrolo[2,3-b]pyridin-5-yl)methyl)isonicotinamide | A |
| 153 | N-((6-amino-2,4-dimethylpyridin-3-yl)methyl)-2-((6-chloropyrrolo [1,2-c]pyrimidin-3-yl)methyl)isonicotinamide | A |
| 154 | N-((6-chloro-[1,2,4]triazolo[4,3-a]pyridin-3-yl)methyl)-2-((3-chloroquinolin-6-yl)methyl)isonicotinamide | B |
| 155 | 2-((3-chloroquinolin-6-yl)methyl)-N-((5-methyl-[1,2,3]triazolo[1,5-a]pyridin-3-yl)methyl)isonicotinamide | B |
| 156 | 2-((3-chloroquinolin-6-yl)methyl)-N-((7-methylimidazo[1,5-a]pyridin-1-yl)methyl)isonicotinamide | A |
| 157 | N-((6-chloroimidazo[1,2-a]pyridin-3-yl)methyl)-2-((3-chloroquinolin-6-yl)methyl)isonicotinamide | D |
| 158 | 2-((3-chloroquinolin-6-yl)methyl)-N-((3,7-dimethylimidazo[1,5-a]pyridin-1-yl)methyl)isonicotinamide | B |
| 159 | N-((3,7-dimethylimidazo[1,5-a]pyridin-1-yl)methyl)-2-((3-(trifluoromethyl)quinolin-6-yl)methyl)isonicotinamide | B |
| 160 | 2-((3-chloroquinolin-6-yl)methyl)-N-((7-methyl-3-(trifluoromethyl)imidazo[1,5-a]pyridin-1-yl)methyl)isonicotinamide | D |
| 161 | 2-((3-chloroquinolin-6-yl)methyl)-N-((6-methyl-2,3-dihydro-1H-pyrrolo[2,3-b]pyridin-5-yl)methyl)isonicotinamide | B |
| 162 | N-((6-methyl-2,3-dihydro-1H-pyrrolo[2,3-b]pyridin-5-yl)methyl)-2-((3-(trifluoromethyl)quinolin-6-yl)methyl)isonicotinamide | B |
| 163 | 2-((3-chloroquinolin-6-yl)methyl)-N-((2-methyl-6,7-dihydro-5H-pyrrolo[3,4-b]pyridin-3-yl)methyl)isonicotinamide | D |
| 164 | N-((2-methyl-6,7-dihydro-5H-pyrrolo[3,4-b]pyridin-3-yl)methyl)-2-((3-(trifluoromethyl)quinolin-6-yl)methyl)isonicotinamide | D |
| 165 | N-((6-amino-2-methyl-4-(trifluoromethyl)pyridin-3-yl)methyl)-2-((3-chloroquinolin-6-yl)methyl)isonicotinamide | B |
| 166 | N-((6-amino-4-methoxy-2-methylpyridin-3-yl)methyl)-2-((3-chloroquinolin-6-yl)methyl)isonicotinamide | D |
| 167 | N-((6-amino-4-cyano-2-methylpyridin-3-yl)methyl)-2-((3-chloroquinolin-6-yl)methyl)isonicotinamide | D |
| 168 | N-(4-(aminomethyl)benzyl)-2-((3-chloroquinolin-6-yl)methyl)isonicotinamide | B |
| 169 | N-((6-(aminomethyl)pyridin-3-yl)methyl)-2-((3-chloroquinolin-6-yl)methyl)isonicotinamide | D |
| 170 | N-((5-(aminomethyl)pyridin-2-yl)methyl)-2-((3-chloroquinolin-6-yl)methyl)isonicotinamide | D |
| 171 | N-((6-(aminomethyl)-2,4-dimethylpyridin-3-yl)methyl)-2-((3-chloroquinolin-6-yl)methyl)isonicotinamide | A |
| 172 | N-((6-(aminomethyl)-2,4-dimethylpyridin-3-yl)methyl)-2-((3-(trifluoromethyl)quinolin-6-yl)methyl)isonicotinamide | A |
| 173 | N-((6-(1-aminoethyl)-2,4-dimethylpyridin-3-yl)methyl)-2-((3-chloroquinolin-6-yl)methyl)isonicotinamide | C |
| 174 | N-((6-(2-hydroxypropan-2-yl)-2,4-dimethylpyridin-3-yl)methyl)-2-((3-(trifluoromethyl)quinolin-6-yl)methyl)isonicotinamide | D |
| 175 | 2-((3-chloroquinolin-6-yl)methyl)-N-((4,6-dimethyl-2,3-dihydro-1H-pyrrolo[2,3-b]pyridin-5-yl)methyl)isonicotinamide | A |
| 176 | N-((4,6-dimethyl-2,3-dihydro-1H-pyrrolo[2,3-b]pyridin-5-yl)methyl)-2-((3-(trifluoromethyl)quinolin-6-yl)methyl)isonicotinamide | A |
| 177 | N-((1-amino-5-methylisoquinolin-6-yl)methyl)-2-((3-chloroquinolin-6-yl)methyl)isonicotinamide | A |
| 178 | N-((1-amino-5-fluoroisoquinolin-6-yl)methyl)-2-((3-chloroquinolin-6-yl)methyl)isonicotinamide | A |
| 179 | N-((1-aminoisoquinolin-6-yl)methyl)-2-((3-chloroquinolin-6-yl)methyl)isonicotinamide | A |
| 180 | N-((1-amino-7-fluoroisoquinolin-6-yl)methyl)-2-((3-chloroquinolin-6-yl)methyl)isonicotinamide | A |
| 181 | N-((1-amino-7-methylisoquinolin-6-yl)methyl)-2-((3-chloroquinolin-6-yl)methyl)isonicotinamide | A |
| 182 | N-((1-amino-7-fluoroisoquinolin-6-yl)methyl)-2-((3-(trifluoromethyl)quinolin-6-yl)methyl)isonicotinamide | A |
| 183 | N-((1-amino-7-methylisoquinolin-6-yl)methyl)-2-((3-(trifluoromethyl)quinolin-6-yl)methyl)isonicotinamide | A |
| 184 | N-((1-amino-5-methylisoquinolin-6-yl)methyl)-2-((3-(trifluoromethyl)quinolin-6-yl)methyl)isonicotinamide | A |
| 185 | 2-((3-chloroquinolin-6-yl)methyl)-N-((3-(trifluoromethyl)imidazo[1,5-a]pyridin-6-yl)methyl)isonicotinamide | D |
| 186 | N-((1-amino-3-(trifluoromethyl)imidazo[1,5-a]pyridin-6-yl)methyl)-2-((3-chloroquinolin-6-yl)methyl)isonicotinamide | A |
| 187 | N-((3-aminoimidazo[1,5-a]pyridin-7-yl)methyl)-2-((3-chloroquinolin-6-yl)methyl)isonicotinamide | B |
| 188 | 2-((3-chloroquinolin-6-yl)methyl)-N-((7-methylimidazo[1,5-a]pyridin-6-yl)methyl)isonicotinamide | D |

TABLE 3-continued

| Chemical Synthesis Example | Name | hPK IC$_{50}$ |
|---|---|---|
| 189 | N-((3-chloro-4-methyl-1H-pyrrolo[2,3-b]pyridin-5-yl)methyl)-2-((3-chloroquinolin-6-yl)methyl)isonicotinamide | B |
| 190 | N-((3-chloro-6-methyl-1H-indol-5-yl)methyl)-2-((3-chloroquinolin-6-yl)methyl)isonicotinamide | B |
| 191 | N-((3-chloro-6-methyl-1H-pyrrolo[2,3-b]pyridin-5-yl)methyl)-2-((3-chloroquinolin-6-yl)methyl)isonicotinamide | A |
| 192 | N-((3-chloro-4,6-dimethyl-1H-pyrrolo[2,3-b]pyridin-5-yl)methyl)-2-((3-chloroquinolin-6-yl)methyl)isonicotinamide | B |
| 193 | N-((6-acetamido-2,4-dimethylpyridin-3-yl)methyl)-2-((3-chloroquinolin-6-yl)methyl)isonicotinamide | C |
| 194 | 2-((3-chloroquinolin-6-yl)methyl)-N-((2,4,6-trimethylpyridin-3-yl)methyl)isonicotinamide | C |
| 195 | 2-((3-chloroquinolin-6-yl)methyl)-N-((2,4-dimethyl-5,6,7,8-tetrahydro-1,8-naphthyridin-3-yl)methyl)isonicotinamide | A |
| 196 | N-((6-amino-2,4-dimethylpyridin-3-yl)methyl)-2-((3-chloroquinolin-6-yl)methyl)-6-(5-oxo-4,5-dihydro-1H-1,2,4-triazol-3-yl)isonicotinamide | A |
| 197 | N-((6-amino-2-methylpyridin-3-yl)methyl)-2-((3-chloroquinolin-6-yl)methyl)isonicotinamide | A |
| 198 | N-((6-amino-2,4-dimethylpyridin-3-yl)methyl)-2-((5-chloro-1H-indazol-1-yl)methyl)isonicotinamide | A |
| 199 | N-((6-amino-2,4-dimethylpyridin-3-yl)methyl)-2-((5-chloro-2H-indazol-2-yl)methyl)isonicotinamide | A |
| 200 | N-((6-amino-2,4-dimethylpyridin-3-yl)methyl)-2-((5-methyl-2H-indazol-2-yl)methyl)isonicotinamide | B |
| 201 | N-((6-amino-2,4-dimethylpyridin-3-yl)methyl)-2-((5-methyl-3a,7a-dihydro-1H-indazol-1-yl)methyl)isonicotinamide | A |
| 202 | N-((6-amino-2,4-dimethylpyridin-3-yl)methyl)-2-((5-chloro-1H-pyrazolo[3,4-b]pyridin-1-yl)methyl)isonicotinamide | B |
| 203 | N-((6-amino-2,4-dimethylpyridin-3-yl)methyl)-2-((5-chloro-2H-pyrazolo[3,4-b]pyridin-2-yl)methyl)isonicotinamide | B |
| 204 | N-((6-amino-2,4-dimethylpyridin-3-yl)methyl)-2-((6-chloro-1,8-naphthyridin-3-yl)methyl)isonicotinamide | A |
| 205 | N-((6-amino-2-methylpyridin-3-yl)methyl)-2-((6-chloro-1,8-naphthyridin-3-yl)methyl)isonicotinamide | A |
| 206 | N-((3-chloropyrrolo[1,2-a]pyrimidin-6-yl)methyl)-2-((3-chloroquinolin-6-yl)methyl)isonicotinamide | D |
| 207 | N-((6-amino-2,4-dimethylpyridin-3-yl)methyl)-2-((3-chloroquinolin-6-yl)methyl)-6-cyanoisonicotinamide | A |
| 208 | N$^4$-((6-amino-2,4-dimethylpyridin-3-yl)methyl)-6-((3-chloroquinolin-6-yl)methyl)pyridine-2,4-dicarboxamide | A |
| 209 | 4-((6-amino-2,4-dimethylpyridin-3-yl)methylcarbamoyl)-6-((3-chloroquinolin-6-yl)methyl)picolinic acid | A |
| 210 | N-((6-amino-2,4-dimethylpyridin-3-yl)methyl)-2-((3-chloroquinolin-6-yl)methyl)-6-(2-hydroxypropan-2-yl)isonicotinamide | A |
| 211 | N-((6-amino-2,4-dimethylpyridin-3-yl)methyl)-2-(aminomethyl)-6-((3-chloroquinolin-6-yl)methyl)isonicotinamide | A |
| 212 | N-((6-amino-2,4-dimethylpyridin-3-yl)methyl)-2-((3-chloroquinolin-6-yl)methyl)-6-(hydroxymethyl)isonicotinamide | A |
| 213 | N-((6-amino-2,4-dimethylpyridin-3-yl)methyl)-2-((3-chloroquinolin-6-yl)methyl)-6-(cyanomethyl)isonicotinamide | A |
| 214 | N-((6-amino-2,4-dimethylpyridin-3-yl)methyl)-2-(2-amino-2-oxoethyl)-6-((3-chloroquinolin-6-yl)methyl)isonicotinamide | A |
| 215 | N-((6-amino-2,4-dimethylpyridin-3-yl)methyl)-2-((5-(trifluoromethyl)-1H-pyrrolo[2,3-b]pyridin-2-yl)methyl)isonicotinamide | A |
| 216 | N-((6-amino-2-methylpyridin-3-yl)methyl)-2-((6-chloro-1,8-naphthyridin-3-yl)methyl)-5-cyanoisonicotinamide | B |
| 217 | N-((6-amino-2,4-dimethylpyridin-3-yl)methyl)-2-((8-amino-3-chloroquinolin-6-yl)methyl)isonicotinamide | A |
| 218 | N-((6-amino-2-methylpyridin-3-yl)methyl)-2-((8-amino-3-chloroquinolin-6-yl)methyl)isonicotinamide | A |
| 219 | N-((6-amino-2,4-dimethylpyridin-3-yl)methyl)-2-((3-chloro-8-(2-hydroxypropan-2-yl)quinolin-6-yl)methyl)isonicotinamide | A |
| 220 | N-((6-amino-2-methylpyridin-3-yl)methyl)-2-((3-chloro-8-(2-hydroxypropan-2-yl)quinolin-6-yl)methyl)isonicotinamide | A |
| 221 | N-((3-chloro-6-fluoro-1H-indol-5-yl)methyl)-2-((3-chloro-8-(2-hydroxypropan-2-yl)quinolin-6-yl)methyl)isonicotinamide | A |
| 222 | N-((3-chloro-4-fluoro-1H-indol-5-yl)methyl)-2-((3-chloro-8-(2-hydroxypropan-2-yl)quinolin-6-yl)methyl)isonicotinamide | A |
| 223 | N-((3-chloro-1H-pyrrolo[2,3-b]pyridin-5-yl)methyl)-2-((3-chloro-8-(2-hydroxypropan-2-yl)quinolin-6-yl)methyl)isonicotinamide | A |
| 224 | N-((1-aminoisoquinolin-6-yl)methyl)-2-((3-chloro-8-(2-hydroxypropan-2-yl)quinolin-6-yl)methyl)isonicotinamide | A |
| 225 | N-((5-chloro-1H-indazol-3-yl)methyl)-2-((3-chloro-8-(2-hydroxypropan-2-yl)quinolin-6-yl)methyl)isonicotinamide | A |
| 226 | N-((6-amino-2,4-dimethylpyridin-3-yl)methyl)-2-((6-chloro-7-fluoroquinolin-3-yl)methyl)isonicotinamide | A |

TABLE 3-continued

| Chemical Synthesis Example | Name | hPK IC$_{50}$ |
|---|---|---|
| 227 | N-((6-amino-2-methylpyridin-3-yl)methyl)-2-((6-chloro-7-fluoroquinolin-3-yl)methyl)isonicotinamide | A |
| 228 | N-((6-amino-2,4-dimethylpyridin-3-yl)methyl)-2-((3-(trifluoromethyl)quinolin-6-yl)methyl)isonicotinamide | A |
| 229 | N-((6-amino-2-methylpyridin-3-yl)methyl)-2-((3-(trifluoromethyl)quinolin-6-yl)methyl)isonicotinamide | A |
| 230 | N-((3-chloro-6-fluoro-1H-indol-5-yl)methyl)-2-((3-(trifluoromethyl)quinolin-6-yl)methyl)isonicotinamide | A |
| 231 | N-((3-chloro-1H-pyrrolo[2,3-b]pyridin-5-yl)methyl)-2-((3-(trifluoromethyl)quinolin-6-yl)methyl)isonicotinamide | A |
| 232 | N-((1-aminoisoquinolin-6-yl)methyl)-2-((3-(trifluoromethyl)quinolin-6-yl)methyl)isonicotinamide | A |
| 233 | N-((5-chloro-1H-indazol-3-yl)methyl)-2-((3-(trifluoromethyl)quinolin-6-yl)methyl)isonicotinamide | A |
| 234 | N-((3-chloro-4-fluoro-1H-indol-5-yl)methyl)-2-((3-(trifluoromethyl)quinolin-6-yl)methyl)isonicotinamide | A |
| 235 | N-((6-amino-2,4-dimethylpyridin-3-yl)methyl)-2-((3-chloro-8-sulfamoylquinolin-6-yl)methyl)isonicotinamide | A |
| 236 | N-((6-amino-2-methylpyridin-3-yl)methyl)-2-((3-chloro-8-sulfamoylquinolin-6-yl)methyl)isonicotinamide | A |
| 237 | N-(1-(6-amino-2-methylpyridin-3-yl)ethyl)-2-((3-chloroquinolin-6-yl)methyl)isonicotinamide | C |
| 238 | N-((6-amino-2,4-dimethylpyridin-3-yl)methyl)-2-((3-chloro-2-methylquinolin-6-yl)methyl)isonicotinamide | A |
| 239 | N-((6-amino-2-methylpyridin-3-yl)methyl)-2-((3-chloro-2-methylquinolin-6-yl)methyl)isonicotinamide | A |
| 240 | N-((6-amino-2,4-dimethylpyridin-3-yl)methyl)-2-(3-(5-oxo-4,5-dihydro-1,2,4-oxadiazol-3-yl)benzyl)isonicotinamide | D |
| 241 | N-((6-amino-2,4-dimethylpyridin-3-yl)methyl)-2-((8-(aminomethyl)-3-chloroquinolin-6-yl)methyl)isonicotinamide | A |
| 242 | 2-((3-chloroquinolin-6-yl)methyl)-N-((6-((2-methoxyethyl)amino)-2-methylpyridin-3-yl)methyl)isonicotinamide | B |
| 243 | N-((6-amino-2,4-dimethylpyridin-3-yl)methyl)-2-((3-cyclopropylquinolin-6-yl)methyl)isonicotinamide | A |
| 244 | N-((6-amino-2-methylpyridin-3-yl)methyl)-2-((3-cyclopropylquinolin-6-yl)methyl)isonicotinamide | A |
| 245 | N-((3-chloro-6-fluoro-1H-indol-5-yl)methyl)-2-((3-cyclopropylquinolin-6-yl)methyl)isonicotinamide | A |
| 246 | N-((3-chloro-1H-pyrrolo[2,3-b]pyridin-5-yl)methyl)-2-((3-cyclopropylquinolin-6-yl)methyl)isonicotinamide | A |
| 247 | N-((1-aminoisoquinolin-6-yl)methyl)-2-((3-cyclopropylquinolin-6-yl)methyl)isonicotinamide | A |
| 248 | N-((3-chloro-4-fluoro-1H-indol-5-yl)methyl)-2-((3-cyclopropylquinolin-6-yl)methyl)isonicotinamide | A |
| 249 | N-((5-chloro-1H-indazol-3-yl)methyl)-2-((3-cyclopropylquinolin-6-yl)methyl)isonicotinamide | A |
| 250 | 6-((4-(((6-amino-2,4-dimethylpyridin-3-yl)methyl)carbamoyl)pyridin-2-yl)methyl)quinoline-3-carboxamide | B |
| 251 | 6-((4-(((6-amino-2-methylpyridin-3-yl)methyl)carbamoyl)pyridin-2-yl)methyl)quinoline-3-carboxamide | C |
| 252 | 2-((3-chloroquinolin-6-yl)methyl)-N-((6-((2-hydroxyethyl)amino)-2-methylpyridin-3-yl)methyl)isonicotinamide | D |
| 253 | N-((6-amino-2-methylpyridin-3-yl)methyl)-2-((8-(aminomethyl)-3-chloroquinolin-6-yl)methyl)isonicotinamide | A |
| 254 | N-((6-amino-2,4-dimethylpyridin-3-yl)methyl)-2-((3-isopropylquinolin-6-yl)methyl)isonicotinamide | A |
| 255 | N-((6-amino-2,4-dimethylpyridin-3-yl)methyl)-2-((3-propylquinolin-6-yl)methyl)isonicotinamide | A |
| 256 | N-((6-chloroimidazo[1,2-a]pyrimidin-3-yl)methyl)-2-((3-chloroquinolin-6-yl)methyl)isonicotinamide | D |
| 257 | N-((6-amino-2,4-dimethylpyridin-3-yl)methyl)-2-((3-(hydroxymethyl)quinolin-6-yl)methyl)isonicotinamide | A |
| 258 | N-((6-amino-2-methylpyridin-3-yl)methyl)-2-((3-(hydroxymethyl)quinolin-6-yl)methyl)isonicotinamide | B |
| 259 | 2-((3-chloroquinolin-6-yl)methyl)-N-((6-fluoro-1H-indol-5-yl)methyl)isonicotinamide | B |
| 260 | 2-((3-chloroquinolin-6-yl)methyl)-N-((6-fluoro-1H-indazol-5-yl)methyl)isonicotinamide | C |
| 261 | 2-((3-chloroquinolin-6-yl)methyl)-N-((3-methyl-1H-indazol-5-yl)methyl)isonicotinamide | C |
| 262 | N-((6-amino-2,4-dimethylpyridin-3-yl)methyl)-2-((3-(1-hydroxyethyl)quinolin-6-yl)methyl)isonicotinamide | A |
| 263 | N-((6-amino-2-methylpyridin-3-yl)methyl)-2-((3-(1-hydroxyethyl)quinolin-6-yl)methyl)isonicotinamide | B |
| 264 | N-((6-amino-2,4-dimethylpyridin-3-yl)methyl)-2-((3-methoxyquinolin-6-yl)methyl)isonicotinamide | A |

TABLE 3-continued

| Chemical Synthesis Example | Name | hPK IC$_{50}$ |
|---|---|---|
| 265 | N-((6-amino-2-methylpyridin-3-yl)methyl)-2-((3-methoxyquinolin-6-yl)methyl)isonicotinamide | A |
| 266 | 2-((3-chloroquinolin-6-yl)methyl)-N-((3-methyl-1H-pyrazolo[3,4-b]pyridin-5-yl)methyl)isonicotinamide | C |
| 267 | 2-((3-chloroquinolin-6-yl)methyl)-N-((3-(trifluoromethyl)-1H-indazol-5-yl)methyl)isonicotinamide | C |
| 268 | N-((5-chloro-1H-indol-3-yl)methyl)-2-((3-chloroquinolin-6-yl)methyl)isonicotinamide | B |
| 269 | N-((5-chloro-1H-pyrrolo[2,3-b]pyridin-3-yl)methyl)-2-((3-chloroquinolin-6-yl)methyl)isonicotinamide | C |
| 270 | N-((5-chloro-2-methyl-1H-indol-3-yl)methyl)-2-((3-chloroquinolin-6-yl)methyl)isonicotinamide | B |
| 271 | 2-((3-chloroquinolin-6-yl)methyl)-N-((3-(trifluoromethyl)-1H-pyrazolo[3,4-b]pyridin-5-yl)methyl)isonicotinamide | B |
| 272 | N-((6-amino-2,4-dimethylpyridin-3-yl)methyl)-2-((3-chloro-8-(1H-tetrazol-5-yl)quinolin-6-yl)methyl)isonicotinamide | A |
| 273 | N-((6-amino-2-methylpyridin-3-yl)methyl)-2-((3-chloro-8-(1H-tetrazol-5-yl)quinolin-6-yl)methyl)isonicotinamide | B |
| 274 | N-((6-amino-2,4-dimethylpyridin-3-yl)methyl)-2-(3-chloroquinoline-6-carbonyl)isonicotinamide | B |
| 275 | N-((6-amino-2,4-dimethylpyridin-3-yl)methyl)-2-((3-chloroquinolin-6-yl)(hydroxy)methyl)isonicotinamide | A |
| 276 | 2-[Amino-(3-chloro-quinolin-6-yl)-methyl]-N-(6-amino-2,4-dimethyl-pyridin-3-ylmethyl)-isonicotinamide | A |
| 277 | N-((6-amino-2,4-dimethylpyridin-3-yl)methyl)-2-(1-(3-chloroquinolin-6-yl)-1-hydroxyethyl)isonicotinamide | B |
| 278 | N-((6-amino-2,4-dimethylpyridin-3-yl)methyl)-2-((3-(2,2-difluoroethyl)quinolin-6-yl)methyl)isonicotinamide | A |
| 279 | N-((6-amino-2-methylpyridin-3-yl)methyl)-2-((3-(2,2-difluoroethyl)quinolin-6-yl)methyl)isonicotinamide | A |
| 280 | N-((3-chloro-6-fluoro-1H-indol-5-yl)methyl)-2-((3-ethylquinolin-6-yl)methyl)isonicotinamide | A |
| 281 | N-((3-chloro-1H-pyrrolo[2,3-b]pyridin-5-yl)methyl)-2-((3-ethylquinolin-6-yl)methyl)isonicotinamide | A |
| 282 | N-((3-chloro-4-fluoro-1H-indol-5-yl)methyl)-2-((3-ethylquinolin-6-yl)methyl)isonicotinamide | A |
| 283 | N-((1-aminoisoquinolin-6-yl)methyl)-2-((3-ethylquinolin-6-yl)methyl)isonicotinamide | A |
| 284 | N-((5-chloro-1H-indazol-3-yl)methyl)-2-((3-ethylquinolin-6-yl)methyl)isonicotinamide | A |
| 285 | N-((6-amino-2-methylpyridin-3-yl)methyl)-2-((3-ethylquinolin-6-yl)methyl)isonicotinamide | A |
| 286 | N-((6-amino-2,4-dimethylpyridin-3-yl)methyl)-2-((3-ethylquinolin-6-yl)methyl)isonicotinamide | A |
| 287 | N-((3-chloro-6-fluoro-1H-indol-5-yl)methyl)-2-((3-methyl-8-sulfamoylquinolin-6-yl)methyl)isonicotinamide | A |
| 288 | N-((5-chloro-1H-indazol-3-yl)methyl)-2-((3-methyl-8-sulfamoylquinolin-6-yl)methyl)isonicotinamide | A |
| 289 | N-((1-aminoisoquinolin-6-yl)methyl)-2-((3-methyl-8-sulfamoylquinolin-6-yl)methyl)isonicotinamide | A |
| 290 | N-((3-chloro-4-fluoro-1H-indol-5-yl)methyl)-2-((3-methyl-8-sulfamoylquinolin-6-yl)methyl)isonicotinamide | A |
| 291 | N-((3-chloro-1H-pyrrolo[2,3-b]pyridin-5-yl)methyl)-2-((3-methyl-8-sulfamoylquinolin-6-yl)methyl)isonicotinamide | A |
| 292 | N-((3-chloro-6-fluoro-1H-indol-5-yl)methyl)-2-((3-morpholinoquinolin-6-yl)methyl)isonicotinamide | C |
| 293 | N-((1-aminoisoquinolin-6-yl)methyl)-2-((3-morpholinoquinolin-6-yl)methyl)isonicotinamide | C |
| 294 | N-((3-chloro-1H-pyrrolo[2,3-b]pyridin-5-yl)methyl)-2-((3-morpholinoquinolin-6-yl)methyl)isonicotinamide | C |
| 295 | N-((5-chloro-1H-indazol-3-yl)methyl)-2-((3-morpholinoquinolin-6-yl)methyl)isonicotinamide | C |
| 296 | N-((6-amino-2,4-dimethylpyridin-3-yl)methyl)-2-((3-chloroquinolin-6-yl)(methoxy)methyl)isonicotinamide | A |
| 297 | 2-((3-aminoquinolin-6-yl)methyl)-N-((3-chloro-6-fluoro-1H-indol-5-yl)methyl)isonicotinamide | B |
| 298 | N-((1-aminoisoquinolin-6-yl)methyl)-2-((3-aminoquinolin-6-yl)methyl)isonicotinamide | B |
| 299 | 2-((3-aminoquinolin-6-yl)methyl)-N-((5-chloro-1H-indazol-3-yl)methyl)isonicotinamide | C |
| 300 | 2-((3-aminoquinolin-6-yl)methyl)-N-((3-chloro-1H-pyrrolo[2,3-b]pyridin-5-yl)methyl)isonicotinamide | C |
| 301 | 2-((3-aminoquinolin-6-yl)methyl)-N-((3-chloro-4-fluoro-1H-indol-5-yl)methyl)isonicotinamide | B |
| 302 | N-((3-chloro-6-fluoro-1H-indol-5-yl)methyl)-2-((3-(piperidin-1-yl)quinolin-6-yl)methyl)isonicotinamide | C |

TABLE 3-continued

| Chemical Synthesis Example | Name | hPK IC$_{50}$ |
|---|---|---|
| 303 | N-((1-aminoisoquinolin-6-yl)methyl)-2-((3-(piperidin-1-yl)quinolin-6-yl)methyl)isonicotinamide | C |
| 304 | N-((5-chloro-1H-indazol-3-yl)methyl)-2-((3-(piperidin-1-yl)quinolin-6-yl)methyl)isonicotinamide | |
| 305 | N-((3-chloro-4-fluoro-1H-indol-5-yl)methyl)-2-((3-(piperidin-1-yl)quinolin-6-yl)methyl)isonicotinamide | D |
| 306 | N-((3-chloro-1H-pyrrolo[2,3-b]pyridin-5-yl)methyl)-2-((3-(piperidin-1-yl)quinolin-6-yl)methyl)isonicotinamide | C |
| 307 | N-((3-chloro-6-fluoro-1H-indol-5-yl)methyl)-2-((3-(pyrrolidin-1-yl)quinolin-6-yl)methyl)isonicotinamide | B |
| 308 | N-((1-aminoisoquinolin-6-yl)methyl)-2-((3-(pyrrolidin-1-yl)quinolin-6-yl)methyl)isonicotinamide | A |
| 309 | N-((5-chloro-1H-indazol-3-yl)methyl)-2-((3-(pyrrolidin-1-yl)quinolin-6-yl)methyl)isonicotinamide | B |
| 310 | N-((3-chloro-1H-pyrrolo[2,3-b]pyridin-5-yl)methyl)-2-((3-(pyrrolidin-1-yl)quinolin-6-yl)methyl)isonicotinamide | B |
| 311 | N-((3-chloro-4-fluoro-1H-indol-5-yl)methyl)-2-((3-(pyrrolidin-1-yl)quinolin-6-yl)methyl)isonicotinamide | B |
| 312 | N-((5-chloro-1H-indazol-3-yl)methyl)-2-((3-(piperazin-1-yl)quinolin-6-yl)methyl)isonicotinamide | C |
| 313 | N-((3-chloro-6-fluoro-1H-indol-5-yl)methyl)-2-((3-(piperazin-1-yl)quinolin-6-yl)methyl)isonicotinamide | C |
| 314 | N-((3-chloro-6-fluoro-1H-indol-5-yl)methyl)-2-((8-(2-hydroxypropan-2-yl)-3-methylquinolin-6-yl)methyl)isonicotinamide | A |
| 315 | N-((3-chloro-4-fluoro-1H-indol-5-yl)methyl)-2-((8-(2-hydroxypropan-2-yl)-3-methylquinolin-6-yl)methyl)isonicotinamide | A |
| 316 | N-((3-chloro-1H-pyrrolo[2,3-b]pyridin-5-yl)methyl)-2-((8-(2-hydroxypropan-2-yl)-3-methylquinolin-6-yl)methyl)isonicotinamide | A |
| 317 | N-((5-chloro-1H-indazol-3-yl)methyl)-2-((8-(2-hydroxypropan-2-yl)-3-methylquinolin-6-yl)methyl)isonicotinamide | A |
| 318 | N-((6-amino-2,4-dimethylpyridin-3-yl)methyl)-2-((8-(2-hydroxypropan-2-yl)-3-methylquinolin-6-yl)methyl)isonicotinamide | A |
| 319 | N-((1-aminoisoquinolin-6-yl)methyl)-2-((8-(2-hydroxypropan-2-yl)-3-methylquinolin-6-yl)methyl)isonicotinamide | A |
| 320 | 2-((3-(azetidin-1-yl)quinolin-6-yl)methyl)-N-((3-chloro-6-fluoro-1H-indol-5-yl)methyl)isonicotinamide | A |

Note:
Biochemical assay IC$_{50}$ data are designated within the following ranges:
A: ≤0.10 μM
B: >0.10 μM to ≤1.0 μM
C: >1.0 μM to ≤10 μM
D: >10 μM Example 2: In Vitro Cellular Assay The ability of the compounds disclosed herein to inhibit cellular kallikrein activity was quantified and the respective EC$_{50}$ value was determined.

Materials:

Plasma kallikrein inhibitor C1NH (Athens Research & Technology, Cat#16-16-031509); Ellagic acid (Sigma, E2250); Substrate Z-FR-2-AMC (GL Biochem, Cat#55352); Nunc™ 96-Well Polypropylene MicroWell™ Plates (Nunc, Cat#267342)

Methods:

All dilutions were prepared in an assay buffer comprising 50 mM Tris-HCl pH 7.2, 150 mM NaCl, and 0.01% Triton X-100.

Four fold serial dilutions were prepared from a 107.53 μM plasma kallikrein inhibitor C1NH stock solution, to yield ten solutions with concentrations between 20 μM and 0.76 nM. Similarly, four fold serial dilutions were prepared from 10 mM stock solutions of various test compounds, to yield ten solutions with concentrations between 4 mM and 0.015 M. The ten solutions of the test compounds, prepared by serial dilution, were further diluted 50-fold in the assay buffer.

Human plasma is thawed on ice and centrifuged for 15 min at 4° C. to remove platelets. A 1 mM stock solution of ellagic acid is diluted to 8 μM and mixed with human plasma, after removing platelets, at a ratio of 1:0.8. The mixture of human plasma and ellagic acid was further diluted 32-fold in the assay buffer, to yield the final mixture for use in the inhibition assay.

A 22.5 μL volume of the final mixture of human plasma and ellagic acid was added to a 96-well microwell plate and the plate was incubated for 15 min at 37° C.

The CINH inhibitor at various concentrations, prepared by serial dilutions as described above, were added to the inhibitor control wells. The volume of CINH inhibitor added to each inhibitor control well was 12.5 μL, to yield final concentrations of 5 μM, 1.25 μM, 312.5 nM, 78.125 nM, 19.531 nM, 4.883 nM, 1.221 nM, 0.305 nM, 0.076 nM, and 0.019 nM. Each CINH concentration is tested in duplicates.

The test compounds at various concentrations, also prepared by serial dilutions as described above, are added to the test wells. The volume of test compound added to each test well was 12.5 μL, to yield final concentrations of 20 μM, 5 μM, 1.25 μM, 312.5 nM, 78.125 nM, 19.531 nM, 4.883 nM, 1.221 nM, 0.305 nM, and 0.076 nM. Each test compound concentration was tested in duplicates.

In addition to the inhibitor control and test wells, the 96 well assay plate includes positive control wells which contained the mixture of human plasma and ellagic acid without C1NH inhibitor or test compounds, and background wells which contained neither the mixture of human plasma and ellagic acid nor the test compounds. The total volume of liquid in positive control and background wells was brought up to 35 µL, using the assay buffer.

The assay plate containing C1NH inhibitors and test compounds mixed with human plasma and ellagic acid and appropriate controls was incubated at 37° C. for 5 min. A 10 mM stock solution of substrate Z-FR-2-AMC was diluted to 133.2 µM in the assay buffer, and 15 µL of the diluted substrate was added to each well, to yield a final substrate concentration of 40 M in each well. The reagents were mixed well by shaking the plate gently for 30 sec.

The enzyme reaction was quantified by immediate kinetic reading of the assay plate using excitation/emission wavelengths of 330 nm/440 nm respectively. Fluorescence intensity was recorded for 60 min, using a time interval of 43 sec.

The inhibition activity of the test compounds were evaluated using the $EC_{50}$ values, calculated according to the dose-response curve of the test compounds, fitted using the "log(inhibitor)-response(variable slope)" equation in GraphPadPrism software (GraphPad Software, Inc.).

The percentage inhibition was calculated using the following equation:

$$\text{Inhibition \%} = 100 - \frac{\text{Sample value} - \text{Mean}(BG)}{\text{Mean}(PC) - \text{Mean}(BG)} \times 100$$

where, Mean(BG) is the average value of the fluorescence intensity of the background wells and Mean(PC) is the average value of the fluorescence intensity of the positive control wells.

Table 4 provides the $EC_{50}$ values of various compounds disclosed herein.

TABLE 4

| Chemical Synthesis Example | Name | Contact Assay $EC_{50}$ |
|---|---|---|
| 15 | N-((6-amino-2,4-dimethylpyridin-3-yl)methyl)-2-((3-methyl-8-(methylsulfonyl)quinolin-6-yl)methyl)isonicotinamide | A |
| 16 | N-((1-aminoisoquinolin-6-yl)methyl)-2-((3-methyl-8-(methylsulfonyl)quinolin-6-yl)methyl)isonicotinamide | A |
| 17 | N-((3-chloro-6-fluoro-1H-indol-5-yl)methyl)-2-((3-methyl-8-(methylsulfonyl)quinolin-6-yl)methyl)isonicotinamide | A |
| 18 | N-((6-fluoro-1H-indol-5-yl)methyl)-2-((3-methyl-8-(methylsulfonyl)quinolin-6-yl)methyl)isonicotinamide | B |
| 20 | N-((5-chloro-1H-indazol-3-yl)methyl)-2-((3-methyl-8-(methylsulfonyl)quinolin-6-yl)methyl)isonicotinamide | A |
| 21 | N-((3-chloro-4-fluoro-1H-indol-5-yl)methyl)-2-((3-methyl-8-(methylsulfonyl)quinolin-6-yl)methyl)isonicotinamide | A |
| 31 | N-((1-aminoisoquinolin-6-yl)methyl)-2-((3-chloroquinolin-6-yl)methyl)isonicotinamide | A |
| 33 | N-((3-chloro-6-fluoro-1H-indol-5-yl)methyl)-2-((3-chloroquinolin-6-yl)methyl)isonicotinamide | B |
| 34 | N-((6-amino-2-methylpyridin-3-yl)methyl)-2-((3-chloroquinolin-6-yl)methyl)isonicotinamide | A |
| 35 | N-((6-amino-2,4-dimethylpyridin-3-yl)methyl)-2-((3-chloroquinolin-6-yl)methyl)isonicotinamide | A |
| 38 | N-((3-chloro-1H-pyrrolo[2,3-b]pyridin-5-yl)methyl)-2-((3-chloroquinolin-6-yl)methyl)isonicotinamide | B |
| 40 | N-((3-chloro-4-fluoro-1H-indol-5-yl)methyl)-2-((3-chloroquinolin-6-yl)methyl)isonicotinamide | B |
| 50 | N-((6-amino-2,4-dimethylpyridin-3-yl)methyl)-2-((3-chloro-8-cyanoquinolin-6-yl)methyl)isonicotinamide | A |
| 56 | N-((6-amino-2-methylpyridin-3-yl)methyl)-2-((3-chloro-8-cyanoquinolin-6-yl)methyl)isonicotinamide | B |
| 57 | N-((1-aminoisoquinolin-6-yl)methyl)-2-((3-chloro-8-cyanoquinolin-6-yl)methyl)isonicotinamide | B |
| 58 | 6-((4-(((6-amino-2,4-dimethylpyridin-3-yl)methyl)carbamoyl)pyridin-2-yl)methyl)-3-chloroquinoline-8-carboxamide | A |
| 59 | 3-chloro-6-((4-(((3-chloro-6-fluoro-1H-indol-5-yl)methyl)carbamoyl)pyridin-2-yl)methyl)quinoline-8-carboxamide | B |
| 60 | 3-chloro-6-((4-(((5-chloro-1H-indazol-3-yl)methyl)carbamoyl)pyridin-2-yl)methyl)quinoline-8-carboxamide | B |
| 61 | 3-chloro-6-((4-(((3-chloro-1H-pyrrolo[2,3-b]pyridin-5-yl)methyl)carbamoyl)pyridin-2-yl)methyl)quinoline-8-carboxamide | B |
| 62 | 6-((4-(((6-amino-2-methylpyridin-3-yl)methyl)carbamoyl)pyridin-2-yl)methyl)-3-chloroquinoline-8-carboxamide | A |
| 64 | 6-((4-(((1-aminoisoquinolin-6-yl)methyl)carbamoyl)pyridin-2-yl)methyl)-3-chloroquinoline-8-carboxamide | A |
| 65 | 3-chloro-6-((4-(((3-chloro-4-fluoro-1H-indol-5-yl)methyl)carbamoyl)pyridin-2-yl)methyl)quinoline-8-carboxamide | A |
| 66 | 3-chloro-6-((4-(((6-fluoro-1H-indol-5-yl)methyl)carbamoyl)pyridin-2-yl)methyl)quinoline-8-carboxamide | B |
| 67 | N-((6-amino-2,4-dimethylpyridin-3-yl)methyl)-2-((3-chloro-8-(methylsulfonyl)quinolin-6-yl)methyl)isonicotinamide | A |
| 68 | N-((3-chloro-6-fluoro-1H-indol-5-yl)methyl)-2-((3-chloro-8-(methylsulfonyl)quinolin-6-yl)methyl)isonicotinamide | A |
| 69 | N-((6-amino-2-methylpyridin-3-yl)methyl)-2-((3-chloro-8-(methylsulfonyl)quinolin-6-yl)methyl)isonicotinamide | A |
| 70 | N-((6-amino-2,4-dimethylpyridin-3-yl)methyl)-2-((8-cyano-3-methylquinolin-6-yl)methyl)isonicotinamide | A |

TABLE 4-continued

| Chemical Synthesis Example | Name | Contact Assay $EC_{50}$ |
|---|---|---|
| 71 | N-((1-aminoisoquinolin-6-yl)methyl)-2-((8-cyano-3-methylquinolin-6-yl)methyl)isonicotinamide | A |
| 72 | N-((3-chloro-6-fluoro-1H-indol-5-yl)methyl)-2-((8-cyano-3-methylquinolin-6-yl)methyl)isonicotinamide | B |
| 73 | N-((3-chloro-1H-pyrrolo[2,3-b]pyridin-5-yl)methyl)-2-((8-cyano-3-methylquinolin-6-yl)methyl)isonicotinamide | B |
| 77 | 6-((4-(((6-amino-2,4-dimethylpyridin-3-yl)methyl)carbamoyl)pyridin-2-yl)methyl)-3-methylquinoline-8-carboxamide | A |
| 78 | 6-((4-(((3-chloro-6-fluoro-1H-indol-5-yl)methyl)carbamoyl)pyridin-2-yl)methyl)-3-methylquinoline-8-carboxamide | A |
| 79 | 6-((4-(((1-aminoisoquinolin-6-yl)methyl)carbamoyl)pyridin-2-yl)methyl)-3-methylquinoline-8-carboxamide | A |
| 80 | 6-((4-(((3-chloro-1H-pyrrolo[2,3-b]pyridin-5-yl)methyl)carbamoyl)pyridin-2-yl)methyl)-3-methylquinoline-8-carboxamide | A |
| 81 | 6-((4-(((3-chloro-4-fluoro-1H-indol-5-yl)methyl)carbamoyl)pyridin-2-yl)methyl)-3-methylquinoline-8-carboxamide | B |
| 82 | 6-((4-(((5-chloro-1H-indazol-3-yl)methyl)carbamoyl)pyridin-2-yl)methyl)-3-methylquinoline-8-carboxamide | B |
| 83 | 6-((4-(((6-fluoro-1H-indol-5-yl)methyl)carbamoyl)pyridin-2-yl)methyl)-3-methylquinoline-8-carboxamide | B |
| 84 | 6-((4-(((6-amino-2,4-dimethylpyridin-3-yl)methyl)carbamoyl)pyridin-2-yl)methyl)-3-methylquinoline-8-carboxylic acid | A |
| 89 | N-((6-amino-2,4-dimethylpyridin-3-yl)methyl)-2-((3-chloro-8-fluoroquinolin-6-yl)methyl)isonicotinamide | A |
| 91 | N-((6-amino-2-methylpyridin-3-yl)methyl)-2-((3-chloro-8-fluoroquinolin-6-yl)methyl)isonicotinamide | A |
| 92 | methyl 6-((4-(((6-amino-2,4-dimethylpyridin-3-yl)methyl)carbamoyl)pyridin-2-yl)methyl)-3-chloroquinoline-8-carboxylate | A |
| 93 | 6-((4-(((6-amino-2,4-dimethylpyridin-3-yl)methyl)carbamoyl)pyridin-2-yl)methyl)-3-chloroquinoline-8-carboxylic acid | A |
| 97 | N-((6-amino-2-methylpyridin-3-yl)methyl)-2-((3-chloro-8-(hydroxymethyl)quinolin-6-yl)methyl)isonicotinamide | A |
| 99 | 6-((4-(((6-amino-2,4-dimethylpyridin-3-yl)methyl)carbamoyl)pyridin-2-yl)methyl)-3-chloroquinoline 1-oxide | A |
| 100 | N-((6-amino-2,4-dimethylpyridin-3-yl)methyl)-2-((3,8-dichloroquinolin-6-yl)methyl)isonicotinamide | A |
| 101 | N-((6-amino-2-methylpyridin-3-yl)methyl)-2-((3,8-dichloroquinolin-6-yl)methyl)isonicotinamide | A |
| 102 | N-((6-amino-2,4-dimethylpyridin-3-yl)methyl)-2-((3-chloro-5-fluoroquinolin-6-yl)methyl)isonicotinamide | B |
| 104 | N-((6-amino-2,4-dimethylpyridin-3-yl)methyl)-2-((3-chloroquinolin-6-yl)methyl)-6-methylisonicotinamide | A |
| 110 | N-((3-chloro-6-fluoro-1H-indol-5-yl)methyl)-2-((2-methylquinolin-6-yl)methyl)isonicotinamide | B |
| 111 | N-((1-aminoisoquinolin-6-yl)methyl)-2-((2-methylquinolin-6-yl)methyl)isonicotinamide | B |
| 113 | N-((6-amino-2,4-dimethylpyridin-3-yl)methyl)-2-((2-methylquinolin-6-yl)methyl)isonicotinamide | A |
| 114 | N-((6-amino-2,4-dimethylpyridin-3-yl)methyl)-2-((6-methylquinolin-3-yl)methyl)isonicotinamide | A |
| 115 | N-((1-aminoisoquinolin-6-yl)methyl)-2-((6-methylquinolin-3-yl)methyl)isonicotinamide | A |
| 116 | N-((3-chloro-6-fluoro-1H-indol-5-yl)methyl)-2-((6-methylquinolin-3-yl)methyl)isonicotinamide | B |
| 117 | N-((6-amino-2-methylpyridin-3-yl)methyl)-2-((6-methylquinolin-3-yl)methyl)isonicotinamide | B |
| 118 | N-((1-aminoisoquinolin-6-yl)methyl)-2-((6-fluoroquinolin-3-yl)methyl)isonicotinamide | A |
| 132 | N-((1-aminoisoquinolin-6-yl)methyl)-2-((3-methylisoquinolin-6-yl)methyl)isonicotinamide | B |
| 142 | N-((1-aminoisoquinolin-6-yl)methyl)-2-((3-methylquinolin-6-yl)methyl)isonicotinamide | A |
| 143 | N-((3-chloro-6-fluoro-1H-indol-5-yl)methyl)-2-((3-methylquinolin-6-yl)methyl)isonicotinamide | B |
| 144 | N-((6-amino-2,4-dimethylpyridin-3-yl)methyl)-2-((3-methylquinolin-6-yl)methyl)isonicotinamide | A |
| 145 | N-((6-amino-2,4-dimethylpyridin-3-yl)methyl)-2-((3-methylisoquinolin-6-yl)methyl)isonicotinamide | A |
| 148 | N-((6-amino-2,4-dimethylpyridin-3-yl)methyl)-2-((3-chloro-1,7-naphthyridin-6-yl)methyl)isonicotinamide | A |
| 149 | N-((6-amino-2-methylpyridin-3-yl)methyl)-2-((3-chloro-1,7-naphthyridin-6-yl)methyl)isonicotinamide | A |

TABLE 4-continued

| Chemical Synthesis Example | Name | Contact Assay EC$_{50}$ |
|---|---|---|
| 152 | N-((6-amino-2,4-dimethylpyridin-3-yl)methyl)-2-((2-(trifluoromethyl)-1H-pyrrolo[2,3-b]pyridin-5-yl)methyl)isonicotinamide | B |
| 153 | N-((6-amino-2,4-dimethylpyridin-3-yl)methyl)-2-((6-chloropyrrolo[1,2-c]pyrimidin-3-yl)methyl)isonicotinamide | A |
| 156 | 2-((3-chloroquinolin-6-yl)methyl)-N-((7-methylimidazo[1,5-a]pyridin-1-yl)methyl)isonicotinamide | B |
| 171 | N-((6-(aminomethyl)-2,4-dimethylpyridin-3-yl)methyl)-2-((3-chloroquinolin-6-yl)methyl)isonicotinamide | B |
| 172 | N-((6-(aminomethyl)-2,4-dimethylpyridin-3-yl)methyl)-2-((3-(trifluoromethyl)quinolin-6-yl)methyl)isonicotinamide | A |
| 176 | N-((4,6-dimethyl-2,3-dihydro-1H-pyrrolo[2,3-b]pyridin-5-yl)methyl)-2-((3-(trifluoromethyl)quinolin-6-yl)methyl)isonicotinamide | B |
| 177 | N-((1-amino-5-methylisoquinolin-6-yl)methyl)-2-((3-chloroquinolin-6-yl)methyl)isonicotinamide | A |
| 178 | N-((1-amino-5-fluoroisoquinolin-6-yl)methyl)-2-((3-chloroquinolin-6-yl)methyl)isonicotinamide | A |
| 179 | N-((1-aminoisoquinolin-6-yl)methyl)-2-((3-chloroquinolin-6-yl)methyl)isonicotinamide | A |
| 180 | N-((1-amino-7-fluoroisoquinolin-6-yl)methyl)-2-((3-chloroquinolin-6-yl)methyl)isonicotinamide | B |
| 181 | N-((1-amino-7-methylisoquinolin-6-yl)methyl)-2-((3-chloroquinolin-6-yl)methyl)isonicotinamide | A |
| 182 | N-((1-amino-7-fluoroisoquinolin-6-yl)methyl)-2-((3-(trifluoromethyl)quinolin-6-yl)methyl)isonicotinamide | B |
| 183 | N-((1-amino-7-methylisoquinolin-6-yl)methyl)-2-((3-(trifluoromethyl)quinolin-6-yl)methyl)isonicotinamide | A |
| 184 | N-((1-amino-5-methylisoquinolin-6-yl)methyl)-2-((3-(trifluoromethyl)quinolin-6-yl)methyl)isonicotinamide | A |
| 186 | N-((1-amino-3-(trifluoromethyl)imidazo[1,5-a]pyridin-6-yl)methyl)-2-((3-chloroquinolin-6-yl)methyl)isonicotinamide | A |
| 197 | N-((6-amino-2-methylpyridin-3-yl)methyl)-2-((3-chloroquinolin-6-yl)methyl)isonicotinamide | A |
| 204 | N-((6-amino-2,4-dimethylpyridin-3-yl)methyl)-2-((6-chloro-1,8-naphthyridin-3-yl)methyl)isonicotinamide | A |
| 208 | N$^4$-((6-amino-2,4-dimethylpyridin-3-yl)methyl)-6-((3-chloroquinolin-6-yl)methyl)pyridine-2,4-dicarboxamide | A |
| 209 | 4-((6-amino-2,4-dimethylpyridin-3-yl)methylcarbamoyl)-6-((3-chloroquinolin-6-yl)methyl)picolinic acid | B |
| 210 | N-((6-amino-2,4-dimethylpyridin-3-yl)methyl)-2-((3-chloroquinolin-6-yl)methyl)-6-(2-hydroxypropan-2-yl)isonicotinamide | A |
| 211 | N-((6-amino-2,4-dimethylpyridin-3-yl)methyl)-2-(aminomethyl)-6-((3-chloroquinolin-6-yl)methyl)isonicotinamide | A |
| 212 | N-((6-amino-2,4-dimethylpyridin-3-yl)methyl)-2-((3-chloroquinolin-6-yl)methyl)-6-(hydroxymethyl)isonicotinamide | A |
| 213 | N-((6-amino-2,4-dimethylpyridin-3-yl)methyl)-2-((3-chloroquinolin-6-yl)methyl)-6-(cyanomethyl)isonicotinamide | A |
| 214 | N-((6-amino-2,4-dimethylpyridin-3-yl)methyl)-2-(2-amino-2-oxoethyl)-6-((3-chloroquinolin-6-yl)methyl)isonicotinamide | A |
| 215 | N-((6-amino-2,4-dimethylpyridin-3-yl)methyl)-2-((5-(trifluoromethyl)-1H-pyrrolo[2,3-b]pyridin-2-yl)methyl)isonicotinamide | B |
| 217 | N-((6-amino-2,4-dimethylpyridin-3-yl)methyl)-2-((8-amino-3-chloroquinolin-6-yl)methyl)isonicotinamide | A |
| 219 | N-((6-amino-2,4-dimethylpyridin-3-yl)methyl)-2-((3-chloro-8-(2-hydroxypropan-2-yl)quinolin-6-yl)methyl)isonicotinamide | A |
| 220 | N-((6-amino-2-methylpyridin-3-yl)methyl)-2-((3-chloro-8-(2-hydroxypropan-2-yl)quinolin-6-yl)methyl)isonicotinamide | A |
| 221 | N-((3-chloro-6-fluoro-1H-indol-5-yl)methyl)-2-((3-chloro-8-(2-hydroxypropan-2-yl)quinolin-6-yl)methyl)isonicotinamide | B |
| 222 | N-((3-chloro-4-fluoro-1H-indol-5-yl)methyl)-2-((3-chloro-8-(2-hydroxypropan-2-yl)quinolin-6-yl)methyl)isonicotinamide | B |
| 223 | N-((3-chloro-1H-pyrrolo[2,3-b]pyridin-5-yl)methyl)-2-((3-chloro-8-(2-hydroxypropan-2-yl)quinolin-6-yl)methyl)isonicotinamide | A |
| 224 | N-((1-aminoisoquinolin-6-yl)methyl)-2-((3-chloro-8-(2-hydroxypropan-2-yl)quinolin-6-yl)methyl)isonicotinamide | A |
| 225 | N-((5-chloro-1H-indazol-3-yl)methyl)-2-((3-chloro-8-(2-hydroxypropan-2-yl)quinolin-6-yl)methyl)isonicotinamide | B |
| 226 | N-((6-amino-2,4-dimethylpyridin-3-yl)methyl)-2-((6-chloro-7-fluoroquinolin-3-yl)methyl)isonicotinamide | A |
| 228 | N-((6-amino-2,4-dimethylpyridin-3-yl)methyl)-2-((3-(trifluoromethyl)quinolin-6-yl)methyl)isonicotinamide | A |
| 229 | N-((6-amino-2-methylpyridin-3-yl)methyl)-2-((3-(trifluoromethyl)quinolin-6-yl)methyl)isonicotinamide | A |
| 230 | N-((3-chloro-6-fluoro-1H-indol-5-yl)methyl)-2-((3-(trifluoromethyl)quinolin-6-yl)methyl)isonicotinamide | B |

TABLE 4-continued

| Chemical Synthesis Example | Name | Contact Assay $EC_{50}$ |
|---|---|---|
| 231 | N-((3-chloro-1H-pyrrolo[2,3-b]pyridin-5-yl)methyl)-2-((3-(trifluoromethyl)quinolin-6-yl)methyl)isonicotinamide | B |
| 232 | N-((1-aminoisoquinolin-6-yl)methyl)-2-((3-(trifluoromethyl)quinolin-6-yl)methyl)isonicotinamide | A |
| 234 | N-((3-chloro-4-fluoro-1H-indol-5-yl)methyl)-2-((3-(trifluoromethyl)quinolin-6-yl)methyl)isonicotinamide | B |
| 235 | N-((6-amino-2,4-dimethylpyridin-3-yl)methyl)-2-((3-chloro-8-sulfamoylquinolin-6-yl)methyl)isonicotinamide | A |
| 236 | N-((6-amino-2-methylpyridin-3-yl)methyl)-2-((3-chloro-8-sulfamoylquinolin-6-yl)methyl)isonicotinamide | A |
| 238 | N-((6-amino-2,4-dimethylpyridin-3-yl)methyl)-2-((3-chloro-2-methylquinolin-6-yl)methyl)isonicotinamide | A |
| 239 | N-((6-amino-2-methylpyridin-3-yl)methyl)-2-((3-chloro-2-methylquinolin-6-yl)methyl)isonicotinamide | B |
| 241 | N-((6-amino-2,4-dimethylpyridin-3-yl)methyl)-2-((8-(aminomethyl)-3-chloroquinolin-6-yl)methyl)isonicotinamide | A |
| 243 | N-((6-amino-2,4-dimethylpyridin-3-yl)methyl)-2-((3-cyclopropylquinolin-6-yl)methyl)isonicotinamide | A |
| 244 | N-((6-amino-2-methylpyridin-3-yl)methyl)-2-((3-cyclopropylquinolin-6-yl)methyl)isonicotinamide | A |
| 245 | N-((3-chloro-6-fluoro-1H-indol-5-yl)methyl)-2-((3-cyclopropylquinolin-6-yl)methyl)isonicotinamide | B |
| 246 | N-((3-chloro-1H-pyrrolo[2,3-b]pyridin-5-yl)methyl)-2-((3-cyclopropylquinolin-6-yl)methyl)isonicotinamide | B |
| 247 | N-((1-aminoisoquinolin-6-yl)methyl)-2-((3-cyclopropylquinolin-6-yl)methyl)isonicotinamide | A |
| 248 | N-((3-chloro-4-fluoro-1H-indol-5-yl)methyl)-2-((3-cyclopropylquinolin-6-yl)methyl)isonicotinamide | B |
| 249 | N-((5-chloro-1H-indazol-3-yl)methyl)-2-((3-cyclopropylquinolin-6-yl)methyl)isonicotinamide | B |
| 253 | N-((6-amino-2-methylpyridin-3-yl)methyl)-2-((8-(aminomethyl)-3-chloroquinolin-6-yl)methyl)isonicotinamide | A |
| 254 | N-((6-amino-2,4-dimethylpyridin-3-yl)methyl)-2-((3-isopropylquinolin-6-yl)methyl)isonicotinamide | A |
| 255 | N-((6-amino-2,4-dimethylpyridin-3-yl)methyl)-2-((3-propylquinolin-6-yl)methyl)isonicotinamide | A |
| 264 | N-((6-amino-2,4-dimethylpyridin-3-yl)methyl)-2-((3-methoxyquinolin-6-yl)methyl)isonicotinamide | A |
| 272 | N-((6-amino-2,4-dimethylpyridin-3-yl)methyl)-2-((3-chloro-8-(1H-tetrazol-5-yl)quinolin-6-yl)methyl)isonicotinamide | B |
| 275 | N-((6-amino-2,4-dimethylpyridin-3-yl)methyl)-2-((3-chloroquinolin-6-yl)(hydroxy)methyl)isonicotinamide | B |
| 276 | 2-[Amino-(3-chloro-quinolin-6-yl)-methyl]-N-(6-amino-2,4-dimethyl-pyridin-3-ylmethyl)-isonicotinamide | B |
| 277 | N-((6-amino-2,4-dimethylpyridin-3-yl)methyl)-2-(1-(3-chloroquinolin-6-yl)-1-hydroxyethyl)isonicotinamide | B |
| 278 | N-((6-amino-2,4-dimethylpyridin-3-yl)methyl)-2-((3-(2,2-difluoroethyl)quinolin-6-yl)methyl)isonicotinamide | A |
| 279 | N-((6-amino-2-methylpyridin-3-yl)methyl)-2-((3-(2,2-difluoroethyl)quinolin-6-yl)methyl)isonicotinamide | B |
| 283 | N-((1-aminoisoquinolin-6-yl)methyl)-2-((3-ethylquinolin-6-yl)methyl)isonicotinamide | A |
| 286 | N-((6-amino-2,4-dimethylpyridin-3-yl)methyl)-2-((3-ethylquinolin-6-yl)methyl)isonicotinamide | A |
| 287 | N-((3-chloro-6-fluoro-1H-indol-5-yl)methyl)-2-((3-methyl-8-sulfamoylquinolin-6-yl)methyl)isonicotinamide | A |
| 288 | N-((5-chloro-1H-indazol-3-yl)methyl)-2-((3-methyl-8-sulfamoylquinolin-6-yl)methyl)isonicotinamide | B |
| 289 | N-((1-aminoisoquinolin-6-yl)methyl)-2-((3-methyl-8-sulfamoylquinolin-6-yl)methyl)isonicotinamide | A |
| 290 | N-((3-chloro-4-fluoro-1H-indol-5-yl)methyl)-2-((3-methyl-8-sulfamoylquinolin-6-yl)methyl)isonicotinamide | B |
| 291 | N-((3-chloro-1H-pyrrolo[2,3-b]pyridin-5-yl)methyl)-2-((3-methyl-8-sulfamoylquinolin-6-yl)methyl)isonicotinamide | A |

Note:
Assay $EC_{50}$ data are designated within the following ranges:
A: ≤0.10 μM
B: >0.10 μM to ≤1.0 μM
C: >1.0 μM to ≤10 μM
D: >10 μM III. Preparation of Pharmaceutical Dosage Forms Example 1: Oral Tablet A tablet is prepared by mixing 48% by weigh of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound, or a pharmaceutically acceptable salt thereof, having the structure of Formula (I):

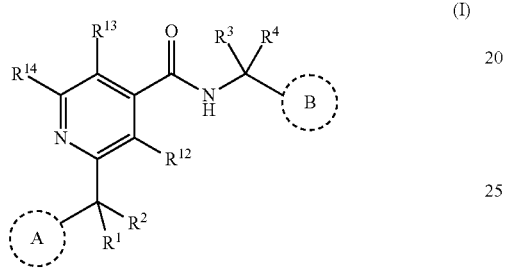

(I)

wherein,
Ring A is an optionally substituted bicyclic heteroaryl ring selected from optionally substituted quinolyl, optionally substituted indolyl, optionally substituted indazolyl, optionally substituted benzimidazolyl, optionally substituted isoquinolyl, optionally substituted cinnolinyl, optionally substituted phthalazinyl, optionally substituted quinazolinyl, optionally substituted naphthyridinyl, or optionally substituted benzoisoxazolyl;

Ring B is an optionally substituted monocyclic heteroaryl ring selected from optionally substituted imidazolyl, optionally substituted pyrazolyl, optionally substituted pyridinyl, optionally substituted pyridazinyl, optionally substituted pyrimidinyl, or optionally substituted pyrazinyl; or optionally substituted bicyclic heteroaryl ring selected from optionally substituted quinolinyl, optionally substituted isoquinolinyl, optionally substituted quinazolinyl, optionally substituted indolyl, optionally substituted indazolyl, optionally substituted 1H-pyrrolo[2,3-b]pyridinyl, optionally substituted benzoxazolyl, optionally substituted benzoisoxazolyl, or optionally substituted benzimidazolyl;

$R^{12}$ is hydrogen;

$R^{13}$ is selected from cyano, halo, hydroxy, azido, amino, nitro, —$CO_2H$, —$S(O)$—$R^{20}$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl;

$R^{14}$ is selected from hydrogen, cyano, halo, hydroxy, azido, amino, nitro, —$CO_2H$, —$S(O)$—$R^{20}$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl;

each $R^1$ or $R^2$ is independently selected from hydrogen, halo, hydroxy, amino, —$CO_2H$, —$S(O)$—$R^{20}$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl; or optionally, $R^1$ and $R^2$ are optionally substituted C1-C5 alkyl and join to form a ring; or optionally, $R^1$ and $R^2$ together form an oxo;

each $R^3$ or $R^4$ is independently selected from hydrogen, —$CO_2H$, optionally substituted alkyl, optionally substituted cycloalkyl, optionally substituted alkenyl, optionally substituted aryl, optionally substituted heteroaryl, optionally substituted heterocyclyl, —CO—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl; or optionally, $R^3$ and $R^4$ are optionally substituted C1-C5 alkyl and join to form a ring;

each $R^{20}$ is selected from optionally substituted alkyl, optionally substituted cycloalkyl, optionally substituted aryl, optionally substituted heteroaryl, or optionally substituted heterocyclyl;

each $R^{21}$ is selected from hydrogen, optionally substituted alkyl, optionally substituted cycloalkyl, optionally substituted aryl, optionally substituted heteroaryl, or optionally substituted heterocyclyl; and each $R^{22}$ is selected from hydrogen, —CN, optionally substituted alkyl, optionally substituted cycloalkyl, optionally substituted aryl, optionally substituted heteroaryl, or optionally substituted heterocyclyl.

2. The compound of claim 1, or a pharmaceutically acceptable salt thereof, wherein $R^{14}$ is hydrogen.

3. The compound of claim 1, or a pharmaceutically acceptable salt thereof, wherein $R^{14}$ is independently selected from —$S(O)$—$R^{20}$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, or —$C(=NR^{22})$—$(NR^{21})_2$.

4. The compound of claim 1, or a pharmaceutically acceptable salt thereof, wherein $R^{14}$ is independently selected from optionally substituted alkyl, optionally substituted cycloalkyl, optionally substituted alkenyl, optionally substituted aryl, optionally substituted heteroaryl, optionally substituted heterocyclyl, or optionally substituted alkynyl.

5. The compound of claim 1, or a pharmaceutically acceptable salt thereof, wherein $R^{14}$ is optionally substituted alkyl, or optionally substituted cycloalkyl.

6. The compound of claim 1, or a pharmaceutically acceptable salt thereof, wherein $R^{13}$ is independently selected from $-S(O)-R^{20}$, $-S-R^{20}$, $-S(O)_2-R^{20}$, optionally substituted alkoxy, optionally substituted aryloxy, optionally substituted heteroaryloxy, optionally substituted (heterocyclyl)-O—, optionally substituted heteroaryl, optionally substituted heterocyclyl, optionally substituted alkylamino, optionally substituted dialkylamino, $-CO-R^{20}$, $-CO_2-R^{20}$, $-CO(NR^{21})_2$, $-SO_2(NR^{21})_2$, or $-C(=NR^{22})-(NR^{21})_2$.

7. The compound of claim 1, or a pharmaceutically acceptable salt thereof, wherein $R^{13}$ is independently selected from optionally substituted alkyl, optionally substituted cycloalkyl, optionally substituted alkenyl, optionally substituted aryl, optionally substituted heteroaryl, optionally substituted heterocyclyl, or optionally substituted alkynyl.

8. The compound of claim 1, or a pharmaceutically acceptable salt thereof, wherein $R^{13}$ is optionally substituted alkyl.

9. The compound of claim 1, or a pharmaceutically acceptable salt thereof, wherein $R^{13}$ is optionally substituted cycloalkyl.

10. The compound of claim 1, or a pharmaceutically acceptable salt thereof, wherein $R^3$ and $R^4$ are hydrogen.

11. The compound of claim 1, or a pharmaceutically acceptable salt thereof, wherein $R^3$ is hydrogen.

12. The compound of claim 1, or a pharmaceutically acceptable salt thereof, wherein $R^4$ is hydrogen.

13. The compound of claim 1, or a pharmaceutically acceptable salt thereof, wherein $R^3$ is optionally substituted alkyl.

14. The compound of claim 1, or a pharmaceutically acceptable salt thereof, wherein $R^4$ is optionally substituted alkyl.

15. The compound of claim 1, or a pharmaceutically acceptable salt thereof, wherein $R^1$ and $R^2$ are hydrogen.

16. The compound of claim 1, or a pharmaceutically acceptable salt thereof, wherein $R^1$ is hydrogen.

17. The compound of claim 1, or a pharmaceutically acceptable salt thereof, wherein $R^2$ is hydrogen.

18. The compound of claim 1, or a pharmaceutically acceptable salt thereof, wherein $R^1$ is optionally substituted alkyl.

19. The compound of claim 1, or a pharmaceutically acceptable salt thereof, wherein $R^2$ is optionally substituted alkyl.

20. The compound of claim 1, or a pharmaceutically acceptable salt thereof, wherein $R^1$ is optionally substituted alkoxy.

21. The compound of claim 1, or a pharmaceutically acceptable salt thereof, wherein $R^2$ is optionally substituted alkoxy.

22. The compound of claim 1, or a pharmaceutically acceptable salt thereof, wherein Ring A is selected from optionally substituted benzo[d]isoxazol-7-yl, optionally substituted 4-aminoquinazolin-5-yl, optionally substituted indol-5-yl; optionally substituted quinolin-3-yl; quinoxalin-2-yl; optionally substituted isoquinolin-1(2H)-on-2-yl; or optionally substituted quinolin-6-yl.

23. The compound of claim 1, or a pharmaceutically acceptable salt thereof, wherein Ring A is an optionally substituted quinolin-6-yl.

24. The compound of claim 23, or a pharmaceutically acceptable salt thereof, wherein the optionally substituted quinolin-6-yl is substituted with at least one substituent selected from optionally substituted C1-C3 alkyl, halogen, $-CN$, $-SO_2Me$, $-SO_2NH_2$, $-CONH_2$, $-CH_2NHAc$, $-CO_2Me$, $-CO_2H$, $-CH_2OH$, $-CH_2NH_2$, $-NH_2$, $-OH$, or $-OMe$.

25. The compound of claim 23, or a pharmaceutically acceptable salt thereof, wherein the optionally substituted quinolin-6-yl is substituted at least at the 3-position.

26. The compound of claim 25, or a pharmaceutically acceptable salt thereof, wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl.

27. The compound of claim 1, or a pharmaceutically acceptable salt thereof, wherein Ring A is an optionally substituted quinolin-3-yl.

28. The compound of claim 27, or a pharmaceutically acceptable salt thereof, wherein the optionally substituted quinolin-3-yl is substituted at least at the 6-position or the 7-position.

29. The compound of claim 27, or a pharmaceutically acceptable salt thereof, wherein the optionally substituted quinolin-3-yl is substituted with at least one substituent selected from optionally substituted C1-C3 alkyl, halogen, $-CN$, $-SO_2Me$, $-SO_2NH_2$, $-CONH_2$, $-CH_2NHAc$, $-CO_2Me$, $-CO_2H$, $-CH_2OH$, $-CH_2NH_2$, $-NH_2$, $-OH$, or $-OMe$.

30. The compound of claim 1, or a pharmaceutically acceptable salt thereof, wherein Ring B is an optionally substituted pyridinyl.

31. The compound of claim 30, or a pharmaceutically acceptable salt thereof, wherein the optionally substituted pyridinyl is an optionally substituted aminopyridinyl.

32. The compound of claim 31, or a pharmaceutically acceptable salt thereof, wherein the optionally substituted aminopyridinyl is an optionally substituted 6-aminopyridin-3-yl.

33. The compound of claim 1, or a pharmaceutically acceptable salt thereof, wherein Ring A is selected from optionally substituted quinol-3-yl; and Ring B is selected from an optionally substituted 6-aminopyridin-3-yl.

34. The compound of claim 1, or a pharmaceutically acceptable salt thereof, wherein Ring B is an optionally substituted indolyl.

35. The compound of claim 1, or a pharmaceutically acceptable salt thereof, wherein Ring B is an optionally substituted indazolyl.

36. The compound of claim 34, or a pharmaceutically acceptable salt thereof, wherein the optionally substituted indolyl is an optionally substituted indol-5-yl.

37. The compound of claim 35, or a pharmaceutically acceptable salt thereof, wherein the optionally substituted indazolyl is an optionally substituted indazol-5-yl.

38. The compound of claim 1, or a pharmaceutically acceptable salt thereof, wherein Ring B is an optionally substituted 1H-pyrrolo[2,3-b]pyridinyl.

39. The compound of claim 1, or a pharmaceutically acceptable salt thereof, wherein Ring A is selected from optionally substituted quinolyl; and Ring B is selected from an optionally substituted indolyl, an optionally substituted indazolyl, and an optionally substituted 1H-pyrrolo[2,3-b]pyridinyl.

40. A pharmaceutical composition comprising a compound of Formula (I) as described in claim 1, or a pharmaceutically acceptable salt thereof, and a pharmaceutically acceptable excipient.

41. A method of inhibiting kallikrein enzyme comprising contacting the kallikrein enzyme with a compound of Formula (I) as described in claim 1.

42. A method for treating angioedema in a patient in need thereof comprising administering to the patient a composition comprising a compound of Formula (I) as described in claim 1, or a pharmaceutically acceptable salt thereof.

* * * * *